US009725453B2

(12) United States Patent
Bursavich et al.

(10) Patent No.: US 9,725,453 B2
(45) Date of Patent: Aug. 8, 2017

(54) IMIDAZOTRIAZINONE COMPOUNDS

(71) Applicant: Ironwood Pharmaceuticals, Inc., Cambridge, MA (US)

(72) Inventors: Matthew Gregory Bursavich, Needham, MA (US); Andrew J. McRiner, Winchester, MA (US); Amy Ripka, Reading, MA (US); Gideon Shapiro, Gainesville, FL (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/490,036

(22) Filed: Sep. 18, 2014

(65) Prior Publication Data

US 2015/0191476 A1 Jul. 9, 2015

Related U.S. Application Data

(63) Continuation of application No. PCT/US2013/031516, filed on Mar. 14, 2013.

(60) Provisional application No. 61/612,866, filed on Mar. 19, 2012.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .................................................. C07D 487/00
See application file for complete search history.

(56) References Cited

U.S. PATENT DOCUMENTS

| | | | |
|---|---|---|---|
| 2004/0067945 A1 | 4/2004 | Niewohner et al. | |
| 2004/0220186 A1 | 11/2004 | Bell et al. | |
| 2004/0254187 A1 | 12/2004 | Alonso-Alija et al. | |
| 2006/0264624 A1 | 11/2006 | Heim-Riether et al. | |
| 2009/0030003 A1 | 1/2009 | Verhoest et al. | |
| 2009/0163521 A1 | 6/2009 | Tadiparthi et al. | |
| 2011/0183976 A1 | 7/2011 | Ripka et al. | |
| 2012/0157458 A1 | 6/2012 | Ripka et al. | |
| 2014/0330014 A1 | 11/2014 | Chesworth et al. | |

FOREIGN PATENT DOCUMENTS

| | | | |
|---|---|---|---|
| EP | 039051 A2 | 11/1981 | |
| JP | 2005535646 A | 11/2005 | |
| WO | WO-03037432 A1 | 5/2003 | |
| WO | WO-2004078163 A2 | 9/2004 | |
| WO | WO-2004096811 A1 | 11/2004 | |
| WO | WO-2008139293 A1 | 11/2008 | |
| WO | PCT/CN2012/070718 | 1/2012 | |
| WO | WO-2012/040230 A1 | 3/2012 | |
| WO | PCT/CN2012/080208 | 8/2012 | |
| WO | WO-2013110768 A1 | 8/2013 | |
| WO | WO-2013142269 A1 | 9/2013 | |

OTHER PUBLICATIONS

Fisher et al., "Isolation and Characterization of PDE9A, a Novel Human cGMP-specific Phosphodiesterase," The Journal of Biological Chemistry, vol. 273, No. 25, Dec. 22, 1997 (pp. 15559-15564).
Hutson et al., "The Selective Phosphodiesterase 9 (PDE9) Inhibitor PF-04447943 (6[3S,4S)-4-methyl-1-(pyrimidin-2ylmethyl)pyrrolidon-3-yl]-1-(tetrahydro-2H-pyran-4-yl)-1,5-dihydro-4H-pyrazolo[3,4-d]pyrimidin-4-one) Enhances Synaptic Plasticity and Cognitive Function in Rodents," Neuropharmacology, May 2011 (pp. 665-676).
International Search Report and Written Opinion issued by the United States Patent and Trademark Office as Searching Authority for International Application No. PCT/US13/31516 mailed May 24, 2013 (32 pages).
International Search Report and Written Opinion issued by the United States Patent and Trademark Office as Searching Authority for International Application No. PCT/US2011/052399 mailed Nov. 24, 2011 (11 pages).
Lazorthes et al., "Advances and Technical Standards in Neurosurgery," vol. 18, Springer-Verlag, Wien New York, No Month Listed 1991 (52 pages).
Minto et al., "Pharmacokinetics and Pharmacodynamics of Nandrolone Esters in Oil Vehicle: Effects of Ester, Injection Site and Injection Volume," The Journal of Pharmacology and Experimetnal Therapeutics, vol. 281, No. 1, No Month Listed 1997 (11 pages).
Ommaya, "Implantable Devices for Chronic Access and Drug Delivery to the Central Nervous System," Cancer Drug Delivery, vol. 1 No. 2, No Month Listed 1984 (12 pages).
Van Der Staay et al., "The Novel Selective PDE9 Inhibitor BAY 73-6691 Improves Learning and Memory in Rodents," Nueropharmacology, Jul. 4, 2008 (pp. 908-918).
Wermuth, "Molecular Variations Based on Isosteric Replacements," Practice of Medicinal Chemistry XP-002190259, No Month Listed 1996 (pp. 203-237).
Extended European Search Report issued by the European Patent Office for Application No. 13763450.7 dated Aug. 21, 2015 (6 pages ).

*Primary Examiner* — Paul V Ward
(74) *Attorney, Agent, or Firm* — McCarter & English, LLP; Steven G. Davis; Xin Zhang

(57) ABSTRACT

The present invention provides imidazotriazinone compounds which are inhibitors of phosphodiesterase 9 and pharmaceutically acceptable salt thereof. The present invention further provides processes, pharmaceutical compositions, pharmaceutical preparations and pharmaceutical use of the compounds in the treatment of PDE9 associated diseases or disorders in mammals, including humans.

2 Claims, No Drawings

IMIDAZOTRIAZINONE COMPOUNDS

RELATED APPLICATION

This application is a continuation of International Application PCT/US2013/31516 filed Mar. 14, 2013, which claims priority to U.S. Provisional Application Ser. No. 61/612,866, filed on Mar. 19, 2012, the entire disclosures of which are expressly incorporated by reference herein in their entirety.

BACKGROUND OF THE INVENTION

The phosphodiesterases (PDEs) are a superfamily of enzymes with eleven members encoded by 21 genes that regulate intracellular cyclic nucleotide signaling (i.e., cyclic adenosine monophosphate (cAMP) and cyclic guanosine monophosphate (cGMP)). The PDEs contain a variable N-terminal regulatory domain and a highly conserved C-terminal catalytic domain and differ in their substrate specificity, expression and localization in cellular and tissue compartments, including the CNS. In neurons these cyclic nucleotides serve as second messengers in the signaling cascade of G-protein coupled receptors and lead to the activation of kinases which, in turn, will phosphorylate proteins involved in the regulation of synaptic transmission and homeostasis.

The PDE9 enzyme selectively hydrolyzes cGMP over cAMP and has the highest affinity of any PDE for cGMP, $K_m$ ~170 nM (Fisher et al., *Journal of Biological Chemistry* 1998, 273 (25), 15559-15564). PDE9 is found to be present in a variety of human tissues including prostate, colon, small intestine, spleen, kidney, brain and skeletal muscle. Specifically, PDE9 mRNA is found in the hippocampal formation further suggesting a role in learning and memory. Studies have also implicated cGMP pathways in synaptic plasticity. In PDE9 knockout mice, long term potentiation (LTP) is enhanced suggesting that PDE9 inhibition can improve learning and memory. Indeed, a selective PDE9 inhibitor was shown to potentiate LTP at the Schaeffer collateral/CA1 synapse, a region of the hippocampus known to be involved in learning and memory (Van der Staay et al., *Neuropharmacology*, 2008, 55 (5), 908-918; Huttson et al., *Neuropharmacology*, 2011, 61 (4), 665-676). In multiple studies, selective PDE9 inhibitors were effective in attenuating the deficits observed in passive avoidance, novel object recognition, social recognition, and T-maze behavioral assays (Van der Staay et al., *Neuropharmacology*, 2008, 55 (5), 908-918). Furthermore, in two studies, neurite outgrowth, a measure of synaptic plasticity, was increased following PDE9 inhibition (Huttson et al., *Neuropharmacology*, 2011, 61 (4), 665-676; Menitti, ICAD, 2009). Overall the data suggest that modulation of neuronal cGMP via inhibition of PDE9 can alter synaptic processes including learning and memory.

As such, there remains a strong need for novel PDE9 inhibitors for use in increasing synaptic plasticity and synaptic processes, for example, involved in learning, memory, as well as CNS diseases or disorders related to modulation of cGMP levels.

SUMMARY OF THE INVENTION

The present invention provides imidazotriazinone compounds and pharmaceutical acceptable salts thereof which are inhibitors of phosphodiesterase 9. The present invention further provides processes, pharmaceutical compositions, pharmaceutical preparations and pharmaceutical use of the compounds or pharmaceutical acceptable salts thereof in the treatment of PDE9 associated diseases or disorders in mammals, including human(s). In particular embodiments, the compounds of the invention are useful for treating central nervous system (CNS) diseases and disorders, as well as other disorders that may affect CNS function, which are related to the modulation of cGMP levels. In a specific embodiment, the compounds of the invention are useful for treating diseases or disorders that would benefit from increased synaptic plasticity and synaptic processes, including learning and memory.

Accordingly, one aspect of the invention provides compounds of Formula (I)

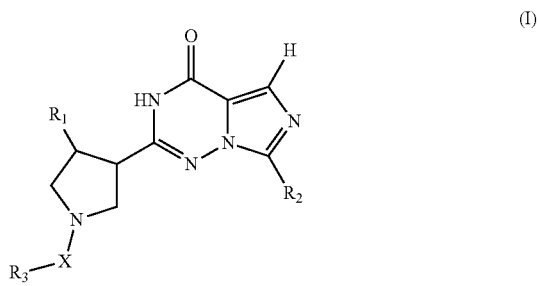

or a pharmaceutically acceptable salt thereof,
wherein:

X is selected from the group consisting of a bond, C(O) and $S(O)_2$;

$R_1$ is independently selected from the group consisting of H, $(C_1-C_6)$ alkyl, $(C_1-C_6)$ alkoxy, $(C_3-C_7)$ cycloalkyl, $(C_3-C_7)$ cycloalkyl$(C_1-C_4)$ alkyl, $(C_3-C_7)$ cycloalkyloxy, heterocycloalkyl, heterocycloalkyl$(C_1-C_4)$alkyl and heterocycloalkyloxy, each of which may be optionally substituted with one or more substituents selected from the group consisting of halogen, $—S(O)_2(C_1-C_4)$alkyl, OH, —C(O)—$(C_1-C_4)$alkyl, oxo, CN, $(C_1-C_6)$alkyl, $(C_1-C_4)$alkoxy, $(C_3-C_7)$cycloalkyl, —C(O)NH$(C_1-C_4)$alkyl, —C(O)N[$(C_1-C_4)$alkyl$(C_1-C_4)$alkyl], $(C_1-C_4$ alkyl)-C(O)—, $(C_1-C_4)$alkylsulfonyl, —S(O)$_2$NH$(C_1-C_4)$alkyl, and —S(O)$_2$N[$(C_1-C_4)$alkyl$(C_1-C_4)$alkyl];

$R_2$ is independently selected from the group consisting of $(C_1-C_6)$ alkyl, $(C_3-C_{10})$cycloalkyl, $(C_3-C_7)$cycloalkyl$(C_1-C_4)$ alkyl, heterocycloalkyl, heterocycloalkyl$(C_1-C_4)$alkyl, heteroaryl, heteroaryl$(C_1-C_4)$alkyl, restricted phenyl and restricted phenyl$(C_1-C_4)$alkyl, each of which may be optionally substituted with one or more substituents selected from the group consisting of halogen, $—S(O)_2(C_1-C_4)$alkyl, OH, —C(O)—$(C_1-C_4)$alkyl, oxo, CN, $(C_1-C_6)$alkyl, $(C_1-C_4)$ alkoxy, $(C_3-C_7)$cycloalkyl, —C(O)NH$(C_1-C_4)$alkyl, —C(O)N[$(C_1-C_4)$alkyl$(C_1-C_4)$alkyl], $(C_1-C_4$ alkyl)-C(O)—, $(C_1-C_4)$alkylsulfonyl, —S(O)$_2$NH$(C_1-C_4)$alkyl, and —S(O)$_2$N[$(C_1-C_4)$alkyl$(C_1-C_4)$alkyl]; and $R_3$ is independently selected from the group consisting of $(C_1-C_6)$ alkyl, $(C_3-C_7)$ cycloalkyl, $(C_3-C_7)$cycloalkyl$(C_1-C_4)$alkyl, heterocycloalkyl, heterocycloalkyl$(C_1-C_4)$alkyl, heteroaryl, heteroaryl$(C_1-C_4)$alkyl, restricted phenyl and restricted phenyl$(C_1-C_4)$alkyl, each of which may be optionally substituted with one or more substituents selected from the group consisting of halogen, $—S(O)_2(C_1-C_4)$alkyl, OH, —C(O)—$(C_1-C_4)$alkyl, oxo, CN, $(C_1-C_6)$alkyl, $(C_1-C_4)$ alkoxy, $(C_3-C_7)$cycloalkyl, —C(O)NH$(C_1-C_4)$alkyl, —C(O)N$[(C_1-C_4)$alkyl$(C_1-C_4)$alkyl$]$, $(C_1-C_4$ alkyl$)$-C(O)—, $(C_1-C_4)$alkylsulfonyl, —S(O)$_2$NH$(C_1-C_4)$alkyl, and —S(O)$_2$N$[(C_1-C_4)$alkyl$(C_1-C_4)$alkyl$]$.

In some embodiments, the substituents are selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, $R_1$ is selected from the group consisting of $(C_1-C_6)$ alkyl (e.g., methyl).

In some embodiments, $R_2$ is selected from the group consisting of heterocycloalkyl, $(C_3-C_{10})$cycloalkyl, and restricted phenyl, which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy. In some embodiments, the heterocycloalkyl is tetrahydropyranyl or piperidinyl, which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, $R_3$ is selected from the group consisting of a mono or bicyclic heteroaryl$(C_1-C_4)$alkyl and restricted phenyl$(C_1-C_4)$alkyl, which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, $R_3$ is pyrimidinylmethyl-, which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, $R_3$ is (restricted phenyl)methyl-, which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, X is a bond.

In some embodiments, each occurrence of halogen is, independently, F, Cl, Br or I.

Another aspect of the invention provides a compound of Formula (I)

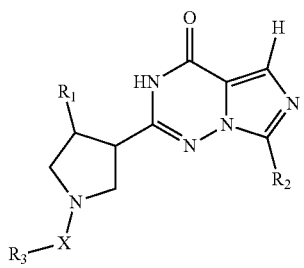

or a pharmaceutically acceptable salt thereof, wherein:
X is selected from the group consisting of a bond, C(O) and S(O)$_2$;
$R_1$ is $(C_1-C_6)$ alkyl;
$R_2$ is selected from the group consisting of heterocycloalkyl, $(C_3-C_{10})$cycloalkyl, e.g., adamantyl, and restricted phenyl, each of which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy; and $R_3$ is selected from the group consisting of a mono or bicyclic heteroaryl$(C_1-C_4)$alkyl and restricted phenyl$(C_1-C_4)$alkyl, each of which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, X is a bond.
In some embodiments, $R_1$ is methyl.
In some embodiments, the heterocycloalkyl is tetrahydropyranyl or piperidinyl, which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, $R_3$ is pyrimidinylmethyl-, which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, $R_3$ is (restricted phenyl)methyl-, which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, each occurrence of halogen is, independently, F or Cl.

In another aspect, the invention provides a compound of Formula (I)

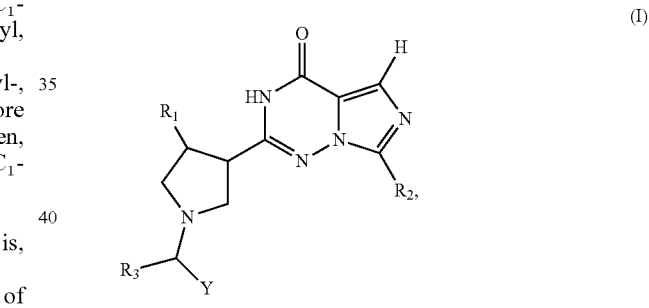

or a pharmaceutically acceptable salt thereof, wherein:
Y is H or $(C_1-C_3)$ alkyl;
$R_1$ is $(C_1-C_6)$ alkyl;
$R_2$ is selected from the group consisting of heterocycloalkyl, $(C_3-C_{10})$cycloalkyl, e.g., adamantyl, and restricted phenyl, each of which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy; and $R_3$ is selected from the group consisting of a mono or bicyclic heteroaryl and restricted phenyl, each of which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, Y is H.
In some embodiments, $R_1$ is methyl.
In some embodiments, the heterocycloalkyl is tetrahydropyranyl or piperidinyl, which may be optionally substituted with one or more substituents selected from the group consisting of halogen, —S(O)$_2(C_1-C_4)$alkyl, OH, —C(O)—$(C_1-C_4)$alkyl, CN, $(C_1-C_6)$alkyl, and $(C_1-C_4)$alkoxy.

In some embodiments, each occurrence of halogen is, independently, F or Cl.

In some embodiments, $R_3$ is pyrimidinyl, which may be optionally substituted with one or more substituents selected from the group consisting of halogen, —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

In some embodiments, $R_3$ is restricted phenyl, which may be optionally substituted with one or more substituents selected from the group consisting of halogen, —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

In some embodiments, $R_3$ is pyrimidinylmethyl-, which may be optionally substituted with one or more substituents selected from the group consisting of halogen, —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

In some embodiments, $R_3$ is (restricted phenyl)methyl-, which may be optionally substituted with one or more substituents selected from the group consisting of halogen, —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

In yet another aspect, the present invention provides a compound selected from the group consisting of:

(−)-2-((3,4-trans)-1-benzyl-4-methylpyrrolidin-3-yl)-7-(tetrahydro-2H-pyran-4-yl)imidazo[1,5-f][1,2,4]triazin-4(3H)-one;

(+)-2-((3,4-trans)-1-benzyl-4-methylpyrrolidin-3-yl)-7-(tetrahydro-2H-pyran-4-yl)imidazo[1,5-f][1,2,4]triazin-4(3H)-one;

(+)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one;

(+)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;

(−)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;

(+)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;

(+)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one;

(+)-7-((1s,3R)-adamantan-1-yl)-2-((3,4-trans)-1-benzyl-4-methylpyrrolidin-3-yl)imidazo[5,1-f][1,2,4]triazin-4(3H)-one;

(−)-7-((1s,3R)-adamantan-1-yl)-2-((3,4-trans)-1-benzyl-4-methylpyrrolidin-3-yl)imidazo[5,1-f][1,2,4]triazin-4(3H)-one;

(−)-2-((3,4-trans)-1-benzyl-4-methylpyrrolidin-3-yl)-7-(5-chloro-2-methylphenyl)imidazo[5,1-f][1,2,4]triazin-4(3H)-one;

(+)-2-((3,4-trans)-1-benzyl-4-methylpyrrolidin-3-yl)-7-(5-chloro-2-methylphenyl)imidazo[5,1-f][1,2,4]triazin-4(3H)-one;

(+)-2-((3,4-trans)-1-benzyl-4-methylpyrrolidin-3-yl)-7-(4-fluoro-2-methylphenyl)imidazo[5,1-f][1,2,4]triazin-4(3H)-one;

(−)-2-((3,4-trans)-1-benzyl-4-methylpyrrolidin-3-yl)-7-(4-fluoro-2-methylphenyl)imidazo[5,1-f][1,2,4]triazin-4(3H)-one;

(+)-2-((3,4-trans)-1-benzyl-4-methylpyrrolidin-3-yl)-7-(4,4-difluorocyclohexyl)imidazo[5,1-f][1,2,4]triazin-4(3H)-one;

(−)-2-((3,4-trans)-1-benzyl-4-methylpyrrolidin-3-yl)-7-(4,4-difluorocyclohexyl)imidazo[5,1-f][1,2,4]triazin-4(3H)-one;

(−)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one;

(−)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one;

(+)-7-((1s,3R)-adamantan-1-yl)-2-((3,4-trans)-4-methyl-1-(pyrimidin-2-ylmethyl)pyrrolidin-3-yl)imidazo[5,1-f][1,2,4]triazin-4(3H)-one;

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 1;

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 2;

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 3;

(+)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one;

(−)-7-(4-fluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one;

(+)-7-(4,4-difluorocyclohexyl)-2-((3,4-trans)-4-methyl-1-(pyrimidin-2-ylmethyl)pyrrolidin-3-yl)imidazo[5,1-f][1,2,4]triazin-4(3H)-one;
(−)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one;
(+)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one;
(−)-7-(5-chloro-2-methylphenyl)-2-((3,4-trans)-4-methylpyrrolidin-3-yl)imidazo[5,1-f][1,2,4]triazin-4(3H)-one;
(+)-2-((3,4-trans)-1-benzyl-4-methylpyrrolidin-3-yl)-7-(furan-3-yl)imidazo[5,1-f][1,2,4]triazin-4(3H)-one;
(−)-2-((3,4-trans)-1-benzyl-4-methylpyrrolidin-3-yl)-7-(furan-3-yl)imidazo[5,1-f][1,2,4]triazin-4(3H)-one;
(−)-7-(1-acetylpiperidin-4-yl)-2-((3,4-trans)-1-benzyl-4-methylpyrrolidin-3-yl)imidazo[5,1-f][1,2,4]triazin-4(3H)-one;
(+)-7-(1-acetylpiperidin-4-yl)-2-((3,4-trans)-1-benzyl-4-methylpyrrolidin-3-yl)imidazo[5,1-f][1,2,4]triazin-4(3H)-one
(−)-2-((3,4-trans)-1-benzyl-4-methylpyrrolidin-3-yl)-7-(2-hydroxypropan-2-yl)imidazo[5,1-f][1,2,4]triazin-4(3H)-one;
(+)-2-((3,4-trans)-1-benzyl-4-methylpyrrolidin-3-yl)-7-(2-hydroxypropan-2-yl)imidazo[5,1-f][1,2,4]triazin-4(3H)-one;
(+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one;
(−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one;
(−)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one
(+)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one;
(+)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one; (−)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one;
or a pharmaceutically acceptable salt thereof.

In one aspect, compounds having Formula (I), or a pharmaceutically acceptable salt thereof, are featured:

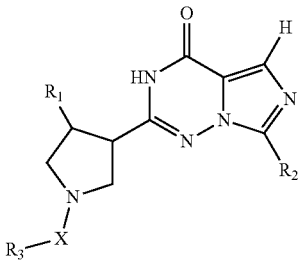

or a pharmaceutically acceptable salt thereof, wherein:
X is selected from the group consisting of a bond, C(O) and S(O)$_2$;

$R_1$ is selected from the group consisting of:
(i) $(C_1-C_6)$ alkyl, which is optionally substituted with one or more $R^a$;
(ii) $(C_1-C_6)$haloalkyl, which is optionally substituted with one or more $R^a$;
(iii) $(C_1-C_6)$ alkoxy, which is optionally substituted with one or more $R^a$;
(iv) $(C_3-C_7)$ cycloalkyl, which is optionally substituted with one or more $R^b$;
(v) $(C_3-C_7)$ cycloalkyl$(C_1-C_4)$ alkyl, wherein the alkyl portion is optionally substituted with one or more $R^{a'}$, and the cycloalkyl portion is optionally substituted with one or more $R^b$;
(vi) $(C_3-C_7)$ cycloalkyloxy, which is optionally substituted with one or more $R^b$;
(vii) heterocycloalkyl, which is optionally substituted with one or more $R^b$;
(viii) heterocycloalkyl$(C_1-C_4)$alkyl, wherein the alkyl portion is optionally substituted with one or more $R^{a'}$, and the cycloalkyl portion is optionally substituted with one or more $R^b$; and
(ix) heterocycloalkyloxy, which is optionally substituted with one or more $R^b$;

$R_2$ is selected from the group consisting of:
(i) heterocycloalkyl, which is optionally substituted with one or more $R^c$;
(ii) heterocycloalkyl$(C_1-C_4)$alkyl, wherein the alkyl portion is optionally substituted with one or more $R^{d'}$, and the cycloalkyl portion is optionally substituted with one or more $R^c$;
(iii) $(C_3-C_7)$ cycloalkyl, which is optionally substituted with one or more $R^c$;
(iv) $(C_3-C_7)$ cycloalkyl$(C_1-C_4)$ alkyl, wherein the alkyl portion is optionally substituted with one or more $R^{d'}$, and the cycloalkyl portion is optionally substituted with one or more $R^c$;
(v) phenyl, which is optionally substituted with one or more $R^e$;
(vi) phenyl$(C_1-C_4)$alkyl, wherein the alkyl portion is optionally substituted with one or more $R^{d'}$, and the phenyl portion is optionally substituted with one or more $R^e$;
(vii) heteroaryl, which is optionally substituted with one or more $R^e$;
(viii) heteroaryl$(C_1-C_4)$alkyl, wherein the alkyl portion is optionally substituted with one or more $R^{d'}$, and the heteroaryl portion is optionally substituted with one or more $R^e$;
(ix) $(C_1-C_6)$ alkyl, which is optionally substituted with one or more $R^d$; and
(x) $(C_1-C_6)$haloalkyl, which is optionally substituted with one or more $R^d$;

$R_3$ is selected from the group consisting of:
(i) heteroaryl, which is optionally substituted with one or more $R^f$;
(ii) heteroaryl$(C_1-C_4)$alkyl, wherein the alkyl portion is optionally substituted with one or more $R^{g'}$, and the heteroaryl portion is optionally substituted with one or more $R^f$;
(iii) phenyl, which is optionally substituted with one or more $R^f$;
(iv) phenyl$(C_1-C_4)$alkyl, wherein the alkyl portion is optionally substituted with one or more $R^{g'}$, and the phenyl portion is optionally substituted with one or more $R^f$;
(v) $(C_3-C_7)$ cycloalkyl, which is optionally substituted with one or more $R^h$;

(vi) ($C_3$-$C_7$) cycloalkyl($C_1$-$C_4$) alkyl, wherein the alkyl portion is optionally substituted with one or more $R^{g'}$, and the cycloalkyl portion is optionally substituted with one or more $R^h$;

(vii) heterocycloalkyl, which is optionally substituted with one or more $R^h$;

(viii) heterocycloalkyl($C_1$-$C_4$)alkyl, wherein the alkyl portion is optionally substituted with one or more $R^{g'}$, and the cycloalkyl portion is optionally substituted with one or more $R^h$;

(ix) ($C_1$-$C_6$) alkyl, which is optionally substituted with one or more $R^g$; and (x) ($C_1$-$C_6$)haloalkyl, which is optionally substituted with one or more $R^g$;

each occurrence of $R^a$, $R^d$, and $R^g$ is independently selected from the group consisting of —S(O)$_2$($C_1$-$C_4$)alkyl, —OH, —C(O)—($C_1$-$C_4$)alkyl, oxo, —CN, ($C_1$-$C_4$)alkoxy, ($C_1$-$C_4$)haloalkoxy, ($C_3$-$C_7$)cycloalkyl, ($C_3$-$C_6$)cycloalkyloxy, ($C_1$-$C_4$)alkylthio, ($C_3$-$C_6$)cycloalkylthio-, —C(O)NH$_2$, —C(O)NH($C_1$-$C_4$)alkyl, —C(O)N[($C_1$-$C_4$)alkyl]$_2$, —NH$_2$, —NH($C_1$-$C_4$)alkyl, —N[($C_1$-$C_4$)alkyl]$_2$, —S(O)$_2$NH($C_1$-$C_4$)alkyl, and —S(O)$_2$N[($C_1$-$C_4$)alkyl]$_2$;

each occurrence of $R^{a'}$, $R^{d'}$, and $R^{g'}$ is independently selected from the group consisting of halo, —S(O)$_2$($C_1$-$C_4$)alkyl, —OH, —C(O)—($C_1$-$C_4$)alkyl, oxo, —CN, ($C_1$-$C_4$)alkoxy, ($C_1$-$C_4$)haloalkoxy, ($C_3$-$C_7$)cycloalkyl, ($C_3$-$C_6$)cycloalkyloxy, ($C_1$-$C_4$)alkylthio, ($C_3$-$C_6$)cycloalkylthio-, —C(O)NH$_2$, —C(O)NH($C_1$-$C_4$)alkyl, —C(O)N[($C_1$-$C_4$)alkyl]$_2$, —S(O)$_2$NH($C_1$-$C_4$)alkyl, and —S(O)$_2$N[($C_1$-$C_4$)alkyl]$_2$;

each occurrence of $R^b$, $R^c$, and $R^h$ is independently selected from the group consisting of halo, —S(O)$_2$($C_1$-$C_4$)alkyl, —OH, —C(O)—($C_1$-$C_4$)alkyl, —C(O)—O—($C_1$-$C_6$)alkyl, —CN, ($C_1$-$C_6$)alkyl, ($C_1$-$C_4$)haloalkyl, ($C_1$-$C_4$)alkoxy, ($C_1$-$C_4$)haloalkoxy, ($C_3$-$C_7$)cycloalkyl, ($C_3$-$C_6$)cycloalkyloxy, ($C_1$-$C_4$)alkylthio, ($C_3$-$C_6$)cycloalkylthio-, —C(O)NH$_2$, —C(O)NH($C_1$-$C_4$)alkyl, —C(O)N[($C_1$-$C_4$)alkyl]$_2$, —S(O)$_2$NH($C_1$-$C_4$)alkyl, and —S(O)$_2$N[($C_1$-$C_4$)alkyl]$_2$; and each occurrence of $R^e$ and $R^f$ is independently selected from the group consisting of halo; —S(O)$_2$($C_1$-$C_4$)alkyl; —OH; —C(O)—($C_1$-$C_4$)alkyl; —C(O)—O—($C_1$-$C_6$)alkyl; —CN; —C(O)OH; ($C_1$-$C_6$)alkyl that is optionally substituted with —OH or —OCH$_3$; ($C_1$-$C_4$)haloalkyl; ($C_1$-$C_4$)alkoxy; ($C_1$-$C_4$)haloalkoxy; ($C_3$-$C_7$)cycloalkyl, that is optionally substituted with from 1-3 substituents independently selected from the group consisting of ($C_1$-$C_4$)alkyl; ($C_3$-$C_6$)cycloalkyloxy; ($C_1$-$C_4$)alkylthio; ($C_3$-$C_6$)cycloalkylthio-; —C(O)NH$_2$; —C(O)NH($C_1$-$C_4$)alkyl; —C(O)N[($C_1$-$C_4$)alkyl]$_2$; —NH$_2$; —NH($C_1$-$C_4$)alkyl; —N[($C_1$-$C_4$)alkyl]$_2$; —NH—C(O)—($C_1$-$C_4$)alkyl; —S(O)$_2$NH($C_1$-$C_4$)alkyl; —S(O)$_2$N[($C_1$-$C_4$)alkyl]$_2$; heterocycloalkyl that is optionally substituted with from 1-3 substituents independently selected from the group consisting of ($C_1$-$C_4$)alkyl; phenyl that is optionally substituted with from 1-3 substituents independently selected from the group consisting of —F, —Cl, ($C_1$-$C_4$)alkyl, —CF$_3$, —OCH$_3$, and —CN; and heteroaryl including from 5 to 6 ring atoms independently selected from the group consisting of N, O, and S, wherein said heteroaryl is optionally substituted with from 1-3 substituents independently selected from the group consisting of ($C_1$-$C_4$)alkyl, —CF$_3$, and —OCH$_3$.

In yet another aspect, the present invention provides a compound selected from the group consisting of the compounds described in Tables 1-3, or a pharmaceutical acceptable salt thereof.

As used herein, the phrase "halogen" or "halo" includes F, Cl, Br, and I.

Embodiments can include any one or more of the following features described throughout sections [I]-[VI] below.

[I] Variable X

[A] In some embodiments, X is a bond.
[B] In some embodiments, X is C(O) or S(O)$_2$.

[II] Variable $R_2$

[A]
In some embodiments, $R_2$ is selected from the group consisting of:
(i) heterocycloalkyl, which is optionally substituted with one or more $R^c$;
(ii) ($C_3$-$C_7$) cycloalkyl, which is optionally substituted with one or more $R^c$;
(iii) phenyl, which is optionally substituted with one or more $R^e$; and
(iv) ($C_1$-$C_6$) alkyl which is optionally substituted with one or more $R^d$.

In some embodiments, $R_2$ is selected from the group consisting of:
(i) heterocycloalkyl, which is optionally substituted with one or more $R^e$;
(ii) ($C_3$-$C_2$) cycloalkyl, which is optionally substituted with one or more $R^c$;
and
(iii) phenyl, which is optionally substituted with one or more $R^c$.

In some embodiments, $R_2$ is selected from the group consisting of:
(i) heterocycloalkyl, which is optionally substituted with one or more $R^c$; and
(ii) ($C_3$-$C_2$) cycloalkyl, which is optionally substituted with one or more $R^c$.

[B]
In some embodiments, $R_2$ is heterocycloalkyl, which is optionally substituted with one or more (e.g., 1-3, 1-2, 1) $R^c$. Embodiments in which $R_2$ is heterocycloalkyl, which is optionally substituted with one or more (e.g., 1-3, 1-2, 1) $R^c$ can include any one or more of the following features.

In some embodiments, $R_2$ is a monocyclic heterocycloalkyl including from 5 to 7 ring atoms, which is optionally substituted with one or more (e.g., 1-3, 1-2, 1) $R^c$.

In some embodiments, $R_2$ is a saturated monocyclic heterocycloalkyl including from 5 to 7 ring atoms, which is optionally substituted with one or more (e.g., 1-3, 1-2, 1) $R^c$, and wherein from 1-2 of the ring atoms are independently selected from the group consisting of N—H, N—$R^c$, and O.

In some embodiments, $R_2$ is a saturated monocyclic heterocycloalkyl including from 5 to 7 ring atoms, which is optionally substituted with one or more (e.g., 1-3, 1-2, 1) $R^c$, and wherein 1 of the ring atoms is selected from the group consisting of N—H, N—$R^c$, and O.

In some embodiments, $R_2$ is a saturated monocyclic heterocycloalkyl including from 5 to 7 ring atoms, which is optionally substituted with one or more (e.g., 1-3, 1-2, 1) $R^c$, and wherein 1 of the ring atoms is O.

In some embodiments, $R_2$ is a saturated monocyclic heterocycloalkyl including from 5 to 7 ring atoms, wherein 1 of the ring atoms is O.

In some embodiments, $R_2$ is tetrahydro-2H-pyran-4-yl.

[C]

In some embodiments, $R_2$ is $(C_3-C_{10})$cycloalkyl, which is optionally substituted with one or more (e.g., 1-3, 1-2, 1) $R^c$. Embodiments in which $R_2$ is $(C_3-C_{10})$cycloalkyl, which is optionally substituted with one or more (e.g., 1-3, 1-2, 1) $R^b$ can include any one or more of the following features.

In some embodiments, $R_2$ is $(C_5-C_{10})$cycloalkyl, which is optionally substituted with one or more (e.g., 1-3, 1-2, 1) $R^c$.

In some embodiments, each $R^c$ is independently selected from the group consisting of halo and $(C_1-C_6)$alkyl. For example, each $R^c$ is independently selected from the group consisting of halo (e.g., fluoro).

In some embodiments, $R_2$ is cyclohexyl, 4-fluorocyclohexan-1-yl, or 4,4-difluorocyclohexan-1-yl.

In some embodiments, $R_2$ is adamantyl.

[D]

In some embodiments, $R_2$ is phenyl that is optionally substituted with one or more (e.g., 1-3, 1-2, 1) $R^e$. In certain embodiments, each $R^e$ is independently selected from the group consisting of halo, $(C_1-C_6)$alkyl, and $(C_1-C_6)$haloalkyl.

[III] Variable $R_3$

[A]

In some embodiments, $R_3$ is selected from the group consisting of:
(i) heteroaryl$(C_1-C_4)$alkyl, wherein the alkyl portion is optionally substituted with one or more $R^{g'}$, and the heteroaryl portion is optionally substituted with one or more $R^f$;
(ii) phenyl$(C_1-C_4)$alkyl, wherein the alkyl portion is optionally substituted with one or more $R^{g'}$, and the phenyl portion is optionally substituted with one or more $R^f$;
(iii) $(C_3-C_7)$ cycloalkyl$(C_1-C_4)$ alkyl, wherein the alkyl portion is optionally substituted with one or more $R^{g'}$, and the cycloalkyl portion is optionally substituted with one or more $R^h$; and
(iv) heterocycloalkyl$(C_1-C_4)$alkyl, wherein the alkyl portion is optionally substituted with one or more $R^{g'}$, and the cycloalkyl portion is optionally substituted with one or more $R^h$.

In some embodiments, $R_3$ is selected from the group consisting of:
(i) heteroaryl$(C_1-C_4)$alkyl, wherein the alkyl portion is optionally substituted with one or more $R^{g'}$, and the heteroaryl portion is optionally substituted with one or more $R^f$; and
(ii) phenyl$(C_1-C_4)$alkyl, wherein the alkyl portion is optionally substituted with one or more $R^{g'}$, and the phenyl portion is optionally substituted with one or more $R^f$.

[B]

In some embodiments, $R_3$ is heteroaryl$(C_1-C_4)$alkyl, wherein the alkyl portion is optionally substituted with one or more $R^{g'}$, and the heteroaryl portion is optionally substituted with one or more $R^f$. Embodiments in which $R_3$ is heteroaryl$(C_1-C_4)$alkyl, wherein the alkyl portion is optionally substituted with one or more $R^{g'}$, and the heteroaryl portion is optionally substituted with one or more $R^f$, can include any one or more of the following features described throughout sections [1] through [4] below. In certain embodiments, any one of the features described throughout section [1] can be combined with any one or more of the features described throughout sections [2] and/or [3] and/or [4] below. In certain embodiments, the heteroaryl portion can include any one or more of the features described throughout sections [2] and/or [3] and/or [4] below.

[1]

In some embodiments, $R_3$ is heteroaryl$(C_1-C_2)$alkyl, wherein the heteroaryl portion is optionally substituted with one or more $R^f$.

In some embodiments, $R_3$ is heteroaryl$(C_1)$alkyl, wherein the heteroaryl portion is optionally substituted with one or more $R^f$.

[2]

In some embodiments, the heteroaryl portion is monocyclic heteroaryl including from 5-6 ring atoms, wherein from 1-3 of the ring atoms are independently selected from the group consisting of N, O, and S and wherein the monocyclic heteroaryl is optionally substituted with one or more $R^f$.

In some embodiments, the heteroaryl portion is monocyclic heteroaryl including 6 ring atoms, wherein from 1-3 of the ring atoms are N and wherein the monocyclic heteroaryl is optionally substituted with one or more $R^f$.

In some embodiments, the heteroaryl portion is pyrimidinyl, pyridyl, or pyrazinyl, each of which is optionally substituted with one or more $R^f$.

In some embodiments, $R_3$ is pyrimidinylmethyl (e.g., 2-pyrimidinylmethyl), which is optionally substituted with one or more $R^f$.

In some embodiments, $R_3$ is unsubstituted pyrimidinylmethyl.

In some embodiments, each $R^f$ is independently selected from the group consisting of halo (e.g., F), $(C_1-C_6)$alkyl (e.g., $CH_3$), $(C_1-C_4)$haloalkyl (e.g., $CF_3$), and $(C_1-C_4)$alkoxy (e.g., $OCH_3$).

[3]

In some embodiments, the heteroaryl portion is:
(i) a bicyclic aromatic ring system including from 8-12 ring atoms, wherein from 1-4 of the ring atoms are independently selected from the group consisting of N, O, and S, and which is optionally substituted with one or more $R^f$; or
(ii) a heterobicyclic ring system including from 8-12 ring atoms, wherein the aromatic portion is optionally substituted with one or more $R^f$.

In some embodiments, the heteroaryl portion is selected from the group consisting of 1,5-naphthyridyl, 1,2,3,4-tetrahydro-1,5-naphthyridyl 1,6-naphthyridyl, 1,2,3,4-tetrahydro-1,6-naphthyridyl 1,7-naphthyridyl, 1,2,3,4-tetrahydro-1,7-naphthyridinyl 1,8-naphthyridyl, 1,2,3,4-tetrahydro-1,8-naphthyridyl, 2,6-naphthyridyl, 2,7-naphthyridyl, cinnolyl, isoquinolyl, tetrahydroisoquinolinyl, phthalazyl, quinazolyl, 1,2,3,4-tetrahydroquinazolinyl, quinolyl, tetrahydroquinolinyl, quinoxalyl and tetrahydroquinoxalinyl, each of which is optionally substituted with one or more $R^f$.

In some embodiments, the heteroaryl portion is selected from the group consisting of benzo[d][1,2,3]triazyl, benzo[e][1,2,4]triazyl, pyrido[2,3-b]pyrazyl, pyrido[2,3-c]pyridazyl, pyrido[2,3-d]pyrimidyl, pyrido[3,2-b]pyrazyl, pyrido[3,2-c]pyridazyl, pyrido[3,2-d]pyrimidyl, pyrido[3,4-b]pyrazyl, pyrido[3,4-c]pyridazyl, pyrido[3,4-d]pyrimidyl, pyrido[4,3-b]pyrazyl, pyrido[4,3-c]pyridazyl, pyrido[4,3-d]pyrimidyl, quinazolyl, 1H-benzo[d][1,2,3]triazoyl, 1H-benzo[d]imidazoyl, 1H-indazoyl, 1H-indoyl, 2H-benzo[d][1,2,3]triazoyl, 2H-pyrazolo[3,4-b]pyridinyl, 2H-pyrazolo[4,3-b]pyridinyl, [1,2,3]triazolo[1,5-a]pyridinyl, [1,2,4]triazolo[1,5-a]pyridinyl and [1,2,4]triazolo[4,3-a]pyridinyl, each of which is optionally substituted with one or more $R^f$.

In some embodiments, the heteroaryl portion is selected from the group consisting of benzo[b]thienyl, benzo[c][1,2, 5]oxadiazyl, benzo[c][1,2,5]thiadiazolyl, benzo[d]isothiazoyl, benzo[d]isoxazoyl, benzo[d]oxazoyl, benzo[d]thiazoyl, benzofuryl, imidazo[1,2-a]pyrazyl, imidazo[1,2-a]pyridinyl, imidazo[1,2-a]pyrimidyl, imidazo[1,2-b]pyridazyl, imidazo[1,2-c]pyrimidyl, imidazo[1,5-a]pyrazyl, imidazo[1,5-a]pyridinyl, imidazo[1,5-a]pyrimidyl, imidazo[1,5-b]pyridazyl, imidazo[1,5-c]pyrimidyl, indolizyl, pyrazolo[1,5-a]pyrazyl, pyrazolo[1,5-a]pyridinyl, pyrazolo[1,5-a]pyrimidyl, pyrazolo[1,5-b]pyridazine, pyrazolo[1,5-c]pyrimidine, pyrrolo[1,2-a]pyrazine, pyrrolo[1,2-a]pyrimidyl, pyrrolo[1,2-b]pyridazyl, pyrrolo[1,2-c]pyrimidyl, 1H-imidazo[4,5-b]pyridinyl, 1H-imidazo[4,5-c]pyridinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-c]pyridinyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, 2H-indazoyl, 3H-imidazo[4,5-b]pyridinyl and 3H-imidazo[4,5-c]pyridinyl, each of which is optionally substituted with one or more $R^f$.

In some embodiments, the heteroaryl portion is selected from the group consisting of benzo[c]isothiazyl, benzo[c]isoxazyl, furo[2,3-b]pyridinyl, furo[2,3-c]pyridinyl, furo[3,2-b]pyridinyl, furo[3,2-c]pyridiyl, isothiazolo[4,5-b]pyridinyl, isothiazolo[4,5-c]pyridinyl, isothiazolo[5,4-b]pyridinyl, isothiazolo[5,4-c]pyridinyl, isoxazolo[4,5-b]pyridinyl, isoxazolo[4,5-c]pyridinyl, isoxazolo[5,4-b]pyridinyl, isoxazolo[5,4-c]pyridinyl, oxazolo[4,5-b]pyridinyl, oxazolo[4,5-c]pyridinyl, oxazolo[5,4-b]pyridinyl, oxazolo[5,4-c]pyridinyl, thiazolo[4,5-b]pyridiyl, thiazolo[4,5-c]pyridinyl, thiazolo[5,4-b]pyridinyl, thiazolo[5,4-c]pyridinyl, thieno[2,3-b]pyridinyl, thieno[2,3-c]pyridinyl, thieno[3,2-b]pyridinyl and thieno[3,2-c]pyridinyl, each of which is optionally substituted with one or more $R^f$.

[4]

In some embodiments, the heteroaryl portion is monocyclic heteroaryl including 5 ring atoms, wherein from 1-3 of the ring atoms are independently selected from the group consisting of N, O, and S and wherein the monocyclic heteroaryl is optionally substituted with one or more $R^f$.

In some embodiments, the heteroaryl portion is selected from the group consisting of thiophenyl, furanyl, thiazolyl, isothiazolyl, oxazolyl, isoxazolyl, 1,2,4-oxadiazolyl, 1,3,4-oxadiazolyl, pyrrazolyl, imidazolyl, 1,2,3-triazolyl, and 1,3,4-triazolyl, each of which is optionally substituted with one or more $R^f$.

[C]

In some embodiments, $R_3$ is phenyl($C_1$-$C_4$)alkyl, wherein the alkyl portion is optionally substituted with one or more $R^{g'}$, and the phenyl portion is optionally substituted with one or more $R^f$. Embodiments in which $R_3$ is phenyl($C_1$-$C_4$)alkyl, wherein the alkyl portion is optionally substituted with one or more $R^{g'}$, and the phenyl portion is optionally substituted with one or more $R^f$, can include any one or more of the following features described throughout sections [1] through [3] below. In certain embodiments, any one of the features described throughout section [1] can be combined with any one or more of the features described throughout sections [2] and/or [3] below. In other embodiments, any one or more of the features described throughout section [2] can be combined with any one or more of the features described throughout section [3] below.

[1]

In certain embodiments, $R_3$ is phenyl($C_1$-$C_2$)alkyl, wherein the phenyl portion is optionally substituted with from 1-3 $R^f$ (embodiments include optionally substituted benzyl, phenylethyl, and α-methylbenzyl).

In certain embodiments, $R_3$ is phenyl($C_1$)alkyl, wherein the phenyl portion is optionally substituted with from 1-3 (e.g., 1-2, 1) $R^f$.

[2]

In some embodiments, each $R^f$ is independently selected from the group consisting of halo; —CN; —C(O)OH; ($C_1$-$C_6$)alkyl that is optionally substituted with —OH or —OCH$_3$; ($C_1$-$C_4$)haloalkyl; ($C_1$-$C_4$)alkoxy; ($C_1$-$C_4$)haloalkoxy; ($C_3$-$C_7$)cycloalkyl, that is optionally substituted with from 1-3 substituents independently selected from the group consisting of ($C_1$-$C_4$)alkyl; —C(O)N[($C_1$-$C_4$)alkyl]$_2$; —N[($C_1$-$C_4$)alkyl]$_2$; heterocycloalkyl that is optionally substituted with from 1-3 substituents independently selected from the group consisting of ($C_1$-$C_4$)alkyl; phenyl that is optionally substituted with from 1-3 substituents independently selected from the group consisting of —F, —Cl, ($C_1$-$C_4$)alkyl, —CF$_3$, —OCH$_3$, and —CN; and heteroaryl including from 5 to 6 ring atoms independently selected from the group consisting of N, O, and S, wherein said heteroaryl is optionally substituted with from 1-3 substituents independently selected from the group consisting of ($C_1$-$C_4$)alkyl, —CF$_3$, and —OCH$_3$. For example, each $R^f$ can be independently selected from the group consisting of —F, —Cl, —Br, —CN, —C(O)OH, —CH$_3$, —CF$_3$, —OCH$_3$, —OCF$_3$, cyclopropyl, —C(O)N(CH$_3$)$_2$, —N(CH$_3$)$_2$, pyrrolidinyl, phenyl, pyridyl, and pyrrazolyl.

Embodiments can include one or more of the following subsets of substituents.

In some embodiments, each $R^f$ is independently selected from the group consisting of halo; —CN; ($C_1$-$C_6$)alkyl that is optionally substituted with —OH or —OCH$_3$; ($C_1$-$C_4$)haloalkyl; and ($C_1$-$C_4$)alkoxy. For example, each $R^f$ can be independently selected from the group consisting of —F, —Cl, —CN, —CH$_3$, —CF$_3$, and —OCH$_3$.

In some embodiments, each $R^f$ is independently selected from the group consisting of halo; —CN; and ($C_1$-$C_4$)haloalkyl. For example, each $R^f$ can be independently selected from the group consisting of —F, —Cl, —CN, and —CF$_3$.

In some embodiments, each $R^f$ is independently selected from the group consisting of halo and ($C_1$-$C_4$)haloalkyl. For example, each $R^f$ can be independently selected from the group consisting of —F, —Cl, and —CF$_3$.

In some embodiments, each $R^f$ is independently selected from the group consisting of halo (e.g., —F, or —Cl, e.g., —F).

[3]

In some embodiments, the phenyl portion is mono-substituted.

In some embodiments, the phenyl portion is mono-substituted (e.g., ortho, meta, or para substituted). For instance, $R_3$ may be 2-, 3-, or 4-fluorobenzyl or 2-, 3-, or 4-trifluoromethylbenzyl.

In some embodiments, the phenyl portion is di-substituted (e.g., 2,3-, 2,4-, 2,5-, 2,6-, 3,4-, or 3,5 di-substituted). For instance, $R_3$ may be 2,4-difluorobenzyl; 2,6-difluorobenzyl; 3,5-difluorobenzyl; 2,4-dichlorobenzyl; 3,5-dichlorobenzyl; 2,3-dichlorobenzyl; 3,4-dichlorobenzyl; 2-fluoro-5-chlorobenzyl; 5-fluoro-2-chlorobenzyl; 3-fluoro-4-chlorobenzyl; 4-fluoro-3-chlorobenzyl; 3-trifluoromethyl-4-fluorobenzyl; 3-trifluoromethyl-4-chlorobenzyl; or 3-methyl-4-chlorobenzyl.

[D]

In some embodiments, $R_3$ is ($C_3$-$C_7$) cycloalkyl($C_1$-$C_4$)alkyl, wherein the alkyl portion is optionally substituted with one or more $R^{g'}$, and the cycloalkyl portion is optionally substituted with one or more $R^h$. Embodiments in which $R_3$ is $(C_3-C_7)$ cycloalkyl$(C_1-C_4)$ alkyl, wherein the alkyl portion is optionally substituted with one or more $R^{g'}$, and the cycloalkyl portion is optionally substituted with one or more $R^h$, can include any one or more of the following features described below.

In some embodiments, $R_3$ is $(C_3-C_7)$ cycloalkyl$(C_1-C_2)$ alkyl, wherein the cycloalkyl portion is optionally substituted with one or more $R^h$.

In some embodiments, $R_3$ is $(C_3-C_7)$ cycloalkyl $(C_1)$alkyl, wherein the cycloalkyl portion is optionally substituted with from 1-3 (e.g., 1-2, 1) $R^h$.

In some embodiments, the cycloalkyl portion can be cyclohexyl, cyclopentyl, or cyclopropyl, each of which is optionally substituted with from 1-3 (e.g., 1-2, 1) $R^h$.

In some embodiments, each $R^h$ is independently selected from the group consisting of halo and $(C_1-C_4)$ alkyl. For example, each $R^f$ can be independently selected from the group consisting of —F and —$CH_3$.

[E]

In some embodiments, $R_3$ is selected from the group consisting of:
  (i) heteroaryl, which is optionally substituted with one or more $R^f$; and
  (ii) phenyl, which is optionally substituted with one or more $R^f$.

Embodiments can include one or more of the following features.

In some embodiments, $R_3$ is phenyl, which is optionally substituted with one or more $R^f$. In certain embodiments, the phenyl ring can be unsubstituted or substituted and include any one or more of the features described in one or both of sections [III][C][2] and [III][C][3].

In some embodiments, $R_3$ is heteroaryl, which is optionally substituted with one or more $R^f$.

[IV] Variable $R_1$

In some embodiments, $R_1$ is $(C_1-C_6)$ alkyl, which is optionally substituted with one or more $R^a$. In certain embodiments, $R_1$ is $(C_1-C_6)$ alkyl, e.g., $(C_1-C_4)$ alkyl, $(C_1-C_2)$ alkyl, e.g., $CH_3$.

In some embodiments, $R_1$ is anti with respect to the imidazo-triazine ring containing $R_2$.

In some embodiments, the carbon that is directly attached to $R_1$ has the R-configuration.

In some embodiments, the carbon that is directly attached to $R_1$ has the S-configuration.

In some embodiments, $R_1$ is anti with respect to the imidazo-triazine ring containing $R_2$, and the carbon that is directly attached to $R_1$ has the R-configuration.

In some embodiments, $R_1$ is anti with respect to the imidazo-triazine ring containing $R_2$, and the carbon that is directly attached to $R_1$ has the S-configuration.

[V] Non-Limiting Combinations of Variables X, $R_1$, $R_2$, and $R_3$

[A]

In some embodiments, the feature described in section [I][A] is combined with any one or more of the features described throughout section [III][A].

In some embodiments, the feature described in section [I][A] is combined with any one or more of the features described throughout section [III][A], and any one or more of the features described throughout section [II][A].

In some embodiments, the feature described in section [I][A] is combined with any one or more of the features described throughout section [III][A], and any one or more of the features described throughout any one, two, or three of sections [II][B], [II][C], and [II][D] (e.g., combined with any one or more of the features described throughout section [II][B]; e.g., $R_2$ is tetrahydro-2H-pyran-4-yl).

In some embodiments, the feature described in section [I][A] is combined with any one or more of the features described throughout section [III][A], and any one or more of the features described throughout section [IV] (e.g., $R_1$ is methyl).

In some embodiments, the feature described in section [I][A] is combined with any one or more of the features described throughout section [III][A], and any one or more of the features described throughout section [II][A], and any one or more of the features described throughout section [IV] (e.g., $R_1$ is methyl).

In some embodiments, the feature described in section [I][A] is combined with any one or more of the features described throughout section [III][A], and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl), and any one or more of the features described throughout section [IV] (e.g., $R_1$ is methyl).

[B]

In some embodiments, the feature described in section [I][A] is combined with any one or more of the features described throughout section [III][B] (for purposes of clarification, including those features described in sub-sections [1]-[4]).

In some embodiments, the feature described in section [I][A] is combined with any one or more of the features described throughout section [III][B] (for purposes of clarification, including those features described in sub-sections [1]-[4]), and any one or more of the features described throughout section [II][A].

In some embodiments, the feature described in section [I][A] is combined with any one or more of the features described throughout section [III][B] (for purposes of clarification, including those features described in sub-sections [1]-[4]), and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl).

In some embodiments, the feature described in section [I][A] is combined with any one or more of the features described throughout section [III][B] (for purposes of clarification, including those features described in sub-sections [1]-[4]), and any one or more of the features described throughout section [IV] (e.g., $R_1$ is methyl).

In some embodiments, the feature described in section [I][A] is combined with any one or more of the features described throughout section [III][B] (for purposes of clarification, including those features described in sub-sections [1]-[4]), and any one or more of the features described throughout section [II][A], and any one or more of the features described throughout section [IV] (e.g., $R_1$ is methyl).

In some embodiments, the feature described in section [I][A] is combined with any one or more of the features described throughout section [III][B] (for purposes of clarification, including those features described in sub-sections [1]-[4]), and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl), and any one or more of the features described throughout section [IV] (e.g., $R_1$ is methyl).

In certain embodiments, any one of the features described throughout section [III][B][1] can be combined with any one or more of the features described throughout sections [III][B][2] and/or [III][B][3] and/or [III][B][4]. In certain embodiments, the heteroaryl portion can include any one or more of the features described throughout sections [III][B][2] and/or [III][B][3] and/or [III][B][4].

[C]

In some embodiments, the feature described in section [I][A] is combined with any one or more of the features described throughout section [III][C] (for purposes of clarification, including those features described in sub-sections [1]-[3]).

In some embodiments, the feature described in section [I][A] is combined with any one or more of the features described throughout section [III][C] (for purposes of clarification, including those features described in sub-sections [1]-[3]), and any one or more of the features described throughout section [II][A].

In some embodiments, the feature described in section [I][A] is combined with any one or more of the features described throughout section [III][C] (for purposes of clarification, including those features described in sub-sections [1]-[3]), and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl).

In some embodiments, the feature described in section [I][A] is combined with any one or more of the features described throughout section [III][C] (for purposes of clarification, including those features described in sub-sections [1]-[3]), and any one or more of the features described throughout section [IV] (e.g., $R_1$ is methyl).

In some embodiments, the feature described in section [I][A] is combined with any one or more of the features described throughout section [III][C] (for purposes of clarification, including those features described in sub-sections [1]-[3]), and any one or more of the features described throughout section [II][A], and any one or more of the features described throughout section [IV] (e.g., $R_1$ is methyl).

In some embodiments, the feature described in section [I][A] is combined with any one or more of the features described throughout section [III][C] (for purposes of clarification, including those features described in sub-sections [1]-[3]), and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl), and any one or more of the features described throughout section [IV] (e.g., $R_1$ is methyl).

In certain embodiments, any one of the features described throughout section [III][C][1] can be combined with any one or more of the features described throughout sections [III][C][2] and/or [III][C][3]. In other embodiments, any one or more of the features described throughout section [III][C][2] can be combined with any one or more of the features described in section [III][C][3].

[D]

In some embodiments, the feature described in section [I][A] is combined with any one or more of the features described throughout section [III][D].

In some embodiments, the feature described in section [I][A] is combined with any one or more of the features described throughout section [III][D], and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl).

In some embodiments, the feature described in section [I][A] is combined with any one or more of the features described throughout section [III][D], and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl), and any one or more of the features described throughout section [IV] (e.g., $R_1$ is methyl).

[E]

In some embodiments, any one or more of the features described throughout section [I][B] are combined with any one or more of the features described throughout section [III][E].

In some embodiments, any one or more of the features described throughout section [I][B] are combined with any one or more of the features described throughout section [III][E], and any one or more of the features described throughout section [II][A].

In some embodiments, any one or more of the features described throughout section [I][B] are combined with any one or more of the features described throughout section [III][E], and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl).

In some embodiments, any one or more of the features described throughout section [I][B] are combined with any one or more of the features described throughout section [III][E], and any one or more of the features described throughout section [IV] (e.g., $R_1$ is methyl).

In some embodiments, any one or more of the features described throughout section [I][B] are combined with any one or more of the features described throughout section [III][E], and any one or more of the features described throughout section [II][A], and any one or more of the features described throughout section [IV] (e.g., $R_1$ is methyl).

In some embodiments, any one or more of the features described throughout section [I][B] are combined with any one or more of the features described throughout section [III][E], and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl), and any one or more of the features described throughout section [IV] (e.g., $R_1$ is methyl).

[VI] Other Embodiments

In some embodiments, one or more of the following apply.

In some embodiments, the compound or salt is selected from the group consisting of the final compounds described in Examples B.1.-6, 6A, 6B, and 7-205.

In some embodiments, the compound or salt is other than one or more (e.g., all) of the final compound described in Examples B.1.-6, 6A, 6B, and 7-205.

In some embodiments, when X is a bond, $R_1$ is $CH_3$, and $R_2$ is tetrahydro-2H-pyran-4-yl or tetrahydro-2H-pyran-3-yl, then $R_3$ is not benzyl, 2-fluorobenzyl, 3-fluorobenzyl, 4-fluorobenzyl, 2-cyanobenzyl, 3-cyanobenzyl, 4-cyanobenzyl, or α-methylbenzyl.

In some embodiments, when X is a bond, $R_1$ is $CH_3$, and $R_2$ is tetrahydro-2H-pyran-4-yl, then $R_3$ is not pyrimidin-2-ylmethyl, imidazo[1,2-b]pyridazin-2-ylmethyl, imidazo[1,2-b]pyridazin-6-ylmethyl, 6-methoxypyridin-2-yl)methyl, pyrazin-2-ylmethyl, pyridin-2-ylmethyl, quinazolin-2-ylmethyl, or quinolin-2-ylmethyl.

In some embodiments, when X is a bond, $R_1$ is $CH_3$, and $R_2$ is adamantan-1-yl or 4,4-difluorocyclohexan-1-yl, then $R_3$ is not benzyl.

In some embodiments, when X is a bond, $R_1$ is $CH_3$, and $R_2$ is adamantan-1-yl or 4,4-difluorocyclohexan-1-yl, then $R_3$ is not pyrimidin-2-ylmethyl.

In some embodiments, when X is a bond, $R_1$ is $CH_3$, and $R_2$ is 1-(ethylsulfonyl)piperidin-4-yl or 1-acetylpiperidin-4-yl, then $R_3$ is not benzyl.

In some embodiments, when X is a bond, $R_1$ is $CH_3$, and $R_2$ is 1-(ethylsulfonyl)piperidin-4-yl or 1-acetylpiperidin-4-yl, then $R_3$ is not pyrimidin-2-ylmethyl.

In some embodiments, when X is a bond, $R_1$ is $CH_3$, and $R_2$ is furan-3-yl, then $R_3$ is not benzyl.

In some embodiments, when X is a bond, $R_1$ is $CH_3$, and $R_2$ is 2-hydroxypropan-2-yl, then $R_3$ is not benzyl.

In some embodiments, when X is a bond, $R_1$ is $CH_3$, and $R_2$ is 4-fluoro-2-methylphenyl, 5-chloro-2-methylphenyl, or o-tolyl, then $R_3$ is not pyrimidin-2-ylmethyl.

In some embodiments, when X is a bond, $R_1$ is $CH_3$, and $R_2$ is 4-fluoro-2-methylphenyl or 5-chloro-2-methylphenyl, then $R_3$ is not benzyl.

In some embodiments, the compound is selected from the group consisting of the compounds having the following combinations of $R_1$, $R_2$, and $R_3$. In other embodiments, the compound is other than one having the following combinations of $R_1$, $R_2$, and $R_3$.

| R1 | R2 | R3 |
|---|---|---|
| Me | 4-pyran | 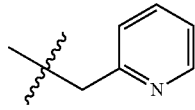 [SMILES: *Cc1ccccn1] |
| Me | 4-pyran | 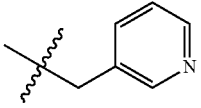 [SMILES: *Cc1cccnc1] |
| Me | 4-pyran | 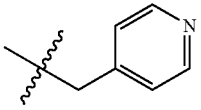 [SMILES: *Cc1ccncc1] |
| Me | 4-pyran | 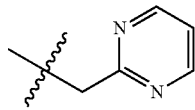 [SMILES: *Cc1ncccn1] |
| Me | 4-pyran | (pyrazine) |
| Me | 4-pyran | (pyrimidine) |
| Me | 4-pyran | (pyridazine) |
| Me | 4-pyran | (pyridazine isomer) |
| Me | 4-pyran | (triazine) |
| Me | 4-pyran | (imidazo[1,2-b]pyridazine) |
| Me | 4-pyran | (imidazo[1,2-b]pyridazine isomer) |
| Me | 4-pyran | ([1,2,4]triazolo[1,5-a]pyridine) |
| Me | 4-pyran | (imidazo[1,2-a]pyridine) |
| Me | 4-pyran | (imidazo[1,2-a]pyrimidine) |
| Me | 4-pyran | (1H-benzimidazole) |

-continued

| R1 | R2 | R3 |
|---|---|---|
| Me | 4-pyran | benzimidazol-2-ylmethyl |
| Me | 4-pyran | quinoxalin-2-ylmethyl |
| Me | 4-pyran | quinoxalin-2-ylmethyl |
| Me | 4-pyran | quinolin-2-ylmethyl |
| Me | 4-pyran | quinoxalin-6-ylmethyl |
| Me | 4-pyran | quinazolin-6-ylmethyl |
| Me | 4-pyran | quinazolin-7-ylmethyl |
| Me | 4-pyran | benzyl |

In all of the embodiments or aspects disclosed herein, the invention includes compounds disclosed herein and pharmaceutically acceptable salts thereof.

Another aspect of the invention provides a pharmaceutical composition comprising a compound of the invention, e.g., a compound of Formula (I), or a pharmaceutical acceptable salt thereof, and a pharmaceutically acceptable carrier or excipient.

Another aspect of the invention provides a method for treating a PDE9 associated disease or disorder comprising administering to a subject an effective amount of a compound of the invention or a pharmaceutical acceptable salt thereof, e.g., in a pharmaceutical composition of the invention, such that the PDE9 associated disease or disorder is treated.

In another aspect, the invention provides a method of inhibiting PDE9 in a subject, wherein the method comprises administering to the subject a therapeutically effective amount of a compound of the invention, e.g., a compound of Formula (I), or a pharmaceutical acceptable salt thereof, such that PDE9 is inhibited in the subject.

DETAILED DESCRIPTION OF THE INVENTION

The present invention provides imidazotriazinone compounds or pharmaceutically acceptable salts thereof which are inhibitors of phosphodiesterase 9. The present invention further provides processes, pharmaceutical compositions, pharmaceutical preparations and pharmaceutical use of the compounds in the treatment of PDE9 associated diseases or disorders in mammals, including human(s). The present invention, including compounds, methods, and pharmaceutical compositions will be described with reference to the following definitions that, for convenience, are set forth below. Unless otherwise specified, the below terms used herein are defined as follows:

I. DEFINITIONS

As used herein, the term "a," "an," "the" and similar terms used in the context of the present invention (especially in the context of the claims) are to be construed to cover both the singular and plural unless otherwise indicated herein or clearly contradicted by the context.

As used herein, the language "PDE9 associated diseases or disorders" describes the class of disorders associated with abnormal PDE9 activity, or aberrant levels of cGMP. In certain embodiments, the PDE9 associated disease or disorder is a central nervous system (CNS) disease or disorder, a neurodegeneration disorder, or a disorder that may affect CNS function, wherein each of these diseases or disorders is related to the modulation of cGMP levels. In certain embodiments, the PDE9 associated disease or disorder is a disease or disorder caused by a relative reduction in synaptic plasticity and synaptic processes, e.g., as in learning or memory. In a particular embodiment, the compounds of the invention serve to treat these disorders by acting to increase synaptic plasticity and synaptic processes, wherein the language increasing synaptic plasticity and synaptic process includes induction of synaptic plasticity and synaptic processes.

Exemplary CNS disorders include Alzheimer's disease, amyotrophic lateral sclerosis (ALS or Lou Gerig's disease), Binswanger's dementia (subcortical arteriosclerotic encephalopathy), bipolar disorders, Down's syndrome, frontotemporal lobar degeneration or dementia, glaucoma, Huntington's disease (chorea), HIV-associated dementia, Lewy body dementia, multiple sclerosis, multiple system atrophy, Parkinson's disease, presenile dementia (mild cognitive impairment), schizophrenia, spinocerebellar ataxies, Steel-Richardson-Olszewski disease (progressive supranuclear palsy), vascular dementia, attention deficit disorder (ADD) and attention deficit hyperactivity disorder (ADHD). Exemplary neurodegeneration disorders include either traumatic (closed or open, penetrating head injuries) or non-traumatic (stroke, aneurism, hypoxia) injury to the brain. In certain embodiments, PDE9 associated diseases or disorders characterized by aberrant levels of cGMP may also include dystonia, including for example, generalized, focal, segmental, sexual, intermediate, acute dystonic reaction, and genetic/primary dystonia; and dyskinesia, including for example, acute, pharmacological, chronic/tardive, and nonmotor dyskinesia. In certain embodiments, PDE9 associated diseases or disorders characterized by a relative reduction in synaptic plasticity and synaptic processes include, for example, obsessive compulsive disorder, Fragile X, Rhett's, Williams syndrome, Renpenning's syndrome, autism spectrum disorders, including autism, Asperger's syndrome, pervasive development disorder, Rhettt's syndrome, and childhood disintegrative disorder.

As used herein, the term "modulation" refers to a relative increase or decrease in the levels of a particular cellular indicator, e.g., cGMP. In this respect, the diseases/disorders described herein are characterized by relatively decreased levels of cGMP levels, wherein the compounds of the present invention serve to increase the level of cGMP through inhibition of PDE9.

As used herein, the term "pharmaceutically acceptable" refers to salts prepared from pharmaceutically acceptable non-toxic bases and acids, including inorganic and organic bases and inorganic and organic acids. Salts derived from inorganic bases include, but are not limited to lithium, sodium, potassium, magnesium, calcium and zinc. Salts derived from organic bases include, but are not limited to, ammonia, primary (e.g. Tromethamine), secondary and tertiary amines, and amino acids (e.g. Lysine). Salts derived from inorganic acids include, but are not limited to, sulfuric, hydrochloric, phosphoric, methanesulfonic, hydrobromic. Salts derived from organic acids include, but are not limited to $C_{1-6}$ alkyl carboxylic acids, di-carboxylic acids and tri-carboxylic acids such as acetic acid, propionic acid, fumaric acid, maleic acid, succinic acid, tartaric acid, adipic acid and citric acid, and alkylsulfonic acids such as methanesulfonic and aryl sulfonic acids such as para-toluene sulfonic acid and benzene sulfonic acid. For detailed list of salts see P. H. Stahl and C. G. Wermuth (eds.) "Handbook of Pharmaceutical Salts, Properties, Selection and Use" Wiley-VCH (ISBN 3-906390-26-8), which is incorporated by reference.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the advancement or worsening of the disease or disorder resulting from the administration of a compound of the invention to a patient with such a disease or disorder. In some embodiments, the terms refer to the administration of a compound provided herein, with or without other additional active agents, after the onset of symptoms of the particular disease. The terms "treating", "treatment", or the like, as used herein covers the treatment of a disease-state in a subject, e.g., a mammal, and includes at least one of: (i) inhibiting the disease-state, i.e., partially or completely halting its progression; (ii) relieving the disease-state, i.e. causing regression of symptoms of the disease-state, or ameliorating a symptom of the disease; and (iii) reversal or regression of the disease-state, preferably eliminating or curing of the disease. In a particular embodiment the terms "treating", "treatment", or the like, covers the treatment of a disease-state in a mammal, e.g., a primate, e.g., a human, and includes at least one of (i), (ii), and (iii) above. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

As used herein, the terms "subject" and "patient" are used interchangeably. The terms "subject" and "patient" refer to an animal (e.g., a bird such as a chicken, quail or turkey) or a mammal including non-primates (e.g., a cow, pig, horse, sheep, rabbit, guinea pig, rat, cat, dog, and mouse) and primates (e.g., a monkey, chimpanzee and a human). In a particular embodiment, the subject is a human.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the administration of a compound provided herein to a subject, with or without other additional active compound, prior to the onset of symptoms, particularly to patients at risk of diseases or disorders provided herein. The terms encompass the inhibition or reduction of a symptom of the particular disease. Subjects with familial history of a disease in particular are candidates for preventive regimens in certain embodiments. In addition, subjects who have a history of recurring symptoms are also potential candidates for the prevention. In this regard, the term "prevention" may be interchangeably used with the term "prophylactic treatment." In certain embodiments, the prevention is achieved by administration of a prophylactically effective amount of a compound of the invention.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent e.g. cholinesterase inhibitors, donepezil, rivastigmine, galantamine and/or memantine.

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Alkyl is meant to denote a linear or branched saturated or unsaturated aliphatic $C_1$-$C_8$ hydrocarbon, unless some other number of carbon atoms is specified. Unsaturation in the form of a double or triple carbon-carbon bond may be internal or terminally located and, in the case of a double bond, both cis and trans isomers are included. An optionally substituted alkyl can be independently substituted with one or more substituents selected from the group consisting of F, oxo, OH, $(C_1$-$C_4)$alkoxy, $(C_3$-$C_6)$cycloalkyloxy, $(C_1$-$C_4)$alkylthio, $(C_3$-$C_6)$cycloalkylthio-, —C(O)NH$_2$, —C(O)NH$(C_1$-$C_4)$alkyl, —C(O)N[$(C_1$-$C_4)$alkyl$(C_1$-$C_4)$alkyl], $(C_1$-$C_4$ alkyl)-C(O)—, $(C_1$-$C_4)$alkylsulfonyl, —S(O)$_2$NH$_2$, —S(O)$_2$NH$(C_1$-$C_4)$alkyl, —S(O)$_2$N[$(C_1$-$C_4)$alkyl$(C_1$-$C_4)$alkyl].

Examples of alkyl groups include, but are not limited to, methyl, trifluoromethyl, ethyl, trifluoroethyl, isobutyl, neopentyl, cis- and trans-2-butenyl, isobutenyl and propargyl. $C_1$-$C_4$ alkyl is the subset of alkyl limited to a total of up to 4 carbon atoms. In other cases, an optionally substituted alkyl can be independently substituted with one or more substituents selected from the group consisting of F, OH, oxo, and ($C_1$-$C_4$)alkoxy. In other cases, an optionally substituted alkyl can be independently substituted with up to three fluorines. In still other cases, an alkyl substituted with one or more halogens (e.g., fluoro) is sometimes referred to herein as "haloalkyl."

In each case in which a size range for the number of atoms in a ring or chain is disclosed, all subsets are disclosed. Thus, $C_x$-$C_y$ includes all subsets, e.g., $C_1$-$C_4$ includes $C_1$-$C_2$, $C_2$-$C_4$, and $C_1$-$C_3$ as well as $C_1$, $C_2$, $C_3$ and $C_4$.

Acyl is an alkyl-C(O)— group wherein alkyl is as defined above. Examples of acyl groups include but are not limited to acetyl and proprionyl.

Alkoxy is an alkyl-O— group wherein alkyl is as defined above, including the optional substitutions. $C_1$-$C_4$ alkoxy is the subset of alkyl-O— where the subset of alkyl is limited to a total of up to 4 carbon atoms. Examples of alkoxy groups include, but are not limited to, methoxy, trifluoromethoxy, ethoxy, trifluoroethoxy, and propoxy.

Alkoxyalkyl is an alkyl-O—($C_1$-$C_4$ alkyl)- group wherein alkyl is as defined above. Examples of alkoxyalkyl groups include, but are not limited to, methoxymethyl and ethoxymethyl.

Alkoxyalkyloxy is an alkoxy-alkyl-O— group wherein alkoxy and alkyl are as defined above. Examples of alkoxyalkyloxy groups include, but are not limited to, methoxymethyloxy ($CH_3OCH_2O$—) and methoxyethyloxy ($CH_3OCH_2CH_2O$—) groups.

Alkylthio is alkyl-S— group wherein alkyl is as defined above. $C_1$-$C_4$ alkylthio is the subset of alkyl-S— where the subset of alkyl is limited to a total of up to 4 carbon atoms.

Alkylsulfonyl is alkyl-$SO_2$— wherein alkyl is as defined above. Examples of alkylsulfonyl groups include, but are not limited to, methanesulfonyl and isopropylsulfonyl.

Alkylamino is alkyl-NH— wherein alkyl is as defined above.

Dialkylamino is (alkyl)$_2$-N— wherein alkyl is as defined above.

Amido is $H_2NC(O)$—.

Alkylamido is alkyl-NHC(O)— wherein alkyl is as defined above.

Dialkylamido is (alkyl)$_2$-NC(O)— wherein alkyl is as defined above.

Aromatic is heteroaryl or aryl wherein heteroaryl and aryl are as defined below.

Aryl is a phenyl or napthyl group. An optionally substituted aryl can be independently substituted with one or more substituents selected from the group consisting of halogen, $CF_3$, CN, OH, ($C_1$-$C_4$)alkoxy, ($C_1$-$C_4$)alkylthio, ($C_3$-$C_7$)cycloalkylthio, ($C_3$-$C_7$)cycloalkyloxy, aryloxy, ($C_1$-$C_4$)alkoxy($C_1$-$C_4$)alkyloxy, hetero($C_3$-$C_7$)cycloalkyloxy, heteroaryloxy, —OC(O)$R_a$, —OC(O)NH$R_a$, —OC(O)N($R_a$)($R_b$), —S(O)$R_a$, —NH$R_a$, —N($R_a$)($R_b$), —NHC(O)$R_a$, —N($R_a$)C(O)$R_b$, —NHC(O)O$R_a$, —N($R_a$)C(O)O$R_b$, —N($R_a$)—C(O)—NH($R_b$), —N($R_a$)—C(O)—N($R_b$)$_2$, —C(O)NH$_2$, —C(O)NH$R_a$, —C(O)N($R_a$)($R_b$), —CO$_2$H, —CO$_2R_a$, —COR$_a$ and $R_c$ wherein $R_a$, $R_b$ and $R_c$ are independently chosen from ($C_1$-$C_6$)alkyl, ($C_1$-$C_4$)alkoxy($C_1$-$C_4$)alkyl, —CH$_2$CH$_2$OH, —CH$_2$CH$_2$OMe, ($C_3$-$C_7$)cycloalkyl, ($C_3$-$C_7$)cycloalkyl($C_1$-$C_4$)alkyl, aryl, arylalkyl, heteroaryl, heteroarylalkyl, hetero($C_3$-$C_7$)cycloalkyl, and hetero($C_3$-$C_7$)cycloalkyl($C_1$-$C_4$)alkyl, each of which is optionally and independently substituted with up to three groups selected from the group consisting of halogen, ($C_1$-$C_6$)alkyl, ($C_3$-$C_7$)cycloalkyl, ($C_3$-$C_7$)cycloalkyloxy, ($C_3$-$C_7$)cycloalkylalkoxy, CN, CHF$_2$, CF$_3$, CH$_2$CF$_3$, NHMe, NMe$_2$, piperidnyl, morpholinyl, N-Me-piperazinyl, piperazinyl, OCF$_3$, OCHF$_2$, OCH$_2$CF$_3$, SMe, each of which are attached via carbon-carbon or carbon-nitrogen or carbon-oxygen single bonds, and none of which are substituted; or $R_a$ and $R_b$ taken together with the atom(s) to which they are attached form a 5-6 membered ring. In other cases, an optionally substituted aryl can be independently substituted with one or more substituents selected from the group consisting of halogen, CF$_3$, CN, ($C_1$-$C_6$)alkyl, ($C_3$-$C_7$)cycloalkyl, ($C_1$-$C_4$)alkoxy, ($C_3$-$C_7$)cycloalkylthio, ($C_3$-$C_7$)cycloalkyloxy, hetero($C_3$-$C_7$)cycloalkyl, C(O)NH$_2$, —C(O)NHR$_a$, and —C(O)N($R_a$)($R_b$) wherein $R_a$ and $R_b$ are defined as above. In further cases, an optionally substituted aryl can be independently substituted with one or more substituents selected from the group consisting of halogen, CF$_3$, CN, ($C_1$-$C_6$)alkyl, ($C_3$-$C_7$)cycloalkyl, ($C_3$-$C_7$)cycloalkyloxy, and hetero($C_3$-$C_7$)cycloalkyl.

Arylalkyl is an aryl-alkyl- group wherein aryl and alkyl are as defined above, including the optional substitutions.

Aryloxy is an aryl-O— group wherein aryl is as defined above, including the optional substitutions.

Arylalkoxy is an aryl-($C_1$-$C_4$ alkyl)-O— group wherein aryl is as defined above, including the optional substitutions.

Carboxy is a CO$_2$H or CO$_2R_d$ group wherein $R_d$ is independently chosen from ($C_1$-$C_6$)alkyl, ($C_3$-$C_7$)cycloalkyl, aryl($C_1$-$C_3$)alkyl, ($C_3$-$C_7$)cycloalkyl($C_1$-$C_3$)alkyl, and alkoxyalkyl, wherein alkyl, cycloalkyl, aryl and alkoxy are as defined above, including the optional substitutions.

Cycloalkyl is a $C_3$-$C_{10}$ cyclic non-aromatic hydrocarbon, e.g., a $C_3$-$C_7$, cyclic non-aromatic hydrocarbon, which may contain a single double bond. An optionally substituted cycloalkyl can be independently substituted with one or more substituents selected from the group consisting of F, oxo, OH, ($C_1$-$C_6$)alkyl, ($C_1$-$C_4$)alkoxy, —($C_3$-$C_7$)cycloalkyl, ($C_3$-$C_7$)cycloalkylalkyl, ($C_3$-$C_7$)cycloalkyloxy, ($C_1$-$C_4$)alkylthio, ($C_3$-$C_6$)cycloalkylthio-, —C(O)NH$_2$, —C(O)NH($C_1$-$C_4$)alkyl, —C(O)N[($C_1$-$C_4$)alkyl($C_1$-$C_4$) alkyl], ($C_1$-$C_4$ alkyl)-C(O)—, ($C_1$-$C_4$)alkylsulfonyl, —S(O)$_2$NH$_2$, —S(O)$_2$NH($C_1$-$C_4$)alkyl, —S(O)$_2$N[($C_1$-$C_4$)alkyl($C_1$-$C_4$)alkyl]. In other cases, an optionally substituted cycloalkyl can be independently substituted with one or more substituents selected from the group consisting of F, oxo, ($C_1$-$C_4$)alkoxy, ($C_3$-$C_7$)cycloalkyl, —C(O)NH($C_1$-$C_4$)alkyl, —C(O)N[($C_1$-$C_4$)alkyl($C_1$-$C_4$)alkyl], ($C_1$-$C_4$ alkyl)-C(O)—, ($C_1$-$C_4$)alkylsulfonyl, —S(O)$_2$NH($C_1$-$C_4$)alkyl, —S(O)$_2$N[($C_1$-$C_4$)alkyl($C_1$-$C_4$)alkyl]. In further cases, an optionally substituted cycloalkyl can be independently substituted with one substituent selected from the group consisting of oxo, OH, ($C_1$-$C_6$)alkyl, ($C_1$-$C_4$)alkoxy, ($C_3$-$C_7$)cycloalkylalkyl, ($C_3$-$C_7$)cycloalkyloxy, ($C_1$-$C_4$)alkylthio, ($C_3$-$C_6$)cycloalkylthio-, —C(O)NH$_2$, —C(O)NH($C_1$-$C_4$)alkyl, —C(O)N[($C_1$-$C_4$)alkyl($C_1$-$C_4$)alkyl], ($C_1$-$C_4$ alkyl)-C(O)—, ($C_1$-$C_4$)alkylsulfonyl, —S(O)$_2$NH$_2$, —S(O)$_2$NH($C_1$-$C_4$)alkyl, —S(O)$_2$N[($C_1$-$C_4$)alkyl($C_1$-$C_4$)alkyl]. In other cases, an optionally substituted cycloalkyl can be independently substituted with one substituent selected from the group consisting of oxo, OH, ($C_1$-$C_6$)alkyl, ($C_1$-$C_4$)alkoxy, ($C_3$-$C_7$)cycloalkylalkyl and ($C_3$-$C_7$)cycloalkyloxy.

Examples of cycloalkyl groups include, but are not limited to, cyclopropyl, cyclobutyl, cyclopentyl, cyclohexyl, cyclopentenyl, and adamantyl.

Cycloalkyloxy is a cycloalkyl-O— group wherein cycloalkyl is as defined above, including the optional substitutions. Examples include, but are not limited to, cyclopropyloxy, cyclobutyloxy and cyclopentyloxy. $C_3$-$C_6$ cycloalkyloxy is the subset of cycloalkyl-O— where cycloalkyl contains 3-6 carbon atoms.

Cycloalkylthio is a cycloalkyl-S— group wherein cycloalkyl is as defined above, including the optional substitutions. Examples include, but are not limited to, cyclopropylthio, cyclobutylthio and cyclopentylthio.

Cycloalkylalkyl is a cycloalkyl-($C_1$-$C_4$ alkyl)- group wherein cycloalkyl and alkyl are defined above, including the optional substitutions. Examples include, but are not limited to, cyclopropylmethyl, cyclopropylethyl, cyclohexylmethyl and cyclohexylethyl.

Cycloalkylalkoxy is a cycloalkyl-($C_1$-$C_4$ alkyl)-O— group wherein cycloalkyl and alkoxy are as defined above, including the optional substitutions. Examples of cycloalkylalkoxy groups include, but are not limited to, cyclopropylmethoxy, cyclopentylmethoxy and cyclohexylmethoxy.

Cycloalkylalkylthio is a cycloalkyl-($C_1$-$C_4$)alkyl-S— group wherein cycloalkyl and alkyl are as defined above. Examples of cycloalkylalkylthio groups include, but are not limited to, cyclopropylmethanethio, cyclobutylmethanethio and cyclopentylmethanethio.

Halogen is F, Cl, Br or I. In particular embodiments, halogens are F, Cl and Br. In a specific embodiment, the halogen is F.

A heteroaryl group can be: (a) a tetrazole, (b) 1,2,3,4-oxatriazole, (c) 1,2,3,5-oxatriazole, or (d) a mono or bicyclic aromatic ring system, or a heterobicyclic ring system with one aromatic ring having 5 to 10 ring atoms independently selected from the group consisting of C, N, O and S, provided that not more than 3 ring atoms in any single ring are other than C. Examples of heteroaryl groups include, but are not limited to, thiophenyl, furanyl, thiazolyl, isothiazolyl, oxazolyl, isoxazolyl, 1,2,4-oxadiazolyl, 1,3,4-oxadiazolyl, pyrrazolyl, imidazolyl, 1,2,3-triazolyl, 1,3,4-triazolyl, pyrimidinyl, pyrazinyl, indolyl, quinolyl, tetrahydroquinolyl, isoquinolyl, tetrahydroisoquinolyl, indazolyl, benzthiadiazololyl, benzoxadiazolyl and benzimidazolyl. An optionally substituted heteroaryl can be independently substituted with one or more substituents selected from the group consisting of halogen, $CF_3$, CN, OH, ($C_1$-$C_4$)alkoxy, ($C_1$-$C_4$)alkylthio, ($C_3$-$C_7$)cycloalkylthio, ($C_3$-$C_7$)cycloalkyloxy, aryloxy, ($C_1$-$C_4$)alkoxy($C_1$-$C_4$)alkyloxy, hetero($C_3$-$C_7$)cycloalkyloxy, heteroaryloxy, —OC(O)$R_a$, —OC(O)NH$R_a$, —OC(O)N($R_a$)($R_b$), —S(O)$R_a$, —NH$_2$, —NH$R_a$, —N($R_a$)($R_b$), —NHC(O)$R_a$, —N($R_a$)C(O)$R_b$, —NHC(O)OR$_a$, —N($R_a$)C(O)OR$_b$, —N($R_a$)—C(O)—NH($R_b$), —N($R_a$)—C(O)—N($R_b$)$_2$, —C(O)NH$_2$, —C(O)NH$R_a$, —C(O)N($R_a$)($R_b$), —CO$_2$H, —CO$_2$$R_a$, —COR$_a$ and $R_c$ wherein $R_a$, $R_b$ and $R_c$, are independently chosen from ($C_1$-$C_6$)alkyl, ($C_1$-$C_4$)alkoxy($C_1$-$C_4$)alkyl, —CH$_2$CH$_2$OH, —CH$_2$CH$_2$OMe, ($C_3$-$C_7$)cycloalkyl, ($C_3$-$C_7$)cycloalkyl($C_1$-$C_4$)alkyl, aryl, arylalkyl, heteroaryl, heteroarylalkyl, hetero($C_3$-$C_7$)cycloalkyl, and hetero($C_3$-$C_7$)cycloalkyl($C_1$-$C_4$)alkyl, each of which is optionally and independently substituted with up to three groups selected from the group consisting of halogen, ($C_1$-$C_6$)alkyl, ($C_3$-$C_7$)cycloalkyl, ($C_3$-$C_7$)cycloalkyloxy, ($C_3$-$C_7$)cycloalkylalkoxy, CN, NO$_2$, NH$_2$, CHF$_2$, CF$_3$, CH$_2$CF$_3$, NHMe, NMe$_2$, piperidnyl, morpholinyl, N-Me-piperazinyl, piperazinyl, OCF$_3$, OCHF$_2$, OCH$_2$CF$_3$, and SMe, each of which are attached via carbon-carbon or carbon-nitrogen or carbon-oxygen single bonds, and none of which are substituted; or $R_a$ and $R_b$ taken together with the atom(s) to which they are attached form a 5-6 membered ring. In other cases, an optionally substituted heteroaryl can be independently substituted with one or more substituents selected from the group consisting of halogen $CF_3$, CN, ($C_1$-$C_6$)alkyl, ($C_3$-$C_7$)cycloalkyl, ($C_1$-$C_4$) alkoxy, ($C_3$-$C_7$)cycloalkylthio, ($C_3$-$C_7$)cycloalkyloxy, hetero($C_3$-$C_7$)cycloalkyl, C(O)NH$_2$, —C(O)NHR$_a$, and —C(O)N($R_a$)($R_b$) wherein $R_a$ and $R_b$ are defined as above. In further cases, an optionally substituted heteroaryl can be independently substituted with one or more substituents selected from the group consisting of halogen, $CF_3$, CN, ($C_1$-$C_6$)alkyl, ($C_3$-$C_7$)cycloalkyl, ($C_3$-$C_7$)cycloalkyloxy, and hetero($C_3$-$C_7$)cycloalkyl.

Heteroarylalkyl is a heteroaryl-($C_1$-$C_4$ alkyl)- group wherein heteroaryl and alkyl are as defined above, including the optional substitutions. Examples of heteroarylalkyl groups include, but are not limited to, 4-pyridinylmethyl and 4-pyridinylethyl.

Heteroaryloxy is a heteroaryl-O group wherein heteroaryl is as defined above, including the optional substitutions.

Heteroarylalkoxy is a heteroaryl-($C_1$-$C_4$ alkyl)-O— group wherein heteroaryl and alkoxy are as defined above, including the optional substitutions. Examples of heteroarylalkyl groups include but are not limited to 4-pyridinylmethoxy and 4-pyridinylethoxy.

Heterobicyclic ring system is a bicyclic ring system having 8-10 atoms independently selected from the group consisting of C, N, O and S, provided that not more than 3 ring atoms in any single ring are other than carbon and provided that at least one of the rings is aromatic. An optionally substituted heterobicyclic ring system can be independently substituted with one or more substituents selected from the group consisting of ($C_1$-$C_6$)alkyl, ($C_1$-$C_4$) alkoxy, ($C_3$-$C_7$)cycloalkyl, ($C_3$-$C_7$)cycloalkyloxy, ($C_3$-$C_7$) cycloalkyl($C_1$-$C_3$)alkyl, halogen, alkylsulfonyl and cyano. In other cases, an optionally substituted heterobicyclic ring system can be independently substituted with one or more substituents selected from the group consisting of ($C_1$-$C_6$) alkyl, ($C_3$-$C_7$)cycloalkyl, ($C_3$-$C_7$)cycloalkyloxy, halogen and cyano. Examples of 8-10 membered heterobicyclic ring systems include, but are not limited to, 1,5-naphthyridyl, 1,2,3,4-tetrahydro-1,5-naphthyridyl 1,6-naphthyridyl, 1,2,3,4-tetrahydro-1,6-naphthyridyl 1,7-naphthyridyl, 1,2,3,4-tetrahydro-1,7-naphthyridinyl 1,8-naphthyridyl, 1,2,3,4-tetrahydro-1,8-naphthyridyl, 2,6-naphthyridyl, 2,7-naphthyridyl, cinnolyl, isoquinolyl, tetrahydroisoquinolinyl, phthalazyl, quinazolyl, 1,2,3,4-tetrahydroquinazolinyl, quinolyl, tetrahydroquinolinyl, quinoxalyl, tetrahydroquinoxalinyl, benzo[d][1,2,3]triazyl, benzo[e][1,2,4]triazyl, pyrido[2,3-b]pyrazyl, pyrido[2,3-c]pyridazyl, pyrido[2,3-d]pyrimidyl, pyrido[3,2-b]pyrazyl, pyrido[3,2-c]pyridazyl, pyrido[3,2-d]pyrimidyl, pyrido[3,4-b]pyrazyl, pyrido[3,4-c]pyridazyl, pyrido[3,4-d]pyrimidyl, pyrido[4,3-b]pyrazyl, pyrido[4,3-c]pyridazyl, pyrido[4,3-d]pyrimidyl, quinazolyl, 1H-benzo[d][1,2,3]triazoyl, 1H-benzo[d]imidazoyl, 1H-indazoyl, 1H-indoyl, 2H-benzo[d][1,2,3]triazoyl, 2H-pyrazolo[3,4-b]pyridinyl, 2H-pyrazolo[4,3-b]pyridinyl, [1,2,3]triazolo[1,5-a]pyridinyl, [1,2,4]triazolo[1,5-a]pyridinyl, [1,2,4]triazolo[4,3-a]pyridinyl, benzo[b]thienyl, benzo[c][1,2,5]oxadiazyl, benzo[c][1,2,5]thiadiazolyl, benzo[d]isothiazoyl, benzo[d]isoxazolyl, benzo[d]oxazoyl, benzo[d]thiazoyl, benzofuryl, imidazo[1,2-a]pyrazyl, imidazo[1,2-a]pyridinyl, imidazo[1,2-a]pyrimidyl, imidazo[1,2-b]pyridazyl, imidazo[1,2-c]pyrimidyl, imidazo[1,5-a]pyrazyl, imidazo[1,5-a]pyridinyl, imidazo[1,5-a]pyrimidyl, imidazo[1,5-b]pyridazyl, imidazo[1,5-c]pyrimidyl, indolizyl, pyrazolo[1,5-a]pyrazyl, pyrazolo[1,5-a]pyridinyl, pyrazolo[1,5-a]pyrimidyl, pyrazolo[1,5-b]pyridazine, pyrazolo[1,5-c]pyrimidine, pyrrolo[1,2-a]pyrazine, pyrrolo[1,2-a]pyrimidyl, pyrrolo[1,2-b]pyridazyl, pyrrolo[1,2-c]pyrimidyl, 1H-imidazo[4,5-b]pyridinyl, 1H-imidazo[4,5-c]pyridinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-c]pyridinyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, 2H-indazoyl, 3H-imidazo[4,5-b]pyridinyl, 3H-imidazo[4,5-c]pyridinyl, benzo[c]isothiazyl, benzo[c]isoxazyl, furo[2,3-b]pyridinyl, furo[2,3-c]pyridinyl, furo[3,2-b]pyridinyl, furo[3,2-c]pyridiyl, isothiazolo[4,5-b]pyridinyl, isothiazolo[4,5-c]pyridinyl, isothiazolo[5,4-b]pyridinyl, isothiazolo[5,4-c]pyridinyl, isoxazolo[4,5-b]pyridinyl, isoxazolo[4,5-c]pyridinyl, isoxazolo[5,4-b]pyridinyl, isoxazolo[5,4-c]pyridinyl, oxazolo[4,5-b]pyridinyl, oxazolo[4,5-c]pyridinyl, oxazolo[5,4-b]pyridinyl, oxazolo[5,4-c]pyridinyl, thiazolo[4,5-b]pyridiyl, thiazolo[4,5-c]pyridinyl, thiazolo[5,4-b]pyridinyl, thiazolo[5,4-c]pyridinyl, thieno[2,3-b]pyridinyl, thieno[2,3-c]pyridinyl, thieno[3,2-b]pyridinyl and thieno[3,2-c]pyridinyl. In some cases, an optionally substituted heterobicyclic system can be independently substituted on carbon with one or more substituents selected from the group consisting of halogen, $CF_3$, CN, $(C_1-C_6)$alkyl, $(C_1-C_4)$alkoxy, $(C_3-C_7)$cycloalkyl, $(C_3-C_7)$cycloalkyloxy, and hetero$(C_3-C_7)$cycloalkyl.

Heterocycloalkyl is a non-aromatic, monocyclic or bicyclic saturated or partially unsaturated ring system comprising 5-10 ring atoms selected from the group consisting of C, N, O and S, provided that not more than 2 ring atoms in any single ring are other than C. An optionally substituted heterocycloalkyl can be independently substituted on a carbon atom with one or more substituents selected from the group consisting of OH, $(C_1-C_6)$alkyl and $(C_1-C_4)$alkoxy groups and up to two oxo groups. In one case where the heterocycloalkyl group contains a nitrogen, an optionally substituted heterocycloalkyl can be independently substituted on said nitrogen with one or more substituents selected from the group consisting of $(C_1-C_6)$alkyl, $(C_3-C_7)$cycloalkyl, $(C_3-C_7)$cycloalkyl$(C_1-C_3)$alkyl, acyl, —C(O)O—$(C_1-C_4)$alkyl, —C(O)NH—$(C_1-C_4)$alkyl or a —C(O)N(($C_1-C_4$)alkyl)$_2$ group. In other cases where the heterocycloalkyl group contains a nitrogen, an optionally substituted heterocycloalkyl can be independently substituted on said nitrogen with one or more substituents selected from the group consisting of $(C_1-C_6)$alkyl, $(C_3-C_7)$cycloalkyl, $(C_3-C_7)$cycloalkyl$(C_1-C_3)$alkyl and acyl. Heterocycloalkyl groups may be linked to the rest of the molecule via either carbon or nitrogen ring atoms. Examples of heterocycloalkyl groups include tetrahydrofuranyl, tetrahydrothienyl, tetrahydro-2H-pyranyl, tetrahydro-2H-thiopyranyl, pyrrolidinyl, pyrrolidonyl, succinimidyl, piperidinyl, piperazinyl, N-methylpiperazinyl, morpholinyl, morpholin-3-one, thiomorpholinyl, thiomorpholin-3-one, 2,5-diazabicyclo[2.2.2]octanyl, 2,5-diazabicyclo[2.2.1]heptanyl, 2-azabicyclo[2.2.2]octane, 2-azabicyclo[2.2.1]heptane and octahydro-1H-pyrido[1,2-a]pyrazine.

Heterocycloalkylalkyl is a heterocycloalkyl-($C_1$-$C_4$ alkyl)- group wherein heterocycloalkyl and alkyl are as defined above, including the optional substitutions.

Heterocycloalkyloxy is a heterocycloalkyl-O— group wherein heterocycloalkyl is as defined above, including the optional substitutions.

Heterocycloalkylalkoxy is a heterocycloalkyl-($C_1$-$C_4$ alkyl)-O— group wherein heterocycloalkyl and alkyl are as defined above, including the optional substitutions.

Oxo is a —C(O)— group.

Phenyl is a benzene ring. An optionally substituted phenyl can be independently substituted with one or more substituents selected from the group consisting of halogen, $CF_3$, CN, OH, $(C_1-C_4)$alkoxy, $(C_1-C_4)$alkylthio, $(C_3-C_7)$cycloalkylthio, $(C_3-C_7)$cycloalkyloxy, aryloxy, $(C_1-C_4)$alkoxy$(C_1-C_4)$alkyloxy, hetero$(C_3-C_7)$cycloalkyloxy, heteroaryloxy, —OC(O)$R_a$, —OC(O)NH$R_a$, —OC(O)N($R_a$)($R_b$), —S(O)$R_a$, —NH$R_a$, —N($R_a$)($R_b$), —NHC(O)$R_a$, —N($R_a$)C(O)$R_b$, —NHC(O)O$R_a$, —N($R_a$)C(O)O$R_b$, —N($R_a$)—C(O)—NH($R_b$), —N($R_a$)—C(O)—N($R_b$)$_2$, —C(O)NH$_2$, —C(O)NH$R_a$, —C(O)N($R_a$)($R_b$), —CO$_2$H, —CO$_2$$R_a$, —COR$_a$ and $R_c$ wherein $R_a$, $R_b$ and $R_c$ are independently chosen from $(C_1-C_6)$alkyl, $(C_1-C_4)$alkoxy$(C_1-C_4)$alkyl, —CH$_2$CH$_2$OH, —CH$_2$CH$_2$OMe, $(C_3-C_7)$cycloalkyl, $(C_3-C_7)$cycloalkyl$(C_1-C_4)$alkyl, aryl, arylalkyl, heteroaryl, heteroarylalkyl, hetero$(C_3-C_7)$cycloalkyl, and hetero$(C_3-C_7)$cycloalkyl$(C_1-C_4)$alkyl, each of which is optionally and independently substituted with up to three groups selected from the group consisting of halogen, $(C_1-C_6)$alkyl, $(C_3-C_7)$cycloalkyl, $(C_3-C_7)$cycloalkyloxy, $(C_3-C_7)$cycloalkylalkoxy, CN, NO$_2$, NH$_2$, CHF$_2$, CF$_3$, CH$_2$CF$_3$, NHMe, NMe$_2$, piperidnyl, morpholinyl, N-Me-piperazinyl, piperazinyl, OCF$_3$, OCHF$_2$, OCH$_2$CF$_3$, SMe, each of which are attached via carbon-carbon or carbon-nitrogen or carbon-oxygen single bonds, and none of which are substituted; or $R_a$ and $R_b$ taken together with the atom(s) to which they are attached form a 5-6 membered ring. In other cases, an optionally substituted phenyl can be independently substituted with one or more substituents selected from the group consisting of halogen $CF_3$, CN, $(C_1-C_6)$alkyl, $(C_3-C_7)$cycloalkyl, $(C_1-C_4)$alkoxy, $(C_3-C_7)$cycloalkylthio, $(C_3-C_7)$cycloalkyloxy, hetero$(C_3-C_7)$cycloalkyl, C(O)NH$_2$, —C(O)NH$R_a$, —C(O)N($R_a$)($R_b$) wherein $R_a$ and $R_b$ are defined as above. In further cases, an optionally substituted phenyl can be independently substituted with one or more substituents selected from the group consisting of halogen, $CF_3$, CN, $(C_1-C_6)$alkyl, $(C_3-C_7)$cycloalkyl, $(C_3-C_7)$cycloalkyloxy, and hetero$(C_3-C_7)$cycloalkyl.

Restricted phenyl is a optionally substituted benzene ring which can be independently substituted with up to three groups selected from the group consisting of halogen, $CF_3$, CN, $(C_1-C_4)$alkoxy, $(C_1-C_4)$alkylthio, $(C_3-C_7)$cycloalkylthio, $(C_3-C_7)$cycloalkyloxy, $(C_1-C_4)$alkoxy$(C_1-C_4)$alkyloxy, hetero$(C_3-C_7)$cycloalkyloxy, —OC(O)NH$R_a$, —OC(O)N($R_a$)($R_b$), —C(O)NH$_2$, —C(O)NH$R_a$, —C(O)N($R_a$)($R_b$), —COR$_a$ and $R_c$ wherein $R_a$, $R_b$ and $R_c$ are independently chosen from $(C_1-C_6)$alkyl, $(C_1-C_4)$alkoxy$(C_1-C_4)$alkyl, —CH$_2$CH$_2$OH, —CH$_2$CH$_2$OMe, $(C_3-C_7)$cycloalkyl, $(C_3-C_7)$cycloalkyl$(C_1-C_4)$alkyl, aryl, arylalkyl, heteroaryl, heteroarylalkyl, hetero$(C_3-C_7)$cycloalkyl, and hetero$(C_3-C_7)$cycloalkyl$(C_1-C_4)$alkyl, each of which is optionally and independently substituted with up to three groups selected from the group consisting of halogen, $(C_1-C_6)$alkyl, $(C_3-C_7)$cycloalkyl, $(C_3-C_7)$cycloalkyloxy, $(C_3-C_7)$cycloalkylalkoxy, CN, CHF$_2$, CF$_3$, CH$_2$CF$_3$, piperidnyl, morpholinyl, N-Me-piperazinyl, piperazinyl, OCF$_3$, OCHF$_2$, OCH$_2$CF$_3$, and SMe, each of which are attached via carbon-carbon or carbon-nitrogen or carbon-oxygen single bonds, and none of which are substituted; or $R_a$ and $R_b$ taken together with the atom(s) to which they are attached form a 5-6 membered ring.

Restricted phenyllalkyl is a restricted phenyl-($C_1$-$C_4$ alkyl)- group wherein restricted phenyl and alkyl are as defined above, including the optional substitutions. Examples of restricted phenylalkyl groups include, but are not limited to, 4-cyano-phenylmethyl and 3-chloro-phenylethyl.

Abbreviations used in the following examples and preparations include:
Ac Acyl (Me-C(O)—)
AcN Acetonitrile
ACN Acetonitrile
BINAP 2,2'-bis(diphenylphosphino)-1,1'-binaphthyl
Bn Benzyl
Celite® Diatomaceous earth
DABCO 1,4-diazabicyclo[2.2.2]octane
DBU 1,8-Diazabicyclo[5.4.0]undec-7-ene
DCC N,N', Dicyclohexylcarbodiimide
DCM Dichloromethane
DIEA Di-isopropylethyl amine
DIPEA Di-isopropylethyl amine
DMAP 4-Dimethylaminopyridine
DMF Dimethylformamide
DMP Dess Martin Periodinane
DMSO Dimethyl sulfoxide
Dppf 1,4-Bis(diphenylphosphino) ferrocene
EDC 1-(3-Dimethylaminopropyl)-3-ethylcarbodiimide Hydrochloride
Et₃N Triethylamine
g gram(s)
h Hour(s)
hr Hour(s)
HATU 2-(7-Aza-1H-benzotriazole-1-yl)-1,1,3,3-tetramethyluronium hexafluorophosphate
HMDS Hexamethyldisilazide
HOBt 1-Hydroxybenzotriazole
HPLC High Pressure Liquid Chromatography
HRMS High resolution mass spectrometry
i.v. Intravenous
KHMDS Potassium Hexamethydisilazide
LDA Lithium Di-isopropylamide
IPA Isopropyl alcohol
m Multiplet
m- meta
MEM Methoxyethoxymethyl
MeOH Methyl Alcohol or Methanol
min Minute(s)
mmol millimoles
mmole millimoles
Ms Mesylate
MS Mass Spectrometry
MW Molecular Weight
NBS N-Bromosuccinamide
NIS N-Iodosuccinamide
NMR Nuclear Magnetic Resonance
NMM N-Methyl Morpholine
NMP N-Methyl-2-pyrrolidone
o ortho
o/n overnight
p para
PCC Pyridinium Chlorochromate
PEPPSI 1,3-Bis(2,6-diisopropylphenyl)imidazolidene)(3-chloropyridinyl) palladium(II) dichloride
PhNTf₂ 1,1,1-trifluoro-N-phenyl-N-(trifluoromethylsulfonyl)methanesulfonamide
POPd Dihydrogen dichlorobis(di-tert-butylphosphinito-kp) palladate (2-)
p.s.i. Pounds per square inch
PPA Polyphosphoric acid
PPAA 1-Propanephosphonic Acid Cyclic Anhydride
PTSA p-Toluenesulfonic acid
PyBOP® Benzotriazol-1-yl-oxytripyrrolidinophosphonium hexafluorophosphate
RT (or rt) room temperature (about 20-25° C.)
s Singlet
sat. Saturated
SuOH N-hydroxy succinimide
t Triplet
TBAF Tetra-butyl ammonium fluoride
TEA Triethylamine
TFA Trifluoroacetic Acid
THF Tetrahydrofuran
TLC Thin layer chromatography
TMS Trimethylsilyl
Tf Triflate
Tof-MS Time of Flight Mass Spectrometry
Ts Tosylate
v/v volume/volume
wt/v weight/volume

II. COMPOUNDS OF THE INVENTION

In one embodiment, the invention provides compounds of Formula (I)

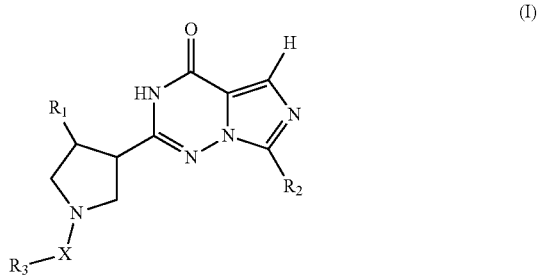

or a pharmaceutically acceptable salt thereof,
wherein:
X is selected from the group consisting of a bond, C(O) and S(O)₂;
R₁ is independently selected from the group consisting of H, (C₁-C₆) alkyl, (C₁-C₆) alkoxy, (C₃-C₇) cycloalkyl, (C₃-C₇) cycloalkyl(C₁-C₄) alkyl, (C₃-C₇) cycloalkyloxy, heterocycloalkyl, heterocycloalkyl(C₁-C₄)alkyl and heterocycloalkyloxy, each of which may be optionally substituted with one or more substituents selected from the group consisting of halogen (e.g., F or Cl), —S(O)₂(C₁-C₄)alkyl, OH, —C(O)—(C₁-C₄)alkyl, oxo, CN, (C₁-C₆)alkyl, (C₁-C₄) alkoxy, (C₃-C₇)cycloalkyl, —C(O)NH(C₁-C₄)alkyl, —C(O)N[(C₁-C₄)alkyl(C₁-C₄)alkyl], (C₁-C₄ alkyl)-C(O)—, (C₁-C₄)alkylsulfonyl, —S(O)₂NH(C₁-C₄)alkyl, and —S(O)₂N[(C₁-C₄)alkyl(C₁-C₄)alkyl];

R₂ is independently selected from the group consisting of (C₁-C₆) alkyl, (C₃-C₁₀)cycloalkyl, (C₃-C₇)cycloalkyl(C₁-C₄) alkyl, heterocycloalkyl, heterocycloalkyl(C₁-C₄)alkyl, heteroaryl, heteroaryl(C₁-C₄)alkyl, restricted phenyl and restricted phenyl(C₁-C₄)alkyl, each of which may be optionally substituted with one or more substituents selected from the group consisting of halogen (e.g., F or Cl), —S(O)₂(C₁-C₄)alkyl, OH,
—C(O)—(C₁-C₄)alkyl, oxo, CN, (C₁-C₆)alkyl, (C₁-C₄) alkoxy, (C₃-C₇)cycloalkyl, —C(O)NH(C₁-C₄)alkyl, —C(O)N[(C₁-C₄)alkyl(C₁-C₄)alkyl], (C₁-C₄ alkyl)-C(O)—, (C₁-C₄)alkylsulfonyl, —S(O)₂NH(C₁-C₄)alkyl, and —S(O)₂N[(C₁-C₄)alkyl(C₁-C₄)alkyl]; and R₃ is independently selected from the group consisting of (C₁-C₆) alkyl, (C₃-C₇) cycloalkyl, (C₃-C₇)cycloalkyl(C₁-C₄)alkyl, heterocycloalkyl, heterocycloalkyl(C₁-C₄)alkyl, heteroaryl, heteroaryl(C₁-C₄)alkyl, restricted phenyl and restricted phenyl(C₁-C₄)alkyl, each of which may be optionally substituted with one or more substituents selected from the group consisting of halogen (e.g., F or Cl), —S(O)₂(C₁-C₄)alkyl, OH, —C(O)—(C₁-C₄)alkyl, oxo, CN, (C₁-C₆)alkyl, (C₁-C₄) alkoxy, (C₃-C₇)cycloalkyl, —C(O)NH(C₁-C₄)alkyl, —C(O)N[(C₁-C₄)alkyl(C₁-C₄)alkyl], (C₁-C₄ alkyl)-C(O)—, (C₁-C₄)alkylsulfonyl, —S(O)₂NH(C₁-C₄)alkyl, and —S(O)₂N[(C₁-C₄)alkyl(C₁-C₄)alkyl]. In certain embodiments the substituents are selected from the group consisting of halogen (e.g., F or Cl), CN, (C₁-C₆)alkyl, and (C₁-C₄)alkoxy. In certain embodiments, R₁ is selected from the group consisting of (C₁-C₆) alkyl, e.g., methyl. In certain embodiments, R₂ is selected from the group consisting of heterocycloalkyl, e.g., tetrahydropyranyl or piperidinyl, (C₃-C₁₀)cycloalkyl, e.g., adamantyl, and restricted phenyl, which may be optionally substituted with one or more substituents selected from the group consisting of halogen, —S(O)₂(C₁-C₄)alkyl, OH, —C(O)—(C₁-C₄)alkyl, CN, (C₁-C₆)alkyl, and (C₁-C₄) alkoxy. In certain embodiments, R₃ is selected from the group consisting of a mono or bicyclic heteroaryl(C₁-C₄) alkyl and restricted phenyl(C₁-C₄)alkyl, which may be optionally substituted with one or more substituents selected from the group consisting of halogen, —S(O)₂(C₁-C₄)alkyl, OH, —C(O)—(C₁-C₄)alkyl, CN, (C₁-C₆)alkyl, and (C₁-C₄) alkoxy. In certain embodiments, X is a bond. In certain embodiments, R₃ is pyrimidinylmethyl-, which may be optionally substituted with one or more substituents selected from the group consisting of halogen (e.g., F or Cl), —S(O)₂(C₁-C₄)alkyl, OH, —C(O)—(C₁-C₄)alkyl, CN, (C₁-C₆)alkyl, and (C₁-C₄)alkoxy. In certain alternative embodiments, R₃ is (restricted phenyl)methyl-, which may be optionally substituted with one or more substituents selected from the group consisting of halogen (e.g., F or Cl), —S(O)₂(C₁-C₄)alkyl, OH, —C(O)—(C₁-C₄)alkyl, CN, (C₁-C₆)alkyl, and (C₁-C₄)alkoxy.

In another embodiment, the invention provides compounds of Formula (I) or a pharmaceutically acceptable salt thereof,

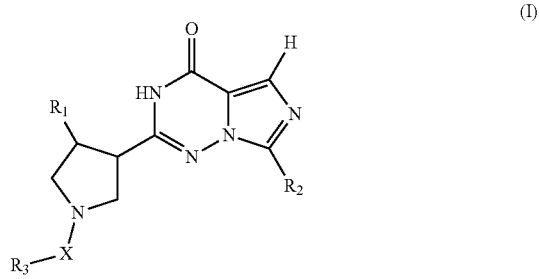

(I)

wherein:

X is selected from the group consisting of a bond, C(O) and S(O)₂;

R₁ is independently selected from the group consisting of H, (C₁-C₆) alkyl, (C₁-C₆) alkoxy, (C₃-C₇) cycloalkyl, (C₃-C₇) cycloalkyl (C₁-C₄) alkyl, (C₃-C₇) cycloalkyloxy, heterocycloalkyl, heterocycloalkyl(C₁-C₄)alkyl and heterocycloalkyloxy, all of which may be optionally substituted;

R₂ is independently selected from the group consisting of (C₁-C₆) alkyl, (C₃-C₇) cycloalkyl, (C₃-C₇) cycloalkyl (C₁-C₄) alkyl, heterocycloalkyl, heterocycloalkyl(C₁-C₄)alkyl, heteroaryl, heteroaryl(C₁-C₄)alkyl, restricted phenyl and restricted phenyl (C₁-C₄) alkyl, all of which can be optionally substituted; and R₃ is independently selected from the group consisting of (C₁-C₆) alkyl, (C₃-C₇) cycloalkyl, (C₃-C₇) cycloalkyl (C₁-C₄) alkyl, heterocycloalkyl, heterocycloalkyl(C₁-C₄)alkyl, heteroaryl, heteroaryl(C₁-C₄)alkyl, restricted phenyl and restricted phenyl (C₁-C₄) alkyl, all of which can be optionally substituted.

In yet another embodiment, the invention provides compounds of Formula (I)

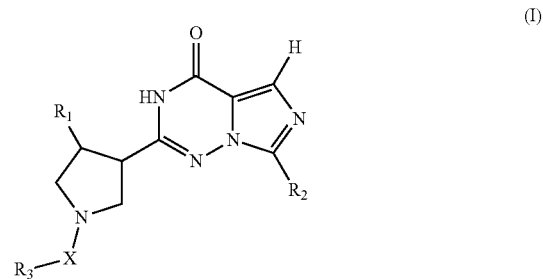

(I)

or a pharmaceutically acceptable salt thereof,
wherein:

X is selected from the group consisting of a bond, C(O) and S(O)₂;

R₁ is (C₁-C₆) alkyl, e.g., methyl;

R₂ is selected from the group consisting of heterocycloalkyl, e.g., tetrahydropyranyl or piperidinyl, (C₃-C₁₀) cycloalkyl, e.g., adamantyl, and restricted phenyl, each of which may be optionally substituted with one or more substituents selected from the group consisting of halogen (e.g., F or Cl), —S(O)₂(C₁-C₄)alkyl, OH, —C(O)—(C₁-C₄) alkyl, CN, (C₁-C₆)alkyl, and (C₁-C₄)alkoxy; and R₃ is selected from the group consisting of a mono or bicyclic heteroaryl(C₁-C₄)alkyl and restricted phenyl(C₁-C₄)alkyl, each of which may be optionally substituted with one or more substituents selected from the group consisting of halogen (e.g., F or CO, —S(O)₂(C₁-C₄)alkyl, OH, —C(O)—(C₁-C₄)alkyl, CN, (C₁-C₆)alkyl, and (C₁-C₄) alkoxy.

A further embodiment of Formula (I) may be represented as

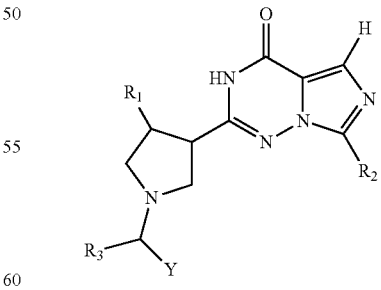

or a pharmaceutically acceptable salt thereof,
wherein:

Y is H or (C₁-C₃) alkyl, e.g., methyl or ethyl;

R₁ is (C₁-C₆) alkyl, e.g., methyl;

R₂ is selected from the group consisting of heterocycloalkyl, e.g., tetrahydropyranyl or piperidinyl, (C₃-C₁₀)

cycloalkyl, e.g., adamantyl, and restricted phenyl, each of which may be optionally substituted with one or more substituents selected from the group consisting of halogen (e.g., F or CO, —S(O)$_2$(C$_1$-C$_4$)alkyl, e.g., —S(O)$_2$CH$_2$CH$_3$, OH, —C(O)—(C$_1$-C$_4$)alkyl, e.g., —C(O)CH$_3$, CN, (C$_1$-C$_6$) alkyl, and (C$_1$-C$_4$)alkoxy; and R$_3$ is selected from the group consisting of a mono or bicyclic heteroaryl and restricted phenyl, each of which may be optionally substituted with one or more substituents selected from the group consisting of halogen (e.g., F or CO, —S(O)$_2$(C$_1$-C$_4$)alkyl, e.g., —S(O)$_2$CH$_2$CH$_3$, OH, —C(O)—(C$_1$-C$_4$)alkyl, e.g., —C(O)CH$_3$, CN, (C$_1$-C$_6$)alkyl, and (C$_1$-C$_4$)alkoxy. In certain embodiments, R$_3$ is pyrimidinyl, which may be optionally substituted with one or more substituents selected from the group consisting of halogen (e.g., F or CO, —S(O)$_2$(C$_1$-C$_4$)alkyl, e.g., —S(O)$_2$CH$_2$CH$_3$, OH, —C(O)—(C$_1$-C$_4$)alkyl, e.g., —C(O)CH$_3$, CN, (C$_1$-C$_6$) alkyl, and (C$_1$-C$_4$)alkoxy. In certain alternative embodiments, R$_3$ is restricted phenyl, which may be optionally substituted with one or more substituents selected from the group consisting of halogen (e.g., F or Cl), —S(O)$_2$(C$_1$-C$_4$)alkyl, e.g., —S(O)$_2$CH$_2$CH$_3$, OH, —C(O)—(C$_1$-C$_4$)alkyl, e.g., —C(O)CH$_3$, CN, (C$_1$-C$_6$)alkyl, and (C$_1$-C$_4$)alkoxy.

In certain embodiments of the invention, where R$_1$ is H, the compound of the invention is the trans (−) stereoisomer.

In certain embodiments of the invention, where R$_1$ is H, the compound of the invention is the trans (+) stereoisomer.

A. Additional Embodiments of the Invention

In one embodiment, alkyl groups are fully saturated whether present on their own or as part of another group (e.g. alkylamino).

In certain embodiments, substituent groups are not further substituted.

In various embodiments, any group that is defined as being optionally substituted can be independently singly or multiply optionally substituted.

In one embodiment, compounds of the invention contain one alkyl group which is substituted with 1-3 fluorine atoms. Such alkyl groups are sometimes referred to herein as an example of a haloalkyl group.

In another embodiment, compounds of the invention contain one alkyl group which contains a double bond.

In one embodiment compounds of the invention contain two alkyl groups which are substituted with 1-3 fluorine atoms.

In another embodiment, compounds of the invention contain one alkyl group which contains a triple bond.

In another embodiment, compounds of the invention contain one alkyl group which is substituted with an oxo group.

In another embodiment, compounds of the invention contain one alkyl group which is substituted with a hydroxyl group.

In another embodiment, compounds of the invention contain one alkyl group which is substituted with a (C$_1$-C$_4$) alkoxy group.

In another embodiment, compounds of the invention contain one alkyl group which is substituted with a (C$_1$-C$_4$) alkylsulfonyl group.

In another embodiment, compounds of the invention contain one alkoxy group which is substituted with 1-3 fluorine atoms.

In one embodiment, saturated monocyclic heterocycloalkyl groups are substituted on carbon with up to 2 groups selected from the group consisting of OH, (C$_1$-C$_6$)alkyl and (C$_1$-C$_4$)alkoxy group.

In one embodiment, saturated monocyclic heterocycloalkyl groups are substituted on nitrogen with a group selected from the group consisting of —S(O)$_2$(C$_1$-C$_4$)alkyl, e.g., —S(O)$_2$-ethyl, and —C(O)—(C$_1$-C$_4$)alkyl, e.g., —C(O)CH$_3$.

In one embodiment, saturated monocyclic heterocycloalkyl groups are substituted on nitrogen with groups selected from the group consisting of (C$_1$-C$_6$)alkyl, acyl, —C(O)O—(C$_1$-C$_4$)alkyl, —C(O)NH—(C$_1$-C$_4$)alkyl, C(O) N((C$_1$-C$_4$)alkyl)$_2$ and (C$_1$-C$_4$)alkylsulfonyl.

In one embodiment heteroaryl groups are substituted on carbon with 1-3 groups selected from the group consisting of halogen, CN, OH, (C$_1$-C$_4$)alkyl, (C$_3$-C$_6$)cycloalkyl, (C$_1$-C$_4$) alkoxy and (C$_1$-C$_4$)alkylsulfonyl.

In one embodiment, restricted phenyl groups are substituted with 1-3 groups selected from the group consisting of halogen, CN, OH, (C$_1$-C$_4$)alkyl, (C$_3$-C$_6$)cycloalkyl, (C$_1$-C$_4$) alkoxy and (C$_1$-C$_4$)alkylsulfonyl.

In various embodiments, heteroaryl may be defined as tetrazolyl, thiophenyl, furanyl, thiazolyl, isothiazolyl, oxazolyl, isoxazolyl, 1,2,4-oxadiazolyl, 1,3,4-oxadiazolyl, pyrrazolyl, imidazolyl, 1,2,3-triazolyl, 1,3,4-triazolyl, pyrimidinyl and pyrazinyl, all of which may be optionally substituted. In a particular embodiment, the heteroaryl is pyrimidinyl.

In other embodiments, heteroaryl may be defined as 1,5-naphthyridyl, 1,2,3,4-tetrahydro-1,5-naphthyridyl 1,6-naphthyridyl, 1,2,3,4-tetrahydro-1,6-naphthyridyl 1,7-naphthyridyl, 1,2,3,4-tetrahydro-1,7-naphthyridinyl 1,8-naphthyridyl, 1,2,3,4-tetrahydro-1,8-naphthyridyl, 2,6-naphthyridyl, 2,7-naphthyridyl, cinnolyl, isoquinolyl, tetrahydroisoquinolinyl, phthalazyl, quinazolyl, 1,2,3,4-tetrahydroquinazolinyl, quinolyl, tetrahydroquinolinyl, quinoxalyl and tetrahydroquinoxalinyl, all of which may be optionally substituted.

In further embodiments, heteroaryl may be defined as benzo[d][1,2,3]triazyl, benzo[e][1,2,4]triazyl, pyrido[2,3-b]pyrazyl, pyrido[2,3-c]pyridazyl, pyrido[2,3-d]pyrimidyl, pyrido[3,2-b]pyrazyl, pyrido[3,2-c]pyridazyl, pyrido[3,2-d]pyrimidyl, pyrido[3,4-b]pyrazyl, pyrido[3,4-c]pyridazyl, pyrido[3,4-d]pyrimidyl, pyrido[4,3-b]pyrazyl, pyrido[4,3-c]pyridazyl, pyrido[4,3-d]pyrimidyl, quinazolyl, 1H-benzo[d][1,2,3]triazoyl, 1H-benzo[d]imidazoyl, 1H-indazoyl, 1H-indoyl, 2H-benzo[d][1,2,3]triazoyl, 2H-pyrazolo[3,4-b]pyridinyl, 2H-pyrazolo[4,3-b]pyridinyl, [1,2,3]triazolo[1,5-a]pyridinyl, [1,2,4]triazolo[1,5-a]pyridinyl and [1,2,4]triazolo[4,3-a]pyridinyl, all of which may be optionally substituted.

In yet other embodiments, heteroaryl may be defined as benzo[b]thienyl, benzo[c][1,2,5]oxadiazyl, benzo[c][1,2,5]thiadiazolyl, benzo[d]isothiazoyl, benzo[d]isoxazoyl, benzo[d]oxazoyl, benzo[d]thiazoyl, benzofuryl, imidazo[1,2-a]pyrazyl, imidazo[1,2-a]pyridinyl, imidazo[1,2-a]pyrimidyl, imidazo[1,2-b]pyridazyl, imidazo[1,2-c]pyrimidyl, imidazo[1,5-a]pyrazyl, imidazo[1,5-a]pyridinyl, imidazo[1,5-a]pyrimidyl, imidazo[1,5-b]pyridazyl, imidazo[1,5-c]pyrimidyl, indolizyl, pyrazolo[1,5-a]pyrazyl, pyrazolo[1,5-a]pyridinyl, pyrazolo[1,5-a]pyrimidyl, pyrazolo[1,5-b]pyridazine, pyrazolo[1,5-c]pyrimidine, pyrrolo[1,2-a]pyrazine, pyrrolo[1,2-a]pyrimidyl, pyrrolo[1,2-b]pyridazyl, pyrrolo[1,2-c]pyrimidyl, 1H-imidazo[4,5-b]pyridinyl, 1H-imidazo[4,5-c]pyridinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-c]pyridinyl, 1H-pyrrolo[2,3-b]pyridinyl, 1H-pyrrolo[2,3-c]

pyridinyl, 1H-pyrrolo[3,2-b]pyridinyl, 1H-pyrrolo[3,2-c]pyridinyl, 2H-indazoyl, 3H-imidazo[4,5-b]pyridinyl and 3H-imidazo[4,5-c]pyridinyl, all of which may be optionally substituted.

In further embodiments, heteroaryl may be defined as benzo[c]isothiazyl, benzo[c]isoxazyl, furo[2,3-b]pyridinyl, furo[2,3-c]pyridinyl, furo[3,2-b]pyridinyl, furo[3,2-c]pyridiyl, isothiazolo[4,5-b]pyridinyl, isothiazolo[4,5-c]pyridinyl, isothiazolo[5,4-b]pyridinyl, isothiazolo[5,4-c]pyridinyl, isoxazolo[4,5-b]pyridinyl, isoxazolo[4,5-c]pyridinyl, isoxazolo[5,4-b]pyridinyl, isoxazolo[5,4-c]pyridinyl, oxazolo[4,5-b]pyridinyl, oxazolo[4,5-c]pyridinyl, oxazolo[5,4-b]pyridinyl, oxazolo[5,4-c]pyridinyl, thiazolo[4,5-b]pyridiyl, thiazolo[4,5-c]pyridiyl, thiazolo[5,4-b]pyridinyl, thiazolo[5,4-c]pyridinyl, thieno[2,3-b]pyridinyl, thieno[2,3-c]pyridinyl, thieno[3,2-b]pyridinyl and thieno[3,2-c]pyridinyl, all of which may be optionally substituted.

In one embodiment, X is selected from the group consisting of C(O) and S(O)$_2$.

In another embodiment, X is C(O).

In a further embodiment, X is S(O)$_2$.

In another embodiment, X is a bond.

In another embodiment, Y is H.

In another embodiment, Y is (C$_1$-C$_3$) alkyl, e.g., methyl or ethyl.

In one embodiment, R$_1$ is selected from the group consisting of H, (C$_1$-C$_6$) alkyl, (C$_3$-C$_7$) cycloalkyl and (C$_3$-C$_7$) cycloalkyl (C$_1$-C$_4$) alkyl.

In another embodiment, R$_1$ is selected from the group consisting of (C$_1$-C$_6$) alkyl, (C$_3$-C$_7$) cycloalkyl and (C$_3$-C$_7$) cycloalkyl (C$_1$-C$_4$) alkyl.

In another embodiment, R$_1$ is selected from the group consisting of (C$_1$-C$_6$) alkoxy and (C$_3$-C$_7$) cycloalkyloxy.

In another embodiment, R$_1$ is selected from the group consisting of (C$_1$-C$_6$) alkyl and (C$_1$-C$_6$) alkoxy.

In a further embodiment, R$_1$ is selected from the group consisting of (C$_1$-C$_6$) alkyl and (C$_3$-C$_7$) cycloalkyl.

In a further embodiment, R$_1$ is selected from the group consisting of heterocycloalkyl, heterocycloalkyl(C$_1$-C$_4$) alkyl and heterocycloalkyloxy.

In another embodiment, R$_1$ is H.

In another embodiment, R$_1$ is (C$_1$-C$_6$) alkyl.

In another embodiment, R$_1$ is (C$_1$-C$_3$) alkyl.

In another embodiment, R$_1$ is methyl.

In an additional embodiment, R$_1$ is (C$_1$-C$_6$) alkoxy.

In an additional embodiment, R$_1$ is (C$_1$-C$_3$) alkoxy.

In a further embodiment, R$_1$ is (C$_3$-C$_7$) cycloalkyl.

In a further embodiment, R$_1$ is (C$_3$-C$_5$) cycloalkyl.

In another embodiment, R$_1$ is (C$_3$-C$_7$) cycloalkyl (C$_1$-C$_4$) alkyl.

In another embodiment, R$_1$ is (C$_3$-C$_5$) cycloalkyl (C$_1$-C$_2$) alkyl.

In another embodiment, R$_1$ is (C$_3$-C$_7$) cycloalkyloxy.

In another embodiment, R$_1$ is (C$_3$-C$_5$) cycloalkyloxy.

In another embodiment, R$_1$ is heterocycloalkyl.

In a further embodiment, R$_1$ is heterocycloalkyl having only 6 ring atoms. Examples include but are not limited to morpholino, piperidinyl, piperazinyl N-Me-piperazinyl and pyranyl.

In another embodiment, R$_1$ is heterocycloalkyl having only 5 ring atoms. Examples include, but are not limited to, tetrahydrofuranyl and pyrrolidinyl.

In another embodiment, R$_1$ is a heterocycloalkyl group selected from the group consisting of Formulas B1-B16 depicted below:

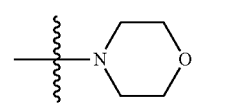 B1

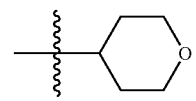 B2

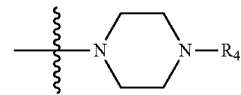 B3

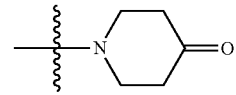 B4

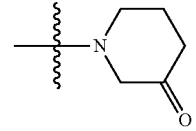 B5

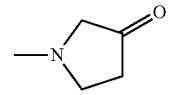 B6

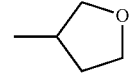 B7

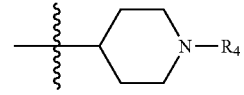 B8

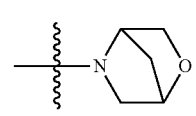 B9

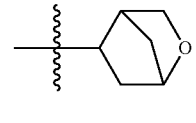 B10

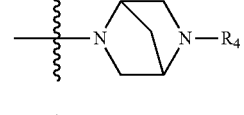 B11

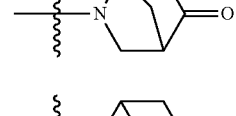 B12

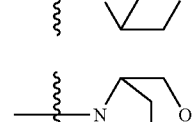 B13

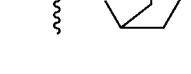 B14

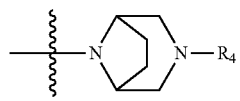
B15

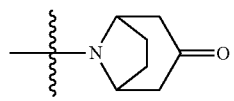
B16 wherein $R_4$ is selected from the group consisting of hydrogen, $C_1$-$C_6$ alkyl, $C_3$-$C_6$ cycloalkyl and $C_3$-$C_6$ cycloalkylalkyl.

In another embodiment, $R_1$ is heterocycloalkyl($C_1$-$C_4$) alkyl.

In a further embodiment, $R_1$ is heterocycloalkyloxy.

In one embodiment, $R_2$ is selected from the group consisting of ($C_1$-$C_6$) alkyl, ($C_3$-$C_{10}$) cycloalkyl and ($C_3$-$C_7$) cycloalkyl ($C_1$-$C_4$) alkyl.

In one embodiment, $R_2$ is selected from the group consisting of ($C_1$-$C_6$) alkyl, ($C_3$-$C_7$) cycloalkyl and ($C_3$-$C_7$) cycloalkyl ($C_1$-$C_4$) alkyl.

In one embodiment, $R_2$ is selected from the group consisting of heterocycloalkyl, ($C_3$-$C_{10}$)cycloalkyl, and restricted phenyl.

In another embodiment, $R_2$ is selected from the group consisting of heterocycloalkyl and heterocycloalkyl($C_1$-$C_4$) alkyl.

In a further embodiment, $R_2$ is selected from the group consisting of restricted phenyl, restricted phenyl($C_1$-$C_4$) alkyl, heteroaryl and heteroaryl($C_1$-$C_4$)alkyl.

In a further embodiment, $R_2$ is selected from the group consisting of heteroaryl and heteroaryl($C_1$-$C_4$)alkyl.

In another embodiment, $R_2$ is selected from the group consisting of ($C_3$-$C_7$) cycloalkyl, heterocycloalkyl, heteroaryl and restricted phenyl.

In another embodiment, $R_2$ is selected from the group consisting of ($C_3$-$C_7$) cycloalkyl, heterocycloalkyl and heteroaryl.

In another embodiment, $R_2$ is ($C_1$-$C_6$) alkyl.

In another embodiment, $R_2$ is ($C_1$-$C_3$) alkyl.

In an additional embodiment, $R_2$ is ($C_3$-$C_2$) cycloalkyl.

In an additional embodiment, $R_2$ is ($C_3$-$C_2$) cycloalkyl substituted with one or two fluoro.

In an additional embodiment, $R_2$ is ($C_3$-$C_{10}$) cycloalkyl.

In an additional embodiment, $R_2$ is ($C_3$-$C_{10}$) cycloalkyl substituted with one or two fluoro.

In an additional embodiment, $R_2$ is ($C_3$-$C_5$) cycloalkyl.

In an additional embodiment, $R_2$ is ($C_3$-$C_2$) cycloalkyl ($C_1$-$C_4$) alkyl.

In an additional embodiment, $R_2$ is ($C_3$-$C_5$) cycloalkyl ($C_1$-$C_2$) alkyl.

In another embodiment, $R_2$ is heterocycloalkyl.

In a further embodiment, $R_2$ is heterocycloalkyl having only 6 ring atoms. Examples include, but are not limited to, morpholino, piperidinyl, piperazinyl N-Me-piperazinyl and pyranyl. Additional examples include 4-piperidinyl, 3-tetrahydropyranyl and 4-tetrahydropyranyl, which may be optionally substituted with one or more groups selected from the group consisting of halogen (e.g., F or Cl), —S(O)$_2$($C_1$-$C_4$)alkyl, OH, —C(O)—($C_1$-$C_4$)alkyl, CN, ($C_1$-$C_6$)alkyl, and ($C_1$-$C_4$) alkoxy.

In another embodiment, $R_2$ is heterocycloalkyl having only 5 ring atoms. Examples include, but are not limited to, tetrahydrofuranyl and pyrrolidinyl.

In another embodiment, $R_2$ is a heterocycloalkyl group selected from the group consisting of Formulas B1-B16 depicted below:

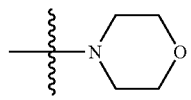
B1

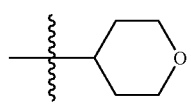
B2

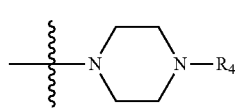
B3

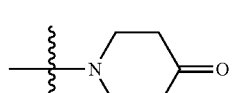
B4

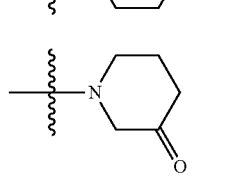
B5

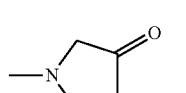
B6

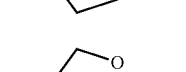
B7

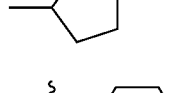
B8

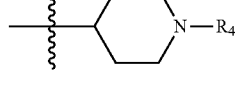
B9

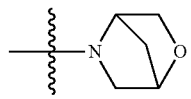
B10

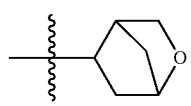
B11

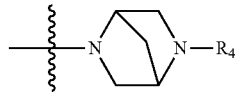
B12

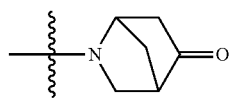
B13

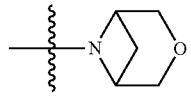

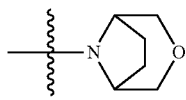

B14

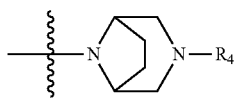

B15

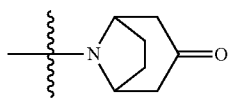

B16 wherein $R_4$ is selected from the group consisting of hydrogen, $C_1$-$C_6$ alkyl, $C_3$-$C_6$ cycloalkyl and $C_3$-$C_6$ cycloalkylalkyl.

In another embodiment, $R_2$ is heterocycloalkyl($C_1$-$C_4$) alkyl.

In an additional embodiment, $R_2$ is heteroaryl.

In a further embodiment, $R_2$ is a heterobicyclic ring system.

In another embodiment, $R_2$ is a monocyclic aromatic ring having 5-6 atoms selected from the group consisting of C, O, S and N provided that not more than 3 ring atoms are not C and where said ring may be optionally and independently substituted with up to two groups selected from the group consisting of $C_1$-$C_4$ alkyl, cycloalkyl, cycloalkyloxy, $C_1$-$C_4$ alkoxy, $CF_3$, carboxyl, alkoxyalkyl, $C_1$-$C_4$ cycloalkylalkoxy, amino, alkylamino, dialkylamino, amido, alkylamido, dialkylamido, thioalkyl, halogen, cyano, and nitro.

In a further embodiment, $R_2$ is a monocyclic aromatic ring containing 5 atoms selected from the group consisting of C, O, S, and N provided that not more than 3 ring atoms are not C and where said ring may be optionally and independently substituted with up to two groups selected from the group consisting of $C_1$-$C_4$ alkyl, cycloalkyl, cycloalkyloxy, $C_1$-$C_4$ alkoxy, $CF_3$, carboxyl, alkoxyalkyl, $C_1$-$C_4$ cycloalkylalkoxy, amino, alkylamino, dialkylamino, amido, alkylamido, dialkylamido, thioalkyl, halogen, cyano, and nitro.

In a further embodiment, $R_2$ is a monocyclic aromatic ring containing 6 atoms selected from the group consisting of C and N provided that not more than 3 ring atoms are not C and where said ring may be optionally and independently substituted with up to two groups selected from the group consisting of $C_1$-$C_4$ alkyl, e.g., methyl, cycloalkyl, cycloalkyloxy, $C_1$-$C_4$ alkoxy, $CF_3$, carboxyl, alkoxyalkyl, $C_1$-$C_4$ cycloalkylalkoxy, amino, alkylamino, dialkylamino, amido, alkylamido, dialkylamido, thioalkyl, halogen (e.g., F or Cl), cyano, and nitro.

In a further embodiment, $R_2$ is heteroaryl($C_1$-$C_4$)alkyl.

In a further embodiment, $R_2$ is restricted phenyl.

In another embodiment, $R_2$ is restricted phenyl($C_1$-$C_4$) alkyl.

In one embodiment, $R_3$ is selected from the group consisting of ($C_1$-$C_6$) alkyl, ($C_3$-$C_7$) cycloalkyl, heterocycloalkyl, heteroaryl and restricted phenyl.

In one embodiment, $R_3$ is selected from the group consisting of ($C_1$-$C_6$) alkyl, ($C_3$-$C_7$) cycloalkyl, heterocycloalkyl and heteroaryl.

In another embodiment, $R_3$ is selected from the group consisting of ($C_3$-$C_7$) cycloalkyl ($C_1$-$C_4$) alkyl, heterocycloalkyl($C_1$-$C_4$)alkyl and heteroaryl($C_1$-$C_4$)alkyl.

In a further embodiment, $R_3$ is selected from the group consisting of heterocycloalkyl($C_1$-$C_4$)alkyl and heteroaryl ($C_1$-$C_4$)alkyl.

In a further embodiment, $R_3$ is selected from the group consisting of heterocycloalkyl and heteroaryl.

In another embodiment, $R_3$ is ($C_1$-$C_6$) alkyl.

In another embodiment, $R_3$ is ($C_1$-$C_3$) alkyl.

In an additional embodiment, $R_3$ is ($C_3$-$C_2$) cycloalkyl.

In an additional embodiment, $R_3$ is ($C_3$-$C_5$) cycloalkyl.

In a further embodiment, $R_3$ is ($C_3$-$C_2$) cycloalkyl ($C_1$-$C_4$) alkyl.

In a further embodiment, $R_3$ is ($C_3$-$C_5$) cycloalkyl ($C_1$-$C_2$) alkyl.

In an additional embodiment, $R_3$ is heterocycloalkyl.

In a further embodiment $R_3$ is heterocycloalkyl having only 6 ring atoms. Examples include, but are not limited to, morpholino, piperidinyl, piperazinyl N-Me-piperazinyl and pyranyl.

In another embodiment, $R_3$ is heterocycloalkyl having only 5 ring atoms. Examples include, but are not limited to, tetrahydrofuranyl and pyrrolidinyl.

In another embodiment, $R_3$ is a heterocycloalkyl group selected from the group consisting of Formulas B1-B16 depicted below:

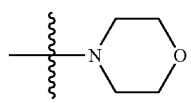

B1

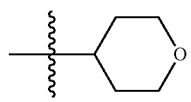

B2

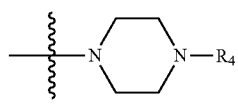

B3

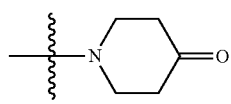

B4

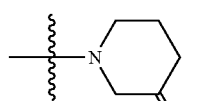

B5

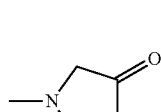

B6

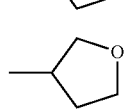

B7

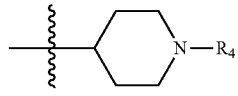

B8

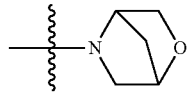

B9

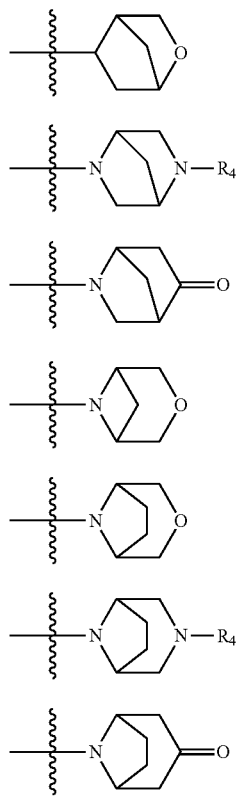

wherein R$_4$ is selected from the group consisting of hydrogen, C$_1$-C$_6$ alkyl, C$_3$-C$_6$ cycloalkyl and C$_3$-C$_6$ cycloalkylalkyl.

In another embodiment, R$_3$ is selected from the group consisting of a monocyclic heteroaryl, bicyclic heteroaryl and restricted phenyl.

In another embodiment, R$_3$ is pyrimidinylmethyl-, which may be optionally substituted with one or more substituents selected from the group consisting of halogen (e.g., F or Cl), —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

In another embodiment, R$_3$ is (restricted phenyl)methyl-, which may be optionally substituted with one or more substituents selected from the group consisting of halogen (e.g., F or Cl), —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

In another embodiment, R$_3$ is heterocycloalkyl(C$_1$-C$_4$)alkyl.

In another embodiment, R$_3$ is heteroaryl, e.g., mono or bicyclic heteroaryl.

In a further embodiment, R$_3$ is a heterobicyclic ring system.

In another embodiment, R$_3$ is a monocyclic aromatic ring having 5-6 atoms selected from the group consisting of C, O, S and N provided that not more than 3 ring atoms are not C and where said ring may be optionally and independently substituted with up to two groups selected from the group consisting of C$_1$-C$_4$ alkyl, cycloalkyl, cycloalkyloxy, C$_1$-C$_4$ alkoxy, CF$_3$, carboxyl, alkoxyalkyl, C$_1$-C$_4$ cycloalkylalkoxy, amino, alkylamino, dialkylamino, amido, alkylamido, dialkylamido, thioalkyl, halogen, cyano, and nitro.

In a further embodiment, R$_3$ is a monocyclic aromatic ring containing 5 atoms selected from the group consisting of C, O, S, and N provided that not more than 3 ring atoms are not C and where said ring may be optionally and independently substituted with up to two groups selected from the group consisting of C$_1$-C$_4$ alkyl, cycloalkyl, cycloalkyloxy, C$_1$-C$_4$ alkoxy, CF$_3$, carboxyl, alkoxyalkyl, C$_1$-C$_4$ cycloalkylalkoxy, amino, alkylamino, dialkylamino, amido, alkylamido, dialkylamido, thioalkyl, halogen, cyano, and nitro.

In a further embodiment, R$_3$ is a monocyclic aromatic ring containing 6 atoms selected from the group consisting of C and N provided that not more than 3 ring atoms are not C and where said ring may be optionally and independently substituted with up to two groups selected from the group consisting of C$_1$-C$_4$ alkyl, cycloalkyl, cycloalkyloxy, C$_1$-C$_4$ alkoxy, e.g., —OMe, CF$_3$, carboxyl, alkoxyalkyl, C$_1$-C$_4$ cycloalkylalkoxy, amino, alkylamino, dialkylamino, amido, alkylamido, dialkylamido, thioalkyl, halogen, e.g., F, cyano, and nitro.

In another embodiment, R$_3$ is selected from the group consisting of a mono or bicyclic heteroaryl(C$_1$-C$_4$)alkyl and restricted phenyl(C$_1$-C$_4$)alkyl.

In another embodiment, R$_3$ is pyrimidinyl, which may be optionally substituted with one or more substituents selected from the group consisting of halogen (e.g., F or Cl), —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

In another embodiment, R$_3$ is restricted phenyl, which may be optionally substituted with one or more substituents selected from the group consisting of halogen (e.g., F or Cl), —S(O)$_2$(C$_1$-C$_4$)alkyl, OH, —C(O)—(C$_1$-C$_4$)alkyl, CN, (C$_1$-C$_6$)alkyl, and (C$_1$-C$_4$)alkoxy.

In a further embodiment, R$_3$ is heteroaryl(C$_1$-C$_4$)alkyl.

In a further embodiment, R$_2$ is heteroaryl-CH$_2$—.

In a further embodiment, R$_3$ is restricted phenyl.

In a further embodiment, R$_3$ is restricted phenyl(C$_1$-C$_4$)alkyl.

In a further embodiment, R$_3$ is restricted phenyl-CH$_2$—.

In certain embodiments, the substituents are selected from the group consisting of halogen, CN, (C$_1$-C$_6$)alkyl, and (C$_1$-C$_4$)alkoxy.

In certain embodiments, heterocycloalkyl is tetrahydropyranyl.

In certain embodiments, heterocycloalkyl is piperidinyl.

In certain embodiments, halogen is F or Cl.

Embodiments can include any one or more of the following features described throughout sections [I]-[VI] below.

[I] Variable X

[A] In some embodiments, X is a bond.

[B] In some embodiments, X is C(O) or S(O)$_2$.

[II] Variable R$_2$

[A]

In some embodiments, R$_2$ is selected from the group consisting of:
 (i) heterocycloalkyl, which is optionally substituted with one or more R$^c$;
 (ii) (C$_3$-C$_2$) cycloalkyl, which is optionally substituted with one or more R$^c$;
 (iii) phenyl, which is optionally substituted with one or more R$^c$; and
 (iv) (C$_1$-C$_6$) alkyl which is optionally substituted with one or more R$^d$.

In some embodiments, $R_2$ is selected from the group consisting of:
  (i) heterocycloalkyl, which is optionally substituted with one or more $R^c$;
  (ii) $(C_3-C_2)$ cycloalkyl, which is optionally substituted with one or more $R^c$; and
  (iii) phenyl, which is optionally substituted with one or more $R^c$.

In some embodiments, $R_2$ is selected from the group consisting of:
  (i) heterocycloalkyl, which is optionally substituted with one or more $R^c$; and
  (ii) $(C_3-C_7)$ cycloalkyl, which is optionally substituted with one or more $R^c$.

[B]

In some embodiments, $R_2$ is heterocycloalkyl, which is optionally substituted with one or more (e.g., 1-3, 1-2, 1) $R^c$. Embodiments in which $R_2$ is heterocycloalkyl, which is optionally substituted with one or more (e.g., 1-3, 1-2, 1) $R^c$ can include any one or more of the following features.

In some embodiments, $R_2$ is a monocyclic heterocycloalkyl including from 5 to 7 ring atoms, which is optionally substituted with one or more (e.g., 1-3, 1-2, 1) $R^c$.

In some embodiments, $R_2$ is a saturated monocyclic heterocycloalkyl including from 5 to 7 ring atoms, which is optionally substituted with one or more (e.g., 1-3, 1-2, 1) $R^c$, and wherein from 1-2 of the ring atoms are independently selected from the group consisting of N—H, N—$R^c$, and O.

In some embodiments, $R_2$ is a saturated monocyclic heterocycloalkyl including from 5 to 7 ring atoms, which is optionally substituted with one or more (e.g., 1-3, 1-2, 1) $R^c$, and wherein 1 of the ring atoms is selected from the group consisting of N—H, N—$R^c$, and O.

In some embodiments, $R_2$ is a saturated monocyclic heterocycloalkyl including from 5 to 7 ring atoms, which is optionally substituted with one or more (e.g., 1-3, 1-2, 1) $R^c$, and wherein 1 of the ring atoms is O.

In some embodiments, $R_2$ is a saturated monocyclic heterocycloalkyl including from 5 to 7 ring atoms, wherein 1 of the ring atoms is O.

In some embodiments, $R_2$ is tetrahydro-2H-pyran-4-yl.

[C]

In some embodiments, $R_2$ is $(C_3-C_{10})$cycloalkyl, which is optionally substituted with one or more (e.g., 1-3, 1-2, 1) $R^c$. Embodiments in which $R_2$ is $(C_3-C_{10})$cycloalkyl, which is optionally substituted with one or more (e.g., 1-3, 1-2, 1) $R^b$ can include any one or more of the following features.

In some embodiments, $R_2$ is $(C_5-C_{10})$cycloalkyl, which is optionally substituted with one or more (e.g., 1-3, 1-2, 1) $R^c$.

In some embodiments, each $R^c$ is independently selected from the group consisting of halo and $(C_1-C_6)$alkyl. For example, each $R^c$ is independently selected from the group consisting of halogens (e.g., fluoro).

In some embodiments, $R_2$ is cyclohexyl, 4-fluorocyclohexan-1-yl, or 4,4-difluorocyclohexan-1-yl.

In some embodiments, $R_2$ is adamantyl.

[D]

In some embodiments, $R_2$ is phenyl that is optionally substituted with one or more (e.g., 1-3, 1-2, 1) $R^e$. In certain embodiments, each $R^e$ is independently selected from the group consisting of halo, $(C_1-C_6)$alkyl, and $(C_1-C_6)$haloalkyl.

[III] Variable $R_3$

[A]

In some embodiments, $R_3$ is selected from the group consisting of:
  (i) heteroaryl$(C_1-C_4)$alkyl, wherein the alkyl portion is optionally substituted with one or more $R^{g'}$, and the heteroaryl portion is optionally substituted with one or more $R^f$;
  (ii) phenyl$(C_1-C_4)$alkyl, wherein the alkyl portion is optionally substituted with one or more $R^{g'}$, and the phenyl portion is optionally substituted with one or more $R^f$;
  (iii) $(C_3-C_7)$ cycloalkyl$(C_1-C_4)$ alkyl, wherein the alkyl portion is optionally substituted with one or more $R^{g'}$, and the cycloalkyl portion is optionally substituted with one or more $R^h$; and
  (iv) heterocycloalkyl$(C_1-C_4)$alkyl, wherein the alkyl portion is optionally substituted with one or more $R^{g'}$, and the cycloalkyl portion is optionally substituted with one or more $R^h$.

In some embodiments, $R_3$ is selected from the group consisting of:
  (i) heteroaryl$(C_1-C_4)$alkyl, wherein the alkyl portion is optionally substituted with one or more $R^{g'}$, and the heteroaryl portion is optionally substituted with one or more $R^f$; and
  (ii) phenyl$(C_1-C_4)$alkyl, wherein the alkyl portion is optionally substituted with one or more $R^{g'}$, and the phenyl portion is optionally substituted with one or more $R^f$.

[B]

In some embodiments, $R_3$ is heteroaryl$(C_1-C_4)$alkyl, wherein the alkyl portion is optionally substituted with one or more $R^{g'}$, and the heteroaryl portion is optionally substituted with one or more $R^f$. Embodiments in which $R_3$ is heteroaryl$(C_1-C_4)$alkyl, wherein the alkyl portion is optionally substituted with one or more $R^{g'}$, and the heteroaryl portion is optionally substituted with one or more $R^f$ can include any one or more of the following features described throughout sections [1] through [4] below. In certain embodiments, any one of the features described throughout section [1] can be combined with any one or more of the features described throughout sections [2] and/or [3] and/or [4] below. In certain embodiments, the heteroaryl portion can include any one or more of the features described throughout sections [2] and/or [3] and/or [4] below.

[1]

In some embodiments, $R_3$ is heteroaryl$(C_1-C_2)$alkyl, wherein the heteroaryl portion is optionally substituted with one or more $R^f$.

In some embodiments, $R_3$ is heteroaryl$(C_1)$alkyl, wherein the heteroaryl portion is optionally substituted with one or more $R^f$.

[2]

In some embodiments, the heteroaryl portion is monocyclic heteroaryl including from 5-6 ring atoms, wherein from 1-3 of the ring atoms are independently selected from the group consisting of N, O, and S and wherein the monocyclic heteroaryl is optionally substituted with one or more $R^f$.

In some embodiments, the heteroaryl portion is monocyclic heteroaryl including 6 ring atoms, wherein from 1-3 of the ring atoms are N and wherein the monocyclic heteroaryl is optionally substituted with one or more $R^f$.

In some embodiments, the heteroaryl portion is pyrimidinyl, pyridyl, or pyrazinyl, each of which is optionally substituted with one or more $R^f$.

In some embodiments, $R_3$ is pyrimidinylmethyl (e.g., 2-pyrimidinylmethyl), which is optionally substituted with one or more $R^f$. $R_3$ is unsubstituted pyrimidinylmethyl.

In some embodiments, each $R^f$ is independently selected from the group consisting of halo (e.g., F), ($C_1$-$C_6$)alkyl (e.g., $CH_3$), ($C_1$-$C_4$)haloalkyl (e.g., $CF_3$), and ($C_1$-$C_4$)alkoxy (e.g., $OCH_3$).

[3]

In some embodiments, the heteroaryl portion is:
(i) a bicyclic aromatic ring system including from 8-12 ring atoms, wherein from 1-4 of the ring atoms are independently selected from the group consisting of N, O, and S, and which is optionally substituted with one or more $R^f$; or
(ii) a heterobicyclic ring system including from 8-12 ring atoms, wherein the aromatic portion is optionally substituted with one or more $R^f$.

In some embodiments, the heteroaryl portion is selected from the group consisting of 1,5-naphthyridyl, 1,2,3,4-tetrahydro-1,5-naphthyridyl 1,6-naphthyridyl, 1,2,3,4-tetrahydro-1,6-naphthyridyl 1,7-naphthyridyl, 1,2,3,4-tetrahydro-1,7-naphthyridinyl 1,8-naphthyridyl, 1,2,3,4-tetrahydro-1,8-naphthyridyl, 2,6-naphthyridyl, 2,7-naphthyridyl, cinnolyl, isoquinolyl, tetrahydroisoquinolinyl, phthalazyl, quinazolyl, 1,2,3,4-tetrahydroquinazolinyl, quinolyl, tetrahydroquinolinyl, quinoxalyl and tetrahydroquinoxalinyl, each of which is optionally substituted with one or more $R^f$.

In some embodiments, the heteroaryl portion is selected from the group consisting of benzo[d][1,2,3]triazyl, benzo[e][1,2,4]triazyl, pyrido[2,3-b]pyrazyl, pyrido[2,3-c]pyridazyl, pyrido[2,3-d]pyrimidyl, pyrido[3,2-b]pyrazyl, pyrido[3,2-c]pyridazyl, pyrido[3,2-d]pyrimidyl, pyrido[3,4-b]pyrazyl, pyrido[3,4-c]pyridazyl, pyrido[3,4-d]pyrimidyl, pyrido[4,3-b]pyrazyl, pyrido[4,3-c]pyridazyl, pyrido[4,3-d]pyrimidyl, quinazolyl, 1H-benzo[d][1,2,3]triazoyl, 1H-benzo[d]imidazoyl, 1H-indazoyl, 1H-indoyl, 2H-benzo[d][1,2,3]triazoyl, 2H-pyrazolo[3,4-b]pyridinyl, 2H-pyrazolo[4,3-b]pyridinyl, [1,2,3]triazolo[1,5-a]pyridinyl, [1,2,4]triazolo[1,5-a]pyridinyl and [1,2,4]triazolo[4,3-a]pyridinyl, each of which is optionally substituted with one or more $R^f$.

In some embodiments, the heteroaryl portion is selected from the group consisting of benzo[b]thienyl, benzo[c][1,2,5]oxadiazyl, benzo[c][1,2,5]thiadiazolyl, benzo[d]isothiazoyl, benzo[d]isoxazoyl, benzo[d]oxazoyl, benzo[d]thiazoyl, benzofuryl, imidazo[1,2-c]pyrazyl, imidazo[1,2-c]pyridinyl, imidazo[1,2-c]pyrimidyl, imidazo[1,2-b]pyridazyl, imidazo[1,2-c]pyrimidyl, imidazo[1,5-c]pyrazyl, imidazo[1,5-c]pyridinyl, imidazo[1,5-a]pyridinyl, imidazo[1,5-b]pyridazyl, imidazo[1,5-c]pyrimidyl, indolizyl, pyrazolo[1,5-c]pyrazyl, pyrazolo[1,5-c]pyridinyl, pyrazolo[1,5-a]pyrimidyl, pyrazolo[1,5-b]pyridazine, pyrazolo[1,5-c]pyrimidine, pyrrolo[1,2-c]pyrazine, pyrrolo[1,2-c]pyrimidyl, pyrrolo[1,2-b]pyridazyl, pyrrolo[1,2-c]pyrimidyl, 1H-imidazo[4,5-b]pyridinyl, 1H-imidazo[4,5-c]pyridinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-c]pyridinyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, 2H-indazoyl, 3H-imidazo[4,5-b]pyridinyl and 3H-imidazo[4,5-c]pyridinyl, each of which is optionally substituted with one or more $R^f$.

In some embodiments, the heteroaryl portion is selected from the group consisting of benzo[c]isothiazyl, benzo[c]isoxazyl, furo[2,3-b]pyridinyl, furo[2,3-c]pyridinyl, furo[3,2-b]pyridinyl, furo[3,2-c]pyridiyl, isothiazolo[4,5-b]pyridinyl, isothiazolo[4,5-c]pyridinyl, isothiazolo[5,4-b]pyridinyl, isothiazolo[5,4-c]pyridinyl, isoxazolo[4,5-b]pyridinyl, isoxazolo[4,5-c]pyridinyl, isoxazolo[5,4-b]pyridinyl, isoxazolo[5,4-c]pyridinyl, oxazolo[4,5-b]pyridinyl, oxazolo[4,5-c]pyridinyl, oxazolo[5,4-b]pyridinyl, oxazolo[5,4-c]pyridinyl, thiazolo[4,5-b]pyridiyl, thiazolo[4,5-c]pyridinyl, thiazolo[5,4-b]pyridinyl, thiazolo[5,4-c]pyridinyl, thieno[2,3-b]pyridinyl, thieno[2,3-c]pyridinyl, thieno[3,2-b]pyridinyl and thieno[3,2-c]pyridinyl, each of which is optionally substituted with one or more $R^f$.

[4]

In some embodiments, the heteroaryl portion is monocyclic heteroaryl including 5 ring atoms, wherein from 1-3 of the ring atoms are independently selected from the group consisting of N, O, and S and wherein the monocyclic heteroaryl is optionally substituted with one or more $R^f$.

In some embodiments, the heteroaryl portion is selected from the group consisting of thiophenyl, furanyl, thiazolyl, isothiazolyl, oxazolyl, isoxazolyl, 1,2,4-oxadiazolyl, 1,3,4-oxadiazolyl, pyrrazolyl, imidazolyl, 1,2,3-triazolyl, and 1,3,4-triazolyl, each of which is optionally substituted with one or more $R^f$.

[C]

In some embodiments, $R_3$ is phenyl($C_1$-$C_4$)alkyl, wherein the alkyl portion is optionally substituted with one or more $R^{g'}$, and the phenyl portion is optionally substituted with one or more $R^f$. Embodiments in which $R_3$ is phenyl($C_1$-$C_4$)alkyl, wherein the alkyl portion is optionally substituted with one or more $R^{g'}$, and the phenyl portion is optionally substituted with one or more $R^f$ can include any one or more of the following features described throughout sections [1] through [3] below. In certain embodiments, any one of the features described throughout section [1] can be combined with any one or more of the features described throughout sections [2] and/or [3] below. In other embodiments, any one or more of the features described throughout section [2] can be combined with any one or more of the features described throughout section [3] below.

[1]

In certain embodiments, $R_3$ is phenyl($C_1$-$C_2$)alkyl, wherein the phenyl portion is optionally substituted with from 1-3 $R^f$ (embodiments include optionally substituted benzyl, phenylethyl, and α-methylbenzyl).

In certain embodiments, $R_3$ is phenyl($C_1$)alkyl, wherein the phenyl portion is optionally substituted with from 1-3 (e.g., 1-2, 1) $R^f$.

[2]

In some embodiments, each $R^f$ is independently selected from the group consisting of halo; —CN; —C(O)OH; ($C_1$-$C_6$)alkyl that is optionally substituted with —OH or —$OCH_3$; ($C_1$-$C_4$)haloalkyl; ($C_1$-$C_4$)alkoxy; ($C_1$-$C_4$)haloalkoxy; ($C_3$-$C_7$)cycloalkyl, that is optionally substituted with from 1-3 substituents independently selected from the group consisting of ($C_1$-$C_4$)alkyl; —C(O)N[($C_1$-$C_4$)alkyl]$_2$; —N[($C_1$-$C_4$)alkyl]$_2$; heterocycloalkyl that is optionally substituted with from 1-3 substituents independently selected from the group consisting of ($C_1$-$C_4$)alkyl; phenyl that is optionally substituted with from 1-3 substituents independently selected from the group consisting of —F, —Cl, ($C_1$-$C_4$)alkyl, —$CF_3$, —$OCH_3$, and —CN; and heteroaryl including from 5 to 6 ring atoms independently selected from the group consisting of N, O, and S, wherein said heteroaryl is optionally substituted with from 1-3 substituents independently selected from the group consisting of ($C_1$-$C_4$)alkyl, —$CF_3$, and —$OCH_3$. For example, each $R^f$ can be independently selected from the group consisting of —F, —Cl, —Br, —CN, —C(O)OH, —$CH_3$, —$CF_3$, —$OCH_3$, —OCF$_3$, cyclopropyl, —C(O)N(CH$_3$)$_2$, —N(CH$_3$)$_2$, pyrrolidinyl, phenyl, pyridyl, and pyrrazolyl.

Embodiments can include one or more of the following subsets of substituents.

In some embodiments, each R$^f$ is independently selected from the group consisting of halo; —CN; (C$_1$-C$_6$)alkyl that is optionally substituted with —OH or —OCH$_3$; (C$_1$-C$_4$) haloalkyl; and (C$_1$-C$_4$)alkoxy. For example, each R$^f$ can be independently selected from the group consisting of —F, —Cl, —CN, —CH$_3$, —CF$_3$, and —OCH$_3$.

In some embodiments, each R$^f$ is independently selected from the group consisting of halo; —CN; and (C$_1$-C$_4$) haloalkyl. For example, each R$^f$ can be independently selected from the group consisting of —F, —Cl, —CN, and —CF$_3$.

In some embodiments, each R$^f$ is independently selected from the group consisting of halo and (C$_1$-C$_4$)haloalkyl. For example, each R$^f$ can be independently selected from the group consisting of —F, —Cl, and —CF$_3$.

In some embodiments, each R$^f$ is independently selected from the group consisting of halo (e.g., —F, or —Cl, e.g., —F).

[3]

In some embodiments, the phenyl portion is mono-substituted.

In some embodiments, the phenyl portion is mono-substituted (e.g., ortho, meta, or para substituted). E.g., R$_3$ is 2-, 3-, or 4-fluorobenzyl or 2-, 3-, or 4-trifluoromethylbenzyl.

In some embodiments, the phenyl portion is di-substituted (e.g., 2,3-, 2,4-, 2,5-, 2,6-, 3,4-, or 3,5 di-substituted). E.g., R$_3$ can be 2,4-difluorobenzyl; 2,6-difluorobenzyl; 3,5-difluorobenzyl; 2,4-dichlorobenzyl; 3,5-dichlorobenzyl; 2,3-dichlorobenzyl; 3,4-dichlorobenzyl; 2-fluoro-5-chlorobenzyl; 5-fluoro-2-chlorobenzyl; 3-fluoro-4-chlorobenzyl; 4-fluoro-3-chlorobenzyl; 3-trifluoromethyl-4-fluorobenzyl; 3-trifluoromethyl-4-chlorobenzyl; or 3-methyl-4-chlorobenzyl.

[D]

In some embodiments, R$_3$ is (C$_3$-C$_7$) cycloalkyl(C$_1$-C$_4$) alkyl, wherein the alkyl portion is optionally substituted with one or more R$^{g'}$, and the cycloalkyl portion is optionally substituted with one or more R$^h$. Embodiments in which R$_3$ is (C$_3$-C$_7$) cycloalkyl(C$_1$-C$_4$) alkyl, wherein the alkyl portion is optionally substituted with one or more R$^{g'}$, and the cycloalkyl portion is optionally substituted with one or more R$^h$ can include any one or more of the following features described below.

In some embodiments, R$_3$ is (C$_3$-C$_7$) cycloalkyl(C$_1$-C$_2$) alkyl, wherein the cycloalkyl portion is optionally substituted with one or more R$^h$.

In some embodiments, R$_3$ is (C$_3$-C$_7$) cycloalkyl (C$_1$)alkyl, wherein the cycloalkyl portion is optionally substituted with from 1-3 (e.g., 1-2, 1) R$^h$.

In some embodiments, the cycloalkyl portion can be cyclohexyl, cyclopentyl, or cyclopropyl, each of which is optionally substituted with from 1-3 (e.g., 1-2, 1) R$^h$.

In some embodiments, each R$^h$ is independently selected from the group consisting of halo and (C$_1$-C$_4$) alkyl. For example, each R$^f$ can be independently selected from the group consisting of —F and —CH$_3$.

[E]

In some embodiments, R$_3$ is selected from the group consisting of:
 (i) heteroaryl, which is optionally substituted with one or more R$^f$; and
 (ii) phenyl, which is optionally substituted with one or more R$^f$.

Embodiments can include one or more of the following features.

In some embodiments, R$_3$ is phenyl, which is optionally substituted with one or more R$^f$. In certain embodiments, the phenyl ring can be unsubstituted or substituted and include any one or more of the features described in one or both of sections [III][C][2] and [III][C][3].

In some embodiments, R$_3$ is heteroaryl, which is optionally substituted with one or more R$^f$.

[IV] Variable R$_1$

In some embodiments, R$_1$ is (C$_1$-C$_6$) alkyl, which is optionally substituted with one or more R$^a$. In certain embodiments, R$_1$ is (C$_1$-C$_6$) alkyl, e.g., (C$_1$-C$_4$) alkyl, (C$_1$-C$_2$) alkyl, e.g., CH$_3$.

In some embodiments, R$_1$ is anti with respect to the imidazo-triazine ring containing R$_2$.

In some embodiments, the carbon that is directly attached to R$_1$ has the R-configuration.

In some embodiments, the carbon that is directly attached to R$_1$ has the 5-configuration.

In some embodiments, R$_1$ is anti with respect to the imidazo-triazine ring containing R$_2$, and the carbon that is directly attached to R$_1$ has the R-configuration.

In some embodiments, R$_1$ is anti with respect to the imidazo-triazine ring containing R$_2$, and the carbon that is directly attached to R$_1$ has the S-configuration.

[V] Non-limiting Combinations of Variables X, R$_1$, R$_2$, and R$_3$

[A]

In some embodiments, the feature described in section [I][A] is combined with any one or more of the features described throughout section [III][A].

In some embodiments, the feature described in section [I][A] is combined with any one or more of the features described throughout section [III][A], and any one or more of the features described throughout section [II][A].

In some embodiments, the feature described in section [I][A] is combined with any one or more of the features described throughout section [III][A], and any one or more of the features described throughout any one, two, or three of sections [II][B], [II][C], and [II][D] (e.g., combined with any one or more of the features described throughout section [II][B]; e.g., R$_2$ is tetrahydro-2H-pyran-4-yl).

In some embodiments, the feature described in section [I][A] is combined with any one or more of the features described throughout section [III][A], and any one or more of the features described throughout section [IV] (e.g., R$_1$ is methyl).

In some embodiments, the feature described in section [I][A] is combined with any one or more of the features described throughout section [III][A], and any one or more of the features described throughout section [II][A], and any one or more of the features described throughout section [IV] (e.g., R$_1$ is methyl).

In some embodiments, the feature described in section [I][A] is combined with any one or more of the features described throughout section [III][A], and any one or more of the features described throughout any one, two, or three of sections [II][B], [II][C], and [II][D] (e.g., any one or more of the features described throughout section [II][B]; e.g., R$_2$ is tetrahydro-2H-pyran-4-yl), and any one or more of the features described throughout section [IV] (e.g., R$_1$ is methyl).

[B]

In some embodiments, the feature described in section [I][A] is combined with any one or more of the features described throughout section [III][B] (for purposes of clarification, including those features described in sub-sections [1]-[4]).

In some embodiments, the feature described in section [I][A] is combined with any one or more of the features described throughout section [III][B] (for purposes of clarification, including those features described in sub-sections [1]-[4]), and any one or more of the features described throughout section [II][A].

In some embodiments, the feature described in section [I][A] is combined with any one or more of the features described throughout section [III][B] (for purposes of clarification, including those features described in sub-sections [1]-[4]), and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl).

In some embodiments, the feature described in section [I][A] is combined with any one or more of the features described throughout section [III][B] (for purposes of clarification, including those features described in sub-sections [1]-[4]), and any one or more of the features described throughout section [IV] (e.g., $R_1$ is methyl).

In some embodiments, the feature described in section [I][A] is combined with any one or more of the features described throughout section [III][B] (for purposes of clarification, including those features described in sub-sections [1]-[4]), and any one or more of the features described throughout section [II][A], and any one or more of the features described throughout section [IV] (e.g., $R_1$ is methyl).

In some embodiments, the feature described in section [I][A] is combined with any one or more of the features described throughout section [III][B] (for purposes of clarification, including those features described in sub-sections [1]-[4]), and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl), and any one or more of the features described throughout section [IV] (e.g., $R_1$ is methyl).

In certain embodiments, any one of the features described throughout section [III][B][1] can be combined with any one or more of the features described throughout sections [III][B][2] and/or [III][B][3] and/or [III][B][4]. In certain embodiments, the heteroaryl portion can include any one or more of the features described throughout sections [III][B][2] and/or [III][B][3] and/or [III][B][4].

[C]

In some embodiments, the feature described in section [I][A] is combined with any one or more of the features described throughout section [III][C] (for purposes of clarification, including those features described in sub-sections [1]-[3]).

In some embodiments, the feature described in section [I][A] is combined with any one or more of the features described throughout section [III][C] (for purposes of clarification, including those features described in sub-sections [1]-[3]), and any one or more of the features described throughout section [II][A].

In some embodiments, the feature described in section [I][A] is combined with any one or more of the features described throughout section [III][C] (for purposes of clarification, including those features described in sub-sections [1]-[3]), and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl).

In some embodiments, the feature described in section [I][A] is combined with any one or more of the features described throughout section [III][C] (for purposes of clarification, including those features described in sub-sections [1]-[3]), and any one or more of the features described throughout section [IV] (e.g., $R_1$ is methyl).

In some embodiments, the feature described in section [I][A] is combined with any one or more of the features described throughout section [III][C] (for purposes of clarification, including those features described in sub-sections [1]-[3]), and any one or more of the features described throughout section [II][A], and any one or more of the features described throughout section [IV] (e.g., $R_1$ is methyl).

In some embodiments, the feature described in section [I][A] is combined with any one or more of the features described throughout section [III][C] (for purposes of clarification, including those features described in sub-sections [1]-[3]), and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl), and any one or more of the features described throughout section [IV] (e.g., $R_1$ is methyl).

In certain embodiments, any one of the features described throughout section [III][C][1] can be combined with any one or more of the features described throughout sections [III][C][2] and/or [III][C][3]. In other embodiments, any one or more of the features described throughout section [III][C][2] can be combined with any one or more of the features described in section [III][C][3].

[D]

In some embodiments, the feature described in section [I][A] is combined with any one or more of the features described throughout section [III][D].

In some embodiments, the feature described in section [I][A] is combined with any one or more of the features described throughout section [III][D], and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl).

In some embodiments, the feature described in section [I][A] is combined with any one or more of the features described throughout section [III][D], and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl), and any one or more of the features described throughout section [IV] (e.g., $R_1$ is methyl).

[E]

In some embodiments, any one or more of the features described throughout section [I][B] are combined with any one or more of the features described throughout section [III][E].

In some embodiments, any one or more of the features described throughout section [I][B] are combined with any one or more of the features described throughout section [III][E], and any one or more of the features described throughout section [II][A].

In some embodiments, any one or more of the features described throughout section [I][B] are combined with any one or more of the features described throughout section [III][E], and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl).

In some embodiments, any one or more of the features described throughout section [I][B] are combined with any one or more of the features described throughout section [III][E], and any one or more of the features described throughout section [IV] (e.g., $R_1$ is methyl).

In some embodiments, any one or more of the features described throughout section [I][B] are combined with any one or more of the features described throughout section [III][E], and any one or more of the features described throughout section [II][A], and any one or more of the features described throughout section [IV] (e.g., $R_1$ is methyl).

In some embodiments, any one or more of the features described throughout section [I][B] are combined with any one or more of the features described throughout section [III][E], and any one or more of the features described throughout any one, two, or three of sections [II][B], [II][C], and [II][D] (e.g., any one or more of the features described throughout section [II][B]; e.g., $R_2$ is tetrahydro-2H-pyran-4-yl), and any one or more of the features described throughout section [IV] (e.g., $R_1$ is methyl).

[VI] Other Embodiments

In some embodiments, one or more of the following apply.

In some embodiments, the compound or salt is other than one or more (e.g., all) of the final compound described in Examples B.1-6, 6A, and 7-205.

In some embodiments, when X is a bond, $R_1$ is $CH_3$, and $R_2$ is tetrahydro-2H-pyran-4-yl or tetrahydro-2H-pyran-3-yl, then $R_3$ is not benzyl, 2-fluorobenzyl, 3-fluorobenzyl, 4-fluorobenzyl, 2-cyanobenzyl, 3-cyanobenzyl, 4-cyanobenzyl, or α-methylbenzyl.

In some embodiments, when X is a bond, $R_1$ is $CH_3$, and $R_2$ is tetrahydro-2H-pyran-4-yl, then $R_3$ is not pyrimidin-2-ylmethyl, imidazo[1,2-b]pyridazin-2-ylmethyl, imidazo[1,2-b]pyridazin-6-ylmethyl, 6-methoxypyridin-2-yl)methyl, pyrazin-2-ylmethyl, pyridin-2-ylmethyl, quinazolin-2-ylmethyl, or quinolin-2-ylmethyl.

In some embodiments, when X is a bond, $R_1$ is $CH_3$, and $R_2$ is adamantan-1-yl or 4,4-difluorocyclohexan-1-yl, then $R_3$ is not benzyl.

In some embodiments, when X is a bond, $R_1$ is $CH_3$, and $R_2$ is adamantan-1-yl or 4,4-difluorocyclohexan-1-yl, then $R_3$ is not pyrimidin-2-ylmethyl.

In some embodiments, when X is a bond, $R_1$ is $CH_3$, and $R_2$ is 1-(ethylsulfonyl)piperidin-4-yl or 1-acetylpiperidin-4-yl, then $R_3$ is not benzyl.

In some embodiments, when X is a bond, $R_1$ is $CH_3$, and $R_2$ is 1-(ethylsulfonyl)piperidin-4-yl or 1-acetylpiperidin-4-yl, then $R_3$ is not pyrimidin-2-ylmethyl.

In some embodiments, when X is a bond, $R_1$ is $CH_3$, and $R_2$ is furan-3-yl, then $R_3$ is not benzyl. In some embodiments, when X is a bond, $R_1$ is $CH_3$, and $R_2$ is 2-hydroxypropan-2-yl, then $R_3$ is not benzyl.

In some embodiments, when X is a bond, $R_1$ is $CH_3$, and $R_2$ is 4-fluoro-2-methylphenyl, 5-chloro-2-methylphenyl, or o-tolyl, then $R_3$ is not pyrimidin-2-ylmethyl.

In some embodiments, when X is a bond, $R_1$ is $CH_3$, and $R_2$ is 4-fluoro-2-methylphenyl or 5-chloro-2-methylphenyl, then $R_3$ is not benzyl.

In some embodiments, the compound is selected from the groups consisting of compounds having the following combinations of $R_1$, $R_2$, and $R_3$. In other embodiments, the compound is other than one having the following combinations of $R_1$, $R_2$, and $R_3$.

| R1 | R2 | R3 |
|----|----|----|
| Me | 4-pyran | 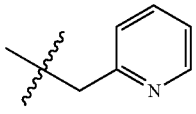 [SMILES: *Cc1ccccn1] |
| Me | 4-pyran | 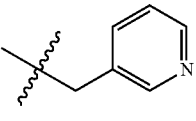 [SMILES: *Cc1cccnc1] |
| Me | 4-pyran | 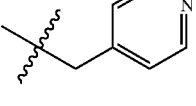 |
| Me | 4-pyran | 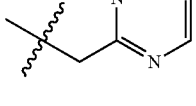 |
| Me | 4-pyran | 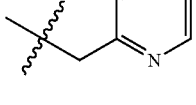 |
| Me | 4-pyran | 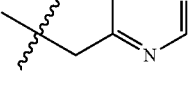 |
| Me | 4-pyran | 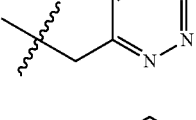 |
| Me | 4-pyran | 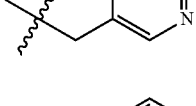 |
| Me | 4-pyran | 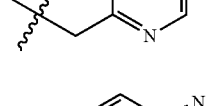 |
| Me | 4-pyran | 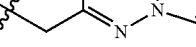 |

| R1 | R2 | R3 |
|---|---|---|
| Me | 4-pyran | -CH2-imidazo[1,2-b]pyridazine |
| Me | 4-pyran | -CH2-[1,2,4]triazolo[1,5-a]pyridine |
| Me | 4-pyran | -CH2-imidazo[1,2-a]pyridine |
| Me | 4-pyran | -CH2-imidazo[1,2-a]pyrimidine |
| Me | 4-pyran | -CH2-1H-benzimidazole |
| Me | 4-pyran | -CH2-1-methyl-benzimidazole |
| Me | 4-pyran | -CH2-quinazoline |
| Me | 4-pyran | -CH2-quinoxaline |
| Me | 4-pyran | -CH2-quinoline |
| Me | 4-pyran | -CH2-quinoxaline (isomer) |
| Me | 4-pyran | -CH2-quinazoline (isomer) |
| Me | 4-pyran | -CH2-quinazoline (isomer) |
| Me | 4-pyran | -CH2-phenyl |

In a particular embodiment, the compound of the invention is selected from the group consisting of following list of individual compounds, each of which is intended to be a separate embodiment, and which is provided in table/list format solely as a convenience:

(−)-2-((3,4-trans)-1-benzyl-4-methylpyrrolidin-3-yl)-7-(tetrahydro-2H-pyran-4-yl)imidazo[1,5-f][1,2,4]triazin-4(3H)-one;

(+)-2-((3,4-trans)-1-benzyl-4-methylpyrrolidin-3-yl)-7-(tetrahydro-2H-pyran-4-yl)imidazo[1,5-f][1,2,4]triazin-4(3H)-one;

(+)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one;

(+)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;

(+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;

(+)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;

(+)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one;

(+)-7-((1s,3R)-adamantan-1-yl)-2-((3,4-trans)-1-benzyl-4-methylpyrrolidin-3-yl)imidazo[5,1-f][1,2,4]triazin-4(3H)-one;

(−)-7-((1s,3R)-adamantan-1-yl)-2-((3,4-trans)-1-benzyl-4-methylpyrrolidin-3-yl)imidazo[5,1-f][1,2,4]triazin-4(3H)-one;

(−)-2-((3,4-trans)-1-benzyl-4-methylpyrrolidin-3-yl)-7-(5-chloro-2-methylphenyl)imidazo[5,1-f][1,2,4]triazin-4(3H)-one;

(+)-2-((3,4-trans)-1-benzyl-4-methylpyrrolidin-3-yl)-7-(5-chloro-2-methylphenyl)imidazo[5,1-f][1,2,4]triazin-4(3H)-one;

(+)-2-((3,4-trans)-1-benzyl-4-methylpyrrolidin-3-yl)-7-(4-fluoro-2-methylphenyl)imidazo[5,1-f][1,2,4]triazin-4(3H)-one;

(+)-2-(3,4-trans)-1-benzyl-4-methylpyrrolidin-3-yl)-7-(4-fluoro-2-methylphenyl)imidazo[5,1-f][1,2,4]triazin-4(3H)-one;

(+)-2-((3,4-trans)-1-benzyl-4-methylpyrrolidin-3-yl)-7-(4,4-difluorocyclohexyl)imidazo[5,1-f][1,2,4]triazin-4(3H)-one;

(−)-2-((3,4-trans)-1-benzyl-4-methylpyrrolidin-3-yl)-7-(4,4-difluorocyclohexyl)imidazo[5,1-f][1,2,4]triazin-4(3H)-one;

(−)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one;

(−)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one;

(+)-7-((1s,3R)-adamantan-1-yl)-2-((3,4-trans)-4-methyl-1-(pyrimidin-2-ylmethyl)pyrrolidin-3-yl)imidazo[5,1-f][1,2,4]triazin-4(3H)-one;

2-(3,4-trans)-1-benzyl-4-methylpyrrolidin-3-yl)-7-(tetrahydro-2H-pyran-3-yl)imidazo[5,1-f][1,2,4]triazin-4(3H)-one fraction 1;

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 2;

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 3;

(+)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one;

(+)-7-(4-fluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one;

(+)-7-(4,4-difluorocyclohexyl)-2-((3,4-trans)-4-methyl-1-(pyrimidin-2-ylmethyl)pyrrolidin-3-yl)imidazo[5,1-f][1,2,4]triazin-4(3H)-one;

(−)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one;

(+)-7-(5-chloro-2-methylphenyl)-2-((3,4-trans)-4-methylpyrrolidin-3-yl)imidazo[5,1-f][1,2,4]triazin-4(3H)-one;

(+)-2-((3,4-trans)-1-benzyl-4-methylpyrrolidin-3-yl)-7-(furan-3-yl)imidazo[5,1-f][1,2,4]triazin-4(3H)-one;

(−)-2-((3,4-trans)-1-benzyl-4-methylpyrrolidin-3-yl)-7-(furan-3-yl)imidazo[5,1-f][1,2,4]triazin-4(3H)-one;

(−)-7-(1-acetylpiperidin-4-yl)-2-((3,4-trans)-1-benzyl-4-methylpyrrolidin-3-yl)imidazo[5,1-f][1,2,4]triazin-4(3H)-one;

(+)-7-(1-acetylpiperidin-4-yl)-2-((3,4-trans)-1-benzyl-4-methylpyrrolidin-3-yl)imidazo[5,1-f][1,2,4]triazin-4(3H)-one;

(−)-2-((3,4-trans)-1-benzyl-4-methylpyrrolidin-3-yl)-7-(2-hydroxypropan-2-yl)imidazo[5,1-f][1,2,4]triazin-4(3H)-one;

(+)-2-((3,4-trans)-1-benzyl-4-methylpyrrolidin-3-yl)-7-(2-hydroxypropan-2-yl)imidazo[5,1-f][1,2,4]triazin-4(3H)-one;

(+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one;

(−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one;

(−)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one;

(+)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one;

(+)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one;

(−)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one;

(−)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(−)-isomer] fraction 1;

(−)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(−)-isomer] fraction 2;

(−)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate;

(+)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate (+)-2-((3,4-trans)-1-benzyl-4-methylpyrrolidin-3-yl)-7-(5-fluoro-2-methylphenyl)imidazo[1,5-f][1,2,4]triazin-4(3H)-one;

(−)-2-((3,4-trans)-1-benzyl-4-methylpyrrolidin-3-yl)-7-(5-fluoro-2-methylphenyl)imidazo[1,5-f][1,2,4]triazin-4(3H)-one;

(+)-7-(5-fluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one;

(+)-7-(5-fluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one;

(−)-2-((3,4-trans)-1-benzyl-4-methylpyrrolidin-3-yl)-7-(piperidin-4-yl)imidazo[1,5-f][1,2,4]triazin-4(3H)-one [piperidine NH fraction 1];

(+)-2-((3,4-trans)-1-benzyl-4-methylpyrrolidin-3-yl)-7-(piperidin-4-yl)imidazo[1,5-f][1,2,4]triazin-4(3H)-one [piperidine NH fraction 2];

(+)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(+)-isomer] fraction 1;

(+)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(+)-isomer] fraction 2;

(−)-2-(1-(3,4-trans)-benzyl-4-methylpyrrolidin-3-yl)-7-(tetrahydrofuran-3-yl)imidazo[5,1-f][1,2,4]triazin-4(3H)-one [furan-(−)-isomer] fraction 1;

(−)-2-(1-(3,4-trans)-benzyl-4-methylpyrrolidin-3-yl)-7-(tetrahydrofuran-3-yl)imidazo[5,1-f][1,2,4]triazin-4(3H)-one [furan-(−)-isomer] fraction 2;

(−)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;

(+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;

(−)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one;

(−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one;

(−)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;

(−)-2-((3,4-trans)-1-benzyl-4-methylpyrrolidin-3-yl)-7-(furan-3-yl)imidazo[5,1-f][1,2,4]triazin-4(3H)-one [furan-(+)-isomer] fraction 1;

(+)-2-((3,4-trans)-1-benzyl-4-methylpyrrolidin-3-yl)-7-(furan-3-yl)imidazo[5,1-f][1,2,4]triazin-4(3H)-one [furan-(+)-isomer] fraction 2;

2-((3,4-trans)-1-benzyl-4-methylpyrrolidin-3-yl)-7-(1-methylpiperidin-4-yl)imidazo[5,1-f][1,2,4]triazin-4(3H)-one [from piperidine NH fraction 1];

2-((3,4-trans)-1-benzyl-4-methylpyrrolidin-3-yl)-7-(1-methylpiperidin-4-yl)imidazo[5,1-f][1,2,4]triazin-4(3H)-one [from piperidine NH fraction 2];

(+)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(4-(trifluoromethyl)benzyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(3-(trifluoromethyl)benzyl)pyrrolidin-3-yl)-7-(tetrahydro-2H-pyran-4-yl)imidazo[5,1-f][1,2,4]triazin-4(3H)-one;

(+)-2-((3,4-trans)-1-(3-chlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2,4-difluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(2-(trifluoromethyl)benzyl)pyrrolidin-3-yl)-7-(tetrahydro-2H-pyran-4-yl)imidazo[5,1-f][1,2,4]triazin-4(3H)-one;

(+)-2-((3,4-trans)-1-(2-fluoro-5-methoxybenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(isoquinolin-7-ylmethyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinolin-6-ylmethyl)pyrrolidin-3-yl)-7-(tetrahydro-2H-pyran-4-yl)imidazo[5,1-f][1,2,4]triazin-4(3H)-one;

(+)-2-((3,4-trans)-1-(2-chlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-chlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2,5-difluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2,3-difluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one;

(+)-2-((3,4-trans)-4-methyl-1-(pyridin-4-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-1-(isoquinolin-6-ylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(quinolin-7-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((2-oxo-1,2-dihydropyridin-3-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyridazin-3-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyridazin-4-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinazolin-6-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinoxalin-6-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinoxalin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((1-methyl-1H-benzo[d]imidazol-2-yl)methyl)pyrrolidin-3-yl)-7-(tetrahydro-2H-pyran-4-yl)imidazo[5,1-f][1,2,4]triazin-4(3H)-one;

(−)-2-((3,4-trans)-1-((1H-benzo[d]imidazol-2-yl)methyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(imidazo[1,2-a]pyridin-2-ylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-benzoyl-4-methylpyrrolidin-3-yl)-7-(tetrahydro-2H-pyran-4-yl)imidazo[5,1-f][1,2,4]triazin-4(3H)-one;

(−)-2-((3,4-trans)-1-(2-fluorobenzoyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(3-fluorobenzoyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(4-fluorobenzoyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-nicotinoylpyrrolidin-3-yl)-7-(tetrahydro-2H-pyran-4-yl)imidazo[5,1-f][1,2,4]triazin-4(3H)-one;

(+)-2-((3,4-trans)-1-(4-fluorobenzoyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-benzoyl-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyridin-3-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((2-methylpyrimidin-4-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrimidin-4-ylmethyl)pyrrolidin-3-yl)-7-(tetrahydro-2H-pyran-4-yl)imidazo[5,1-f][1,2,4]triazin-4(3H)-one;

(−)-2-((3,4-trans)-1-(imidazo[1,2-a]pyrimidin-2-ylmethyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(phenylsulfonyl)pyrrolidin-3-yl)-7-(tetrahydro-2H-pyran-4-yl)imidazo[5,1-f][1,2,4]triazin-4(3H)-one;

(+)-2-((3,4-trans)-1-((2-fluorophenyl)sulfonyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-((4-fluorophenyl)sulfonyl)-4-methylpyrrolidin-3-yl)-7-(tetrahydro-2H-pyran-4-yl)imidazo[5,1-f][1,2,4]triazin-4(3H)-one;

(+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile;

(−)-2-((3,4-trans)-4-methyl-1-(phenylsulfonyl)pyrrolidin-3-yl)-7-(tetrahydro-2H-pyran-4-yl)imidazo[5,1-f][1,2,4]triazin-4(3H)-one;

(−)-2-((3,4-trans)-1-((4-fluorophenyl)sulfonyl)-4-methylpyrrolidin-3-yl)-7-(tetrahydro-2H-pyran-4-yl)imidazo[5,1-f][1,2,4]triazin-4(3H)-one;

(+)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile;

(+)-2-((3,4-trans)-4-methyl-1-(pyrimidin-5-ylmethyl)pyrrolidin-3-yl)-7-(tetrahydro-2H-pyran-4-yl)imidazo[5,1-f][1,2,4]triazin-4(3H)-one;

(−)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile;

(+)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile;

(−)-2-((3,4-trans)-4-methyl-1-(pyrimidine-2-carbonyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrimidine-2-carbonyl)pyrrolidin-3-yl)-7-(tetrahydro-2H-pyran-4-yl)imidazo[5,1-f][1,2,4]triazin-4(3H)-one;

(−)-2-((3,4-trans)-1-isonicotinoyl-4-methylpyrrolidin-3-yl)-7-(tetrahydro-2H-pyran-4-yl)imidazo[5,1-f][1,2,4]triazin-4(3H)-one;

(+)-4-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile;

(−)-2-((3,4-trans)-4-methyl-1-(pyrimidine-5-carbonyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyrazine-2-carbonyl)pyrrolidin-3-yl)-7-(tetrahydro-2H-pyran-4-yl)imidazo[5,1-f][1,2,4]triazin-4(3H)-one;

(+)-2-((3,4-trans)-1-((3-fluorophenyl)sulfonyl)-4-methylpyrrolidin-3-yl)-7-(tetrahydro-2H-pyran-4-yl)imidazo[5,1-f][1,2,4]triazin-4(3H)-one;

(+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile;

(+)-2-((3,4-trans)-4-methyl-1-(quinolin-7-ylmethyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-picolinoylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(quinoline-2-carbonyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyrimidine-4-carbonyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyridin-3-ylsulfonyl)pyrrolidin-3-yl)-7-(tetrahydro-2H-pyran-4-yl)imidazo[5,1-f][1,2,4]triazin-4(3H)-one;

(+)-2-((3,4-trans)-1-(2-methoxybenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3-methoxybenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-methoxybenzyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(quinazoline-2-carbonyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(2-methylbenzyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(3-methylbenzyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(4-methylbenzyl)pyrrolidin-3-yl)-7-(tetrahydro-2H-pyran-4-yl)imidazo[5,1-f][1,2,4]triazin-4(3H)-one;

(−)-2-((3,4-trans)-1-(ethylsulfonyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(ethylsulfonyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(cyclohexylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(4-(pyrrolidin-1-yl)benzyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(2-(pyrrolidin-1-yl)benzyl)pyrrolidin-3-yl)-7-(tetrahydro-2H-pyran-4-yl)imidazo[5,1-f][1,2,4]triazin-4(3H)-one;

(+)-2-((3,4-trans)-1-(2-(dimethylamino)benzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3-(dimethylamino)benzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-(dimethylamino)benzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-phenethylpyrrolidin-3-yl)-7-(tetrahydro-2H-pyran-4-yl)imidazo[5,1-f][1,2,4]triazin-4(3H)-one;

(+)-2-((3,4-trans)-1-((6-methoxypyridin-3-yl)methyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrimidin-2-yl)pyrrolidin-3-yl)-7-(tetrahydro-2H-pyran-4-yl)imidazo[5,1-f][1,2,4]triazin-4(3H)-one;

(+)-2-((3,4-trans)-1-(2,6-difluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3-cyclopropylbenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-cyclopropylbenzyl)-4-methylpyrrolidin-3-yl)-7-(tetrahydro-2H-pyran-4-yl)imidazo[5,1-f][1,2,4]triazin-4(3H)-one;

(+)-((3,4-trans)-1,4-dimethylpyrrolidin-3-yl)-7-(tetrahydro-2H-pyran-4-yl)imidazo[5,1-f][1,2,4]triazin-4(3H)-one;

(−)-2-((3,4-trans)-1-(2-cyclopropylbenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3-(1H-pyrazol-1-yl)benzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinolin-4-ylmethyl)pyrrolidin-3-yl)-7-(tetrahydro-2H-pyran-4-yl)imidazo[5,1-f][1,2,4]triazin-4(3H)-one;

(+)-2-((3,4-trans)-1-((1,3-dimethyl-1H-pyrazol-5-yl)methyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-((2-methylpyrimidin-5-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((2-methylthiazol-5-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((6-methylpyridin-3-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((5-methylpyrazin-2-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((5-methylpyrazin-2-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(3-(pyrrolidin-1-yl)benzyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((6-(trifluoromethyl)pyridin-3-yl)methyl)pyrrolidin-3-yl)-7-(tetrahydro-2H-pyran-4-yl)imidazo[5,1-f][1,2,4]triazin-4(3H)-one;

(+)-2-((3,4-trans)-1-((2-ethylpyrimidin-5-yl)methyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3-bromobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2,4-dichlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-bromobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3,5-dichlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(3-(trifluoromethoxy)benzyl)pyrrolidin-3-yl)-7-(tetrahydro-2H-pyran-4-yl)imidazo[5,1-f][1,2,4]triazin-4(3H)-one;

(+)-2-((3,4-trans)-1-(2-chloro-4-fluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2-bromobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4,4-difluorocyclohexyl)imidazo[5,1-f][1,2,4]triazin-4(3H)-one;

(+)-2-((3,4-trans)-1-(4-chloro-3-fluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(4-(trifluoromethoxy)benzyl)pyrrolidin-3-yl)-7-(tetrahydro-2H-pyran-4-yl)imidazo[5,1-f][1,2,4]triazin-4(3H)-one;

(+)-2-((3,4-trans)-1-(4-fluoro-3-(trifluoromethyl)benzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2,5-dichlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3,5-difluorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(3,4-dichlorobenzyl)-4-methylpyrrolidin-3-yl)-7-(tetrahydro-2H-pyran-4-yl)imidazo[1,5-f][1,2,4]triazin-4(3H)-one;

(+)-(4,4-difluorocyclohexyl)-2-((3,4-trans)-1-(4-fluorobenzyl)-4-methylpyrrolidin-3-yl)imidazo[5,1-f][1,2,4]triazin-4(3H)-one;

(+)-2-((3,4-trans)-1-(4-chlorobenzyl)-4-methylpyrrolidin-3-yl)-7-(4,4-difluorocyclohexyl)imidazo[5,1-f][1,2,4]triazin-4(3H)-one;

(+)-7-(4,4-difluorocyclohexyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-2-((3,4-trans)-1-((3aH-benzo[d]imidazol-2-yl)methyl)-4-methylpyrrolidin-3-yl)-7-(4,4-difluorocyclohexyl)imidazo[1,5-f][1,2,4]triazin-4(3H)-one;

(+)-7-(4,4-difluorocyclohexyl)-2-((3,4-trans)-4-methyl-1-(pyridin-2-ylmethyl)pyrrolidin-3-yl)imidazo[1,5-f][1,2,4]triazin-4(3H)-one;

(+)-7-(4,4-difluorocyclohexyl)-2-((3,4-trans)-4-methyl-1-(pyridin-3-ylmethyl)pyrrolidin-3-yl)imidazo[1,5-f][1,2,4]triazin-4(3H)-one;

(+)-7-(4,4-difluorocyclohexyl)-2-((3,4-trans)-4-methyl-1-(pyrazin-2-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(5-fluoro-2-methylphenyl)imidazo[1,5-f][1,2,4]triazin-4(3H)-one;

(+)-2-((3,4-trans)-1-(4-chlorobenzyl)-4-methylpyrrolidin-3-yl)-7-(5-fluoro-2-methylphenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(5-fluoro-2-methylphenyl)imidazo[1,5-f][1,2,4]triazin-4(3H)-one;

(+)-7-(5-fluoro-2-methylphenyl)-2-((3,4-trans)-1-(4-fluorobenzyl)-4-methylpyrrolidin-3-yl)imidazo[1,5-f][1,2,4]triazin-4(3H)-one;

(+)-7-(5-fluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(5-fluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(+)-7-(5-fluoro-2-methylphenyl)-2-((3,4-trans)-4-methyl-1-(pyridin-2-ylmethyl)pyrrolidin-3-yl)imidazo[1,5-f][1,2,4]triazin-4(3H)-one;

(+)-(+)-7-(5-fluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(4-fluorocyclohexyl)imidazo[1,5-f][1,2,4]triazin-4(3H)-one;

(+)-2-((3,4-trans)-1-(4-chlorobenzyl)-4-methylpyrrolidin-3-yl)-7-(4-fluorocyclohexyl)imidazo[1,5-f][1,2,4]triazin-4(3H)-one;

(+)-2-((3,4-trans)-1-(4-fluorobenzyl)-4-methylpyrrolidin-3-yl)-7-(4-fluorocyclohexyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4-fluorocyclohexyl)imidazo[1,5-f][1,2,4]triazin-4(3H)-one;

(+)-2-((3,4-trans)-1-benzyl-4-methylpyrrolidin-3-yl)-7-(4-fluorocyclohexyl)imidazo[1,5-f][1,2,4]triazin-4(3H)-one;

(+)-2-((3,4-trans)-1-benzyl-4-methylpyrrolidin-3-yl)-7-(4-fluorocyclohexyl)imidazo[1,5-f][1,2,4]triazin-4(3H)-one;

(+)-7-(4-fluorocyclohexyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(4-fluorocyclohexyl)-2-((3,4-trans)-4-methyl-1-(pyrazin-2-ylmethyl)pyrrolidin-3-yl)imidazo[1,5-f][1,2,4]triazin-4(3H)-one;

(+)-7-(4-fluorocyclohexyl)-2-((3,4-trans)-4-methyl-1-(pyridin-2-ylmethyl)pyrrolidin-3-yl)imidazo[1,5-f][1,2,4]triazin-4(3H)-one;

(+)-7-(4-fluorocyclohexyl)-2-((3,4-trans)-4-methyl-1-(pyridin-3-ylmethyl)pyrrolidin-3-yl)imidazo[1,5-f][1,2,4]triazin-4(3H)-one;

(+)-7-(4-fluorocyclohexyl)-2-((3,4-trans)-4-methyl-1-(pyrimidin-2-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(4-fluorophenyl)imidazo[1,5-f][1,2,4]triazin-4(3H)-one;

(+)-2-((3,4-trans)-1-(4-chlorobenzyl)-4-methylpyrrolidin-3-yl)-7-(4-fluorophenyl)imidazo[1,5-f][1,2,4]triazin-4(3H)-one;

(+)-2-((3,4-trans)-1-(4-fluorobenzyl)-4-methylpyrrolidin-3-yl)-7-(4-fluorophenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4-fluorophenyl)imidazo[1,5-f][1,2,4]triazin-4(3H)-one;

(+)-2-((3,4-trans)-1-benzyl-4-methylpyrrolidin-3-yl)-7-(4-fluorophenyl)imidazo[1,5-f][1,2,4]triazin-4(3H)-one;

(+)-7-(4-fluorophenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(4-fluorophenyl)-2-((3,4-trans)-4-methyl-1-(pyrazin-2-ylmethyl)pyrrolidin-3-yl)imidazo[1,5-f][1,2,4]triazin-4(3H)-one;

(+)-7-(4-fluorophenyl)-2-((3,4-trans)-4-methyl-1-(pyridin-2-ylmethyl)pyrrolidin-3-yl)imidazo[1,5-f][1,2,4]triazin-4(3H)-one;

(+)-7-(4-fluorophenyl)-2-((3,4-trans)-4-methyl-1-(pyridin-3-ylmethyl)pyrrolidin-3-yl)imidazo[1,5-f][1,2,4]triazin-4(3H)-one;

(+)-7-(4-fluorophenyl)-2-((3,4-trans)-4-methyl-1-(pyrimidin-2-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(3-fluorophenyl)imidazo[1,5-f][1,2,4]triazin-4(3H)-one;

(+)-2-((3,4-trans)-1-(4-chlorobenzyl)-4-methylpyrrolidin-3-yl)-7-(3-fluorophenyl)imidazo[1,5-f][1,2,4]triazin-4(3H)-one;

(+)-2-((3,4-trans)-1-(4-fluorobenzyl)-4-methylpyrrolidin-3-yl)-7-(3-fluorophenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(3-fluorophenyl)imidazo[1,5-f][1,2,4]triazin-4(3H)-one;

(+)-2-((3,4-trans)-1-benzyl-4-methylpyrrolidin-3-yl)-7-(3-fluorophenyl)imidazo[1,5-f][1,2,4]triazin-4(3H)-one;

(+)-7-(3-fluorophenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(3-fluorophenyl)-2-((3,4-trans)-4-methyl-1-(pyrazin-2-ylmethyl)pyrrolidin-3-yl)imidazo[1,5-f][1,2,4]triazin-4(3H)-one;

(+)-7-(3-fluorophenyl)-2-((3,4-trans)-4-methyl-1-(pyridin-2-ylmethyl)pyrrolidin-3-yl)imidazo[1,5-f][1,2,4]triazin-4(3H)-one;

(+)-7-(3-fluorophenyl)-2-((3,4-trans)-4-methyl-1-(pyridin-3-ylmethyl)pyrrolidin-3-yl)imidazo[1,5-f][1,2,4]triazin-4(3H)-one;

(+)-7-(3-fluorophenyl)-2-((3,4-trans)-4-methyl-1-(pyrimidin-2-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-o-tolylimidazo[1,5-f][1,2,4]triazin-4(3H)-one;

(+)-2-((3,4-trans)-1-(4-chlorobenzyl)-4-methylpyrrolidin-3-yl)-7-o-tolylimidazo[1,5-f][1,2,4]triazin-4(3H)-one;

(+)-2-((3,4-trans)-1-(4-fluorobenzyl)-4-methylpyrrolidin-3-yl)-7-o-tolylimidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-o-tolylimidazo[1,5-f][1,2,4]triazin-4(3H)-one;

(+)-2-((3,4-trans)-1-(imidazo[1,2-a]pyridin-2-ylmethyl)-4-methylpyrrolidin-3-yl)-7-o-tolylimidazo[1,5-f][1,2,4]triazin-4(3H)-one;

(+)-2-((3,4-trans)-1-benzyl-4-methylpyrrolidin-3-yl)-7-o-tolylimidazo[1,5-f][1,2,4]triazin-4(3H)-one;

(+)-2-((3,4-trans)-4-methyl-1-(pyrazin-2-ylmethyl)pyrrolidin-3-yl)-7-O—tolylimidazo[1,5-f][1,2,4]triazin-4(3H)-one;

(+)-2-((3,4-trans)-4-methyl-1-(pyridin-2-ylmethyl)pyrrolidin-3-yl)-7-O—tolylimidazo[1,5-f][1,2,4]triazin-4(3H)-one;

(+)-2-((3,4-trans)-4-methyl-1-(pyridin-3-ylmethyl)pyrrolidin-3-yl)-7-O—tolylimidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(4,5-difluoro-2-methylphenyl)imidazo[1,5-f][1,2,4]triazin-4(3H)-one;

(+)-2-((3,4-trans)-1-(4-chlorobenzyl)-4-methylpyrrolidin-3-yl)-7-(4,5-difluoro-2-methylphenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4,5-difluoro-2-methylphenyl)imidazo[1,5-f][1,2,4]triazin-4(3H)-one;

(+)-2-((3,4-trans)-1-benzyl-4-methylpyrrolidin-3-yl)-7-(4,5-difluoro-2-methylphenyl)imidazo[1,5-f][1,2,4]triazin-4(3H)-one;

(+)-7-(4,5-difluoro-2-methylphenyl)-2-((3,4-trans)-1-(4-fluorobenzyl)-4-methylpyrrolidin-3-yl)imidazo[1,5-f][1,2,4]triazin-4(3H)-one;

(+)-7-(4,5-difluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(4,5-difluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(+)-7-(4,5-difluoro-2-methylphenyl)-2-((3,4-trans)-4-methyl-1-(pyridin-2-ylmethyl)pyrrolidin-3-yl)imidazo[1,5-f][1,2,4]triazin-4(3H)-one;

(+)-7-(4,5-difluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(+)-7-(4,5-difluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-phenylimidazo[1,5-f][1,2,4]triazin-4(3H)-one;

(+)-2-((3,4-trans)-1-(4-chlorobenzyl)-4-methylpyrrolidin-3-yl)-7-phenylimidazo[1,5-f][1,2,4]triazin-4(3H)-one;

(+)-2-((3,4-trans)-1-(4-fluorobenzyl)-4-methylpyrrolidin-3-yl)-7-phenylimidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-phenylimidazo[1,5-f][1,2,4]triazin-4(3H)-one;

(+)-2-((3,4-trans)-1-(imidazo[1,2-a]pyridin-2-ylmethyl)-4-methylpyrrolidin-3-yl)-7-phenylimidazo[1,5-f][1,2,4]triazin-4(3H)-one;

(+)-2-((3,4-trans)-1-benzyl-4-methylpyrrolidin-3-yl)-7-phenylimidazo[1,5-f][1,2,4]triazin-4(3H)-one;

(+)-2-((3,4-trans)-4-methyl-1-(pyrazin-2-ylmethyl)pyrrolidin-3-yl)-7-phenylimidazo[1,5-f][1,2,4]triazin-4(3H)-one;

(+)-2-((3,4-trans)-4-methyl-1-(pyridin-2-ylmethyl)pyrrolidin-3-yl)-7-phenylimidazo[1,5-f][1,2,4]triazin-4(3H)-one;

(+)-2-((3,4-trans)-4-methyl-1-(pyridin-3-ylmethyl)pyrrolidin-3-yl)-7-phenylimidazo[1,5-f][1,2,4]triazin-4(3H)-one;

(+)-2-((3,4-trans)-4-methyl-1-(pyrimidin-2-ylmethyl)pyrrolidin-3-yl)-7-phenylimidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(4-(trifluoromethyl)phenyl)imidazo[1,5-f][1,2,4]triazin-4(3H)-one;

(+)-2-((3,4-trans)-1-(4-chlorobenzyl)-4-methylpyrrolidin-3-yl)-7-(4-(trifluoromethyl)phenyl)imidazo[1,5-f][1,2,4]triazin-4(3H)-one;

(+)-2-((3,4-trans)-1-(4-fluorobenzyl)-4-methylpyrrolidin-3-yl)-7-(4-(trifluoromethyl)phenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4-(trifluoromethyl)phenyl)imidazo[1,5-f][1,2,4]triazin-4(3H)-one;

(+)-2-((3,4-trans)-1-(imidazo[1,2-a]pyridin-2-ylmethyl)-4-methylpyrrolidin-3-yl)-7-(4-(trifluoromethyl)phenyl)imidazo[1,5-f][1,2,4]triazin-4(3H)-one;

(+)-2-((3,4-trans)-1-benzyl-4-methylpyrrolidin-3-yl)-7-(4-(trifluoromethyl)phenyl)imidazo[1,5-f][1,2,4]triazin-4(3H)-one;

(+)-2-((3,4-trans)-4-methyl-1-(pyrazin-2-ylmethyl)pyrrolidin-3-yl)-7-(4-(trifluoromethyl)phenyl)imidazo[1,5-f][1,2,4]triazin-4(3H)-one;

(+)-2-((3,4-trans)-4-methyl-1-(pyridin-2-ylmethyl)pyrrolidin-3-yl)-7-(4-(trifluoromethyl)phenyl)imidazo[1,5-f][1,2,4]triazin-4(3H)-one;

(+)-2-((3,4-trans)-4-methyl-1-(pyridin-3-ylmethyl)pyrrolidin-3-yl)-7-(4-(trifluoromethyl)phenyl)imidazo[1,5-f][1,2,4]triazin-4(3H)-one;

(+)-2-((3,4-trans)-4-methyl-1-(pyrimidin-2-ylmethyl)pyrrolidin-3-yl)-7-(4-(trifluoromethyl)phenyl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(4-fluoro-2-methylphenyl)imidazo[1,5-f][1,2,4]triazin-4(3H)-one;

(+)-2-((3,4-trans)-1-(4-chlorobenzyl)-4-methylpyrrolidin-3-yl)-7-(4-fluoro-2-methylphenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4-fluoro-2-methylphenyl)imidazo[1,5-f][1,2,4]triazin-4(3H)-one;

(+)-7-(4-fluoro-2-methylphenyl)-2-((3,4-trans)-1-(4-fluorobenzyl)-4-methylpyrrolidin-3-yl)imidazo[1,5-f][1,2,4]triazin-4(3H)-one;

(+)-7-(4-fluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(4-fluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(+)-7-(4-fluoro-2-methylphenyl)-2-((3,4-trans)-4-methyl-1-(pyridin-2-ylmethyl)pyrrolidin-3-yl)imidazo[1,5-f][1,2,4]triazin-4(3H)-one;

(+)-7-(4-fluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(+)-2-((3,4-trans)-4-methyl-1-(4-(trifluoromethyl)pyrimidin-2-yl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(2,2,2-trifluoroethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((2-methylpyridin-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(quinolin-8-ylmethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((3-methylpyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((2-methylpyridin-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((2-propylpyrimidin-5-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(2-(pyrimidin-2-yl)ethyl)pyrrolidin-3-yl)-7-(tetrahydro-2H-pyran-4-yl)imidazo[1,5-f][1,2,4]triazin-4(3H)-one;

(+)-2-((3,4-trans)-1-((1,5-naphthyridin-4-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((1,8-naphthyridin-4-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((2-(dimethylamino)pyrimidin-4-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(cinnolin-3-ylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((4,5,6,7-tetrahydropyrazolo[1,5-a]pyridin-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(2-(pyrimidin-5-yl)ethyl)pyrrolidin-3-yl)-7-(tetrahydro-2H-pyran-4-yl)imidazo[1,5-f][1,2,4]triazin-4(3H)-one;

(+)-2-((3,4-trans)-1-((8-fluoroquinolin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(benzo[c][1,2,5]thiadiazol-5-ylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-imidazol-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-imidazol-5-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-pyrazol-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-pyrazol-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-pyrazol-5-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(thiazol-2-ylmethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(quinuclidin-4-ylmethyl)pyrrolidin-3-yl)-7-(tetrahydro-2H-pyran-4-yl)imidazo[1,5-f][1,2,4]triazin-4(3H)-one;

(+)-2-((3,4-trans)-1-((1,3,5-triazin-2-yl)methyl)-4-methylpyrrolidin-3-yl)-7-(tetrahydro-2H-pyran-4-yl)imidazo[1,5-f][1,2,4]triazin-4(3H)-one;

(+)-2-fluoro-5-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzonitrile;

(+)-2-((3,4-trans)-1-((4,6-dimethylpyrimidin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chloropyrimidin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(2,3-dichlorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(3-chloro-4-fluorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((4-methylpyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((6-methylpyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(pyrido[2,3-d]pyrimidin-2-ylmethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(pyrido[3,2-b]pyrazin-3-ylmethyl)pyrrolidin-3-yl)-7-(tetrahydro-2H-pyran-4-yl)imidazo[1,5-f][1,2,4]triazin-4(3H)-one;

(+)-tert-butyl 4-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)piperidine-1-carboxylate;

(+)-2-((3,4-trans)-1-((1,2,4-oxadiazol-5-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((4,4-difluorocyclohexyl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chlorofuran-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chlorofuran-3-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chlorothiophen-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chlorothiophen-3-yl)methyl)-4-methylpyrrolidin-3-yl)-7-(tetrahydro-2H-pyran-4-yl)imidazo[1,5-f][1,2,4]triazin-4(3H)-one (+)-2-((3,4-trans)-1-(cyclopentylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(cyclopropylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(furan-2-ylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(furan-3-ylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methylpiperidin-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((tetrahydro-2H-pyran-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(piperidin-4-ylmethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(thiophen-2-ylmethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(thiophen-3-ylmethyl)pyrrolidin-3-yl)-7-(tetrahydro-2H-pyran-4-yl)imidazo[1,5-f][1,2,4]triazin-4(3H)-one;

(+)-2-((3,4-trans)-1-((2-methoxypyridin-4-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((2-methoxypyrimidin-5-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((4-methoxypyridin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chloropyridin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-fluoropyridin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-methoxypyridin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-methoxypyridin-3-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(2-chloro-5-fluorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(4-chloro-3-(trifluoromethyl)benzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(4-chloro-3-methylbenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(5-chloro-2-fluorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((5-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((6-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(2-(trifluoromethoxy)benzyl)pyrrolidin-3-yl)-7-(tetrahydro-2H-pyran-4-yl)imidazo[1,5-f][1,2,4]triazin-4(3H)-one;

(+)-2-((3,4-trans)-1-((2-methoxypyridin-4-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-methoxypyridin-3-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(2-chloro-3,6-difluorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(2-chloro-6-fluorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(3-chloro-5-(trifluoromethyl)benzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((3-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((4-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((5-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((6-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-N,N-dimethyl-2-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(+)-N,N-dimethyl-3-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(+)-N,N-dimethyl-4-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(+)-2-((3,4-trans)-1-((1,2,4-oxadiazol-3-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((1,3,4-oxadiazol-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(biphenyl-4-ylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-1,2,4-triazol-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-imidazol-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((2-methylthiazol-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((5-(trifluoromethyl)-1,2,4-oxadiazol-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((5-methyl-1,2,4-oxadiazol-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((5-methyl-1H-1,2,4-triazol-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(4-(pyridin-4-yl)benzyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(oxazol-2-ylmethyl)pyrrolidin-3-yl)-7-(tetrahydro-2H-pyran-4-yl)imidazo[1,5-f][1,2,4]triazin-4(3H)-one;

(−)-7-(4,4-difluorocyclohexyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-2-((3,4-trans)-1-((3aH-benzo[d]imidazol-2-yl)methyl)-4-methylpyrrolidin-3-yl)-7-(4,4-difluorocyclohexyl)imidazo[1,5-f][1,2,4]triazin-4(3H)-one;

(−)-7-(4,4-difluorocyclohexyl)-2-((3,4-trans)-4-methyl-1-(pyridin-2-ylmethyl)pyrrolidin-3-yl)imidazo[1,5-f][1,2,4]triazin-4(3H)-one;

(−)-7-(4,4-difluorocyclohexyl)-2-((3,4-trans)-4-methyl-1-(pyridin-3-ylmethyl)pyrrolidin-3-yl)imidazo[1,5-f][1,2,4]triazin-4(3H)-one;

(−)-7-(4,4-difluorocyclohexyl)-2-((3,4-trans)-4-methyl-1-(pyrazin-2-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(5-fluoro-2-methylphenyl)imidazo[1,5-f][1,2,4]triazin-4(3H)-one;

(−)-2-((3,4-trans)-1-(4-chlorobenzyl)-4-methylpyrrolidin-3-yl)-7-(5-fluoro-2-methylphenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(5-fluoro-2-methylphenyl)imidazo[1,5-f][1,2,4]triazin-4(3H)-one;

(−)-7-(5-fluoro-2-methylphenyl)-2-((3,4-trans)-1-(4-fluorobenzyl)-4-methylpyrrolidin-3-yl)imidazo[1,5-f][1,2,4]triazin-4(3H)-one;

(−)-7-(5-fluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(5-fluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(−)-7-(5-fluoro-2-methylphenyl)-2-((3,4-trans)-4-methyl-1-(pyridin-2-ylmethyl)pyrrolidin-3-yl)imidazo[1,5-f][1,2,4]triazin-4(3H)-one;

(−)-(−)-7-(5-fluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(4-fluorocyclohexyl)imidazo[1,5-f][1,2,4]triazin-4(3H)-one;

(−)-2-((3,4-trans)-1-(4-chlorobenzyl)-4-methylpyrrolidin-3-yl)-7-(4-fluorocyclohexyl)imidazo[1,5-f][1,2,4]triazin-4(3H)-one;

(−)-2-((3,4-trans)-1-(4-fluorobenzyl)-4-methylpyrrolidin-3-yl)-7-(4-fluorocyclohexyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(4-fluorocyclohexyl)imidazo[1,5-f][1,2,4]triazin-4(3H)-one;

(−)-2-((3,4-trans)-1-benzyl-4-methylpyrrolidin-3-yl)-7-(4-fluorocyclohexyl)imidazo[1,5-f][1,2,4]triazin-4(3H)-one;

(−)-2-((3,4-trans)-1-benzyl-4-methylpyrrolidin-3-yl)-7-(4-fluorocyclohexyl)imidazo[1,5-f][1,2,4]triazin-4(3H)-one;

(−)-7-(4-fluorocyclohexyl)-2((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(4-fluorocyclohexyl)-2-((3,4-trans)-4-methyl-1-(pyrazin-2-ylmethyl)pyrrolidin-3-yl)imidazo[1,5-f][1,2,4]triazin-4(3H)-one;

(−)-7-(4-fluorocyclohexyl)-2-((3,4-trans)-4-methyl-1-(pyridin-2-ylmethyl)pyrrolidin-3-yl)imidazo[1,5-f][1,2,4]triazin-4(3H)-one;

(−)-7-(4-fluorocyclohexyl)-2-((3,4-trans)-4-methyl-1-(pyridin-3-ylmethyl)pyrrolidin-3-yl)imidazo[1,5-f][1,2,4]triazin-4(3H)-one;

(−)-7-(4-fluorocyclohexyl)-2-((3,4-trans)-4-methyl-1-(pyrimidin-2-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(4-fluorophenyl)imidazo[1,5-f][1,2,4]triazin-4(3H)-one;

(−)-2-((3,4-trans)-1-(4-chlorobenzyl)-4-methylpyrrolidin-3-yl)-7-(4-fluorophenyl)imidazo[1,5-f][1,2,4]triazin-4(3H)-one;

(−)-2-((3,4-trans)-1-(4-fluorobenzyl)-4-methylpyrrolidin-3-yl)-7-(4-fluorophenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(4-fluorophenyl)imidazo[1,5-f][1,2,4]triazin-4(3H)-one;

(−)-2-((3,4-trans)-1-benzyl-4-methylpyrrolidin-3-yl)-7-(4-fluorophenyl)imidazo[1,5-f][1,2,4]triazin-4(3H)-one;

(−)-7-(4-fluorophenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(4-fluorophenyl)-2-((3,4-trans)-4-methyl-1-(pyrazin-2-ylmethyl)pyrrolidin-3-yl)imidazo[1,5-f][1,2,4]triazin-4(3H)-one;

(−)-7-(4-fluorophenyl)-2-((3,4-trans)-4-methyl-1-(pyridin-2-ylmethyl)pyrrolidin-3-yl)imidazo[1,5-f][1,2,4]triazin-4(3H)-one;

(−)-7-(4-fluorophenyl)-2-((3,4-trans)-4-methyl-1-(pyridin-3-ylmethyl)pyrrolidin-3-yl)imidazo[1,5-f][1,2,4]triazin-4(3H)-one;

(−)-7-(4-fluorophenyl)-2-((3,4-trans)-4-methyl-1-(pyrimidin-2-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(3-fluorophenyl)imidazo[1,5-f][1,2,4]triazin-4(3H)-one;

(−)-2-((3,4-trans)-1-(4-chlorobenzyl)-4-methylpyrrolidin-3-yl)-7-(3-fluorophenyl)imidazo[1,5-f][1,2,4]triazin-4(3H)-one;

(−)-2-((3,4-trans)-1-(4-fluorobenzyl)-4-methylpyrrolidin-3-yl)-7-(3-fluorophenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(3-fluorophenyl)imidazo[1,5-f][1,2,4]triazin-4(3H)-one;

(−)-2-((3,4-trans)-1-benzyl-4-methylpyrrolidin-3-yl)-7-(3-fluorophenyl)imidazo[1,5-f][1,2,4]triazin-4(3H)-one;

(−)-7-(3-fluorophenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(3-fluorophenyl)-2-((3,4-trans)-4-methyl-1-(pyrazin-2-ylmethyl)pyrrolidin-3-yl)imidazo[1,5-f][1,2,4]triazin-4(3H)-one;

(−)-7-(3-fluorophenyl)-2-((3,4-trans)-4-methyl-1-(pyridin-2-ylmethyl)pyrrolidin-3-yl)imidazo[1,5-f][1,2,4]triazin-4(3H)-one;

(−)-7-(3-fluorophenyl)-2-((3,4-trans)-4-methyl-1-(pyridin-3-ylmethyl)pyrrolidin-3-yl)imidazo[1,5-f][1,2,4]triazin-4(3H)-one;

(−)-7-(3-fluorophenyl)-2-((3,4-trans)-4-methyl-1-(pyrimidin-2-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-o-tolylimidazo[1,5-f][1,2,4]triazin-4(3H)-one;

(−)-2-((3,4-trans)-1-(4-chlorobenzyl)-4-methylpyrrolidin-3-yl)-7-o-tolylimidazo[1,5-f][1,2,4]triazin-4(3H)-one;

(−)-2-((3,4-trans)-1-(4-fluorobenzyl)-4-methylpyrrolidin-3-yl)-7-o-tolylimidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-o-tolylimidazo[1,5-f][1,2,4]triazin-4(3H)-one;

(−)-2-((3,4-trans)-1-(imidazo[1,2-a]pyridin-2-ylmethyl)-4-methylpyrrolidin-3-yl)-7-o-tolylimidazo[1,5-f][1,2,4]triazin-4(3H)-one;

(−)-2-((3,4-trans)-1-benzyl-4-methylpyrrolidin-3-yl)-7-o-tolylimidazo[1,5-f][1,2,4]triazin-4(3H)-one;

(−)-2-((3,4-trans)-4-methyl-1-(pyrazin-2-ylmethyl)pyrrolidin-3-yl)-7-o-tolylimidazo[1,5-f][1,2,4]triazin-4(3H)-one;

(−)-2-((3,4-trans)-4-methyl-1-(pyridin-2-ylmethyl)pyrrolidin-3-yl)-7-o-tolylimidazo[1,5-f][1,2,4]triazin-4(3H)-one;

(−)-2-((3,4-trans)-4-methyl-1-(pyridin-3-ylmethyl)pyrrolidin-3-yl)-7-o-tolylimidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(4,5-difluoro-2-methylphenyl)imidazo[1,5-f][1,2,4]triazin-4(3H)-one;

(−)-2-((3,4-trans)-1-(4-chlorobenzyl)-4-methylpyrrolidin-3-yl)-7-(4,5-difluoro-2-methylphenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(4,5-difluoro-2-methylphenyl)imidazo[1,5-f][1,2,4]triazin-4(3H)-one;

(−)-2-((3,4-trans)-1-benzyl-4-methylpyrrolidin-3-yl)-7-(4,5-difluoro-2-methylphenyl)imidazo[1,5-f][1,2,4]triazin-4(3H)-one;

(−)-7-(4,5-difluoro-2-methylphenyl)-2-((3,4-trans)-1-(4-fluorobenzyl)-4-methylpyrrolidin-3-yl)imidazo[1,5-f][1,2,4]triazin-4(3H)-one;

(−)-7-(4,5-difluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(4,5-difluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(−)-7-(4,5-difluoro-2-methylphenyl)-2-((3,4-trans)-4-methyl-1-(pyridin-2-ylmethyl)pyrrolidin-3-yl)imidazo[1,5-f][1,2,4]triazin-4(3H)-one (−)-7-(4,5-difluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(−)-7-(4,5-difluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-phenylimidazo[1,5-f][1,2,4]triazin-4(3H)-one;

(−)-2-((3,4-trans)-1-(4-chlorobenzyl)-4-methylpyrrolidin-3-yl)-7-phenylimidazo[1,5-f][1,2,4]triazin-4(3H)-one;

(−)-2-((3,4-trans)-1-(4-fluorobenzyl)-4-methylpyrrolidin-3-yl)-7-phenylimidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-phenylimidazo[1,5-f][1,2,4]triazin-4(3H)-one;

(−)-2-((3,4-trans)-1-(imidazo[1,2-a]pyridin-2-ylmethyl)-4-methylpyrrolidin-3-yl)-7-phenylimidazo[1,5-f][1,2,4]triazin-4(3H)-one;

(−)-2-((3,4-trans)-1-benzyl-4-methylpyrrolidin-3-yl)-7-phenylimidazo[1,5-f][1,2,4]triazin-4(3H)-one;

(−)-2-((3,4-trans)-4-methyl-1-(pyrazin-2-ylmethyl)pyrrolidin-3-yl)-7-phenylimidazo[1,5-f][1,2,4]triazin-4(3H)-one;

(−)-2-((3,4-trans)-4-methyl-1-(pyridin-2-ylmethyl)pyrrolidin-3-yl)-7-phenylimidazo[1,5-f][1,2,4]triazin-4(3H)-one;

(−)-2-((3,4-trans)-4-methyl-1-(pyridin-3-ylmethyl)pyrrolidin-3-yl)-7-phenylimidazo[1,5-f][1,2,4]triazin-4(3H)-one;

(−)-2-((3,4-trans)-4-methyl-1-(pyrimidin-2-ylmethyl)pyrrolidin-3-yl)-7-phenylimidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(4-(trifluoromethyl)phenyl)imidazo[1,5-f][1,2,4]triazin-4(3H)-one;

(−)-2-((3,4-trans)-1-(4-chlorobenzyl)-4-methylpyrrolidin-3-yl)-7-(4-(trifluoromethyl)phenyl)imidazo[1,5-f][1,2,4]triazin-4(3H)-one (−)-2-((3,4-trans)-1-(4-fluorobenzyl)-4-methylpyrrolidin-3-yl)-7-(4-(trifluoromethyl)phenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(4-(trifluoromethyl)phenyl)imidazo[1,5-f][1,2,4]triazin-4(3H)-one;

(−)-2-((3,4-trans)-1-(imidazo[1,2-a]pyridin-2-ylmethyl)-4-methylpyrrolidin-3-yl)-7-(4-(trifluoromethyl)phenyl)imidazo[1,5-f][1,2,4]triazin-4(3H)-one;

(−)-2-((3,4-trans)-1-benzyl-4-methylpyrrolidin-3-yl)-7-(4-(trifluoromethyl)phenyl)imidazo[1,5-f][1,2,4]triazin-4(3H)-one;

(−)-2-((3,4-trans)-4-methyl-1-(pyrazin-2-ylmethyl)pyrrolidin-3-yl)-7-(4-(trifluoromethyl)phenyl)imidazo[1,5-f][1,2,4]triazin-4(3H)-one (−)-2-((3,4-trans)-4-methyl-1-(pyridin-2-ylmethyl)pyrrolidin-3-yl)-7-(4-(trifluoromethyl)phenyl)imidazo[1,5-f][1,2,4]triazin-4(3H)-one (−)-2-((3,4-trans)-4-methyl-1-(pyridin-3-ylmethyl)pyrrolidin-3-yl)-7-(4-(trifluoromethyl)phenyl)imidazo[1,5-f][1,2,4]triazin-4(3H)-one;

(−)-2-((3,4-trans)-4-methyl-1-(pyrimidin-2-ylmethyl)pyrrolidin-3-yl)-7-(4-(trifluoromethyl)phenyl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(4-fluoro-2-methylphenyl)imidazo[1,5-f][1,2,4]triazin-4(3H)-one;

(−)-2-((3,4-trans)-1-(4-chlorobenzyl)-4-methylpyrrolidin-3-yl)-7-(4-fluoro-2-methylphenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(4-fluoro-2-methylphenyl)imidazo[1,5-f][1,2,4]triazin-4(3H)-one;

(−)-7-(4-fluoro-2-methylphenyl)-2-((3,4-trans)-1-(4-fluorobenzyl)-4-methylpyrrolidin-3-yl)imidazo[1,5-f][1,2,4]triazin-4(3H)-one;

(−)-7-(4-fluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(4-fluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(−)-7-(4-fluoro-2-methylphenyl)-2-((3,4-trans)-4-methyl-1-(pyridin-2-ylmethyl)pyrrolidin-3-yl)imidazo[1,5-f][1,2,4]triazin-4(3H)-one;

(−)-7-(4-fluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(−)-2-((3,4-trans)-4-methyl-1-(4-(trifluoromethyl)pyrimidin-2-yl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(2,2,2-trifluoroethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((2-methylpyridin-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(quinolin-8-ylmethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((3-methylpyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((2-methylpyridin-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((2-propylpyrimidin-5-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(2-(pyrimidin-2-yl)ethyl)pyrrolidin-3-yl)-7-(tetrahydro-2H-pyran-4-yl)imidazo[1,5-f][1,2,4]triazin-4(3H)-one;

(−)-2-((3,4-trans)-1-((1,5-naphthyridin-4-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((1,8-naphthyridin-4-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((2-(dimethylamino)pyrimidin-4-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(cinnolin-3-ylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((4,5,6,7-tetrahydropyrazolo[1,5-a]pyridin-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(2-(pyrimidin-5-yl)ethyl)pyrrolidin-3-yl)-7-(tetrahydro-2H-pyran-4-yl)imidazo[1,5-f][1,2,4]triazin-4(3H)-one;

(−)-2-((3,4-trans)-1-((8-fluoroquinolin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(benzo[c][1,2,5]thiadiazol-5-ylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-imidazol-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-imidazol-5-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-pyrazol-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-pyrazol-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-pyrazol-5-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(thiazol-2-ylmethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(quinuclidin-4-ylmethyl)pyrrolidin-3-yl)-7-(tetrahydro-2H-pyran-4-yl)imidazo[1,5-f][1,2,4]triazin-4(3H)-one;

(−)-2-((3,4-trans)-1-((1,3,5-triazin-2-yl)methyl)-4-methylpyrrolidin-3-yl)-7-(tetrahydro-2H-pyran-4-yl)imidazo[1,5-f][1,2,4]triazin-4(3H)-one;

(+2-fluoro-5-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzonitrile;

(−)-2-((3,4-trans)-1-((4,6-dimethylpyrimidin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chloropyrimidin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(2,3-dichlorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(3-chloro-4-fluorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((4-methylpyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((6-methylpyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(pyrido[2,3-d]pyrimidin-2-ylmethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(pyrido[3,2-b]pyrazin-3-ylmethyl)pyrrolidin-3-yl)-7-(tetrahydro-2H-pyran-4-yl)imidazo[1,5-f][1,2,4]triazin-4(3H)-one;

(−)-tert-butyl 4-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)piperidine-1-carboxylate;

(−)-2-((3,4-trans)-1-(((1,2,4-oxadiazol-5-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((4,4-difluorocyclohexyl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chlorofuran-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chlorofuran-3-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chlorothiophen-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chlorothiophen-3-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-cyclopentylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(cyclopropylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(furan-2-ylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(furan-3-ylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methylpiperidin-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((tetrahydro-2H-pyran-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(piperidin-4-ylmethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(thiophen-2-ylmethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(thiophen-3-ylmethyl)pyrrolidin-3-yl)-7-(tetrahydro-2H-pyran-4-yl)imidazo[1,5-f][1,2,4]triazin-4(3H)-one;

(−)-2-((3,4-trans)-1-((2-methoxypyridin-4-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((2-methoxypyrimidin-5-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((4-methoxypyridin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chloropyridin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-fluoropyridin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-methoxypyridin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-methoxypyridin-3-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(2-chloro-5-fluorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(4-chloro-3-(trifluoromethyl)benzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(4-chloro-3-methylbenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(5-chloro-2-fluorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((5-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((6-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(2-(trifluoromethoxy)benzyl)pyrrolidin-3-yl)-7-(tetrahydro-2H-pyran-4-yl)imidazo[1,5-f][1,2,4]triazin-4(3H)-one;

(−)-2-((3,4-trans)-1-((2-methoxypyridin-4-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-methoxypyridin-3-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(2-chloro-3,6-difluorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(2-chloro-6-fluorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(3-chloro-5-(trifluoromethyl)benzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((3-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((4-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((5-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((6-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-N,N-dimethyl-2-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(−)-N,N-dimethyl-3-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(−)-N,N-dimethyl-4-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(−)-2-((3,4-trans)-1-((1,2,4-oxadiazol-3-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((1,3,4-oxadiazol-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(biphenyl-4-ylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-1,2,4-triazol-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-imidazol-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((2-methylthiazol-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((5-(trifluoromethyl)-1,2,4-oxadiazol-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((5-methyl-1,2,4-oxadiazol-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((5-methyl-1H-1,2,4-triazol-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(4-(pyridin-4-yl)benzyl)pyrrolidin-3-yl)-7-(tetrahydro-2H-pyran-4-yl)imidazo[1,5-f][1,2,4]triazin-4(3H)-one; and (−)-2-((3,4-trans)-4-methyl-1-(oxazol-2-ylmethyl)pyrrolidin-3-yl)-7-(tetrahydro-2H-pyran-4-yl)imidazo[1,5-f][1,2,4]triazin-4(3H)-one;

or a pharmaceutically acceptable salt thereof.

In a further embodiment of Formula (I), the compounds of the disclosure are embodied by the examples listed in the table below, each of which is intended to be a separate embodiment, and which is provided in table/list format solely as a convenience:

| R1 | R2 | R3 |
| --- | --- | --- |
| Me | 4-pyran | 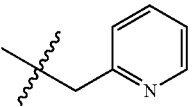 [SMILES: *Cc1ccccn1] |
| Me | 4-pyran | 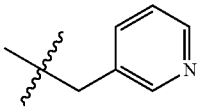 [SMILES: *Cc1cccnc1] |

-continued

| R1 | R2 | R3 |
|---|---|---|
| Me | 4-pyran |  |
| Me | 4-pyran | 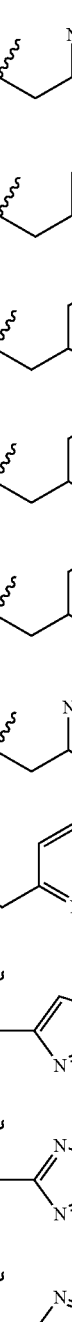 |
| Me | 4-pyran | 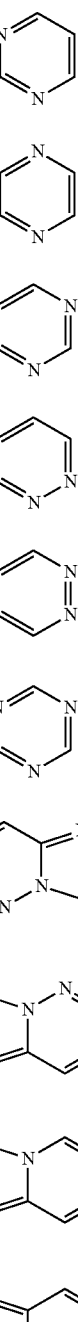 |
| Me | 4-pyran |  |
| Me | 4-pyran |  |
| Me | 4-pyran | 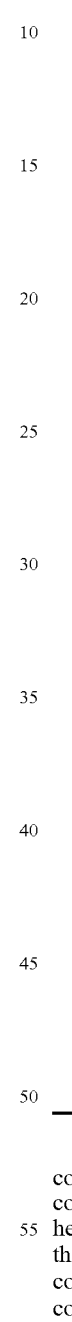 |
| Me | 4-pyran |  |
| Me | 4-pyran |  |
| Me | 4-pyran |  |
| Me | 4-pyran |  |
| Me | 4-pyran | 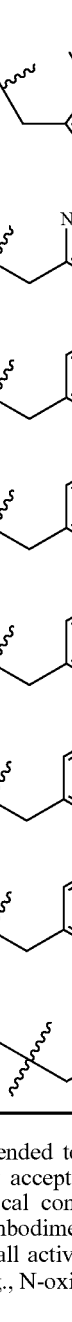 |
| Me | 4-pyran | 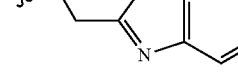 |

-continued

| R1 | R2 | R3 |
|---|---|---|
| Me | 4-pyran | 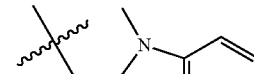 |
| Me | 4-pyran | 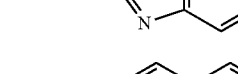 |
| Me | 4-pyran | 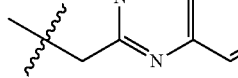 |
| Me | 4-pyran | 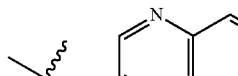 |
| Me | 4-pyran | 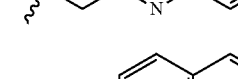 |
| Me | 4-pyran | 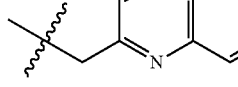 |
| Me | 4-pyran | 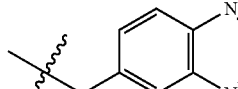 |
| Me | 4-pyran |  |
| Me | 4-pyran | 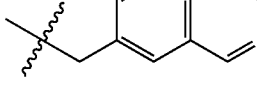 |

The present invention is intended to include any novel compound or pharmaceutically acceptable salt thereof, or composition, e.g., pharmaceutical composition, described herein. In addition, in certain embodiments of the invention, the present invention includes all active metabolites of the compounds of the invention, e.g., N-oxide derivatives of the compounds of Formula (I).

Compounds in the disclosure, e.g., compounds of Formula (I), may be in the form of pharmaceutically acceptable salts The phrase "pharmaceutically acceptable" refers to salts prepared from pharmaceutically acceptable non-toxic bases and acids, including inorganic and organic bases and inorganic and organic acids. Salts derived from inorganic bases include, but are not limited to, lithium, sodium, potassium, magnesium, calcium and zinc. Salts derived from organic bases include, but are not limited to, ammonia, primary (e.g. Tromethamine), secondary and tertiary amines, and amino acids (e.g. Lysine). Salts derived from inorganic acids include, but are not limited to, sulfuric, hydrochloric, phosphoric, methanesulfonic, hydrobromic. Salts derived from organic acids include, but are not limited to, $C_{1-6}$ alkyl carboxylic acids, di-carboxylic acids and tricarboxylic acids such as acetic acid, propionic acid, fumaric acid, maleic acid, succinic acid, tartaric acid, adipic acid and citric acid, and alkylsulfonic acids such as methanesulfonic and aryl sulfonic acids such as para-toluene sulfonic acid and benzene sulfonic acid. For detailed list of salts see P. H. Stahl and C. G. Wermuth (eds.) "Handbook of Pharmaceutical Salts, Properties, Selection and Use" Wiley-VCH (ISBN 3-906390-26-8)

As noted herein, the present invention also includes enantiomers, diastereomers or racemates of the compound. Enantiomers are a pair of stereoisomers that are non-superimposable mirror images of each other. A 1:1 mixture of a pair of enantiomers is a racemic mixture. The term "enantiomers" is used to designate a racemic mixture where appropriate. Diastereoisomers are stereoisomers that have at least two asymmetric atoms, but which are not mirror-images of each other. The absolute stereochemistry may be specified according to the Cahn-lngold-Prelog R-S system. When a compound is a pure enantiomer the stereochemistry at each chiral carbon may be specified by either R or S. Resolved compounds can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

In addition, compounds in the invention may exist in tautomeric forms which can be in equilibrium with each other. All tautomeric forms of Formula (I) are encompassed in the invention.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. For example, substitution with heavier isotopes such as deuterium ($^2H$) may offer certain therapeutic advantages resulting from greater metabolic stability which could be preferable and lead to longer in vivo half-life or dose reduction in a mammal or human. The invention includes various isotopically labeled compounds as defined herein, for example, those into which radioactive isotopes, such as $^3H$, $^{13}C$, and $^{14}C$, are present. Such isotopically labeled compounds may also be useful in metabolic studies (with $^{14}C$), reaction kinetic studies (with, for example, $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example, increased in vivo half-life or reduced dosage requirements or an improvement in therapeutic index. It is understood that deuterium in this context is regarded as a substituent of a compound of the Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of Formula (I) can generally be prepared by conventional techniques known to those skilled in the art or by processes analogous to those described in the accompanying Examples and Preparations using an appropriate isotopically-labeled reagents in place of the non-labeled reagent previously employed.

Compounds in the disclosure may exist in different crystal forms. Crystal forms include single-component crystal forms and multiple-component crystal forms, and include, but are not limited to, polymorphs, solvates, hydrates, and/or other molecular complexes. In certain embodiments, a crystalline form is substantially pure, isolated or enriched in one crystalline form, and/or is substantially free of amorphous forms and/or other crystal forms.

Furthermore, in certain embodiments, compounds and pharmaceutically acceptable salts thereof may be in the form of a solvate, i.e., a substance formed by chemical union of two or more elements or ingredients in definite proportion by weight. In certain embodiments, this occurs when a compound of Formula (I) crystallize in a manner that it incorporates solvent molecules into the crystal lattice. Examples of solvents forming solvates are water (hydrates), MeOH, EtOH, iPrOH, and acetone. Formula (I) covers all solvates of the depicted compounds. Pharmaceutically acceptable solvates in accordance with the invention also include those wherein the solvent of crystallization may be isotopically substituted, e.g. $D_2O$, $d_6$-acetone, $d_6$-DMSO.

Compounds of the invention, i.e. compounds of Formula (I) that contain groups capable of acting as donors and/or acceptors for hydrogen bonds may be capable of forming co-crystals with suitable co-crystal formers. These co-crystals may be prepared from compounds of Formula (I) by known co-crystal forming procedures. Such procedures include grinding, heating, co-subliming, co-melting, or contacting in solution compounds of Formula (I) with the co-crystal former under crystallization conditions and isolating co-crystals thereby formed. Suitable co-crystal formers include those described in WO 2004/078163. Hence the invention further provides co-crystals comprising a compound of Formula (I).

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that convert in vivo to the compounds of the present invention. A pro-drug is a compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound that contains one or more protective groups and is converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)); and hydroxy groups have been masked as esters and ethers. EP 039,051 (Sloan and Little) discloses Mannich-base hydroxamic acid prodrugs, their preparation and use.

Practitioners of the art will recognize that certain electrophilic ketones, may exist in a hydrated form. The scope of this disclosure is to include all such hydrated forms. For example, a trifluoromethyl ketone may exist in a hydrated form via addition of water to the carbonyl group. This is depicted in figure below. This example is not meant to be limiting in the scope of hydrated forms.

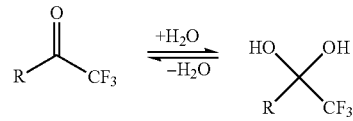

Other therapeutic agents may be administered either simultaneously with, before, or after compounds of the present invention. The compounds of the present invention may be administered separately, by the same or different route of administration, or together in the same pharmaceutical composition as the other agent(s).

In one embodiment, the invention provides a product comprising a compound of Formula (I) and at least one other therapeutic agent as a combined preparation for simultaneous, separate, or sequential use in therapy. In one embodiment, the therapy is the treatment of a disease or condition mediated by PDE9 or cGMP levels. Products provided as a combined preparation include a composition comprising the compound of Formula (I) and the other therapeutic agent(s) together in the same pharmaceutical composition, or the compound of Formula (I) and the other therapeutic agent(s) in separate form, e.g., in the form of a kit.

Compounds of the disclosure may also be used in mammals and humans in conjunction with conventional cognition enhancing or neuroprotective medications including donepezil, rivastigmine, galantamine and memantine. Additional medications could include additional cholinesterase inhibitors, NMDA receptor antagonists, nicotinic agonists (including α7 agonists), muscarinic agonists (including $M_1$ agonists) and 5-$HT_6$ antagonists. The combination of a compound of Formula (I) with a subtherapeutic dose of an aforementioned conventional cognition enhancer or neuroprotective medication may afford certain treatment advantages including improved side effect profiles and lower dosing requirements.

III. METHODS OF THE INVENTION

Compounds in the disclosure and their pharmaceutically acceptable salts, prodrugs, as well as metabolites of the compounds, may also be used to treat PDE9 associated diseases or disorders, e.g., CNS disorders and conditions, urogenital disorders and cardiovascular disorders. In certain embodiments, the imidazotriazinone compounds of Formula (I) are useful as inhibitors of at least one phosphodiesterase 9. Moreover, in particular embodiments, a compound of Formula (I) selectively inhibits PDE9A.

Another aspect of the invention provides a method for treating a PDE9 associated disease or disorder comprising administering to a subject an effective amount of a compound of the invention, e.g., in a pharmaceutical composition of the invention.

In another aspect, the invention provides a method of inhibiting PDE9 in a subject, wherein the method comprises administering to the subject a therapeutically effective amount of a compound of the invention, e.g., a compound of Formula (I), A. Methods of Use Another embodiment of the invention provides a method of treating a PDE9 associated disease or disorder comprising administering to a subject an effective amount of a compound of the invention, e.g., in a pharmaceutical composition of the invention, such that PDE9 is inhibited in the subject. The PDE9 associated diseases or disorders that may be treated by the compounds of the invention are those disorders or diseases associated with abnormal PDE9 activity, or aberrant levels of cGMP. In certain embodiments, the PDE9 associated disease or disorder is a central nervous system (CNS) disease or disorder, a neurodegeneration disorder, or a disorder that may affect CNS function, wherein each of these diseases or disorders is related to the modulation of cGMP levels. In certain embodiments, the PDE9 associated disease or disorder is a disease or disorder caused by a relative reduction in synaptic plasticity and synaptic processes, e.g., as in learning or memory. In a particular embodiment, the compounds of the invention serve to treat these disorders by acting to increase synaptic plasticity and synaptic processes.

Exemplary CNS disorders include Alzheimer's disease, amyotrophic lateral sclerosis (ALS or Lou Gerig's disease), Binswanger's dementia (subcortical arteriosclerotic encephalopathy), bipolar disorders, Down's syndrome, frontotemporal lobar degeneration or dementia, glaucoma, Huntington's diseases (chorea), HIV-associated dementia, Lewy body dementia, multiple sclerosis, multiple system atrophy, Parkinson's disease, presenile dementia (mild cognitive impairment), schizophrenia, spinocerebellar ataxies, Steel-Richardson-Olszewski disease (progressive supranuclear palsy), vascular dementia, attention deficit disorder (ADD) and attention deficit hyperactivity disorder (ADHD). Exemplary neurodegeneration disorders include either traumatic (closed or open, penetrating head injuries) or non-traumatic (stroke, aneurism, hypoxia) injury to the brain. In certain embodiments, PDE9 associated diseases or disorders characterized by aberrant levels of cGMP may also include dystonia, including for example, generalized, focal, segmental, sexual, intermediate, acute dystonic reaction, and genetic/primary dystonia; and dyskinesia, including for example, acute, chronic/tardive, and non-motor. In certain embodiments, PDE9 associated diseases or disorders characterized by a relative reduction in synaptic plasticity and synaptic processes include, for example, obsessive compulsive disorder, Fragile X, Rhett's, Williams syndrome, Renpenning's syndrome, autism spectrum disorders, including autism, Asperger's syndrome, pervasive development disorder, Rhettt's syndrome, and childhood disintegrative disorder In one embodiment, the treatment of PDE9 associated diseases or disorders by the compounds of the disclosure can include Alzheimer's disease, amyotrophic lateral sclerosis (ALS or Lou Gerig's disease), Binswanger's dementia (subcortical arteriosclerotic encephalopathy), bipolar disorders, Down's syndrome, frontotemporal lobar degeneration or dementia, glaucoma, Huntington's diseases (chorea), HIV-associated dementia, Lewy body dementia, multiple sclerosis, multiple system atrophy, Parkinson's disease, presenile dementia (mild cognitive impairment), schizophrenia, spinocerebellar ataxies, Steel-Richardson-Olszewski disease (progressive supranuclear palsy), vascular dementia, attention deficit disorder (ADD) and attention deficit hyperactivity disorder (ADHD).

In another embodiment, the treatment of CNS disorders and conditions by the compounds of the disclosure can include Alzheimer's disease, amyotrophic lateral sclerosis (ALS or Lou Gehrig's disease), bipolar disorders, frontotemporal dementia, multiple system atrophy, Parkinson's disease, presenile dementia (mild cognitive impairment) and vascular dementia.

In another embodiment, compounds of the disclosure may be used for the treatment of neurodegeneration disorders caused by either traumatic (closed or open, penetrating head injuries) or non-traumatic (stroke, aneurism, hypoxia) injury to the brain. The present invention may also be useful for the treatment of cognitive impairment or dysfunction resulting from brain injuries or neurogenerative disorders.

In another embodiment, of the invention provides a method of treating a PDE9 associated disease or disorder comprising administering to a subject an effective amount of a compound of the invention, e.g., in a pharmaceutical composition of the invention, in combination with a second therapeutic agent suitable to offer advantages of single administration, including for example, improved therapeutic effectiveness and reduction of therapeutic dose of the compound of the invention. In particular embodiments, the methods of the present invention may include an additional step of administering the second therapeutic agent. Compounds of the disclosure may also be used, e.g., in mammals and humans, in conjunction with conventional cognition enhancing or neuroprotective medications including donepezil, rivastigmine, galantamine and memantine. Additional medications could include additional cholinesterase inhibitors, NMDA receptor antagonists, nicotinic agonists (including α7 agonists), muscarinic agonists (including $M_1$ agonists) and 5-$HT_6$ antagonists. The combination of a compound of Formula (I) with a subtherapeutic dose of an aforementioned conventional cognition enhancer or neuroprotective medication may afford certain treatment advantages including improved side effect profiles and lower dosing requirements.

In certain embodiments, the subject has been diagnosed with Alzheimer's disease or pre-Alzheimer's disease. In certain embodiments, the subject has been diagnosed with mild to moderate Alzheimer's disease. In certain embodiments, the subject has been diagnosed with moderate to severe Alzheimer's disease. In certain embodiments, the subject has been diagnosed with schizophrenia or schizoaffective disorder.

In any of the methods described herein, the method may improve one or more facets of cognition impairment, for example, related to Alzheimer's disease, selected from the group consisting of, but not limited to, learning, delayed memory, attention, working memory, visual learning, speed of processing, vigilance, verbal learning, visual motor function, social cognition, long term memory or executive function.

In another embodiment, the methods described herein may be used to treat Alzheimer's disease (AD), also called Alzheimer disease, senile dementia of the Alzheimer type, primary degenerative dementia of the Alzheimer's type, or simply Alzheimer's, which is the most common form of dementia. It is a degenerative disease most often diagnosed in subjects over 65 years old. Without wishing to be bound by theory, the first symptoms of Alzheimer's are often mistaken as related to aging and stress. The early symptoms can affect most daily living activities, including feeding oneself, bathing, dressing, grooming, work, homemaking, leisure activities, and memory loss. This pre-dementia period has also been termed mild Alzheimer's (a term well known in the art), or mild cognitive impairment, and includes subtle problems with executive functions of attentiveness, planning, flexibility, and abstract thinking, as well as impairments in semantic memory. Moderate AD (a term also well known in the art) is characterized by speech difficulties, impairment of reading and writing skills, and complex motor sequences becoming less coordinated making the risk of falling increasingly higher. During moderate AD, memory problems worsen, and the subject may fail to recognize close relatives. Long term memory also becomes impaired. Moderate AD often leads to advanced, or severe AD (both terms well known in the art), where the subject is completely dependent on caregivers. Language is reduced to simple phrases or even single words, eventually leading to complete loss of speech. Despite the loss of verbal language abilities, subjects can often understand and return emotional signals. Although aggressiveness can still be present, extreme apathy and exhaustion are much more common results. Subjects will ultimately not be able to perform even the simplest tasks without assistance. Muscle mass and mobility deteriorate to the point where they are bedridden, and they lose the ability to feed themselves.

In another embodiment, the invention provides a method of inhibiting PDE9 in a subject, wherein the method comprises administering to the subject a therapeutically effective amount of a compound of the invention, e.g., a compound of Formula (I), such that PDE9 is inhibited in the subject.

In an additional embodiment, the compounds of the present invention may be used to improve or enhance PDE9 related function, for example, related to memory and cognition, through modulation of cGMP levels.

In another embodiment, the compounds of the present invention may be used for the treatment of retinal disorders, e.g., retinopathy (e.g., hypertensive retinopathy, diabetic retinopathy, retinopathy of prematurity), retinal detachment and breaks; retinal vascular occlusions; macular degeneration (e.g., age-related macular degeneration); epiretinal membrane; peripheral retinal degeneration; hereditary retinal dystrophy; retinitis pigmentosa; retinal haemorrhage; separation of retinal layers; and macular edema.

B. Methods of Preparation

Certain compounds of the present invention were prepared using novel methods of the invention as shown herein in the schemes and description of the Exemplification section. Such methods are intended to be included with the present invention, including minor variations as would be understood by the skilled artisan, and which would not involve undue experimentation, for example, minor modifications in general reaction controls of temperature, reaction time, and relative amounts of starting materials, as well as minor modifications to any purification, separation, or isolation techniques.

IV. PHARMACEUTICAL COMPOSITIONS OF THE INVENTION

The present invention also provides pharmaceutical compositions for treating a subject having a PDE9 associated disease or disorder.

In one embodiment, the present invention provides a pharmaceutical composition for treating a PDE9 associated disease or disorder comprising a therapeutically effective amount of a compound of the invention, e.g., a compound of Formula (I), or a pharmaceutically acceptable salt thereof, and a pharmaceutically acceptable excipient, carrier or diluent.

The pharmaceutical compositions can be administered in a variety of dosage forms including, but not limited to, a solid dosage form or in a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension or combinations thereof. The dosage can be an oral dosage form that is a controlled release dosage form. The oral dosage form can be a tablet or a caplet. The compounds can be administered, for example, by oral or parenteral routes, including intravenous, intramuscular, intraperitoneal, subcutaneous, transdermal, airway (aerosol), rectal, vaginal and topical (including buccal and sublingual) administration. In one embodiment, the compounds or pharmaceutical compositions comprising the compounds are delivered to a desired site, such as the brain, by continuous injection via a shunt.

In another embodiment, the compound can be administered parenterally, such as intravenous (i.v.) administration. The formulations for administration will commonly comprise a solution of the compound of the Formula (I) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of compound of Formula (I) in these formulations can vary widely, and will be selected primarily based on fluid volumes, viscosities, body weight, and the like, in accordance with the particular mode of administration selected and the patient's needs. For i.v. administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In one embodiment, a compound of Formula (I) can be administered by introduction into the central nervous system of the subject, e.g., into the cerebrospinal fluid of the subject. The formulations for administration will commonly comprise a solution of the compound of Formula (I) dissolved in a pharmaceutically acceptable carrier. In certain aspects, the compound of Formula (I) is introduced intrathecally, e.g., into a cerebral ventricle, the lumbar area, or the cisterna magna. In another aspect, the compound of Formula (I) is introduced intraocularly, to thereby contact retinal ganglion cells.

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

In one embodiment, the pharmaceutical composition comprising a compound of Formula (I) is administered into a subject intrathecally. As used herein, the term "intrathecal administration" is intended to include delivering a pharmaceutical composition comprising a compound of Formula (I) directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a compound of Formula (I) to any of the above mentioned sites can be achieved by direct injection of the pharmaceutical composition comprising the compound of Formula (I) or by the use of infusion pumps. For injection, the pharmaceutical compositions can be formulated in liquid solutions, preferably in physiologically compatible buffers such as Hank's solution or Ringer's solution. In addition, the pharmaceutical compositions may be formulated in solid form and re-dissolved or suspended immediately prior to use. Lyophilized forms are also included. The injection can be, for example, in the form of a bolus injection or continuous infusion (e.g., using infusion pumps) of pharmaceutical composition.

In one embodiment, the pharmaceutical composition comprising a compound of Formula (I) is administered by lateral cerebro ventricular injection into the brain of a subject. The injection can be made, for example, through a burr hole made in the subject's skull. In another embodiment, the encapsulated therapeutic agent is administered through a surgically inserted shunt into the cerebral ventricle of a subject. For example, the injection can be made into the lateral ventricles, which are larger, even though injection into the third and fourth smaller ventricles can also be made.

In yet another embodiment, the pharmaceutical composition is administered by injection into the cisterna magna, or lumbar area of a subject.

For oral administration, the compounds will generally be provided in unit dosage forms of a tablet, pill, dragee, lozenge or capsule; as a powder or granules; or as an aqueous solution, suspension, liquid, gels, syrup, slurry, etc. suitable for ingestion by the patient. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include, but are not limited to, sodium and calcium carbonate, sodium and calcium phosphate, and lactose, while corn starch and alginic acid are suitable disintegrating agents. Binding agents may include, but are not limited to, starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutical preparations for oral use can be obtained through combination of a compound of Formula (I) with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethyl-cellulose or sodium carboxymethyl-cellulose; and gums including arabic and tragacanth, as well as proteins such as gelatin and collagen. If desired, disintegrating or solubilizing agents may be added, such as the cross-linked polyvinyl pyrrolidone, agar, alginic acid, or a salt thereof, such as sodium alginate.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For transmucosal administration (e.g., buccal, rectal, nasal, ocular, etc.), penetrants appropriate to the barrier to be permeated are used in the formulation. Such penetrants are generally known in the art.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing, in addition to the active ingredient, such carriers as are known in the art to be appropriate. For intramuscular, intraperitoneal, subcutaneous and intravenous use, the compounds will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The suppositories for rectal administration of the drug can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds can be delivered transdermally by a topical route, formulated as applicator sticks, solutions, suspensions, emulsions, gels, creams, ointments, pastes, jellies, paints, powders, or aerosols.

The compounds may also be presented as aqueous or liposome formulations. Aqueous suspensions can contain a compound of Formula (I) in admixture with excipients suitable for the manufacture of aqueous suspensions. Such excipients include, but are not limited to, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a compound of Formula (I) in a vegetable oil, such as arachis oil, olive oil, sesame oil or coconut oil, or in a mineral oil such as liquid paraffin, or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g., gelatin for use in an inhaler or insufflator, may be formulated containing a powder mix of the compound and a suitable powder base such as lactose or starch.

In general, a suitable dose will be in the range of 0.001 to 150 mg per kilogram body weight of the recipient per day, e.g., in the range of 0.01 to 100 mg per kilogram body weight of the recipient per day, e.g., in the range of 0.2 to 10 mg per kilogram body weight per day. In a particular embodiment, the desired dose is presented once daily, but may be dosed as two, three, four, five, six or more sub-doses administered at appropriate intervals throughout the day.

The compounds can be administered as the sole active agent, or in combination with other known therapeutics to be beneficial in the treatment of neurological disorders. In any event, the administering physician can provide a method of treatment that is prophylactic or therapeutic by adjusting the amount and timing of drug administration on the basis of observations of one or more symptoms (e.g., motor or cognitive function as measured by standard clinical scales or assessments) of the disorder being treated.

Details on techniques for formulation and administration are well described in the scientific and patent literature, see, e.g., the latest edition of Remington's Pharmaceutical Sciences, Maack Publishing Co, Easton Pa. ("Remington's"). After a pharmaceutical composition has been formulated in an acceptable carrier, it can be placed in an appropriate container and labeled for treatment of an indicated condition. For administration of the compounds of Formula (I), such labeling would include, e.g., instructions concerning the amount, frequency and method of administration.

EXEMPLIFICATION

The present invention is illustrated by the following examples, which are not intended to be limiting in any way.

I. Biological Assays

Example 1

Phosphodiesterase Enzyme Screening Assay

Compounds of the invention were screened against PDE1A, PDE1B, PDE2A, PDE3A, PDE3B, PDE4A1A, PDE4B1, PDE4D3, PDE5A1, PDE6C, PDE7A, PDE8A1, PDE9A2, PDE10A2 AND PDE11A isoforms of the phosphodiesterase enzyme to determine activity and overall selectivity through comparative analysis. The assay generally consists of testing the compounds of the invention at 10 concentrations. Where 8-methoxy-IBMX and Zaprinast were used as reference inhibitors.

Materials and Methods:

The phosphodiesterase enzyme isoforms were obtained from a commercial retailer (Reaction Biology Corporation, Malvern, Pa.) for use in the instant screening assay.

The analysis was completed using the Caliper LabChip 3000 and a 12-sipper LabChip. LabChip assays are separations-based, meaning that the product and substrate are electrophoretically separated, thereby minimizing interferences and yielding the highest data quality available on any screening platform. Z' factors for both the EZ Reader and LC3000 enzymatic assays are routinely in the 0.8 to 0.9 range. High Z' values, few false positives, few false negatives and analytical quality reproducibility are the reasons cited for the increasing reliance on the LabChip assays.

The off-chip incubation mobility-shift phosphodiesterase assay uses a microfluidic chip to measure the conversion of a fluorescent cyclic AMP substrate to a 5'-AMP product, or a cyclic GMP substrate to a 5'-GMP product. The reaction mixture, from a microtiter plate well, is introduced through a capillary sipper onto the chip, where the fluorescent substrate and product are separated by electrophoresis and detected via laser-induced fluorescence. The signature of the fluorescence signal over time reveals the extent of the reaction. The precision of microfluidics allows researchers to detect subtle interactions between drug candidates and therapeutic targets. The technology is able to detect both strong and weak inhibitors with high accuracy, and routinely identifies drug candidates that conventional techniques miss.

EXPERIMENTAL

Reactions were carried out in 100 mM HEPES (pH 7.5), 5 mM $MgCl_2$, 1 mM DTT, 0.003% Brij, 4.0 µM cGMP substrate. The reaction was started by addition of cGMP or cAMP and incubated for 1 hour at R.T. The reaction was terminated by the addition of stop buffer containing 100 mM HEPES (pH 7.5), 15 mM EDTA, 0.015% Brij-35, 5% DMSO. Cyclic AMP/GMP substrate and 5'-AMP/5'-GMP product were separated by charge using electrophoretic mobility shift. Product formed was compared to control wells to determine inhibition or enhancement of enzyme activity.

One or more reference compounds, depending on phosphodiesterase isoform, selected from 8-methoxy-IBMX, Zaprinast, Trequinsin, Pentoxifyline, Rolipram, and Vinpocetine, Dipyridamole, and BRL-50481, were run alongside client samples to ensure data quality. The resulting IC50 is compared against the historical average and must be within 3-fold of this average.

Data points were averages of quadruplicate wells and error bars represented the SEM for each point. IC50s were determined using GraphPad Prism Version 5.01 and the log(inhibitor) vs. response—variable slope curve fit. Selectivity values shown in the table below were made by comparison of IC50 values for the various isoforms, and calculated, for example, as a ratio of the IC50 of PDE9A2 to the IC50 of PDE1A or PDE1B; wherein a value greater than 1 indicates a greater selectivity for PDE9A2.

In some embodiments, the compounds disclosed herein are selected from the group consisting of the compounds described in Tables 1, 2, and 3. Tables 1 and 2 provide certain compounds according to one or more embodiments and their corresponding biological activities. Table 3 provides certain compounds according to one or more embodiments and methods of making thereof, starting materials and reagents used for the methods of making thereof, and biological activities thereof

TABLE 1

| Example name | Band (PDE9A2 $IC_{50}$) | PDE1A selectivity (versus PDE9A2) | PDE1B selectivity (versus PDE9A2) |
|---|---|---|---|
| (−)-2-((3,4-trans)-1-benzyl-4-methylpyrrolidin-3-yl)-7-(tetrahydro-2H-pyran-4-yl)imidazo[1,5-f][1,2,4]triazin-4(3H)-one | A | 465 | 550 |
| (+)-2-((3,4-trans)-1-benzyl-4-methylpyrrolidin-3-yl)-7-(tetrahydro-2H-pyran-4-yl)imidazo[1,5-f][1,2,4]triazin-4(3H)-one | A | 5 | 5 |
| (+)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one | A | 1005 | 1413 |
| (+)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one | A | 232 | 633 |
| (−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one | A | 1110 | 1140 |
| (+)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one | A | 664 | 714 |
| (+)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile | A | 942 | 343 |

TABLE 1-continued

| Example name | Band (PDE9A2 IC$_{50}$) | PDE1A selectivity (versus PDE9A2) | PDE1B selectivity (versus PDE9A2) |
| --- | --- | --- | --- |
| (−)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile | A | 640 | 1445 |
| (+)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one | A | 300 | 442 |
| (+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile | A | 241 | 220 |
| (+)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one | A | 373 | 470 |
| (+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one | A | 621 | 1400 |
| (+)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one | A | 973 | 1360 |
| (−)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one | A | 56 | 48 |
| (+)-7-((1s,3R)-adamantan-1-yl)-2-((3,4-trans)-1-benzyl-4-methylpyrrolidin-3-yl)imidazo[5,1-f][1,2,4]triazin-4(3H)-one | A | — | — |
| (−)-7-((1s,3R)-adamantan-1-yl)-2-((3,4-trans)-1-benzyl-4-methylpyrrolidin-3-yl)imidazo[5,1-f][1,2,4]triazin-4(3H)-one | C | — | — |
| (−)-2-((3,4-trans)-1-benzyl-4-methylpyrrolidin-3-yl)-7-(5-chloro-2-methylphenyl)imidazo[5,1-f][1,2,4]triazin-4(3H)-one | B | — | — |
| (+)-2-((3,4-trans)-1-benzyl-4-methylpyrrolidin-3-yl)-7-(5-chloro-2-methylphenyl)imidazo[5,1-f][1,2,4]triazin-4(3H)-one | A | 276 | 142 |
| (+)-2-((3,4-trans)-1-benzyl-4-methylpyrrolidin-3-yl)-7-(4-fluoro-2-methylphenyl)imidazo[5,1-f][1,2,4]triazin-4(3H)-one | A | 257 | 225 |
| (−)-2-((3,4-trans)-1-benzyl-4-methylpyrrolidin-3-yl)-7-(4-fluoro-2-methylphenyl)imidazo[5,1-f][1,2,4]triazin-4(3H)-one | C | — | — |
| (+)-2-((3,4-trans)-1-benzyl-4-methylpyrrolidin-3-yl)-7-(4,4-difluorocyclohexyl)imidazo[5,1-f][1,2,4]triazin-4(3H)-one | A | 309 | 496 |
| (−)-2-((3,4-trans)-1-benzyl-4-methylpyrrolidin-3-yl)-7-(4,4-difluorocyclohexyl)imidazo[5,1-f][1,2,4]triazin-4(3H)-one | A | — | — |
| (−)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one | A | 1213 | 2000 |
| (−)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one | A | 8 | 12 |
| (−)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one | A | — | — |

TABLE 1-continued

| Example name | Band (PDE9A2 IC$_{50}$) | PDE1A selectivity (versus PDE9A2) | PDE1B selectivity (versus PDE9A2) |
|---|---|---|---|
| (−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one | C | 0 | 0 |
| (+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one | A | 393 | 386 |
| (−)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one | B | — | — |
| (+)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one | A | 202 | 178 |
| (+)-7-((1s,3R)-adamantan-1-yl)-2-((3,4-trans)-4-methyl-1-(pyrimidin-2-ylmethyl)pyrrolidin-3-yl)imidazo[5,1-f][1,2,4]triazin-4(3H)-one | A | — | — |
| 2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 1 | A | 28 | 38 |
| 2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 2 | B | — | — |
| 2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 3 | B | — | — |
| (+)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one | A | 579 | 571 |
| (−)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one | B | — | — |
| (−)-7-(4-fluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one | A | 132 | 175 |
| (+)-7-(4,4-difluorocyclohexyl)-2-((3,4-trans)-4-methyl-1-(pyrimidin-2-ylmethyl)pyrrolidin-3-yl)imidazo[5,1-f][1,2,4]triazin-4(3H)-one | A | 165 | 313 |
| (−)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one | A | — | — |
| (+)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one | A | 51 | 99 |
| (−)-7-(5-chloro-2-methylphenyl)-2-((3,4-trans)-4-methylpyrrolidin-3-yl)imidazo[5,1-f][1,2,4]triazin-4(3H)-one | B | — | — |
| (+)-2-((3,4-trans)-1-benzyl-4-methylpyrrolidin-3-yl)-7-(furan-3-yl)imidazo[5,1-f][1,2,4]triazin-4(3H)-one | A | 81 | 80 |
| (−)-2-((3,4-trans)-1-benzyl-4-methylpyrrolidin-3-yl)-7-(furan-3-yl)imidazo[5,1-f][1,2,4]triazin-4(3H)-one | B | — | — |
| (−)-7-(1-acetylpiperidin-4-yl)-2-((3,4-trans)-1-benzyl-4-methylpyrrolidin-3-yl)imidazo[5,1-f][1,2,4]triazin-4(3H)-one | C | — | — |

TABLE 1-continued

| Example name | Band (PDE9A2 IC$_{50}$) | PDE1A selectivity (versus PDE9A2) | PDE1B selectivity (versus PDE9A2) |
|---|---|---|---|
| (+)-7-(1-acetylpiperidin-4-yl)-2-((3,4-trans)-1-benzyl-4-methylpyrrolidin-3-yl)imidazo[5,1-f][1,2,4]triazin-4(3H)-one | A | 177 | 232 |
| (−)-2-((3,4-trans)-1-benzyl-4-methylpyrrolidin-3-yl)-7-(2-hydroxypropan-2-yl)imidazo[5,1-f][1,2,4]triazin-4(3H)-one | C | — | — |
| (+)-2-((3,4-trans)-1-benzyl-4-methylpyrrolidin-3-yl)-7-(2-hydroxypropan-2-yl)imidazo[5,1-f][1,2,4]triazin-4(3H)-one | B | — | — |
| (+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one | A | — | — |
| (−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one | C | — | — |
| (−)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one | C | — | — |
| (+)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one | B | — | — |
| (+)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one | B | — | — |
| (−)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one | C | — | — |
| (−)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one[furan-(−)-isomer] fraction 1 | B | — | — |
| (−)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one[furan-(−)-isomer] fraction 2 | C | — | — |
| (−)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate | C | — | — |
| (+)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate | B | — | — |
| (+)-2-((3,4-trans)-1-benzyl-4-methylpyrrolidin-3-yl)-7-(5-fluoro-2-methylphenyl)imidazo[1,5-f][1,2,4]triazin-4(3H)-one | A | 247 | 109 |
| (−)-2-((3,4-trans)-1-benzyl-4-methylpyrrolidin-3-yl)-7-(5-fluoro-2-methylphenyl)imidazo[1,5-f][1,2,4]triazin-4(3H)-one | B | — | — |
| (+)-7-(5-fluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one | A | 158 | 102 |
| (−)-7-(5-fluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one | B | — | — |
| (−)-2-((3,4-trans)-1-benzyl-4-methylpyrrolidin-3-yl)-7-(piperidin-4-yl)imidazo[1,5-f][1,2,4]triazin-4(3H)-one[piperidine NH fraction 1] | C | — | — |

TABLE 1-continued

| Example name | Band (PDE9A2 IC$_{50}$) | PDE1A selectivity (versus PDE9A2) | PDE1B selectivity (versus PDE9A2) |
|---|---|---|---|
| (+)-2-((3,4-trans)-1-benzyl-4-methylpyrrolidin-3-yl)-7-(piperidin-4-yl)imidazo[1,5-f][1,2,4]triazin-4(3H)-one[piperidine NH fraction 2] | B | — | — |
| (+)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one[furan-(+)-isomer] fraction 1 | A | — | — |
| (+)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one[furan-(+)-isomer] fraction 2 | A | 28 | 58 |
| (−)-2-(1-(3,4-trans)-benzyl-4-methylpyrrolidin-3-yl)-7-(tetrahydrofuran-3-yl)imidazo[5,1-f][1,2,4]triazin-4(3H)-one[furan-(−)-isomer] fraction 1 | B | — | — |
| (−)-2-(1-(3,4-trans)-benzyl-4-methylpyrrolidin-3-yl)-7-(tetrahydrofuran-3-yl)imidazo[5,1-f][1,2,4]triazin-4(3H)-one [furan-(−)-isomer] fraction 2 | B | — | — |
| (−)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile | A | — | — |
| (+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile | A | — | — |
| (−)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one | A | — | — |
| (−)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one | A | — | — |
| (−)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one | A | — | — |
| (−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one | A | — | — |
| (−)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one | A | — | — |
| (−)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile | A | — | — |
| (−)-2-((3,4-trans)-1-benzyl-4-methylpyrrolidin-3-yl)-7-(furan-3-yl)imidazo[5,1-f][1,2,4]triazin-4(3H)-one [furan-(+)-isomer] fraction 1 | A | 162 | 263 |
| (+)-2-((3,4-trans)-1-benzyl-4-methylpyrrolidin-3-yl)-7-(furan-3-yl)imidazo[5,1-f][1,2,4]triazin-4(3H)-one [furan-(+)-isomer] fraction 2 | A | — | — |
| 2-((3,4-trans)-1-benzyl-4-methylpyrrolidin-3-yl)-7-(1-methylpiperidin-4-yl)imidazo[5,1-f][1,2,4]triazin-4(3H)-one [from piperidine NH fraction 1] | B | — | — |
| 2-((3,4-trans)-1-benzyl-4-methylpyrrolidin-3-yl)-7-(1-methylpiperidin-4-yl)imidazo[5,1-f][1,2,4]triazin-4(3H)-one [from piperidine NH fraction 2]: | B | — | — |

TABLE 1-continued

| Example name | Band (PDE9A2 IC$_{50}$) | PDE1A selectivity (versus PDE9A2) | PDE1B selectivity (versus PDE9A2) |
|---|---|---|---|
| (+)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one | B | — | — |
| (−)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one | A | — | — |
| (+)-2-((3,4-trans)-4-methyl-1-(4-(trifluoromethyl)benzyl)pyrrolidin-3-yl)-7-(tetrahydro-2H-pyran-4-yl)imidazo[5,1-f][1,2,4]triazin-4(3H)-one | A | 109 | 122 |
| (+)-2-((3,4-trans)-4-methyl-1-(3-(trifluoromethyl)benzyl)pyrrolidin-3-yl)-7-(tetrahydro-2H-pyran-4-yl)imidazo[5,1-f][1,2,4]triazin-4(3H)-one | A | 203 | 86 |
| (+)-2-((3,4-trans)-1-(3-chlorobenzyl)-4-methylpyrrolidin-3-yl)-7-(tetrahydro-2H-pyran-4-yl)imidazo[5,1-f][1,2,4]triazin-4(3H)-one | A | 470 | 331 |
| (+)-2-((3,4-trans)-1-(2,4-difluorobenzyl)-4-methylpyrrolidin-3-yl)-7-(tetrahydro-2H-pyran-4-yl)imidazo[5,1-f][1,2,4]triazin-4(3H)-one | A | 271 | 579 |
| (+)-2-((3,4-trans)-4-methyl-1-(2-(trifluoromethyl)benzyl)pyrrolidin-3-yl)-7-(tetrahydro-2H-pyran-4-yl)imidazo[5,1-f][1,2,4]triazin-4(3H)-one | A | 73 | 16 |
| (+)-2-((3,4-trans)-1-(2-fluoro-5-methoxybenzyl)-4-methylpyrrolidin-3-yl)-7-(tetrahydro-2H-pyran-4-yl)imidazo[5,1-f][1,2,4]triazin-4(3H)-one | A | 340 | 255 |
| (+)-2-((3,4-trans)-1-(isoquinolin-7-ylmethyl)-4-methylpyrrolidin-3-yl)-7-(tetrahydro-2H-pyran-4-yl) imidazo [5,1-f][1,2,4] triazin-4(3H)-one | A | 223 | 893 |
| (+)-2-((3,4-trans)-4-methyl-1-(quinolin-6-ylmethyl)pyrrolidin-3-yl)-7-(tetrahydro-2H-pyran-4-yl)imidazo[5,1-f][1,2,4]triazin-4(3H)-one | A | 520 | 1525 |
| (+)-2-((3,4-trans)-1-(2-chlorobenzyl)-4-methylpyrrolidin-3-yl)-7-(tetrahydro-2H-pyran-4-yl)imidazo[5,1-f][1,2,4]triazin-4(3H)-one | A | 92 | 48 |
| (+)-2-((3,4-trans)-1-(4-chlorobenzyl)-4-methylpyrrolidin-3-yl)-7-(tetrahydro-2H-pyran-4-yl)imidazo[5,1-f][1,2,4]triazin-4(3H)-one | A | 193 | 491 |
| (+)-2-((3,4-trans)-1-(2,5-difluorobenzyl)-4-methylpyrrolidin-3-yl)-7-(tetrahydro-2H-pyran-4-yl)imidazo[5,1-f][1,2,4]triazin-4(3H)-one | A | 97 | 118 |
| (+)-2-((3,4-trans)-1-(2,3-difluorobenzyl)-4-methylpyrrolidin-3-yl)-7-(tetrahydro-2H-pyran-4-yl)imidazo[5,1-f][1,2,4]triazin-4(3H)-one | A | 159 | 218 |
| (+)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one | A | 84 | 119 |
| (+)-2-((3,4-trans)-4-methyl-1-(pyridin-4-ylmethyl)pyrrolidin-3-yl)-7-(tetrahydro-2H-pyran-4-yl)imidazo[5,1-f][1,2,4]triazin-4(3H)-one | A | 156 | 321 |
| (+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one | A | 238 | 193 |

TABLE 1-continued

| Example name | Band (PDE9A2 IC$_{50}$) | PDE1A selectivity (versus PDE9A2) | PDE1B selectivity (versus PDE9A2) |
|---|---|---|---|
| (+)-2-((3,4-trans)-1-(isoquinolin-6-ylmethyl)-4-methylpyrrolidin-3-yl)-7-(tetrahydro-2H-pyran-4-yl)imidazo[5,1-f][1,2,4]triazin-4(3H)-one | A | 145 | 335 |
| (−)-2-((3,4-trans)-4-methyl-1-(quinolin-7-ylmethyl)pyrrolidin-3-yl)-7-(tetrahydro-2H-pyran-4-yl)imidazo[5,1-f][1,2,4]triazin-4(3H)-one | A | 334 | 2610 |
| (+)-2-((3,4-trans)-4-methyl-1-((2-oxo-1,2-dihydropyridin-3-yl)methyl)pyrrolidin-3-yl)-7-(tetrahydro-2H-pyran-4-yl)imidazo[5,1-f][1,2,4]triazin-4(3H)-one | A | 424 | 940 |
| (+)-2-((3,4-trans)-4-methyl-1-(pyridazin-3-ylmethyl)pyrrolidin-3-yl)-7-(tetrahydro-2H-pyran-4-yl)imidazo[5,1-f][1,2,4]triazin-4(3H)-one | A | 182 | 276 |
| (+)-2-((3,4-trans)-4-methyl-1-(pyridazin-4-ylmethyl)pyrrolidin-3-yl)-7-(tetrahydro-2H-pyran-4-yl)imidazo[5,1-f][1,2,4]triazin-4(3H)-one | A | 71 | 99 |
| (+)-2-((3,4-trans)-4-methyl-1-(quinazolin-6-ylmethyl)pyrrolidin-3-yl)-7-(tetrahydro-2H-pyran-4-yl)imidazo[5,1-f][1,2,4]triazin-4(3H)-one | A | 890 | 1067 |
| (+)-2-((3,4-trans)-4-methyl-1-(quinoxalin-6-ylmethyl)pyrrolidin-3-yl)-7-(tetrahydro-2H-pyran-4-yl)imidazo[5,1-f][1,2,4]triazin-4(3H)-one | A | 459 | 815 |
| (+)-2-((3,4-trans)-4-methyl-1-(quinoxalin-2-ylmethyl)pyrrolidin-3-yl)-7-(tetrahydro-2H-pyran-4-yl)imidazo[5,1-f][1,2,4]triazin-4(3H)-one | A | 453 | 1130 |
| (+)-2-((3,4-trans)-4-methyl-1-((1-methyl-1H-benzo[d]imidazol-2-yl)methyl)pyrrolidin-3-yl)-7-(tetrahydro-2H-pyran-4-yl)imidazo[5,1-f][1,2,4]triazin-4(3H)-one | A | 181 | 356 |
| (−)-2-((3,4-trans)-1-((1H-benzo[d]imidazol-2-yl)methyl)-4-methylpyrrolidin-3-yl)-7-(tetrahydro-2H-pyran-4-yl)imidazo[5,1-f][1,2,4]triazin-4(3H)-one | A | 433 | 540 |
| (+)-2-((3,4-trans)-1-(imidazo[1,2-a]pyridin-2-ylmethyl)-4-methylpyrrolidin-3-yl)-7-(tetrahydro-2H-pyran-4-yl)imidazo[5,1-f][1,2,4]triazin-4(3H)-one | A | 754 | 734 |
| (−)-2-((3,4-trans)-1-benzoyl-4-methylpyrrolidin-3-yl)-7-(tetrahydro-2H-pyran-4-yl)imidazo[5,1-f][1,2,4]triazin-4(3H)-one | A | 26 | 32 |
| (−)-2-((3,4-trans)-1-(2-fluorobenzoyl)-4-methylpyrrolidin-3-yl)-7-(tetrahydro-2H-pyran-4-yl)imidazo[5,1-f][1,2,4]triazin-4(3H)-one | A | 9 | 7 |
| (−)-2-((3,4-trans)-1-(3-fluorobenzoyl)-4-methylpyrrolidin-3-yl)-7-(tetrahydro-2H-pyran-4-yl)imidazo[5,1-f][1,2,4]triazin-4(3H)-one | A | 26 | 26 |
| (−)-2-((3,4-trans)-1-(4-fluorobenzoyl)-4-methylpyrrolidin-3-yl)-7-(tetrahydro-2H-pyran-4-yl)imidazo[5,1-f][1,2,4]triazin-4(3H)-one | A | 12 | 23 |
| (−)-2-((3,4-trans)-4-methyl-1-nicotinoylpyrrolidin-3-yl)-7-(tetrahydro-2H-pyran-4-yl)imidazo[5,1-f][1,2,4]triazin-4(3H)-one | A | 36 | 50 |
| (+)-2-((3,4-trans)-1-(4-fluorobenzoyl)-4-methylpyrrolidin-3-yl)-7-(tetrahydro-2H-pyran-4-yl)imidazo[5,1-f][1,2,4]triazin-4(3H)-one | B | — | — |

TABLE 1-continued

| Example name | Band (PDE9A2 IC$_{50}$) | PDE1A selectivity (versus PDE9A2) | PDE1B selectivity (versus PDE9A2) |
|---|---|---|---|
| (+)-2-((3,4-trans)-1-benzoyl-4-methylpyrrolidin-3-yl)-7-(tetrahydro-2H-pyran-4-yl)imidazo[5,1-f][1,2,4]triazin-4(3H)-one | B | — | — |
| (+)-2-((3,4-trans)-4-methyl-1-(pyridin-3-ylmethyl)pyrrolidin-3-yl)-7-(tetrahydro-2H-pyran-4-yl)imidazo[5,1-f][1,2,4]triazin-4(3H)-one | A | 542 | 666 |
| (+)-2-((3,4-trans)-4-methyl-1-((2-methylpyrimidin-4-yl)methyl)pyrrolidin-3-yl)-7-(tetrahydro-2H-pyran-4-yl)imidazo[5,1-f][1,2,4]triazin-4(3H)-one | A | 184 | 400 |
| (+)-2-((3,4-trans)-4-methyl-1-(pyrimidin-4-ylmethyl)pyrrolidin-3-yl)-7-(tetrahydro-2H-pyran-4-yl)imidazo[5,1-f][1,2,4]triazin-4(3H)-one | A | 136 | 174 |
| (−)-2-((3,4-trans)-1-(imidazo[1,2-a]pyrimidin-2-ylmethyl)-4-methylpyrrolidin-3-yl)-7-(tetrahydro-2H-pyran-4-yl)imidazo[5,1-f][1,2,4]triazin-4(3H)-one | A | 188 | 591 |
| (+)-2-((3,4-trans)-1-([1,2,4]triazolo[1,5-a]pyridin-2-ylmethyl)-4-methylpyrrolidin-3-yl)-7-(tetrahydro-2H-pyran-4-yl)imidazo[5,1-f][1,2,4]triazin-4(3H)-one | A | 563 | 457 |
| (+)-2-((3,4-trans)-4-methyl-1-(phenylsulfonyl)pyrrolidin-3-yl)-7-(tetrahydro-2H-pyran-4-yl)imidazo[5,1-f][1,2,4]triazin-4(3H)-one | A | — | — |
| (+)-2-((3,4-trans)-1-((2-fluorophenyl)sulfonyl)-4-methylpyrrolidin-3-yl)-7-(tetrahydro-2H-pyran-4-yl)imidazo[5,1-f][1,2,4]triazin-4(3H)-one | A | — | — |
| (+)-2-((3,4-trans)-1-((4-fluorophenyl)sulfonyl)-4-methylpyrrolidin-3-yl)-7-(tetrahydro-2H-pyran-4-yl)imidazo[5,1-f][1,2,4]triazin-4(3H)-one | A | — | — |
| (−)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile | A | — | — |
| (−)-2-((3,4-trans)-4-methyl-1-(phenylsulfonyl)pyrrolidin-3-yl)-7-(tetrahydro-2H-pyran-4-yl)imidazo[5,1-f][1,2,4]triazin-4(3H)-one | B | — | — |
| (−)-2-((3,4-trans)-1-((4-fluorophenyl)sulfonyl)-4-methylpyrrolidin-3-yl)-7-(tetrahydro-2H-pyran-4-yl)imidazo[5,1-f][1,2,4]triazin-4(3H)-one | B | — | — |
| (+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile | B | — | — |
| (+)-2-((3,4-trans)-4-methyl-1-(pyrimidin-5-ylmethyl)pyrrolidin-3-yl)-7-(tetrahydro-2H-pyran-4-yl)imidazo[5,1-f][1,2,4]triazin-4(3H)-one | A | 331 | 545 |
| (−)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile | A | — | — |
| (+)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile | B | — | — |
| (−)-2-((3,4-trans)-4-methyl-1-(pyrimidine-2-carbonyl)pyrrolidin-3-yl)-7-(tetrahydro-2H-pyran-4-yl)imidazo[5,1-f][1,2,4]triazin-4(3H)-one | A | — | — |

TABLE 1-continued

| Example name | Band (PDE9A2 IC$_{50}$) | PDE1A selectivity (versus PDE9A2) | PDE1B selectivity (versus PDE9A2) |
|---|---|---|---|
| (+)-2-((3,4-trans)-4-methyl-1-(pyrimidine-2-carbonyl)pyrrolidin-3-yl)-7-(tetrahydro-2H-pyran-4-yl)imidazo[5,1-f][1,2,4]triazin-4(3H)-one | B | — | — |
| (−)-2-((3,4-trans)-1-isonicotinoyl-4-methylpyrrolidin-3-yl)-7-(tetrahydro-2H-pyran-4-yl)imidazo[5,1-f][1,2,4]triazin-4(3H)-one | A | — | — |
| (−)-4-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile | A | 14 | 21 |
| (−)-2-((3,4-trans)-4-methyl-1-(pyrimidine-5-carbonyl)pyrrolidin-3-yl)-7-(tetrahydro-2H-pyran-4-yl)imidazo[5,1-f][1,2,4]triazin-4(3H)-one | A | — | — |
| (−)-2-((3,4-trans)-4-methyl-1-(pyrazine-2-carbonyl)pyrrolidin-3-yl)-7-(tetrahydro-2H-pyran-4-yl)imidazo[5,1-f][1,2,4]triazin-4(3H)-one | A | — | — |
| (+)-2-((3,4-trans)-1-((3-fluorophenyl)sulfonyl)-4-methylpyrrolidin-3-yl)-7-(tetrahydro-2H-pyran-4-yl)imidazo[5,1-f][1,2,4]triazin-4(3H)-one | A | — | — |
| (+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile | C | — | — |
| (+)-2-((3,4-trans)-4-methyl-1-(quinolin-7-ylmethyl)pyrrolidin-3-yl)-7-(tetrahydro-2H-pyran-4-yl)imidazo[5,1-f][1,2,4]triazin-4(3H)-one | A | 5020 | 5180 |
| (−)-2-((3,4-trans)-4-methyl-1-picolinoylpyrrolidin-3-yl)-7-(tetrahydro-2H-pyran-4-yl)imidazo[5,1-f][1,2,4]triazin-4(3H)-one | A | — | — |
| (−)-2-((3,4-trans)-4-methyl-1-(quinoline-2-carbonyl)pyrrolidin-3-yl)-7-(tetrahydro-2H-pyran-4-yl)imidazo[5,1-f][1,2,4]triazin-4(3H)-one | A | 25 | 59 |
| (−)-2-((3,4-trans)-4-methyl-1-(pyrimidine-4-carbonyl)pyrrolidin-3-yl)-7-(tetrahydro-2H-pyran-4-yl)imidazo[5,1-f][1,2,4]triazin-4(3H)-one | A | — | — |
| (+)-2-((3,4-trans)-4-methyl-1-(pyridin-3-ylsulfonyl)pyrrolidin-3-yl)-7-(tetrahydro-2H-pyran-4-yl)imidazo[5,1-f][1,2,4]triazin-4(3H)-one | A | — | — |
| (+)-2-((3,4-trans)-1-(2-methoxybenzyl)-4-methylpyrrolidin-3-yl)-7-(tetrahydro-2H-pyran-4-yl)imidazo[5,1-f][1,2,4]triazin-4(3H)-one | A | 337 | 230 |
| (+)-2-((3,4-trans)-1-(3-methoxybenzyl)-4-methylpyrrolidin-3-yl)-7-(tetrahydro-2H-pyran-4-yl)imidazo[5,1-f][1,2,4]triazin-4(3H)-one | A | 1347 | 477 |
| (+)-2-((3,4-trans)-1-(4-methoxybenzyl)-4-methylpyrrolidin-3-yl)-7-(tetrahydro-2H-pyran-4-yl)imidazo[5,1-f][1,2,4]triazin-4(3H)-one | A | 539 | 409 |
| (−)-2-((3,4-trans)-4-methyl-1-(quinazoline-2-carbonyl)pyrrolidin-3-yl)-7-(tetrahydro-2H-pyran-4-yl)imidazo[5,1-f][1,2,4]triazin-4(3H)-one | A | 32 | 50 |
| (+)-2-((3,4-trans)-4-methyl-1-(2-methylbenzyl)pyrrolidin-3-yl)-7-(tetrahydro-2H-pyran-4-yl)imidazo[5,1-f][1,2,4]triazin-4(3H)-one | A | 249 | 105 |

TABLE 1-continued

| Example name | Band (PDE9A2 IC$_{50}$) | PDE1A selectivity (versus PDE9A2) | PDE1B selectivity (versus PDE9A2) |
|---|---|---|---|
| (+)-2-((3,4-trans)-4-methyl-1-(3-methylbenzyl)pyrrolidin-3-yl)-7-(tetrahydro-2H-pyran-4-yl)imidazo[5,1-f][1,2,4]triazin-4(3H)-one | A | 442 | 402 |
| (+)-2-((3,4-trans)-4-methyl-1-(4-methylbenzyl)pyrrolidin-3-yl)-7-(tetrahydro-2H-pyran-4-yl)imidazo[5,1-f][1,2,4]triazin-4(3H)-one | A | 288 | 365 |
| (−)-2-((3,4-trans)-1-(ethylsulfonyl)-4-methylpyrrolidin-3-yl)-7-(tetrahydro-2H-pyran-4-yl)imidazo[5,1-f][1,2,4]triazin-4(3H)-one | A | — | — |
| (+)-2-((3,4-trans)-1-(ethylsulfonyl)-4-methylpyrrolidin-3-yl)-7-(tetrahydro-2H-pyran-4-yl)imidazo[5,1-f][1,2,4]triazin-4(3H)-one | B | — | — |
| (−)-2-((3,4-trans)-1-(cyclohexylmethyl)-4-methylpyrrolidin-3-yl)-7-(tetrahydro-2H-pyran-4-yl)imidazo[5,1-f][1,2,4]triazin-4(3H)-one | A | 65 | 52 |
| (−)-2-((3,4-trans)-4-methyl-1-(4-(pyrrolidin-1-yl)benzyl)pyrrolidin-3-yl)-7-(tetrahydro-2H-pyran-4-yl)imidazo[5,1-f][1,2,4]triazin-4(3H)-one | A | 365 | 552 |
| (+)-2-((3,4-trans)-4-methyl-1-(2-(pyrrolidin-1-yl)benzyl)pyrrolidin-3-yl)-7-(tetrahydro-2H-pyran-4-yl)imidazo[5,1-f][1,2,4]triazin-4(3H)-one | A | 184 | 213 |
| (+)-2-((3,4-trans)-1-(2-(dimethylamino)benzyl)-4-methylpyrrolidin-3-yl)-7-(tetrahydro-2H-pyran-4-yl)imidazo[5,1-f][1,2,4]triazin-4(3H)-one | A | 363 | 279 |
| (+)-2-((3,4-trans)-1-(3-(dimethylamino)benzyl)-4-methylpyrrolidin-3-yl)-7-(tetrahydro-2H-pyran-4-yl)imidazo[5,1-f][1,2,4]triazin-4(3H)-one | A | 680 | 923 |
| (+)-2-((3,4-trans)-1-(4-(dimethylamino)benzyl)-4-methylpyrrolidin-3-yl)-7-(tetrahydro-2H-pyran-4-yl)imidazo[5,1-f][1,2,4]triazin-4(3H)-one | A | 209 | 465 |
| (+)-2-((3,4-trans)-4-methyl-1-phenethylpyrrolidin-3-yl)-7-(tetrahydro-2H-pyran-4-yl)imidazo[5,1-f][1,2,4]triazin-4(3H)-one | A | 28 | 23 |
| (+)-2-((3,4-trans)-1-((6-methoxypyridin-3-yl)methyl)-4-methylpyrrolidin-3-yl)-7-(tetrahydro-2H-pyran-4-yl)imidazo[5,1-f][1,2,4]triazin-4(3H)-one | A | 215 | 515 |
| (+)-2-((3,4-trans)-4-methyl-1-(pyrimidin-2-yl)pyrrolidin-3-yl)-7-(tetrahydro-2H-pyran-4-yl)imidazo[5,1-f][1,2,4]triazin-4(3H)-one | A | 1 | 1 |
| (+)-2-((3,4-trans)-1-(2,6-difluorobenzyl)-4-methylpyrrolidin-3-yl)-7-(tetrahydro-2H-pyran-4-yl)imidazo[5,1-f][1,2,4]triazin-4(3H)-one | A | 56 | 83 |
| (+)-2-((3,4-trans)-1-(3-cyclopropylbenzyl)-4-methylpyrrolidin-3-yl)-7-(tetrahydro-2H-pyran-4-yl)imidazo[5,1-f][1,2,4]triazin-4(3H)-one | A | 703 | 903 |
| (+)-2-((3,4-trans)-1-(4-cyclopropylbenzyl)-4-methylpyrrolidin-3-yl)-7-(tetrahydro-2H-pyran-4-yl)imidazo[5,1-f][1,2,4]triazin-4(3H)-one | A | 260 | 605 |
| (+)-((3,4-trans)-1,4-dimethylpyrrolidin-3-yl)-7-(tetrahydro-2H-pyran-4-yl)imidazo[5,1-f][1,2,4]triazin-4(3H)-one | A | 75 | 121 |

TABLE 1-continued

| Example name | Band (PDE9A2 IC$_{50}$) | PDE1A selectivity (versus PDE9A2) | PDE1B selectivity (versus PDE9A2) |
|---|---|---|---|
| (−)-2-((3,4-trans)-1-(2-cyclopropylbenzyl)-4-methylpyrrolidin-3-yl)-7-(tetrahydro-2H-pyran-4-yl)imidazo[5,1-f][1,2,4]triazin-4(3H)-one | A | 685 | 505 |
| (+)-2-((3,4-trans)-1-(3-(1H-pyrazol-1-yl)benzyl)-4-methylpyrrolidin-3-yl)-7-(tetrahydro-2H-pyran-4-yl)imidazo[5,1-f][1,2,4]triazin-4(3H)-one | A | 612 | 1490 |
| (+)-2-((3,4-trans)-4-methyl-1-(quinolin-4-ylmethyl)pyrrolidin-3-yl)-7-(tetrahydro-2H-pyran-4-yl)imidazo[5,1-f][1,2,4]triazin-4(3H)-one | A | 471 | 987 |
| (+)-2-((3,4-trans)-1-((1,3-dimethyl-1H-pyrazol-5-yl)methyl)-4-methylpyrrolidin-3-yl)-7-(tetrahydro-2H-pyran-4-yl)imidazo[5,1-f][1,2,4]triazin-4(3H)-one | A | 487 | 670 |
| (+)-2-((3,4-trans)-4-methyl-1-((2-methylpyrimidin-5-yl)methyl)pyrrolidin-3-yl)-7-(tetrahydro-2H-pyran-4-yl)imidazo[5,1-f][1,2,4]triazin-4(3H)-one | A | 80 | 60 |
| (+)-2-((3,4-trans)-4-methyl-1-((2-methylthiazol-5-yl)methyl)pyrrolidin-3-yl)-7-(tetrahydro-2H-pyran-4-yl)imidazo[5,1-f][1,2,4]triazin-4(3H)-one | A | 129 | 243 |
| (+)-2-((3,4-trans)-4-methyl-1-((6-methylpyridin-3-yl)methyl)pyrrolidin-3-yl)-7-(tetrahydro-2H-pyran-4-yl)imidazo[5,1-f][1,2,4]triazin-4(3H)-one | A | 97 | 177 |
| (+)-2-((3,4-trans)-4-methyl-1-((5-methylpyrazin-2-yl)methyl)pyrrolidin-3-yl)-7-(tetrahydro-2H-pyran-4-yl)imidazo[5,1-f][1,2,4]triazin-4(3H)-one | A | 63 | 117 |
| (+)-2-((3,4-trans)-4-methyl-1-((5-methylpyrazin-2-yl)methyl)pyrrolidin-3-yl)-7-(tetrahydro-2H-pyran-4-yl)imidazo[5,1-f][1,2,4]triazin-4(3H)-one | A | 191 | 463 |
| (+)-2-((3,4-trans)-4-methyl-1-(3-(pyrrolidin-1-yl)benzyl)pyrrolidin-3-yl)-7-(tetrahydro-2H-pyran-4-yl)imidazo[5,1-f][1,2,4]triazin-4(3H)-one | A | 700 | 1190 |
| (+)-2-((3,4-trans)-4-methyl-1-((6-(trifluoromethyl)pyridin-3-yl)methyl)pyrrolidin-3-yl)-7-(tetrahydro-2H-pyran-4-yl)imidazo[5,1-f][1,2,4]triazin-4(3H)-one | A | 333 | 980 |
| (+)-2-((3,4-trans)-1-((2-ethylpyrimidin-5-yl)methyl)-4-methylpyrrolidin-3-yl)-7-(tetrahydro-2H-pyran-4-yl)imidazo[5,1-f][1,2,4]triazin-4(3H)-one | A | 855 | 1920 |
| (+)-2-((3,4-trans)-1-(3-bromobenzyl)-4-methylpyrrolidin-3-yl)-7-(tetrahydro-2H-pyran-4-yl)imidazo[5,1-f][1,2,4]triazin-4(3H)-one | A | 243 | 92 |
| (+)-2-((3,4-trans)-1-(2,4-dichlorobenzyl)-4-methylpyrrolidin-3-yl)-7-(tetrahydro-2H-pyran-4-yl)imidazo[5,1-f][1,2,4]triazin-4(3H)-one | A | 598 | 994 |
| (+)-2-((3,4-trans)-1-(4-bromobenzyl)-4-methylpyrrolidin-3-yl)-7-(tetrahydro-2H-pyran-4-yl)imidazo[5,1-f][1,2,4]triazin-4(3H)-one | A | 476 | 1105 |
| (+)-2-((3,4-trans)-1-(3,5-dichlorobenzyl)-4-methylpyrrolidin-3-yl)-7-(tetrahydro-2H-pyran-4-yl)imidazo[5,1-f][1,2,4]triazin-4(3H)-one | A | 93 | 92 |

TABLE 1-continued

| Example name | Band (PDE9A2 IC$_{50}$) | PDE1A selectivity (versus PDE9A2) | PDE1B selectivity (versus PDE9A2) |
|---|---|---|---|
| (+)-2-((3,4-trans)-4-methyl-1-(3-(trifluoromethoxy)benzyl)pyrrolidin-3-yl)-7-(tetrahydro-2H-pyran-4-yl)imidazo[5,1-f][1,2,4]triazin-4(3H)-one | A | 261 | 99 |
| (+)-2-((3,4-trans)-1-(2-chloro-4-fluorobenzyl)-4-methylpyrrolidin-3-yl)-7-(tetrahydro-2H-pyran-4-yl)imidazo[5,1-f][1,2,4]triazin-4(3H)-one | A | 75 | 75 |
| (+)-2-((3,4-trans)-1-(2-bromobenzyl)-4-methylpyrrolidin-3-yl)-7-(tetrahydro-2H-pyran-4-yl)imidazo[5,1-f][1,2,4]triazin-4(3H)-one | A | 104 | 28 |
| (+)-2-((3,4-trans)-1-([1,2,4]triazolo[1,5-a]pyridin-2-ylmethyl)-4-methylpyrrolidin-3-yl)-7-(4,4-difluorocyclohexyl)imidazo[5,1-f][1,2,4]triazin-4(3H)-one | A | 597 | 1847 |
| (+)-2-((3,4-trans)-1-(4-chloro-3-fluorobenzyl)-4-methylpyrrolidin-3-yl)-7-(tetrahydro-2H-pyran-4-yl)imidazo[5,1-f][1,2,4]triazin-4(3H)-one | A | 3575 | 6575 |
| (+)-2-((3,4-trans)-4-methyl-1-(4-(trifluoromethoxy)benzyl)pyrrolidin-3-yl)-7-(tetrahydro-2H-pyran-4-yl)imidazo[5,1-f][1,2,4]triazin-4(3H)-one | A | 2063 | 4067 |
| (+)-2-((3,4-trans)-1-(4-fluoro-3-(trifluoromethyl)benzyl)-4-methylpyrrolidin-3-yl)-7-(tetrahydro-2H-pyran-4-yl)imidazo[5,1-f][1,2,4]triazin-4(3H)-one | A | 1687 | 1097 |
| (+)-2-((3,4-trans)-1-(2,5-dichlorobenzyl)-4-methylpyrrolidin-3-yl)-7-(tetrahydro-2H-pyran-4-yl)imidazo[5,1-f][1,2,4]triazin-4(3H)-one | A | 274 | 90 |
| (+)-2-((3,4-trans)-1-(3,5-difluorobenzyl)-4-methylpyrrolidin-3-yl)-7-(tetrahydro-2H-pyran-4-yl)imidazo[1,5-f][1,2,4]triazin-4(3H)-one | A | 1710 | 1043 |
| (+)-2-((3,4-trans)-1-(3,4-dichlorobenzyl)-4-methylpyrrolidin-3-yl)-7-(tetrahydro-2H-pyran-4-yl)imidazo[1,5-f][1,2,4]triazin-4(3H)-one | A | 1297 | 2627 |
| (+)-(4,4-difluorocyclohexyl)-2-((3,4-trans)-1-(4-fluorobenzyl)-4-methylpyrrolidin-3-yl)imidazo[5,1-f][1,2,4]triazin-4(3H)-one | A | 1453 | 2980 |
| (+)-2-((3,4-trans)-1-(4-chlorobenzyl)-4-methylpyrrolidin-3-yl)-7-(4,4-difluorocyclohexyl)imidazo[5,1-f][1,2,4]triazin-4(3H)-one | A | 595 | 1210 |

A <1 μM
B 1 μM-10 μM
C >10 μM
N/A Not Available

TABLE 2

| Example name | Band (PDE9A2 IC$_{50}$) | PDE1A selectivity (versus PDE9A2) | PDE1B selectivity (versus PDE9A2) |
|---|---|---|---|
| (+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)pyrimidine-5-carbonitrile | A | 22 | 65 |

TABLE 2-continued

| Example name | Band (PDE9A2 IC$_{50}$) | PDE1A selectivity (versus PDE9A2) | PDE1B selectivity (versus PDE9A2) |
|---|---|---|---|
| (+)-2-((3,4-trans)-1-((5-chloropyrimidin-2-yl)methyl)-4-methylpyrrolidin-3-yl)-7-(tetrahydro-2H-pyran-4-yl)imidazo[5,1-f][1,2,4]triazin-4(3H)-one | A | 95 | 154 |
| (+)-2-((3,4-trans)-1-((4,6-dimethylpyrimidin-2-yl)methyl)-4-methylpyrrolidin-3-yl)-7-(tetrahydro-2H-pyran-4-yl)imidazo[5,1-f][1,2,4]triazin-4(3H)-one | A | 947 | 767 |
| (+)-2-((3,4-trans)-1-((5-methoxypyrimidin-2-yl)methyl)-4-methylpyrrolidin-3-yl)-7-(tetrahydro-2H-pyran-4-yl)imidazo[5,1-f][1,2,4]triazin-4(3H)-one | A | 26 | 64 |
| (+)-2-((3,4-trans)-4-methyl-1-((4-(trifluoromethyl)pyrimidin-2-yl)methyl)pyrrolidin-3-yl)-7-(tetrahydro-2H-pyran-4-yl)imidazo[5,1-f][1,2,4]triazin-4(3H)-one | A | 585 | 566 |
| (+)-2-((3,4-trans)-4-methyl-1-((5-methylpyrimidin-2-yl)methyl)pyrrolidin-3-yl)-7-(tetrahydro-2H-pyran-4-yl)imidazo[5,1-f][1,2,4]triazin-4(3H)-one | A | 42 | 76 |
| (+)-2-((3,4-trans)-4-methyl-1-((4-methylpyrimidin-2-yl)methyl)pyrrolidin-3-yl)-7-(tetrahydro-2H-pyran-4-yl)imidazo[5,1-f][1,2,4]triazin-4(3H)-one | A | 182 | 220 |
| (+)-2-((3,4-trans)-1-((4-(dimethylamino)pyrimidin-2-yl)methyl)-4-methylpyrrolidin-3-yl)-7-(tetrahydro-2H-pyran-4-yl)imidazo[5,1-f][1,2,4]triazin-4(3H)-one | A | 117 | 177 |
| (+)-2-((3,4-trans)-1-((5-fluoropyrimidin-2-yl)methyl)-4-methylpyrrolidin-3-yl)-7-(tetrahydro-2H-pyran-4-yl)imidazo[5,1-f][1,2,4]triazin-4(3H)-one | A | 133 | 279 |
| (+)-2-((3,4-trans)-1-((5-cyclopropylpyrimidin-2-yl)methyl)-4-methylpyrrolidin-3-yl)-7-(tetrahydro-2H-pyran-4-yl)imidazo[5,1-f][1,2,4]triazin-4(3H)-one | A | 151 | 670 |
| (+)-2-((3,4-trans)-4-methyl-1-((5-(pyrrolidin-1-yl)pyrimidin-2-yl)methyl)pyrrolidin-3-yl)-7-(tetrahydro-2H-pyran-4-yl)imidazo[5,1-f][1,2,4]triazin-4(3H)-one | A | 105 | 496 |
| (+)-2-((3,4-trans)-1-((5-fluoro-4-morpholinopyrimidin-2-yl)methyl)-4-methylpyrrolidin-3-yl)-7-(tetrahydro-2H-pyran-4-yl)imidazo[5,1-f][1,2,4]triazin-4(3H)-one | A | — | — |
| (+)-2-((3,4-trans)-1-((4-cyclopropylpyrimidin-2-yl)methyl)-4-methylpyrrolidin-3-yl)-7-(tetrahydro-2H-pyran-4-yl)imidazo[5,1-f][1,2,4]triazin-4(3H)-one | A | 229 | 403 |
| (+)-2-((3,4-trans)-4-methyl-1-((5-(methylthio)pyrimidin-2-yl)methyl)pyrrolidin-3-yl)-7-(tetrahydro-2H-pyran-4-yl)imidazo[5,1-f][1,2,4]triazin-4(3H)-one | A | — | — |
| (+)-2-((3,4-trans)-4-methyl-1-((5-(trifluoromethyl)pyrimidin-2-yl)methyl)pyrrolidin-3-yl)-7-(tetrahydro-2H-pyran-4-yl)imidazo[5,1-f][1,2,4]triazin-4(3H)-one | A | — | — |
| (+)-2-((3,4-trans)-1-((4,6-bis(trifluoromethyl)pyrimidin-2-yl)methyl)-4-methylpyrrolidin-3-yl)-7-(tetrahydro-2H-pyran-4-yl)imidazo[5,1-f][1,2,4]triazin-4(3H)-one | A | — | — |

TABLE 2-continued

| Example name | Band (PDE9A2 IC$_{50}$) | PDE1A selectivity (versus PDE9A2) | PDE1B selectivity (versus PDE9A2) |
|---|---|---|---|
| (+)-2-((3,4-trans)-4-methyl-1-(2,2,2-trifluoroethyl)pyrrolidin-3-yl)-7-(tetrahydro-2H-pyran-4-yl)imidazo[5,1-f][1,2,4]triazin-4(3H)-one | A | — | — |
| (+)-2-((3,4-trans)-4-methyl-1-(2-(pyrimidin-5-yl)acetyl)pyrrolidin-3-yl)-7-(tetrahydro-2H-pyran-4-yl)imidazo[5,1-f][1,2,4]triazin-4(3H)-one | B | — | — |
| (+)-2-((3,4-trans)-4-methyl-1-(2-(pyrimidin-5-yl)ethyl)pyrrolidin-3-yl)-7-(tetrahydro-2H-pyran-4-yl)imidazo[5,1-f][1,2,4]triazin-4(3H)-one | A | 71 | 89 |

A <1 μM
B 1 μM-10 μM
C >10 μM
N/A Not Available

TABLE 3

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 2-methylpyridine-4-carbaldehyde | B | (+)-2-((3,4-trans)-4-methyl-1-((2-methylpyridin-4-yl)methyl)pyrrolidin-3-yl)-7-(tetrahydro-2H-pyran-4-yl)imidazo[5,1-f][1,2,4]triazin-4(3H)-one | A | 232 | 421 | 1H-NMR (DMSO-d6, 400 MHz): δ 8.42-8.35 (d, 1H), 7.67 (s, 1H), 7.25-7.15 (s, 1H), 7.15-7.10 (d, 1H), 3.96-3.94 (d, 2H), 3.72-3.60 (m, 2H), 3.55-3.48 (m, 3H), 3.02-2.98 (m, 1H), 2.95-2.94 (m, 3H), 2.84-2.75 (m, 1H), 2.55-2.50 (s, 3H), 2.35-2.27 (m, 1H), 1.84-1.79 (m, 4H), 1.08 (d, 3H); Mass (ESI): 409 [M+ + 1]; LC-MS: 99.07%; 409.4 (M+ + 1); (column; XDB C-18, (150 × 4.6 mm, 5 μm); RT 5.58 min. 0.05% TFA (Aq): ACN; 1.0 mL/min); UPLC (purity): 99.54%; (column: Acquity UPLC HSS-T3 (100 × 2.1 mm, 1.8 μm; RT 2.82 min. 0.025% TFA (Aq): ACN; 0.3 mL/min.; Chiral HPLC: 100%, Rt = 22.21 min (Chiralpak IA, 250 × 4.6 mm, 5μ; mobile phase (A) 0.1% DEA in n-Hexane (B) CH2Cl2:MeOH (80:20) (A:B :: 85:15); flow Rate: 1.0 mL/min); Optical rotation [α]D20: +22.40° (c = 0.25, CH2Cl2). TLC: 10% MeOH/CH2Cl2 (Rf: 0.5). |
| (−)-2-((3,4-trans)-4-methylpyrrolidin-3-yl)-7- | 2-methylpyridine-3-carbaldehyde | B | (+)-2-((3,4-trans)-4-methyl-1-((2-methylpyridin- | A | 139 | 201 | 1H-NMR (DMSO-d6, 400 MHz): 11.50-11.40 (br s, 1H), 8.40-8.35 (d, 1H), 7.70-7.65 (m, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (tetrahydro-2H-pyran-4-yl)imidazo[5,1-f][1,2,4]triazin-4(3H)-one | | | 3-yl)methyl)pyrrolidin-3-yl)-7-(tetrahydro-2H-pyran-4-yl)imidazo[5,1-f][1,2,4]triazin-4(3H)-one | | | | 2H), 7.20-7.15 (d, 1H), 3.98-3.96 (m, 2H), 3.60-3.56 (s, 2H), 3.55-3.50 (m, 2H), 3.30 (m, 1H), 2.92-2.88 (m, 4H), 2.70-2.65 (m, 1H), 2.60-2.55 (s, 3H), 2.32-2.25 (m, 1H), 1.86-1.81 (m, 4H), 1.08 (d, 3H); Mass (ESI): 409 [M+ + 1]; LC-MS: 98.17%; 409.4 (M+ + 1) (column; XDB, C-18, (150 × 4.6 mm, 5μm); RT 5.57 min. 0.05% TFA (Aq): ACN; 1.0 mL/min); UPLC (purity): 99.79%; (column: Acquity UPLC HSS-T3 (100 × 2.1 mm, 1.8 μm); RT 2.82 min. 0.025% TFA (Aq): ACN; 0.3 mL/min; Chiral HPLC: 100%, Rt = 10.70 min (Chiralpak IA, 250 × 4.6 mm, 5μ; mobile phase (A) 0.1% DEA in n-Hexane (B) CH2Cl2:MeOH (80:20) (A:B :: 80:20); flow Rate: 1.00 mL/min); Optical rotation [α]D20: +16.73° (c = 0.25, CH2Cl2); TLC: 10% MeOH/CH2Cl2 (Rf: 0.5). |
| (−)-2-((3,4-trans)-4-methylpyrrolidin-3-yl)-7-(tetrahydro-2H-pyran-4-yl)imidazo[5,1-f][1,2,4]triazin-4(3H)-one | 2,3-dichloro benzaldehyde | B | (+)-2-((3,4-trans)-1-(2,3-dichlorobenzyl)-4-methylpyrrolidin-3-yl)-7-(tetrahydro-2H-pyran-4-yl)imidazo[5,1-f][1,2,4]triazin-4(3H)-one | A | 195 | 199 | 1H-NMR (DMSO-d6, 400 MHz); δ 11.52 (br s, 1H), 7.65 (s, 1H), 7.54-7.42 (m, 2H), 7.32 (t, 1H), 3.92 (d, 2H), 3.78 (s, 2H), 3.48-3.36 (m, 3H), 3.06-2.98 (m, 1H), 2.94-2.78 (m, 3H), 2.72-2.66 (m, 1H), 2.42-2.36 (m, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | 1.92-1.82 (m, 4H), 1.10 (d, 3H); Mass (ESI): 462 [M] +; LC-MS: 97.57%; 462.3 (M) +; (column; X-bridge C-18, (50 × 3.0 mm, 3.5 μm); RT 2.32 min. 0.05% TFA: ACN; 0.8 ml/min; HPLC (purity): 96.5%; (column: Eclipse XDB-C18 (150 × 4.6 mm, 5.0 μm); RT 11.29 min. 5 mM aq. NH4OAc: ACN: Water; 1.0 mL/min; Chiral HPLC: 97.35%, Rt = 22.95 min (Chiralpak IA, 250 × 4.6 mm, 5μ mobile phase (A) 0.1% DEA in n-Hexane (B) CH2Cl2:MeOH (80:20) (A:B :: 90:10); flow Rate: 1.0 mL/min); Optical rotation [α]D20: +23.24° (c = 0.25, CH2Cl2); TLC: 10% MeOH/CH2Cl2 (Rf: 0.4). |
| (−)-2-((3,4-trans)-4-methylpyrrolidin-3-yl)-7-(tetrahydro-2H-pyran-4-yl)imidazo[5,1-f][1,2,4]triazin-4(3H)-one | 4-chloro-3-methylbenzaldehyde | B | (+)-2-((3,4-trans)-4-chloro-3-methylpyrrolidin-1-(4-chloro-3-methylbenzyl)-4-methylpyrrolidin-3-yl)-7-(tetrahydro-2H-pyran-4-yl)imidazo[5,1-f][1,2,4]triazin-4(3H)-one | A | 466 | 818 | 1H-NMR (DMSO-d6, 400 MHz): δ 7.64 (s, 1H), 7.33 (d, 1H), 7.26 (d, 1H), 7.12 (d, 1H), 3.92 (d, 2H), 3.56 (d, 2H), 3.46-3.40 (m, 2H), 3.38-3.32 (m, 2H), 2.96 (t, 1H), 2.90-2.84 (m, 1H), 2.78-2.72 (m, 2H), 2.68-2.62 (m, 1H), 2.38-2.32 (m, 3H), 2.26 (t, 1H), 1.90-1.78 (m, 4H), 1.08 (d, 3H); Mass (ESI): 442 [M] +; LC-MS: 99.30%; 442 (M) +; (column; X-bridge C-18, (50 × 3.0 mm, 3.5 μm); RT 3.75 min. 5 mM NH4OAc: ACN; 0.8 ml/min; |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | | | | | HPLC (purity): 99.58%; (column: Eclipse XDB-C18 (150 × 4.6 mm, 5.0 μm; RT 11.26 min. 5 mM aqueous NH4OAc: ACN: Water; 1.0 mL/min.; Chiral HPLC: 96.41%, Rt = 23.32 min (Chiralpak IA, 250 × 4.6 mm, 5μ; mobile phase (A) 0.1% DEA in n-Hexane (B) CH2Cl2:MeOH (80:20) (A:B :: 90:10); flow Rate: 1.00 mL/min); Optical rotation [α]D20: +23.45° (c = 0.25, CH2Cl2); TLC: 10% MeOH/CH2Cl2 (Rf: 0.4). |
| | 3-chloro-4-fluorobenzaldehyde | B | (+)-2-((3,4-trans)-1-(3-chloro-4-fluorobenzyl)-4-methylpyrrolidin-3-yl)-7-(tetrahydro-2H-pyran-4-yl)imidazo[5,1-f][1,2,4]triazin-4(3H)-one | A | 604 | 430 | 1H-NMR (DMSO-d6, 400 MHz): δ 7.62 (s, 1H), 7.45 (d, 1H), 7.30 (d, 2H), 3.94 (d, 2H), 3.65-3.50 (t, 2H), 3.48-3.41 (t, 2H), 3.35-3.30 (m, 1H), 2.93-2.87 (m, 1H), 2.84-2.76 (m, 3H), 2.60-2.54 (m, 1H), 2.21 (t, 1H), 1.90-1.78 (m, 4H), 1.04 (s, 3H); Mass (ESI): 446 [M + 1] +; LC-MS: 99.18%; 446 (M + 1); (column; X-bridge C-18, (50 × 3.0 mm, 3.5 μm); RT 2.31 min. 0.05% aq.TFA: ACN; 0.8 ml/min); UPLC (purity): 99.37%; (column; Acquity BEH C-18 (50 × 2.1 mm, 1.7μ; RT 1.59 min. 0.025% TFA: ACN: Water; 0.5 mL/min.; Chiral HPLC: 99.07%, Rt = 11.70 min (Chiralpak IA, 250 × 4.6 mm, 5μ; mobile |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)imidazo[5,1-f][1,2,4]triazin-4(3H)-one-7-(tetrahydro-2H-pyran-4-yl)imidazo[5,1-f][1,2,4]triazin-4(3H)-one | | | | | | | phase (A) 0.1% DEA in n-Hexane (B) CH2Cl2:MeOH (80:20) (A:B :: 85:15); Flow Rate: 1.00 mL/min); Optical rotation [α]D20: +16.19° (c = 0.25, CH2Cl2); TLC: 10% MeOH/CH2Cl2 (Rf: 0.6). |
| | 4-chloro-3-(trifluoromethyl)benzaldehyde | B | (+)-2-((3,4-trans)-1-(4-chloro-3-(trifluoromethyl)benzyl)-4-methylpyrrolidin-3-yl)-7-(tetrahydro-2H-pyran-4-yl)imidazo[5,1-f][1,2,4]triazin-4(3H)-one | A | 196 | 406 | 1H-NMR (DMSO-d6, 400 MHz): δ 11.62 (br s, 1H), 7.82 (s, 1H), 7.70-7.58 (m, 3H), 3.94 (d, 2H), 3.80-3.60 (m, 2H), 3.50-3.40 (m, 2H), 3.38-3.30 (m, 1H), 3.02 (m, 1H), 2.92-2.72 (m, 3H), 2.70-2.62 (m, 1H), 2.30-2.22 (m, 1H), 1.90-1.82 (m, 4H), 1.04 (d, 3H); Mass (ESI): 496 [M+ + 1]; LC-MS: 99.25%; 496.5 (M+ + 1); (column; X-bridge C-18, (50 × 3.0 mm, 3.5 μm); RT 3.21 min. 0.05% TFA: ACN; 0.8 mL/min); UPLC (purity): 97.31%; (column; Acquity BEH C-18, 50 × 2.1 mm, 1.7μ; RT 1.80 min. 0.025% aqueous TFA: ACN: Water; 0.50 ml/min; Chiral HPLC: 96.95%, Rt = 20.42 min (Chiralpak IA, 250 × 4.6 mm, 5μ; mobile phase (A) 0.1% DEA in n-Hexane (B) CH2Cl2:MeOH (80:20) (A:B :: 90:10); Flow Rate: 1.00 mL/min); Optical rotation [α]D20: +2.99° (c = 0.25, MeOH); TLC: 10% |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 2-chloro-5-fluorobenzaldehyde | B | (+)-2-((3,4-trans)-1-(2-chloro-5-fluorobenzyl)-4-methylpyrrolidin-3-yl)-7-(tetrahydro-2H-pyran-4-yl)imidazo[5,1-f][1,2,4]triazin-4(3H)-one | A | 177 | 73 | 1H-NMR (DMSO-d6, 500 MHz): δ 11.56 (bs, 1H), 7.63 (s, 1H), 7.45-7.42 (q, 1H), 7.29-7.26 (m, 1H), 7.19-7.16 (m, 1H), 3.92 (d, 2H), 3.72 (s, 2H), 3.52-3.42 (m, 2H), 3.40-3.32 (m, 1H), 3.01 (t, 1H), 2.95 (t, 1H), 2.88 (t, 1H), 2.84-2.78 (m, 1H), 2.68-2.60 (m, 1H), 2.38-2.32 (m, 1H), 1.86-1.82 (m, 4H), 1.14 (d, 3H); Mass (ESI): 446 [M+ + 1]; LC-MS: 94.63%; 446.2 (M+ + 1); (column: X-bridge C-18, (50 × 3.0 mm, 3.5 μm); RT 2.13 min. 0.05% aqueous TFA: ACN; 0.8 mL/min); UPLC (purity): 95.78%; (column: Acquity BEH-C18, 50 × 2.1 mm, 1.7μ; RT 1.50 min. 0.025% aq TFA: ACN; Water: 0.50 mL/min; Chiral HPLC: 95.55%, Rt = 9.73 min (Chiralpak IA, 250 × 4.6 mm, 5 μm; mobile phase (A) 0.1% DEA in n-Hexane (B) CH2Cl2:MeOH (80:20) (A:B :: 80:20); flow Rate: 1.00 mL/min); Optical rotation [α]D20: +18.12° (c = 0.25, CH2Cl2); TLC: 10% MeOH/CH2Cl2 (Rf: 0.6). |
| (−)-2-((3,4-trans)-4-methylpyrrolidin-3-yl)- | 2-methoxypyrimidine-5-carbaldehyde | B | (+)-2-((3,4-trans)-1-((2-methoxypyrimidin-5- | A | 1210 | 3650 | 1H-NMR (DMSO-d6, 400 MHz): δ 8.60 (s, 2H), 7.70 (s, 1H), 3.96-3.94 (m, 5H), |

TABLE 3-continued

| SM name | Reagent | Method | Example name | Band | PDE9A2 IC$_{50}$ | PDE1A selectivity (versus PDE9A2) | PDE1B selectivity (versus PDE9A2) | Analytical Data |
|---|---|---|---|---|---|---|---|---|
| (tetrahydro-2H-pyran-4-yl)imidazo[5,1-f][1,2,4]triazin-4(3H)-one | | | yl)methyl)-4-methylpyrrolidin-3-yl)-7-(tetrahydro-2H-pyran-4-yl)imidazo[5,1-f][1,2,4]triazin-4(3H)-one | | | | | 3.80-3.78 (m, 1H), 3.65-3.55 (m, 3H), 3.40-3.35 (m, 1H), 3.02-2.98 (m, 2H), 2.90-2.85 (m, 2H), 2.75-2.60 (m, 1H), 2.27-2.21 (m, 1H), 1.84-1.79 (m, 4H), 1.08 (d, 3H); Mass (ESI): 426 [M+ + 1]; LC-MS: 94.60%; 426 (M+ + 1); (column; X-bridge C-18, (50 × 3.0 mm, 3.5 μm); RT 2.59 min. 5.0 mM NH4OAC: ACN; 0.8 mL/min); HPLC (purity): 96.10%; (column: Eclipse-XDB-C-18 (150 × 4.6 mm, 5.0 μm; RT 7.74 min. 5.0 mM NH4OAC (Aq): ACN; 1.0 mL/min.; Chiral HPLC: 97.82%, Rt = 25.88 min (Chiralpak IA, 250 × 4.6 mm, 5μ; mobile phase (A) 0.1% DEA in n-Hexane (B) CH2Cl2:MeOH (80:20) (A:B :: 85:15); flow Rate: 1.0 mL/min); Optical rotation [α]D20: +2.00° (c = 0.25%, CH2Cl2); TLC: 10% MeOH/CH2Cl2 (Rf: 0.5). |
| (−)-2-((3,4-trans)-4-methylpyrrolidin-3-yl)-7-(tetrahydro-2H-pyran-4-yl)imidazo[5,1-f][1,2,4]triazin-4(3H)-one | 3-chloro-5-trifluoromethyl benzaldehyde | B | (+)-2-((3,4-trans)-1-(3-chloro-5-(trifluoromethyl)benzyl)-4-methylpyrrolidin-3-yl)-7-(tetrahydro-2H-pyran-4-yl)imidazo[5,1-f][1,2,4]triazin-4(3H)-one | A | | 236 | 105 | 1H-NMR (DMSO-d6, 400 MHz): 7.75-7.70 (d, 2H), 7.65-7.60 (d, 2H), 3.96-3.94 (m, 2H), 3.82-3.80 (s, 2H), 3.55-3.45 (t, 2H), 3.40-3.35 (m, 1H), 3.02-2.98 (m, 1H), 2.92-2.86 (m, 1H), 2.82-2.75 (m, 2H), 2.68-2.60 (m, 1H), 2.27-2.21 (m, 1H), 1.84-1.79 (m, 4H), 1.08 (d, 3H); Mass |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | (ESI): 496 [M+ + 1]; LC-MS: 93.10%; 496.6 (M+ + 1); (column; X-bridge C-18, (50 × 3.0 mm, 3.5 μm); RT 3.16 min. 0.05% TFA (Aq): ACN; 0.8 mL/min); UPLC (purity): 95.19%; (column; Acquity BEH C-18 (50 × 2.1 mm, 1.7 μm; RT 1.78 min. 0.025% TFA (Aq): ACN; 0.5 mL/min.; Chiral HPLC: 95.68%, Rt = 17.39 min (Chiralpak IA, 250 × 4.6 mm, 5μ mobile phase (A) 0.1% DEA in n-Hexane (B) CH2Cl2:MeOH (A:B :: 90:10); flow Rate: 1.0 mL/min); Optical rotation [α]D20: +5.16° (c = 0.25, CH2Cl2); TLC: 10% MeOH/CH2Cl2 (Rf: 0.5) |
| (−)-2-((3,4-trans)-4-methylpyrrolidin-3-yl)-7-(tetrahydro-2H-pyran-4-yl)imidazo[5,1-f][1,2,4]triazin-4(3H)-one | 2-chloro-6-fluorobenzaldehyde | B | (+)-2-((3,4-trans)-1-(2-chloro-6-fluorobenzyl)-4-methylpyrrolidin-3-yl)-7-(tetrahydro-2H-pyran-4-yl)imidazo[5,1-f][1,2,4]triazin-4(3H)-one | A | 196 | 252 | 1H-NMR (DMSO-d6, 400 MHz): δ 11.50-11.35 (bs, 1H), 7.67 (s, 1H), 7.35-7.30 (m, 2H), 7.28-7.20 (m, 1H), 3.96-3.94 (m, 2H), 3.92-3.88 (m, 2H), 3.55-3.50 (m, 3H), 3.40-3.35 (m, 1H), 3.02-2.95 (m, 1H), 2.86 (m, 1H), 2.77-2.72 (m, 1H), 2.65-2.60 (m, 1H), 2.27-2.21 (m, 1H), 1.84-1.79 (m, 4H), 1.08 (d, 3H); Mass (ESI): 446 [M+ + 1]; LC-MS: 95.57%; 446.8 (M+ + 1); (column; X-bridge C-18, (50 × 3.0 mm, 3.5 μm); RT 2.62 min. 0.05% TFA (Aq): ACN; |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | 0.8 mL/min); UPLC (purity): 96.25%; (column: Acquity BEH C-18 (50 × 2.1 mm, 1.7 μm; RT 1.45 min. 0.025% TFA (Aq): ACN; 0.5 mL/min.; Chiral HPLC: 97.88%, Rt = 7.78 min (Chiralpak IA, 250 × 4.6 mm, 5μ; mobile phase (A) 0.1% DEA in n-Hexane (B) CH2Cl2:MeOH (A:B :: 80:20); flow Rate: 1.0 mL/min); Optical rotation [α]D20: +25.52° (c = 0.25, CH2Cl2); TLC: 10% MeOH/CH2Cl2 (Rf 0.5). |
| (−)-2-((3,4-trans)-4-methylpyrrolidin-3-yl)-7-(tetrahydro-2H-pyran-4-yl)imidazo[5,1-f][1,2,4]triazin-4(3H)-one | 2-chloro-3,6-difluorobenzaldehyde | B | (+)-2-((3,4-trans)-1-(2-chloro-3,6-difluorobenzyl)-4-methylpyrrolidin-3-yl)-7-(tetrahydro-2H-pyran-4-yl)imidazo[5,1-f][1,2,4]triazin-4(3H)-one | A | 118 | 231 | 1H-NMR (DMSO-d6, 400 MHz): δ 11.50-11.40 (bs, 1H), 7.67 (s, 1H), 7.43-7.41 (m, 1H), 7.35-7.30 (m, 1H), 3.96-3.94 (m, 2H), 3.92-3.88 (m, 2H), 3.72-3.60 (m, 2H), 3.48-3.25 (m, 1H), 3.02-2.90 (m, 3H), 2.84 (m, 1H), 2.77-2.72 (m, 1H), 2.27-2.21 (m, 1H), 1.84-1.79 (m, 4H), 1.08 (d, 3H); Mass (ESI): 464 [M+ + 1]; LC-MS: 96.69%; 464.4 (M+ + 1); (column: X-bridge C-18, (50 × 3.0 mm, 3.5 μm); RT 2.66 min. 0.05% TFA (Aq): ACN; 0.8 mL/min); UPLC (purity): 98.33%; (column: Acquity BEH C-18 (50 × 2.1 mm, 1.7 μm; RT 1.49 min. 0.025% TFA (Aq): ACN; 0.5 mL/min. |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 5-methoxy nicotinaldehyde | B | (+)-2-((3,4-trans)-1-((5-methoxypyridin-3-yl)methyl)-4-methylpyrrolidin-3-yl)-7-(tetrahydro-2H-pyran-4-yl)imidazo[5,1-f][1,2,4]triazin-4(3H)-one | A | 1060 | 1780 | (IP1203O408); Chiral HPLC: 95.18%, Rt = 9.85 min (Chiralpak IA, 250 × 4.6 mm, 5μ; mobile phase (A) 0.1% DEA in n-Hexane (B) (A:B:: 80:20); flow Rate: 1.0 mL/min); Optical rotation [α]D20: +4.51° (c = 0.25, CH2Cl2); TLC: 10% MeOH/CH2Cl2 (Rf: 0.5). 1H-NMR (DMSO-d6, 400 MHz): δ 8.20 (s, 1H), 8.16 (s, 1H), 7.68 (s, 1H), 7.30 (s, 1H), 3.94-3.92 (m, 2H), 3.82 (s, 3H), 3.70 (d, 1H), 3.64 (d, 1H), 3.52-3.49 (m, 3H), 2.96-2.90 (m, 2H), 2.81-2.79 (m, 2H), 2.66-2.64 (m, 1H), 2.30-2.28 (m, 1H), 1.90-1.80 (m, 4H), 1.10 (d, 3H); Mass (ESI): 425 [M+ + 1]; LC-MS: 93.60%; 425.4 (M+ + 1); (column: Eclipse XDB C-18, 150 × 4.6 mm, 5.0 μm); RT 5.88 min. 0.1% TFA (aq.): ACN; 1.0 mL/min); UPLC (purity): 94.09%; (column: Acquity BEH C-18, (50 × 2.1 mm, 1.7μ): RT 1.14 min. ACN: 0.025% TFA (Aq): 0.5 mL/min; Chiral HPLC: 99.31%, Rt = 13.62 min (Chiralpak IA, 250 × 4.6 mm, 5μ); mobile phase (A) 0.1% DEA in n-Hexane (B) CH2Cl2:MeOH (80:20) (A:B: 80:20); flow Rate: 1.0 mL/min); |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 2-(trifluoromethoxy)benzaldehyde | B | (+)-2-((3,4-trans)-4-methyl-1-(2-(trifluoromethoxy)benzyl)pyrrolidin-3-yl)-7-(tetrahydro-2H-pyran-4-yl)imidazo[5,1-f][1,2,4]triazin-4(3H)-one | A | 173 | 24 | Optical rotation [α]D20: +5.96° (c = 0.25, CH2Cl2); TLC: 10% MeOH/CH2Cl2 (Rf: 0.4). 1H-NMR (DMSO-d6, 400 MHz): δ 11.60 (br s, 1H), 7.64 (s, 1H), 7.60-7.59 (m, 1H), 7.42-7.34 (m, 3H), 3.96-3.94 (m, 2H), 3.71-3.70 (m, 2H), 3.50-3.47 (m, 2H), 3.38-3.36 (m, 1H), 3.00-2.98 (m, 1H), 2.90-2.78 (m, 3H), 2.64-2.62 (m, 1H), 2.32-2.30 (m, 1H), 1.90-1.80 (m, 4H), 1.10 (d, 3H); Mass (ESI): 478 [M+ + 1]; LC-MS: 98.50%; 478.4 (M+ + 1); (column: X-Bridge C-18, 50 × 3.0 mm, 3.5 μm); RT 2.97 min. 0.05% TFA:ACN; 0.8 mL/min); UPLC (purity): 98.76%; (column: Acquity BEH C-18, (50 × 2.1 mm, 1.7μ); RT 1.63 min. ACN: 0.025% TFA (Aq); 0.5 mL/min.; Chiral HPLC: 99.24%, Rt = 8.48 min (Chiralpak IA, 250 × 4.6 mm, 5μ); mobile phase (A) 0.1% DEA in n-Hexane (B) CH2Cl2:MeOH (80:20) (A:B: 85:15); flow Rate: 1.0 mL/min); Optical rotation [α]D20.01: +13.88° (c = 0.25, CH2Cl2); TLC: 10% MeOH/CH2Cl2 (Rf: 0.4). |
| (−)-2-((3,4- | 2- | A | (+)-2-((3,4- | A | 7 | 1 | 1H-NMR (DMSO-d6, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| 4-methylpyrrolidin-3-yl)-7-(tetrahydro-2H-pyran-4-yl)imidazo[5,1-f][1,2,4]triazin-4(3H)-one | chloro-4-(trifluoromethyl)pyrimidine | | trans)-4-methyl-1-(4-(trifluoromethyl)pyrimidin-2-yl)pyrrolidin-3-yl)-7-(tetrahydro-2H-pyran-4-yl)imidazo[5,1-f][1,2,4]triazin-4(3H)-one | | | | 400 MHz): δ 11.90 (br s, 1H), 8.70 (s, 1H), 7.68 (s, 1H), 7.04 (d, 1H), 4.02-3.74 (m, 5H), 3.28-3.22 (m, 4H), 3.10 (q, 1H), 2.78-2.74 (m, 1H), 1.86-1.70 (m, 4H), 1.20 (d, 3H); Mass (ESI): 450 [M+ +1]; LC-MS: 95.62%; 450.3 (M+ + 1); (column: X-bridge C-18, (50 × 3.0 mm, 3.5 μm); RT 2.89 min. 0.05% TFA (Aq): ACN; 0.8 mL/min); UPLC (purity): 95.82%; (column: Acquity BEH C-18 (50 × 2.1 mm, 1.7μ); RT 2.09 min. ACN: 0.025% TFA (Aq); 0.5 mL/min.: Chiral HPLC: 96.79%, Rt = 17.97 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D20: +16.43° (c = 0.25, CH2Cl2); TLC: 10% MeOH/CH2Cl2 (Rf: 0.6). |
| (−)-2-(3,4-trans)-4-methylpyrrolidin-3-yl)-4-(tetrahydro-2H-pyran-4-yl)imidazo[5,1-f][1,2,4]triazin-4(3H)-one | 6-methylpicolinaldehyde | B | (+)-2-(3,4-trans)-4-methyl-1-((6-methylpyridin-2-yl)methyl)pyrrolidin-3-yl)-7-(tetrahydro-2H-pyran-4-yl)imidazo[5,1-f][1,2,4]triazin-4(3H)-one | A | 780 | 1005 | 1H-NMR (DMSO-d6, 400 MHz): δ 7.70-7.64 (m, 2H), 7.22 (d, 1H), 7.10 (d, 1H), 3.96-3.90 (m, 2H), 3.80 (d, 1H), 3.68 (d, 1H), 3.51-3.49 (m, 3H), 3.02-2.98 (m, 2H), 2.86-2.78 (m, 2H), 2.66-2.64 (m, 1H), 2.42 (s, 3H), 2.32-2.30 (m, 1H), 1.92-1.80 (m, 4H), 1.12 (d, 3H); |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | Mass (ESI): 409.4 [M+ + 1]; LC-MS: 94.06%; 409.4 (M+ + 1); (column: Eclipse XDB C-18, 150 × 4.6 mm, 5.0 μm); RT 6.37 min. 0.05% Aq TFA: ACN; 1.0 mL/min); UPLC (purity): 96.48%; (column: Acquity BEH C-18, (50 × 2.1 mm, 1.7μ); RT 1.34 min. ACN: 0.025% TFA (Aq); 0.5 mL/min.; Chiral HPLC: 96.88%, Rt = 21.10 min (Chiralpak IA, 250 × 4.6 mm, 5μ); mobile phase (A) 0.1% DEA in n-Hexane (B) CH2Cl2:MeOH (80:20) (A:B: 90:10); flow Rate: 1.0 mL/min); Optical rotation [α]D20: +74.78° (c = 0.25, CH2Cl2); TLC: 10% MeOH/CH2Cl2 (Rf: 0.5). |
| (−)-2-((3,4-trans)-4-methylpyrrolidin-3-yl)-7-(tetrahydro-2H-pyran-4-yl)imidazo[5,1-f][1,2,4]triazin-4(3H)-one | 2-fluoro-5-formylbenzonitrile | B | (+)-2-fluoro-5-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile | A | 61 | 58 | 1H-NMR (DMSO-d6, 500 MHz): δ 7.83 (d, 1H), 7.75-7.70 (m, 1H), 7.61 (s, 1H), 7.48 (t, 1H), 3.88-3.84 (m, 2H), 3.66-3.62 (m, 2H), 3.52-3.44 (m, 2H), 3.40-3.38 (m, 1H), 2.96 (t, 1H), 2.86 (t, 1H), 2.80-2.76 (m, 2H), 2.66-2.64 (m, 1H), 2.28-2.26 (m, 1H), 1.90-1.80 (m, 4H), 1.12 (d, 3H); Mass (ESI): 437 [M+ + 1]; LC-MS: 98.11%; 437.4 (M+ + 1); (column: X-bridge C-18, 50 × 3.0 mm, 3.5 μm); RT 2.10 min. 0.05% TFA (aq.): |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 4-methyl pyridine-2-carbaldehyde | B | (+)-2-((3,4-trans)-4-methyl-1-((4-methylpyridin-2-yl)methyl)pyrrolidin-3-yl)-7-(tetrahydro-2H-pyran-4-yl)imidazo[5,1-f][1,2,4]triazin-4(3H)-one | A | 143 | 116 | ACN: 0.8 mL/min); UPLC (purity): 97.33%; (column: Acquity BEH C-18, (50 × 2.1 mm, 1.7µ); RT 1.46 min. ACN: 0.025% TFA (Aq); 0.5 mL/min; Chiral HPLC: 97.90%, Rt = 12.30 min (Chiralpak IA, 250 × 4.6 mm, 5 µm); mobile phase (A) 0.1% DEA in n-Hexane (B) CH2Cl2:MeOH (80:20) (A:B: 80:20); flow Rate: 1.0 mL/min); Optical rotation [α]D20: +10.16° (c = 0.25, CH2Cl2); TLC: 10% MeOH/CH2Cl2 (Rf. 0.5). 1H-NMR (DMSO-d6, 400 MHz): δ 8.37 (d, 1H), 7.72-7.70 (s, 1H), 7.35-7.30 (d, 1H), 7.10-7.05 (d, 1H), 3.98-3.96 (m, 2H), 3.80-3.67 (m, 2H), 3.60-3.45 (m, 2H), 3.00-2.95 (m, 2H), 2.92-2.88 (m, 2H), 2.60-2.55 (m, 1H), 2.50-2.45 (m, 2H), 2.32-2.25 (m, 3H), 1.86-1.81 (m, 4H), 1.08 (d, 3H); Mass (ESI): 409 [M+ + 1]; LC-MS: 93.30%; 409.3 (M+ + 1); (column; X-bridge C-18, (50 × 3.0 mm, 3.5µ); RT 1.89 min. 0.05% TFA (Aq); ACN: 0.8 ml/min); HPLC (purity): 92.92%; (column: Eclipse XDB-C 18 (150 × 4.6 mm, 5.0µ; RT 8.56 min. 5 mM NH4OAc (Aq): |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | | | | | ACN; 1.0 ml/min.; Chiral HPLC: 89.00%, Rt = 12.51 min (Chiralpak IA, 250 × 4.6 mm, 5μ; mobile phase (A) 0.1% DEA in n-Hexane (B) CH2Cl2:MeOH (80:20) (A:B: 85:15); flow Rate: 1.00 mL/min); Optical rotation [α]D20: +92.49° (c = 0.25, CH2Cl2). TLC: 10% MeOH/CH2Cl2 (Rf: 0.5) |
| | 2-thiophene carbaldehyde | B | (+)-2-((3,4-trans)-4-methyl-1-(thiophen-2-ylmethyl)pyrrolidin-3-yl)-7-(tetrahydro-2H-pyran-4-yl)imidazo[5,1-f][1,2,4]triazin-4(3H)-one | A | 91 | 140 | 1H-NMR (DMSO-d6, 400 MHz): δ 7.67 (s, 1H), 7.43-7.41 (m, 1H), 6.97-6.94 (t, 2H), 3.96-3.94 (t, 2H), 3.92-3.88 (t, 2H), 3.72-3.60 (m, 2H), 3.48-3.25 (m, 1H), 3.02-2.98 (m, 1H), 2.95-2.94 (m, 1H), 2.84 (m, 2H), 2.77-2.72 (m, 1H), 2.27-2.21 (m, 1H), 1.84-1.79 (m, 4H), 1.08 (d, 3H); Mass (ESI): 400 [M+ + 1]; LC-MS: 97.44%; 400.3 (M+ + 1); (column: X-bridge C-18, (50 × 3.0 mm, 3.5 μm); RT 1.86 min. 0.05% TFA (Aq): ACN; 0.8 mL/min); UPLC (purity): 98.92%; (column: Acquity BEH C-18 (50 × 2.1 mm, 1.7 μm; RT 1.32 min. 0.025% TFA (Aq); ACN; 0.5 mL/min.; Chiral HPLC: 99.68%, Rt = 9.80 min (Chiralpak IA, 250 × 4.6 mm, 5 μm; mobile phase (A) 0.1% DEA in n-Hexane (B) CH2Cl2:MeOH |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 5-chloro-2-formyl pyridine | B | (+)-2-((3,4-trans)-1-((5-chloropyridin-2-yl)methyl)-4-methylpyrrolidin-3-yl)-7-(tetrahydro-2H-pyran-4-yl)imidazo[5,1-f][1,2,4]triazin-4(3H)-one | A | 107 | 184 | (80:20) (A:B: 80:20); flow Rate: 1.0 mL/min); Optical rotation [α]D20: +33.93° (c = 0.25, CH2Cl2). TLC: 10% MeOH/CH2Cl2 (Rf: 0.5). 1H-NMR (DMSO-d6, 400 MHz): δ 11.75-11.35 (bs, 1H), 8.62-8.55 (s, 1H), 7.90-7.85 (d, 1H), 7.72-7.65 (s, 1H), 7.52-7.45 (d, 1H), 3.96-3.94 (m, 2H), 3.92-3.88 (m, 2H), 3.82-3.70 (m, 2H), 3.52-3.48 (m, 1H), 3.52-3.25 (m, 1H), 2.95-2.94 (m, 1H), 2.84 (m, 2H), 2.77-2.72 (m, 1H), 2.27-2.21 (m, 1H), 1.84-1.79 (m, 4H), 1.08 (d, 3H); Mass (ESI): 429 [M+ + 1]; LC-MS: 98.07%; 429.3 (M+ + 1); (column; X-bridge C-18, (50 × 3.0 mm, 3.5 μm); RT 2.03 min. 0.05% TFA (Aq): ACN; 0.8 ml/min); HPLC (purity): 93.25%; (column: Eclipse XDB-C 18 (150 × 4.6 mm, 5.0μ; RT 9.32 min. 5 mM NH4OAc (Aq): ACN; 1.0 ml/min.; Chiral HPLC: 93.62%, Rt = 9.77 min (Chiralpak IA, 250 × 4.6 mm, 5μ; mobile phase (A) 0.1% DEA in n-Hexane (B) CH2Cl2:MeOH (80:20) (A:B: 80:20); flow Rate: 1.00 mL/min); Optical rotation [α]D20: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 2-fluoro-5-chloro benzaldehyde | B | (+)-2-((3,4-trans)-1-(5-chloro-2-fluorobenzyl)-4-methylpyrrolidin-3-yl)-7-(tetrahydro-2H-pyran-4-yl)imidazo[5,1-f][1,2,4]triazin-4(3H)-one | A | 15 | 16 | +48.44° (c = 0.25, CH2Cl2). TLC: 10% MeOH/CH2Cl2 (Rf: 0.5) 1H-NMR (DMSO-d6, 400 MHz): δ 11.65-11.40 (bs, 1H), 7.65 (s, 1H), 7.55-7.45 (d, 1H), 7.42-7.35 (d, 1H), 7.25-7.15 (d, 1H), 3.96-3.94 (m, 2H), 3.74 (s, 2H), 3.51-3.46 (m, 2H), 3.39-3.27 (m, 1H), 3.02-2.98 (t, 1H), 2.91-2.82 (m, 1H), 2.72-2.65 (m, 2H), 2.53-2.45 (d, 1H), 2.34-2.32 (m, 1H), 1.89-1.84 (m, 4H), 1.08 (d, 3H); Mass (ESI): 446.3 [M+ + 1]; LC-MS: 96.98%; 446.5 (M+ + 1); (column; X-bridge C-18, (50 × 3.0 mm, 3.5 μm); RT 2.74 min. 0.05% TFA (Aq); ACN; 0.8 ml/min); UPLC (purity): 98.15%; (column; Acquity BEH C-18, 50 × 2.1 mm, 1.7μ; RT 1.52 min. 0.025% TFA (Aq); ACN; 0.50 ml/min.; Chiral HPLC: 92.96%, Rt = 22.28 min (Chiralpak IA, 250 × 4.6 mm, 5μ; mobile phase (A) 0.1% DEA in n-Hexane (B) CH2Cl2:MeOH (80:20) (A:B: 90:10); flow Rate: 1.00 mL/min); Optical rotation [α]D20: +3.02° (c = 0.25, CH2Cl2); TLC: 10% MeOH/CH2Cl2 (Rf: 0.4). |
| (−)-2-((3,4-trans)- | 3-furan | B | (+)-2-((3,4- | A | 68 | 123 | 1H-NMR (DMSO-d6, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| 4-methylpyrrolidin-3-yl)-7-(tetrahydro-2H-pyran-4-yl)imidazo[5,1-f][1,2,4]triazin-4(3H)-one | aldehyde | | trans)-1-(furan-3-ylmethyl)-4-methylpyrrolidin-3-yl)-7-(tetrahydro-2H-pyran-4-yl)imidazo[5,1-f][1,2,4]triazin-4(3H)-one | | | | 400 MHz): δ 7.66 (s, 1H), 7.63-7.59 (t, 1H), 7.57-7.56 (d, 1H), 6.45 (s, 1H), 3.98-3.96 (m, 2H), 3.60-3.56 (m, 4H), 3.45-3.35 (m, 1H), 2.92-2.88 (m, 2H), 2.70-2.65 (m, 2H), 2.60-2.55 (m, 1H), 2.32-2.25 (m, 1H), 1.86-1.81 (m, 4H), 1.08 (d, 3H); Mass (ESI): 384.3 [M+ + 1]; LC-MS: 99.03%; 384.2 (M+ + 1); (column; X-bridge C-18, (50 × 3.0 mm, 3.5 μm); RT 1.75 min. 0.05% TFA (Aq): ACN; 0.8 mL/min); UPLC (purity): 97.81%; (column: Acquity BEH C-18 (50 × 2.1 mm, 1.7 μm; RT 1.23 min. 0.025% TFA (Aq): ACN; 0.5 mL/min.; Chiral HPLC: 98.47%, Rt = 13.15 min (Chiralpak IA, 250 × 4.6 mm, 5μ; mobile phase (A) 0.1% DEA in n-Hexane (B) CH2Cl2:MeOH (80:20) (A:B: 85:15); flow Rate: 1.00 mL/min); Optical rotation [α]D20: +27.76° (c = 0.25, CH2Cl2); TLC: 10% MeOH/CH2Cl2 (Rf: 0.5). |
| (−)-2-((3,4-trans)-4-methylpyrrolidin-3-yl)-7-(tetrahydro-2H-pyran-4-yl)imidazo[5,1-f][1,2,4]triazin-4(3H)-one | Thiophene-3-carbaxaldehyde | B | (+)-2-((3,4-trans)-4-methyl-1-(thiophen-3-ylmethyl)pyrrolidin-3-yl)-7-(tetrahydro-2H-pyran-4-yl)imidazo[5,1-f][1,2,4]triazin-4(3H)-one | A | 176 | 209 | 1H-NMR (DMSO-d6, 400 MHz): δ 7.64 (s, 1H), 7.58 (d, 1H), 7.34 (s, 1H), 7.09 (d, 1H), 3.96-3.94 (m, 2H), 3.67-3.65 (m, 2H), 3.51-3.48 (m, 2H), 3.42-3.41 (m, 1H), 2.98-2.97 (m, 2H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | f][1,2,4]triazin-4(3H)-one | | | | 2.83-2.79 (m, 2H), 2.74-2.72 (m, 1H), 2.33-2.31 (m, 1H), 1.87-1.81 (m, 4H), 1.08 (d, 3H); Mass (ESI): 400.3 [M+ + 1]; LC-MS: 94.64%; 400.3 (M+ + 1); (column; X-bridge C-18, (50 × 3.0 mm, 3.5 μm); RT 1.92 min. 0.05% TFA (Aq): ACN; 0.8 mL/min); UPLC (purity): 97.45%; (column: Acquity BEH C-18, 50 × 2.1 mm, 1.7μ; RT 1.35 min. 0.025% TFA (Aq): ACN; 0.5 mL/min.; Chiral HPLC: 98.18%, Rt = 8.22 min (Chiralpak IA, 250 × 4.6 mm, 5μ; mobile phase (A) 0.1% DEA in n-Hexane (B) CH2Cl2:MeOH (80:20) (A:B: 80:20); flow Rate: 1.0 mL/min); Optical rotation [α]D20: +29.88° (c = 0.25, CH2Cl2); TLC: 5% MeOH/CH2Cl2 (Rf: 0.5). |
| | 5-chlorothiophene-2-carbaldehyde | B | (+)-2-((3,4-trans)-1-((5-chlorothiophen-2-yl)methyl)-4-methylpyrrolidin-3-yl)-7-(tetrahydro-2H-pyran-4-yl)imidazo[5,1-f][1,2,4]triazin-4(3H)-one | A | 209 | 126 | 1H-NMR (DMSO-d6, 400 MHz): δ 11.63-1149 (bs, 1H), 7.64 (s, 1H), 6.95 (d, 1H), 6.85 (d, 1H), 3.96-3.94 (m, 2H), 3.67-3.65 (m, 2H), 3.51-3.48 (m, 2H), 3.42-3.41 (m, 1H), 2.98-2.85 (m, 4H), 2.72-2.65 (m, 1H), 2.33-2.31 (m, 1H), 1.87-1.81 (m, 4H), 1.08 (d, 3H); Mass (ESI): 434.4 [M+ + 1]; LC-MS: 95.07%; 434.6 (M+ + 1); (column; X- |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | bridge C-18 (50 × 3.0 mm, 3.5 μm); RT 2.74 min. 0.05% TFA (Aq): ACN; 0.8 mL/min); HPLC (purity): 95.09%; (column Eclipse XDB C-18, 150 × 4.6 mm, 5.0 μm; RT 10.41 min. 5 mM NH4OAc (Aq): ACN; 1.0 mL/min; Chiral HPLC: 98.33%, Rt = 12.04 min (Chiralpak IA, 250 × 4.6 mm, 5μ; mobile phase (A) 0.1% DEA in n-Hexane (B) CH2Cl2:MeOH (80:20) (A:B: 85:15); flow Rate: 1.0 mL/min); Optical rotation [α]D20: +10.99° (c = 0.25, CH2Cl2); TLC: 5% MeOH/CH2Cl2 (Rf: 0.5). |
| (−)-2-((3,4-trans)-4-methylpyrrolidin-3-yl)-7-(tetrahydro-2H-pyran-4-yl)imidazo[5,1-f][1,2,4]triazin-4(3H)-one | 5-chlorofuran-2-carbaldehyde | B | (+)-2-((3,4-trans)-1-((5-chlorofuran-2-yl)methyl)-4-methylpyrrolidin-3-yl)-7-(tetrahydro-2H-pyran-4-yl)imidazo[5,1-f][1,2,4]triazin-4(3H)-one | A | 653 | 476 | 1H-NMR (DMSO-d6, 400 MHz): δ 11.80-11.22 (br s, 1H), 7.64 (s, 1H), 6.45 (d, 2H), 3.96-3.94 (m, 2H), 3.67-3.65 (m, 2H), 3.51-3.48 (m, 3H), 3.42-3.41 (m, 1H), 2.98-2.85 (m, 1H), 2.72-2.65 (m, 2H), 2.33-2.31 (m, 2H), 2.30-2.25 (m, 1H), 1.87-1.81 (m, 4H), 1.08 (d, 3H); Mass (ESI): 418.2 [M+ + 1]; LC-MS: 97.20%; 418.2 (M+ + 1); (column: X-bridge C-18, (50 × 3.0 mm, 3.5 μm); RT 2.02 min. 0.05% TFA (Aq): ACN; 0.8 mL/min); UPLC (purity): 98.39%; (column: Acquity BEH C-18, 50 × 2.1 mm, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 2-methoxy isonicotinaldehyde | B | (+)-2-((3,4-trans)-1-((2-methoxypyridin-4-yl)methyl)-4-methylpyrrolidin-3-yl)-7-(tetrahydro-2H-pyran-4-yl)imidazo[5,1-f][1,2,4]triazin-4(3H)-one | A | 317 | 607 | 1.7µ; RT 1.42 min. 0.025% TFA (Aq): ACN; 0.5 mL/min.; Chiral HPLC: 92.76%, Rt = 8.86 min (Chiralpak IA, 250 × 4.6 mm, 5 µm; mobile phase (A) 0.1% DEA in n-Hexane (B) CH2Cl2:MeOH (80:20) (A:B: 80:20); flow Rate: 1.00 mL/min); Optical rotation [α]D20: +35.48° (c = 0.25, CH2Cl2); TLC: 5% MeOH/CH2Cl2 (Rf: 0.5). 1H-NMR (DMSO-d6, 400 MHz): δ 8.10 (d, 1H), 7.64 (s, 1H), 6.95 (d, 1H), 6.75 (s, 1H), 3.96-3.94 (m, 2H), 3.85 (s, 3H), 3.65-3.55 (m, 2H), 3.45-3.41 (m, 2H), 3.35-3.33 (m, 1H), 2.95 (t, 1H), 2.85 (m, 1H), 2.75-2.70 (m, 2H), 2.65-2.60 (m, 1H), 2.45-2.40 (m, 1H), 1.87-1.81 (m, 4H), 1.08 (d, 3H); Mass (ESI): 425.3 [M+ + 1]; LC-MS: 97.73%; 425.4 (M+ + 1); (column; X-bridge C-18, (50 × 3.0 mm, 3.5 µm); RT 2.14 min. 0.05% TFA (Aq): ACN; 0.8 mL/min); UPLC (purity): 99.88%; (column: Acquity BEH C-18, 50 × 2.1 mm, 1.7µ; RT 1.29 min. 0.025% TFA (Aq): ACN; 0.5 mL/min.; Chiral HPLC: 99.21%, Rt = 10.96 min (Chiralpak IA, 250 × 4.6 mm, 5 µm; mobile |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | phase (A) 0.1% DEA in n-Hexane (B) CH2Cl2:MeOH (80:20) (A:B: 80:20); flow Rate: 1.00 mL/min); Optical rotation [α]D20: +10.76° (c = 0.25, CH2Cl2); TLC: 5% MeOH/CH2Cl2 (Rf: 0.5). |
| (−)-2-((3,4-trans)-4-methylpyrrolidin-3-yl)-7-(tetrahydro-2H-pyran-4-yl)imidazo[5,1-f][1,2,4]triazin-4(3H)-one | 6-(trifluoromethyl)picolinaldehyde | B | (+)-2-((3,4-trans)-4-methyl-1-((6-(trifluoromethyl)pyridin-2-yl)methyl)pyrrolidin-3-yl)-7-(tetrahydro-2H-pyran-4-yl)imidazo[5,1-f][1,2,4]triazin-4(3H)-one | A | 708 | 389 | 1H-NMR (DMSO-d6, 400 MHz): δ 11.70-11.35 (bs, 1H), 8.10 (t, 1H), 7.53 (m, 2H), 7.65 (s, 1H), 3.96-3.94 (m, 4H), 3.55-3.53 (m, 2H), 3.45-3.40 (m, 1H), 3.10-3.0 (m, 1H), 2.95-2.90 (m, 3H), 2.65-2.63 (m, 1H), 2.35-2.30 (m, 1H), 1.87-1.81 (m, 4H), 1.08 (d, 3H); Mass (ESI): 463 [M+ + 1]; LC-MS: 93.06%; 463.4 (M+ + 1); (column: X-bridge C-18, (50 × 3.0 mm, 3.5 μm); RT 2.19 min. 0.05% TFA (Aq): ACN; 0.8 mL/min); UPLC (purity): 92.09%; (column: Acquity BEH C-18, 50 × 2.1 mm, 1.7μ; RT 1.52 min. 0.025% TFA (Aq): ACN; 0.5 mL/min.; Chiral HPLC: 87.35%, Rt = 8.26 min (Chiralpak IA, 250 × 4.6 mm, 5μ; mobile phase (A) 0.1% DEA in n-Hexane (B) CH2Cl2:MeOH (80:20) (A:B: 80:20); flow Rate: 1.0 mL/min); Optical rotation [α]D20: +30.73° (c = 0.25, CH2Cl2). TLC: 5% |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | added 3-trifluoromethyl pyridine-2-carbaldehyde | B | (+)-2-((3,4-trans)-4-methyl-1-((3-(trifluoromethyl)pyridin-2-yl)methyl)pyrrolidin-3-yl)-7-(tetrahydro-2H-pyran-4-yl)imidazo[5,1-f][1,2,4]triazin-4(3H)-one | A | 123 | 58 | MeOH/CH2Cl2 (Rf: 0.5). 1H-NMR (DMSO-d6, 400 MHz): δ 8.85-8.80 (d, 1H), 8.20 (d, 1H), 7.70 (m, 1H), 7.60-7.55 (d, 1H), 4.10-4.00 (m, 1H), 3.96-3.94 (m, 3H), 3.72-3.60 (m, 2H), 3.48-3.25 (m, 1H), 3.12-3.08 (m, 1H), 2.95-2.94 (m, 2H), 2.84 (m, 1H), 2.57-2.50 (m, 1H), 2.30-2.27 (m, 1H), 1.84-1.79 (m, 4H), 1.08 (d, 3H); Mass (ESI): 463 [M+ + 1]; LC-MS: 95.19%; 463.4 (M+ + 1); (column: X-bridge C-18, (50 × 3.0 mm, 3.5 μm); RT 2.09 min. 0.05% TFA (Aq): ACN; 0.8 mL/min); UPLC (purity): 93.34%; (column: Acquity BEH C-18 (50 × 2.1 mm, 1.7 μm; RT 1.46 min. 0.025% TFA (Aq): ACN; 0.5 mL/min.; Chiral HPLC: 90.02%, Rt = 7.21 min (Chiralpak IA, 250 × 4.6 mm, 5μ; mobile phase (A) 0.1% DEA in n-Hexane (B) CH2Cl2:MeOH (80:20) (A:B: 80:20); flow Rate: 1.0 mL/min); Optical rotation [α]D20: +104.36° (c = 0.25%, CH2Cl2); TLC: 10% MeOH/CH2Cl2 (Rf: 0.5). |
| (−)-2-((3,4-trans)-4-methylpyrrolidin-3-yl)-7- | 5-fluoropicolinaldehyde | B | (+)-2-((3,4-trans)-1-((5-fluoropyridin-2-yl)methyl)- | A | 273 | 377 | 1H-NMR (DMSO-d6, 400 MHz): δ 8.49 (s, 1H), 7.71-7.65 (m, 2H), 7.49-7.43 (m, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (tetrahydro-2H-pyran-4-yl)imidazo[5,1-f][1,2,4]triazin-4(3H)-one | | | 4-methylpyrrolidin-3-yl)-7-(tetrahydro-2H-pyran-4-yl)imidazo[5,1-f][1,2,4]triazin-4(3H)-one | | | | 3.94-3.90 (m, 2H), 3.73 (q, 2H), 3.51-3.48 (m, 3H), 2.99-2.89 (m, 2H), 2.88-2.77 (m, 2H), 2.68-2.60 (m, 1H), 2.30 (t, 1H), 1.89-1.79 (m, 4H), 1.09 (d, 3H); Mass (ESI): 413 [M+ +1]; LC-MS: 92.22%; 413 (M+ +1); (column: X-bridge C-18, (50 × 3.0 mm, 3.5 µm); RT 2.78 min. mobile phase A: 5.0 mM NH4OAc, B: ACN (Gradient) Flow rate: 0.8 mL/min); HPLC (purity): 91.61%; (column: Eclipse XDB-C18 (150 × 4.6 mm, 5.0 µm); RT 8.48 min. ACN: 5 mM NH4OAc (aq); 1.0 mL/min.; Chiral HPLC: 92.53%, Rt = 9.94 min (Chiralpak IA, 250 × 4.6 mm, 5µ; mobile phase (A) 0.1% DEA in n-Hexane (B) CH2Cl2:MeOH (80:20) (A:B: 80:20); flow Rate: 1.0 mL/min); Optical rotation [α]D20: +56.70° (c = 0.25, CH2Cl2). TLC: 10% MeOH/CH2Cl2 (Rf: 0.4). |
| (−)-2-((3,4-trans)-4-methylpyrrolidin-3-yl)-7-(tetrahydro-2H-pyran-4-yl)imidazo[5,1-f][1,2,4]triazin-4(3H)-one | 8-fluoroquinoline-2-carbaldehyde | B | (+)-2-((3,4-trans)-1-((8-fluoroquinolin-2-yl)methyl)-4-methylpyrrolidin-3-yl)-7-(tetrahydro-2H-pyran-4-yl)imidazo[5,1-f][1,2,4]triazin- | A | 39 | 76 | 1H-NMR (DMSO-d6, 400 MHz): δ 8.41 (d, 1H), 7.80 (d, 1H), 7.73 (d, 1H), 7.66 (s, 1H), 7.57 (d, 2H), 4.00-3.88 (m, 3H), 3.52-3.48 (m, 2H), 3.07-3.04 (m, 2H), 2.98 (t, 2H), 2.91-2.80 (m, 2H), 1.72-1.68 (m, 1H), 1.39-1.37 (m, 1H), 1.91-1.80 (m, 4H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | 4(3H)-one | | | | 1.10 (d, 3H); Mass (ESI): 463.3 [M+ + 1]; LC-MS: 95.20%; 464.3 (M+ + 1); (column: X-bridge C-18, (50 × 3.0 mm, 3.5 μm); RT 2.99 min. mobile phase A: 5.0 mM NH4OAc, B: ACN (Gradient) Flow rate: 0.8 mL/min); HPLC (purity): 98.35%; (column: Eclipse XDB-C18 (150 × 4.6 mm, 5.0 μm); RT 9.37 min. ACN: 5 mM NH4OAc (aq.); 1.0 mL/min; Chiral HPLC: 94.21%, Rt = 15.33 min (Chiralpak IA, 250 × 4.6 mm, 5μ mobile phase (A) 0.1% TFA in n-Hexane (B) CH2Cl2:MeOH (80:20) (A:B: 80:20); flow Rate: 1.0 mL/min); Optical rotation [α]D20: +31.68° (c = 0.25, CH2Cl2); TLC: 10% MeOH/CH2Cl2 (Rf: 0.5). |
| (−)-2-((3,4-trans)-4-methylpyrrolidin-3-yl)-7-(tetrahydro-2H-pyran-4-yl)imidazo[5,1-f][1,2,4]triazin-4(3H)-one | 1-methyl-1H-pyrazole-5-carbaldehyde | B | (+)-2-((3,4-trans)-4-methyl-1-((1-methyl-1H-pyrazol-5-yl)methyl)pyrrolidin-3-yl)-7-(tetrahydro-2H-pyran-4-yl)imidazo[5,1-f][1,2,4]triazin-4(3H)-one | A | 243 | 370 | 1H-NMR (DMSO-d6, 400 MHz): δ 11.60-11.50 (bs, 1H), 7.62 (s, 1H), 7.30 (s, 1H), 6.11 (s, 1H), 3.98-3.94 (m, 2H), 3.80 (s, 3H), 3.72-3.68 (m, 2H), 3.62-3.58 (m, 2H), 3.42-3.40 (m, 1H), 2.98-2.96 (m, 1H), 2.92-2.88 (m, 1H), 2.78-2.74 (m, 2H), 2.62-2.56 (m, 1H), 2.26-2.22 (m, 1H), 1.90-1.84 (m, 4H), 1.08 (d, 3H); Mass (ESI): 398.3 [M+ + 1]; LC-MS: 97.17%; 398.3 (M+ + 1); |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | (column: X-bridge C-18, (50 × 3.0 mm, 3.5 μm); RT 3.34 min. 5 mM NH4OAc: ACN; 0.8 mL/min); UPLC (purity): 99.25%; (column: Acquity UPLC HSS T3 (2.1 × 100 mm, 1.8μ; RT 2.90 min. 0.025% TFA (Aq): ACN; 0.3 mL/min.; Chiral HPLC: 96.15%, Rt = 12.52 min (Chiralpak IA, 250 × 4.6 mm, 5μ; mobile phase (A) 0.1% DEA in n-Hexane (B) CH2Cl2:MeOH (80:20) (A:B :: 80:20); flow Rate: 1.0 mL/min); Optical rotation [α]D20: +20.75° (c = 0.25, CH2Cl2); TLC: 5% MeOH/CH2Cl2 (Rf: 0.4). |
| (−)-2-((3,4-trans)-4-methylpyrrolidin-3-yl)-7-(tetrahydro-2H-pyran-4-yl)imidazo[5,1-f][1,2,4]triazin-4(3H)-one | furan-2-carbaldehyde | B | (+)-2-((3,4-trans)-1-(furan-2-ylmethyl)-4-methylpyrrolidin-3-yl)-7-(tetrahydro-2H-pyran-4-yl)imidazo[5,1-f][1,2,4]triazin-4(3H)-one | A | 161 | 149 | 1H-NMR (DMSO-d6, 400 MHz): δ 7.67 (s, 1H), 7.59-7.56 (m, 1H), 6.42-6.38 (m, 1H), 6.31-6.26 (m, 1H), 4.02-3.98 (m, 2H), 3.78-3.72 (m, 2H), 3.62-3.48 (m, 2H), 3.62-3.48 (m, 1H), 3.10-2.90 (m, 1H), 2.90-2.85 (m, 1H), 2.65-2.60 (m, 2H), 2.50-2.45 (m, 1H), 2.35-2.30 (m, 1H), 1.92-1.82 (m, 4H), 1.12 (d. 3H); Mass (ESI): 384.3 [M+ + 1]; LC-MS: 93.82%; 384.3 (M+ + 1); (column: X-bridge C-18 (50 × 3.0 mm, 3.5 μm); RT 2.77 min. 5 mM NH4OAc: ACN: 0.8 mL/min); |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | | | | | UPLC (purity): 96.25%; (column: Acquity BEH C-18, 50 × 2.1 mm, 1.7μ; RT 1.25 min. 0.025% TFA: ACN; 0.5 mL/min.; Chiral HPLC: 95.57%, Rt = 9.33 min (Chiralpak IA, 250 × 4.6 mm, 5 μm; mobile phase (A) 0.1% DEA in n-Hexane (B) CH2Cl2:MeOH (80:20) (A:B :: 80:20); flow Rate: 1.0 mL/min); Optical rotation [α]D20: +33.20° (c = 0.25, CH2Cl2); TLC: 5% MeOH/CH2Cl2 (Rf 0.4). |
| | 5-(trifluoromethyl) picolinal dehyde ( | B | (+)-2-((3,4-trans)-4-methyl-1-((5-(trifluoromethyl)pyridin-2-yl)methyl)pyrrolidin-3-yl)-7-(tetrahydro-2H-pyran-4-yl)imidazo[5,1-f][1,2,4]triazin-4(3H)-one | A | 258 | 560 | 1H-NMR (DMSO-d6, 400 MHz): δ 11.70-11.40 (bs, 1H), 8.90 (s, 1H), 8.20 (d, 1H), 7.78 (m, 2H), 3.98-3.90 (m, 4H), 3.52-3.48 (m, 2H), 3.38-3.36 (m, 1H), 3.02-2.96 (m, 2H), 2.92-2.88 (m, 2H), 2.62-2.60 (m, 1H), 2.40-2.38 (m, 1H), 1.91-1.87 (m, 4H), 1.12 (d, 3H); Mass (ESI): 463.2 [M+ + 1]; LC-MS: 96.76%; 463.4 (M+ + 1); (column; X-bridge C-18, (50 × 3.0 mm, 3.5 μm); RT 2.76 min. 0.05% TEA (Aq); ACN; 0.8 mL/min); UPLC (purity): 99.31%; (column: Acquity BEH C-18, 50 × 2.1 mm, 1.7 μm; RT 1.54 min. 0.025% TFA (Aq); ACN; 0.5 mL/min.; Chiral HPLC: 100%, Rt = 11.29 min (Chiralpak |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | IA, 250 × 4.6 mm, 5 μm; mobile phase (A) 0.1% DEA in n-Hexane (B) CH2Cl2:MeOH (80:20) (A:B:85:15); flow Rate: 1.0 mL/min); Optical rotation [α]D19.99: +84.01° (c = 0.25, CH2Cl2); TLC: 5% MeOH/CH2Cl2 (Rf: 0.5). |
| (−)-2-((3,4-trans)-4-methylpyrrolidin-3-yl)-7-(tetrahydro-2H-pyran-4-yl)imidazo[5,1-f][1,2,4]triazin-4(3H)-one | 1-methyl-1H-pyrazole-4-carbaldehyde | B | (+)-2-((3,4-trans)-4-methyl-1-((1-methyl-1H-pyrazol-4-yl)methyl)pyrrolidin-4-yl)-7-(tetrahydro-2H-pyran-4-yl)imidazo[5,1-f][1,2,4]triazin-4(3H)-one | A | 247 | 434 | 1H-NMR (DMSO-d6, 400 MHz): δ 7.67 (s, 1H), 7.55 (s, 1H), 7.30 (s, 1H), 3.96-3.94 (m, 2H), 3.75 (s, 3H), 3.50-3.45 (m, 3H), 3.35-3.30 (m, 2H), 2.98-2.97 (m, 1H), 2.85-2.80 (m, 1H), 2.74-2.72 (m, 2H), 2.60-2.55 (m, 1H), 2.21 (t, 1H), 1.87-1.81 (m, 4H), 1.08 (d, 3H); Mass (ESI): 398.3 [M+ + 1]; LC-MS: 94.98%; 398.3 (M+ + 1); (column; Eclipse XDB C-18, 150 × 4.6 mm, 5.0 um); RT 5.82 min. 0.05% TFA (Aq); ACN; 1.0 mL/min); UPLC (purity): 97.47%; (column: Acquity UPLC HSS T3 (2.1 × 100 mm, 1.8 u), RT 2.88 min. 0.025% TFA (Aq): ACN; 0.3 mL/min. Chiral HPLC: 96.41%, Rt = 22.05 min (Chiralpak IA, 250 × 4.6 mm, 5μ mobile phase (A) 0.1% DEA in n-Hexane (B) CH2Cl2:MeOH (80:20) (A:B :: 85:15); flow Rate: 1.0 mL/min); Optical |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-4-yl)-7-(tetrahydro-2H-pyran-4-yl)imidazo[5,1-f][1,2,4]triazin-4(3H)-one | 3-methylpicolinaldehyde | B | (+)-2-((3,4-trans)-4-methyl-1-((3-methylpyridin-2-yl)methyl)pyrrolidin-3-yl)-7-(tetrahydro-2H-pyran-4-yl)imidazo[5,1-f][1,2,4]triazin-4(3H)-one | A | 242 | 298 | rotation [α]D20: +20.56° (c = 0.25, CH2Cl2); TLC: 5% MeOH/CH2Cl2 (Rf: 0.5). 1H-NMR (DMSO-d6, 400 MHz): δ 8.32 (d, 1H), 7.64 (s, 1H), 7.54 (d, 1H), 7.18 (t, 1H), 3.94-3.92 (m, 2H), 3.78 (q, 2H), 3.52-3.46 (m, 2H), 3.42 (m, 1H), 2.98 (t, 1H), 2.88-2.86 (m, 2H), 2.80 (t, 1H), 2.58-2.56 (m, 1H), 2.34 (s, 3H), 2.24 (t, 1H), 1.88-1.74 (m, 4H), 1.08 (d, 3H); Mass (ESI): 409.4 [M+ + 1]; LC-MS: 98.30%; 409 (M+ + 1); (column; X-bridge C-18, (50 × 3.0 mm, 3.5 μm); RT 2.90 min. 5 mM NH4OAc: ACN; 0.8 mL/min); HPLC (purity): 98.77%; (column; Eclipse XDB-C18 (150 × 4.6 mm, 5.0 μm); RT 9.04 min. ACN: 5 mM NH4OAc 1.0 mL/min; Chiral HPLC: 99.30%, Rt = 12.22 min (Chiralpak IA, 250 × 4.6 mm, 5 μm; mobile phase (A) 0.1% DEA in n-Hexane (B) CH2Cl2:MeOH (80:20) (A:B :: 85:15); flow Rate: 1.0 mL/min); Optical rotation [α]D20: +94.94° (c = 0.25, CH2Cl2); TLC: 10% MeOH/CH2Cl2 (Rf: 0.6). |
| (−)-2-((3,4-trans)-4-methylpyrrolidin- | 4-(pyridin-4- | B | (−)-2-((3,4-trans)-4-methyl-1-(4- | A | 679 | 1560 | 1H-NMR (DMSO-d6, 400 MHz): δ 8.61 (d, 2H), 7.76 (d, 2H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| 3-yl)-7-(tetrahydro-2H-pyran-4-yl)imidazo[5,1-f][1,2,4]triazin-4(3H)-one | y)benzaldehyde | | (pyridin-4-yl)benzyl)pyrrolidin-3-yl)-7-(tetrahydro-2H-pyran-4-yl)imidazo[5,1-f][1,2,4]triazin-4(3H)-one | | | | 7.64 (d, 2H), 7.62 (s, 1H), 7.44 (d, 2H), 3.84 (d, 2H), 3.62 (q, 2H), 3.53-3.51 (m, 2H), 3.41-3.39 (m, 1H), 3.38-3.08 (m, 1H), 2.88 (t, 1H), 2.82-2.76 (m, 2H), 2.64-2.62 (m, 1H), 2.26-2.24 (m, 1H), 1.86-1.78 (m, 4H), 1.08 (d, 3H); Mass (ESI): 471.4 [M+ + 1]; LC-MS: 98.28%; 471.4 (M+ + 1); (column; X-bridge C-18, (50 × 3.0 mm, 3.5 μm; RT 4.01 min. 5 mM NH4OAc: ACN; 0.8 mL/min); HPLC: (purity): 98.96%; (column: Eclipse XDB-C18, 150 × 4.6 mm, 5.0 μm; RT 9.50 min. ACN: 5 mM NH4OAc; 1.0 mL/min.; Chiral HPLC: 99.82%, Rt = 18.25 min (Chiralpak IA, 250 × 4.6 mm, 5μ; mobile phase (A) 0.1% DEA in n-Hexane (B) CH2Cl2:MeOH (80:20) (A:B :: 80:20); flow Rate: 1.0 mL/min); Optical rotation [α]D20: −3.088° (c = 0.25, CH2Cl2); TLC: 10% MeOH/CH2Cl2 (Rf: 0.6). |
| (−)-2-((3,4-trans)-4-methylpyrrolidin-3-yl)-7-(tetrahydro-2H-pyran-4-yl)imidazo[5,1-f][1,2,4]triazin-4(3H)-one | 1-methyl-1H-pyrazole-3-carbaldehyde | B | (+)-2-((3,4-trans)-4-methyl-1-((1-methyl-1H-pyrazol-3-yl)methyl)pyrrolidin-3-yl)-7-(tetrahydro-2H-pyran-4-yl)imidazo[5,1-f][1,2,4]triazin-4(3H)-one | A | 628 | 721 | 1H-NMR (DMSO-d6, 400 MHz): δ 7.68 (s, 1H), 7.57 (s, 1H), 6.12 (s, 1H), 3.94-3.92 (m, 2H), 3.80-3.77 (m, 3H), 3.64-3.60 (m, 2H), 3.46-3.42 (m, 2H), 3.36-3.34 (m, 1H), 2.96-2.92 (m, 2H), 2.81-2.77 (m, 2H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | f][1,2,4]triazin-4(3H)-one | | | | 2.61-2.59 (m, 1H), 2.28-2.26 (m, 1H), 1.88-1.84 (m, 4H), 1.12 (d, 3H); Mass (ESI): 398.3 [M+ + 1]; LC-MS: 94.16%; 398.3 (M+ + 1); (column; Eclipse XDB C-18 (150 × 4.6 mm, 5.0 μm); RT 5.94 min. 0.05% TFA: ACN: 1.0 mL/min); UPLC (purity): 96.05%; (column: Acquity BEH C-18, 50 × 2.1 mm, 1.7μ; RT 1.13 min. 0.025% TFA: ACN; 0.5 mL/min.; Chiral HPLC: 94.87%, Rt = 14.31 min (Chiralpak IA, 250 × 4.6 mm, 5μ; mobile phase (A) 0.1% DEA in n-Hexane (B) CH2Cl2:MeOH (80:20) (A:B :: 85:15); flow Rate: 1.0 mL/min); Optical rotation [α]D20,01: +43.55° (c = 0.25, CH2Cl2); TLC: 5% MeOH/CH2Cl2 (Rf: 0.7). |
| | 4-methoxypicolinaldehyde | B | (+)-2-((3,4-trans)-1-((4-methoxypyridin-2-yl)methyl)-4-methylpyrrolidin-3-yl)-7-(tetrahydro-2H-pyran-4-yl)imidazo[5,1-f][1,2,4]triazin-4(3H)-one | A | 466 | 456 | 1H-NMR (DMSO-d6, 400 MHz): δ 8.28 (d, 1H), 7.68 (s, 1H), 6.98 (s, 1H), 6.82 (d, 1H), 3.92 (d, 2H), 3.78 (s, 3H), 3.72 (d, 1H), 3.64 (d, 1H), 3.47-3.45 (m, 2H), 3.38-3.36 (m, 1H), 2.99-2.97 (m, 2H), 2.91-2.89 (m, 1H), 2.81-2.79 (m, 1H), 2.64-2.60 (m, 1H), 2.32-2.30 (m, 1H), 1.90-1.84 (m, 4H), 1.22 (d, 3H); Mass (ESI): 425.3 [M+ + 1]; LC-MS: 98.93%; |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | | | | | 425.4 (M+ + 1); (column; X-bridge C-18, (50 × 3.0 mm, 3.5 µm); RT 2.11 min. 0.05% TFA (Aq): ACN; 0.8 mL/min); UPLC (purity): 99.79%; (column: Acquity BEH C-18, 50 × 2.1 mm, 1.7µ; RT 1.31 min. 0.025% TFA (Aq): ACN; 0.5 mL/min.; Chiral HPLC: 99.66%, Rt = 9.44 min (Chiralpak IA, 250 × 4.6 mm, 5µ; mobile phase (A) 0.1% DEA in n-Hexane (B) CH2Cl2:MeOH (80:20) (A:B :: 80:20); flow Rate: 1.0 mL/min); Optical rotation [α]D20.02: +66.06° (c = 0.25, CH2Cl2); TLC: 5% MeOH/CH2Cl2 (Rf: 0.3). |
| (+)-2-((3,4-trans)-1-(benzo[c][1,2,5]thiadiazol-5-ylmethyl)-4-methylpyrrolidin-3-yl)-7-(tetrahydro-2H-pyran-4-yl)imidazo[5,1-f][1,2,4]triazin-4(3H)-one | benzo[c][1,2,5]thiadiazole-5-carbaldehyde | B | | A | 212 | 473 | 1H-NMR (DMSO-d6, 400 MHz): δ 8.05 (d, 1H), 8.00 (s, 1H), 7.73 (d, 1H), 7.65 (s, 1H), 3.93-3.90 (m, 2H), 3.86-3.82 (m, 2H), 3.60-3.56 (m, 3H), 3.04-3.00 (m, 1H), 2.98-2.94 (m, 1H), 2.88-2.84 (m, 2H), 2.66-2.61 (m, 1H), 2.34-2.32 (m, 1H), 1.88-1.84 (m, 4H), 1.12 (d, 3H); Mass (ESI): 452.2 [M+ + 1]; LC-MS: 99.68%; 452.3 (M+ + 1); (column; X-bridge C-18, (50 × 3.0 mm, 3.5 µm); RT 2.71 min. 0.05% aq. TFA: ACN; 0.8 mL/min); UPLC (purity): 99.34%; (column: Acquity BEH |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | | | | | C-18 (50 × 2.1 mm, 1.7μ; RT 1.40 min. 0.025% TFA (Aq): ACN; 0.5 mL/min.; Chiral HPLC: 97.86%, Rt = 11.72 min (Chiralpak IA, 250 × 4.6 mm, 5μ; mobile phase (A) 0.1% DEA in n-Hexane (B) CH2Cl2:MeOH (80:20) (A:B :: 80:20); flow Rate: 1.0 mL/min); Optical rotation [α]D19.99: +15.39° (c = 0.25, CH2Cl2); TLC: 5% MeOH/CH2Cl2 (Rf: 0.4). |
| | quinoline-8-carbaldehyde | B | (+)-2-((3,4-trans)-4-methyl-1-(quinolin-8-ylmethyl)pyrrolidin-3-yl)-7-(tetrahydro-2H-pyran-4-yl)imidazo[5,1-f][1,2,4]triazin-4(3H)-one | A | 647 | 673 | 1H-NMR (DMSO-d6, 400 MHz): δ 8.92 (d, 1H), 8.36 (d, 1H), 7.84 (dd, 2H), 7.64 (s, 1H), 7.58 (d, 1H), 7.56-7.54 (m, 1H), 4.32 (d, 2H), 3.92 (d, 2H), 3.50-3.46 (m, 3H), 3.06-3.02 (m, 2H), 2.86-2.84 (m, 1H), 2.64-2.62 (m, 1H), 2.54-2.52 (m, 1H), 2.39-2.37 (m, 1H), 1.86-1.80 (m, 4H), 1.12 (d, 3H); Mass (ESI): 445.3 [M+ + 1]; LC-MS: 93.17%; 445.4 (M+ + 1); (column; X-bridge C-18, (50 × 3.0 mm, 3.5 μm); RT 2.84 min. 0.05% TFA (Aq): ACN; 0.8 mL/min); UPLC (purity): 95.79%; (column: Acquity BEH C-18, (50 × 2.1 mm, 1.7μ); RT 1.49 min. ACN: 0.025% TFA (Aq), 0.5 mL/min.; Chiral HPLC: 95.59%, Rt = 13.24 min (Chiralpak IA, 250 × 4.6 mm, |

TABLE 3-continued

| SM name | Reagent | Method | Example name | Band | PDE9A2 IC$_{50}$ | PDE1A selectivity (versus PDE9A2) | PDE1B selectivity (versus PDE9A2) | Analytical Data |
|---|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | | | | | | 5 μm); mobile phase (A) 0.1% DEA in n-Hexane (B) CH2Cl2:MeOH (80:20) (A:B :: 85:15); flow Rate: 1.0 mL/min); Optical rotation [α]D19.99: +36.38° (c = 0.25, CH2Cl2); TLC: 5% MeOH/CH2Cl2 (Rf: 0.4). |
| | 1-methyl-1H-imidazole-5-carbaldehyde | B | (+)-2-((3,4-trans)-4-methyl-1-((1-methyl-1H-imidazol-5-yl)methyl)pyrrolidin-3-yl)-7-(tetrahydro-2H-pyran-4-yl)imidazo[5,1-f][1,2,4]triazin-4(3H)-one | A | | 214 | 456 | 1H-NMR (DMSO-d6, 400 MHz): δ 7.78 (s, 1H), 7.50 (s, 1H), 6.74 (s, 1H), 3.92 (d, 2H), 3.64 (s, 3H), 3.61 (d, 2H), 3.51-3.49 (m, 2H), 3.41-3.39 (m, 1H), 2.88 (t, 2H), 2.76-2.74 (m, 2H), 2.61-2.58 (m, 1H), 2.18-2.16 (m, 1H), 1.84-1.80 (m, 4H), 1.08 (d, 3H). Mass (ESI): 398.3 [M+ + 1]; LC-MS: 97.75%; 398.3 (M+ + 1); (column; Eclipse XDB-C18, (150 × 4.6 mm, 5.0 μm); RT 5.76 min. 0.05% TFA (Aq); ACN; 1.0 mL/min); UPLC (purity): 99.81%; (column: Acquity UPLC HSS T3, 2.1 × 100 mm, 1.8μ; RT 2.72 min. ACN: 0.025% TFA (Aq); 0.3 mL/min.; Chiral HPLC: 100%, Rt = 15.27 min (Chiralpak IA, 250 × 4.6 mm, 5μ mobile phase (A) 0.1% DEA in n-Hexane (B) CH2Cl2:MeOH (80:20) (A:B :: 80:20); flow Rate: 1.0 mL/min); Optical rotation [α]D20: +15.58° (c = 0.25, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 5-methoxy picolinaldehyde | B | (+)-2-((3,4-trans)-1-((5-methoxypyridin-2-yl)methyl)-4-methylpyrrolidin-3-yl)-7-(tetrahydro-2H-pyran-4-yl)imidazo[5,1-f][1,2,4]triazin-4(3H)-one | A | 216 | 540 | CH2Cl2); TLC: 10% MeOH/CH2Cl2 (Rf: 0.4). 1H-NMR (DMSO-d6, 400 MHz): δ 8.21 (s, 1H), 7.62 (s, 1H), 7.34-7.32 (m, 2H), 3.94 (d, 2H), 3.82 (s, 3H), 3.74-3.68 (m, 2H), 3.52-3.48 (m, 2H), 3.40-3.38 (m, 1H), 2.98-2.94 (m, 2H), 2.84-2.78 (m, 2H), 2.62-2.60 (m, 1H), 2.32-2.28 (m, 1H), 1.90-1.78 (m, 4H), 1.12 (d, 3H); Mass (ESI): 425.4 [M+ + 1]; LC-MS: 94.93%; 425.4 (M+ + 1); (column: X-bridge C-18, (50 × 3.0 mm, 3.5 μm); RT 2.59 min. 0.05% TFA (Aq): ACN; 0.8 mL/min); UPLC (purity): 98.30%; (column: Acquity BEH C-18, 50 × 2.1 mm, 1.7μ; RT 1.33 min. ACN: 0.025% TFA (Aq): 0.5 mL/min.; Chiral HPLC: 98.97%, Rt = 21.99 min (Chiralpak IA, 250 × 4.6 mm, 5μ; mobile phase (A) 0.1% DEA in n-Hexane (B) CH2Cl2:MeOH (80:20) (A:B :: 88:12); flow Rate: 1.0 mL/min); Optical rotation [α]D20: +68.99° (c = 0.25, CH2Cl2); TLC: 10% MeOH/CH2Cl2 (Rf: 0.4) |
| (−)-2-((3,4-trans)-4-methylpyrrolidin-3-yl)-7-(tetrahydro-2H-pyran-4- | tetrahydro-2H-pyran-4-carbaldehyde | B | (+)-2-((3,4-trans)-4-methyl-1-((tetrahydro-2H-pyran-4-yl)methyl)pyrrolidin- | A | 77 | 93 | 1H-NMR (DMSO-d6, 400 MHz): δ 7.61 (s, 1H), 3.94-3.92 (m, 2H), 3.80-3.78 (m, 2H), 3.46-3.42 (m, 2H), 3.36-3.34 (m, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | 3-yl)-7-(tetrahydro-2H-pyran-4-yl)imidazo[5,1-f][1,2,4]triazin-4(3H)-one | | | | 3.22-3.18 (m, 2H), 2.86-2.74 (m, 4H), 2.56-2.54 (m, 1H), 2.40-2.24 (m, 3H), 1.86-1.78 (m, 4H), 1.64-1.58 (m, 3H), 1.18-1.14 (m, 2H), 1.04 (d, 3H); Mass (ESI): 402.3 [M+ + 1]; LC-MS: 97.54%; 402.4 (M+ + 1); (column; X-bridge C-18, (50 × 3.0 mm, 3.5 μm); RT 2.32 min. 5 mM NH4OAc: ACN; 0.8 mL/min); UPLC (purity): 98.04%; (column; Acquity UPLC HSS T3 (2.1 × 100 mm, 1.8 μm); RT 2.92 min. ACN: 0.025% TFA (Aq); 0.3 mL/min.; Chiral HPLC: 98.31%, Rt = 9.29 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D20: +17.82° (c = 0.25, CH2Cl2); TLC: 10% MeOH/CH2Cl2 (Rf: 0.6). |
| | 1-methyl-1H-imidazole-2-carbaldehyde | B | (+)-2-((3,4-trans)-4-methyl-1-((1-methyl-1H-imidazol-2-yl)methyl)pyrrolidin-3-yl)-7-(tetrahydro-2H-pyran-4-yl)imidazo[5,1-f][1,2,4]triazin-4(3H)-one | A | 197 | 107 | 1H-NMR (DMSO-d6, 400 MHz): δ 7.64 (s, 1H), 7.05 (d, 1H), 6.71 (d, 1H), 3.94-3.92 (m, 2H), 3.68-3.66 (m, 2H), 3.62-3.58 (m, 3H), 3.52-3.50 (m, 2H), 3.40-3.38 (m, 1H), 2.92-2.88 (m, 2H), 2.80-2.76 (m, 2H), 2.61-2.59 (m, 1H), 2.26-2.24 (m, 1H), 1.86-1.82 (m, 4H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | | | | | 1.04 (d, 3H); Mass (ESI): 398.3 [M+ + 1]; LC-MS: 96.71%; 398.4 (M+ + 1); (column; XDB C-18, (150 × 4.6 mm, 5 μm); RT 6.08 min. 0.05% TFA: ACN; 1.0 mL/min); UPLC (purity): 98.46%; (column: Acquity BEH C-18 (50 × 2.1 mm, 1.7μm); RT 1.19 min. ACN: 0.025% TFA (Aq); 0.5 mL/min.; Chiral HPLC: 94.62%, Rt = 17.80 min (Chiralpak IC, 250 × 4.6 mm, 5 μm); mobile phase (A) 0.1% DEA in n-Hexane (B) CH2Cl2:MeOH (80:20) (A:B :: 60-40); flow Rate: 1.0 mL/min); Optical rotation [α]D20: +25.20° (c = 0.25, CH2Cl2); TLC: 10% MeOH/CH2Cl2 (Rf: 0.6). |
| | thiazole-2-carbaldehyde | B | (+)-2-((3,4-trans)-4-methyl-1-(thiazol-2-ylmethyl)pyrrolidin-3-yl)-7-(tetrahydro-2H-pyran-4-yl)imidazo[5,1-f][1,2,4]triazin-4(3H)-one | A | 150 | 147 | 1H-NMR (DMSO-d6, 400 MHz): δ 11.80-11.40 (br s, 1H), 7.70 (d, 3H), 4.10-3.98 (m, 4H), 3.56-3.54 (m, 2H), 3.46-3.44 (m, 1H), 3.10-3.08 (m, 1H), 2.98-2.96 (m, 2H), 2.84-2.82 (m, 1H), 2.64-2.62 (m, 1H), 2.54-2.52 (m, 1H), 1.86-1.82 (m, 4H), 1.12 (d, 3H). Mass (ESI): 401.3 [M+ + 1]; LC-MS: 98.90%; 401.4 (M+ + 1); (column; Eclipse XDB C-18, (150 × 4.6 mm, 5.0 μm); RT 6.16 min. 0.05% TFA (Aq): ACN; |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | [1,1′-biphenyl]-4- | B | (−)-2-((3,4-trans)-1-([1,1′-biphenyl]-4-ylmethyl)-4-methylpyrrolidin-3-yl)-7-(tetrahydro-2H-pyran-4-yl)imidazo[5,1-f][1,2,4]triazin-4(3H)-one | A | 2875 | 2060 | 1.0 mL/min); UPLC (purity): 99.44%; (column: Acquity BEH C-18, (50 × 2.1 mm, 1.7 μm); RT 1.14 min. ACN: 0.025% TFA (Aq); 0.5 mL/min; Chiral HPLC: 99.51%, Rt = 11.77 min (Chiralpak IA, 250 × 4.6 mm, 5 μm); mobile phase (A) 0.1% DEA in n-Hexane (B) CH2Cl2:MeOH (80:20) (A:B: 80 :: 20); flow Rate: 1.0 mL/min); Optical rotation [α]D20: +30.06° (c = 0.25, CH2Cl2). TLC: 10% MeOH/CH2Cl2 (Rf: 0.6). 1H-NMR (DMSO-d6, 400 MHz): δ 7.71 (s, 1H), 7.66-7.62 (m, 4H), 7.46-7.42 (m, 4H), 7.36 (t, 1H), 3.92 (d, 2H), 3.66-3.64 (m, 2H), 3.48-3.46 (m, 2H), 3.40-3.38 (m, 1H), 3.00-2.98 (m, 1H), 2.90-2.88 (m, 1H), 2.80-2.78 (m, 2H), 2.64-2.62 (m, 1H), 2.28-2.26 (m, 1H), 1.84-1.80 (m, 4H), 1.14 (d, 3H). Mass (ESI): 470 [M+ + 1]; LC-MS: 99.00%; 470 (M+ + 1); (column; X-bridge C-18, (50 × 3.0 mm, 3.5 μm); RT 2.71 min. 0.05% TFA (Aq); ACN: 0.8 mL/min); UPLC (purity): 98.44%; (column: Acquity BEH C-18, 50 × 2.1 mm, 1.7 μm); RT 1.83 min. ACN: 0.025% TFA |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | cyclopropanecarbaldehyde | B | (+)-2-((3,4-trans)-1-(cyclopropylmethyl)-4-methylpyrrolidin-3-yl)-7-(tetrahydro-2H-pyran-4-yl)imidazo[5,1-f][1,2,4]triazin-4(3H)-one | B | — | — | (Aq); 0.5 mL/min.; Chiral HPLC: 98.32%, Rt = 8.26 min (Chiralpak IA, 250 × 4.6 mm, 5 μm; mobile phase (A) 0.1% DEA in n-Hexane (B) CH2Cl2:MeOH (80:20) (A:B :: 80:20); flow Rate: 1.0 mL/min); Optical rotation [α]D20: −11.95° (c = 0.25, CH2Cl2). TLC: 10% MeOH/CH2Cl2 (Rf: 0.7). 1H-NMR (DMSO-d6, 400 MHz): δ 7.66 (s, 1H), 3.94 (d, 2H), 3.34-3.32 (m, 3H), 2.94-2.92 (m, 2H), 2.82-2.78 (m, 2H), 2.62-2.60 (m, 1H), 2.32-2.28 (m, 3H), 1.90-1.84 (m, 4H), 1.10 (d, 3H), 0.86-0.84 (m, 1H), 0.46-0.42 (m, 2H), 0.12-0.08 (m, 2H); Mass (ESI): 358 [M+ + 1]; LC-MS: 97.40%; 358 (M+ + 1); (column: X-bridge C-18, (50 × 3.0 mm, 3.5 μm); RT 2.59 min. 0.05% TFA (Aq): ACN; 0.8 mL/min); UPLC (purity): 96.16%; (column: Acquity BEH C-18, 50 × 2.1 mm, 1.7 μm); RT 1.15 min. ACN: 0.025% TFA (Aq); 0.5 mL/min.; Chiral HPLC: 94.68%, Rt = 7.26 min (Chiralpak IA, 250 × 4.6 mm, 5 μm; mobile phase (A) 0.1% DEA in n-Hexane (B) CH2Cl2:MeOH (80:20) (A:B :: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | cyclopentanecarbaldehyde | B | (+)-2-((3,4-trans)-1-(cyclopentylmethyl)-4-methylpyrrolidin-3-yl)-7-(tetrahydro-2H-pyran-4-yl)imidazo[5,1-f][1,2,4]triazin-4(3H)-one | A | — | — | 80:20); flow Rate: 1.0 mL/min); Optical rotation [α]D19.98: +4.52° (c = 0.25, CH2Cl2); TLC: 10% MeOH/CH2Cl2 (Rf: 0.8). 1H-NMR (DMSO-d6, 400 MHz): δ 7.64 (s, 1H), 3.92 (d, 2H), 3.52-3.48 (m, 4H), 2.96-2.94 (m, 1H), 2.84-2.82 (m, 2H), 2.72-2.70 (m, 1H), 2.60-2.58 (m, 1H), 2.42-2.36 (m, 2H), 2.18-2.16 (m, 1H), 2.02-1.98 (m, 1H), 1.90-1.86 (m, 3H), 1.72-1.68 (m, 2H), 1.54-1.48 (m, 4H), 1.22-1.18 (m, 2H), 1.08 (d, 3H); Mass (ESI): 386 [M+ + 1]; LC-MS: 386 [M+ + 1]; 98.57%; 386 (M+ + 1); (column: X-bridge C-18, 50 × 3.0 mm, 3.5 μm); RT 2.20 min. 0.05% TFA (Aq): ACN; 0.8 mL/min); UPLC (purity): 99.82%; (column: Acquity BEH C-18, 50 × 2.1 mm, 1.7 μm); RT 1.42 min. ACN: 0.025% TFA (Aq); 0.5 mL/min; Chiral HPLC: 99.07%, Rt = 7.21 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D19.99: +10.83° (c = 0.25, CH2Cl2); TLC: 10% |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | tert-butyl 4-formylpiperidine-1-carboxylate | B | (−)-tert-butyl (−)-4-((3,4-trans)-3-methyl-7-oxo-7-(tetrahydro-2H-pyran-4-yl)-3,4-dihydroimidazo[5,1-f][1,2,4]triazin-2-yl)pyrrolidin-1-yl)methyl)piperidine-1-carboxylate | A | 129 | 262 | MeOH/CH2Cl2 (Rf: 0.8). 1H-NMR (DMSO-d6, 400 MHz): δ 7.64 (s, 1H), 3.96-3.88 (m, 4H), 3.50-3.48 (m, 2H), 3.41-3.40 (m, 1H), 2.88-2.70 (m, 5H), 2.61-2.59 (m, 2H), 2.36-2.20 (m, 3H), 1.90-1.82 (m, 4H), 1.78-1.62 (m, 3H), 1.40 (s, 9H), 1.12 (d, 3H), 1.00-0.92 (m, 2H); Mass (ESI): 501 [M+ + 1]; LC-MS: 96.53%; 501 (M+ + 1); (column: XBridge C-18, 50 × 3.0 mm, 3.5 μm); RT 2.48 min. 0.05% TFA (aq.): ACN; 0.8 mL/min); HPLC (purity): 95.73%; (column: Eclipse-XDB-C-18, (150 × 4.6 mm, 5 μm); RT 11.52 min. ACN: 5 mM NH4OAc; 1.0 mL/min; Chiral HPLC: 94.51%, Rt = 14.46 min (Chiralpak IA, 250 × 4.6 mm, 5μ); mobile phase (A) 0.1% DEA in n-Hexane (B) CH2Cl2:MeOH (80:20) (A:B: 85:15); flow Rate: 1.0 mL/min); Optical rotation [α]D20: −5.68° (c = 0.25, CH2Cl2); TLC: 10% MeOH/CH2Cl2 (Rf: 0.6). |
| (−)-2-((3,4-trans)-4-methylpyrrolidin-3-yl)-7-(tetrahydro-2H-pyran-4-yl)imidazo[5,1- | oxazole-2-carbaldehyde | B | (+)-2-((3,4-trans)-4-methyl-1-(oxazol-2-ylmethyl)pyrrolidin-3-yl)-7-(tetrahydro- | A | 81 | 119 | 1H-NMR (DMSO-d6, 400 MHz): δ 11.70-11.40 (br s, 1H), 8.04 (s, 1H), 7.64 (d, 1H), 7.16 (d, 1H), 3.92 (d, 2H), 3.82-3.80 (m, 2H), 3.50-3.46 (m, 3H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | 2H-pyran-4-yl)imidazo[5,1-f][1,2,4]triazin-4(3H)-one | | | | 3.06-3.04 (m, 1H), 2.92-2.90 (m, 1H), 2.84-2.82 (m, 1H), 2.74-2.72 (m, 1H), 2.62-2.60 (m, 1H), 2.34-2.32 (m, 1H), 1.88-1.84 (m, 4H), 1.10 (d, 3H); Mass (ESI): 385.3 [M+ + 1]; LC-MS: 94.98%; 385.3 (M+ + 1); (column: X-bridge C-18, 50 × 3.0 mm, 3.5 μm); RT 2.44 min. 5 mM NH4OAc: ACN; 0.8 mL/min); UPLC (purity): 96.62%; (column: Acquity UPLC HSS T3, 2.1 × 100 mm, 1.8 μm); RT 2.87 min. ACN: 0.025% TFA (Aq): 0.3 mL/min.; Chiral HPLC: 94.03%, Rt = 14.87 min (Chiralpak IA, 250 × 4.6 mm, 5 μm; mobile phase (A) 0.1% DEA in n-Hexane (B) CH2Cl2:MeOH (80:20) (A:B :: 80:20); flow Rate: 1.0 mL/min); Optical rotation [α]D20: +27.90° (c = 0.25, CH2Cl2); TLC: 10% MeOH/CH2Cl2 (Rf: 0.8). |
| | 4,4-difluorocyclohexanecarbaldehyde | B | (+)-2-(3,4-trans)-1-((4,4-difluorocyclohexyl)methyl)-4-methylpyrrolidin-3-yl)-7-(tetrahydro-2H-pyran-4-yl)imidazo[5,1-f][1,2,4]triazin-4(3H)-one | A | 51 | 68 | 1H-NMR (DMSO-d6, 400 MHz): δ 7.66 (s, 1H), 3.94 (d, 2H), 3.51-3.49 (m, 2H), 3.40-3.38 (m, 1H), 2.90-2.88 (m, 2H), 2.80-2.78 (m, 2H), 2.60-2.58 (m, 1H), 2.32-2.28 (m, 2H), 2.20-2.18 (m, 1H), 2.02-1.98 (m, 2H), 1.90-1.76 (m, 8H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | 1.56-1.54 (m, 1H), 1.16-1.14 (m, 2H), 1.06 (d, 3H); Mass (ESI): 436 [M+ + 1]; LC-MS: 97.40%; 436.4 (M+ + 1); (column: X-bridge C-18, 50 × 3.0 mm, 3.5 μm); RT 3.20 min. 5 mM NH4OAc: ACN; 0.8 mL/min); HPLC (purity): 97.82%; (column: Eclipse XDB-C18, 150 × 4.6 mm, 5.0 μm); RT 10.10 min. ACN: 5 mM NH4OAc (Aq); 1.0 mL/min.; Chiral HPLC: 97.27%, Rt = 8.79 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D20: +7.28° (c = 0.25, CH2Cl2); TLC: 10% MeOH/CH2Cl2 (Rf: 0.8). |
| tert-butyl 4-(((3S,4S)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)piperidine-1-carboxylate | — | — | (+)-2-((3,4-trans)-4-methyl-1-(piperidin-4-ylmethyl)pyrrolidin-3-yl)-7-(tetrahydro-2H-pyran-4-yl)imidazo[5,1-f][1,2,4]triazin-4 (3H)-one | A | — | — | 1H-NMR (DMSO-d6, 400 MHz): δ 7.54 (s, 1H), 3.94 (d, 2H), 3.50-3.48 (m, 2H), 3.36-3.34 (m, 2H), 2.99 (d, 2H), 2.90-2.88 (m, 3H), 2.80-2.76 (m, 1H), 2.60-2.58 (m, 2H), 2.42-2.40 (m, 1H), 2.30-2.28 (m, 1H), 2.20-2.18 (m, 1H), 2.10-2.08 (m, 1H), 1.88-1.84 (m, 4H), 1.70-1.68 (m, 2H), 1.52-1.48 (m, 1H), 1.10-1.06 (d, 3H), 0.98-0.96 (m, 2H). Mass (ESI): 401.4 [M+ + 1]; LC-MS: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | | | | | 96.31%; 401.4 (M+ + 1); (column: X-bridge C-18, 50 × 3.0 mm, 3.5 μm); RT 2.00 min. 5 mM NH4OAc: ACN; 0.8 mL/min); UPLC (purity): 97.51%; (column: Acquity UPLC HSS T3; 2.1 × 100 mm, 1.8 μm); RT 2.72 min. ACN: 0.025% TFA (Aq); 0.3 mL/min.; Chiral HPLC: 99.38%, Rt = 15.34 min (Chiralpak IA, 250 × 4.6 mm, 5 μm); mobile phase (A) 0.1% DEA in n-Hexane (B) CH2Cl2:MeOH (80:20) (A:B :: 75:25); flow Rate: 1.0 mL/min); Optical rotation [α]D19.99: +8.65° (c = 0.25, CH2Cl2). TLC: 10% MeOH/CH2Cl2 (Rf: 0.4). |
| (+)-2-((3,4-trans)-4-methyl-1-((4,5,6,7-tetrahydropyrazolo[1,5-a]pyridin-3-yl)methyl)pyrrolidin-3-yl)-7-(tetrahydro-2H-pyran-4-yl)imidazo[5,1-f][1,2,4]triazin-4(3H)-one | 4,5,6,7-tetrahydropyrazolo[1,5-a]pyridine-3-carbaldehyde | B | | A | 337 | 337 | 1H-NMR (DMSO-d6, 400 MHz): δ 7.68 (s, 1H), 7.26 (s, 1H), 4.02-3.90 (m, 5H), 3.51-3.49 (m, 3H), 2.90-2.88 (m, 2H), 2.78-2.68 (m, 5H), 2.60-2.58 (m, 1H), 2.18-2.16 (m, 1H), 1.94-1.72 (m, 8H), 1.08 (d, 3H); Mass (ESI): 438.3 [M+ + 1]; LC-MS: 98.52%; 438 (M+ + 1); (column: X-bridge C-18, 50 × 3.0 mm, 3.5 μm); RT 1.97 min. 0.05% Aq TFA: ACN; 0.8 mL/min); UPLC (purity): 93.86%; (column: Acquity BEH C-18, (50 × 2.1 mm, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | | | | | 1.7μ); RT 1.28 min. ACN: 0.025% TFA (Aq); 0.5 mL/min.; Chiral HPLC: 91.74%, Rt = 11.88 min (Chiralpak IA, 250 × 4.6 mm, 5μ); mobile phase (A) 0.1% DEA in n-Hexane (B) CH2Cl2:MeOH (80:20) (A:B: 80:20); flow Rate: 1.0 mL/min); Optical rotation [α]D19.99: +15.60° (c = 0.25, CH2Cl2); TLC: 10% MeOH/CH2Cl2 (Rf: 0.6). |
| | 1-methylpiperidine-4-carbaldehyde | B | (+)-2-((3,4-trans)-4-methyl-1-((1-methylpiperidin-4-yl)methyl)pyrrolidin-3-yl)-7-(tetrahydro-2H-pyran-4-yl)imidazo[5,1-f][1,2,4]triazin-4(3H)-one | B | — | — | 1H-NMR (DMSO-d6, 400 MHz): δ 7.67 (s, 1H), 3.94 (d, 2H), 3.51-3.46 (m, 3H), 2.90-2.84 (m, 3H), 2.82-2.76 (m, 3H), 2.60-2.58 (m, 1H), 2.34-2.28 (m, 2H), 2.18-2.12 (m, 4H), 1.90-1.78 (m, 6H), 1.66-1.64 (m, 2H), 1.38-1.36 (m, 1H), 1.10-1.08 (m, 2H), 1.04 (d, 3H); Mass (ESI): 415.4 [M+ + 1]; LC-MS: 98.61%; 415.4 (M+ + 1); (column: X-bridge C-18, 50 × 3.0 mm, 3.5 μm); RT 2.69 min. 5 mM NH4OAc: ACN; 0.8 mL/min); UPLC (purity): 99.86%; (column: Acquity UPLC HSS T3, 2.1 × 100 mm, 1.8 μm); RT 0.97 min. ACN: 0.025% TFA (Aq); 0.3 mL/min.; Chiral HPLC: 99.72%, Rt = 8.98 min (Chiralpak IA, 250 × 4.6 mm, 5 μm); mobile |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)imidazo[5,1-f][1,2,4]triazin-4(3H)-one | | | | | | | phase (A) 0.1% DEA in n-Hexane (B) CH2Cl2:MeOH (80:20) (A:B: 80:20); flow Rate: 1.0 mL/min); Optical rotation [α]D20: +13.02° (c = 0.25, CH2Cl2); TLC: 10% MeOH/CH2Cl2 (Rf: 0.4). |
| | pyrazolo[1,5-a]pyridine-3-carbaldehyde | B | (+)-2-((3,4-trans)-4-methyl-1-(pyrazolo[1,5-a]pyridin-3-ylmethyl)pyrrolidin-3-yl)imidazo[5,1-f][1,2,4]triazin-4(3H)-one (tetrahydro-2H-pyran-4-yl)imidazo[5,1-f][1,2,4]triazin-4(3H)-one | A | 3240 | 1010 | 1H-NMR (DMSO-d6, 400 MHz): δ 8.62 (d, 1H), 7.92 (s, 1H), 7.70 (d, 1H), 7.62 (s, 1H), 7.11 (t, 1H), 6.81 (t, 1H), 3.91 (d, 2H), 3.80 (s, 2H), 3.51-3.49 (m, 1H), 3.41-3.39 (m, 1H), 3.36-3.34 (m, 1H), 2.91-2.89 (m, 2H), 2.84-2.81 (m, 2H), 2.62-2.60 (m, 1H), 2.24-2.22 (m, 1H), 1.86-1.82 (m, 4H), 1.12 (d, 3H); Mass (ESI): 434.4 [M+ + 1]; LC-MS: 99.89%; 434 (M+ + 1); (column; X-bridge C-18, (50 × 3.0 mm, 3.5 μm); RT 1.99 min. 0.05% TFA (Aq); ACN; 0.8 mL/min); UPLC (purity): 99.17%; (column: Acquity BEH C-18 (50 × 2.1 mm, 1.7 μm); RT 1.28 min. ACN: 0.025% TFA (Aq); 0.5 mL/min.; Chiral HPLC: 99.39%, Rt = 14.73 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D19.99: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 5-(chloromethyl)-1,2,4-oxadiazole | A | (+)-2-((3,4-trans)-1-((1,2,4-oxadiazol-5-yl)methyl)-4-methylpyrrolidin-3-yl)-7-(tetrahydro-2H-pyran-4-yl)imidazo[5,1-f][1,2,4]triazin-4(3H)-one | A | 650 | 1528 | +39.74° (c = 0.25, CH2Cl2); TLC: 10% MeOH/CH2Cl2 (Rf: 0.6) 1H-NMR (DMSO-d6, 400 MHz): δ 11.8 (b s, 1H), 8.96 (s, 1H), 7.68 (s, 1H), 4.08 (q, 2H), 3.90 (d, 2H), 3.50-3.48 (m, 2H), 3.12 (t, 1H), 3.00-2.96 (m, 2H), 2.80 (q, 1H), 2.62-2.60 (m, 1H), 2.42-2.40 (m, 1H), 1.88-1.84 (m, 4H), 1.10 (d, 3H); Mass (ESI): 386.3 [M+ + 1]; LC-MS: 91.08%; 386 (M+ + 1); (column; X-bridge C-18, 50 × 3.0 mm, 3.5 μm); RT 1.87 min. 0.05% TFA (Aq): ACN; 0.8 mL/min); UPLC (purity): 98.84%; (column: Acquity UPLC HSS T3, 2.1 × 100 mm, 1.8 μm); RT 2.96 min. ACN: 0.025% TFA (Aq); 0.3 mL/min.; Chiral HPLC: 97.11%, Rt = 17.35 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D20.01: +4.16° (c = 0.25, CH2Cl2); TLC: 10% MeOH/CH2Cl2 (Rf: 0.6). |
| (−)-2-((3,4-trans)-4-methylpyrrolidin-3-yl)-7-(tetrahydro-2H-pyran- | 3-(chloromethyl)-5-methyl-1,2,4- | A | (+)-2-((3,4-trans)-4-methyl-1-((5-methyl-1,2,4-oxadiazol-3-yl)methyl)pyrrolidin- | A | 20 | 21 | 1H-NMR (DMSO-d6, 400 MHz): δ 11.5 (m, 1H), 7.62 (s, 1H), 3.92 (d, 2H), 3.76 (q, 2H), 3.46 (t, 2H), 3.32-3.30 (m, 1H), 3.06 (t, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| y)imidazo[5,1-f][1,2,4]triazin-4(3H)-one | oxadiazole | | 3-yl)-7-(tetrahydro-2H-pyran-4-yl)imidazo[5,1-f][1,2,4]triazin-4(3H)-one | | | | 2.98 (t, 1H), 2.88 (t, 1H), 2.74 (q, 1H), 2.62-2.60 (m, 1H), 2.50 (s, 3H), 2.40-2.38 (m, 1H), 1.82-1.78 (m, 4H), 1.04 (d, 3H). Mass (ESI): 400.5 [M+ + 1]; LC-MS: 99.48%; 400 (M+ + 1); (column; X-bridge C-18, 50 × 3.0 mm, 3.5 µm); RT 1.87 min. 0.05% TFA (Aq); ACN: 0.8 mL/min); UPLC (purity): 97.48%; (column: Acquity BEH C-18, 50 × 2.1 mm, 1.7 µm); RT 1.14 min. ACN: 0.025% TFA (Aq); 0.5 mL/min.; Chiral HPLC: 98.38%, Rt = 9.80 min (Chiralpak IA, 250 × 4.6 mm, 5 µm); mobile phase (A) 0.1% DEA in n-Hexane (B) CH2Cl2:MeOH (80:20) (A:B: 80:20); flow Rate: 1.0 mL/min); Optical rotation [α]D19.99: +31.40° (c = 0.25, CH2Cl2). TLC: 10% MeOH/CH2Cl2 (Rf: 0.6). |
| (−)-2-((3,4-trans)-4-methylpyrrolidin-3-yl)-7-(tetrahydro-2H-pyran-4-yl)imidazo[5,1-f][1,2,4]triazin-4(3H)-one | 4-(chloromethyl)-2-methylthiazole | A | (+)-2-((3,4-trans)-4-methyl-1-((2-methylthiazol-4-yl)methyl)pyrrolidin-3-yl)-7-(tetrahydro-2H-pyran-4-yl)imidazo[5,1-f][1,2,4]triazin-4(3H)-one | A | 12 | 19 | 1H-NMR (DMSO-d6, 400 MHz): δ 7.62 (s, 1H), 7.26 (s, 1H), 3.92 (d, 2H), 3.70 (q, 2H), 3.50-3.42 (m, 3H), 3.00-2.92 (m, 3H), 2.78-2.74 (m, 1H), 2.60-2.50 (m, 4H), 2.26-2.24 (m, 1H), 1.82-1.72 (m, 4H), 1.04 (d, 3H). Mass (ESI): 415 [M+ + 1]; LC-MS: 97.97%; 415 (M+ + 1); (column; X-bridge C-18, 50 × 3.0 mm, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | 3-(chloromethyl)-1-methyl-1H-1,2,4-triazole hydrochloride | A | (+)-2-((3,4-trans)-4-methyl-1-((1-methyl-1H-1,2,4-triazol-3-yl)methyl)pyrrolidin-3-yl)-7-(tetrahydro-2H-pyran-4-yl)imidazo[5,1-f][1,2,4]triazin-4(3H)-one | A | 208 | 266 | 3.5 μm); RT 2.08 min. 0.05% TFA (Aq); ACN; 0.8 mL/min); UPLC (purity): 97.40%; (column: Acquity BEH C-18, 50 × 2.1 mm, 1.7 μm); RT 1.28 min. ACN: 0.025% TFA (Aq); 0.5 mL/min; Chiral HPLC: 93.00%, Rt = 8.04 min (Chiralpak IA, 250 × 4.6 mm, 5 μm; mobile phase (A) 0.1% DEA in n-Hexane (B) CH2Cl2:MeOH (80:20) (A:B: 80:20); flow Rate: 1.0 mL/min); Optical rotation [α]D20: +60.81° (c = 0.25, CH2Cl2); TLC: 10% MeOH/CH2Cl2 (Rf. 0.4). 1H-NMR (DMSO-d6, 400 MHz): δ 8.34 (s, 1H), 7.66 (s, 1H), 3.92 (d, 2H), 3.82 (s, 3H), 3.64 (q, 2H), 3.50 (t, 3H), 3.02-2.98 (m, 2H), 2.86 (t, 1H), 2.74 (q, 1H), 2.60 (t, 1H), 2.32 (t, 1H), 1.90-1.84 (m, 4H), 1.06 (d, 3H), Mass (ESI): 399.3 [M+ + 1]; LC-MS: 97.82%; 399 (M+ + 1); (column: X-bridge C-18, 50 × 3.0 mm, 3.5 μm); RT 1.41 min. 0.05% TFA (Aq); ACN; 0.8 mL/min); UPLC (purity): 97.57%; (column: Acquity UPLC HSS T3, 2.1 × 100 mm, 1.8 μm); RT 2.87 min. ACN: 0.025% TFA (Aq); 0.3 mL/min.; Chiral HPLC: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (−)-2-((3,4-trans)-4-methylpyrrolidin-3-yl)-7-(tetrahydro-2H-pyran-4-yl)imidazo[5,1-f][1,2,4]triazin-4(3H)-one | | | | | | | 94.56%, Rt = 19.01 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D20: +43.05° (c = 0.25, CH2Cl2). TLC: 10% MeOH/CH2Cl2 (Rf: 0.4). |
| | 3-(chloromethyl)-1,2,4-oxadiazole | A | (+)-2-((3,4-trans)-1-((1,2,4-oxadiazol-3-yl)methyl)-4-methylpyrrolidin-3-yl)-7-(tetrahydro-2H-pyran-4-yl)imidazo[5,1-f][1,2,4]triazin-4(3H)-one | A | 35 | 63 | 1H-NMR (DMSO-d6, 400 MHz): δ 11.70-11.50 (br s, 1H), 9.60 (s, 1H), 7.66 (s, 1H), 3.96-3.88 (m, 4H), 3.51-3.49 (m, 2H), 3.34-3.32 (m, 1H), 3.10 (t, 1H), 2.98 (t, 1H), 2.90 (t, 1H), 2.78-2.76 (m, 1H), 2.62-2.59 (m, 1H), 2.40-2.38 (m, 1H), 1.88-1.78 (m, 4H), 1.06 (d, 3H); Mass (ESI): 386.2 [M+ − 1]; LC-MS: 94.69%; 386.3 (M+ + 1); (column: X-bridge C-18, 50 × 3.0 mm, 3.5 μm); RT 2.53 min. 5 mM NH4OAc: ACN; 0.8 mL/min); UPLC (purity): 98.00%; (column: Acquity UPLC HSS T3; 2.1 × 100 mm, 1.8μ); RT 2.92 min. ACN: 0.025% TFA (Aq); 0.3 mL/min.; Chiral HPLC: 98.48%, Rt = 14.64 min (Chiralpak IA, 250 × 4.6 mm, 5 μm); mobile phase (A) 0.1% DEA in n-Hexane (B) CH2Cl2:MeOH (80:20) |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4,4-difluorocyclohexyl)-2-((3,4-trans)-4-methylpyrrolidin-3-yl) imidazo [5,1-f] [1,2,4] triazin-4 (3H)-one obtained from deprotection of (+)-2-((3,4-trans)-1-benzyl-4-methylpyrrolidin-3-yl)-7-(4,4-difluorocyclohexyl)imidazo[5,1-f][1,2,4]triazin-4(3H)-one | picolinaldehyde | B | (+)-7-(4,4-difluorocyclohexyl)-2-((3,4-trans)-4-methyl-1-(pyridin-2-ylmethyl)pyrrolidin-3-yl)imidazo[5,1-f][1,2,4]triazin-4(3H)-one | A | 167 | 362 | (A:B: 80:20); flow Rate: 1.0 mL/min); Optical rotation [α]D19.99: +27.18° (c = 0.25, CH2Cl2). TLC: 10% MeOH/CH2Cl2 (Rf: 0.4). 1H-NMR (DMSO-d6, 400 MHz): δ 8.48-8.46 (m, 1H), 7.76 (t, 1H), 7.64 (s, 1H), 7.42 (d, 1H), 7.28 (t, 1H), 3.78 (q, 2H), 3.00-2.92 (m, 2H), 2.88-2.87 (m, 1H), 2.71-2.70 (m, 2H), 2.64-2.62 (m, 1H), 2.34-2.32 (m, 1H), 2.18-2.12 (m, 2H), 2.06-1.86 (m, 6H), 1.12 (d. 3H); Mass (ESI): 429 [M+ + 1]; LC-MS: 99.45%; 429.3 (M+ + 1); (column; X-bridge C-18, (50 × 3.0 mm, 3.5 μm); RT 2.28 min. 0.05% TFA (aq.): ACN; 0.8 mL/min. UPLC (purity): 99.17%; (column: Acquity BEH C-18 (50 × 2.1 mm, 1.7μ); RT 1.61 min. ACN: 0.025% TFA (Aq); 0.5 mL/min. Chiral HPLC: 99.56%, Rt = 9.22 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D20.01: +66.89° (c = 0.25, CH2Cl2); TLC: 10% MeOH/CH2Cl2 (Rf: 0.4). |
| The enantiomer of 7-(4,4-difluorocyclohexyl) | nicotinaldehyde | B | (+)-7-(4,4-difluorocyclohexyl)- | A | 181 | 409 | 1H-NMR (DMSO-d6, 400 MHz): δ 8.52 (s, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| difluorocyclohexyl)-2-((3,4-trans)-4-methylpyrrolidin-3-yl) imidazo [5,1-f] [1,2,4] triazin-4 (3H)-one obtained from deprotection of (+)-2-((3,4-trans)-1-benzyl-4-methylpyrrolidin-3-yl)-7-(4,4-difluorocyclohexyl)imidazo[5,1-f][1,2,4]triazin-4(3H)-one | | | 2-((3,4-trans)-4-methyl-1-(pyridin-3-ylmethyl)pyrrolidin-3-yl)imidazo[5,1-f][1,2,4]triazin-4(3H)-one | | | | 1H), 8.45-8.44 (m, 1H), 7.70 (d, 1H), 7.63 (s, 1H), 7.34-7.32 (m, 1H), 3.65 (q, 2H), 3.32-3.30 (m, 1H), 2.94-2.89 (m, 4H), 2.68-2.66 (m, 1H), 2.28-2.26 (m, 1H), 2.16-2.12 (m, 2H), 2.02-1.94 (m, 6H), 1.10 (d, 3H); Mass (ESI): 429 [M+ + 1]; LC-MS: 99.37%; 429.3 (M+ + 1); (column; X-bridge C-18, 50 × 3.0 mm, 3.5 μm); RT 1.99 min. 0.05% TFA (aq.): ACN; 0.8 mL/min); UPLC (purity): 98.45%; (column: Acquity BEH C-18; 50 × 2.1 mm, 1.7μ); RT 1.42 min. ACN: 0.025% TFA (Aq); 0.5 mL/min.; Chiral HPLC: 96.38%, Rt = 10.79 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D19.99: +14.38° (c = 0.25, CH2Cl2); TLC: 10% MeOH/CH2Cl2 (Rf: 0.5). |
| The enantiomer of 7-(4,4-difluorocyclohexyl)-2-((3,4-trans)-4-methylpyrrolidin-3-yl) imidazo [5,1-f] [1,2,4] triazin-4 (3H)-one obtained from deprotection of (+)-2-((3,4-trans)- | 2-(chloromethyl)-1H-benzo[d]imidazole | A | (+)-2-(3,4-trans)-1-((1H-benzo[d]imidazol-2-yl)methyl)-4-methylpyrrolidin-3-yl)-7-(4,4-difluorocyclohexyl)imidazo[5,1-f][1,2,4]triazin-4(3H)-one | A | 90 | 250 | 1H-NMR (CD3OD-d4, 400 MHz): δ 7.71 (s, 1H), 7.54-7.52 (m, 2H), 7.24-7.22 (m, 2H), 4.00 (s, 2H), 3.36-3.34 (m, 1H), 3.20 (t, 1H), 3.12-3.09 (m, 2H), 2.91-2.90 (m, 1H), 2.71-2.69 (m, 1H), 2.40 (t, 1H), 2.20-1.96 (m, 8H), 1.20 (d, 3H); Mass (ESI): |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| 1-benzyl-4-methylpyrrolidin-3-yl)-7-(4,4-difluorocyclohexyl)imidazo[5,1-f][1,2,4]triazin-4(3H)-one | | | | | | | 468 [M+ + 1]; LC-MS: 94.64%; 468.4 (M+ + 1); (column: X-bridge C-18, 50 × 3.0 mm, 3.5 µm); RT 2.46 min. 0.05% TFA (aq.): ACN; 0.8 mL/min); UPLC (purity): 97.20%; (column: Acquity BEH C-18; 50 × 2.1 mm, 1.7µ); RT 1.71 min. ACN: 0.025% TFA (Aq); 0.5 mL/min. Chiral HPLC: 93.30%, Rt = 8.44 min (Chiralpak IA, 250 × 4.6 mm, 5 µm); mobile phase (A) 0.1% DEA in n-Hexane (B) CH2Cl2:MeOH (80:20) (A:B: 80:20); flow Rate: 1.0 mL/min); Optical rotation [α]D20.01: +10.06° (c = 0.25, CH2Cl2); TLC: 10% MeOH/CH2Cl2 (Rf: 0.4). |
| The enantiomer of 7-(4,4-difluorocyclohexyl)-2-((3,4-trans)-4-methylpyrrolidin-3-yl) imidazo [5, 1-f] [1,2,4] triazin-4 (3H)-one obtained from deprotection of (+)-2-((3,4-trans)-1-benzyl-4-methylpyrrolidin-3-yl)-7-(4,4-difluorocyclohexyl)imidazo[5,1-f][1,2,4]triazin-4(3H)-one | 2-(chloromethyl) imidazo [1,2-a] pyridine | A | (+)-7-(4,4-difluorocyclohexyl)-2-(3,4-trans)-1-(imidazo[1,2-a]pyridin-2-ylmethyl)-4-methylpyrrolidin-3-yl)imidazo[5,1-f][1,2,4]triazin-4(3H)-one | A | 405 | 1659 | 1H-NMR (DMSO-d6, 400 MHz): δ 8.46 (d, 1H), 7.80 (s, 1H), 7.60-7.59 (m, 1H), 7.46 (d, 1H), 7.20 (t, 1H), 6.80 (t, 1H), 3.70 (q, 2H), 3.06 (t, 1H), 2.96 (t, 1H), 2.90-2.88 (m, 1H), 2.76-2.74 (m, 2H), 2.64-2.62 (m, 1H), 2.38-2.36 (m, 1H), 2.10-2.08 (m, 2H), 2.00-1.86 (m, 6H), 1.06 (d, 3H); Mass (ESI): 468.4 [M+ + 1]; LC-MS: 95.50%; 468.4 (M+ + 1); (column; X-bridge C-18, (50 × 3.0 mm, 3.5 µm); RT 2.61 min. 0.05% TFA (aq.): ACN; 0.8 mL/min); UPLC (purity): 97.88%; |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4,4-difluorocyclohexyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4,4-difluorocyclohexyl)imidazo[5,1-f][1,2,4]triazin-4(3H)-one | 2-(chloromethyl)pyrazine | A | (+)-7-(4,4-difluorocyclohexyl)-2-((3,4-trans)-4-methyl-1-(pyrazin-2-yl)methyl)pyrrolidin-3-yl)imidazo[5,1-f][1,2,4]triazin-4(3H)-one | A | 233 | 575 | (column: Acquity BEH C-18 (50 × 2.1 mm, 1.7μ); RT 1.50 min. ACN: 0.025% TFA (Aq); 0.5 mL/min. Chiral HPLC: 92.33%, Rt = 11.23 min (Chiralpak IC, 250 × 4.6 mm, 5 μm); mobile phase (A) 0.1% DEA in n-Hexane (B) CH2Cl2:MeOH (80:20) (A:B: 60:40); flow Rate: 1.0 mL/min); Optical rotation [α]D19.99: +4.44° (c = 0.25, MeOH); TLC: 10% MeOH/CH2Cl2 (Rf: 0.5). 1H-NMR (DMSO-d6, 400 MHz): δ 11.60 (br s, 1H), 8.72 (s, 1H), 8.58 (d, 2H), 7.70 (s, 1H), 3.90 (d, 1H), 3.80 (d, 1H), 3.00-2.94 (m, 3H), 2.82-2.80 (m, 1H), 2.66-2.64 (m, 1H), 2.34-2.32 (m, 1H), 2.20-1.86 (m, 8H), 1.10 (d, 3H); Mass (ESI): 430.3 [M+ + 1]; LC-MS: 95.48%; 430.4 (M+ + 1); (column; X-bridge C-18, (50 × 3.0 mm, 3.5 μm); RT 2.61 min. 0.05% TFA (aq.): ACN; 0.8 mL/min); UPLC (purity): 96.07%; (column: Acquity BEH C-18 (50 × 2.1 mm, 1.7μ); RT 1.49 min. ACN: 0.025% TFA (Aq); 0.5 mL/min. Chiral HPLC: 94.66%, Rt = 14.14 min (Chiralpak IA, 250 × 4.6 mm, 5 μm); mobile phase (A) 0.1% DEA in n-Hexane (B) CH2Cl2:MeOH (80:20) |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4-fluoro-2-methylphenyl)-2-((3,4-trans)-4-methylpyrrolidin-3-yl) imidazo [5,1-f] [1,2,4] triazin-4 (3H)-one obtained from debenzylation of (+)-2-(3,4-trans)-1-benzyl-4-methylpyrrolidin-2-methylphenyl)imidazo[5,1-f][1,2,4]triazin-4(3H)-one | [1,2,4] triazolo [1,5-a] pyridine-2-carbaldehyde | B | (+)-2-(3,4-trans)-1-([1,2,4]triazolo[1,5-a]pyridin-2-ylmethyl)-4-methylpyrrolidin-3-yl)-7-(4-fluoro-2-methylphenyl) imidazo[5,1-f][1,2,4]triazin-4(3H)-one | A | 215 | 473 | (A:B: 80:20); flow Rate: 1.0 mL/min); Optical rotation [α]D20: +61.10° (c = 0.25, CH2Cl2); TLC: 10% MeOH/CH2Cl2 (Rf 0.4). 1H-NMR (DMSO-d6, 400 MHz): δ 8.84 (d, 1H), 7.84 (s, 1H), 7.72 (d, 1H), 7.60-7.54 (m, 2H), 7.20-7.12 (m, 3H), 3.82 (q, 2H), 3.00-2.96 (m, 3H), 2.90-2.88 (m, 1H), 2.72-2.70 (m, 1H), 2.34-2.32 (m, 1H), 2.22-2.20 (m, 3H), 1.00 (d, 3H); Mass (ESI): 459.4 [M+ + 1]; LC-MS: 98.16%; 459 (M+ + 1); (column; X-bridge C-18, 50 × 3.0 mm, 3.5 μm); RT 2.59 min. 0.05% TFA (Aq): ACN: 0.8 mL/min); UPLC (purity): 97.58%; (column; Acquity BEH C-18, 50 × 2.1 mm, 1.7μ; RT 1.60 min. ACN: 0.025% TFA (Aq); 0.5 mL/min.; Chiral HPLC: 96.47%, Rt = 13.57 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D19.98: +31.21° (c = 0.25, CH2Cl2); TLC: 10% MeOH/CH2Cl2 (Rf 0.4). |
| The enantiomer of 7-(4-fluoro-2-methylphenyl)-2- | 2-(chloro methyl) | A | (+)-7-(4-fluoro-2-methylphenyl)- | A | 339 | 792 | 1H-NMR (DMSO-d6, 400 MHz): δ 8.41 (d, 1H), 7.86 (s, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| ((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4-fluoro-2-methylphenyl)imidazo[5,1-f][1,2,4]triazin-4(3H)-one | imidazo [1,2-a] pyridine | | 2-((3,4-trans)-1-(imidazo[1,2-a]pyridin-2-ylmethyl)-4-methylpyrrolidin-3-yl)imidazo[5,1-f][1,2,4]triazin-4(3H)-one | | | | 7.72 (s, 1H), 7.54 (d, 1H), 7.42 (d, 1H), 7.20-7.14 (m, 3H), 6.80 (t, 1H), 3.70 (q, 2H), 3.50-3.48 (m, 1H), 3.00-2.98 (m, 1H), 2.90-2.88 (m, 1H), 2.80-2.78 (m, 1H), 2.70-2.68 (m, 1H), 2.50-2.48 (m, 1H), 2.30 (d, 3H), 1.00 (d, 3H); Mass (ESI): 458.4 [M+ + 1]; LC-MS: 98.40%; 458 (M+ + 1); (column: X-bridge C-18, 50 × 3.0 mm, 3.5 μm); RT 2.44 min. |
| The enantiomer of 7-(4-fluoro-2-methylphenyl)-2-((3,4-trans)-4-methylpyrrolidin-3-yl) imidazo [5,1-f] [1,2,4] triazin-4 (3H)-one obtained from debenzylation of (+)-2-((3,4-trans)- | 4-fluorobenzaldehyde | B | (+)-7-(4-fluoro-2-methylphenyl)-2-((3,4-trans)-1-(4-fluorobenzyl)-4-methylpyrrolidin-3-yl)imidazo[5,1-f][1,2,4]triazin- | A | 345 | 493 | UPLC (purity): 94.69%; (column: Acquity BEH C-18 (50 × 2.1 mm, 1.7μ); RT 1.53 min. ACN: 0.025% TFA (Aq): 0.5 mL/min.; Chiral HPLC: 94.53%, Rt = 12.91 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min) Optical rotation [α]D20: +6.41° (c = 0.25, CH2Cl2); TLC: 10% MeOH/ CH2Cl2 (Rf: 0.4). 1H-NMR (DMSO-d6, 400 MHz): δ 7.90 (s, 1H), 7.62-7.60 (m, 1H), 7.30-7.28 (m, 3H), 7.16-7.08 (m, 3H), 3.54 (q, 2H), 2.90 (t, 1H), 2.80-2.74 (m, 3H), 2.56-2.54 (m, 1H), 2.32-2.26 (m, 3H), 2.20 (t, 1H), 1.04 (d, 3H); Mass (ESI): |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| 1-benzyl-4-methylpyrrolidin-3-yl)-7-(4-fluoro-2-methylphenyl)imidazo[5,1-f][1,2,4]triazin-4(3H)-one | | | 4(3H)-one | | | | 436.3 [M+ + 1]; LC-MS: 97.96%; 436 (M+ + 1); (column: X-bridge C-18, 50 × 3.0 mm, 3.5 μm); RT 2.80 min. 0.05% TFA (Aq): ACN; 0.8 mL/min); UPLC (purity): 98.53%; (column: Acquity BEH C-18, 50 × 2.1 mm, 1.7μ); RT 1.83 min. ACN: 0.025% TFA (Aq); 0.5 mL/min.; Chiral HPLC: 99.13%, Rt = 6.60 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D20: +4.83° (c = 0.25, CH2Cl2). TLC: 10% MeOH/CH2Cl2 (Rf: 0.6). |
| The enantiomer of 7-(4-fluoro-2-methylphenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4-fluoro-2-methylphenyl)imidazo[5,1-f][1,2,4]triazin-4(3H)-one | 4-chlorobenzaldehyde | B | (+)-2-((3,4-trans)-1-(4-chlorobenzyl)-4-methylpyrrolidin-3-yl)-7-(4-fluoro-2-methylphenyl) imidazo[5,1-f][1,2,4]triazin-4(3H)-one | A | 468 | 1106 | 1H-NMR (DMSO-d6, 400 MHz): δ 7.88 (s, 1H), 7.58 (t, 1H), 7.32-7.24 (m, 5H), 7.10 (t, 1H), 3.54 (q, 2H), 2.90 (t, 1H), 2.72-2.68 (m, 3H), 2.54-2.52 (m, 1H), 2.30 (s, 3H), 2.14-2.12 (m, 1H), 1.04 (d, 3H); Mass (ESI): 452.3 [M+ + 1]; LC-MS: 97.48%; 452 (M+ + 1); (column: X-bridge C-18, 50 × 3.0 mm, 3.5 μm); RT 2.97 min. 0.05% TFA (Aq): ACN; 0.8 mL/min); UPLC (purity): 95.58%; (column: Acquity BEH C-18, 50 × 2.1 mm, 1.7μ); RT 1.93 min. ACN: 0.025% TFA (Aq); 0.5 mL/min.; Chiral HPLC: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4-fluoro-2-methylphenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4-fluoro-2-methylphenyl)imidazo[5,1-f][1,2,4]triazin-4(3H)-one | 2-(chloromethyl)pyrazine | A | (+)-7-(4-fluoro-2-methylphenyl)-2-((3,4-trans)-4-methyl-1-(pyrazin-2-ylmethyl)pyrrolidin-3-yl)imidazo[5,1-f][1,2,4]triazin-4(3H)-one | A | 342 | 393 | 95.26%, Rt = 16.14 min (Chiralpak IA, 250 × 4.6 mm, 5μ); mobile phase (A) 0.1% DEA in n-Hexane (B) CH2Cl2:MeOH (80:20) (A:B: 90:10); flow Rate: 1.0 mL/min); Optical rotation [α]D20.02: −9.50° (c = 0.25, CH2Cl2); TLC: 5% MeOH/CH2Cl2 (Rf: 0.6). 1H-NMR (DMSO-d6, 400 MHz): δ 8.64 (s, 1H), 8.56 (d, 2H), 7.90 (s, 1H), 7.60 (t, 1H), 7.26 (d, 1H), 7.16 (t, 1H), 3.80 (q, 2H), 3.00 (t, 1H), 2.88 (t, 1H), 2.80-2.78 (m, 2H), 2.56-2.54 (m, 1H), 2.32-2.28 (m, 4H), 1.02 (d, 3H); Mass (ESI): 420.3 [M+ + 1]; LC-MS: 98.77%; 420 (M+ + 1); (column; X-bridge C-18, 50 × 3.0 mm, 3.5 μm); RT 2.32 min. 0.05% TFA (Aq): ACN: 0.8 mL/min; UPLC (purity): 94.38%; (column: Acquity BEH C-18, 50 × 2.1 mm, 1.7μ); RT 1.49 min. ACN: 0.025% TFA (Aq); 0.5 mL/min.; Chiral HPLC: 97.15%, Rt = 11.17 min (Chiralpak IA, 250 × 4.6 mm, 5μ); mobile phase (A) 0.1% DEA in n-Hexane (B) CH2Cl2:MeOH (80:20) (A:B: 80:20); flow Rate: 1.0 mL/min); Optical rotation [α]D20: +48.96° (c = 0.25, CH2Cl2); TLC: 10% |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4-fluoro-2-methylphenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4-fluoro-2-methylphenyl)imidazo[5,1-f][1,2,4]triazin-4(3H)-one | nicotinaldehyde | B | (+)-7-(4-fluoro-2-methylphenyl)-2-((3,4-trans)-4-methyl-1-(pyridin-3-ylmethyl)pyrrolidin-3-yl)imidazo[5,1-f][1,2,4]triazin-4(3H)-one | A | 452 | 492 | MeOH/CH2Cl2 (Rf: 0.4). 1H-NMR (DMSO-d6, 400 MHz): δ 8.42 (d, 2H), 7.90 (s, 1H), 7.66 (d, 1H), 7.60 (t, 1H), 7.36-7.34 (m, 1H), 7.24 (d, 1H), 7.14 (t, 1H), 3.60 (q, 2H), 2.90 (t, 1H), 2.82-2.76 (m, 3H), 2.56-2.54 (m, 1H), 2.30 (s, 3H), 2.20 (t, 1H), 1.00 (d, 3H); Mass (ESI): 419.5 [M+ + 1]; LC-MS: 99.49%; 419 (M+ + 1); (column: X-bridge C-18, 50 × 3.0 mm, 3.5 μm); RT 2.23 min. 0.05% TFA (Aq): ACN; 0.8 mL/min); UPLC (purity): 98.67%; (column: Acquity BEH C-18, 50 × 2.1 mm, 1.7μ; RT 1.43 min. ACN: 0.025% TFA (Aq); 0.5 mL/min.; Chiral HPLC: 99.32%, Rt = 11.07 min (Chiralpak IA, 250 × 4.6 mm, 5μ); mobile phase (A) 0.1% DEA in n-Hexane (B) CH2Cl2:MeOH (80:20) (A:B: 80:20); flow Rate: 1.0 mL/min); Optical rotation [α]D20: +10.72° (c = 0.25, CH2Cl2); TLC: 10% MeOH/CH2Cl2 (Rf: 0.7). |
| The enantiomer of 7-(4-fluoro-2-methylphenyl)-2-((3,4-trans)-4-methylpyrrolidin-3-yl) imidazo [5,1-f] [1,2,4] triazin-4 (3H)-one | picolinaldehyde | B | (+)-7-(4-fluoro-2-methylphenyl)-2-((3,4-trans)-4-methyl-1-(pyridin-2-ylmethyl)pyrrolidin- | A | 5780 | 374 | 1H-NMR (DMSO-d6, 400 MHz): δ 8.48 (d, 1H), 7.90 (s, 1H), 7.72 (t, 1H), 7.60 (t, 1H), 7.36 (d, 1H), 7.24 (d, 2H), 7.14 (t, 1H), 3.80 (d, 1H), 3.64 (d, 1H), 2.92-2.88 (m, 2H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| obtained from debenzylation of (+)-2-((3,4-trans)-methylpyrrolidin-3-yl)-7-(4-fluoro-2-methylphenyl)imidazo[5,1-f][1,2,4]triazin-4(3H)-one | | | 3-yl)imidazo[5,1-f][1,2,4]triazin-4(3H)-one | | | | 2.82-2.78 (m, 3H), 2.32 (s, 3H), 2.24-2.22 (m, 1H), 1.04 (d, 3H); Mass (ESI): 419.4 [M+ + 1]; LC-MS: 98.00%; 419 (M+ + 1); (column: X-bridge C-18, 50 × 3.0 mm, 3.5 μm); RT 2.50 min. 0.05% TFA (Aq): ACN; 0.8 mL/min); UPLC (purity): 98.22%; (column: Acquity BEH C-18, 50 × 2.1 mm, 1.7μ); RT 1.63 min. ACN: 0.025% TFA (Aq); 0.5 mL/min.; Chiral HPLC: 93.61%, Rt = 10.89 min (Chiralpak IA, 250 × 4.6 mm, 5μ; mobile phase (A) 0.1% DEA in n-Hexane (B) CH2Cl2:MeOH (80:20) (A:B: 85:15); flow Rate: 1.0 mL/min); Optical rotation [α]D19.99: +5.84° (c = 0.25, CH2Cl2); TLC: 10% MeOH/CH2Cl2 (Rf: 0.5). |
| The enantiomer of 7-(4-fluoro-2-methylphenyl)-2-((3,4-trans)-4-methylpyrrolidin-3-yl) imidazo [5, 1-f] [1,2,4] triazin-4 (3H)-one obtained from debenzylation of (+)-2-((3,4-trans)-1-benzyl-4-methylpyrrolidin-3-yl)-7-(4-fluoro-2-methylphenyl)imidazo[5,1-f][1,2,4]triazin- | 2-(chloromethyl)-1H-benzo[d]imidazole | A | (+)-2-((3,4-trans)-1-((1H-benzo[d]imidazol-2-yl)methyl)-4-methylpyrrolidin-3-yl)-7-(4-fluoro-2-methylphenyl)imidazo[5,1-f][1,2,4]triazin-4(3H)-one | A | 1438 | 2500 | 1H-NMR (DMSO-d6, 400 MHz): δ 12.22 (br s, 1H), 7.90 (s, 1H), 7.60 (t, 1H), 7.51-7.49 (m, 1H), 7.41-7.39 (m, 1H), 7.20 (d, 1H), 7.11-7.08 (m, 3H), 3.82 (q, 2H), 3.04 (t, 1H), 2.90 (t, 1H), 2.81-2.78 (m, 2H), 2.58-2.56 (m, 1H), 2.36-2.34 (m, 1H), 2.22 (s, 3H), 1.04 (d, 3H); Mass (ESI): 458.4 [M+ + 1]; LC-MS: 96.58%; 458 (M+ + 1); (column: X-bridge C-18, 50 × 3.0 mm, 3.5 μm); RT 2.65 min. |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| 4(3H)-one | | | | | | | 0.05% TFA (Aq): ACN; 0.8 mL/min; UPLC (purity): 92.78%; (column: Acquity BEH C-18, 50 × 2.1 mm, 1.7μ); RT 1.75 min. ACN: 0.025% TFA (Aq); 0.5 mL/min; Chiral HPLC: 94.79%, Rt = 9.85 min (Chiralpak IA, 250 × 4.6 mm, 5μ); mobile phase (A) 0.1% DEA in n-Hexane (B) CH2Cl2:MeOH (80:20) (A:B: 80:20); flow Rate: 1.0 mL/min); Optical rotation [α]D19.99: +8.49° (c = 0.25, MeOH); TLC: 10% MeOH/CH2Cl2 (Rf: 0.4). |
| The enantiomer of 7-(5-fluoro-2-methylphenyl)-2-((3,4-trans)-4-methylpyrrolidin-3-yl) imidazo [5,1-f][1,2,4] triazin-4 (3H)-one obtained from debenzylation of (+)-2-((3,4-trans)-1-benzyl-4-methylpyrrolidin-3-yl)-7-(5-fluoro-2-methylphenyl)imidazo [1,5-f][1,2,4]triazin-4(3H)-one | 4-fluorobenzaldehyde | B | (+)-7-(5-fluoro-2-methylphenyl)-2-((3,4-trans)-4-fluorobenzyl)-4-methylpyrrolidin-3-yl)imidazo[5,1-f][1,2,4]triazin-4(3H)-one | A | 1738 | 393 | 1H-NMR (DMSO-d6, 400 MHz): δ 7.90 (s, 1H), 7.42 (t, 2H), 7.26-7.24 (m, 3H), 7.10 (t, 2H), 3.58 (q, 2H), 2.92 (t, 1H), 2.74-2.72 (m, 3H), 2.56-2.54 (m, 1H), 2.30 (s, 3H), 2.16 (t, 1H), 1.04 (d, 3H). Mass (ESI): 436 [M+ + 1]; LC-MS: 97.97%; 436 (M+ + 1); (column: X-bridge C-18, 50 × 3.0 mm, 3.5 μm); RT 2.82 min. 0.05% TFA (Aq): ACN; 0.8 mL/min; UPLC (purity): 99.51%; (column: Acquity BEH C-18, 50 × 2.1 mm, 1.7μ); RT 1.85 min. ACN: 0.025% TFA (Aq); 0.5 mL/min; Chiral HPLC: 97.96%, Rt = 6.88 min (Chiralpak IA, 250 × 4.6 mm, 5 μm); mobile phase (A) 0.1% DEA in |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(5-fluoro-2-methylphenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(5-fluoro-2-methylphenyl)imidazo[1,5-f][1,2,4]triazin-4(3H)-one | [1,2,4] triazolo [1,5-a] pyridine-2-carbaldehyde | B | (+)-2-((3,4-trans)-1-([1,2,4]triazolo[1,5-a]pyridin-2-ylmethyl)-4-methylpyrrolidin-3-yl)-7-(5-fluoro-2-methylphenyl) imidazo[5,1-f][1,2,4]triazin-4(3H)-one | A | 487 | 473 | n-Hexane (B) CH2Cl2:MeOH (80:20) (A:B: 80:20); flow Rate: 1.0 mL/min); Optical rotation [α]D20: +13.61° (c = 0.25, CH2Cl2). TLC: 5% MeOH/CH2Cl2 (Rf: 0.4). 1H-NMR (DMSO-d6, 500 MHz): δ 8.86 (d, 1H), 7.91 (s, 1H), 7.76 (d, 1H), 7.64 (t, 1H), 7.42 (d, 1H), 7.38 (t, 1H), 7.25 (t, 1H), 7.16 (t, 1H), 3.84 (q, 2H), 3.18 (t, 1H), 3.00 (t, 1H), 2.92 (t, 1H), 2.78 (q, 1H), 2.58-2.56 (m, 1H), 2.41-2.39 (m, 1H), 2.26 (s, 3H), 1.04 (d, 3H). Mass (ESI): 459 [M+ + 1]; LC-MS: 97.01%; 459 (M+ + 1); (column: X-bridge C-18, 50 × 3.0 mm, 3.5 μm); RT 2.46 min. 0.05% TFA (Aq): ACN; 0.8 mL/min); UPLC (purity): 97.82%; (column: Acquity BEH C-18, 50 × 2.1 mm, 1.7μ); RT 1.62 min. ACN: 0.025% TFA (Aq); 0.5 mL/min. Chiral HPLC: 99.04%, Rt = 7.28 min (Chiralpak IA, 250 × 4.6 mm, 5μ); mobile phase (A) 0.1% DEA in n-Hexane (B) CH2Cl2:MeOH (80:20) (A:B: 75:25); flow Rate: 1.0 mL/min); Optical rotation [α]D19.99: +52.06° (c = 0.25, CH2Cl2). TLC: 10% MeOH/CH2Cl2 (Rf: 0.4). |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(5-fluoro-2-methylphenyl)-2-((3,4-trans)-4-methylpyrrolidin-3-yl) imidazo [5,1-f][1,2,4]triazin-4 (3H)-one obtained from debenzylation of (+)-2-((3,4-trans)-1-benzyl-4-methylpyrrolidin-3-yl)-7-(5-fluoro-2-methylphenyl)imidazo[1,5-f][1,2,4]triazin-4(3H)-one | 2-(chloromethyl)imidazo[1,2-a]pyridine | A | (+)-7-(5-fluoro-2-methylphenyl)-2-((3,4-trans)-1-(imidazo[1,2-a]pyridin-2-ylmethyl)-4-methylpyrrolidin-3-yl)imidazo[5,1-f][1,2,4]triazin-4(3H)-one | A | 1437 | 1427 | 1H-NMR (DMSO-d6, 400 MHz): δ 8.42 (d, 1H), 7.90 (s, 1H), 7.72 (s, 1H), 7.44-7.38 (m, 3H), 7.24 (t, 1H), 7.12 (t, 1H), 6.80 (t, 1H), 3.70 (q, 2H), 3.02 (t, 1H), 2.90 (t, 1H), 2.80 (t, 1H), 2.72-2.70 (m, 1H), 2.58-2.56 (m, 1H), 2.32-2.26 (m, 4H), 1.06 (d, 3H); Mass (ESI): 458.3 [M+ + 1]; LC-MS: 96.69%; 458 (M+ + 1); (column: X-bridge C-18, 50 × 3.0 mm, 3.5 μm); RT 2.84 min. 0.05% TFA (Aq.): ACN; 0.8 mL/min); UPLC (purity): 97.72%; (column: Acquity BEH C-18, 50 × 2.1 mm, 1.7μ); RT 1.52 min. ACN: 0.025% TFA (Aq) 0.5 mL/min.; Chiral HPLC: 96.12%, Rt = 19.85 min (Chiralpak IA, 250 × 4.6 mm, 5 μm); mobile phase (A) 0.1% DEA in n-Hexane (B) CH2Cl2:MeOH (80:20) (A:B: 85:15); flow Rate: 1.0 mL/min); Optical rotation [α]D19.99: +9.82° (c = 0.25, CH2Cl2); TLC: 10% MeOH/CH2Cl2 (Rf: 0.6). |
| The enantiomer of 7-(5-fluoro-2-methylphenyl)-2-((3,4-trans)-4-methylpyrrolidin-3-yl) imidazo [5,1-f][1,2,4] triazin-4 (3H)-one obtained from | picolinaldehyde | B | (+)-7-(5-fluoro-2-methylphenyl)-2-((3,4-trans)-4-methyl-1-(pyridin-2-ylmethyl)pyrrolidin-3- | A | 560 | 277 | 1H-NMR (DMSO-d6, 400 MHz): δ 8.46 (d, 1H), 7.90 (s, 1H), 7.70 (t, 1H), 7.48 (t, 2H), 7.38 (d, 1H), 7.26-7.24 (m, 2H), 3.78 (d, 1H), 3.68 (d, 1H), 2.96-2.94 (m, 2H), 2.84-2.82 (m, 2H), 2.60-2.58 (m, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| debenzylation of (+)-2-((3,4-trans)-4-methylpyrrolidin-3-yl)-7-(5-fluoro-2-methylphenyl)imidazo[1,5-f][1,2,4]triazin-4(3H)-one | | | y])imidazo[5,1-f][1,2,4]triazin-4(3H)-one | | | | 2.30 (s, 3H), 2.26-2.24 (m, 1H), 1.08 (d, 3H); Mass (ESI): 419.5 [M+ + 1]; LC-MS: 99.61%; 419 (M+ + 1); (column: X-bridge C-18, 50 × 3.0 mm, 3.5 μm); RT 2.54 min. 0.05% TFA (Aq): ACN; 0.8 mL/min); UPLC (purity): 99.13%; (column: Acquity BEH C-18, 50 × 2.1 mm, 1.7μ); RT 1.65 min. ACN: 0.025% TFA (Aq); 0.5 mL/min. Chiral HPLC: 98.92%, Rt = 7.60 min (Chiralpak IA, 250 × 4.6 mm, 5μ); mobile phase (A) 0.1% DEA in n-Hexane (B) CH2Cl2:MeOH (80:20) (A:B :: 80:20); flow Rate: 1.0 mL/min); Optical rotation [α]D20: +82.57° (c = 0.25, CH2Cl2); TLC: 10% MeOH/CH2Cl2 (Rf: 0.7). |
| The enantiomer of 7-(5-fluoro-2-methylphenyl)-2-((3,4-trans)-4-methylpyrrolidin-3-yl) imidazo [5,1-f] [1,2,4] triazin-4 (3H)-one obtained from debenzylation of (+)-2-((3,4-trans)-4-methylpyrrolidin-3-yl)-7-(5-fluoro-2-methylphenyl)imidazo[1,5-f][1,2,4]triazin-4(3H)-one | nicotinaldehyde | B | (+)-7-(5-fluoro-2-methylphenyl)-2-((3,4-trans)-4-methyl-1-(pyridin-3-yl)methyl)pyrrolidin-3-yl)imidazo[5,1-f][1,2,4]triazin-4(3H)-one | A | 770 | 505 | 1H-NMR (DMSO-d6, 400 MHz): δ 8.48 (d, 2H), 7.94 (s, 1H), 7.70 (d, 1H), 7.48-7.46 (m, 2H), 7.30-7.26 (m, 2H), 3.60 (q, 2H), 2.96 (t, 1H), 2.80-2.76 (m, 3H), 2.54-2.52 (m, 1H), 2.32 (s, 3H), 2.18 (t, 1H), 1.08 (d, 3H). Mass (ESI): 419.4 [M+ + 1]; LC-MS: 99.70%; 419 (M+ + 1); (column: X-bridge C-18, 50 × 3.0 mm, 3.5 μm); RT 2.29 min. 0.05% TFA (Aq): ACN; 0.8 mL/min); UPLC (purity): 95.01%; |

TABLE 3-continued

| SM name | Reagent | Method | Example name | Band | PDE9A2 IC$_{50}$ | PDE1A selectivity (versus PDE9A2) | PDE1B selectivity (versus PDE9A2) | Analytical Data |
|---|---|---|---|---|---|---|---|---|
| The enantiomer of 7-(5-fluoro-2-methylphenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(5-fluoro-2-methylphenyl)imidazo[1,5-f][1,2,4]triazin-4(3H)-one | 4-chlorobenzaldehyde | B | (−)-2-((3,4-trans)-1-(4-chlorobenzyl)-4-methylpyrrolidin-3-yl)-7-(5-fluoro-2-methylphenyl)imidazo[5,1-f][1,2,4]triazin-4(3H)-one | A | | 3375 | 1735 | (column: Acquity BEH C-18, 50 × 2.1 mm, 1.7μ); RT 1.45 min. ACN: 0.025% TFA (Aq); 0.5 mL/min.; Chiral HPLC: 97.56%, Rt = 9.77 min (Chiralpak IA, 250 × 4.6 mm, 5μ); mobile phase (A) 0.1% DEA in n-Hexane (B) CH2Cl2:MeOH (80:20) (A:B: 80:20); flow Rate: 1.0 mL/min); Optical rotation [α]D20: +15.63° (c = 0.25, CH2Cl2); TLC: 10% MeOH/CH2Cl2 (Rf: 0.6). 1H-NMR (DMSO-d6, 400 MHz): δ 7.91 (s, 1H), 7.40 (t, 2H), 7.32-7.28 (m, 5H), 3.60 (q, 2H), 2.92 (t, 1H), 2.78-2.74 (m, 3H), 2.58-2.56 (m, 1H), 2.30 (s, 3H), 2.20 (t, 1H), 1.09 (d, 3H); Mass (ESI): 452.3 [M+ + 1]; LC-MS: 94.74%; 452 (M+ + 1); (column: X-bridge C-18, 50 × 3.0 mm, 3.5 μm); RT 2.99 min. 0.05% TFA (Aq); ACN; 0.8 mL/min); UPLC (purity): 92.08%; (column: Acquity BEH C-18, 50 × 2.1 mm, 1.7μ); RT 1.95 min. ACN: 0.025% TFA (Aq); 0.5 mL/min.; Chiral HPLC: 93.18%, Rt = 14.56 min (Chiralpak IA, 250 × 4.6 mm, 5μ); mobile phase (A) 0.1% DEA in n-Hexane (B) CH2Cl2:MeOH (80:20) (A:B: 90:10); flow Rate: 1.0 mL/min); Optical |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | rotation [α]D20.02: −5.31° (c = 0.25, CH2Cl2); TLC: 5% MeOH/CH2Cl2 (Rf: 0.5). |
| The enantiomer of 7-(5-fluoro-2-methylphenyl)-2-((3,4-trans)-4-methylpyrrolidin-3-yl) imidazo [5,1-f] [1,2,4] triazin-4 (3H)-one obtained from debenzylation of (+)-2-((3,4-trans)-4-methylpyrrolidin-3-yl)-7-(5-fluoro-2-methylphenyl)imidazo[1,5-f][1,2,4]triazin-4(3H)-one | 2-(chloromethyl) pyrazine | A | (+)-7-(5-fluoro-2-methylphenyl)-2-((3,4-trans)-4-methyl-1-(pyrazin-2-ylmethyl)pyrrolidin-3-yl)imidazo[5,1-f][1,2,4]triazin-4(3H)-one | A | 85 | 74 | 1H-NMR (DMSO-d6, 400 MHz): δ 8.76 (s, 1H), 8.52 (d, 2H), 7.94 (s, 1H), 7.44-7.42 (m, 2H), 7.24 (t, 1H), 3.80 (q, 2H), 3.02 (t, 1H), 2.90 (t, 1H), 2.82-2.80 (m, 3H), 2.56-2.54 (m, 1H), 2.32-2.29 (m, 3H), 1.06 (d, 3H); Mass (ESI): 420.3 [M+ + 1]; LC-MS: 96.37%; 420 (M+ + 1); (column; X-bridge C-18, 50 × 3.0 mm, 3.5 μm); RT 2.34 min. 0.05% TFA (Aq): ACN: 0.8 mL/min); UPLC (purity): 92.08%; (column: Acquity BEH C-18, 50 × 2.1 mm, 1.7μ; RT 1.52 min. ACN: 0.025% TFA (Aq); 0.5 mL/min.; Chiral HPLC: 94.12%, Rt = 11.96 min (Chiralpak IA, 250 × 4.6 mm, 5μ); mobile phase (A) 0.1% DEA in n-Hexane (B) CH2Cl2:MeOH (80:20) (A:B: 80:20); flow Rate: 1.0 mL/min); Optical rotation [α]D20: +57.50° (c = 0.25, CH2Cl2). TLC: 10% MeOH/CH2Cl2 (Rf: 0.5). |
| The enantiomer of 7-(5-fluoro-2-methylphenyl)-2-((3,4-trans)-4-methylpyrrolidin-3-yl) imidazo [5,1-f] [1,2,4] | 2-(chloromethyl)-1H-benzo[d] imidazole | A | (+)-2-((3,4-trans)-1-((1H-benzo[d]imidazol-2-yl)methyl)-4-methylpyrrolidin-3-yl)-7-(5- | A | 89 | 130 | 1H-NMR (DMSO-d6, 400 MHz): δ 12.29 (br s, 1H), 7.90 (s, 1H), 7.42 (d, 1H), 7.38-7.34 (m, 3H), 7.26 (t, 1H), 7.14-7.11 (m, 2H), 3.80 (q, 2H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| triazin-4 (3H)-one obtained from debenzylation of (+)-2-((3,4-trans)-1-benzyl-4-methylpyrrolidin-3-yl)-7-(5-fluoro-2-methylphenyl)imidazo[1,5-f][1,2,4]triazin-4(3H)-one | | | fluoro-2-methylphenyl)imidazo[5,1-f][1,2,4]triazin-4(3H)-one | | | | 3.08-3.06 (m, 1H), 2.92 (t, 1H), 2.81-2.79 (m, 2H), 2.60-2.58 (m, 1H), 2.41-2.39 (m, 1H), 2.30 (s, 3H), 1.08 (d, 3H); Mass (ESI): 458.5 [M+ + 1]; LC-MS: 94.08%; 458 (M+ + 1); (column: X-bridge C-18, (50 × 3.0 mm, 3.5 µm); RT 2.70 min. 0.05% TFA (Aq): ACN; 0.8 mL/min); UPLC (purity): 93.00%; (column: Acquity BEH C-18; 50 × 2.1 mm, 1.7µ); RT 1.76 min. ACN: 0.025% TFA (Aq); 0.5 mL/min.; Chiral HPLC: 95.63%, Rt = 9.60 min (Chiralpak IA, 250 × 4.6 mm, 5µ); mobile phase (A) 0.1% DEA in n-Hexane (B) CH2Cl2:MeOH (80:20) (A:B: 80:20); flow Rate: 1.0 mL/min); Optical rotation [α]D20: +6.56° (c = 0.25, MeOH); TLC: 10% MeOH/CH2Cl2 (Rf: 0.5). |
| — | — | — | (+)-2-((3,4-trans)-1-benzyl-4-methylpyrrolidin-3-yl)-7-(4-fluorophenyl)imidazo[5,1-f][1,2,4]triazin-4(3H)-one | A | 220 | 286 | — |
| The enantiomer of 7-(4-fluorophenyl)-2-((3,4-trans)-4-methylpyrrolidin-3-yl) imidazo [5,1-f] [1,2,4] triazin-4 (3H)-one | nicotinaldehyde | B | (+)-7-(4-fluorophenyl)-2-((3,4-trans)-4-methyl-1-(pyridin-3-ylmethyl)pyrrolidin-3-yl)imidazo[5,1- | A | — | — | 1H-NMR (DMSO-d6, 400 MHz): δ 8.52 (s, 1H), 8.46-8.44 (m, 1H), 8.38-8.36 (m, 2H), 7.88 (s, 1H), 7.70 (d, 1H), 7.38-7.34 (m, 3H), 3.70-3.68 (m, 2H), 3.02-3.00 (m, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| obtained from debenzylation of (+)-2-((3,4-trans)-1-benzyl-4-methylpyrrolidin-3-yl)-7-(4-fluorophenyl) imidazo [5,1-f] [1,2,4] triazin-4 (3H)-one | | | f][1,2,4]triazin-4(3H)-one | | | | 2.90-2.86 (m, 3H), 2.70-2.66 (m, 1H), 2.30-2.28 (m, 1H), 1.10 (d, 3H); Mass (ESI): 405.4 [M+ + 1]; LC-MS: 96.83%; 405 (M+ + 1); (column; X-bridge C-18, 50 × 3.0 mm, 3.5 μm); RT 2.27 min. 0.05% TFA (Aq); ACN; 0.8 mL/min; UPLC (purity): 94.17%; (column: Acquity BEH C-18, 50 × 2.1 mm, 1.7 μm); RT 1.47 min. ACN: 0.025% TFA (Aq); 0.5 mL/min; Chiral HPLC: 94.35%, Rt = 15.82 min (Chiralpak IA, 250 × 4.6 mm, 5 μm; mobile phase (A) 0.1% DEA in n-Hexane (B) CH2Cl2:MeOH (80:20) (A:B :: 80:20); flow Rate: 1.0 mL/min); Optical rotation [α]D19.99: +31.21° (c = 0.25, CH2Cl2); TLC: 10% MeOH/CH2Cl2 (Rf: 0.7). |
| The enantiomer of 7-(4-fluorophenyl)-2-((3,4-trans)-4-methylpyrrolidin-3-yl) imidazo [5, 1-f] [1,2,4] triazin-4 (3H)-one obtained from debenzylation of (+)-2-((3,4-trans)-1-benzyl-4-methylpyrrolidin-3-yl)-7-(4-fluorophenyl) imidazo [5,1-f] | [1,2,4]triazolo[1,5-a]pyridine-2-carbaldehyde | B | (+)-2-((3,4-trans)-1-([1,2,4]triazolo[1,5-a]pyridin-2-ylmethyl)-4-methylpyrrolidin-3-yl)-7-(4-fluorophenyl)imidazo[5,1-f][1,2,4]triazin-4(3H)-one | A | 87 | 87 | 1H-NMR (DMSO-d6, 400 MHz): δ 8.87 (d, 1H), 8.39-8.32 (m, 2H), 7.87 (s, 1H), 7.75 (d, 1H), 7.63 (t, 1H), 7.30 (t, 2H), 7.12 (t, 1H), 3.90 (q, 2H), 3.15-3.08 (m, 2H), 3.01-2.99 (m, 1H), 2.87-2.81 (m, 1H), 2.68-2.66 (m, 1H), 2.47-2.45 (m, 1H), 1.10 (d, 3H); Mass (ESI): 445.3 [M+ + 1]; LC-MS: 93.71%; 445 (M+ + 1); (column; X-bridge C-18, (50 × 3.0 mm, 3.5 μm); RT 2.50 min. |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| [1,2,4] triazin-4 (3H)-one | | | | | | | 0.05% TFA (Aq); ACN; 0.8 mL/min); UPLC (purity): 90.04%; (column: Acquity BEH C-18 (50 × 2.1 mm, 1.7μ); RT 1.61 min. ACN: 0.025% TFA (Aq); 0.5 mL/min.; Chiral HPLC: 93.03%, Rt = 23.98 min (Chiralpak IA, 250 × 4.6 mm, 5μ); mobile phase (A) 0.1% DEA in n-Hexane (B) CH2Cl2:MeOH (80:20) (A:B :: 80:20); flow Rate: 1.0 mL/min); Optical rotation [α]D20: +68.92° (c = 0.25, CH2Cl2); TLC: 10% MeOH/CH2Cl2 (Rf: 0.6). |
| The enantiomer of 7-(4-fluorophenyl)-2-((3,4-trans)-4-methylpyrrolidin-3-yl) imidazo [5,1-f] [1,2,4] triazin-4 (3H)-one obtained from debenzylation of (+)-2-(3,4-trans)-1-benzyl-4-methylpyrrolidin-3-yl)-7-(4-fluorophenyl) imidazo [5,1-f] [1,2,4] triazin-4 (3H)-one | 2-(chloromethyl) pyrimidine | A | (+)-7-(4-fluorophenyl)-2-((3,4-trans)-4-methyl-1-(pyrimidin-2-ylmethyl)pyrrolidin-3-yl)imidazo[5,1-f][1,2,4]triazin-4(3H)-one | A | — | — | 1H-NMR (DMSO-d6, 400 MHz): δ 8.80 (d, 2H), 8.40 (t, 2H), 7.86 (s, 1H), 7.40-7.36 (m, 3H), 4.00 (d, 1H), 3.82 (d, 1H), 3.14-3.12 (m, 1H), 3.01-2.99 (m, 2H), 2.84-2.82 (m, 1H), 2.64-2.62 (m, 1H), 2.40-2.38 (m, 1H), 1.10 (d, 3H); Mass (ESI): 406.3 [M+ + 1]; LC-MS: 88.38%; 406.3 (M+ + 1); (column: X-bridge C-18, 50 × 3.0 mm, 3.5 μm); RT 2.92 min. 0.05% TFA (Aq); ACN; 0.8 mL/min; UPLC (purity): 88.85%; (column: Acquity BEH C-18, 50 × 2.1 mm, 1.7 μm); RT 1.55 min. ACN: 0.025% TFA (Aq); 0.5 mL/min.; Chiral HPLC: 95.76%, Rt = 10.73 min |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-4-methylpyrrolidin-3-yl)-7-(4-fluorophenyl) imidazo [5,1-f] [1,2,4] triazin-4 (3H)-one | picolinaldehyde | B | (+)-7-(4-fluorophenyl)-2-((3,4-trans)-4-methyl-1-(pyridin-2-ylmethyl)pyrrolidin-3-yl)imidazo[5,1-f][1,2,4]triazin-4(3H)-one | B | — | — | (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D19.99: +95.53° (c = 0.25, CH2Cl2); TLC: 10% MeOH/CH2Cl2 (Rf: 0.7). 1H-NMR (DMSO-d6, 400 MHz): δ 8.50 (d, 1H), 8.36 (t, 2H), 7.88 (s, 1H), 7.72 (t, 1H), 7.42-7.36 (m, 3H), 7.24 (t, 1H), 3.80 (q, 2H), 3.04-3.02 (m, 2H), 2.90-2.86 (m, 2H), 2.70-2.68 (m, 1H), 2.36-2.34 (m, 1H), 1.12 (d, 3H); Mass (ESI): 405 [M+ + 1]; LC-MS: 99.62%; 405 (M+ + 1); (column; X-bridge C-18, 50 × 3.0 mm, 3.5 μm); RT 2.57 min. 0.05% TFA (Aq): ACN; 0.8 mL/min; HPLC (purity): 98.75%; (column: Eclipse XDB-C18, 150 × 4.6 mm, 5.0 μm); RT 10.12 min. ACN: 5 mM NH4OAc (Aq); 1.0 mL/min; Chiral HPLC: 99.00%, Rt = 7.76 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D19.98: +72.80° (c = 0.25, CH2Cl2); TLC: 5% |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4-fluorophenyl) imidazo [5,1-f] [1,2,4] triazin-4 (3H)-one | 2-(chloro methyl) pyrazine | A | (+)-7-(4-fluorophenyl)-2-((3,4-trans)-4-methyl-1-(pyrazin-2-ylmethyl)pyrrolidin-3-yl)imidazo[5,1-f][1,2,4]triazin-4(3H)-one | A | 9 | 8 | 1H-NMR (DMSO-d6, 400 MHz): δ 8.70 (s, 1H), 8.58 (s, 1H), 8.56 (s, 1H), 8.34 (t, 2H), 7.82 (s, 1H), 7.38 (t, 2H), 3.80 (q, 2H), 3.06-3.04 (m, 1H), 2.98-2.96 (m, 1H), 2.90-2.88 (m, 1H), 2.80-2.78 (m, 1H), 2.68-2.66 (m, 1H), 2.34-2.32 (m, 1H), 1.12 (d, 3H). Mass (ESI): 406.4 [M+ + 1]; LC-MS: 95.49%; 406 (M+ + 1); (column: X-bridge C-18, 50 × 3.0 mm, 3.5 μm); RT 2.43 min. UPLC (purity): 96.39%; (column: Acquity BEH C-18, 50 × 2.1 mm, 1.7 μm); Rt 1.54 min. ACN: 0.025% TFA (Aq); 0.5 mL/min; Chiral HPLC: 98.41%, Rt = 11.53 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D20.01: +77.79° (c = 0.25, CH2Cl2); TLC: 10% MeOH/CH2Cl2 (Rf: 0.5). |
| The enantiomer of 7-(4-fluorophenyl)-2-((3,4-trans)-4-methylpyrrolidin-3-yl) imidazo [5, benzo [d] | 2-(chloro methyl)-1H-benzo [d] | A | (+)-2-((3,4-trans)-1-((1H-benzo[d]imidazol-2-yl)methyl)-4-methylpyrrolidin- | A | — | — | 1H-NMR (DMSO-d6, 400 MHz): δ 12.30 (br s, 1H), 8.39 (t, 2H), 7.90 (s, 1H), 7.60-7.58 (m, 1H), 7.48-7.46 (m, 1H), 7.34 (t, 2H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| 1-f[1,2,4] triazin-4 (3H)-one obtained from debenzylation of (+)-2-((3,4-trans)-4-methylpyrrolidin-3-yl)-7-(4-fluorophenyl) imidazo [5,1-f] [1,2,4] triazin-4 (3H)-one | imidazole | | 3-yl)-7-(4-fluorophenyl)imidazo[5,1-f][1,2,4]triazin-4(3H)-one | | | | 7.24-7.22 (m, 2H), 3.90 (q, 2H), 3.18 (t, 1H), 3.00 (t, 2H), 2.91-2.89 (m, 2H), 2.71-2.69 (m, 1H), 1.20 (d, 3H); Mass (ESI): 444.3 [M+ + 1]; LC-MS: 98.64%; 444 (M+ + 1); (column; X-bridge C-18, 50 × 3.0 mm, 3.5 μm); RT 2.74 min. 0.05% TFA (Aq): ACN; 0.8 mL/min); UPLC (purity): 94.40%; (column: Acquity BEH C-18, 50 × 2.1 mm, 1.7μ); RT 1.77 min. ACN: 0.025% TFA (Aq); 0.5 mL/min.; Chiral HPLC: 92.31%, Rt = 9.97 min (Chiralpak IA, 250 × 4.6 mm, 5μ); mobile phase (A) 0.1% DEA in n-Hexane (B) CH2Cl2:MeOH (80:20) (A:B :: 80:20); flow Rate: 1.0 mL/min); Optical rotation [α]D19.99 +6.97° (c = 0.25, CH2Cl2); TLC: 10% MeOH/CH2Cl2 (Rf: 0.6). |
| The enantiomer of 7-(4-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-4-methylpyrrolidin-3-yl)-7-(4-fluorophenyl) imidazo [5,1-f] | 2-(chloro methyl) imidazo [1,2-a] pyridine | A | (+)-7-(4-fluorophenyl)-2-(3,4-trans)-1-(imidazo[1,2-a]pyridin-2-ylmethyl)-4-methylpyrrolidin-3-yl)imidazo[5,1-f][1,2,4]triazin-4(3H)-one | A | 120 | 209 | 1H-NMR (DMSO-d6, 400 MHz): δ 8.46 (d, 1H), 8.41-8.39 (m, 2H), 7.89 (s, 1H), 7.81 (s, 1H), 7.50 (d, 1H), 7.34 (t, 2H), 7.18 (t, 1H), 6.82 (t, 1H), 3.80 (q, 2H), 3.10 (t, 1H), 3.02 (t, 1H), 2.91-2.89 (m, 1H), 2.84-2.82 (m, 1H), 2.71-2.69 (m, 1H), 2.42-2.40 (m, 1H), 1.14 (d, 3H); Mass (ESI): 444.8 [M+ + 1]; LC-MS: 93.86%; 444 (M+ + 1); (column: X-bridge C-18, 50 × 3.0 mm, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| [1,2,4] triazin-4 (3H)-one | | | | | | | 3.5 μm); RT 2.35 min. 0.05% TFA: ACN; 0.8 mL/min); UPLC (purity): 94.09%; (column: Acquity UPLC BEH C-18, (2.1 × 50 mm, 1.7μ); RT 1.50 min. ACN: 0.025% TFA (Aq); 0.5 mL/min.; Chiral HPLC: 93.07%, Rt = 9.90 min (Chiralpak IA, 250 × 4.6 mm, 5 μm); mobile phase (A) 0.1% DEA in n-Hexane (B) CH2Cl2:MeOH (80:20) (A:B :: 75:25); flow Rate: 1.0 mL/min); Optical rotation [α]D20: +38.01° (c = 0.25, CH2Cl2); TLC: 10% MeOH/CH2Cl2 (Rf: 0.6). |
| — | — | | (+)-2-((3,4-trans)-1-benzyl-4-methylpyrrolidin-3-yl)-7-(3-fluorophenyl)imidazo[5,1-f][1,2,4]triazin-4(3H)-one | A | 70 | 113 | — |
| The enantiomer of 7-(3-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(3-fluorophenyl) imidazo [5,1-f] | 4-chlorobenzaldehyde | B | (+)-2-((3,4-trans)-1-(4-chlorobenzyl)-4-methylpyrrolidin-3-yl)-7-(3-fluorophenyl)imidazo[5,1-f][1,2,4]triazin-4(3H)-one | B | — | — | 1H-NMR (DMSO-d6, 400 MHz): δ 8.20-8.18 (m, 2H), 7.88 (s, 1H), 7.58 (q, 1H), 7.38-7.32 (m, 5H), 3.66-3.64 (m, 2H), 3.02-3.00 (m, 1H), 2.90-2.86 (m, 3H), 2.70-2.68 (m, 1H), 2.32-2.30 (m, 1H), 1.12 (d, 3H); Mass (ESI): 438.3 [M+ + 1]; LC-MS: 94.85%; 438 (M+ + 1); (column: X-bridge C-18, 50 × 3.0 mm, 3.5 μm); RT 2.98 min. 0.05% TFA (Aq.): |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| [1,2,4] triazin-4 (3H)-one | | | | | | | ACN; 0.8 mL/min); UPLC (purity): 94.44%; (column: Acquity BEH C-18, 50 × 2.1 mm, 1.7 μm); RT 1.95 min. ACN: 0.025% TFA (Aq); 0.5 mL/min; Chiral HPLC: 96.98%, Rt = 8.88 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D19.97: +6.16° (c = 0.25, CH2Cl2); TLC: 5% MeOH/CH2Cl2 (Rf. 0.6). |
| The enantiomer of 7-(3-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(3-fluorophenyl) imidazo [5,1-f] [1,2,4] triazin-4 (3H)-one | 4-fluorobenzaldehyde | B | (+)-2-((3,4-trans)-1-(4-fluorobenzyl)-4-methylpyrrolidin-3-yl)-7-(3-fluorophenyl)imidazo[5,1-f][1,2,4]triazin-4(3H)-one | A | 42 | 57 | 1H-NMR (DMSO-d6, 400 MHz): δ 8.22-8.19 (m, 2H), 7.90 (s, 1H), 7.60 (m, 1H), 7.38-7.29 (m, 3H), 7.10 (t, 2H), 3.62 (s, 2H), 3.56-3.53 (m, 1H), 3.01-2.98 (m, 1H), 2.89-2.80 (m, 2H), 2.70-2.68 (m, 1H), 2.31-2.29 (m, 1H), 1.10 (d, 3H); Mass (ESI): 422.4 [M+ + 1]; LC-MS: 93.02%; 422 (M+ + 1); (column: X-Bridge C-18, 50 × 3.0 mm, 3.5 μm); RT 2.84 min. 0.05% Aq TFA: ACN; 0.8 mL/min); UPLC (purity): 94.03%; (column: Acquity BEH C-18, (50 × 2.1 mm, 1.7μ); RT 1.87 min. ACN: 0.025% TFA (Aq); 0.5 mL/min.; Chiral HPLC: 96.97%, Rt = 6.53 min |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | (Chiralpak IA, 250 × 4.6 mm, 5μ); mobile phase (A) 0.1% DEA in n-Hexane (B) CH2Cl2:MeOH (80:20) (A:B: 80:20); flow Rate: 1.0 mL/min); Optical rotation [α]D19.97: +19.68° (c = 0.25, CH2Cl2); TLC: 10% MeOH/CH2Cl2 (Rf: 0.6). |
| The enantiomer of 7-(3-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(3-fluorophenyl) imidazo [5,1-f] [1,2,4] triazin-4 (3H)-one | [1,2,4] triazolo [1,5-a] pyridine-2-carbaldehyde | B | (+)-2-((3,4-trans)-1-([1,2,4]triazolo[1,5-a]pyridin-2-ylmethyl)-4-methylpyrrolidin-3-yl)-7-(3-fluorophenyl)imidazo[5,1-f][1,2,4]triazin-4(3H)-one | A | 3 | 10 | 1H-NMR (DMSO-d6, 400 MHz): δ 8.88 (d, 1H), 8.20 (d, 1H), 8.14 (d, 1H), 7.86 (s, 1H), 7.72 (d, 1H), 7.62-7.56 (m, 2H), 7.24 (t, 1H), 7.12 (t, 1H), 3.90 (q, 2H), 3.20-3.18 (m, 1H), 3.10-3.08 (m, 1H), 3.00 (t, 1H), 2.88 (t, 1H), 2.70-2.68 (m, 1H), 2.40-2.38 (m, 1H), 1.08 (d, 3H); Mass (ESI): 445.4 [M+ + 1]; LC-MS: 96.96%; 445 (M+ + 1); (column; X-bridge C-18, 50 × 3.0 mm, 3.5 μm); RT 2.65 min. 0.05% TFA (Aq): ACN; 0.8 mL/min); UPLC (purity): 98.45%; (column; Acquity BEH C-18, 50 × 2.1 mm, 1.7 μm); RT 1.64 min. ACN: 0.025% TFA (Aq); 0.5 mL/min; Chiral HPLC: 97.52%, Rt = 14.38 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D20: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(3-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(3-fluorophenyl) imidazo [5,1-f] [1,2,4] triazin-4 (3H)-one | 2-(chloro methyl) pyrimidine | A | (+)-7-(3-fluorophenyl)-2-((3,4-trans)-4-methyl-1-(pyrimidin-2-yl)methyl)pyrrolidin-3-yl)imidazo[5,1-f][1,2,4]triazin-4(3H)-one | A | — | — | +70.43° (c = 0.25, CH2Cl2); TLC: 10% MeOH/CH2Cl2 (Rf: 0.4). 1H-NMR (DMSO-d6, 400 MHz): δ 8.80 (d, 2H), 8.22 (d, 1H), 8.12 (d, 1H), 7.90 (s, 1H), 7.58 (q, 1H), 7.40 (t, 1H), 7.32 (t, 1H), 4.00 (d, 1H), 3.84 (d, 1H), 3.24 (t, 1H), 3.04 (d, 2H), 2.88 (q, 1H), 2.66-2.64 (m, 1H), 2.38 (d, 1H), 1.12 (d, 3H). Mass (ESI): 406.3 [M+ + 1]; LC-MS: 95.86%; 406 (M+ + 1); (column: X-bridge C-18, 50 × 3.0 mm, 3.5 μm); RT 2.63 min. 0.05% TFA (Aq): ACN; 0.8 mL/min); HPLC: 96.56%, Rt = 9.60 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D20.01 +85.64° (c = 0.25, CH2Cl2). TLC: 10% MeOH/CH2Cl2 (Rf: 0.7). |
| The enantiomer of 7-(3-fluorophenyl)-2-((3,4-trans)-4-methylpyrrolidin-3-yl) imidazo [5,1-f] [1,2,4] triazin-4 (3H)-one obtained from debenzylation of | 2-(chloro methyl) imidazo [1,2-a] pyridine | A | (+)-7-(3-fluorophenyl)-2-((3,4-trans)-1-(imidazo[1,2-a]pyridin-2-yl)methyl)-4-methylpyrrolidin-3-yl)imidazo[5,1- | A | — | — | 1H-NMR (DMSO-d6, 400 MHz): δ 8.42 (d, 1H), 8.18 (d, 2H), 7.88 (s, 1H), 7.76 (s, 1H), 7.54 (q, 1H), 7.44 (d, 1H), 7.30 (t, 1H), 7.16 (t, 1H), 6.82 (t, 1H), 3.76-3.74 (m, 2H), 3.10 (t, 1H), 3.00 (t, 1H), 2.92 (t, 1H), |

TABLE 3-continued

| SM name | Reagent | Method | Example name | Band | PDE9A2 IC$_{50}$ | PDE1A selectivity (versus PDE9A2) | PDE1B selectivity (versus PDE9A2) | Analytical Data |
|---|---|---|---|---|---|---|---|---|
| (+)-2-((3,4-trans)-1-benzyl-4-methylpyrrolidin-3-yl)-7-(3-fluorophenyl) imidazo [5,1-f] [1,2,4] triazin-4 (3H)-one | | | f][1,2,4]triazin-4(3H)-one | | | | | 2.80 (q, 1H), 2.68 (d, 1H), 2.40 (d, 1H), 1.12 (d, 3H); Mass (ESI): 444.3 [M+ + 1]; LC-MS: 98.18%; 444 (M+ + 1); (column: X-bridge C-18, 50 × 3.0 mm, 3.5 µm); RT 2.43 min. 0.05% TFA (Aq): ACN; 0.8 mL/min); UPLC (purity): 98.88%; (column: Acquity BEH C-18, 50 × 2.1 mm, 1.7 µm); RT 1.56 min. ACN: 0.025% TFA (Aq); 0.5 mL/min; Chiral HPLC: 98.14%; Rt = 12.81 min (Chiralpak IA, 250 × 4.6 mm, 5 µm); mobile phase (A) 0.1% DEA in n-Hexane (B) CH2Cl2:MeOH (80:20) (A:B :: 80:20); flow Rate: 1.0 mL/min); Optical rotation [α]D19.99: +19.48° (c = 0.25, CH2Cl2); TLC: 10% MeOH/CH2Cl2 (Rf: 0.4). |
| The enantiomer of 7-(3-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(3-fluorophenyl) imidazo [5,1-f] [1,2,4] triazin-4 (3H)-one | picolinaldehyde | B | (+)-7-(3-fluorophenyl)-2-((3,4-trans)-4-methyl-1-(pyridin-2-ylmethyl)pyrrolidin-3-yl)imidazo[5,1-f][1,2,4]triazin-4(3H)-one | A | | 190 | 236 | 1H-NMR (DMSO-d6, 400 MHz): δ 8.50 (d, 1H), 8.20 (d, 2H), 7.88 (s, 1H), 7.72 (t, 1H), 7.56 (q, 1H), 7.42 (d, 1H), 7.30 (t, 1H), 7.26 (t, 1H), 3.78 (q, 2H), 3.02-2.94 (m, 4H), 2.70-2.66 (m, 1H), 2.32 (t, 1H), 1.12 (d, 3H); Mass (ESI): 405 [M+ + 1]; LC-MS: 97.07%; 405 (M+ + 1); (column: X-bridge C-18, 50 × 3.0 mm, 3.5 µm); RT 2.60 min. 0.05% TFA (Aq): ACN; 0.8 mL/min; |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(3-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(3-fluorophenyl) imidazo [5,1-f] [1,2,4] triazin-4 (3H)-one | nicotinaldehyde | B | (+)-7-(3-fluorophenyl)-2-((3,4-trans)-4-methyl-1-(pyridin-3-ylmethyl)pyrrolidin-3-yl)imidazo[5,1-f][1,2,4]triazin-4(3H)-one | A | 15 | 37 | UPLC (purity): 96.43%; (column: Acquity BEH C-18, 50 × 2.1 mm, 1.7 μm); RT 1.68 min. ACN: 0.025% TFA (Aq); 0.5 mL/min.; Chiral HPLC: 95.52%, Rt = 8.16 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D20: +86.81° (c = 0.25, CH2Cl2); TLC: 10% MeOH/CH2Cl2 (Rf: 0.4). 1H-NMR (DMSO-d6, 400 MHz): δ 8.50 (s, 1H), 8.42 (d, 1H), 8.20 (d, 2H), 7.84 (s, 1H), 7.70 (d, 1H), 7.58 (q, 1H), 7.32-7.30 (m, 2H), 3.66 (s, 2H), 3.02-3.00 (m, 1H), 2.90-2.86 (m, 3H), 2.68-2.66 (m, 1H), 2.30 (t, 1H), 1.12 (d, 3H); Mass (ESI): 405 [M+ + 1]; LC-MS: 98.76%; 405 (M+ + 1); (column: X-bridge C-18, 50 × 3.0 mm, 3.5 μm); RT 2.28 min. 0.05% TFA (Aq): ACN: 0.8 mL/min; UPLC (purity): 96.36%; (column: Acquity BEH C-18, 50 × 2.1 mm, 1.7 μm); RT 1.49 min. ACN: 0.025% TFA (Aq); 0.5 mL/min.; Chiral HPLC: 97.53%, Rt = 12.35 min (Chiralpak IA, 250 × 4.6 mm, 5 μm); mobile |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | phase (A) 0.1% DEA in n-Hexane (B) CH2Cl2:MeOH (80:20) (A:B: 80:20); flow Rate: 1.0 mL/min); Optical rotation [α]D19.99: +21.77° (c = 0.25, CH2Cl2); TLC: 10% MeOH/CH2Cl2 (Rf: 0.4). |
| The enantiomer of 2-((3,4-trans)-4-methylpyrrolidin-3-yl)-7-(o-tolyl) imidazo [5,1-f] [1,2,4] triazin-4 (3H)-one obtained from debenzylation of (+)-2-((3,4-trans)-1-benzyl-4-methylpyrrolidin-3-yl)-7-(o-tolyl) imidazo[5,1-f] [1,2,4] triazin-4(3H)-one | — | — | (+)-2-((3,4-trans)-1-benzyl-4-methylpyrrolidin-3-yl)-7-(o-tolyl)imidazo[5,1-f][1,2,4]triazin-4(3H)-one | A | 461 | 531 | — |
| | 4-fluorobenzaldehyde | B | (+)-2-((3,4-trans)-1-(4-fluorobenzyl)-4-methylpyrrolidin-3-yl)-7-(o-tolyl)imidazo[5,1-f][1,2,4]triazin-4(3H)-one | A | 963 | 744 | 1H-NMR (DMSO-d6, 500 MHz): δ 7.86 (s, 1H), 7.48 (d, 1H), 7.41 (t, 1H), 7.36 (d, 1H), 7.31-7.25 (m, 3H), 7.17 (t, 2H), 3.56 (dd, 2H), 2.86-2.78 (m, 4H), 2.40 (t, 1H), 2.20 (s, 3H), 2.12 (t, 1H), 1.00 (d, 3H); Mass (ESI): 418.2 [M+ + 1]; LC-MS: 98.63%; 418 (M+ + 1); (column: X-bridge C-18, 50 × 3.0 mm, 3.5 µm); RT 2.69 min. 0.05% TFA (Aq); ACN; 0.8 mL/min); UPLC (purity): 97.96%; (column: Acquity BEH C-18, 50 × 2.1 mm, 1.7 µm); RT 1.76 min. ACN: 0.025% TFA (Aq); 0.5 mL/min.; Chiral HPLC: 99.29%, Rt = 6.10 min (Chiralpak IA, 250 × 4.6 mm, 5 µm); mobile phase (A) 0.1% DEA in n-Hexane (B) CH2Cl2:MeOH |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 2-((3,4-trans)-4-methylpyrrolidin-3-yl)-7-(o-tolyl) imidazo [5,1-f] [1,2,4] triazin-4 (3H)-one obtained from debenzylation of (+)-2-((3,4-trans)-1-benzyl-4-methylpyrrolidin-3-yl)-7-(o-tolyl) imidazo [5,1-f] [1,2,4] triazin-4(3H)-one | 2-(chloromethyl) imidazo [1,2-a] pyridine | A | (+)-2-((3,4-trans)-1-(imidazo[1,2-a]pyridin-2-ylmethyl)-4-methylpyrrolidin-3-yl)-7-(o-tolyl)imidazo[5,1-f][1,2,4]triazin-4(3H)-one | A | 326 | 661 | (80:20) (A:B :: 80:20); flow Rate: 1.0 mL/min); Optical rotation [α]D19.99: +18.59° (c = 0.25, CH2Cl2); TLC: 10% MeOH/CH2Cl2 (Rf: 0.6). 1H-NMR (DMSO-d6, 400 MHz): δ 8.42 (d, 1H), 7.90 (s, 1H), 7.74 (s, 1H), 7.54 (d, 1H), 7.46 (d, 1H), 7.40-7.32 (m, 3H), 7.18 (t, 1H), 6.80 (t, 1H), 3.72-3.70 (m, 2H), 3.06-3.04 (m, 1H), 2.94-2.92 (m, 2H), 2.82-2.80 (m, 1H), 2.72-2.70 (m, 1H), 2.40-2.38 (m, 1H), 2.22 (s, 3H), 1.00 (d, 3H); Mass (ESI): 440 [M+ + 1]; LC-MS: 97.36%; 440 (M+ + 1); UPLC (purity): 96.67%; (column: Acquity BEH C-18, 50 × 2.1 mm, 1.7 μm); RT 1.47 min. ACN: 0.025% TFA (Aq); 0.5 mL/min.; Chiral HPLC: 97.53%, Rt = 13.11 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D19.99: +11.60° (c = 0.25, CH2Cl2); TLC: 5% MeOH/CH2Cl2 (Rf: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 2-((3,4-trans)-4-methylpyrrolidin-3-yl)-7-(o-tolyl) imidazo [5,1-f] [1,2,4] triazin-4 (3H)-one obtained from debenzylation of (+)-2-((3,4-trans)-4-methylpyrrolidin-3-yl)-7-(o-tolyl) imidazo [5,1-f] [1,2,4] triazin-4(3H)-one | 4-chlorobenzaldehyde | B | (+)-2-((3,4-trans)-1-(4-chlorobenzyl)-4-methylpyrrolidin-3-yl)-7-(o-tolyl)imidazo[5,1-f][1,2,4]triazin-4(3H)-one | A | 55 | 109 | 1H-NMR (DMSO-d6, 400 MHz): δ 7.90 (s, 1H), 7.56 (d, 1H), 7.42-7.38 (m, 2H), 7.32-7.24 (m, 5H), 3.58 (q, 2H), 2.88 (t, 1H), 2.76-2.72 (m, 4H), 2.30 (s, 3H), 2.16 (t, 1H), 1.02 (d, 3H); Mass (ESI): 434.2 [M+ + 1]; LC-MS: 94.00%; 434 (M+ + 1); (column; X-bridge C-18, 50 × 3.0 mm, 3.5 μm); RT 2.87 min. 0.05% TFA (Aq); ACN: 0.8 mL/min); UPLC (purity): 95.58%; (column: Acquity BEH C-18, 50 × 2.1 mm, 1.7 μm); RT 1.87 min. ACN: 0.025% TFA (Aq); 0.5 mL/min.; Chiral HPLC: 99.54%, Rt = 7.55 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D20: +5.52° (c = 0.25, CH2Cl2). TLC: 5% MeOH/ CH2Cl2 (Rf: 0.7). |
| The enantiomer of 2-((3,4-trans)-4-methylpyrrolidin-3-yl)-7-(o-tolyl) imidazo[5,1-f] [1,2,4] triazin-4 (3H)-one obtained from debenzylation of (+)-2-((3,4-trans)-1-benzyl-4- | picolinaldehyde | B | (+)-2-((3,4-trans)-4-methyl-1-(pyridin-2-ylmethyl)pyrrolidin-3-yl)-7-(o-tolyl)imidazo[5,1-f][1,2,4]triazin-4(3H)-one | A | 73 | 148 | 1H-NMR (DMSO-d6, 400 MHz): δ 8.48 (s, 1H), 7.90 (s, 1H), 7.72 (t, 1H), 7.58 (d, 1H), 7.42-7.30 (m, 4H), 7.20 (d, 1H), 3.80 (d, 1H), 3.70 (d, 1H), 2.92-2.88 (m, 2H), 2.80-2.76 (m, 2H), 2.52-2.50 (m, 1H), 2.30 (s, 3H), 2.22-2.20 (m, 1H), 1.02 (d, 3H). Mass |

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| methylpyrrolidin-3-yl)-7-(o-tolyl) imidazo [5,1-f] [1,2,4] triazin-4(3H)-one | | | | | | | (ESI): 401.3 [M+ + 1]; LC-MS: 99.48%; 401 (M+ + 1); (column; X-bridge C-18, 50 × 3.0 mm, 3.5 µm); RT 2.41 min. 0.05% TFA (Aq): ACN; 0.8 mL/min); UPLC (purity): 98.94%; (column: Acquity BEH C-18, 50 × 2.1 mm, 1.7 µm); RT 1.56 min. ACN: 0.025% TFA (Aq); 0.5 mL/min; Chiral HPLC: 100%, Rt = 7.44 min (Chiralpak IA, 250 × 4.6 mm, 5 µm); mobile phase (A) 0.1% DEA in n-Hexane (B) CH2Cl2:MeOH (80:20) (A:B :: 80:20); flow Rate: 1.0 mL/min); Optical rotation [α]D20: +70.04° (c = 0.25, CH2Cl2). TLC: 5% MeOH/CH2Cl2 (Rf: 0.6). |
| The enantiomer of 2-((3,4-trans)-4-methylpyrrolidin-3-yl)-7-(o-tolyl) imidazo [5,1-f] [1,2,4] triazin-4 (3H)-one obtained from debenzylation of (+)-2-((3,4-trans)-1-benzyl-4-methylpyrrolidin-3-yl)-7-(o-tolyl) imidazo [5,1-f] [1,2,4] triazin-4(3H)-one | [1,2,4] triazolo [1,5-a] pyridine-2-carbaldehyde | B | (+)-2-((3,4-trans)-1-([1,2,4]triazolo[1,5-a]pyridin-2-ylmethyl)-4-methylpyrrolidin-3-yl)-7-(o-tolyl)imidazo[5,1-f][1,2,4]triazin-4(3H)-one | A | 490 | 429 | 1H-NMR (DMSO-d6, 400 MHz): δ 8.90 (d, 1H), 7.90 (s, 1H), 7.80 (d, 1H), 7.64 (t, 1H), 7.52 (d, 1H), 7.42 (d, 1H), 7.34 (d, 1H), 7.26 (t, 2H), 7.14 (t, 1H), 3.90 (q, 2H), 3.02-2.99 (m, 2H), 2.86 (t, 1H), 2.71-2.69 (m, 1H), 2.38 (t, 1H), 2.26-2.24 (m, 3H), 1.06 (d, 3H); Mass (ESI): 441 [M+ + 1]; LC-MS: 98.88%; 441 (M+ + 1); (column: X-bridge C-18, 50 × 3.0 mm, 3.5 µm); RT 2.46 min. 0.05% TFA (Aq): ACN; 0.8 mL/min); UPLC (purity): 95.11%; |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 2-((3,4-trans)-4-methylpyrrolidin-3-yl)-7-(o-tolyl) imidazo [5,1-f] [1,2,4] triazin-4 (3H)-one obtained from debenzylation of (+)-2-((3,4-trans)-1-benzyl-4-methylpyrrolidin-3-yl)-7-(o-tolyl) imidazo [5,1-f] [1,2,4] triazin-4(3H)-one | 2-(chloro methyl)-1H-benzo [d] imidazole | A | (+)-2-((3,4-trans)-1-((1H-benzo[d]imidazol-2-yl)methyl)-4-methylpyrrolidin-3-yl)-7-(o-tolyl)imidazo[5,1-f][1,2,4]triazin-4(3H)-one | A | 1740 | 2990 | (column: Acquity BEH C-18, 50 × 2.1 mm, 1.7 μm); RT 1.53 min. ACN: 0.025% TFA (Aq); 0.5 mL/min.; Chiral HPLC: 94.37%, Rt = 9.67 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D19.99: +29.64° (c = 0.25, CH2Cl2); TLC: 5% MeOH/CH2Cl2 (Rf: 0.4). 1H-NMR (DMSO-d6, 400 MHz): δ 12.22 (b, 1H), 7.90 (s, 1H), 7.56 (d, 2H), 7.41-7.39 (m, 2H), 7.34 (d, 1H), 7.20 (d, 1H), 7.10 (m, 2H), 3.82 (q, 2H), 3.06-3.04 (m, 1H), 2.90 (t, 1H), 2.80-2.77 (m, 2H), 2.51-2.49 (m, 1H), 2.34-2.32 (m, 1H), 2.22 (s, 3H), 1.00 (d, 3H); Mass (ESI): 440.3 [M+ + 1]; LC-MS: 95.12%; 440 (M+ + 1); (column: X-bridge C-18, 50 × 3.0 mm, 3.5 μm); RT 2.66 min. 0.05% TFA (Aq): ACN: 0.8 mL/min); UPLC (purity): 95.04%; (column: Acquity BEH C-18, 50 × 2.1 mm, 1.7 μm); RT 1.70 min. ACN: 0.025% TFA (Aq); 0.5 mL/min.; Chiral HPLC: 96.53%, Rt = 9.06 min (Chiralpak IA, 250 × 4.6 mm, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | 5 μm); mobile phase (A) 0.1% DEA in n-Hexane (B) CH2Cl2:MeOH (80:20) (A:B :: 80:20); flow Rate: 1.0 mL/min); Optical rotation [α]D19.99: +5.47° (c = 0.25, CH2Cl2); TLC: 5% MeOH/CH2Cl2 (Rf: 0.6). |
| The enantiomer of 2-((3,4-trans)-4-methylpyrrolidin-3-yl)-7-(o-tolyl) imidazo [5,1-f] [1,2,4] triazin-4 (3H)-one obtained from debenzylation of (+)-2-((3,4-trans)-1-benzyl-4-methylpyrrolidin-3-yl)-7-(o-tolyl) imidazo [5,1-f] [1,2,4] triazin-4(3H)-one | nicotinaldehyde | B | (+)-2-(3,4-trans)-4-methyl-1-(pyridin-3-ylmethyl)pyrrolidin-3-yl)-7-(o-tolyl)imidazo[5,1-f][1,2,4]triazin-4(3H)-one | A | 103 | 183 | 1H-NMR (DMSO-d6, 400 MHz): δ 8.46-8.45 (m, 2H), 7.88 (s, 1H), 7.66-7.64 (m, 1H), 7.56-7.54 (m, 1H), 7.42-7.40 (m, 2H), 7.32-7.30 (m, 2H), 3.60 (q, 2H), 2.92 (t, 1H), 2.80-2.70 (m, 4H), 2.30 (s, 3H), 2.22-2.20 (m, 1H), 1.04 (d, 3H); Mass (ESI): 401.3 [M+ + 1]; LC-MS: 95.18%; 401 (M+ + 1); (column; X-bridge C-18, (50 × 3.0 mm, 3.5 μm); RT 2.06 min. 0.05% TFA (aq.): ACN; 0.8 mL/min); UPLC (purity): 97.72%; (column: Acquity BEH C-18 (50 × 2.1 mm, 1.7μ); RT 1.36 min. ACN: 0.025% TFA (Aq); 0.5 mL/min.; Chiral HPLC: 97.24%, Rt = 9.78 min (Chiralpak IA, 250 × 4.6 mm, 5μ); mobile phase (A) 0.1% DEA in n-Hexane (B) CH2Cl2:MeOH (80:20) (A:B: 80:20); flow Rate: 1.0 mL/min); Optical rotation [α]D19.99: +14.64° (c = 0.25, CH2Cl2); TLC: 5% MeOH/CH2Cl2 (Rf: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 2-((3,4-trans)-4-methylpyrrolidin-3-yl)-7-(o-tolyl) imidazo [5,1-f] [1,2,4] triazin-4 (3H)-one obtained from debenzylation of (+)-2-((3,4-trans)-1-benzyl-4-methylpyrrolidin-3-yl)-7-(o-tolyl) imidazo [5,1-f] [1,2,4] triazin-4(3H)-one | 2-(chloromethyl) pyrazine | A | (+)-2-((3,4-trans)-4-methyl-1-(pyrazin-2-ylmethyl)pyrrolidin-3-yl)-7-(o-tolyl)imidazo[5,1-f][1,2,4]triazin-4(3H)-one | A | 387 | 469 | 1H-NMR (DMSO-d6, 400 MHz): δ 8.70 (s, 1H), 8.54 (d, 2H), 7.90 (s, 1H), 7.56 (d, 1H), 7.42-7.26 (m, 3H), 3.80 (q, 2H), 3.00 (t, 1H), 2.90-2.74 (m, 3H), 2.60-2.58 (m, 1H), 2.34-2.28 (m, 4H), 1.08 (d, 3H); Mass (ESI): 402.3 [M+ + 1]; LC-MS: 94.44%; 402 (M+ + 1); (column; X-bridge C-18, 50 × 3.0 mm, 3.5 μm); RT 2.20 min. 0.05% TFA (aq.): ACN; 0.8 mL/min); UPLC (purity): 92.69%; (column: Acquity BEH C-18; 50 × 2.1 mm, 1.7μ); RT 1.43 min. ACN: 0.025% TFA (Aq); 0.5 mL/min.; Chiral HPLC: 95.34%, Rt = 10.08 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D20: +64.60° (c = 0.25, CH2Cl2); TLC: 5% MeOH/CH2Cl2 (Rf: 0.3). |
| — | — | — | (+)-2-((3,4-trans)-1-benzyl-4-methylpyrrolidin-3-yl)-7-(4,5-difluoro-2-methylphenyl) imidazo[5,1-f][1,2,4]triazin-4(3H)-one | A | 174 | 143 | — |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4,5-difluoro-2-methylphenyl)-2-((3,4-trans)-4-methylpyrrolidin-3-yl) imidazo [5,1-f] [1,2,4] triazin-4 (3H)-one obtained from debenzylation of (+)-2-(3,4-trans)-1-benzyl-4-methylpyrrolidin-3-yl)-7-(4,5-difluoro-2-methylphenyl)imidazo[5,1-f][1,2,4]triazin-4(3H)-one | 4-fluorobenzaldehyde | B | (+)-7-(4,5-difluoro-2-methylphenyl)-2-((3,4-trans)-1-(4-fluorobenzyl)-4-methylpyrrolidin-3-yl)imidazo[5,1-f][1,2,4]triazin-4(3H)-one | A | 232 | 179 | 1H-NMR (DMSO-d6, 400 MHz): δ 7.92 (s, 1H), 7.70 (t, 1H), 7.52 (t, 1H), 7.31-7.28 (m, 2H), 7.10 (t, 2H), 3.56 (q, 2H), 2.90 (t, 1H), 2.80-2.70 (m, 3H), 2.56-2.54 (m, 1H), 2.32 (s, 3H), 2.22 (t, 1H), 1.08 (d, 3H), Mass (ESI): 454 [M+ + 1]; LC-MS: 98.96%; 454 (M+ + 1); (column: X-bridge C-18, 50 × 3.0 mm, 3.5 μm); RT 3.03 min. 0.05% TFA: ACN; 0.8 mL/min); UPLC (purity): 97.61%; (column: Acquity BEH C-18, (50 × 2.1 mm, 1.7 μm); RT 1.89 min. ACN: 0.025% TFA (Aq); 0.5 mL/min; Chiral HPLC: 95.27%, Rt = 13.02 min (Chiralpak IA, 250 × 4.6 mm, 5 μm; mobile phase (A) 0.1% DEA in n-Hexane (B) DCM:MeOH (80:20) (A:B :: 88:12); flow Rate: 1.0 mL/min); Optical rotation [α]D20: +24.35° (c = 0.25, DCM), TLC: 10% MeOH/DCM (Rf: 0.7). |
| The enantiomer of 7-(4,5-difluoro-2-methylphenyl)-2-((3,4-trans)-4-methylpyrrolidin-3-yl) imidazo [5,1-f] [1,2,4] triazin-4 (3H)-one obtained from debenzylation of | [1,2,4]triazolo[1,5-a]pyridine-2-carbaldehyde | B | (+)-2-((3,4-trans)-1-([1,2,4]triazolo[1,5-a]pyridin-2-ylmethyl)-4-methylpyrrolidin-3-yl)-7-(4,5-difluoro-2-methylphenyl) | A | 1000 | 2140 | 1H-NMR (DMSO-d6, 400 MHz): δ 8.86 (d, 1H), 7.90 (s, 1H), 7.74 (d, 1H), 7.62 (q, 2H), 7.44 (t, 1H), 7.14 (t, 1H), 3.85 (q, 2H), 3.06 (t, 1H), 3.00 (t, 1H), 2.90 (t, 1H), 2.76-2.74 (m, 1H), 2.54-2.52 (m, 1H), 2.41-2.39 (m, 1H), 2.30 (s, 3H), 1.04 (d, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| (+)-2-((3,4-trans)-1-benzyl-4-methylpyrrolidin-3-yl)-7-(4,5-difluoro-2-methylphenyl)imidazo[5,1-f][1,2,4]triazin-4(3H)-one | | | imidazo[5,1-f][1,2,4]triazin-4(3H)-one | | | | 3H), Mass (ESI): 477.4 [M+ + 1]; LC-MS: 98.04%; 477 (M+ + 1); (column; X-bridge C-18, 50 × 3.0 mm, 3.5 µm); RT 2.60 min. 0.05% TFA (aq.): ACN; 0.8 mL/min; UPLC (purity): 96.22%; (column: Acquity BEH C-18; 50 × 2.1 mm, 1.7µ); RT 1.68 min. ACN: 0.025% TFA (Aq); 0.5 mL/min.; Chiral HPLC: 96.61%, Rt = 12.40 min (Chiralpak IA, 250 × 4.6 mm, 5µ); mobile phase (A) 0.1% DEA in n-Hexane (B) DCM:MeOH (80:20) (A:B :: 80:20); flow Rate: 1.0 mL/min); Optical rotation [α]D19.97: +40° (c = 0.25, DCM); TLC: 10% MeOH/DCM (Rf: 0.4). |
| The enantiomer of 7-(4,5-difluoro-2-methylphenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4,5-difluoro-2-methylphenyl)imidazo[5,1-f][1,2,4]triazin-4(3H)-one | 2-(chloro methyl) pyrimidine | A | (+)-7-(4,5-difluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one | A | 44 | 85 | 1H-NMR (DMSO-d6, 400 MHz): δ 8.78 (d, 2H), 7.90 (s, 1H), 7.68 (t, 1H), 7.50 (t, 1H), 7.40 (t, 1H), 3.98 (d, 1H), 3.80 (d, 1H), 3.10 (t, 1H), 2.94-2.92 (m, 2H), 2.74-2.72 (m, 1H), 2.34-2.32 (m, 2H), 2.28 (s, 3H), 1.06 (d, 3H). Mass (ESI): 436.5 [M+ − 1]; LC-MS: 96.13%; 438 (M+ + 1); (column: X-bridge C-18, (50 × 3.0 mm, 3.5 µm); RT 2.58 min. 0.05% TFA (Aq): ACN; 0.8 mL/min); UPLC (purity): 95.18%; (column: Acquity BEH C-18 (50 × 2.1 mm, 1.7 µm); RT 1.63 min. |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4,5-difluoro-2-methylphenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4,5-difluoro-2-methylphenyl)imidazo[5,1-f][1,2,4]triazin-4(3H)-one | 2-(chloromethyl) imidazo [1,2-a] pyridine | A | (+)-7-(4,5-difluoro-2-methylphenyl)-2-((3,4-trans)-1-(imidazo[1,2-a]pyridin-2-ylmethyl)-4-methylpyrrolidin-3-yl)imidazo[5,1-f][1,2,4]triazin-4(3H)-one | A | 2510 | 9350 | ACN: 0.025% TFA (Aq); 0.5 mL/min.; Chiral HPLC: 95.05%, Rt = 9.03 min (Chiralpak IA, 250 × 4.6 mm, 5µ; mobile phase (A) 0.1% DEA in n-Hexane (B) DCM:MeOH (80:20) (A:B: 80:20); flow Rate: 1.0 mL/min); Optical rotation [α]D20: +78.94° (c = 0.25, DCM). TLC: 10% MeOH/DCM (Rf: 0.6). 1H-NMR (DMSO-d6, 400 MHz): δ 8.46 (d, 1H), 7.90 (s, 1H), 7.79 (s, 1H), 7.69 (t, 1H), 7.46 (d, 2H), 7.20 (t, 1H), 6.80 (t, 1H), 3.72 (q, 2H), 3.02 (t, 1H), 2.92 (t, 1H), 2.82 (t, 1H), 2.72 (t, 1H), 2.60-2.58 (m, 1H), 2.38-2.36 (m, 1H), 2.28 (s, 3H), 1.09 (d, 3H). Mass (ESI): 476.4 [M+ + 1]; LC-MS: 96.49%; 476 (M+ + 1); (column: X-bridge C-18, 50 × 3.0 mm, 3.5 µm); RT 2.45 min. 0.05% TFA (aq.): ACN; 0.8 mL/min); UPLC (purity): 94.67%; (column: Acquity BEH C-18; 50 × 2.1 mm, 1.7µ); RT 1.62 min. ACN: 0.025% TFA (Aq); 0.5 mL/min.; Chiral HPLC: 95.20%, Rt = 12.05 min (Chiralpak IA, 250 × 4.6 mm, 5 µm; mobile phase (A) 0.1% DEA in n-Hexane (B) DCM:MeOH (80:20) (A:B :: 80:20); flow |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | — | — | (+)-2-((3,4-trans)-1-benzyl-4-methylpyrrolidin-3-yl)-7-phenylimidazo[5,1-f][1,2,4]triazin-4(3H)-one | | | | Rate: 1.0 mL/min); Optical rotation [α]D20: +12.94° (c = 0.25, DCM). TLC: 10% MeOH/DCM (Rf: 0.4). |
| | — | — | | A | 4 | 12 | — |
| The enantiomer of 2-((3,4-trans)-4-methylpyrrolidin-3-yl)-7-phenylimidazo[5,1-f][1,2,4]triazin-4(3H)-one obtained from debenzylation of (+)-2-((3,4-trans)-1-benzyl-4-methylpyrrolidin-3-yl)-7-phenylimidazo[5,1-f][1,2,4]triazin-4(3H)-one | 4-fluorobenzaldehyde | B | (+)-2-((3,4-trans)-1-(4-fluorobenzyl)-4-methylpyrrolidin-3-yl)-7-phenylimidazo[5,1-f][1,2,4]triazin-4(3H)-one | A | 3 | 7 | 1H-NMR (DMSO-d6, 500 MHz): δ 8.36 (d, 2H), 7.86 (s, 1H), 7.58-7.46 (m, 3H), 7.38-7.36 (m, 2H), 7.12 (t, 2H), 3.62 (s, 2H), 3.01-2.99 (m, 1H), 2.90-2.78 (m, 3H), 2.66-2.64 (m, 1H), 2.28 (t, 1H), 1.14 (d, 3H). Mass (ESI): 404.4 [M+ + 1]; LC-MS: 95.36%; 404 (M+ + 1); (column: X-bridge C-18, 50 × 3.0 mm, 3.5 μm); RT 2.76 min. 0.05% TFA (aq.): ACN; 0.8 mL/min); UPLC (purity): 95.80%; (column: Acquity BEH C-18; 50 × 2.1 mm, 1.7μ); RT 1.77 min. ACN: 0.025% TFA (Aq); 0.5 mL/min.; Chiral HPLC: 93.40%, Rt = 7.37 min (Chiralpak IA, 250 × 4.6 mm, 5 μm; mobile phase (A) 0.1% DEA in n-Hexane (B) DCM: MeOH (80:20) (A:B :: 80:20); flow Rate: 1.0 mL/min); Optical rotation [α]D20: +25.21° (c = 0.25, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 2-((3,4-trans)-4-methylpyrrolidin-3-yl)-7-phenylimidazo[5,1-f][1,2,4]triazin-4(3H)-one obtained from debenzylation of (+)-2-((3,4-trans)-1-benzyl-4-methylpyrrolidin-3-yl)-7-phenylimidazo[5,1-f][1,2,4]triazin-4(3H)-one | 2-(chloromethyl)pyrimidine | A | (+)-2-((3,4-trans)-4-methyl-1-(pyrimidin-2-ylmethyl)pyrrolidin-3-yl)-7-phenylimidazo[5,1-f][1,2,4]triazin-4(3H)-one | A | — | — | DCM). TLC: 5% MeOH/DCM (Rf: 0.6). 1H-NMR (DMSO-d6, 400 MHz): δ 8.80 (d, 2H), 8.34 (d, 2H), 7.80 (s, 1H), 7.52 (t, 2H), 7.44 (d, 1H), 7.36 (t, 1H), 4.00 (d, 1H), 3.84 (d, 1H), 3.10 (t, 1H), 3.04 (d, 2H), 2.82-2.80 (m, 1H), 2.64-2.62 (m, 1H), 2.41-2.38 (m, 1H), 1.12 (d, 3H). Mass (ESI): 388 [M+ + 1]; LC-MS: 95.68%; 388 (M+ + 1); (column; X-bridge C-18, 50 × 3.0 mm, 3.5 μm); RT 2.29 min. 0.05% TFA (aq.): ACN; 0.8 mL/min); UPLC (purity): 98.96%; (column: Acquity UPLC BEH C-18; 2.1 × 50 mm, 1.7μ); RT 1.44 min. ACN: 0.025% TFA (Aq) 0.5 mL/min.; Chiral HPLC: 98.86%, Rt = 11.79 min (Chiralpak IA, 250 × 4.6 mm, 5 μm); mobile phase (A) 0.1% DEA in n-Hexane (B) DCM:MeOH (80:20) (A:B :: 80:20); flow Rate: 1.0 mL/min); Optical rotation [α]D20.01: +70.83° (c = 0.25, DCM). TLC: 5% MeOH/DCM (Rf: 0.4). |
| The enantiomer of 2-((3,4-trans)-4-methylpyrrolidin-3-yl)-7-phenylimidazo[5,1-f][1,2,4]triazin-4(3H)-one | [1,2,4]triazolo[1,5-a]pyridine-2-carbaldehyde | B | (+)-2-((3,4-trans)-1-([1,2,4]triazolo[1,5-a]pyridin-2-ylmethyl)-4-methylpyrrolidin-3-yl)-7- | A | — | — | 1H-NMR (DMSO-d6, 400 MHz): δ 8.90 (d, 1H), 8.32 (d, 2H), 7.90 (s, 1H), 7.76 (d, 1H), 7.62 (t, 1H), 7.52-7.42 (m, 3H), 7.16 (t, 1H), 3.92 (q, 2H), 3.12-3.08 (m, 2H), 3.00 (t, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| obtained from debenzylation of (+)-2-((3,4-trans)-1-benzyl-4-methylpyrrolidin-3-yl)-7-phenylimidazo[5,1-f][1,2,4]triazin-4(3H)-one | | | | | | | 2.86-2.84 (m, 1H), 2.70-2.66 (m, 1H), 2.44-2.42 (m, 1H), 1.12 (d, 3H). Mass (ESI): 427.6 [M+ + 1]; LC-MS: 93.40%; 427 (M+ + 1); (column; X-bridge C-18, 50 × 3.0 mm, 3.5 μm); RT 2.42 min. 0.05% TFA (aq.); ACN; 0.8 mL/min); UPLC (purity): 93.80%; (column: Acquity BEH C-18; 50 × 2.1 mm, 1.7μ); RT 1.54 min. ACN: 0.025% TFA (Aq); 0.5 mL/min.; Chiral HPLC: 96.03%, Rt = 9.21 min (Chiralpak IA, 250 × 4.6 mm, 5 μm); mobile phase (A) 0.1% DEA in n-Hexane (B) DCM: MeOH (80:20) (A:B :: 85:15); flow Rate: 1.0 mL/min); Optical rotation [α]D19.99: +51.44° (c = 0.25, DCM). TLC: 10% MeOH/DCM (Rf: 0.4). |
| The enantiomer of 2-((3,4-trans)-4-methylpyrrolidin-3-yl)-7-phenylimidazo [5,1-f] [1,2,4] triazin-4 (3H)-one obtained from debenzylation of (+)-2-((3,4-trans)-1-benzyl-4-methylpyrrolidin-3-yl)-7-phenylimidazo[5,1-f][1,2,4]triazin-4(3H)-one | 2-(chloro methyl) imidazo [1,2-a] pyridine | A | (+)-2-(3,4-trans)-1-(imidazo[1,2-a]pyridin-2-ylmethyl)-4-methylpyrrolidin-3-yl)-7-phenylimidazo[5,1-f][1,2,4]triazin-4(3H)-one | A | — | — | 1H-NMR (DMSO-d6, 400 MHz): δ 8.46 (d, 1H), 8.34 (d, 2H), 7.86 (s, 1H), 7.78 (s, 1H), 7.54-7.42 (m, 4H), 7.18 (t, 1H), 6.82 (t, 1H), 3.80 (q, 2H), 3.10 (t, 1H), 3.04 (t, 1H), 2.92-2.90 (m, 1H), 2.84-2.82 (m, 1H), 2.70-2.64 (m, 1H), 2.40-2.38 (m, 1H), 1.12 (d, 3H); Mass (ESI): 426.7 [M+ + 1]; LC-MS: 97.32%; 426 (M+ + 1); (column; X-bridge C-18, 50 × 3.0 mm, 3.5 μm); RT 2.23 min. 0.05% TFA (aq.); |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4-methylpyridin-3-yl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4-methylpyridin-3-yl)imidazo[5,1-f][1,2,4]triazin- | — | — | (+)-2-((3,4-trans)-1-benzyl-4-methylpyrrolidin-3-yl)-7-(4-methylpyridin-3-yl)imidazo[5,1-f][1,2,4]triazin-4(3H)-one | A | 148 | 379 | ACN; 0.8 mL/min); UPLC (purity): 98.29%; (column: Acquity BEH C-18; 50 × 2.1 mm, 1.7µ); RT 1.47 min. ACN: 0.025% TFA (Aq): 0.5 mL/min.; Chiral HPLC: 99.24%, Rt = 16.12 min (Chiralpak IC, 250 × 4.6 mm, 5µ); mobile phase (A) 0.1% DEA in n-Hexane (B) CH2Cl2:MeOH (80:20) (A:B: 65:35); flow Rate: 1.0 mL/min); Optical rotation [α]D20: +43.45° (c = 0.25, CH2Cl2); TLC: 10% MeOH/CH2Cl2 (Rf: 0.6). |
| | 2-(chloromethyl)pyrimidine | A | (+)-2-((3,4-trans)-4-methyl-1-(pyrimidin-2-ylmethyl)pyrrolidin-3-yl)-7-(4-methylpyridin-3-yl)imidazo[5,1-f][1,2,4]triazin-4(3H)-one | A | 85 | 127 | 1H-NMR (DMSO-d6, 400 MHz): δ 8.80 (d, 2H), 8.72 (s, 1H), 8.52 (d, 1H), 7.94 (s, 1H), 7.42-7.34 (m, 2H), 4.00 (d, 1H), 3.80 (d, 1H), 3.06 (t, 1H), 2.96-2.90 (m, 2H), 2.78-2.74 (m, 1H), 2.44-2.42 (m, 1H), 2.36-2.30 (m, 4H), 1.10 (d, 3H); Mass (ESI): 403.3 [M+ + 1]; LC-MS: 94.57%; 403 (M+ + 1); (column: X-bridge C-18, 50 × 3.0 mm, 3.5 µm); RT 2.48 min. 5 mM NH4OAc: ACN; |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| 4(3H)-one | | | | | | | 0.8 mL/min); UPLC (purity): 94.33%; (column: Acquity UPLC HSS T3; 2.1 × 100 mm, 1.8μ); RT 2.80 min. ACN: 0.025% TFA (Aq); 0.3 mL/min.; Chiral HPLC: 93.89%, Rt = 17.23 min (Chiralpak IA, 250 × 4.6 mm, 5 μm); mobile phase (A) 0.1% DEA in n-Hexane (B) CH2Cl2:MeOH (80:20) (A:B:: 80:20); flow Rate: 1.0 mL/min); Optical rotation [α]D20: +79.37° (c = 0.25, CH2Cl2); TLC: 10% MeOH/CH2Cl2 (Rf: 0.5). |
| The enantiomer of 7-(4-methylpyridin-3-yl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4-methylpyridin-3-yl)imidazo[5,1-f][1,2,4]triazin-4(3H)-one | 4-fluorobenzaldehyde | B | (+)-2-((3,4-trans)-1-(4-fluorobenzyl)-4-methylpyrrolidin-3-yl)-7-(4-methylpyridin-3-yl)imidazo[5,1-f][1,2,4]triazin-4(3H)-one | A | — | — | 1H-NMR (DMSO-d6, 400 MHz): δ 8.74 (s, 1H), 8.52 (d, 1H), 7.92 (s, 1H), 7.44 (d, 1H), 7.30 (t, 2H), 7.12 (t, 2H), 3.56 (q, 2H), 2.90 (t, 1H), 2.78-2.64 (m, 4H), 2.38 (s, 3H), 2.21-2.19 (m, 1H), 1.04 (d, 3H); Mass (ESI): 419.3 [M+ + 1]; LC-MS: 94.46%; 419 (M+ + 1); (column: X-bridge C-18, 50 × 3.0 mm, 3.5 μm); RT 2.11 min. 0.05% TFA: ACN; 0.8 mL/min); UPLC (purity): 93.22%; (column: Acquity UPLC HSS T3, (2.1 × 100 mm, 1.8μ); RT 3.18 min. ACN: 0.025% TFA (Aq); 0.3 mL/min.; Chiral HPLC: 94.23%, Rt = 9.62 min (Chiralpak IA, 250 × 4.6 mm, 5 μm); mobile |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4-methylpyrrolidin-3-yl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4-methylpyrrolidin-3-yl)imidazo[5,1-f][1,2,4]triazin-4(3H)-one | [1,2,4]triazolo[1,5-a]pyridine-2-carbaldehyde | B | (+)-2-((3,4-trans)-1-([1,2,4]triazolo[1,5-a]pyridin-2-ylmethyl)-4-methylpyrrolidin-3-yl)-7-(4-methylpyrrolidin-3-yl)imidazo[5,1-f][1,2,4]triazin-4(3H)-one | A | 56 | 115 | 1H-NMR (DMSO-d6, 400 MHz): δ 8.90 (d, 1H), 8.72 (s, 1H), 8.52 (d, 1H), 7.96 (s, 1H), 7.78 (d, 1H), 7.64-7.62 (m, 1H), 7.39 (d, 1H), 7.16 (t, 1H), 3.88 (q, 2H), 3.10 (t, 1H), 3.00 (t, 1H), 2.91-2.89 (m, 1H), 2.80-2.78 (m, 1H), 2.61-2.59 (m, 1H), 2.41-2.39 (m, 1H), 2.30 (s, 3H), 1.08 (d, 3H); Mass (ESI): 443 [M+ + 2]; LC-MS: 93.66%; 442 (M+ + 1); (column; X-bridge C-18, 50 × 3.0 mm, 3.5 μm); RT 1.69 min. 0.05% TFA (aq.): ACN; 0.8 mL/min); UPLC (purity): 97.70%; (column: Acquity UPLC HSS T3; 2.1 × 100 mm, 1.8μ); RT 2.90 min. ACN: 0.025% TFA (Aq); 0.3 mL/min, Chiral HPLC: 95.37%, Rt = 17.12 min (Chiralpak IC, 250 × 4.6 mm, 5μ; mobile phase (A) 0.1% DEA in n-Hexane (B) CH2Cl2:MeOH (80:20) (A:B :: 50:50); flow Rate: 1.0 mL/min); Optical rotation [α]D20: +38.08° (c = 0.25, | phase (A) 0.1% DEA in n-Hexane (B) CH2Cl2:MeOH (80:20) (A:B: 80:20); flow Rate: 1.0 mL/min); Optical rotation [α]D20.01: +19.93° (c = 0.25, CH2Cl2); TLC: 10% MeOH/CH2Cl2 (Rf: 0.6)

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(4-methylpyrrolidin-3-yl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(4-methylpyrrolidin-3-yl)imidazo[5,1-f][1,2,4]triazin-4(3H)-one | 2-(chloromethyl) imidazo [1,2-a] pyridine | A | (+)-2-((3,4-trans)-1-(imidazo[1,2-a]pyridin-2-ylmethyl)-4-methylpyrrolidin-3-yl)-7-(4-methylpyrrolidin-3-yl)imidazo[5,1-f][1,2,4]triazin-4(3H)-one | A | 128 | 230 | CH2Cl2); TLC: 10% MeOH/CH2Cl2 (Rf: 0.2). 1H-NMR (DMSO-d6, 400 MHz): δ 8.76 (s, 1H), 8.54 (d, 1H), 8.46 (d, 1H), 7.94 (s, 1H), 7.74 (s, 1H), 7.46 (d, 1H), 7.40 (d, 1H), 7.17 (t, 1H), 6.84 (t, 1H), 3.70 (q, 2H), 3.02 (t, 1H), 2.92 (t, 1H), 2.84-2.82 (m, 1H), 2.76-2.74 (m, 1H), 2.56-2.54 (m, 1H), 2.40 (s, 3H), 2.31-2.29 (m, 1H), 1.04 (d, 3H); Mass (ESI): 441.5 [M+ + 1]; LC-MS: 99.39%; 441 (M+ + 1); (column; X-bridge C-18, 50 × 3.0 mm, 3.5 μm); RT 2.55 min. 0.05% TFA (aq.): ACN; 0.8 mL/min); UPLC (purity): 98.45%; (column: Acquity UPLC HSS T3; 2.1 × 100 mm, 1.8μ); RT 2.84 min. ACN: 0.025% TFA (Aq): 0.3 mL/min.; Chiral HPLC: 99.75%, Rt = 18.19 min (Chiralpak IC, 250 × 4.6 mm, 5μ); mobile phase (A) 0.1% DEA in n-Hexane (B) CH2Cl2:MeOH (80:20) (A:B: 50:50); flow Rate: 1.0 mL/min); Optical rotation [α]D20: +23.50° (c = 0.25, CH2Cl2); TLC: 10% MeOH/CH2Cl2 (Rf: 0.2). |
| — | — | — | (+)-2-((3,4-trans)-1-benzyl-4-methylpyrrolidin- | A | — | — | — |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-cyclopentyl-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-cyclopentylimidazo[5,1-f][1,2,4]triazin-4(3H)-one | 4-fluorobenzaldehyde | B | (+)-7-cyclopentyl-2-((3,4-trans)-1-(4-fluorobenzyl)-4-methylpyrrolidin-3-yl)imidazo[5,1-f][1,2,4]triazin-4(3H)-one | A | 41 | 104 | 1H-NMR (DMSO-d6, 400 MHz): δ 7.60 (s, 1H), 7.36 (t, 2H), 7.10 (t, 2H), 3.60 (q, 2H), 3.46 (t, 1H), 2.96-2.94 (m, 1H), 2.80 (t, 1H), 2.74-2.72 (m, 2H), 2.64-2.62 (m, 1H), 2.28 (t, 1H), 2.01-1.97 (m, 2H), 1.86-1.84 (m, 2H), 1.76-1.74 (m, 2H), 1.64-1.62 (m, 2H), 1.08 (d, 3H); Mass (ESI): 396.4 [M+ + 1]; LC-MS: 99.90%; 396 (M+ + 1); (column; X-bridge C-18, 50 × 3.0 mm, 3.5 μm); RT 2.49 min. 0.05% TFA (Aq): ACN; 0.8 mL/min); UPLC (purity): 96.90%; (column: Acquity BEH C-18, 50 × 2.1 mm, 1.7μ); RT 1.65 min. ACN: 0.025% TFA (Aq): 0.5 mL/min.; Chiral HPLC: 99.52%, Rt = 7.13 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D19.99 +15.31° (c = 0.25, CH2Cl2); TLC: 10% MeOH/CH2Cl2 (Rf: 0.7). |
| The enantiomer of 7-cyclopentyl-2-((3,4-trans)-4-methylpyrrolidin- | 2-(chloromethyl) pyrimidine | A | (+)-7-cyclopentyl-2-((3,4-trans)-4-methyl-1- | A | 60 | 45 | 1H-NMR (DMSO-d6, 400 MHz): δ 8.80 (d, 2H), 7.62 (s, 1H), 7.42 (t, 1H), 4.02 (d, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| 3-yl) imidazo [5,1-f] [1,2,4] triazin-4 (3H)-one obtained from debenzylation of (+)-2-((3,4-trans)-1-benzyl-4-methylpyrrolidin-3-yl)-7-cyclopentylimidazo[5,1-f][1,2,4]triazin-4(3H)-one | | | (pyrimidin-2-ylmethyl)pyrrolidin-3-yl)imidazo[5,1-f][1,2,4]triazin-4(3H)-one | | | | 3.80 (d, 1H), 3.50 (t, 1H), 3.14 (t, 1H), 3.02-2.98 (m, 2H), 2.80-2.78 (m, 1H), 2.60-2.58 (m, 1H), 2.40-2.36 (m, 1H), 2.05-2.00 (m, 2H), 1.86-1.84 (m, 2H), 1.72-1.69 (m, 2H), 1.62-1.59 (m, 2H), 1.10 (d, 3H); Mass (ESI): 380 [M+ + 1]; LC-MS: 99.19%; 380 (M+ + 1); (column: X-bridge C-18, 50 × 3.0 mm, 3.5 μm); RT 2.03 min. 0.05% TFA (aq.): ACN; 0.8 mL/min); UPLC (purity): 97.03%; (column: Acquity BEH C-18; 50 × 2.1 mm, 1.7μ); RT 1.33 min. ACN: 0.025% TFA (Aq); 0.5 mL/min.; Chiral HPLC: 97.13%, Rt = 11.21 min (Chiralpak IA, 250 × 4.6 mm, 5μ); mobile phase (A) 0.1% DEA in n-Hexane (B) CH2Cl2:MeOH (80:20), (A:B :: 80:20); flow Rate: 1.0 mL/min); Optical rotation [α]D19.99: +67.07° (c = 0.25, CH2Cl2); TLC: 10% MeOH/CH2Cl2 (Rf: 0.6). |
| The enantiomer of 7-cyclopentyl-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4- | [1,2,4]triazolo[1,5-a]pyridine-2-carbaldehyde | B | (+)-2-((3,4-trans)-1-([1,2,4]triazolo[1,5-a]pyridin-2-ylmethyl)-4-methylpyrrolidin-3-yl)-7-cyclopentylimidazo[5,1-f][1,2,4]triazin- | A | 98 | 204 | 1H-NMR (DMSO-d6, 400 MHz): δ 8.90 (d, 1H), 7.78 (d, 1H), 7.66-7.62 (m, 2H), 7.18 (t, 1H), 3.90 (q, 2H), 3.50-3.46 (m, 1H), 3.12-3.08 (m, 2H), 2.98-2.96 (m, 1H), 2.78-2.74 (m, 1H), 2.64-2.60 (m, 1H), 2.41-2.39 (m, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| methylpyrrolidin-3-yl)-7-cyclopentylimidazo[5,1-f][1,2,4]triazin-4(3H)-one | | | 4(3H)-one | | | | 2.02-1.98 (m, 2H), 1.88-1.84 (m, 2H), 1.74-1.70 (m, 2H), 1.64-1.60 (m, 2H), 1.10 (d, 3H); Mass (ESI): 419.3 [M+ + 1]; LC-MS: 99.16%; 419 (M+ + 1); (column: X-bridge C-18, 50 × 3.0 mm, 3.5 µm); RT 2.16 min. 0.05% TFA (aq.): ACN; 0.8 mL/min); UPLC (purity): 96.47%; (column: Acquity BEH C-18; 50 × 2.1 mm, 1.7µ; RT 1.42 min. ACN: 0.025% TFA (Aq) 0.5 mL/min.; Chiral HPLC: 97.96%, Rt = 14.20 min (Chiralpak IA, 250 × 4.6 mm, 5 µm); mobile phase (A) 0.1% DEA in n-Hexane (B) CH2Cl2:MeOH (80:20) (A:B :: 80:20); flow Rate: 1.0 mL/min); Optical rotation [α]D20: +90.40° (c = 0.25, CH2Cl2); TLC: 10% MeOH/CH2Cl2 (Rf: 0.6) |
| The enantiomer of 7-cyclopentyl-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-cyclopentylimidazo[5,1-f][1,2,4]triazin-4(3H)-one | 2-(chloromethyl) imidazo [1,2-a] pyridine | A | (+)-7-cyclopentyl-2-((3,4-trans)-1-(imidazo[1,2-a]pyridin-2-ylmethyl)-4-methylpyrrolidin-3-yl)imidazo[5,1-f][1,2,4]triazin-4(3H)-one | A | 57 | 125 | 1H-NMR (DMSO-d6, 400 MHz): δ 8.46 (d, 1H), 7.80 (s, 1H), 7.62 (s, 1H), 7.48 (d, 1H), 7.20 (t, 1H), 6.88 (t, 1H), 3.78 (q, 2H), 3.51-3.49 (m, 1H), 3.08 (t, 1H), 2.98 (t, 1H), 2.88-2.86 (m, 1H), 2.74-2.72 (m, 1H), 2.62-2.60 (m, 1H), 2.36-2.34 (m, 1H), 2.02-1.98 (m, 2H), 1.86-1.58 (m, 6H), 1.10 (d, 3H); Mass (ESI): 418.6 [M+ + 1]; LC-MS: 98.69%; 418 (M+ + 1); |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | | | | | | | (column: X-bridge C-18, 50 × 3.0 mm, 3.5 μm); RT 2.04 min. 0.05% TFA (aq.): ACN; 0.8 mL/min); UPLC (purity): 99.19%; (column: Acquity UPLC BEH C-18; 2.1 × 50 mm, 1.7μ); RT 1.31 min. ACN: 0.025% TFA (Aq); 0.5 mL/min.; Chiral HPLC: 98.02%, Rt = 14.81 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D20: +36.92° (c = 0.25, CH2Cl2); TLC: 10% MeOH/CH2Cl2 (Rf: 0.5). |
| | — | — | (+)-2-((3,4-trans)-1-benzyl-4-methylpyrrolidin-3-yl)-7-(pentan-3-yl)imidazo[5,1-f][1,2,4]triazin-4(3H)-one | A | 175 | 86 | — |
| The enantiomer of 2-((3,4-trans)-4-methylpyrrolidin-3-yl)-7-(pentan-3-yl) imidazo [5,1-f] [1,2,4] triazin 4 (3H)-one obtained from debenzylation of (+)-2-((3,4-trans)-1-benzyl-4-methylpyrrolidin-3-yl)-7-(pentan-3- | 4-fluorobenzaldehyde | B | (+)-2-((3,4-trans)-1-(4-fluorobenzyl)-4-methylpyrrolidin-3-yl)-7-(pentan-3-yl)imidazo[5,1-f][1,2,4]triazin-4(3H)-one | A | 70 | 27 | 1H-NMR (DMSO-d6, 400 MHz): δ 7.70 (s, 1H), 7.34-7.30 (m, 2H), 7.12 (t, 2H), 3.60 (q, 2H), 3.16-3.14 (m, 1H), 2.92-2.90 (m, 1H), 2.84-2.72 (m, 3H), 2.64-2.62 (m, 1H), 2.28 (t, 1H), 1.80-1.70 (m, 4H), 1.10 (d, 3H), 0.76-0.68 (m, 6H). Mass (ESI): 398 [M+ + 1]; LC-MS: 99.92%; 398 (M+ + 1); |

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| yl)imidazo[5,1-f][1,2,4]triazin-4(3H)-one | | | | | | | (column: X-bridge C-18, 50 × 3.0 mm, 3.5 μm); RT 2.55 min. 0.05% TFA (aq.): ACN; 0.8 mL/min); UPLC (purity): 96.87%; (column: Acquity BEH C-18; 50 × 2.1 mm, 1.7μ); RT 1.71 min. ACN: 0.025% TFA (Aq); 0.5 mL/min.; Chiral HPLC: 96.23%, Rt = 6.11 min (Chiralpak IA, 250 × 4.6 mm, 5μ); mobile phase (A) n-Hexane (B) DCM:MeOH (80:20) (A:B :: 85:15); flow Rate: 1.0 mL/min); Optical rotation [α]D20: +15.29° (c = 0.25, DCM). TLC: 10% MeOH/DCM (Rf: 0.6). |
| The enantiomer of 2-((3,4-trans)-4-methylpyrrolidin-3-yl)-7-(pentan-3-yl) imidazo [5,1-f] [1,2,4] triazin-4 (3H)-one obtained from debenzylation of (+)-2-(3,4-trans)-1-benzyl-4-methylpyrrolidin-3-yl)-7-(pentan-3-yl)imidazo[5,1-f][1,2,4]triazin-4(3H)-one | 2-(chloro methyl) pyrimidine | A | (+)-2-((3,4-trans)-4-methyl-1-(pyrimidin-2-yl)methyl)pyrrolidin-3-yl)-7-(pentan-3-yl)imidazo[5,1-f][1,2,4]triazin-4(3H)-one | A | — | — | 1H-NMR (DMSO-d6, 400 MHz): δ 8.80 (d, 2H), 7.70 (s, 1H), 7.40 (t, 1H), 4.02 (d, 1H), 3.82 (d, 1H), 3.14-3.12 (m, 2H), 2.96 (d, 2H), 2.80-2.78 (m, 1H), 2.62-2.60 (m, 1H), 2.40 (t, 1H), 1.78-1.70 (m, 4H), 1.12 (d, 3H), 0.78-0.70 (m, 6H). Mass (ESI): 382.4 [M+ + 1]; LC-MS: 97.70%; 382 (M+ + 1); (column: X-bridge C-18, 50 × 3.0 mm, 3.5 μm); RT 2.10 min. 0.05% TFA (aq): ACN; 0.8 mL/min); HPLC (purity): 97.60%; (column: Eclipse XDB C-18; 150 × 4.6 mm, 5.0 μm); RT 9.60 min. ACN: 5 mM NH4OAc; 1.0 mL/min.; Chiral HPLC: 98.94%, Rt = 7.68 min |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 2-((3,4-trans)-4-methylpyrrolidin-3-yl)-7-(pentan-3-yl)imidazo[5,1-f][1,2,4]triazin-4(3H)-one obtained from debenzylation of (+)-2-((3,4-trans)-1-benzyl-4-methylpyrrolidin-3-yl)-7-(pentan-3-yl)imidazo[5,1-f][1,2,4]triazin-4(3H)-one | [1,2,4]triazolo[1,5-a]pyridine-2-carbaldehyde | B | (+)-2-((3,4-trans)-1-([1,2,4]triazolo[1,5-a]pyridin-2-ylmethyl)-4-methylpyrrolidin-3-yl)-7-(pentan-3-yl)imidazo[5,1-f][1,2,4]triazin-4(3H)-one | A | 386 | 306 | (Chiralpak IA, 250 × 4.6 mm, 5μ); mobile phase (A) 0.1% DEA in n-Hexane (B) DCM:MeOH (80:20) (A:B: 80:20); flow Rate: 1.0 mL/min); Optical rotation [α]D20: +96.12° (c = 0.25, DCM). TLC: 10% MeOH/DCM (Rf: 0.6). 1H-NMR (DMSO-d6, 400 MHz): δ 11.50 (br s, 1H), 8.90 (d, 1H), 7.80 (d, 1H), 7.68-7.60 (m, 2H), 7.18 (t, 1H), 3.90 (q, 2H), 3.14-3.06 (m, 3H), 2.96-2.94 (m, 1H), 2.81-2.79 (m, 1H), 2.64-2.60 (m, 1H), 2.44-2.42 (m, 1H), 1.76-1.62 (m, 4H), 1.08 (d, 3H), 0.74-0.66 (m, 6H); Mass (ESI): 421.6 [M+ + 1]; LC-MS: 99.49%; 421 (M+ + 1); (column: X-bridge C-18, 50 × 3.0 mm, 3.5 μm); RT 2.23 min. 0.05% TFA (aq.): ACN; 0.8 mL/min); UPLC (purity): 94.84%; (column: Acquity BEH C-18; 50 × 2.1 mm, 1.7μ); RT 1.45 min. ACN: 0.025% TFA (Aq); 0.5 mL/min.; Chiral HPLC: 96.06%, Rt = 8.94 min (Chiralpak IA, 250 × 4.6 mm, 5 μm); mobile phase (A) 0.1% DEA in n-Hexane (B) CH2Cl2:MeOH (80:20) (A:B :: 80:20); flow Rate: 1.0 mL/min); Optical rotation [α]D19.99: +17.98° (c = 0.25, CH2Cl2). TLC: 15% |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 2-((3,4-trans)-4-methylpyrrolidin-3-yl)-7-(pentan-3-yl) imidazo [5,1-f] [1,2,4] triazin-4 (3H)-one obtained from debenzylation of (+)-2-((3,4-trans)-1-benzyl-4-methylpyrrolidin-3-yl)-7-(pentan-3-yl)imidazo[5,1-f][1,2,4]triazin-4(3H)-one | 2-(chloromethyl) imidazo [1,2-a] pyridine | A | (+)-2-((3,4-trans)-1-(imidazo[1,2-a]pyridin-2-ylmethyl)-4-methylpyrrolidin-3-yl)-7-(pentan-3-yl)imidazo[5,1-f][1,2,4]triazin-4(3H)-one | A | 51 | 48 | MeOH/CH2Cl2 (Rf: 0.4). 1H-NMR (DMSO-d6, 400 MHz): δ 8.48 (d, 1H), 7.80 (s, 1H), 7.68 (s, 1H), 7.46 (d, 1H), 7.16 (t, 1H), 6.84 (t, 1H), 3.81-3.79 (m, 2H), 3.11-3.09 (m, 2H), 3.01-2.99 (m, 1H), 2.90-2.88 (m, 1H), 2.80-2.78 (m, 1H), 2.61-2.59 (m, 1H), 2.41-2.39 (m, 1H), 1.80-1.66 (m, 4H), 1.10 (d, 3H), 0.76-0.68 (m, 6H); Mass (ESI): 420 [M+ + 1]; LC-MS: 98.95%; 420.6 (M+ + 1); (column: X-bridge C-18, 50 × 3.0 mm, 3.5 μm); RT 2.62 min. 0.05% TFA (aq.): 0.05% ACN; 0.8 mL/min). UPLC (purity): 94.86%; (column: Acquity BEH C-18; 50 × 2.1 mm, 1.7μ); RT 1.40 min. ACN: 0.025% TFA (Aq); 0.5 mL/min.; Chiral HPLC: 93.48%, Rt = 12.22 min (Chiralpak IC, 250 × 4.6 mm, 5 μm); mobile phase (A) 0.1% DEA in n-Hexane (B) CH2Cl2:MeOH (80:20) (A:B: 65:35); flow Rate: 1.0 mL/min); Optical rotation [α]D19.99: +41.44° (c = 0.25, CH2Cl2). TLC: 10% MeOH/CH2Cl2 (Rf: 0.4). |
| | | — | (+)-2-((3,4-trans)-1-benzyl-4-methylpyrrolidin- | A | 167 | 144 | — |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(3-methylpyridin-4-yl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(3-methylpyridin-4-yl) imidazo [5,1-f] [1,2,4] triazin-4 (3H)-one | 2-(chloromethyl) pyrimidine | A | (+)-2-((3,4-trans)-4-methyl-1-(pyrimidin-2-ylmethyl)pyrrolidin-3-yl)-7-(3-methylpyridin-4-yl)imidazo[5,1-f][1,2,4]triazin-4(3H)-one | A | 85 | 63 | 1H-NMR (DMSO-d6, 400 MHz): δ 8.80 (d, 2H), 8.60 (s, 1H), 8.53-8.52 (m, 1H), 7.96 (s, 1H), 7.69-7.68 (m, 1H), 7.40 (t, 1H), 4.00 (d, 1H), 3.82 (d, 1H), 3.10 (t, 1H), 3.00-2.98 (m, 2H), 2.79-2.78 (m, 1H), 2.56-2.55 (m, 1H), 2.38-2.36 (m, 4H), 1.07 (d. 3H); Mass (ESI): 403 [M+ + 1]; LC-MS: 98.42%; 403.5 (M+ + 1); (column; X-bridge C-18, (50 × 3.0 mm, 3.5 µm); RT 2.36 min. 0.05% TFA (aq.): ACN; 0.8 mL/min); UPLC (purity): 99.49%; (column: Acquity UPLC HSS T3 (2.1 × 100 mm, 1.8µ); RT 2.75 min. ACN: 0.025% TFA (Aq); 0.3 mL/min.; Chiral HPLC: 90.05%, Rt = 24.06 min (Chiralpak IA, 250 × 4.6 mm, 5 µm); mobile phase (A) 0.1% DEA in n-Hexane (B) CH2Cl2:MeOH (80:20) (A:B: 85:15); flow Rate: 1.0 mL/min); Optical rotation [α]D20.01: +70.06° (c = 0.25, CH2Cl2); TLC: 10% MeOH/CH2Cl2 (Rf: 0.5). |
| The enantiomer of 7-(3-methylpyridin-4- | 4-fluorobenzaldehyde | B | (+)-2-((3,4-trans)-1-(4-fluorobenzyl)- | A | — | — | 1H-NMR (CDCl3, 400 MHz): δ 8.62 (s, 1H), 8.56 (d, 1H), 8.10 (s, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| yl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(3-methylpyridin-4-yl) imidazo [5,1-f] [1,2,4] triazin-4 (3H)-one | | | 4-methylpyrrolidin-3-yl)-7-(3-methylpyridin-4-yl) imidazo [5,1-f] [1,2,4] triazin-4 (3H)-one | | | | 1H), 7.58 (d, 1H), 7.34-7.32 (m, 2H), 7.10-7.08 (m, 2H), 3.80 (d, 1H), 3.57 (d, 1H), 3.40 (t, 1H), 2.98 (d, 1H), 2.71-2.70 (m, 1H), 2.50-2.49 (m, 1H), 2.44-2.43 (m, 1H), 2.40 (s, 3H), 1.92 (t, 1H), 1.20 (d, 3H); Mass (ESI): 419.3 [M+ + 1]; LC-MS: 99.62%; 419.4 (M+ + 1); (column: X-bridge C-18, (50 × 3.0 mm, 3.5 µm); RT 2.08 min. 0.025% TFA (Aq): 0.3 mL/min.; Chiral HPLC: 98.84%, Rt = 7.92 min (Chiralpak IA, 250 × 4.6 mm, 5 µm); mobile phase (A) 0.1% DEA in n-Hexane (B) CH2Cl2:MeOH (80:20) (A:B: 80:20); flow Rate: 1.0 mL/min); Optical rotation [α]D19.99: +20.67° (c = 0.25, CH2Cl2); TLC: 10% MeOH/CH2Cl2 (Rf 0.5). |
| The enantiomer of 7-(3-methylpyridin-4-yl)-2-((3,4-trans)-4-methylpyrrolidin-3-yl) imidazo [5,1-f] [1,2,4] triazin-4 (3H)-one obtained from | 2-(chloromethyl) imidazo [1,2-a] pyridine | A | (+)-2-((3,4-trans)-1-(imidazo[1,2-a]pyridin-2-ylmethyl)-4-methylpyrrolidin-3-yl)-7-(3-methylpyridin-4-yl)imidazo[5,1-f] | A | 155 | 149 | 1H-NMR (CDCl3, 400 MHz): δ 8.60 (s, 1H), 8.58 (d, 1H), 8.10 (d, 1H), 8.02 (s, 1H), 7.70 (d, 1H), 7.62-7.60 (m, 2H), 7.20 (t, 1H), 6.80 (t, 1H), 4.12 (d, 1H), 3.79 (d, 1H), 3.51-3.49 (m, 1H), 3.14 (d, 1H), 2.76-2.74 (m, 1H), |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| debenzylation of (+)-2-((3,4-trans)-1-benzyl-4-methylpyrrolidin-3-yl)-7-(3-methylpyridin-4-yl) imidazo [5,1-f] [1,2,4] triazin-4 (3H)-one | | | f][1,2,4]triazin-4(3H)-one | | | | 2.60-2.58 (m, 1H), 2.49-2.48 (m, 1H), 2.41-2.38 (m, 4H), 1.22 (d, 3H); Mass (ESI): 441.5 [M+ + 1]; LC-MS: 99.95%; 441.5 (M+ + 1); (column; X-bridge C-18, (50 × 3.0 mm, 3.5 µm); RT 2.15 min. 0.05% TFA (aq.); ACN; 0.8 mL/min); UPLC (purity): 95.67%; (column: Acquity UPLC HSS T3 (2.1 × 100 mm, 1.8µ); RT 2.80 min. ACN: 0.025% TFA (Aq) 0.3 mL/min.; Chiral HPLC: 100%, Rt = 17.98 min (Chiralpak IA, 250 × 4.6 mm, 5 µm); mobile phase (A) 0.1% DEA in n-Hexane (B) CH2Cl2:MeOH (80:20) (A:B: 80:20); flow Rate: 1.0 mL/min); Optical rotation [α]D20: +29.71° (c = 0.25, CH2Cl2); TLC: 10% MeOH/CH2Cl2 (Rf: 0.4). |
| The enantiomer of 7-(3-methylpyridin-4-yl)-2-((3,4-trans)-4-methylpyrrolidin-3-yl) imidazo [5, 1-f] [1,2,4] triazin-4 (3H)-one obtained from debenzylation of (+)-2-((3,4-trans)-1-benzyl-4-methylpyrrolidin-3-yl)-7-(3-methylpyridin-4-yl) imidazo [5,1- | [1,2,4] triazolo [1,5-a] pyridine-2-carbaldehyde | B | (+)-2-((3,4-trans)-1-([1,2,4]triazolo[1,5-a]pyridin-2-ylmethyl)-4-methylpyrrolidin-3-yl)-7-(3-methylpyridin-4-yl)imidazo[5,1-f][1,2,4]triazin-4(3H)-one | A | — | — | 1H-NMR (CD3OD-d4, 400 MHz): δ 8.80-8.79 (m, 1H), 8.60 (s, 1H), 8.50-8.49 (m, 1H), 7.99 (s, 1H), 7.74-7.70 (m, 3H), 7.20 (t, 1H), 4.08 (d, 1H), 3.92 (d, 1H), 3.29-3.28 (m, 1H), 3.20-3.19 (m, 1H), 3.01-2.99 (m, 1H), 2.90-2.88 (m, 1H), 2.60-2.59 (m, 1H), 2.39-2.37 (m, 4H), 1.16 (d, 3H); Mass (ESI): 442.5 [M+ + 1]; LC-MS: 98.33%; 442.5 (M+ + 1); (column; X- |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| f] [1,2,4] triazin-4 (3H)-one | | | | | | | bridge C-18, (50 × 3.0 mm, 3.5 μm); RT 1.76 min. 0.05% TFA (aq.): ACN; 0.8 mL/min); UPLC (purity): 98.09%; (column: Acquity UPLC HSS T3 (2.1 × 100 mm, 1.8μ); RT 2.88 min. ACN: 0.025% TFA (Aq); 0.3 mL/min.; Chiral HPLC: 97.68%, Rt = 17.18 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D20: +55.68° (c = 0.25, CH2Cl2); TLC: 10% MeOH/CH2Cl2 (Rf: 0.4). |
| | — | — | (+)-2-((3,4-trans)-1-benzyl-4-methylpyrrolidin-3-yl)-7-(2-fluorophenyl)imidazo[5,1-f][1,2,4]triazin-4(3H)-one | A | 76 | 83 | — |
| The enantiomer of 7-(2-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(2-fluorophenyl)imidazo[5, | 2-(chloromethyl) pyrimidine | A | (+)-7-(2-fluorophenyl)-2-((3,4-trans)-4-methyl-1-(pyrimidin-2-yl)methyl)pyrrolidin-3-yl)imidazo[5,1-f][1,2,4]triazin-4(3H)-one | A | 19 | 39 | 1H-NMR (CD3OD-d4, 400 MHz): δ 8.82 (d, 2H), 7.93 (s, 1H), 7.72 (t, 1H), 7.60-7.58 (m, 1H), 7.34-7.31 (m, 3H), 4.11 (d, 1H), 3.90 (d, 1H), 3.26-3.24 (m, 2H), 2.90-2.87 (m, 2H), 2.60-2.59 (m, 1H), 2.31-2.29 (m, 1H), 1.12 (d, 3H); Mass (ESI): 406.4 [M+ + 1]; LC-MS: 98.02%; 406.4 (M+ + 1); (column; X-bridge C-18, (50 × 3.0 mm, |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| 1-f][1,2,4]triazin-4(3H)-one | | | | | | | 3.5 μm); RT 2.15 min. 0.05% TFA (aq.): ACN; 0.8 mL/min); UPLC (purity): 94.80%; (column: Acquity BEH C-18 (50 × 2.1 mm, 1.7μ); RT 1.42 min. ACN: 0.025% TFA (Aq): 0.5 mL/min.; Chiral HPLC: 99.07%, Rt = 10.94 min (Chiralpak IA, 250 × 4.6 mm, 5 μm); mobile phase (A) 0.1% DEA in n-Hexane (B) CH2Cl2:MeOH (80:20) (A:B: 80:20); flow Rate: 1.0 mL/min); Optical rotation [α]D20.01: +85.28° (c = 0.25, CH2Cl2); TLC: 10% MeOH/CH2Cl2 (Rf: 0.4). |
| The enantiomer of 7-(2-fluorophenyl)-2-((3,4-trans)-4-methylpyrrolidin-3-yl) imidazo [5,1-f] [1,2,4] triazin-4 (3H)-one obtained from debenzylation of (+)-2-(3,4-trans)-1-benzyl-4-methylpyrrolidin-3-yl)-7-(2-fluorophenyl)imidazo[5,1-f][1,2,4]triazin-4(3H)-one | 4-fluorobenzaldehyde | B | (+)-2-((3,4-trans)-1-(4-fluorobenzyl)-4-methylpyrrolidin-3-yl)-7-(2-fluorophenyl)imidazo[5,1-f][1,2,4]triazin-4(3H)-one | A | 62 | 165 | 1H-NMR (CDCl3, 400 MHz): δ 8.01 (s, 1H), 7.78 (t, 1H), 7.50-7.48 (m, 1H), 7.35-7.33 (m, 2H), 7.28-7.27 (m, 1H), 7.18-7.16 (m, 1H), 7.06-7.04 (m, 2H), 3.79 (d, 1H), 3.60 (d, 1H), 3.39 (t, 1H), 3.00 (d, 1H), 2.72-2.70 (m, 1H), 2.51-2.49 (m, 2H), 1.90 (t, 1H), 1.20 (d, 3H); Mass (ESI): 422.4 [M+ + 1]; LC-MS: 97.28%; 422.4 (M+ + 1); (column: X-bridge C-18, (50 × 3.0 mm, 3.5 μm); RT 2.67 min. 0.05% TFA (aq.): ACN; 0.8 mL/min); UPLC (purity): 93.01%; (column: Acquity BEH C-18 (50 × 2.1 mm, 1.7μ); RT 1.70 min. ACN: 0.025% TFA (Aq): 0.5 mL/min.; Chiral HPLC: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 7-(2-fluorophenyl)-2-((3,4-trans)-4-methylpyrrolidin-3-yl) imidazo [5,1-f] [1,2,4] triazin-4 (3H)-one obtained from debenzylation of (+)-2-((3,4-trans)-1-benzyl-4-methylpyrrolidin-3-yl)-7-(2-fluorophenyl)imidazo[5,1-f][1,2,4]triazin-4(3H)-one | | | | | | | 94.31%, Rt = 22.80 min (Chiralpak IC, 250 × 4.6 mm, 5 µm); mobile phase (A) 0.1% DEA in n-Hexane (B) CH2Cl2:MeOH (80:20) (A:B: 80:20); flow Rate: 1.0 mL/min); Optical rotation [α]D19.99: +29.01° (c = 0.25, CH2Cl2); TLC: 10% MeOH/CH2Cl2 (Rf: 0.5). |
| | [1,2,4] triazolo [1,5-a] pyridine-2-carbaldehyde | B | (+)-2-(3,4-trans)-1-([1,2,4]triazolo[1,5-a]pyridin-2-ylmethyl)-4-methylpyrrolidin-3-yl)-7-(2-fluorophenyl)imidazo[5,1-f][1,2,4]triazin-4(3H)-one | A | — | — | 1H-NMR (CDCl3, 400 MHz): δ 8.80 (d, 1H), 8.04 (s, 1H), 7.80-7.76 (m, 2H), 7.51-7.48 (m, 2H), 7.30-7.29 (m, 1H), 7.20-7.19 (m, 1H), 7.03-7.01 (m, 1H), 4.28 (d, 1H), 3.90 (d, 1H), 3.53 (t, 1H), 3.32 (d, 1H), 2.81-2.80 (m, 1H), 2.62-2.60 (m, 1H), 2.51-2.50 (m, 1H), 2.23 (t, 1H), 1.20 (d, 3H); Mass (ESI): 445.3 [M+ + 1]; LC-MS: 98.05%; 445.5 (M+ + 1); (column: X-bridge C-18, (50 × 3.0 mm, 3.5 µm); RT 2.34 min. 0.05% TFA (aq.): ACN; 0.8 mL/min); HPLC (purity): 94.31%; (column: Eclipse XDB C-18 (150 × 4.6 mm, 5µ); RT 8.60 min. ACN: 5 mM NH4OAc; 1.0 mL/min; Chiral HPLC: 98.08%, Rt = 14.62 min (Chiralpak IA, 250 × 4.6 mm, 5 µm); mobile phase (A) 0.1% DEA in n-Hexane (B) CH2Cl2:MeOH (80:20) (A:B: 80:20); flow Rate: 1.0 mL/min). |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 2-((3,4-trans)-4-methylpyrrolidin-3-yl)-7-(2,2,2-trifluoroethyl) imidazo [5,1-f] [1,2,4] triazin-4 (3H)-one obtained from debenzylation of (+)-2-((3,4-trans)-1-benzyl-4-methylpyrrolidin-3-yl)-7-(2,2,2-trifluoroethyl) imidazo [5,1-f] [1,2,4] triazin-4 (3H)-one | — | — | (+)-2-((3,4-trans)-1-benzyl-4-methylpyrrolidin-3-yl)-7-(2,2,2-trifluoroethyl) imidazo [5,1-f] [1,2,4] triazin-4 (3H)-one | A | — | — | Optical rotation [α]D19.99: +68.00° (c = 0.25, CH2Cl2); TLC: 10% MeOH/CH2Cl2 (Rf: 0.3). |
| | [1,2,4]triazolo[1,5-a]pyridine-2-carbaldehyde | B | 2-((3,4-trans)-1-([1,2,4]triazolo[1,5-a]pyridin-2-ylmethyl)-4-methylpyrrolidin-3-yl)-7-(2,2,2-trifluoroethyl)imidazo[5,1-f][1,2,4]triazin-4(3H)-one | A | — | — | 1H-NMR (DMSO-d6, 500 MHz): δ 8.86-8.84 (m, 1H), 7.78-7.76 (m, 2H), 7.62-7.60 (m, 1H), 7.18-7.16 (m, 1H), 4.12-4.08 (m, 2H), 3.90 (q, 2H), 3.12 (t, 1H), 3.06 (t, 1H), 2.96 (t, 1H), 2.84-2.82 (m, 1H), 2.74-2.72 (m, 1H), 2.40-2.38 (m, 1H), 1.10 (d, 3H); Mass: m/z 433.4 [M + 1]+; LC-MS: 99.78%; 433.2 (M+ + 1); (column: X-Bridge C-18, 50 × 3.0 mm, 3.5 µm); RT 3.21 min. 0.05% TFA: ACN; 0.8 mL/min); UPLC (purity): 99.94%; (column: Acquity UPLC BEH-C18 (50 × 2.1 mm, 1.7µ); RT 1.38 min. ACN: 0.025% TFA (Aq); 0.5 mL/min.; Chiral HPLC: 99.37%, Rt = 8.12 min (Chiralpak IC, 250 × 4.6 mm, 5 µm); mobile phase (A) 0.1% DEA in n-Hexane (B) CH2Cl2:MeOH (50:50) (A:B: |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| | — | — | (+)-2-((3,4-trans)-1-benzyl-4-methylpyrrolidin-3-yl)-7-(2-(trifluoromethyl)phenyl) imidazo [5,1-f] [1,2,4] triazin-4 (3H)-one | A | — | — | 60:40); flow Rate: 1.0 mL/min); Optical rotation [α]D20: +127.74° (c = 0.25, CH2Cl2); TLC: 5% MeOH/CH2Cl2 (Rf: 0.3). |
| The enantiomer of 2-((3,4-trans)-4-methylpyrrolidin-3-yl)-7-(2-(trifluoromethyl)phenyl) imidazo [5,1-f] [1,2,4] triazin-4 (3H)-one obtained from debenzylation of (+)-2-((3,4-trans)-1-benzyl-4-methylpyrrolidin-3-yl)-7-(2-(trifluoromethyl)phenyl) imidazo [5,1-f] [1,2,4] triazin-4 (3H)-one | 2-(chloromethyl) pyrimidine | A | (+)-2-((3,4-trans)-4-methyl-1-(pyrimidin-2-ylmethyl)pyrrolidin-3-yl)-7-(2-(trifluoromethyl)phenyl) imidazo [5,1-f] [1,2,4] triazin-4 (3H)-one | A | — | — | 1H-NMR (DMSO-d6, 400 MHz): δ 8.80 (d, 2H), 7.92-7.90 (m, 2H), 7.81-7.79 (m, 2H), 7.71-7.70 (m, 1H), 7.41-7.40 (m, 1H), 3.96 (d, 1H), 3.80 (d, 1H), 3.06 (t, 1H), 2.90-2.88 (m, 2H), 2.70-2.69 (m, 1H), 2.45-2.43 (m, 1H), 2.31-2.30 (m, 1H), 1.00 (d, 3H); Mass (ESI): 456.3 [M+ + 1]; LC-MS: 97.59%; 456.3 (M+ + 1); (column: X-bridge C-18, (50 × 3.0 mm, 3.5 μm); RT 2.43 min. 0.05% TFA (aq.): ACN; 0.8 mL/min); UPLC (purity): 98.12%; (column: Acquity UPLC BEH-C18 (2.1 × 50 mm, 1.7μ); RT 1.52 min. ACN: 0.025% TFA (Aq): 0.5 mL/min.; Chiral HPLC: 97.71%, Rt = 9.55 min (Chiralpak IA, 250 × 4.6 mm, 5 μm); mobile |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 2-((3,4-trans)-4-methylpyrrolidin-3-yl)-7-(2-(trifluoromethyl)phenyl) imidazo [5,1-f] [1,2,4] triazin-4 (3H)-one obtained from debenzylation of (+)-2-((3,4-trans)-1-benzyl-4-methylpyrrolidin-3-yl)-7-(2-(trifluoromethyl)phenyl) imidazo [5,1-f] [1,2,4] triazin-4 (3H)-one | 4-fluorobenzaldehyde | B | (+)-2-((3,4-trans)-1-(4-fluorobenzyl)-4-methylpyrrolidin-3-yl)-7-(2-(trifluoromethyl)phenyl) imidazo [5,1-f] [1,2,4] triazin-4 (3H)-one | A | — | — | phase (A) 0.1% DEA in n-Hexane (B) CH2Cl2:MeOH (80:20) (A:B: 80:20); flow Rate: 1.0 mL/min); Optical rotation [α]D20.01: +71.74° (c = 0.25, CH2Cl2); TLC: 10% MeOH/CH2Cl2 (Rf: 0.6). 1H-NMR (DMSO-d6, 500 MHz): δ 7.96 (d, 1H), 7.90 (s, 1H), 7.86-7.78 (m, 2H), 7.72 (d, 1H), 7.28 (t, 2H), 7.10 (t, 2H), 3.58-3.54 (m, 2H), 2.96-2.94 (m, 1H), 2.78-2.64 (m, 3H), 2.44-2.42 (m, 1H), 2.21-2.19 (m, 1H), 1.00 (d, 3H); Mass: m/z 472.5 [M + 1]+; LC-MS: 99.64%; UPLC BEH-C18 (50 × 2.1 mm, 1.7μ); RT 1.78 min. ACN: 0.025% TFA (Aq); 0.5 mL/min.; 472.3 (M+ + 1); (column: X-Bridge C-18, 50 × 3.0 mm, 3.5 μm); RT 2.86 min. 0.05% TFA: ACN; 0.8 mL/min); UPLC (purity): 98.73%; (column: Acquity Chiral HPLC: 94.28%, Rt = 15.56 min (Chiralpak IA, 250 × 4.6 mm, 5 μm); mobile phase (A) 0.1% DEA in n-Hexane (B) CH2Cl2:MeOH (80:20) (A:B: 90:10); flow Rate: 1.0 mL/min); Optical rotation [α]D20: +6.32° (c = 0.25, CH2Cl2); TLC: 10% MeOH/CH2Cl2 (Rf: 0.5). |

TABLE 3-continued

| SM name | Reagent | Method | Example name | Band (PDE9A2 IC$_{50}$) | PDE1A selectivity (versus PDE9A2) | PDE1B selectivity (versus PDE9A2) | Analytical Data |
|---|---|---|---|---|---|---|---|
| The enantiomer of 2-((3,4-trans)-4-methylpyrrolidin-3-yl)-7-(2-(trifluoromethyl)phenyl) imidazo [5,1-f] [1,2,4] triazin-4 (3H)-one obtained from debenzylation of (+)-2-((3,4-trans)-1-benzyl-4-methylpyrrolidin-3-yl)-7-(2-(trifluoromethyl)phenyl) imidazo [5,1-f] [1,2,4] triazin-4 (3H)-one | [1,2,4] triazolo [1,5-a] pyridine-2-carbaldehyde | B | (+)-2-((3,4-trans)-1-([1,2,4]triazolo[1,5-a]pyridin-2-ylmethyl)-4-methylpyrrolidin-3-yl)-7-(2-(trifluoromethyl)phenyl)imidazo[5,1-f][1,2,4]triazin-4(3H)-one | A | — | — | 1H-NMR (DMSO-d6, 500 MHz): δ 11.80 (br s, 1H), 8.86 (d, 1H), 7.92 (d, 2H), 7.82-7.76 (m, 3H), 7.70 (d, 1H), 7.63 (t, 1H), 7.18 (t, 1H), 3.84 (q, 2H), 3.04 (t, 1H), 2.95 (t, 1H), 2.86 (t, 1H), 2.71 (q, 1H), 2.46 (q, 1H), 2.34 (t, 1H), 1.00 (d, 3H); Mass: m/z 495.6 [M + 1]+; LC-MS: 99.57%; 495.3 (M+ + 1); (column: X-Bridge C-18, 50 × 3.0 mm, 3.5 μm); RT 2.54 min. 0.05% TFA: ACN; 0.8 mL/min; UPLC (purity): 98.62%; (column: Acquity UPLC BEH-C18 (50 × 2.1 mm, 1.7μ); RT 1.58 min. ACN: 0.025% TFA (Aq); 0.5 mL/min.; Chiral HPLC: 94.82%, Rt = 22.09 min (Chiralpak IA, 250 × 4.6 mm, 5 μm); mobile phase (A) 0.1% DEA in n-Hexane (B) CH2Cl2:MeOH (80:20) (A:B: 85:15); flow Rate: 1.0 mL/min); Optical rotation [α]D19.99: +45.84° (c = 0.25, CH2Cl2); TLC: 10% MeOH/CH2Cl2 (Rf: 0.6). |

A <1 μM
B 1 μM-10 μM
C >10 μM
N/A Not Available

In Table 3, "SM" refers to the starting material of the reaction to make the corresponding example. "Reagent" refers to the reagent used in the reaction using the starting material to make the corresponding example. Generally, two methods, shown as Method A or Method B in Table 3, can be used to make these examples in Table 3.

In some embodiments, the compounds disclosed herein may be synthesized using Method A, described in Scheme 1; or Method B, described in Scheme 2. As shown in Scheme 1, intermediate amine I' may be alkylated using intermediate III' bearing a leaving group X' to give final produce II'. Non-limiting examples of X' include Cl, Br, I, OTs, OMs, and OTf. Other leaving groups known in the art can be used. An inorganic or organic base may be used in this reaction. Non-limiting examples of bases include $Et_3N$, DIPEA, imidazole, pyridine, $K_2CO_3$, $Li_2CO_3$, $Na_2CO_3$, and $Cs_2CO_3$. Other bases known in the art can be used. A solvent may be used in this reaction. Non-limiting examples of solvents include $CH_2Cl_2$, $CH_3CN$, toluene, DMSO, and DMF. Other solvents known in the art can be used. Optionally, a catalyst may be used to facilitate the reaction. Non-limiting examples of catalysts include KI, NaI, and $Fe(OTf)_3$. Other catalysts known in the art can be used. The reaction may be carried out at room temperate or under heating conditions, e.g., at 40° C., 50° C., 60° C., 80° C., 100° C., or 120° C. Other suitable temperatures are contemplated. In one particular embodiment, the compounds are synthesized by Method A using $Fe(OTf)_3$, $Cs_2CO_3$ under heating at 50° C. for 3 h in $CH_3CN$.

Method A

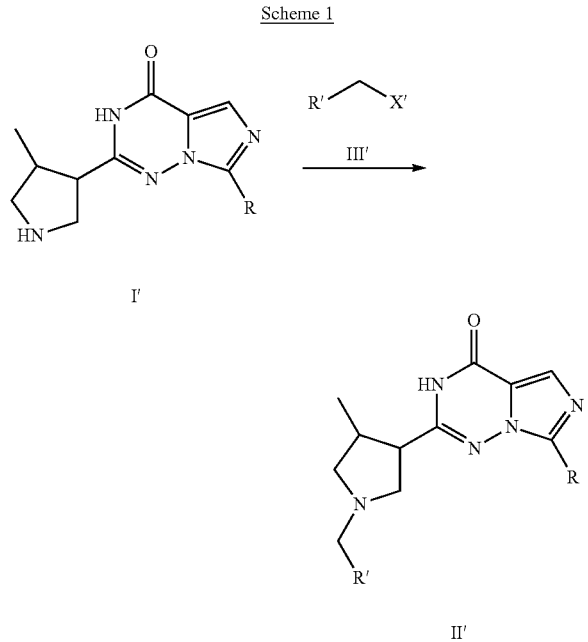

In other embodiments, final product VI' may be synthesized using Method B as described in Scheme 2. Intermediate amine IV' may undergo reductive amination with aldehyde V' to give final produce VI'. A reducing agent used in this reaction. Non-limiting examples of reducing agents include $H_2$, $NaBH_4$, $NaCNBH_3$, $BH_3$, $NaBH(OAc)_3$, $B_{10}H_{14}$, $Et_3SiH$, and tert-butyl dimethylsilane. Other reducing agents known in the art can be used. A solvent may be used in this reaction. Non-limiting examples of solvents include $CH_2Cl_2$, $CH_3CN$, toluene, DMSO, AcOH, MeOH, EtOH, and DMF. Other solvents known in the art can be used. Optionally, a small amount of acid may be used to facilitate the reaction. Non-limiting examples of acids include HCOOH, AcOH, and propanoic acid. Other acids known in the art can be used. The reaction may be optionally carried out at room temperature under heating conditions, e.g., at 40° C., 50° C., 60° C., 80° C., 100° C., or 120° C. Other suitable temperatures are contemplated. In one particular embodiment, the compounds are synthesized by Method B using $NaCNBH_3$ and AcOH in MeOH.

Method B

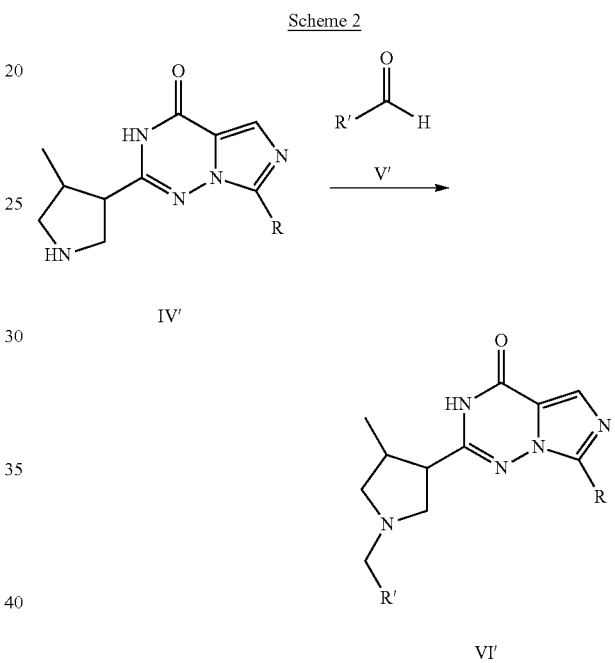

In some embodiments, R' is selected from the group consisting of
(i) heteroaryl, which is optionally substituted with one or more $R^f$;
(ii) heteroaryl($C_1$-$C_4$)alkyl, wherein the alkyl portion is optionally substituted with one or more $R^{g'}$, and the heteroaryl portion is optionally substituted with one or more $R^f$;
(iii) phenyl, which is optionally substituted with one or more $R^f$;
(iv) phenyl($C_1$-$C_4$)alkyl, wherein the alkyl portion is optionally substituted with one or more $R^{g'}$, and the phenyl portion is optionally substituted with one or more $R^f$;
(v) ($C_3$-$C_7$) cycloalkyl, which is optionally substituted with one or more $R^h$;
(vi) ($C_3$-$C_7$) cycloalkyl($C_1$-$C_4$) alkyl, wherein the alkyl portion is optionally substituted with one or more $R^{g'}$, and the cycloalkyl portion is optionally substituted with one or more $R^h$;
(vii) heterocycloalkyl, which is optionally substituted with one or more $R^h$;
(viii) heterocycloalkyl($C_1$-$C_4$)alkyl, wherein the alkyl portion is optionally substituted with one or more $R^{g'}$, and the cycloalkyl portion is optionally substituted with one or more $R^h$;

(ix) (C$_1$-C$_6$) alkyl, which is optionally substituted with one or more R$^g$; and (x) (C$_1$-C$_6$)haloalkyl, which is optionally substituted with one or more R$^g$;

wherein R$^f$, R$^h$, and R$^g$ are as defined herein.

II. Synthetic Preparation of Compounds of the Invention

A. Synthesis of Building Blocks i. 2,5-dioxopyrrolidin-1-yl tetrahydro-2H-pyran-4-carboxylate

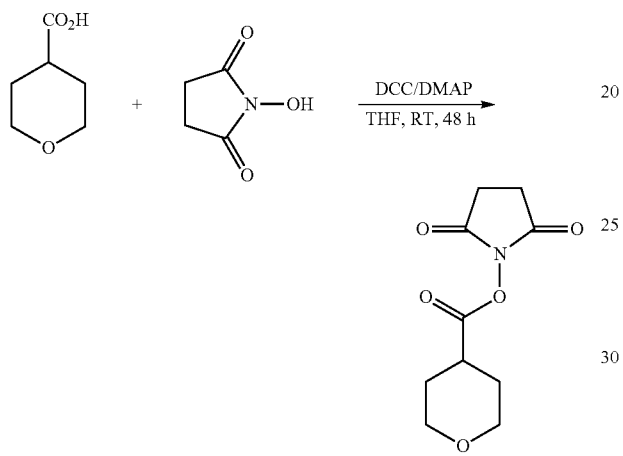

Synthesis of 2,5-dioxopyrrolidin-1-yl tetrahydro-2H-pyran-4-carboxylate

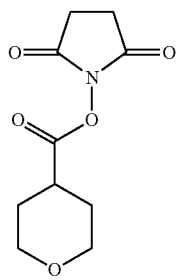 [SMILES: O=C(ON1C(=O)CCC1=O)C1CCOCC1]

Typical experimental procedure: To a solution of tetra-hydro-pyran-4-carboxylic acid (11.28 g, 86.7 mmol), N-hydroxysuccininmide (10.97 g, 95.3 mmol), and DMAP (1.16 g, 0.95 mmol) in THF (430 mL) was added DCC (19.67 g, 95.3 mmol) slowly under argon atmosphere at RT. The reaction mixture was stirred at RT for 48 h. The reaction mixture cooled in a freezer and was then filtered and the filter cake was rinsed with dichloromethane (2×100 mL). The combined filtrates were concentrated under reduced pressure to give a light yellow solid (24.50 g). Flash chromatography (50% EtOAc/heptane—ETOAc only) provided 2,5-dioxopyrrolidin-1-yl tetrahydro-2H-pyran-4-carboxylate (17.24 g, 84%) as white solid. $^1$H NMR (300 MHz, CDCl$_3$) δ 4.02 (t, 1H, J=3.8 Hz), 3.98 (t, 1H, J=3.8 Hz), 3.56-3.46 (m, 2H), 2.99-2.86 (m, 1H), 2.85 (s, 3H), 2.04-1.87 (m, 4H); $^{13}$C NMR (75 MHz, CDCl$_3$) δ 169.4, 168.9, 66.5, 37.6, 28.3, 25.6.

ii. 2-(chloromethyl)pyrimidine

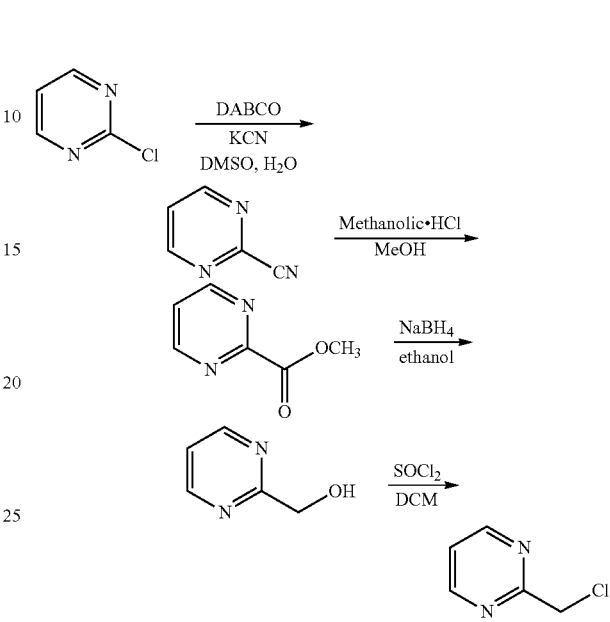

Synthesis of Pyrimidine-2-carbonitrile

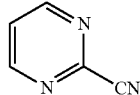

To a stirred solution of 2-chloropyrimidine (20.0 g, 174.6 mmol) in DMSO (40 mL) were added DABCO (3.72 g, 33.17 mmol), KCN (12.48 g, 192 mmol) and drop-wise addition of H$_2$O (15 mL) at RT. The resulting solution was stirred at RT for 48 h. After consumption of starting material by TLC, the reaction mixture was diluted with water and extracted with EtOAc. Combined organic layer was dried over sodium sulphate, filtered and concentrated in vacuo to obtain the crude product. The crude material was triturated with Hexane to afford pyrimidine-2-carbonitrile (12 g, 65%) as dark brown solid. $^1$H-NMR (DMSO-d$_6$, 400 MHz): δ 9.04 (s, 2H), 8.92 (d, 1H); LC-MS: 99.41%; 107.6 (M+2); (column; X-bridge C-18, (50×3.0 mm, 3.5μ); RT 1.14 min. 0.1% Aq TFA: ACN; 0.8 ml/min); TLC: 30% EtOAc/Hexane (Rf: 0.2)

Synthesis of methylpyrimidine-2-carboxylate

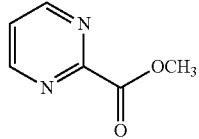

To a stirred solution of pyrimidine-2-carbonitrile (12.0 g, 114.28 mmol) in MeOH (20 mL) was added methanolic HCl (180 mL) at 0° C. and stirred for 16 h. After completion of starting material by TLC, the volatiles were evaporated under reduced pressure. The residue was neutralized with saturated NaHCO$_3$ solution and extracted with EtOAc. The combined organic layer was dried over sodium sulphate, filtered and concentrated in vacuo to obtain the crude product. The crude material was triturated with Hexane to afford methylpyrimidine-2-carboxylate (10.0 g, crude) as yellow solid. $^1$H-NMR (DMSO-d$_6$, 400 MHz): δ 9.08 (d, 2H), 7.76 (t, 1H), 3.92 (s, 3H); LC-MS: 94.32%; 139 (M$^+$+1) (column; Chromolith RP-18, (100×4.6 mm); RT 2.85 min. 5 mM NH$_4$OAc: ACN; 0.8 ml/min); TLC: 70% EtOAc/Hexane (Rf: 0.2).

Synthesis of pyrimidin-2-ylmethanol

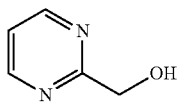

To a stirred solution of methylpyrimidine-2-carboxylate (10.0 g, 72.46 mmol) in EtOH (100 mL) was added NaBH$_4$ (3.85 g, 101.31 mmol) portion wise at 0° C. under inert atmosphere. The reaction mixture was warmed to RT and stirred for 2 h. After completion of starting material by TLC, the volatiles were evaporated under reduced pressure. The residue was diluted with saturated K$_2$CO$_3$ solution and extracted with EtOAc. The combined organic layer was dried over sodium sulphate, filtered and concentrated in vacuo to afford pyrimidin-2-ylmethanol (4.5 g, crude) as yellow semi-solid. $^1$H-NMR (DMSO-d$_6$, 400 MHz): δ 8.76 (d, 2H), 7.42 (t, 1H), 5.29 (br s, 1H), 4.61 (s, 2H); LC-MS: 94.12%; 111 (M$^+$+1) (column; Chromolith RP-18, (100×4.6 mm); RT 2.24 min. 5 mM NH$_4$OAc: ACN; 0.8 ml/min); TLC: 100% EtOAc (Rf: 0.2).

Synthesis of 2-(chloromethyl)pyrimidine

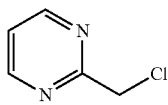

To a stirred solution of pyrimidin-2-ylmethanol (4.5 g 40.90 mmol) in DCM (50 mL) was added SOCl$_2$ (10 mL) at 0° C. under inert atmosphere. The reaction mixture was heated up to 50° C. and stirred for 2 h. After completion of starting material (by TLC), the volatiles were evaporated under reduced pressure. The residue was quenched with ice cold water followed by saturated NaHCO$_3$ and extracted with EtOAc. Combined organic layer was dried over sodium sulphate, filtered and concentrated in vacuo to obtain the crude product. The crude material was purified by silica gel column chromatography to afford 2-(chloromethyl)pyrimidine (960 mg, 18%) as brown liquid. $^1$H-NMR (DMSO-d$_6$, 400 MHz): δ 8.84 (d, 2H), 7.52 (t, 1H), 4.82 (s, 2H); Mass (ESI): 128.5 [M+1]; LC-MS: 95.09%; 129 (M$^+$+1) (column; Chromolith RP-18, (100×4.6 mm); RT 3.86 min. 5 mM NH$_4$OAc: ACN; 0.8 ml/min); TLC: 70% EtOAc/Hexane (Rf: 0.6).

iii. 2-(chloromethyl)pyrimidine

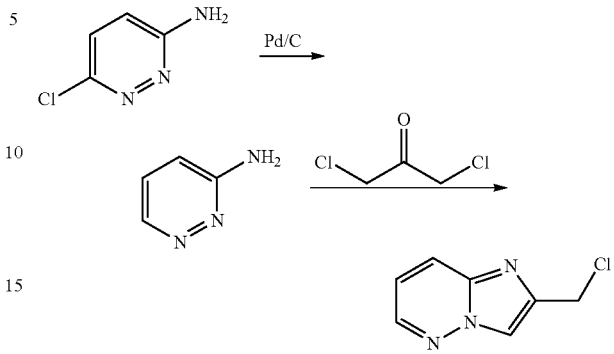

Synthesis of pyridazin-3-amine

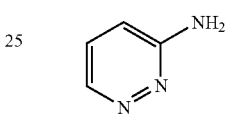

To a stirred solution of 6-chloropyridazin-3-amine (10 g, 77.19 mmol) in MeOH (100 mL) was added 10% Pd—C (2.5 g), diethyl amine (16.0 mL, 154.38 mmol) and stirred at RT for 16 h under H$_2$ atmosphere (balloon pressure). The reaction mixture was passed through a pad of celite and washed with MeOH (10 mL). Volatiles were dried in vacuo to afford pyridazin-3-amine (7.3 g) as a crude. This was used for next step without further purification. $^1$H-NMR (DMSO d$_6$, 500 MHz): δ 8.84 (br s, 2H), 8.41-8.38 (m, 1H), 7.22-7.18 (m, 1H), 6.74 (d, 1H); LC-MS: 78.43%; 95.9 (M$^+$+1); (column; X-bridge C-18, (50×3.0 mm, 3.5μ); RT 0.68 min. 5 mM AA in water: ACN; 0.5 ml/min); TLC: 100% EtOAc (Rf: 0.2).

Synthesis of 2-(chloromethyl)imidazo[1,2-b]pyridazine

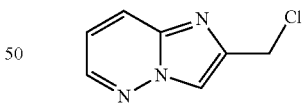

To a stirred solution of pyridazin-3-amine (7.3 g, 77.65 mmol) in ACN (100 mL) was added 1,3-dichloropropan-2-one (19.7 g, 155.3 mmol) at RT under inert atmosphere. The reaction mixture was stirred under reflux for 16 h. After full consumption of starting material (by TLC), the reaction mixture was cooled to RT and volatiles were evaporated under reduced pressure. The residue was neutralized with NaHCO$_3$ solution and extracted with EtOAc. The combined organic layer was dried over sodium sulphate, filtered and concentrated in vacuo to obtain the crude product. The crude material was purified by silica gel column chromatography to afford 2-(chloromethyl)imidazo[1,2-b]pyridazine (1.5 g, 12%) as a red solid. $^1$H-NMR (DMSO d$_6$, 500 MHz): δ 8.57-8.54 (m, 1H), 8.38 (s, 1H), 8.17 (d, 1H), 7.25-7.21 (m, 1H), 4.96 (s, 2H); LC-MS: 98.16%; 168.0 (M⁺+1); (column; X-bridge C-18, (50×3.0 mm, 3.5µ); RT 2.02 min. 5 mM AA in water: ACN; 0.8 ml/min); TLC: 100% EtOAc (Rf: 0.6).

iv. 6-(chloromethyl)imidazo[1,2-b]pyridazine

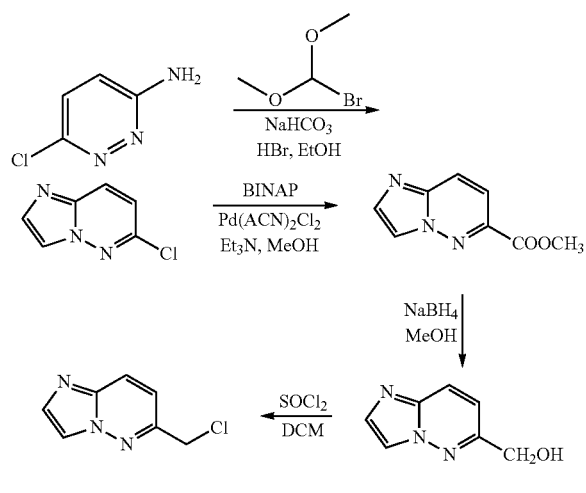

Synthesis of 6-Chloroimidazo[1,2-b]pyridazine

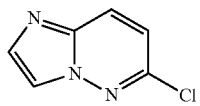

A mixture of 2-bromo-1,1-dimethoxyethane (45.67 mg, 0.27 mmol) and 48% of aqueous HBr (9 mL) was heated up to 120° C. and stirred for 30 min under inert atmosphere. The reaction mixture was cooled to 0° C., NaHCO₃ (10 g, 119.69 mmol) and a solution of 6-chloropyridazin-3-amine (5.0 g, 38.61 mmol) in EtOH (250 mL) was added to the reaction mixture at 0° C. The resultant reaction mixture was heated up to 80° C. and stirring was continued for another 2 h. After consumption of starting material by TLC, the volatiles were removed under reduced pressure. The residue was diluted with NaHCO₃ solution and extracted with EtOAc. Combined organic layer was dried over sodium sulphate, filtered and concentrated in vacuo to obtain the crude product. The crude material was purified by silica gel column chromatography to afford 6-chloroimidazo[1,2-b]pyridazine (3 g, 50%) as white solid. ¹H-NMR (DMSO-d₆, 400 MHz): δ 8.32 (s, 1H), 8.18 (d, 1H), 7.81 (s, 1H), 7.34 (d, 1H); LC-MS: 99.59%; 154.0 (M+1); (column; X-bridge C-18, (50×3.0 mm, 3.5µ); RT 2.60 min. 5 mM NH₄OAc in water: ACN; 0.8 ml/min); TLC: 70% EtOAc/Hexane (Rf: 0.5).

Synthesis of methyl imidazo[1,2-b]pyridazine-6-carboxylate

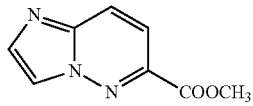

To a stirred solution of 6-chloroimidazo[1,2-b]pyridazine (2.0 g, 13.15 mmol) in ACN:MeOH (60 mL, 1:1) under N₂ bubbling atmosphere were added BINAP (818 mg, 1.31 mmol), Pd(ACN)₂Cl₂ (341 mg, 1.31 mmol) and Et₃N (1.60 g, 15.78 mmol) in a steel bomb. The resultant reaction mixture was agitated under CO atmosphere (150 psi) at 100° C. for 16 h. After full consumption of starting material by TLC, the reaction was diluted with water and extracted with EtOAc. The combined organic layer was dried over sodium sulphate, filtered and concentrated in vacuo to obtain the crude product. The crude material was purified by silica gel column chromatography to afford imidazo[1,2-b]pyridazine-6-carboxylate (1.3 g, 65%) as brown solid. ¹H-NMR (DMSO-d₆, 500 MHz): δ 8.51 (s, 1H), 8.27 (d, 1H), 7.94 (s, 1H), 7.72 (d, 1H), 3.97 (s, 3H); LC-MS: 91.14%; 178 (M⁺+1) (column; X-bridge C-18, (50×3.0 mm, 3.5µ); RT 2.28 min. 5 mM NH₄OAc: ACN; 0.8 ml/min); TLC: 70% EtOAc/Hexane (Rf: 0.5).

Synthesis of imidazo[1,2-b]pyridazin-6-ylmethanol

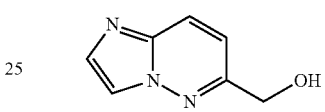

To a stirred solution of imidazo[1,2-b]pyridazine-6-carboxylate (3.5 g, 22.77 mmol) in MeOH:THF (45 mL, 1:2) was added NaBH₄ (1.72 g, 45.26 mmol) portion wise at 0° C. and stirred for 2 h. After full consumption of starting material by TLC, the reaction was diluted with saturated Na₂CO₃ solution and extracted with EtOAc. The combined organic layer was dried over sodium sulphate, filtered and concentrated in vacuo to obtain the crude product. The crude material was washed with 50% EtOAc/Hexane to afford crude imidazo[1,2-b]pyridazin-6-ylmethanol (2.5 g). ¹H-NMR (DMSO-d₆, 400 MHz): δ 8.21 (s, 1H), 8.06 (d, 1H), 7.21 (s, 1H), 7.24 (d, 1H), 5.68 (br s, 1H), 4.59 (s, 2H); LC-MS: 85.80%; 149.6 (M⁺+1) (column; X-Select C-18, (50×3.0 mm, 3.5µ); RT 0.72 min. 5 mM NH₄OAc in water: ACN; 0.8 ml/min); TLC: 100% EtOAc (Rf: 0.2).

Synthesis of 6-(chloromethyl)imidazo[1,2-b]pyridazine

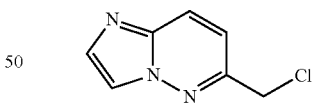

To a stirred solution of imidazo[1,2-b]pyridazin-6-ylmethanol (2.5 g 16.77 mmol) in DCM (20 mL) was added SOCl₂ (8 mL) at 0° C. under inert atmosphere. The reaction mixture was heated up to 50° C. and stirred for 3 h. After complete consumption of starting material (by TLC), the volatiles were evaporated under reduced pressure. The residue was quenched with ice cold water followed by saturated Na₂SO₄ and extracted with EtOAc. Combined organic layer was dried over sodium sulphate, filtered and concentrated in vacuo to obtain the crude product. The crude material was purified by silica gel column chromatography to afford 6-(chloromethyl)imidazo[1,2-b]pyridazine (1.4 g, 50%) as an off-white solid. ¹H-NMR (DMSO-d₆, 500 MHz): δ 8.31 (s, 1H), 8.18 (d, 1H), 7.82 (s, 1H), 7.36 (d, 1H), 4.92 (s, 2H); LC-MS: 83.93%; 167.6 (M⁺+1) (column X-Select C-18, (50×3.0 mm, 3.5μ); RT 2.29 min. 5 mM NH₄OAc in water: ACN; 0.8 ml/min); UPLC (purity): 92.54%; (column; Acquity UPLC HSS T3, 2.1×100 mm, 1.7μ); RT 2.93 min. 0.025% Aq TFA: ACN; 0.3 ml/min.; TLC: 70% EtOAc/Hexane (Rf 0.6).

v. 6-(chloromethyl)imidazo[1,2-b]pyridazine

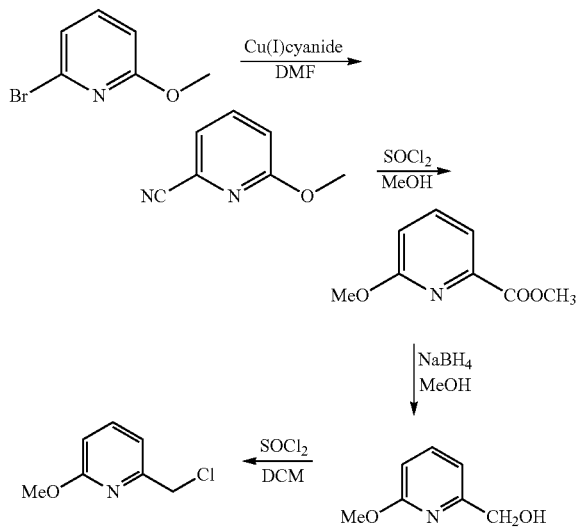

Synthesis of 6-methoxypicolinonitrile

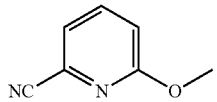

To a stirred solution of 2-bromo-6-methoxypyridine (5.0 g, 26.59 mmol) in DMF (50 mL) was added Cu(I)cyanide (7.14 g, 79.77 mmol) at room temperature. The resulting reaction mixture was heated at 100° C. and stirred for 16 h. The reaction mixture was diluted with water, filtered through a pad of celite and the filtrate was extracted with EtOAc. Combined organic layer was dried over sodium sulphate, filtered and concentrated in vacuo to obtain the crude product. The crude material was purified by silica gel column chromatography to afford 6-methoxypicolinonitrile (1.4 g, 39%) as white solid. ¹H-NMR (DMSO d₆, 400 MHz): δ 7.94 (t, 1H), 7.64 (d, 1H), 7.18 (d, 1H), 3.92 (s, 3H); LC-MS: 99.14%; 135.8 (M⁺+1); (column; X-bridge C-18, (50×3.0 mm, 3.5μ); RT 3.31 min. 0.1% Aq TFA: ACN; 0.8 ml/min); TLC: 10% EtOAc/Hexane (Rf: 0.3).

Synthesis of methyl 6-methoxypicolinate

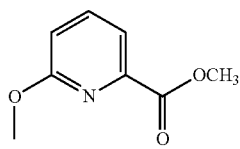

To a stirred solution of 6-methoxypicolinonitrile (1.4 g 10.44 mmol) in MeOH (30 mL) was added SOCl₂ (4 mL) at 0° C. The resultant reaction mixture was heated at 70° C. for 16 h. After full consumption of starting material (by TLC), the volatiles were evaporated under reduced pressure. The residue was quenched with ice cold water and saturated NaHCO₃ and extracted with EtOAc. Combined organic layer was dried over sodium sulphate, filtered and concentrated in vacuo to afford methyl 6-methoxypicolinate (1.2 g) as crude. LC-MS: 79.02%; 167.5 (M⁺+1); (column; X-select C-18, (50×3.0 mm, 3.5μ); RT 3.39 min. 5 mM NH₄OAc in water: ACN; 0.50 ml/min); TLC: 10% EtOAc/Hexane (Rf: 0.4).

Synthesis of (6-methoxypyridin-2-yl)methanol

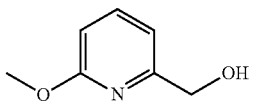

To a stirred solution of methyl 6-methoxypicolinate (1.2 g, 7.18 mmol) in ethanol (30 mL) was added NaBH₄ (409 mg, 10.77 mmol) portion wise at 0° C. and stirred for 3 h at RT. Progress of the reaction was monitored by TLC. Volatiles were evaporated under reduced pressure. The residue was diluted with water and extracted with EtOAc (2×25 mL). Combined organic layer was dried over sodium sulphate, filtered and concentrated in vacuo to afford crude (6-methoxypyridin-2-yl)methanol (0.7 g). LC-MS: 52.48%; 139.5 (M⁺+1); (column; X-select C-18, (50×3.0 mm, 3.5μ); RT 2.55 min. 5 mM NH₄OAc in water: ACN; 0.50 ml/min); TLC: 20% EtOAc/Hexane (Rf: 0.2).

Synthesis of 2-(chloromethyl)-6-methoxypyridine

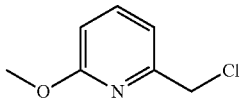

To a stirred solution of (6-methoxypyridin-2-yl)methanol (0.7 g 5.03 mmol) in CH₂Cl₂ (20 mL) was added SOCl₂ (2 mL) at 0° C. under inert atmosphere. The resultant reaction mixture was heated up to 50° C. and stirred for 2 h. After completion of starting material (by TLC), the volatiles were evaporated under reduced pressure. The residue was quenched with ice cold water and saturated NaHCO₃ and extracted with EtOAc. Combined organic layer was dried over sodium sulphate, filtered and concentrated in vacuo. The crude material was purified by silica gel column chromatography to afford 2-(chloromethyl)-6-methoxypyridine (180 mg, 24%) as a liquid. ¹H-NMR (DMSO d₆, 500 MHz): δ 7.72 (t, 1H), 7.12 (d, 1H), 6.87 (d, 1H), 4.64 (s, 2H), 3.82 (s, 3H); LC-MS: 98.62%; 158.0 (M⁺+1); (column; X-select C-18, (50×3.0 mm, 3.5μ); RT 4.12 min. 5 mM NH₄OAc in water: ACN; 0.50 ml/min); TLC: 10% EtOAc/Hexane (Rf: 0.6).

vi. (R)-(1-Chloroethyl)benzene

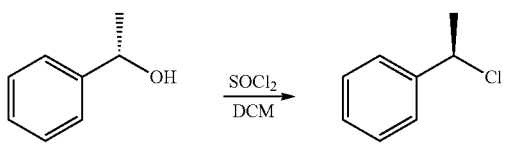

Synthesis of (R)-(1-Chloroethyl)benzene

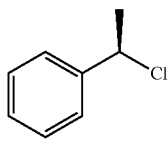

To a stirred solution of (S)-1-phenylethanol (0.5 g 4.09 mmol) in DCM (5 mL) was added $SOCl_2$ (1.48 mL, 20.49 mmol) at 0° C. under inert atmosphere. The resultant reaction mixture was heated up to 50° C. and stirred for 2 h. After complete consumption of starting material (by TLC), the volatiles were evaporated under reduced pressure. The residue was quenched with saturated $NaHCO_3$ and extracted with EtOAc. Combined organic layer was dried over sodium sulphate, filtered and concentrated in vacuo to afford (R)-(1-Chloroethyl)benzene (0.4 g, crude) as pale yellow liquid. $^1$H-NMR (DMSO $d_6$, 400 MHz): δ 7.51-7.47 (m, 2H), 7.38-7.29 (m, 3H), 5.38-5.31 (m, 1H), 1.89 (d, 3H); TLC: 10% EtOAc/Hexane (Rf: 0.7).

vii. (S)-(1-Chloroethyl)benzene

Synthesis of (S)-(1-chloroethyl)benzene

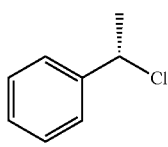

To a stirred solution of (R)-1-phenylethanol (0.5 g 4.09 mmol) in DCM (10 mL) was added $SOCl_2$ (2.438 g, 20.49 mmol) at 0° C. under inert atmosphere. The resultant reaction mixture was heated up to 50° C. and stirred for 3 h. After completion of starting material (by TLC), the volatiles were evaporated under reduced pressure. The residue was quenched with saturated $NaHCO_3$ and extracted with EtOAc. Combined organic layer was dried over sodium sulphate, filtered and concentrated in vacuo to afford (S)-(1-chloroethyl)benzene (0.38 g, 66%) as pale yellow liquid. $^1$H-NMR (DMSO $d_6$, 400 MHz): δ 7.48-7.46 (m, 2H), 7.38-7.29 (m, 3H), 5.36-5.32 (m, 1H), 1.87 (d, 3H); TLC: 10% EtOAc/Hexane (Rf: 0.7).

viii. methyl pyrazine-2-carboxylate

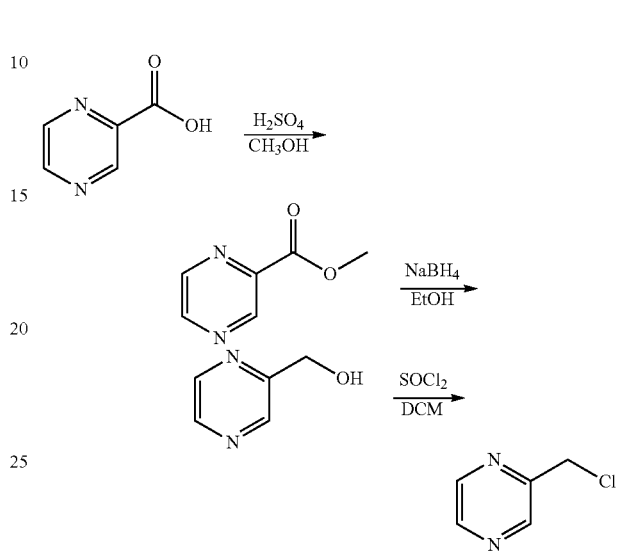

Synthesis of methyl pyrazine-2-carboxylate

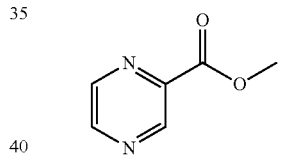

To a stirred solution of pyrazine-2-carboxylic acid (5 g, 40.29 mmol) in MeOH (20 mL) was added concentrated $H_2SO_4$ (1 mL) drop-wise and stirred under reflux for 5 h. The reaction mixture was cooled to RT; volatiles were evaporated under reduced pressure. The residue was diluted with water and basified to pH~8.5 using $NaHCO_3$ and extracted with EtOAc. Combined organic layer was dried over sodium sulphate, filtered and concentrated in vacuo to afford methyl pyrazine-2-carboxylate (3.5 g, 63.63%) as an off-white solid. $^1$H-NMR (DMSO $d_6$, 400 MHz): δ 9.21 (s, 1H), 8.91 (d, 1H), 8.82 (d, 1H), 3.92 (s, 3H); TLC: 50% EtOAc/Hexane (Rf: 0.4).

Synthesis of pyrazin-2-ylmethanol

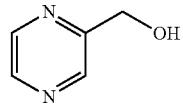

To a stirred solution of methyl pyrazine-2-carboxylate (0.5 g, 3.62 mmol) in $H_2O$ (10 mL) was added $NaBH_4$ (685 g, 18.02 mmol) portion wise at 0° C., and the reaction mixture was allowed to warm to RT and stirred for 30 min under inert atmosphere. To this saturated K₂CO₃ (10 mL) and EtOH (5 mL) was added and stirring was continued for another 1 h at RT. The progress of the reaction was monitored by TLC; the reaction mixture was extracted with EtOAc. The combined organic layer was dried over sodium sulphate, filtered and concentrated in vacuo to afford crude pyrazin-2-ylmethanol (0.3 g). LC-MS: 99.91%; 111.9 (M⁺+1) (column; X-bridge C-18, (50×3.0 mm, 3.5μ); RT 0.72 min. 0.1% TFA in water: ACN; 0.8 ml/min); TLC: 100% EtOAc (Rf: 0.2).

Synthesis of 2-(chloromethyl)pyrazine

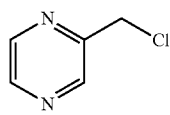

To a stirred solution of pyrazin-2-ylmethanol (0.3 g 2.72 mmol) in DCM (10 mL) was added SOCl₂ (1 mL) at 0° C. under inert atmosphere. The reaction mixture was heated up to 50° C. and stirred for 2 h. After completion of starting material (by TLC), the volatiles were evaporated under reduced pressure. The residue was quenched with ice cold water followed by saturated NaHCO₃ and extracted with EtOAc. Combined organic layer was dried over sodium sulphate, filtered and concentrated in vacuo to obtain the crude product. The crude material was purified by silica gel column chromatography to afford 2-(chloromethyl)pyrazine (110 mg, 20.4%) as liquid. ¹H-NMR (CDCl₃, 400 MHz): δ 8.74 (s, 1H), 8.58-8.56 (m, 2H), 4.71 (s, 2H); LC-MS: 98.86%; 129 (M⁺+1) (column; Eclipse XDB C-18, (150×4.6 mm, 5.0μ); RT 4.83 min. 5 mM NH₄OAc: ACN; 1.0 ml/min); TLC: 70% EtOAc/Hexane (Rf: 0.6).

ix. (3r,5r,7r)-2,5-dioxopyrrolidin-1-yl adamantane-1-carboxylate

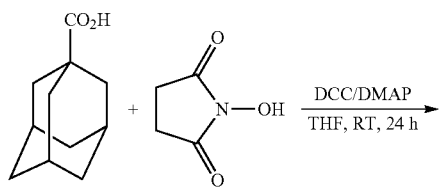

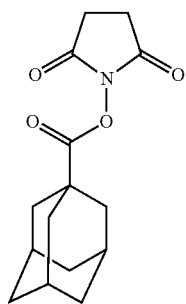 [SMILES: O=C1CCC(=O)N1OC(=O)C12CC3CC(CC(C3)C1)C2]

Synthesis of (3r,5r,7r)-2,5-dioxopyrrolidin-1-yl adamantane-1-carboxylate

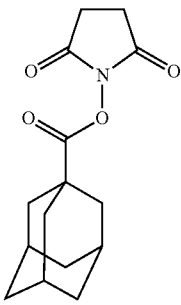

To a stirred solution of adamantine-1-carboxylic acid (1.80 g, 10 mmol), N-hydroxysuccininmide (1.15 g, 10 mmol), and DMAP (0.12 g, 1.0 mmol) in dry THF (40 mL) was added DCC (2.27 g, 11 mmol) slowly under argon atmosphere at RT. The reaction mixture was stirred at RT for 24 h. The resulting suspension was filtered through a Celite pad and the filter cake was rinsed with dichloromethane. The combined filtrates were concentrated under reduced pressure to give a white solid. This solid was redissolved in dichloromethane (20 mL) and filtered. The filtrate was concentrated under reduced pressure to give crude product (3.19 g) as white solid. Flash chromatography (10-60% ETOAc/heptane) provided (3r,5r,7r)-2,5-dioxopyrrolidin-1-yl adamantane-1-carboxylate as white solid (2.12 g, 77% yield). ¹H NMR (300 MHz, CDCl₃) δ 2.82 (s, 4H), 2.08 (br s, 9H), 1.76 (br s, 6H); ¹³C NMR (75 MHz, CDCl₃) δ 172.1, 169.1, 40.4, 38.4, 36.2, 27.6, 25.7.

x. 5-chloro-2-methylbenzoyl chloride

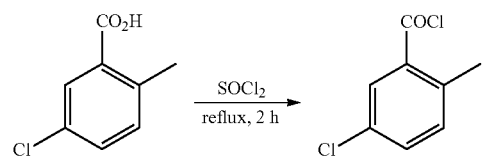

Synthesis of 5-chloro-2-methylbenzoyl chloride

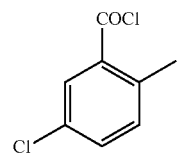

A suspension of 5-chloro-2-methyl-benzoic acid (2.00 g, 11.7 mmol) in thionyl chloride (10 mL) was heated to reflux for 2 h. After this time the mixture was cooled to RT and evaporated to dryness. Toluene (20 mL) was added and the resulting mixture was evaporated to dryness again to give 5-chloro-2-methylbenzoyl chloride (1.73 g, 78% yield) as brown oil. ¹H NMR (300 MHz, CDCl₃) δ 8.16 (s, 1H), 7.47

(s, 1H), 7.24 (s, 1H), 2.53 (s, 3H); $^{13}$C NMR (75 MHz, CDCl$_3$) δ 166.4, 139.4, 133.9, 133.6, 133.1, 132.0, 21.5.

xi. 4-fluoro-2-methylbenzoyl chloride

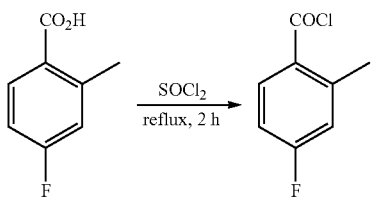

Synthesis of 4-fluoro-2-methylbenzoyl chloride

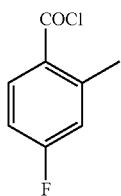

A suspension of 4-fluoro-2-methylbenzoic acid (1.54 g, 10 mmol) in thionyl chloride (10 mL) was heated to reflux for 2 h. After this time the mixture was cooled to RT. The excess thionyl chloride was evaporated and the residue was rotovaped twice with toluene (2×20 mL) to give 1.74 g crude 6 (3:1 molar ratio of 6 with toluene, 86% yield) as brown oil. $^1$H NMR (300 MHz, CDCl$_3$) δ 8.32-8.24 (m, 1H), 7.07-6.95 (m, 2H), 2.58 (s, 3H); $^{13}$C NMR (75 MHz, CDCl$_3$) δ 166.1, 165.6 (d, J=257 Hz), 145.2 (d, J=9.5 Hz), 137.1 (d, J=10 Hz), 128.5, 118.8 (d, J=22 Hz), 113.5 (d, J=22 Hz), 22.4.

xii. 2,5-dioxopyrrolidin-1-yl 4,4-difluorocyclohexanecarboxylate

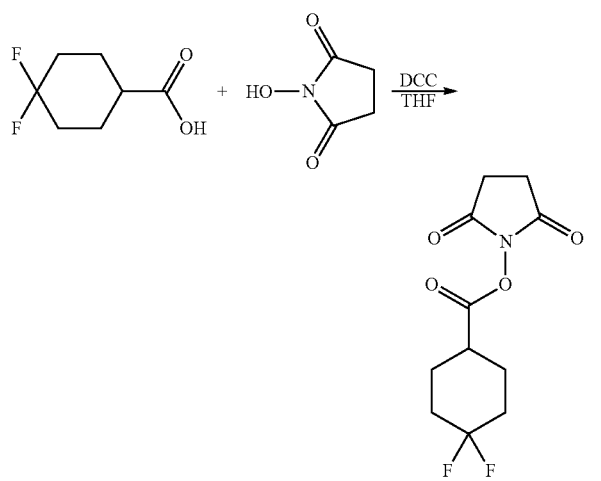

Synthesis of 2,5-dioxopyrrolidin-1-yl 4,4-difluorocyclohexanecarboxylate

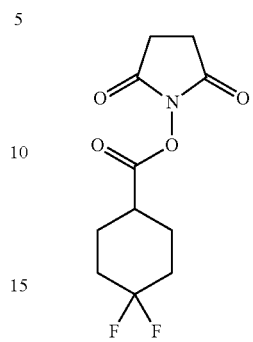

DCC (1.38 g, 6.7 mmol) was added to 4,4-difluorocyclohexanecarboxylic acid (1.0 g, 6.1 mmol) in THF (50 mL) at 0° C. The reaction mixture was stirred at room temperature for 1 h and cooled down to 0° C. N-Hydroxysuccinimide (0.77 g, 6.7 mmol) was added and stirring was continued overnight at room temperature. The reaction mixture was filtered, the solvent was evaporated, the residue was purified by column chromatography (silica gel, EtOAc/Hept, 1:1-1:0) to prepare 2,5-dioxopyrrolidin-1-yl 4,4-difluorocyclohexanecarboxylate (1.5 g, 94% yield). $^1$H NMR (300 MHz, CDCl$_3$/TMS): δ 2.81 (s, 4H), 2.2-1.8 (m, 8H), 1.2 (m, 1H).

xiii. 2,5-dioxopyrrolidin-1-yl furan-3-carboxylate

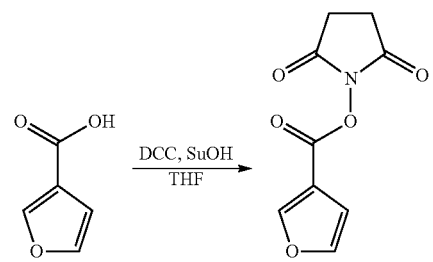 [SMILES: O=C(O)c1ccoc1 ; O=C(ON1C(=O)CCC1=O)c1ccoc1 ; "THF"]

Synthesis of 2,5-dioxopyrrolidin-1-yl furan-3-carboxylate

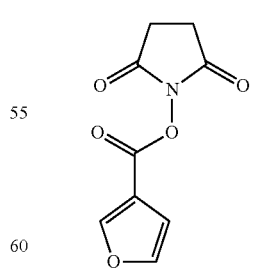

DCC (6.8 g, 33 mmol) was added to furan-3-carboxylic acid (3.36 g, 30 mmol) in THF (70 mL) at 0° C. The reaction mixture was stirred at room temperature for 1 h and cooled down to 0° C. N-hydroxysuccinimide (3.8 g, 33 mmol) was added and stirring was continued overnight at room temperature. The reaction mixture was filtered, the solvent was evaporated, the residue was purified by column chromatography (silica gel, EtOAc/Hept, 1:1) to prepare 2,5-dioxopyrrolidin-1-yl furan-3-carboxylate (2.7 g, 43% yield). $^1$H NMR (300 MHz, CDCl$_3$/TMS): δ 8.21 (s, 1H), 7.51 (s, 1H), 6.80 (s, 1H), 2.83 (s, 4H).

xiv. 1-(((9H-fluoren-9-yl)methoxy)carbonyl)piperidine-4-carboxylic acid

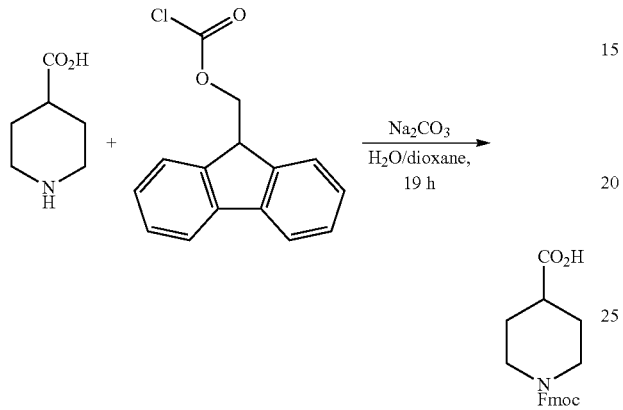

Synthesis of 1-(((9H-fluoren-9-yl)methoxy)carbonyl)piperidine-4-carboxylic acid

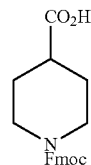

Fmoc chloride (3.30 g, 12.8 mmol) in dioxane (50 mL) was added to a solution of isonipecotic acid (1.50 g, 11.6 mmol) and sodium carbonate (6.15 g, 58.0 mmol) in water (50 mL) at RT. The resulting white suspension was stirred at RT for 19 h. After this time the mixture was diluted with water (75 mL), and extracted with ether (3×90 mL). The aqueous layer was acidified with 2N HCl aqueous solution to pH=2, and was extracted with EtOAc (3×100 mL). The combined organic phase was washed with brine (50 mL), dried over MgSO$_4$. Filtration, concentration and dried over high vacuum gave 1-(((9H-fluoren-9-yl)methoxy)carbonyl)piperidine-4-carboxylic acid (3.90 g, 95% yield) as white solid. $^1$H NMR (300 MHz, CDCl$_3$) δ 7.76 (d, 2H, J=7.2 Hz), 7.57 (d, 2H, J=6.9 Hz), 7.39 (t, 2H, J=7.4 Hz), 7.31 (t, 2H, J=7.4 Hz), 4.43 (s, 2H), 4.24 (t, 1H, J=6.5 Hz), 4.09-3.94 (m, 2H), 2.95 (t, 2H, J=11.4 Hz), 2.51 (t, 1H, J=10.4 Hz), 1.90 (br s, 2H), 1.64 (br s, 2H); $^{13}$C NMR (75 MHz, CDCl$_3$) δ 179.6, 155.0, 143.8, 141.2, 127.6, 126.9, 124.8, 119.9, 67.3, 47.4, 43.2, 40.6, 27.6.

xv. (9H-fluoren-9-yl)methyl 4-(chlorocarbonyl)piperidine-1-carboxylate

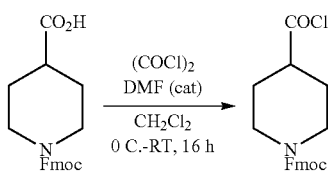

Synthesis of (9H-fluoren-9-yl)methyl 4-(chlorocarbonyl)piperidine-1-carboxylate

To a stirred suspension of 1-(((9H-fluoren-9-yl)methoxy)carbonyl)piperidine-4-carboxylic acid (3.88 g, 11 mmol) and DMF (0.4 mL) in CH$_2$Cl$_2$ (50 mL) was added oxalyl chloride (2.80 g, 22 mmol) drop-wise at 0° C. The reaction mixture turned to clear solution in 5 min, and then stirred for 16 h at RT. The reaction mixture was then concentrated at reduced pressure to afford (9H-fluoren-9-yl)methyl 4-(chlorocarbonyl)piperidine-1-carboxylate (4.07 g) as light yellow oily wax, which was used without further purification.

xvi. 2,5-dioxopyrrolidin-1-yl 2-(benzyloxy)-2-methylpropanoate

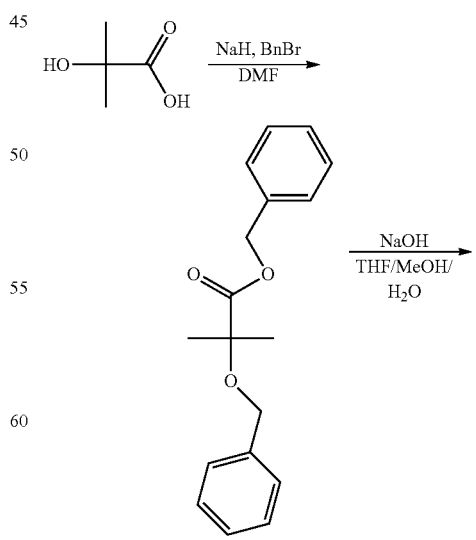

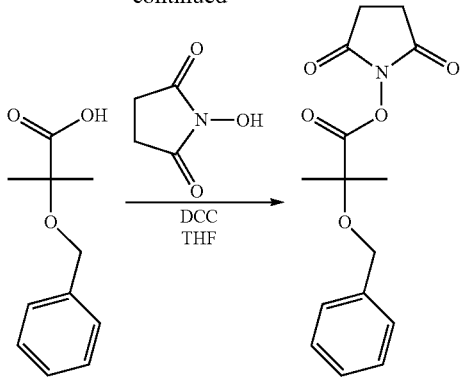

Synthesis of benzyl 2-(benzyloxy)-2-methylpropanoate

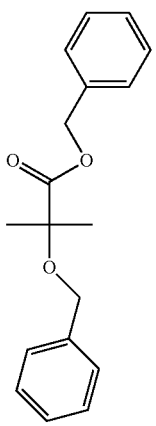 [SMILES: CC(C)(OCc1ccccc1)C(=O)OCc1ccccc1]

Sodium hydride (2.64 g, 60% in oil, 66 mmol) was added to 2-hydroxy-2-methyl-propionic acid (3.12 g, 30 mmol) in DMF (30 mL) at 0° C. The reaction mixture was stirred for 30 min at room temperature. Benzyl bromide (10.03 g, 60 mmol) was added and the reaction mixture was stirred at room temperature overnight. The reaction mixture was quenched with HCl (1M) and extracted with Et2O (3×50 mL). The organic solution was washed with water, brine, and dried over MgSO₄. The solvent was evaporated and residue was purified by column to prepare benzyl 2-(benzyloxy)-2-methylpropanoate (3.6 g, 42% yield). ¹H NMR (300 MHz, CDCl3/TMS): δ 7.39-7.29 (m, 10H), 5.24 (s, 2H), 4.49 (s, 2H), 1.58 (s, 6H).

Synthesis of benzyl 2-(benzyloxy)-2-methylpropanoic acid

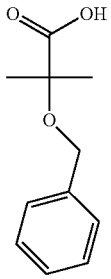

The benzyl 2-(benzyloxy)-2-methylpropanoate (3.6 g, 13 mmol) was refluxed in aqueous THF/MeOH/NaOH solution (2.0 g, 40/40/40 mL) for 1 h. The reaction mixture was acidified with HCl to pH=2 and extracted with CH₂Cl₂ (2×50 mL). The CH₂Cl₂ was evaporated, the residue was dissolved in aqueous NaOH (1M, 40 mL). The aqueous solution was extracted with chloroform (2×30 mL). The aqueous solution was again acidified with HCl to pH=2 and extracted with chloroform. The organic solution was washed with water, brine, dried over MgSO₄, and evaporated to prepare benzyl 2-(benzyloxy)-2-methylpropanoic acid (2.4 g, 99% yield). ¹H NMR (300 MHz, CDCl₃/TMS): δ 7.45-7.28 (m, 5H), 4.58 (s, 2H), 1.62 (s, 6H).

Synthesis of benzyl 2,5-dioxopyrrolidin-1-yl 2-(benzyloxy)-2-methylpropanoate

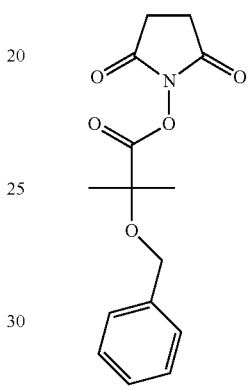

DCC (2.79 g, 13.5 mmol) was added to benzyl 2-(benzyloxy)-2-methylpropanoic acid (2.4 g, 12.3 mmol) in THF (70 mL) at 0° C. The reaction mixture was stirred at room temperature for 1 h and cooled down to 0° C. N-Hydroxysuccinimide (1.56 g, 13.5 mmol) was added and stirring was continued overnight at room temperature. The reaction mixture was filtered, the solvent was evaporated, the residue was purified by column chromatography (silica gel, EtOAc/Hept, 1:1) to prepare 2,5-dioxopyrrolidin-1-yl 2-(benzyloxy)-2-methylpropanoate (2.2 g, 61% yield). ¹H NMR (300 MHz, CDCl₃/TMS): δ 7.42-7.24 (m, 5H), 4.59 (s, 2H), 2.81 (s, 4H), 1.67 (6H).

xvii. 2,5-dioxopyrrolidin-1-yl tetrahydro-2H-pyran-3-carboxylate

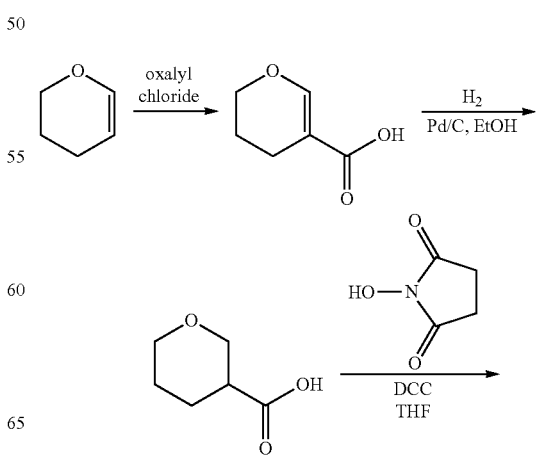

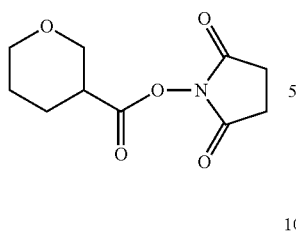

Synthesis of 3,4-dihydro-2H-pyran-5-carboxylic acid

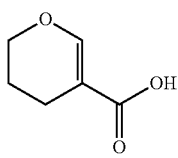

3,4-dihydro-2H-pyran-5-carboxylic acid was prepared as described in *J. Het. Chem.*, 2010, 47, p. 1171. Oxalyl chloride (7.2 mL, 83 mmol) was cooled to 0° C. and 3,4-dihydro-2H-pyrane (5.0 mL, 55.4 mmol) was added. The solution was slowly warmed to ambient temperature and stirring was continued for 1 h. Excess oxalyl chloride was evaporated in vacuo at 30° C. The mixture was then heated to 120° C. for 0.5 h, cooled to ambient temperature, and poured into ice-cold aqueous solution of $Na_2CO_3$. The alkaline solution was extracted with $CH_2Cl_2$ and then acidified with HCl (6 M). The aqueous layer was extracted with $CH_2Cl_2$ and the organic solution was dried over $MgSO_4$, filtered, and evaporated to yield 3,4-dihydro-2H-pyran-5-carboxylic acid (5.1 g, 67% yield). $^1$H NMR (300 MHz, $CDCl_3$/TMS): δ 11.4 (br s, 1H), 7.70 (s, 1H), 4.08 (t, J=5 Hz, 2H), 2.26 (t, J=7 Hz, 2H), 1.89 (m, 2H).

Synthesis of tetrahydro-2H-pyran-3-carboxylic acid

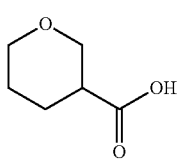

3,4-dihydro-2H-pyran-5-carboxylic acid (5.0 g, 39 mmol) was hydrogenated with $H_2$ under Pd/C (30%, 500 mg) in EtOH (100 mL) for 2 days at room temperature. The solution was filtered, EtOH was evaporated, and crude tetrahydro-2H-pyran-3-carboxylic acid (4.5 g) was used for next step without purification. $^1$H NMR (300 MHz, $CDCl_3$/TMS): δ 11.0 (br s, 1H), 4.00 (m, 1H), 3.78 (m, 1H), 3.60 (1H), 3.45 (m, 1H), 2.59 (m, 1H), 1.99 (m, 1H), 1.76-1.59 (m, 3H).

Synthesis of tetrahydro-2H-pyran-3-carboxylic acid

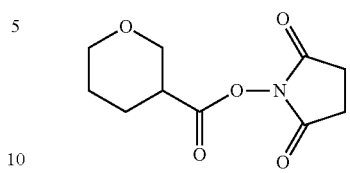

DCC (7.85 g, 38.1 mmol) was added to tetrahydro-2H-pyran-3-carboxylic acid (4.5 g, 34.6 mmol) in THF (100 mL) at 0° C. The reaction mixture was stirred at room temperature for 1 h and cooled down to 0° C. N-Hydroxysuccinimide (4.78 g, 41.5 mmol) was added and stirring was continued overnight at room temperature. The reaction mixture was filtered, the solvent was evaporated, and the residue was purified by column chromatography (silica gel, EtOAc/Hept, 1:1-1:0) to prepare 2,5-dioxopyrrolidin-1-yl tetrahydro-2H-pyran-3-carboxylate (6.5 g, 83% yield). $^1$H NMR (300 MHz, $CDCl_3$/TMS): δ 4.14-4.06 (m, 1H), 3.88-3.79 (m, 1H), 3.71-3.64 (m, 1H), 3.54-3.44 (m, 1H), 2.99-2.89 (m, 1H), 2.81 (s, 4H), 22.2-2.14 (m, 1H), 1.95-1.84 (m, 1H), 1.78-1.64 (m, 3H).

xviii. 2-(dimethylamino)benzaldehyde

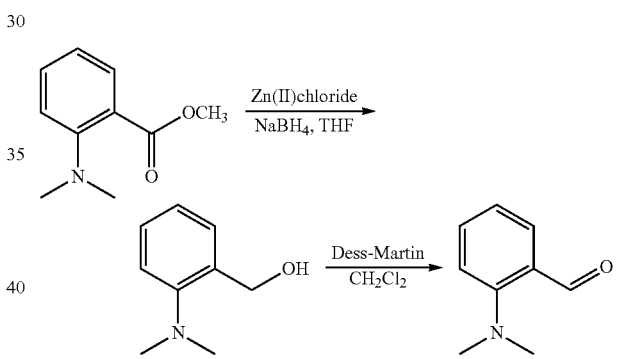

Synthesis of (2-(dimethylamino)phenyl)methanol

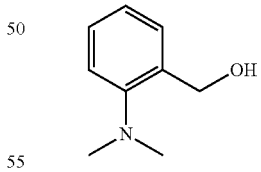

To a stirred solution of methyl 2-(dimethylamino)benzoate (1.0 g, 5.58 mmol) in THF (30 mL) was added Zn(II) chloride (1.52 g, 11.16 mmol) followed by $NaBH_4$ (254 mg, 6.69 mmol) at 0° C. under argon atmosphere. The resulting reaction mixture was heated to 65° C. and stirred for 2 h. The reaction mixture was allowed to cool to RT, filtered through a pad of celite, the filtrate was diluted with water and extracted with EtOAc (2×30 mL). The combined organic extracts were dried over sodium sulphate, filtered and concentrated in vacuo to obtain the crude product. The crude material was purified by silica gel column chromatography to afford (2-(dimethylamino)phenyl)methanol (0.5 g, 60%) as a liquid. ¹H-NMR (CDCl₃, 400 MHz): δ 7.25-7.05 (m, 4H), 5.56 (bs, 1H), 4.82 (s, 2H), 2.72 (s, 6H).

Synthesis of 2-(dimethylamino)benzaldehyde

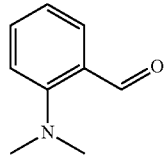

To a stirred solution of (2-(dimethylamino)phenyl)methanol (0.5 g, 3.02 mmol) in CH₂Cl₂ (20 mL) was added Dess-Martin periodinane (2.56 g, 6.02 mmol) at 0° C. under argon atmosphere. The resulting reaction mixture was stirred for 2 h at RT; the reaction mixture was then neutralized with saturated NaHCO₃ solution and extracted with DCM (2×30 mL). The combined organic extracts were dried over sodium sulphate, filtered and concentrated in vacuo to obtain the crude product. The crude material was purified by silica gel column chromatography to afford 2-(dimethylamino)benzaldehyde (0.35 g, 78%) as a liquid. LC-MS: 55.66%; 150.1 [M⁺+1]; (column; Eclipse XDB C-18, (150×4.6 mm, 5.0µ); RT 4.10 min. 0.05% TFA in water: ACN; 1.0 ml/min);

xix. 3-(dimethylamino)benzaldehyde

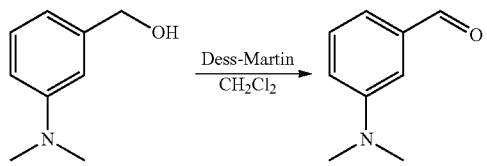

Synthesis of 3-(dimethylamino)benzaldehyde

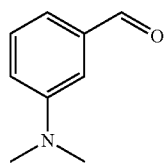

To a stirred solution of (3-(dimethylamino)phenyl)methanol (1.0 g, 6.05 mmol) in CH₂Cl₂ (20 mL) was added Dess-Martin periodinane (5.1 g, 12.10 mmol) at 0° C. under argon atmosphere. The resulting reaction mixture was stirred for 2 h at RT; the reaction mixture was then neutralized with saturated NaHCO₃ solution and extracted with DCM (2×30 mL). The combined organic extracts were dried over sodium sulphate, filtered and concentrated in vacuo to obtain the crude product. The crude material was purified by silica gel column chromatography to afford 3-(dimethylamino)benzaldehyde (0.4 g, 44%) as pale-grn liquid. ¹H-NMR (DMSO d₆, 400 MHz): δ 9.94 (bs, 1H), 7.38 (t, 1H), 7.16-7.12 (m, 2H), 7.05 (d, 1H), 2.97 (s, 6H); LC-MS: 99.55%; 191 [M⁺+1]; (column; X-bridge C-18, (50×3.0 mm, 3.5µ); RT 3.29 min. 5 mM NH₄OAc: ACN; 0.8 ml/min).

xx. quinazoline-7-carbaldehyde

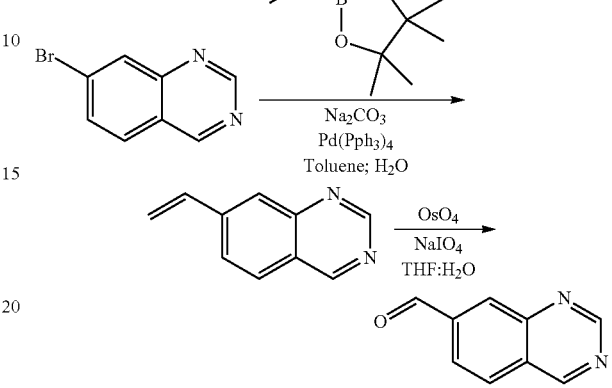

Synthesis of 7-vinylquinazoline

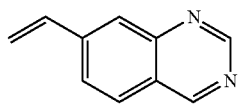

To a stirred solution of 7-bromoquinazoline (200 mg, 0.95 mmol) in Toluene: H2O (3 mL, (4:1)) was added 4,4,5,5-tetramethyl-2-vinyl-1,3,2-dioxaborolane (221 mg, 1.43 mmol), Na₂CO₃ (304 mg, 2.86 mmol), and Pd(PPh₃)₄ (55 mg, 0.04 mmol) at RT. The reaction mixture was allowed to warm 90° C. stirred for 2 h in seal tube. The reaction mixture was filtered, the solvent was evaporated, the crude material was purified by silica gel column chromatography to afford 7-vinylquinazoline (105 mg, 70.4%) as a thick syrup. ¹H-NMR (CDCl₃, 400 MHz): δ 9.31 (d, 2H), 7.95 (s, 1H), 7.86 (d, 1H), 6.98-6.85 (m, 1H), 6.05 (d, 1H), 5.55 (d, 1H); LC-MS: 98.77%; 157.0 (M⁺+1); (column; X-Bridge C-18, (50×3.0 mm, 3.5µ); RT 2.51 min. A: 5 Mm NH₄OAc in water, B: CH₃CN, 0.8 ml/min); TLC: 30% EtOAc/Hexane (Rf: 0.3).

Synthesis of quinazoline-7-carbaldehyde

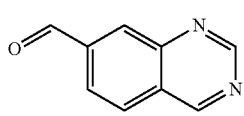

To a stirred solution of 7-vinylquinazoline (105 mg, 0.67 mmol) in THF:H₂O (3 mL, (2:1)) was added osmium tetroxide (4M in Toluene, 0.3 ml, 0.06 mmol), sodium periodate (288 mg, 1.3 mmol), 1 h, at room temperature The reaction mixture was quenched with water and extracted with CHCl₃ (2×10 ml). The combined organic layer was dried over sodium sulphate, filtered and concentrated in vacuo to obtain the crude product. The crude material was directly taken for next reaction without purification to afford quinazoline-7-carbaldehyde (100 mg, 94%) as an pale yellow solid. $^1$H-NMR (CDCl$_3$, 400 MHz): δ 10.32 (s, 1H), 9.51 (d, 2H), 8.5 (s, 1H), 8.21 (d, 1H), 8.11 (d, 1H); LC-MS: 96.12%; 159.0 (M$^+$+1); (column; X-Bridge C-18, (50×3.0 mm, 3.5μ); RT 1.81 min. A: 5 Mm NH$_4$OAc in water, B: CH$_3$CN, 0.8 ml/min); TLC: 30% EtOAc/Hexane (Rf: 0.3).

xxi. 3-(pyrrolidin-1-yl)benzaldehyde

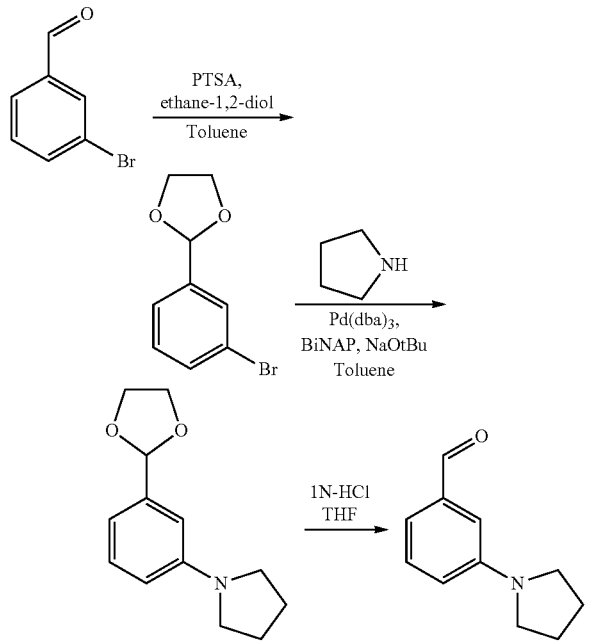

Synthesis of 2-(3-bromophenyl)-1,3-dioxolane

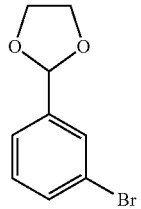

To a stirred solution of 3-bromobenzaldehyde (1.0 g, 5.40 mmol) in toluene (20 mL) was added ethane-1,2-diol (1.0 g, 16.21 mmol) followed by catalytic amount of p-Toluenesulfonic acid at RT. The resulting reaction mixture was agitated for 2 h under H$_2$ atmosphere (balloon pressure) at reflux temperature; progress of the reaction was monitored by TLC. The volatiles were evaporated under reduced pressure. The residue was diluted with EtOAc, washed with NaHCO$_3$ solution. Combined organic layer was dried over sodium sulphate, filtered and concentrated in vacuo to afford 2-(3-bromophenyl)-1,3-dioxolane (1.0 g, 82%) as colorless liquid. This was used in the next step without further purification; TLC: 5% EtOAc/Hexane (Rf: 0.3).

Synthesis of 1-(3-(1,3-dioxolan-2-yl)phenyl)pyrrolidine

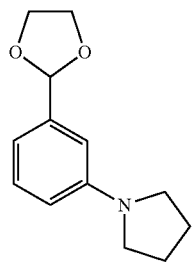 [SMILES: c1cc(C2OCCO2)cc(N2CCCC2)c1]

To a stirred solution of 2-(3-bromophenyl)-1,3-dioxolane (0.3 g, 1.32 mmol) in toluene (15 mL) were added pyrrolidine (93 mg, 1.32 mmol), Pd(dba)$_3$ (24 mg, 0.026 mmol), BINAP (21 mg, 0.033 mmol) and NaO$^t$Bu (190 mg, 1.98 mmol) at RT and degassed with argon for 15 min. The resulting reaction mixture was heated to 70° C. and stirred for 16 h; progress of the reaction was monitored by TLC. The reaction mixture was allowed to cool to RT, filtered through a pad of celite and the filtrate was concentrated under reduced pressure to obtain the crude. The crude material was purified by silica gel column chromatography to afford 1-(3-(1,3-dioxolan-2-yl)phenyl)pyrrolidine (0.15 g, 52%) as pale-yellow liquid; $^1$H-NMR (CDCl$_3$, 400 MHz): δ 7.24-7.21 (m, 1H), 6.78 (d, 1H), 6.65 (s, 1H), 6.54 (d, 1H), 5.79 (s, 1H), 4.14-3.98 (m, 4H), 3.32 (t, 4H), 1.98 (t, 4H); TLC: 5% EtOAc/Hexane (Rf: 0.2).

Synthesis of 3-(pyrrolidin-1-yl)benzaldehyde

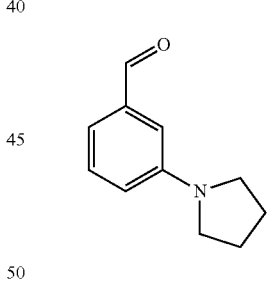

To a stirred solution of 1-(3-(1,3-dioxolan-2-yl)phenyl) pyrrolidine (0.15 g, 0.68 mmol) in THF (5 mL) was added 1N HCl (3 mL) at 0° C. under nitrogen atmosphere. The resulting reaction mixture was allowed to warm to RT and stirred for 4 h. The progress of the reaction was monitored by TLC; the volatiles were evaporated under reduced pressure and obtained residue was diluted EtOAc and washed with bicarbonate solution. The separated organic layer was dried over sodium sulphate, filtered and concentrated in vacuo to obtain the crude. The crude material was purified by silica gel column chromatography to afford 3-(pyrrolidin-1-yl)benzaldehyde (0.11 g, 92%) as colorless liquid. $^1$H-NMR (CDCl$_3$, 500 MHz): δ 9.94 (bs, 1H), 7.37 (t, 1H), 7.16-7.14 (m, 1H), 7.04 (d, 1H), 6.84-6.81 (m, 1H), 3.37 (t, 4H), 2.08 (t, 4H); TLC: 10% EtOAc/Hexane (Rf: 0.4).

xxii. 5-Fluoro-2-methylbenzoyl chloride

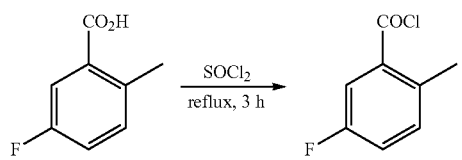

Synthesis of 5-Fluoro-2-methylbenzoyl chloride

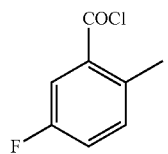

A suspension of 5-fluoro-2-methyl-benzoic acid (1.54 g, 10 mmol) in thionyl chloride (10 mL) was heated to reflux for 3 h. After this time the mixture was cooled to RT. The excess thionyl chloride was evaporated and the residue was dissolved in toluene (2×10 mL) and concentrated under reduced pressure, and then put placed under high vacuum for 1 h to afford 5-Fluoro-2-methylbenzoyl chloride (1.32 g, 77% yield) as yellow oil.

$^1$H NMR (300 MHz, CDCl$_3$) δ 7.89 (dd, 1H, J=9.4, 2.2 Hz), 7.30-7.18 (m, 2H), 2.52 (s, 3H); $^{13}$C NMR (75 MHz, CDCl$_3$) δ 166.3, 160.2 (d, J=244 Hz), 136.8 (d, J=3 Hz), 133.5 (d, J=7 Hz), 133.3 (d, J=7 Hz), 121.1 (d, J=21 Hz), 120.0 (d, J=24 Hz), 21.2.

xxiii. 2-(chloromethyl)-4,6-dimethylpyrimidine

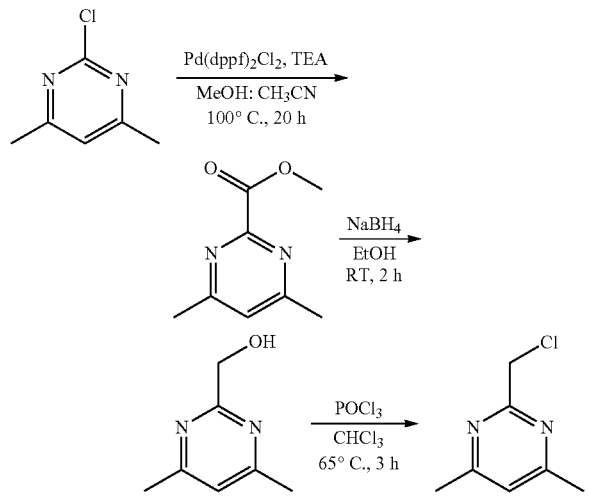

Synthesis of methyl 4,6-dimethylpyrimidine-2-carboxylate

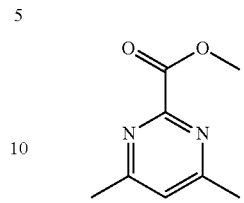

To a stirred solution of 2-chloro-4,6-dimethylpyrimidine (1 g, 7.05 mmol) in MeOH:CH$_3$CN (4:1, 20 mL) under argon atmosphere were added triethyl amine (1.98 mL, 14.02 mmol) and Pd(dppf)$_2$Cl$_2$ (1 g, 1.40 mmol) at room temperature; heated to 100° C. and stirred for 20 h under CO pressure in steel bomb. The reaction was monitored by TLC; after completion of the reaction, the reaction mixture was filtered through celite and the filtrate was concentrated in vacuo to obtain the crude. The crude was purified through silica gel column chromatography using 30% EtOAc/Hexanes to afford methyl 4,6-dimethylpyrimidine-2-carboxylate (400 mg, 34%) as an off-white solid.

$^1$H-NMR (CDCl$_3$, 400 MHz): δ 7.20 (s, 1H), 4.07 (s, 3H), 2.61 (s, 6H); LC-MS: 87.29%; 167.2 (M$^+$+1); (column: X-Bridge C-18, 50×3.0 mm, 3.5 μm); RT 1.47 min. 0.05% Aq TFA: ACN; 0.8 mL/min); TLC: 30% EtOAc/Hexanes (R$_f$: 0.3).

Synthesis of (4,6-dimethylpyrimidin-2-yl)methanol

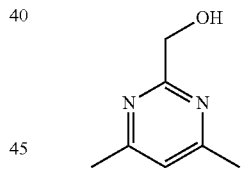

To a stirred solution of methyl 4,6-dimethylpyrimidine-2-carboxylate (400 mg, 2.40 mmol) in ethanol (10 mL) under argon atmosphere was added sodium borohydride (137 mg, 3.60 mmol) at 0° C.; warmed to room temperature and stirred for 2 h. The reaction was monitored by TLC; after completion of the reaction, the reaction mixture was quenched with water (15 mL) and extracted with CH$_2$Cl$_2$ (2×30 mL). The combined organic extracts were dried over sodium sulphate, filtered and concentrated in vacuo to obtain the crude (4,6-dimethylpyrimidin-2-yl)methanol (285 mg, 86%) as thick syrup. The crude was carried to the next step without any further purification.

$^1$H-NMR (CDCl$_3$, 400 MHz): δ 6.91 (s, 1H), 4.71 (s, 2H), 2.50 (s, 6H); LC-MS: 96.66%; 139.3 (M$^+$+1); (column: Eclipse XDB C-18, 150×4.6 mm, 5 μm); RT 4.03 min. 0.05% TFA: ACN; 1.0 mL/min); TLC: 40% EtOAc/Hexanes (R$_f$: 0.5).

Synthesis of 2-(chloromethyl)-4,6-dimethylpyrimidine

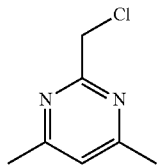

To a stirred solution of (4,6-dimethylpyrimidin-2-yl)methanol (285 mg, 2.06 mmol) in chloroform (8 mL) under argon atmosphere was added phosphoryl chloride (792 mg, 5.16 mmol) at 0° C.; heated to 65° C. and stirred for 3 h. The reaction was monitored by TLC; after completion of the reaction, the reaction mixture was neutralized with saturated sodium bicarbonate solution (15 mL) and extracted with CH$_2$Cl$_2$ (2×25 mL). The combined organic extracts were dried over sodium sulphate, filtered and concentrated in vacuo to obtain the crude 2-(chloromethyl)-4,6-dimethylpyrimidine (225 mg, 68%) as semi solid. The crude was carried to the next step without any further purification.

$^1$H-NMR (CDCl$_3$, 400 MHz): δ 7.48 (s, 1H), 5.00 (s, 2H), 2.8 (s 6H); LC-MS: 88.37%; 157 (M$^+$+1); (column: X Bridge C-18, 50×3.0 mm, 3.5 µm); RT 2.05 min. 0.05% TFA in water: ACN; 0.8 mL/min); TLC: 20% EtOAc/Hexanes (R$_f$: 0.7).

xxiv. 2-(chloromethyl)-5-methoxypyrimidine

Synthesis of methyl 5-methoxypyrimidine-2-carboxylate

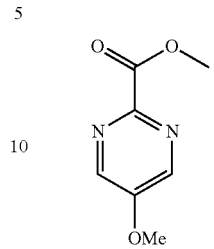

To a stirred solution of 2-chloro-5-methoxypyrimidine (1 g, 6.92 mmol) in MeOH:CH$_3$CN (4:1, 20 mL) under argon atmosphere were added Pd(dppf)Cl$_2$ (1 g, 1.38 mmol) and triethyl amine (1.9 mL, 13.84 mmol) at RT; heated to 100° C. and stirred for 16 h in steel bomb under CO pressure. The reaction was monitored by TLC; after completion of the reaction, the reaction mixture was filtered through celite and the filtrate was concentrated in vacuo to obtain the crude. The crude was purified through silica gel column chromatography using 60% EtOAc/Hexanes to afford methyl 5-methoxypyrimidine-2-carboxylate (600 mg, 52%) as brown solid.

$^1$H-NMR (CDCl$_3$, 400 MHz): δ 8.54 (s, 2H), 4.06 (s, 3H), 4.00 (s, 3H); LC-MS: 98.52%; 169 (M$^+$+1); (column: X Bridge C-18, 50×3.0 mm, 3.5 µm); RT 2.26 min. 0.05% Aq TFA: ACN; 0.8 mL/min); TLC: 70% EtOAc/Hexanes (R$_f$: 0.2).

Synthesis of (5-methoxypyrimidin-2-yl)methanol

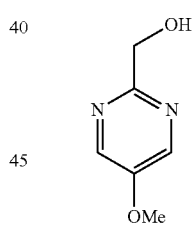

To a stirred solution of methyl 5-methoxypyrimidine-2-carboxylate (500 mg, 2.97 mmol) in EtOH (10 mL) under argon atmosphere was added sodium borohydride (226 mg, 5.95 mmol) at 0° C.; warmed to RT and stirred for 4 h. The reaction was monitored by TLC; after completion of the reaction, the reaction mixture was quenched with water (20 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 2% MeOH/CH$_2$Cl$_2$ to afford (5-methoxypyrimidin-2-yl)methanol (200 mg, 48%) as brown solid.

$^1$H-NMR (CDCl$_3$, 400 MHz): δ 8.40 (s, 2H), 4.80 (d, 2H), 3.92 (s, 3H), 3.48 (t, 1H); LC-MS: 96.34%; 141 (M$^+$+1); (column: X Bridge C-18, 50×3.0 mm, 3.5 µm); RT 1.01 min. 0.05% Aq TFA: ACN; 0.8 mL/min); TLC: 5% MeOH/CH$_2$Cl$_2$ (R$_f$: 0.3).

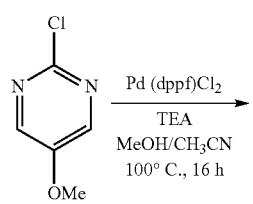

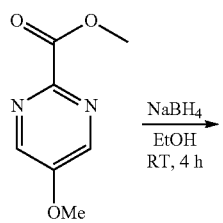

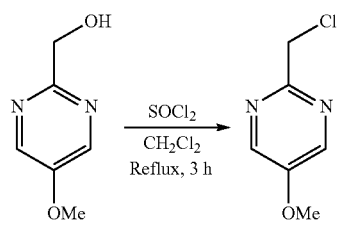

377

Synthesis of 2-(chloromethyl)-5-methoxypyrimidine

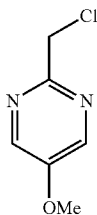

To a stirred solution of (5-methoxypyrimidin-2-yl)methanol (100 mg, 0.71 mmol) in CH$_2$Cl$_2$ (3 mL) under argon atmosphere was added thionyl chloride (0.15 mL, 2.14 mmol) at RT; heated to reflux and stirred for 3 h. The reaction was monitored by TLC; after completion of the reaction, the volatiles were removed in vacuo. The residue was basified with saturated NaHCO$_3$ solution (15 mL) to pH~8 and extracted with CH$_2$Cl$_2$ (2×20 mL). The combined organic extracts were dried over sodium sulfate, filtered and concentrated in vacuo to obtain 2-(chloromethyl)-5-methoxypyrimidine (80 mg, 70%) as colorless syrup.

$^1$H-NMR (CDCl$_3$, 400 MHz): δ 8.40 (s, 2H), 4.70 (s, 2H), 3.92 (s, 3H); LC-MS: 97.97%; 159 (M$^+$+1); (column: X Bridge C-18, 50×3.0 mm, 3.5 μm); RT 2.92 min. 0.05% Aq TFA: ACN; 0.8 mL/min); TLC: 5% MeOH/CH$_2$Cl$_2$ (R$_f$: 0.7).

xxv. 4-(trifluoromethyl)pyrimidine-2-carbaldehyde

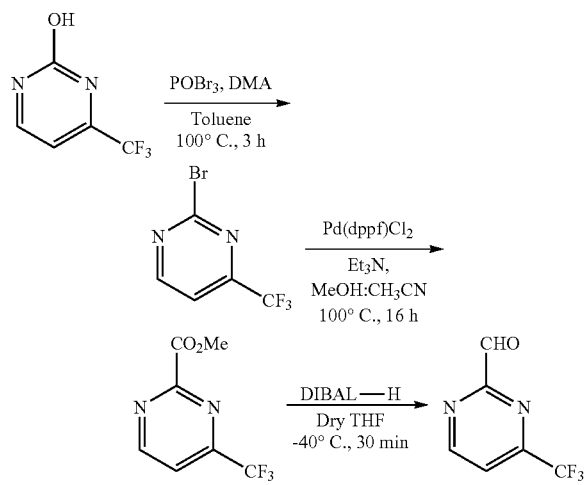

Synthesis of 2-bromo-4-(trifluoromethyl)pyrimidine

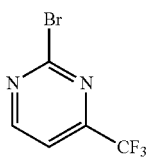

To a stirred solution of 6-(trifluoromethyl)-1,2-dihydropyrimidin-2-ol (2 g, 12.19 mmol) in toluene (40 mL) under argon atmosphere were added phosphorous oxybromide (5.24 g, 18.20 mmol), N,N-dimethyl aniline (156 mg, 1.20 mmol) at RT; heated to 100° C. and stirred for 3 h. The reaction was monitored by TLC; after completion of the reaction, the reaction mixture was diluted with water (50 mL) and extracted with hexanes (2×50 mL). The combined organic extracts were washed with water (50 mL), dried over sodium sulphate, and concentrated in vacuo to obtain 2-bromo-4-(trifluoromethyl)pyrimidine (800 mg, 29%) as light yellow oil.

$^1$H-NMR (CDCl$_3$, 500 MHz): δ 8.82 (d, 1H), 7.64 (d, 1H); TLC: 10% EtOAc/Hexanes (R$_f$: 0.8).

Synthesis of methyl 4-(trifluoromethyl)pyrimidine-2-carboxylate

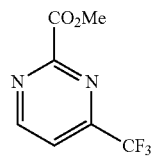

To a stirred solution of 2-bromo-4-(trifluoromethyl)pyrimidine (800 mg, 3.52 mmol) in MeOH:CH$_3$CN (4:1, 5 mL) under argon atmosphere was added Pd(dppf)$_2$Cl$_2$ (503 mg, 0.70 mmol), triethyl amine (1.0 mL, 7.04 mmol) at RT; heated to 100° C. and stirred for 16 h under CO pressure. The reaction was monitored by TLC; after completion of the reaction, the volatiles were removed in vacuo to obtain the crude. The crude was purified through silica gel column chromatography using 25% EtOAc/Hexanes to afford methyl 4-(trifluoromethyl)pyrimidine-2-carboxylate (300 mg, 41%) as Light pink solid.

$^1$H-NMR (CDCl$_3$, 500 MHz): δ 9.20 (d, 1H), 7.82 (d, 1H), 4.10 (s, 3H); LC-MS: 96.04%; 207 (M$^+$+1); (column; X-bridge C-18, (50×3.0 mm, 3.5μ); RT 2.48 min. 0.05% TFA (aq.): ACN; 0.8 mL/min); TLC: 50% EtOAc/Hexanes (R$_f$: 0.3).

Synthesis of 4-(trifluoromethyl)pyrimidine-2-carbaldehyde

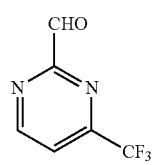

To a stirred solution of methyl 4-(trifluoromethyl)pyrimidine-2-carboxylate (300 mg, 1.45 mmol) in dry THF (12 mL) under argon atmosphere was added DIBAL-H (4.34 mL, 4.36 mmol) at −40 C, and stirred for 30 min at −40 C. The reaction was monitored by TLC; after completion of the reaction, the reaction mixture was quenched with sodium potassium tartrate solution (50 mL) and extracted with EtOAc (2×100 mL). The combined organic extracts were washed with water (25 mL), dried over sodium sulphate, and concentrated in vacuo to obtain the crude 4-(trifluoromethyl)

pyrimidine-2-carbaldehyde (180 mg) as brown colour syrup. The crude was carried to the next step without further purification.

$^1$H-NMR (CDCl$_3$, 400 MHz): δ 10.19 (s, 1H), 9.26 (d, 1H), 7.84 (d, 1H); LC-MS: 91.25%; 177.1 (M$^+$+1); (column; X-bridge C-18, (50×3.0 mm, 3.5μ); RT 0.97 min. 0.05% TFA (aq.): ACN; 0.8 mL/min); TLC: 5% MeOH/CH$_2$Cl$_2$ (R$_f$: 0.6).

xxvi. 5-methylpyrimidine-2-carbaldehyde

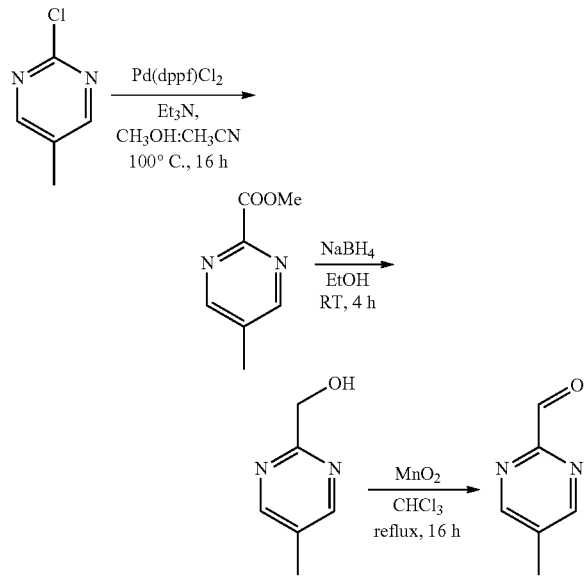

Synthesis of methyl 5-methylpyrimidine-2-carboxylate

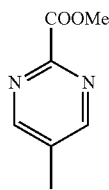

To a stirred solution of 2-chloro-5-methylpyrimidine (200 mg, 1.55 mmol) in MeOH:CH$_3$CN (4:1, 10 mL) under argon atmosphere were added Pd(dppf)Cl$_2$ (227 mg, 0.31 mmol) and triethyl amine (0.45 mL, 3.11 mmol) at RT; heated to 100° C. and stirred for 16 h in steel bomb under CO pressure. The reaction was monitored by TLC; after completion of the reaction, the reaction mixture was filtered through celite and the filtrate was concentrated in vacuo to obtain the crude. The crude was purified through silica gel column chromatography using 60% EtOAc/Hexanes to afford 5-methylpyrimidine-2-carboxylate (146 mg, 62%) as brick red solid.

$^1$H-NMR (CDCl$_3$, 400 MHz): δ 8.74 (s, 2H), 4.08 (s, 3H), 2.42 (s, 3H); LC-MS: 81.73%; 153 (M$^+$+1); (column: X Bridge C-18, 50×3.0 mm, 3.5 μm); RT 2.10 min. 0.05% Aq TFA: ACN; 0.8 mL/min); TLC: 70% EtOAc/Hexanes (R$_f$: 0.2).

Synthesis of (5-methylpyrimidin-2-yl)methanol

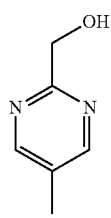

To a stirred solution of 5-methylpyrimidine-2-carboxylate (500 mg, 3.28 mmol) in EtOH (8 mL) under argon atmosphere was added sodium borohydride (250 mg, 6.57 mmol) at 0° C.; warmed to RT and stirred for 4 h. The reaction was monitored by TLC; after completion of the reaction, the reaction mixture was diluted with water (15 mL) and extracted with CH$_2$Cl$_2$ (3×25 mL). The combined organic extracts were dried over sodium sulfate, filtered and concentrated in vacuo to obtain the crude. The crude was purified through silica gel column chromatography using 2-3% MeOH/CH$_2$Cl$_2$ to afford (5-methylpyrimidin-2-yl) methanol (240 mg, 59%) as brown solid.

$^1$H-NMR (CDCl$_3$, 400 MHz): δ 8.56 (s, 2H), 4.80 (d, 2H), 3.64 (t, 1H), 2.36 (s, 3H); LC-MS: 92.72%; 125.3 (M$^+$+1); (column: Eclipse XDB C-18, 150×4.6 mm, 5.0 μm); RT 5.23 min. 0.05% Aq TFA: ACN; 1.0 mL/min); TLC: 5% MeOH/CH$_2$Cl$_2$ (R$_f$: 0.4).

Synthesis of 5-methylpyrimidine-2-carbaldehyde

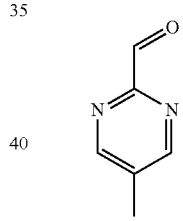

To a stirred solution of (5-methylpyrimidin-2-yl)methanol (50 mg, 0.40 mmol) in CHCl$_3$ (10 mL) under argon atmosphere was added manganese dioxide (350 mg, 4.03 mmol) at RT; heated to reflux and stirred for 16 h. The reaction was monitored by TLC; after completion of the reaction, the reaction mixture was filtered through celite and the filtrate was concentrated in vacuo to obtain crude 5-methylpyrimidine-2-carbaldehyde (40 mg) as brown solid. The crude was carried to the next step without further purification.

$^1$H-NMR (CDCl$_3$, 400 MHz): δ 10.10 (s, 1H), 8.82-8.78 (m, 2H), 2.45 (s, 3H); TLC: 5% MeOH/CH$_2$Cl$_2$ (R$_f$: 0.7).

xxvii. 2-(chloromethyl)-4-methylpyrimidine

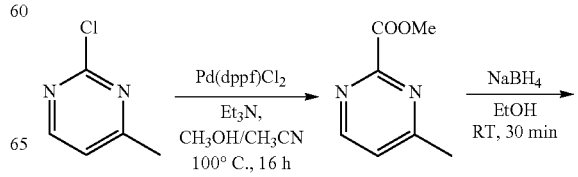

-continued

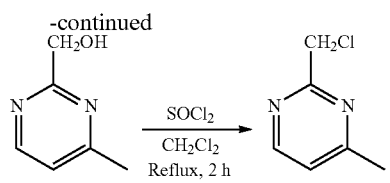

Synthesis of methyl
4-methylpyrimidine-2-carboxylate

To a stirred solution of 2-chloro-4-methylpyrimidine (370 mg, 2.87 mmol) in MeOH:CH$_3$CN (4:1, 20 mL) under argon atmosphere were added Pd(dppf)Cl$_2$ (420 mg, 0.57 mmol) and triethyl amine (0.8 mL, 5.75 mmol) at RT; heated to 100° C. and stirred for 16 h in steel bomb under CO pressure. The reaction was monitored by TLC; after completion of the reaction, the volatiles were removed in vacuo to obtain the crude. The crude was purified through silica gel column chromatography using 40% EtOAc/Hexanes to afford methyl 4-methylpyrimidine-2-carboxylate (330 mg, 75%) as an off-white solid.

$^1$H-NMR (CDCl$_3$, 400 MHz): δ 8.78 (d, 1H), 7.31 (d, 1H), 4.01 (s, 3H), 2.68 (s, 3H); LC-MS: 97.40%; 153.2 (M$^+$+1); (column: X Bridge C-18, 50×3.0 mm, 3.5 µm); RT 0.68 min. 5 mM NH$_4$OAc: ACN; 0.8 mL/min); TLC: 50% EtOAc/Hexanes (R$_f$: 0.2).

Synthesis of (4-methylpyrimidin-2-yl)methanol

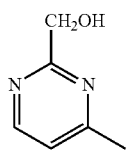

To a stirred solution of 4-methylpyrimidine-2-carboxylate (320 mg, 2.10 mmol) in EtOH (5 mL) under argon atmosphere was added sodium borohydride (159 mg, 4.20 mmol) at 0° C.; warmed to RT and stirred for 30 min. The reaction was monitored by TLC; after completion of the reaction, the reaction mixture was quenched with ice cold water (10 mL) and extracted with CH$_2$Cl$_2$ (2×25 mL). The combined organic extracts were dried over sodium sulfate, filtered and concentrated in vacuo to obtain the crude. The crude was purified through silica gel column chromatography using 2-3% MeOH/CH$_2$Cl$_2$ to afford (4-methylpyrimidin-2-yl)methanol (130 mg, 50%) as brown syrup.

$^1$H-NMR (CDCl$_3$, 400 MHz): δ 8.54 (d, 1H), 7.05 (d, 1H), 4.77 (d, 2H), 3.77 (t, 1H), 2.55 (s, 3H); LC-MS: 97.48%; 151.6 (M$^+$+1); (column: Eclipse XDB C-18, 150×4.6 mm, 5.0 µm); RT 3.24 min. 0.05% Aq TFA: ACN; 1.0 mL/min); TLC: 5% MeOH/CH$_2$Cl$_2$ (R$_f$: 0.5).

Synthesis of 2-(chloromethyl)-4-methylpyrimidine

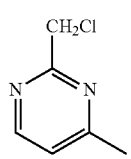

To a stirred solution of (4-methylpyrimidin-2-yl)methanol (50 mg, 0.40 mmol) in CH$_2$Cl$_2$ (3 mL) under argon atmosphere was added thionyl chloride (0.09 mL, 1.20 mmol) at RT; heated to reflux and stirred for 2 h. The reaction was monitored by TLC; after completion of the reaction, the volatiles were removed in vacuo. The residue was basified with saturated NaHCO$_3$ solution (7 mL) to pH~8 and extracted with CH$_2$Cl$_2$ (2×15 mL). The combined organic extracts were dried over sodium sulfate, filtered and concentrated in vacuo to obtain crude 2-(chloromethyl)-4-methylpyrimidine. This crude material was carried to the next step without further purification.

xxviii.
2-(chloromethyl)-N,N-dimethylpyrimidin-4-amine

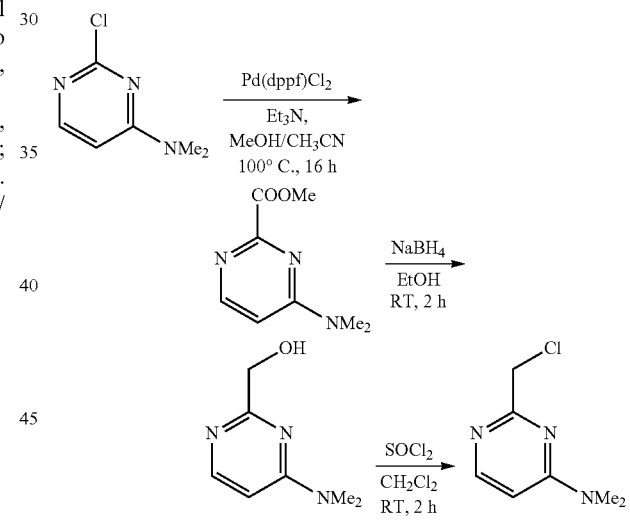

Synthesis of methyl
4-(dimethylamino)pyrimidine-2-carboxylate

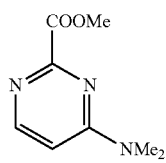

To a stirred solution of 2-chloro-N,N-dimethylpyrimidin-4-amine (500 mg, 3.17 mmol) in MeOH:CH$_3$CN (4:1, 10 mL) under argon atmosphere were added Pd(dppf)Cl$_2$ (463 mg, 0.63 mmol) and triethyl amine (0.90 mL, 6.34 mmol) at RT; heated to 110° C. and stirred for 16 h in steel bomb under CO pressure. The reaction was monitored by TLC; after completion of the reaction, the reaction mixture was filtered through celite and the filtrate was concentrated in vacuo to obtain the crude. The crude was purified through silica gel column chromatography using 60% EtOAc/Hexanes to afford methyl 4-(dimethylamino)pyrimidine-2-carboxylate (335 mg, 58%) as brick red solid.

$^1$H-NMR (CDCl$_3$, 400 MHz): δ 8.30 (d, 1H), 6.50 (d, 1H), 4.00 (s, 3H), 3.19 (s, 6H); LC-MS: 82.57%; 182.1 (M$^+$+1); (column: X Bridge C-18, 50×3.0 mm, 3.5 µm); RT 2.38 mM. 5 mM NH$_4$OAc: ACN; 0.8 mL/min); TLC: 70% EtOAc/Hexanes (R$_f$: 0.3).

Synthesis of (4-(dimethylamino)pyrimidin-2-yl)methanol

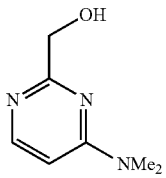 [SMILES: CN(C)c1ccnc(CO)n1]

To a stirred solution of methyl 4-(dimethylamino)pyrimidine-2-carboxylate (330 mg, 1.82 mmol) in EtOH (8 mL) under argon atmosphere was added sodium borohydride (138 mg, 3.64 mmol) at 0° C.; warmed to RT and stirred for 2 h. The reaction was monitored by TLC; after completion of the reaction, the reaction mixture was quenched with ice cold water (10 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 2% MeOH/CH$_2$Cl$_2$ to afford (4-(dimethylamino)pyrimidin-2-yl)methanol (160 mg, 57%) as an off-white solid.

$^1$H-NMR (CDCl$_3$, 400 MHz): δ 8.18 (d, 1H), 6.30 (d, 1H), 4.60 (s, 2H), 3.92-3.88 (m, 1H), 3.13 (s, 6H); LC-MS: 98.52%; 154.2 (M$^+$+1); (column: Eclipse XDB C-18, 150× 4.6 mm, 5.0 µm); RT 5.45 min. 0.05% Aq TFA: ACN; 1.0 mL/min); TLC: 5% MeOH/CH$_2$Cl$_2$ (R$_f$: 0.3).

Synthesis of 2-(chloromethyl)-N,N-dimethylpyrimidin-4-amine

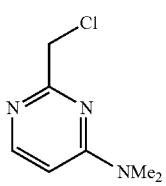 [SMILES: CN(C)c1ccnc(CCl)n1]

To a stirred solution of (4-(dimethylamino)pyrimidin-2-yl)methanol (20 mg, 0.13 mmol) in CHCl$_3$ (5 mL) under argon atmosphere was added thionyl chloride (0.03 mL, 0.39 mmol) at 0° C.; warmed to RT and stirred for 2 h. The reaction was monitored by TLC; after completion of the reaction, the volatiles were removed in vacuo. The residue was triturated with n-pentane (2×4 mL) to afford 2-(chloromethyl)-N,N-dimethylpyrimidin-4-amine (16 mg, 72%) as an off-white solid.

$^1$H-NMR (DMSO-d$_6$, 400 MHz): δ 8.31-8.30 (m, 1H), 6.96-6.94 (m, 1H), 4.76 (s, 2H), 3.24 (s, 6H); LC-MS: 99.60%; 172 (M$^+$+1); (column: X Bridge C-18, 50×3.0 mm, 3.5 µm); RT 1.09 min. 0.05% Aq TFA: ACN; 0.8 mL/min); TLC: 5% MeOH/CH$_2$Cl$_2$ (R$_f$: 0.6).

xxix. 5-fluoropyrimidine-2-carbaldehyde

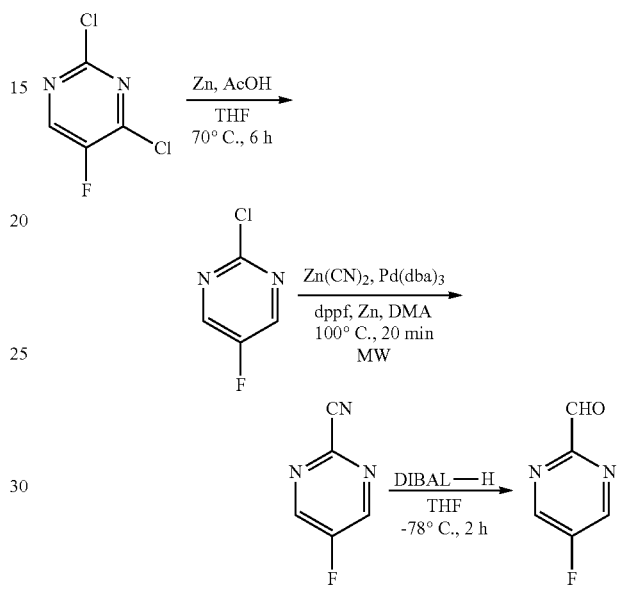

Synthesis of 2-chloro-5-fluoropyrimidine

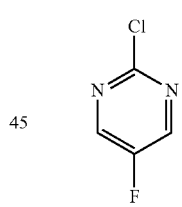

To a stirred solution of 2,4-dichloro-5-fluoropyrimidine (1 g, 5.98 mmol) in THF (10 mL) under argon atmosphere was added zinc (1.13 g, 17.96 mmol) at room temperature, heated to 70° C.; then added acetic acid (0.36 mL, 5.98 mmol) and stirred for 6 h. The reaction was monitored by TLC; after completion of the reaction, the reaction mixture was filtered and the filtrate was concentrated in vacuo to obtain the crude. The crude was purified through silica gel column chromatography using 10% EtOAc/Hexanes to afford 2-chloro-5-fluoropyrimidine (280 mg, 35%) as colorless liquid.

$^1$H-NMR (CDCl$_3$, 400 MHz): δ 8.52 (s, 2H); LC-MS: 90.01%; 133.1 (M$^+$+1); (column: X-Bridge C-18, 50×3.0 mm, 3.5 µm); RT 1.29 min. 0.05% TFA (aq.): ACN; 0.8 mL/min); TLC: 10% EtOAc/Hexanes (R$_f$: 0.5).

Synthesis of 5-fluoropyrimidine-2-carbonitrile

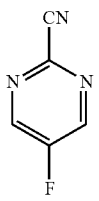

To a stirred solution of 2-chloro-5-fluoropyrimidine (280 mg, 2.11 mmol) in DMA (6 mL) under argon atmosphere were added zinc cyanide (161 mg, 1.37 mmol), $Pd_2(dba)_3$ (77 mg, 0.08 mmol), dppf (93 mg, 0.16 mmol) and zinc (32 mg, 0.50 mmol) at room temperature; heated to 100° C. and stirred for 20 min under Micro Wave irradiation. The reaction was monitored by TLC; after completion of the reaction, the reaction mixture was diluted with water (30 mL) and extracted with EtOAc (2×45 mL). The combined organic extracts were washed with water (40 mL), dried over sodium sulphate, filtered and concentrated in vacuo to obtain the crude. The crude was purified through silica gel column chromatography using 7% EtOAc/Hexanes to afford 5-fluoropyrimidine-2-carbonitrile (60 mg, 23%) as an off-white solid.

$^1$H-NMR (CDCl$_3$, 400 MHz): δ 8.73 (s, 2H); TLC: 10% EtOAc/Hexanes (R$_f$: 0.4).

Synthesis of 5-fluoropyrimidine-2-carbaldehyde

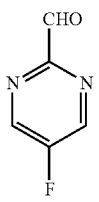

To a stirred solution of 5-fluoropyrimidine-2-carbonitrile (60 mg, 0.48 mmol) in THF (3 mL) under argon atmosphere were added DIBAL-H (0.73 mL, 0.73 mmol) at −78° C. and stirred for 2 h. The reaction was monitored by TLC; after completion of the reaction, the reaction mixture was diluted with methanol (10 mL), diluted HCl solution (20 mL) and extracted with EtOAc (3×30 mL). The combined organic extracts were dried over sodium sulphate, filtered and concentrated in vacuo to obtain crude 5-fluoropyrimidine-2-carbaldehyde (50 mg). The crude was carried for the next step without further purification.

$^1$H-NMR (CDCl$_3$, 400 MHz, crude): δ 10.09 (s, 1H), 8.81 (s, 1H), 8.70 (s, 1H); TLC: 5% MeOH/CH$_2$Cl$_2$ (R$_f$: 0.5).

xxx. 2-(bromomethyl)-5-cyclopropylpyrimidine

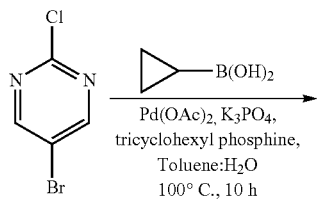

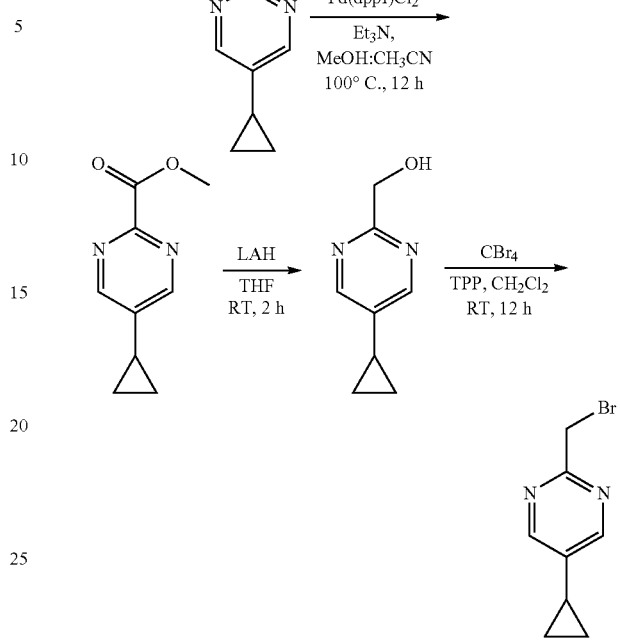

Synthesis of 2-chloro-5-cyclopropylpyrimidine

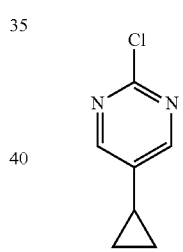

To a stirred solution of 5-bromo-2-chloropyrimidine (1.5 g, 9.43 mmol) in toluene:H$_2$O (4:1, 20 mL) under argon atmosphere were added cyclopropyl boronic acid (972 mg, 11.32 mmol), potassium phosphate (6 g, 28.32 mmol), tricyclohexyl phosphine (260 mg, 0.94 mmol) and purged under argon for 10 min. Then palladium acetate (104 mg, 0.47 mmol) was added to the reaction mass; heated to 100° C. and stirred for 10 h. The reaction was monitored by TLC; after completion of the reaction, the reaction mixture was diluted with water (35 mL) and extracted with EtOAc (3×60 mL). The combined organic extracts were dried over sodium sulfate, filtered and concentrated in vacuo to obtain the crude. The crude was purified through silica gel column chromatography using 10% EtOAc/Hexanes to afford 2-chloro-5-cyclopropylpyrimidine (1 g, 69%) as an off-white solid.

$^1$H-NMR (CDCl$_3$, 400 MHz): δ 8.30 (s, 2H), 1.98-1.96 (m, 1H), 1.12 (t, 2H), 0.78 (t, 2H); LC-MS: 99.19%; 155 (M$^+$+1); (column: X Bridge C-18, 50×3.0 mm, 3.5 µm); RT 3.19 min. 0.05% Aq TFA: ACN; 0.8 mL/min); TLC: 20% EtOAc/Hexanes (R$_f$: 0.3).

Synthesis of methyl 5-cyclopropylpyrimidine-2-carboxylate

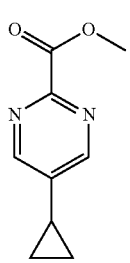

To a stirred solution of 2-chloro-5-cyclopropylpyrimidine (120 mg, 0.77 mmol) in MeOH:CH₃CN (4:1, 10 mL) under argon atmosphere were added Pd(dppf)Cl₂ (113.9 mg, 0.15 mmol) and triethyl amine (0.22 ml, 1.55 mmol) at RT; heated to 100° C. and stirred for 12 h in steel bomb under CO pressure. The reaction was monitored by TLC; after completion of the reaction, the volatiles were removed in vacuo to obtain the crude. The crude was purified through silica gel column chromatography using 50% EtOAc/Hexanes to afford methyl 5-cyclopropylpyrimidine-2-carboxylate (53 mg, 38%) as brown liquid.

$^1$H-NMR (CDCl$_3$, 500 MHz): δ 8.60 (s, 2H), 4.04 (s, 3H), 1.98-1.96 (m, 1H), 1.13-1.10 (m, 2H), 0.88-0.84 (m, 2H); m/z: 178 (M$^+$+1); TLC: 70% EtOAc/Hexanes (R$_f$: 0.3).

Synthesis of (5-cyclopropylpyrimidin-2-yl)methanol

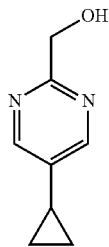

To a stirred solution of methyl 5-cyclopropylpyrimidine-2-carboxylate (250 mg, 1.62 mmol) in THF (10 mL) under argon atmosphere was added LAH (90.09 mg, 2.43 mmol) portion wise for 10 min at 0° C.; warmed to RT and stirred for 2 h. The reaction was monitored by TLC; after completion of the reaction, the reaction mixture was quenched with ice cold water (15 mL) and extracted with EtOAc (2×20 mL). The combined organic extracts were dried over sodium sulfate, filtered and concentrated in vacuo to obtain the crude. The crude was purified through silica gel column chromatography using 60% EtOAc/Hexanes to afford (5-cyclopropylpyrimidin-2-yl)methanol (80 mg, 33%) as colorless oil.

$^1$H-NMR (CDCl$_3$, 500 MHz): δ 8.51-8.50 (m, 1H), 7.68-7.66 (m, 1H), 4.90-4.88 (m, 2H), 1.98-1.96 (m, 1H), 1.18-1.16 (m, 2H), 0.81-0.80 (m, 2H); LC-MS: 63.99%; 151 (M$^+$+1); (column: X Bridge C-18, 50×3.0 mm, 3.5 μm); RT 1.02 min. 0.05% Aq TFA: ACN; 0.8 mL/min); TLC: 70% EtOAc/Hexanes (R$_f$: 0.4).

Synthesis of 2-(bromomethyl)-5-cyclopropylpyrimidine

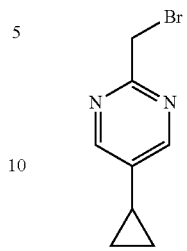

To a stirred solution of (5-cyclopropylpyrimidin-2-yl)methanol (60 mg, 0.40 mmol) in CH₂Cl₂ (10 mL) under argon atmosphere were added carbon tetrabromide (172 mg, 0.52 mmol) and triphenyl phosphine (136 mg, 0.52 mmol) at 0° C.; warmed to RT and stirred for 12 h. The reaction was monitored by TLC; after completion of the reaction, the volatiles were removed in vacuo to obtain the crude. The crude was purified through silica gel column chromatography using 30% EtOAc/Hexanes to afford 2-(bromomethyl)-5-cyclopropylpyrimidine (10 mg, 12%) as colorless oil.

$^1$H-NMR (CDCl$_3$, 400 MHz): δ 8.46 (s, 2H), 4.58 (s, 2H), 1.90-1.88 (m, 1H), 1.14-1.12 (m, 2H), 0.88-0.86 (m, 2H); LC-MS: 96.01%; 213 (M$^+$+2); (column: X Bridge C-18, 50×3.0 mm, 3.5 μm); RT 3.05 min. 0.05% Aq TFA: ACN; 0.8 mL/min); TLC: 70% EtOAc/Hexanes (R$_f$: 0.6).

xxxi. 5-(pyrrolidin-1-yl)pyrimidine-2-carbaldehyde

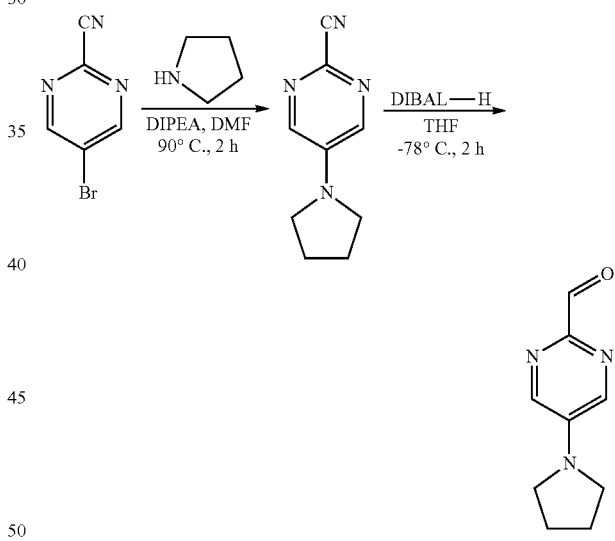

Synthesis of 5-(pyrrolidin-1-yl)pyrimidine-2-carbonitrile

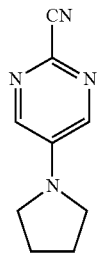

To a stirred solution of 5-bromopyrimidine-2-carbonitrile (150 mg, 0.81 mmol) in DMF (6 mL) under argon atmosphere were added pyrrolidine (82.7 mg, 1.21 mmol), diisopropyl ethyl amine (0.28 mL, 1.62 mmol) at RT; heated to 90° C. and stirred for 2 h. The reaction was monitored by TLC; after completion of the reaction, the reaction mixture was diluted with water (20 mL) and extracted with $CH_2Cl_2$ (2×30 mL). The combined organic extracts were dried over sodium sulfate, filtered and concentrated in vacuo to obtain the crude. The crude was purified through silica gel column chromatography using 30% EtOAc/Hexanes to afford 5-(pyrrolidin-1-yl)pyrimidine-2-carbonitrile (32 mg, 21%) as an off-white solid.

$^1$H-NMR (CDCl$_3$, 400 MHz): δ 8.02 (s, 2H), 3.40-3.38 (m, 4H), 2.11-2.09 (m, 4H); LC-MS: 99%; 175.1 (M$^+$+1); (column; Eclipse XDB C18, (150×4.6 mm, 5.0 μm); RT 7.46 min. 0.05% TFA (aq.): ACN; 1.0 mL/min); TLC: 30% EtOAc/Hexanes (R$_f$: 0.2).

Synthesis of
5-(pyrrolidin-1-yl)pyrimidine-2-carbaldehyde

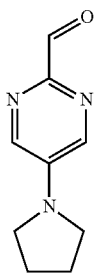

To a stirred solution of 5-(pyrrolidin-1-yl)pyrimidine-2-carbonitrile (50 mg, 0.28 mmol) in THF (3 mL) under argon atmosphere was added DIBAL-H (1 M in toluene) (1.42 mL, 1.43 mmol) at −78° C. and stirred for 2 h. The reaction was monitored by TLC; after completion of the reaction, the reaction mixture was quenched with MeOH (2 mL); warmed to RT and 1 N HCl (5 mL) was added. The compound was extracted with $CH_2Cl_2$ (2×15 mL). The combined organic extracts dried over sodium sulfate, filtered and concentrated in vacuo to afford crude 5-(pyrrolidin-1-yl)pyrimidine-2-carbaldehyde (45 mg) as thick syrup. The crude was carried to the next step without further purification.

$^1$H-NMR (CDCl$_3$, 400 MHz crude): δ 9.91 (s, 1H), 8.2 (s, 2H), 3.44-3.40 (m, 4H), 2.10-2.06 (m, 4H); TLC: 5% MeOH/CH$_2$Cl$_2$ (R$_f$: 0.5).

xxxii.
5-fluoro-4-morpholinopyrimidine-2-carbaldehyde

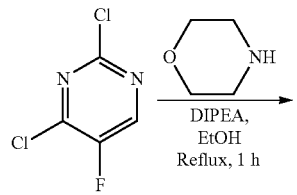

-continued

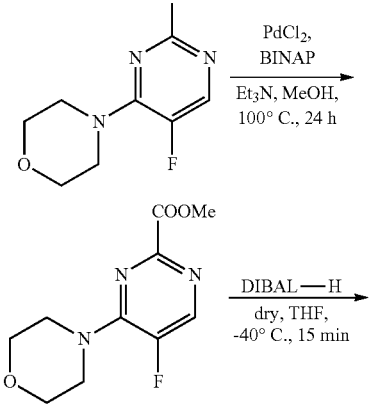

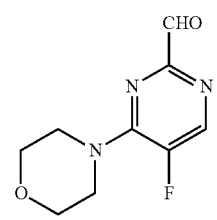

Synthesis of
4-(2-chloro-5-fluoropyrimidin-4-yl)morpholine

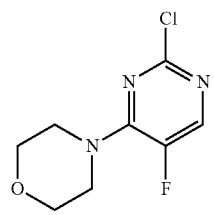 [SMILES: Fc1cnc(Cl)nc1N1CCOCC1]

To a stirred solution of morpholine (260 mg, 2.99 mmol) in EtOH (10 mL) under argon atmosphere were added DIPEA (1.15 g, 8.98 mmol) and 2,4-dichloro-5-fluoropyrimidine (500 mg, 2.99 mmol) at RT; heated to reflux and stirred for 1 h. The reaction was monitored by TLC; after completion of the reaction, the volatiles were removed in vacuo. The residue was diluted with water (20 mL) and extracted with EtOAc (2×30 mL). The combined organic extracts were dried over sodium sulphate, filtered and concentrated in vacuo to obtain the crude. The crude was purified through silica gel column chromatography using 15% EtOAc/Hexanes to afford 4-(2-chloro-5-fluoropyrimidin-4-yl)morpholine (550 mg, 85%) as an off-white solid.

$^1$H-NMR (CDCl$_3$, 500 MHz): δ 7.96 (d, 1H), 3.82-3.76 (m, 8H); LC-MS: 99.56%; 218.1 (M$^+$+1); (column: X-Bridge C-18, 50×3.0 mm, 3.5 μm); RT 2.88 min. 0.05% TFA: ACN; 0.8 mL/min); TLC: 20% EtOAc/Hexanes (R$_f$: 0.3).

Synthesis of methyl 5-fluoro-4-morpholinopyrimidine-2-carboxylate

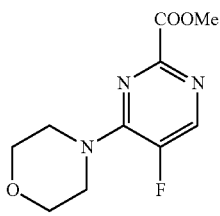 [SMILES: COC(=O)c1ncc(F)c(N2CCOCC2)n1]

To a stirred solution of 4-(2-chloro-5-fluoropyrimidin-4-yl)morpholine (500 mg, 2.30 mmol) in MeOH (10 mL) under argon atmosphere were added palladium chloride (4 mg, 0.02 mmol), BINAP (14.3 mg, 0.02 mmol) and triethyl amine (0.6 mL, 4.60 mmol) at room temperature; heated to 100° C. and stirred for 24 h in steel bomb. The reaction was monitored by TLC; after completion of the reaction, the reaction mixture was filtered and the filtrate was concentrated in vacuo to obtain the crude. The crude was purified through silica gel column chromatography using 2% MeOH/CH$_2$Cl$_2$ to afford methyl 5-fluoro-4-morpholinopyrimidine-2-carboxylate (110 mg, 22%) as off white solid.

$^1$H-NMR (CDCl$_3$, 400 MHz): δ 8.18 (d, 1H), 3.99 (s, 3H), 3.91 (t, 4H), 3.79 (t, 4H); LC-MS: 96.09%; 242.2 (M$^+$+1); (column: X-Bridge C-18, 50×3.0 mm, 3.5 μm); RT 2.20 min. 0.05% TFA (aq.): ACN; 0.8 mL/min); TLC: 5% MeOH/CH$_2$Cl$_2$ (R$_f$: 0.5).

Synthesis of 5-fluoro-4-morpholinopyrimidine-2-carbaldehyde

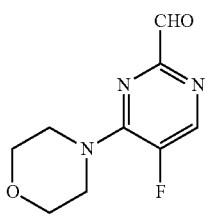

To a stirred solution of methyl 5-fluoro-4-morpholinopyrimidine-2-carboxylate (100 mg, 0.41 mmol) in dry THF (10 mL) under argon atmosphere was added DIBAL-H (1 M in toluene) (2.5 mL, 1.24 mmol) at −40° C. and stirred for 15 min. The reaction was monitored by TLC; after completion of the reaction, the reaction mixture was quenched with saturated sodium potassium tartrate solution (15 mL) and extracted with EtOAc (2×25 mL). The combined organic extracts dried over sodium sulphate, filtered and concentrated in vacuo to obtain crude 5-fluoro-4-morpholinopyrimidine-2-carbaldehyde (70 mg) as brown syrup. The crude was carried to the next step without further purification.

$^1$H-NMR (CDCl$_3$, 400 MHz): δ 9.90 (s, 1H), 8.28 (d, 1H), 3.94-3.91 (m, 4H), 3.81-3.78 (m, 4H); TLC: 5% MeOH/CH$_2$Cl$_2$ (R$_f$: 0.4).

xxxiii. 4-cyclopropylpyrimidine-2-carbaldehyde

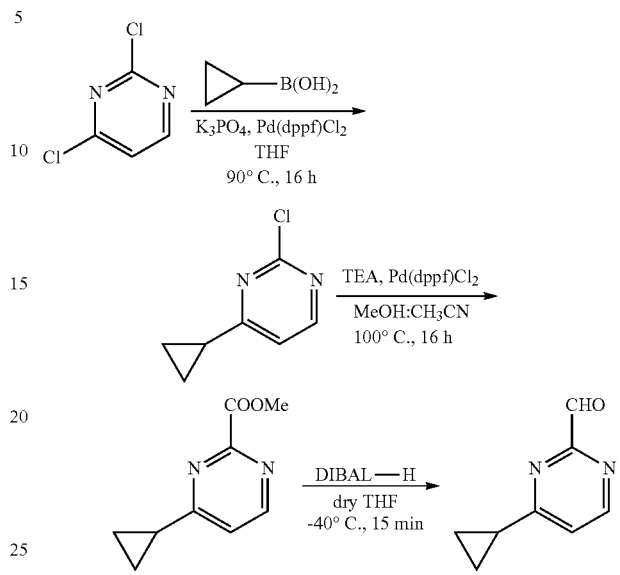

Synthesis of 2-chloro-4-cyclopropylpyrimidine

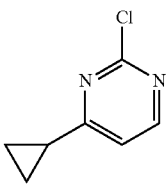

To a stirred solution of 2,4-dichloropyrimidine (500 mg, 3.35 mmol) in THF (20 mL) under argon atmosphere were added cyclopropyl boronic acid (288 mg, 3.35 mmol), potassium phosphate (1.7 g, 8.38 mmol) at RT and purged under argon for 20 min. Then pd(dppf)Cl$_2$ (245 mg, 0.33 mmol) was added to the reaction mass and stirred at 90° C. for 16 h in a sealed tube. The reaction was monitored by TLC; after completion of the reaction, the reaction mixture was diluted with water (20 mL) and extracted with EtOAc (2×20 mL). The combined organic extracts were washed with water (10 mL), dried over sodium sulphate, filtered and concentrated in vacuo to obtain the crude. The crude was purified through silica gel column chromatography using 30% EtOAc/Hexanes to afford 2-chloro-4-cyclopropylpyrimidine (200 mg, 38%) as an off-white solid.

$^1$H-NMR (CDCl$_3$, 500 MHz): δ 8.38 (d, 1H), 7.06 (d, 1H), 2.00-1.98 (m, 1H), 1.22-1.20 (m, 2H), 1.18-1.16 (m, 2H); LC-MS: 96.31%; 155.0 (M$^+$+1); (column: X-Bridge C-18, 50×3.0 mm, 3.5 μm); RT 2.84 min. 0.05% TFA: ACN; 0.8 mL/min); TLC: 20% EtOAc/Hexanes (R$_f$: 0.6).

Synthesis of methyl 4-cyclopropylpyrimidine-2-carboxylate

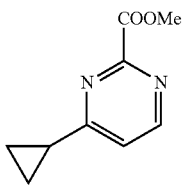 [SMILES: COC(=O)c1nccc(C2CC2)n1]

To a stirred solution of 2-chloro-4-cyclopropylpyrimidine (65 mg, 0.42 mmol) in MeOH:CH$_3$CN (4:1, 5 mL) under argon atmosphere was added triethyl amine (85 mg, 0.84 mmol) at RT and purged with argon for 20 min. Then Pd(dppf)Cl$_2$ (61 mg, 0.08 mmol) was added to the reaction mass; heated to 100° C. and stirred for 16 h in steel bomb under CO atmosphere. The reaction was monitored by TLC; after completion of the reaction, the reaction mixture was filtered and the filtrate was concentrated in vacuo to obtain the crude. The crude was purified through silica gel column chromatography using 30% EtOAc/Hexanes to afford methyl 4-cyclopropylpyrimidine-2-carboxylate (45 mg, 60%) as an off-white solid.

$^1$H-NMR (CDCl$_3$, 400 MHz): δ 8.64 (d, 1H), 7.20 (d, 1H), 4.00 (s, 3H), 2.11-2.10 (m, 1H), 1.27-1.25 (m, 2H), 1.20-1.18 (m, 2H); LC-MS: 99.63%; 179.2 (M$^+$+1); (column: X-Bridge C-18, 50×3.0 mm, 3.5 μm); RT 2.45 min. 0.05% TFA: ACN; 0.8 mL/min); UPLC (purity): 99.95%; (column: Acquity UPLC BEH C-18 (2.1×50 mm, 1.7μ); RT 1.33 min. ACN: 0.025% TFA (Aq); 0.5 mL/min. (IP12120578); TLC: 30% EtOAc/Hexane (R$_f$: 0.2).

Synthesis of 4-cyclopropylpyrimidine-2-carbaldehyde

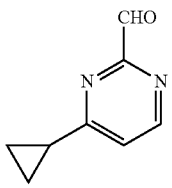

To a stirred solution of methyl 4-cyclopropylpyrimidine-2-carboxylate (100 mg, 0.56 mmol) in dry THF (6 mL) under argon atmosphere was added DIBAL-H (1 M in toluene; 1.7 ml, 1.68 mmol) at −40° C. and stirred for 15 min. The reaction was monitored by TLC; after completion of the reaction, the reaction mixture was quenched with saturated sodium potassium tartrate solution (10 mL) and extracted with EtOAc (2×15 mL). The combined organic extracts were washed with water (10 mL), dried over sodium sulphate, filtered and concentrated in vacuo to obtain crude 4-cyclopropylpyrimidine-2-carbaldehyde (80 mg) as brown solid. The crude was carried to the next step without further purification.

$^1$H-NMR (CDCl$_3$, 500 MHz): δ 10.01 (s, 1H), 8.71 (d, 1H), 7.31 (d, 1H), 2.08-1.99 (m, 1H), 1.31-1.30 (m, 2H), 1.28-1.26 (m, 2H).

xxxiv. 5-(methylthio)pyrimidine-2-carbaldehyde

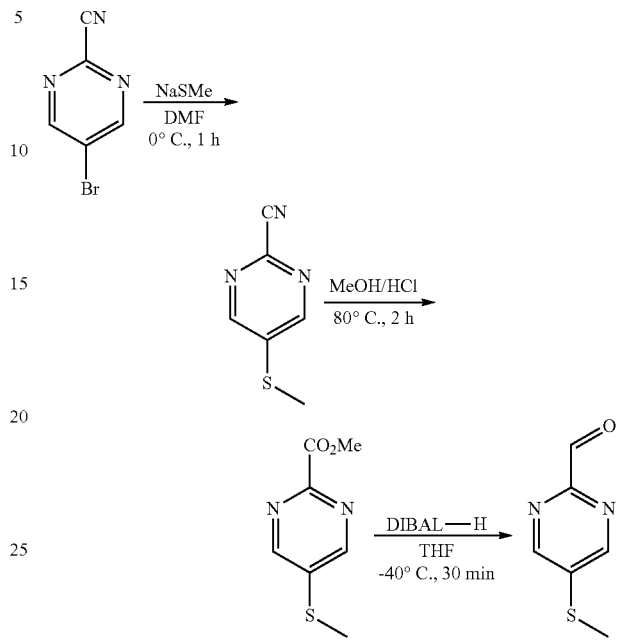

Synthesis of 5-(methylthio)pyrimidine-2-carbonitrile

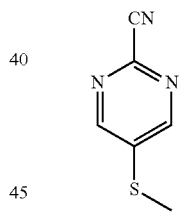

To a stirred solution of 5-bromopyrimidine-2-carbonitrile (1 g, 5.40 mmol) in DMF (20 mL) under argon atmosphere was added sodium methanethiolate (454 mg, 6.48 mmol) at 0° C. and stirred for 1 h. The reaction was monitored by TLC; after completion of the reaction, the reaction mixture was diluted with water (30 mL) and extracted with EtOAc (2×40 mL). The combined organic extracts were dried over sodium sulphate, filtered and concentrated in vacuo to obtain the crude. The crude was purified through silica gel column chromatography using 10% EtOAc/Hexanes to afford 5-(methylthio)pyrimidine-2-carbonitrile (350 mg, 42%) as white solid.

$^1$H-NMR (CDCl$_3$, 500 MHz): δ 8.60 (s, 2H), 2.63 (s, 3H); LC-MS: 99.56%; 151.8 (M$^+$+1); (column; X-bridge C-18, (50×3.0 mm, 3.5μ); RT 2.58 min. 0.05% TFA (aq.): ACN; 0.8 mL/min); TLC: 20% EtOAc/Hexanes (R$_f$: 0.3).

Synthesis of methyl 5-(methylthio)pyrimidine-2-carboxylate

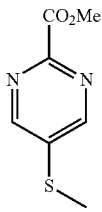

A stirred solution of 5-(methylthio)pyrimidine-2-carbonitrile (350 mg, 2.31 mmol) in MeOH/HCl (20 mL) under argon atmosphere was heated to 80° C. and stirred for 2 h. The reaction was monitored by TLC; after completion of the reaction, the reaction mixture was diluted with saturated NaHCO₃ solution (20 mL) and extracted with EtOAc (2×30 mL). The combined organic extracts were dried over sodium sulphate, filtered and concentrated in vacuo to obtain the crude. The crude was triturated with n-hexane (2×5 mL) to afford methyl 5-(methylthio)pyrimidine-2-carboxylate (300 mg, 70%) as white solid.

$^1$H-NMR (CDCl₃, 500 MHz): δ 8.72 (s, 2H), 4.60 (s, 3H), 2.60 (s, 3H); LC-MS: 98.88%; 184.9 (M$^+$+1); (column; X-bridge C-18, (50×3.0 mm, 3.5μ); RT 1.91 min. 0.05% TFA (aq.): ACN; 0.8 mL/min); TLC: 50% EtOAc/Hexanes (R$_f$: 0.3).

Synthesis of 5-(methylthio)pyrimidine-2-carbaldehyde

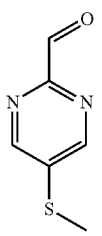

To a stirred solution of methyl 5-(methylthio)pyrimidine-2-carboxylate (300 mg, 1.63 mmol) in dry THF (10 mL) under argon atmosphere was added DIBAL-H (4.8 mL, 4.89 mmol) at −40 C; stirred for 30 min at −40 C. The reaction was monitored by TLC; after completion of the reaction, the reaction mixture was quenched with sodium potassium tartrate solution (15 mL) and extracted with EtOAc (2×30 mL). The combined organic extracts were dried over sodium sulphate, filtered and concentrated in vacuo to obtain the crude 5-(methylthio)pyrimidine-2-carbaldehyde (150 mg, 70%) as Colorless syrup. The crude was carried to the next step without further purification.

$^1$H-NMR (CDCl₃, 500 MHz): δ 10.02 (s, 1H), 8.78 (s, 2H), 2.62 (s, 3H); TLC: 5% MeOH/CH₂Cl₂ (R$_f$: 0.8).

xxxv. 2-(chloromethyl)-5-(trifluoromethyl)pyrimidine

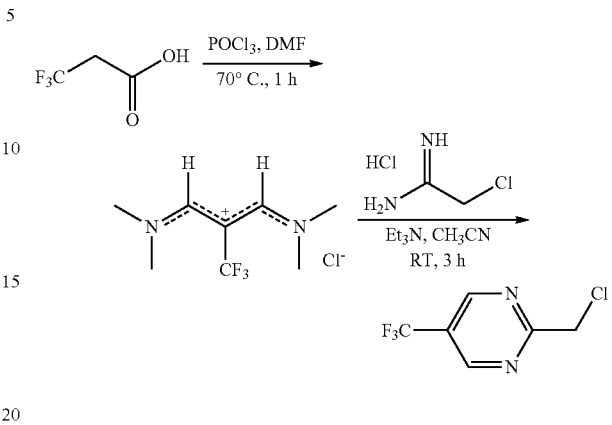

Synthesis of 1,5-diaza-3-(trifluoromethyl)-1,3-pentadieniumchloride

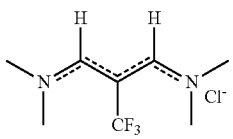

To a stirred solution of 3,3,3-trifluoropropanoic acid (500 mg, 3.90 mmol) in DMF (4 mL) under argon atmosphere was added phosphorous oxychloride (1.09 mL, 11.70 mmol) at RT; heated to 70° C. and stirred for 1 h. The reaction was monitored by TLC; after completion of the reaction, the reaction mixture was diluted with EtOAc (20 mL) and purified by silica gel column by using EtOAc:THF (1:1) and compound eluting with ethanol to afford 1,5-diaza-3-(trifluoromethyl)-1,3-pentadieniumchloride (375 mg, 41%) as thick colorless syrup.

$^1$H-NMR (CD₃OD-d₄, 500 MHz): δ 8.00 (s, 2H), 3.52 (s, 6H), 3.34 (s, 6H), 2.65 (s, 1H); LC-MS: 90.84%; 195 (M$^+$+1); (column; X-bridge C-18, (50×3.0 mm, 3.5μ); RT 1.54 min. 0.05% TFA (aq.): ACN; 0.8 mL/min); TLC: 5% MeOH/CH₂Cl₂ (R$_f$: 0.2).

Synthesis of 2-(chloromethyl)-5-(trifluoromethyl)pyrimidine

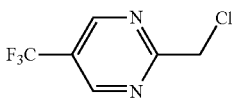

To a stirred solution of compound 2 (275 mg, 1.18 mmol) in CH3CN (5.5 mL) under argon atmosphere were added 2-chloroacetimidamide (182 mg, 1.42 mmol) and triethyl amine (0.2 mL, 1.42 mmol) at RT and stirred for 3 h. The reaction was monitored by TLC; after completion of the reaction, the reaction mixture was diluted with water (50 mL) and extracted with ether (2×25 mL). The combined organic extracts were washed with water (20 mL), dried over sodium sulphate, filtered and concentrated in vacuo to obtain the crude 2-(chloromethyl)-5-(trifluoromethyl)pyrimidine (70 mg) as colorless liquid.

$^1$H-NMR (CDCl$_3$, 500 MHz): δ 9.06 (s, 2H), 4.80 (s, 2H); TLC: 10% EtOAc/Hexanes (R$_f$: 0.8).

xxxvi. 2-(chloromethyl)-4,6-bis(trifluoromethyl)-1,4,5,6-tetrahydropyrimidine-4,6-diol

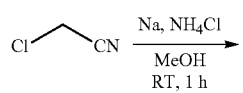

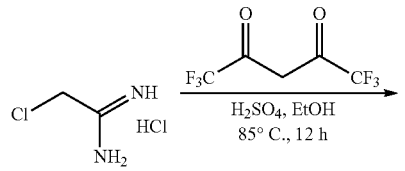

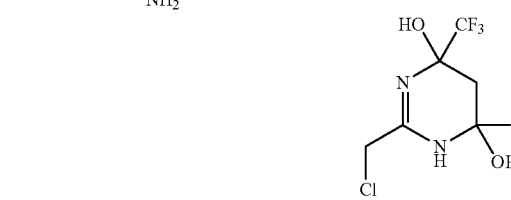

Synthesis of 2-chloroacetimidamide hydrochloride

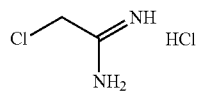

To a stirred solution of sodium (153 mg, 6.65 mmol) in MeOH (16.5 mL) under argon atmosphere were added 2-chloroacetonitrile (5 g, 66.67 mmol) drop wise for 5 min at RT and stirred for 1 h. Then ammonium chloride (3.8 g, 71.69 mmol) was added portion wise for 10 min to the reaction mass and stirred for 1 h. The reaction was monitored by TLC; after completion of the reaction, the volatiles were removed in vacuo the crude. The crude was triturated with ether (2×20 mL) to afford crude 2-chloroacetimidamide hydrochloride (6 g) as black solid. The crude compound was carried to the next step without further purification.

Synthesis of 2-(chloromethyl)-4,6-bis(trifluoromethyl)-1,4,5,6-tetrahydropyrimidine-4,6-diol

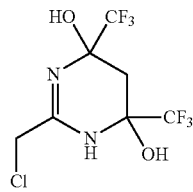 [SMILES: OC1(C(F)(F)F)CC(O)(C(F)(F)F)NC(CCl)=N1]

To a stirred solution of 2-chloroacetimidamide hydrochloride (1 g, 10.75 mmol) in EtOH (50 mL) under argon atmosphere were added 1,1,1,5,5,5-hexafluoropentane-2,4-dione (2.23 g, 10.75 mmol), sulphuric acid (2 drops) at RT; heated to 85° C. and stirred for 12 h. The reaction was monitored by TLC; after completion of the reaction, the volatiles were removed in vacuo. The residue was diluted with water (20 mL), basified with saturated sodium carbonate solution (10 mL) to pH~7 and extracted with EtOAc (2×30 mL). The combined organic extracts were dried over sodium sulfate, filtered and concentrated in vacuo to obtain the crude 2-(chloromethyl)-4,6-bis(trifluoromethyl)-1,4,5,6-tetrahydropyrimidine-4,6-diol (790 mg) as an off-white solid.

$^1$H-NMR (CDCl$_3$, 500 MHz): δ 5.06-5.04 (m, 1H), 4.20 (s, 2H), 2.60 (d, 1H), 2.18 (d, 1H); TLC: 50% EtOAc/Hexanes (R$_f$: 0.4).

xxxvii. 4,5,6,7-tetrahydropyrazolo[1,5-a]pyridine-3-carbaldehyde

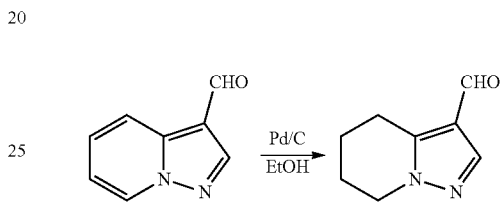

Synthesis of 4,5,6,7-tetrahydropyrazolo[1,5-a]pyridine-3-carbaldehyde

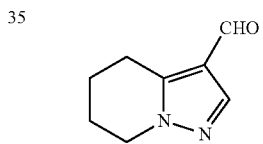

To a stirred solution of pyrazolo[1,5-a]pyridine-3-carbaldehyde (100 mg, 0.68 mmol) in ethanol (5 mL) under argon atmosphere was added Pd/C (10 mg) at room temperature; heated to 60° C. and stirred under hydrogen atmosphere (balloon pressure) for 16 h. The reaction was monitored by TLC; after completion of the reaction, the reaction mixture was filtered through celite and the filtrate was concentrated in vacuo to obtain 4,5,6,7-tetrahydropyrazolo[1,5-a]pyridine-3-carbaldehyde (80 mg, crude aldehyde directly taken up for next reaction.) as thick syrup. LC-MS: 30.75%; 151 (M$^+$+1); (column; X-bridge C-18, (50×3.0 mm, 3.5 μm); RT 1.89 min. 0.05% TFA (Aq): ACN; 0.8 mL/min); TLC: 30% EtOAc/Hexanes (R$_f$: 0.2).

xxxviii. pyrazolo[1,5-a]pyridine-3-carbaldehyde

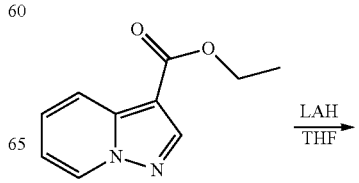

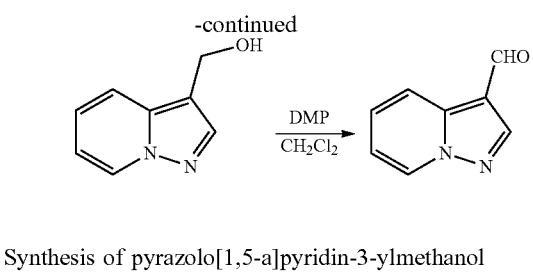

Synthesis of pyrazolo[1,5-a]pyridin-3-ylmethanol

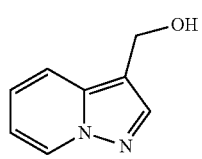 [SMILES: OCc1cnn2ccccc12]

To a stirred solution of ethyl pyrazolo[1,5-a]pyridine-3-carboxylate (200 mg, 1.04 mmol) in THF (5 mL) under argon atmosphere was added lithium aluminum hydride (60 mg, 1.57 mmol) at 0° C.; warmed to RT and stirred for 1 h. The reaction was monitored by TLC; after completion of the reaction, the reaction mixture was quenched with ice water (15 mL) and extracted with EtOAc (2×20 mL). The combined organic extracts were dried over sodium sulphate, filtered and concentrated in vacuo to obtain pyrazolo[1,5-a]pyridin-3-ylmethanol (125 mg, crude) as thick syrup. The crude was carried to the next step without further purification.

$^1$H-NMR (CDCl$_3$, 500 MHz): δ 8.42 (d, 1H), 7.94 (s, 1H), 7.61 (d, 1H), 7.14 (t, 1H), 6.79 (t, 1H), 4.93-4.90 (m, 2H); LC-MS: 80.48%; 149.1 (M$^+$+1); (column; X-bridge C-18, (150×4.6 mm, 5 μm); RT 6.25 min. 0.05% TFA (Aq): ACN; 1.0 mL/min); TLC: 50% EtOAc/Hexanes (R$_f$: 0.3).

Synthesis of pyrazolo[1,5-a]pyridine-3-carbaldehyde

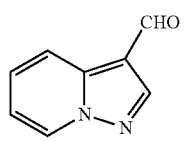 [SMILES: O=Cc1cnn2ccccc12]

To a stirred solution of pyrazolo[1,5-a]pyridin-3-ylmethanol (25 mg, 0.16 mmol) in CH$_2$Cl$_2$ (5 mL) under argon atmosphere was added dessmartin periodinane (143 mg, 0.33 mmol) at 0° C.; warmed to RT and stirred for 1.5 h. The reaction was monitored by TLC; after completion of the reaction, the reaction mixture was quenched with saturated sodium bicarbonate solution (10 mL) and extracted with CH$_2$Cl$_2$ (2×15 mL). The combined organic extracts were dried over sodium sulphate, filtered and concentrated in vacuo to obtain pyrazolo[1,5-a]pyridine-3-carbaldehyde (40 mg, crude). The crude was carried to the next step without further purification.

$^1$H-NMR (CDCl$_3$, 500 MHz): δ 10.01 (s, 1H), 8.60 (d, 1H), 8.48 (d, 1H), 8.38 (s, 1H), 7.52 (t, 1H), 7.04 (t, 1H). LC-MS: 26.29%; 147.1 (M$^+$+1); (column; XDB C-18, (150×4.6 mm, 5 μm); RT 6.90 min. 0.05% TFA: ACN; 1.0 mL/min); TLC: 50% EtOAc/Hexanes (R$_f$: 0.3).

xxxix. 5-(2-chloroethyl)pyrimidine

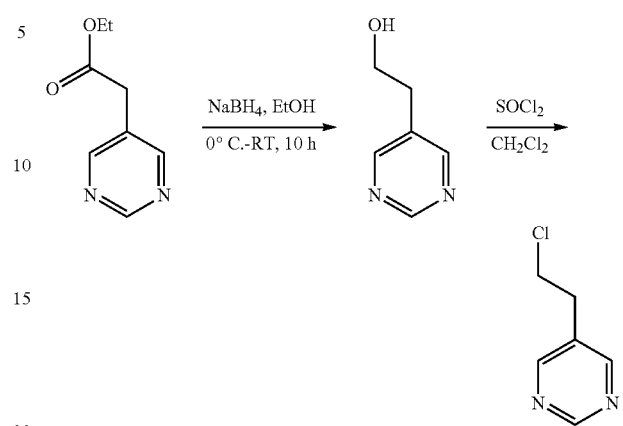

Synthesis of 2-(pyrimidin-5-yl)ethanol

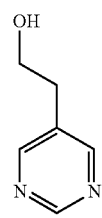

To a stirred solution of ethyl 2-(pyrimidin-5-yl)acetate (200 mg, 1.20 mmol) in ethanol (15 mL) under argon atmosphere was added sodium borohydride (91 mg, 2.40 mmol) at 0° C.; warmed to room temperature and stirred for 16 h. The reaction was monitored by TLC; after completion of the reaction, the reaction mass was quenched with ice-water (2 mL) and the volatiles were removed in vacuo to obtain the crude. The crude was purified through silica gel column chromatography using 4% MeOH/CH$_2$Cl$_2$ to afford 2-(pyrimidin-5-yl)ethanol (45 mg, 30%) as colorless syrup.

$^1$H-NMR (DMSO-d$_6$, 500 MHz): δ 9.01 (s, 1H), 8.62 (s, 2H), 4.76 (t, 1H), 3.66-3.64 (m, 2H), 2.78-2.76 (t, 2H); LC-MS: 98.71%; 125 (M$^+$+1); (column; Eclipse XDB C-18, 150×4.6 mm, 5 μm); RT 3.75 min. 0.05% TFA (aq.): ACN; 1.0 mL/min); UPLC (purity): 96.67%; (column: Acquity UPLC HSS T3, 2.1×100 mm, 1.8 μm); RT 1.86 min. ACN: 0.025% TFA (Aq); 0.3 mL/min. (IP12060040); TLC: 10% MeOH/CH$_2$Cl$_2$ (R$_f$: 0.4).

Synthesis of 5-(2-chloroethyl)pyrimidine

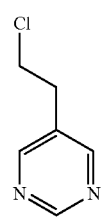

To a stirred solution of 2-(pyrimidin-5-yl)ethanol (20 mg, 0.16 mmol) in CH$_2$Cl$_2$ (4 mL) under argon atmosphere was added sulfurous dichloride (0.02 mL, 0.32 mmol) at 0° C.; heated to 50° C. and stirred for 4 h. The reaction was monitored by TLC; after completion of the reaction, the reaction mass was cooled to room temperature and pH was adjusted to ~8 using saturated NaHCO$_3$ solution (5 mL) and the compound was extracted with CH$_2$Cl$_2$ (2×10 mL). The combined organic extracts were dried over sodium sulphate, filtered and concentrated in vacuo to obtain the crude. The crude was purified through silica gel column chromatography using 2% MeOH/CH$_2$Cl$_2$ to afford 5-(2-chloroethyl)pyrimidine (18 mg, 77%) as colorless syrup.

$^1$H-NMR (CDCl$_3$, 400 MHz): δ 9.16 (s, 1H), 8.66 (s, 2H), 3.78 (t, 2H), 3.12 (t, 2H); LC-MS: 97.54%; 143 (M$^+$+1); (column; Xbridge C-18, 50×3.0 mm, 3.5 μm); RT 1.80 min. 0.05% TFA (aq.): ACN; 0.8 mL/min); UPLC (purity): 99.22%; (column: Acquity BEH C-18, 50×2.1 mm, 1.7μ); RT 1.15 min. ACN: 0.025% TFA (Aq); 0.5 mL/min. (IP12060335); TLC: 10% MeOH/CH$_2$Cl$_2$ (R$_f$: 0.7).

xxxx. 2-cyclopropylbenzaldehyde

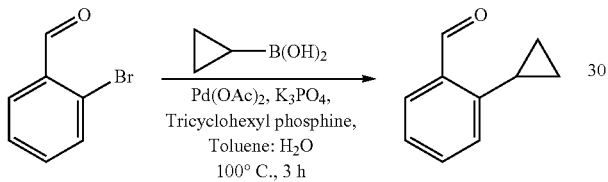

Synthesis of 2-cyclopropylbenzaldehyde

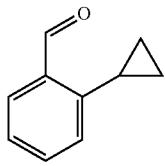 [SMILES: O=Cc1ccccc1C1CC1]

To a stirred solution of 2-bromo benzaldehyde (400 mg, 2.16 mmol) in toluene:H$_2$O (4:1, 10 mL) under argon atmosphere were added cyclopropyl boronic acid (223 mg, 2.59 mmol), potassium phosphate (1.37 g, 6.48 mmol) and tricyclohexyl phosphine (catalytic amount) at RT and purged under argon for 30 min. Then palladium acetate (catalytic amount) was added to the reaction mass; heated to 100° C. and stirred for 3 h. The reaction was monitored by TLC; after completion of the reaction, the volatiles were removed in vacuo to obtain the crude. The crude was purified through silica gel column chromatography using 5% EtOAc/Hexanes to afford 2-cyclopropylbenzaldehyde (200 mg, 64%) as colorless thick syrup.

$^1$H-NMR (CDCl$_3$, 400 MHz): δ 10.61 (s, 1H), 7.81 (d, 1H), 7.50 (t, 1H), 7.30 (t, 1H), 7.12 (d, 1H), 2.66-2.63 (m, 1H), 1.11-1.09 (m, 2H), 0.80-0.77 (m, 2H); TLC: 5% EtOAc/Hexanes (R$_f$: 0.7).

xxxxi. 4-cyclopropylbenzaldehyde

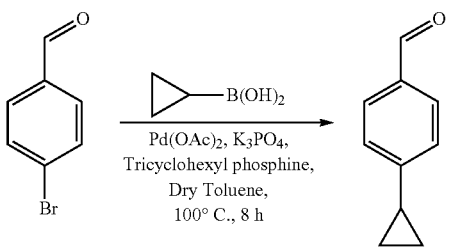 [SMILES: O=Cc1ccc(Br)cc1 ; OB(O)C1CC1 ; O=Cc1ccc(C2CC2)cc1]

Synthesis of 4-cyclopropylbenzaldehyde

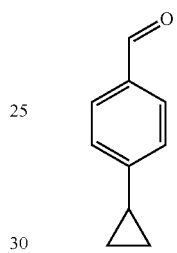

To a stirred solution of 4-bromobenzaldehyde (500 mg, 2.70 mmol) in toluene (20 mL) under argon atmosphere were added cyclopropyl boronic acid (300 mg, 3.51 mmol), potassium phosphate (1.72 g, 8.10 mmol) and tricyclohexyl phosphine (38 mg, 0.13 mmol) at RT and purged under argon for 30 min. Then palladium acetate (30 mg, 0.13 mmol) was added to the reaction mass; heated to 100° C. and stirred for 8 h. The reaction was monitored by TLC; after completion of the reaction, the reaction mixture was filtered through celite and the filtrate was concentrated in vacuo. The residue was diluted with ice cold water (25 mL) and extracted with EtOAc (2×30 mL). The combined organic extracts were washed with saturated NaHCO$_3$ solution (15 mL), dried over sodium sulfate, filtered and concentrated in vacuo to obtain the crude. The crude was purified through silica gel column chromatography using 10% EtOAc/Hexanes to afford 4-cyclopropylbenzaldehyde (240 mg, 61%) as pale yellow liquid.

$^1$H-NMR (CDCl$_3$, 400 MHz): δ 9.94 (s, 1H), 7.78 (d, 2H), 7.20 (d, 2H), 2.00-1.95 (m, 1H), 1.12-1.07 (m, 2H), 0.84-0.78 (m, 2H); TLC: 20% EtOAc/Hexanes (R$_f$: 0.5).

xxxxii. 3-cyclopropylbenzaldehyde

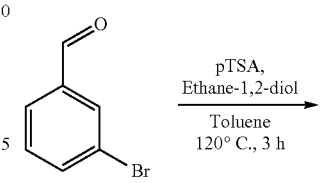

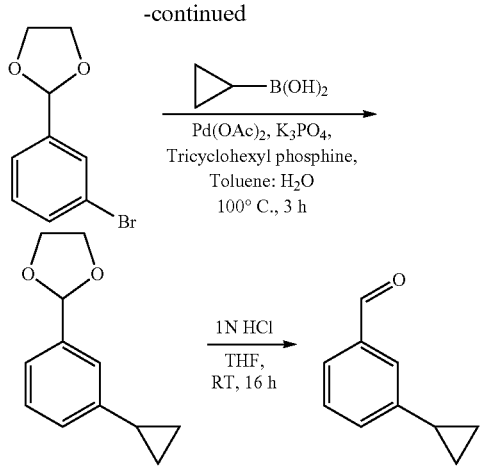

Synthesis of 2-(3-bromophenyl)-1,3-dioxolane (2)

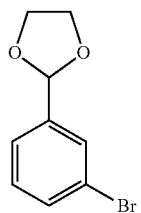

To a stirred solution of 3-bromobenzaldehyde (500 mg, 2.70 mmol) in toluene (10 mL) under argon atmosphere were added pTSA (catalytic amount), ethane-1,2-diol (0.5 mL, 8.10 mmol) at RT; heated to 120° C. and stirred for 3 h. The reaction was monitored by TLC; after completion of the reaction, the reaction mixture was quenched with ice cold water (20 mL) and extracted with EtOAc (2×30 mL). The combined organic extracts were washed with saturated NaHCO$_3$ solution (20 mL), dried over sodium sulfate, filtered and concentrated in vacuo to obtain the crude 2-(3-bromophenyl)-1,3-dioxolane (550 mg, 89%) as colorless liquid. The crude was carried to the next step without further purification.

$^1$H-NMR (CDCl$_3$, 400 MHz): δ 7.64 (s, 1H), 7.50 (d, 1H), 7.41 (d, 1H), 7.18-7.17 (m, 1H), 5.80 (s, 1H), 4.14 (t, 2H), 4.06 (t, 2H); LC-MS: 84.41%; 231.1 (M$^+$+2); (column; X-bridge C-18, (50×3.0 mm, 3.5 μm); RT 3.42 min. 0.05% TFA (aq.): ACN; 0.8 mL/min); TLC: 10% EtOAc/Hexanes (R$_f$: 0.6).

Synthesis of 2-(3-cyclopropylphenyl)-1,3-dioxolane

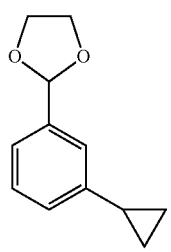 [SMILES: c1cc(C2CC2)cc(C2OCCO2)c1]

To a stirred solution of 2-(3-bromophenyl)-1,3-dioxolane (400 mg, 1.84 mmol) in toluene:H2O (4:1, 10 mL) under argon atmosphere were added cyclopropyl boronic acid (190 mg, 2.21 mmol), potassium phosphate (1.17 g, 5.52 mmol) and tricyclohexyl phosphine (catalytic amount) at RT and purged under argon for 30 min. Then palladium acetate (catalytic amount) was added to the reaction mass; heated to 100° C. and stirred for 3 h. The reaction was monitored by TLC; after completion of the reaction, the volatiles were removed in vacuo to obtain the crude. The crude was purified through silica gel column chromatography using 4% EtOAc/Hexanes to afford 2-(3-cyclopropylphenyl)-1,3-dioxolane (200 mg, 61%) as colorless liquid.

$^1$H-NMR (CDCl$_3$, 400 MHz): δ 7.30-7.28 (m, 2H), 7.20 (s, 1H), 7.10 (t, 1H), 5.80 (s, 1H), 4.14 (t, 2H), 4.06 (t, 2H), 1.98-1.94 (m, 1H), 0.99-0.96 (m, 2H), 0.74-0.71 (m, 2H); TLC: 10% EtOAc/Hexanes (R$_f$: 0.6).

Synthesis of 3-cyclopropylbenzaldehyde

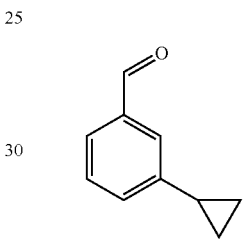

To a stirred solution of 2-(3-cyclopropylphenyl)-1,3-dioxolane (200 mg, 1.12 mmol) in THF (5 mL) under argon atmosphere was added 1N HCl (3 mL) at 0° C.; warmed to RT and stirred for 16 h. The reaction was monitored by TLC; after completion of the reaction, the reaction mixture was quenched with ice cold water (15 mL) and extracted with EtOAc (2×20 mL). The combined organic extracts were washed with saturated NaHCO$_3$ solution (15 mL), dried over sodium sulfate, filtered and concentrated in vacuo to obtain the crude. The crude was purified through silica gel column chromatography using 3% EtOAc/Hexanes to afford 3-cyclopropylbenzaldehyde (120 mg, 74%) as colorless thick syrup.

$^1$H-NMR (CDCl$_3$, 400 MHz): δ 10.00 (s, 1H), 7.66 (d, 1H), 7.59 (s, 1H), 7.40 (t, 1H), 7.34 (d, 1H), 1.99-1.95 (m, 1H), 1.04-1.00 (m, 2H), 0.76-0.73 (m, 2H); TLC: 10% EtOAc/Hexanes (R$_f$: 0.6).

xxxxiii. 3-(dimethylamino)benzaldehyde

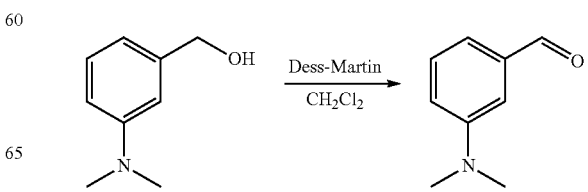

Synthesis of 3-(dimethylamino)benzaldehyde

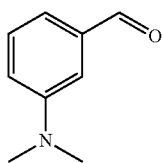

To a stirred solution of (3-(dimethylamino)phenyl)methanol (1.0 g, 6.05 mmol) in $CH_2Cl_2$ (20 mL) was added Dess-Martin periodinane (5.1 g, 12.10 mmol) at 0° C. under argon atmosphere. The resulting reaction mixture was stirred for 2 h at RT; the reaction mixture was then neutralized with saturated $NaHCO_3$ solution and extracted with DCM (2×30 mL). The combined organic extracts were dried over sodium sulphate, filtered and concentrated in vacuo to obtain the crude product. The crude material was purified by silica gel column chromatography to afford 3-(dimethylamino)benzaldehyde (0.4 g, 44%) as pale-grn liquid. $^1$H-NMR (DMSO $d_6$, 400 MHz): δ 9.94 (bs, 1H), 7.38 (t, 1H), 7.16-7.12 (m, 2H), 7.05 (d, 1H), 2.97 (s, 6H); LC-MS: 99.55%; 191 [M$^+$+1]; (column; X-bridge C-18, (50×3.0 mm, 3.5µ); RT 3.29 min. 5 mM $NH_4OAc$: ACN; 0.8 ml/min);

xxxxiv. 2-(dimethylamino)benzaldehyde

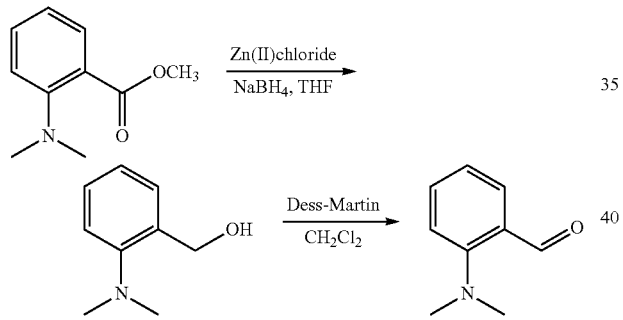

Synthesis of (2-(dimethylamino)phenyl)methanol

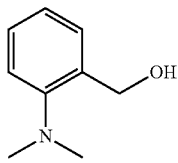

To a stirred solution of methyl 2-(dimethylamino)benzoate (1.0 g, 5.58 mmol) in THF (30 mL) was added Zn(II) chloride (1.52 g, 11.16 mmol) followed by $NaBH_4$ (254 mg, 6.69 mmol) at 0° C. under argon atmosphere. The resulting reaction mixture was heated to 65° C. and stirred for 2 h. The reaction mixture was allowed to cool to RT, filtered through a pad of celite, the filtrate was diluted with water and extracted with EtOAc (2×30 mL). The combined organic extracts were dried over sodium sulphate, filtered and concentrated in vacuo to obtain the crude product. The crude material was purified by silica gel column chromatography to afford (2-(dimethylamino)phenyl)methanol (0.5 g, 60%) as a liquid. $^1$H-NMR (CDCl$_3$, 400 MHz): δ 7.25-7.05 (m, 4H), 5.56 (bs, 1H), 4.82 (s, 2H), 2.72 (s, 6H).

Synthesis of 2-(dimethylamino)benzaldehyde

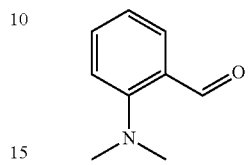

To a stirred solution of (2-(dimethylamino)phenyl)methanol (0.5 g, 3.02 mmol) in $CH_2Cl_2$ (20 mL) was added Dess-Martin periodinane (2.56 g, 6.02 mmol) at 0° C. under argon atmosphere. The resulting reaction mixture was stirred for 2 h at RT; the reaction mixture was then neutralized with saturated $NaHCO_3$ solution and extracted with DCM (2×30 mL). The combined organic extracts were dried over sodium sulphate, filtered and concentrated in vacuo to obtain the crude product. The crude material was purified by silica gel column chromatography to afford 2-(dimethylamino)benzaldehyde (0.35 g, 78%) as a liquid. LC-MS: 55.66%; 150.1 [M$^+$+1]; (column; Eclipse XDB C-18, (150×4.6 mm, 5.0µ); RT 4.10 min. 0.05% TFA in water: ACN; 1.0 ml/min).

xxxxv. 2-(pyrrolidin-1-yl)benzaldehyde

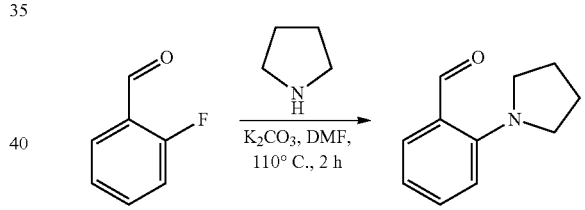

Synthesis of 2-(pyrrolidin-1-yl)benzaldehyde

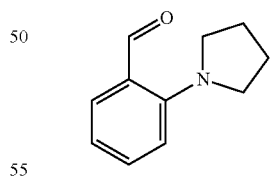

To a stirred solution of 2-fluorobenzaldehyde (200 mg, 1.61 mmol) in DMF (5 mL) under argon atmosphere were added pyrrolidine (345 mg, 4.83 mmol) and potassium carbonate (667 mg, 4.83 mmol) at RT; heated to 110° C. and stirred for 2 h. The reaction was monitored by TLC; after completion of the reaction, the reaction mixture was quenched with ice cold water (15 mL) and extracted with EtOAc (2×25 mL). The combined organic extracts were washed with saturated $NaHCO_3$ solution (15 mL), dried over sodium sulfate, filtered and concentrated in vacuo to obtain the crude. The crude was purified through silica gel column chromatography using 8% EtOAc/Hexanes to afford 2-(pyrrolidin-1-yl)benzaldehyde (230 mg, 82%) as colorless thick syrup.

¹H-NMR (CDCl₃, 400 MHz): δ 10.10 (s, 1H), 7.70 (d, 1H), 7.40 (t, 1H), 6.84-6.80 (m, 2H), 3.40-3.37 (m, 4H), 2.01-1.97 (m, 4H); LC-MS: 99.81%; 176.1 (M⁺+1); (column; X-bridge C-18, (50×3.0 mm, 3.5 μm); RT 2.36 min. 0.05% TFA (aq.): ACN; 0.8 mL/min); TLC: 20% EtOAc/Hexanes ($R_f$: 0.6).

xxxxvi. 4-(pyrrolidin-1-yl)benzaldehyde

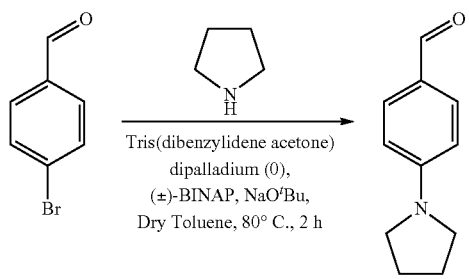 [SMILES: O=Cc1ccc(Br)cc1 ; C1CCNC1 ; O=Cc1ccc(N2CCCC2)cc1]

Synthesis of 4-(pyrrolidin-1-yl)benzaldehyde

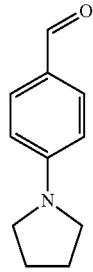

To a stirred solution of 4-bromobenzaldehyde (1 g, 5.40 mmol) in dry toluene (20 mL) under argon atmosphere were added tris(dibenzylidene acetone) dipalladium (0) (100 mg, 0.10 mmol), (±)-BINAP (84 mg, 0.13 mmol) and sodium tertiary butoxide (780 mg, 8.10 mmol) at RT and purged under argon for 30 min; heated to 80° C. and stirred for 2 h. The reaction was monitored by TLC; after completion of the reaction, the reaction mixture was diluted with ice cold water (30 mL) and extracted with EtOAc (2×40 mL). The combined organic extracts were washed with water (25 mL), dried over sodium sulfate, filtered and concentrated in vacuo to obtain the crude. The crude was purified through silica gel column chromatography using 15% EtOAc/Hexanes to afford 4-(pyrrolidin-1-yl)benzaldehyde (300 mg, 32%) as yellow solid.

¹H-NMR (CDCl₃, 400 MHz): δ 9.70 (s, 1H), 7.71 (d, 2H), 6.60 (d, 2H), 3.41-3.38 (m, 4H), 2.08-2.03 (m, 4H); LC-MS: 99.78%; 176.1 (M⁺+1); (column; X-bridge C-18, (50×3.0 mm, 3.5 μm); RT 3.18 min. 0.05% TFA (aq.): ACN; 0.8 mL/min); TLC: 20% EtOAc/Hexanes ($R_f$: 0.3).

xxxxvii. pyrimidine-5-carbaldehyde

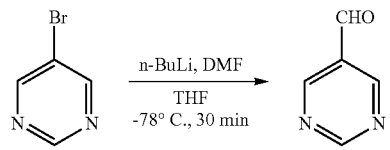 [SMILES: Brc1cncnc1 ; O=Cc1cncnc1]

Synthesis of pyrimidine-5-carbaldehyde

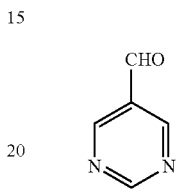

To a stirred solution of 5-bromopyrimidine (5 g, 31.66 mmol) in THF (50 mL) under argon atmosphere was added n-butyl lithium (2.2 g, 34.83 mmol) drop wise for 10 min at −78° C. and stirred for 20 min. To this was added DMF (2.3 g, 31.66 mmol) at −78° C. and stirred for 30 min. The reaction was monitored by TLC; after completion of the reaction, the reaction mixture was quenched with saturated ammonium chloride solution (40 mL) and extracted with EtOAc (3×40 mL). The combined organic extracts were washed with water (30 mL), brine (30 mL), dried over sodium sulfate, filtered and concentrated in vacuo to obtain the crude. The crude was purified through silica gel column chromatography using 25% EtOAc/Hexanes to afford pyrimidine-5-carbaldehyde (200 mg, 3%) as colorless thick syrup. TLC: 30% EtOAc/Hexanes ($R_f$: 0.2).

xxxxviii. 4-(bromomethyl)pyrimidine

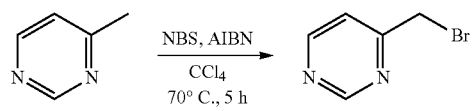

Synthesis of 4-(bromomethyl)pyrimidine

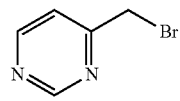

To a stirred solution of 4-methylpyrimidine (1 g, 10.63 mmol) in CCl₄ (40 mL) under argon atmosphere were added N-bromo succinimide (2.08 g, 11.70 mmol) portion wise for 15 min and AIBN (100 mg) at 0° C. and stirred for 30 min; heated to 70° C. and stirred for 5 h. The reaction was monitored by TLC; after completion of the reaction, the volatiles were removed in vacuo to obtain the crude. The crude was purified through silica gel column chromatography using 25% EtOAc/Hexanes to afford 4-(bromomethyl) pyrimidine (200 mg, 11%) as pink liquid.

¹H-NMR (CDCl₃, 400 MHz): δ 9.20 (s, 1H), 8.79 (d, 1H), 7.56 (d, 1H), 4.60-4.47 (m, 2H); TLC: 50% EtOAc/Hexanes (R_f: 0.4).

xxxxix.
2-(chloromethyl)-[1,2,4]triazolo[1,5-a]pyridine

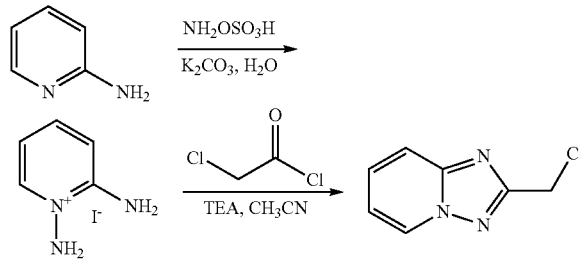

Synthesis of 1,2-diaminopyridin-1-ium iodide

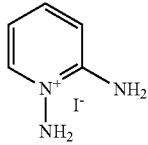

To a stirred solution of hydroxylamine-O-sulfonic acid (1.13 g, 10.05 mmol) in water (6 mL) was added 2-amino pyridine (1.41 g, 15.0 mmol) at RT; heated to 85-90° C. for 3 h. The reaction was monitored by TLC; after completion of the reaction, the reaction mass was cooled to RT, then potassium carbonate (1.38 g, 10.05 mmol) was added and stirred for 10 min; water was removed at 45° C. under reduced pressure. The residue was stirred with absolute ethanol (8 mL) for 5 min and filtered. The filtrate was treated with 57% HI (1.4 mL) and stirred at −20° C. for 90 min (no crystal was formed); concentrated and dried under reduced pressure, co-distilled with toluene (2×10 mL) and triturated with n-hexane (2×10 mL) to afford crude 1,2-diaminopyridin-1-ium iodide (1.8 g) as pale black solid.

Synthesis of 2-(chloromethyl)-[1,2,4]triazolo[1,5-a]pyridine

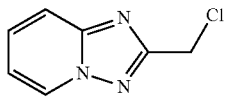 [SMILES: ClCc1nc2ccccn2n1]

To a stirred solution of 1,2-diaminopyridin-1-ium iodide (1 g, 4.21 mmol) in CH₃CN (10 mL) under argon atmosphere was added 2-chloroacetyl chloride (0.68 mL, 8.43 mmol) at 0° C. and stirred for 20 min. Then triethyl amine (1.2 mL, 8.43 mmol) was added to the reaction mass at 0° C.; warmed to RT and stirred for 16 h. The reaction was monitored by TLC; after completion of the reaction, the reaction mixture was diluted with water (15 mL) and extracted with EtOAc (2×20 mL). The combined organic extracts were dried over sodium sulfate, filtered and concentrated under reduced pressure to obtain the crude. The crude was purified through silica gel column chromatography using 20% EtOAc/Hexanes to afford 2-(chloromethyl)-[1,2,4]triazolo[1,5-a]pyridine (200 mg, 28%) as an off-white solid.

¹H-NMR (CDCl₃, 400 MHz): δ 8.59 (d, 1H), 7.78 (d, 1H), 7.56 (t, 1H), 7.06 (t, 1H), 4.80 (s, 2H); LC-MS: 98.70%; 168 (M⁺+1); (column; X-bridge C-18, (50×3.0 mm, 3.5 μm); RT 2.00 min. 0.05% TFA (aq.): ACN; 0.8 mL/min); UPLC (purity): 99.86%; (column: Acquity BEH C-18 (50×2.1 mm, 1.7μ); RT 1.30 min. ACN: 0.025% TFA (Aq); 0.5 mL/min.

xxxxx. 7-(4-fluorophenyl)-2-((3,4-trans)-4-methyl-pyrrolidin-3-yl)imidazo[5,1-f][1,2,4]triazin-4(3H)-one

Synthesis of 7-(4-fluorophenyl)-2-((3,4-trans)-4-methylpyrrolidin-3-yl) imidazo[5,1-f][1,2,4]triazin-4(3H)-one

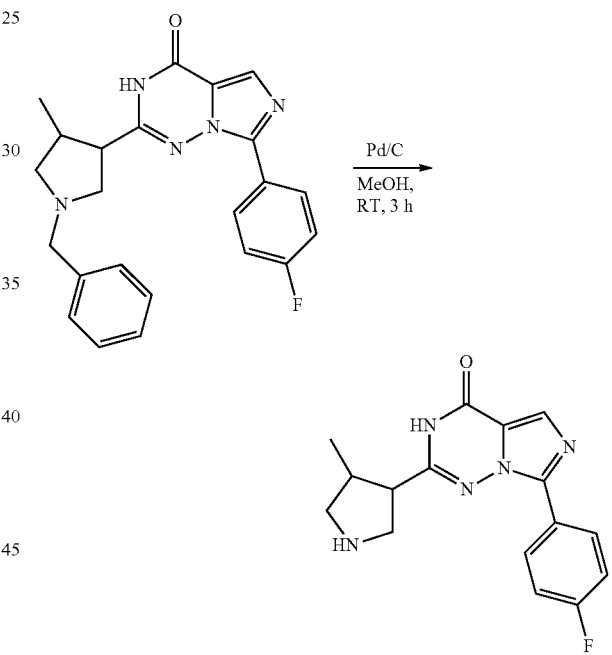

To a stirred solution of (+)-2-((3,4-trans)-1-benzyl-4-methylpyrrolidin-3-yl)-7-(4-fluorophenyl)imidazo[5,1-f][1,2,4]triazin-4(3H)-one (250 mg, 0.62 mmol) in MeOH (10 mL) under argon atmosphere was added 10% Pd/C (150 mg) at RT and stirred under hydrogen atmosphere (balloon pressure) and stirred for 3 h. The reaction was monitored by TLC; the reaction mixture was filtered through celite and the filtrate was concentrated in vacuo to obtain the crude. The crude was triturated with n-pentane (2×5 mL) to afford 7-(4-fluorophenyl)-2-((3,4-trans)-4-methylpyrrolidin-3-yl) imidazo[5,1-f][1,2,4]triazin-4(3H)-one (150 mg, 77%) as white solid.

¹H-NMR (CD₃OD-d₄, 400 MHz): δ 8.36-8.34 (m, 2H), 7.70 (s, 1H), 7.28 (t, 2H), 3.54-3.51 (m, 3H), 3.36-3.34 (m, 1H), 3.00 (q, 1H), 2.81-2.80 (m, 1H), 2.71-2.69 (m, 1H), 1.20 (d, 3H); LC-MS: 96.72%; 314 (M⁺+1); (column; X-bridge C-18, 50×3.0 mm, 3.5 μm); RT 2.40 min. 0.05%

TFA (Aq): ACN; 0.8 mL/min); UPLC (purity): 95.24%; (column: Acquity BEH C-18, 50×2.1 mm, 1.7μ); RT 1.48 min. ACN: 0.025% TFA (Aq); 0.5 mL/min.

xxxxxi. 7-(3-fluorophenyl)-2-((3,4-trans)-4-methyl-pyrrolidin-3-yl) imidazo[5,1-f][1,2,4]triazin-4(3H)-one Synthesis of 7-(3-fluorophenyl)-2-((3,4-trans)-4-methylpyrrolidin-3-yl) imidazo[5,1-f][1,2,4]triazin-4(3H)-one

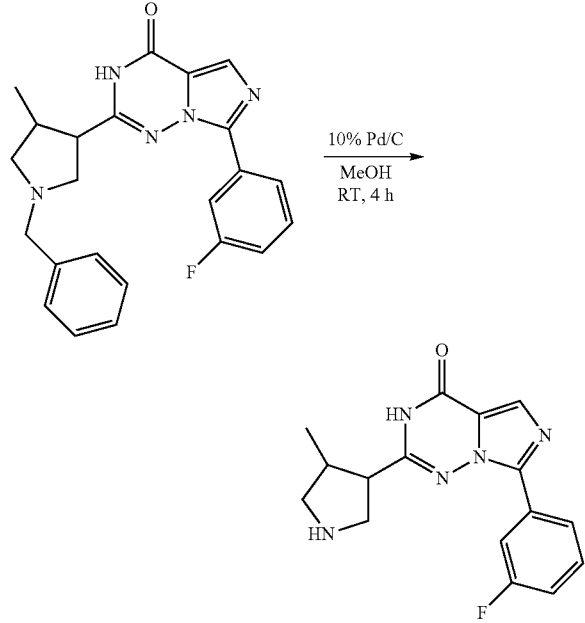

To a stirred solution of (+)-2-((3,4-trans)-1-benzyl-4-methylpyrrolidin-3-yl)-7-(3-fluorophenyl)imidazo[5,1-f][1,2,4]triazin-4(3H)-one (180 mg, 0.44 mmol) in MeOH (15 mL) under argon atmosphere was added 10% Pd/C (50 mg) at room temperature and stirred under hydrogen atmosphere (balloon pressure) for 4 h. The reaction was monitored by TLC; after completion of the reaction, the reaction mixture was filtered through celite and the filtrate was concentrated in vacuo to afford 7-(3-fluorophenyl)-2-((3,4-trans)-4-methylpyrrolidin-3-yl) imidazo[5,1-f][1,2,4]triazin-4(3H)-one (120 mg, 86%) as an off-white solid.

$^1$H-NMR (DMSO-$d_6$, 400 MHz): δ 8.22 (d, 2H), 7.69 (s, 1H), 7.48-7.50 (m, 1H), 7.24-7.21 (m, 1H), 3.45-3.41 (m, 1H), 3.38-3.28 (m, 2H), 2.82-2.79 (m, 1H), 2.69-2.66 (m, 1H), 2.62-2.59 (m, 1H), 1.11 (d, 3H); LC-MS: 91.33%; 314 (M$^+$+1); (column: X-Bridge C-18, 50×3.0 mm, 3.5 μm); RT 2.26 min. 0.05% aq TFA: ACN; 0.8 mL/min); UPLC (purity): 84.83%; (column: Acquity BEH C-18, (50×2.1 mm, 1.7μ); RT 1.49 min. ACN: 0.025% TFA (Aq); 0.5 mL/min.; TLC: 10% MeOH/CH$_2$Cl$_2$ (R$_f$: 0.2).

xxxxxii. 2-((3,4-trans)-4-methylpyrrolidin-3-yl)-7-(o-tolyl)imidazo[5,1-f][1,2,4]triazin-4(3H)-one Synthesis of 2-((3,4-trans)-4-methylpyrrolidin-3-yl)-7-(o-tolyl)imidazo[5,1-f][1,2,4]triazin-4(3H)-one

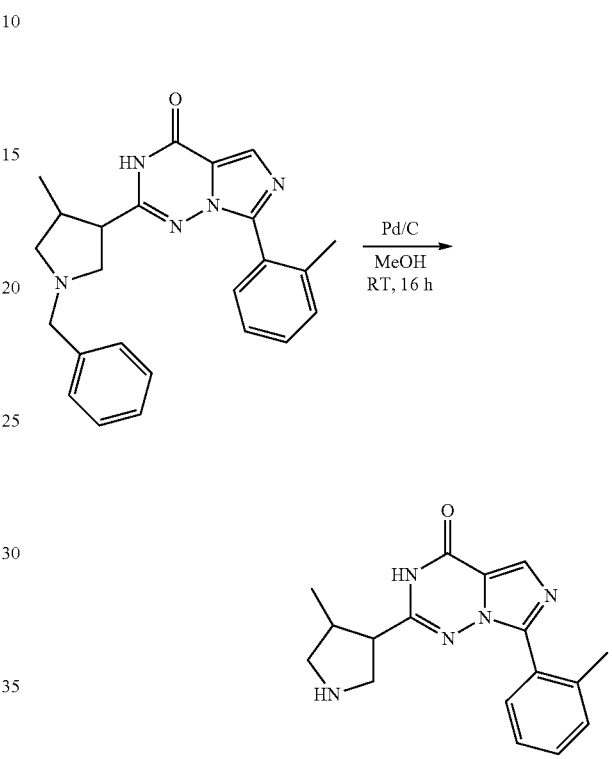

To a stirred solution of (+)-2-((3,4-trans)-1-benzyl-4-methylpyrrolidin-3-yl)-7-(o-tolyl)imidazo[5,1-f][1,2,4]triazin-4(3H)-one (210 mg, 0.52 mmol) in MeOH (20 mL) under argon atmosphere was added 10% Pd/C (60 mg) at RT and stirred under hydrogen atmosphere (balloon pressure) for 16 h. The reaction was monitored by TLC; after completion of the reaction, the reaction mixture was filtered through celite and the filtrate was concentrated in vacuo to obtain the crude. The crude was triturated with n-pentane (2×15 mL) to afford 2-((3,4-trans)-4-methylpyrrolidin-3-yl)-7-(o-tolyl) imidazo[5,1-f][1,2,4]triazin-4(3H)-one (140 mg, 87%) as white solid.

$^1$H-NMR (DMSO-$d_6$, 400 MHz): δ 7.87 (s, 1H), 7.51-7.49 (m, 1H), 7.40-7.22 (m, 3H), 3.32-3.08 (m, 3H), 2.80-2.60 (m, 2H), 2.42-2.42 (m, 1H), 2.28 (s, 3H), 1.00-0.98 (m, 3H); LC-MS: 93.90%; 310 (M$^+$+1); (column: X Bridge C-18, 50×3.0 mm, 3.5 μm); RT 2.12 min. 0.05% Aq TFA: ACN; 0.8 mL/min); UPLC (purity): 96.22%; (column: Acquity BEH C-18 (50×2.1 mm, 1.7μ); RT 1.37 min. ACN: 0.025% TFA (Aq); 0.5 mL/min. (IP12050312); TLC: 10% MeOH/CH$_2$Cl$_2$ (R$_f$: 0.1).

xxxxxiii. 7-(4,5-difluoro-2-methylphenyl)-2-((3,4-trans)-4-methylpyrrolidin-3-yl)imidazo[5,1-f][1,2,4]triazin-4(3H)-one Synthesis of 7-(4,5-difluoro-2-methylphenyl)-2-((3,4-trans)-4-methylpyrrolidin-3-yl)imidazo[5,1-f][1,2,4]triazin-4 (3H)-one

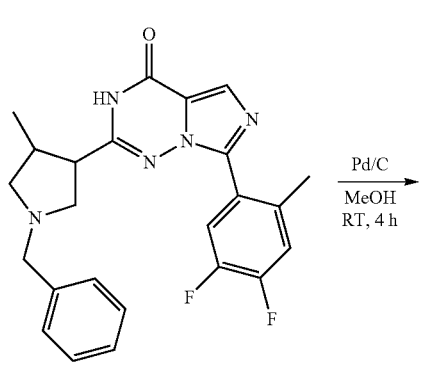

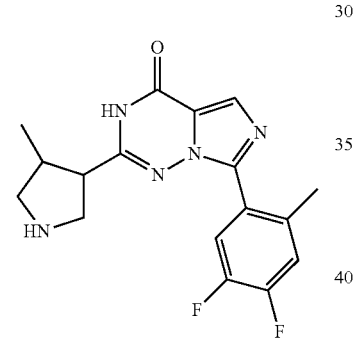

To a stirred solution of (+)-2-((3,4-trans)-1-benzyl-4-methylpyrrolidin-3-yl)-7-(4,5-difluoro-2-methylphenyl)imidazo[5,1-f][1,2,4]triazin-4(3H)-one (300 mg, 0.68 mmol) in MeOH (10 mL) was added 10% Pd/C (60 mg) at RT and stirred under hydrogen atmosphere (balloon pressure) for 4 h. The reaction was monitored by TLC; after completion of the reaction, the reaction mixture was filtered through celite and the filtrate was concentrated in vacuo to afford 7-(4,5-difluoro-2-methylphenyl)-2-((3,4-trans)-4-methylpyrrolidin-3-yl)imidazo[5,1-f][1,2,4]triazin-4(3H)-one (200 mg, 85%) as an off-white solid.

$^1$H-NMR (DMSO-d$_6$, 400 MHz): δ 7.71-7.69 (m, 2H), 7.48-7.44 (m, 1H), 3.36-3.34 (m, 1H), 3.28-3.26 (m, 1H), 3.20-3.18 (m, 1H), 2.71-2.69 (m, 1H), 2.58-2.56 (m, 1H), 2.40-2.38 (m, 1H), 2.30 (s, 3H), 1.06 (d, 3H); UPLC (purity): 91.34%; (column: Acquity BEH C-18 (50×2.1 mm, 1.7µ); RT 1.55 min. ACN: 0.025% TFA (Aq); 0.5 mL/min. (IP12100545); TLC: 10% MeOH/CH$_2$Cl$_2$ (R$_f$: 0.2).

xxxxxiv. 2-((3,4-trans)-4-methylpyrrolidin-3-yl)-7-phenylimidazo[5,1-f][1,2,4]triazin-4(3H)-one Synthesis of 2-((3,4-trans)-4-methylpyrrolidin-3-yl)-7-phenylimidazo[5,1-f][1,2,4]triazin-4(3H)-one

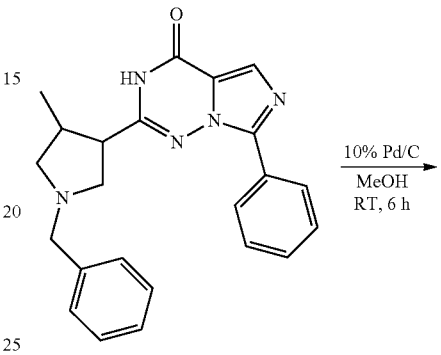

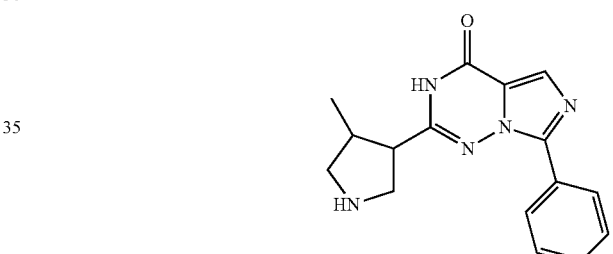

To a stirred solution of (+)-2-((3,4-trans)-1-benzyl-4-methylpyrrolidin-3-yl)-7-phenylimidazo[5,1-f][1,2,4]triazin-4(3H)-one (200 mg, 0.51 mmol) in MeOH (10 mL) under argon atmosphere was added 10% Pd/C (60 mg) at room temperature and stirred under hydrogen atmosphere (balloon pressure) for 6 h. The reaction was monitored by TLC; after completion of the reaction, the reaction mixture was filtered through celite and the filtrate was concentrated in vacuo to obtain 2-((3,4-trans)-4-methylpyrrolidin-3-yl)-7-phenylimidazo[5,1-f][1,2,4]triazin-4(3H)-one (135 mg, 85%) as white solid.

$^1$H-NMR (DMSO-d$_6$, 400 MHz): δ 8.33 (d, 2H), 7.80 (s, 1H), 7.55-7.49 (m, 2H), 7.44-7.39 (m, 1H), 3.52-3.49 (m, 1H), 3.39-3.29 (m, 2H), 2.90 (d, 1H), 2.70 (t, 1H), 2.63-2.59 (m, 1H), 1.10 (d, 3H); LC-MS: 82.38%; 296 (M$^+$+1); (column: X Bridge C-18, 50×3.0 mm, 3.5 µm); RT 2.10 min. 0.05% aq TFA: ACN; 0.8 mL/min); UPLC (purity): 85.31%; (column: Acquity BEH C-18, (50×2.1 mm, 1.7µ); RT 1.39 min. ACN: 0.025% TFA (Aq); 0.5 mL/min. (IP12051263); TLC: 10% MeOH/CH$_2$Cl$_2$ (R$_f$: 0.1).

xxxxxv. 7-(4-methylpyridin-3-yl)-2-((3,4-trans)-4-methylpyrrolidin-3-yl)imidazo[5,1-f][1,2,4]triazin-4(3H)-one Synthesis of 7-(4-methylpyridin-3-yl)-2-((3,4-trans)-4-methylpyrrolidin-3-yl)imidazo[5,1-f][1,2,4]triazin-4 (3H)-one xxxxxvi. 7-cyclopentyl-2-((3,4-trans)-4-methylpyrrolidin-3-yl)imidazo[5,1-f][1,2,4]triazin-4(3H)-one Synthesis of 7-cyclopentyl-2-((3,4-trans)-4-methylpyrrolidin-3-yl)imidazo[5,1-f][1,2,4]triazin-4(3H)-one

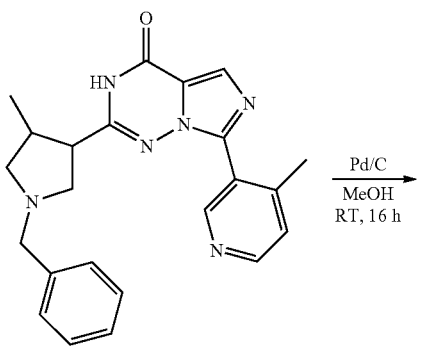

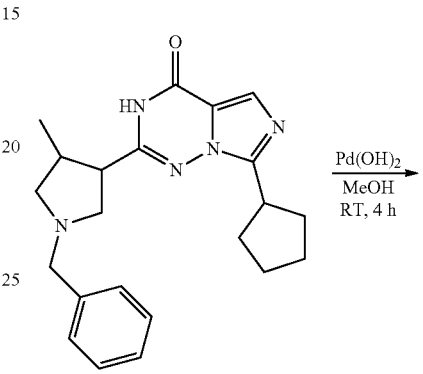

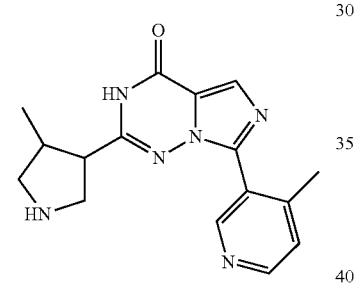

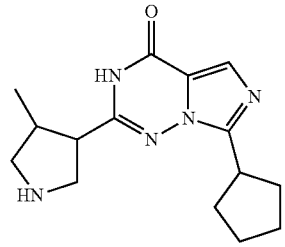

To a stirred solution of (+)-2-((3,4-trans)-1-benzyl-4-methylpyrrolidin-3-yl)-7-(4-methylpyridin-3-yl)imidazo[5,1-f][1,2,4]triazin-4(3H)-one (50 mg, 0.12 mmol) in MeOH (10 mL) under argon atmosphere was added Pd/C (10 mg) at room temperature and stirred under hydrogen atmosphere (balloon pressure) for 16 h. The reaction was monitored by TLC; after completion of the reaction, the reaction mixture was filtered through celite and the filtrate was concentrated in vacuo to afford 7-(4-methylpyridin-3-yl)-2-((3,4-trans)-4-methylpyrrolidin-3-yl)imidazo[5,1-f][1,2,4]triazin-4(3H)-one (30 mg, 80%) as an off-white solid.

$^1$H-NMR (DMSO-$d_6$, 400 MHz): δ 8.78 (s, 1H), 8.50 (d, 1H), 7.76 (s, 1H), 7.40 (d, 1H), 3.38-3.36 (m, 1H), 3.24-3.22 (m, 2H), 2.72-2.70 (m, 1H), 2.61-2.59 (m, 1H), 2.42-2.40 (m, 1H), 2.37 (s, 3H), 1.06 (d, 3H); LC-MS: 85.71%; 311.5 (M$^+$+1); (column: Eclipse XDB C-18, 150×4.6 mm, 5.0 μm); RT 6.12 min. 0.05% TFA (aq.): ACN; 1.0 mL/min); UPLC (purity): 86.86%; (column: Acquity UPLC HSS T3, (2.1×100 mm, 1.8μ); RT 2.66 min. ACN: 0.025% TFA (Aq); 0.3 mL/min.; TLC: 10% MeOH/CH$_2$Cl$_2$ (R$_f$: 0.1).

To a stirred solution of (+)-2-((3,4-trans)-1-benzyl-4-methylpyrrolidin-3-yl)-7-cyclopentylimidazo[5,1-f][1,2,4]triazin-4(3H)-one (150 mg, 0.39 mmol) in MeOH (10 mL) under argon atmosphere was added 20% palladium hydroxide (30 mg) at room temperature and stirred under hydrogen atmosphere (balloon pressure) for 4 h. The reaction was monitored by TLC; after completion of the reaction, the reaction mixture was filtered through celite and the filtrate was concentrated in vacuo to afford 7-cyclopentyl-2-((3,4-trans)-4-methylpyrrolidin-3-yl)imidazo[5,1-f][1,2,4]triazin-4(3H)-one (80 mg, 70%) as an off-white solid.

$^1$H-NMR (DMSO-$d_6$, 400 MHz): δ 7.54 (s, 1H), 3.51-3.50 (m, 2H), 3.22-3.14 (m, 2H), 3.04-3.02 (m, 1H), 2.68-2.64 (m, 1H), 2.41-2.39 (m, 2H), 2.02-1.98 (m, 2H), 1.88-1.85 (m, 2H), 1.76-1.74 (m, 2H), 1.66-1.64 (m, 2H), 1.06 (d, 3H); LC-MS: 95.78%; 288.2 (M$^+$+1); (column: X-Bridge C-18, 50×3.0 mm, 3.5 μm); RT 2.05 min. 5 mM NH$_4$OAc: ACN; 0.8 mL/min); TLC: 10% MeOH/CH$_2$Cl$_2$ (R$_f$: 0.1).

xxxxxvii. 2-((3,4-trans)-4-methylpyrrolidin-3-yl)-7-(pentan-3-yl)imidazo[5,1-f][1,2,4]triazin-4(3H)-one Synthesis of 2-((3,4-trans)-4-methylpyrrolidin-3-yl)-7-(pentan-3-yl)imidazo[5,1-f][1,2,4]triazin-4(3H)-one

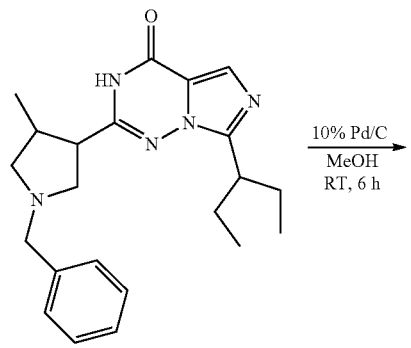

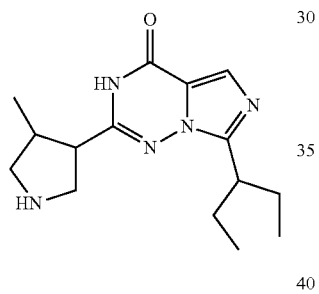

To a stirred solution of (+)-2-((3,4-trans)-1-benzyl-4-methylpyrrolidin-3-yl)-7-(pentan-3-yl)imidazo[5,1-f][1,2,4]triazin-4(3H)-one (140 mg, 0.36 mmol) in MeOH (10 mL) under argon atmosphere was added 10% Pd/C (40 mg) at room temperature and stirred under hydrogen atmosphere (balloon pressure) for 6 h. The reaction was monitored by TLC; after completion of the reaction, the reaction mixture was filtered through celite and the filtrate was concentrated in vacuo to obtain 24(3,4-trans)-4-methylpyrrolidin-3-yl)-7-(pentan-3-yl)imidazo[5,1-f][1,2,4]triazin-4(3H)-one (85 mg, 80%) as an off-white solid.

$^1$H-NMR (DMSO-$d_6$, 400 MHz): δ 7.64 (s, 1H), 4.69 (d, 1H), 3.28-3.20 (m, 1H), 3.18-3.10 (m, 3H), 2.92-2.89 (m, 1H), 2.78 (d, 1H), 2.69-2.63 (m, 1H), 2.44-2.42 (m, 2H), 1.24 (s, 1H), 1.08-1.00 (m, 3H), 0.91 (d, 1H), 0.73-0.69 (m, 6H); LC-MS: 82.78%; 290 (M$^+$+1); (column: X Bridge C-18, 50×3.0 mm, 3.5 μm); RT 1.98 min. 0.05% TFA (aq.): ACN; 0.8 mL/min); UPLC (purity): 87.45%; (column: Acquity BEH C-18, (50×2.1 mm, 1.7μ); RT 1.27 min. ACN: 0.025% TFA (Aq); 0.5 mL/min. TLC: 10% MeOH/CH$_2$Cl$_2$ (R$_f$: 0.1).

xxxxxviii. 7-(3-methylpyridin-4-yl)-2-((3,4-trans)-4-methylpyrrolidin-3-yl)imidazo[5,1-f][1,2,4]triazin-4(3H)-one Synthesis of 7-(3-methylpyridin-4-yl)-2-((3,4-trans)-4-methylpyrrolidin-3-yl)imidazo[5,1-f][1,2,4]triazin-4(3H)-one

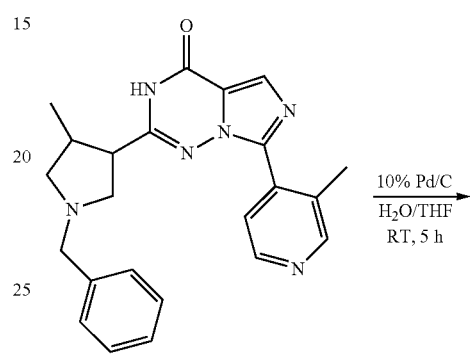

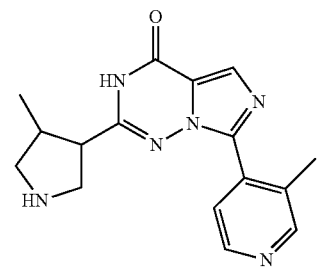

To a stirred solution of (+)-2-((3,4-trans)-1-benzyl-4-methylpyrrolidin-3-yl)-7-(3-methylpyridin-4-yl)imidazo[5,1-f][1,2,4]triazin-4(3H)-one (30 mg, 0.07 mmol) in H$_2$O: THF (1:0.1, 3.3 mL) was added 10% Pd/C (10 mg) at RT and stirred under hydrogen atmosphere (balloon pressure) for 5 h. The reaction was monitored by TLC; after completion of the reaction, the reaction mixture was filtered through celite and the filtrate was concentrated in vacuo to afford 7-(3-methylpyridin-4-yl)-2-((3,4-trans)-4-methylpyrrolidin-3-yl)imidazo[5,1-f][1,2,4]triazin-4(3H)-one (20 mg, 86%) as an off-white solid.

$^1$H-NMR (DMSO-$d_6$, 400 MHz): δ 8.60 (s, 1H), 8.50 (d, 1H), 7.80 (d, 1H), 7.70 (s, 1H), 3.38-3.24 (m, 4H), 2.70-2.68 (m, 1H), 2.60-2.58 (m, 1H), 2.40-2.36 (m, 4H), 1.08 (d, 3H); LC-MS: 97.67%; 311.3 (M$^+$+1); (column: X-Bridge C-18, 50×3.0 mm, 3.5 μm); RT 1.78 min. 0.05% Aq TFA: ACN; 0.8 mL/min); UPLC (purity): 93.28%; (column: Acquity UPLC HSS T3 (2.1×100 mm, 1.8μ); RT 2.78 min. ACN: 0.025% TFA (Aq); 0.3 mL/min. (IP12100657); TLC: 10% MeOH/CH$_2$Cl$_2$ (R$_f$: 0.2).

xxxxxix. 7-(2-fluorophenyl)-2-((3,4-trans)-4-methyl-pyrrolidin-3-yl)imidazo[5,1-f][1,2,4]triazin-4(3H)-one Synthesis of 7-(2-fluorophenyl)-2-((3,4-trans)-4-methylpyrrolidin-3-yl)imidazo[5,1-f][1,2,4]triazin-4(3H)-one

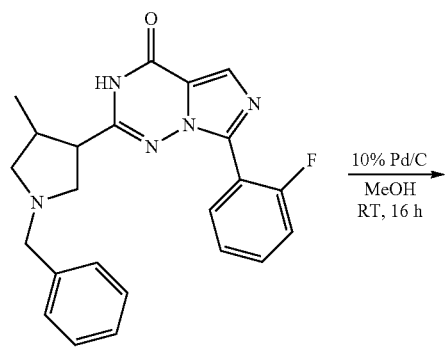

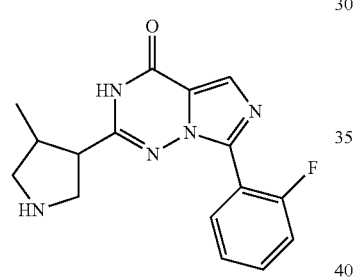

To a stirred solution of (+)-2-((3,4-trans)-1-benzyl-4-methylpyrrolidin-3-yl)-7-(2-fluorophenyl)imidazo[5,1-f][1,2,4]triazin-4(3H)-one (30 mg, 0.07 mmol) in MeOH (3 mL) under argon atmosphere was added 10% Pd/C (9 mg) at RT and stirred under hydrogen atmosphere (balloon pressure) for 16 h. The reaction was monitored by TLC; after completion of the reaction, the reaction mixture was filtered through celite and the solid was washed with 30% MeOH/CH$_2$Cl$_2$ (2×15 mL). The combined filtrates were concentrated in vacuo to afford 7-(2-fluorophenyl)-2-((3,4-trans)-4-methyl-pyrrolidin-3-yl)imidazo[5,1-f][1,2,4]triazin-4(3H)-one (20 mg, 86%) as an off-white solid.

$^1$H-NMR (CDCl$_3$, 400 MHz): δ 8.04 (s, 1H), 7.78 (t, 1H), 7.48-7.45 (m, 1H), 7.31-7.29 (m, 1H), 7.20-7.18 (m, 1H), 3.50 (t, 1H), 3.30 (d, 1H), 3.16-3.14 (m, 1H), 2.76-2.74 (m, 1H), 2.50-2.44 (m, 4H), 1.20 (d, 3H); LC-MS: 91.66%; 314.3 (M$^+$+1); (column: X-Bridge C-18, 50×3.0 mm, 3.5 μm); RT 2.24 min. 0.05% Aq TFA: ACN; 0.8 mL/min); TLC: 10% MeOH/CH$_2$Cl$_2$ (R$_f$: 0.2).

xxxxxxx. 2-((3,4-trans)-4-methylpyrrolidin-3-yl)-7-(2,2,2-trifluoroethyl)imidazo[5,1-f][1,2,4]triazin-4(3H)-one Synthesis of 2-((3,4-trans)-4-methylpyrrolidin-3-yl)-7-(2,2,2-trifluoroethyl)imidazo[5,1-f][1,2,4]triazin-4(3H)-one

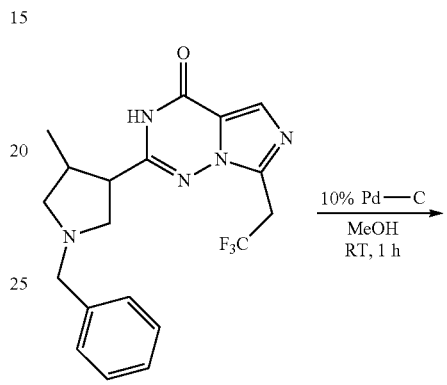

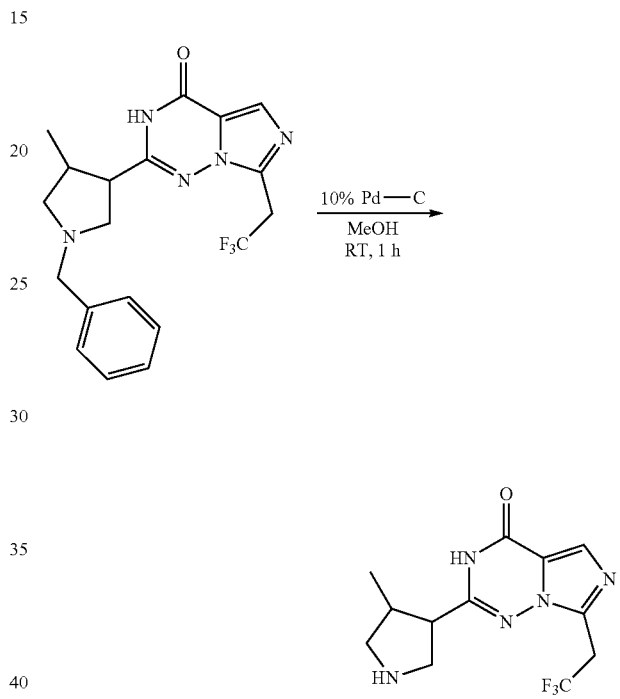

To a stirred solution of (+)-2-((3,4-trans)-1-benzyl-4-methylpyrrolidin-3-yl)-7-(2,2,2-trifluoroethyl)imidazo[5,1-f][1,2,4]triazin-4(3H)-one (100 mg, 0.24 mmol) in MeOH (10 mL) under argon atmosphere was added 10% Pd/C (25 mg) at RT and stirred under hydrogen atmosphere (balloon pressure) for 1 h. The reaction was monitored by TLC; after completion of the reaction, the reaction mixture was filtered through celite and the filtrate was concentrated in vacuo to afford 2-((3,4-trans)-4-methylpyrrolidin-3-yl)-7-(2,2,2-trifluoroethyl)imidazo[5,1-f][1,2,4]triazin-4(3H)-one (35 mg, 48%) as an off-white solid.

$^1$H-NMR (DMSO-d$_6$, 500 MHz): δ 7.54 (s, 1H), 4.04 (q, 2H), 3.34-3.22 (m, 4H), 2.96-2.94 (m, 1H), 2.76-2.74 (m, 2H), 2.58-2.57 (m, 1H), 1.06 (d, 3H); LC-MS: 97.11%; 302 (M$^+$+1); (column: X-Bridge C-18, 50×3.0 mm, 3.5 μm); RT 1.95 min. 0.05% Aq TFA: ACN; 0.8 mL/min); TLC: 10% MeOH/CH$_2$Cl$_2$ (R$_f$: 0.2).

xxxxxxi. 2-((3,4-trans)-4-methylpyrrolidin-3-yl)-7-(2-(trifluoromethyl)phenyl)imidazo[5,1-f][1,2,4]triazin-4(3H)-one Synthesis of 2-((3,4-trans)-4-methylpyrrolidin-3-yl)-7-(2-(trifluoromethyl)phenyl)imidazo[5,1-f][1,2,4]triazin-4(3H)-one

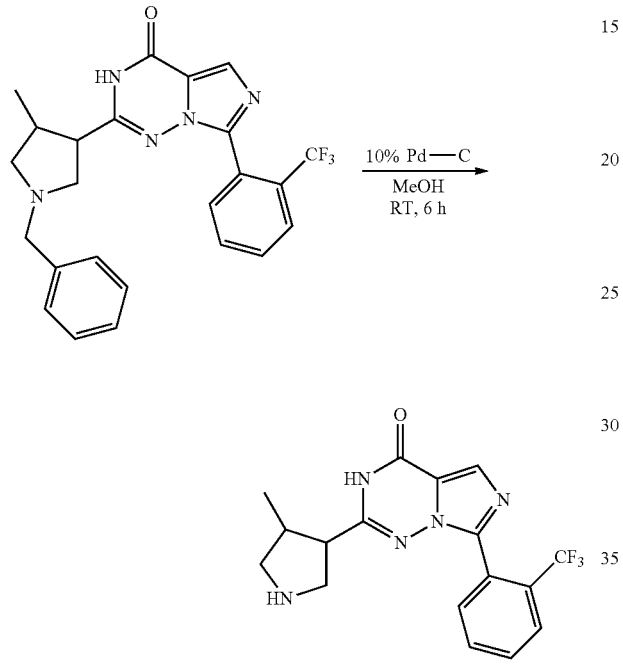

To a stirred solution of (+)-2-((3,4-trans)-1-benzyl-4-methylpyrrolidin-3-yl)-7-(2-(trifluoromethyl)phenyl)imidazo[5,1-f][1,2,4]triazin-4(3H)-one (300 mg, 0.66 mmol) in MeOH (30 mL) under argon atmosphere was added 10% Pd/C (150 mg) at RT and stirred under hydrogen atmosphere (balloon pressure) for 6 h. The reaction was monitored by TLC; after completion of the reaction, the reaction mixture was filtered through celite and the filtrate was extracted with 50% MeOH/CH$_2$Cl$_2$ (2×30 mL). The combined organic extracts were concentrated in vacuo to afford 2-((3,4-trans)-4-methylpyrrolidin-3-yl)-7-(2-(trifluoromethyl)phenyl)imidazo[5,1-f][1,2,4]triazin-4(3H)-one (170 mg, 71%) as an off-white solid.

$^1$H-NMR (CD$_3$OD-d$_4$, 400 MHz): δ 7.90 (d, 1H), 7.74 (s, 3H), 7.60 (d, 1H), 3.48-3.44 (m, 3H), 2.82 (q, 1H), 2.72 (t, 1H), 2.56-2.54 (m, 1H), 1.10 (d, 3H); LC-MS: 86.78%; 364.3 (M$^+$+1); (column: Eclipse XDB-C18, 150×4.6 mm, 5 μm); RT 6.24 min. 0.05% Aq TFA: ACN; 1.0 mL/min); UPLC (purity): 94.24%; (column: Acquity UPLC BEH-C18 (50×2.1 mm, 1.7μ); RT 1.47 min. ACN: 0.025% TFA (Aq); 0.5 mL/min.; TLC: 10% MeOH/CH$_2$Cl$_2$ (R$_f$: 0.2).

B. Synthesis of Final Products

1. Asymmetric synthesis of 2-((3S,4S)-1-benzyl-4-methylpyrrolidin-3-yl)-7-(tetrahydro-2H-pyran-4-yl)imidazo[5,1-f][1,2,4]-triazin-4(3H)-one

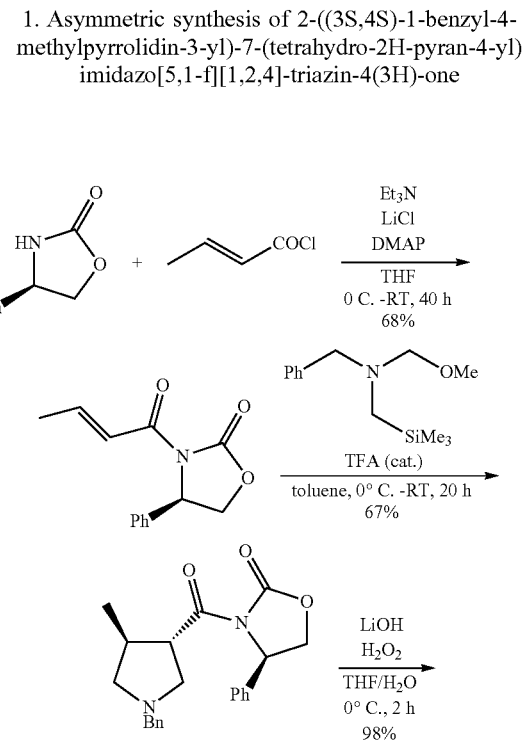

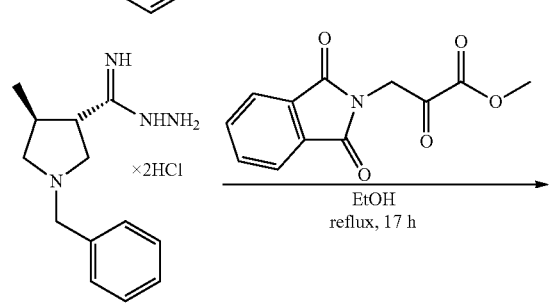

Synthesis of (R,E)-3-but-2-enoyl-4-phenyloxazolidin-2-one

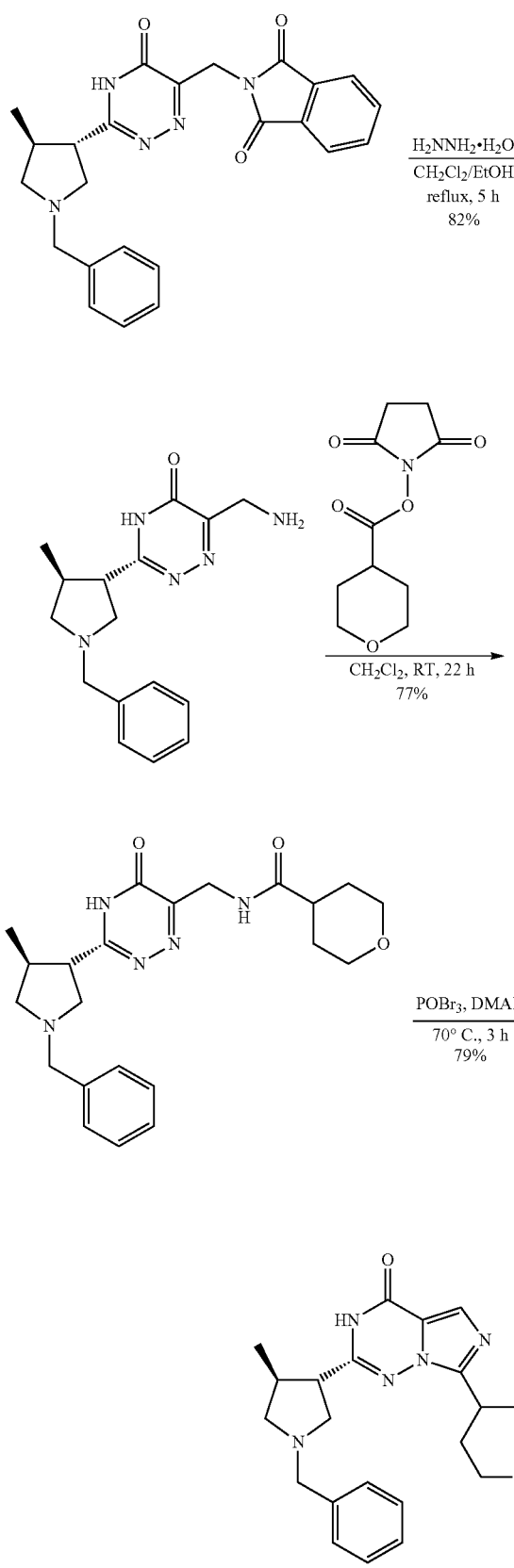

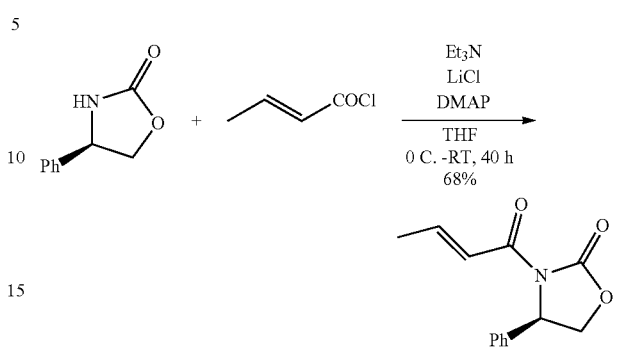

To a solution of (R)-4-phenyloxazolidin-2-one (8.30 g, 50.9 mmol) in anhydrous THF (80 mL) were added LiCl (2.48 g, 58.5 mmol) and triethylamine (10.30 g, 101.8 mmol). The resulting solution was stirred at RT for 20 minutes, and was then cooled by an ice-water bath. DMAP (0.63 g, 5.1 mmol) was added followed by drop-wise addition of (E)-but-2-enoyl chloride (6.11 g, 58.5 mmol). The resulting yellow suspension was stirred at 0° C. for 0.5 h, then at RT for 16 h. Water (160 mL) was added to quench the reaction, and the mixture was extracted with EtOAc (1×150 mL, 2×100 mL). The combined organic phases were washed with brine (50 mL), dried over magnesium sulfate. The solvent was removed under reduced pressure to give crude product as yellowish oily wax, which was purified by chromatography (0-50% EtOAc/heptane) to obtain (R,E)-3-but-2-enoyl-4-phenyloxazolidin-2-one as light yellow wax (8.0 g, 68%). $^1$H NMR (300 MHz, CDCl$_3$/TMS): δ 7.50-7.20 (m, 6H), 7.18-7.00 (m, 1H), 5.48 (dd, 1H, J=8.7, 3.9 Hz), 4.69 (t, 1H, J=8.7 Hz), 4.27 (dd, 1H, J=8.7, 3.9 Hz), 1.93 (dd, 3H, J=6.7, 1.3 Hz); $^{13}$C NMR (75 MHz, CDCl$_3$/TMS): δ 164.2, 153.5, 146.9, 138.9, 128.9, 128.3, 125.7, 121.5, 69.8, 57.6, 18.5.

Synthesis of (R)-3-((3S,4S)-1-benzyl-4-methylpyrrolidine-3-carbonyl)-4-phenyloxazolidin-2-one

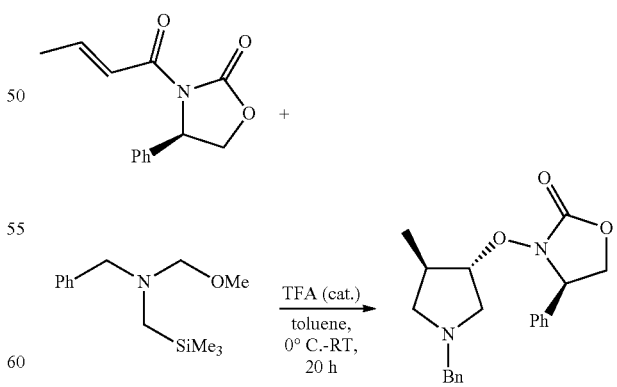

A solution of (R,E)-3-but-2-enoyl-4-phenyloxazolidin-2-one (8.04 g, 34.8 mmol) in dry toluene (150 mL) was flushed with argon. To this solution was added N-benzyl-1-methoxy-N-((trimethylsilyl)methyl)methanamine (9.92 g, 41.8 mmol) at 0° C., and the resulting solution was stirred at this temperature for 0.5 h. A solution of TFA in CH$_2$Cl$_2$ (1M, 3.5 mL) was added drop-wise over 10 minutes at 0° C. After addition was complete, the reaction mixture was stirred at 0° C. for 0.5 h and then at room temperature under argon for 20 h. The reaction mixture was washed with 5% NaHCO$_3$ aqueous solution (100 mL), brine (50 mL), and dried over magnesium sulfate. The solvent was removed under reduced pressure to give crude product as yellowish oily wax, which was separated by chromatography (10-100% EtOAc/heptane) to obtain (R)-3-((3S,4S)-1-benzyl-4-methylpyrrolidine-3-carbonyl)-4-phenyloxazolidin-2-one (8.10 g, 64%) and (R)-3-((3R,4R)-1-benzyl-4-methylpyrrolidine-3-carbonyl)-4-phenyloxazolidin-2-one (2.10 g, 17%).

(R)-3-((3S,4S)-1-benzyl-4-methylpyrrolidine-3-carbonyl)-4-phenyloxazolidin-2-one: light yellow oily wax; [α]$_D^{22}$ -69.7 (c 0.9, CHCl$_3$); $^1$H NMR (300 MHz, CDCl$_3$/TMS): δ 7.60-7.10 (m, 10H), 5.42 (dd, 1H, J=8.7, 3.9 Hz), 4.65 (t, 1H, J=9.0 Hz), 4.20 (dd, 1H, J=8.7, 3.9 Hz), 3.76-3.66 (m, 1H), 3.64 (d, 1H, J=13.5 Hz), 3.46 (d, 1H, J=12.9 Hz), 2.99 (t, 1H, J=9.3 Hz), 2.88 (t, 1H, J=8.0 Hz), 2.83-2.72 (m, 1H), 2.66 (dd, 1H, J=10.0, 5.2 Hz), 2.25-2.10 (m, 1H), 1.06 (d, 3H, J=6.6 Hz); $^{13}$C NMR (75 MHz, CDCl$_3$/TMS): δ 173.4, 153.2, 138.8, 129.0, 128.4, 128.3, 127.9, 126.6, 125.5, 69.7, 61.6, 59.7, 57.7, 57.2, 50.2, 34.4, 19.0.

(R)-3-((3R,4R)-1-benzyl-4-methylpyrrolidine-3-carbonyl)-4-phenyloxazolidin-2-one: light yellow oily wax; $^1$H NMR (300 MHz, CDCl$_3$/TMS): δ 7.40-7.15 (m, 10H), 5.36 (dd, 1H, J=8.4, 3.9 Hz), 4.58 (t, 1H, J=8.8 Hz), 4.17 (dd, 1H, J=8.8, 3.9 Hz), 3.86-3.75 (m, 1H), 3.63 (d, 1H, J=13.2 Hz), 3.53 (d, 1H, J=12.9 Hz), 2.94 (t, 1H, J=9.4 Hz), 2.88-2.75 (m, 2H), 2.61-2.49 (m, 1H), 2.25-2.10 (m, 1H), 1.02 (d, 3H, J=6.9 Hz); $^{13}$C NMR (75 MHz, CDCl$_3$/TMS): δ 173.7, 153.3, 138.9, 138.8, 128.9, 128.4, 127.9, 126.6, 125.5, 69.6, 61.4, 59.8, 57.8, 57.0, 49.6, 36.2, 18.8.

Synthesis of (3S,4S)-1-benzyl-4-methylpyrrolidine-3-carboxylic acid

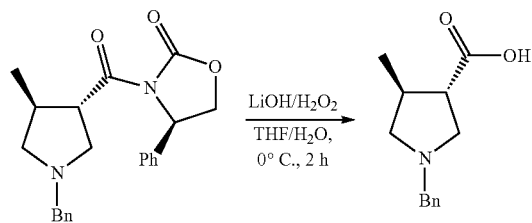 [SMILES: C[C@@H]1CN(Cc2ccccc2)C[C@H]1C(=O)N1C(=O)OC[C@H]1c1ccccc1 ; C[C@@H]1CN(Cc2ccccc2)C[C@H]1C(=O)O]

A solution of LiOH (1.32 g, 54.9 mmol) and H$_2$O$_2$ (35%, 4.26 g, 43.8 mmol) in water (35 mL) was added to a solution of (R)-3-((3S,4S)-1-benzyl-4-methylpyrrolidine-3-carbonyl)-4-phenyloxazolidin-2-one (8.00 g, 21.9 mmol) in THF (120 mL) drop-wise at 0° C., and the resulting mixture was stirred at this temperature for 2 h, then diluted with water (150 mL). Sodium sulfite (5.77 g, 45.8 mmol) was added, and the solution was extracted with EtOAc (2×50 mL). The aqueous phase was adjusted to pH 4.6 with NaH$_2$PO$_4$.H$_2$O (10.3 g, 73 mmol) and 10% HCl, then saturated with NaCl. The solution was extracted with i-PrOH/CH$_2$Cl$_2$ (1:3, 5×120 mL). The combined organic phase was washed with brine (100 mL), dried over magnesium sulfate. The solvent was removed under reduced pressure to give crude (3S,4S)-1-benzyl-4-methylpyrrolidine-3-carboxylic acid (4.33 g, 90%)

as highly hygroscopic, yellowish wax, which was used for next step without further purification; $^1$H NMR (300 MHz, CD$_3$OD/TMS): δ 7.55-7.45 (m, 5H), 4.39 (s, 2H), 3.68 (dd, 1H, J=12.3, 7.2 Hz), 3.61-3.51 (m, 2H), 3.00 (t, 1H, J=10.8 Hz), 2.90 (dd, 1H, J=16.5, 8.7 Hz), 2.67-3.55 (m, 1H), 1.26 (d, 3H, J=6.6 Hz); $^{13}$C NMR (75 MHz, CD$_3$OD/TMS): δ 174.6, 131.6, 131.3, 131.0, 130.3, 61.1, 59.9, 56.7, 50.3, 38.0, 17.2.

Synthesis of (3S,4S)-methyl 1-benzyl-4-methylpyrrolidine-3-carboxylate

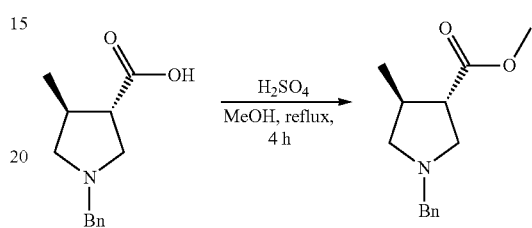

To a solution of (3S,4S)-1-benzyl-4-methylpyrrolidine-3-carboxylic acid (4.30 g, 19.6 mmol) in anhydrous methanol (100 mL) was added conc. H$_2$SO$_4$ (3 mL) at RT, and the resulting solution was stirred and heated under reflux for 4 h. The solvent was removed under reduced pressure, and the residue was dissolved in EtOAc (200 mL), treated with saturated NaHCO$_3$ aqueous solution (100 mL). The phases were separated, and the aqueous phase was extracted with EtOAc (2×50 mL). The combined organic phase was washed with brine (50 mL), and dried over magnesium sulfate. The solvent was removed under reduced pressure to give crude product as yellowish oil, which was purified by chromatography (0.1/6/94-0.5/15/85 Et$_3$N/EtOAc/heptane) to obtain (3S,4S)-methyl 1-benzyl-4-methylpyrrolidine-3-carboxylate (3.51 g, 68%) as light yellow oil. $^1$H NMR (300 MHz, CDCl$_3$/TMS): δ 7.38-7.20 (m, 5H), 3.67 (s, 3H), 3.64 (d, 1H, J=12.9 Hz), 3.56 (d, 1H, J=12.9 Hz), 2.91-2.73 (m, 3H), 2.60-2.42 (m, 2H), 2.21 (dd, 1H, J=8.7, 6.6 Hz), 1.13 (d, 3H, J=6.6 Hz); $^{13}$C NMR (75 MHz, CDCl$_3$/TMS): δ 174.8, 138.6, 128.5, 128.0, 126.7, 61.5, 60.0, 56.6, 51.7, 50.4, 36.7, 19.7.

Synthesis of (3S,4S)-1-benzyl-4-methylpyrrolidine-3-carboximidamide hydrochloride

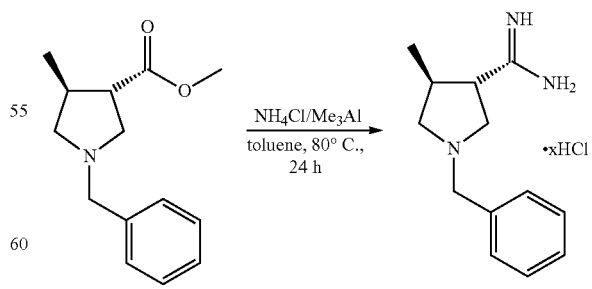

Ammonium chloride (4.01 g, 7.5 mmol) was suspended in dry toluene (90 mL) and the mixture was then cooled to 0° C. under argon. A solution of trimethylaluminum in heptane (37.5 mL, 2.0 M, 7.5 mmol) was added drop-wise and the resulting mixture was stirred at room temperature until no more evolution of gas was observed (about 2 hours). After addition of (3S,4S)-methyl 1-benzyl-4-methylpyrrolidine-3-carboxylate (3.50 g, 1.5 mmol) at RT, resulting reaction mixture was stirred at RT for 0.5 h, then heated at 80° C. for 24 h. The reaction mixture was cooled to 0° C., quenched by slow addition of methanol (75 mL) and then stirred vigorously at room temperature for one hour. The mixture was filtered and the filter cake was washed with methanol (2×20 mL). The combined filtrates were concentrated under reduced pressure to give a yellow solid. The solid was triturated with dichloromethane/methanol (1:1, 50 mL), and filtered. The filtrate was concentrated under reduced pressure to give crude (3S,4S)-1-benzyl-4-methylpyrrolidine-3-carboximidamide hydrochloride as yellow wax (4.10 g, 94%). This compound was used for next step without further purification. $^1$H NMR (300 MHz, CD$_3$OD): δ 7.60-7.25 (m, 5H), 4.06 (br s, 2H), 3.46-3.16 (m, 3H), 2.94 (br s, 1H), 2.62 (br s, 2H), 1.19 (d, 3H, J=6.3 Hz); $^{13}$C NMR (75 MHz, CDCl$_3$) δ 173.4, 135.8, 130.8, 129.9, 129.7, 61.3, 60.1, 57.3, 50.0, 40.3, 18.1.

Synthesis of (3S,4S)-1-benzyl-4-methylpyrrolidine-3-carboximidhydrazide hydrochloride

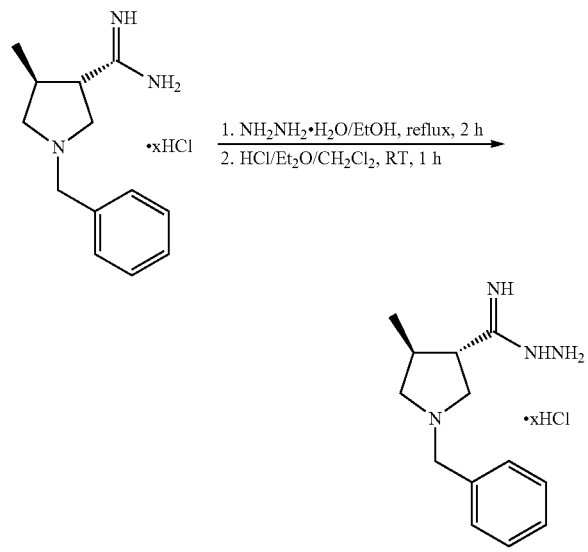

A solution of hydrazine monohydrate (0.69 g, 13.7 mmol) in EtOH (2 mL) was added slowly to a solution of (3S,4S)-1-benzyl-4-methylpyrrolidine-3-carboximidamide hydrochloride (3.98 g, 13.7 mmol) in ethanol (58 mL) at RT. The resulting light yellow suspension was stirred at reflux for 2 h. The reaction mixture was cooled to RT and the white solid was filtered. The filtrate was concentrated under reduced pressure to give a light pink wax. The material was dissolved in a minimum CH$_2$Cl$_2$ (10 mL), and to this stick solution was added 2M HCl in ether (18 mL) drop-wise at RT with stirring. Then anhydrous ether (20 mL) was added. The resulting yellow suspension was stirred at RT under argon for 0.5 h. The solid was filtered and rinsed with ether, dried over high vacuum to provide crude (3S,4S)-1-benzyl-4-methylpyrrolidine-3-carboximidhydrazide hydrochloride (4.20 g, 100%). This material was used for the next step without further purification.

Synthesis of 2-((3-((3S,4S)-1-benzyl-4-methylpyrrolidin-3-yl)-5-oxo-4,5-dihydro-1,2,4-triazin-6-yl)methyl)isoindoline-1,3-dione

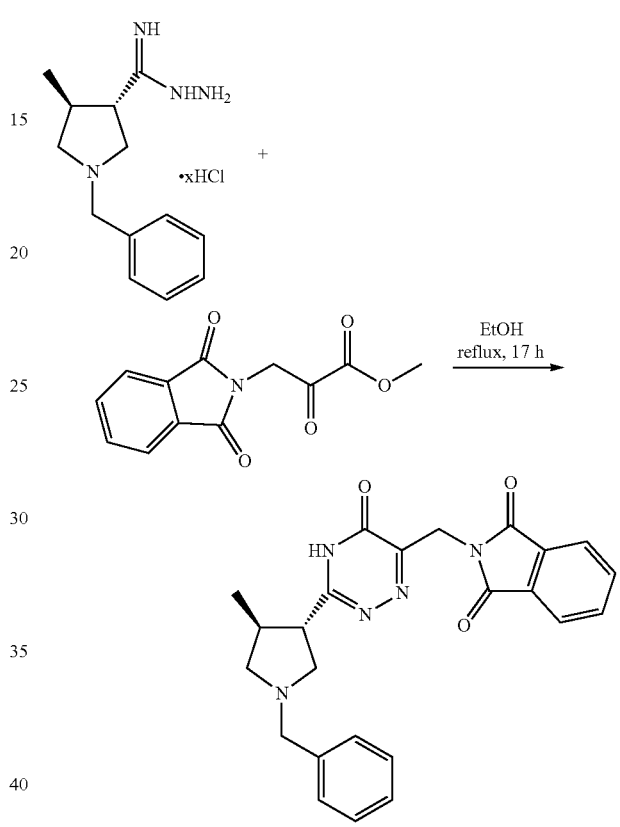

The mixture of (3S,4S)-1-benzyl-4-methylpyrrolidine-3-carboximidhydrazide hydrochloride (4.00 g, 13.1 mmol) and methyl 3-(1,3-dioxoisoindolin-2-yl)-2-oxopropanoate (3.24 g, 13.1 mmol) in anhydrous ethanol (45 mL) was heated under reflux and argon for 17 h. The cooled reaction mixture was concentrated under reduced pressure and the residue was dissolved in CHCl3 (100 mL), and the pH value was adjusted to 8 with saturated NaHCO$_3$. The organic phase was separated from aqueous phase, and the latter was extracted with CHCl$_3$ (2×20 mL). The combined organic phase was dried over MgSO$_4$. After concentration the residue purified by flash chromatography over silica gel column (0.1/1.5/98.4-0.5/7.5/92 NH$_4$OH/MeOH/CH$_2$Cl$_2$) to give 2-((3-((3S,4S)-1-benzyl-4-methylpyrrolidin-3-yl)-5-oxo-4,5-dihydro-1,2,4-triazin-6-yl)methyl)isoindoline-1,3-dione (2.14 g, 38%) as yellow solid. $^1$H NMR (300 MHz, CDCl$_3$/TMS) δ 9.81 (br s, 1H), 7.86 (dd, 2H, J=5.6, 2.8 Hz), 7.72 (dd, 2H, J=5.3, 3.1 Hz), 7.30 (m, 5H), 5.01 (s, 2H), 3.97 (br s, 1H), 3.81 (d, 1H, J=10.5 Hz), 3.40-3.00 (m, 4H), 2.60-2.50 (m, 2H), 0.95 (d, 3H, J=6.0 Hz); $^{13}$C NMR (75 MHz, CDCl$_3$/TMS) δ 167.8, 165.0, 162.6, 148.7, 133.7, 132.2, 129.3, 128.7, 128.5, 123.1, 60.2, 59.3, 56.5, 50.3, 38.5, 37.6, 17.6.

429
Synthesis of 6-(aminomethyl)-3-((3S,4S)-1-benzyl-4-methylpyrrolidin-3-yl)-1,2,4-triazin-5(4H)-one

430
Synthesis of N-((3-((3S,4S)-1-benzyl-4-methylpyrrolidin-3-yl)-5-oxo-4,5-dihydro-1,2,4-triazin-6-yl)methyl)tetrahydro-2H-pyran-4-carboxamide

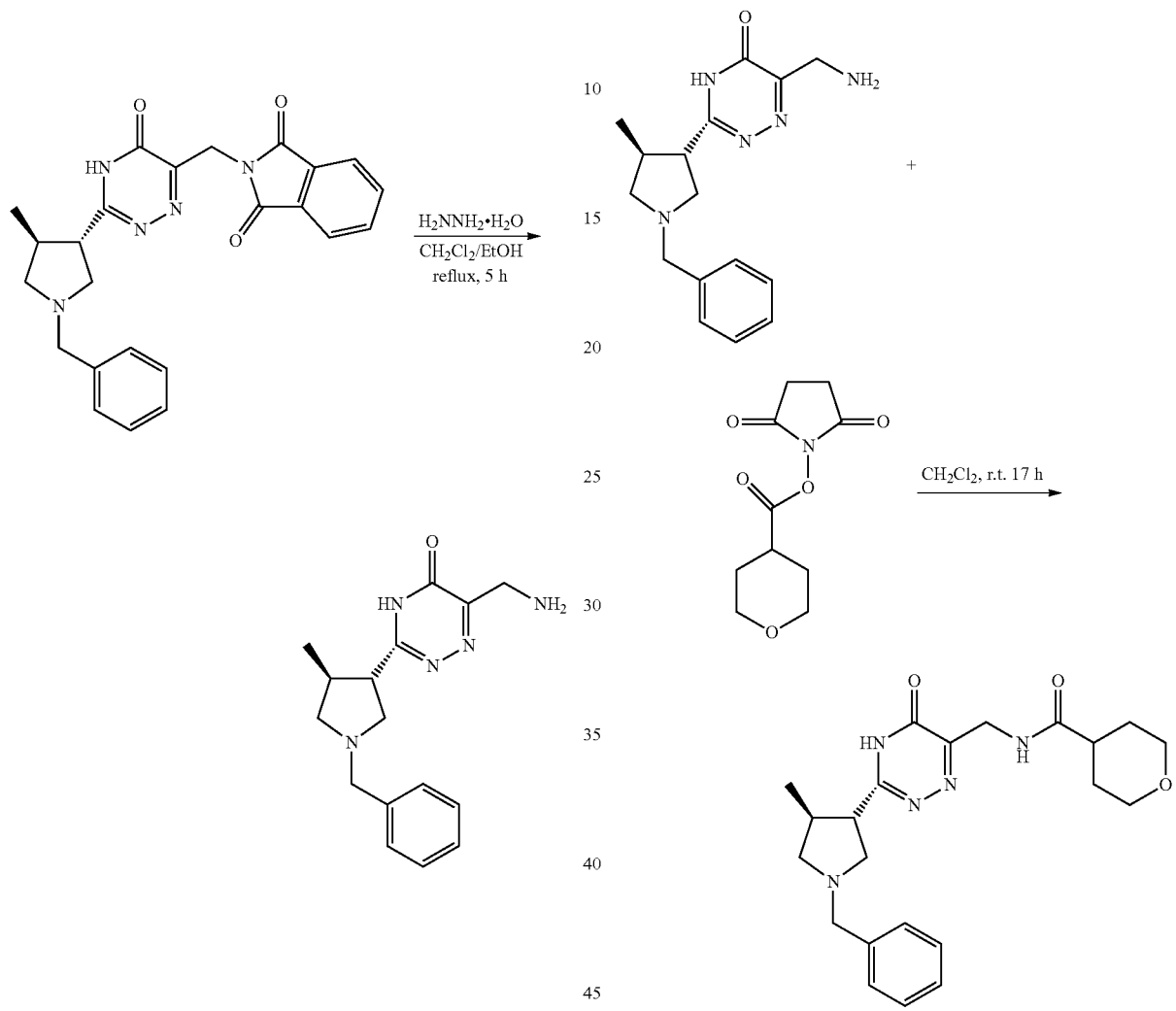

To a mixture of 2-((3-((3S,4S)-1-benzyl-4-methylpyrrolidin-3-yl)-5-oxo-4,5-dihydro-1,2,4-triazin-6-yl)methyl)isoindoline-1,3-dione (2.10 g, 4.88 mmol) in dichloromethane/ethanol (1:1, 80 mL) was added hydrazine monohydrate (0.62 g, 12.2 mmol) at RT, and the resulting solution was stirred and heated to reflux for 5 h. The cooled reaction mixture was filtered and the filter cake was rinsed with dichloromethane/ethanol (1:1, 60 mL). The combined filtrates were concentrated under reduced pressure to give crude mixture, which was purified by flash chromatography column (0.5/7.5/92-1/15/84 $NH_4OH/MeOH/CH_2Cl_2$) to provide 6-(aminomethyl)-3-((3S,4S)-1-benzyl-4-methylpyrrolidin-3-yl)-1,2,4-triazin-5(4H)-one (1.19 g, 81%) as yellow wax. $^1$H NMR (300 MHz, $CD_3OD$) δ 7.40-7.22 (m, 5H), 4.04 (s, 2H), 3.86 (d, 1H, J=12.6 Hz), 3.78 (d, 1H, J=12.6 Hz), 3.20-2.92 (m, 4H), 2.64-2.53 (m, 2H), 1.08 (d, 3H, J=6.3 Hz); $^{13}$C NMR (75 MHz, $CD_3OD$/TMS) δ 170.0, 166.5, 150.3, 138.0, 130.6, 129.5, 128.8, 62.5, 61.3, 60.2, 53.3, 41.4, 39.9, 18.8.

To a solution of 6-(aminomethyl)-3-((3S,4S)-1-benzyl-4-methylpyrrolidin-3-yl)-1,2,4-triazin-5(4H)-one (1.10 g, 3.68 mmol) in $CH_2Cl_2$ (60 mL) was added 2,5-dioxopyrrolidin-1-yl tetrahydro-2H-pyran-4-carboxylate (1.30 g, 5.51 mmol) at RT. The resulting solution was stirred at room temperature for 20 h. The reaction mixture was filtered. The filtrate was washed with sat. $NaHCO_3$ (2×20 mL). The aqueous phase was extracted with $CHCl_3$ (2×20 mL). The combined organic phase was dried over $MgSO_4$. Concentration and purification by flash chromatography over silica gel column (0.1/1.5/98.4-1/15/84 $NH_4OH/MeOH/CH_2Cl_2$) to give N-((3-((3S,4S)-1-benzyl-4-methylpyrrolidin-3-yl)-5-oxo-4,5-dihydro-1,2,4-triazin-6-yl)methyl)tetrahydro-2H-pyran-4-carboxamide (1.07 g, 71%) as a yellow solid. $^1$H NMR (300 MHz, $CDCl_3$) δ 7.46-7.30 (m, 5H), 7.00 (br s, 1H), 6.84 (br s, 1H), 4.52 (br s, 2H), 4.08-3.82 (m, 4H), 3.48-3.38 (m, 3H), 3.29 (br s, 1H), 3.22-3.04 (m, 2H), 2.70-2.38 (m, 3H), 1.92-1.77 (m, 4H), 1.06 (d, 3H, J=6.3 Hz); $^{13}$C NMR (75 MHz, $CDCl_3$) δ 174.3, 165.3, 162.7, 150.7, 134.2, 129.2, 128.7, 128.4, 67.2, 60.4, 59.6, 56.6, 50.3, 42.0, 39.7, 38.6, 29.2, 18.3.

431

Synthesis of 2-((3S,4S)-1-benzyl-4-methylpyrrolidin-3-yl)-7-(tetrahydro-2H-pyran-4-yl)imidazo[1,5-f][1,2,4]triazin-4(3H)-one

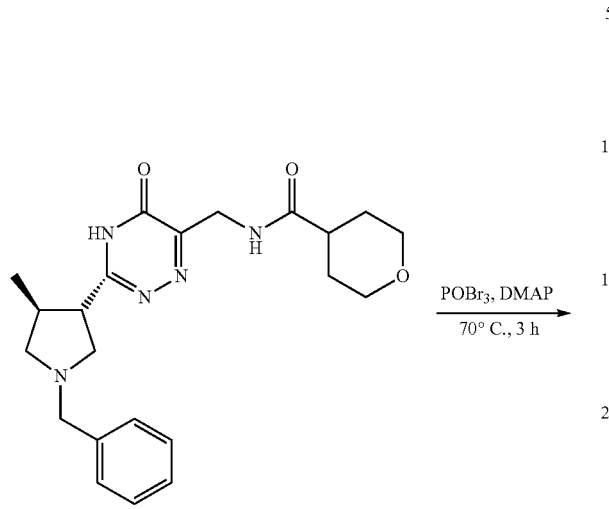

To a solution of N-((3-((3S,4S)-1-benzyl-4-methylpyrrolidin-3-yl)-5-oxo-4,5-dihydro-1,2,4-triazin-6-yl)methyl)tetrahydro-2H-pyran-4-carboxamide (1.04 g, 2.53 mmol), DMAP (34 mg, 0.25 mmol) in acetonitrile (65 mL) was added a solution of POBr$_3$ (2.18 g, 7.61 mmol) in acetonitrile (25 mL) at RT, and the resulting suspension was heated to 70° C. for 3 h. After the mixture was cooled to room temperature, it was poured into saturated NaHCO$_3$ solution (200 mL), and stirred vigorously for 0.5 h, then extracted with CH$_2$Cl$_2$ (1×90 mL, 2×40 mL). The organic extract was dried over MgSO$_4$ and concentrated under reduced pressure. The residue was purified by flash chromatography over silica gel (0.1/1.5/98.4-0.3/4.5/95.2 NH$_4$OH/MeOH/CH$_2$Cl$_2$) to furnish 2-((3S,4S)-1-benzyl-4-methylpyrrolidin-3-yl)-7-(tetrahydro-2H-pyran-4-yl)imidazo[1,5-f][1,2,4]triazin-4(3H)-one (0.72 g, 70%) as a white wax. $^1$H NMR (300 MHz, CDCl$_3$/TMS) δ 8.33 (br s, 1H), 7.78 (s, 1H), 7.42-7.22 (m, 5H), 4.13-4.02 (m, 2H), 3.81 (d, 1H, J=12.6 Hz), 3.65-3.52 (m, 3H), 3.50-3.34 (m, 2H), 2.99 (d, 1H, J=9.9 Hz), 2.83-2.75 (m, 1H), 2.57 (dd, 1H, J=9.9, 6.3 Hz), 2.52-2.40 (m, 1H), 2.19-1.84 (m, 5H), 1.23 (d, 3H, J=6.9 Hz); $^{13}$C NMR (75 MHz, CDCl$_3$/TMS) δ 154.25, 153.53, 148.32, 137.16, 128.49, 128.44, 127.34, 127.22, 118.67, 67.42, 67.38, 60.95, 59.15, 55.93, 47.78, 38.15, 32.47, 30.23, 29.97, 19.97.

432

2. Racemic synthesis of (+/−)-2-((3,4-trans)-1-benzyl-4-methylpyrrolidin-3-yl)-7-(tetrahydro-2H-pyran-4-yl)imidazo[5,1-f][1,2,4]-triazin-4(3H)-one

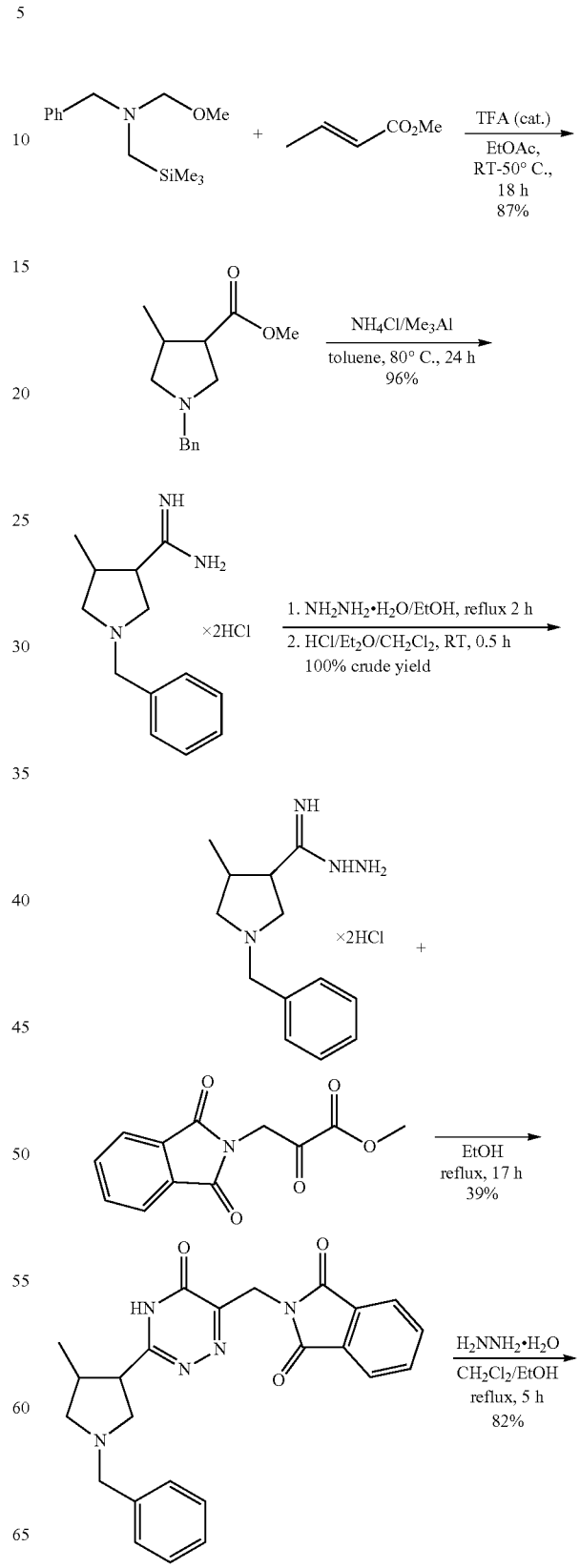

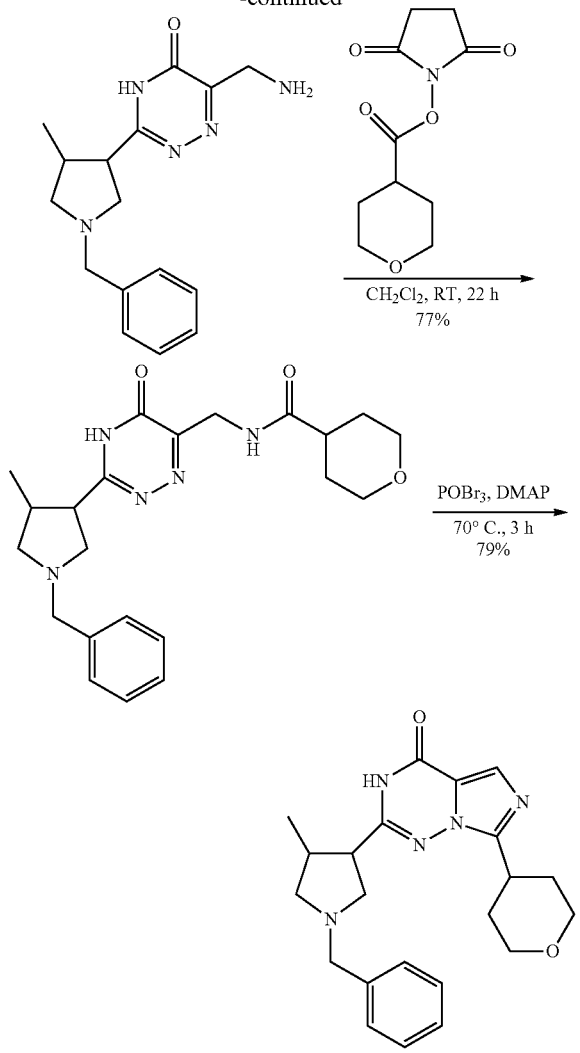

Synthesis of (+/−)-(3,4-trans)-methyl 1-benzyl-4-methylpyrrolidine-3-carboxylate

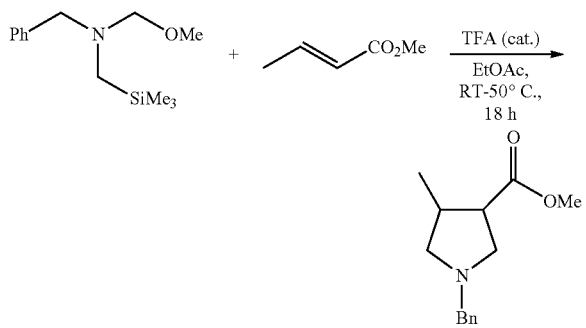

Benzylmethoxymethyl-trimethylsilanylmethylamine (118.71 g, 500 mmole) was added drop-wise to a stirred solution of methyl trans-2-pentenoate (50.00 g, 500 mmol) and TFA (1.0 mL) in dry ethyl acetate (1000 mL) at a rate to maintain the temperature below 50° C. After the addition was complete, the reaction mixture was stirred at room temperature under argon for 5 hours. Saturated NaHCO₃ (200 mL) was added and the mixture was stirred for 0.5 hour. The organic phase was separated from aqueous phase, and the latter was extracted with EtOAc (150 mL). The combined organic phases were washed with brine (100 mL), dried over magnesium sulfate. The solvent was removed under reduced pressure to give crude product as yellowish oil, which was purified by chromatography (1/20/79-1/30/69 Et₃N/EtOAc/heptane) to obtain 101.37 g of (+/−)-(3 (3,4-trans)-methyl 1-benzyl-4-methylpyrrolidine-3-carboxylate as light yellow oil (87%). ¹H NMR (300 MHz, CDCl₃/TMS): δ 7.35-7.18 (m, 5H), 3.68 (s, 3H), 3.64 (d, 1H, J=12.9 Hz), 3.56 (d, 1H, J=12.9 Hz), 2.95-2.74 (m, 3H), 2.60-2.44 (m, 2H), 2.25-2.18 (m, 1H), 1.13 (d, 3H, J=6.6 Hz); ¹³C NMR (75 MHz, CDCl₃/TMS): δ 174.9, 138.8, 128.5, 128.1, 126.8, 61.6, 60.1, 56.6, 51.7, 50.5, 36.8, 19.8.

Synthesis of (+/−)-(3,4-trans)-1-benzyl-4-methylpyrrolidine-3-carboximidamide hydricholoride

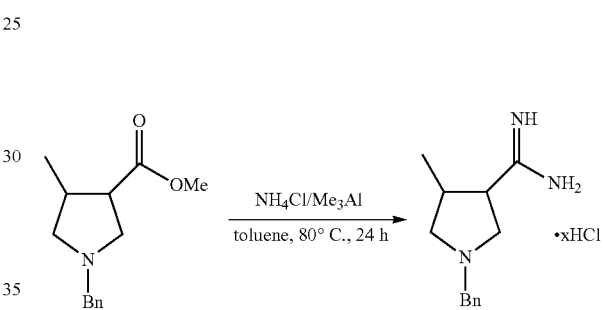

Ammonium chloride (26.75 g, 500 mmol) was suspended in dry toluene (600 mL) and the mixture was then cooled to 0° C. A solution of trimethylaluminum in hexane (250 mL, 2.0 M, 500 mmol) was added drop-wise and the resulting mixture was stirred at room temperature until no more evolution of gas was observed (about 3 hours). (+/−)-(3 (3,4-Trans)-methyl 1-benzyl-4-methylpyrrolidine-3-carboxylate (23.33 g, 100 mmol) was added and the resulting mixture was heated at 80° C. for 24 h. After cooling to 0° C., the reaction mixture was quenched by slow addition of methanol (500 mL) and then stirred vigorously at room temperature for one hour. The mixture was filtered and the filter cake was washed with methanol (3×150 mL). The combined filtrates were concentrated under reduced pressure to give a yellow solid. The solid was triturated with dichloromethane/methanol (1:1, 300 mL). The filtrate was concentrated under reduced pressure to give (+/−)-(3,4-trans)-1-benzyl-4-methylpyrrolidine-3-carboximidamide hydrochloride as a yellow wax (28.00 g, 96%). This compound was used for next step without further purification. ¹H NMR (300 MHz, CDCl₃): δ 7.60-7.25 (m, 5H), 4.08 (br s, 2H), 3.46-3.16 (m, 3H), 3.03-2.90 (m, 1H), 2.72-2.50 (m, 2H), 1.19 (d, 3H, J=6.3 Hz); ¹³C NMR (75 MHz, CDCl₃) δ 173.2, 135.7, 130.8, 129.9, 129.7, 61.2, 60.0, 57.2, 50.0, 40.3, 18.0.

Synthesis of (+/−)-(3,4-trans)-1-benzyl-4-methylpyrrolidine-3-carboximidhydrazide hydrochloride

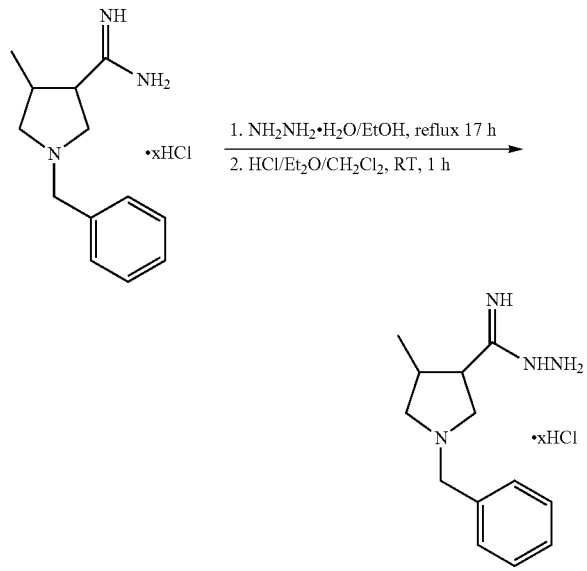

A solution of hydrazine monohydrate (2.62 g, 52.4 mmol) in EtOH (20 mL) was added slowly to a solution of (+/−)-(3,4-trans)-1-benzyl-4-methylpyrrolidine-3-carboximidamide hydrochloride (15.21 g, 52.4 mmol) in ethanol (200 mL). The resulting white suspension was stirred at reflux for 2 h. The reaction mixture was cooled to RT and the white solid was filtered. The filtrate was concentrated under reduced pressure to give a light pink wax. The material was dissolved in a minimum $CH_2Cl_2$ (20 mL), and to this stick solution was added 2M HCl in ether (70 mL) drop-wise at RT with stirring. Then anhydrous ether (50 mL) was added. The resulting yellow suspension was stirred at RT under argon for 0.5 h. The solid was filtered and rinsed with ether, dried over high vacuum to provide crude salt (+/−)-(3,4-trans)-1-benzyl-4-methylpyrrolidine-3-carboximidhydrazide hydrochloride (16.50 g, 103%). This material was used for next step without further purification.

Synthesis of (+/−)-2-((3-((3,4-trans)-1-benzyl-4-methylpyrrolidin-3-yl)-5-oxo-4,5-dihydro-1,2,4-triazin-6-yl)methyl)isoindoline-1,3-dione

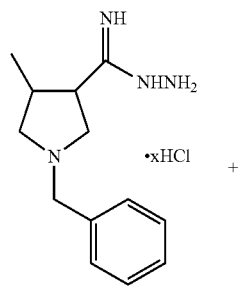

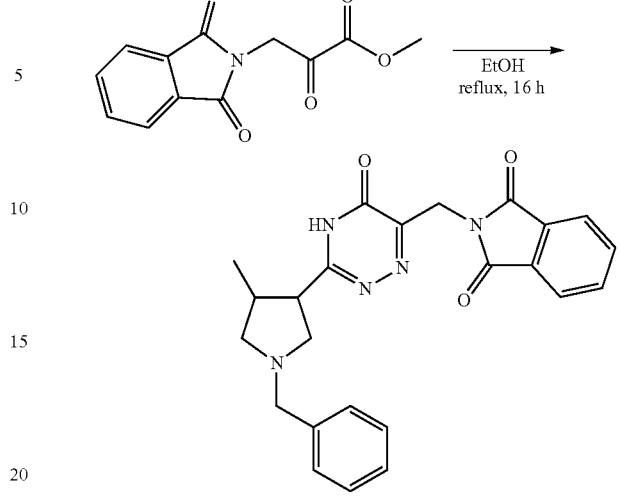

The mixture of (+/−)-(3,4-trans)-1-benzyl-4-methylpyrrolidine-3-carboximidhydrazide hydrochloride (2.69 g, 8.8 mmol) and methyl 3-(1,3-dioxoisoindolin-2-yl)-2-oxopropanoate (2.18 g, 8.8 mmol) in anhydrous ethanol (25 mL) was heated under reflux and argon for 17 h. The cooled reaction mixture was concentrated under reduced pressure and the residue was triturated with 2% $MeOH/CH_2Cl_2$ (20 mL) to give a yellow solid. The solid was suspended in $CHCl_3$ (25 mL) and the pH value was adjusted to 8 with saturated $NaHCO_3$. The organic phase was separated from aqueous phase, and the latter was extracted with $CHCl_3$ (2×10 mL). The combined organic phase was dried over $MgSO_4$. After concentration the residue purified by flash chromatography over silica gel column (0.1/1.5/98.4-0.6/9/90.4 $NH_4OH/MeOH/CH_2Cl_2$) to give (+/−)-2-((3-((3,4-trans)-1-benzyl-4-methylpyrrolidin-3-yl)-5-oxo-4,5-dihydro-1,2,4-triazin-6-yl)methyl)isoindoline-1,3-dione (1.46 g, 39%) as light yellow solid. $^1$H NMR (300 MHz, $CD_3OD$/$CDCl_3$) δ 7.92-7.85 (m, 2H), 7.81-7.74 (m, 2H), 7.34 (m, 5H), 4.97 (s, 2H), 3.98 (d, 1H, J=12.3 Hz), 3.89 (d, 1H, J=12.3 Hz), 3.40-3.24 (m, 1H), 3.22-3.17 (m, 2H), 3.08-2.98 (m, 1H), 2.65-2.50 (m, 2H), 1.03 (d, 3H, J=6.0 Hz); $^{13}$C NMR (75 MHz, $CD_3OD$/$CDCl_3$) δ 168.3, 165.7, 163.7, 148.6, 134.3, 134.0, 132.2, 129.6, 128.9, 128.7, 123.4, 60.6, 59.6, 57.4, 50.3, 38.8, 37.7, 17.6.

Synthesis of (+/−)-6-(aminomethyl)-3-((3,4-trans)-1-benzyl-4-methylpyrrolidin-3-yl)-1,2,4-triazin-5(4H)-one

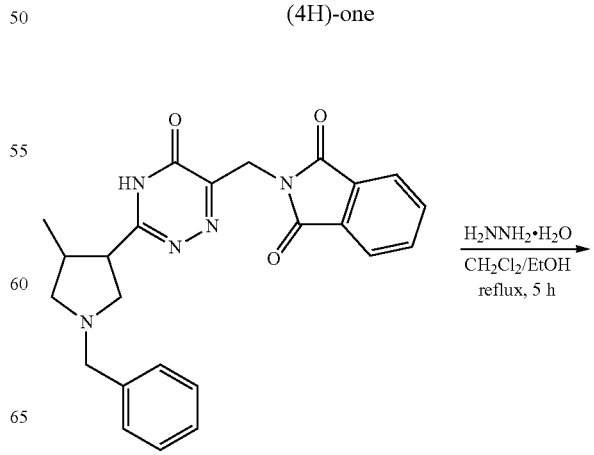

-continued

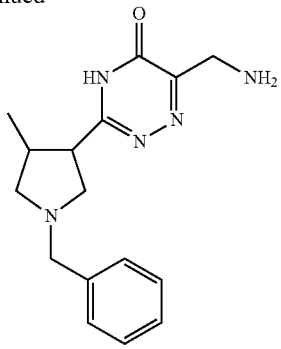

To a mixture of (+/−)-2-((3-((3,4-trans)-1-benzyl-4-methylpyrrolidin-3-yl)-5-oxo-4,5-dihydro-1,2,4-triazin-6-yl)methyl)isoindoline-1,3-dione (2.19 g, 5.1 mmol) in dichloromethane/ethanol (1:1, 80 mL) was added hydrazine monohydrate (0.64 g, 12.7 mmol) at RT, and the resulting suspension was stirred and heated to reflux for 5 h. The cooled reaction mixture was filtered and the filter cake was rinsed with dichloromethane/ethanol (1:1, 80 mL). The combined filtrates were concentrated under reduced pressure to give crude mixture, which was purified by flash chromatography column (0.5/7.5/92-1/15/84 NH$_4$OH/MeOH/CH$_2$Cl$_2$) to provide (+/−)-6-(aminomethyl)-3-((3,4-trans)-1-benzyl-4-methylpyrrolidin-3-yl)-1,2,4-triazin-5(4H)-one (1.25 g, 82%) as off-white wax. $^1$H NMR (300 MHz, CD$_3$OD) δ 7.45-7.27 (m, 5H), 4.04 (br s, 2H), 3.88 (d, 1H, J=12.6 Hz), 3.80 (d, 1H, J=12.6 Hz), 3.20-2.92 (m, 4H), 2.63-2.55 (m, 2H), 1.08 (d, 3H, J=5.7 Hz); $^{13}$C NMR (75 MHz, CD$_3$OD) δ 170.0, 166.5, 150.1, 137.8, 130.6, 129.6, 128.9, 62.4, 61.3, 60.1, 53.2, 41.3, 39.9, 18.8.

Synthesis of (+/−)-N-((3-((3,4-trans)-1-benzyl-4-methylpyrrolidin-3-yl)-5-oxo-4,5-dihydro-1,2,4-triazin-6-yl)methyl)tetrahydro-2H-pyran-4-carboxamide

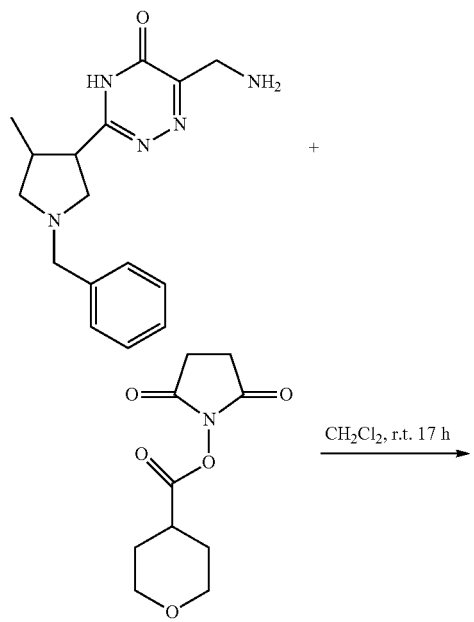

-continued

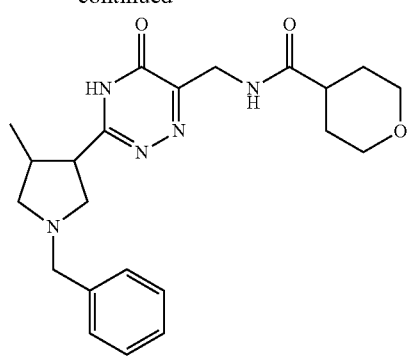

To a suspension of (+/−)-6-(aminomethyl)-3-((3,4-trans)-1-benzyl-4-methylpyrrolidin-3-yl)-1,2,4-triazin-5(4H)-one (1.00 g, 3.34 mmol) in CH$_2$Cl$_2$ (45 mL) was added 2,5-dioxopyrrolidin-1-yl tetrahydro-2H-pyran-4-carboxylate (1.19 g, 5.01 mmol) at room temperature. The resulting solution was stirred at room temperature for 22 h. The reaction mixture was filtered. The filtrate was washed with sat. NaHCO$_3$ (2×10 mL). The aqueous phase was extracted with CHCl$_2$ (3×10 mL). The combined organic phase was dried over MgSO$_4$. Concentration and purification by flash chromatography over silica gel column (0.1/1.5/98.4-1/15/84 NH$_4$OH/MeOH/CH$_2$Cl$_2$) to give (+/−)-N-((3-((3,4-trans)-1-benzyl-4-methylpyrrolidin-3-yl)-5-oxo-4,5-dihydro-1,2,4-triazin-6-yl)methyl)tetrahydro-2H-pyran-4-carboxamide (1.06 g, 77%) as a yellow solid. $^1$H NMR (300 MHz, CDCl$_3$) δ 9.99 (br s, 1H, br), 7.36-7.26 (m, 5H), 6.81 (br s, 1H), 4.50 (d, 2H, J=4.5 Hz), 4.04-3.78 (m, 4H), 3.46-3.37 (m, 3H), 3.20 (br s, 1H), 3.04-2.75 (m, 2H), 2.60-2.28 (m, 2H), 2.28-2.15 (m, 1H), 1.91-1.77 (m, 4H), 1.13 (d, 3H, J=6.3 Hz); $^{13}$C NMR (75 MHz, CDCl$_3$) δ 174.2, 165.8, 162.3, 151.0, 134.8, 129.0, 128.8, 128.2, 67.3, 60.5, 59.6, 56.4, 50.0, 42.2, 39.9, 38.8, 29.2, 19.5.

Synthesis of (+)-2-((3,4-trans)-1-benzyl-4-methylpyrrolidin-3-yl)-7-(tetrahydro-2H-pyran-4-yl)imidazo[1,5-f][1,2,4]triazin-4(3H)-one and (−)-2-((3,4-trans)-1-benzyl-4-methylpyrrolidin-3-yl)-7-(tetrahydro-2H-pyran-4-yl)imidazo[1,5-f][1,2,4]triazin-4(3H)-one

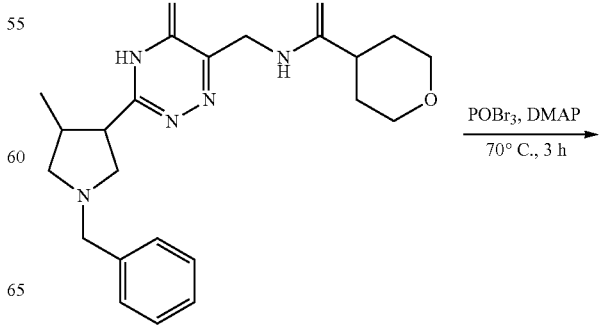

-continued

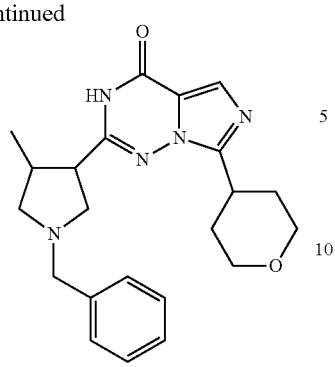

To a solution of (+/−)-N-((3-((3,4-trans)-1-benzyl-4-methylpyrrolidin-3-yl)-5-oxo-4,5-dihydro-1,2,4-triazin-6-yl)methyl)tetrahydro-2H-pyran-4-carboxamide (500 mg, 1.2 mmol), DMAP (15 mg, 0.12 mmol) in acetonitrile (25 mL) was added a solution of $POBr_3$ (1045 mg, 3.6 mmol) in acetonitrile (5 mL) at RT, and the resulting suspension was heated to 70° C. for 3 h. After the mixture was cooled to room temperature, it was poured into saturated $NaHCO_3$ solution (100 mL), and stirred vigorously for 0.5 h, then extracted with $CH_2Cl_2$ (3×25 mL). The organic extract was dried over $MgSO_4$ and concentrated under reduced pressure. The residue was purified by flash chromatography over silica gel (0.1/1.5/98.4-0.5/7.5/92 $NH_4OH$/MeOH/$CH_2Cl_2$) to furnish (+/−)-2-((3,4-trans)-1-benzyl-4-methylpyrrolidin-3-yl)-7-(tetrahydro-2H-pyran-4-yl)imidazo[1,5-f][1,2,4]triazin-4(3H)-one (380 mg, 79%) as a yellow wax.

Racemic (+/−)-2-((3,4-trans)-1-benzyl-4-methylpyrrolidin-3-yl)-7-(tetrahydro-2H-pyran-4-yl)imidazo[1,5-f][1,2,4]triazin-4(3H)-one was purified by Chiralpak IA, 250×20 mm, 5 um (100 mg loading; 0.1% TEA in n-Hexane:IPA (90:10) as mobile phase) to obtain (−)-2-((3,4-trans)-1-benzyl-4-methylpyrrolidin-3-yl)-7-(tetrahydro-2H-pyran-4-yl)imidazo[1,5-f][1,2,4]triazin-4(3H)-one and (+)-2-((3,4-trans)-1-benzyl-4-methylpyrrolidin-3-yl)-7-(tetrahydro-2H-pyran-4-yl)imidazo[1,5-f][1,2,4]triazin-4(3H)-one.

(−)-2-((3,4-trans)-1-benzyl-4-methylpyrrolidin-3-yl)-7-(tetrahydro-2H-pyran-4-yl)imidazo[1,5-f][1,2,4]triazin-4(3H)-one: H-NMR (DMSO $d_6$, 400 MHz): δ 7.65 (s, 1H), 7.34-7.29 (m, 4H), 7.24-7.21 (m, 1H), 3.94-3.92 (m, 2H), 3.68-3.64 (m, 2H), 3.52-3.47 (m, 4H), 2.98-2.87 (m, 4H), 2.64-2.61 (m, 1H), 2.28-2.24 (m, 1H), 1.89-1.82 (m, 4H), 1.09 (d, 3H); Mass (ESI): 394 [$M^+$+1]; UPLC (purity): 99.07%; (column; Acquity BEH C-18, 50×2.1 mm, 1.7μ; RT 1.42 min. 0.025% TFA (Aq): ACN:Water; 0.50 ml/min.; Chiral HPLC: 99.34% ee $R_t$=17.21 min (Chiralpak IA, 250×4.6 mm, 5μ; mobile phase (A) 0.1% TEA in n-Hexane (B) Ethanol (A:B:90:10); flow Rate: 1.00 mL/min); Optical rotation $[α]_D^{27}$: −22.72° (c=0.25, DCM).

(+)-2-((3,4-trans)-1-benzyl-4-methylpyrrolidin-3-yl)-7-(tetrahydro-2H-pyran-4-yl)imidazo[1,5-f][1,2,4]triazin-4(3H)-one: H-NMR (DMSO $d_6$, 400 MHz): δ 7.64 (s, 1H), 7.32-7.29 (m, 4H), 7.24-7.21 (m, 1H), 3.94-3.92 (m, 2H), 3.68-3.64 (m, 2H), 3.52-3.47 (m, 2H), 3.42-3.39 (m, 2H), 2.94-2.91 (m, 2H), 2.82-2.78 (m, 2H), 2.68-2.64 (m, 1H), 2.32-2.27 (m, 1H), 1.92-1.87 (m, 4H), 1.09 (d, 3H); Mass (ESI): 394 [$M^+$+1]; UPLC (purity): 99.73%; (column; Acquity BEH C-18, 50×2.1 mm, 1.7μ; RT 1.42 min. 0.025% TFA (Aq): ACN:Water; 0.50 ml/min.; Chiral HPLC: 99.55% ee $R_t$=21.37 min (Chiralpak IA, 250×4.6 mm, 5μ; mobile phase (A) 0.1% TEA in n-Hexane (B) Ethanol (A:B:90:10); flow Rate: 1.00 mL/min); Optical rotation $[α]_D^{27}$: +22.22° (c=0.25, DCM).

3. Synthesis of (+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one

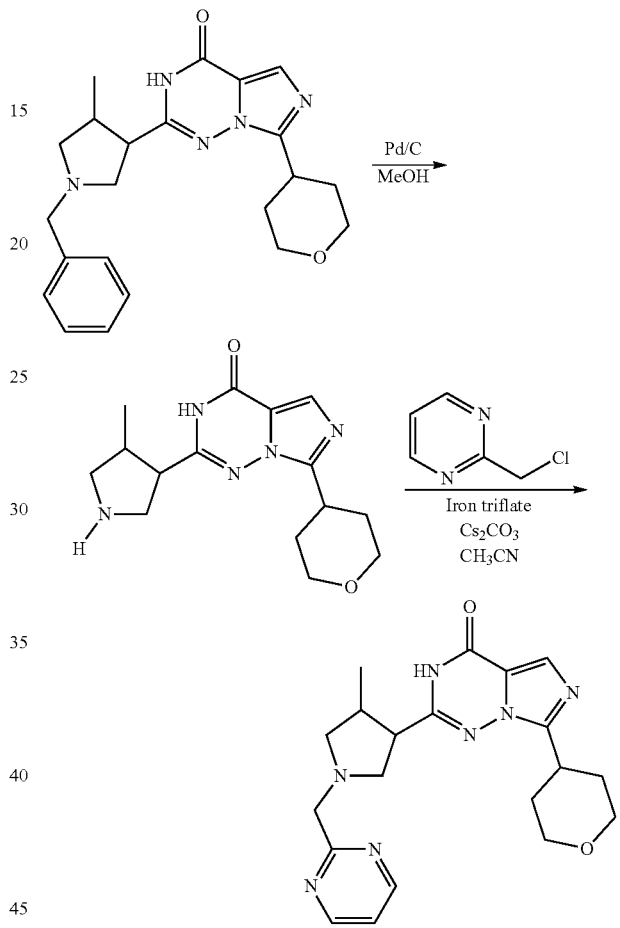

Synthesis of (−)-2-((3,4-trans)-4-methylpyrrolidin-3-yl)-7-(tetrahydro-2H-pyran-4-yl)imidazo[5,1-f][1,2,4]triazin-4(3H)-one

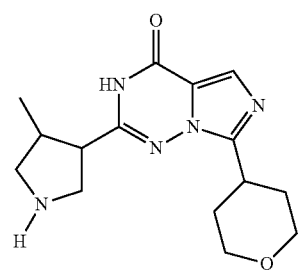 [SMILES: CC1CNCC1c1nn2c(C3CCOCC3)ncc2c(=O)[nH]1]

To a stirred solution of (−)-2-((3,4-trans)-1-benzyl-4-methylpyrrolidin-3-yl)-7-(tetrahydro-2H-pyran-4-yl)imidazo[1,5-f][1,2,4]triazin-4(3H)-one (0.5 g 1.27 mmol) in MeOH (30 mL) was added 10% Pd—C (150 mg) and stirred at RT for 16 h under H₂ atmosphere (balloon pressure). The reaction mixture was passed through a pad of celite and dried in vacuo to obtain crude. The crude material was triturated with pentane to afford (−)-2-((3,4-trans)-4-methylpyrrolidin-3-yl)-7-(tetrahydro-2H-pyran-4-yl)imidazo[5, 1-f][1,2,4]triazin-4(3H)-one (360 mg, 1.18 mmol, 94%) as an off-white solid. ¹H-NMR (DMSO d₆, 400 MHz): δ 7.58 (s, 1H), 3.95-3.85 (m, 4H), 3.54-3.48 (m, 2H), 3.38-3.32 (m, 1H), 3.24-3.22 (m, 2H), 3.07-3.02 (m, 1H), 2.68-2.64 (m, 1H), 2.44-2.41 (m, 2H), 1.87-1.82 (m, 4H), 1.04 (d, 3H); Mass (ESI): 304 [M⁺+1]; LC-MS: 98.57%; 304 (M⁺+1); (column; X-bridge C-18, (50×3.0 mm, 3.5µ); RT 1.77 min. 5 mM NH₄OAc: ACN; 0.8 ml/min); UPLC (purity): 97.43%; (column; Acquity UPLC HSS T3, 2.1×100 mm, 1.7µ; RT 2.83 min. 0.025% aqueous TFA: ACN:Water; 0.3 ml/min.; TLC: 10% MeOH/CH₂Cl₂ (Rf: 0.2); Optical rotation $[\alpha]_D^{27}$: −69° (c=0.25, DMF).

Synthesis of (+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one

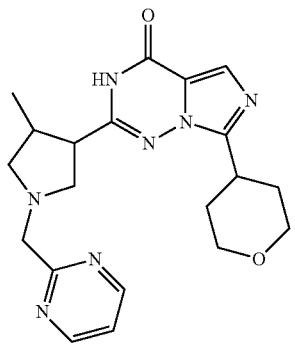 [SMILES: CC1CN(Cc2ncccn2)CC1c1nn2c(C3CCOCC3)ncc2c(=O)[nH]1]

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 2-(chloromethyl)pyrimidine (46.46 mg, 0.36 mmol), iron triflate (33.20 mg, 0.066 mmol) and Cs₂CO₃ (236 mg, 0.72 mmol) at RT under inert atmosphere. The reaction mixture was heated to 70° C. and stirred for 4 h. After completion of starting material (by TLC), the reaction mixture was diluted with water and extracted with EtOAc (3×25 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one (60 mg, 46%) as an off-white solid. ¹H-NMR (DMSO d₆, 500 MHz): δ 8.78 (d, 2H), 7.62 (s, 1H), 7.29 (t, 1H), 4.02-3.98 (m, 1H), 3.94-3.87 (m, 2H), 3.85-3.82 (m, 1H), 3.48-3.42 (m, 2H), 3.38-3.34 (m, 2H), 3.18-3.12 (m, 1H), 2.29-2.27 (m, 2H), 2.81-2.76 (m, 1H), 2.62-2.59 (m, 1H), 2.18-2.16 (m, 1H), 1.84-1.79 (m, 4H), 1.04 (d, 3H); Mass (ESI): 396.5 [M⁺+1]; LC-MS: 95.73%; 396.4 (M⁺+1); (column; X-bridge C-18, (50×3.0 mm, 3.5µ); RT 2.91 min. 5 mM NH₄OAc: ACN; 0.8 ml/min); UPLC (purity): 99.06%; (column; Acquity UPLC HSS T3, 2.1×100 mm, 1.7µ; RT 2.75 min. 0.025% TFA (Aq): ACN:Water; 0.3 ml/min.; Chiral HPLC: 100% ee R$_t$=26.48 min (Chiralpak IC, 250× 4.6 mm, 5µ; mobile phase (A) 0.1% TEA in n-Hexane (B) ethanol (A:B:50:50); flow Rate: 1.00 mL/min); Optical rotation $[\alpha]_D^{25}$: +115.88° (c=0.5, DCM); TLC: 10% MeOH/ DCM (Rf: 0.7).

4. Synthesis of (−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one

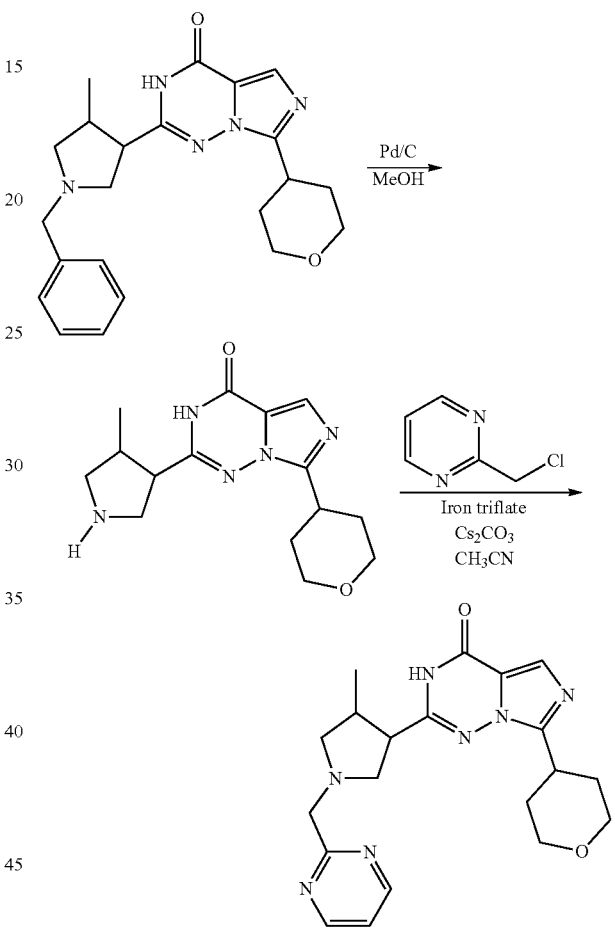

Synthesis of (+)-2-((3,4-trans)-4-methylpyrrolidin-3-yl)-7-(tetrahydro-2H-pyran-4-yl)imidazo[5,1-f][1,2,4]triazin-4(3H)-one

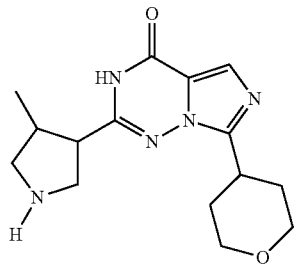 [SMILES: CC1CNCC1c1nn2c(C3CCOCC3)ncc2c(=O)[nH]1]

To a stirred solution of (+)-2-((3,4-trans)-1-benzyl-4-methylpyrrolidin-3-yl)-7-(tetrahydro-2H-pyran-4-yl)imidazo[5,1-f][1,2,4]triazin-4(3H)-one (0.5 g 1.27 mmol) in MeOH (30 mL) was added 10% Pd—C (150 mg) and stirred at RT for 16 h under H$_2$ atmosphere (balloon pressure). The reaction mixture was passed through a pad of celite and dried in vacuo to obtain crude. The crude material was triturated with n-pentane to afford (+)-2-((3,4-trans)-4-methylpyrrolidin-3-yl)-7-(tetrahydro-2H-pyran-4-yl)imidazo[5,1-f][1,2,4]triazin-4(3H)-one (365 mg, 1.20 mmol, 95%) as an off-white solid. $^1$H-NMR (DMSO d$_6$, 400 MHz): δ 7.56 (s, 1H), 3.96-3.87 (m, 5H), 3.52-3.48 (m, 3H), 3.42-3.37 (m, 1H), 3.28-3.21 (m, 2H), 3.18-3.14 (m, 1H), 2.67-2.64 (m, 1H), 2.42-2.38 (m, 2H), 1.89-1.86 (m, 2H), 0.96 (d, 3H); LC-MS: 98.34%; 304.8 (M$^+$+1); (column; Chromolith RP-18e, (100×4.6 mm); RT 3.47 min. 5 mM NH$_4$OAc: ACN; 1.0 ml/min); UPLC (purity): 98.81%; (column; Acquity HSS T3, 2.1×100 mm, 1.7μ; RT 2.77 min. 0.025% aqueous TFA: ACN: Water; 0.3 ml/min.; TLC: 10% MeOH/CH$_2$Cl$_2$ (Rf: 0.2); Optical rotation [α]$_D^{27}$: +61° (c=0.25, DMF).

Synthesis of (−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one

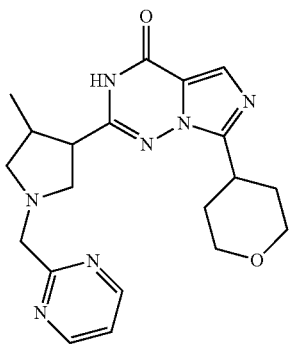 [SMILES: CC1CN(Cc2ncccn2)CC1c1nn2c(C3CCOCC3)ncc2c(=O)[nH]1]

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added 2-(chloromethyl)pyrimidine (34 mg, 0.27 mmol), iron triflate (24 mg, 0.047 mmol) and Cs$_2$CO$_3$ (161 mg, 0.49 mmol) at RT under inert atmosphere. The reaction mixture was heated to 70° C. and stirred for 4 h. After completion of starting material (by TLC), the reaction mixture was diluted with water and extracted with EtOAc (3×25 mL). Combined organic layer was dried over sodium sulphate, filtered and concentrated in vacuo to obtain the crude product. The crude material was purified by silica gel column chromatography and then further washed with pentane to afford (−)-2-((3,4-trans)-4-methyl-1-(pyrimidin-2-ylmethyl)pyrrolidin-3-yl)-7-(tetrahydro-2H-pyran-4-yl)imidazo[5,1-f][1,2,4]triazin-4(3H)-one (50 mg, 52%) as an off-white solid. $^1$H-NMR (DMSO d$_6$, 400 MHz): δ 11.67 (br s, 1H), 8.79 (s, 2H), 7.62 (s, 1H), 7.42 (t, 1H), 4.18-4.12 (m, 1H), 3.96-3.92 (m, 2H), 3.82-3.78 (m, 1H), 3.52-3.48 (m, 2H), 3.41-3.38 (m, 2H), 3.18-3.14 (m, 1H), 3.06-2.98 (m, 2H), 2.82-2.78 (m, 1H), 2.62-2.59 (m, 1H), 1.86-1.82 (m, 4H), 1.14 (d, 3H); Mass (ESI): 396 [M$^+$+1]; LC-MS: 96.67%; 396 (M$^+$+1); (column; X-bridge C-18, (50×3.0 mm, 3.5μ); RT 2.64 min. 5 mM NH$_4$OAc: ACN; 0.8 ml/min); UPLC (purity): 99.80%; (column; Acquity UPLC HSS T3, 2.1×100 mm, 1.7μ; RT 2.94 min. 0.025% TFA (Aq): ACN: Water; 0.3 ml/min.; Chiral HPLC: 99.35% ee R$_t$=41.20 min (Chiralpak IC, 250×4.6 mm, 5μ; mobile phase (A) 0.1% TEA in n-Hexane (B) ethanol (A:B:50:50); flow Rate: 1.00 mL/min); Optical rotation [α]$_D^{24}$: −116.01° (c=0.5, DCM); TLC: 10% MeOH/DCM (Rf:0.5).

5. Synthesis of (+)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one

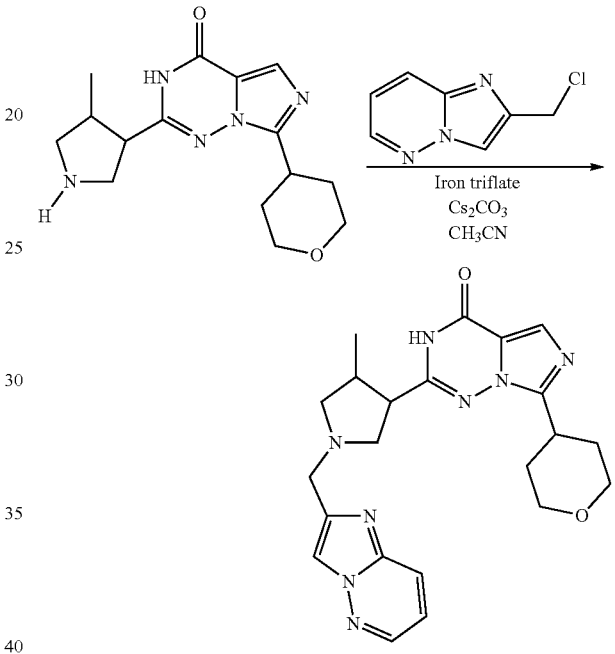

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (0.1 g, 0.33 mmol) in ACN (10 mL) were added 2-(chloromethyl)imidazo[1,2-b]pyridazine (60.62 mg, 0.36 mmol), iron triflate (33.20 mg, 0.066 mmol) and Cs$_2$CO$_3$ (236 mg, 0.72 mmol) at RT under inert atmosphere. The reaction mixture was heated to 70° C. and stirred for 4 h. After completion of starting material (by TLC), the reaction mixture was cooled to RT; diluted with water and extracted with EtOAc (3×25 mL). Combined organic layer was dried over sodium sulphate, filtered and concentrated in vacuo to obtain the crude product. The crude material was purified by silica gel column chromatography to afford (+)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one (70 mg, 51.95%) as an off-white solid. $^1$H-NMR (DMSO d$_6$, 400 MHz): δ 8.45 (d, 1H), 8.14 (s, 1H), 8.02 (d, 1H), 7.64 (s, 1H), 7.18-7.12 (m, 1H), 3.92-3.84 (m, 5H), 3.08-3.04 (m, 4H), 2.94-2.91 (m, 2H), 2.82-2.78 (m, 1H), 2.69-2.64 (m, 1H), 2.34-2.31 (m, 1H), 1.87-1.82 (m, 4H), 1.08 (d, 3H); Mass (ESI): 435 [M$^+$+1]; LC-MS: 93.22%; 435 (M$^+$+1); (column; X-bridge C-18, (50×3.0 mm, 3.5μ); RT 2.62 min. 5 mM NH$_4$OAc: ACN; 0.8 ml/min); HPLC (purity): 99.91%; (column; Acquity BEH C-18, 50×2.1 mm, 1.7μ; RT 1.21 min. 0.025% TFA (Aq): ACN:Water; 0.50 ml/min.; Chiral HPLC: 99.14% ee $R_t$=22.18 min (Chiralpak IC, 250×4.6 mm, 5μ; mobile phase (A) 0.1% TEA in n-Hexane (B) ethanol (A:B:40:60); flow Rate: 1.00 mL/min); Optical rotation $[\alpha]_D^{25}$: +48.76° (c=0.5, DCM); TLC: 10% MeOH/DCM (Rf: 0.5).

6. Synthesis of (−)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]-triazin-4(3H)-one

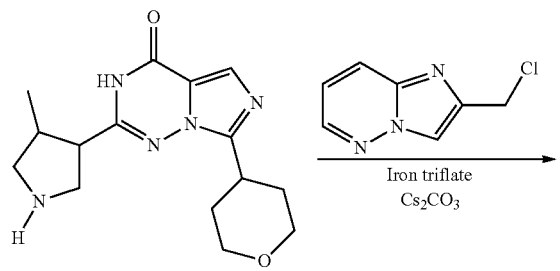

(B) ethanol (A:B:40:60); flow Rate: 1.00 mL/min); Optical rotation $[\alpha]_D^{25}$: −45.21° (c=0.5, DCM). TLC: 10% MeOH/DCM (Rf: 0.5).

6a. (−)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one

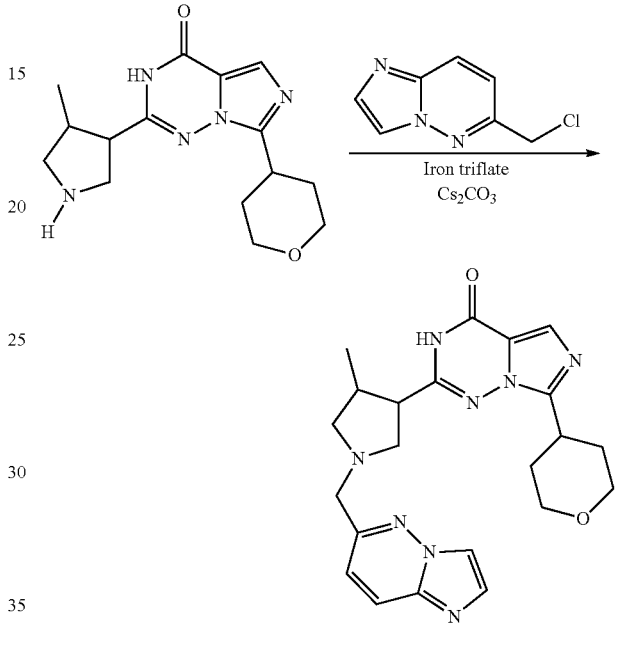

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in ACN (20 mL) were added 2-(chloromethyl)imidazo[1,2-b]pyridazine (90 mg, 0.54 mmol), iron triflate (48 mg, 0.095 mmol) and $Cs_2CO_3$ (322 mg, 0.99 mmol) at RT under inert atmosphere. The reaction mixture was heated to 70° C. and stirred for 4 h. After completion of starting material (by TLC), the reaction mixture was diluted with water and extracted with EtOAc (3×25 mL). Combined organic layer was dried over sodium sulphate, filtered and concentrated in vacuo to obtain the crude product. The crude material was purified by silica gel column chromatography and then further triturated with n-pentane to afford (−)-2-((3,4-trans)-1-(imidazo[1,2-b]pyridazin-2-ylmethyl)-4-methylpyrrolidin-3-yl)-7-(tetrahydro-2H-pyran-4-yl)imidazo[5,1-f][1,2,4]triazin-4(3H)-one (78 mg, 36%) as an off-white solid. $^1$H-NMR (DMSO $d_6$, 400 MHz): δ 8.48 (t, 1H), 8.16 (s, 1H), 8.04 (d, 1H), 7.64 (s, 1H), 7.21-7.16 (m, 1H), 3.46-3.34 (m, 6H), 3.12-3.04 (m, 3H), 2.96-2.94 (m, 1H), 2.84-2.78 (m, 1H), 2.69-2.64 (m, 1H), 2.41-2.36 (m, 1H), 1.86-1.82 (m, 4H), 1.09 (d, 3H); Mass (ESI): 435 [M$^+$+1]; LC-MS: 97.00%; 435 (M$^+$+1); (column; X-bridge C-18, (50×3.0 mm, 3.5μ); RT 2.54 min. 5 mM NH$_4$OAc: ACN; 0.8 ml/min); UPLC (purity): 99.79%; (column; Acquity BEH C-18, 50×2.1 mm, 1.7μ; RT 1.20 min. 0.025% TFA (Aq): ACN:Water; 0.50 ml/min.; Chiral HPLC: 99.32% ee $R_t$=36.69 min (Chiralpak IC, 250×4.6 mm, 5μ; mobile phase (A) 0.1% TEA in n-Hexane To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 6-(chloromethyl)imidazo[1,2-b]pyridazine (60.6 mg, 0.33 mmol), iron triflate (33.2 mg, 0.066 mmol) and $Cs_2CO_3$ (215 mg, 0.66 mmol) at RT under inert atmosphere. The reaction mixture was heated to 70° C. and stirred for 4 h. After completed consumption of starting material (by TLC), the reaction mixture was diluted with water and extracted with EtOAc (3×25 mL). The combined organic layers were dried over sodium sulfate, filtered and concentrated in vacuo to obtain the crude product. The crude material was purified by silica gel column chromatography and then further washed with 20% DCM/ether to afford (−)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one (55 mg, 38%) as an off-white solid. $^1$H-NMR (DMSO $d_6$, 400 MHz): δ 11.67 (br s, 1H), 8.21 (s, 1H), 8.06 (d, 1H), 7.74 (s, 1H), 7.64 (s, 1H), 7.21 (d, 1H), 3.94-3.78 (m, 4H), 3.52-3.48 (m, 3H), 3.18-2.82 (m, 4H), 2.72-2.68 (m, 1H), 2.38-2.32 (m, 1H), 1.92-1.84 (m, 4H), 1.12 (d, 3H); Mass (ESI): 435.5 [M$^+$+1]; LC-MS: 96.67%; 435.6 (M$^+$+1); (column; X-Select C-18, (50×3.0 mm, 3.5μ); RT 2.54 min. 5 mM NH$_4$OAc in water: ACN; 0.8 ml/min); UPLC (purity): 95.02%; (column; Acquity UPLC HSS T3, 2.1×100 mm, 1.7μ; RT 2.86 min. 0.025% TFA (Aq): ACN:Water; 0.3 ml/min.; Chiral HPLC: 100% ee $R_t$=35.95 min (Chiralpak IC, 250×4.6 mm, 5μ; mobile phase (A) 0.1% TEA in n-Hexane (B) ethanol (A:B:25:75); flow Rate: 1.00 mL/min); Optical rotation [α]$_D^{25}$: −101.22° (c=0.5, DCM). TLC: 10% MeOH/DCM (Rf: 0.5).

7. (+)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one

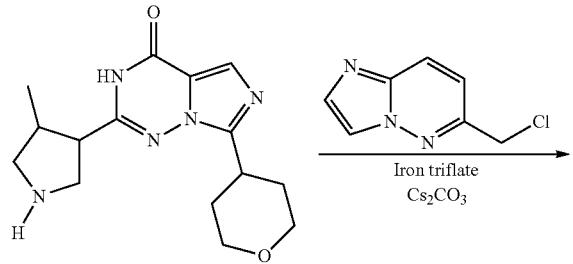

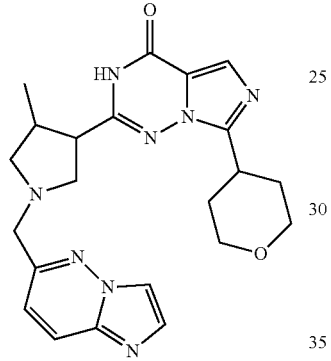

8. (+)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one

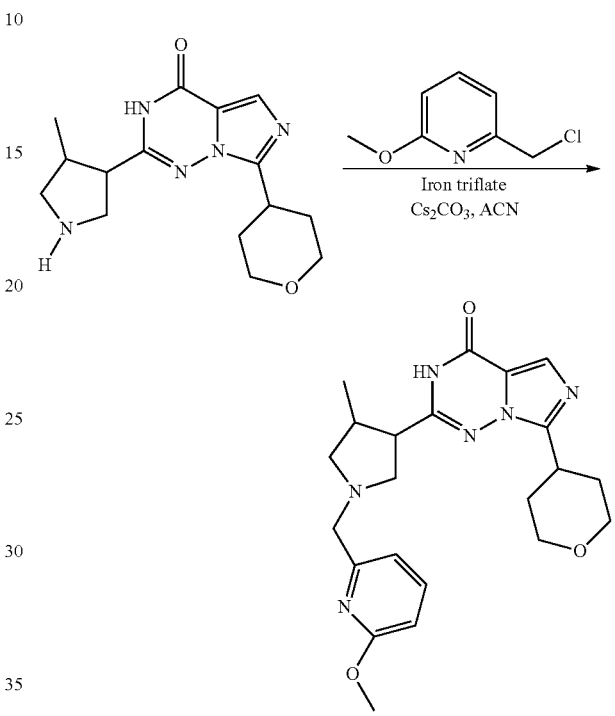

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 6-(chloromethyl)imidazo[1,2-b]pyridazine (60.62 mg, 0.36 mmol), iron triflate (33.2 mg, 0.066 mmol) and Cs$_2$CO$_3$ (236 mg, 0.72 mmol) at RT under inert atmosphere. The reaction mixture was heated to 70° C. and stirred for 4 h. After full consumption of starting material (by TLC), the reaction mixture was diluted with water and extracted with EtOAc (3×25 mL). The combined organic layers were dried over sodium sulfate, filtered and concentrated in vacuo to obtain the crude product. The crude material was purified by silica gel column chromatography and then further washed with 20% DCM/ether to afford (+)-2-((3,4-trans)-1-(imidazo[1,2-b]pyridazin-6-ylmethyl)-4-methylpyrrolidin-3-yl)-7-(tetrahydro-2H-pyran-4-yl)imidazo[5,1-f][1,2,4]triazin-4(3H)-one (70 mg, 49%) as an off-white solid. $^1$H-NMR (DMSO d$_6$, 400 MHz): δ 11.62 (br s, 1H), 8.21 (s, 1H), 8.04 (d, 1H), 7.72 (s, 1H), 7.68 (s, 1H), 7.25 (d, 1H), 3.92-3.74 (m, 4H), 3.52-3.49 (m, 2H), 3.47-3.42 (m, 1H), 3.04-2.97 (m, 4H), 2.68-2.62 (m, 1H), 2.34-2.32 (m, 1H), 1.89-1.84 (m, 4H), 1.04 (d, 3H); Mass (ESI): 435.5 [M$^+$+1]; LC-MS: 94.75%; 435.5 (M$^+$+1); (column; X-bridge C-18, (50×3.0 mm, 3.5μ); RT 3.04 min. 5 mM NH$_4$OAc in water: ACN; 0.8 ml/min); UPLC (purity): 97.45%; (column; Acquity UPLC HSS T3, 2.1×100 mm, 1.7μ; RT 2.89 min. 0.025% TFA (Aq): ACN:Water; 0.3 ml/min.; Chiral HPLC: 98.98% ee R$_t$=53.89 min (Chiralpak IC, 250×4.6 mm, 5μ; mobile phase (A) 0.1% TEA in n-Hexane (B) ethanol (A:B:25:75); flow Rate: 1.00 mL/min); Optical rotation [α]$_D^{24}$: +118.00° (c=0.5, DCM); TLC: 10% MeOH/DCM (Rf:0.54).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added 2-(chloromethyl)-6-methoxypyridine (39 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×15 mL). Combined organic layer was dried over sodium sulphate, filtered and concentrated in vacuo to obtain the crude product. The crude material was purified by silica gel column chromatography to afford (+)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one (55 mg, 52%) as pale green solid. $^1$H-NMR (DMSO d$_6$, 400 MHz): δ 11.48 (br s, 1H), 7.68-7.61 (m, 2H), 7.02 (d, 1H), 6.68 (d, 1H), 3.94-3.92 (m, 2H), 3.84 (s, 3H), 3.78-3.72 (m, 2H), 3.51-3.48 (m, 2H), 3.42-3.39 (m, 1H), 3.07-3.00 (m, 2H), 2.98-2.97 (m, 1H), 2.89-2.85 (m, 1H), 2.64-2.62 (m, 1H), 2.38-2.28 (m, 1H), 1.92-1.87 (m, 4H), 1.14 (d, 3H); Mass (ESI): 425.4 [M$^+$+1]; LC-MS: 95.85%; 425 (M$^+$+1); (column; X-bridge C-18, (50×3.0 mm, 3.5μ); RT 3.05 min. 5 mM NH$_4$OAc: ACN; 0.8 ml/min); UPLC (purity): 97.10%; (column; Acquity UPLC BEH C-18, (2.1×50 mm, 1.7μ); RT 1.35 min. 0.025% TFA (Aq): ACN:Water; 0.5 ml/min.; Chiral HPLC: 95.11% ee, R$_t$=12.04 min (Chiralpak IC, 250×4.6 mm, 5μ; mobile phase (A) 0.1% TEA in n-Hexane (B) ethanol (A:B:50:50); flow Rate: 1.00 mL/min); Optical rotation $[\alpha]_D^{25}$: +7.28° (c=0.5, DCM). TLC: 10% MeOH/DCM (Rf: 0.6).

9. (−)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one

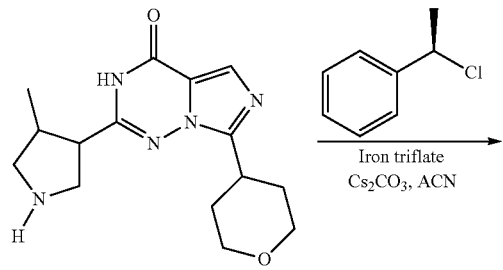

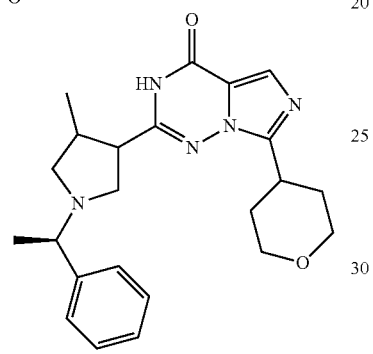

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added (R)-(1-Chloroethyl)benzene (38 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×25 mL). Combined organic layer was dried over sodium sulphate, filtered and concentrated in vacuo to obtain the crude product. The crude material was purified by silica gel column chromatography to afford the desired product as a racemic mixture, which upon chiral preparative HPLC purification to afforded (−)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one (9 mg, 9%) as an off-white solid. $^1$H-NMR (DMSO d$_6$, 400 MHz): δ 7.62 (s, 1H), 7.34-7.29 (m, 4H), 7.21-7.18 (m, 1H), 3.97-3.93 (m, 2H), 3.54-3.47 (m, 4H), 3.34-3.31 (m, 1H), 2.84-2.81 (m, 4H), 2.78-2.72 (m, 1H), 2.31-2.27 (m, 1H), 1.89-1.82 (m, 4H), 1.28 (d, 3H), 1.07 (d, 3H); Mass (ESI): 406 [M$^-$−1]; LC-MS: 86.11%; 408.5 (M$^+$+1); (column; X-bridge C-18, (50×3.0 mm, 3.5μ); RT 2.69 min. 0.1% Aq TFA: ACN; 0.8 ml/min); UPLC (purity): 87.57%; (column; Acquity UPLC BEH C-18, 2.1×50 mm, 1.7μ; RT 1.43 min. 0.025% TFA (Aq): ACN:Water; 0.50 ml/min; Chiral HPLC: 100% ee R$_t$=8.82 min (Chiralpak IC, 250×4.6 mm, 5μ; mobile phase (A) 0.1% TEA in n-Hexane (B) ethanol (A:B:50:50); flow Rate: 1.00 mL/min); Optical rotation $[\alpha]_D^{24}$: −85.66° (c=0.5, DCM). TLC: 10% MeOH/DCM (Rf: 0.6).

10. (+)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one

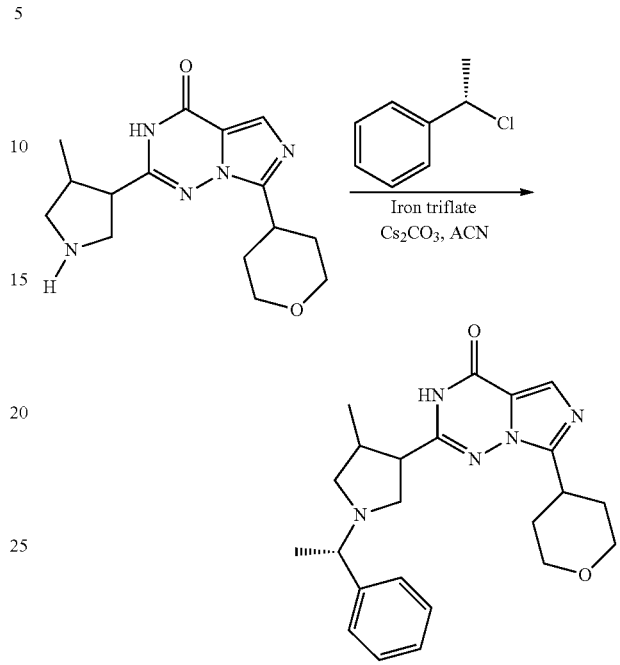

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added (S)-(1-chloroethyl)benzene (38 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×15 mL). Combined organic layer was dried over sodium sulphate, filtered and concentrated in vacuo to obtain the crude product. The crude material was purified by silica gel column chromatography to afford the desired product as a racemic mixture, which upon chiral preparative HPLC purification to afforded (+)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one (12 mg, 12%) as an off-white solid. $^1$H-NMR (DMSO d$_6$, 400 MHz): δ 7.64 (s, 1H), 7.34-7.31 (m, 4H), 7.21-7.18 (m, 1H), 3.56-3.52 (m, 3H), 3.42-3.37 (m, 4H), 2.94 (t, 2H), 2.75-2.71 (m, 1H), 2.68-2.65 (m, 1H), 2.61-2.58 (m, 1H), 2.14-2.11 (m, 1H), 1.89-1.82 (m, 4H), 1.32 (d, 3H), 1.04 (d, 3H); Mass (ESI): 408 [M$^+$+1]; LC-MS: 86.88%; 408.5 (M$^+$+1); (column; X-bridge C-18, (50×3.0 mm, 3.5μ); RT 2.67 min. 0.1% Aq TFA: ACN; 0.8 ml/min); UPLC (purity): 87.11%; (column; Acquity UPLC BEH C-18, 2.1×50 mm, 1.7μ; RT 1.42 min. 0.025% TFA (Aq): ACN:Water; 0.50 ml/min.; Chiral HPLC: 99.44% ee R$_t$=11.01 min (Chiralpak IC, 250×4.6 mm, 5μ; mobile phase (A) 0.1% TEA in n-Hexane (B) ethanol (A:B:50:50); flow Rate: 1.00 mL/min); Optical rotation $[\alpha]_D^{25}$: +96.90° (c=0.5, DCM). TLC: 10% MeOH/DCM (Rf:0.4).

451

11. (−)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one

452

12. (+)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one

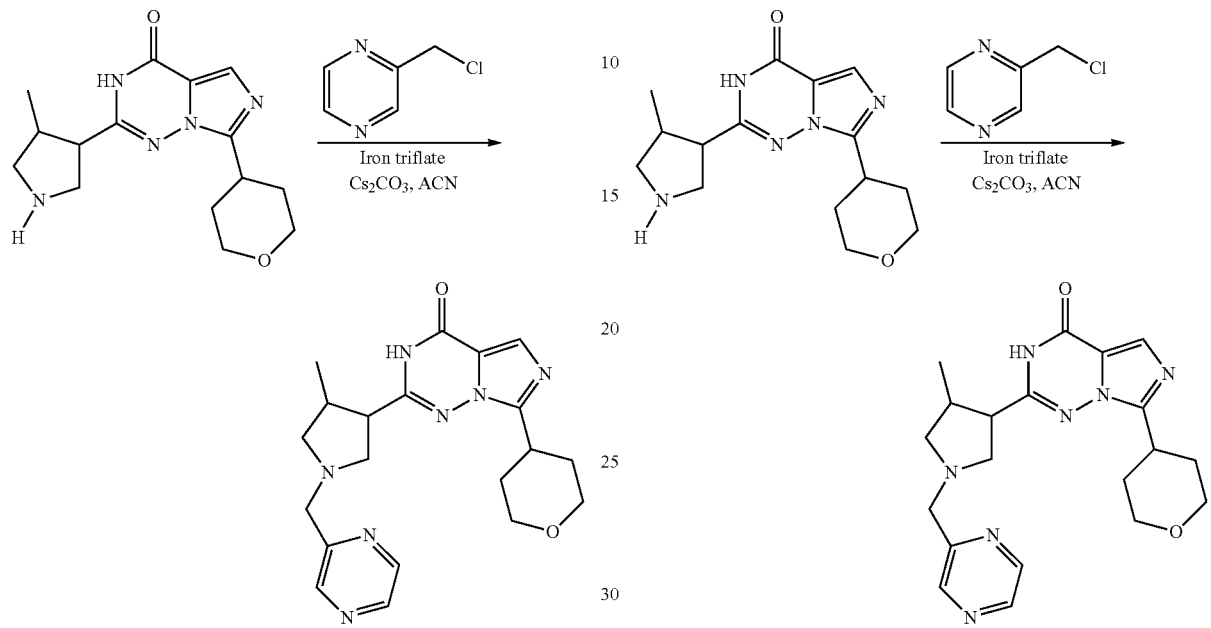

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(chloromethyl)pyrazine (34.85 mg, 0.27 mmol), iron triflate (24.90 mg, 0.049 mmol) and $Cs_2CO_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (3×25 mL). Combined organic layer was dried over sodium sulphate, filtered and concentrated in vacuo to obtain the crude product. The crude material was purified by silica gel column chromatography to afford (−)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one (45 mg, 46%) as an off-white solid. $^1$H-NMR (DMSO $d_6$, 400 MHz): δ 11.78 (br s, 1H), 8.72 (s, 1H), 8.58-8.54 (m, 2H), 7.61 (s, 1H), 3.97-3.94 (m, 3H), 3.81-3.76 (m, 1H), 3.52-3.47 (m, 2H), 3.41-3.37 (m, 1H), 3.02-2.94 (m, 4H), 2.67-2.62 (m, 1H), 2.34-2.31 (m, 1H), 1.89-1.74 (m, 4H), 1.04 (d, 3H); Mass (ESI): 396 [M$^+$+1]; LC-MS: 97.39%; 396 (M$^+$+1); (column; X-bridge C-18, (50×3.0 mm, 3.5μ); RT 2.44 min. 5 mM $NH_4OAc$: ACN; 0.8 ml/min); UPLC (purity): 98.61%; (column; Acquity UPLC HSS T3 (2.1×100 mm, 1.7μ); RT 2.89 min. 0.025% TFA (Aq): ACN:Water; 0.3 ml/min.; Chiral HPLC: 99.90% ee $R_t$=38.93 min (Chiralpak IC, 250×4.6 mm, 5μ); mobile phase (A) 0.1% TEA in n-Hexane (B) ethanol (A:B:50:50); flow Rate: 1.00 mL/min); Optical rotation $[α]_D^{24}$: −67.24° (c=0.5, DCM); TLC: 10% MeOH/DCM (Rf:0.46).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(chloromethyl)pyrazine (34.85 mg, 0.27 mmol), iron triflate (24.90 mg, 0.049 mmol) and $Cs_2CO_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (3×25 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyrazin-2-ylmethyl)pyrrolidin-3-yl)-7-(tetrahydro-2H-pyran-4-yl)imidazo[5,1-f][1,2,4]triazin-4(3H)-one (42 mg, 43%) as an off-white solid. $^1$H-NMR (DMSO $d_6$, 400 MHz): δ 11.67 (br s, 1H), 8.72 (s, 1H), 8.54 (d, 2H), 7.64 (s, 1H), 3.94-3.91 (m, 3H), 3.81-3.77 (m, 1H), 3.42-3.38 (m, 2H), 3.04-3.01 (m, 2H), 2.94-2.92 (m, 2H), 2.84-2.81 (m, 1H), 2.67-2.62 (m, 1H), 2.34-2.31 (m, 1H), 1.89-1.82 (m, 4H), 1.04 (d, 3H); Mass (ESI): 396 [M$^+$+1]; LC-MS: 94.22%; 396 (M$^+$+1); (column; Eclipse XDB C-18, (150×4.6 mm, 5.0μ); RT 5.35 min. 5 mM $NH_4OAc$: ACN; 1.0 ml/min); UPLC (purity): 95.66%; (column; Acquity BEH C-18 (50×2.1 mm, 1.7μ; RT 1.11 min. 0.025% TFA (Aq): ACN:Water; 0.50 ml/min.; Chiral HPLC: 100% ee $R_t$=25.25 min (Chiralpak IC, 250×4.6 mm, 5μ; mobile phase (A) 0.1% TEA in n-Hexane (B) ethanol (A:B:50:50); flow Rate: 1.00 mL/min); Optical rotation $[α]_D^{26}$: +60.52° (c=0.5, DCM); TLC: 10% MeOH/DCM (Rf: 0.46).

13. (+)-2-((3,4-trans)-1-(2-fluorobenzyl)-4-methyl-pyrrolidin-3-yl)-7-(tetrahydro-2H-pyran-4-yl)imidazo[5,1-f][1,2,4]triazin-4(3H)-one

14. (−)-2-((3,4-trans)-1-(3-fluorobenzyl)-4-methyl-pyrrolidin-3-yl)-7-(tetrahydro-2H-pyran-4-yl)imidazo[5,1-f][1,2,4]triazin-4(3H)-one

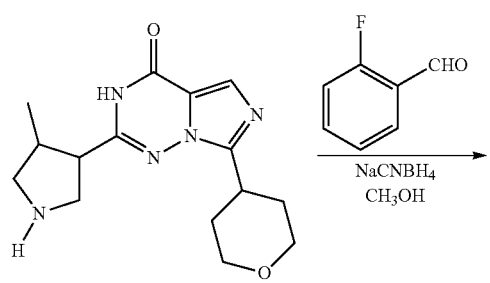

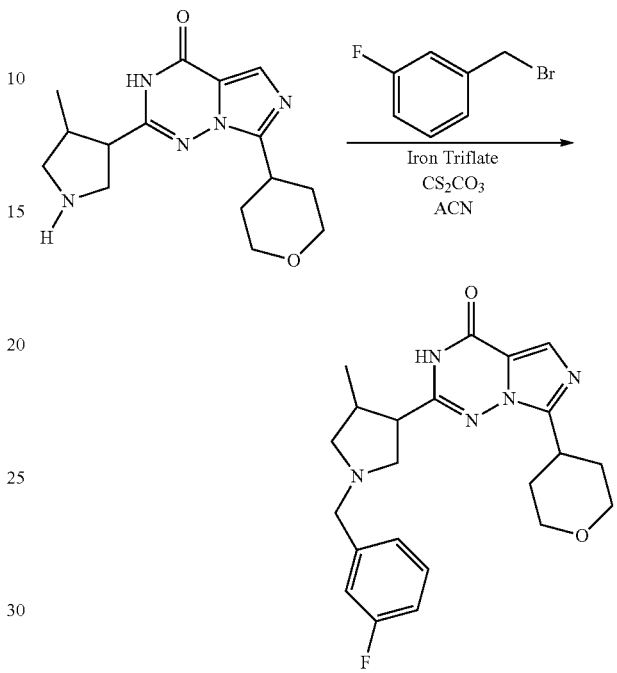

A mixture of (−)-2-((3,4-trans)-4-methylpyrrolidin-3-yl)-7-(tetrahydro-2H-pyran-4-yl)imidazo[5,1-f][1,2,4]triazin-4(3H)-one (60 mg, 0.198 mmol) and 2-fluorobenzaldehyde (27 mg, 0.22 mmol) in MeOH (5 mL) at RT and stirred for 2 h under inert atmosphere. To this NaCNBH$_4$ (37 mg, 0.59 mmol) was added and stirring was continued for another 6 h at RT. After completion of starting material (by TLC), the volatiles were evaporated under reduced pressure. The residue was diluted with water and extracted with DCM (2×15 mL). Combined organic layer was dried over sodium sulphate, filtered and concentrated in vacuo to obtain the crude product. The crude material was purified by silica gel column chromatography to afford (+)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one (0.06 g, 75%) as sticky solid. $^1$H-NMR (DMSO d$_6$, 400 MHz): δ 7.67 (s, 1H), 7.46-7.42 (m, 1H), 7.34-7.31 (m, 1H), 7.21-7.18 (m, 2H), 3.68 (s, 2H), 3.53-3.49 (m, 3H), 3.41-3.37 (m, 3H), 2.99-2.97 (m, 1H), 2.94-2.91 (m, 1H), 2.87-2.82 (m, 2H), 2.65-2.63 (m, 1H), 2.34-2.32 (m, 1H), 1.84-1.81 (m, 4H), 1.07 (d, 3H); Mass (ESI): 412.4 [M$^+$+1]; LC-MS: 97.97%; 412.6 (M$^+$+1); (column; X-bridge C-18, (50×4.6 mm, 5.0μ); RT 2.55 min. 0.1% TFA: ACN; 0.8 ml/min); UPLC (purity): 96.92%; (column; Acquity UPLC BEH C-18, (2.1×50 mm, 1.7μ); RT 1.37 min. 0.025% TFA (Aq); ACN:Water; 0.5 ml/min.; Optical rotation $[α]_D^{25}$: +14.83° (c=0.5, DCM). TLC: 5% MeOH/DCM (Rf: 0.7).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one hydrochloride (50 mg, 0.16 mmol) in ACN (5 mL) were added 1-(bromomethyl)-3-fluorobenzene (37.7 mg, 0.19 mmol), iron triflate (16.6 mg, 0.03 mmol) and Cs$_2$CO$_3$ (118 mg, 0.36 mmol) at RT under inert atmosphere. The reaction mixture was heated to 70° C. and stirred for 12 h. After completion of starting material (by TLC), the reaction mixture was diluted with water and extracted with EtOAc (2×15 mL). Combined organic layer was dried over sodium sulphate, filtered and concentrated in vacuo to obtain the crude product. The crude material was purified by preparative HPLC to afford (−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one (15 mg, 22%) as sticky solid. $^1$H-NMR (DMSO d$_6$, 400 MHz): δ 7.64 (s, 1H), 7.39-7.34 (m, 1H), 7.18-7.09 (m, 3H), 3.92-3.89 (m, 2H), 3.67-3.61 (m, 2H), 3.52-3.48 (m, 3H), 2.94-2.91 (m, 3H), 2.81-2.78 (m, 2H), 2.68-2.64 (m, 1H), 2.29-2.26 (m, 1H), 1.89-1.87 (m, 4H), 1.07 (d, 3H); Mass (ESI): 412.5 [M$^+$+1]; LC-MS: 94.10%; 412.4 (M$^+$+1); (column; X-bridge C-18, (50×3.0 mm, 3.5μ); RT 3.87 min. 5 mM NH$_4$OAc: ACN; 0.8 ml/min); UPLC (purity): 96.81%; (column; Acquity UPLC BEH C-18, (50×2.1 mm, 1.7μ); RT 1.41 min. 0.025% TFA (Aq): ACN:Water; 0.50 ml/min.; Optical rotation $[α]_D^{25}$: −1.216° (c=0.5, MeOH). TLC: 5% MeOH/DCM (Rf:0.6).

15. (+)-2-((3,4-trans)-1-(4-fluorobenzyl)-4-methyl-pyrrolidin-3-yl)-7-(tetrahydro-2H-pyran-4-yl)imidazo[5,1-f][1,2,4]triazin-4(3H)-one

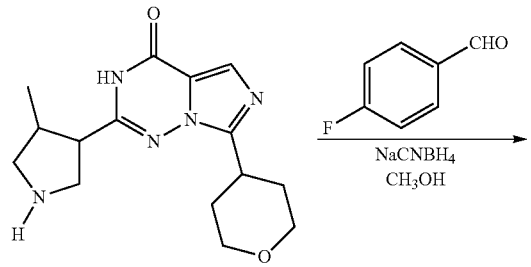

A mixture of (−)-2-((3,4-trans)-4-methylpyrrolidin-3-yl)-7-(tetrahydro-2H-pyran-4-yl)imidazo[5,1-f][1,2,4]triazin-4(3H)-one (50 mg, 0.16 mmol) and 4-fluorobenzaldehyde (22.5 mg, 0.18 mmol) in MeOH (5 mL) at RT and stirred for 2 h under inert atmosphere. To this NaCNBH₄ (31 mg, 0.49 mmol) was added and stirring was continued for another 6 h at RT. After completion of starting material (by TLC), the volatiles were evaporated under reduced pressure. The residue was diluted with ice cold water and extracted with DCM (2×15 mL). Combined organic layer was dried over sodium sulphate, filtered and concentrated in vacuo to obtain the crude product. The crude material was purified by silica gel column chromatography then triturated with n-pentane to afford (+)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one (45 mg, 66%) as an off-white solid. ¹H-NMR (DMSO d₆, 400 MHz): δ 7.62 (s, 1H), 7.38-7.32 (m, 2H), 7.17-7.12 (m, 2H), 3.96-3.94 (m, 2H), 3.67-3.64 (m, 2H), 3.57-3.55 (m, 2H), 3.42-3.36 (m, 4H), 2.95-2.93 (m, 1H), 2.84-2.79 (m, 1H), 2.64-2.62 (m, 1H), 2.24-2.21 (m, 1H), 1.92-1.87 (m, 4H), 1.07 (d, 3H); LC-MS: 94.33%; 412.5 (M⁺+1); (column; X-bridge C-18, (50×3.0 mm, 3.5μ); RT 2.71 min. 0.1% TFA: ACN; 0.8 ml/min); UPLC (purity): 95.95%; (column; Acquity BEH C-18, (50×2.1 mm, 1.7μ); RT 1.51 min. 0.025% TFA (Aq): ACN:Water; 0.50 ml/min.; Optical rotation [α]$_D^{24}$: +16.44° (c=0.5, DCM). TLC: 5% MeOH/DCM (Rf: 0.8).

16. (+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile

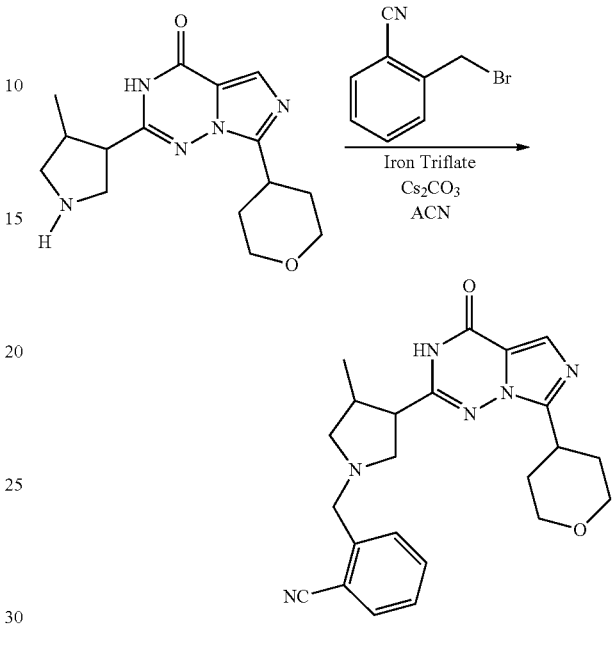

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(bromomethyl)benzonitrile (53.37 mg, 0.27 mmol), iron triflate (24.90 mg, 0.049 mmol) and Cs₂CO₃ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile (35 mg, 34%) as an off-white solid. ¹H-NMR (DMSO d₆, 500 MHz): δ 11.62 (br s, 1H), 7.87-7.84 (m, 1H), 7.72-7.67 (m, 2H), 7.62-7.58 (m, 1H), 7.52-7.47 (m, 1H), 3.97-3.92 (m, 2H), 3.84-3.82 (m, 2H), 3.53-3.49 (m, 2H), 3.41-3.37 (m, 1H), 3.04-3.00 (m, 1H), 2.96-2.92 (m, 2H), 2.87-2.84 (m, 1H), 2.68-2.64 (m, 1H), 2.37-2.34 (m, 1H), 1.86-1.81 (m, 4H), 1.04 (d, 3H); Mass (ESI): 419.4 [M⁺+1]; LC-MS: 95.93%; 419.7 (M⁺+1); (column; Eclipse XDB C-18, (150×4.6 mm, 5.0μ); RT 7.21 min. 5 mM NH₄OAc: ACN; 1.0 ml/min); UPLC (purity): 99.32%; (column; Acquity BEH C-18 (50×2.1 mm, 1.7μ); RT 1.41 min. 0.025% TFA (Aq): ACN:Water; 0.50 ml/min.; Optical rotation [α]$_D^{25}$: +7.28° (c=0.5, DCM). TLC: 5% MeOH/DCM (Rf: 0.5).

17. (+)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile

18. (−)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile

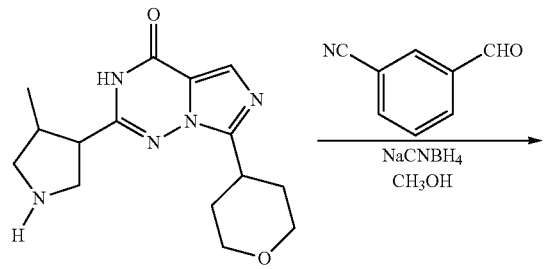

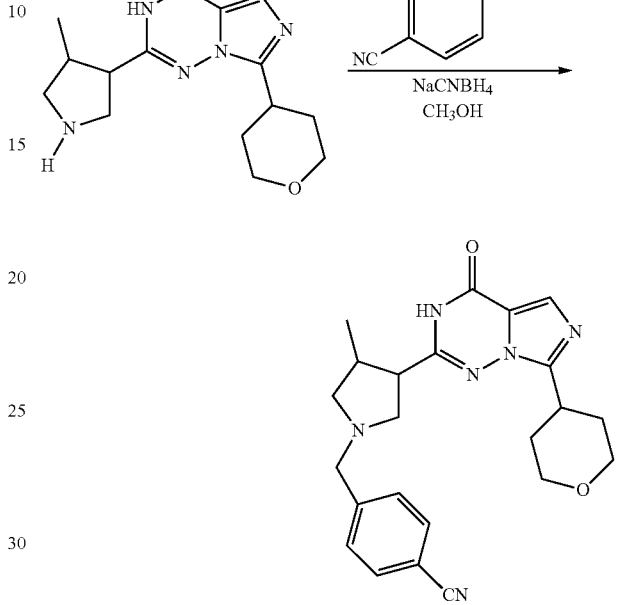

A mixture of (−)-2-((3,4-trans)-4-methylpyrrolidin-3-yl)-7-(tetrahydro-2H-pyran-4-yl)imidazo[5,1-f][1,2,4]triazin-4(3H)-one (50 mg, 0.16 mmol) and 3-formylbenzonitrile (23.7 mg, 0.18 mmol) in MeOH (5 mL) at RT and stirred for 2 h under inert atmosphere. To this NaCNBH$_4$ (31 mg, 0.49 mmol) was added and stirring was continued for another 6 h at RT. After completion of starting material (by TLC), the volatiles were evaporated under reduced pressure. The residue was diluted with ice cold water and extracted with DCM (2×15 mL). Combined organic layer was dried over sodium sulphate, filtered and concentrated in vacuo to obtain the crude product. The crude material was purified by preparative HPLC to afford (+)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile (40 mg, 58%) as an off-white solid. $^1$H-NMR (DMSO d$_6$, 400 MHz): δ 7.78-7.74 (m, 1H), 7.72-7.68 (m, 1H), 7.64 (s, 2H), 7.56-7.51 (m, 1H), 3.97-3.94 (m, 2H), 3.71 (s, 2H), 3.52-3.47 (m, 2H), 3.42-3.38 (m, 2H), 2.97-2.94 (m, 1H), 2.89-2.87 (m, 1H), 2.81-2.77 (m, 2H), 2.68-2.64 (m, 1H), 2.31-2.27 (m, 1H), 1.87-1.82 (m, 4H), 1.12 (d, 3H); LC-MS: 97.10%; 419.7 (M$^+$+1); (column; X-bridge C-18, (50×4.6 mm, 5µ); RT 2.49 min. 0.1% TFA: ACN; 0.8 ml/min); UPLC (purity): 96.81%; (column; Acquity BEH C-18, (50×2.1 mm, 1.7µ); RT 1.44 min. 0.025% TFA (Aq): ACN:Water; 0.50 ml/min.; Optical rotation [α]$_D^{23}$: +5.11° (c=0.5, DCM). TLC: 5% MeOH/DCM (Rf: 0.8).

A mixture of (−)-2-((3,4-trans)-4-methylpyrrolidin-3-yl)-7-(tetrahydro-2H-pyran-4-yl)imidazo[5,1-f][1,2,4]triazin-4(3H)-one (50 mg, 0.16 mmol) and 4-formylbenzonitrile (23.7 mg, 0.18 mmol) in MeOH (5 mL) at RT and stirred for 2 h under inert atmosphere. To this NaCNBH$_4$ (31 mg, 0.49 mmol) was added and stirring was continued for another 6 h at RT. After completion of starting material (by TLC), the volatiles were evaporated under reduced pressure. The residue was diluted with ice cold water and extracted with DCM (2×15 mL). Combined organic layer was dried over sodium sulphate, filtered and concentrated in vacuo to obtain the crude product. The crude material was purified by preparative HPLC to afford (−)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile (40 mg, 58%) as an off-white solid. $^1$H-NMR (DMSO d$_6$, 400 MHz): δ 7.78 (d, 2H), 7.68 (s, 1H), 7.54 (d, 2H), 4.95-4.91 (m, 2H), 3.78-3.72 (m, 2H), 3.54-3.51 (m, 2H), 3.42-3.37 (m, 2H), 2.99-2.97 (m, 1H), 2.87-2.81 (m, 3H), 2.68-2.64 (m, 1H), 2.34-2.28 (m, 1H), 1.87-1.82 (m, 4H), 1.12 (d, 3H); Mass (ESI): 419.5 [M$^+$+1]; LC-MS: 97.59%; 419.6 (M$^+$+1); (column; X-bridge C-18, (50×3.0 mm, 3.5µ); RT 2.46 min. 0.1% TFA: ACN; 0.8 ml/min); UPLC (purity): 98.56%; (column; Acquity BEH C-18, (50×2.1 mm, 1.7µ); RT 1.43 min. 0.025% TFA (Aq): ACN:Water; 0.50 ml/min.; Optical rotation [α]$_D^{23}$: −5.368° (c=0.5, DCM). TLC: 5% MeOH/DCM (Rf: 0.7).

19. (+)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one

20. (−)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one

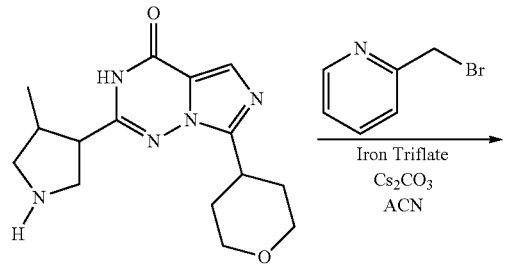

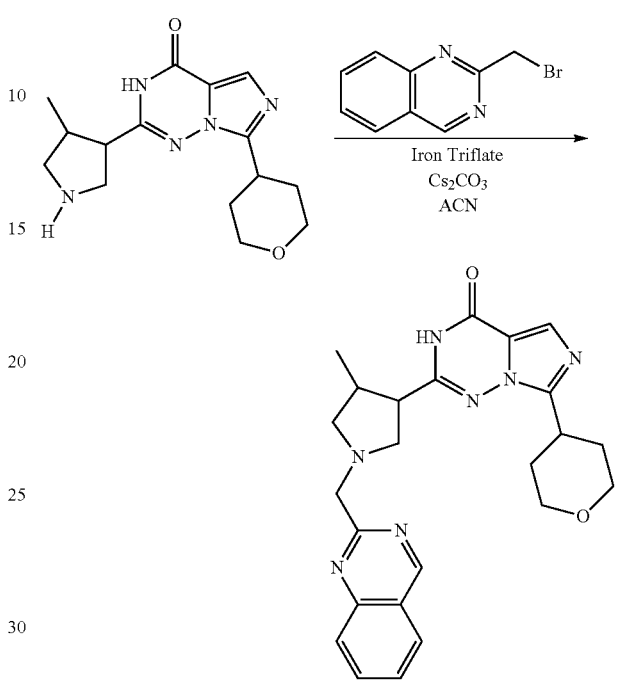

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(chloromethyl)pyridine (44.46 mg, 0.27 mmol), iron triflate (24.90 mg, 0.049 mmol) and $Cs_2CO_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one (20 mg, 20%) as sticky solid. $^1$H-NMR (DMSO $d_6$, 500 MHz): δ 8.47 (d, 1H), 7.78-7.74 (m, 1H), 7.68 (s, 1H), 7.42 (d, 1H), 7.24-7.21 (m, 1H), 3.96-3.92 (m, 2H), 3.84-3.81 (m, 1H), 3.74-3.68 (m, 1H), 3.54-3.48 (m, 2H), 3.42-3.38 (m, 2H), 3.01-3.27 (m, 2H), 2.87-2.79 (m, 2H), 2.64-2.62 (m, 1H), 2.37-2.34 (m, 1H), 1.85-1.82 (m, 4H), 1.12 (d, 3H); Mass (ESI): 395.3 [M$^+$+1]; LC-MS: 98.60%; 395.2 (M$^+$+1); (column; X-bridge C-18, (50×3.0 mm, 3.5µ); RT 2.16 min. 0.1% TFA in water: ACN; 0.50 ml/min); UPLC (purity): 97.79%; (column; Acquity UPLC BEH C-18 (2.1×50 mm, 1.7µ); RT 1.23 min. 0.025% TFA (Aq): ACN:Water; 0.5 ml/min.; Optical rotation $[α]_D^{25}$: +11.24° (c=0.5, DCM). TLC: 10% MeOH/DCM (Rf: 0.6).

To a stirred solution of compound (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.247 mmol) in ACN (5 mL) were added 2-(chloromethyl)quinazoline (48.6 mg, 0.272 mmol), iron triflate (24.9 mg, 0.049 mmol) and $Cs_2CO_3$ (177.5 mg, 0.54 mmol) at RT under inert atmosphere. The resultant reaction mixture was heated to 70° C. and stirred for 6 h. After completion of starting material (by TLC), the reaction mixture was diluted with water and extracted with EtOAc (3×25 mL). Combined organic layers were dried over anhydrous sodium sulphate, filtered and concentrated in vacuo to obtain the crude product. The crude material was purified by silica gel column chromatography to afford (−)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one (50 mg, 45%) as an off-white solid. $^1$H-NMR (DMSO $d_6$, 400 MHz): δ 9.63 (s, 1H), 8.18 (d, 1H), 8.09-8.01 (m, 2H), 7.77 (t, 2H), 4.24 (d, 1H), 4.01-3.92 (m, 3H), 3.52 (t, 2H), 3.25-3.20 (m, 2H), 3.14 (t, 1H), 2.98 (t, 1H), 2.81 (q, 1H), 2.63-2.59 (m, 1H), 2.41 (t, 1H), 1.85 (s, 4H), 1.14 (d, 3H); Mass (ESI): 446 [M$^+$+1]; LC-MS: 97.83%; 447.1 (M$^+$+1); (column; XDB C-18, (150× 4.6 mm, 5 um); RT 5.04 min. 0.1% TFA in water: ACN; 1.0 ml/min); UPLC (purity): 99.01%; (column; Acquity BEH C-18, 50×2.1 mm, 1.7µ; RT 1.42 min. 0.025% TFA (Aq): ACN:DMSO; 0.50 ml/min.; TLC: 5% MeOH/DCM (Rf: 0.5). Chiral HPLC: 96.49% ee R$_t$=43.76 min (Chiralpak IC, 250×4.6 mm, 5µ; mobile phase (A) 0.1% TEA in n-Hexane (B) ethanol (A:B:50:50); flow Rate: 1.00 mL/min); Optical rotation $[α]_D^{24}$: −128.77° (c=0.5, DCM).

21. (+)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one

22. (−)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one

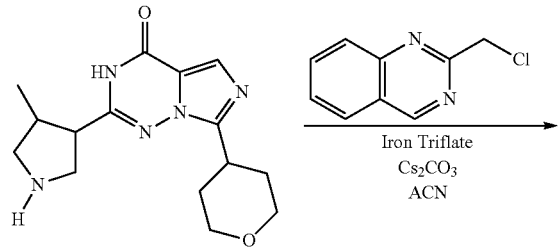

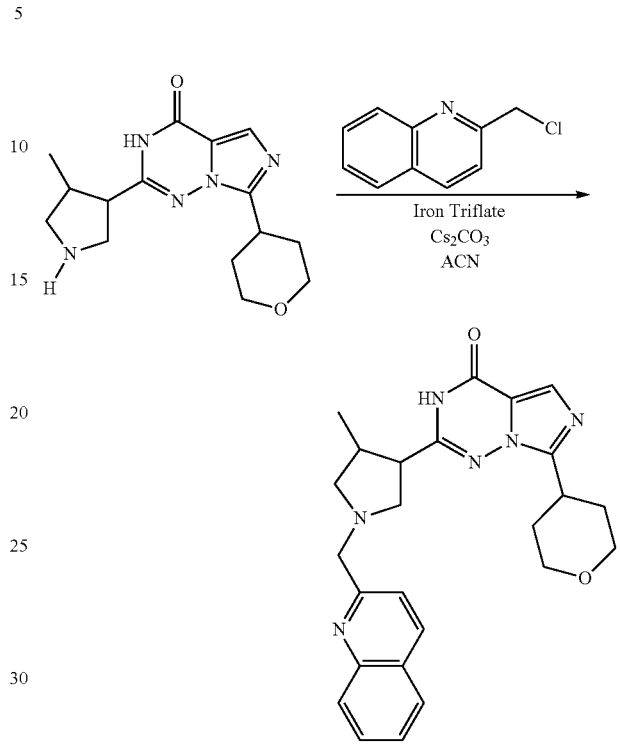

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(chloromethyl)quinazoline (48.46 mg, 0.27 mmol), iron triflate (24.90 mg, 0.049 mmol) and Cs$_2$CO$_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinazolin-2-ylmethyl)pyrrolidin-3-yl)-7-(tetrahydro-2H-pyran-4-yl)imidazo[5,1-f][1,2,4]triazin-4(3H)-one (40.2 mg, 37%) as an off-white solid. $^1$H-NMR (DMSO d$_6$, 400 MHz): δ 9.58 (s, 1H), 8.14 (d, 1H), 8.07-8.02 (m, 2H), 7.78-7.65 (m, 2H), 4.24-4.21 (m, 1H), 4.01-3.95 (m, 3H), 3.52-3.48 (m, 2H), 3.28-3.24 (m, 2H), 3.14-3.11 (m, 1H), 2.98-2.94 (m, 1H), 2.87-2.85 (m, 1H), 2.67-2.64 (m, 1H), 2.42-2.37 (m, 1H), 1.94-1.87 (m, 4H), 1.12 (d, 3H); Mass (ESI): 446.3 [M$^+$+1]; LC-MS: 96.13%; 446.6 (M$^+$+1); (column; Eclipse XDB C-18, (150×4.6 mm, 5μ); RT 6.84 min. 5.0 mM NH$_4$OAc: ACN; 1.0 ml/min); UPLC (purity): 97.52%; (column; Acquity BEH C-18 (50×2.1 mm, 1.7μ); RT 1.46 min. 0.025% TFA (Aq): ACN:Water; 0.50 ml/min.; Optical rotation [α]$_D^{25}$: +130.89° (c=0.5, DCM). TLC: 10% MeOH/DCM (Rf:0.7).

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.247 mmol) in ACN (10 mL) were added 2-(chloromethyl)quinoline (58.3 mg, 0.272 mmol), Iron triflate (24 mg, 0.049 mmol) and Cs$_2$CO$_3$ (177 mg, 0.54 mmol) at RT under inert atmosphere. The resultant reaction mixture was heated to 70° C. and stirred for 6 h. After completion of the reaction, the reaction mixture was diluted with water and extracted with EtOAc (3×25 mL). Combined organic layers were dried over anhydrous sodium sulphate, filtered and concentrated in vacuo to obtain the crude product. The crude material was purified by silica gel column chromatography to afford (−)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one (50 mg, 42%) as an off-white solid. $^1$H-NMR (DMSO d$_6$, 400 MHz): δ 8.33 (d, 1H), 8.01-7.98 (m, 2H), 7.77-7.52 (m, 4H), 4.01-3.97 (m, 4H), 3.52-3.48 (m, 4H), 3.04 (t, 2H), 2.85 (q, 1H), 2.75 (t, 1H), 2.71-2.69 (m, 1H), 2.39 (t, 1H), 1.82 (s, 3H), 1.12 (d, 3H); Mass (ESI): 445 [M$^+$+1]; LC-MS: 93.62%; 445.5 (M$^+$+1); (column; XDB C-18, (150×4.6 mm, 3.5 um); RT 5.39 min. 0.1% Aqueous TFA: ACN; 1.0 ml/min); UPLC (purity): 96.63%; (column; Acquity BEH C-18, 50×2.1 mm, 1.7μ; RT 1.59 min. 0.025% TFA (Aq): ACN:Water; 0.50 ml/min.; TLC: 5% MeOH/DCM (Rf:0.5). Chiral HPLC: 99.12% ee R$_t$=20.83 min (Chiralpak IC, 250×4.6 mm, 5μ; mobile phase (A) 0.1% TEA in n-Hexane (B) ethanol (A:B:50:50); flow Rate: 1.00 mL/min); Optical rotation [α]$_D^{24}$: −87.99° (c=0.5, DCM).

23. (+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one

24. (+)-7-((1s,3R)-adamantan-1-yl)-2-((3,4-trans)-1-benzyl-4-methylpyrrolidin-3-yl)imidazo[5,1-f][1,2,4]triazin-4(3H)-one and (−)-7-((1s,3R)-adamantan-1-yl)-2-((3,4-trans)-1-benzyl-4-methylpyrrolidin-3-yl)imidazo[5,1-f][1,2,4]triazin-4(3H)-one

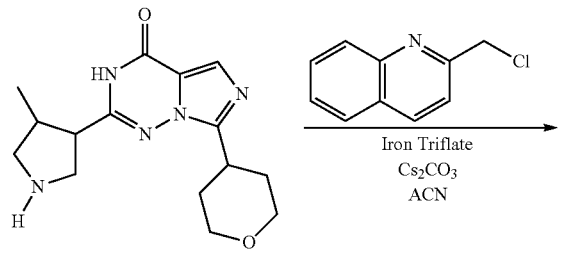

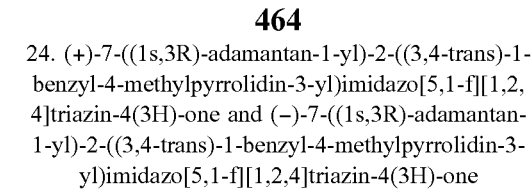

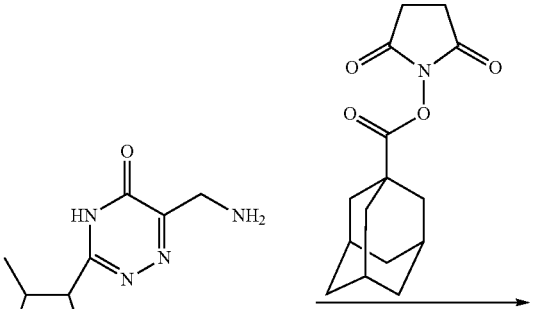

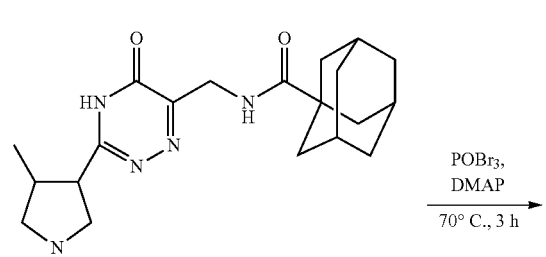

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added 2-(chloromethyl)quinoline (63 mg, 0.29 mmol), iron triflate (24 mg, 0.049 mmol) and $Cs_2CO_3$ (177 mg, 0.54 mmol) at RT under inert atmosphere. The reaction mixture was heated to 70° C. and stirred for 4 h. After completion of starting material (by TLC), the reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-one (65 mg, 59%) as sticky solid. $^1$H-NMR (DMSO $d_6$, 400 MHz): δ 8.32 (d, 1H), 8.07-7.95 (m, 2H), 7.76 (t, 1H), 7.68 (s, 1H), 7.64-7.61 (m, 1H), 7.59-7.57 (m, 1H), 4.08-3.92 (m, 4H), 3.57-3.47 (m, 2H), 3.42-3.38 (m, 2H), 3.06-3.02 (m, 2H), 2.87-2.84 (m, 1H), 2.71-2.65 (m, 1H), 2.37-2.34 (m, 1H), 1.92-1.84 (m, 4H), 1.12 (d, 3H); Mass (ESI): 445.7 [M$^+$+1]; LC-MS: 94.58%; 445.2 (M$^+$+1); (column; X-bridge C-18, (50×3.0 mm, 3.5μ); RT 2.21 min. 0.1% TFA in water: ACN; 0.80 ml/min); UPLC (purity): 94.28%; (column; Acquity BEH C-18 (50×2.1 mm, 1.7μ); RT 1.56 min. 0.025% TFA (Aq): ACN:Water; 0.50 ml/min.; Optical rotation $[α]_D^{21}$: +78.42° (c=0.5, DCM). TLC: 5% MeOH/DCM (Rf: 0.6).

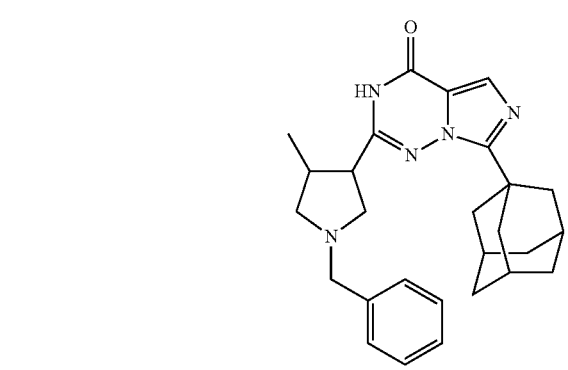

465

Synthesis of (+/−)-(3S,5S,7S)—N-((3-((3,4-trans)-1-benzyl-4-methylpyrrolidin-3-yl)-5-oxo-4,5-dihydro-1,2,4-triazin-6-yl)methyl)adamantane-1-carboxamide

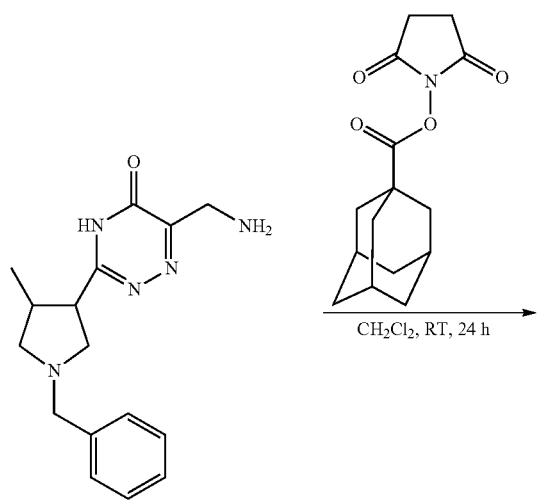

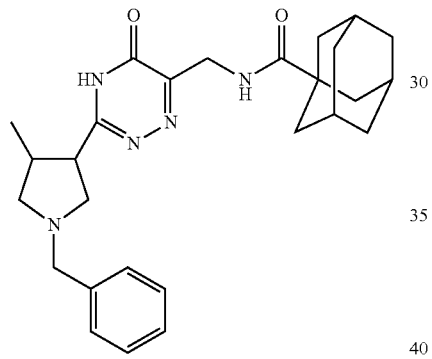

To a suspension of (+/−)-6-(aminomethyl)-3-((3,4-trans)-1-benzyl-4-methylpyrrolidin-3-yl)-1,2,4-triazin-5(4H)-one (1.05 g, 3.51 mmol) in CH$_2$Cl$_2$ (45 mL) was added (3r,5r,7r)-2,5-dioxopyrrolidin-1-yl adamantane-1-carboxylate (1.46 g, 5.26 mmol) at RT. The resulting solution was stirred at room temperature for 24 h. The solvent was removed under reduced pressure to give a yellow solid. Flash chromatography over silica gel column (0.1/1.5/98.4-1/15/84 NH$_4$OH/MeOH/CH$_2$Cl$_2$) provided (+/−)-(3S,5S,7S)—N-((3-((3,4-trans)-1-benzyl-4-methylpyrrolidin-3-yl)-5-oxo-4,5-dihydro-1,2,4-triazin-6-yl)methyl)adamantane-1-carboxamide (1.19 g, 74% yield) as a yellow solid. $^1$H NMR (300 MHz, CDCl$_3$) δ 10.41 (br s, 1H), 7.38-7.30 (m, 5H), 7.07 (br s, 1H), 4.49 (d, 2H, J=4.8 Hz), 4.04 (d, 1H, J=12.6 Hz), 3.92 (d, 1H, J=12.9 Hz), 3.45-3.37 (m, 1H), 3.34-3.22 (m, 1H), 3.22-3.10 (m, 2H), 2.70-2.45 (m, 2H), 2.03 (br s, 3H), 1.90 (br s, 6H), 1.72 (br s, 6H), 1.08 (d, 3H, J=6.3 Hz); $^{13}$C NMR (75 MHz, CDCl$_3$) δ 178.0, 165.1, 162.8, 150.7, 134.3, 131.9, 129.2, 128.6, 128.3, 60.3, 59.5, 56.8, 50.1, 40.7, 39.7, 39.1, 38.5, 36.4, 28.0, 18.3.

466

Synthesis of (+)-7-((1s,3R)-adamantan-1-yl)-2-((3,4-trans)-1-benzyl-4-methylpyrrolidin-3-yl)imidazo[5,1-f][1,2,4]triazin-4(3H)-one and (−)-7-((1s,3R)-adamantan-1-yl)-2-((3,4-trans)-1-benzyl-4-methylpyrrolidin-3-yl)imidazo[5,1-f][1,2,4]triazin-4(3H)-one

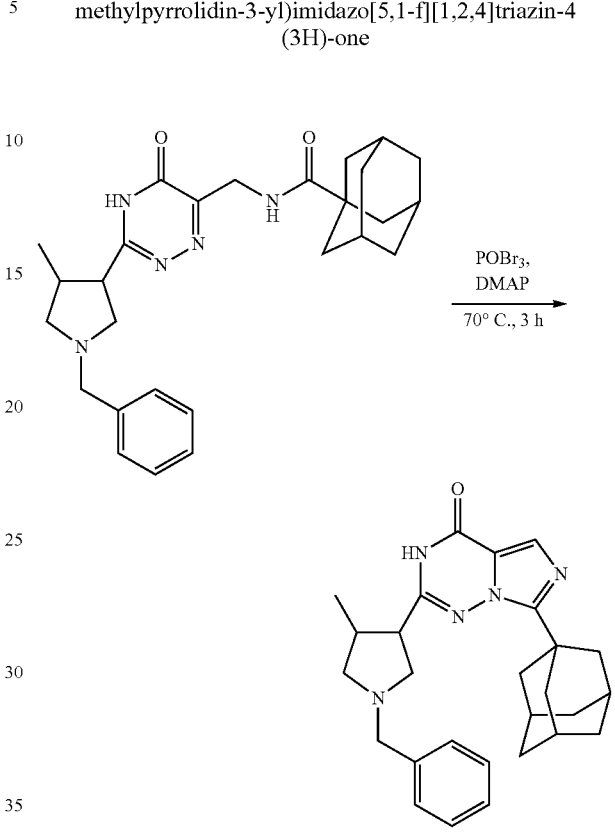

To a solution of (+/−)-(3S,5S,7S)—N-((3-((3,4-trans)-1-benzyl-4-methylpyrrolidin-3-yl)-5-oxo-4,5-dihydro-1,2,4-triazin-6-yl)methyl)adamantane-1-carboxamide (200 mg, 0.43 mmol), DMAP (5 mg, 0.04 mmol) in acetonitrile (8 mL) was added a solution of POBr$_3$ (373 mg, 1.3 mmol) in acetonitrile (2 mL) at RT, and the resulting suspension was heated to 70° C. for 3 h. After the mixture was cooled to room temperature, it was poured into cold saturated NaHCO$_3$ solution (30 mL), and stirred vigorously for 0.5 h, then extracted with CH$_2$Cl$_2$ (3×10 mL). The organic extract was dried over MgSO$_4$ and concentrated under reduced pressure. The residue was purified by flash chromatography over silica gel (0.1/1.5/98.4-0.3/4.5/95.2 NH$_4$OH/MeOH/CH$_2$Cl$_2$) to furnish (+/−)-7-((1s,3R)-adamantan-1-yl)-2-((3,4-trans)-1-benzyl-4-methylpyrrolidin-3-yl)imidazo[5,1-f][1,2,4]triazin-4(3H)-one (120 mg, 62% yield) as a white foam. Purity (HPLC): 96.1%; $^1$H NMR (300 MHz, CDCl$_3$/TMS) δ 9.10 (br s, 1H), 7.76 (s, 1H), 7.50-7.24 (m, 5H), 3.81 (d, J=12.3 Hz, 1H), 3.57 (d, J=12.6 Hz, 1H), 3.36 (t, J=8.5 Hz, 1H), 2.99 (d, J=10.2 Hz, 1H), 2.76 (dd, J=6.2, 2.4 Hz, 1H), 2.55 (dd, J=9.9, 6.6 Hz, 1H), 2.52-2.40 (m, 1H), 2.26 (br s, 6H), 2.08 (br s, 3H), 2.02-1.93 (m, 1H), 1.80 (br s, 6H), 1.22 (d, J=6.6 Hz, 3H); $^{13}$C NMR (75 MHz, CDCl$_3$/TMS) δ 154.61, 152.15, 151.79, 137.29, 128.53, 128.50, 127.40, 126.89, 119.35, 61.12, 59.32, 56.10, 48.15, 39.09, 38.24, 36.71, 36.06, 28.25, 20.14; HRMS: calculated for C$_{27}$H$_{34}$N$_5$O$_2$ (MH$^+$), 444.2758. found, 444.2768.

Racemic (+/−)-7-((1s,3R)-adamantan-1-yl)-2-((3,4-trans)-1-benzyl-4-methylpyrrolidin-3-yl)imidazo[5,1-f][1,2,4]triazin-4(3H)-one was purified by Chiralpak IC, 250×20 mm, 5 um (80 mg loading; 0.1% TEA in n-Hexane:Ethanol (90:10) as mobile phase) to obtain pure fraction 1 ((+)-7-((1s,3R)-adamantan-1-yl)-2-((3,4-trans)-1-benzyl-4-methylpyrrolidin-3-yl)imidazo[5,1-f][1,2,4]triazin-4(3H)-one) and pure fraction 2 ((−)-7-((1s,3R)-adamantan-1-yl)-2-((3,4-trans)-1-benzyl-4-methylpyrrolidin-3-yl)imidazo[5,1-f][1,2,4]triazin-4(3H)-one). Characterization details of are as follows:

(+)-7-((1s,3R)-adamantan-1-yl)-2-((3,4-trans)-1-benzyl-4-methylpyrrolidin-3-yl)imidazo[5,1-f][1,2,4]triazin-4(3H)-one: $^1$H-NMR (DMSO d$_6$, 400 MHz): δ 7.62 (s, 1H), 7.34-7.29 (m, 4H), 7.24-7.21 (m, 1H), 3.64-3.62 (m, 2H), 3.08-3.02 (m, 2H), 2.82-2.78 (m, 3H), 2.65-2.62 (m, 1H), 2.28-2.25 (m, 6H), 2.09-2.07 (m, 3H), 1.78-1.74 (m, 6H), 1.14 (d, 3H); Mass (ESI): 444 [M$^+$+1]; LC-MS: 97.86%; 444 (M$^+$+1); (column; X-bridge C-18, (50×3.0 mm, 3.5μ); RT 4.44 min. 5 mM NH$_4$OAc: ACN; 0.8 ml/min); UPLC (purity): 99.51%; (column; Acquity BEH C-18, 50×2.1 mm, 1.7μ; RT 2.00 min. 0.025% TFA (Aq): ACN:Water; 0.50 ml/min.; Chiral HPLC: 99.73% ee R$_t$=9.70 min (Chiralpak IC, 250×4.6 mm, 5μ; mobile phase (A) 0.1% TEA in n-Hexane (B) ethanol (A:B:80:20); flow Rate: 1.00 mL/min); Optical rotation [α]$_D^{24}$: +16.15° (c=0.5, DCM). 16874

(−)-7-((1s,3R)-adamantan-1-yl)-2-((3,4-trans)-1-benzyl-4-methylpyrrolidin-3-yl)imidazo[5,1-f][1,2,4]triazin-4(3H)-one: $^1$H-NMR (DMSO d$_6$, 400 MHz): δ 7.62 (s, 1H), 7.34-7.29 (m, 4H), 7.24-7.21 (m, 1H), 4.34-4.28 (m, 1H), 3.68-3.64 (m, 2H), 3.48-3.42 (m, 2H), 3.02-2.98 (m, 1H), 2.89-2.81 (m, 3H), 2.68-2.62 (m, 1H), 2.28-2.23 (m, 1H), 2.24-2.18 (m, 6H), 2.07-2.02 (m, 3H), 1.78-1.74 (m, 4H), 1.18 (d, 3H); Mass (ESI): 444 [M$^+$+1]; LC-MS: 98.74%; 444 (M$^+$+1); (column; X-bridge C-18, (50×3.0 mm, 3.5μ); RT 4.43 min. 5 mM NH$_4$OAc: ACN; 0.8 ml/min); UPLC (purity): 99.17%; (column; Acquity BEH C-18, 50×2.1 mm, 1.7μ; RT 1.99 min. 0.025% TFA (Aq): ACN:Water; 0.50 ml/min.; Chiral HPLC: 98.98% ee R$_t$=12.32 min (Chiralpak IC, 250×4.6 mm, 5μ; mobile phase (A) 0.1% TEA in n-Hexane (B) ethanol (A:B:80:20); flow Rate: 1.00 mL/min); Optical rotation [α]$_D^{25}$: −20.78° (c=0.5, DCM). 16875.

25. (+)-7-((1s,3R)-adamantan-1-yl)-2-((3,4-trans)-4-methyl-1-(pyrimidin-2-ylmethyl)pyrrolidin-3-yl)imidazo[5,1-f][1,2,4]triazin-4(3H)-one

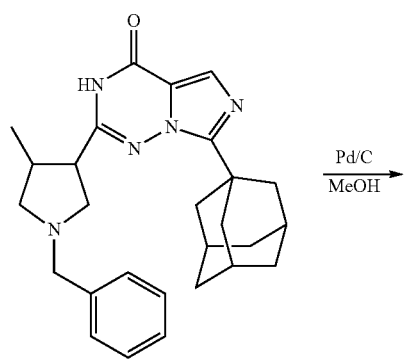

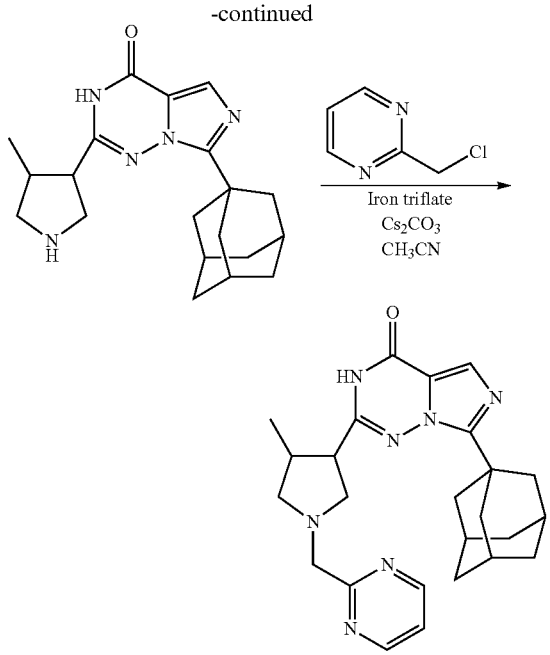

To a stirred solution of (+)-7-((1s,3R)-adamantan-1-yl)-2-((3,4-trans)-1-benzyl-4-methylpyrrolidin-3-yl)imidazo[5,1-f][1,2,4]triazin-4(3H)-one (160 mg, 0.36 mmol) in MeOH (10 mL) was added Pd/C (55 mg, catalytic) under N$_2$ atmosphere. The reaction was stirred at RT for 16 h under H$_2$ atmosphere (balloon pressure). The reaction mixture was passed through a pad of celite and volatiles were dried in vacuo. Obtained residue was washed with n-pentane (2 times) and dried under reduced pressure to afford 7-((1s,3R)-adamantan-1-yl)-2-((3,4-trans)-4-methylpyrrolidin-3-yl)imidazo[5,1-f][1,2,4]triazin-4(3H)-one (95 mg, 75%) as off-white solid. $^1$H-NMR (DMSO d$_6$, 400 MHz): δ 7.59 (s, 1H), 3.31 (t, 1H), 3.25 (t, 1H), 3.02-2.99 (m, 1H), 2.71 (q, 1H), 2.21 (s, 6H), 2.05 (s, 3H), 1.76 (s, 6H), 1.05 (d, 3H); LC-MS: 92.03%; 355.5 [(M$^+$+2)]; (column; Eclipse XDBC-18, (150×4.6 mm, 5 um); RT 5.35 min. 0.1% Aqueous TFA: ACN; 1.0 ml/min); UPLC (purity): 96.4%; (column; Acquity BEH C18, 2.1×50 mm, 1.7μ; RT 1.61 min. 0.025% aqueous TFA: ACN:Water; 0.5 ml/min.; TLC: 5% MeOH/CH$_2$Cl$_2$ (R$_f$ 0.1).

To a stirred solution of 7-((1s,3R)-adamantan-1-yl)-2-((3,4-trans)-4-methylpyrrolidin-3-yl)imidazo[5,1-f][1,2,4]triazin-4(3H)-one (50 mg, 0.14 mmol) in ACN (5 mL) was added 2-(chloromethyl)pyrimidine (19 mg, 0.1 mmol), iron triflate (14 mg, 0.02 mmol) followed by Cs$_2$CO$_3$ (92 mg, 0.2 mmol) at RT under inert atmosphere. The reaction mixture was heated to 70° C. and stirred for 4 h. After consumption of starting material (by TLC), the reaction was diluted with water and extracted with EtOAc (2×30 mL). Combined organic layers were dried over anhydrous sodium sulphate, filtered and concentrated in vacuo to obtain the crude product. The crude material was purified by silica gel column chromatography to afford (+)-7-((1s,3R)-adamantan-1-yl)-2-((3,4-trans)-4-methyl-1-(pyrimidin-2-ylmethyl)pyrrolidin-3-yl)imidazo[5,1-f][1,2,4]triazin-4(3H)-one (20 mg, 32%) as an off-white solid. $^1$H-NMR (DMSO d$_6$, 400 MHz): δ 8.79 (d, 2H), 7.61 (s, 1H), 7.42 (t, 1H), 3.99 (d, 1H), 3.85 (d, 1H), 3.09 (q, 2H), 2.98 (t, 1H), 2.80 (q, 1H), 2.62-2.58 (m, 1H), 2.42 (t, 1H), 2.19 (s, 6H), 2.04 (br s, 3H), 1.75 (s, 6H), 1.12 (d, 3H); Mass (ESI): 446 [(M$^+$+1)];

LC-MS: 97.27%; 446 [(M++1)]; (column; X-bridge C-18, (50×3.0 mm, 3.5µ); RT 3.91 min. 5 mM NH4OAc: ACN; 0.8 ml/min); UPLC (purity): 97.78%; (column; Acquity UPLC BEH C18, 2.1×50 mm, 1.7µ; RT 1.63 min. 0.025% aqueous TFA: ACN:Water; 0.5 ml/min.; Chiral HPLC: 99.28% ee $R_t$=10.92 min (Chiralpak IC, 250×4.6 mm, 5µ; mobile phase (A) 0.1% TEA in n-Hexane (B) ethanol (A:B:50:50); flow Rate: 1.00 mL/min); Optical rotation $[\alpha]_D^{25}$: +98.4° (c=0.5, DCM).

26. (+)-2-((3,4-trans)-1-benzyl-4-methylpyrrolidin-3-yl)-7-(5-chloro-2-methylphenyl)imidazo[5,1-f][1,2,4]triazin-4(3H)-one and (−)-2-((3,4-trans)-1-benzyl-4-methylpyrrolidin-3-yl)-7-(5-chloro-2-methylphenyl)imidazo[5,1-f][1,2,4]triazin-4(3H)-one

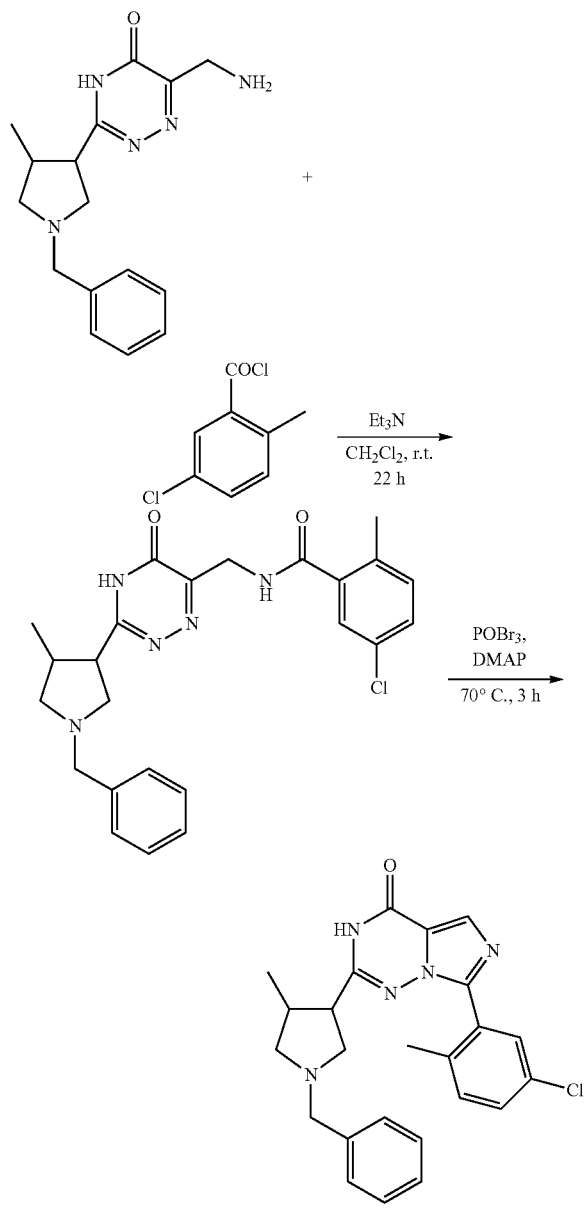

Synthesis of (+/+N-((3-((3,4-trans)-1-benzyl-4-methylpyrrolidin-3-yl)-5-oxo-4,5-dihydro-1,2,4-triazin-6-yl)methyl)-5-chloro-2-methylbenzamide

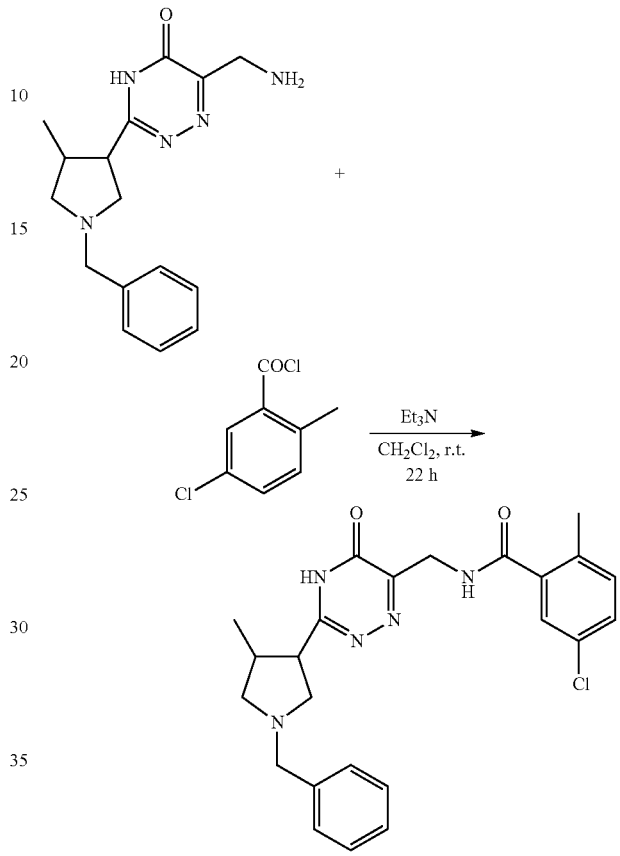

To a suspension of (+/−)-6-(aminomethyl)-3-((3,4-trans)-1-benzyl-4-methylpyrrolidin-3-yl)-1,2,4-triazin-5(4H)-one (1.02 g, 3.41 mmol) and triethylamine (1.04 g, 10.23 mmol) in CH$_2$Cl$_2$ (45 mL) was added 5-chloro-2-methylbenzoyl chloride (0.97 g, 5.11 mmol) drop-wise at RT. The resulting solution was stirred at room temperature for 22 h. After which time the precipitate was filtered and the filter cake was washed with CHCl$_3$. The filtrated was mixed with saturated NaHCO$_3$ (30 mL). The organic phase was separated from the aqueous phase, and the latter was extracted with CHCl$_3$ (20 mL). The combined organic phase was dried over MgSO$_4$. Filtration and concentration gave a yellow foam. Flash chromatography over silica gel column (0.1/1.5/98.4-1/15/84 NH$_4$OH/MeOH/CH$_2$Cl$_2$) provided (+/−)-N-((3-((3,4-trans)-1-benzyl-4-methylpyrrolidin-3-yl)-5-oxo-4,5-dihydro-1,2,4-triazin-6-yl)methyl)-5-chloro-2-methylbenzamide (1.10 g, 71% yield) as a yellow solid. $^1$H NMR (300 MHz, CDCl$_3$) δ 7.41 (d, 1H, J=1.8 Hz), 7.38-7.30 (m, 5H), 7.24 (dd, 1H, J=7.8, 2.1 Hz), 7.14 (d, 1H, J=7.8 Hz), 6.97 (br s, 1H), 4.66 (d, 2H, J=5.1 Hz), 3.91 (d, 1H, J=12.3 Hz), 3.78 (d, 1H, J=12.3 Hz), 3.48-3.37 (m, 1H), 3.25-3.14 (m, 1H), 3.05-2.78 (m, 2H), 2.58-2.42 (m, 1H), 2.41 (s, 3H), 2.30-2.14 (m, 1H), 1.13 (d, 3H, J=6.6 Hz); $^{13}$C NMR (75 MHz, CDCl$_3$) δ 168.3, 165.8, 160.7, 151.0, 1137.3, 135.9, 134.6, 132.2, 131.3, 129.8, 128.8, 128.7, 128.0, 126.9, 60.6, 59.5, 56.3, 49.8, 40.1, 38.9, 19.8, 19.4.

Synthesis of (+)-2-((3,4-trans)-1-benzyl-4-methyl-pyrrolidin-3-yl)-7-(5-chloro-2-methylphenyl)imidazo[5,1-f][1,2,4]triazin-4(3H)-one and (−)-2-((3,4-trans)-1-benzyl-4-methylpyrrolidin-3-yl)-7-(5-chloro-2-methylphenyl)imidazo[5,1-f][1,2,4]triazin-4(3H)-one

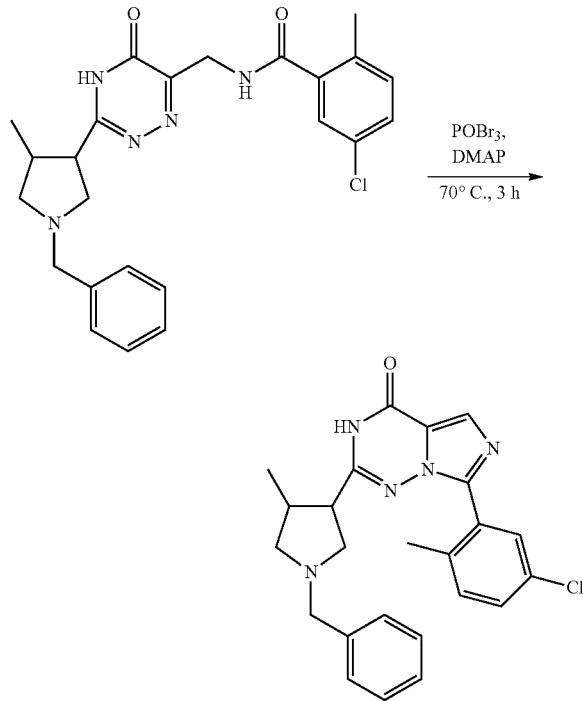

To a solution of (+/−)-N-((3-((3,4-trans)-1-benzyl-4-methylpyrrolidin-3-yl)-5-oxo-4,5-dihydro-1,2,4-triazin-6-yl)methyl)-5-chloro-2-methylbenzamide (110 mg, 0.24 mmol), DMAP (4 mg, 0.03 mmol) in acetonitrile (5 mL) was added a solution of POBr₃ (210 mg, 0.73 mmol) in acetonitrile (1 mL) at RT, and the resulting suspension was heated to 70° C. for 3 h. After the mixture was cooled to room temperature, it was poured into cold saturated NaHCO₃ solution (20 mL), and stirred vigorously for 0.5 h, then extracted with CH₂Cl₂ (3×10 mL). The organic extract was dried over MgSO₄ and concentrated under reduced pressure. The residue was purified by flash chromatography over silica gel (0.05/0.75/99.2-0.3/4.5/95.2 NH₄OH/MeOH/CH₂Cl₂) to furnish (+/−)-2-((3,4-trans)-1-benzyl-4-methylpyrrolidin-3-yl)-7-(5-chloro-2-methylphenyl)imidazo[5,1-f][1,2,4]triazin-4(3H)-one (68 mg, 64% yield) as a white foam. Purity (HPLC): 97.2%; ¹H NMR (300 MHz, CDCl₃/TMS) δ 7.98 (s, 1H), 7.54 (d, J=1.8 Hz, 1H) 7.42-7.21 (m, 7H), 3.82 (d, J=12.3 Hz, 1H), 3.57 (d, J=12.6 Hz, 1H), 3.40 (t, J=8.6 Hz, 1H), 2.97 (d, J=10.5 Hz, 1H), 2.72-2.68 (m, 1H), 2.52-2.37 (m, 2H), 2.30 (s, 3H), 1.92 (t, J=8.7 Hz, 1H), 1.17 (d, J=7.2 Hz, 3H); ¹³C NMR (75 MHz, CDCl₃/TMS) δ 154.51, 154.25, 143.18, 137.17, 136.86, 131.73, 130.92, 130.66, 129.68, 129.49, 128.70, 128.67, 128.49, 127.65, 119.30, 61.10, 59.32, 55.96, 47.75, 38.50, 20.25, 20.00; HRMS: calculated for C₂₄H₂₅ClN₅O (MH⁺), 434.1742. found, 434.1742.

(+/−)-2-((3,4-trans)-1-benzyl-4-methylpyrrolidin-3-yl)-7-(5-chloro-2-methylphenyl)imidazo[5,1-f][1,2,4]triazin-4(3H)-one was purified by Chiralpak AD-H, 250×20 mm, 5 um (160 mg loading; 0.1% TEA in n-Hexane:Ethanol (95:05) as mobile phase) to obtain pure fraction 1 ((−)-2-((3,4-trans)-1-benzyl-4-methylpyrrolidin-3-yl)-7-(5-chloro-2-methylphenyl)imidazo[5,1-f][1,2,4]triazin-4(3H)-one) and pure fraction 2 ((+)-2-((3,4-trans)-1-benzyl-4-methylpyrrolidin-3-yl)-7-(5-chloro-2-methylphenyl)imidazo[5,1-f][1,2,4]triazin-4(3H)-one). Characterization details of both fractions are as follows:

(−)-2-((3,4-trans)-1-benzyl-4-methylpyrrolidin-3-yl)-7-(5-chloro-2-methylphenyl)imidazo[5,1-f][1,2,4]triazin-4(3H)-one: H-NMR (DMSO d₆, 400 MHz): δ 7.92 (s, 1H), 7.68 (s, 1H), 7.48 (d, 1H), 7.42 (d, 1H), 7.32-7.29 (m, 5H), 3.62-3.57 (m, 4H), 2.94-2.91 (m, 1H), 2.82-2.78 (m, 3H), 2.34 (s, 3H), 2.22-2.18 (m, 1H), 1.07 (d, 3H); Mass (ESI): 434 [M⁺+1]; LC-MS: 96.91%; 434 (M⁺+1); (column; X-bridge C-18, (50×3.0 mm, 3.5μ); RT 3.71 min. 5 mM NH₄OAc: ACN; 0.8 ml/min); UPLC (purity): 99.01%; (column; Acquity BEH C-18, 50×2.1 mm, 1.7μ; RT 1.95 min. 0.025% TFA (Aq): ACN:Water; 0.50 ml/min.; Chiral HPLC: 99.65% ee R$_f$=10.64 min (Chiralpak AD-H, 250×4.6 mm, 5μ; mobile phase (A) 0.1% TEA in n-Hexane (B) Ethanol (A:B:90:10); flow Rate: 1.00 mL/min); Optical rotation [α]$_D^{25}$: −28.52° (c=0.5, DCM).

(+)-2-((3,4-trans)-1-benzyl-4-methylpyrrolidin-3-yl)-7-(5-chloro-2-methylphenyl)imidazo[5,1-f][1,2,4]triazin-4(3H)-one: H-NMR (DMSO d₆, 400 MHz): δ 7.92 (s, 1H), 7.69 (s, 1H), 7.48 (d, 1H), 7.42 (d, 1H), 7.36-7.29 (m, 5H), 3.62-3.57 (m, 4H), 2.94-2.91 (m, 1H), 2.82-2.777 (m, 3H), 2.34 (s, 3H), 2.24-2.21 (m, 1H), 1.07 (d, 3H); Mass (ESI): 434 [M⁺+1]; LC-MS: 95.15%; 434 (M⁺+1); (column; X-bridge C-18, (50×3.0 mm, 3.5μ); RT 3.71 min. 5 mM NH₄OAc: ACN; 0.8 ml/min); UPLC (purity): 98.14%; (column; Acquity BEH C-18, 50×2.1 mm, 1.7μ; RT 1.95 min. 0.025% TFA (Aq): ACN:Water; 0.50 ml/min.; Chiral HPLC: 99.94% ee R$_f$=18.33 min (Chiralpak AD-H, 250×4.6 mm, 5μ; mobile phase (A) 0.1% TEA in n-Hexane (B) Ethanol (A:B:90:10); flow Rate: 1.00 mL/min); Optical rotation [α]$_D^{25}$: +23.42° (c=0.5, DCM).

27. (−)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one

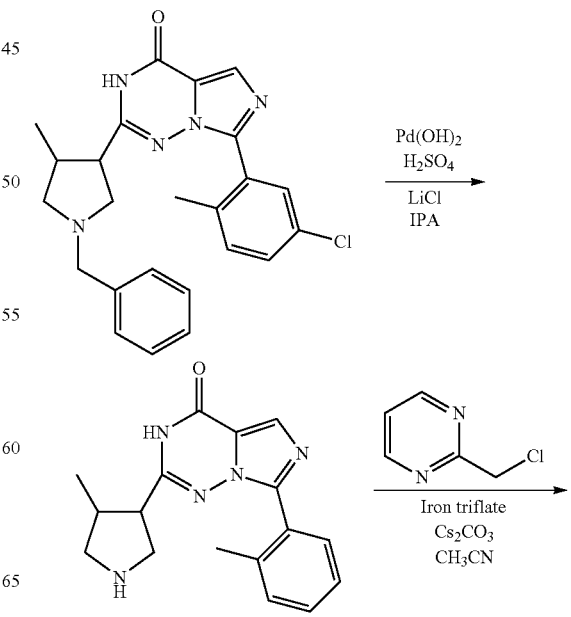

28. (−)-7-(5-chloro-2-methylphenyl)-2-((3,4-trans)-4-methylpyrrolidin-3-yl)imidazo[5,1-f][1,2,4]triazin-4(3H)-one

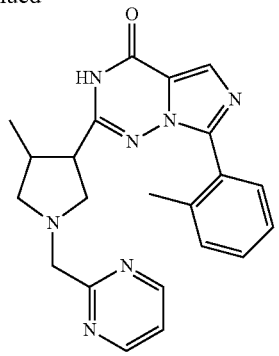

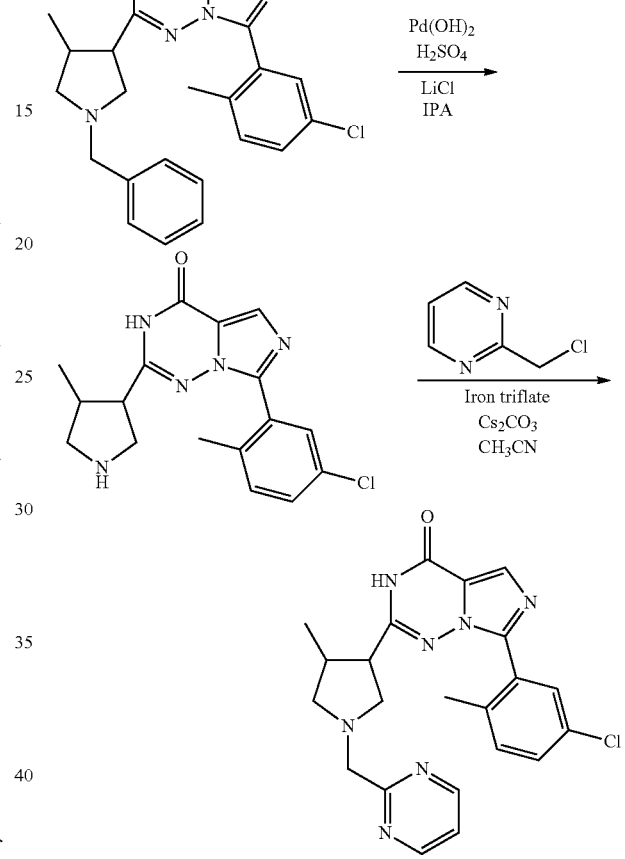

To a stirred solution of (−)-2-((3,4-trans)-1-benzyl-4-methylpyrrolidin-3-yl)-7-(5-chloro-2-methylphenyl)imidazo[5,1-f][1,2,4]triazin-4(3H)-one (150 mg, 0.34 mmol) in MeOH (10 mL) was added Pd/C (50 mg) under $N_2$ atmosphere. The reaction was stirred at RT for 3 h under $H_2$ atmosphere (balloon pressure). The reaction mixture was passed through a pad of celite and volatiles were dried in vacuo. Obtained residue was washed with n-pentane (2 times) to afford 2-((3,4-trans)-4-methylpyrrolidin-3-yl)-7-(o-tolyl)imidazo[5,1-f][1,2,4]triazin-4(3H)-one (100 mg, 94%) as solid. $^1$H-NMR (DMSO $d_6$, 400 MHz): δ 12.34 (br s, 1H), 9.65 (br s, 1H), 7.92 (s, 1H), 7.60 (d, 1H), 7.55-7.32 (m, 3H), 3.65 (t, 1H), 3.46-3.40 (m, 2H), 3.01 (q, 1H), 2.83 (t, 1H), 2.61-2.57 (m, 1H), 2.34 (s, 3H), 1.09 (d, 3H); LC-MS: 91.38%; 310 ($M^+$+1); (column; Eclipse XDB C-18, (150×4.6 mm, 5.0μ); RT 5.30 min. 5 mM NH4Oac: ACN; 1.0 ml/min); TLC: 5% MeOH/$CH_2Cl_2$ ($R_f$ 0.1).

To a stirred solution of 2-((3,4-trans)-4-methylpyrrolidin-3-yl)-7-(o-tolyl)imidazo[5,1-f][1,2,4]triazin-4(3H)-one (100 mg, 0.29 mmol) in ACN (10 mL) was added 2-(chloromethyl)pyrimidine (41 mg, 0.32 mmol), Irontriflate (29.32 mg, 0.06 mmol) followed by $Cs_2CO_3$ (209 mg, 0.641 mmol) at RT under inert atmosphere The reaction mixture was heated to 70° C. and stirred for 3 h. After consumption of starting material (by TLC), the reaction was diluted with water and extracted with EtOAc (2×30 ml). Combined organic layers were dried over anhydrous sodium sulphate, filtered and concentrated in vacuo to obtain the crude product. The crude material was purified by silica gel column chromatography and further purified by preparative to afford (−)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one (42 mg, 36%) as an off-white solid. $^1$H-NMR (DMSO $d_6$, 400 MHz): δ 8.79 (d, 2H), 7.90 (s, 1H), 7.53 (d, 1H), 7.41-7.25 (m, 4H), 3.98 (d, 1H), 3.82 (d, 1H), 3.09 (t, 2H), 2.99-2.90 (m, 3H), 2.72 (q, 1H), 2.34 (d, 1H), 2.28 (s, 3H), 1.05 (d, 3H); Mass (ESI): 402 [($M^+$+1)]; LC-MS: 97.87%; 403.7 [($M^+$+2)]; (column; X-bridge C-18, (50×3.0 mm, 3.5μ); RT 2.66 min. 0.1% aq. TFA: ACN; 0.8 ml/min); UPLC (purity): 98.7%; (column; Acquity UPLC BEH C18, 2.1×50 mm, 1.7μ; RT 1.41 min. 0.025% aqueous TFA: ACN:Water; 0.5 ml/min.; Chiral HPLC: 100% ee $R_t$=33.0 min (Chiralpak IC, 250×4.6 mm, 5μ; mobile phase (A) 0.1% TEA in n-Hexane (B) ethanol (A:B:50:50); flow Rate: 1.00 mL/min); Optical rotation $[α]_D^{24}$: −86.78° (c=0.5, DCM). TLC: 10% MeOH/$CH_2Cl_2$ ($R_f$ 0.5).

To a stirred solution of (−)-2-((3,4-trans)-1-benzyl-4-methylpyrrolidin-3-yl)-7-(5-chloro-2-methylphenyl)imidazo[5,1-f][1,2,4]triazin-4(3H)-one (120 mg, 0.276 mmol) in IPA (20 mL) were added LiCl (24 mg), Pd(OH)$_2$ (36 mg) followed by $H_2SO_4$ (36 mg) under $N_2$ atmosphere. The reaction was stirred at RT for 8 h under $H_2$ atmosphere (balloon pressure). The reaction mixture was passed through a pad of celite and volatiles were dried in vacuo. Obtained residue was co-distilled with toluene (2×20 ml) to afford 7-(5-chloro-2-methylphenyl)-2-((3,4-trans)-4-methylpyrrolidin-3-yl)imidazo[5,1-f][1,2,4]triazin-4(3H)-one (140 mg, crude) as solid. This was directly used for the next step without further purification. Mass (ESI): 344 [$M^+$+1]; LC-MS: 34.66%; 344.9 ($M^+$+1); (column; X-bridge C-18, (50× 3.0 mm, 3.5μ); RT 2.94 min. 0.1% TFA: ACN; 0.8 ml/min); UPLC (purity): 37.41%; (column; Acquity BEH C18, 2.1× 100 mm, 1.7μ; RT 1.63 min. 0.025% aqueous TFA:ACN: Water; 0.5 ml/min.; TLC: 10% MeOH/$CH_2Cl_2$ (Rf 0.2).

To a stirred solution of 7-(5-chloro-2-methylphenyl)-2-((3,4-trans)-4-methylpyrrolidin-3-yl)imidazo[5,1-f][1,2,4]triazin-4(3H)-one (60 mg, 0.174 mmol) in ACN (10 mL) was added 2-(chloromethyl)pyrimidine (24.6 mg, 0.19 mmol), iron triflate (17.5 mg, 0.03 mmol) followed by Cs$_2$CO$_3$ (114 mg, 0.34 mmol) at RT under inert atmosphere. The reaction mixture was heated to 70° C. and stirred for 4 h. After consumption of starting material (by TLC), the reaction was diluted with water and extracted with EtOAc. Combined organic layers were dried over anhydrous sodium sulphate, filtered and concentrated in vacuo to obtain the crude product. The crude material was purified by silica gel column chromatography and further purified by preparative to afford (−)-7-(5-chloro-2-methylphenyl)-2-((3,4-trans)-4-methylpyrrolidin-3-yl)imidazo[5,1-f][1,2,4]triazin-4(3H)-one (12 mg, 16%) as an off-white solid. $^1$H-NMR (DMSO d$_6$, 500 MHz): δ 8.79 (s, 2H), 7.95 (s, 1H), 7.64 (s, 1H), 7.46 (d, 1H), 7.41 (d, 2H), 4.03 (d, 1H), 3.82-3.80 (m, 1H), 3.54 (s, 1H), 3.15 (t, 1H), 3.03-2.97 (m, 3H), 2.79 (q, 1H), 2.38 (t, 1H), 2.09 (s, 3H), 1.05 (d, 3H); Mass (ESI): 436 [M$^+$]; LC-MS: 87.85%; 436 (M$^+$); (column; X-bridge C-18, (50× 3.0 mm, 3.5μ); RT 3.68 min. 5 mM NH4OAc: ACN; 0.8 ml/min); UPLC (purity): 87.41%; (column; Acquity BEH C18, 2.1×100 mm, 1.7μ; RT 1.66 min. 0.025% aqueous TFA: ACN:Water; 0.5 ml/min.; Chiral HPLC: 98.3% ee R$_t$=23.57 min (Chiralpak IC, 250×4.6 mm, 5μ; mobile phase (A) 0.1% TEA in n-Hexane (B) ethanol (A:B:40:60); flow Rate: 1.00 mL/min); Optical rotation [α]$_D^{25}$: −64.53° (c=0.25, DCM). TLC: 5% MeOH/CH$_2$Cl$_2$ (R$_f$ 0.35).

29. (+)-2-((3,4-trans)-1-benzyl-4-methylpyrrolidin-3-yl)-7-(4-fluoro-2-methylphenyl)imidazo[5,1-f][1,2,4]triazin-4(3H)-one and (−)-2-((3,4-trans)-1-benzyl-4-methylpyrrolidin-3-yl)-7-(4-fluoro-2-methylphenyl)imidazo[5,1-f][1,2,4]triazin-4(3H)-one

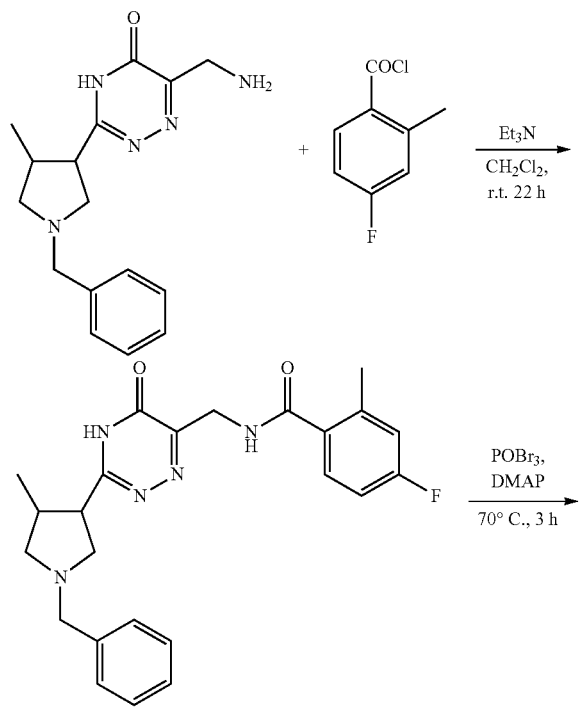

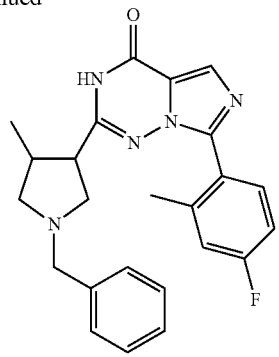

Synthesis of (+/−)-N-((3-((3,4-trans)-1-benzyl-4-methylpyrrolidin-3-yl)-5-oxo-4,5-dihydro-1,2,4-triazin-6-yl)methyl)-4-fluoro-2-methylbenzamide

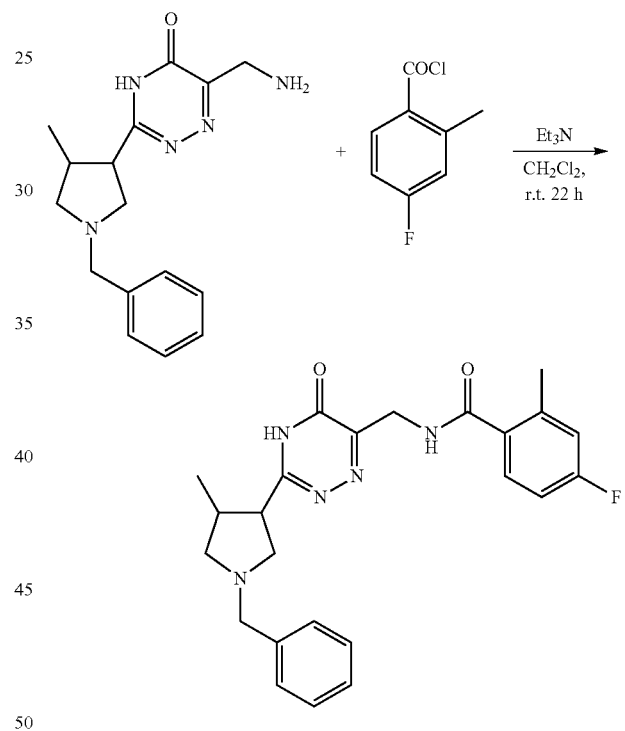

To a suspension of (+/−)-6-(aminomethyl)-3-((3,4-trans)-1-benzyl-4-methylpyrrolidin-3-yl)-1,2,4-triazin-5(4H)-one (1.02 g, 3.41 mmol) and triethylamine (1.04 g, 10.23 mmol) in CH$_2$Cl$_2$ (40 mL) was added a solution of 4-fluoro-2-methylbenzoyl chloride (0.88 g, 5.11 mmol) in CH$_2$Cl$_2$ (5 mL) drop-wise at RT. The resulting solution was stirred at room temperature for 17 h. After which time the precipitate was filtered and the filter cake was washed with CHCl$_3$. The filtrated was concentrated to give a yellow solid. Flash chromatography over silica gel column (0.1/1.5/98.4-0.8/12/87.2 NH$_4$OH/MeOH/CH$_2$Cl$_2$) provided (+/−)-N-((3-((3,4-trans)-1-benzyl-4-methylpyrrolidin-3-yl)-5-oxo-4,5-dihydro-1,2,4-triazin-6-yl)methyl)-4-fluoro-2-methylbenzamide (1.17 g, 79% yield) as a yellow solid. $^1$H NMR (300 MHz, CDCl$_3$) δ 9.43 (br s, 1H), 7.45 (dd, 1H, J=8.4, 6.0 Hz), 7.40-7.26 (m, 5H), 7.05 (br s, 1H), 6.94-6.82

(m, 2H), 4.67 (d, 2H, J=5.4 Hz), 3.96 (d, 1H, J=11.4 Hz), 3.84 (d, 1H, J=11.4 Hz), 3.48-3.37 (m, 1H), 3.30-3.20 (m, 1H), 3.15-2.85 (m, 2H), 2.60-2.45 (m, 1H), 2.48 (s, 3H), 2.39-2.25 (m, 1H), 1.11 (d, 3H, J=6.9 Hz); $^{13}$C NMR (75 MHz, CDCl$_3$) δ 168.9, 165.5, 163.1 (d, J=247 Hz), 150.8, 139.4 (d, J=8.4 Hz), 131.8, 129.0, 128.7, 128.3, 117.6 (d, J=22 Hz), 112.4 (d, J=21 Hz), 60.4, 59.5, 56.4, 49.9, 40.2, 38.7, 20.2, 19.0.

Synthesis of (+)-2-((3,4-trans)-1-benzyl-4-methyl-pyrrolidin-3-yl)-7-(4-fluoro-2-methylphenyl)imidazo[5,1-f][1,2,4]triazin-4(3H)-one and (−)-2-((3,4-trans)-1-benzyl-4-methylpyrrolidin-3-yl)-7-(4-fluoro-2-methylphenyl)imidazo[5,1-f][1,2,4]triazin-4(3H)-one

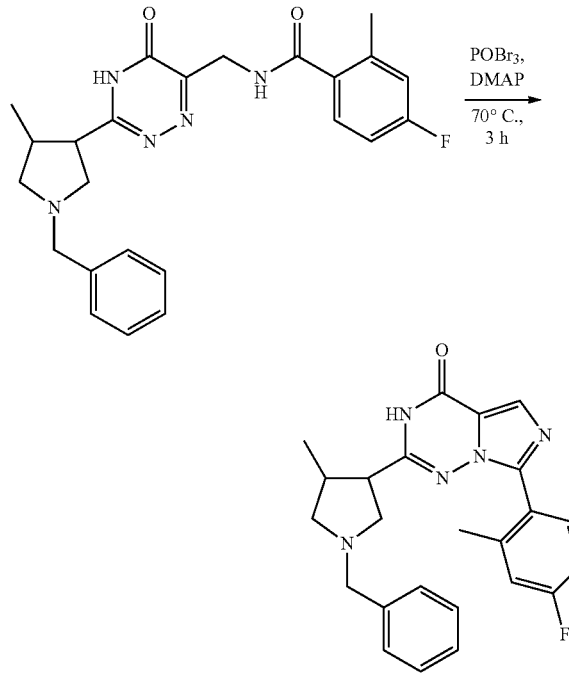

To a solution of (+/−)-N-((3-((3,4-trans)-1-benzyl-4-methylpyrrolidin-3-yl)-5-oxo-4,5-dihydro-1,2,4-triazin-6-yl)methyl)-4-fluoro-2-methylbenzamide (1.17 g, 2.69 mmol), DMAP (33 mg, 0.27 mmol) in acetonitrile (50 mL) was added a solution of POBr$_3$ (2.31 g, 8.06 mmol) in acetonitrile (10 mL) at RT, and the resulting suspension was heated to 70° C. for 3 h. After the mixture was cooled to room temperature, it was poured into cold saturated NaHCO$_3$ solution (200 mL), and stirred vigorously for 0.5 h, then extracted with CH$_2$Cl$_2$ (3×60 mL). The organic extract was dried over MgSO$_4$ and concentrated under reduced pressure. The residue was purified by flash chromatography over silica gel (0.05/0.75/99.2-0.3/4.5/95.2 NH$_4$OH/MeOH/CH$_2$Cl$_2$) to furnish (+/−)-2-((3,4-trans)-1-benzyl-4-methyl-pyrrolidin-3-yl)-7-(4-fluoro-2-methylphenyl)imidazo[5,1-f][1,2,4]triazin-4(3H)-one (0.72 g, 64% yield) as a white foam. Purity (HPLC): 96.9%; $^1$H NMR (300 MHz, CDCl$_3$/TMS) δ 7.98 (s, 1H), 7.51 (dd, J=8.4, 6.0 Hz, 1H) 7.44-7.24 (m, 5H), 7.06-6.94 (m, 2H), 3.82 (d, J=12.3 Hz, 1H), 3.56 (d, J=12.9 Hz, 1H), 3.39 (t, J=8.3 Hz, 1H), 2.96 (d, J=9.9 Hz, 1H), 2.72-2.66 (m, 1H), 2.52-2.37 (m, 2H), 2.33 (s, 3H), 1.91 (t, J=8.7 Hz, 1H), 1.16 (d, J=7.2 Hz, 3H); $^{13}$C NMR (75 MHz, CDCl$_3$/TMS) δ 163.12 (d, J=247 Hz), 154.22, 143.73, 141.20 (d, J=8.4 Hz), 137.13, 132.62 (d, J=9.0 Hz), 128.62, 128.58, 128.33, 127.55, 124.41, 119.12, 117.10 (d, J=21.5 Hz), 112.39 (d, J=21.5 Hz), 61.07, 59.27, 55.94, 47.84, 38.44, 20.47, 20.11; HRMS: calculated for C$_{24}$H$_{25}$FN$_5$O (MH$^+$), 418.2038. found, 418.2043.

(+/−)-2-((3,4-trans)-1-benzyl-4-methylpyrrolidin-3-yl)-7-(4-fluoro-2-methylphenyl)imidazo[5,1-f][1,2,4]triazin-4(3H)-one was purified by Chiralpak AD-H, 250×20 mm, 5 um (135 mg loading; 0.1% TEA in n-Hexane:Ethanol (90:10) as mobile phase) to obtain pure fraction 1 ((+)-2-((3,4-trans)-1-benzyl-4-methylpyrrolidin-3-yl)-7-(4-fluoro-2-methylphenyl)imidazo[5,1-f][1,2,4]triazin-4(3H)-one) and pure fraction 2 ((−)-2-((3,4-trans)-1-benzyl-4-methylpyrrolidin-3-yl)-7-(4-fluoro-2-methylphenyl)imidazo[5,1-f][1,2,4]triazin-4(3H)-one). Characterization details of both fractions are as follows:

(+)-2-((3,4-trans)-1-benzyl-4-methylpyrrolidin-3-yl)-7-(4-fluoro-2-methylphenyl)imidazo[5,1-f][1,2,4]triazin-4(3H)-one: H-NMR (DMSO d$_6$, 400 MHz): δ 7.89 (s, 1H), 7.64-7.61 (m, 1H), 7.34-7.29 (m, 6H), 7.21-7.16 (m, 1H), 3.64-3.58 (m, 3H), 2.92-2.87 (m, 1H), 2.82-2.74 (m, 3H), 2.57-2.52 (m, 1H), 2.32 (s, 3H), 2.23-2.18 (m, 1H), 1.07 (d, 3H); Mass (ESI): 418 [M$^+$+1]; LC-MS: 95.17%; 418 (M$^+$+1); (column; X-bridge C-18, (50×3.0 mm, 3.5μ); RT 3.44 min. 5 mM NH$_4$OAc: ACN; 0.8 ml/min); UPLC (purity): 97.01%; (column; Acquity BEH C-18, 50×2.1 mm, 1.7μ; RT 1.83 min. 0.025% TFA (Aq): ACN:Water; 0.50 ml/min.; Chiral HPLC: 100% ee R$_t$=27.33 min (Chiralpak IA, 250× 4.6 mm, 5μ; mobile phase (A) 0.1% TEA in n-Hexane (B) IPA (A:B:95:05); flow Rate: 1.00 mL/min); Optical rotation [α]$_D^{24}$: +11.61° (c=0.5, DCM).

(−)-2-((3,4-trans)-1-benzyl-4-methylpyrrolidin-3-yl)-7-(4-fluoro-2-methylphenyl)imidazo[5,1-f][1,2,4]triazin-4(3H)-one: H-NMR (DMSO d$_6$, 400 MHz): δ 7.89 (s, 1H), 7.62-7.57 (m, 1H), 7.34-7.29 (m, 6H), 7.19-7.14 (m, 1H), 3.64-3.58 (m, 3H), 2.92-2.87 (m, 1H), 2.82-2.76 (m, 3H), 2.57-2.52 (m, 1H), 2.32 (s, 3H), 2.21-2.17 (m, 1H), 1.04 (d, 3H); Mass (ESI): 418 [M$^+$+1]; LC-MS: 97.42%; 418 (M$^+$+1); (column; X-bridge C-18, (50×3.0 mm, 3.5μ); RT 3.44 min. 5 mM NH$_4$OAc: ACN; 0.8 ml/min); UPLC (purity): 99.30%; (column; Acquity BEH C-18, 50×2.1 mm, 1.7μ; RT 1.83 min. 0.025% TFA (Aq): ACN:Water; 0.50 ml/min.; Chiral HPLC: 100% ee R$_t$=34.31 min (Chiralpak IA, 250× 4.6 mm, 5μ; mobile phase (A) 0.1% TEA in n-Hexane (B) IPA (A:B:95:05); flow Rate: 1.00 mL/min); Optical rotation [α]$_D^{24}$: −19.16° (c=0.5, DCM).

30. (−)-7-(4-fluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one

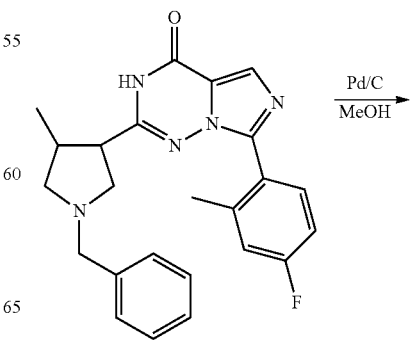

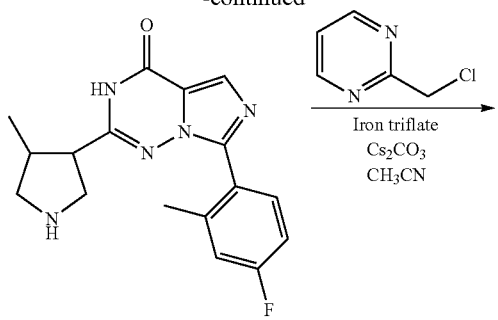

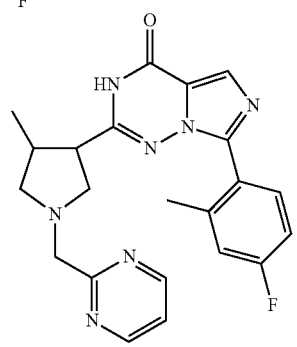

To a stirred solution of (+)-2-((3,4-trans)-1-benzyl-4-methylpyrrolidin-3-yl)-7-(4-fluoro-2-methylphenyl)imidazo[5,1-f][1,2,4]triazin-4(3H)-one (100 mg, 0.24 mmol) in MeOH (5 mL) was added dry Pd/C (30 mg) under $N_2$ atmosphere. The reaction was stirred at RT for 8 h under $H_2$ atmosphere (balloon pressure). The reaction mixture was passed through a pad of celite; the bed was washed with MeOH/$CH_2Cl_2$ and volatiles were dried in vacuo. Obtained residue was washed with n-pentane (2 times) to afford 7-(4-fluoro-2-methylphenyl)-2-((3,4-trans)-4-methylpyrrolidin-3-yl)imidazo[5,1-f][1,2,4]triazin-4(3H)-one (75 mg, 96%) as off-white solid. $^1$H-NMR (DMSO $d_6$, 400 MHz): δ 7.73 (s, 1H), 7.67 (t, 1H), 7.21 (dd, 2H), 3.31-3.20 (m, 4H), 2.67-2.55 (m, 1H), 2.47-2.38 (m, 2H), 2.34 (s, 3H), 1.02 (d, 3H); LC-MS: 93.25%; 328 [(M$^+$+1)]; (column; X-Bridge C-18, (50×3.0 mm, 5.0μ); RT 2.36 min. 5 mM NH4Oac: ACN; 0.8 ml/min); TLC: 5% MeOH/$CH_2Cl_2$ (Rf 0.05).

To a stirred solution of compound 7-(4-fluoro-2-methylphenyl)-2-((3,4-trans)-4-methylpyrrolidin-3-yl)imidazo[5,1-f][1,2,4]triazin-4(3H)-one (75 mg, 0.23 mmol) in ACN (10 mL) was added 2-(chloromethyl)pyrimidine (32.29 mg, 0.253 mmol), iron triflate (23 mg, 0.045 mmol) followed by $Cs_2CO_3$ (164 mg, 0.504 mmol) at RT under inert atmosphere. The reaction mixture was heated to 70° C. and stirred for 4 h. After consumption of starting material (by TLC), the reaction was diluted with water and extracted with EtOAc (2×30 ml). Combined organic layers were dried over anhydrous sodium sulphate, filtered and concentrated in vacuo to obtain the crude product. The crude material was purified by silica gel column chromatography to afford (−)-7-(4-fluoro-2-methylphenyl)-2-((3,4-trans)-4-methyl-1-(pyrimidin-2-ylmethyl)pyrrolidin-3-yl)imidazo[5,1-f][1,2,4]triazin-4(3H)-one (60 mg, 63%) as an off-white solid. $^1$H-NMR (DMSO $d_6$, 400 MHz): δ 8.83 (d, 2H), 7.92 (s, 1H), 7.65 (t, 1H), 7.44 (t, 1H), 7.29 (dd, 1H), 7.20 (t, 1H), 4.01 (d, 1H), 3.85 (d, 1H), 3.13 (t, 1H), 2.99-2.90 (m, 2H), 2.79 (q, 1H), 2.59 (s, 1H), 2.35 (s, 4H), 1.12 (d, 3H); Mass (ESI): 420 [(M$^+$+1)]; LC-MS: 97.74%; 420 [(M$^+$+1)]; (column; X-bridge C-18, (50×3.0 mm, 3.5μ); RT 3.24 min. 5.0 mM NH4OAc: ACN; 0.8 ml/min); UPLC (purity): 99.07%; (column; Acquity UPLC BEH C18, 2.1×50 mm, 1.7μ; RT 1.51 min. 0.025% aqueous TFA: ACN:Water; 0.5 ml/min.; Chiral HPLC: 98.87% ee $R_t$=17.71 min (Chiralpak IC, 250×4.6 mm, 5μ; mobile phase (A) 0.1% TEA in n-Hexane (B) ethanol (A:B:50:50); flow Rate: 1.00 mL/min); Optical rotation $[α]_D^{24}$: −70.93° (c=0.5, DCM). TLC: 10% MeOH/$CH_2Cl_2$ (Rf 0.55).

31. (+)-2-((3,4-trans)-1-benzyl-4-methylpyrrolidin-3-yl)-7-(4,4-difluorocyclohexybimidazo[5,1-f][1,2,4]triazin-4(3H)-one and (−)-2-((3,4-trans)-1-benzyl-4-methylpyrrolidin-3-yl)-7-(4,4-difluorocyclohexybimidazo[5,1-f][1,2,4]triazin-4(3H)-one

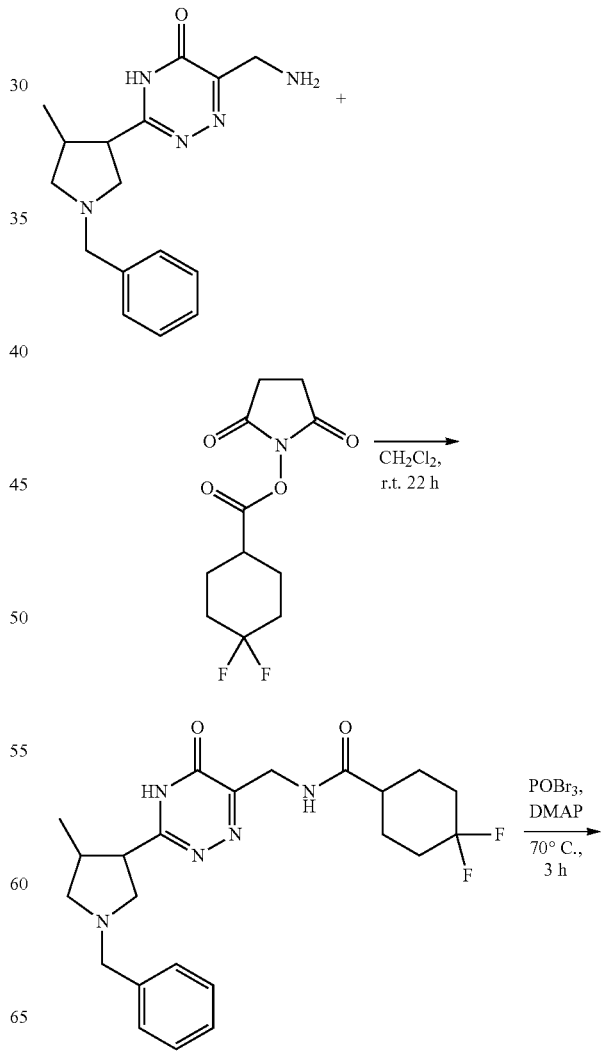

Synthesis of (+/−)-N-((3-((3,4-trans)-1-benzyl-4-methylpyrrolidin-3-yl)-5-oxo-4,5-dihydro-1,2,4-triazin-6-yl)methyl)-4,4-difluorocyclohexanecarboxamide

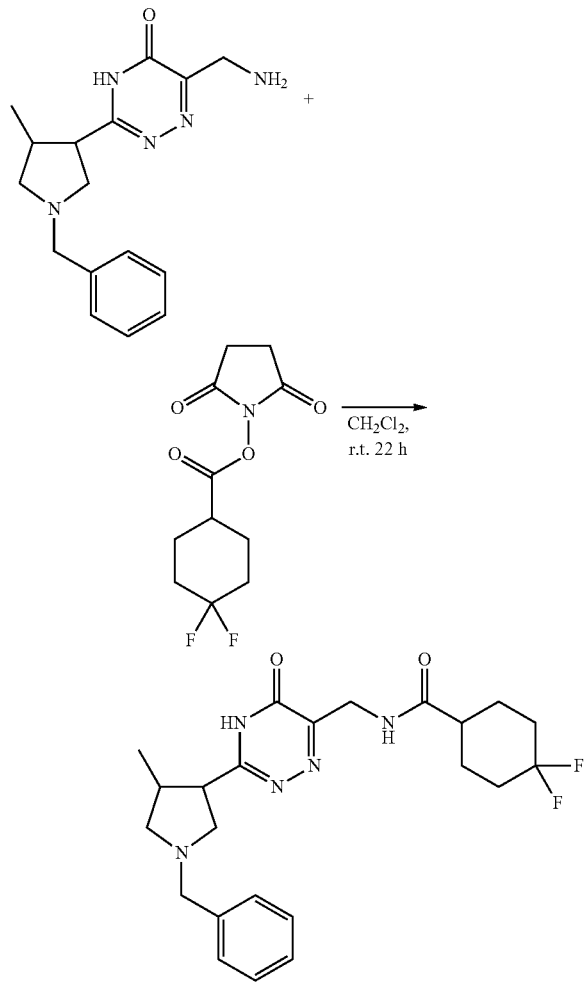

The mixture of (+/−)-6-(aminomethyl)-3-((3,4-trans)-1-benzyl-4-methylpyrrolidin-3-yl)-1,2,4-triazin-5(4H)-one (1.0 g, 3.3 mmol) and 2,5-dioxopyrrolidin-1-yl 4,4-difluorocyclohexanecarboxylate (1.0 g, 3.8 mmol) in CH₂Cl₂ (50 mL) was stirred at room temperature overnight. The precipitate was filtered and the filtrate was washed with water. The aqueous solution was extracted with chloroform (4×100 ml). The CH₂Cl₂ solution and chloroform extracts were combined and the solvents were evaporated. The residue was purified by column chromatography (silica gel, CH₂Cl₂/MeOH/NH₄OH, 10:1:0.5%) to prepare (+/−)-N-((3-((3,4-trans)-1-benzyl-4-methylpyrrolidin-3-yl)-5-oxo-4,5-dihydro-1,2,4-triazin-6-yl)methyl)-4,4-difluorocyclohexanecarboxamide (670 mg, 45% yield). $^1$H NMR (300 MHz, CDCl₃/TMS): δ 7.31 (m, 5H), 4.46 (d, J=4 Hz, 2H), 4.00 (d, J=12 Hz, 1H), 3.86 (d, J=12 Hz, 1H), 3.39 (t, J=9 Hz, 1H), 3.25 (m, 1H), 3.08 (m, 2H), 2.53-2.43 (m, 2H), 2.25 (m, 1H), 2.13-1.60 (m, 9H), 1.04 (d, J=7 Hz, 3H).

Synthesis of (+)-2-((3,4-trans)-1-benzyl-4-methylpyrrolidin-3-yl)-7-(4,4-difluorocyclohexyl)imidazo[5,1-f][1,2,4]triazin-4(3H)-one and (−)-2-((3,4-trans)-1-benzyl-4-methylpyrrolidin-3-yl)-7-(4,4-difluorocyclohexyl)imidazo[5,1-f][1,2,4]triazin-4(3H)-one

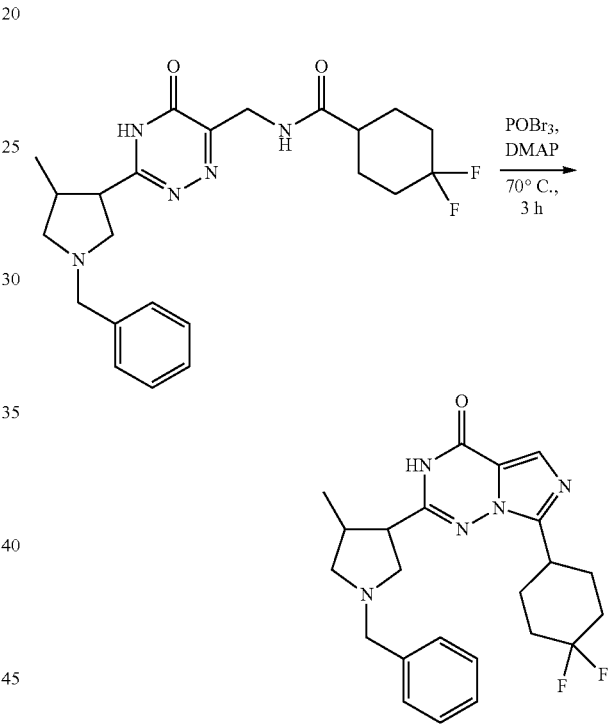

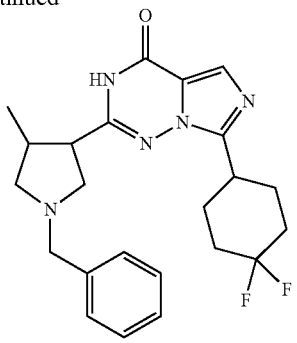

Phosphorus oxybromide (1.26 g, 4.4 mmol) was dissolved in MeCN (10 mL) and the solution was added to (+/−)-N-((3-((3,4-trans)-1-benzyl-4-methylpyrrolidin-3-yl)-5-oxo-4,5-dihydro-1,2,4-triazin-6-yl)methyl)-4,4-difluorocyclohexanecarboxamide (670 mg, 1.5 mmol) and DMAP (50 mg) in MeCN (30 mL) at room temperature drop-wise. The reaction mixture was heat up to 70° C. and stirred for 3 h. The reaction mixture was purred into the cold concentrated aqueous solution of NaHCO₃ (100 mL). The organics were extracted with CH₂Cl₂ (3×50 mL). The organic solution was washed with brine and dried over MgSO₄. The solvent was evaporated and residue was purified by column chromatography (silica gel, CH₂Cl₂/MeOH/NH₄OH, 10:1:1%) to prepare (+/−)-2-((3,4-trans)-1-benzyl-4-methylpyrrolidin-3-yl)-7-(4,4-difluorocyclohexyl)imidazo[5,1-f][1,2,4]triazin-4(3H)-one (380 mg, 59% yield). Purity (HPLC): 97.2%; $^1$H NMR (300 MHz, CDCl₃/TMS): δ 7.75 (s, 1H), 7.34-7.24 (m, 5H), 3.80 (d, J=12.6 Hz, 1H), 3.54 (d, J=12.6 Hz, 1H), 3.37 (t, J=8.5 Hz, 1H), 3.23 (m, 1H), 2.95 (d, J=9.0 Hz, 1H), 2.73-2.72 (m, 1H), 2.53-2.38 (m, 2H), 2.24-1.81 (m, 9H), 1.19 (d, J=7.0 Hz, 3H); $^{13}$C NMR (75 MHz, CDCl$_3$/TMS): δ 154.6, 154.2, 148.3, 137.5, 128.9, 127.9, 127.7, 123.1 (t, J=241. Hz), 119.2, 61.4, 59.6, 56.3, 48.2, 38.7, 33.8, 33.5, 33.1, 27.0 (dd, J=9.0 Hz, J=10.0 Hz), 20.5; $^{19}$F NMR (282 MHz, CDCl$_3$/TMS): δ−93.10 (d, J=236 Hz), 101.1 (d, J=236 Hz).

(+/−)-2-((3,4-trans)-1-benzyl-4-methylpyrrolidin-3-yl)-7-(4,4-difluorocyclohexyl)imidazo[5,1-f][1,2,4]triazin-4(3H)-one was purified by Chiralpak IC, 250×20 mm, 5 um (45 mg loading; 0.1% TEA in n-Hexane:Ethanol (90:10) as mobile phase) to obtain pure fraction 1 ((+)-2-((3,4-trans)-1-benzyl-4-methylpyrrolidin-3-yl)-7-(4,4-difluorocyclohexyl)imidazo[5,1-f][1,2,4]triazin-4(3H)-one) and pure fraction 2 ((−)-2-((3,4-trans)-1-benzyl-4-methylpyrrolidin-3-yl)-7-(4,4-difluorocyclohexyl)imidazo[5,1-f][1,2,4]triazin-4(3H)-one). Characterization details of both fractions are as follows:

(+)-2-((3,4-trans)-1-benzyl-4-methylpyrrolidin-3-yl)-7-(4,4-difluorocyclohexyl)imidazo[5,1-f][1,2,4]triazin-4(3H)-one: H-NMR (DMSO d$_6$, 400 MHz): δ 7.64 (s, 1H), 7.34-7.29 (m, 4H), 7.24-7.21 (m, 1H), 3.68-3.62 (m, 3H), 3.38-3.32 (m, 3H), 2.98-2.96 (m, 1H), 2.87-2.82 (m, 1H), 2.79-2.74 (m, 2H), 2.65-2.62 (m, 1H), 2.18-2.15 (m, 2H), 2.08-1.96 (m, 4H), 1.07 (d, 3H); Mass (ESI): 428 [M$^+$+1]; LC-MS: 97.43%; 428 (M$^+$+1); (column; X-bridge C-18, (50×3.0 mm, 3.5μ); RT 3.40 min. 5 mM NH$_4$OAc: ACN; 0.8 ml/min); UPLC (purity): 99.76%; (column; Acquity BEH C-18, 50×2.1 mm, 1.7μ; RT 1.81 min. 0.025% TFA (Aq): ACN:Water; 0.50 ml/min.; Chiral HPLC: 100% ee R$_t$=24.69 min (Chiralpak IC, 250×4.6 mm, 5μ; mobile phase (A) 0.1% TEA in n-Hexane (B) Ethanol (A:B:90:10); flow Rate: 1.00 mL/min.) Optical rotation [α]$_D^{24}$: +20.19° (c=0.5, DCM).

(−)-2-((3,4-trans)-1-benzyl-4-methylpyrrolidin-3-yl)-7-(4,4-difluorocyclohexyl)imidazo[5,1-f][1,2,4]triazin-4(3H)-one: H-NMR (DMSO d$_6$, 400 MHz): δ 7.62 (s, 1H), 7.37-7.29 (m, 4H), 7.24-7.21 (m, 1H), 3.68-3.61 (m, 3H), 3.34-3.31 (m, 3H), 2.98-2.96 (m, 1H), 2.86-2.84 (m, 1H), 2.79-2.74 (m, 2H), 2.65-2.63 (m, 1H), 2.28-2.26 (m, 1H), 2.18-2.14 (m, 2H), 2.09-1.97 (m, 4H), 1.09 (d, 3H); Mass (ESI): 428 [M$^+$+1]; LC-MS: 98.16%; 428 (M$^+$+1); (column; X-bridge C-18, (50×3.0 mm, 3.5μ); RT 3.42 min. 5 mM NH$_4$OAc: ACN; 0.8 ml/min); UPLC (purity): 99.58%; (column; Acquity BEH C-18, 50×2.1 mm, 1.7μ; RT 1.81 min. 0.025% TFA (Aq): ACN:Water; 0.50 ml/min.; Chiral HPLC: 98.94% ee R$_t$=28.81 min (Chiralpak IC, 250×4.6 mm, 5μ; mobile phase (A) 0.1% TEA in n-Hexane (B) Ethanol (A:B:90:10); flow Rate: 1.00 mL/min.) Optical rotation [α]$_D^{24}$: −24.91° (c=0.5, DCM).

32. (+)-7-(4,4-difluorocyclohexyl)-2-((3,4-trans)-4-methyl-1-(pyrimidin-2-ylmethyl)pyrrolidin-3-yl)imidazo[5,1-f][1,2,4]triazin-4(3H)-one

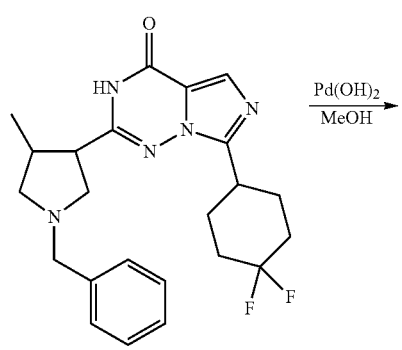

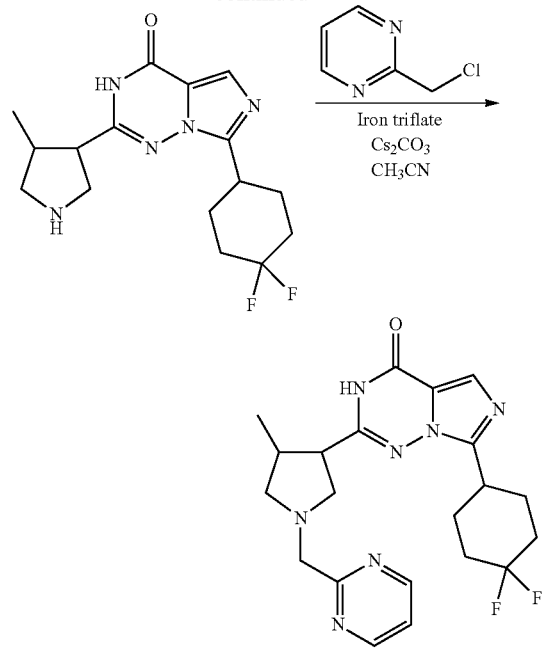

To a stirred solution of (+)-2-((3,4-trans)-1-benzyl-4-methylpyrrolidin-3-yl)-7-(4,4-difluorocyclohexyl)imidazo[5,1-f][1,2,4]triazin-4(3H)-one (125 mg, 0.3 mmol) in MeOH (15 mL) was added 10% Pd(OH)$_2$ (38 mg, catalytic) under N$_2$ atmosphere. The reaction was stirred at RT for 8 h under H$_2$ atmosphere (balloon pressure). The reaction mixture was passed through a pad of celite; the bed was washed with MeOH & CH$_2$Cl$_2$ and volatiles were dried in vacuo. Obtained residue was washed with n-pentane (2 times) and dried under reduced pressure to afford 7-(4,4-difluorocyclohexyl)-2-((3,4-trans)-4-methylpyrrolidin-3-yl)imidazo[5,1-f][1,2,4]triazin-4(3H)-one as off-white solid (95 mg, 97%). LC-MS: 77.88%; 338 [(M$^+$+1)]; (column; X-Bridge C-18, (50×3.0 mm, 3.5 um); RT 2.38 min. 5 mM NH4Oac: ACN; 0.8 ml/min); UPLC (purity): 96.84%; (column; Acquity UPLC BEH C18, 2.1×50 mm, 1.7μ; RT 1.35 min. 0.025% aqueous TFA: ACN:Water; 0.5 ml/min.; TLC: 10% MeOH/CH$_2$Cl$_2$ (Rf 0.1).

To a stirred solution of 7-(4,4-difluorocyclohexyl)-2-((3,4-trans)-4-methylpyrrolidin-3-yl)imidazo[5,1-f][1,2,4]triazin-4(3H)-one (75 mg, 0.22 mmol) in ACN (10 mL) was added 2-(chloromethyl)pyrimidine (31.33 mg, 0.24 mmol), iron triflate (22.4 mg, 0.04 mmol) followed by Cs$_2$CO$_3$ (145 mg, 0.4 mmol) at RT under inert atmosphere. The reaction mixture was heated to 70° C. and stirred for 3 h. After consumption of starting material (by TLC), the reaction was diluted with water and extracted with EtOAc (3×25 mL). Combined organic layers were dried over anhydrous sodium sulphate, filtered and concentrated in vacuo to obtain the crude product. The crude material was purified by silica gel column chromatography to afford (+)-7-(4,4-difluorocyclohexyl)-2-((3,4-trans)-4-methyl-1-(pyrimidin-2-ylmethyl)pyrrolidin-3-yl)imidazo[5,1-f][1,2,4]triazin-4(3H)-one (50 mg, 53%) as an off-white solid. $^1$H-NMR (DMSO d$_6$, 400 MHz): δ 8.79 (d, 2H), 7.68 (s, 1H), 7.44 (t, 1H), 4.04 (d, 1H), 3.85 (d, 1H), 3.15 (t, 1H), 3.02-2.98 (m, 2H), 2.78 (q, 1H), 2.63-2.58 (m, 1H), 2.38 (t, 1H), 2.21-1.98 (m, 9H), 1.13 (d, 3H); Mass (ESI): 430 [(M$^+$+1)]; LC-MS: 99.05%; 430.9 [(M$^+$+1)]; (column; X-bridge C-18, (50×3.0 mm, 3.5μ); RT 2.67 min. 0.1% TFA: ACN; 0.8 ml/min); UPLC (purity):

99.04%; (column; Acquity BEH C18, 2.1×50 mm, 1.7µ; RT 1.56 min. 0.025% aqueous TFA: ACN:Water; 0.5 ml/min.; Chiral HPLC: 100% ee R$_t$=9.04 min (Chiralpak IC, 250×4.6 mm, 5µ; mobile phase (A) 0.1% TEA in n-Hexane (B) ethanol (A:B:40:60); flow Rate: 1.00 mL/min); Optical rotation $[\alpha]_D^{25}$: +103.4° (c=0.5, DCM). TLC: 10% MeOH/ CH$_2$Cl$_2$ (Rf 0.5).

33. (+)-2-((3,4-trans)-1-benzyl-4-methylpyrrolidin-3-yl)-7-(furan-3-yl)imidazo[5,1-f][1,2,4]triazin-4(3H)-one and (−)-2-((3,4-trans)-1-benzyl-4-methylpyrrolidin-3-yl)-7-(furan-3-yl)imidazo[5,1-f][1,2,4]triazin-4(3H)-one

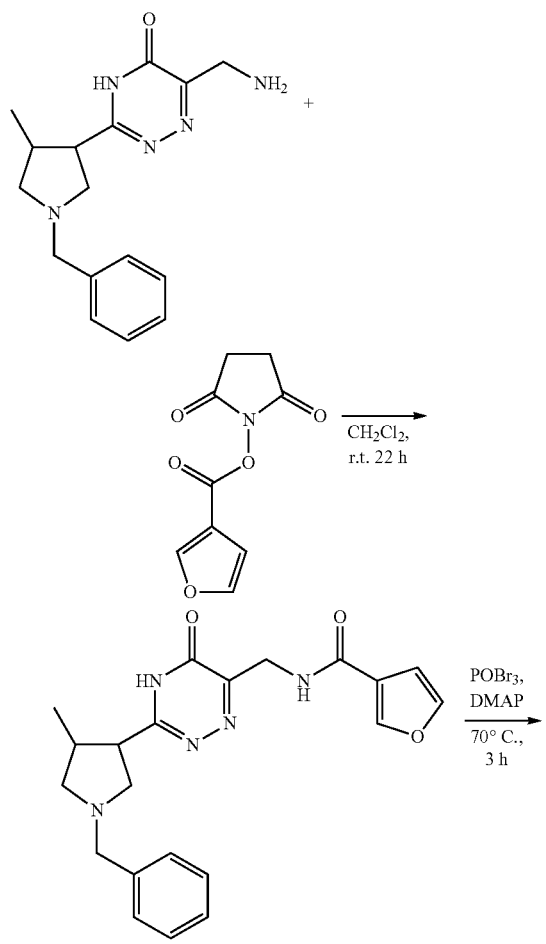

Synthesis of (+/−)-N-((3-((3,4-trans)-1-benzyl-4-methylpyrrolidin-3-yl)-5-oxo-4,5-dihydro-1,2,4-triazin-6-yl)methyl)furan-3-carboxamide

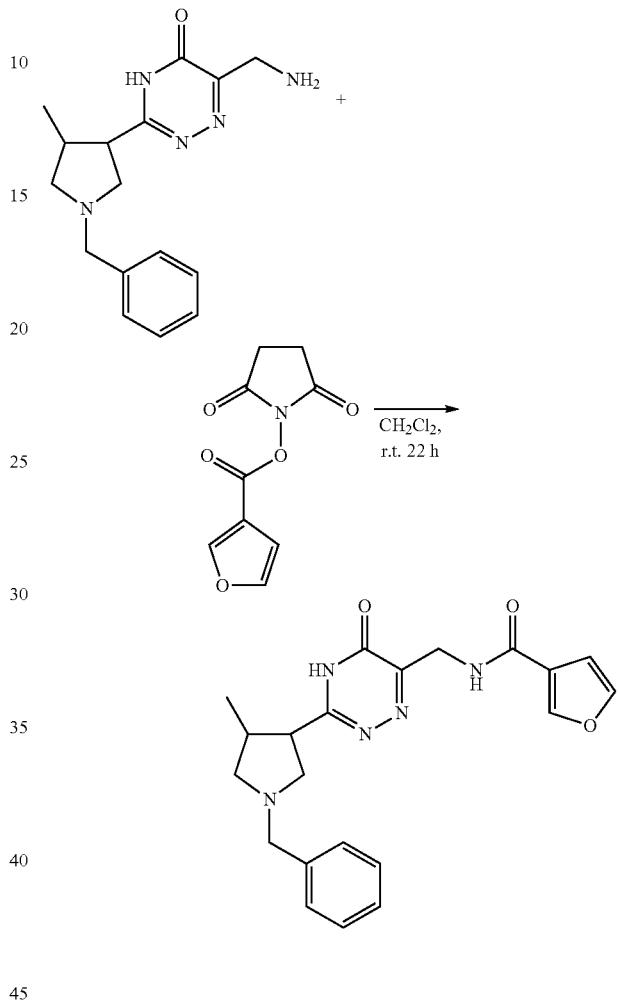

The mixture of (+/−)-6-(aminomethyl)-3-((3,4-trans)-1-benzyl-4-methylpyrrolidin-3-yl)-1,2,4-triazin-5(4H)-one (1.5 g, 5.0 mmol) and furan-2,5-dioxopyrrolidin-1-yl furan-3-carboxylate (1.15 g, 5.5 mmol) in CH$_2$Cl$_2$ (50 mL) was stirred at room temperature overnight. The precipitate was filtered and the filtrate was washed with water. The aqueous solution was extracted with chloroform (4×100 mL). The CH$_2$Cl$_2$ solution and chloroform extracts were combined and the solvents were evaporated and the residue was purified by column chromatography (silica gel, CH$_2$Cl$_2$/ MeOH/NH$_4$OH, 10:1:0.5%) to prepare (+/−)-N-((3-((3,4-trans)-1-benzyl-4-methylpyrrolidin-3-yl)-5-oxo-4,5-dihydro-1,2,4-triazin-6-yl)methyl)furan-3-carboxamide (1.05 g, 45% yield). $^1$H NMR (300 MHz, CDCl$_3$/TMS): δ 7.98 (s, 1H), 7.54 (s, 1H), 7.36-7.26 (m, 5H), 6.70 (s, 1H), 4.60 (d, J=4 Hz, 2H), 4.00 (d, J=12 Hz, 1H), 3.90 (d, J=12 Hz, 1H), 3.44-3.13 (m, 4H), 2.60-2.45 (m, 2H), 1.02 (d, J=6 Hz, 3H).

Synthesis of (+)-2-((3,4-trans)-1-benzyl-4-methyl-pyrrolidin-3-yl)-7-(furan-3-yl)imidazo[5,1-f][1,2,4]triazin-4(3H)-one and (−)-2-((3,4-trans)-1-benzyl-4-methylpyrrolidin-3-yl)-7-(furan-3-yl)imidazo[5,1-f][1,2,4]triazin-4(3H)-one

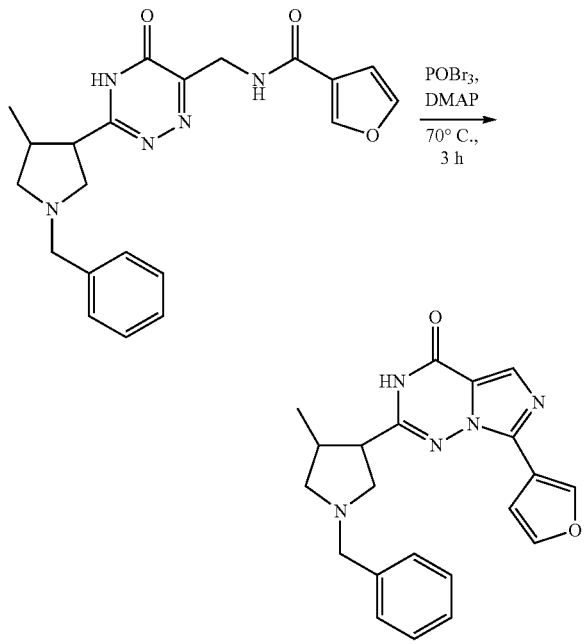

Phosphorus oxybromide (2.31 g, 8.0 mmol) was dissolved in acetonitrile (20 mL) and the solution was added to (+/−)-N-((3-((3,4-trans)-1-benzyl-4-methylpyrrolidin-3-yl)-5-oxo-4,5-dihydro-1,2,4-triazin-6-yl)methyl)furan-3-carboxamide (1.05 g, 2.7 mmol) and DMAP (50 mg) in acetonitrile (40 mL) at room temperature drop-wise. The reaction mixture was heat up to 70° C. and stirred for 3 h. The reaction mixture was purred into the cold concentrated aqueous solution of NaHCO$_3$ (100 mL). The organics were extracted with CH$_2$Cl$_2$ (3×50 mL), the organic solution was washed with brine and dried over MgSO$_4$, the solvent was evaporated and residue was purified by column chromatography (silica gel, CH$_2$Cl$_2$/MeOH/NH$_4$OH, 30:1:1%) to obtain (+/−)-2-((3,4-trans)-1-benzyl-4-methylpyrrolidin-3-yl)-7-(furan-3-yl)imidazo[5,1-f][1,2,4]triazin-4(3H)-one (370 mg, 37% yield). Purity by HPLC:97.3%; $^1$H NMR (300 MHz, CDCl$_3$/TMS): δ 8.39 (s, 1H), 7.90 (s, 1H), 7.49 (s, 1H), 7.37-7.28 (m, 5H), 7.12 (s, 1H), 3.81 (d, J=12 Hz, 1H), 3.58 (d, J=12 Hz, 1H), 3.39 (t, J=8 Hz, 1H), 3.00 (d, J=10 Hz, 1H), 2.77 (m, 1H), 2.56-2.42 (m, 2H), 1.93 (t, J=10 Hz, 1H), 1.21 (d, J=7 Hz, 3H); $^{13}$C NMR (75 MHz, CDCl$_3$/TMS): δ 154.4, 154.0, 142.8, 142.6, 138.7, 137.0, 128.8, 128.6, 127.5, 119.2, 115.4, 109.2, 60.9, 59.2, 55.9, 48.1, 38.4, 20.2.

(+/−)-2-((3,4-trans)-1-benzyl-4-methylpyrrolidin-3-yl)-7-(furan-3-yl)imidazo[5,1-f][1,2,4]triazin-4(3H)-one was purified by Chiralpak IC, 250×20 mm, 5 um (20 mg loading; 0.1% TEA in n-Hexane:ethanol (70:30) as mobile phase) to obtain pure fraction 1 ((+)-2-((3,4-trans)-1-benzyl-4-methylpyrrolidin-3-yl)-7-(furan-3-yl)imidazo[5,1-f][1,2,4]triazin-4(3H)-one) and pure fraction 2 ((−)-2-((3,4-trans)-1-benzyl-4-methylpyrrolidin-3-yl)-7-(furan-3-yl)imidazo[5,1-f][1,2,4]triazin-4(3H)-one). Characterization details of both fractions are as follows:

(+)-2-((3,4-trans)-1-benzyl-4-methylpyrrolidin-3-yl)-7-(furan-3-yl)imidazo[5,1-f][1,2,4]triazin-4(3H)-one:
$^1$H-NMR (DMSO d$_6$, 500 MHz): δ 8.43 (s, 1H), 7.86 (s, 1H), 7.82 (s, 1H), 7.34 (s, 4H), 7.24 (br s, 1H), 7.13 (s, 1H), 3.63 (q, 2H), 2.99 (t, 1H), 2.90-2.83 (m, 4H), 2.73-2.65 (m, 1H), 2.29 (t, 1H), 1.16 (d, 3H); LC-MS: 99.09%; 376.5 (M$^+$+1); (column; X select C-18, (50×3.0 mm, 3.5μ); RT 3.43 min. ACN: 5 mM NH$_4$OAc in water; 0.8 ml/min); UPLC (purity): 99.9%; (column; Acquity BEH C-18, 50×2.1 mm, 1.7μ; RT 1.62 min. 0.025% TFA (Aq): ACN:Water; 0.50 ml/min.; Chiral HPLC: 98.99% ee R$_t$=8.18 min (Chiralpak IC, 250× 4.6 mm, 5μ; mobile phase (A) 0.1% TEA in n-Hexane (B) Ethanol (A:B:70:30); flow Rate: 1.00 mL/min); Optical rotation [α]$_D^{25}$: +28.12° (c=0.25, DCM).

(−)-2-((3,4-trans)-1-benzyl-4-methylpyrrolidin-3-yl)-7-(furan-3-yl)imidazo[5,1-f][1,2,4]triazin-4(3H)-one:
$^1$H-NMR (DMSO d$_6$, 400 MHz): δ 12.72-10.80 (m, 1H), 8.45 (s, 1H), 7.89 (s, 1H), 7.80 (s, 1H), 7.34 (s, 4H), 7.34 (br s, 1H), 7.10 (s, 1H), 3.62 (q, 2H), 2.99-2.79 (m, 4H), 2.71-2.60 (m, 1H), 2.29 (t, 1H), 1.13 (d, 3H); LC-MS: 95.47%; 376.5 (M$^+$+1); (column; X-bridge C-18, (50×3.0 mm, 3.5μ); RT 5.19 min. 5 mM NH$_4$OAc: ACN; 0.8 ml/min); UPLC (purity): 99.94%; (column; Acquity BEH C-18, 50×2.1 mm, 1.7μ; RT 1.60 min. 0.025% TFA (Aq): ACN:Water; 0.50 ml/min.; Chiral HPLC: 99.29% ee R$_t$=10.3 min (Chiralpak IC, 250×4.6 mm, 5μ; mobile phase (A) 0.1% TEA in n-Hexane (B) Ethanol (A:B:70:30); flow Rate: 1.00 mL/min); Optical rotation [α]$_D^{24}$: −36.51° (c=0.25, DCM).

34. (+)-7-(1-acetylpiperidin-4-yl)-2-((3,4-trans)-1-benzyl-4-methylpyrrolidin-3-yl)imidazo[5,1-f][1,2,4]triazin-4(3H)-one and (−)-7-(1-acetylpiperidin-4-yl)-2-((3,4-trans)-1-benzyl-4-methylpyrrolidin-3-yl)imidazo[5,1-f][1,2,4]triazin-4(3H)-one

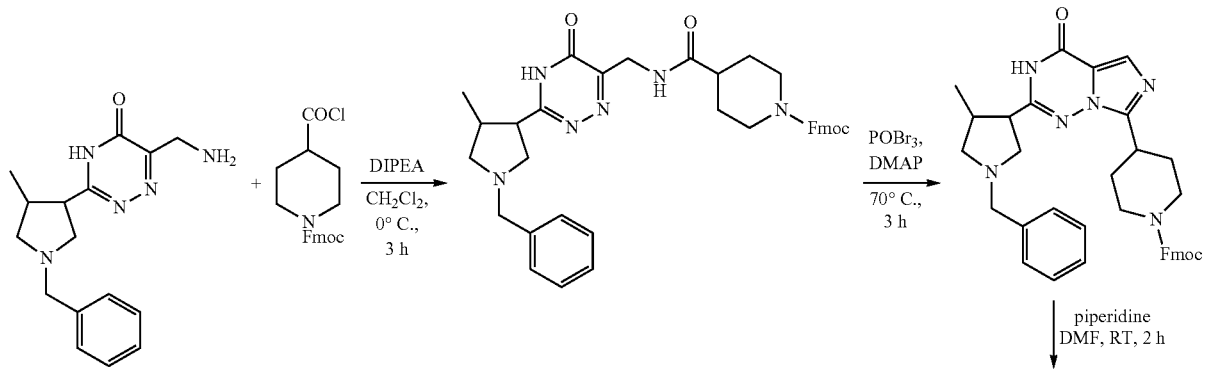

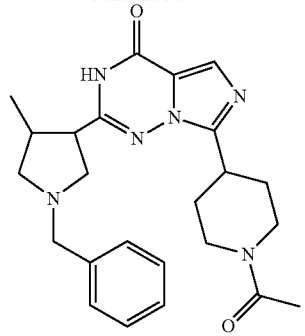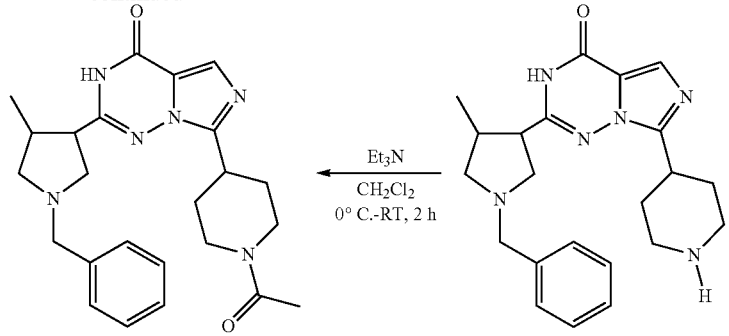

Synthesis of (+/−)-(9H-fluoren-9-yl)methyl 4-(((3-((3,4-trans)-1-benzyl-4-methylpyrrolidin-3-yl)-5-oxo-4,5-dihydro-1,2,4-triazin-6-yl)methyl)carbamoyl)piperidine-1-carboxylate

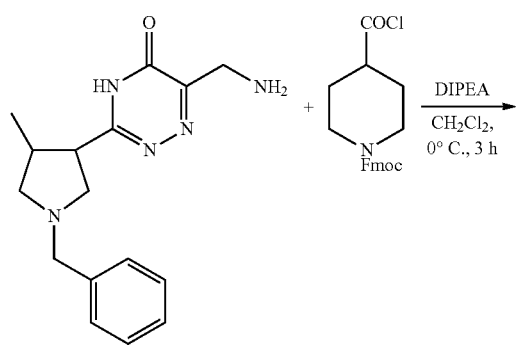

To a solution of (9H-fluoren-9-yl)methyl 4-(chlorocarbonyl)piperidine-1-carboxylate (2.45 g, 6.6 mmol) in CH$_2$Cl$_2$ (75 mL) was added a solution of (+/−)-6-(aminomethyl)-3-((3,4-trans)-1-benzyl-4-methylpyrrolidin-3-yl)-1,2,4-triazin-5(4H)-one (1.80 g, 6.0 mmol) and diisopropylethylamine (0.93 g, 7.2 mmol) in CH$_2$Cl$_2$ (75 mL) drop-wise at 0° C. The resulting solution was stirred at this temperature for 3 h. After which time the precipitate was filtered and the filter cake was washed with CHCl$_3$. The filtrated was treated with saturated NaHCO$_3$ (50 mL). The phases were separated, and the aqueous phase was extracted with CHCl$_3$ (2×20 mL). The combined organic phase was dried over MgSO$_4$. Concentration and purification by chromatography (0-10% MeOH/CH$_2$Cl$_2$) provided (+/−)-(9H-fluoren-9-yl)methyl 4-(((3-((3,4-trans)-1-benzyl-4-methylpyrrolidin-3-yl)-5-oxo-4,5-dihydro-1,2,4-triazin-6-yl)methyl)carbamoyl)piperidine-1-carboxylate (2.06 g, 54% yield) as a yellow solid. $^1$H NMR (300 MHz, CDCl$_3$) δ 7.76 (d, 2H, J=7.5 Hz), 7.57 (d, 2H, J=7.8 Hz), 7.43-7.24 (m, 9H), 6.74 (br s, 1H), 4.55-4.35 (m, 4H), 4.28-4.05 (m, 3H), 3.90-3.70 (m, 2H), 3.45-3.35 (m, 1H), 3.20-3.10 (m, 1H), 2.98-2.70 (m, 4H), 2.55-2.40 (m, 1H), 2.38-2.27 (m, 1H), 2.25-2.00 (m, 1H), 1.90-1.80 (m, 2H), 1.74-1.58 (m, 2H), 1.15 (d, 3H, J=6.3 Hz); $^{13}$C NMR (75 MHz, CDCl$_3$) δ 174.1, 165.3, 162.6, 154.8, 150.5, 143.7, 141.0, 134.3, 129.2, 128.7, 128.3, 127.4, 126.8, 124.7, 119.7, 67.2, 60.3, 59.5, 56.6, 50.2, 47.2, 43.3, 42.8, 39.7, 38.5, 28.4, 18.4.

Synthesis of (+/−)-(9H-fluoren-9-yl)methyl 4-(2-((3,4-trans)-1-benzyl-4-methylpyrrolidin-3-yl)-4-oxo-3,4-dihydroimidazo[5,1-f][1,2,4]triazin-7-yl)piperidine-1-carboxylate

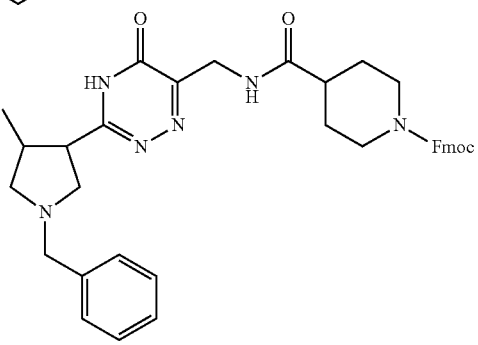
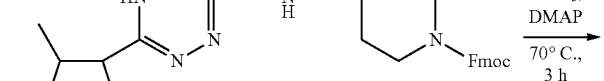
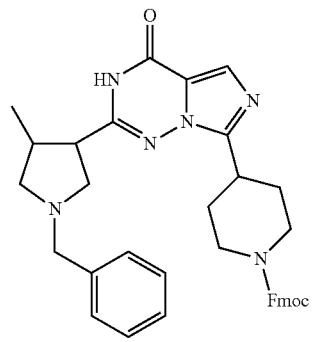

To a solution of (+/−)-(9H-fluoren-9-yl)methyl 4-(((3-((3,4-trans)-1-benzyl-4-methylpyrrolidin-3-yl)-5-oxo-4,5-dihydro-1,2,4-triazin-6-yl)methyl)carbamoyl)piperidine-1-carboxylate (2.14 g, 3.38 mmol) and DMAP (40 mg, 0.34 mmol) in acetonitrile (100 mL) was added a solution of POBr$_3$ (2.91 g, 10.15 mmol) in acetonitrile (70 mL) at RT, and the resulting suspension was heated to 70° C. for 3 h. After the mixture was cooled to room temperature, it was poured into cold saturated NaHCO₃ solution (250 mL), and stirred vigorously for 0.5 h, then extracted with CH₂Cl₂ (1×150 mL, 2×50 mL). The combined organic extracts were dried over MgSO₄ and concentrated under reduced pressure. The residue was purified by gradient flash chromatography over silica gel (0-10% MeOH/CH₂Cl₂) to furnish (+/−)-(9H-fluoren-9-yl)methyl 4-(2-((3,4-trans)-1-benzyl-4-methyl-pyrrolidin-3-yl)-4-oxo-3,4-dihydroimidazo[5,1-f][1,2,4]tri-azin-7-yl)piperidine-1-carboxylate (1.67 g, 80% yield) as a white foam. ¹H NMR (300 MHz, CDCl₃/TMS) δ 9.40 (br s, 1H), 7.79 (s, 1H), 7.74 (d, J=7.8 Hz, 2H), 7.58 (d, J=7.5 Hz, 2H), 7.44-7.22 (m, 9H), 4.52-4.16 (m, 5H), 3.79 (d, J=12.3 Hz, 1H), 3.53 (d, J=12.6 Hz, 1H), 3.35 (t, J=8.3 Hz, 2H), 3.20-2.88 (m, 3H), 2.80-2.64 (m, 1H), 2.60-2.34 (m, 2H), 2.14-1.80 (m, 5H), 1.19 (d, J=6.9 Hz, 3H); ¹³C NMR (75 MHz, CDCl₃/TMS) δ 154.8, 154.1, 153.7, 148.0, 143.8, 141.0, 137.1, 128.5, 127.4, 127.3, 126.8, 124.7, 119.7, 118.8, 67.2, 60.9, 59.1, 55.8, 47.7, 47.2, 43.6, 38.2, 33.1, 29.4, 29.1, 20.1.

Synthesis of (+/−)-2-((3,4-trans)-1-benzyl-4-methyl-pyrrolidin-3-yl)-7-(piperidin-4-yl)imidazo[5,1-f][1,2,4]triazin-4(3H)-one

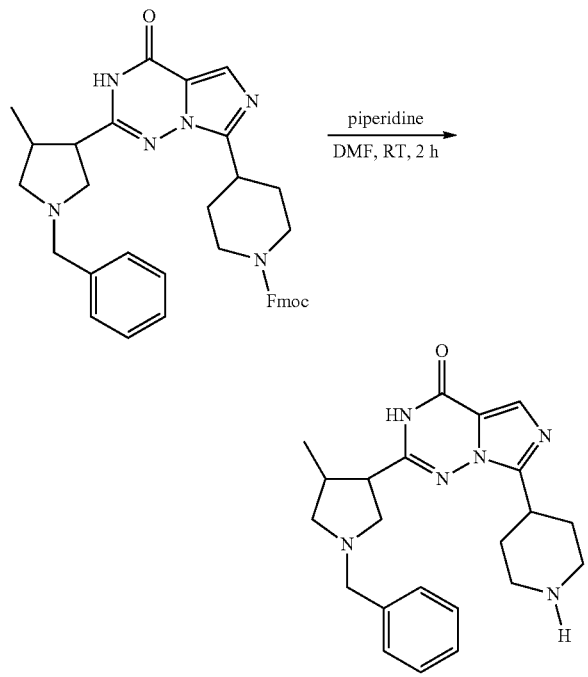

To a solution of (+/−)-(9H-fluoren-9-yl)methyl 4-(2-((3,4-trans)-1-benzyl-4-methylpyrrolidin-3-yl)-4-oxo-3,4-dihydroimidazo[5,1-f][1,2,4]triazin-7-yl)piperidine-1-carboxylate (1.67 g, 3.24 mmol) in DMF (50 mL) was added piperidine (5.53 g, 64.90 mmol) at RT, and the resulting solution was stirred at RT for 2 h. The solvent and excess piperidine was removed under reduced pressure. The residue was purified by flash chromatography over silica gel (0.1/1.5/98.4-1/15/84 NH₄OH/MeOH/CH₂Cl₂) to furnish (+/−)-2-((3,4-trans)-1-benzyl-4-methylpyrrolidin-3-yl)-7-(piperi-din-4-yl)imidazo[5,1-f][1,2,4]triazin-4(3H)-one (0.75 g, 70% yield) as an off-white foam. Purity (HPLC): 99.5%; ¹H NMR (300 MHz, CDCl₃/TMS) δ 7.78 (s, 1H), 7.40-7.24 (m, 5H), 5.25 (br s, 2H), 3.82 (d, 1H, J=12.6 Hz), 3.57 (d, 1H, J=12.6 Hz), 3.42-3.16 (m, 4H), 2.97 (d, 1H, J=9.9 Hz), 2.87-2.72 (m, 3H), 2.58-2.36 (m, 2H), 2.02-1.76 (m, 5H), 1.22 (d, 3H, J=7.2 Hz); ¹³C NMR (75 MHz, CDCl₃/TMS) δ 154.35, 153.55, 149.11, 137.14, 128.54, 127.47, 127.42, 118.57, 61.07, 59.25, 55.95, 47.80, 46.17, 38.27, 33.72, 30.89, 30.63, 20.11; HRMS: calculated for C₂₂H₂₉N₆O (MH⁺), 393.2397. found: 393.2410.

Synthesis of (+)-7-(1-acetylpiperidin-4-yl)-2-((3,4-trans)-1-benzyl-4-methylpyrrolidin-3-yl)imidazo[5,1-f][1,2,4]triazin-4(3H)-one and (−)-7-(1-acetylpip-eridin-4-yl)-2-((3,4-trans)-1-benzyl-4-methylpyrrolidin-3-yl)imidazo[5,1-f][1,2,4]triazin-4(3H)-one

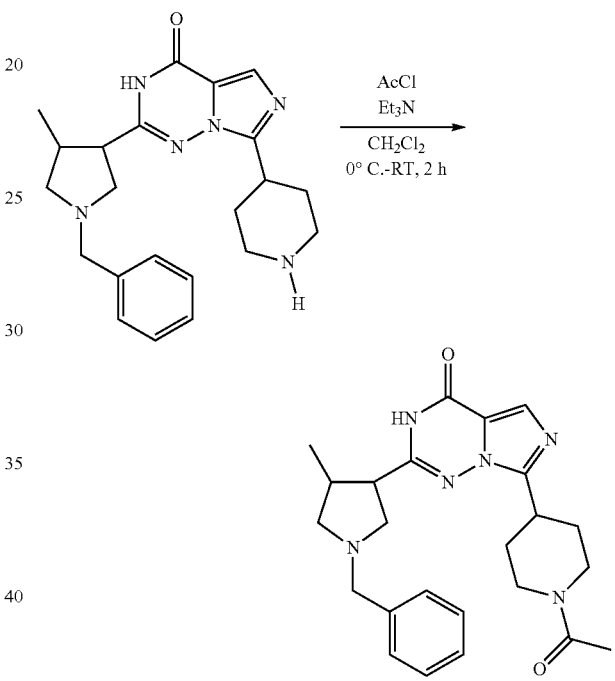

To a solution of (+/−)-2-((3,4-trans)-1-benzyl-4-methyl-pyrrolidin-3-yl)-7-(piperidin-4-yl)imidazo[5,1-f][1,2,4]tri-azin-4(3H)-one (0.30 g, 0.76 mmol) and triethylamine (0.23 g, 2.29 mmol) in CH₂Cl₂ (5 mL) was added acetyl chloride (0.09 g, 1.15 mmol) drop-wise at 0° C. After complete of addition, the ice-water bath was removed and the reaction mixture was stirred at RT for 2 h. The reaction mixture was diluted with CH₂Cl₂ (15 mL) and washed with saturated NaHCO₃ (5 mL), dried over MgSO₄. Concentration and purification by flash chromatography over silica gel (0.1/1.5/98.4-0.4/6.0/93.6 NH₄OH/MeOH/CH₂Cl₂) to furnish (+/−)-7-(1-acetylpiperidin-4-yl)-2-((3,4-trans)-1-benzyl-4-methylpyrrolidin-3-yl)imidazo[5,1-f][1,2,4]triazin-4(3H)-one (0.29 g, 87% yield) as a colorless wax. Purity (HPLC): 99.3%; ¹H NMR (300 MHz, CDCl₃/TMS) δ 8.58 (br s, 1H), 7.76 (s, 1H), 7.42-7.23 (m, 5H), 4.62 (t, 1H, J=12.3 Hz), 3.94 (t, 1H, J=11.3 Hz), 3.82 (d, 1H, J=12.6 Hz), 3.57 (d, 1H, J=12.6 Hz), 3.50-3.34 (m, 2H), 3.32-3.18 (m, 1H), 2.98 (d, 1H, J=9.9 Hz), 2.90-2.74 (m, 2H), 2.60-2.52 (m, 1H), 2.50-2.40 (m, 1H), 2.12 (s, 3H), 2.08-1.72 (m, 5H), 1.23 (d, 3H, J=6.9 Hz); ¹³C NMR (75 MHz, CDCl₃/TMS) δ 168.54, 154.16, 153.80, 147.83, 137.15, 128.49, 127.40, 127.29, 118.78, 60.97, 59.17, 55.92, 47.75, 46.11, 41.16, 38.19, 33.11, 29.88, 29.59, 29.48, 29.23, 21.40, 20.09.

(+/−)-7-(1-acetylpiperidin-4-yl)-2-((3,4-trans)-1-benzyl-4-methylpyrrolidin-3-yl)imidazo[5,1-f][1,2,4]triazin-4(3H)-one was purified by Chiralcel OJ-H, 250×20 mm, 5 um (30 mg loading; 0.1% TEA in n-Hexane:Ethanol (90:10) as mobile phase) to obtain pure fraction 1 (yl)-7-(1-acetylpiperidin-4-yl)-2-((3,4-trans)-1-benzyl-4-methylpyrrolidin-3-yl)imidazo[5,1-f][1,2,4]triazin-4(3H)-one) and pure fraction 2 ((+)-7-(1-acetylpiperidin-4-yl)-2-((3,4-trans)-1-benzyl-4-methylpyrrolidin-3-yl)imidazo[5,1-f][1,2,4]triazin-4(3H)-one). Characterization details of both fractions are as follows:

(−)-7-(1-acetylpiperidin-4-yl)-2-((3,4-trans)-1-benzyl-4-methylpyrrolidin-3-yl)imidazo[5,1-f][1,2,4]triazin-4(3H)-one: H-NMR (DMSO $d_6$, 400 MHz): δ 7.64 (s, 1H), 7.37-7.32 (m, 4H), 7.24-7.21 (m, 1H), 4.39-4.32 (m, 1H), 3.92-3.86 (m, 1H), 3.67-3.62 (m, 2H), 3.48-3.47 (m, 1H), 2.98-2.94 (m, 6H), 2.72-2.67 (m, 2H), 2.34-2.31 (m, 1H), 2.04 (s, 3H), 1.98-1.96 (m, 2H), 1.84-1.81 (m, 1H), 1.68-1.62 (m, 1H), 1.09 (d, 3H); LC-MS: 93.15%; 435 ($M^+$+1); (column; X-bridge C-18, (50×3.0 mm, 3.5μ); RT 2.86 min. 5 mM $NH_4OAc$: ACN; 0.8 ml/min); UPLC (purity): 100%; (column; Acquity BEH C-18, 50×2.1 mm, 1.7μ; RT 1.36 min. 0.025% TFA (Aq): ACN:Water; 0.50 ml/min.; Chiral HPLC: 100% ee $R_t$=38.92 min (Chiralcel OJ-H, 250×4.6 mm, 5μ; mobile phase (A) 0.1% TEA in n-Hexane (B) ethanol (A:B:90:10); flow Rate: 1.00 mL/min); Optical rotation $[α]_D^{25}$: −25.72° (c=0.25, DCM).

(+)-7-(1-acetylpiperidin-4-yl)-2-((3,4-trans)-1-benzyl-4-methylpyrrolidin-3-yl)imidazo[5,1-f][1,2,4]triazin-4(3H)-one: H-NMR (DMSO $d_6$, 400 MHz): δ 7.62 (s, 1H), 7.34-7.29 (m, 4H), 7.24-7.22 (m, 1H), 4.36-4.34 (m, 1H), 3.92-3.89 (m, 1H), 3.68-3.62 (m, 2H), 3.47-3.41 (m, 2H), 3.28-3.26 (m, 2H), 2.98-2.96 (m, 1H), 2.67-2.63 (m, 2H), 2.29-2.27 (m, 1H), 2.02 (s, 3H), 1.98-1.94 (m, 2H), 1.84-1.82 (m, 1H), 1.64-1.61 (m, 1H), 1.08 (d, 3H); LC-MS: 91.25%; 435 ($M^+$+1); (column; X-bridge C-18, (50×3.0 mm, 3.5μ); RT 2.85 min. 5 mM $NH_4OAc$: ACN; 0.8 ml/min); UPLC (purity): 99.35%; (column; Acquity BEH C-18, 50×2.1 mm, 1.7μ; RT 1.35 min. 0.025% TFA (Aq): ACN:Water; 0.50 ml/min.; Chiral HPLC: 100% ee $R_t$=45.10 min (Chiralcel OJ-H, 250×4.6 mm, 5μ; mobile phase (A) 0.1% TEA in n-Hexane (B) ethanol (A:B:90:10); flow Rate: 1.00 mL/min); Optical rotation $[α]_D^{25}$: +26.38° (c=0.25, DCM).

35. (−)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one

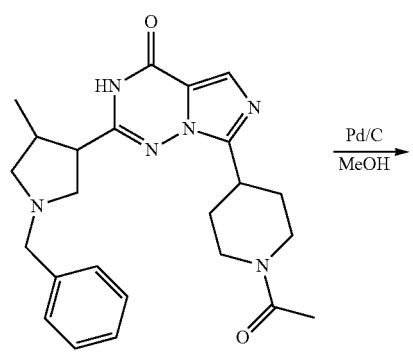

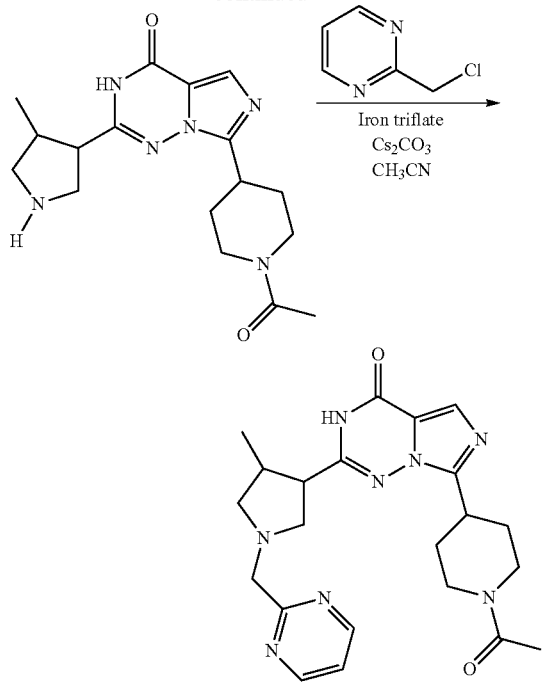

To a stirred solution of (−)-7-(1-acetylpiperidin-4-yl)-2-((3,4-trans)-1-benzyl-4-methylpyrrolidin-3-yl)imidazo[5,1-f][1,2,4]triazin-4(3H)-one (25 mg 0.057 mmol) in MeOH (8 mL) was added 10% Pd—C (6 mg) under a $N_2$ atmosphere. The reaction mixture was stirred at RT for 10 h under $H_2$ atmosphere (balloon pressure). The reaction mixture was passed through a pad of celite and dried in vacuo to obtain crude. The crude material was washed with n-pentane to afford 7-(1-acetylpiperidin-4-yl)-2-((3,4-trans)-4-methylpyrrolidin-3-yl)imidazo[5,1-f][1,2,4]triazin-4(3H)-one (16 mg, crude) as an off-white solid. $^1$H-NMR (DMSO $d_6$, 400 MHz): δ 7.65 (s, 1H), 7.47 (br s, 1H), 4.76 (q, 1H), 4.41-4.35 (m, 1H), 3.85-3.80 (m, 1H), 3.35-3.30 (m, 3H), 2.97 (d, 1H), 2.82 (t, 2H), 2.64-2.60 (m, 1H), 2.46-2.41 (m, 1H), 2.01 (s, 3H), 1.91-1.80 (m, 2H), 1.72-1.70 (m, 2H), 1.01 (s, 3H); Mass (ESI): 345 [($M^+$+1)]; LC-MS: 48.83%; 345 ($M^+$+1); (column; X-bridge C-18, (50×3.0 mm, 3.5 um); RT 1.69 min. 5 mM $NH_4OAc$: ACN; 0.8 ml/min); TLC: 10% MeOH/$CH_2Cl_2$ (Rf 0.1).

To a stirred solution of 7-(1-acetylpiperidin-4-yl)-2-((3,4-trans)-4-methylpyrrolidin-3-yl)imidazo[5,1-f][1,2,4]triazin-4(3H)-one (35 mg, 0.1 mmol) in ACN (10 mL) were added 2-(chloromethyl)pyrimidine (14.3 mg, 0.11 mmol), iron triflate (10 mg, 0.02 mmol) and $Cs_2CO_3$ (66 mg, 0.2 mmol) at RT under inert atmosphere. The resultant reaction mixture was heated at 70° C. and stirred for 3 h. After full consumption of starting material (by TLC), the reaction mixture was diluted with water and extracted with EtOAc (2×25 mL). Combined organic layers were dried over anhydrous sodium sulfate, filtered and concentrated in vacuo to obtain the crude product. The crude material was purified by silica gel column chromatography to afford (−)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one (20 mg, 22%) as an off-white solid. $^1$H-NMR (DMSO $d_6$, 400 MHz): δ 8.79 (d, 2H), 7.68 (s, 1H), 7.44 (t, 1H), 4.39-4.30 (m, 1H), 4.02 (d, 1H), 3.89 (d, 2H), 3.45-3.40 (m, 1H), 3.28-3.25 (m, 1H), 3.14 (t, 2H), 3.03-2.97 (m, 2H), 2.81-2.76 (m, 2H), 2.64-2.60 (m, 1H), 2.38 (t, 1H), 2.02 (s, 3H), 1.95 (t, 2H), 1.80-1.72 (m, 2H), 1.11 (d, 3H); Mass (ESI): 437.6 [M$^+$+1]; LC-MS: 97.43%; 437.5 (M$^+$+1); (column; Xbridge C-18, (50×3.0 mm, 3.5 um); RT 2.73 min. 5 mM NH4OAC: ACN; 0.8 ml/min); UPLC (purity): 96.67%; (column; Acquity UPLC HSS T3, 100×2.1 mm, 1.7μ; RT 2.95 min. 0.025% TFA (Aq): ACN:Water; 0.3 ml/min.; TLC: 10% MeOH/DCM (Rf:0.5). Chiral HPLC: 99.44% ee R$_t$=14.61 min (Chiralpak IA, 250×4.6 mm, 5 um; mobile phase (A) 0.1% DBA in n-Hexane (B) IPA (A:B:60:40); flow Rate: 1.00 mL/min); Optical rotation [α]$_D^{23}$: −29.92° (c=0.125, DCM).

36. (+)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one

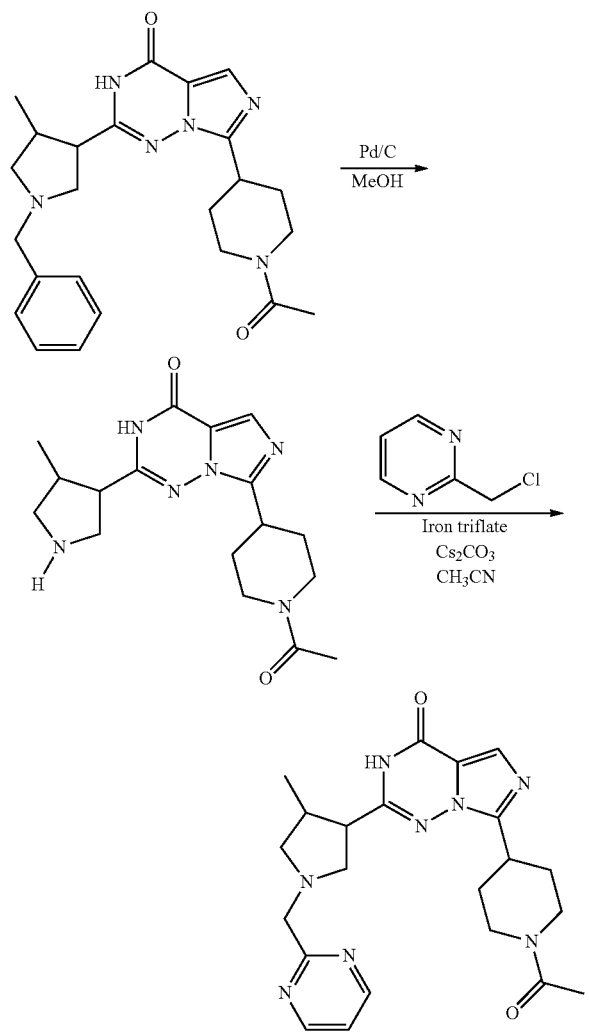

To a stirred solution of (+)-7-(1-acetylpiperidin-4-yl)-2-((3,4-trans)-1-benzyl-4-methylpyrrolidin-3-yl)imidazo[5,1-f][1,2,4]triazin-4(3H)-one (90 mg 0.207 mmol) in MeOH (10 mL) was added 10% Pd—C (25 mg) under N$_2$ atmosphere. The reaction mixture was stirred at RT for 10 h under H$_2$ atmosphere (balloon pressure). The reaction mixture was passed through a pad of celite and dried in vacuo to obtain crude 7-(1-acetylpiperidin-4-yl)-2-((3,4-trans)-4-methylpyrrolidin-3-yl)imidazo[5,1-f][1,2,4]triazin-4(3H)-one (75 mg, crude) as an off-white solid. Mass (ESI): 345 [(M$^+$+1)]; LC-MS: 87.06%; 345 (M$^+$+1); (column; X-bridge C-18, (50×3.0 mm, 3.5 um); RT 1.82 min. 5 mM NH$_4$OAc: ACN; 0.8 ml/min); TLC: 5% MeOH/CH$_2$Cl$_2$ (Rf 0.1).

To a stirred solution of 7-(1-acetylpiperidin-4-yl)-2-((3,4-trans)-4-methylpyrrolidin-3-yl)imidazo[5,1-f][1,2,4]triazin-4(3H)-one (75 mg, 0.2 mmol) in ACN (5 mL) were added 2-(chloromethyl)pyrimidine (30 mg, 0.23 mmol), iron triflate (21 mg, 0.04 mmol) and Cs$_2$CO$_3$ (142 mg, 0.4 mmol) at RT under inert atmosphere. The resultant reaction mixture was heated to 70° C. and stirred for 4 h. After full consumption of starting material (by TLC), the reaction mixture was diluted with water and extracted with EtOAc (3×25 mL). Combined organic layers were dried over anhydrous sodium sulphate, filtered and concentrated in vacuo to obtain the crude product. The crude material was purified by silica gel column chromatography to afford (+)-7-(1-acetylpiperidin-4-yl)-2-((3,4-trans)-4-methyl-1-(pyrimidin-2-ylmethyl)pyrrolidin-3-yl)imidazo[5,1-f][1,2,4]triazin-4(3H)-one (20 mg, 21%) as an off-white solid. $^1$H-NMR (DMSO d$_6$, 400 MHz): δ 8.79 (d, 2H), 7.68 (s, 1H), 7.44 (t, 1H), 4.39-4.30 (m, 1H), 4.02 (d, 1H), 3.89 (d, 2H), 3.45-3.40 (m, 1H), 3.14 (t, 1H), 3.03-2.97 (m, 2H), 2.81-2.76 (m, 2H), 2.64-2.60 (m, 2H), 2.38 (t, 1H), 2.02 (s, 3H), 1.95 (t, 2H), 1.80-1.72 (m, 2H), 1.11 (d, 3H); Mass (ESI): 437.6 [M$^+$+1]; LC-MS: 95.86%; 437.6 (M$^+$+1); (column; Xbridge C-18, (50×3.0 mm, 3.5 um); RT 2.78 min. 0.1% Aqueous TFA: ACN; 0.8 ml/min); HPLC (purity): 96.55%; (column; Eclipse XDB C-18, 150× 3.0 mm, 3 um; RT 7.42 min. ACN: 5 mM NH4OAC: ACN:Water; 1.0 ml/min.; TLC: 5% MeOH/DCM (Rf:0.4). Chiral HPLC: 98.67% ee R$_t$=11.24 min (Chiralpak IA, 250×4.6 mm, 5 um; mobile phase (A) 0.1% DBA in n-Hexane (B) IPA (A:B:60:40); flow Rate: 1.00 mL/min); Optical rotation [α]$_D^{23}$: +140.64° (c=0.125, DCM).

37. (+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one and (−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one

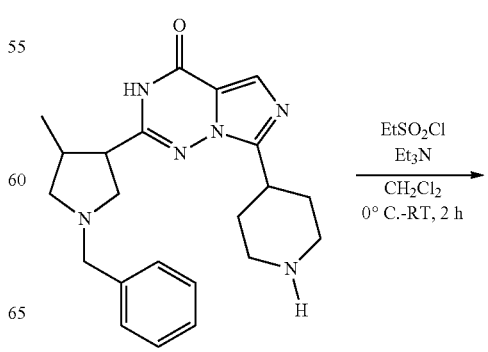

-continued

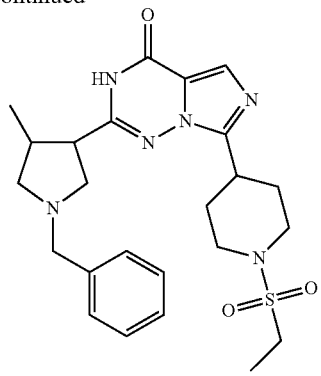

To a solution of (+/−)-2-((3,4-trans)-1-benzyl-4-methyl-pyrrolidin-3-yl)-7-(piperidin-4-yl)imidazo[5,1-f][1,2,4]triazin-4(3H)-one (0.31 g, 0.79 mmol) and triethylamine (0.24 g, 2.37 mmol) in CH$_2$Cl$_2$ (5 mL) was added ethanesulfonyl chloride (0.15 g, 1.18 mmol) drop-wise at 0° C. After complete of addition, the ice-water bath was removed and the reaction mixture was stirred at RT for 2 h. The reaction mixture was diluted with CH$_2$Cl$_2$ (15 mL) and washed with saturated NaHCO$_3$ (5 mL), dried over MgSO$_4$. Concentration and purification by flash chromatography over silica gel (0.1/1.5/98.4-0.3/4.5/95.2 NH$_4$OH/MeOH/CH$_2$Cl$_2$) gave (+/−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one (0.33 g, 86% yield) as a white foam. HPLC: 98.0% (rt=11.09 min); $^1$H NMR (300 MHz, CDCl$_3$/TMS) δ 7.78 (s, 1H), 7.47-7.24 (m, 5H), 4.00-3.79 (m, 3H), 3.56 (d, 1H, J=12.3 Hz), 3.45-3.25 (m, 2H), 3.15-2.94 (m, 5H), 2.82-2.72 (m, 1H), 2.60-2.46 (m, 2H), 2.20-1.90 (m, 5H), 1.39 (t, 3H, J=7.4 Hz) 1.22 (d, 3H, J=6.6 Hz); $^{13}$C NMR (75 MHz, CDCl$_3$/TMS) δ 154.12, 153.94, 147.55, 137.07, 128.57, 127.52, 127.41, 118.92, 61.02, 59.20, 55.86, 47.77, 45.34, 45.31, 44.54, 38.31, 32.60, 29.49, 29.20, 20.16, 7.98.

(+/−)-2-((3,4-Trans)-1-benzyl-4-methylpyrrolidin-3-yl)-7-(1-(ethylsulfonyl)piperidin-4-yl)imidazo[5,1-f][1,2,4]triazin-4(3H)-one was purified by Chiralcel OJ-H, 250×20 mm, 5 um (40 mg loading; 0.1% TEA in n-Hexane:Ethanol (50:50) as mobile phase) to obtain pure fraction 1 ((+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one) and pure fraction 2 ((−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one). Characterization details of both fractions are as follows:

(+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one: H-NMR (DMSO d$_6$, 400 MHz): δ 7.58 (s, 1H), 7.34-7.28 (m, 4H), 7.24-7.21 (m, 1H), 3.68-3.62 (m, 4H), 3.18-3.14 (m, 4H), 3.94-3.92 (m, 2H), 3.87-3.84 (m, 1H), 2.79-2.74 (m, 2H), 2.68-2.62 (m, 1H), 2.24-2.21 (m, 1H), 2.02-1.97 (m, 2H), 1.89-1.82 (m, 2H), 1.24 (t, 3H), 1.08 (d, 3H); Mass (ESI): 485 [M$^+$+1]; LC-MS: 97.97%; 485 (M$^+$+1); (column; X-bridge C-18, (50×3.0 mm, 3.5μ); RT 3.34 min. 5 mM NH$_4$OAc: ACN; 0.8 ml/min); UPLC (purity): 99.85%; (column; Acquity BEH C-18, 50×2.1 mm, 1.7μ; RT 1.56 min. 0.025% TFA (Aq): ACN:Water; 0.50 ml/min.; Chiral HPLC: 100% ee R$_t$=13.31 min (Chiralcel OJ-H, 250×4.6 mm, 5μ; mobile phase (A) 0.1% TEA in n-Hexane (B) ethanol (A:B:50:50); flow Rate: 1.00 mL/min); Optical rotation [α]$_D^{24}$: +18.32° (c=0.25, DCM).

(−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one: H-NMR (DMSO d$_6$, 400 MHz): δ 7.68 (s, 1H), 7.34-7.29 (m, 4H), 7.24-7.21 (m, 1H), 3.72-3.65 (m, 4H), 3.38-3.32 (m, 1H), 3.12-3.07 (m, 4H), 2.98-2.96 (m, 1H), 2.87-2.84 (m, 1H), 2.79-2.77 (m, 2H), 2.64-2.62 (m, 1H), 2.29-2.27 (m, 1H), 2.07-2.03 (m, 2H), 1.89-1.84 (m, 2H), 1.26 (t, 3H), 1.07 (d, 3H); Mass (ESI): 485 [M$^+$+1]; LC-MS: 94.38%; 485 (M$^+$+1); (column; X-bridge C-18, (50×3.0 mm, 3.5μ); RT 3.28 min. 5 mM NH$_4$OAc: ACN; 0.8 ml/min); UPLC (purity): 99.05%; (column; Acquity BEH C-18, 50×2.1 mm, 1.7μ; RT 1.58 min. 0.025% TFA (Aq): ACN:Water; 0.50 ml/min.; Chiral HPLC: 98.67% ee R$_t$=20.84 min (Chiralcel OJ-H, 250×4.6 mm, 5μ; mobile phase (A) 0.1% TEA in n-Hexane (B) ethanol (A:B:50:50); flow Rate: 1.00 mL/min); Optical rotation [α]$_D^{25}$: −21.98° (c=0.25, DCM).

38. (+)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one

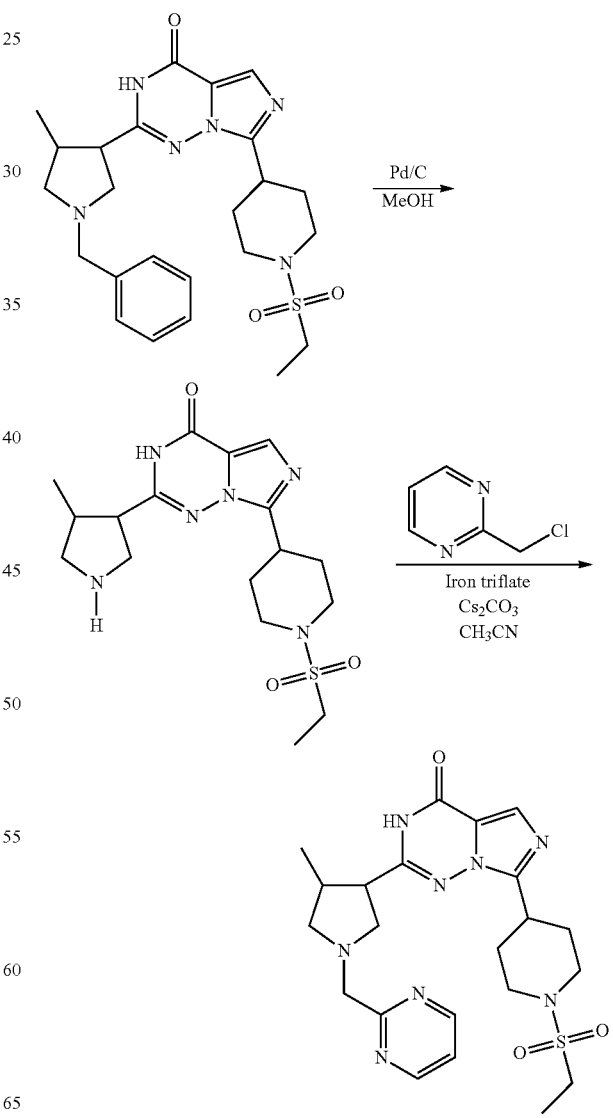

To a stirred solution of (+)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one (80 mg 0.165 mmol) in MeOH (10 mL) was added 10% Pd—C (25 mg) under $N_2$ atmosphere. The reaction mixture was stirred at RT for 10 h under $H_2$ atmosphere (balloon pressure). The reaction mixture was passed through a pad of celite and dried in vacuo to obtain crude 7-(1-(ethylsulfonyl)piperidin-4-yl)-2-((3,4-trans)-4-methylpyrrolidin-3-yl)imidazo[5,1-f][1,2,4]triazin-4(3H)-one (100 mg, crude) as an off-white solid. LC-MS: 88.31%; 395.5 ($M^+$+1); (column; X-bridge C-18, (50×3.0 mm, 3.5 um); RT 2.16 min. 5 mM $NH_4OAc$: ACN; 0.8 ml/min); TLC: 10% MeOH/$CH_2Cl_2$ (Rf 0.1).

To a stirred solution of 7-(1-(ethylsulfonyl)piperidin-4-yl)-2-((3,4-trans)-4-methylpyrrolidin-3-yl)imidazo[5,1-f][1,2,4]triazin-4(3H)-one (100 mg, 0.2 mmol) in ACN (10 mL) were added 2-(chloromethyl)pyrimidine (35 mg, 0.27 mmol), iron triflate (25 mg, 0.05 mmol) and $Cs_2CO_3$ (165 mg, 0.5 mmol) at RT under inert atmosphere. The resultant reaction mixture was heated at 70° C. and stirred for 4 h. After full consumption of starting material (by TLC), the reaction mixture was diluted with water and extracted with EtOAc (3×25 mL). Combined organic layers were dried over anhydrous sodium sulphate, filtered and concentrated in vacuo to obtain the crude product. The crude material was purified by silica gel column chromatography and further purified by preparative to afford (+)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one (20 mg, 16%) as semi solid. $^1$H-NMR (DMSO $d_6$, 400 MHz): δ 8.79 (d, 2H), 7.68 (s, 1H), 7.44 (t, 1H), 4.02 (d, 1H), 3.89 (d, 1H), 3.71-3.65 (m, 2H), 3.39-3.20 (m, 1H), 3.18-3.10 (m, 3H), 2.78 (q, 1H), 2.67-2.60 (m, 1H), 2.61-2.55 (m, 1H), 2.37 (t, 1H), 2.01 (d, 2H), 1.85-1.80 (m, 2H), 1.52 (t, 2H), 1.34-1.30 (m, 2H), 1.25 (s, 3H), 1.12 (d, 3H); Mass (ESI): 487.6 [$M^+$+1]; LC-MS: 96.31%; 487.9 ($M^+$+1); (column; Xbridge C-18, (50×3.0 mm, 3.5 um); RT 2.45 min. 0.1% Aqueous TFA: ACN; 0.8 ml/min); UPLC (purity): 96.89%; (column; Aquity BEH C-18, 50×2.1 mm, 1.7μ; RT 1.34 min. ACN: 0.025% Aqueous TFA: ACN:Water; 0.5 ml/min.; TLC: 5% MeOH/DCM (Rf:0.4). Chiral UPLC: 99.63% ee $R_t$=12.15 min (Chiralpak IA, 250×4.6 mm, 5 um; mobile phase (A) 0.1% DBA in n-Hexane (B) IPA (A:B:60:40); flow Rate: 1.00 mL/min); Optical rotation $[α]_D^{24}$: +53.12° (c=0.125, DCM).

39. (−)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one

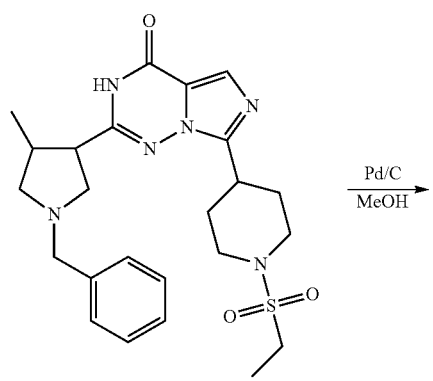

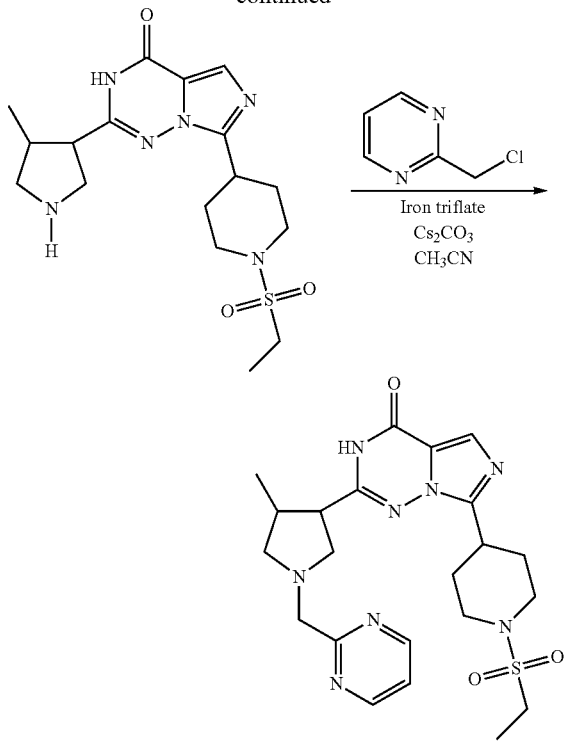

To a stirred solution of (−)-2-((3,4-trans)-1-benzyl-4-methylpyrrolidin-3-yl)-7-(1-(ethylsulfonyl)piperidin-4-yl)imidazo[5,1-f][1,2,4]triazin-4(3H)-one (90 mg, 0.185 mmol) in MeOH (10 mL) was added 10% Pd—C (25 mg) under $N_2$ atmosphere. The reaction mixture was stirred at RT for 10 h under $H_2$ atmosphere (balloon pressure). The reaction mixture was passed through a pad of celite and dried in vacuo to obtain crude 7-(1-(ethylsulfonyl)piperidin-4-yl)-2-((3,4-trans)-4-methylpyrrolidin-3-yl)imidazo[5,1-f][1,2,4]triazin-4(3H)-one (80 mg, crude) as an off-white solid. LC-MS: 47.32%; 395 ($M^+$+1); (column; X-bridge C-18, (50×3.0 mm, 3.5 um); RT 2.04 min. 5 mM $NH_4OAc$: ACN; 0.8 ml/min); TLC: 5% MeOH/$CH_2Cl_2$ (Rf 0.1).

To a stirred solution of 7-(1-(ethylsulfonyl)piperidin-4-yl)-2-((3,4-trans)-4-methylpyrrolidin-3-yl)imidazo[5,1-f][1,2,4]triazin-4(3H)-one (80 mg, 0.2 mmol) in ACN (5 mL) were added 2-(chloromethyl)pyrimidine (28 mg, 0.22 mmol), iron triflate (20 mg, 0.04 mmol) and $Cs_2CO_3$ (132 mg, 0.4 mmol) at RT. The resultant reaction mixture was heated up to 70° C. and stirred for 4 h. After full consumption of starting material (by TLC), the reaction mixture was diluted with water and extracted with EtOAc (2×25 mL) & $CH_2Cl_2$ (2×25 mL). Combined organic layers were dried over anhydrous sodium sulphate, filtered and concentrated in vacuo to obtain the crude product. The crude material was purified by silica gel column chromatography to afford (−)-7-(1-(ethylsulfonyl)piperidin-4-yl)-2-((3,4-trans)-4-methyl-1-(pyrimidin-2-ylmethyl)pyrrolidin-3-yl)imidazo[5,1-f][1,2,4]triazin-4(3H)-one (22 mg, 22%) as an off-white solid. $^1$H-NMR (DMSO $d_6$, 400 MHz): δ 8.79 (d, 2H), 7.68 (s, 1H), 7.44 (t, 1H), 4.02 (d, 1H), 3.89 (d, 1H), 3.71-3.65 (m, 2H), 3.29-3.19 (m, 8H), 2.78 (q, 1H), 2.67-2.60 (m, 1H), 2.41 (t, 1H), 2.02 (d, 2H), 1.85-1.80 (m, 2H), 1.25 (t, 4H), 1.12 (d, 3H); Mass (ESI): 487 [M++1]; LC-MS: 96.21%; 487.6 (M++1); (column; Xbridge C-18, (50×3.0 mm, 3.5 um); RT 3.22 min. 5 mM NH4OAC: ACN; 0.8 ml/min); HPLC (purity): 98.53%; (column; Eclipse XDB C-18, 150× 4.6 mm, 5 um; RT 8.29 min. ACN: 5 mM NH4OAC: ACN:Water; 1.0 ml/min.; TLC: 5% MeOH/DCM (Rf:0.45). Chiral HPLC: 99.12% ee Rt=16.93 min (Chiralpak IA, 250×4.6 mm, 5 um; mobile phase (A) 0.1% DBA in n-Hexane (B) IPA (A:B:60:40); flow Rate: 1.00 mL/min); Optical rotation $[\alpha]_D^{26}$: −83.3° (c=0.125, DCM).

40. (+)-2-((3,4-trans)-1-benzyl-4-methylpyrrolidin-3-yl)-7-(2-hydroxypropan-2-yl)imidazo[5,1-f][1,2,4]triazin-4(3H)-one and (−)-2-((3,4-trans)-1-benzyl-4-methylpyrrolidin-3-yl)-7-(2-hydroxypropan-2-yl)imidazo[5,1-f][1,2,4]triazin-4(3H)-one

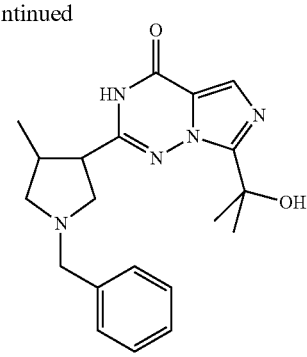

Synthesis of (+/−)-N-((3-((3,4-trans)-1-benzyl-4-methylpyrrolidin-3-yl)-5-oxo-4,5-dihydro-1,2,4-triazin-6-yl)methyl)-2-(benzyloxy)-2-methylpropanamide

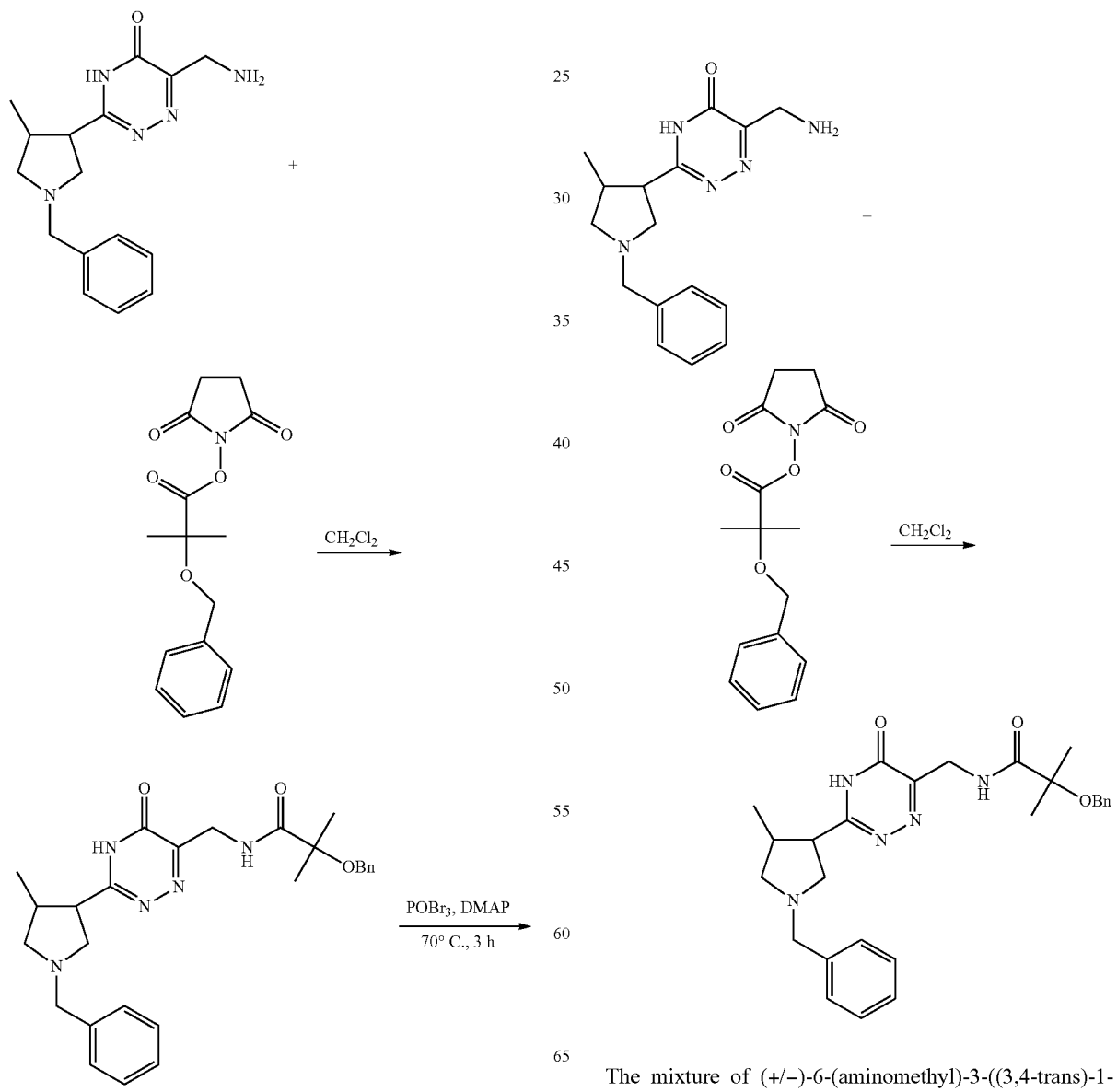

The mixture of (+/−)-6-(aminomethyl)-3-((3,4-trans)-1-benzyl-4-methylpyrrolidin-3-yl)-1,2,4-triazin-5(4H)-one (1.3 g, 4.3 mmol) and 2,5-dioxopyrrolidin-1-yl 2-(benzyloxy)-2-methylpropanoate (1.4 g, 4.8 mmol) in CH$_2$Cl$_2$ (50 mL) was stirred at room temperature overnight. The precipitate was filtered and the filtrate was washed with water. The aqueous solution was extracted with chloroform (4×100 ml). The CH$_2$Cl$_2$ solution and chloroform extracts were combined, the solvents were evaporated, and the residue was purified by column chromatography (silica gel, CH$_2$Cl$_2$/MeOH/NH$_4$OH, 10:1:0.5%) to prepare (+/−)-N-((3-((3,4-trans)-1-benzyl-4-methylpyrrolidin-3-yl)-5-oxo-4,5-dihydro-1,2,4-triazin-6-yl)methyl)-2-(benzyloxy)-2-methylpropanamide (2.0 g, 100% yield). $^1$H NMR (300 MHz, CDCl$_3$/TMS): δ 8.4 (br s, 1H), 7.34-7.22 (m, 10H), 4.50 (s, 2H), 4.02 (s, 2H), 3.44-3.30 (m, 4H), 2.69 (m, 1H), 1.48 (s, 3H), 1.48 (s, 6H), 1.09 (s, 3H).

Synthesis of (+)-2-((3,4-trans)-1-benzyl-4-methylpyrrolidin-3-yl)-7-(2-hydroxypropan-2-yl)imidazo[5,1-f][1,2,4]triazin-4(3H)-one and (−)-2-((3,4-trans)-1-benzyl-4-methylpyrrolidin-3-yl)-7-(2-hydroxypropan-2-yl)imidazo[5,1-f][1,2,4]triazin-4(3H)-one

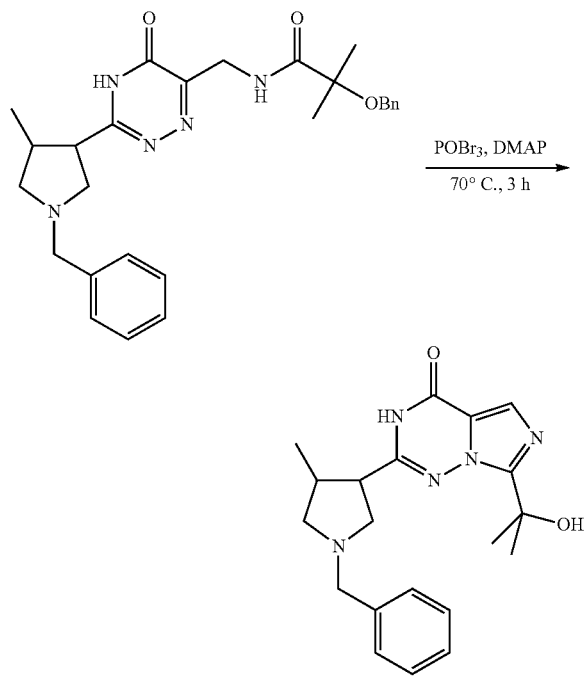

Phosphorus oxybromide (3.65 g, 12.6 mmol) was dissolved in MeCN (30 mL) and the solution was added to (+/−)-N-((3-((3,4-trans)-1-benzyl-4-methylpyrrolidin-3-yl)-5-oxo-4,5-dihydro-1,2,4-triazin-6-yl)methyl)-2-(benzyloxy)-2-methylpropanamide (2.0 g, 4.2 mmol) and DMAP (100 mg) in MeCN (40 mL) at room temperature dropwise. The reaction mixture was heat at 70° C. and stirred for 3 h. The reaction mixture was poured into a cold solution of concentrated aqueous NaHCO$_3$ (100 mL). The organics were extracted with CH$_2$Cl$_2$ (3×50 mL). The organic solution was washed with brine, dried over MgSO$_4$, the solvent was evaporated, and residue was purified by column chromatography (silica gel, CH$_2$Cl$_2$/MeOH/NH$_4$OH, 30:1:0.5%) to prepare (+/−)-2-((3,4-trans)-1-benzyl-4-methylpyrrolidin-3-yl)-7-(2-hydroxypropan-2-yl)imidazo[5,1-f][1,2,4]triazin-4(3H)-one (135 mg, 9% yield). Purity (HPLC): 96.6%; $^1$H NMR (300 MHz, CDCl$_3$/TMS): δ 7.77 (s, 1H), 7.39-7.29 (m, 5H), 3.85 (d, J=12 Hz, 1H), 3.58 (d, J=12 Hz, 1H), 3.42 (t, J=8 Hz, 1H), 3.01 (d, J=10 Hz, 1H), 2.76-2.74 (m, 1H), 2.57-2.43 (m, 2H), 1.96 (t, J=10 Hz, 1H), 1.72 (d, 5 Hz, 6H), 1.22 (d, J=7 Hz, 3H); $^{13}$C NMR (75 MHz, CDCl$_3$/TMS): δ 153.9, 149.4, 136.9, 128.6, 128.5, 127.5, 126.8, 119.4, 70.4, 60.9, 59.1, 55.8, 53.3, 47.8, 38.4, 28.5, 28.3, 20.1.

(+/−)-2-((3,4-trans)-1-benzyl-4-methylpyrrolidin-3-yl)-7-(2-hydroxypropan-2-yl)imidazo[5,1-f][1,2,4]triazin-4(3H)-one was purified by Chiralcel OJ-H, 250×20 mm, 5 um (15 mg loading; 0.1% TEA in n-Hexane:Ethanol (90:10) as mobile phase) to obtain pure fraction 1 ((−)-2-((3,4-trans)-1-benzyl-4-methylpyrrolidin-3-yl)-7-(2-hydroxypropan-2-yl)imidazo[5,1-f][1,2,4]triazin-4(3H)-one) and pure fraction 2 ((+)-2-((3,4-trans)-1-benzyl-4-methylpyrrolidin-3-yl)-7-(2-hydroxypropan-2-yl)imidazo[5,1-f][1,2,4]triazin-4(3H)-one). Characterization details of both fractions are as follows:

(−)-2-((3,4-trans)-1-benzyl-4-methylpyrrolidin-3-yl)-7-(2-hydroxypropan-2-yl)imidazo[5,1-f][1,2,4]triazin-4(3H)-one: $^1$H-NMR (DMSO d$_6$, 400 MHz): δ 7.65 (s, 1H), 7.32 (s, 5H), 5.15 (br s, 1H), 3.66 (q, 2H), 2.99 (t, 1H), 2.85-2.60 (m, 3H), 2.59-2.50 (m, 1H), 2.25 (t, 1H), 1.63 (s, 6H), 1.12 (d, 3H); Mass (ESI): 368.5 [M$^+$+1]; LC-MS: 98.01%; 368.5 (M$^+$+1); (column; X Select C-18, (50×3.0 mm, 3.5μ); RT 2.81 min. ACN: 5 mM NH$_4$OAc; 0.8 ml/min); UPLC (purity): 98.29%; (column; Acquity BEH C-18, 50×2.1 mm, 1.7μ; RT 1.36 min. 0.025% TFA (Aq): ACN:Water; 0.50 ml/min.; Chiral HPLC: 100% ee R$_t$=14.72 min (Chiralcel OJ-H, 250×4.6 mm, 5μ; mobile phase (A) 0.1% TEA in n-Hexane (B) ethanol (A:B:90:10); flow Rate: 1.00 mL/min); Optical rotation [α]$_D^{21}$: −12.64° (c=0.125, DCM).

(+)-2-((3,4-trans)-1-benzyl-4-methylpyrrolidin-3-yl)-7-(2-hydroxypropan-2-yl)imidazo[5,1-f][1,2,4]triazin-4(3H)-one: $^1$H-NMR (DMSO d$_6$, 400 MHz): δ 7.65 (s, 1H), 7.32 (s, 5H), 5.15 (br s, 1H), 3.66 (q, 2H), 2.99 (t, 1H), 2.85-2.60 (m, 4H), 2.25 (t, 1H), 1.63 (s, 6H), 1.12 (d, 3H); Mass (ESI): 368.5 [M$^+$+1]; LC-MS: 98.81%; 368.5 (M$^+$+1); (column; X select C-18, (50×3.0 mm, 3.5μ); RT 2.82 min. ACN: 5 mM NH$_4$OAc; 0.8 ml/min); UPLC (purity): 97.17%; (column; Acquity BEH C-18, 50×2.1 mm, 1.7μ; RT 1.36 min. 0.025% TFA (Aq): ACN:Water; 0.50 ml/min.; Chiral HPLC: 96.74% ee R$_t$=16.74 min (Chiralcel OJ-H, 250×4.6 mm, 5μ; mobile phase (A) 0.1% TEA in n-Hexane (B) ethanol (A:B:90:10); flow Rate: 1.00 mL/min); Optical rotation [α]$_D^{21}$: 21.44° (c=0.125, DCM).

41. 2-((3,4-trans)-1-benzyl-4-methylpyrrolidin-3-yl)-7-(tetrahydro-2H-pyran-3-yl)imidazo[5,1-f][1,2,4]-triazin-4(3H)-one

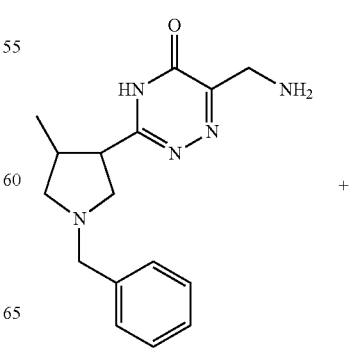

505
-continued

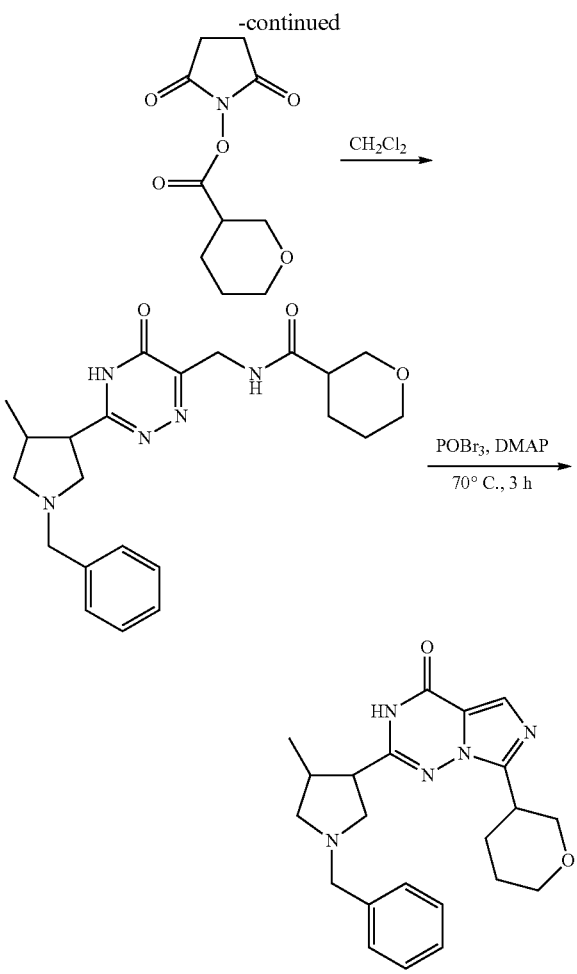

506
-continued

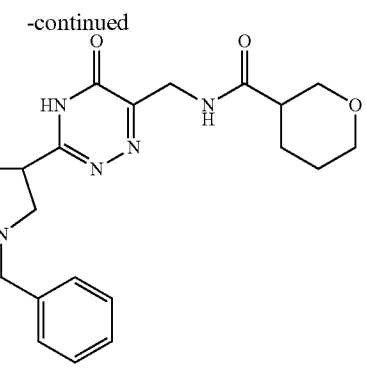

The mixture of (+/−)-6-(aminomethyl)-3-((3,4-trans)-1-benzyl-4-methylpyrrolidin-3-yl)-1,2,4-triazin-5(4H)-one (1.0 g, 3.3 mmol) and 2,5-dioxopyrrolidin-1-yl tetrahydro-2H-pyran-3-carboxylate (0.99 g, 4.4 mmol) in $CH_2Cl_2$ (50 mL) was stirred at room temperature overnight. The precipitate was filtered, the filtrate was concentrated and the residue was purified by column chromatography (silica gel, $CH_2Cl_2$/MeOH, 10:1). The obtained product (1.63 g) was dissolved in $CH_2Cl_2$ (50 mL) and washed with water (3×20 mL). The aqueous solution was extracted with chloroform (4×100 mL). The $CH_2Cl_2$ solution and chloroform extracts were combined and the solvents were evaporated to prepare N-((3-((3,4-trans)-1-benzyl-4-methylpyrrolidin-3-yl)-5-oxo-4,5-dihydro-1,2,4-triazin-6-yl)methyl)tetrahydro-2H-pyran-3-carboxamide (750 mg, 55% yield). $^1$H NMR (300 MHz, $CDCl_3$/TMS): δ 7.42-7.34 (m, 5H), 4.37 (d, 2 Hz, 1H), 4.07-3.58 (m, 4H), 3.51-3.27 (m, 6H), 3.00 (m, 1H), 2.63 (m, 1H), 2.55 (m, 2H), 2.00-1.50 (m, 5H), 1.09 (d, J=6 Hz, 3H).

Synthesis of 2-((3,4-trans)-1-benzyl-4-methylpyrrolidin-3-yl)-7-(tetrahydro-2H-pyran-3-yl)imidazo[5,1-f][1,2,4]triazin-4(3H)-one Synthesis of N-((3-((3,4-trans)-1-benzyl-4-methylpyrrolidin-3-yl)-5-oxo-4,5-dihydro-1,2,4-triazin-6-yl)methyl)tetrahydro-2H-pyran-3-carboxamide

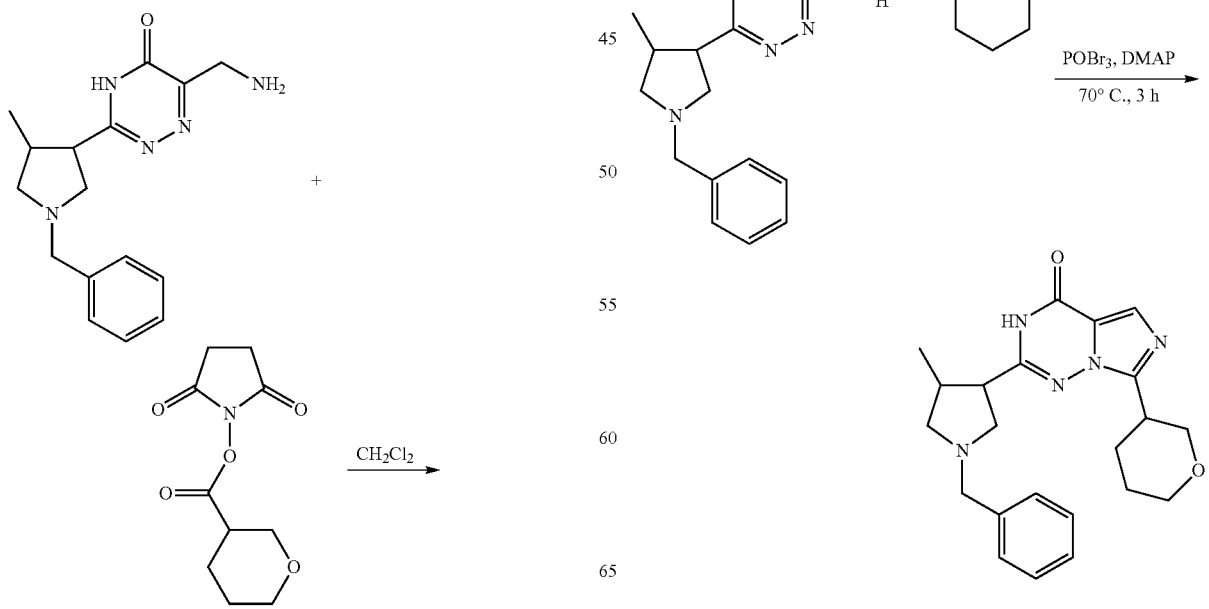

Phosphorous oxybromide (1.57 g, 5.4 mmol) was dissolved in MeCN (10 mL) and the solution was added to N-((3-((3,4-trans)-1-benzyl-4-methylpyrrolidin-3-yl)-5-oxo-4,5-dihydro-1,2,4-triazin-6-yl)methyl)tetrahydro-2H-pyran-3-carboxamide (750 mg, 1.8 mmol) and DMAP (50 mg) in MeCN (30 mL) at room temperature drop-wise. The reaction mixture was heat up to 70° C. and stirred for 3 h. The reaction mixture was purred into the ice-cold concentrated aqueous solution of $NaHCO_3$ (100 mL). The organics were extracted with $CH_2Cl_2$ (3×50 mL), washed with brine, and dried over $MgSO_4$. The $CH_2Cl_2$ solvent was evaporated and residue was purified by column chromatography (silica gel, $CH_2Cl_2$/MeOH/$NH_4OH$, 10:1:1%) to prepare 2-((3,4-trans)-1-benzyl-4-methylpyrrolidin-3-yl)-7-(tetrahydro-2H-pyran-3-yl)imidazo[5,1-f][1,2,4]triazin-4(3H)-one as a colorless glass (330 mg, 46% yield). Purity by HPLC: 95.9%; $^1$H NMR (300 MHz, $CDCl_3$/TMS): δ 7.73 (s, 1H), 7.73-7.21 (m, 5H), 4.07 (m, 1H), 3.96-3.93 (m, 1H), 3.79-3.74 (m, 1H), 3.63-3.43 (m, 4H), 3.28 (t, J=8.5 Hz, 1H), 2.94 (d, J=9.9 Hz, 1H), 2.71 (m, 1H), 2.58 (m, 1H), 2.41-2.39 (m, 1H), 2.09-1.88 (m, 3H), 1.77-1.72 (m, 2H), 1.16 (d, J=8.8 Hz, 3H); $^{13}$C NMR (75 MHz, $CDCl_3$/TMS): δ 148.9, 148.4, 140.9, 140.8, 131.8, 123.2, 123.1, 122.1, 113.4, 64.8, 64.7, 62.8, 55.7, 53.9, 50.6, 42.5, 32.9, 28.7, 28.6, 22.2, 21.9, 20.1, 14.7 (mixture of four stereoisomers).

2-((3,4-trans)-1-benzyl-4-methylpyrrolidin-3-yl)-7-(tetrahydro-2H-pyran-3-yl)imidazo[5,1-f][1,2,4]triazin-4(3H)-one was purified by Chiralpak AD-H, 250×20 mm, 5 um (35 mg loading; 0.1% TEA in n-Hexane:Ethanol (90:10) as mobile phase) to obtain pure fraction 1 (2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 1), pure fraction 2 (2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 2) and fraction 3 (2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 3). Characterization details of all fractions are as follows:

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 1:
$^1$H-NMR ($CDCl_3$, 400 MHz): δ 7.79 (s, 1H), 7.37 (s, 4H), 7.29 (s, 1H), 4.13 (t, 1H), 4.01 (d, 1H), 3.83 (d, 1H), 3.71 (t, 1H), 3.58-3.50 (m, 3H), 3.41 (t, 1H), 2.99 (d, 1H), 2.75 (d, 1H), 2.52-2.49 (m, 1H), 2.41 (q, 1H), 2.16-2.02 (m, 2H), 1.91 (t, 1H), 1.87-1.70 (m, 3H), 1.20 (d, 3H); Chiral HPLC: 100% ee $R_t$=21.15 min (Chiralpak IC, 250×4.6 mm, 5μ; mobile phase (A) 0.1% TEA in n-Hexane (B) ethanol (A:B:80:20); flow Rate: 1.00 mL/min); Optical rotation $[α]_D^{25}$: +19.71° (c=0.5, DCM).

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 2:
$^1$H-NMR ($CDCl_3$, 400 MHz): δ 7.79 (s, 1H), 7.37 (s, 4H), 7.29 (s, 1H), 4.13 (dd, 1H), 4.01 (d, 1H), 3.83 (d, 1H), 3.71 (t, 1H), 3.58-3.50 (m, 3H), 3.41 (t, 1H), 2.99 (d, 1H), 2.75 (d, 1H), 2.52-2.49 (m, 1H), 2.41 (q, 1H), 2.16-2.02 (m, 2H), 1.91 (t, 1H), 1.87-1.70 (m, 3H), 1.20 (d, 3H); Chiral HPLC: 98.44% ee $R_t$=22.79 min (Chiralpak IC, 250×4.6 mm, 5μ; mobile phase (A) 0.1% TEA in n-Hexane (B) ethanol (A:B:80:20); flow Rate: 1.00 mL/min); Optical rotation $[α]_D^{25}$: −15.46° (c=0.5, DCM).

2-((3,4-trans)-1-benzyl-4-methylpyrrolidin-3-yl)-7-(tetrahydro-2H-pyran-3-yl)imidazo[5,1-f][1,2,4]triazin-4(3H)-one fraction 3:
$^1$H-NMR ($CDCl_3$, 400 MHz): δ 7.79 (s, 1H), 7.37 (s, 4H), 7.29-2.5 (m, 2H), 4.13 (dd, 1H), 4.01 (d, 1H), 3.83 (d, 1H), 3.61-3.40 (m, 5H), 2.99 (d, 1H), 2.75 (d, 1H), 2.52-2.49 (m, 1H), 2.41 (q, 1H), 2.16-2.02 (m, 2H), 1.91 (t, 1H), 1.87-1.70 (m, 2H), 1.20 (d, 3H), 0.01 (s, 2H); Chiral HPLC: 96.69% ee $R_t$=24.95 min (Chiralpak IC, 250×4.6 mm, 5μ; mobile phase (A) 0.1% TEA in n-Hexane (B) ethanol (A:B:80:20); flow Rate: 1.00 mL/min); Optical rotation $[α]_D^{25}$: −17.65° (c=0.5, DCM).

42. (+)-2-((3,4-trans)-4-methyl-1-(pyrimidin-2-ylmethyl)pyrrolidin-3-yl)-7-(tetrahydrofuran-3-yl)imidazo[5,1-f][,1,2,4]-triazin-4(3H)-one [furan-(+)-isomer] fraction 1 and (+)-2-((3,4-trans)-4-methyl-1-(pyrimidin-2-ylmethyl)pyrrolidin-3-yl)-7-(tetrahydrofuran-3-yl)imidazo[5,1-f][,1,2,4]-triazin-4(3H)-one [furan-(+)-isomer]fraction 2

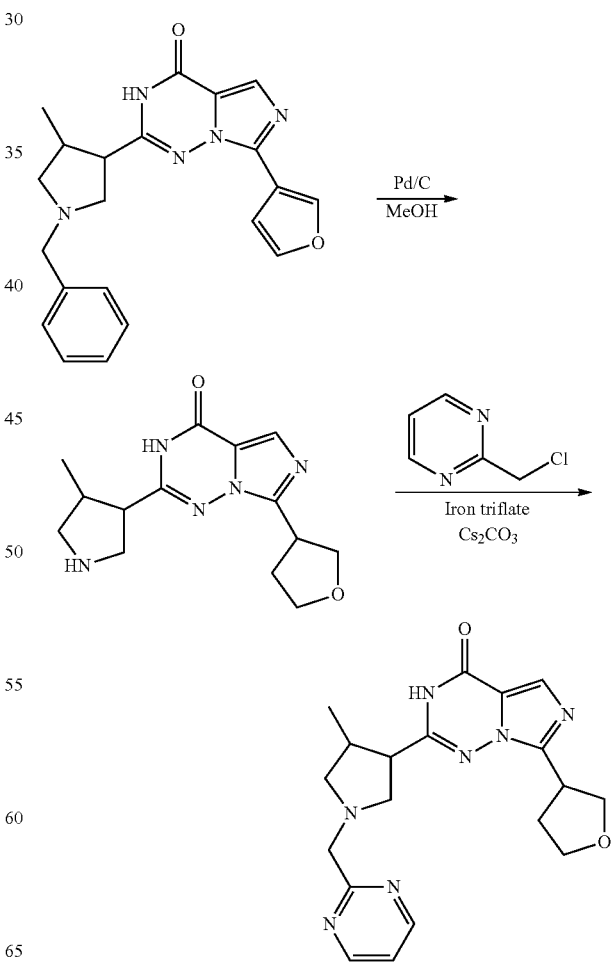

Synthesis of 2-((3,4-trans)-4-methylpyrrolidin-3-yl)-7-(tetrahydrofuran-3-yl)imidazo[5,1-f][1,2,4]triazin-4(3H)-one [furan-(+)-isomer]

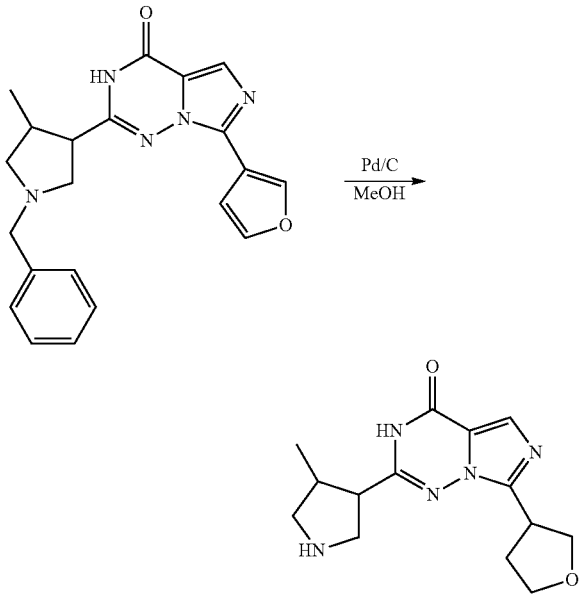

To a stirred solution of (+)-2-((3,4-trans)-1-benzyl-4-methylpyrrolidin-3-yl)-7-(furan-3-yl)imidazo[5,1-f][1,2,4]triazin-4(3H)-one (100 mg, 0.26 mmol) in MeOH (15 mL) was added 10% Pd—C (30 mg) and stirred at room temperature for 20 h under $H_2$ atmosphere (balloon pressure). The reaction mixture was passed through a pad of celite and dried in vacuo to afford 2-((3,4-trans)-4-methylpyrrolidin-3-yl)-7-(tetrahydrofuran-3-yl)imidazo[5,1-f][1,2,4]triazin-4(3H)-one [furan-(+)-isomer] (80 mg, crude) as an off-white solid. This was used in the next step without further purification; LC-MS: 95.26%; 290 (M$^+$+1); (column; X-select C-18, (50×3.0 mm, 3.5μ); RT 0.57 min. 0.1% TFA in water: ACN; 0.8 ml/min); TLC: 10% MeOH/CH$_2$Cl$_2$ (R$_f$: 0.2)

Synthesis of 2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(+)-isomer]

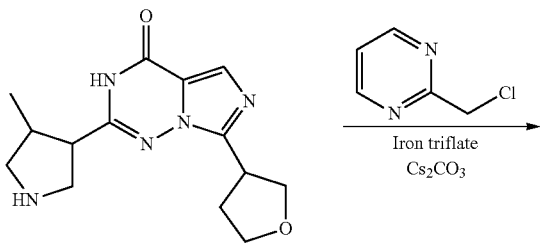 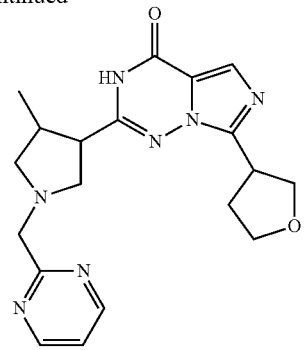

To a stirred solution of 2-((3,4-trans)-4-methylpyrrolidin-3-yl)-7-(tetrahydrofuran-3-yl)imidazo[5,1-f][1,2,4]triazin-4(3H)-one [furan-(+)-isomer] (100 mg, 0.34 mmol) in ACN (15 mL) were added Cs$_2$CO$_3$ (225 mg, 0.69 mmol), Iron triflate (34 mg, 0.69 mmol) and 2-(chloromethyl)pyrimidine (48 mg, 0.34 mmol) at room temperature under argon atmosphere. The resulting reaction mixture was heated to 70° C. and stirred for 4 h. The reaction mixture was diluted with water and extracted with EtOAc (2×30 mL). Combined organic layer was dried over sodium sulphate, filtered and concentrated in vacuo to obtain the crude product. The crude material was purified by silica gel column chromatography to afford 2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(+)-isomer] (50 mg, 38%) as an off-white solid.

The diastereimeric mixture of 2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one (furan-(+)-isomer) was purified by Chiralcel OJ-H, 250×19 mm, 5 um (5 mg loading; n-Hexane:ethanol (92:08) as mobile phase) to obtain pure fraction 1 ((+)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(+)-isomer] fraction 1) (9.8 mg) and pure fraction 2 ((+)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(+)-isomer] fraction 2) (7.2 mg). Characterization details of both fractions are as follows:

(+)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(+)-isomer] fraction 1:

$^1$H-NMR (DMSO d$_6$, 400 MHz): δ 11.57 (bs, 1H), 8.76 (s, 2H), 7.68 (s, 1H), 7.41 (t, 1H), 4.06 (t, 1H), 3.96-3.94 (m, 1H), 3.87-3.78 (m, 5H), 3.12 (t, 1H), 2.98-2.96 (m, 2H), 2.75-2.71 (m, 1H), 2.64-2.61 (m, 1H), 2.34-2.27 (m, 3H), 1.09 (d, 3H); Mass (ESI): 382 [M$^+$+1]; LC-MS: 97.14%; 382 (M$^+$+1); (column; X bridge C-18, (50×3.0 mm, 3.5μ); RT 3.29 min. ACN: 5 mM NH$_4$OAc; 0.8 ml/min); UPLC (purity): 98.41%; (column; Acquity UPLC HSS T3, 2.1×100 mm, 1.7μ; RT 2.50 min. 0.025% TFA (Aq): ACN; 0.3 ml/min.; Chiral HPLC: 100% R$_t$=17.80 min (Chiralcel OJ-H, 250×4.6 mm, 5μ; mobile phase (A) n-Hexane (B) Ethanol (A:B:88:12); flow Rate: 1.00 mL/min); Optical rotation [α]$_D^{20}$: +102.49° (c=0.125, DCM).

511

(+)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(+)-isomer] fraction 2:

$^1$H-NMR (DMSO d$_6$, 400 MHz): δ 8.78 (d, 2H), 7.62 (s, 1H), 7.41 (t, 1H), 4.06-4.04 (m, 1H), 3.99-3.97 (m, 1H), 3.87-3.81 (m, 5H), 3.12 (t, 1H), 2.98-2.96 (m, 2H), 2.75-2.71 (m, 1H), 2.62-2.57 (m, 1H), 2.37-2.29 (m, 3H), 1.12 (d, 3H); Mass (ESI): 382 [M$^+$+1]; LC-MS: 92.18%; 382 (M$^+$+1); (column; X-bridge C-18, (50×3.0 mm, 3.5μ); RT 3.45 min. ACN: 5 mM NH$_4$OAc; 0.8 ml/min); UPLC (purity): 98.32%; (column; Acquity UPLC HSS T3, 2.1×100 mm, 1.7μ; RT 2.51 min. 0.025% TFA (Aq): ACN; 0.3 ml/min; Chiral HPLC: 95.51% R$_t$=19.10 min (Chiralcel OJ-H, 250× 4.6 mm, 5μ; mobile phase (A) n-Hexane (B) Ethanol (A:B: 88:12); flow Rate: 1.00 mL/min); Optical rotation [α]$_D^{20}$: +63.93° (c=0.125, DCM).

43. (−)-2-((3,4-trans)-4-methyl-1-(pyrimidin-2-ylmethyl)pyrrolidin-3-yl)-7-(tetrahydrofuran-3-yl)imidazo[5,1-f][1,2,4]-triazin-4(3H)-one [furan-(−)-isomer] fraction 1 and (−)-2-((3,4-trans)-4-methyl-1-(pyrimidin-2-ylmethyl)pyrrolidin-3-yl)-7-(tetrahydrofuran-3-yl)imidazo[5,1-f][1,2,4]-triazin-4(3H)-one [furan-(−)-isomer] fraction 2

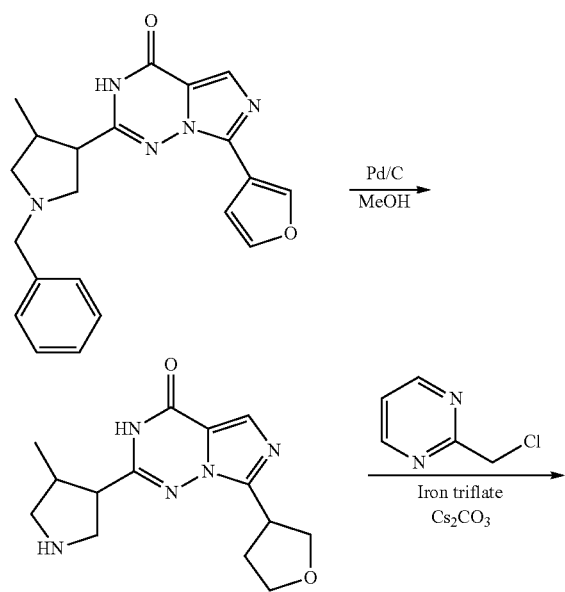

512

Synthesis of 2-((3,4-trans)-4-methylpyrrolidin-3-yl)-7-(tetrahydrofuran-3-yl)imidazo[5,1-f][1,2,4]triazin-4(3H)-one

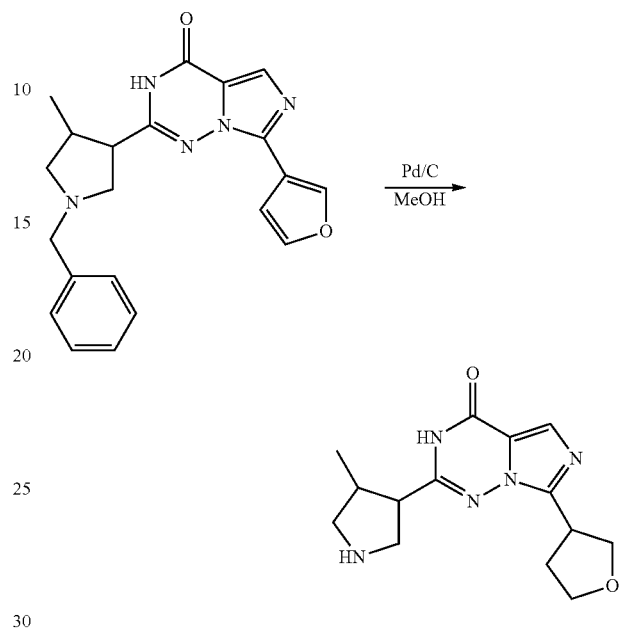

To a stirred solution of (−)-2-((3,4-trans)-1-benzyl-4-methylpyrrolidin-3-yl)-7-(furan-3-yl)imidazo[5,1-f][1,2,4]triazin-4(3H)-one (100 mg, 0.26 mmol) in MeOH (20 mL) was added 10% Pd—C (30 mg) and stirred at room temperature for 20 h under H2 atmosphere (balloon pressure). The reaction mixture was passed through a pad of celite and dried in vacuo to afford 2-((3,4-trans)-4-methylpyrrolidin-3-yl)-7-(tetrahydrofuran-3-yl)imidazo[5,1-f][1,2,4]triazin-4(3H)-one [furan-(−)-isomer] (85 mg, crude) as an off-white solid. This was used in the next step without further purification; LC-MS: 91.80%; 290 (M$^+$+1); (column; X-select C-18, (50×3.0 mm, 3.5μ); RT 0.92 min. 5 mM NH4OAc in water: ACN; 0.8 ml/min); TLC: 10% MeOH/CH$_2$Cl$_2$ (Rf: 0.2).

Synthesis of 2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(−)-isomer]

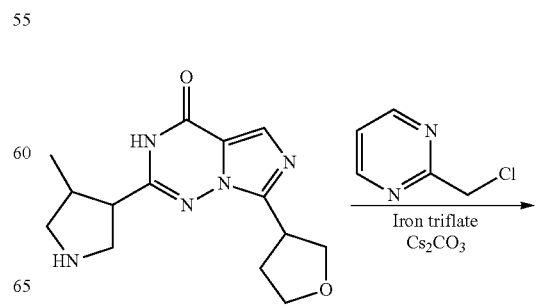

-continued

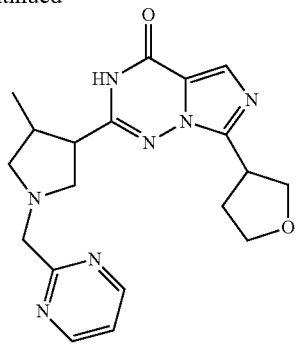

To a stirred solution of 2-((3,4-trans)-4-methylpyrrolidin-3-yl)-7-(tetrahydrofuran-3-yl)imidazo[5,1-f][1,2,4]triazin-4(3H)-one [furan-(−)-isomer] (94 mg, 0.32 mmol) in ACN (20 mL) were added $Cs_2CO_3$ (212 mg, 0.65 mmol) Iron triflate (32.72 mg, 0.064 mmol) and 2-(chloromethyl)pyrimidine (45.78 mg, 0.35 mmol) at room temperature under argon atmosphere. The resulting reaction mixture was heated to 70° C. and stirred for 4 h. The reaction mixture was diluted with water and extracted with EtOAc (2×30 mL). Combined organic layer was dried over sodium sulphate, filtered and concentrated in vacuo to obtain the crude product. The crude material was purified by silica gel column chromatography to afford 2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(−)-isomer] (40 mg, 32%) as an off-white solid.

The diastereimeric mixture 2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(−)-isomer] was purified by Chiralcel OJ-H, 250×19 mm, 5 um (25 mg loading; n-Hexane:ethanol (88:12) as mobile phase) to obtain pure fraction 1 ((−)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(−)-isomer] fraction 1) (15.3 mg) and pure fraction 2((−)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(−)-isomer] fraction 2) (14 mg). Characterization details of both fractions are as follows:

(−)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(−)-isomer] fraction 1:

$^1$H-NMR (DMSO $d_6$, 400 MHz): δ 8.79 (d, 2H), 7.67 (s, 1H), 7.38 (t, 1H), 4.08-4.06 (m, 1H), 4.01-3.99 (m, 1H), 3.87-3.82 (m, 5H), 3.14-3.09 (m, 1H), 3.00-2.98 (m, 2H), 2.78-2.76 (m, 1H), 2.62-2.59 (m, 1H), 2.37-2.32 (m, 1H), 2.27-2.21 (m, 2H), 1.12 (d, 3H); Mass (ESI): 382 [M$^+$+1]; LC-MS: 99.78%; 382 (M$^+$+1); (column; X bridge C-18, (50×3.0 mm, 3.5µ); RT 2.65 min. ACN: 5 mM $NH_4OAc$; 0.8 ml/min); UPLC (purity): 99.40%; (column; Eclipse XDB C-18, 150×4.6 mm, 5µ; RT 7.63 min. 5 mM $NH_4OAc$: ACN; 1.0 ml/min.; Chiral HPLC: 100% $R_t$=19.61 min (Chiralcel OJ-H, 250×4.6 mm, 5µ; mobile phase (A) n-Hexane (B) Ethanol (A:B:88:12); flow Rate: 1.00 mL/min); Optical rotation $[α]_D^{20}$: −86.97° (c=0.125, DCM).

(−)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one [furan-(−)-isomer] fraction 2:

$^1$H-NMR (DMSO $d_6$, 400 MHz): δ 8.78 (d, 2H), 7.64 (s, 1H), 7.38 (t, 1H), 4.08-4.06 (m, 1H), 3.96-3.94 (m, 1H), 3.87-3.792 (m, 5H), 3.12 (t, 1H), 2.96 (s, 2H), 2.77-2.76 (m, 1H), 2.62-2.59 (m, 1H), 2.34-2.29 (m, 1H), 2.27-2.25 (m, 2H), 1.12 (d, 3H); Mass (ESI): 382 [M$^+$+1]; LC-MS: 99%; 382 (M$^+$+1); (column; X-bridge C-18, (50×3.0 mm, 3.5µ); RT 2.66 min. ACN: 5 mM $NH_4OAc$; 0.8 ml/min); UPLC (purity): 98.37%; (column; Eclipse XDB C-18, 150×4.6 mm, 5µ; RT 7.63 min. 5 mM $NH_4OAc$: ACN; 1.0 ml/min.; Chiral HPLC: 100% $R_t$=26.66 min (Chiralcel OJ-H, 250× 4.6 mm, 5µ; mobile phase (A) n-Hexane (B) Ethanol (A:B: 88:12); flow Rate: 1.00 mL/min); Optical rotation $[α]_D^{25}$: −129.56° (c=0.125, DCM).

44. (−)-2-((3,4-trans)-1-benzyl-4-methylpyrrolidin-3-yl)-7-(furan-3-yl)imidazo[5,1-f][1,2,4]triazin-4(3H)-one [furan-(+)-isomer] fraction 1 and (+)-2-((3,4-trans)-1-benzyl-4-methylpyrrolidin-3-yl)-7-(furan-3-yl)imidazo[5,1-f][1,2,4]triazin-4(3H)-one [furan-(+)-isomer] fraction 2

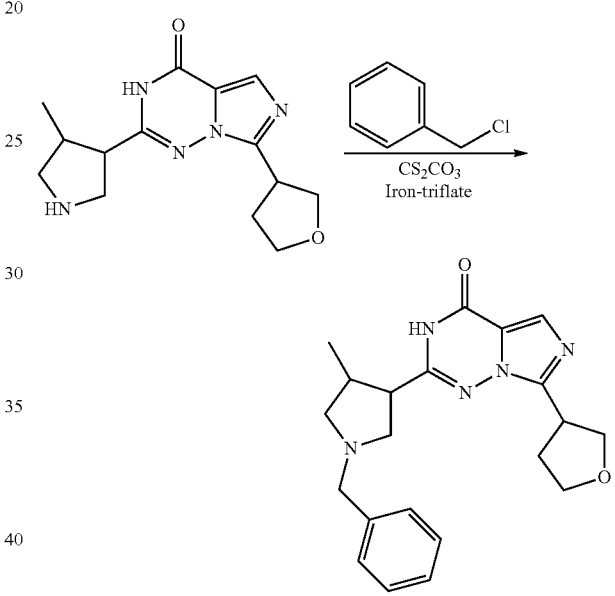

Synthesis of 2-(1-(3,4-trans)-benzyl-4-methylpyrrolidin-3-yl)-7-(tetrahydrofuran-3-yl)imidazo[5,1-f][1,2,4]triazin-4(3H)-one [furan-(+)-isomer]

To a stirred solution of 2-((3,4-trans)-4-methylpyrrolidin-3-yl)-7-(tetrahydrofuran-3-yl)imidazo[5,1-f][1,2,4]triazin-4(3H)-one [furan-(+)-isomer] (40 mg, 0.138 mmol) in ACN (10 mL) were added $Cs_2CO_3$ (99.26 mg, 0.30 mmol), Iron triflate (13.9 mg, 0.027 mmol) and (chloromethyl)benzene (19 mg, 0.15 mmol) at room temperature under argon atmosphere. The resulting reaction mixture was heated to 70° C. and stirred for 3 h. The reaction mixture was cooled to room temperature; diluted with water and extracted with EtOAc (2×10 mL). Combined organic layer was dried over sodium sulphate, filtered and concentrated in vacuo to obtain the crude product. The crude material was purified by silica gel column chromatography to afford 2-(1-(3,4-trans)-benzyl-4-methylpyrrolidin-3-yl)-7-(tetrahydrofuran-3-yl)imidazo[5,1-f][1,2,4]triazin-4(3H)-one [furan-(+)-isomer] (40 mg, 77%) as an off-white solid.

The diastereimeric mixture 2-(1-(3,4-trans)-benzyl-4-methylpyrrolidin-3-yl)-7-(tetrahydrofuran-3-yl)imidazo[5,1-f][1,2,4]triazin-4(3H)-one [furan-(+)-isomer] was purified by Chiralpak AD-H, 250×90 mm, 5 um (5 mg loading; 0.1% DEA in n-Hexane:ethanol (85:15) as mobile phase) to obtain pure fraction 1((−)-2-((3,4-trans)-1-benzyl-4-methylpyrrolidin-3-yl)-7-(furan-3-yl)imidazo[5,1-f][1,2,4]triazin-4(3H)-one [furan-(+)-isomer] fraction 1) (9 mg) and pure fraction 2 ((+)-2-((3,4-trans)-1-benzyl-4-methylpyrrolidin-3-yl)-7-(furan-3-yl)imidazo[5,1-f][1,2,4]triazin-4(3H)-one [furan-(+)-isomer] fraction 1) (8.4 mg). Characterization details of both fractions are as follows:

(−)-2-((3,4-trans)-1-benzyl-4-methylpyrrolidin-3-yl)-7-(furan-3-yl)imidazo[5,1-f][1,2,4]triazin-4(3H)-one [furan-(+)-isomer] fraction 1:

$^1$H-NMR (CD$_3$OD, 400 MHz): δ 7.69 (s, 1H), 7.39-7.28 (m, 5H), 4.12 (t, 1H), 4.04-3.87 (m, 6H), 3.27-3.21 (m, 1H), 3.14-3.10 (m, 1H), 3.05-2.99 (m, 1H), 2.91-2.87 (m, 1H), 2.65-2.61 (m, 1H), 2.37-2.31 (m, 3H), 1.12 (d, 3H); LC-MS: 94.62%; 380 (M$^+$+1); (column; X-select C-18, (50×3.0 mm, 3.5μ); RT 2.99 min. ACN: 5 mM NH$_4$OAc; 0.8 ml/min); UPLC (purity): 92.44%; (column; Acquity BEH C-18, 50×2.1 mm, 1.7μ; RT 1.45 min. 0.025% TFA (Aq): ACN; 0.50 ml/min.; Chiral HPLC: 100% R$_t$=23.55 min (Chiralpak AD-H, 250×4.6 mm, 5μ; mobile phase (A) 0.1% DEA in n-Hexane (B) Ethanol (A:B:85:15); flow Rate: 1.00 mL/min); Optical rotation [α]$_D^{20}$: −4.12° (c=0.25, DCM). TLC: 10% MeOH/CH$_2$Cl$_2$ (R$_f$: 0.8).

(+)-2-((3,4-trans)-1-benzyl-4-methylpyrrolidin-3-yl)-7-(furan-3-yl)imidazo[5,1-f][1,2,4]triazin-4(3H)-one [furan-(+)-isomer] fraction 2:

$^1$H-NMR (CD$_3$OD, 400 MHz): δ 7.71 (s, 1H), 7.41-7.28 (m, 5H), 4.16 (t, 1H), 4.02-3.87 (m, 6H), 3.28-3.27 (m, 1H), 3.21-3.17 (m, 2H), 2.94-2.88 (m, 1H), 2.71-2.67 (m, 1H), 2.47-2.42 (m, 1H), 2.34-2.31 (m, 2H), 1.12 (d, 3H); LC-MS: 93.21%; 380 (M++1); (column; X-select C-18, (50×3.0 mm, 3.5μ); RT 2.99 min. ACN: 5 mM NH4OAc; 0.8 ml/min); UPLC (purity): 92.44%; (column; Acquity BEH C-18, 50×2.1 mm, 1.7μ; RT 1.45 min. 0.025% TFA (Aq): ACN; 0.50 ml/min. (IP11100452); Chiral HPLC: 100% Rt=31.19 min (Chiralpak AD-H, 250×4.6 mm, 5μ; mobile phase (A) 0.1% DEA in n-Hexane (B) Ethanol (A:B:85:15); flow Rate: 1.00 mL/min); Optical rotation [α]D20: +17.98° (c=0.25, DCM).

45. (−)-2-(1-(3,4-trans)-benzyl-4-methylpyrrolidin-3-yl)-7-(tetrahydrofuran-3-yl)imidazo[5,1-f][1,2,4]-triazin-4(3H)-one [furan-(−)-isomer] fraction 1 and (−)-2-(1-(3,4-trans)-benzyl-4-methylpyrrolidin-3-yl)-7-(tetrahydrofuran-3-yl)imidazo[5,1-f][1,2,4]-triazin-4(3H)-one [furan-(−)-isomer] fraction 2

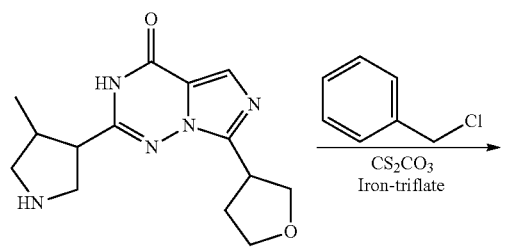

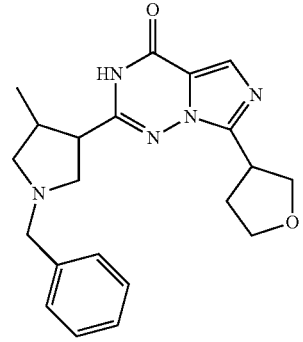

Synthesis of 2-(1-(3,4-trans)-benzyl-4-methylpyrrolidin-3-yl)-7-(tetrahydrofuran-3-yl)imidazo[5,1-f][1,2,4]triazin-4(3H)-one [furan-(−)-isomer]

To a stirred solution of 2-((3,4-trans)-4-methylpyrrolidin-3-yl)-7-(tetrahydrofuran-3-yl)imidazo[5,1-f][1,2,4]triazin-4(3H)-one [furan-(−)-isomer] (40 mg, 0.138 mmol) in ACN (5 mL) were added Cs$_2$CO$_3$ (99.26 mg, 0.30 mmol), Iron triflate (13.9 mg, 0.027 mmol) and (chloromethyl)benzene (19 mg, 0.15 mmol) at room temperature under argon atmosphere. The resulting reaction mixture was heated to 70° C. and stirred for 3 h. The reaction mixture was cooled to room temperature; diluted with water and extracted with EtOAc (2×15 mL). Combined organic layer was dried over sodium sulphate, filtered and concentrated in vacuo to obtain the crude product. The crude material was purified by silica gel column chromatography to afford 2-(1-(3,4-trans)-benzyl-4-methylpyrrolidin-3-yl)-7-(tetrahydrofuran-3-yl)imidazo[5,1-f][1,2,4]triazin-4(3H)-one [furan-(−)-isomer] (41 mg, 78%) as an off-white solid. TLC: 10% MeOH/CH$_2$Cl$_2$ (Rf: 0.5).

The diastereimeric mixture 2-(1-(3,4-trans)-benzyl-4-methylpyrrolidin-3-yl)-7-(tetrahydrofuran-3-yl)imidazo[5,1-f][1,2,4]triazin-4(3H)-one [furan-(−)-isomer] was purified by Chiralpak IC, 250×19 mm, 5μ; (15 mg loading; 0.1% DEA in n-Hexane: DCM:Methanol (80:20) (76:24) as mobile phase) to obtain pure fraction 1 ((−)-2-(1-(3,4-trans)-benzyl-4-methylpyrrolidin-3-yl)-7-(tetrahydrofuran-3-yl)imidazo[5,1-f][1,2,4]triazin-4(3H)-one [furan-(−)-isomer] fraction 1) (9.7 mg) and pure fraction 2 ((+)-2-(1-(3,4-trans)-benzyl-4-methylpyrrolidin-3-yl)-7-(tetrahydrofuran-3-yl)imidazo[5,1-f][1,2,4]triazin-4(3H)-one [furan-(−)-isomer] fraction 2) (9.3 mg). Characterization details of both fractions are as follows:

(−)-2-(1-(3,4-trans)-benzyl-4-methylpyrrolidin-3-yl)-7-(tetrahydrofuran-3-yl)imidazo[5,1-f][1,2,4]triazin-4(3H)-one [furan-(−)-isomer] fraction 1

$^1$H-NMR (DMSO-d6, 400 MHz): δ 7.68 (s, 1H), 7.32-7.29 (m, 5H), 4.07-4.03 (m, 1H), 3.89-3.79 (m, 4H), 3.64-3.58 (m, 2H), 2.96-2.94 (m, 1H), 2.86-2.85 (m, 1H), 2.78-2.72 (m, 2H), 2.66-2.64 (m, 1H), 2.31-2.24 (m, 3H), 1.07 (d, 3H); Mass: 380 (M$^+$+1); LC-MS: 99.17%; 380 (M$^+$+1); (column; X-select C-18, (50×3.0 mm, 3.5μ); RT 2.26 min. ACN: 0.1% TFA in water; 0.8 ml/min); UPLC (purity): 97.53%; (column; Acquity BEH C-18, 50×2.1 mm, 1.7μ; RT 1.44 min. 0.025% TFA (Aq): ACN; 0.50 ml/min.; Chiral HPLC: 100% Rt=23.09 min, Chiralpak IC, 250×4.6 mm, 5μ; mobile phase (A) 0.1% DEA in n-Hexane (B) DCM:Methanol (80:20) (A:B:76:24); flow Rate: 1.00 mL/min); Optical rotation [α]D20: −2.30° (c=0.25, DCM).

(−)-2-(1-(3,4-trans)-benzyl-4-methylpyrrolidin-3-yl)-7-(tetrahydrofuran-3-yl)imidazo[5,1-f][1,2,4]triazin-4(3H)-one [furan-(−)-isomer] fraction 2

¹H-NMR (DMSO-d6, 400 MHz): δ 7.67 (s, 1H), 7.32-7.29 (m, 5H), 4.08 (t, 1H), 3.89-3.81 (m, 4H), 3.64-3.58 (m, 2H), 2.96-2.94 (m, 1H), 2.89-2.86 (m, 2H), 2.79-2.74 (m, 2H), 2.67-2.64 (m, 1H), 2.30-2.26 (m, 3H), 1.07 (d, 3H); Mass: 380 (M++1); LC-MS: 99.55%; 380 (M++1); (column; X-bridge C-18, (50×3.0 mm, 3.5µ); RT 2.30 min. ACN: 0.1% TFA in water; 0.8 ml/min); UPLC (purity): 99.62%; (column; Acquity BEH C-18, 50×2.1 mm, 1.7µ; RT 1.44 min. 0.025% TFA (Aq): ACN; 0.50 ml/min.; Chiral HPLC: 100% Rt=26.55 min (Chiralpak IC, 250×4.6 mm, 5µ; mobile phase (A) 0.1% DEA in n-Hexane (B) DCM:Methanol (80:20) (A:B:76:24); flow Rate: 1.00 mL/min); Optical rotation [α]D20: −39.56° (c=0.25, DCM).

46. (+)-tert-butyl 4-(2-((3,4-trans)-1-benzyl-4-methylpyrrolidin-3-yl)-4-oxo-3,4-dihydroimidazo[5,1-f][1,2,4]triazin-7-yl)piperidine-1-carboxylate and (−)-tert-butyl 4-(2-((3,4-trans)-1-benzyl-4-methylpyrrolidin-3-yl)-4-oxo-3,4-dihydroimidazo[5,1-f][1,2,4]triazin-7-yl)piperidine-1-carboxylate

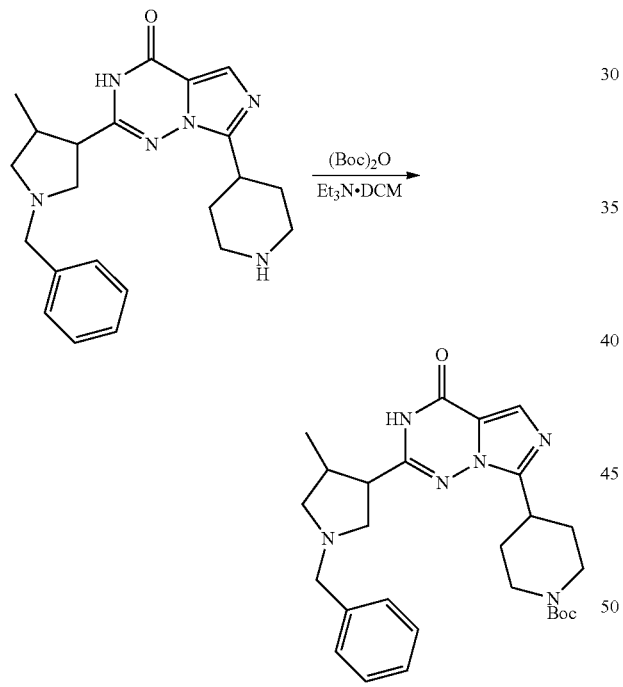

To a stirred solution of (+/−)-2-((3,4-trans)-1-benzyl-4-methylpyrrolidin-3-yl)-7-(piperidin-4-yl)imidazo[5,1-f][1,2,4]triazin-4(3H)-one (75 mg, 0.19 mmol) in DCM (10 mL) was added (Boc)₂O (45 mg, 0.21 mmol) followed by Et₃N (38 mg, 0.38 mmol) at 0° C. under nitrogen atmosphere. The resulting reaction mixture was allowed to warm to room temperature and stirred for 16 h. The reaction mixture was diluted with water and extracted with CH₂Cl₂ (2×20 mL). Combined organic layer was dried over sodium sulphate, filtered and concentrated in vacuo to obtain the crude product. The crude material was purified by silica gel column chromatography to afford (+/−)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate (75 mg, 80%) as an off-white solid. TLC: 5% MeOH/CH2Cl2 (Rf: 0.5).

Racemic tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate was purified by Chiralcel OJ-H, 250×19 mm, 5 um (10 mg loading; 0.1% DEA in n-Hexane: Ethanol (90:10) as mobile phase) to obtain pure fraction 1((−)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate) (5 mg) and pure fraction 2 ((+)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate) (5 mg). Characterization details of both fractions are as follows:

(−)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate:

¹H-NMR (DMSO-d6, 400 MHz): δ 7.67 (s, 1H), 7.33-7.29 (m, 4H), 7.24-7.21 (m, 1H), 4.01-3.98 (m, 2H), 3.64-3.59 (m, 2H), 2.98-2.92 (m, 4H), 2.89-2.86 (m, 1H), 2.76-2.72 (m, 2H), 2.65-2.61 (m, 1H), 2.24-2.21 (m, 1H), 1.92-1.87 (m, 2H), 1.74-1.69 (m, 2H), 1.42 (s, 9H), 1.08 (d, 3H); LC-MS: 97.70%; 493 (M++1); (column; X-bridge C-18, (50×3.0 mm, 3.5µ); RT 3.89 min. ACN: 5 mM NH4OAc; 0.8 ml/min); UPLC (purity): 99.69%; (column; Acquity BEH C-18, 50×2.1 mm, 1.7µ; RT 1.91 min. 0.025% TFA (Aq): ACN; 0.50 ml/min.; Chiral HPLC: 100% Rt=15.04 min (Chiralcel OJ-H, 250×4.6 mm, 5µ; mobile phase (A) 0.1% DEA in n-Hexane (B) Ethanol (A:B:90:10); flow Rate: 1.00 mL/min); Optical rotation [α]D20: −17.05° (c=0.125, DCM).

(+)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate:

¹H-NMR (DMSO-d6, 400 MHz): δ 7.68 (s, 1H), 7.34-7.29 (m, 5H), 4.01-3.98 (m, 2H), 3.64-3.58 (m, 2H), 2.98-2.94 (m, 4H), 2.89-2.88 (m, 1H), 2.79-2.75 (m, 2H), 2.67-2.65 (m, 1H), 2.25-2.21 (m, 1H), 1.92-1.87 (m, 2H), 1.74-1.69 (m, 2H), 1.42 (s, 9H), 1.08 (d, 3H); LC-MS: 96.75%; 493 (M++1); (column; X-bridge C-18, (50×3.0 mm, 3.5µ); RT 4.13 min. ACN: 5 mM NH4OAc; 0.8 ml/min); UPLC (purity): 98.62%; (column; Acquity BEH C-18, 50×2.1 mm, 1.7µ; RT 1.90 min. 0.025% TFA (Aq): ACN; 0.50 ml/min.; Chiral HPLC: 99.77% Rt=20.15 min (Chiralcel OJ-H, 250×4.6 mm, 5µ; mobile phase (A) 0.1% DEA in n-Hexane (B) Ethanol (A:B:90:10); flow Rate: 1.00 mL/min); Optical rotation [α]D20: +19.96° (c=0.125, DCM).

47. (−)-2-((3,4-trans)-1-benzyl-4-methylpyrrolidin-3-yl)-7-(piperidin-4-yl)imidazo[1,5-f][1,2,4]triazin-4(3H)-one [piperidine NH fraction 1]

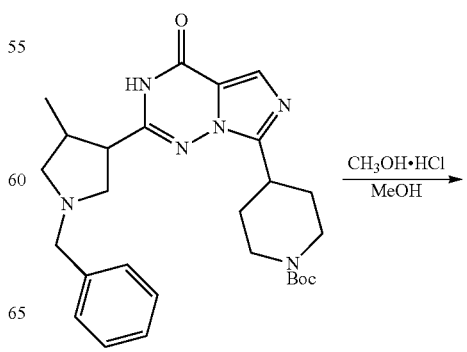

-continued

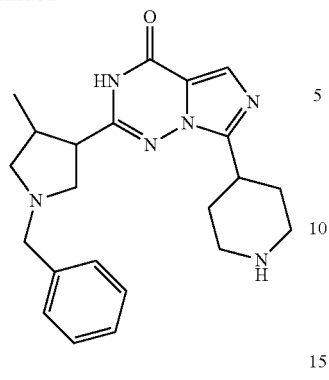

-continued

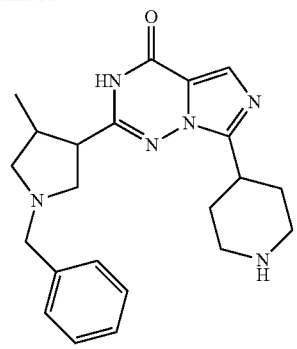

To a stirred solution of (−)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate (20 mg, 0.040 mmol) in CH$_3$OH (2 mL) was added CH$_3$OH·HCl (5 mL) at 0° C. under argon atmosphere. The resulting reaction mixture was allowed to warm to room temperature and stirred for 8 h. The volatiles were evaporated under reduced pressure. The residue was diluted with saturated NaHCO$_3$ and extracted with DCM (2×15 mL). Combined organic layer was dried over sodium sulphate, filtered and concentrated in vacuo to obtain the crude product. The crude material was purified by silica gel column chromatography to afford (−)-2-((3,4-trans)-1-benzyl-4-methylpyrrolidin-3-yl)-7-(piperidin-4-yl)imidazo[1,5-f][1,2,4]triazin-4(3H)-one [piperidine NH fraction 1] (10 mg, 62%) as an off-white solid.

$^1$H-NMR (DMSO d$_6$, 400 MHz): δ 7.58 (s, 1H), 7.34-7.31 (m, 4H), 7.24-7.21 (m, 1H), 3.68-3.57 (m, 2H), 3.24-3.19 (m, 2H), 3.05-3.01 (m, 1H), 2.92-2.89 (m, 2H), 2.85-2.81 (m, 1H), 2.78-2.72 (m, 1H), 2.68-2.61 (m, 5H), 2.27-2.24 (m, 1H), 1.87-1.82 (m, 2H), 1.76-1.72 (m, 2H), 1.08 (d, 3H); Mass (ESI): 393 [M$^+$+1]; LC-MS: 97.24%; 393 (M$^+$+1); (column; X bridge C-18, (50×3.0 mm, 3.5μ); RT 2.59 min. ACN: 5 mM NH$_4$OAc; 0.8 ml/min); UPLC (purity): 99.08%; (column; Acquity UPLC HSS T3, 2.1×100 mm, 1.7μ; RT 3.45 min. 0.025% TFA (Aq): ACN; 0.3 ml/min.; Optical rotation [α]$_D^{20}$: −11.26° (c=0.25, DCM); TLC: 10% MeOH/CH$_2$Cl$_2$ (R$_f$: 0.3).

48. (+)-2-((3,4-trans)-1-benzyl-4-methylpyrrolidin-3-yl)-7-(piperidin-4-yl)imidazo[1,5-f][1,2,4]triazin-4(3H)-one [piperidine NH fraction 2]

To a stirred solution of (−)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate (20 mg, 0.040 mmol) in CH$_3$OH (2 mL) was added CH$_3$OH·HCl (5 mL) at 0° C. under argon atmosphere. The resulting reaction mixture was allowed to warm to room temperature and stirred for 8 h. The volatiles were evaporated under reduced pressure. The residue was diluted with saturated NaHCO$_3$ and extracted with DCM (2×15 mL). Combined organic layer was dried over sodium sulphate, filtered and concentrated in vacuo to obtain the crude product. The crude material was purified by silica gel column chromatography to afford (+)-2-((3,4-trans)-1-benzyl-4-methylpyrrolidin-3-yl)-7-(piperidin-4-yl)imidazo[1,5-f][1,2,4]triazin-4(3H)-one [piperidine NH fraction 2] (10 mg, 62%) as an off-white solid.

$^1$H-NMR (DMSO d$_6$, 400 MHz): δ 7.57 (s, 1H), 7.32-7.30 (m, 4H), 7.25-7.21 (m, 1H), 3.69-3.62 (m, 2H), 3.24-3.19 (m, 3H), 3.07-3.01 (m, 2H), 2.92-2.89 (m, 1H), 2.89-2.84 (m, 1H), 2.78-2.71 (m, 2H), 2.67-2.61 (m, 3H), 2.25-2.21 (m, 1H), 1.87-1.84 (m, 2H), 1.76-1.69 (m, 2H), 1.08 (d, 3H); Mass (ESI): 393 [M$^+$+1]; LC-MS: 98.51%; 393 (M$^+$+1); (column; X bridge C-18, (50×3.0 mm, 3.5μ); RT 2.64 min. ACN: 5 mM NH$_4$OAc; 0.8 ml/min); UPLC (purity): 99.45%; (column; Acquity UPLC HSS T3, 2.1×100 mm, 1.7μ; RT 3.61 min. 0.025% TFA (Aq): ACN; 0.3 ml/min.; Optical rotation [α]β20: +12.40° (c=0.25, DCM); TLC: 10% MeOH/CH$_2$Cl$_2$ (R$_f$: 0.2).

49. 2-((3,4-trans)-1-benzyl-4-methylpyrrolidin-3-yl)-7-(1-methylpiperidin-4-yl)imidazo[5,1-f][1,2,4]triazin-4(3H)-one [from piperidine NH fraction 1]

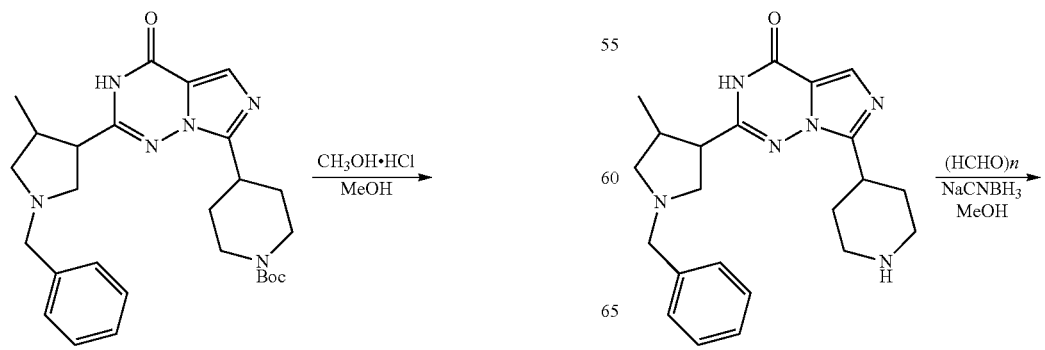

521

-continued

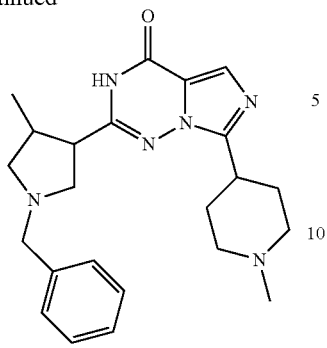

522

-continued

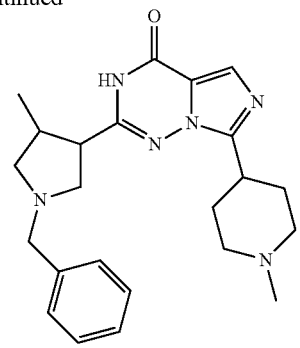

To a stirred solution of (−)-2-((3,4-trans)-1-benzyl-4-methylpyrrolidin-3-yl)-7-(piperidin-4-yl)imidazo[1,5-f][1,2,4]triazin-4(3H)-one [piperidine NH fraction 1] (20 mg, 0.05 mmol) in MeOH (4 mL) was added paraformaldehyde (4.89 mg, 0.10 mmol) at room temperature and stirred for 2 h under argon atmosphere. To the resulting solution was added NaCNBH$_3$ (9.4 mg, 0.15 mmol) and stirring was continued for another 8 h at room temperature. The volatiles were evaporated under reduced pressure. The residue was diluted with water and extracted with CH$_2$Cl$_2$ (2×30 mL). Combined organic layer was dried over sodium sulphate, filtered and concentrated in vacuo to obtain the crude product. The crude material was purified by silica gel column chromatography to afford (−)-2-((3,4-trans)-1-benzyl-4-methylpyrrolidin-3-yl)-7-(1-methylpiperidin-4-yl)imidazo[5,1-f][1,2,4]triazin-4(3H)-one [from piperidine NH fraction 1 (11.6 mg, 60%) as an off-white solid.

$^1$H-NMR (DMSO-d$_6$, 400 MHz): δ 7.68 (s, 1H), 7.34-7.31 (m, 4H), 7.25-7.21 (m, 1H), 3.68 (s, 2H), 2.96-2.94 (m, 1H), 2.85-2.83 (m, 4H), 2.78-2.71 (m, 5H), 2.69-2.61 (m, 4H), 2.37-2.35 (m, 1H), 2.01 (s, 3H), 1.08 (d, 3H); Mass (ESI): 407.4 [M$^+$+1]; LC-MS: 96.01%; 407.4 (M$^+$+1); (column; X-select C-18, (50×3.0 mm, 3.5μ); RT 2.58 min. 5 mM ammonium acetate: ACN; 0.8 ml/min); UPLC (purity): 95.60%; (column; Acquity BEH C-18, 50×2.1 mm, 1.7μ; RT 1.17 min. 0.025% TFA (Aq): ACN; 0.50 ml/min.; Chiral HPLC: 96.92%, R$_t$=32.96 min (Chiralcel OJ-H, 250×4.6 mm, 5μ; mobile phase (A) 0.1% DEA in n-Hexane (B) Ethanol (A:B:96:4); flow Rate: 1.00 mL/min); TLC: 10% MeOH/DCM (R$_f$: 0.5).

50. 2-((3,4-trans)-1-benzyl-4-methylpyrrolidin-3-yl)-7-(1-methylpiperidin-4-yl)imidazo[5,1-f][1,2,4]triazin-4(3H)-one [from piperidine NH fraction 2]

To a stirred solution of (+)-2-((3,4-trans)-1-benzyl-4-methylpyrrolidin-3-yl)-7-(piperidin-4-yl)imidazo[1,5-f][1,2,4]triazin-4(3H)-one [piperidine NH fraction 2] (20 mg, 0.05 mmol) in MeOH (4 mL) was added paraformaldehyde (4.89 mg, 0.10 mmol) at room temperature and stirred for 2 h under argon atmosphere. To the resulting solution was added NaCNBH$_3$ (9.48 mg, 0.15 mmol) and stirring was continued for another 8 h at room temperature. The volatiles were evaporated under reduced pressure. The residue was diluted with water and extracted with CH$_2$Cl$_2$ (2×30 mL). Combined organic layer was dried over sodium sulphate, filtered and concentrated in vacuo to obtain the crude product. The crude material was purified by silica gel column chromatography to afford 2-((3,4-trans)-1-benzyl-4-methylpyrrolidin-3-yl)-7-(1-methylpiperidin-4-yl)imidazo[5,1-f][1,2,4]triazin-4(3H)-one [from piperidine NH fraction 2] (13.4 mg, 72%) as an off-white solid.

$^1$H-NMR (CD$_3$OD, 400 MHz): δ 7.72 (s, 1H), 7.39-7.29 (m, 5H), 3.79-3.72 (m, 2H), 3.51-3.47 (m, 1H), 3.42-3.37 (m, 2H), 3.19-3.16 (m, 1H), 3.04-2.97 (m, 1H), 2.92-2.84 (m, 4H), 2.71 (s, 3H), 2.65-2.61 (m, 1H), 2.27-2.21 (m, 1H), 2.19-2.14 (m, 4H), 1.12 (d, 3H); Mass (ESI): 407 [M$^+$+1]; LC-MS: 92.41%; 407.4 (M$^+$+1); (column; X-select C-18, (50×3.0 mm, 3.5μ); RT 3.12 min. 0.1% TFA (Aq): ACN; 0.8 ml/min); UPLC (purity): 93.36%; (column; Acquity BEH C-18, 50×2.1 mm, 1.7μ; RT 1.17 min. 0.025% TFA (Aq): ACN; 0.50 ml/min.; Chiral HPLC: 98.60%, R$_t$=28.60 min (Chiralcel OJ-H, 250×4.6 mm, 5μ; mobile phase (A) 0.1% DEA in n-Hexane (B) Ethanol (A:B:96:4); flow Rate: 1.00 mL/min); TLC: 10% MeOH/DCM (R$_f$: 0.5).

51. (+)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one

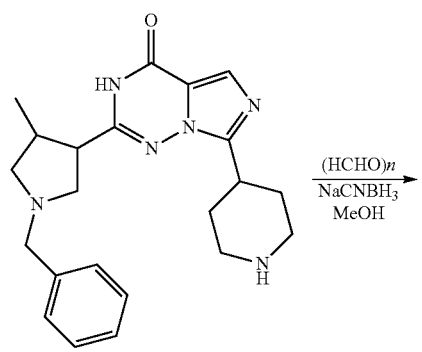

(HCHO)n
⎯⎯⎯⎯→
NaCNBH$_3$
MeOH

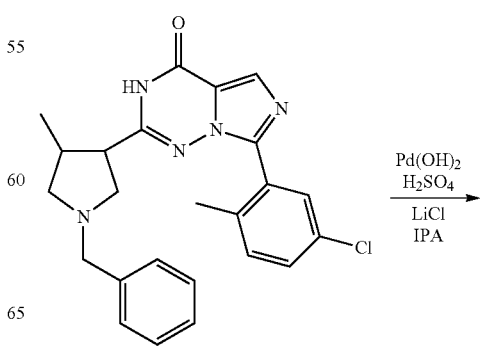

Pd(OH)$_2$
H$_2$SO$_4$
⎯⎯⎯⎯→
LiCl
IPA

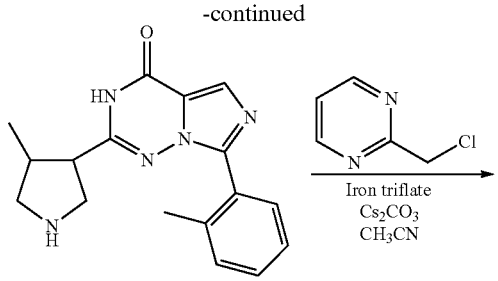

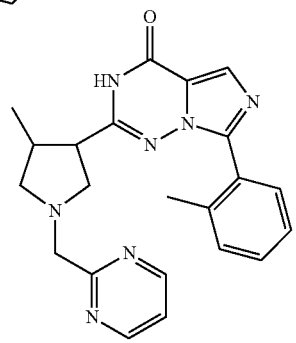

To a stirred solution of (+)-2-((3,4-trans)-1-benzyl-4-methylpyrrolidin-3-yl)-7-(5-chloro-2-methylphenyl)imidazo[5,1-f][1,2,4]triazin-4(3H)-one (30 mg, 0.13 mmol) in MeOH (30 mL) was added 10% Pd—C (20 mg) and stirred at room temperature for 20 h under $H_2$ atmosphere (balloon pressure). The reaction mixture was passed through a pad of celite and dried in vacuo to afford 2-((3,4-trans)-4-methylpyrrolidin-3-yl)-7-o-tolylimidazo[1,5-f][1,2,4]triazin-4(3H)-one (40 mg, crude) as an off-white solid. This was used in the next step without further purification; LC-MS: 93.36%; 310 ($M^+$+1); (column; X-bridge C-18, (50×3.0 mm, 3.5μ); RT 2.17 min. 5 mM $NH_4OAc$ in water: ACN; 0.8 ml/min); TLC: 5% MeOH/$CH_2Cl_2$ ($R_f$: 0.2).

To a stirred solution of 2-((3,4-trans)-4-methylpyrrolidin-3-yl)-7-o-tolylimidazo[1,5-f][1,2,4]triazin-4(3H)-one (80 mg, 0.2 mmol) in ACN (20 mL) were added $Cs_2CO_3$ (168 mg, 0.5 mmol) Iron triflate (26 mg, 0.05 mmol) and 2-(chloromethyl)pyrimidine (36 mg, 0.28 mmol) at room temperature under argon atmosphere. To the resulting reaction mixture was heated to 70° C. and stirred for 3 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one (45 mg, 57%) as an off-white solid.

$^1$H-NMR (DMSO-$d_6$, 400 MHz): δ 12.04 (bs, 1H), 8.78 (d, 2H), 7.87 (s, 1H), 7.52 (d, 1H), 7.39-7.31 (m, 4H), 3.92 (d, 1H), 3.76 (d, 1H), 3.04 (t, 1H), 2.96-2.92 (m, 2H), 2.71-2.68 (m, 2H), 2.26-2.25 (m, 1H), 2.24 (s, 3H), 1.08 (d, 3H); Mass (ESI): 402 [$M^+$+1]; LC-MS: 97.09%; 402 ($M^+$+1); (column; X-bridge C-18, (50×3.0 mm, 3.5μ); RT 2.90 min. ACN: 5 mM $NH_4OAc$; 0.8 ml/min); UPLC (purity): 98.51%; (column; Acquity BEH C-18, 50×2.1 mm, 1.7μ; RT 1.63 min. 0.025% TFA (Aq): ACN; 0.5o 0 ml/min.; Chiral HPLC: 100% $R_t$=18.82 min (Chiralpak IC, 250×4.6 mm, 5μ; mobile phase (A) 0.1% TEA in n-Hexane (B) Ethanol (A:B:50:50); flow Rate: 1.00 mL/min); Optical rotation [α]$_D^{20}$: +66.11° (c=0.25, DCM). TLC: 5% MeOH/$CH_2Cl_2$ ($R_f$: 0.5).

52. (+)-2-((3,4-trans)-1-benzyl-4-methylpyrrolidin-3-yl)-7-(5-fluoro-2-methylphenyl)imidazo[1,5-f][1,2,4]triazin-4(3H)-one and (−)-2-((3,4-trans)-1-benzyl-4-methylpyrrolidin-3-yl)-7-(5-fluoro-2-methylphenyl)imidazo[1,5-f][1,2,4]triazin-4(3H)-one

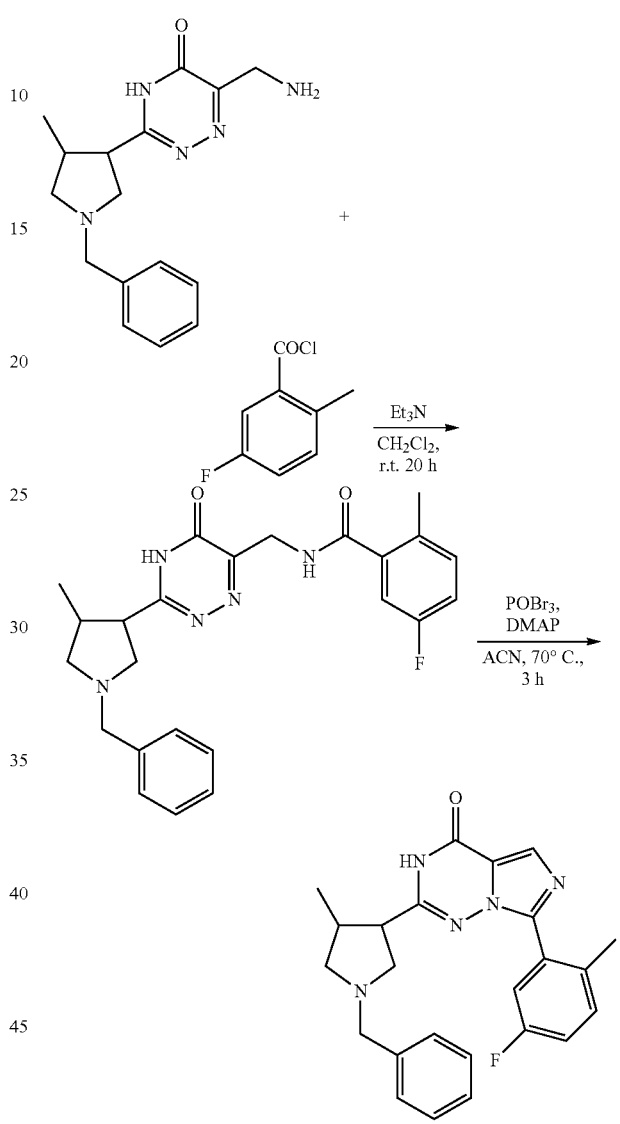

Synthesis of (+/−)-N-((3-((3,4-trans)-1-benzyl-4-methylpyrrolidin-3-yl)-5-oxo-4,5-dihydro-1,2,4-triazin-6-yl)methyl)-5-fluoro-2-methylbenzamide

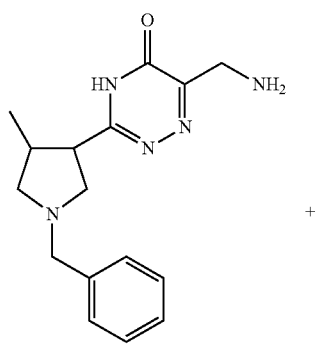

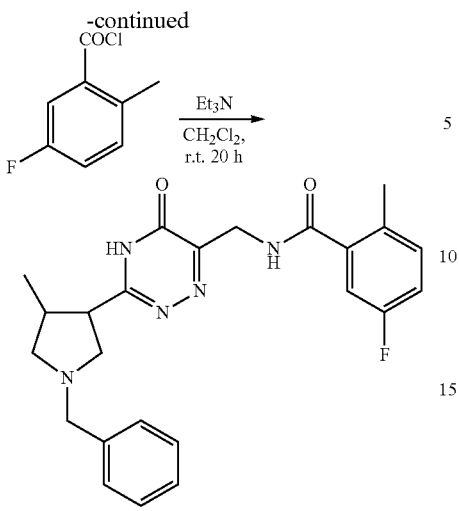

To a solution of (+/−)-6-(aminomethyl)-3-((3,4-trans)-1-benzyl-4-methylpyrrolidin-3-yl)-1,2,4-triazin-5(4H)-one (0.40 g, 1.34 mmol) and triethylamine (0.41 g, 4.00 mmol) in CH$_2$Cl$_2$ (20 mL) was added 5-fluoro-2-methylbenzoyl chloride (0.35 g, 2.00 mmol) drop-wise at RT. The resulting solution was stirred at room temperature for 20 h. After which time the reaction was quenched by addition of saturated NaHCO$_3$ aqueous solution (20 mL). The phases were separated, and the aqueous phase was extracted with CHCl$_3$ (2×10 mL). The combined organic phase was dried over MgSO$_4$. Concentration and purification by flash chromatography over silica gel column (0.1/1.5/98.4-0.8/12/87.2 NH$_4$OH/MeOH/CH$_2$Cl$_2$) provided (+/−)-N-((3-((3,4-trans)-1-benzyl-4-methylpyrrolidin-3-yl)-5-oxo-4,5-dihydro-1,2,4-triazin-6-yl)methyl)-5-fluoro-2-methylbenzamide (0.38 g, 65% yield) as a yellow solid.

$^1$H NMR (300 MHz, CDCl$_3$) δ 11.02 (br s, 1H), 7.64-7.56 (m, 1H), 7.46-7.26 (m, 5H), 7.18-7.08 (m, 2H), 6.94 (t, 1H, J=8.4 Hz), 4.69 (s, 2H), 4.04 (d, 1H, J=12.3 Hz), 3.92 (d, 1H, J=12.3 Hz), 3.48-3.10 (m, 4H), 2.80-2.50 (m, 2H), 2.38 (s, 3H), 1.00 (d, 3H, J=5.1 Hz); $^{13}$C NMR (75 MHz, CDCl$_3$) δ 168.6, 165.6, 163.7, 160.2 (d, J=243 Hz), 149.9, 137.2 (d, J=6 Hz), 134.2, 132.2 (d, J=7 Hz), 131.5 (d, J=3 Hz), 129.3, 128.5, 128.2, 116.4 (d, J=20 Hz), 113.9 (d, J=22 Hz), 60.4, 59.5, 57.1, 50.3, 40.0, 38.4, 19.1, 17.6.

Synthesis of (+/−)-2-((3,4-trans)-1-benzyl-4-methylpyrrolidin-3-yl)-7-(5-fluoro-2-methylphenyl)imidazo[1,5-f][1,2,4]triazin-4(3H)-one

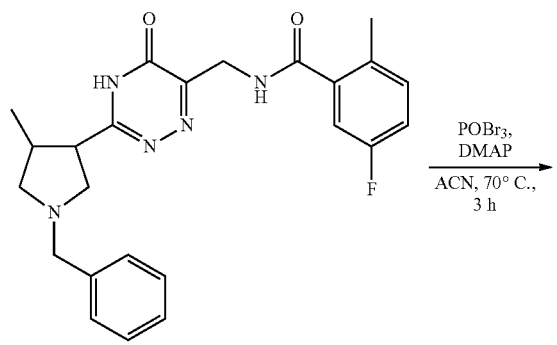

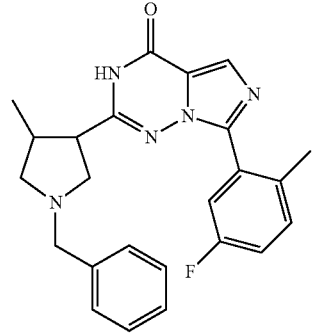

To a solution of (+/−)-N-((3-((3,4-trans)-1-benzyl-4-methylpyrrolidin-3-yl)-5-oxo-4,5-dihydro-1,2,4-triazin-6-yl)methyl)-5-fluoro-2-methylbenzamide (0.38 g, 0.87 mmol) and DMAP (11 mg, 0.09 mmol) in acetonitrile (15 mL) was added a solution of POBr$_3$ (0.75 g, 2.62 mmol) in acetonitrile (5 mL) at RT, and the resulting suspension was heated to 70° C. for 3 h. After the mixture was cooled to room temperature, it was poured into cold saturated NaHCO$_3$ solution (50 mL), and stirred vigorously for 0.5 h, then extracted with CH$_2$Cl$_2$ (3×20 mL). The organic extract was dried over MgSO$_4$ and concentrated under reduced pressure. The residue was purified by flash chromatography over silica gel (0.05/0.75/99.2-0.3/4.5/95.2 NH$_4$OH/MeOH/CH$_2$Cl$_2$) to furnish (+/−)-2-((3,4-trans)-1-benzyl-4-methylpyrrolidin-3-yl)-7-(5-fluoro-2-methylphenyl)imidazo[1,5-f][1,2,4]triazin-4(3H)-one (0.25 g, 68% yield) as white foam. Purity (HPLC): 95.3%; $^1$H NMR (300 MHz, CDCl$_3$/TMS) 67.98 (s, 1H), 7.50-7.24 (m, 7H), 7.10-7.02 (m, 1H), 3.81 (d, J=12.3 Hz, 1H), 3.56 (d, J=12.9 Hz, 1H), 3.38 (t, J=8.4 Hz, 1H), 2.97 (d, J=9.9 Hz, 1H), 2.78-2.68 (m, 1H), 2.60-2.37 (m, 2H), 2.31 (s, 3H), 1.92 (t, J=8.4 Hz, 1H), 1.16 (d, J=6.9 Hz, 3H); $^{13}$C NMR (75 MHz, CDCl$_3$/TMS) δ 160.12 (d, J=242 Hz), 154.31, 154.17, 143.17, 137.11, 133.98, 131.71 (d, J=8.4 Hz), 129.34 (d, J=8.4 Hz), 128.54, 128.25, 127.48, 119.16, 117.43 (d, J=22.7 Hz), 116.29 (d, J=20.3 Hz), 60.96, 59.18, 55.87, 47.70, 38.33, 20.05, 19.69.

Racemic (+/−)-2-((3,4-trans)-1-benzyl-4-methylpyrrolidin-3-yl)-7-(5-fluoro-2-methylphenyl)imidazo[1,5-f][1,2,4]triazin-4(3H)-one was purified by Chiralpak IA, 250×19 mm, 5 um (30 mg loading; 0.1% TEA in n-Hexane:IPA (95:05) as mobile phase) to obtain pure fraction 1((+)-2-((3,4-trans)-1-benzyl-4-methylpyrrolidin-3-yl)-7-(5-fluoro-2-methylphenyl)imidazo[1,5-f][1,2,4]triazin-4(3H)-one) (5 mg) and pure fraction 2 ((−)-2-((3,4-trans)-1-benzyl-4-methylpyrrolidin-3-yl)-7-(5-fluoro-2-methylphenyl)imidazo[1,5-f][1,2,4]triazin-4(3H)-one) (5 mg). Characterization details of both fractions are as follows:

(+)-2-((3,4-trans)-1-benzyl-4-methylpyrrolidin-3-yl)-7-(5-fluoro-2-methylphenyl)imidazo[1,5-f][1,2,4]triazin-4(3H)-one:

$^1$H-NMR (DMSO-d$_6$, 400 MHz): δ 7.92 (s, 1H), 7.47-7.39 (m, 2H), 7.30-7.21 (m, 6H), 3.57-3.52 (m, 2H), 2.92-2.88 (m, 1H), 2.81-2.75 (m, 3H), 2.54-2.51 (m, 1H), 2.34 (s, 3H), 2.24-2.21 (m, 1H), 1.08 (d, 3H); Mass: 418 (M$^+$+1); LC-MS: 99.31%; 418 (M$^+$+1); (column; X-bridge C-18, (50×3.0 mm, 3.5μ); RT 3.80 min. ACN: 5 mM NH$_4$OAc; 0.8 ml/min); UPLC (purity): 99.98%; (column; Acquity BEH C-18, 50×2.1 mm, 1.7μ; RT 1.82 min. 0.025% TFA (Aq): ACN; 0.50 ml/min.; Chiral HPLC: 100% R$_t$=19.85 min (Chiralpak IA, 250×4.6 mm, 5μ; mobile phase (A) 0.1%

TEA in n-Hexane (B) IPA (A:B:95:05); flow Rate: 1.00 mL/min); Optical rotation $[\alpha]_D^{20}$: +20.35° (c=0.125, DCM).

(−)-2-((3,4-trans)-1-benzyl-4-methylpyrrolidin-3-yl)-7-(5-fluoro-2-methylphenyl)imidazo[1,5-f][1,2,4]triazin-4(3H)-one:

$^1$H-NMR (DMSO-d$_6$, 400 MHz): δ 7.91 (s, 1H), 7.47-7.39 (m, 2H), 7.31-7.21 (m, 6H), 3.57-3.52 (m, 2H), 2.94-2.89 (m, 1H), 2.81-2.75 (m, 3H), 2.54-2.51 (m, 1H), 2.32 (s, 3H), 2.24-2.19 (m, 1H), 1.08 (d, 3H); Mass: 418 (M$^+$+1); LC-MS: 99.46%; 418 (M$^+$+1); (column; X-bridge C-18, (50×3.0 mm, 3.5μ); RT 3.80 min. ACN: 5 mM NH$_4$OAc; 0.8 ml/min); UPLC (purity): 99.97%; (column; Acquity BEH C-18, 50×2.1 mm, 1.7μ; RT 1.82 min. 0.025% TFA (Aq): ACN; 0.50 ml/min.; Chiral HPLC: 99.72% R$_f$=25.10 min (Chiralpak IA, 250×4.6 mm, 5μ; mobile phase (A) 0.1% TEA in n-Hexane (B) IPA (A:B:95:05); flow Rate: 1.00 mL/min); Optical rotation $[\alpha]_D^{20}$: −18.08° (c=0.25, DCM).

53. (+)-7-(5-fluoro-2-methylphenyl)-2-((3,4-trans)-4-methyl-1-(pyrimidin-2-ylmethyl)pyrrolidin-3-yl) imidazo[1,5-f][1,2,4]triazin-4(3H)-one

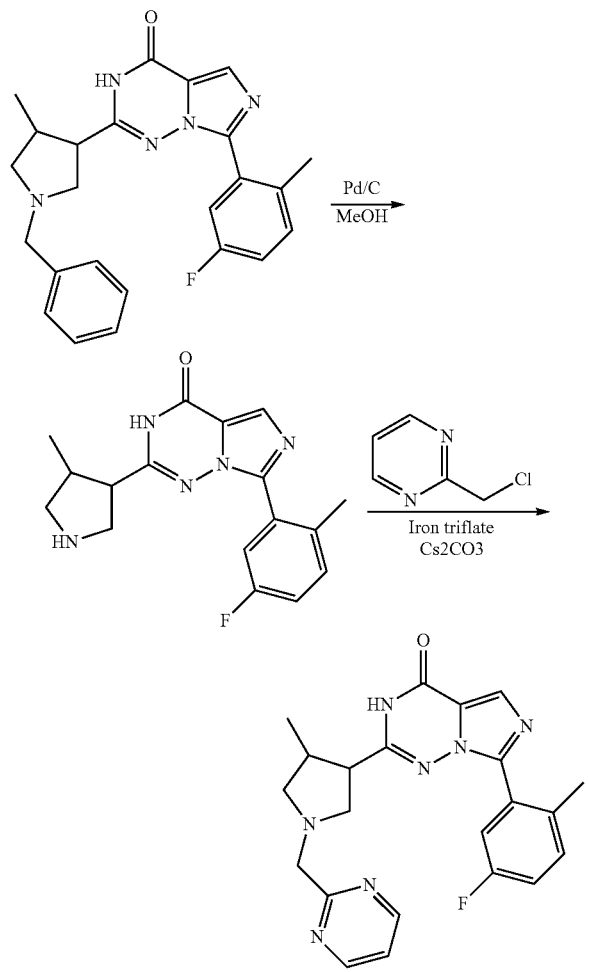

Synthesis of 7-(5-fluoro-2-methylphenyl)-2-((3,4-trans)-4-methylpyrrolidin-3-yl)imidazo[5,1-f][1,2,4]triazin-4(3H)-one To a stirred solution of (+)-2-((3,4-trans)-1-benzyl-4-methylpyrrolidin-3-yl)-7-(5-fluoro-2-methylphenyl)imidazo[1,5-f][1,2,4]triazin-4(3H)-one (80 mg, 0.19 mmol) in MeOH (15 mL) was added 10% Pd—C (20 mg) and stirred at room temperature for 16 h under H$_2$ atmosphere (balloon pressure). The reaction mixture was passed through a pad of celite and dried in vacuo to obtain the crude. The obtained crude material was triturated with pentane to afford 7-(5-fluoro-2-methylphenyl)-2-((3,4-trans)-4-methylpyrrolidin-3-yl)imidazo[1,5-f][1,2,4]triazin-4(3H)-one (60 mg, 95%) as an off-white solid.

$^1$H-NMR (DMSO-d$_6$, 400 MHz): δ 7.69 (s, 1H), 7.47 (d, 1H), 7.37-7.35 (m, 1H), 2.25-7.16 (m, 1H), 3.34-3.24 (m, 4H), 3.16-3.15 (m, 2H), 2.67-2.61 (m, 1H), 2.32 (s, 3H), 1.08 (d, 3H); Mass (ESI): 328 [M$^+$+1]; LC-MS: 95.10%; 328 (M$^+$+1); (column; X-bridge C-18, (50×3.0 mm, 3.5μ); RT 2.66 min. 5 mM NH$_4$OAc: ACN; 0.8 ml/min); TLC: 10% MeOH/CH$_2$Cl$_2$ (R$_f$; 0.2).

Synthesis of (+)-7-(5-fluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one To a stirred solution of 7-(5-fluoro-2-methylphenyl)-2-((3,4-trans)-4-methylpyrrolidin-3-yl)imidazo[1,5-f][1,2,4]triazin-4(3H)-one (60 mg, 0.18 mmol) in ACN (10 mL) were added Cs$_2$CO$_3$ (131 mg, 0.40 mmol) Iron triflate (18.45 mg, 0.036 mmol) and 2-(chloromethyl)pyrimidine (25.83 mg, 0.20 mmol) at room temperature under argon atmosphere. The resulting reaction mixture was heated to 70° C. and stirred for 3 h. The reaction mixture was diluted with water and extracted with EtOAc (2×30 mL). Combined organic layer was dried over sodium sulphate, filtered and concentrated in vacuo to obtain the crude product. The crude material was purified by silica gel column chromatography to afford (+)-7-(5-fluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one (45 mg, 58%) as an off-white solid. $^1$H-NMR (DMSO d$_6$, 400 MHz): δ 8.78 (d, 2H), 7.89 (s, 1H), 7.42-7.37 (m, 3H), 7.24-7.21 (m, 1H), 3.97 (d, 1H), 3.74 (d, 1H), 3.07 (t, 1H), 2.97-2.94 (m, 2H), 2.74-2.72 (m, 2H), 2.50-2.46 (m, 1H), 2.24 (s, 3H), 1.07 (d, 3H); Mass (ESI): 420 [M$^+$+1]; LC-MS: 97.43%; 420 (M$^+$+1); (column; X bridge C-18, (50×3.0 mm, 3.5μ); RT 3.17 min. ACN: 5 mM NH$_4$OAc; 0.8 ml/min); UPLC (purity): 97.76%; (column; Eclipse XDB C-18, 150×4.6 mm, 5.0μ; RT 9.85 min. 5 mM NH$_4$OAc: ACN; 1.0 ml/min.; Chiral HPLC: 100% R$_f$=13.97 min (Chiralpak IA, 250×4.6 mm, 5μ; mobile phase (A) 0.1% DEA in n-Hexane (B) Ethanol (A:B:80:20); flow Rate: 1.00 mL/min); Optical rotation $[\alpha]_D^{20}$: +87.96° (c=0.125, DCM); TLC: 10% MeOH/CH$_2$Cl$_2$ (R$_f$; 0.6).

54. (−)-7-(5-fluoro-2-methylphenyl)-2-((3,4-trans)-4-methyl-1-(pyrimidin-2-ylmethyl)pyrrolidin-3-yl) imidazo[1,5-f][1,2,4]triazin-4(3H)-one

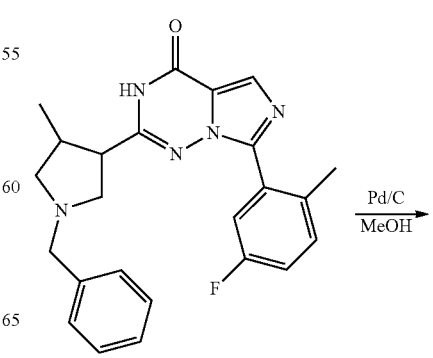

-continued

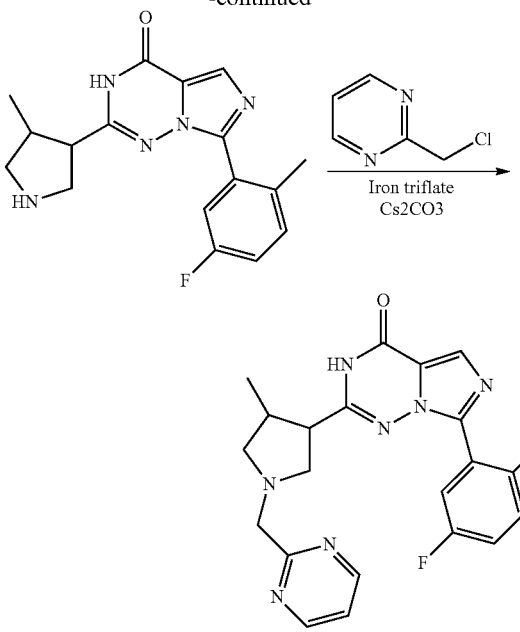

Synthesis of 7-(5-fluoro-2-methylphenyl)-2-((3,4-trans)-4-methylpyrrolidin-3-yl)imidazo[5,1-f][1,2,4]triazin-4(3H)-one To a stirred solution of (−)-2-((3,4-trans)-1-benzyl-4-methylpyrrolidin-3-yl)-7-(5-fluoro-2-methylphenyl)imidazo[1,5-f][1,2,4]triazin-4(3H)-one (80 mg, 0.19 mmol) in MeOH (10 mL) was added 10% Pd—C (20 mg) and stirred at room temperature for 16 h under $H_2$ atmosphere (balloon pressure). The reaction mixture was passed through a pad of celite and dried in vacuo to obtain the crude. The obtained crude material was triturated with pentane to afford 7-(5-fluoro-2-methylphenyl)-2-((3,4-trans)-4-methylpyrrolidin-3-yl)imidazo[5,1-f][1,2,4]triazin-4(3H)-one (59 mg, 94%) as an off-white solid. LC-MS: 94%; 328 (M$^+$+1); (column; X-bridge C-18, (50×3.0 mm, 3.5µ); RT 2.65 min. 5 mM $NH_4OAc$: ACN; 0.8 ml/min); TLC: 10% MeOH/$CH_2Cl_2$ ($R_f$: 0.3).

Synthesis of (−)-7-(5-fluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one To a stirred solution of 7-(5-fluoro-2-methylphenyl)-2-((3,4-trans)-4-methylpyrrolidin-3-yl)imidazo[5,1-f][1,2,4]triazin-4(3H)-one (60 mg, 0.18 mmol) in ACN (10 mL) were added Cs2CO3 (131 mg, 0.40 mmol), Iron triflate (18.45 mg, 0.036 mmol) and 2-(chloromethyl)pyrimidine (25.63 mg, 0.20 mmol) at room temperature under argon atmosphere. The resulting reaction mixture was heated to 70° C. and stirred for 3 h. The reaction mixture was diluted with water and extracted with EtOAc (2×30 mL). Combined organic layer was dried over sodium sulphate, filtered and concentrated in vacuo to obtain the crude product. The crude material was purified by silica gel column chromatography to afford (−)-7-(5-fluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one (42 mg, 55%) as an off-white solid.

$^1$H-NMR (DMSO d$_6$, 400 MHz): δ 8.76 (d, 2H), 7.89 (s, 1H), 7.45-7.37 (m, 3H), 7.28-7.27 (m, 1H), 3.96 (d, 1H), 3.78 (d, 1H), 3.06 (t, 1H), 2.97-2.96 (m, 2H), 2.74-2.72 (m, 1H), 2.51-2.48 (m, 1H), 2.38-2.29 (m, 1H), 2.27 (s, 3H), 1.07 (d, 3H); Mass (ESI): 420 [M$^+$+1]; LC-MS: 98.95%; 420 (M$^+$+1); (column; X bridge C-18, (50×3.0 mm, 3.5µ); RT 3.61 min. ACN: 5 mM $NH_4OAc$; 0.8 ml/min); UPLC (purity): 99.56%; (column; Eclipse XDB C-18, 150×4.6 mm, 5.0µ; RT 9.84 min. 5 mM $NH_4OAc$: ACN; 1.0 ml/min.; Chiral HPLC: 99.64% $R_t$=16.09 min (Chiralpak IA, 250×4.6 mm, 5µ; mobile phase (A) 0.1% DEA in n-Hexane (B) Ethanol (A:B:80:20); flow Rate: 1.00 mL/min); Optical rotation $[α]_D^{20}$: −92.76° (c=0.125, DCM); TLC: 10% MeOH/$CH_2Cl_2$ ($R_f$: 0.7).

55. (+)-2-((3,4-trans)-1-([1,2,4]triazolo[1,5-a]pyridin-2-ylmethyl)-4-methylpyrrolidin-3-yl)-7-(4,4-difluorocyclohexyl)imidazo[5,1-f][1,2,4]triazin-4(3H)-one

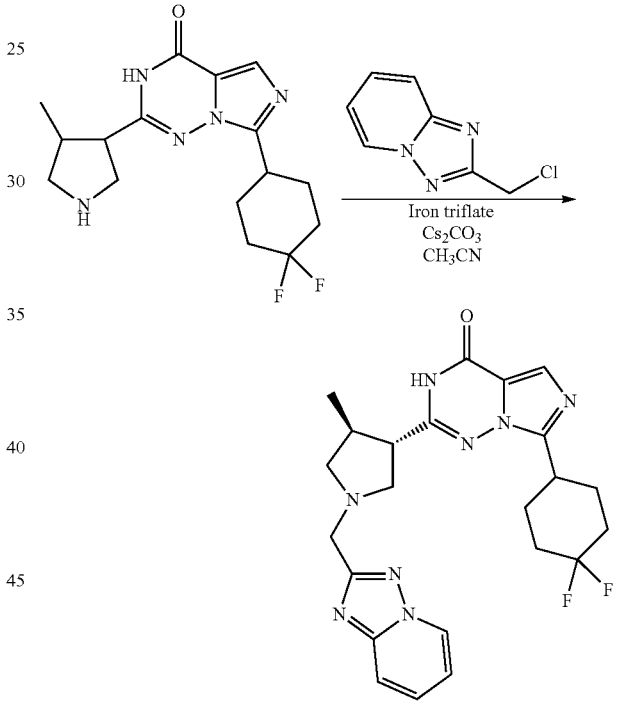

To a stirred solution of (+)-2-((3,4-trans)-1-benzyl-4-methylpyrrolidin-3-yl)-7-(4,4-difluorocyclohexyl)imidazo[5,1-f][1,2,4]triazin-4(3H)-one (60 mg, 0.17 mmol) in ACN (5 mL) was added 2-(chloromethyl)-[1,2,4]triazolo[1,5-a]pyridine (36 mg, 0.21 mmol), iron(III)trifluoromethanesulfonate (18 mg, 0.03 mmol) and $Cs_2CO_3$ (74 mg, 0.53 mmol) at room temperature and stirred for 3 h at 70° C. under argon atmosphere. The volatiles were evaporated under reduced pressure. The residue was diluted with water and extracted with $CH_2Cl_2$ (2×20 mL). Combined organic layer was dried over sodium sulphate, filtered and concentrated in vacuo to obtain the crude product. The crude material was purified by silica gel column chromatography to afford (+)-2-((3,4-trans)-1-([1,2,4]triazolo[1,5-a]pyridin-2-ylmethyl)-4-methylpyrrolidin-3-yl)-7-(4,4-difluorocyclohexyl)imidazo[5,1-f][1,2,4]triazin-4(3H)-one (25 mg, 30%) as an white solid.

$^1$H-NMR (DMSO d$_6$, 400 MHz): δ 8.85 (d, 1H), 7.78 (d, 1H), 7.65-7.60 (m, 2H), 7.14 (t, 1H), 3.91 (q, 2H), 3.31-3.23 (m, 1H), 3.12-3.02 (m, 2H), 2.95-2.90 (m, 1H), 2.81-2.72 (m, 1H), 2.70-2.62 (m, 1H), 2.56-2.48 (m, 1H), 2.15-1.81 (m, 8H), 1.12 (d, 3H); Mass (ESI): 469.3 [M$^+$+1]; LC-MS: 98.27%; 469.3 (M$^+$+1); (column; Eclipse XDB C-18, (150× 4.6 mm, 5.0μ); RT 1.57 min. 0.05% TFA: ACN; 0.8 ml/min); UPLC (purity): 99.16%; (column; Acquity UPLC BEH C-18, 50×2.1 mm, 1.7μ; RT 2.89 min. 0.025% TFA (Aq): ACN; 0.50 ml/min.; Chiral HPLC: 99.47%, R$_t$=10.56 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +91.07° (c=0.25%, DCM). TLC: 5% MeOH/DCM (R$_f$: 0.4).

56. (−)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile

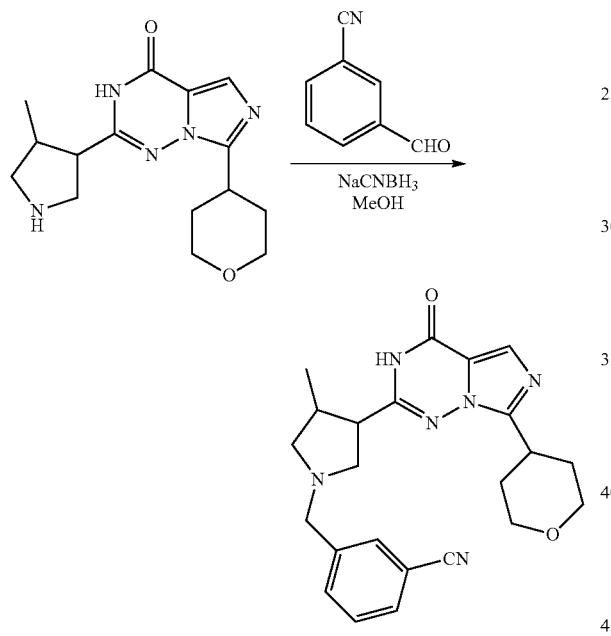

A mixture of (+)-2-((3,4-trans)-4-methylpyrrolidin-3-yl)-7-(tetrahydro-2H-pyran-4-yl)imidazo[5,1-f][1,2,4]triazin-4 (3H)-one (75 mg, 0.24 mmol) and 3-formylbenzonitrile (35.66 mg, 0.27 mmol) in MeOH (10 mL) at room temperature and stirred for 2 h under argon atmosphere. To this NaCNBH$_3$ (46.78 mg, 0.74 mmol) was added and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (−)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl) methyl)benzonitrile (55 mg, 53%) as an off-white solid. $^1$H-NMR (DMSO-d$_6$, 400 MHz): δ 11.78 (bs, 1H), 7.78-7.67 (m, 4H), 7.58-7.53 (m, 1H), 3.98-3.94 (m, 2H), 3.68 (s, 2H), 3.52-3.47 (m, 2H), 3.39-3.37 (m, 2H), 2.98-2.96 (m, 1H), 2.88-2.68 (m, 3H), 2.29-2.24 (m, 1H), 1.92-1.87 (m, 4H), 1.12 (d, 3H); Mass (ESI): 419.2 [M$^+$+1]; LC-MS: 96%; 419.2 (M$^+$+1); (column; X-bridge C-18, (50×3.0 mm, 3.5μ); RT 3.52 min. 5 mM NH$_4$OAc: ACN; 0.8 ml/min); UPLC (purity): 96%; (column; Acquity BEH C-18, 50×2.1 mm, 1.7μ; RT 1.42 min. 0.025% TFA (Aq): ACN:Water; 0.50 ml/min; Chiral HPLC: 98%, R$_t$=15.54 min (Chiralpak IC, 250×4.6 mm, 5μ; mobile phase (A) 0.1% DEA in n-Hexane (B) ethanol (A:B:50:50); flow Rate: 1.00 mL/min); Optical rotation [α]$_D^{20}$: −17.36° (c=0.5, DCM). TLC: 10% MeOH/DCM (R$_f$: 0.5).

57. (+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile

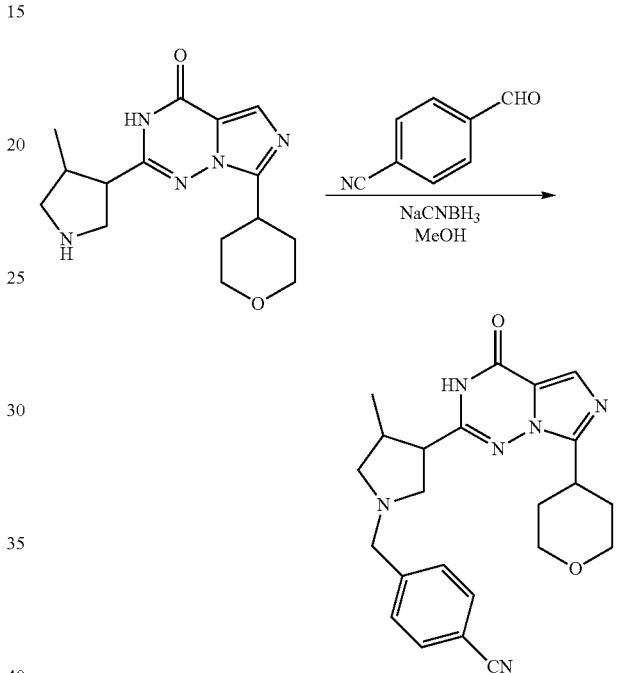

A mixture of (+)-2-((3,4-trans)-4-methylpyrrolidin-3-yl)-7-(tetrahydro-2H-pyran-4-yl)imidazo[5,1-f][1,2,4]triazin-4 (3H)-one (75 mg, 0.24 mmol) and 4-formylbenzonitrile (35.66 mg, 0.27 mmol) in MeOH (10 mL) at room temperature and stirred for 2 h under argon atmosphere. To this NaCNBH$_3$ (46.78 mg, 0.74 mmol) was added and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl) methyl)benzonitrile (50 mg, 48%) as an off-white solid. $^1$H-NMR (DMSO-d$_6$, 400 MHz): δ 7.84 (d, 2H), 7.65 (s, 1H), 7.56 (d, 2H), 3.96-3.94 (m, 2H), 3.78-3.74 (m, 2H), 3.52-3.47 (m, 2H), 3.39-3.76 (m, 1H), 3.01-2.98 (m, 1H), 3.86-3.78 (m, 3H), 2.67-2.64 (m, 1H), 2.32-2.27 (m, 1H), 1.87-1.84 (m, 4H), 1.07 (d, 3H); Mass (ESI): 419.4 [M$^+$+1]; LC-MS: 98%; 419.3 (M$^+$+1); (column; X-select C-18, (50× 3.0 mm, 3.5μ); RT 3.04 min. 5 mM NH$_4$OAc: ACN; 0.8 ml/min); UPLC (purity): 97%; (column; Acquity BEH C-18, 50×2.1 mm, 1.7μ; RT 1.42 min. 0.025% TFA (Aq): ACN: Water; 0.50 ml/min; Chiral HPLC: 98.53%, R$_t$=17.77 min (Chiralpak IC, 250×4.6 mm, 5µ; mobile phase (A) 0.1% DEA in n-Hexane (B) ethanol (A:B:50:50); flow Rate: 1.00 mL/min); Optical rotation $[\alpha]_D20$: +7.98° (c=0.5, DCM). TLC: 10% MeOH/DCM ($R_f$: 0.5).

58. (−)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]-triazin-4(3H)-one

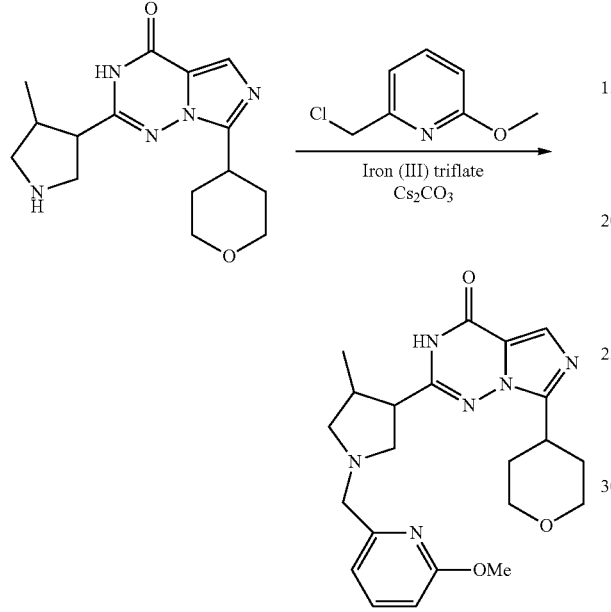

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (15 mL) were added 2-(chloromethyl)-6-methoxypyridine (42.74 mg, 0.27 mmol), Iron triflate (24.90 mg, 0.049 mmol) and $Cs_2CO_3$ (177 mg, 0.54 mmol) at room temperature under argon atmosphere. The resultant reaction mixture was heated to 65° C. and stirred for 3 h. The reaction mixture was diluted with water and extracted with EtOAc (3×15 mL). Combined organic layer was washed with brine, dried over sodium sulphate, filtered and concentrated in vacuo to obtain the crude product. The crude material was purified by silica gel column chromatography to afford (−)-2-((3,4-trans)-1-(6-methoxypyridin-2-yl)methyl)-4-methylpyrrolidin-3-yl)-7-(tetrahydro-2H-pyran-4-yl)imidazo[5,1-f][1,2,4]triazin-4 (3H)-one (25 mg, 18%) as an off-white solid. $^1$H-NMR (DM.SO-$d_6$, 400 MHz): δ 7.68 (t, 2H), 7.02 (d, 1H), 6.67 (d, 1H), 3.96 (s, 2H), 3.82 (s, 3H), 3.76-3.74 (m, 3H), 3.68-3.66 (m, 2H), 3.09-2.97 (m, 2H), 2.96-2.93 (m, 1H), 2.82-2.79 (m, 1H), 2.68-2.64 (m, 1H), 2.36-2.34 (m, 1H), 1.89-1.84 (m, 4H), 1.09 (d, 3H); Mass (ESI): 425.4 [M$^+$+1]; LC-MS: 99.84%; 425 (M$^+$+1); (column; X-bridge C-18, (50×3.0 mm, 3.5µ); RT 3.23 min. 5 mM NH$_4$OAc in water: ACN; 0.8 ml/min); UPLC (purity): 99.66%; (column; Acquity BEH C-18, 50×2.1 mm, 1.7µ; RT 1.48 min. 0.025% TFA (Aq): ACN:Water; 0.50 ml/min; Chiral HPLC: 99%, $R_t$=10.08 min (Chiralpak IC, 250×4.6 mm, 5µ; mobile phase (A) 0.1% DEA in n-Hexane (B) DCM:Methanol (80:20) (A:B:60:40); flow Rate: 1.00 mL/min); Optical rotation $[\alpha]_D^{20}$: −28.04° (C=0.5, DCM). TLC: 10% MeOH/DCM ($R_f$: 0.5).

59. (−)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one

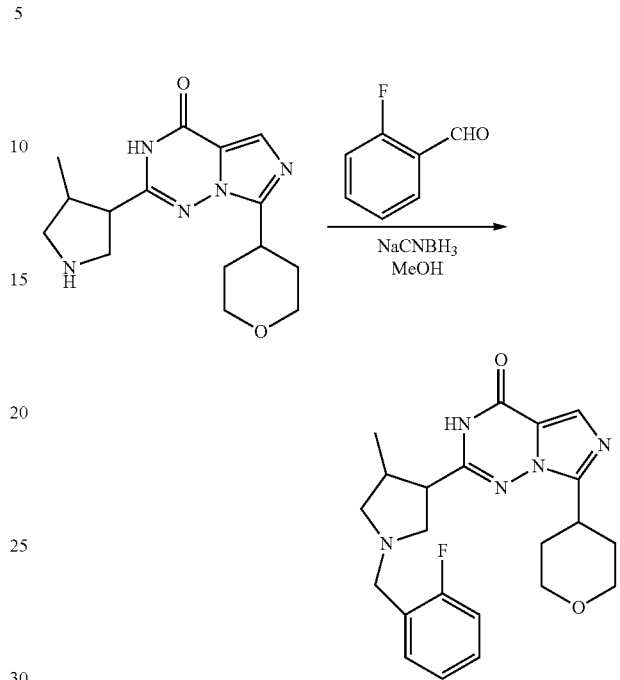

To a stirred solution of (+)-2-((3,4-trans)-4-methylpyrrolidin-3-yl)-7-(tetrahydro-2H-pyran-4-yl)imidazo[5,1-f][1,2, 4]triazin-4(3H)-one (75 mg, 0.24 mmol) in MeOH (5 mL) was added 2-fluorobenzaldehyde (33.7 mg, 0.27 mmol) at room temperature and stirred for 2 h under argon atmosphere. To the above solution, NaCNBH$_3$ (46.7 mg, 0.74 mmol) was added and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (−)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one (40 mg, 40%) as thick syrup. $^1$H-NMR (DMSO-$d_6$, 400 MHz): δ 11.68 (bs, 1H), 7.64 (s, 1H), 7.48-7.42 (m, 1H), 7.36-7.31 (m, 1H), 7.21-7.14 (m, 2H), 3.98-3.92 (m, 2H), 3.72 (s, 2H), 3.52-3.46 (m, 2H), 3.02-2.98 (m, 2H), 2.92-2.89 (m, 1H), 2.86-2.82 (m, 2H), 2.68-2.62 (m, 1H), 2.34-2.28 (m, 1H), 1.89-1.74 (m, 4H), 1.06 (d, 3H); Mass (ESI): 412 [M$^+$+1]; LC-MS: 99.69%; 412 (M$^+$+1); (column; X-bridge C-18, (50×3.0 mm, 3.5µ); RT 3.37 min. 5 mM NH$_4$OAc in water: ACN; 0.8 ml/min); UPLC (purity): 96%; (column; Acquity BEH C-18, 50×2.1 mm, 1.7µ; RT 1.44 min. 0.025% TFA (Aq): ACN:Water; 0.50 ml/min; Chiral HPLC: 100%, $R_t$=16.71 min (Chiralpak IB, 250×4.6 mm, 5µ; mobile phase (A) 0.1% DEA in n-Hexane (B) ethanol (A:B:92:8); flow Rate: 1.00 mL/min); Optical rotation $[\alpha]_D^{20}$: −12.90° (c=0.5, DCM). TLC: 10% MeOH/DCM ($R_f$: 0.6).

60. (−)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one

61. (−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one

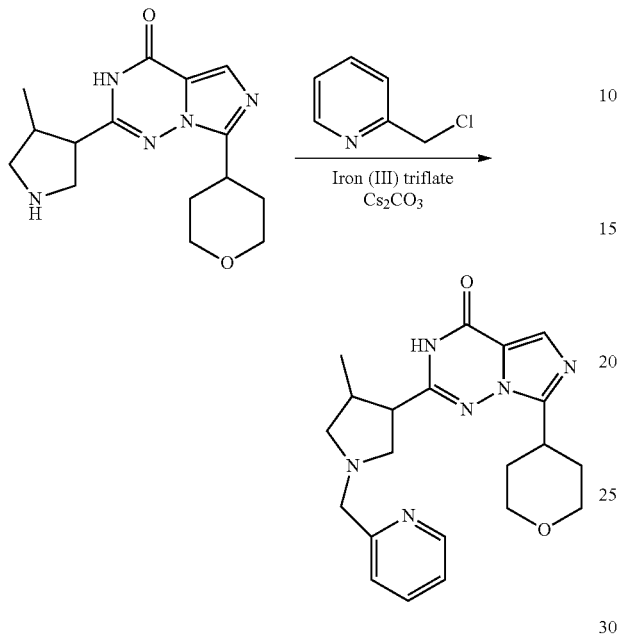

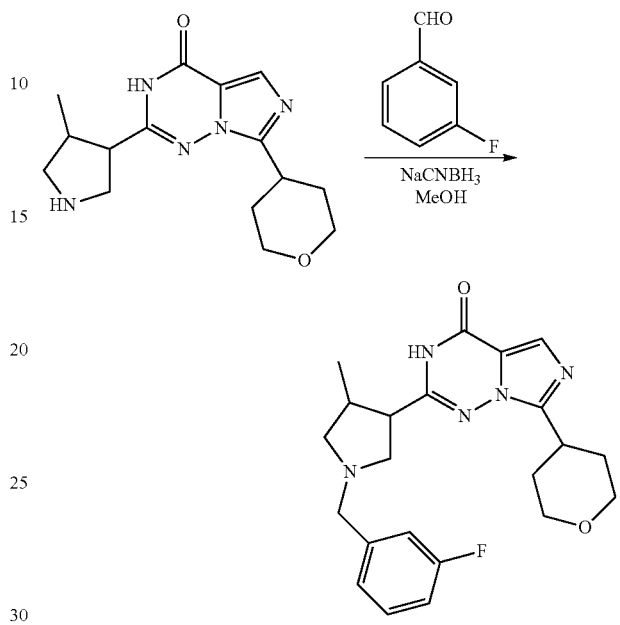

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added 2-(chloromethyl)pyridine (44 mg, 0.27 mmol), iron triflate (24.9 mg, 0.049 mmol) and Cs$_2$CO$_3$ (161.3 mg, 0.49 mmol) at room temperature under argon atmosphere. The resultant reaction mixture was heated to 65° C. and stirred for 3 h. The reaction mixture was diluted with water and extracted with EtOAc (3×15 mL). Combined organic layer was washed with brine, dried over sodium sulphate, filtered and concentrated in vacuo to obtain the crude product. The crude material was purified by silica gel column chromatography to afford (−)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one (45 mg, 46%) as thick syrup. $^1$H-NMR (DMSO-d$_6$, 400 MHz): δ 11.54 (bs, 1H), 7.82 (d, 1H), 7.69-7.62 (m, 3H), 7.48-7.41 (m, 1H), 3.96-3.92 (m, 2H), 3.82 (s, 2H), 3.54-3.48 (m, 2H), 3.37-3.35 (m, 1H), 3.06-3.04 (m, 1H), 2.92-2.84 (m, 3H), 2.67-2.61 (m, 1H), 2.37-2.31 (m, 1H), 1.89-1.81 (m, 4H), 1.07 (d, 3H); Mass (ESI): 395.4 [M$^+$+1]; LC-MS: 96.75%; 395 (M$^+$+1); (column; X-bridge C-18, (50×3.0 mm, 3.5μ); RT 2.67 min. 5 mM NH$_4$OAc in water: ACN; 0.8 ml/min); UPLC (purity): 99.62%; (column; Acquity BEH C-18, 50×2.1 mm, 1.7μ; RT 1.28 min. 0.025% TFA (Aq): ACN:Water; 0.50 ml/min; Chiral HPLC: 100%, R$_t$=20.63 min (Chiralpak IC, 250×4.6 mm, 5μ; mobile phase (A) 0.1% DEA in n-Hexane (B) ethanol (A:B:50:50); flow Rate: 1.00 mL/min); Optical rotation [α]$_D^{20}$: −68.27° (C=0.5, DCM). TLC: 10% MeOH/DCM (R$_f$: 0.5).

To stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (5 mL) was added 3-fluorobenzaldehyde (33.7 mg, 0.27 mmol) at room temperature and stirred for 2 h under argon atmosphere. To this NaCNBH$_3$ (46.7 mg, 0.74 mmol) was added and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (−)-2-((3,4-trans)-1-(3-fluorobenzyl)-4-methylpyrrolidin-3-yl)-7-(tetrahydro-2H-pyran-4-yl)imidazo[5,1-f][1,2,4]triazin-4(3H)-one (60 mg, 59%) as an off-white semi solid. $^1$H-NMR (DMSO-d$_6$, 400 MHz): δ 7.68 (s, 1H), 7.38-7.34 (m, 1H), 7.18-7.14 (m, 3H), 3.98-3.94 (m, 2H), 3.68 (s, 2H), 3.52-3.48 (m, 2H), 3.42-3.39 (m, 1H), 2.98-2.78 (m, 4H), 2.69-2.64 (m, 1H), 2.28-2.24 (m, 1H), 1.89-1.82 (m, 4H), 1.09 (d, 3H); Mass (ESI): 412.4 [M$^+$+1]; LC-MS: 99.38%; 412.5 (M$^+$+1); (column; X-bridge C-18, (50×3.0 mm, 3.5μ); RT 3.21 min. 5 mM NH$_4$OAc in water: ACN; 0.8 ml/min); UPLC (purity): 93%; (column; Eclipse XDB C-18, 150×4.6 mm, 5μ; RT 9.96 min. 5 mM NH$_4$OAc: ACN:Water; 1.0 ml/min; Chiral HPLC: 95.70%, R$_t$=8.49 min (Chiralpak IC, 250×4.6 mm, 5μ; mobile phase (A) 0.1% DEA in n-Hexane (B) ethanol (A:B:50:50); flow Rate: 1.00 mL/min); Optical rotation [α]$_D^{20}$: −14.30° (c=0.5, DCM). TLC: 10% MeOH/DCM (R$_f$: 0.5).

537

62. (−)-2-((3,4-trans)-1-(4-fluorobenzyl)-4-methyl-pyrrolidin-3-yl))-7-(tetrahydro-2H-pyran-4-yl)imidazo[5,1-f][1,2,4]triazin-4(3H)-one

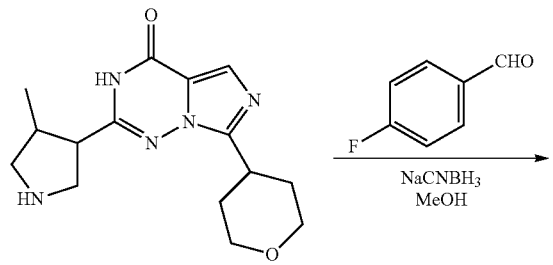

A mixture of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) and 4-fluorobenzaldehyde (33.7 mg, 0.27 mmol) in MeOH (5 mL) at room temperature under argon atmosphere. After being stirred for 2 h; NaCNBH$_3$ (46.7 mg, 0.74 mmol) was added to the reaction mixture and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (−)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one (65 mg, 64%) as white solid. $^1$H-NMR (DMSO-d$_6$, 400 MHz): δ 7.64 (s, 1H), 7.38-7.32 (m, 2H), 7.18-7.13 (m, 2H), 3.98-3.94 (m, 2H), 3.67-3.64 (m, 2H), 3.48 (s, 2H), 3.42-3.37 (m, 1H), 2.97-2.94 (m, 1H), 2.90-2.84 (m, 3H), 2.69-2.64 (m, 1H), 2.24-2.21 (m, 1H), 1.87-1.82 (m, 4H), 1.09 (d, 3H); LC-MS: 99%; 412.5 (M$^+$+1); (column; X-select C-18, (50×3.0 mm, 3.5μ); RT 3.16 min. 5 mM NH$_4$OAc in water: ACN; 0.8 ml/min); UPLC (purity): 94%; (column; Eclipse XDB C-18, 150×4.6 mm, 5μ; RT 9.84 min. 5 mM NH4OAc: ACN:Water; 1 ml/min; Chiral HPLC: 95%, R$_t$=8.46 min (Chiralpak IC, 250×4.6 mm, 5μ; mobile phase (A) 0.1% DEA in n-Hexane (B) ethanol (A:B:50:50); flow Rate: 1.00 mL/min); Optical rotation [α]$_D^{20}$: −13.84° (c=0.5, DCM). TLC: 10% MeOH/DCM (R$_f$: 0.5).

538

63. (−)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile

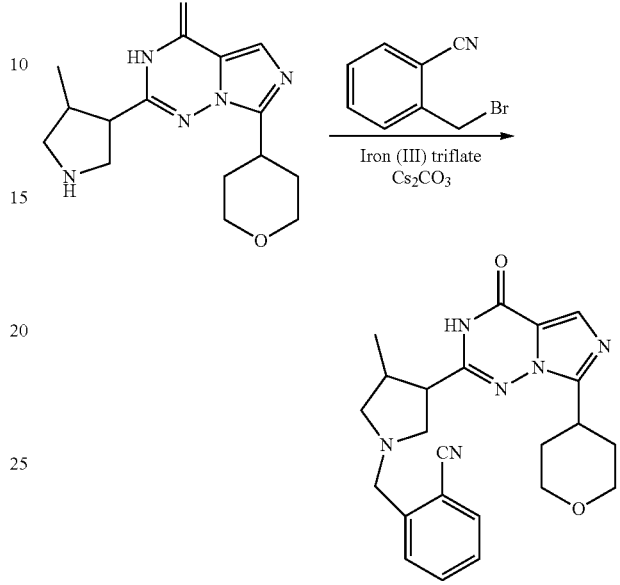

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added 2-(bromomethyl)benzonitrile (53.3 mg, 0.27 mmol), iron triflate (24.9 mg, 0.049 mmol) and Cs$_2$CO$_3$ (161.3 mg, 0.49 mmol) at room temperature under argon atmosphere. The resultant reaction mixture was heated to 65° C. and stirred for 3 h. The reaction mixture was diluted with water and extracted with EtOAc (3×15 mL). Combined organic layer was dried over sodium sulphate, filtered and concentrated in vacuo to obtain the crude product. The crude material was purified by silica gel column chromatography to afford (−)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile (40 mg, 39%) as an off-white semi solid. $^1$H-NMR (DMSO-d$_6$, 400 MHz): δ 11.58 (bs, 1H), 7.82 (d, 1H), 7.69-7.62 (m, 3H), 7.48-7.41 (m, 1H), 3.96-3.92 (m, 2H), 3.82 (s, 2H), 3.54-3.48 (m, 2H), 3.37-3.35 (m, 1H), 3.06-3.04 (m, 1H), 2.92-2.84 (m, 3H), 2.67-2.61 (m, 1H), 2.37-2.31 (m, 1H), 1.89-1.81 (m, 4H), 1.07 (d, 3H); Mass (ESI): 419 [M$^+$+1]; LC-MS: 97%; 419 (M$^+$+1); (column; X-bridge C-18, (50×3.0 mm, 3.5μ); RT 3.50 min. 5 mM NH$_4$OAc in water: ACN; 0.8 ml/min); UPLC (purity): 98%; (column; Eclipse XDB C-18, 150×4.6 mm, 5μ; RT 9.49 min. 5 mM NH$_4$OAc: ACN:Water; 1 ml/min; Chiral HPLC: 100%, R$_t$=10.04 min (Chiralpak IB, 250×4.6 mm, 5μ; mobile phase (A) 0.1% DEA in n-Hexane (B) ethanol (A:B:80:20); flow Rate: 1.00 mL/min); Optical rotation [α]$_D^{24}$: −13.24° (c=0.5, DCM). TLC: 10% MeOH/DCM (R$_f$: 0.5).

64. (+)-2-((3,4-trans)-4-methyl-1-((R)-1-phenyl-ethyl)pyrrolidin-3-yl)-7-(tetrahydro-2H-pyran-4-yl)imidazo[5,1-f][1,2,4]triazin-4(3H)-one 65. (−)-2-((3,4-trans)-4-methyl-1-((S)-1-phenyl-ethyl)pyrrolidin-3-yl)-7-(tetrahydro-2H-pyran-4-yl)imidazo[5,1-f][1,2,4]triazin-4(3H)-one

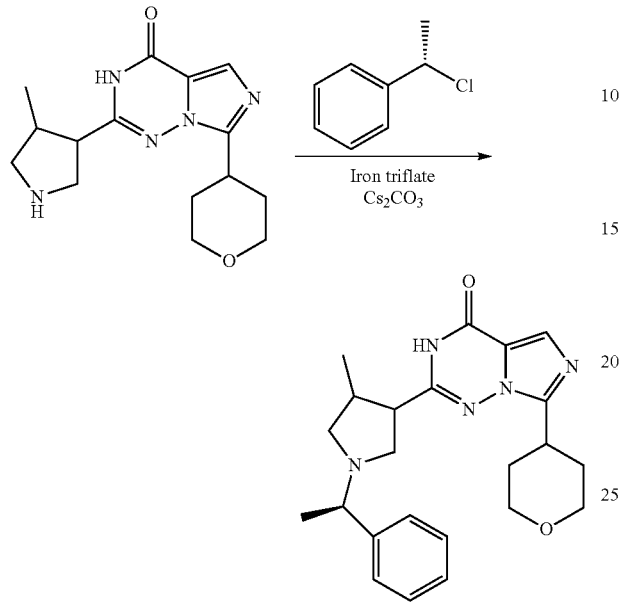

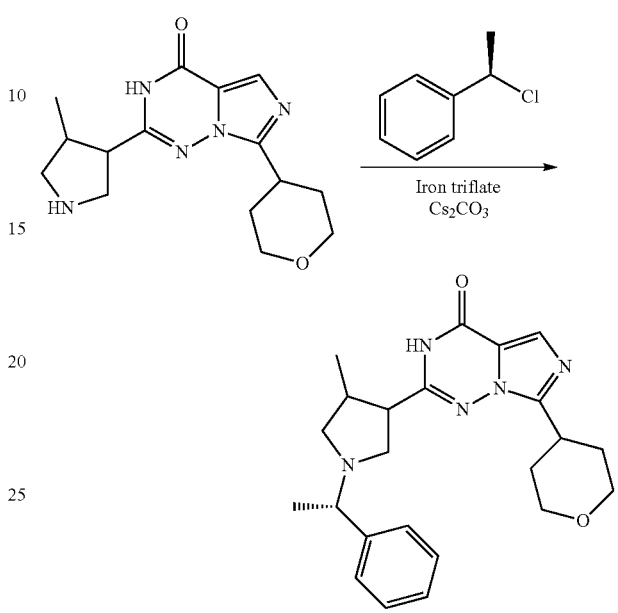

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added (S)-(1-chloroethyl)benzene (38 mg, 0.27 mmol), iron triflate (24.8 mg, 0.049 mmol) and $Cs_2CO_3$ (161 mg, 0.49 mmol) at room temperature under inert atmosphere. The resultant reaction mixture was heated to 65° C. and stirred for 3 h. The reaction mixture was diluted with water and extracted with EtOAc (3×15 mL). Combined organic layer was dried over sodium sulphate, filtered and concentrated in vacuo to obtain the crude product. The crude material was purified by silica gel column chromatography and then further purified by preparative HPLC to afford (+)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one (20 mg, 20%) as an off-white solid. $^1$H-NMR (DMSO-$d_6$, 400 MHz): δ 7.65-7.63 (m, 1H), 7.34-7.29 (m, 5H), 3.97-3.92 (m, 2H), 3.54-3.48 (m, 2H), 3.41-3.37 (m, 2H), 2.85-2.81 (m, 1H), 2.31-2.27 (m, 3H), 2.64-2.61 (m, 1H), 2.35-2.31 (m, 1H), 1.87-1.82 (m, 4H), 1.29 (d, 3H), 1.09 (d, 3H); Mass (ESI): 408 [M$^+$+1]; LC-MS: 97.94%; 408 (M$^+$+1); (column; X-bridge C-18, (50×3.0 mm, 3.5μ); RT 3.26 min. 5 mM $NH_4OAc$ in water: ACN; 0.8 ml/min); UPLC (purity): 98%; (column; Acquity BEH C-18, 50×2.1 mm, 1.7μ; RT=1.49 min. 0.025% TFA(Aq): ACN: Water; 0.50 ml/min; Chiral HPLC: 100%, $R_t$=18.13 min (Chiralpak IA, 250×4.6 mm, 5μ; mobile phase (A) 0.1% DEA in n-Hexane (B) ethanol (A:B:90:10); flow Rate: 1.00 mL/min); Optical rotation $[α]_D^{24}$: +61.04° (c=0.25, DCM). TLC: 10% MeOH/DCM ($R_f$: 0.5).

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (90 mg, 0.29 mmol) in ACN (10 mL) were added (R)-(1-chloroethyl)benzene (54 mg, 0.38 mmol), iron triflate (29.8 mg, 0.059 mmol) and $Cs_2CO_3$ (193 mg, 0.59 mmol) at room temperature under inert atmosphere. The resultant reaction mixture was heated to 65° C. and stirred for 3 h. The reaction mixture was diluted with water and extracted with EtOAc (3×15 mL). Combined organic layer was dried over sodium sulphate, filtered and concentrated in vacuo to obtain the crude product. The crude material was purified by silica gel column chromatography and then further purified by preparative HPLC to afford (−)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one (40 mg, 59.7%) as an off-white solid. $^1$H-NMR (DMSO-$d_6$, 400 MHz): δ 7.64 (s, 1H), 4.39-4.29 (m, 5H), 4.01-3.95 (m, 2H), 3.56-3.52 (m, 3H), 2.97-2.94 (m, 3H), 2.79-2.72 (m, 1H), 2.69-2.61 (m, 2H), 2.14-2.12 (m, 1H), 1.89-1.78 (m, 4H), 1.33 (d, 3H), 1.09 (d, 3H); Mass (ESI): 408 [M$^+$+1]; LC-MS: 98.78%; 408 (M$^+$+1); (column; X-bridge C-18, (50×3.0 mm, 3.5μ); RT 3.26 min. 5 mM $NH_4OAc$ in water: ACN; 0.8 ml/min); UPLC (purity): 97.79%; (column; Acquity BEH C-18, 50×2.1 mm, 1.7μ; RT 1.48 min. 0.025% TFA(Aq): ACN:Water; 0.50 ml/min; Chiral HPLC: 100%, $R_t$=13.97 min (Chiralpak IA, 250×4.6 mm, 5μ; mobile phase (A) 0.1% DEA in n-Hexane (B) ethanol (A:B:90:10); flow Rate: 1.00 mL/min); Optical rotation $[α]_D^{24}$: −103.45° (C=0.25, DCM). TLC: 10% MeOH/DCM ($R_f$: 0.5).

66. (+)-2-((3,4-trans)-4-methyl-1-(4-(trifluoromethyl)benzyl)pyrrolidin-3-yl)-7-(tetrahydro-2H-pyran-4-yl)imidazo[5,1-f][1,2,4]triazin-4(3H)-one

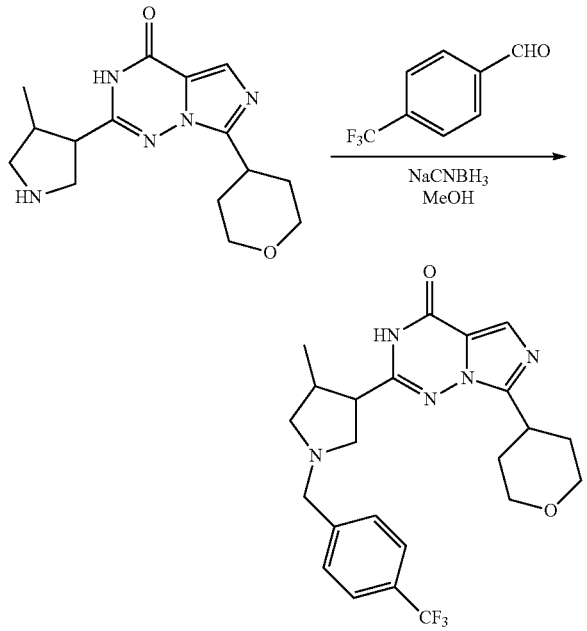

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (7 mL) was added 4-(trifluoromethyl)benzaldehyde (47 mg, 0.27 mmol) at room temperature and stirred for 2 h under argon atmosphere. To the resulting solution was added NaCNBH$_3$ (45 mg, 0.72 mmol) and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-2-((3,4-trans)-4-methyl-1-(4-(trifluoromethyl)benzyl)pyrrolidin-3-yl)-7-(tetrahydro-2H-pyran-4-yl)imidazo[5,1-f][1,2,4]triazin-4(3H)-one (40 mg, 35%) as an off-white solid. $^1$H-NMR (DMSO-d$_6$, 400 MHz): δ 11.52 (bs, 1H), 7.69-7.65 (m, 3H), 7.58-7.52 (m, 2H), 3.96-3.92 (m, 2H), 3.74-3.68 (m, 2H), 3.54-3.49 (m, 2H), 3.42-3.38 (m, 2H), 2.98-2.96 (m, 1H), 2.79-2.74 (m, 2H), 2.71-2.68 (m, 1H), 2.32-2.29 (m, 1H), 1.89-1.82 (m, 4H), 1.12 (d, 3H); Mass (ESI): 462 [M$^+$+1]; LC-MS: 99.30%; 462 (M$^+$+1); (column; X-bridge C-18, (50×3.0 mm, 3.5μ); RT 3.62 min. 5 mM NH$_4$OAc in water: ACN; 0.8 ml/min); UPLC (purity): 95.65%; (column; Eclipse XDB C-18, 150×4.6 mm, 5μ; RT 10.54 min. 5 mM NH$_4$OAc: ACN:Water; 1.0 ml/min; Chiral HPLC: 98.29%, R$_t$=17.14 min (Chiralpak IA, 250×4.6 mm, 5μ; mobile phase (A) 0.1% TEA in n-Hexane (B) IPA (A:B:90:10); flow Rate: 1.00 mL/min); Optical rotation [α]$_D^{20}$: +9.09° (c=0.5, DCM). TLC: 10% MeOH/DCM (R$_f$: 0.5).

67. (+)-2-((3,4-trans)-4-methyl-1-(3-(trifluoromethyl)benzyl)pyrrolidin-3-yl)-7-(tetrahydro-2H-pyran-4-yl)imidazo[5,1-f][1,2,4]triazin-4(3H)-one

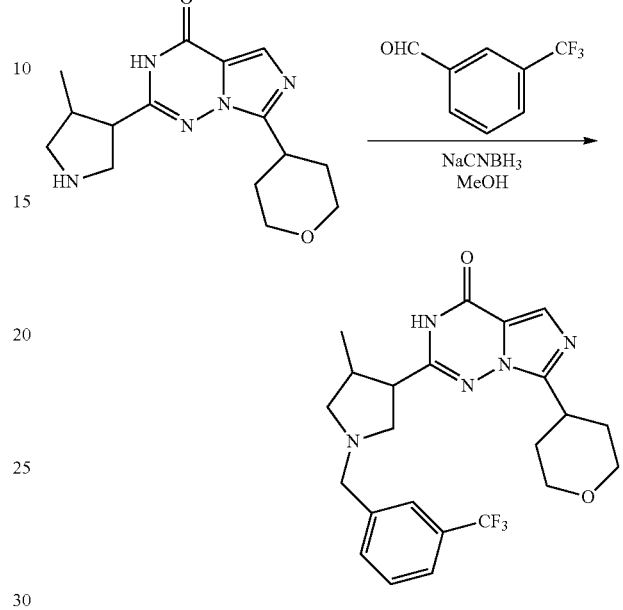

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (5 mL) was added 3-(trifluoromethyl)benzaldehyde (47.3 mg, 0.27 mmol) at room temperature and stirred for 2 h under argon atmosphere. To the resulting solution was added NaCNBH$_3$ (46.7 mg, 0.74 mmol) and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by preparative HPLC to afford (+)-2-((3,4-trans)-4-methyl-1-(3-(trifluoromethyl)benzyl)pyrrolidin-3-yl)-7-(tetrahydro-2H-pyran-4-yl)imidazo[5,1-f][1,2,4]triazin-4(3H)-one (45 mg, 42%) as an off-white solid. $^1$H-NMR (DMSO-d$_6$, 400 MHz): δ 7.69-7.59 (m, 5H), 3.96-3.92 (m, 2H), 3.74-3.71 (m, 2H), 3.52-3.47 (m, 3H), 2.98-2.96 (m, 1H), 2.89-2.86 (m, 3H), 2.69-2.62 (m, 1H), 2.34-2.26 (m, 1H), 1.87-1.74 (m, 4H), 1.09 (d, 3H); Mass (ESI): 462 [M$^+$+1]; LC-MS: 95.90%; 462 (M$^+$+1); (column; X-bridge C-18, (50×3.0 mm, 3.5μ); RT 3.61 min. 5 mM NH$_4$OAc in water: ACN; 0.8 ml/min); UPLC (purity): 95.65%; (column; Eclipse XDB C-18, 150×4.6 mm, 5μ; RT 10.64 min. 5 mM Aq.NH$_4$OAc: ACN:Water; 1.0 ml/min; Chiral HPLC: 100%, R$_t$=14.56 min (Chiralpak IA, 250×4.6 mm, 5μ; mobile phase (A) 0.1% TEA in n-Hexane (B) IPA (A:B:90:10); flow Rate: 1.00 mL/min); Optical rotation [α]$_D^{20}$: +11.00° (c=0.5, DCM). TLC: 10% MeOH/DCM (R$_f$: 0.5).

543

68. (+)-2-((3,4-trans)-1-(3-chlorobenzyl)-4-methyl-pyrrolidin-3-yl)-7-(tetrahydro-2H-pyran-4-yl)imidazo[5,1-f][1,2,4]triazin-4(3H)-one

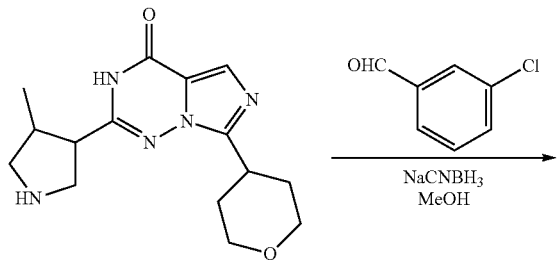

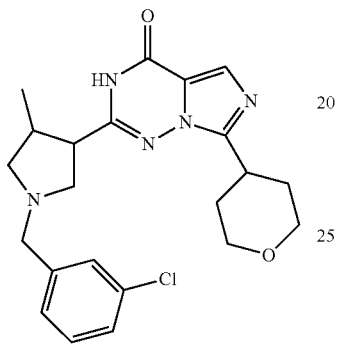

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (5 mL) was added 3-chlorobenzaldehyde (38 mg, 0.27 mmol) at room temperature and stirred for 2 h under argon atmosphere. To this NaCNBH$_3$ (46.7 mg, 0.74 mmol) was added and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography and then further purified by preparative HPLC to afford (+)-2-((3,4-trans)-1-(3-chlorobenzyl)-4-methylpyrrolidin-3-yl)-7-(tetrahydro-2H-pyran-4-yl)imidazo[5,1-f][1,2,4]triazin-4(3H)-one (45 mg, 42%) as thick syrup. $^1$H-NMR (DMSO-d$_6$, 400 MHz): δ 7.68 (s, 1H), 7.39-7.29 (m, 4H), 3.96-3.94 (m, 2H), 3.68-3.65 (m, 2H), 3.52-3.48 (m, 2H), 3.46-3.44 (m, 1H), 2.98-2.96 (m, 1H), 2.87-2.85 (m, 1H), 2.79-2.74 (m, 2H), 2.68-2.65 (m, 1H), 2.31-2.24 (m, 1H), 1.89-1.82 (m, 4H), 1.09 (d, 3H); Mass (ESI): 428 [M$^+$+1]; LC-MS: 96%; 428 (M$^+$+1); (column: X-bridge C-18, (50×3.0 mm, 3.5μ); RT 3.51 min. 5 mM NH$_4$OAc in water: ACN; 0.8 ml/min); UPLC (purity): 98.25%; (column; Eclipse XDB C-18, 150×4.6 mm, 5μ; RT 10.48 min. 5 mM NH$_4$OAc (Aq): ACN:Water; 1.0 ml/min; Chiral HPLC: 100%, R$_t$=17.67 min (Chiralpak IA, 250×4.6 mm, 5μ; mobile phase (A) 0.1% TEA in n-Hexane (B) IPA (A:B:90:10); flow Rate: 1.00 mL/min); Optical rotation [α]$_D^{20}$: +18.21° (c=0.5, DCM). TLC: 10% MeOH/DCM (R$_f$: 0.6).

544

69. (+)-2-((3,4-trans)-1-(2,4-difluorobenzyl)-4-methylpyrrolidin-3-yl)-7-(tetrahydro-2H-pyran-4-yl)imidazo[5,1-f][1,2,4]triazin-4(3H)-one

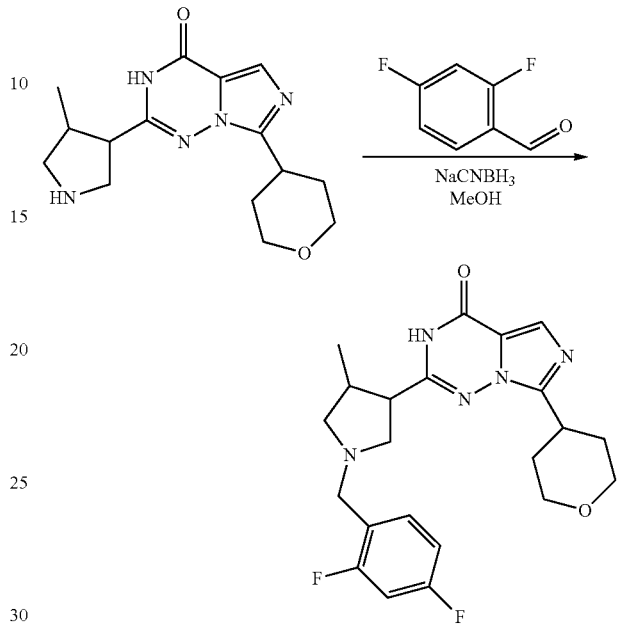

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (5 mL) was added 2,4-difluorobenzaldehyde (38 mg, 0.27 mmol) at room temperature and stirred for 2 h under argon atmosphere. To this NaCNBH$_3$ (45 mg, 0.72 mmol) was added and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-2-((3,4-trans)-1-(2,4-difluorobenzyl)-4-methylpyrrolidin-3-yl)-7-(tetrahydro-2H-pyran-4-yl)imidazo[5,1-f][1,2,4]triazin-4(3H)-one (35 mg, 33%) as an off-white solid. $^1$H-NMR (DMSO-d$_6$, 400 MHz): δ 11.52 (bs, 1H), 7.69 (s, 1H), 7.49-7.42 (m, 1H), 7.24 (t, 1H), 7.06 (t, 1H), 3.98-3.94 (m, 2H), 3.68-3.67 (m, 1H), 3.49-3.42 (m, 2H), 3.38-3.37 (m, 1H), 2.98-2.94 (m, 1H), 2.87-2.84 (m, 1H), 2.77-2.75 (m, 1H), 2.69-2.64 (m, 1H), 2.63-2.62 (m, 1H), 2.56-2.55 (m, 1H), 2.31-2.26 (m, 1H), 1.88-1.81 (m, 4H), 1.09 (d, 3H); Mass (ESI): 430.4 [M$^+$+1]; LC-MS: 95.65%; 430 (M$^+$+1); (column; X-select C-18, (50×3.0 mm, 3.5μ); RT 3.30 min. 5 mM NH$_4$OAc: ACN; 0.8 ml/min); UPLC (purity): 97%; (column; Acquity BEH C-18, 50×2.1 mm, 1.7μ; RT 1.47 min. 0.025% TFA (Aq): ACN:Water; 0.50 ml/min; Chiral HPLC: 100%, R$_t$=18.63 min (Chiralpak IA, 250×4.6 mm, 5μ; mobile phase (A) 0.1% TEA in n-Hexane (B) IPA (A:B:90:10); flow Rate: 1.00 mL/min); Optical rotation [α]$_D^{20}$: +10.82° (c=0.5, DCM). TLC: 10% MeOH/DCM (R$_f$: 0.5).

545

70. (+)-2-((3,4-trans)-4-methyl-1-(2-(trifluoromethyl)benzyl)pyrrolidin-3-yl)-7-(tetrahydro-2H-pyran-4-yl)imidazo[5,1-f][1,2,4]triazin-4(3H)-one

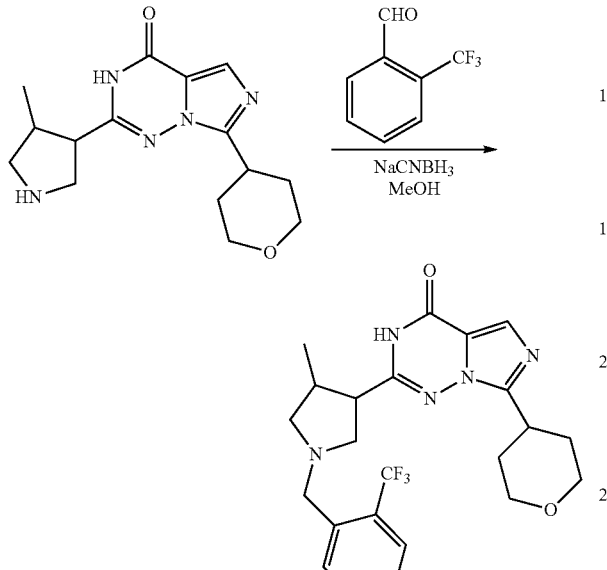

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (5 mL) was added 2-(trifluoromethyl)benzaldehyde (47.3 mg, 0.27 mmol) at room temperature and stirred for 2 h under argon atmosphere. To this NaCNBH$_3$ (46.7 mg, 0.74 mmol) was added and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-2-((3,4-trans)-4-methyl-1-(2-(trifluoromethyl)benzyl)pyrrolidin-3-yl)-7-(tetrahydro-2H-pyran-4-yl)imidazo[5,1-f][1,2,4]triazin-4(3H)-one (50 mg, 43%) as an off-white solid. $^1$H-NMR (DMSO-d$_6$, 400 MHz): δ 11.56 (bs, 1H), 7.78-7.77 (m, 1H), 7.72-7.68 (m, 3H), 7.49-7.45 (m, 1H), 3.98 (d, 2H), 3.82 (s, 2H), 3.56-3.52 (m, 2H), 3.41-3.38 (m, 1H), 3.04-3.01 (m, 1H), 2.91-2.84 (m, 3H), 2.68-2.61 (m, 1H), 2.31-2.28 (m, 1H), 1.89-1.84 (m, 4H), 1.12 (d, 3H); Mass (ESI): 430.4 [M$^+$+1]; LC-MS: 95.54%; 462 (M$^+$+1); (column; X-bridge C-18, (50×3.0 mm, 3.5μ); RT 3.75 min. 5 mM NH$_4$OAc in water: ACN; 0.8 ml/min); UPLC (purity): 96%; (column; Eclipse XDB C-18, 150×4.6 mm, 5μ; RT 11.12 min. 5 mM NH$_4$OAc: ACN:Water; 1.0 ml/min; Chiral HPLC: 100%, R$_t$=12.66 min (Chiralpak IA, 250×4.6 mm, 5μ; mobile phase (A) 0.1% TEA in n-Hexane (B) IPA (A:B:90:10); flow Rate: 1.00 mL/min); Optical rotation [α]$_D^{20}$: +7.72° (c=0.5, DCM). TLC: 10% MeOH/DCM (R$_f$: 0.5).

546

71. (+)-2-((3,4-trans)-1-(2-fluoro-5-methoxybenzyl)-4-methylpyrrolidin-3-yl)-7-(tetrahydro-2H-pyran-4-yl)imidazo[5,1-f][1,2,4]triazin-4(3H)-one

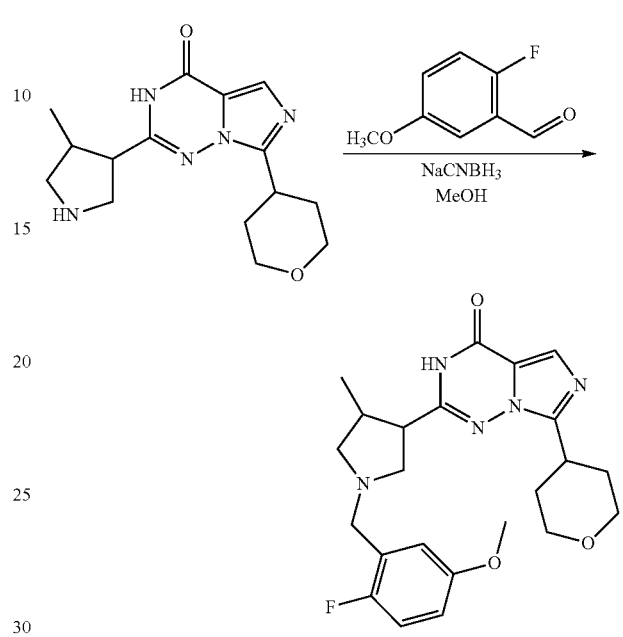

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (5 mL) was added 2-fluoro-5-methoxybenzaldehyde (42 mg, 0.27 mmol) at room temperature and stirred for 2 h under argon atmosphere. To this NaCNBH$_3$ (45 mg, 0.72 mmol) was added and stirring was continued for another 16 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-2-((3,4-trans)-1-(2-fluoro-5-methoxybenzyl)-4-methylpyrrolidin-3-yl)-7-(tetrahydro-2H-pyran-4-yl)imidazo[5,1-f][1,2,4]triazin-4(3H)-one (40 mg, 37%) as an off-white solid. $^1$H-NMR (DMSO-d$_6$, 400 MHz): δ 7.64 (s, 1H), 7.09 (t, 1H), 6.99-6.94 (m, 1H), 6.84-6.82 (m, 1H), 3.98-3.96 (m, 2H), 3.74 (s, 3H), 3.68 (s, 2H), 3.51-3.44 (m, 3H), 2.98-2.96 (m, 1H), 2.92-2.87 (m, 1H), 2.87-2.84 (m, 2H), 2.67-2.64 (m, 1H), 2.32-2.31 (m, 1H), 1.89-1.82 (m, 4H), 1.04 (d, 3H); Mass (ESI): 442.4 [M$^+$+1]; LC-MS: 95.68%; 442.4 (M$^+$+1); (column; X-select C-18, (50×3.0 mm, 3.5μ); RT 3.26 min. 5 mM NH$_4$OAc: ACN; 0.8 ml/min); UPLC (purity): 99%; (column; Eclipse XDB C-18, 150×4.6 mm, 5μ; RT 10.31 min. 5 mM NH$_4$OAc: ACN:Water; 1.0 ml/min; Chiral HPLC: 98.69%, R$_t$=23.81 min (Chiralpak IA, 250×4.6 mm, 5μ; mobile phase (A) 0.1% TEA in n-Hexane (B) IPA (A:B:90:10); flow Rate: 1.00 mL/min); Optical rotation [α]$_D^{20}$: +7.07° (c=0.5, DCM). TLC: 10% MeOH/DCM (R$_f$: 0.5).

72. (+)-2-((3,4-trans)-1-(isoquinolin-7-ylmethyl)-4-methylpyrrolidin-3-yl)-7-(tetrahydro-2H-pyran-4-yl)imidazo[5,1-f][1,2,4]triazin-4(3H)-one

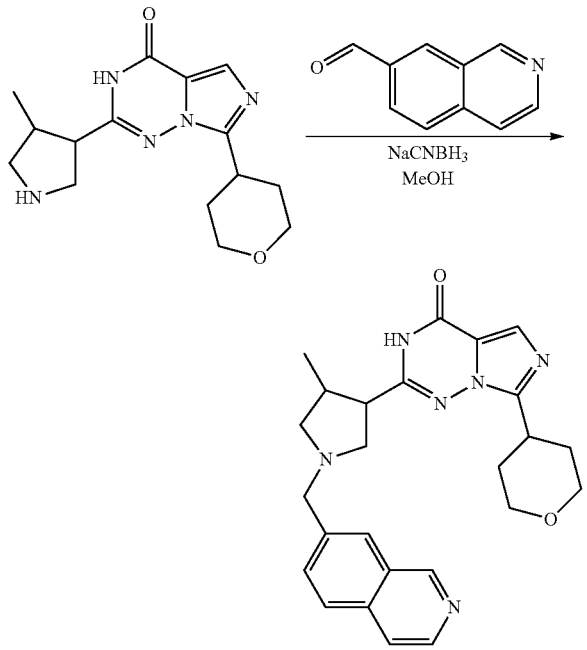

73. (+)-2-((3,4-trans)-4-methyl-1-(Quinolin-6-ylmethyl)pyrrolidin-3-yl)-7-(tetrahydro-2H-pyran-4-yl)imidazo[5,1-f][1,2,4]triazin-4(3H)-one

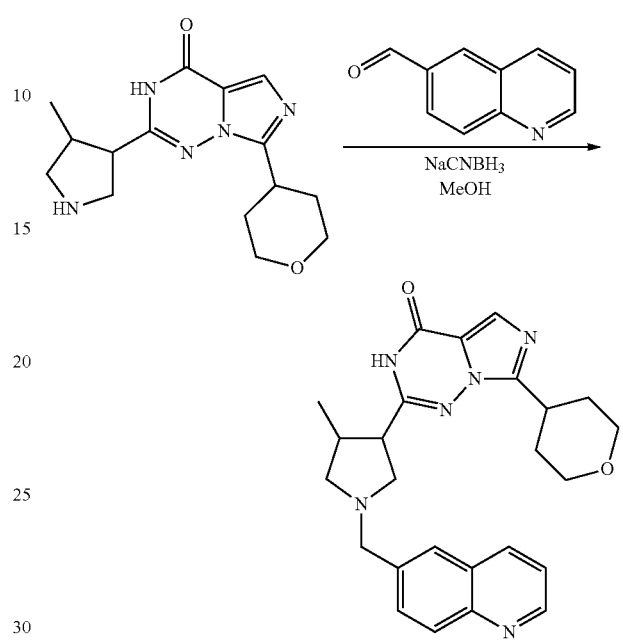

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (5 mL) was added isoquinoline-7-carbaldehyde (62.2 mg, 0.39 mmol) at RT under argon atmosphere. After being stirred for 2 h, NaCNBH$_3$ (37 mg, 0.59 mmol) was added to the reaction mixture and stirring was continued for another 16 h at RT. The volatiles were evaporated under reduced pressure. The residue was diluted with ice-cold water and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-1-(isoquinolin-7-ylmethyl)-4-methylpyrrolidin-3-yl)-7-(tetrahydro-2H-pyran-4-yl)imidazo[5,1-f][1,2,4]triazin-4(3H)-one (50 mg, 34%) as an off-white solid. $^1$H-NMR (DMSO d$_6$, 400 MHz): δ 9.25 (bs, 1H), 8.48 (d, 1H), 8.01 (s, 1H), 7.98 (d, 1H), 7.80-7.76 (m, 2H), 7.64 (s, 1H), 3.94-3.81 (m, 4H), 3.49-3.42 (m, 2H), 3.04-3.01 (m, 2H), 2.96-2.94 (m, 2H), 2.87-2.84 (m, 2H), 2.69-2.64 (m, 1H), 2.34-2.32 (m, 1H), 1.92-1.84 (m, 4H), 1.12 (d, 3H); Mass (ESI): 445.4 [M$^+$+1] & 486.5 [M$^+$+ACN]; LC-MS: 99.89%; 445.3 (M$^+$+1); (column; X-bridge C-18, (50×3.0 mm, 3.5μ); RT 2.85 min. 5 mM NH$_4$OAc in water: ACN; 0.8 ml/min); HPLC (purity): 99.28%; (column; Eclipse XDB C-18, (150×4.6 mm, 5μ); RT 8.82 min. 5 mM NH$_4$OAc (Aq): ACN; 1.0 ml/min; Chiral HPLC: 100%, R$_t$=10.60 min (Chiralpak IA, 250×4.6 mm, 5μ; mobile phase (A) 0.1% DEA in n-Hexane (B) DCM:Methanol (80:20) (A:B:75:25); flow Rate: 1.00 mL/min); Optical rotation [α]$_D^{20}$: +14.17° (c=0.25, DCM). TLC: 5% MeOH/DCM (Rf: 0.4).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (15 mL) was added quinoline-6-carbaldehyde (62.2 mg, 0.39 mmol) at RT under argon atmosphere. After being stirred for 2 h, NaCNBH$_3$ (37 mg, 0.59 mmol) was added to the reaction mixture and stirring was continued for another 16 h at RT. The volatiles were evaporated under reduced pressure. The residue was diluted with ice-cold water and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinolin-6-ylmethyl)pyrrolidin-3-yl)-7-(tetrahydro-2H-pyran-4-yl)imidazo[5,1-f][1,2,4]triazin-4(3H)-one (65 mg, 46%) as an off-white solid. $^1$H-NMR (DMSO d$_6$, 400 MHz): δ 8.98 (bs, 1H), 8.34 (d, 1H), 7.99 (d, 1H), 7.87 (s, 1H), 7.76 (d, 1H), 7.68 (s, 1H), 7.54 (d, 1H), 3.94-3.92 (m, 2H), 3.86-3.84 (m, 2H), 3.49-3.42 (m, 2H), 3.02 (t, 1H), 2.92 (s, 2H), 2.88-2.82 (m, 2H), 2.68-2.64 (m, 1H), 2.34-2.36 (m, 1H), 1.84-1.81 (m, 4H), 1.12 (d, 3H); Mass (ESI): 445 [M$^+$+1]; LC-MS: 97.81%; 445 (M$^+$+1); (column; X-bridge C-18, (50×3.0 mm, 3.5μ); RT 2.82 min. 5 mM NH$_4$OAc in water: ACN; 0.8 ml/min); HPLC (purity): 97.77%; (column; Eclipse XDB C-18, (150×4.6 mm, 5μ); RT 8.72 min. 5 mM NH$_4$OAc (Aq): ACN; 1.0 ml/min.; Chiral HPLC: 98.66%, R$_t$=11.28 min (Chiralpak IA, 250×4.6 mm, 5μ; mobile phase (A) 0.1% DEA in n-Hexane (B) DCM:Methanol (80:20) (A:B:75:25); flow Rate: 1.00 mL/min); Optical rotation [α]$_D^{20}$: +5.500 (c=0.25% in DCM (301111L)). TLC: 5% MeOH/DCM (Rf: 0.4).

74. (+)-2-((3,4-trans)-1-(2-chlorobenzyl)-4-methyl-pyrrolidin-3-yl)-7-(tetrahydro-2H-pyran-4-yl)imidazo[5,1-f][1,2,4]triazin-4(3H)-one

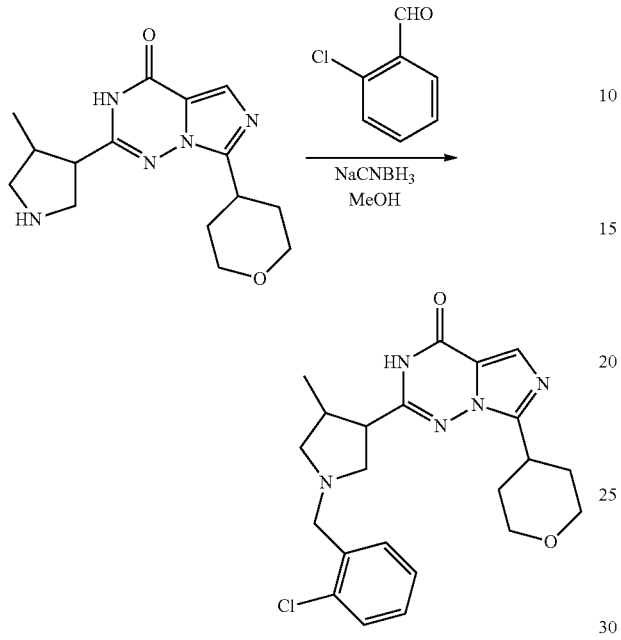

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (5 mL) was added 2-chlorobenzaldehyde (38 mg, 0.27 mmol) at RT under argon atmosphere. After being stirred for 2 h; NaCNBH$_3$ (45 mg, 0.72 mmol) was added to the reaction mixture and stirring was continued for another 5 h at RT. The volatiles were evaporated under reduced pressure. The residue was diluted with ice-cold water and extracted with DCM (2×10 mL). Combined organic layer was dried over sodium sulphate, filtered and concentrated in vacuo to obtain the crude product. The crude material was purified by silica gel column chromatography and then further purified by preparative HPLC to afford (+)-2-((3,4-trans)-1-(2-chlorobenzyl)-4-methylpyrrolidin-3-yl)-7-(tetrahydro-2H-pyran-4-yl)imidazo[5,1-f][1,2,4]triazin-4(3H)-one (30 mg, 29%) as an off-white solid. $^1$H-NMR (DMSO d$_6$, 400 MHz): δ 11.52 (bs, 1H), 7.69-7.67 (m, 1H), 7.54-7.26 (m, 4H), 4.66 (bs, 1H), 3.96-3.94 (m, 2H), 3.78-3.72 (m, 2H), 3.52-3.48 (m, 2H), 3.41-3.38 (m, 2H), 3.01-2.84 (m, 2H), 2.69-2.67 (m, 1H), 2.37-2.29 (m, 1H), 1.98-1.82 (m, 4H), 1.14 (d, 3H); Mass (ESI): 428.6 [M$^+$+1]; LC-MS: 99.36%; 428.4 (M$^+$+1); (column; X-select C-18, (50×3.0 mm, 3.5µ); RT 3.52 min. 5 mM NH$_4$OAc: ACN; 0.8 ml/min); UPLC (purity): 99.33%; (column; Acquity BEH C-18, (50×2.1 mm, 1.7µ); RT 1.66 min. 0.025% TFA (Aq): ACN; 0.50 ml/min; Chiral HPLC: 100%, R$_t$=28.19 min (Chiralpak IC, 250×4.6 mm, 5µ; mobile phase (A) 0.1% DEA in n-Hexane (B) IPA (A:B:50:50); flow Rate: 1.00 mL/min); Optical rotation [α]$_D^{20}$: +11.05° (c=0.25, DCM). TLC: 10% MeOH/DCM (Rf: 0.5).

75. (+)-2-((3,4-trans)-1-(4-chlorobenzyl)-4-methyl-pyrrolidin-3-yl)-7-(tetrahydro-2H-pyran-4-yl)imidazo[5,1-f][1,2,4]triazin-4(3H)-one

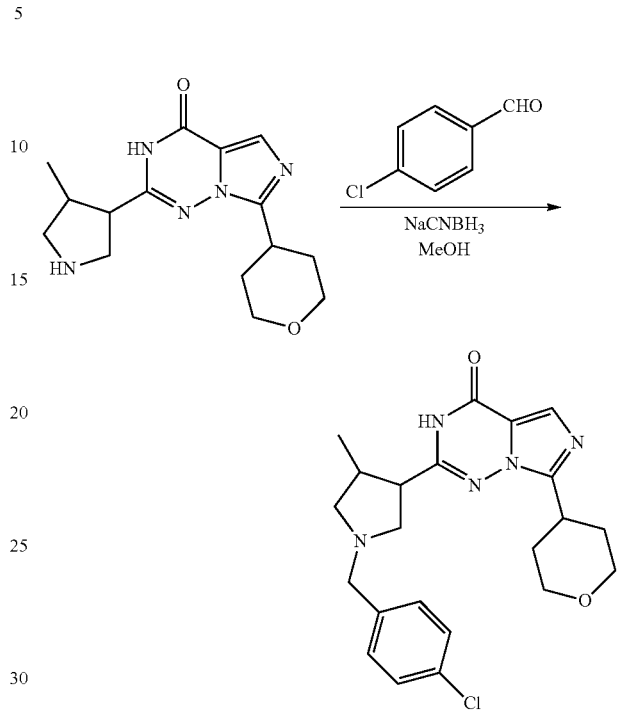

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (80 mg, 0.26 mmol) in MeOH (5 mL) was added 4-chlorobenzaldehyde (40 mg, 0.29 mmol) at RT under argon atmosphere. After being stirred for 2 h, NaCNBH$_3$ (49 mg, 0.78 mmol) was added to the reaction mixture and stirring was continued for another 5 h at RT. The volatiles were evaporated under reduced pressure. The residue was diluted with ice-cold water and extracted with DCM (2×20 mL). Combined organic layer was dried over sodium sulphate, filtered and concentrated in vacuo to obtain the crude product. The crude material was purified by silica gel column chromatography and then further purified by preparative HPLC to afford (+)-2-((3,4-trans)-1-(4-chlorobenzyl)-4-methylpyrrolidin-3-yl)-7-(tetrahydro-2H-pyran-4-yl)imidazo[5,1-f][1,2,4]triazin-4(3H)-one (60 mg, 27%) as an off-white solid. $^1$H-NMR (DMSO d$_6$, 500 MHz): δ 7.64 (s, 1H), 7.38-7.29 (m, 4H), 3.94-3.92 (m, 2H), 3.68-3.66 (m, 2H), 3.51-3.48 (m, 2H), 3.38-3.32 (m, 4H), 2.92-2.90 (m, 1H), 2.86-2.84 (m, 1H), 2.65-2.61 (m, 1H), 2.28-2.21 (m, 1H), 1.89-1.84 (m, 4H), 1.08 (d, 3H); Mass (ESI): 428 [M$^+$+1]; LC-MS: 99.50%; 428 (M$^+$+1); (column; X-bridge C-18, (50×3.0 mm, 3.5µ); RT 3.43 min. 5 mM NH$_4$OAc in water: ACN; 0.8 ml/min); UPLC (purity): 96.52%; (column; Acquity BEH C-18, (50×2.1 mm, 1.7µ); RT 1.77 min. 0.025% TFA (Aq): ACN; 0.50 ml/min; Chiral HPLC: 96.85%, R$_t$=21.98 min (Chiralpak IC, 250×4.6 mm, 5µ; mobile phase (A) 0.1% DEA in n-Hexane (B) IPA (A:B:50:50); flow Rate: 1.00 mL/min); Optical rotation [α]$_D^{20}$: +5.648° (c=0.25, DCM). TLC: 10% MeOH/DCM (Rf: 0.5).

76. (+)-2-((3,4-trans)-1-(2,5-difluorobenzyl)-4-methylpyrrolidin-3-yl)-7-(tetrahydro-2H-pyran-4-yl)imidazo[5,1-f][1,2,4]triazin-4(3H)-one

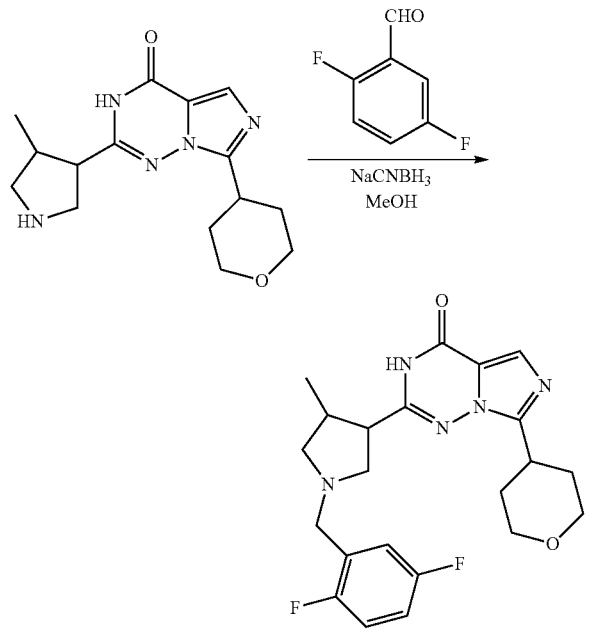

77. (+)-2-((3,4-trans)-1-(2,3-difluorobenzyl)-4-methylpyrrolidin-3-yl)-7-(tetrahydro-2H-pyran-4-yl)imidazo[5,1-f][1,2,4]triazin-4(3H)-one

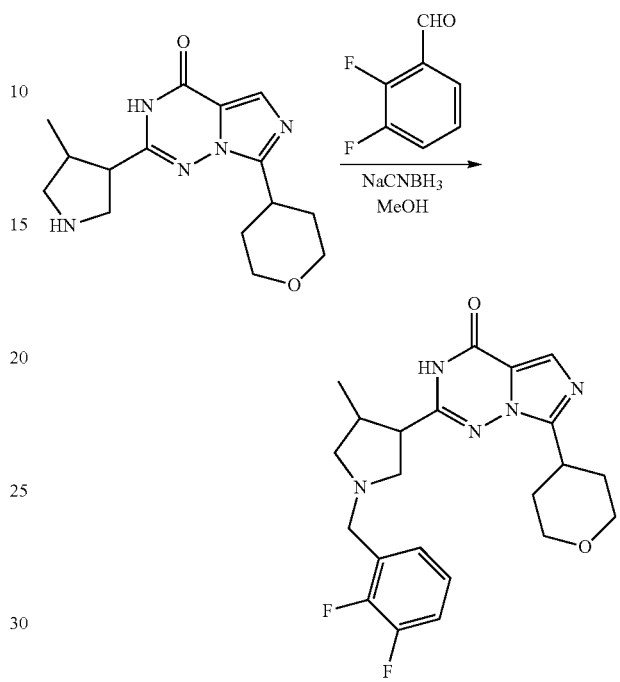

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (11 mg, 0.36 mmol) in MeOH (5 mL) was added 2,5-difluorobenzaldehyde (56 mg, 0.39 mmol) at RT under argon atmosphere. After being stirred for 2 h, NaCNBH$_3$ (68 mg, 108 mmol) was added to the reaction mixture and stirring was continued for another 5 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography and then further purified by preparative HPLC to afford (+)-2-((3,4-trans)-1-(2,5-difluorobenzyl)-4-methylpyrrolidin-3-yl)-7-(tetrahydro-2H-pyran-4-yl)imidazo[5,1-f][1,2,4]triazin-4(3H)-one (50 mg, 33%) as an off-white solid. $^1$H-NMR (DMSO d$_6$, 500 MHz): δ 11.58 (bs, 1H), 7.64 (s, 1H), 7.24-7.16 (m, 4H), 3.91-3.89 (m, 2H), 3.62 (s, 3H), 3.49-3.41 (m, 2H), 3.38-3.36 (m, 2H), 2.98-2.79 (m, 1H), 2.68-2.64 (m, 1H), 2.25-2.21 (m, 1H), 1.89-1.82 (m, 4H), 1.07 (d, 3H); Mass (ESI): 430.4 [M$^+$+1]; LC-MS: 99.62%; 430.4 (M$^+$+1); (column; X-select C-18, (50×3.0 mm, 3.5μ); RT 3.30 min. 5 mM NH$_4$OAc: ACN; 0.8 ml/min); HPLC (purity): 99.58%; (column; Eclipse XDB C-18, (150×4.6 mm, 5.0μ); RT 9.94 min. 5 mM NH$_4$OAc (Aq): ACN; 1.0 ml/min; Chiral HPLC: 100%, R$_t$=18.75 min (Chiralpak IA, 250×4.6 mm, 5μ; mobile phase (A) 0.1% TEA in n-Hexane (B) IPA (A:B:90:10); flow Rate: 1.00 mL/min); Optical rotation [α]$_D^{20}$: +4.65° (c=0.25, DCM). TLC: 10% MeOH/DCM (Rf: 0.9).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (7 mL) was added 2,3-difluorobenzaldehyde (38 mg, 0.27 mmol) at RT under argon atmosphere. After being stirred for 2 h, NaCNBH$_3$ (46 mg, 0.74 mmol) was added to the reaction mixture and stirring was continued for another 5 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-1-(2,3-difluorobenzyl)-4-methylpyrrolidin-3-yl)-7-(tetrahydro-2H-pyran-4-yl)imidazo[5,1-f][1,2,4]triazin-4(3H)-one (30 mg, 28%) as an off-white solid. $^1$H-NMR (DMSO d$_6$, 400 MHz): δ 11.62 (bs, 1H), 7.69 (s, 1H), 7.34-7.16 (m, 3H), 3.94-3.91 (m, 2H), 3.74 (s, 2H), 3.51-3.48 (m, 2H), 3.04-2.98 (m, 2H), 2.89-2.84 (m, 1H), 2.81-2.74 (m, 2H), 2.71-2.64 (m, 1H), 2.34-2.29 (m, 1H), 1.84-1.81 (m, 4H), 1.09 (d, 3H); Mass (ESI): 430 [M$^+$+1]; LC-MS: 96.75%; 430 (M$^+$+1); (column; X-bridge C-18, (50×3.0 mm, 3.5μ); RT 3.35 min. 5 mM NH$_4$OAc in water: ACN; 0.8 ml/min); HPLC (purity): 96.95%; (column; Eclipse XDB C-18, (150×4.6 mm, 5.0μ); RT 9.97 min. 5 mM NH$_4$OAc (Aq): ACN; 1.0 ml/min; Chiral HPLC: 97.68%, R$_t$=19.52 min (Chiralpak IA, 250×4.6 mm, 5μ; mobile phase (A) 0.1% TEA in n-Hexane (B) IPA (A:B:90:10); flow Rate: 1.00 mL/min); Optical rotation [α]$_D^{20}$: +8.59° (c=0.5, DCM). TLC: 10% MeOH/DCM (Rf: 0.5).

78. (+)-2-((3,4-trans)-4-methyl-1-(pyridin-4-ylmethyl)pyrrolidin-3-yl)-7-(tetrahydro-2H-pyran-4-yl)imidazo[5,1-f][1,2,4]triazin-4(3H)-one

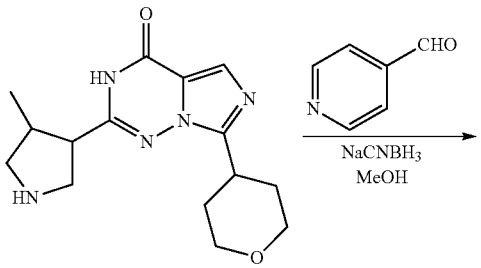

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (20 mL) was added isonicotinaldehyde (38 mg, 0.36 mmol) at RT under argon atmosphere. After being stirred for 2 h, NaCNBH$_3$ (62 mg, 0.99 mmol) was added to the reaction mixture and stirring was continued for another 5 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyridin-4-ylmethyl)pyrrolidin-3-yl)-7-(tetrahydro-2H-pyran-4-yl)imidazo[5,1-f][1,2,4]triazin-4(3H)-one (45 mg, 35%) as an off-white solid. $^1$H-NMR (DMSO d$_6$, 400 MHz): δ 8.54 (s, 2H), 7.68 (s, 1H), 7.36-7.32 (m, 2H), 3.94-3.91 (m, 2H), 3.72-3.64 (m, 2H), 3.51-3.48 (m, 2H), 2.96-2.94 (m, 1H), 2.92-2.84 (m, 4H), 2.69-2.64 (m, 1H), 2.34-2.28 (m, 1H), 1.91-1.84 (m, 4H), 1.09 (d, 3H); Mass (ESI): 395 [M$^+$+1]; LC-MS: 94.70%; 395 (M$^+$+1); (column; X-bridge C-18, (50×3.0 mm, 3.5μ); RT 2.53 min. 5 mM NH$_4$OAc in water: ACN; 0.8 ml/min); HPLC (purity): 95%; (column; Eclipse XDB C-18, (150×4.6 mm, 5.0μ); RT 7.76 min. 5 mM NH$_4$OAc (Aq): ACN; 1.0 ml/min; Chiral HPLC: 100%, R$_t$=10.25 min (Chiralpak IA, 250×4.6 mm, 5μ; mobile phase (A) 0.1% DEA in n-Hexane (B) DCM:MeOH (80:20) (A:B:75:25); flow Rate: 1.00 mL/min); Optical rotation [α]$_D^{20}$: +13.13° (c=0.25, DCM). TLC: 5% MeOH/DCM (Rf: 0.5).

79. (+)-2-((3,4-trans)-4-methyl-1-(Quinolin-2-ylmethyl)pyrrolidin-3-yl)-7-(tetrahydro-2H-pyran-4-yl)imidazo[5,1-f][1,2,4]triazin-4(3H)-one

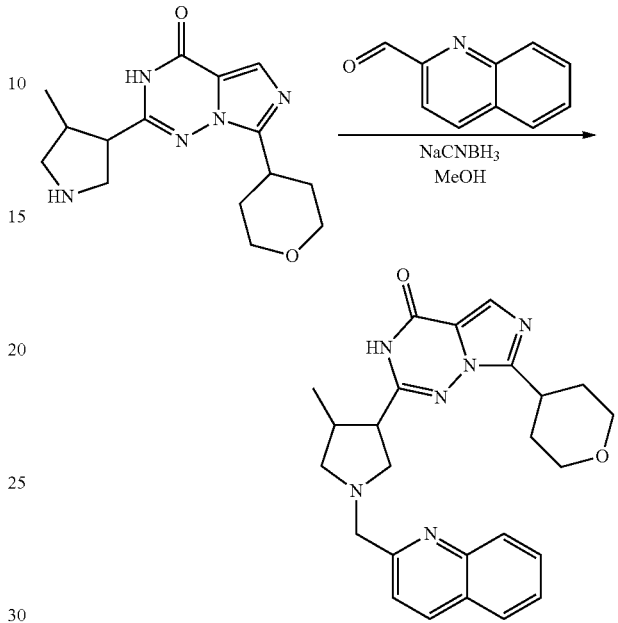

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in MeOH (20 mL) was added quinoline-2-carbaldehyde (77 mg, 0.49 mmol) at RT under argon atmosphere. After being stirred for 2 h, NaCNBH$_3$ (77.9 mg, 1.23 mmol) was added to the reaction mixture and stirring was continued for another 16 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinolin-2-ylmethyl)pyrrolidin-3-yl)-7-(tetrahydro-2H-pyran-4-yl)imidazo[5,1-f][1,2,4]triazin-4(3H)-on (60 mg, 33%) as an off-white solid. $^1$H-NMR (DMSO d$_6$, 400 MHz): δ 9.28 (s, 1H), 8.12 (d, 1H), 7.94 (d, 1H), 7.89 (s, 1H), 7.87-7.84 (m, 1H), 7.68-7.62 (m, 2H), 3.96-3.91 (m, 4H), 3.51-3.48 (m, 2H), 3.47-3.42 (m, 2H), 3.12-2.98 (m, 2H), 2.96-2.2.91 (m, 1H), 2.74-2.68 (m, 1H), 2.66-2.62 (m, 1H), 2.43-2.38 (m, 1H), 1.89-1.84 (m, 4H), 1.12 (d, 3H); Mass (ESI): 445.4 [M$^+$+1]; LC-MS: 98%; 445.4 (M$^+$+1); (column; X-bridge C-18, (50×3.0 mm, 3.5μ); RT 2.87 min. 5 mM NH$_4$OAc: ACN; 0.8 ml/min); HPLC (purity): 99.78%; (column; Eclipse XDB C-18, (150× 4.6 mm, 5.0μ); RT 9.29 min. 5 mM NH$_4$OAc (Aq): ACN; 1.0 ml/min; Chiral HPLC: 97.32%, R$_t$=13.00 min (Chiralpak IA, 250×4.6 mm, 5μ; mobile phase (A) 0.1% DEA in n-Hexane (B) EtOH (A:B:80:20); flow Rate: 1.00 mL/min); Optical rotation [α]$_D^{20}$: +66.92° (c=0.25, DCM). TLC: 5% MeOH/DCM (Rf: 0.5).

80. (+)-2-((3,4-trans)-1-(isoquinolin-6-ylmethyl)-4-methylpyrrolidin-3-yl)-7-(tetrahydro-2H-pyran-4-yl)imidazo[5,1-f][1,2,4]triazin-4(3H)-one

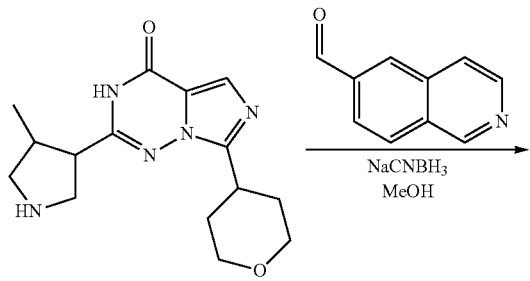

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in MeOH (20 mL) was added isoquinoline-6-carbaldehyde (77 mg, 0.49 mmol) at RT under argon atmosphere. After being stirred for 2 h, NaCNBH$_3$ (77.9 mg, 1.23 mmol) was added to the reaction mixture and stirring was continued for another 16 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-1-(isoquinolin-6-ylmethyl)-4-methylpyrrolidin-3-yl)-7-(tetrahydro-2H-pyran-4-yl)imidazo[5,1-f][1,2,4]triazin-4(3H)-one (40 mg, 22%) as an off-white solid. $^1$H-NMR (DMSO d$_6$, 400 MHz): δ 9.25 (s, 1H), 8.46 (d, 1H), 8.02 (d, 1H), 7.86 (s, 1H), 7.74 (d, 1H), 7.60 (bs, 1H), 7.62 (s, 1H), 3.94-3.82 (m, 4H), 3.49-3.41 (m, 2H), 3.01-2.99 (m, 2H), 2.94-2.91 (m, 2H), 2.86-2.84 (m, 2H), 2.64-2.62 (m, 1H), 2.34-2.30 (m, 1H), 1.84-1.81 (m, 4H), 1.07 (d, 3H); Mass (ESI): 445 [M$^+$+1]; LC-MS: 99.13%; 445 (M$^+$+1); (column; X-bridge C-18, (50×3.0 mm, 3.5μ); RT 2.88 min. 5 mM NH$_4$OAc in water: ACN; 0.8 ml/min); UPLC (purity): 96.95%; (column; Acquity BEH C-18, (50×2.1 mm, 1.7μ); RT 1.26 min. 0.025% TFA (Aq): ACN; 0.50 ml/min; Chiral HPLC: 99.40%, R$_t$=16.61 min (Chiralpak IA, 250×4.6 mm, 5μ; mobile phase (A) 0.1% DEA in n-Hexane (B) EtOH (A:B:80:20); flow Rate: 1.00 mL/min); Optical rotation [α]$_D^{20}$: +11.18° (c=0.25, DCM). TLC: 5% MeOH/DCM (Rf: 0.5).

81. (−)-2-((3,4-trans)-4-methyl-1-(Quinolin-7-ylmethyl)pyrrolidin-3-yl)-7-(tetrahydro-2H-pyran-4-yl)imidazo[5,1-f][1,2,4]triazin-4(3H)-one

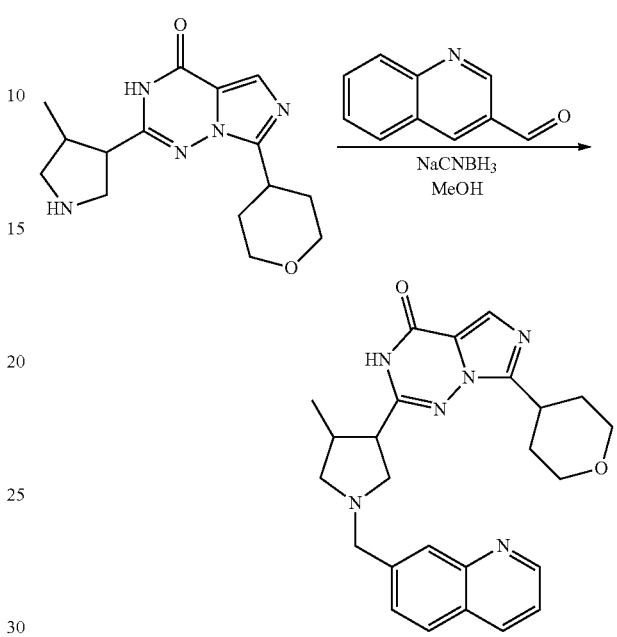

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in MeOH (20 mL) was added quinoline-3-carbaldehyde (77 mg, 0.49 mmol) at RT under argon atmosphere. After being stirred for 2 h, NaCNBH$_3$ (77.9 mg, 1.23 mmol) was added to the reaction mixture and stirring was continued for another 16 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography to afford (−)-2-((3,4-trans)-4-methyl-1-(quinolin-7-ylmethyl)pyrrolidin-3-yl)-7-(tetrahydro-2H-pyran-4-yl)imidazo[5,1-f][1,2,4]triazin-4(3H)-one (95 mg, 52%) as an off-white solid. $^1$H-NMR (CD$_3$OD, 400 MHz): δ 9.01 (s, 1H), 8.54 (s, 1H), 8.12 (d, 1H), 8.02 (d, 1H), 7.89-7.86 (m, 1H), 7.74 (s, 1H), 7.72-7.71 (m, 1H), 4.57-4.53 (m, 2H), 4.04-3.99 (m, 2H), 3.72-3.61 (m, 6H), 3.22-3.18 (m, 1H), 3.09-3.02 (m, 1H), 2.97-2.82 (m, 1H), 2.05-1.85 (m, 4H), 1.32 (d, 3H); Mass (ESI): 445.4 [M$^+$+1]; LC-MS: 99%; 445.5 (M$^+$); (column; X-bridge C-18, (50×3.0 mm, 3.5μ); RT 2.80 min. 5 mM NH$_4$OAc: ACN; 0.8 ml/min); UPLC (purity): 99%; (column; Acquity BEH C-18, (50×2.1 mm, 1.7μ); RT 1.52 min. 0.025% TFA (Aq): ACN; 0.50 ml/min; Chiral HPLC: 98.95%, R$_t$=14.10 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: −22.83° (c=0.25, DCM); TLC: 5% MeOH/DCM (Rf: 0.5).

82. (+)-2-((3,4-trans)-4-methyl-1-((2-oxo-1,2-dihydropyridin-3-yl)methyl)pyrrolidin-3-yl)-7-(tetrahydro-2H-pyran-4-yl)imidazo[5,1-f][1,2,4]triazin-4(3H)-one

83. (+)-2-((3,4-trans)-4-methyl-1-(pyridazin-3-ylmethyl)pyrrolidin-3-yl)-7-(tetrahydro-2H-pyran-4-yl)imidazo[5,1-f][1,2,4]triazin-4(3H)-one

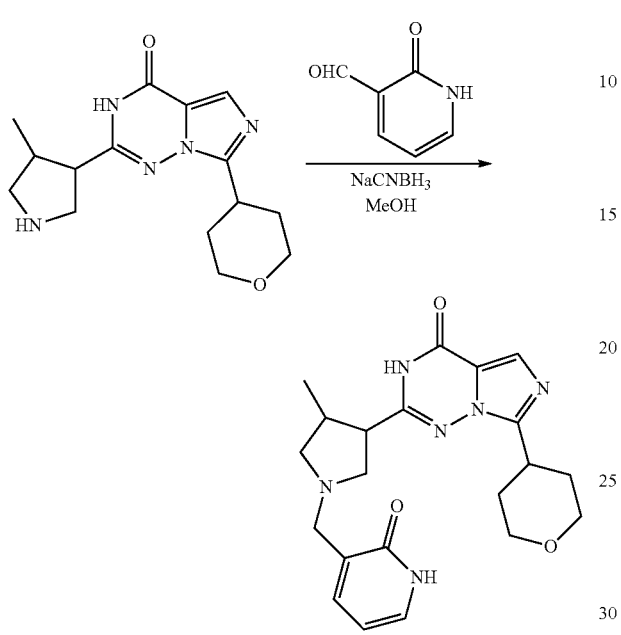

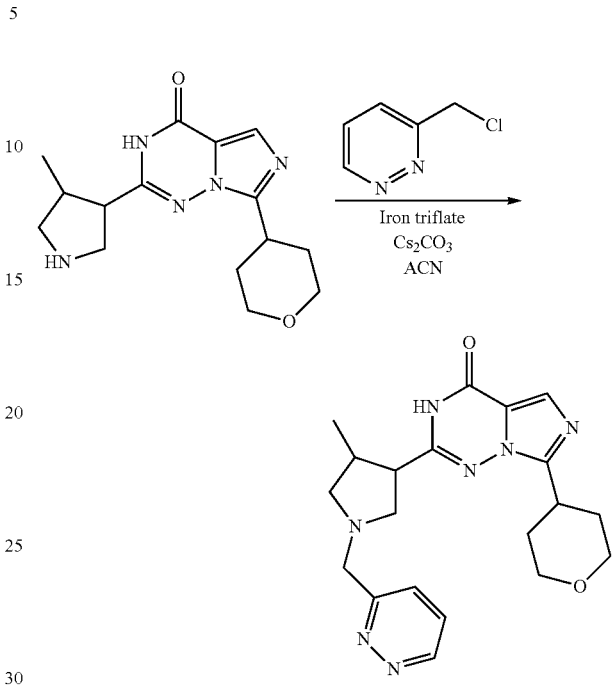

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (110 mg, 0.36 mmol) in MeOH (5 mL) was added 2-oxo-1,2-dihydropyridine-3-carbaldehyde (49 mg, 0.39 mmol) at RT under argon atmosphere. After being stirred for 2 h, NaCNBH$_3$ (68 mg, 1.08 mmol) was added to the reaction mixture and stirring was continued for another 6 h at RT. The volatiles were evaporated under reduced pressure. The residue was diluted with ice-cold water (15 mL) and extracted with DCM (3×20 mL). Combined organic layer was dried over sodium sulphate, filtered and concentrated in vacuo to obtain the crude product. The crude material was purified by silica gel column chromatography and then further purified by preparative HPLC to afford (+)-2-((3,4-trans)-4-methyl-1-((2-oxo-1,2-dihydropyridin-3-yl)methyl)pyrrolidin-3-yl)-7-(tetrahydro-2H-pyran-4-yl)imidazo[5,1-f][1,2,4]triazin-4(3H)-one (61 mg, 41%) as an off-white solid. $^1$H-NMR (DMSO d$_6$, 400 MHz): δ 11.58 (bs, 1H), 7.64 (s, 1H), 7.44-7.41 (m, 1H), 7.25-7.20 (m, 1H), 6.14-6.12 (m, 1H), 3.94-3.91 (m, 2H), 3.51-3.44 (m, 5H), 2.99-2.84 (m, 5H), 2.66-2.61 (m, 1H), 2.32-2.30 (m, 1H), 1.86-1.81 (m, 4H), 1.07 (d, 3H); Mass (ESI): 411 [M$^+$+1] & 433 [M$^+$+Na]; LC-MS: 98.85%; 411.3 (M$^+$+1); (column; X-bridge C-18, (50×3.0 mm, 3.5μ); RT 2.02 min. 5 mM NH$_4$OAc: ACN; 0.8 ml/min); HPLC (purity): 98.85%; (column; Eclipse XDB C-18, (150×4.6 mm, 5.0μ); RT 5.80 min. 5 mM NH$_4$OAc (Aq): ACN; 1.0 ml/min; Chiral HPLC: 99.79%, R$_t$=9.55 min (Chiralpak IA, 250×4.6 mm, 5μ; mobile phase (A) 0.1% DEA in n-Hexane (B) EtOH (A:B: 70:30); flow Rate: 1.00 mL/min); Optical rotation [α]$_D^{20}$: +22.12° (c=0.25, DCM). TLC: 5% MeOH/DCM (Rf: 0.4).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in ACN (15 mL) were added 3-(chloromethyl)pyridazine (74.8 mg, 0.45 mmol), Iron triflate (41.5 mg, 0.082 mmol) and Cs$_2$CO$_3$ (268 mg, 0.82 mmol) at RT under argon atmosphere. The resultant reaction mixture was heated to 70° C. and stirred for 3 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyridazin-3-ylmethyl)pyrrolidin-3-yl)-7-(tetrahydro-2H-pyran-4-yl)imidazo[5,1-f][1,2,4]triazin-4(3H)-one (45 mg, 28%) as an off-white solid; $^1$H-NMR (DMSO d$_6$, 400 MHz): δ 11.68 (bs, 1H), 9.12 (s, 1H), 7.68-7.64 (m, 3H), 3.96-3.89 (m, 4H), 3.51-3.47 (m, 2H), 3.41-3.39 (m, 2H), 3.04-3.01 (m, 1H), 2.94-2.91 (m, 1H), 2.87-2.82 (m, 2H), 2.65-2.62 (m, 1H), 2.36-2.32 (m, 1H), 1.89-1.85 (m, 4H), 1.09 (d, 3H); Mass (ESI): 396.3 [M$^+$+1]; LC-MS: 96.43%; 394.4 (M−1); (column; X-bridge C-18, (50×3.0 mm, 3.5μ); RT 2.15 min. 5 mM NH$_4$OAc: ACN; 0.8 ml/min); HPLC (purity): 98.24%; (column; Eclipse XDB C-18, (150×4.6 mm, 5.0μ); RT 6.82 min. 5 mM NH$_4$OAc (Aq): ACN; 1.0 ml/min; Chiral HPLC: 98.52%, R$_t$=8.88 min (Chiralpak IA, 250×4.6 mm, 5μ; mobile phase (A) 0.1% DEA in n-Hexane (B) EtOH (A:B:60:40); flow Rate: 1.00 mL/min); Optical rotation [α]$_D^{20}$: +14.81° (c=0.25, DCM). TLC: 7% MeOH/DCM (Rf: 0.4).

84. (+)-2-((3,4-trans)-4-methyl-1-(pyridazin-4-ylmethyl)pyrrolidin-3-yl)-7-(tetrahydro-2H-pyran-4-yl)imidazo[5,1-f][1,2,4]triazin-4(3H)-one

85. (+)-2-((3,4-trans)-4-methyl-1-(quinazolin-6-ylmethyl)pyrrolidin-3-yl)-7-(tetrahydro-2H-pyran-4-yl)imidazo[5,1-f][1,2,4]triazin-4(3H)-one

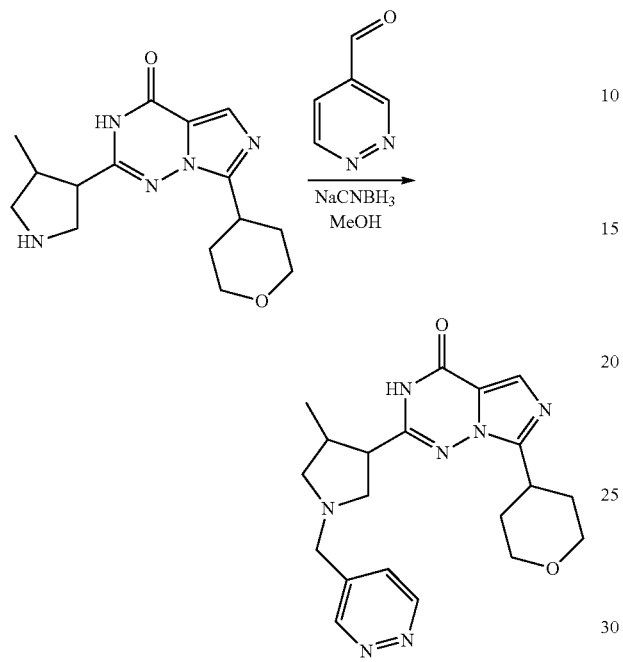

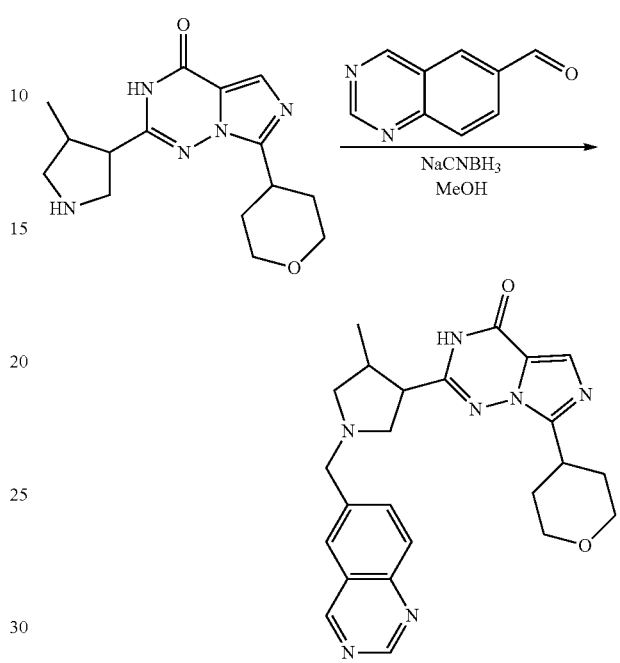

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in MeOH (15 mL) was added pyridazine-4-carbaldehyde (53.5 mg, 0.49 mmol) at RT under argon atmosphere. After being stirred for 2 h, NaCNBH$_3$ (77 mg, 1.23 mmol) was added to the reaction mixture and stirring was continued for another 16 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyridazin-4-ylmethyl)pyrrolidin-3-yl)-7-(tetrahydro-2H-pyran-4-yl)imidazo[5,1-f][1,2,4]triazin-4(3H)-one (35 mg, 22%) as an off-white solid; $^1$H-NMR (DMSO d$_6$, 400 MHz): δ 11.62 (bs, 1H), 9.21 (s, 1H), 9.14 (d, 1H), 7.68 (s, 1H), 7.57-7.55 (m, 1H), 3.96-3.94 (m, 2H), 3.79-3.71 (m, 2H), 3.54-3.51 (m, 2H), 2.99-2.82 (m, 5H), 2.68-2.64 (m, 1H), 2.34-2.31 (m, 1H), 1.87-1.82 (m, 4H), 1.12 (d, 3H); Mass (ESI): 396.3 [M$^+$+1]; LC-MS: 94.26%; 3.96 [M$^+$+1]; (column; X-bridge C-18, (50×3.0 mm, 3.5µ); RT 3.31 min. 5 mM NH$_4$OAc in water: ACN; 0.8 ml/min); HPLC (purity): 95%; (column; Eclipse XDB C-18, (150×4.6 mm, 5.0µ); RT 6.91 min. 5 mM NH$_4$OAc (Aq): ACN; 1.0 ml/min; Chiral HPLC: 96.99%, R$_t$=6.89 min (Chiralpak IA, 250×4.6 mm, 5µ; mobile phase (A) 0.1% DEA in n-Hexane (B) Ethanol (A:B:50:50); flow Rate: 1.00 mL/min); Optical rotation [α]$_D^{20}$: +27.32° (c=0.25, DCM); TLC: 7% MeOH/DCM (Rf: 0.5).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in MeOH (10 mL) was added quinazoline-6-carbaldehyde (98 mg, 0.62 mmol) at RT under argon atmosphere. After being stirred for 2 h, NaCNBH$_3$ (78 mg, 1.23 mmol) was added to the reaction mixture and stirring was continued for another 16 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinazolin-6-ylmethyl)pyrrolidin-3-yl)-7-(tetrahydro-2H-pyran-4-yl)imidazo[5,1-f][1,2,4]triazin-4(3H)-one (70 mg, 38%) as an off-white solid; $^1$H-NMR (DMSO d$_6$, 400 MHz): δ 9.57 (s, 1H), 9.24 (s, 1H), 8.02-7.94 (m, 3H), 7.62 (s, 1H), 3.97-3.88 (m, 4H), 3.51-3.47 (m, 3H), 3.04-3.01 (m, 1H), 3.92-3.87 (m, 1H), 2.85-2.81 (m, 2H), 2.71-2.65 (m, 1H), 2.36-2.32 (m, 1H), 1.87-1.82 (m, 4H), 1.12 (d, 3H); Mass (ESI): 446 [M$^+$+1]; LC-MS: 98.52%; 446 [M$^+$+1]; (column; X-bridge C-18, (50×3.0 mm, 3.5µ); RT 3.86 min. 5 mM NH$_4$OAc in water: ACN; 0.8 ml/min); UPLC (purity): 98.39%; (column; Acquity HSS T3, (2.1×100 mm, 1.8µ); RT 2.77 min. 0.025% TFA (Aq): ACN; 0.3 ml/min; Chiral HPLC: 99.24%, R$_t$=23.63 min (Chiralpak IA, 250×4.6 mm, 5µ; mobile phase (A) 0.1% DEA in n-Hexane (B) Ethanol (A:B:75:25); flow Rate: 1.00 mL/min); Optical rotation [α]$_D^{20}$: +3.76° (c=0.25, DCM); TLC: 10% MeOH/DCM (Rf: 0.3).

86. (+)-2-((3,4-trans)-4-methyl-1-(quinoxalin-6-ylmethyl)pyrrolidin-3-yl)-7-(tetrahydro-2H-pyran-4-yl)imidazo[5,1-f][1,2,4]triazin-4(3H)-one

87. (+)-2-((3,4-trans)-4-methyl-1-(quinoxalin-2-ylmethyl)pyrrolidin-3-yl)-7-(tetrahydro-2H-pyran-4-yl)imidazo[5,1-f][1,2,4]triazin-4(3H)-one

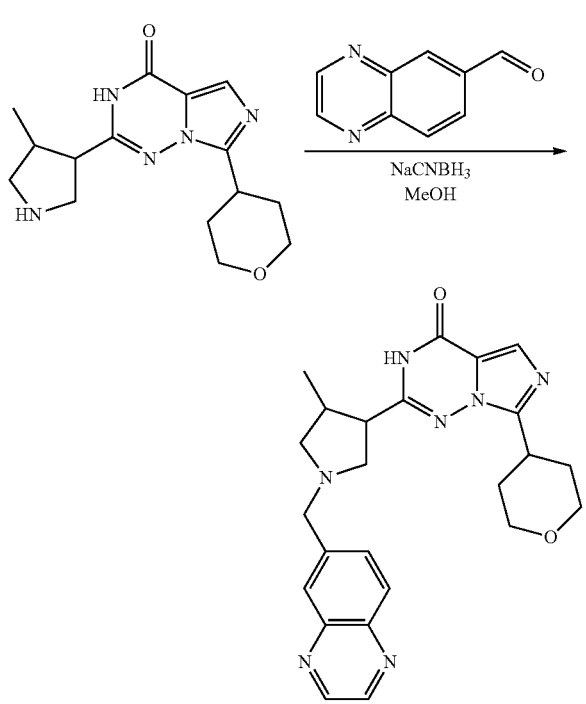

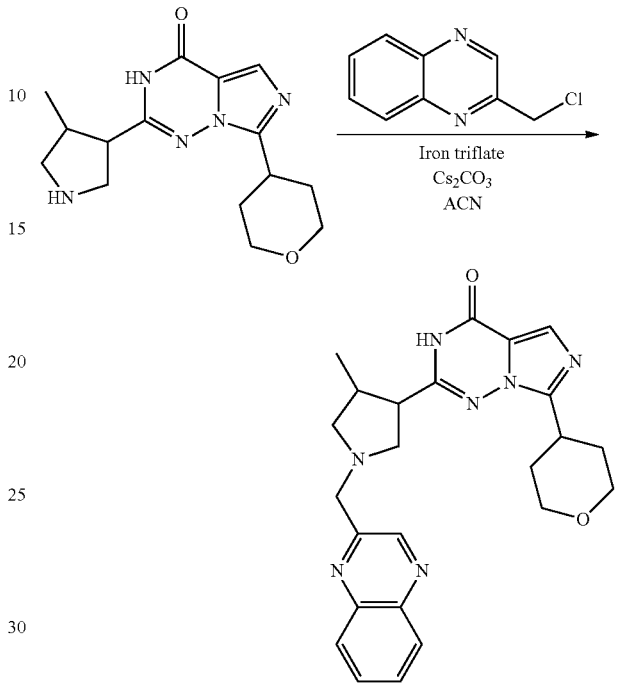

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in MeOH (10 mL) was added quinoxaline-6-carbaldehyde (98 mg, 0.62 mmol) at RT under an argon atmosphere. After being stirred for 2 h, NaCNBH$_3$ (78 mg, 1.23 mmol) was added to the reaction mixture and stirring was continued for another 16 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinoxalin-6-ylmethyl)pyrrolidin-3-yl)-7-(tetrahydro-2H-pyran-4-yl)imidazo[5,1-f][1,2,4]triazin-4(3H)-one (70 mg, 38%) as an off-white solid; $^1$H-NMR (DMSO d$_6$, 400 MHz): δ 8.91 (d, 2H), 8.08 (d, 1H), 8.01 (s, 1H), 7.87 (d, 1H), 7.64 (s, 1H), 3.95-3.91 (m, 4H), 3.54-3.50 (m, 3H), 3.04-3.01 (m, 1H), 2.96-2.94 (m, 1H), 2.87-2.84 (m, 2H), 2.72-2.64 (m, 1H), 2.34-2.31 (m, 1H), 1.87-1.82 (m, 4H), 1.12 (d, 3H); Mass (ESI): 446 [M$^+$+1]; LC-MS: 98.47%; 446 [M$^+$+1]; (column; X-bridge C-18, (50×3.0 mm, 3.5μ); RT 2.72 min. 5 mM NH$_4$OAc in water: ACN; 0.8 ml/min); UPLC (purity): 96.41%; (column; Acquity BEH C-18, (50×2.1 mm, 1.7μ); RT 1.38 min. 0.025% TFA (Aq): ACN; 0.50 ml/min; Chiral HPLC: 99.37%, R$_t$=23.23 min (Chiralpak IA, 250×4.6 mm, 5μ; mobile phase (A) 0.1% TEA in n-Hexane (B) Ethanol (A:B:75:25); flow Rate: 1.00 mL/min); Optical rotation [α]$_D^{20}$: +8.65° (c=0.25, DCM); TLC: 10% MeOH/DCM (Rf: 0.6).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in ACN (10 mL) were added 2-(chloromethyl)quinoxaline (81 mg, 0.45 mmol), Iron triflate (41.5 mg, 0.082 mmol) and Cs$_2$CO$_3$ (268 mg, 0.82 mmol) at RT under an argon atmosphere. The resultant reaction mixture was heated to 70° C. and stirred for 3 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinoxalin-2-ylmethyl)pyrrolidin-3-yl)-7-(tetrahydro-2H-pyran-4-yl)imidazo[5,1-f][1,2,4]triazin-4(3H)-one (50 mg, 27%) as an off-white solid; $^1$H-NMR (DMSO d$_6$, 400 MHz): δ 11.62 (bs, 1H), 9.02 (s, 1H), 8.09-8.07 (m, 2H), 7.85-7.81 (m, 2H), 7.54 (s, 1H), 4.12-4.08 (m, 1H), 3.96-3.92 (m, 3H), 3.51-3.46 (m, 2H), 3.41-3.37 (m, 1H), 3.07-2.98 (m, 3H), 2.89-2.82 (m, 1H), 2.67-2.63 (m, 1H), 2.38-2.31 (m, 1H), 1.89-1.82 (m, 4H), 1.12 (d, 3H); Mass (ESI): 446 [M$^+$+1]; LC-MS: 94.55%; 446 (M−1); (column; X-bridge C-18, (50×3.0 mm, 3.5μ); RT 2.90 min. 5 mM NH$_4$OAc in water: ACN; 0.8 ml/min); HPLC (purity): 95.65%; (column; Eclipse XDB C-18, (150× 4.6 mm, 5.0μ); RT 8.74 min. 5 mM NH$_4$OAc (Aq): ACN; 1.0 ml/min; Chiral HPLC: 99.32%, R$_t$=14.77 min (Chiralpak IA, 250×4.6 mm, 5μ; mobile phase (A) 0.1% DEA in n-Hexane (B) EtOH (A:B:75:25); flow Rate: 1.00 mL/min); Optical rotation [α]$_D^{20}$: +104.92° (c=0.25, DCM); TLC: 7% MeOH/DCM (Rf: 0.4).

563

88. (+)-2-((3,4-trans)-4-methyl-1-((1-methyl-1H-benzo[d]imidazol-2-yl)methyl)pyrrolidin-3-yl)-7-(tetrahydro-2H-pyran-4-yl)imidazo[5,1-f][1,2,4]triazin-4(3H)-one

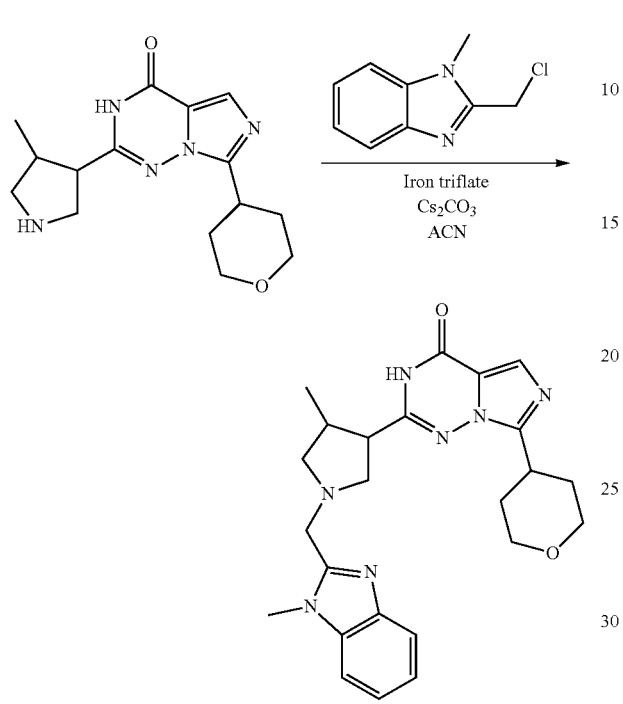

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in ACN (15 mL) were added 2-(chloromethyl)-1-methyl-1H-benzo[d]imidazole (81.9 mg, 0.45 mmol), Iron triflate (41.5 mg, 0.082 mmol) and Cs$_2$CO$_3$ (268 mg, 0.82 mmol) at RT under argon atmosphere. The resultant reaction mixture was heated to 70° C. and stirred for 3 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-((1-methyl-1H-benzo[d]imidazol-2-yl)methyl)pyrrolidin-3-yl)-7-(tetrahydro-2H-pyran-4-yl)imidazo[5,1-f][1,2,4]triazin-4(3H)-one (50 mg, 27%) as an off-white solid; $^1$H-NMR (DMSO d$_6$, 400 MHz): δ 11.57 (bs, 1H), 7.64 (s, 1H), 7.58 (d, 1H), 7.52 (d, 1H), 7.21-7.14 (m, 2H), 3.98-3.94 (m, 4H), 3.86 (s, 3H), 3.51-3.47 (m, 2H), 3.41-3.37 (m, 2H), 3.02-2.97 (m, 1H), 2.95-2.91 (m, 1H), 2.85-2.82 (m, 1H), 2.67-2.63 (m, 1H), 2.34-2.31 (m, 1H), 1.86-1.82 (m, 4H), 1.08 (d, 3H); Mass (ESI): 448 [M$^+$+1]; LC-MS: 98.45%; 448 (M−1); (column; X-bridge C-18, (50×3.0 mm, 3.5μ); RT 4.20 min. 5 mM NH$_4$OAc in water: ACN; 0.8 ml/min); HPLC (purity): 98.46%; (column; Eclipse XDB C-18, (150×4.6 mm, 5.0μ); RT 8.86 min. 5 mM NH$_4$OAc (Aq): ACN; 1.0 ml/min; Chiral HPLC: 99.41%, R$_t$=11.24 min (Chiralpak IA, 250× 4.6 mm, 5μ; mobile phase (A) 0.1% DEA in n-Hexane (B) EtOH (A:B:75:25); flow Rate: 1.00 mL/min); Optical rotation [α]$_D^{20}$: +30.75° (c 0.25, DCM); TLC: 7% MeOH/DCM (Rf: 0.3).

564

89. (−)-2-((3,4-trans)-1-((1H-benzo[d]imidazol-2-yl)methyl)-4-methylpyrrolidin-3-yl)-7-(tetrahydro-2H-pyran-4-yl)imidazo[5,1-f][1,2,4]triazin-4(3H)-one

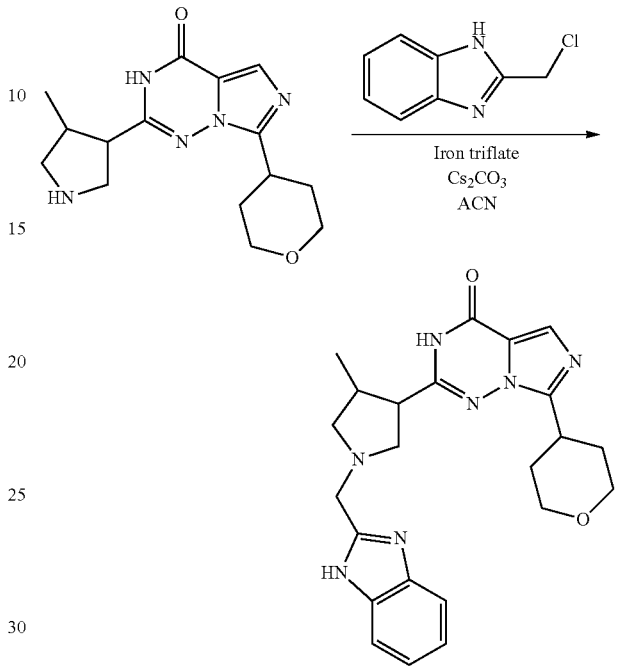

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in ACN (10 mL) were added 2-(chloromethyl)-1H-benzo[d]imidazole (75 mg, 0.45 mmol), Iron triflate (41.5 mg, 0.082 mmol) and Cs$_2$CO$_3$ (268 mg, 0.82 mmol) at RT under argon atmosphere. The resultant reaction mixture was heated to 70° C. and stirred for 3 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (−)-2-((3,4-trans)-1-((1H-benzo[d]imidazol-2-yl)methyl)-4-methylpyrrolidin-3-yl)-7-(tetrahydro-2H-pyran-4-yl)imidazo[5,1-f][1,2,4]triazin-4(3H)-one (30 mg, 24%) as an off-white solid; $^1$H-NMR (DMSO d$_6$, 400 MHz): δ 12.29 (bs, 1H), 7.65 (s, 1H), 7.51-7.47 (m, 2H), 7.16-7.12 (m, 2H), 3.92-3.84 (m, 4H), 3.52-3.47 (m, 2H), 3.41-3.36 (m, 2H), 3.13-3.01 (m, 1H), 2.99-2.95 (m, 1H), 2.87-2.81 (m, 2H), 2.71-2.67 (m, 1H), 2.47-2.41 (m, 1H), 1.88-1.82 (m, 4H), 1.12 (d, 3H); Mass (ESI): 434.4 [M$^+$+1]; LC-MS: 98.07%; 434.3 (M−1); (column; X-bridge C-18, (50×3.0 mm, 3.5μ); RT 3.09 min. 5 mM NH$_4$OAc: ACN; 0.8 ml/min); UPLC (purity): 99.87%; (column; Acquity BEH C-18, (50×2.1 mm, 1.7μ); RT 1.55 min. 0.025% TFA (Aq): ACN; 0.50 ml/min; Chiral HPLC: 91.34%, R$_t$=8.24 min (Chiralpak IA, 250×4.6 mm, 5μ; mobile phase (A) 0.1% TEA in n-Hexane (B) IPA (A:B:75:25); flow Rate: 1.00 mL/min); Optical rotation [α]$_D^{20}$: −13.39° (c=0.25, DCM); TLC: 7% MeOH/DCM (Rf: 0.5).

90. (+)-2-((3,4-trans)-1-(imidazo[1,2-a]pyridin-2-ylmethyl)-4-methylpyrrolidin-3-yl)-7-(tetrahydro-2H-pyran-4-yl)imidazo[5,1-f][1,2,4]triazin-4(3H)-one 91. (−)-2-((3,4-trans)-1-benzoyl-4-methylpyrrolidin-3-yl)-7-(tetrahydro-2H-pyran-4-yl)imidazo[5,1-f][1,2,4]triazin-4(3H)-one

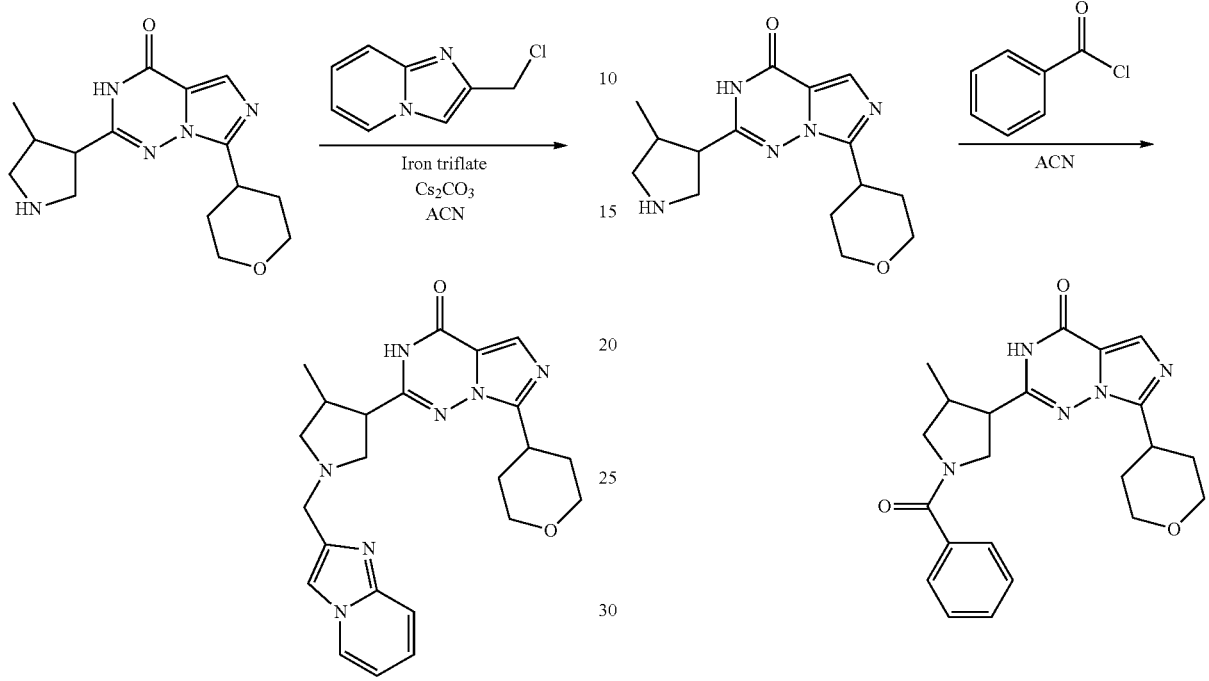

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in ACN (15 mL) were added 2-(chloromethyl)imidazo[1,2-a]pyridine (131 mg, 0.64 mmol), Iron triflate (50 mg, 0.09 mmol) and $Cs_2CO_3$ (482 mg, 1.08 mmol) at RT under argon atmosphere. The resultant reaction mixture was heated to 70° C. and stirred for 5 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-1-(imidazo[1,2-a]pyridin-2-ylmethyl)-4-methylpyrrolidin-3-yl)-7-(tetrahydro-2H-pyran-4-yl)imidazo[5,1-f][1,2,4]triazin-4(3H)-one (20 mg, 14%) as an off-white solid; $^1$H-NMR (DMSO $d_6$, 400 MHz): δ 11.68 (bs, 1H), 8.48 (d, 1H), 7.67 (s, 1H), 7.49-7.47 (m, 1H), 7.20-7.18 (m, 1H), 6.84-6.80 (m, 1H), 3.96-3.91 (m, 2H), 3.81-3.75 (m, 2H), 3.62-3.45 (m, 2H), 3.04-2.99 (m, 3H), 2.91-2.87 (m, 3H), 2.69-2.65 (m, 1H), 2.38-2.31 (m, 1H), 1.82-1.77 (m, 4H), 1.12 (d, 3H); Mass (ESI): 434.6 [M$^+$+1]; LC-MS: 99%; 434 [M$^+$+1]; (column; X-bridge C-18, (150× 4.6 mm, 3.5µ); RT 2.46 min. 5 mM NH$_4$OAc: ACN; 0.8 ml/min); UPLC (purity): 99%; (column; Acquity BEH C-18, (50×2.1 mm, 1.7µ); RT 1.15 min. 0.025% TFA (Aq): ACN; 0.50 ml/min; Chiral HPLC: 99%, R$_t$=8.04 min (Chiralpak IA, 250×4.6 mm, 5µ; mobile phase (A) 0.1% DEA in n-Hexane (B) EtOH (A:B:60:40); flow Rate: 1.00 mL/min); Optical rotation [α]$_D^{20}$: +23.82° (c=0.25, DCM); TLC: 10% MeOH/DCM (Rf: 0.3).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (135 mg, 0.44 mmol) in ACN (25 mL) was added a solution of benzoyl chloride (94 mg, 0.66 mmol) in ACN (25 mL) at 0° C. under argon atmosphere. The resultant reaction mixture was allowed to warm to room temperature and stirred for 20 min. The reaction mixture was diluted with water (50 mL) and extracted with EtOAc (3×50 mL). Combined organic layer was dried over sodium sulphate, filtered and concentrated in vacuo to obtain the crude product. The crude material was purified by silica gel column chromatography to afford (−)-2-((3,4-trans)-1-benzoyl-4-methylpyrrolidin-3-yl)-7-(tetrahydro-2H-pyran-4-yl)imidazo[5,1-f][1,2,4]triazin-4(3H)-one (50 mg, 37%) as an off-white solid; $^1$H-NMR (DMSO $d_6$, 400 MHz): δ 11.95 (bs, 1H), 7.67 (d, 1H), 7.52-7.49 (m, 1H), 7.38-7.29 (m, 3H), 3.99-3.91 (m, 3H), 3.82-3.78 (m, 2H), 3.76-3.72 (m, 2H), 3.39-3.37 (m, 1H), 3.26-3.21 (m, 1H), 3.01-2.94 (m, 1H), 2.72-2.64 (m, 1H), 1.89-1.82 (m, 4H), 1.07 (d, 3H); Mass (ESI): 408 [M$^+$+1]; LC-MS: 99.90%; 408.3 [M$^+$+1]; (column; X-bridge C-18, (50×3.0 mm, 3.5µ); RT 2.33 min. 0.05% TFA in water: ACN; 0.8 ml/min); UPLC (purity): 99.82%; (column; Acquity BEH C-18, (50×2.1 mm, 1.7µ); RT 1.94 min. 0.025% TFA (Aq): ACN; 0.50 ml/min; Chiral HPLC: 99.46%, R$_t$=22.60 min (Chiralpak IA, 250×4.6 mm, 5µ; mobile phase (A) n-Hexane (B) DCM:MeOH (80:20) (A:B:80:20); flow Rate: 1.00 mL/min); Optical rotation [α]$_D^{20}$: −20.00° (c=0.25, DCM); TLC: 10% MeOH/DCM (Rf: 0.7).

92. (−)-2-((3,4-trans)-1-(2-fluorobenzoyl)-4-methyl-pyrrolidin-3-yl)-7-(tetrahydro-2H-pyran-4-yl)imidazo[5,1-f][1,2,4]triazin-4(3H)-one

93. (−)-2-((3,4-trans)-1-(3-fluorobenzoyl)-4-methyl-pyrrolidin-3-yl)-7-(tetrahydro-2H-pyran-4-yl)imidazo[5,1-f][1,2,4]triazin-4(3H)-one

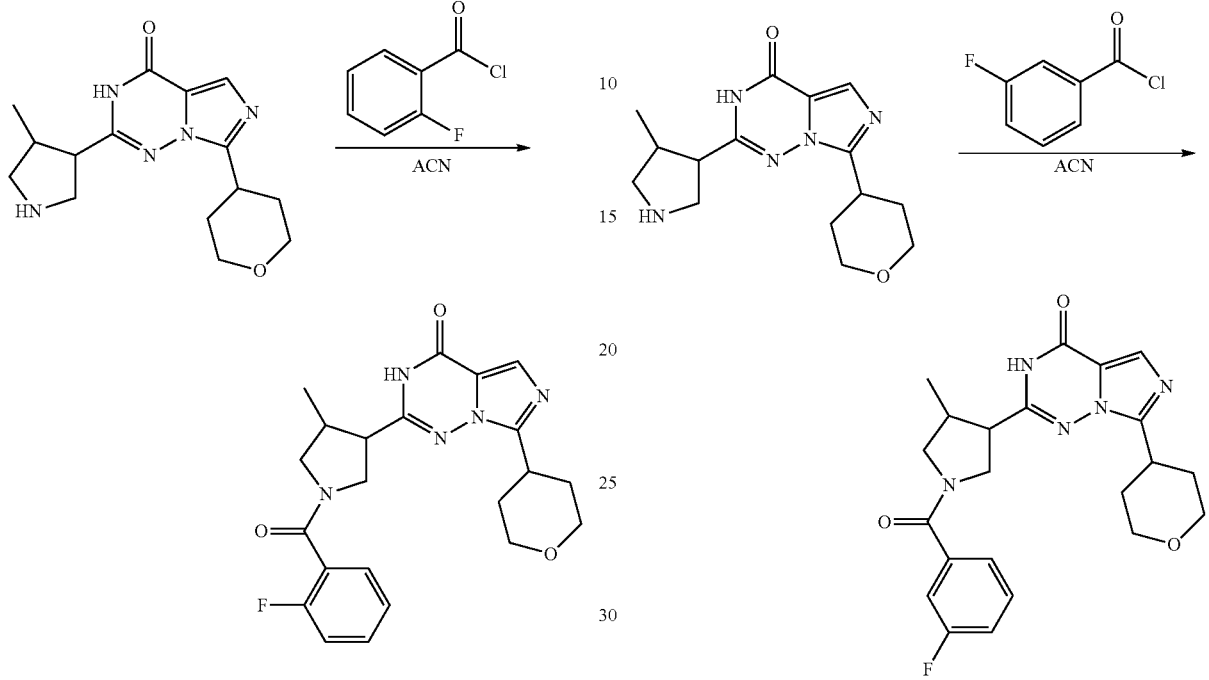

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in ACN (25 mL) was added a solution of 2-fluorobenzoyl chloride (98 mg, 0.61 mmol) in ACN (25 mL) at 0° C. under argon atmosphere. The resultant reaction mixture was allowed to warm to room temperature and stirred for 20 min. The reaction mixture was diluted with water (50 mL) and extracted with EtOAc (3×50 mL). Combined organic layer was dried over sodium sulphate, filtered and concentrated in vacuo to obtain the crude product. The crude material was purified by silica gel column chromatography to afford (−)-2-((3,4-trans)-1-(2-fluorobenzoyl)-4-methylpyrrolidin-3-yl)-7-(tetrahydro-2H-pyran-4-yl)imidazo[5,1-f][1,2,4]triazin-4(3H)-one (73.3 mg, 52%) as an off-white solid; $^1$H-NMR (DMSO d$_6$, 400 MHz): δ 11.95 (bs, 1H), 7.65 (d, 1H), 7.52-7.42 (m, 2H), 7.32-7.29 (m, 2H), 3.97-3.95 (m, 2H), 3.82-3.79 (m, 2H), 3.54-3.42 (m, 4H), 3.33-3.29 (m, 1H), 3.02-2.97 (m, 1H), 2.71-2.68 (m, 1H), 1.87-1.77 (m, 4H), 1.07 (d, 3H); Mass (ESI): 426.4 [M$^+$+1]; LC-MS: 99%; 426.4 [M$^+$+1]; (column; X-bridge C-18, (150×4.6 mm, 3.5µ); RT 2.53 min. 5 mM NH$_4$OAc: ACN; 0.8 ml/min); HPLC (purity): 97.56%; (column; Eclipse XDB C-18, (150×4.6 mm, 5.0µ); RT 7.84 min. 5 mM NH$_4$OAc (Aq): ACN; 1.0 ml/min; Chiral HPLC: 99.57%, R$_t$=11.44 min (Chiralpak IA, 250×4.6 mm, 5µ; mobile phase (A) n-Hexane (B) DCM:MeOH (80:20) (A:B: 75:25); flow Rate: 1.00 mL/min); Optical rotation [α]$_D^{20}$: −17.00° (c=0.25, DCM); TLC: 10% MeOH/DCM (Rf: 0.7).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in ACN (25 mL) was added a solution of 2-fluorobenzoyl chloride (98 mg, 0.61 mmol) in ACN (25 mL) at 0° C. under argon atmosphere. The resultant reaction mixture was allowed to warm to room temperature and stirred for 20 min. The reaction mixture was diluted with water (50 mL) and extracted with EtOAc (3×50 mL). Combined organic layer was dried over sodium sulphate, filtered and concentrated in vacuo to obtain the crude product. The crude material was purified by silica gel column chromatography to afford (−)-2-((3,4-trans)-1-(3-fluorobenzoyl)-4-methylpyrrolidin-3-yl)-7-(tetrahydro-2H-pyran-4-yl)imidazo[5,1-f][1,2,4]triazin-4(3H)-one (50 mg, 36%) as an off-white solid; $^1$H-NMR (DMSO d$_6$, 400 MHz): δ 11.95 (bs, 1H), 7.67 (d, 1H), 7.52-7.49 (m, 1H), 7.38-7.29 (m, 3H), 3.99-3.91 (m, 3H), 3.82-3.78 (m, 2H), 3.76-3.72 (m, 2H), 3.39-3.37 (m, 1H), 3.26-3.21 (m, 1H), 3.01-2.94 (m, 1H), 2.72-2.64 (m, 1H), 1.89-1.82 (m, 4H), 1.07 (d, 3H); Mass (ESI): 426 [M$^+$+1]; LC-MS: 99.60%; 426.4 [M$^+$+1]; (column; X-bridge C-18, (50×3.0 mm, 3.5µ); RT 2.56 min. 5 mM NH$_4$OAc: ACN; 0.8 ml/min); UPLC (purity): 99.78%; (column; Acquity BEH C-18, (50×2.1 mm, 1.7µ); RT 1.85 min. 0.025% TFA (Aq): ACN; 0.50 ml/min; Chiral HPLC: 100%, R$_t$=13.57 min (Chiralpak IA, 250×4.6 mm, 5µ; mobile phase (A) n-Hexane (B) DCM:MeOH (80:20) (A:B:75:25); flow Rate: 1.00 mL/min); Optical rotation [α]$_D^{20}$: −17.85° (c=0.25, DCM); TLC: 10% MeOH/DCM (Rf: 0.7).

94. (−)-2-((3,4-trans)-1-(4-fluorobenzoyl)-4-methyl-pyrrolidin-3-yl)-7-(tetrahydro-2H-pyran-4-yl)imidazo[5,1-f][1,2,4]triazin-4(3H)-one

95. (−)-2-((3,4-trans)-4-methyl-1-nicotinoylpyrrolidin-3-yl)-7-(tetrahydro-2H-pyran-4-yl)imidazo[5,1-f][1,2,4]triazin-4(3H)-one

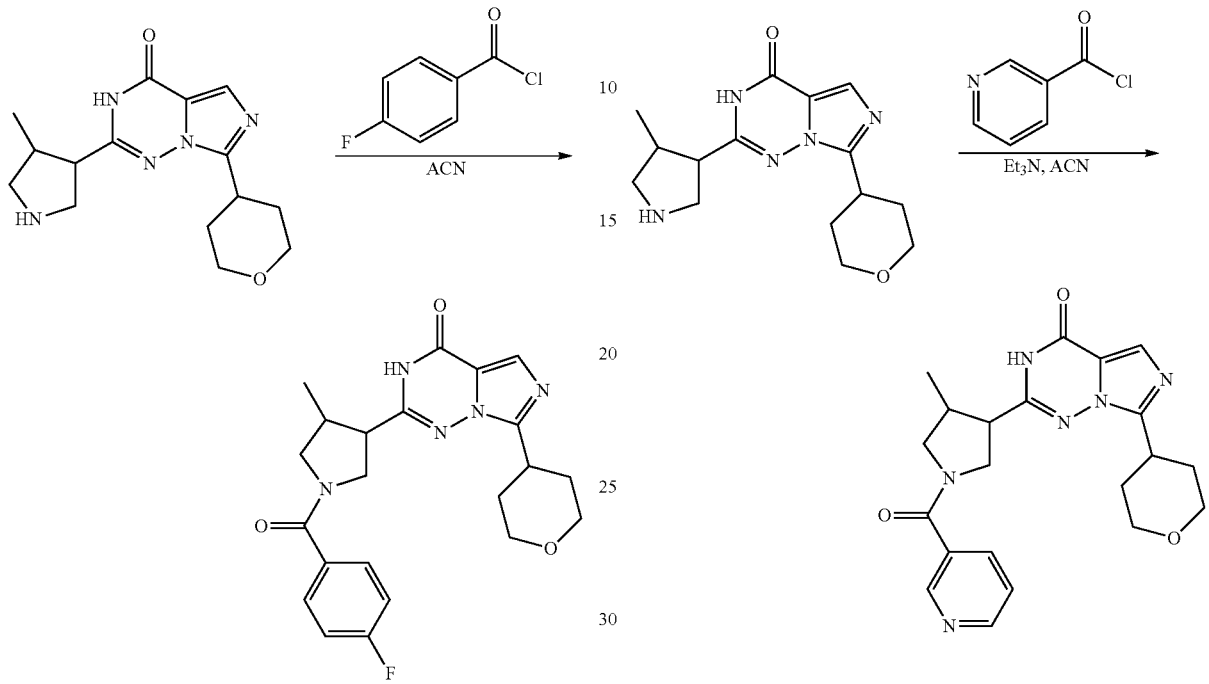

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in ACN (30 mL) was added a solution of 4-fluorobenzoyl chloride (117 mg, 0.74 mmol) in ACN (30 mL) at 0° C. under argon atmosphere. The resultant reaction mixture was allowed to warm to room temperature and stirred for 20 min. The reaction mixture was diluted with water (50 mL) and extracted with EtOAc (3×50 mL). Combined organic layer was dried over sodium sulphate, filtered and concentrated in vacuo to obtain the crude product. The crude material was purified by silica gel column chromatography to afford (−)-2-((3,4-trans)-1-(4-fluorobenzoyl)-4-methylpyrrolidin-3-yl)-7-(tetrahydro-2H-pyran-4-yl)imidazo[5,1-f][1,2,4]triazin-4(3H)-one (43 mg, 36%) as an off-white solid; $^1$H-NMR (DMSO d$_6$, 400 MHz): δ 11.95 (bs, 1H), 7.68-7.58 (m, 3H), 7.31-7.29 (m, 2H), 3.96-3.94 (m, 2H), 3.81-3.74 (m, 2H), 3.72-3.64 (m, 2H), 3.49-3.47 (m, 1H), 3.42-3.38 (m, 1H), 3.29-3.21 (m, 1H), 3.01-2.28 (m, 1H), 2.72-2.64 (m, 1H), 1.92-1.84 (m, 4H), 1.07 (d, 3H); Mass (ESI): 426 [M$^+$+1]; LC-MS: 99.84%; 3.98 [M$^+$+1]; (column; X-bridge C-18, (50×3.0 mm, 3.5μ); RT 3.98 min. 5 mM NH$_4$OAc: ACN; 0.8 ml/min); UPLC (purity): 99.89%; (column; Acquity BEH C-18, (50×2.1 mm, 1.7μ); RT 1.87 min. 0.025% TFA (Aq): ACN; 0.50 ml/min; Chiral HPLC: 99%, R$_t$=21.59 min (Chiralpak IA, 250×4.6 mm, 5μ; mobile phase (A) 0.1 DEA in n-Hexane (B) DCM:MeOH (80:20) (A:B:80:20); flow Rate: 1.00 mL/min); Optical rotation [α]$_D^{20}$: −21.05° (c=0.25, DCM); TLC: 10% MeOH/DCM (Rf: 0.8).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (135 mg, 0.44 mmol) in ACN (30 mL) was added Et$_3$N (0.12 mL, 0.89 mmol) followed by nicotinoyl chloride (120 mg, 0.66 mmol) at 0° C. under argon atmosphere. The resultant reaction mixture was allowed to warm to room temperature and stirred for 4 h. The reaction mixture was diluted with water (100 mL) and extracted with DCM (3×50 mL). Combined organic layer was dried over sodium sulphate, filtered and concentrated in vacuo to obtain the crude product. The crude material was purified by silica gel column chromatography to afford (−)-2-((3,4-trans)-4-methyl-1-nicotinoylpyrrolidin-3-yl)-7-(tetrahydro-2H-pyran-4-yl)imidazo[5,1-f][1,2,4]triazin-4(3H)-one (45 mg, 41%) as an off-white solid; $^1$H-NMR (DMSO d$_6$, 400 MHz): δ 11.95 (bs, 1H), 8.79 (d, 1H), 8.66 (s, 1H), 8.07-7.97 (m, 1H), 7.65 (d, 1H), 7.52-7.48 (m, 1H), 4.02-3.92 (m, 5H), 3.51-3.47 (m, 2H), 3.41-3.38 (m, 1H), 3.36-3.32 (m, 1H), 3.24-3.21 (m, 1H), 2.69-2.54 (m, 1H), 1.91-1.82 (m, 4H), 1.06 (d, 3H); Mass (ESI): 409.3 [M$^+$+1]; LC-MS: 99.18%; 409.3 [M$^+$+1]; (column; X-bridge C-18, (50×3.0 mm, 3.5μ); RT 1.68 min. 0.05% TFA in water: ACN; 0.8 ml/min); UPLC (purity): 99.55%; (column; Acquity BEH C-18, (50×2.1 mm, 1.7μ); RT 1.41 min. 0.025% TFA (Aq): ACN; 0.50 ml/min; Chiral HPLC: 99.50%, R$_t$=12.47 min (Chiralpak IA, 250×4.6 mm, 5μ; mobile phase (A) 0.1% DEA in n-Hexane (B) DCM:MeOH (80:20) (A:B:70:30); flow Rate: 1.00 mL/min); Optical rotation [α]$_D^{20}$: −33.10° (c=0.25, DCM); TLC: 10% MeOH/DCM (Rf: 0.7).

571

96. (+)-2-((3,4-trans)-1-(4-fluorobenzoyl)-4-methyl-pyrrolidin-3-yl)-7-(tetrahydro-2H-pyran-4-yl)imidazo[5,1-f][1,2,4]triazin-4(3H)-one

572

97. (+)-2-((3,4-trans)-1-benzoyl-4-methylpyrrolidin-3-yl)-7-(tetrahydro-2H-pyran-4-yl)imidazo[5,1-f][1,2,4]triazin-4(3H)-one

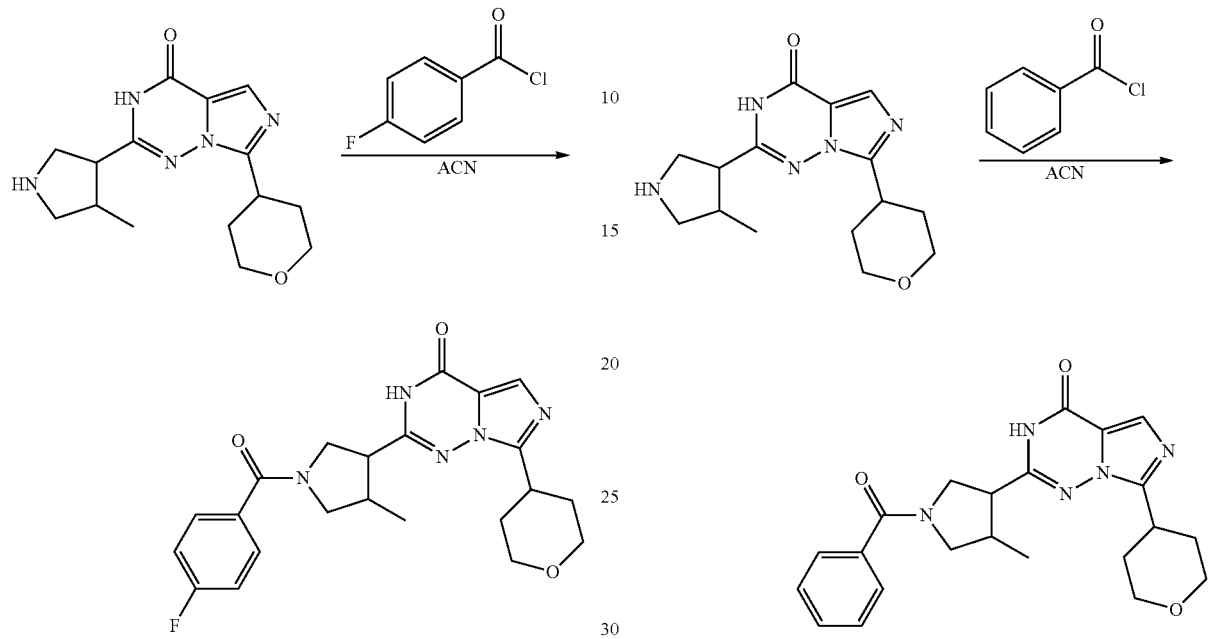

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) was added a solution of 4-fluorobenzoyl chloride (60 mg, 0.37 mmol) in ACN (10 mL) drop-wise at 0° C. under argon atmosphere. The resultant reaction mixture was allowed to warm to room temperature and stirred for 20 min. The reaction mixture was diluted with water (50 mL) and extracted with EtOAc (3×50 mL). Combined organic layer was dried over sodium sulphate, filtered and concentrated in vacuo to obtain the crude product. The crude material was purified by silica gel column chromatography to afford (+)-2-((3,4-trans)-1-(4-fluorobenzoyl)-4-methylpyrrolidin-3-yl)-7-(tetrahydro-2H-pyran-4-yl)imidazo[5,1-f][1,2,4]triazin-4(3H)-one (40 mg, 38%) as an off-white solid; $^1$H-NMR (DMSO $d_6$, 400 MHz): δ 11.92 (bs, 1H), 1.68-1.62 (m, 3H), 7.31-7.24 (m, 2H), 3.98-3.94 (m, 3H), 3.82-3.78 (m, 2H), 3.51-3.47 (m, 3H), 3.21-3.18 (m, 1H), 3.02-2.96 (m, 1H), 2.71-2.67 (m, 1H), 1.92-1.87 (m, 4H), 1.06 (d, 3H); Mass (ESI): 426.3 [M$^+$+1]; LC-MS: 99.07%; 426 [M$^+$+1]; (column; X-bridge C-18, (50×3.0 mm, 3.5μ); RT 2.73 min. 5 mM NH$_4$OAc: ACN; 0.8 ml/min); UPLC (purity): 97.53%; (column; Acquity BEH C-18, (50×2.1 mm, 1.7μ); RT 1.93 min. 0.025% TFA (Aq): ACN; 0.50 ml/min; Chiral HPLC: 99.38%, R$_t$=23.70 min (Chiralpak IA, 250×4.6 mm, 5μ; mobile phase (A) 0.1% DEA in n-Hexane (B) DCM: MeOH (80:20) (A:B:80:20); flow Rate: 1.00 mL/min); Optical rotation [α]$_D^{20}$: +22.81° (c=0.25, DCM); TLC: 10% MeOH/DCM (Rf: 0.7).

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) was added a solution of benzoyl chloride (52 mg, 0.37 mmol) in ACN (10 mL) drop-wise at 0° C. under argon atmosphere. The resultant reaction mixture was allowed to warm to room temperature and stirred for 20 min. The reaction mixture was diluted with water (50 mL) and extracted with EtOAc (3×50 mL). Combined organic layer was dried over sodium sulphate, filtered and concentrated in vacuo to obtain the crude product. The crude material was purified by silica gel column chromatography to afford (+)-2-((3,4-trans)-1-benzoyl-4-methylpyrrolidin-3-yl)-7-(tetrahydro-2H-pyran-4-yl)imidazo[5,1-f][1,2,4]triazin-4(3H)-one (45 mg, 45%) as an off-white solid; $^1$H-NMR (DMSO $d_6$, 400 MHz): δ 11.92 (bs, 1H), 7.68 (d, 1H), 7.58-7.46 (m, 5H), 3.97-3.91 (m, 3H), 3.87-3.80 (m, 2H), 3.52-3.50 (m, 1H), 3.49-3.46 (m, 1H), 3.29-3.19 (m, 1H), 3.01-2.94 (m, 1H), 2.68-2.61 (m, 1H), 1.89-1.82 (m, 4H), 1.17-1.16 (m, 1H), 1.07 (d, 3H); Mass (ESI): 408 [M$^+$+1]; LC-MS: 96.33%; 408.4 [M$^+$+1]; (column; X-bridge C-18, (50×3.0 mm, 3.5μ); RT 2.34 min. 0.05% TFA in water: ACN; 0.8 ml/min); UPLC (purity): 95.79%; (column; Acquity BEH C-18, (50×2.1 mm, 1.7μ); RT 1.70 min. 0.025% TFA (Aq): ACN; 0.50 ml/min; Chiral HPLC: 99.77%, R$_t$=24.36 min (Chiralpak IA, 250×4.6 mm, 5μ; mobile phase (A) n-Hexane (B) DCM:MeOH (80:20) (A:B:80:20); flow Rate: 1.00 mL/min); Optical rotation [α]$_D^{20}$: +21.68° (c=0.25, DCM); TLC: 10% MeOH/DCM (Rf: 0.7).

573

98. (+)-2-((3,4-trans)-4-methyl-1-(pyridin-3-ylmethyl)pyrrolidin-3-yl)-7-(tetrahydro-2H-pyran-4-yl)imidazo[5,1-f][1,2,4]triazin-4(3H)-one

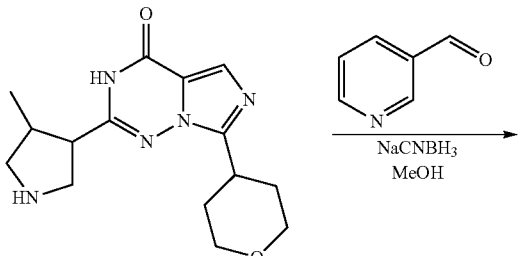

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in MeOH (15 mL) was added nicotinaldehyde (66.2 mg, 0.61 mmol) at RT under argon atmosphere. After being stirred for 2 h; NaCNBH$_3$ (77.9 mg, 1.23 mmol) was added to the reaction mixture and stirring was continued for another 16 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyridin-3-ylmethyl)pyrrolidin-3-yl)-7-(tetrahydro-2H-pyran-4-yl)imidazo[5,1-f][1,2,4]triazin-4(3H)-one (60 mg, 33%) as an off-white solid; $^1$H-NMR (DMSO d$_6$, 400 MHz): δ 8.56-8.48 (m, 2H), 7.74-7.72 (m, 1H), 7.66 (s, 1H), 7.37-7.32 (m, 1H), 3.94-3.91 (m, 2H), 3.72-3.61 (m, 2H), 3.52-2.47 (m, 3H), 2.95-2.91 (m, 2H), 2.81-2.76 (m, 2H), 2.66-2.61 (m, 1H), 1.27-1.22 (m, 1H), 1.89-1.81 (m, 4H), 1.09 (d, 3H); Mass (ESI): 395 [M$^+$+1]; LC-MS: 97.38%; 395.3 [M$^+$+1]; (column; X-bridge C-18, (50×3.0 mm, 3.5μ); RT 2.37 min. 5 mM NH$_4$OAc: ACN; 0.8 ml/min); HPLC (purity): 95.6%; (column; Eclipse XDB C-18, (150×4.6 mm, 5.0μ); RT 7.71 min. 5 mM NH$_4$OAc (Aq): ACN; 1.0 ml/min; Chiral HPLC: 99.55%, R$_t$=9.51 min (Chiralpak IA, 250×4.6 mm, 5μ; mobile phase (A) 0.1% TEA in n-Hexane (B) IPA (A:B:75:25); flow Rate: 1.00 mL/min); Optical rotation [α]$_D^{20}$: +10.06° (c=0.25, DCM); TLC: 7% MeOH/DCM (Rf: 0.5).

574

99. (+)-2-((3,4-trans)-4-methyl-1-((2-methylpyrimidin-4-yl)methyl)pyrrolidin-3-yl)-7-(tetrahydro-2H-pyran-4-yl)imidazo[5,1-f][1,2,4]triazin-4(3H)-one

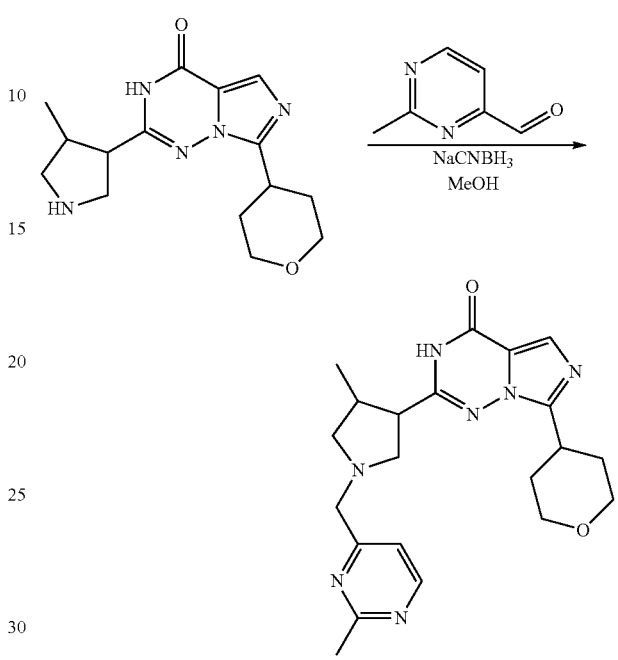

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in MeOH (10 mL) was added 2-methylpyrimidine-4-carbaldehyde (66 mg, 0.54 mmol) at RT under argon atmosphere. After being stirred for 2 h, NaCNBH$_3$ (92 mg, 1.47 mmol) was added to the reaction mixture and stirring was continued for another 16 h at RT. The volatiles were evaporated under reduced pressure. The residue was diluted with ice-cold water (15 mL) and extracted with DCM (2×20 mL). Combined organic layer was dried over sodium sulphate, filtered and concentrated in vacuo to obtain the crude product. The crude material was purified by silica gel column chromatography and then further purified by preparative HPLC to afford (+)-2-((3,4-trans)-4-methyl-1-((2-methylpyrimidin-4-yl)methyl)pyrrolidin-3-yl)-7-(tetrahydro-2H-pyran-4-yl)imidazo[5,1-j][1,2,4]triazin-4(3H)-one (50 mg, 25%) as an off-white solid; $^1$H-NMR (DMSO d$_6$, 400 MHz): δ 11.72 (bs, 1H), 8.64 (d, 1H), 7.67 (s, 1H), 7.32 (d, 1H), 3.97-3.93 (m, 2H), 3.84-3.68 (m, 2H), 3.52-3.47 (m, 2H), 3.41-3.37 (m, 1H), 3.06-2.38 (m, 4H), 2.69-2.65 (m, 2H), 2.58 (s, 3H), 2.37-2.32 (m, 4H), 1.09 (d, 3H); Mass (ESI): 410 [M$^+$+1]; LC-MS: 98.26%; 410.3 [M$^+$+1]; (column; X-bridge C-18, (50×3.0 mm, 3.5μ); RT 2.31 min. 5 mM NH$_4$OAc: ACN; 0.8 ml/min); HPLC (purity): 99.24%; (column; Eclipse XDB C-18, (150×4.6 mm, 5.0μ); RT 7.50 min. 5 mM NH$_4$OAc (Aq): ACN; 1.0 ml/min; Chiral HPLC: 100%, R$_t$=10.36 min (Chiralpak IA, 250×4.6 mm, 5μ; mobile phase (A) 0.1% TEA in n-Hexane (B) IPA (A:B:75:25); flow Rate: 1.00 mL/min); Optical rotation [α]$_D^{20}$: +69.96° (c=0.25, DCM); TLC: 10% MeOH/DCM (Rf: 0.4).

100. (+)-2-((3,4-trans)-4-methyl-1-(pyrimidin-4-ylmethyl)pyrrolidin-3-yl)-7-(tetrahydro-2H-pyran-4-yl)imidazo[5,1-f][1,2,4]triazin-4(3H)-one

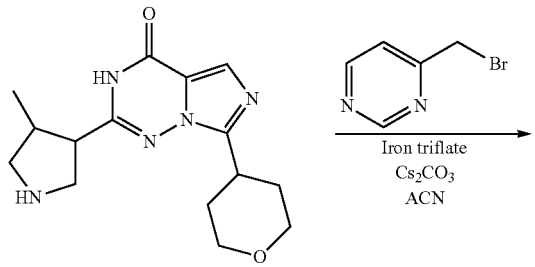

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in ACN (10 mL) were added 4-(bromomethyl)pyrimidine (111 mg, 0.61 mmol), Iron triflate (49.8 mg, 0.09 mmol) and Cs$_2$CO$_3$ (322 mg, 0.98 mmol) at RT under argon atmosphere. The resultant reaction mixture was heated to 70° C. and stirred for 3 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyrimidin-4-ylmethyl)pyrrolidin-3-yl)-7-(tetrahydro-2H-pyran-4-yl)imidazo[5,1-f][1,2,4]triazin-4(3H)-one (15 mg, 8%) as an off-white solid; $^1$H-NMR (DMSO d$_6$, 400 MHz): δ 11.71 (bs, 1H), 9.07 (s, 1H), 8.76 (d, 1H), 7.65 (s, 1H), 7.58 (d, 1H), 3.97-3.88 (m, 2H), 3.86-2.74 (m, 2H), 3.51-3.47 (m, 2H), 3.42-3.89 (m, 2H), 3.09-3.01 (m, 1H), 2.98-2.89 (m, 2H), 2.85-2.81 (m, 1H), 2.69-2.61 (m, 1H), 2.92-2.85 (m, 4H), 1.09 (d, 3H); Mass (ESI): 396 [M$^+$+1]; LC-MS: 98.85%; 396 (M$^+$+1); (column; X-bridge C-18, (50×3.0 mm, 3.5μ); RT 2.43 min. 5 mM NH$_4$OAc: ACN; 0.8 ml/min); UPLC (purity): 99.57%; (column; Acquity HSS T3, (2.1×100 mm, 1.8μ); RT 2.83 min. 0.025% TFA (Aq): ACN; 0.3 ml/min; Chiral HPLC: 100%, R$_t$=11.34 min (Chiralpak IA, 250×4.6 mm, 5μ; mobile phase (A) n-Hexane (B) DCM:MeOH (80:20) (A:B:75:25); flow Rate: 1.00 mL/min); Optical rotation [α]$_D^{20}$: +76.38° (c=0.25, DCM); TLC: 7% MeOH/DCM (Rf: 0.4).

101. (−)-2-((3,4-trans)-1-(imidazo[1,2-a]pyrimidin-2-ylmethyl)-4-methylpyrrolidin-3-yl)-7-(tetrahydro-2H-pyran-4-yl)imidazo[5,1-f][1,2,4]triazin-4(3H)-one

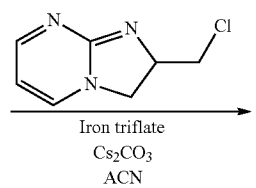

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in ACN (10 mL) were added 2-(chloromethyl)-2,3-dihydroimidazo[1,2-a]pyrimidine (107 mg, 0.64 mmol), iron triflate (49.8 mg, 0.09 mmol) and Cs$_2$CO$_3$ (322 mg, 0.98 mmol) at RT under argon atmosphere. The resultant reaction mixture was heated to 70° C. and stirred for 3 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (−)-2-((3,4-trans)-1-(imidazo[1,2-a]pyrimidin-2-ylmethyl)-4-methylpyrrolidin-3-yl)-7-(tetrahydro-2H-pyran-4-yl)imidazo[5,1-f][1,2,4]triazin-4(3H)-one (14 mg, 7%) as an off-white solid; $^1$H-NMR (DMSO d$_6$, 400 MHz): δ 8.91 (s, 1H), 8.48 (d, 1H), 7.81 (s, 1H), 7.67 (s, 1H), 7.04-7.68 (m, 1H), 4.96-4.91 (m, 2H), 4.86-4.81 (m, 2H), 3.51-3.47 (m, 4H), 3.14-3.11 (m, 2H), 3.07-3.05 (m, 1H), 3.85-3.82 (m, 2H), 2.87-2.84 (m, 1H), 1.89-1.82 (m, 4H), 1.12 (d, 3H); Mass (ESI): 435 [M$^+$+1]; LC-MS: 93.27%; 435 (M$^+$+1); (column; X-bridge C-18, (50×3.0 mm, 3.5μ); RT 2.10 min. 5 mM NH$_4$OAc: ACN; 0.8 ml/min); UPLC (purity): 98%; (column; Acquity BEH C-18, (50×2.1 mm, 1.7μ); RT 1.33 min. 0.025% TFA (Aq): ACN; 0.50 ml/min; Chiral HPLC: 98.98%, R$_t$=18.66 min (Chiralpak IA, 250×4.6 mm, 5μ; mobile phase (A) 0.1% DEA in n-Hexane (B) EtOH (A:B:75:25); flow Rate: 1.00 mL/min); Optical rotation [α]$_D^{20}$: −2.70° (c=0.25, DCM); TLC: 7% MeOH/DCM (Rf: 0.4).

102. (+)-2-((3,4-trans)-1-([1,2,4]triazolo[1,5-a]pyridin-2-ylmethyl)-4-methylpyrrolidin-3-yl)-7-(tetrahydro-2H-pyran-4-yl)imidazo[5,1-f][1,2,4]triazin-4(3H)-one

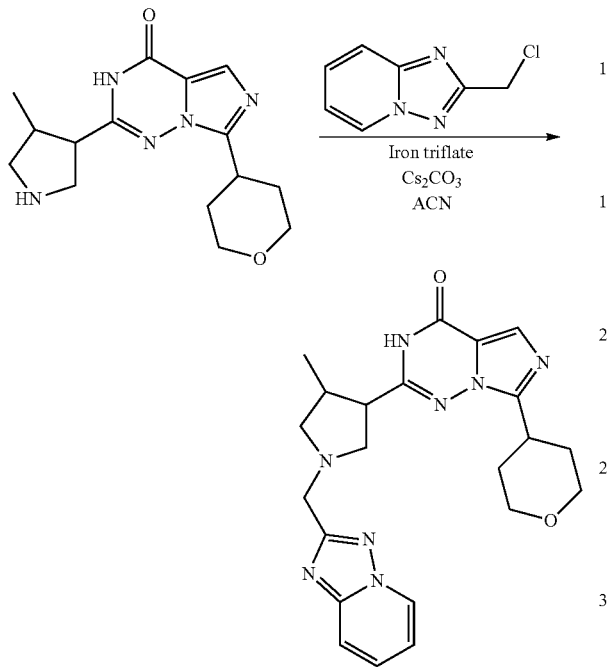

103. (+)-2-((3,4-trans)-4-methyl-1-(phenylsulfonyl)pyrrolidin-3-yl)-7-(tetrahydro-2H-pyran-4-yl)imidazo[5,1-f][1,2,4]triazin-4(3H)-one

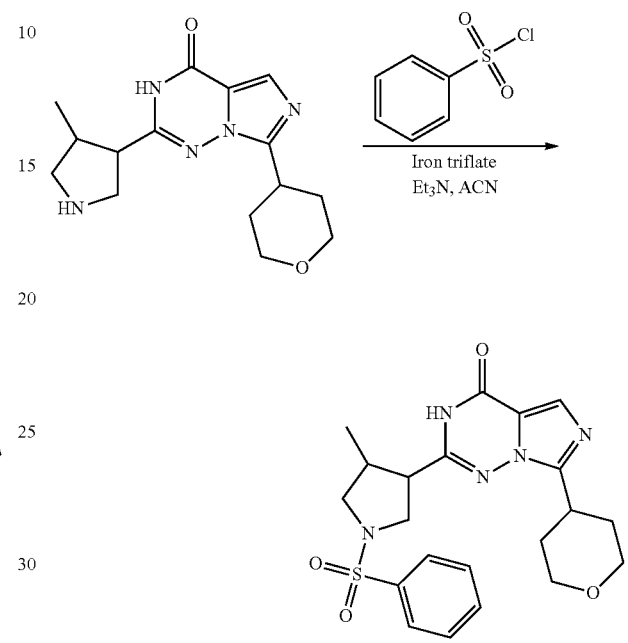

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 2-(chloromethyl)-[1,2,4]triazolo[1,5-a]pyridine (60 mg, 0.36 mmol), Iron triflate (33.2 mg, 0.06 mmol) and $Cs_2CO_3$ (215 mg, 0.65 mmol) at RT under argon atmosphere. The resultant reaction mixture was heated to 70° C. and stirred for 3 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-1-([1,2,4]triazolo[1,5-a]pyridin-2-ylmethyl)-4-methylpyrrolidin-3-yl)-7-(tetrahydro-2H-pyran-4-yl)imidazo[5,1-f][1,2,4]triazin-4(3H)-one (30 mg, 21%) as an off-white solid; $^1$H-NMR (DMSO $d_6$, 400 MHz): δ 11.68 (bs, 1H), 8.89 (s, 1H), 7.78 (s, 1H), 7.66-7.62 (m, 2H), 7.14-7.12 (m, 1H), 3.96-3.91 (m, 4H), 3.49-3.41 (m, 3H), 3.12-2.95 (m, 2H), 2.98-2.96 (m, 1H), 2.79-2.75 (m, 1H), 2.67-2.61 (m, 1H), 2.47-2.41 (m, 1H), 1.89-1.82 (m, 4H), 1.08 (d, 3H); Mass (ESI): 435 [M$^+$+1]; LC-MS: 95.73%; 435.7 [M$^+$+1]; (column; X-bridge C-18, (50×3.0 mm, 3.5μ); RT 1.63 min. 5 mM $NH_4OAc$: ACN; 0.8 ml/min); UPLC (purity): 95%; (column; Acquity BEH C-18, (50×2.1 mm, 1.7μ); RT 1.30 min. 0.025% TFA (Aq): ACN; 0.50 ml/min; Chiral HPLC: 98%, $R_t$=14.91 min (Chiralpak IA, 250×4.6 mm, 5μ; mobile phase (A) n-Hexane (B) DCM:MeOH (80:20) (A:B:80:20); flow Rate: 1.00 mL/min); Optical rotation $[\alpha]_D^{20}$: +75.12° (c=0.25, DCM); TLC: 5% MeOH/DCM (Rf: 0.4).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added benzenesulfonyl chloride (58.2 mg, 0.33 mmol), Iron triflate (33.2 mg, 0.06 mmol) and $Et_3N$ (66.6 mg, 0.99 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(phenylsulfonyl)pyrrolidin-3-yl)-7-(tetrahydro-2H-pyran-4-yl)imidazo[5,1-f][1,2,4]triazin-4(3H)-one (40 mg, 27%) as an off-white solid; $^1$H-NMR (DMSO $d_6$, 400 MHz): δ 11.74 (bs, 1H), 7.89 (d, 2H), 7.61-7.54 (m, 4H), 3.96-3.89 (m, 2H), 3.78-3.75 (m, 1H), 3.62-3.59 (m, 1H), 3.48-3.41 (m, 3H), 3.23-3.20 (m, 2H), 2.94-2.91 (m, 1H), 2.87-2.82 (m, 1H), 1.89-1.81 (m, 4H), 1.02 (d, 3H); Mass (ESI): 444 [M$^+$+1]; LC-MS: 99.77%; 444 (M$^+$+1); (column; X-bridge C-18, (150×4.6 mm, 3.5μ); RT 2.85 min. 5 mM $NH_4OAc$: ACN; 0.8 ml/min); HPLC (purity): 97.42%; (column; Eclipse XDB C-18, (150×4.6 mm, 5.0μ); RT 8.45 min. 5 mM $NH_4OAc$ (Aq): ACN; 1.0 ml/min; Chiral HPLC: 98.77%, $R_t$=21.97 min (Chiralpak IA, 250×4.6 mm, 5μ; mobile phase (A) n-Hexane (B) DCM:MeOH (80:20) (A:B:80:20); flow Rate: 1.00 mL/min); Optical rotation $[\alpha]_D^{20}$: +5.40° (c=0.25, DCM); TLC: 5% MeOH/DCM (Rf: 0.4).

579

104. (+)-2-((3,4-trans)-1-((2-fluorophenyl)sulfonyl)-4-methylpyrrolidin-3-yl)-7-(tetrahydro-2H-pyran-4-yl)imidazo[5,1-f][1,2,4]triazin-4(3H)-one

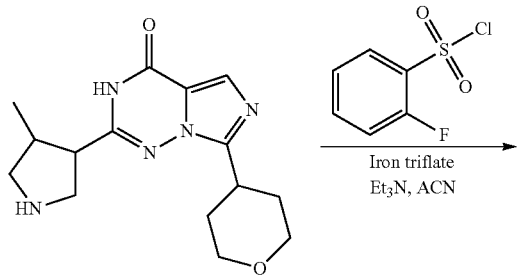

580

105. (+)-2-((3,4-trans)-1-((4-fluorophenyl)sulfonyl)-4-methylpyrrolidin-3-yl)-7-(tetrahydro-2H-pyran-4-yl)imidazo[5,1-f][1,2,4]triazin-4(3H)-one

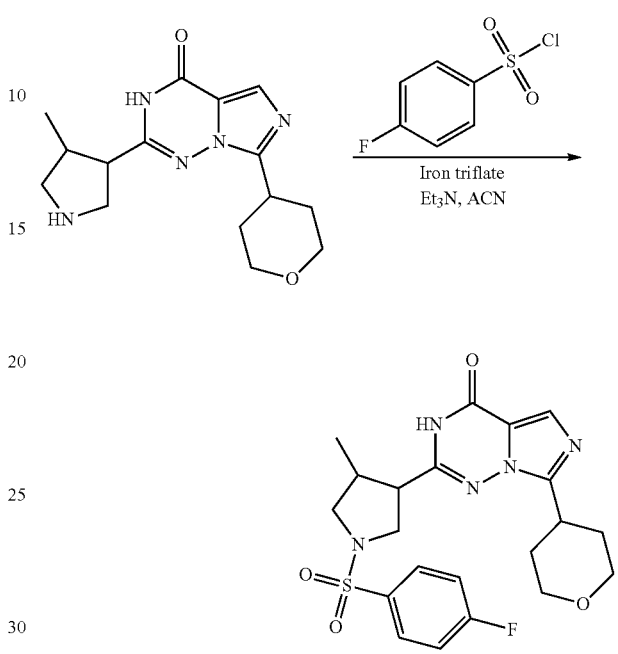

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 2-fluorobenzene-1-sulfonyl chloride (64.2 mg, 0.33 mmol), Iron triflate (33.2 mg, 0.06 mmol) and Et$_3$N (66.6 mg, 0.99 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-1-((2-fluorophenyl)sulfonyl)-4-methylpyrrolidin-3-yl)-7-(tetrahydro-2H-pyran-4-yl)imidazo[5,1-f][1,2,4]triazin-4(3H)-one (50 mg, 33%) as an off-white solid; $^1$H-NMR (DMSO d$_6$, 400 MHz): δ 11.82 (bs, 1H), 7.82-7.79 (m, 1H), 7.67-7.62 (m, 2H), 7.41-7.29 (m, 2H), 3.96-3.94 (m, 2H), 3.79-3.74 (m, 1H), 3.64-3.62 (m, 2H), 3.47-3.41 (m, 2H), 3.21-3.16 (m, 1H), 3.02-2.99 (m, 1H), 2.92-2.89 (m, 1H), 2.65-2.62 (m, 1H), 1.82-1.78 (m, 4H), 1.02 (d, 3H); Mass (ESI): 462.4 [M$^+$+1]; LC-MS: 99.41%; 462.4 (M$^+$+1); (column; X-bridge C-18, (50×3.0 mm, 3.5μ); RT 2.65 min. 0.05% TFA in water: ACN; 0.8 ml/min); UPLC (purity): 99.86%; (column; Acquity BEH C-18, (50×2.1 mm, 1.7μ); RT 1.99 min. 0.025% TFA (Aq): ACN; 0.50 ml/min; Chiral HPLC: 100%, R$_t$=9.11 min (Chiralpak IA, 250×4.6 mm, 5μ; mobile phase (A) 0.1% DEA in n-Hexane (B) EtOH (A:B:70:30); flow Rate: 1.00 mL/min); Optical rotation [α]$_D^{20}$: +5.24° (c=0.25, DCM); TLC: 5% MeOH/DCM (Rf: 0.5).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 4-fluorobenzene-1-sulfonyl chloride (64.2 mg, 0.33 mmol), iron triflate (33.2 mg, 0.06 mmol) and Et$_3$N (66.6 mg, 0.99 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-1-((4-fluorophenyl)sulfonyl)-4-methylpyrrolidin-3-yl)-7-(tetrahydro-2H-pyran-4-yl)imidazo[5,1-f][1,2,4]triazin-4(3H)-one (55 mg, 36%) as an off-white solid; $^1$H-NMR (DMSO d$_6$, 400 MHz): δ 11.74 (bs, 1H), 7.92-7.89 (m, 2H), 7.64 (s, 1H), 7.41-7.36 (m, 2H), 3.96-3.89 (m, 2H), 3.76-3.74 (m, 1H), 3.62-3.57 (m, 1H), 3.49-3.44 (m, 4H), 3.27-3.21 (m, 1H), 2.96-2.92 (m, 1H), 2.81-2.78 (m, 1H), 1.82-1.76 (m, 4H), 0.98 (d, 3H); Mass (ESI): 462 [M$^+$+1]; LC-MS: 98.39%; 462.4 (M$^+$+1); (column; X-bridge C-18, (50×3.0 mm, 3.5μ); RT 2.80 min. 5 mM NH$_4$OAc: ACN; 0.8 ml/min); HPLC (purity): 99.45%; (column; Eclipse XDB C-18, (150×4.6 mm, 5.0μ); RT 8.68 min. 5 mM NH$_4$OAc: ACN; 1.0 ml/min; Chiral HPLC: 98.57%, R$_t$=20.45 min (Chiralpak IC, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +3.37° (c≤0.25, DCM); TLC: 5% MeOH/DCM (Rf: 0.4).

106. (−)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile

107. (−)-2-((3,4-trans)-4-methyl-1-(phenylsulfonyl)pyrrolidin-3-yl)-7-(tetrahydro-2H-pyran-4-yl)imidazo[5,1-f][1,2,4]triazin-4(3H)-one

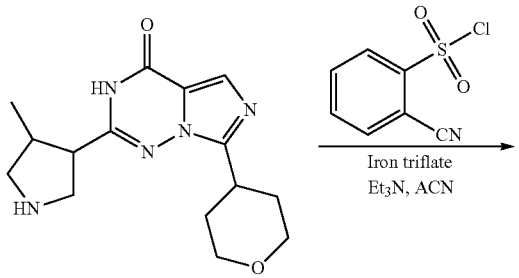

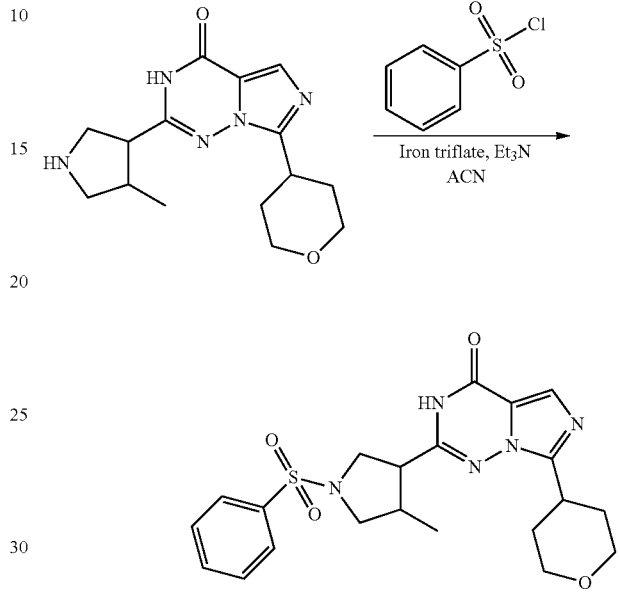

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 2-cyanobenzene-1-sulfonyl chloride (66.5 mg, 0.33 mmol), Iron triflate (33.2 mg, 0.06 mmol) and Et$_3$N (66.6 mg, 0.99 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (−)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile (70 mg, 45%) as an off-white solid; $^1$H-NMR (DMSO d$_6$, 400 MHz): δ 11.81 (bs, 1H), 8.04 (d, 2H), 7.92-7.91 (m, 1H), 7.82-7.76 (m, 1H), 7.64 (s, 1H), 3.96-3.92 (m, 4H), 3.71-3.69 (m, 2H), 3.48-3.46 (m, 2H), 3.24-3.21 (m, 1H), 2.98-2.96 (m, 1H), 2.64-2.62 (m, 1H), 1.82-1.78 (m, 4H), 1.02 (d, 3H); Mass (ESI): 469.4 [M$^+$+1]; LC-MS: 98.31%; 469.4 (M$^+$+1); (column; X-bridge C-18, (50×3.0 mm, 3.5μ); RT 2.57 min. 0.05% TFA in water: ACN; 0.8 ml/min); UPLC (purity): 99.27%; (column; Acquity BEH C-18, (50×2.1 mm, 1.7μ); RT 1.93 min. 0.025% TFA (Aq): ACN; 0.50 ml/min; Chiral HPLC: 98.72%, R$_t$=16.34 min (Chiralpak IC, 250×4.6 mm, 5μ; mobile phase (A) 0.1% DEA in n-Hexane (B) DCM: MeOH (80:20) (A:B:50:50); flow Rate: 1.00 mL/min); Optical rotation [α]$_D^{20}$: −8.03° (c=0.25, MeOH:DCM (1:4)); TLC: 5% MeOH/DCM (Rf: 0.5).

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added iron triflate (24.9 mg, 0.04 mmol), Et$_3$N (49.9 mg, 0.44 mmol) and benzenesulfonyl chloride (43.7 mg, 0.24 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (−)-2-((3,4-trans)-4-methyl-1-(phenylsulfonyl)pyrrolidin-3-yl)-7-(tetrahydro-2H-pyran-4-yl)imidazo[5,1-f][1,2,4]triazin-4(3H)-one (45 mg, 41.28%) as an off-white solid; $^1$H-NMR (DMSO d$_6$, 400 MHz): δ 11.72 (bs, 1H), 7.84 (d, 2H), 7.62 (s, 1H), 7.58-7.54 (m, 3H), 3.96-3.89 (m, 2H), 3.75-3.72 (m, 1H), 3.62-3.59 (m, 1H), 3.51-3.42 (m, 3H), 3.21-3.18 (m, 1H), 2.96-2.91 (m, 1H), 2.92-2.87 (m, 1H), 2.80-2.78 (m, 1H), 1.82-1.75 (m, 4H), 0.94 (d, 3H); Mass (ESI): 444 [M$^+$+1]; LC-MS: 99.94%; 444 (M$^+$+1); (column; X-bridge C-18, (50×3.0 mm, 3.5μ); RT 2.85 min. 5 mM NH$_4$OAc: ACN; 0.8 ml/min); HPLC (purity): 97.64%; (column; Eclipse XDB C-18, (150×4.6 mm, 5.0μ); RT 8.44 min. 5 mM NH$_4$OAc (Aq): ACN; 1.0 ml/min; Chiral HPLC: 98.81%, R$_t$=20.27 min (Chiralpak IA, 250×4.6 mm, 5μ; mobile phase (A) n-Hexane (B) DCM:MeOH (80:20) (A:B: 80:20); flow Rate: 1.00 mL/min); Optical rotation [α]$_D^{20}$: −4.14° (c=0.25, DCM); TLC: 10% MeOH/DCM (Rf: 0.7).

108. (−)-2-((3,4-trans)-1-((4-fluorophenyl)sulfonyl)-4-methylpyrrolidin-3-yl)-7-(tetrahydro-2H-pyran-4-yl)imidazo[5,1-f][1,2,4]triazin-4(3H)-one

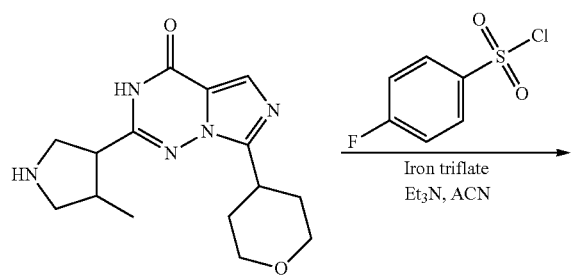

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added 4-fluorobenzene-1-sulfonyl chloride (48.1 mg, 0.24 mmol), iron triflate (24.9 mg, 0.049 mmol) and Et$_3$N (49.9 mg, 0.49 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (−)-2-((3,4-trans)-1-((4-fluorophenyl)sulfonyl)-4-methylpyrrolidin-3-yl)-7-(tetrahydro-2H-pyran-4-yl)imidazo[5,1-f][1,2,4]triazin-4(3H)-on (50 mg, 44%) as an off-white solid; $^1$H-NMR (DMSO d$_6$, 400 MHz): δ 11.74 (bs, 1H), 7.89 (d, 2H), 7.64 (s, 1H), 7.48-7.37 (m, 2H), 3.96-3.94 (m, 2H), 3.76-3.72 (m, 1H), 3.61-3.58 (m, 1H), 3.49-3.40 (m, 3H), 3.24-3.21 (m, 1H), 2.94-2.92 (m, 1H), 2.82-2.74 (m, 1H), 1.81-1.76 (m, 4H), 0.97 (d, 3H); Mass (ESI): 462 [M$^+$+1]; LC-MS: 98.85%; 462.4 (M$^+$+1); (column; X-bridge C-18, (150×4.6 mm, 3.5µ); RT 2.70 min. 0.05% TFA in water: ACN; 0.8 ml/min); HPLC (purity): 94.42%; (column; Eclipse XDB C-18, (150×4.6 mm, 5.0µ); RT 8.66 min. 5 mM NH$_4$OAc (Aq): ACN; 1.0 ml/min; Chiral HPLC: 95.37%, R$_t$=18.85 min (Chiralpak IA, 250×4.6 mm, 5µ; mobile phase (A) 0.1% DEA in n-Hexane (B) DCM:MeOH (80:20) (A:B:80:20); flow Rate: 1.00 mL/min); Optical rotation [α]$_D^{20}$: −4.72° (c=0.25, DCM); TLC: 5% MeOH/DCM (Rf: 0.5).

109. (+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile

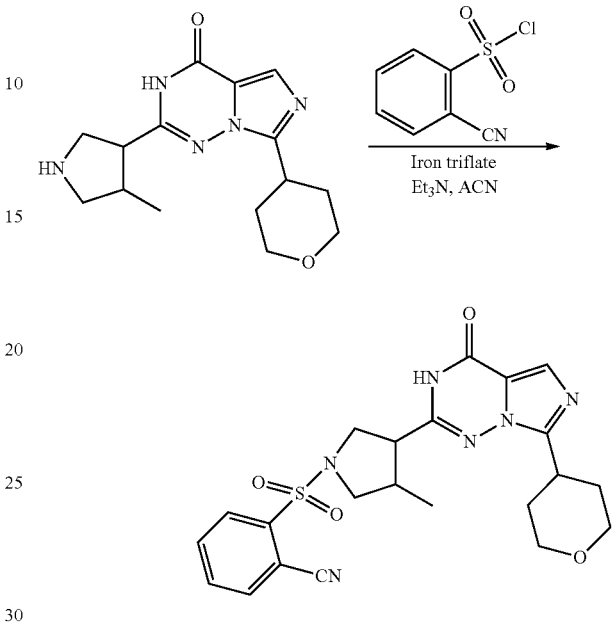

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (10 mL) were added 2-cyanobenzene-1-sulfonyl chloride (49.9 mg, 0.24 mmol), Iron triflate (24.9 mg, 0.049 mmol) and Et$_3$N (49.9 mg, 0.49 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile (55 mg, 47.49%) as an off-white solid; $^1$H-NMR (DMSO d$_6$, 500 MHz): δ 11.79 (bs, 1H), 8.04 (d, 2H), 7.89-7.86 (m, 1H), 7.81-7.74 (m, 1H), 7.62 (s, 1H), 3.94-3.92 (m, 3H), 3.69-3.63 (m, 2H), 3.47-3.41 (m, 2H), 3.26-3.22 (m, 1H), 3.08-3.06 (m, 1H), 2.98-2.95 (m, 1H), 2.64-2.61 (m, 1H), 1.84-1.81 (m, 4H), 1.03 (d, 3H); Mass (ESI): 469.4 [M$^+$+1]; LC-MS: 98.76%; 469.4 (M$^+$+1); (column; X-bridge C-18, (50×3.0 mm, 3.5µ); RT 2.59 min. 0.05% TFA in water: ACN; 0.8 ml/min); UPLC (purity): 98.23%; (column; Acquity BEH C-18, (50×2.1 mm, 1.7µ); RT 1.87 min. 0.025% TFA (Aq): ACN; 0.50 ml/min; Chiral HPLC: 99.48%, R$_t$=21.34 min (Chiralpak IC, 250×4.6 mm, 5µ; mobile phase (A) 0.1% DEA in n-Hexane (B) DCM:MeOH (80:20) (A:B:50:50); flow Rate: 1.00 mL/min); Optical rotation [α]$_D^{20}$: +11.96° (c=0.25, MeOH:DCM (1:4)); TLC: 5% MeOH/DCM (Rf: 0.5).

110. (+)-2-((3,4-trans)-4-methyl-1-(pyrimidin-5-ylmethyl)pyrrolidin-3-yl))-7-(tetrahydro-2H-pyran-4-yl)imidazo[5,1-f][1,2,4]triazin-4(3H)-one

111. (−)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile

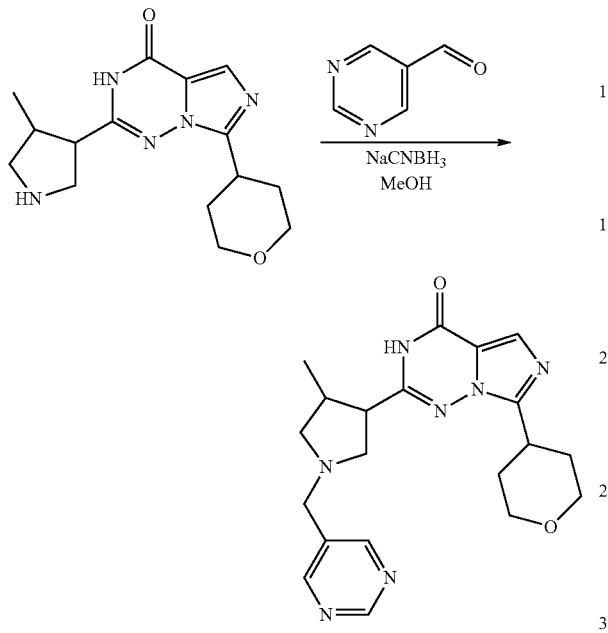

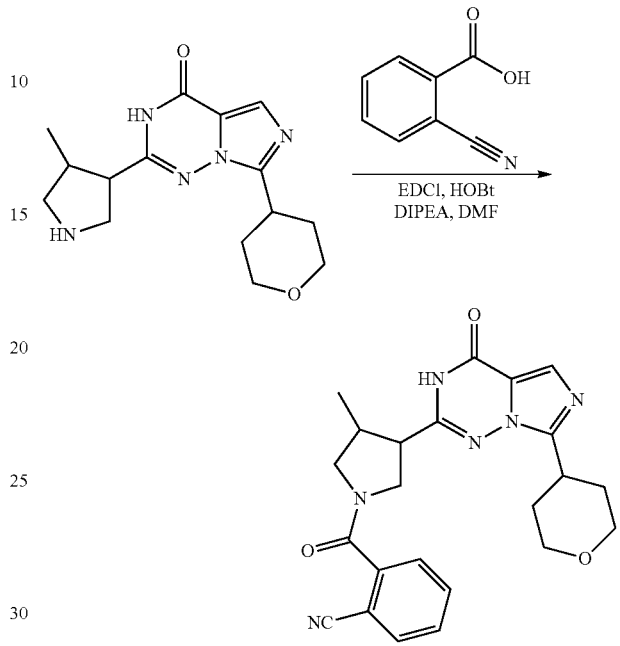

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added pyrimidine-5-carbaldehyde (46.3 mg, 0.42 mmol) at RT under argon atmosphere. After being stirred for 2 h, NaCNBH$_3$ (62.3 mg, 0.99 mmol) was added to the reaction mixture and stirring was continued for another 5 h at RT. The volatiles were evaporated under reduced pressure. The residue was diluted with ice-cold water and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyrimidin-5-ylmethyl)pyrrolidin-3-yl)-7-(tetrahydro-2H-pyran-4-yl)imidazo[5,1-f][1,2,4]triazin-4(3H)-one (35 mg, 27%) as an off-white solid. $^1$H-NMR (DMSO d$_6$, 500 MHz): δ 9.15 (s, 1H), 8.72 (s, 2H), 7.63 (s, 1H), 3.96-3.95 (m, 2H), 3.78-3.76 (m, 1H), 3.67-3.62 (m, 2H), 3.57-3.54 (m, 2H), 3.51-3.47 (m, 1H), 2.97-2.92 (m, 2H), 2.85-2.80 (m, 1H), 2.68-2.64 (m, 1H), 2.31-2.24 (m, 1H), 1.89-1.81 (m, 4H), 1.08 (d, 3H); Mass (ESI): 396.5 [M$^+$+1] LC-MS: 98.58%; 396.4 (M$^+$+1); (column; X-bridge C-18, (50×3.0 mm, 3.5μ); RT 3.21 min. 0.05% TFA in water: ACN; 0.8 ml/min); UPLC (purity): 95%; (column; Acquity HSS T3, (2.1×100 mm, 1.8μ); RT 2.80 min. 0.025% TFA (Aq): ACN; 0.3 ml/min; Chiral HPLC: 98.27%, R$_t$=9.35 min (Chiralpak IA, 250×4.6 mm, 5μ; mobile phase (A) 0.1% DEA in n-Hexane (B) Ethanol (A:B:60:40); flow Rate: 1.00 mL/min); Optical rotation [α]$_D^{20}$: +5.15° (c=0.25, DCM). TLC: 5% MeOH/DCM (Rf: 0.4).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in DMF (10 mL) were added EDCI (120 mg, 0.61 mmol), HOBt (84 mg, 0.61 mmol), DIPEA (160 mg, 1.23 mmol) and 2-cyanobenzoic acid (73 mg, 0.49 mmol) at 0° C. under argon atmosphere. The resulting reaction mixture was allowed to warm to room temperature and stirred for 16 h. The reaction mass was diluted with water (100 mL) and extracted with DCM (3×50 mL). Combined organic layer was dried over sodium sulphate, filtered and concentrated in vacuo to obtain the crude product. The crude material was purified by silica gel column chromatography to afford (−)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile (50 mg, 28%) as an off-white solid. $^1$H-NMR (DMSO d$_6$, 400 MHz): δ 11.95 (bs, 1H), 7.98 (d, 1H), 7.82-7.76 (m, 1H), 7.69-7.64 (m, 3H), 3.95-3.89 (m, 4H), 3.54-3.45 (m, 4H), 3.02-2.97 (m, 2H), 2.71-2.68 (m, 1H), 1.89-1.76 (m, 4H), 1.08 (d, 3H); Mass (ESI): 433 [M$^+$+1] LC-MS: 97.70%; 433.4 (M$^+$+1); (column; X-bridge C-18, (50×3.0 mm, 3.5μ); RT 2.29 min. 0.05% TFA in water: ACN; 0.8 ml/min); UPLC (purity): 97.76%; (column; Acquity BEH C-18, (50×2.1 mm, 1.7μ); RT 1.64 min. 0.025% TFA (Aq): ACN; 0.50 ml/min; Chiral HPLC: 99.15%, R$_t$=27.22 min (Chiralpak IA, 250×4.6 mm, 5μ; mobile phase (A) n-Hexane (B) DCM:MeOH (80:20) (A:B: 80:20); flow Rate: 1.00 mL/min); Optical rotation [α]$_D^{20}$: −18.91° (c=0.25, DCM). TLC: 10% MeOH/DCM (Rf: 0.6).

112. (+)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile

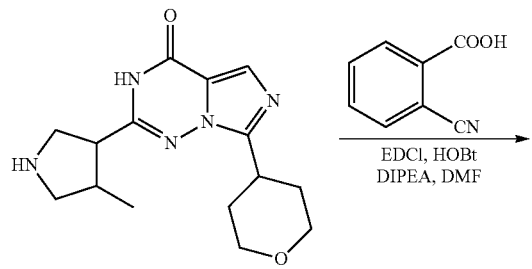

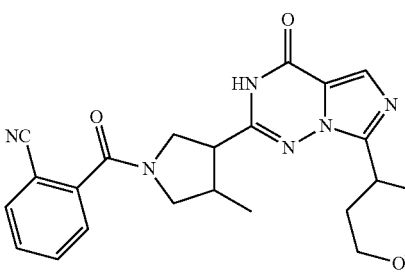

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in DMF (5 mL) were added EDCI (70 mg, 0.37 mmol), HOBt (50 mg, 0.37 mmol), DIPEA (95 mg, 0.74 mmol) and 2-cyanobenzoic acid (47.2 mg, 0.32 mmol) at 0° C. under argon atmosphere. The resulting reaction mixture was allowed to warm to room temperature and stirred for 8 h. The reaction mass was diluted with water (100 mL) and extracted with DCM (2×50 mL). Combined organic layer was dried over sodium sulphate, filtered and concentrated in vacuo to obtain the crude product. The crude material was purified by silica gel column chromatography to afford (+)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile (45 mg, 42%) as an off-white solid. $^1$H-NMR (DMSO d$_6$, 400 MHz): δ 11.95 (bs, 1H), 7.97 (d, 1H), 7.82-7.79 (m, 1H), 7.69-7.64 (m, 3H), 3.98-3.89 (m, 4H), 3.54-3.45 (m, 4H), 3.04-2.97 (m, 2H), 2.71-2.68 (m, 1H), 1.89-1.74 (m, 4H), 1.08 (d, 3H); Mass (ESI): 433 [M$^+$+1] LC-MS: 99%; 433.3 (M$^+$+1); (column; X-bridge C-18, (50×3.0 mm, 3.5μ); RT 2.28 min. 0.05% TFA in water: ACN; 0.8 ml/min); UPLC (purity): 97.94%; (column; Acquity BEH C-18, (50×2.1 mm, 1.7μ); RT 1.62 min. 0.025% TFA (Aq): ACN; 0.50 ml/min; Chiral HPLC: 99.58%, R$_t$=32.45 min (Chiralpak IA, 250×4.6 mm, 5μ; mobile phase (A) n-Hexane (B) DCM:MeOH (80:20) (A:B: 80:20); flow Rate: 1.00 mL/min); Optical rotation [α]$_D^{20}$: +19.61° (c=0.25, DCM). TLC: 10% MeOH/DCM (Rf: 0.6).

113. (−)-2-((3,4-trans)-4-methyl-1-(pyrimidine-2-carbonyl)pyrrolidin-3-yl)-7-(tetrahydro-2H-pyran-4-yl)imidazo[5,1-f][1,2,4]triazin-4(3H)-one

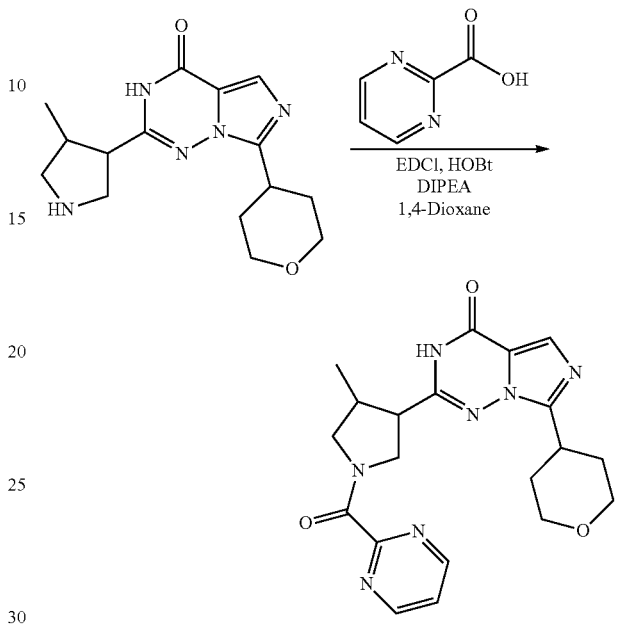

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in 1,4-Dioxane (20 mL) were added EDCI (120 mg, 0.61 mmol), HOBt (84 mg, 0.61 mmol), DIPEA (160 mg, 1.23 mmol) and 2-cyanobenzoic acid (73 mg, 0.49 mmol) at 0° C. under argon atmosphere. The resulting reaction mixture was allowed to warm to room temperature and stirred for 16 h. The reaction mass was diluted with water (100 mL) and extracted with DCM (3×50 mL). Combined organic layer was dried over sodium sulphate, filtered and concentrated in vacuo to obtain the crude product. The crude material was purified by silica gel column chromatography to afford (−)-2-((3,4-trans)-4-methyl-1-(pyrimidine-2-carbonyl)pyrrolidin-3-yl)-7-(tetrahydro-2H-pyran-4-yl)imidazo[5,1-f][1,2,4]triazin-4(3H)-one (60 mg, 36%) as an off-white solid. $^1$H-NMR (DMSO d$_6$, 400 MHz): δ 11.95 (bs, 1H), 8.92 (d, 2H), 7.67 (s, 1H), 7.64-7.61 (m, 1H), 3.98-3.87 (m, 4H), 3.65-3.42 (m, 4H), 3.12-2.97 (m, 2H), 2.68-2.61 (m, 1H), 1.87-1.80 (m, 4H), 1.09 (d, 3H); Mass (ESI): 410 [M$^+$+1] LC-MS: 99.89%; 410.3 (M$^+$+1); (column; X-bridge C-18, (50×3.0 mm, 3.5μ); RT 1.85 min. 0.05% TFA in water: ACN; 0.8 ml/min); UPLC (purity): 99.48%; (column; Eclipse XDB C-18, (150×4.6 mm, 5.0μ); RT 8.17 min. 5 mM NH$_4$OAc (Aq): ACN; 1.0 ml/min; Chiral HPLC: 99.13%, R$_t$=35.50 min (Chiralpak IA, 250×4.6 mm, 5μ; mobile phase (A) n-Hexane (B) DCM:MeOH (80:20) (A:B:80:20); flow Rate: 1.00 mL/min); Optical rotation [α]$_D^{20}$: −12.59° (c=0.25, DCM). TLC: 10% MeOH/DCM (Rf: 0.6).

114. (+)-2-((3,4-trans)-4-methyl-1-(pyrimidine-2-carbonyl)pyrrolidin-3-yl)-7-(tetrahydro-2H-pyran-4-yl)imidazo[5,1-f][1,2,4]triazin-4(3H)-one

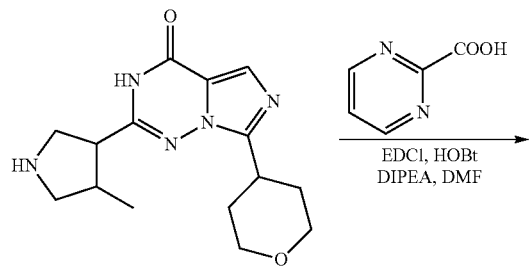

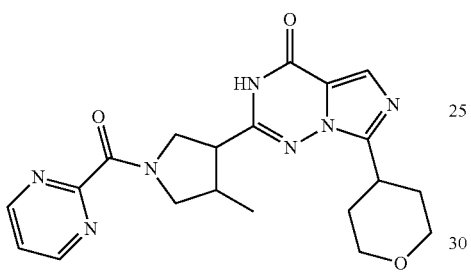

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in DMF (5 mL) were added EDCI (70 mg, 0.37 mmol), HOBt (50 mg, 0.37 mmol), DIPEA (95 mg, 0.74 mmol) and pyrimidine-2-carboxylic acid (40 mg, 0.32 mmol) at 0° C. under inert atmosphere. The resulting reaction mixture was allowed to warm to room temperature and stirred for 8 h. The reaction mass was diluted with water (100 mL) and extracted with DCM (3×50 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyrimidine-2-carbonyl)pyrrolidin-3-yl)-7-(tetrahydro-2H-pyran-4-yl)imidazo[5,1-f][1,2,4]triazin-4(3H)-one (40 mg, 40%) as an off-white solid. $^1$H-NMR (DMSO d$_6$, 400 MHz): δ 11.95 (bs, 1H), 8.97 (d, 2H), 6.69-6.58 (m, 2H), 3.98-3.84 (m, 4H), 3.65-3.57 (m, 4H), 3.22-3.27 (m, 2H), 2.68-2.61 (m, 1H), 1.90-1.84 (m, 4H), 1.08 (d, 3H); Mass (ESI): 410 [M$^+$+1] LC-MS: 98.92%; 410.3 (M$^+$+1); (column; X-bridge C-18, (50×3.0 mm, 3.5µ); RT 1.85 min. 0.05% TFA in water: ACN; 0.8 ml/min); UPLC (purity): 98.76%; (column; Eclipse XDB C-18, (150×4.6 mm, 5.0µ); RT 8.23 min. 5 mM NH$_4$OAc (Aq): ACN; 1.0 ml/min; Chiral HPLC: 99%, R$_t$=37.69 min (Chiralpak IA, 250×4.6 mm, 5µ; mobile phase (A) n-Hexane (B) DCM:MeOH (80:20) (A:B:80:20); flow Rate: 1.00 mL/min); Optical rotation [α]$_D^{20}$: +12.17° (c=0.25, DCM). TLC: 10% MeOH/DCM (Rf: 0.5).

115. (−)-2-((3,4-trans)-1-isonicotinoyl-4-methylpyrrolidin-3-yl)-7-(tetrahydro-2H-pyran-4-yl)imidazo[5,1-f][1,2,4]triazin-4(3H)-one

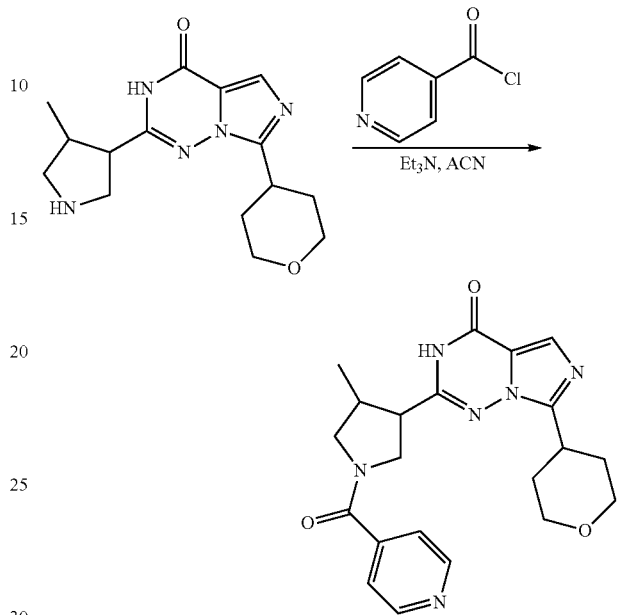

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (90 mg, 0.29 mmol) in ACN (20 mL) was added isonicotinoyl chloride (80 mg, 0.44 mmol) followed by Et$_3$N (60 mg, 0.59 mmol) at 0° C. under argon atmosphere. The resulting reaction mixture was allowed to warm to room temperature and stirred for 30 min. The reaction mass was diluted with water (100 mL) and extracted with DCM (3×50 mL). Combined organic layer was dried over sodium sulphate, filtered and concentrated in vacuo to obtain the crude product. The crude material was purified by silica gel column chromatography to afford (−)-2-((3,4-trans)-1-isonicotinoyl-4-methylpyrrolidin-3-yl)-7-(tetrahydro-2H-pyran-4-yl)imidazo[5,1-f][1,2,4]triazin-4(3H)-one (45 mg, 37%) as an off-white solid. $^1$H-NMR (DMSO d$_6$, 400 MHz): δ 11.95 (bs, 1H), 8.68 (d, 2H), 7.64 (d, 1H), 7.52-7.47 (m, 2H), 4.02-3.94 (m, 3H), 3.89-3.84 (m, 2H), 3.71-3.69 (m, 1H), 3.48-3.41 (m, 2H), 3.40-3.38 (m, 1H), 3.21-2.97 (m, 1H), 2.96-2.92 (m, 1H), 1.87-1.80 (m, 4H), 1.07 (d, 3H); Mass (ESI): 409 [M$^+$+1]; LC-MS: 93.58%; 409 (M$^+$+1); (column; X-bridge C-18, (50×3.0 mm, 3.5µ); RT 2.18 min. 5 mM NH$_4$OAc: ACN; 0.8 ml/min); UPLC (purity): 95%; (column; Acquity BEH C-18, (50×2.1 mm, 1.7µ); RT 1.20 min. 0.025% TFA (Aq): ACN; 0.50 ml/min; Chiral HPLC: 100%, R$_t$=8.73 min (Chiralpak IA, 250×4.6 mm, 5µ; mobile phase (A) 0.1% DEA in n-Hexane (B) EtOH (A:B:70:30); flow Rate: 1.00 mL/min); Optical rotation [α]$_D^{20}$: −28.60° (c=0.25, DCM). TLC: 10% MeOH/DCM (Rf: 0.8).

116. (−)-4-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile

117. (−)-2-((3,4-trans)-4-methyl-1-(pyrimidine-5-carbonyl)pyrrolidin-3-yl)-7-(tetrahydro-2H-pyran-4-yl)imidazo[5,1-f][1,2,4]triazin-4(3H)-one

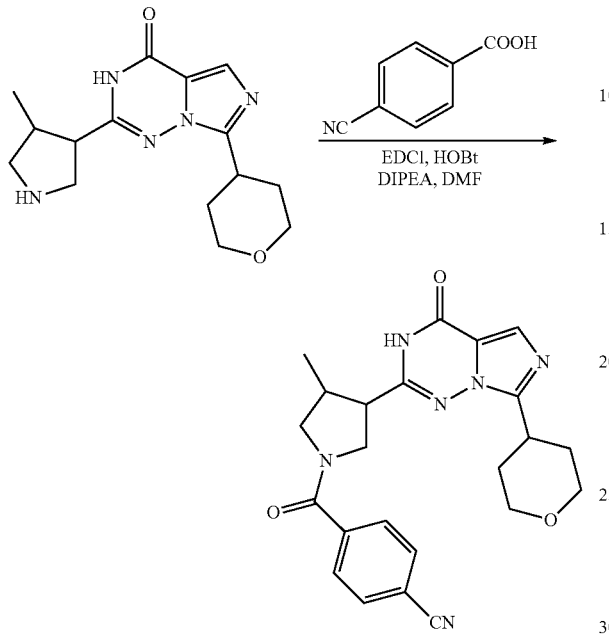
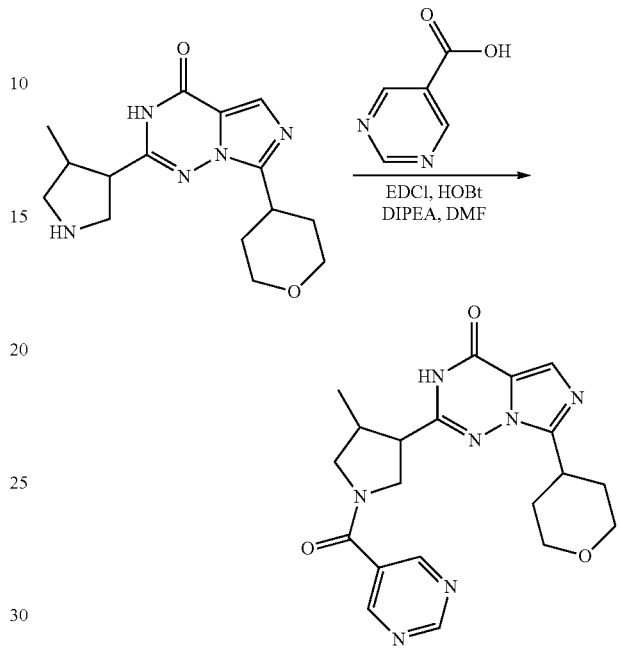

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in DMF (10 mL) were added EDCI (95 mg, 0.49 mmol), HOBt (67 mg, 0.49 mmol), DIPEA (0.18 mL, 0.99 mmol) and 4-cyanobenzoic acid (64 mg, 0.42 mmol) at 0° C. under argon atmosphere. The resulting reaction mixture was allowed to warm to room temperature and stirred for 8 h. The reaction mass was diluted with water (100 mL) and extracted with DCM (3×50 mL). Combined organic layer was dried over sodium sulphate, filtered and concentrated in vacuo to obtain the crude product. The crude material was purified by silica gel column chromatography to afford (−)-4-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile (40 mg, 28%) as an off-white solid. $^1$H-NMR (DMSO d$_6$, 400 MHz): δ 11.95 (bs, 1H), 7.97-7.92 (m, 2H), 7.76-7.70 (m, 3H), 3.97-3.92 (m, 5H), 3.51-3.48 (m, 2H), 3.43-3.40 (m, 1H), 3.26-3.21 (m, 1H), 3.04-2.29 (m, 1H), 2.73-2.69 (m, 1H), 1.97-1.91 (m, 4H), 1.08 (d, 3H); Mass (ESI): 433.4 [M$^+$+1] & 474.3 [M$^+$+1]; LC-MS: 92.64%; 433.3 (M$^+$+1) & 474.4 [M$^+$+1]; (column; X-bridge C-18, (50×3.0 mm, 3.5μ); RT 2.31 min. 0.05% TFA in water: ACN; 0.8 ml/min); UPLC (purity): 93%; (column; Acquity HSS T$_3$, (2.1×100 mm, 1.8μ); RT 1.57 min. 0.025% TFA (Aq): ACN; 0.3 ml/min; Chiral HPLC: 100%, R$_t$=13.18 min (Chiralpak IA, 250×4.6 mm, 5μ; mobile phase (A) 0.1% DEA in n-Hexane (B) EtOH (A:B:70:30); flow Rate: 1.00 mL/min); Optical rotation [α]$_D^{20}$: −19.96° (c=0.25, DCM). TLC: 10% MeOH/DCM (Rf: 0.7).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in DMF (10 mL) were added EDCI (95 mg, 0.49 mmol), HOBt (67 mg, 0.49 mmol), DIPEA (0.2 mL, 0.99 mmol) and pyrimidine-5-carboxylic acid (53 mg, 0.42 mmol) at 0° C. under argon atmosphere. The resulting reaction mixture was allowed to warm to room temperature and stirred for 8 h. The reaction mass was diluted with water (100 mL) and extracted with DCM (3×50 mL). Combined organic layer was dried over sodium sulphate, filtered and concentrated in vacuo to obtain the crude product. The crude material was purified by silica gel column chromatography to afford (−)-2-((3,4-trans)-4-methyl-1-(pyrimidine-5-carbonyl)pyrrolidin-3-yl)-7-(tetrahydro-2H-pyran-4-yl)imidazo[5,1-f][1,2,4]triazin-4(3H)-one (50 mg, 37%) as an off-white solid. $^1$H-NMR (DMSO d$_6$, 400 MHz): δ 9.28 (s, 1H), 9.02 (d, 2H), 7.62-7.60 (m, 1H), 4.01-3.96 (m, 4H), 3.81-3.74 (m, 2H), 3.50-3.47 (m, 2H), 3.24-3.21 (m, 1H), 3.01-2.96 (m, 1H), 2.71-2.64 (m, 1H), 1.87-1.81 (m, 4H), 1.08 (d, 3H); Mass (ESI): 410.4 [M$^+$+1]; LC-MS: 93.25%; 410.3 (M$^+$+1); (column; X-bridge C-18, (50×3.0 mm, 3.5μ); RT 1.76 min. 0.05% TFA in water: ACN; 0.8 ml/min); UPLC (purity): 98.82%; (column; Acquity BEH C-18, (50×2.1 mm, 1.7μ); RT 1.26 min. 0.025% TFA (Aq): ACN; 0.50 ml/min; Chiral HPLC: 100%, R$_t$=13.15 min (Chiralpak IA, 250×4.6 mm, 5μ; mobile phase (A) 0.1% DEA in n-Hexane (B) DCM:MeOH (70:30) (A:B: 70:30); flow Rate: 1.00 mL/min); Optical rotation [α]$_D^{20}$: −27.21° (c=0.25, DCM). TLC: 10% MeOH/DCM (Rf: 0.7).

118. (−)-2-((3,4-trans)-4-methyl-1-(pyrazine-2-carbonyl)pyrrolidin-3-yl)-7-(tetrahydro-2H-pyran-4-yl)imidazo[5,1-f][1,2,4]triazin-4(3H)-one

119. (+)-2-((3,4-trans)-1-((3-fluorophenyl)sulfonyl)-4-methylpyrrolidin-3-yl)-7-(tetrahydro-2H-pyran-4-yl)imidazo[5,1-f][1,2,4]triazin-4(3H)-one

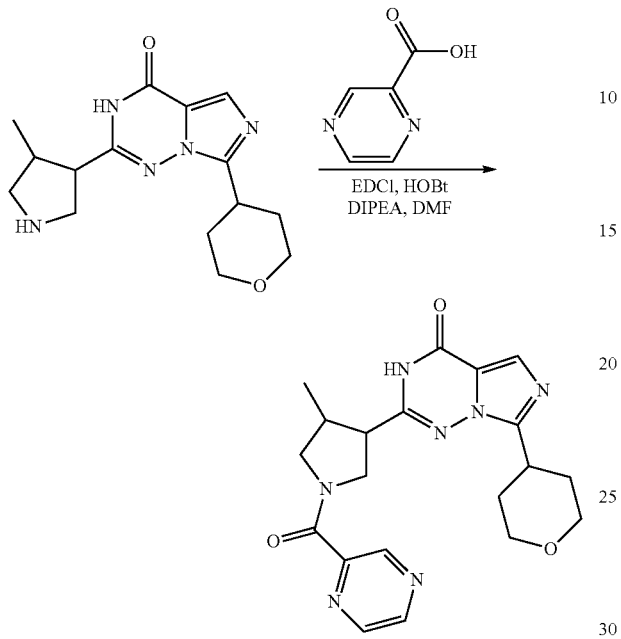

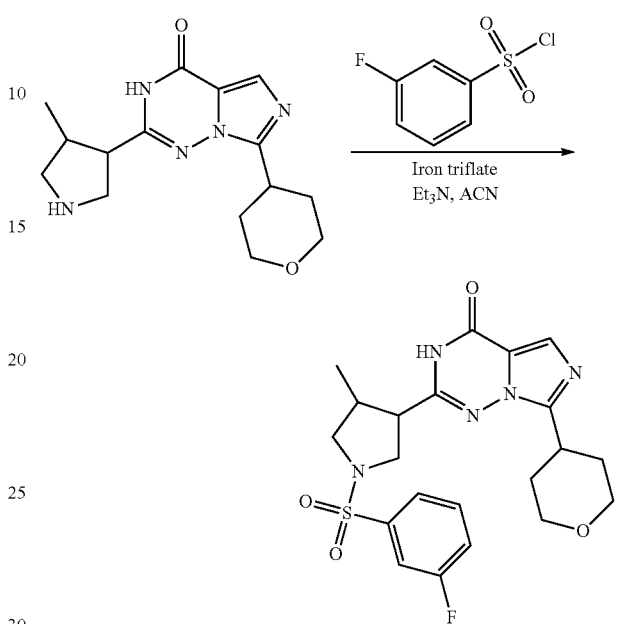

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in DMF (5 mL) were added EDCI (94.5 mg, 0.49 mmol), HOBt (66.8 mg, 0.49 mmol), DIPEA (127 mg, 0.99 mmol) and pyrazine-2-carboxylic acid (53 mg, 0.42 mmol) at 0° C. under argon atmosphere. The resulting reaction mixture was allowed to warm to room temperature and stirred for 16 h. The reaction mass was diluted with water (100 mL) and extracted with DCM (3×20 mL). Combined organic layer was dried over sodium sulphate, filtered and concentrated in vacuo to obtain the crude product. The crude material was purified by silica gel column chromatography to afford (−)-2-((3,4-trans)-4-methyl-1-(pyrazine-2-carbonyl)pyrrolidin-3-yl)-7-(tetrahydro-2H-pyran-4-yl)imidazo[5,1-f][1,2,4]triazin-4(3H)-one (60 mg, 44.45%) as an off-white solid. $^1$H-NMR (DMSO d$_6$, 500 MHz): δ 11.96 (bs, 1H), 9.02 (d, 1H), 8.76 (d, 2H), 7.62 (d, 1H), 4.28-4.21 (m, 1H), 4.18-3.96 (m, 1H), 4.16-3.95 (m, 2H), 3.92-3.86 (m, 1H), 3.49-3.41 (m, 2H), 3.14-3.10 (m, 1H), 3.02-2.297 (m, 1H), 2.65-2.62 (m, 2H), 1.92-1.87 (m, 4H), 1.08 (d, 3H); Mass (ESI): 410.3 [M$^+$+1]; LC-MS: 99.88%; 410.3 (M$^+$+1); (column; X-bridge C-18, (50×3.0 mm, 3.5μ); RT 1.93 min. 0.05% TFA in water: ACN; 0.8 ml/min); UPLC (purity): 99.69%; (column; Acquity BEH C-18, (50×2.1 mm, 1.7μ); RT 1.37 min. 0.025% TFA (Aq): ACN; 0.50 ml/min; Chiral HPLC: 100%, R$_t$=14.12 min (Chiralpak IA, 250×4.6 mm, 5μ; mobile phase (A) 0.1% DEA in n-Hexane (B) EtOH (A:B:70:30); flow Rate: 1.00 mL/min); Optical rotation [α]$_D^{20}$: −13.92° (c=0.25, DCM). TLC: 10% MeOH/DCM (Rf: 0.7).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 3-fluorobenzene-1-sulfonyl chloride (64.2 mg, 0.33 mmol), Iron triflate (33.2 mg, 0.06 mmol) and Et$_3$N (66.6 mg, 0.99 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-1-((3-fluorophenyl)sulfonyl)-4-methylpyrrolidin-3-yl)-7-(tetrahydro-2H-pyran-4-yl)imidazo[5,1-f][1,2,4]triazin-4(3H)-one (35 mg, 66%) as an off-white solid; $^1$H-NMR (DMSO d$_6$, 400 MHz): δ 11.68 (bs, 1H), 9.12 (s, 1H), 7.68-7.64 (m, 3H), 3.96-3.89 (m, 4H), 3.51-3.47 (m, 2H), 3.41-3.39 (m, 2H), 3.04-3.01 (m, 1H), 2.94-2.91 (m, 1H), 2.87-2.82 (m, 2H), 2.65-2.62 (m, 1H), 2.36-2.32 (m, 1H), 1.89-1.85 (m, 4H), 1.09 (d, 3H); Mass (ESI): 462 [M$^+$+1]; LC-MS: 97%; 462.3 (M$^+$+1); (column; X-bridge C-18, (50×3.0 mm, 3.5μ); RT 2.70 min. 0.05% TFA in water: ACN; 0.8 ml/min); UPLC (purity): 97%; (column; Acquity BEH C-18, (50×2.1 mm, 1.7μ); RT 1.93 min. 0.025% TFA (Aq): ACN; 0.50 ml/min; Chiral HPLC: 98.75% R$_t$=19.57 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +4.22° (c=0.25, DCM); TLC: 5% MeOH/DCM (Rf: 0.4).

120. (+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile

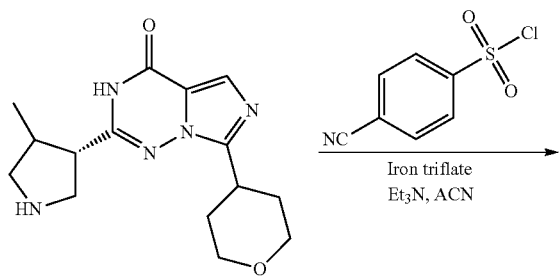

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added 4-cyanobenzene-1-sulfonyl chloride (66.5 mg, 0.33 mmol), Iron triflate (33.2 mg, 0.06 mmol) and Et₃N (66.6 mg, 0.99 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile (60 mg, 39%) as an off-white solid; ¹H-NMR (DMSO d₆, 400 MHz): δ 11.74 (bs, 1H), 8.10-7.96 (m, 4H), 7.64 (s, 1H), 3.97-3.91 (m, 2H), 3.80-3.77 (m, 1H), 3.66-3.61 (m, 1H), 3.49-3.42 (m, 3H), 3.24-3.21 (m, 1H), 2.96-2.94 (m, 1H), 2.81-2.76 (m, 1H), 2.54-2.51 (m, 1H), 1.87-1.76 (m, 4H), 0.98 (d, 3H); Mass (ESI): 467 [M−1]; LC-MS: 96%; 469.3 (M⁺+1); (column; X-bridge C-18, (50×3.0 mm, 3.5μ); RT 2.65 min. 0.05% TFA in water: ACN; 0.8 ml/min); HPLC (purity): 95.63%; (column; Acquity BEH C-18, (50×2.1 mm, 1.7μ); RT 8.48 min. 5 mM NH₄OAc: ACN; 1.0 ml/min); Chiral HPLC: 100%, R$_f$=11.76 min (Chiralpak IC, 250×4.6 mm, 5μ; mobile phase (A) n-Hexane (B) EtOH (A:B:50:50); flow Rate: 1.00 mL/min); Optical rotation [α]$_D^{20}$: +11.12° (c=0.25, DCM); TLC: 5% MeOH/DCM (Rf: 0.5).

121. (+)-2-((3,4-trans)-4-methyl-1-(quinolin-7-ylmethyl)pyrrolidin-3-yl)-7-(tetrahydro-2H-pyran-4-yl)imidazo[5,1-f][1,2,4]triazin-4(3H)-one

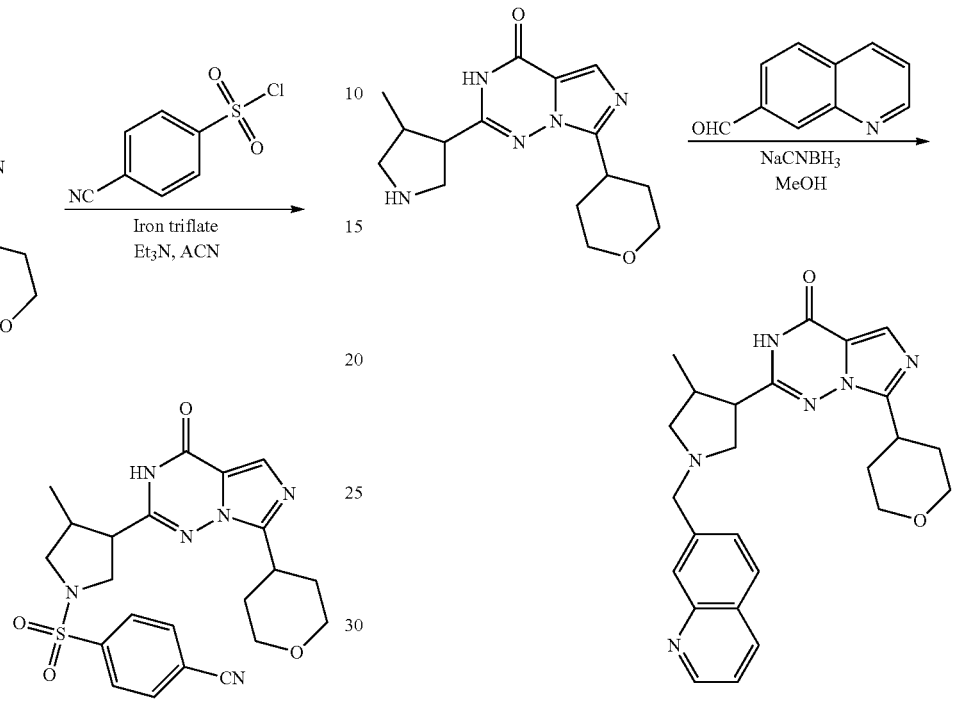

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added quinoline-7-carbaldehyde (62 mg, 0.39 mmol) at RT under argon atmosphere. After being stirred for 2 h, NaCNBH₃ (62.3 mg, 0.99 mmol) was added to the reaction mixture and stirring was continued for another 5 h at RT. The volatiles were evaporated under reduced pressure. The residue was diluted with ice-cold water and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinolin-7-ylmethyl)pyrrolidin-3-yl)-7-(tetrahydro-2H-pyran-4-yl)imidazo[5,1-f][1,2,4]triazin-4(3H)-one (32 mg, 22%) as an off-white solid. ¹H-NMR (DMSO d₆, 400 MHz): δ 11.69 (bs, 1H), 8.87 (d, 1H), 8.34 (d, 1H), 7.96-7.93 (m, 2H), 7.67 (s, 2H), 7.58 (d, 2H), 7.49-7.45 (m, 1H), 3.97-3.92 (m, 4H), 3.56-3.52 (m, 2H), 3.42-3.39 (m, 1H), 3.07-3.01 (m, 1H), 2.96-2.94 (m, 1H), 2.89-2.87 (m, 2H), 2.69-2.67 (m, 1H), 2.34-2.99 (m, 1H), 1.87-1.82 (m, 4H), 1.12 (d, 3H); Mass (ESI): 396.5 [M⁺+1] LC-MS: 98.58%; 396.4 (M⁺+1); (column; X-bridge C-18, (50×3.0 mm, 3.5μ); RT 3.21 min. 0.05% TFA in water: ACN; 0.8 ml/min); UPLC (purity): 95%; (column; Acquity HSS T3, (2.1×100 mm, 1.8μ); RT 2.80 min. 0.025% TFA (Aq): ACN; 0.3 ml/min; Chiral HPLC: 98.27%, R$_f$=9.35 min (Chiralpak IA, 250×4.6 mm, 5μ; mobile phase (A) 0.1% DEA in n-Hexane (B) Ethanol (A:B:60:40); flow Rate: 1.00 mL/min); Optical rotation [α]$_D^{20}$: +5.15° (c=0.25, DCM). TLC: 5% MeOH/DCM (Rf: 0.4).

122. (−)-2-((3,4-trans)-4-methyl-1-picolinoylpyrrolidin-3-yl)-7-(tetrahydro-2H-pyran-4-yl)imidazo[5,1-f][1,2,4]triazin-4(3H)-one

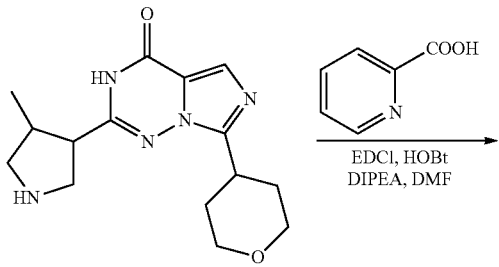

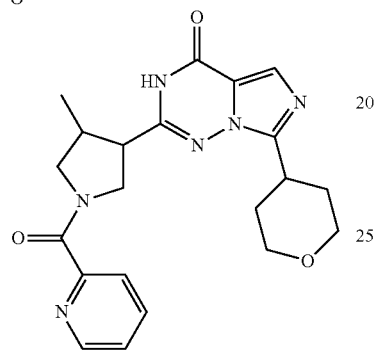

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in DMF (10 mL) were added EDCI (95 mg, 0.49 mmol), HOBt (67 mg, 0.49 mmol), DIPEA (0.18 mL, 0.99 mmol) and picolinic acid (53 mg, 0.42 mmol) at 0° C. under argon atmosphere. The resulting reaction mixture was allowed to warm to room temperature and stirred for 8 h. The reaction mass was diluted with water (100 mL) and extracted with DCM (3×50 mL). Combined organic layer was dried over sodium sulphate, filtered and concentrated in vacuo to obtain the crude product. The crude material was purified by silica gel column chromatography to afford (−)-2-((3,4-trans)-4-methyl-1-picolinoylpyrrolidin-3-yl)-7-(tetrahydro-2H-pyran-4-yl)imidazo[5,1-f][1,2,4]triazin-4(3H)-one (40 mg, 30%) as pale-yellow solid. $^1$H-NMR (DMSO d$_6$, 400 MHz): δ 11.82 (bs, 1H), 8.61 (d, 1H), 7.98-7.95 (m, 1H), 7.79-7.73 (m, 1H), 7.64 (d, 1H), 7.51-7.47 (m, 1H), 4.14-3.87 (m, 5H), 3.46-3.41 (m, 3H), 3.24-3.21 (m, 1H), 3.02-2.96 (m, 1H), 2.67-2.62 (m, 1H), 1.87-1.79 (m, 4H), 1.07 (d, 3H); Mass (ESI): 409 [M$^+$+1] & 431 [M$^+$+Na]; LC-MS: 95.29%; 409.3 (M$^+$+1); (column; X-bridge C-18, (50×3.0 mm, 3.5μ); RT 2.02 min. 0.05% TFA in water: ACN; 0.8 ml/min); UPLC (purity): 95%; (column; Acquity BEH C-18, (50×2.1 mm, 1.7μ); RT 1.45 min. 0.025% TFA (Aq): ACN; 0.50 ml/min; Chiral HPLC: 100%, R$_t$=10.40 min (Chiralpak IA, 250×4.6 mm, 5μ; mobile phase (A) 0.1% DEA in n-Hexane (B) Ethanol (A:B:70:30); flow Rate: 1.00 mL/min); Optical rotation [α]$_D^{20}$: −10.06° (c=0.25, DCM). TLC: 10% MeOH/DCM (Rf: 0.8).

123. (−)-2-((3,4-trans)-4-methyl-1-(quinoline-2-carbonyl)pyrrolidin-3-yl)-7-(tetrahydro-2H-pyran-4-yl)imidazo[5,1-f][1,2,4]triazin-4(3H)-one

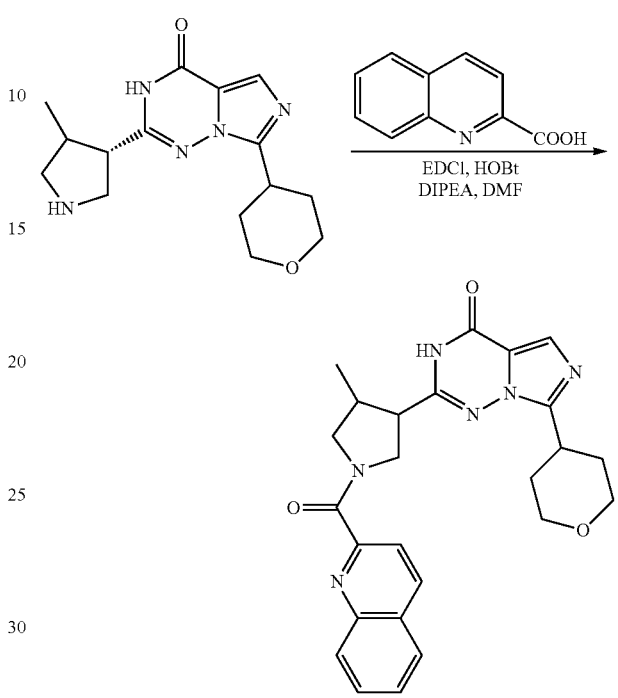

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in DMF (5 mL) were added EDCI (94.5 mg, 0.49 mmol), HOBt (66.8 mg, 0.49 mmol), DIPEA (127 mg, 0.99 mmol) and quinoline-2-carboxylic acid (74.2 mg, 0.49 mmol) at 0° C. under argon atmosphere. The resulting reaction mixture was allowed to warm to room temperature and stirred for 16 h. The reaction mass was diluted with water (50 mL) and extracted with DCM (3×20 mL). Combined organic layer was dried over sodium sulphate, filtered and concentrated in vacuo to obtain the crude product. The crude material was purified by silica gel column chromatography to afford (−)-2-((3,4-trans)-4-methyl-1-(quinoline-2-carbonyl)pyrrolidin-3-yl)-7-(tetrahydro-2H-pyran-4-yl)imidazo[5,1-f][1,2,4]triazin-4(3H)-one (30 mg, 20%) as an off-white solid; $^1$H-NMR (DMSO d$_6$, 500 MHz): δ 11.98 (bs, 1H), 8.52-8.49 (m, 1H), 8.08 (d, 2H), 7.89-7.82 (m, 2H), 7.70-7.65 (m, 2H), 4.22-3.97 (m, 6H), 3.57-3.49 (m, 3H), 3.08-3.05 (m, 1H), 2.74-2.71 (m, 1H), 1.87-1.82 (m, 4H), 1.09 (d, 3H); Mass (ESI): 459.4 [M$^+$+1]; LC-MS: 99.96%; 459.4 (M$^+$+1); (column; X-bridge C-18, (50×3.0 mm, 3.5μ); RT 2.53 min. 0.05% TFA in water: ACN; 0.8 ml/min); UPLC (purity): 99.82%; (column; Acquity BEH C-18, (50×2.1 mm, 1.7μ); RT 1.80 min. 0.025% TFA (Aq): ACN; 0.50 ml/min; Chiral HPLC: 100%, R$_t$=10.70 min (Chiralpak IA, 250×4.6 mm, 5μ; mobile phase (A) 0.1% DEA in n-Hexane (B) Ethanol (A:B:70:30); flow Rate: 1.00 mL/min); Optical rotation [α]$_D^{20}$: −18.96° (c=0.25, DCM). TLC: 7% MeOH/DCM (Rf: 0.4).

124. (−)-2-((3,4-trans)-4-methyl-1-(pyrimidine-4-carbonyl)pyrrolidin-3-yl)-7-(tetrahydro-2H-pyran-4-yl)imidazo[5,1-f][1,2,4]triazin-4(3H)-one

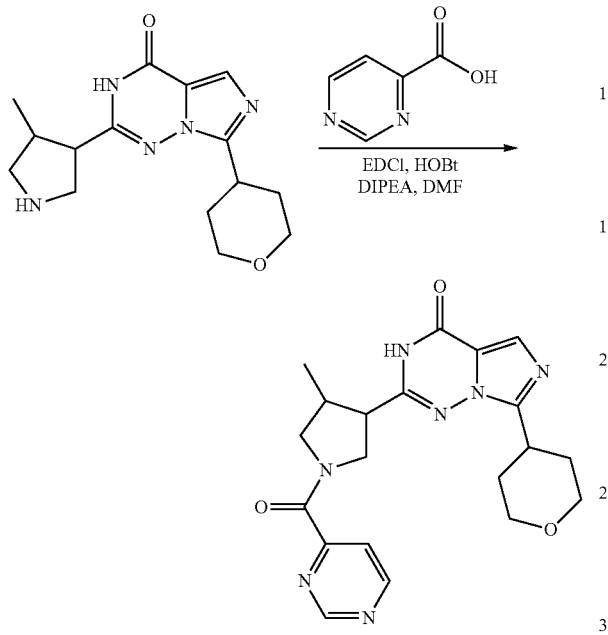

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in DMF (7 mL) were added EDCl (95 mg, 0.49 mmol), HOBt (67 mg, 0.49 mmol), DIPEA (0.2 mL, 0.99 mmol) and pyrimidine-4-carboxylic acid (62 mg, 0.49 mmol) at 0° C. under argon atmosphere. The resulting reaction mixture was allowed to warm to room temperature and stirred for 8 h. The reaction mass was diluted with water (100 mL) and extracted with DCM (4×50 mL). Combined organic layer was dried over sodium sulphate, filtered and concentrated in vacuo to obtain the crude product. The crude material was purified by silica gel column chromatography to afford (−)-2-((3,4-trans)-4-methyl-1-(pyrimidine-4-carbonyl)pyrrolidin-3-yl)-7-(tetrahydro-2H-pyran-4-yl)imidazo[5,1-f][1,2,4]triazin-4(3H)-one (25 mg, 18%) as an off-white solid. $^1$H-NMR (DMSO d$_6$, 500 MHz): δ 11.94 (bs, 1H), 9.27 (s, 1H), 9.04 (d, 1H), 7.94-7.91 (m, 1H), 7.65 (d, 1H), 4.12-3.91 (m, 5H), 3.44-3.39 (m, 3H), 3.26-3.21 (m, 1H), 3.09-3.02 (m, 1H), 2.72-2.68 (m, 1H), 1.87-1.82 (m, 4H), 1.09 (d, 3H); Mass (ESI): 408 [M−1]; LC-MS: 99.22%; 410.3 (M$^+$+1); (column; X-bridge C-18, (50×3.0 mm, 3.5μ); RT 1.85 min. 0.05% TFA in water: ACN; 0.8 ml/min); UPLC (purity): 98.39%; (column; Acquity BEH C-18, (50×2.1 mm, 1.7μ); RT 1.32 min. 0.025% TFA (Aq): ACN; 0.50 ml/min; Chiral HPLC: 100%, R$_t$=6.46 min (Chiralpak IA, 250×4.6 mm, 5μ; mobile phase (A) 0.1% DEA in n-Hexane (B) DCM:MeOH (80:20) (A:B:60:40); flow Rate: 1.00 mL/min); Optical rotation [α]$_D^{20}$: −11.85° (c=0.25, DCM). TLC: 10% MeOH/DCM (Rf: 0.5).

125. (+)-2-((3,4-trans)-4-methyl-1-(pyridin-3-ylsulfonyl)pyrrolidin-3-yl)-7-(tetrahydro-2H-pyran-4-yl)imidazo[5,1-f][1,2,4]triazin-4(3H)-one

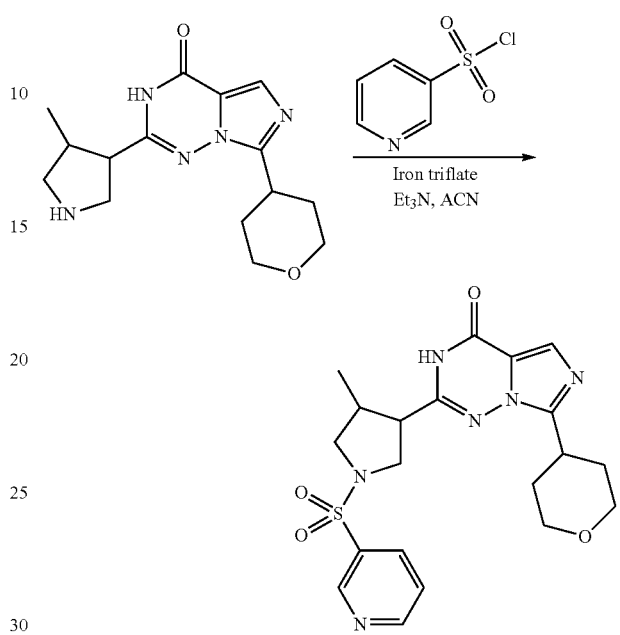

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (10 mL) were added pyridine-3-sulfonyl chloride (58.6 mg, 0.33 mmol), Iron triflate (33.2 mg, 0.06 mmol) and Et$_3$N (66.6 mg, 0.99 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyridin-3-ylsulfonyl)pyrrolidin-3-yl)-7-(tetrahydro-2H-pyran-4-yl)imidazo[5,1-f][1,2,4]triazin-4(3H)-one (46 mg, 32%) as an off-white solid; $^1$H-NMR (DMSO d$_6$, 500 MHz): δ 11.78 (bs, 1H), 8.99 (s, 1H), 8.78 (d, 1H), 8.24 (d, 1H), 7.62 (s, 1H), 7.59-7.54 (m, 1H), 7.65 (d, 1H), 3.96-3.92 (m, 2H), 3.82-3.78 (m, 1H), 3.68-3.62 (m, 1H), 3.49-3.41 (m, 3H), 3.26-3.21 (m, 1H), 2.99-2.95 (m, 1H), 2.82-2.80 (m, 1H), 1.84-1.78 (m, 4H), 0.99 (d, 3H); Mass (ESI): 445 [M$^+$+1]; LC-MS: 99%; 445.3 (M$^+$+1); (column; X-bridge C-18, (50×3.0 mm, 3.5μ); RT 2.26 min. 0.05% TFA in water: ACN; 0.8 ml/min); UPLC (purity): 99.60%; (column; Acquity BEH C-18, (50×2.1 mm, 1.7μ); RT 1.62 min. 0.025% TFA (Aq): ACN; 0.50 ml/min; Chiral HPLC: 99.59%, R$_t$=10.93 min (Chiralpak IA, 250×4.6 mm, 5μ; mobile phase (A) 0.1% DEA in n-Hexane (B) Ethanol (A:B:70:30); flow Rate: 1.00 mL/min); Optical rotation [α]$_D^{20}$: +13.04° (c=0.25, DCM); TLC: 5% MeOH/DCM (Rf: 0.5).

126. (+)-2-((3,4-trans)-1-(2-methoxybenzyl)-4-methylpyrrolidin-3-yl)-7-(tetrahydro-2H-pyran-4-yl)imidazo[5,1-f][1,2,4]triazin-4(3H)-one

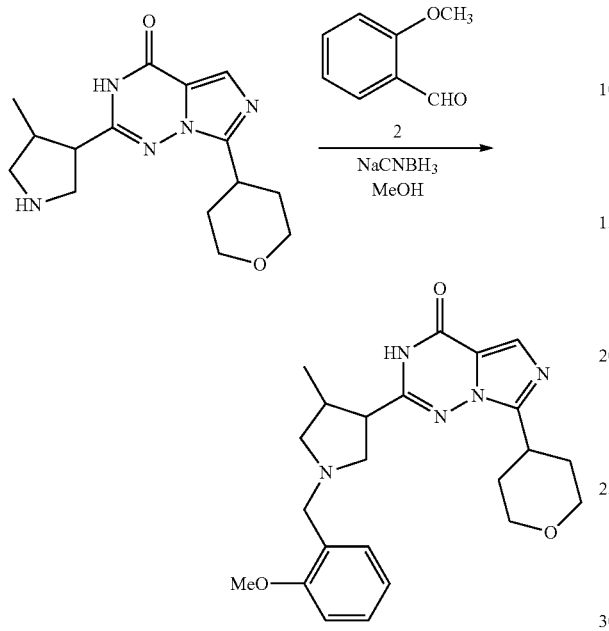

127. (+)-2-((3,4-trans)-1-(3-methoxybenzyl)-4-methylpyrrolidin-3-yl)-7-(tetrahydro-2H-pyran-4-yl)imidazo[5,1-f][1,2,4]triazin-4(3H)-one

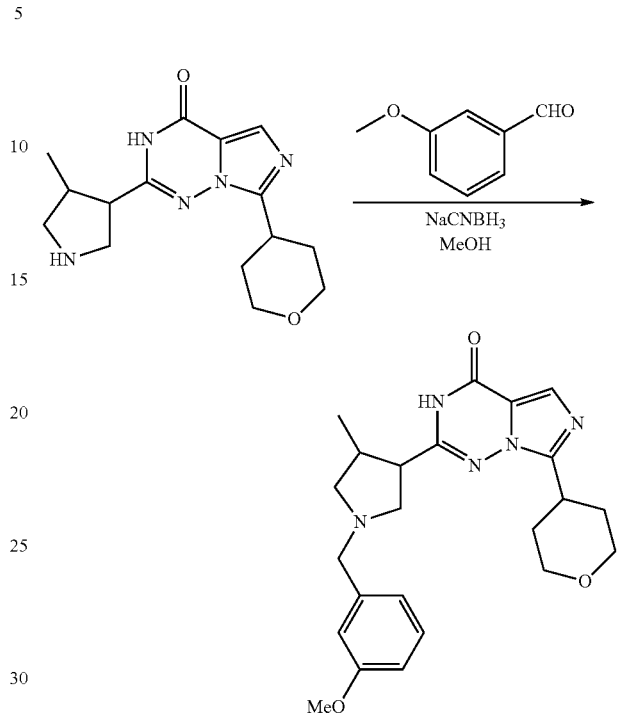

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in MeOH (15 mL) was added 2-methoxybenzaldehyde (85 mg, 0.61 mmol) at RT under argon atmosphere. After being stirred for 2 h, NaCNBH$_3$ (78 mg, 1.23 mmol) was added to the reaction mixture and stirring was continued for another 16 h at RT. After the consumption of starting material (by TLC), the reaction mixture was diluted with ice-cold water (100 mL) and extracted with DCM (3×50 mL). Combined organic layer was dried over sodium sulphate, filtered and concentrated in vacuo to obtain the crude product. The crude material was purified by silica gel column chromatography to afford (+)-2-((3,4-trans)-1-(2-methoxybenzyl)-4-methylpyrrolidin-3-yl)-7-(tetrahydro-2H-pyran-4-yl)imidazo[5,1-f][1,2,4]triazin-4(3H)-one (40 mg, 29%) as an off-white solid. $^1$H-NMR (DMSO d$_6$, 500 MHz): δ 7.68 (s, 1H), 7.34-7.28 (m, 2H), 7.68-7.62 (m, 2H), 3.96-3.94 (m, 2H), 3.82 (s, 3H), 3.66-3.64 (m, 2H), 3.51-3.47 (m, 2H), 3.41-3.37 (m, 1H), 2.96-2.94 (m, 2H), 2.87-2.75 (m, 2H), 2.67-2.62 (m, 1H), 2.24-2.21 (m, 1H), 1.86-1.82 (m, 4H), 1.09 (d, 3H); Mass (ESI): 424.4 [M$^+$+1]; LC-MS: 99%; 424.4 (M$^+$+1); (column; X-bridge C-18, (50×3.0 mm, 3.5μ); RT 2.12 min. 0.05% TFA in water: ACN; 0.8 ml/min); UPLC (purity): 99%; (column; Acquity BEH C-18, (50×2.1 mm, 1.7μ); RT 1.49 min. 0.025% TFA (Aq): ACN; 0.50 ml/min; Chiral HPLC: 99.56%, R$_t$=7.17 min (Chiralpak IA, 250×4.6 mm, 5μ; mobile phase (A) n-Hexane (B) DCM:Methanol (80:20) (A:B:80:20); flow Rate: 1.00 mL/min); Optical rotation [α]$_D^{20}$: +24.48° (c=0.25, DCM); TLC: 10% MeOH/DCM (Rf: 0.6).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (90 mg, 0.29 mmol) in MeOH (10 mL) was added 3-methoxybenzaldehyde (53 mg, 0.38 mmol) at RT under argon atmosphere. After being stirred for 2 h, NaCNBH$_3$ (56 mg, 0.89 mmol) was added to the reaction mixture and stirring was continued for another 16 h at RT. After the consumption of starting material (by TLC), the reaction mixture was diluted with ice-cold water (100 mL) and extracted with DCM (3×50 mL). Combined organic layer was dried over sodium sulphate, filtered and concentrated in vacuo to obtain the crude product. The crude material was purified by silica gel column chromatography to afford (+)-2-((3,4-trans)-1-(3-methoxybenzyl)-4-methylpyrrolidin-3-yl)-7-(tetrahydro-2H-pyran-4-yl)imidazo[5,1-f][1,2,4]triazin-4(3H)-one (45 mg, 36%) as an off-white solid. $^1$H-NMR (DMSO d$_6$, 400 MHz): δ 11.82 (bs, 1H), 7.68 (s, 1H), 7.24 (t, 1H), 6.89-6.87 (m, 2H), 6.78-6.77 (m, 1H), 3.96-3.94 (m, 2H), 3.72 (s, 3H), 3.64-3.58 (m, 2H), 3.51-3.46 (m, 2H), 3.41-3.37 (m, 1H), 2.96-2.89 (m, 2H), 2.80-2.76 (m, 2H), 2.64-2.60 (m, 1H), 2.24-2.21 (m, 1H), 1.87-1.82 (m, 4H), 1.12 (d, 3H); Mass (ESI): 424.4 [M$^+$+1]; LC-MS: 98%; 424.4 (M$^+$+1); (column; X-bridge C-18, (50×3.0 mm, 3.5μ); RT 2.10 min. 0.05% TFA in water: ACN; 0.8 ml/min); UPLC (purity): 97.48%; (column; Acquity BEH C-18, (50×2.1 mm, 1.7μ); RT 1.47 min. 0.025% TFA (Aq): ACN; 0.50 ml/min; Chiral HPLC: 98%, R$_t$=8.41 min (Chiralpak IA, 250×4.6 mm, 5μ; mobile phase (A) n-Hexane (B) DCM:Methanol (80:20) (A:B:80:20); flow Rate: 1.00 mL/min); Optical rotation [α]$_D^{20}$: +27.00° (c=0.25, DCM); TLC: 10% MeOH/DCM (Rf: 0.4).

128. (+)-2-((3,4-trans)-1-(4-methoxybenzyl)-4-methylpyrrolidin-3-yl)-7-(tetrahydro-2H-pyran-4-yl)imidazo[5,1-f][1,2,4]triazin-4(3H)-one

129. (−)-2-((3,4-trans)-4-methyl-1-(quinazoline-2-carbonyl)pyrrolidin-3-yl)-7-(tetrahydro-2H-pyran-4-yl)imidazo[5,1-f][1,2,4]triazin-4(3H)-one

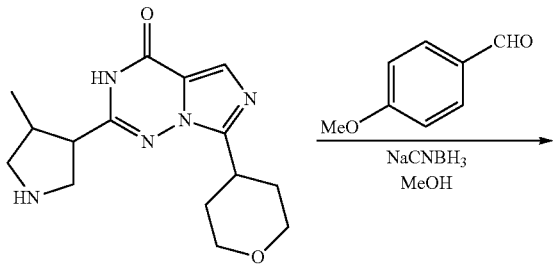

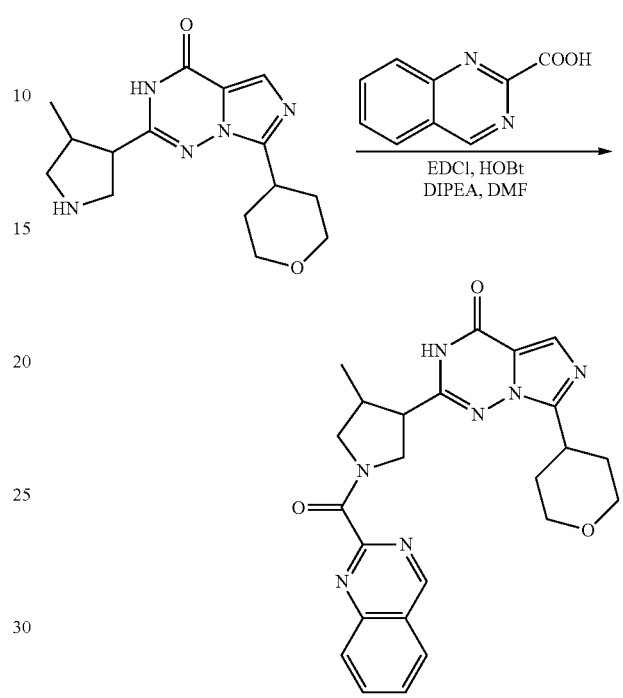

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (125 mg, 0.41 mmol) in MeOH (15 mL) was added 4-methoxybenzaldehyde (85 mg, 0.61 mmol) at RT under argon atmosphere. After being stirred for 2 h, NaCNBH$_3$ (78 mg, 1.23 mmol) was added to the reaction mixture and stirring was continued for another 16 h at RT. After the consumption of starting material (by TLC), the reaction mixture was diluted with ice-cold water (100 mL) and extracted with DCM (3×50 mL). Combined organic layer was dried over sodium sulphate, filtered and concentrated in vacuo to obtain the crude product. The crude material was purified by silica gel column chromatography to afford (+)-2-((3,4-trans)-1-(4-methoxybenzyl)-4-methylpyrrolidin-3-yl)-7-(tetrahydro-2H-pyran-4-yl)imidazo[5,1-f][1,2,4]triazin-4(3H)-one (45 mg, 32%) as an off-white solid. $^1$H-NMR (DMSO d$_6$, 400 MHz): δ 7.68 (s, 1H), 7.21 (d, 2H), 6.87 (d, 2H), 3.96-3.94 (m, 2H), 3.72 (s, 3H), 3.57-3.53 (m, 2H), 3.51-3.47 (m, 2H), 3.41-3.37 (m, 1H), 2.92-2.85 (m, 2H), 2.80-2.74 (m, 2H), 2.64-2.60 (m, 1H), 2.24-2.20 (m, 1H), 1.87-1.82 (m, 4H), 1.09 (d, 3H); Mass (ESI): 424 [M$^+$+1]; LC-MS: 98%; 424.4 (M$^+$+1); (column; X-bridge C-18, (50×3.0 mm, 3.5μ); RT 2.06 min. 0.05% TFA in water: ACN; 0.8 ml/min); UPLC (purity): 97.38%; (column; Acquity BEH C-18, (50×2.1 mm, 1.7μ); RT 1.44 min. 0.025% TFA (Aq): ACN; 0.50 ml/min; Chiral HPLC: 100%, R$_t$=10.04 min (Chiralpak IA, 250×4.6 mm, 5μ; mobile phase (A) 0.1% DEA in n-Hexane (B) Ethanol (A:B:80:20); flow Rate: 1.00 mL/min); Optical rotation [α]$_D^{20}$: +25.16° (c=0.25, DCM); TLC: 5% MeOH/DCM (Rf: 0.4).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in DMF (10 mL) were added EDCI (94.5 mg, 0.49 mmol), HOBt (67 mg, 0.49 mmol), DIPEA (0.2 mL, 0.99 mmol) and quinazoline-2-carboxylic acid (85 mg, 0.49 mmol) at 0° C. under an argon atmosphere. The resulting reaction mixture was allowed to warm to room temperature and stirred for 8 h. The reaction mass was diluted with water (100 mL) and extracted with DCM (4×50 mL). Combined organic layer was dried over sodium sulphate, filtered and concentrated in vacuo to obtain the crude product. The crude material was purified by silica gel column chromatography to afford (−)-2-((3,4-trans)-4-methyl-1-(quinazoline-2-carbonyl)pyrrolidin-3-yl)-7-(tetrahydro-2H-pyran-4-yl)imidazo[5,1-f][1,2,4]triazin-4(3H)-one (45 mg, 34%) as an off-white solid. $^1$H-NMR (DMSO-d$_6$, 400 MHz): δ 11.92 (bs, 1H), 9.74 (s, 1H), 8.26 (d, 1H), 8.18-8.06 (m, 2H), 7.89-7.81 (m, 1H), 7.69-7.61 (m, 1H), 3.97-3.88 (m, 3H), 3.71-3.68 (m, 2H), 3.52-3.43 (m, 3H), 3.21-2.98 (m, 3H), 2.77-2.64 (m, 1H), 1.89-1.82 (m, 4H), 1.06 (d, 3H); Mass (ESI): 460.3 [M$^+$+1]; LC-MS: 97.36%; 460.3 (M$^+$+1); (column; Eclipse XDB C-18, (150×4.6 mm, 5.0μ); RT 6.28 min. 0.05% TFA in water: ACN; 1.0 ml/min); HPLC (purity): 99.80%; (column; Eclipse XDB C-18, (150× 4.6 mm, 5.0μ); RT 7.40 min. 5 mM NH$_4$OAc: ACN; 1.0 ml/min); Chiral HPLC: 98.58%, R$_t$=12.48 min (Chiralpak IA, 250×4.6 mm, 5μ; mobile phase (A) 0.1% DEA in n-Hexane (B) Ethanol (A:B:70:30); flow Rate: 1.00 mL/min); Optical rotation [α]$_D^{20}$: −6.20° (c=0.25, DCM). TLC: 10% MeOH/DCM (Rf: 0.2).

130. (+)-2-((3,4-trans)-4-methyl-1-(2-methylbenzyl)pyrrolidin-3-yl)-7-(tetrahydro-2H-pyran-4-yl)imidazo[5,1-f][1,2,4]triazin-4(3H)-one

131. (+)-2-((3,4-trans)-4-methyl-1-(3-methylbenzyl)pyrrolidin-3-yl)-7-(tetrahydro-2H-pyran-4-yl)imidazo[5,1-f][1,2,4]triazin-4(3H)-one

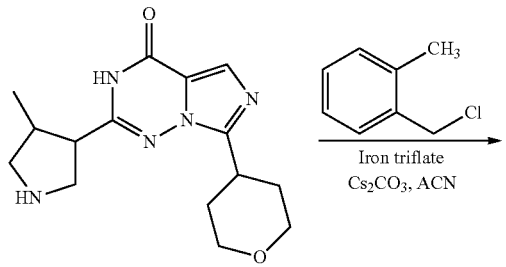

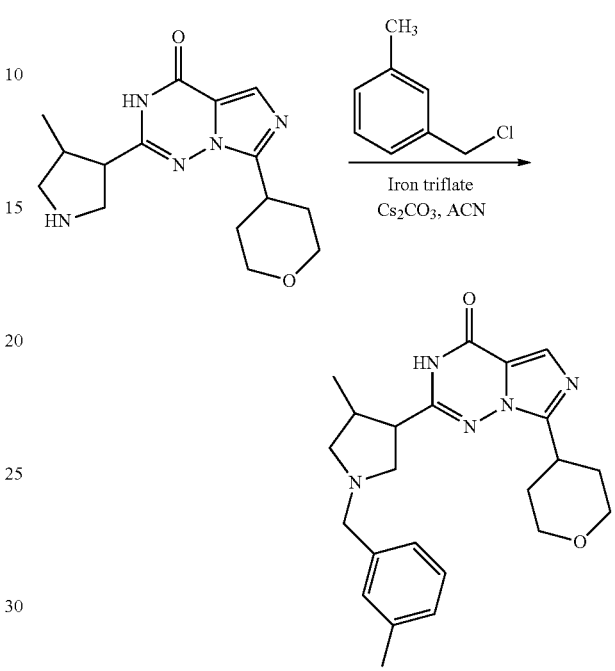

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (90 mg, 0.29 mmol) in ACN (5 mL) were added 1-(chloromethyl)-2-methylbenzene (45.9 mg, 0.32 mmol), Iron triflate (29.8 mg, 0.05 mmol) and $Cs_2CO_3$ (193.6 mg, 0.59 mmol) at RT under argon atmosphere. The resultant reaction mixture was heated to 70° C. and stirred for 1.5 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(2-methylbenzyl)pyrrolidin-3-yl)-7-(tetrahydro-2H-pyran-4-yl)imidazo[5,1-f][1,2,4]triazin-4(3H)-one (42 mg, 35%) as an off-white solid; $^1$H-NMR (DMSO-$d_6$, 400 MHz): δ 11.58 (bs, 1H), 7.65 (s, 1H), 7.29-7.28 (m, 1H), 7.16-7.14 (m, 3H), 3.98-3.96 (m, 2H), 3.57-3.54 (m, 2H), 3.50-3.47 (m, 2H), m 3.369-3.38 (m, 1H), 2.93-2.87 (m, 2H), 2.81-2.79 (m, 2H), 2.64-2.61 (m, 1H), 2.34 (s, 3H), 2.24-2.21 (m, 1H), 1.89-1.80 (m, 4H), 1.12 (d, 3H); Mass (ESI): 408.3 [M$^+$+1]; LC-MS: 95.52%; 408.3 (M$^+$+1); (column; X-bridge C-18, (50×3.0 mm, 3.5µ); RT 2.13 min. 0.05% TFA in water: ACN; 0.8 ml/min); UPLC (purity): 94.15%; (column; Acquity BEH C-18, (50×2.1 mm, 1.7µ); RT 1.50 min. 0.025% TFA (Aq): ACN; 0.50 ml/min; Chiral HPLC: 96.97%, R$_t$=7.16 min (Chiralpak IA, 250×4.6 mm, 5µ; mobile phase (A) 0.1% DEA in n-Hexane (B) Ethanol (A:B:80:20); flow Rate: 1.00 mL/min); Optical rotation [α]$_D^{20}$: +24.70° (c=0.25, DCM). TLC: 5% MeOH/DCM (Rf: 0.5).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (90 mg, 0.29 mmol) in ACN (5 mL) were added 1-(chloromethyl)-3-methylbenzene (45.9 mg, 0.32 mmol), Iron triflate (29.8 mg, 0.05 mmol) and $Cs_2CO_3$ (193.6 mg, 0.59 mmol) at RT under argon atmosphere. The resultant reaction mixture was heated to 70° C. and stirred for 1.5 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(3-methylbenzyl)pyrrolidin-3-yl)-7-(tetrahydro-2H-pyran-4-yl)imidazo[5,1-f][1,2,4]triazin-4(3H)-one (55 mg, 46%) as an off-white solid; $^1$H-NMR (DMSO-$d_6$, 400 MHz): δ 7.68 (s, 1H), 7.24-7.19 (m, 1H), 7.14-7.12 (m, 3H), 3.98-3.96 (m, 2H), 3.59-3.51 (m, 5H), 2.94-2.89 (m, 2H), 2.80-2.76 (m, 2H), 2.67-2.62 (m, 1H), 2.31-2.24 (m, 4H), 1.91-1.84 (m, 4H), 1.09 (d, 3H); Mass (ESI): 408 [M$^+$+1]; LC-MS: 97.68%; 408.3 (M$^+$+1); (column; X-bridge C-18, (50×3.0 mm, 3.5µ); RT 2.18 min. 0.05% TFA in water: ACN; 0.8 ml/min); UPLC (purity): 97.78%; (column; Acquity BEH C-18, (50×2.1 mm, 1.7µ); RT 1.55 min. 0.025% TFA (Aq): ACN; 0.50 ml/min; Chiral HPLC: 99.75%, R$_t$=13.25 min (Chiralpak IA, 250×4.6 mm, 5µ; mobile phase (A) 0.1% DEA in n-Hexane (B) Ethanol (A:B:90:10); flow Rate: 1.00 mL/min); Optical rotation [α]$_D^{20}$: +20.60° (c=0.25, DCM). TLC: 5% MeOH/DCM (Rf: 0.5).

607

132. (+)-2-((3,4-trans)-4-methyl-1-(4-methylbenzyl)pyrrolidin-3-yl)-7-(tetrahydro-2H-pyran-4-yl)imidazo[5,1-f][1,2,4]triazin-4(3H)-one

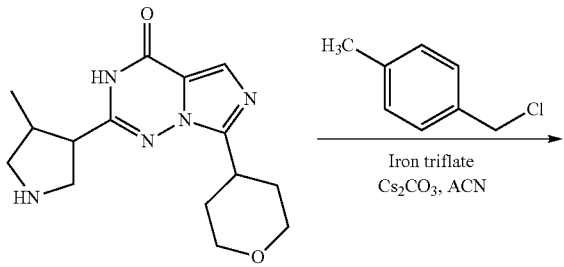

608

133. (−)-2-((3,4-trans)-1-(ethylsulfonyl)-4-methylpyrrolidin-3-yl)-7-(tetrahydro-2H-pyran-4-yl)imidazo[5,1-f][1,2,4]triazin-4(3H)-one

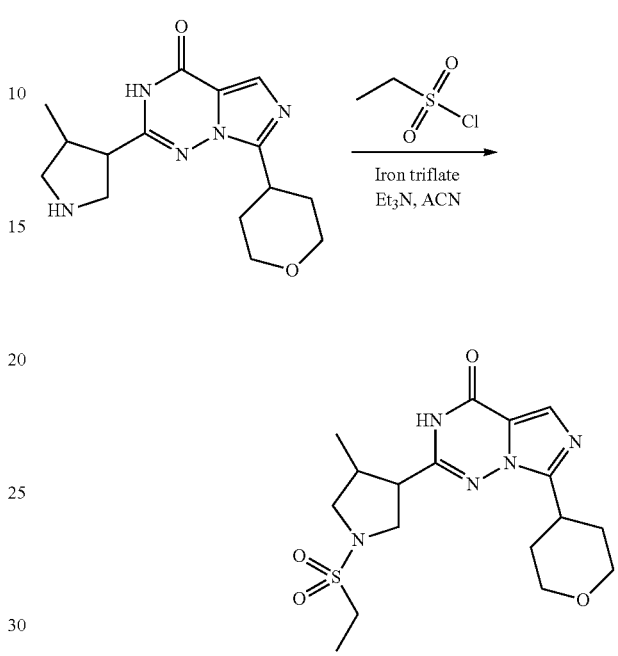

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (15 mL) were added 1-(chloromethyl)-4-methylbenzene (38.2 mg, 0.29 mmol), Iron triflate (24.9 mg, 0.049 mmol) and $Cs_2CO_3$ (161 mg, 0.49 mmol) at RT under argon atmosphere. The resultant reaction mixture was heated to 70° C. and stirred for 2 h. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(4-methylbenzyl)pyrrolidin-3-yl)-7-(tetrahydro-2H-pyran-4-yl)imidazo[5,1-f][1,2,4]triazin-4(3H)-one (41 mg, 41%) as an off-white solid; $^1$H-NMR (DMSO-$d_6$, 500 MHz): δ 7.68 (s, 1H), 7.19-7.12 (m, 4H), 3.96-3.92 (m, 2H), 3.61-3.49 (m, 5H), 2.89-2.85 (m, 2H), 2.76-2.74 (m, 2H), 2.65-2.61 (m, 2H), 2.28 (s, 3H), 2.24-2.22 (m, 1H), 1.88-1.81 (m, 4H), 1.09 (d, 3H); Mass (ESI): 408 [M$^+$+1]; LC-MS: 96.67%; 408.4 (M$^+$+1); (column; X-bridge C-18, (50×3.0 mm, 3.5μ); RT 2.19 min. 0.05% TFA in water: ACN; 0.8 ml/min); UPLC (purity): 95.79%; (column; Acquity BEH C-18, (50×2.1 mm, 1.7μ); RT 1.56 min. 0.025% TFA (Aq): ACN; 0.50 ml/min; Chiral HPLC: 95.19%, $R_t$=7.75 min (Chiralpak IA, 250×4.6 mm, 5μ; mobile phase (A) 0.1% DEA in n-Hexane (B) Ethanol (A:B:80:20); flow Rate: 1.00 mL/min); Optical rotation $[α]_D^{20}$: +12.78° (c=0.25, DCM). TLC: 5% MeOH/DCM (Rf: 0.3).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added ethanesulfonyl chloride (31.8 mg, 0.24 mmol), Iron triflate (24.9 mg, 0.04 mmol) and Et$_3$N (49.9 mg, 0.44 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (−)-2-((3,4-trans)-1-(ethylsulfonyl)-4-methylpyrrolidin-3-yl)-7-(tetrahydro-2H-pyran-4-yl)imidazo[5,1-f][1,2,4]triazin-4(3H)-one (41 mg, 42%) as an off-white solid; $^1$H-NMR (DMSO-$d_6$, 500 MHz): δ 11.84 (bs, 1H), 7.68 (s, 1H), 3.94-3.92 (m, 2H), 3.78-3.75 (m, 1H), 3.64-3.59 (m, 2H), 3.52-3.45 (m, 3H), 3.17-3.14 (m, 2H), 3.05-3.01 (m, 2H), 2.68-2.62 (m, 1H), 1.86-1.82 (m, 4H), 1.28 (t, 3H), 1.12 (d, 3H); Mass (ESI): 396 [M$^+$+1]; LC-MS: 99.16%; 396.3 (M$^+$+1); (column; X-bridge C-18, (50×3.0 mm, 3.5μ); RT 2.16 min. 0.05% TFA in water: ACN; 0.8 ml/min); UPLC (purity): 98.87%; (column; Acquity BEH C-18, (50×2.1 mm, 1.7μ); RT 1.59 min. 0.025% TFA (Aq): ACN; 0.50 ml/min; Chiral HPLC: 98.81%, $R_t$=16.38 min (Chiralpak IC, 250×4.6 mm, 5μ; mobile phase (A) n-Hexane (B) DCM:Methanol (80:20) (A:B:50:50); flow Rate: 1.00 mL/min); Optical rotation $[α]_D^{20}$: −12.24° (c=0.25, DCM). TLC: 5% MeOH/DCM (Rf: 0.3).

134. (+)-2-((3,4-trans)-1-(ethylsulfonyl)-4-methyl-pyrrolidin-3-yl)-7-(tetrahydro-2H-pyran-4-yl)imidazo[5,1-f][1,2,4]triazin-4(3H)-one

135. (−)-2-((3,4-trans)-1-(cyclohexylmethyl)-4-methylpyrrolidin-3-yl)-7-(tetrahydro-2H-pyran-4-yl)imidazo[5,1-f][1,2,4]triazin-4(3H)-one

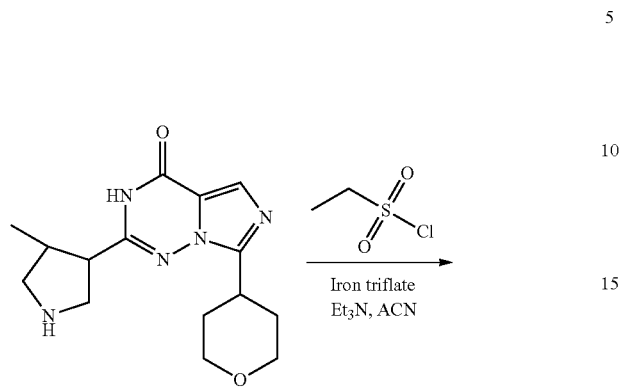

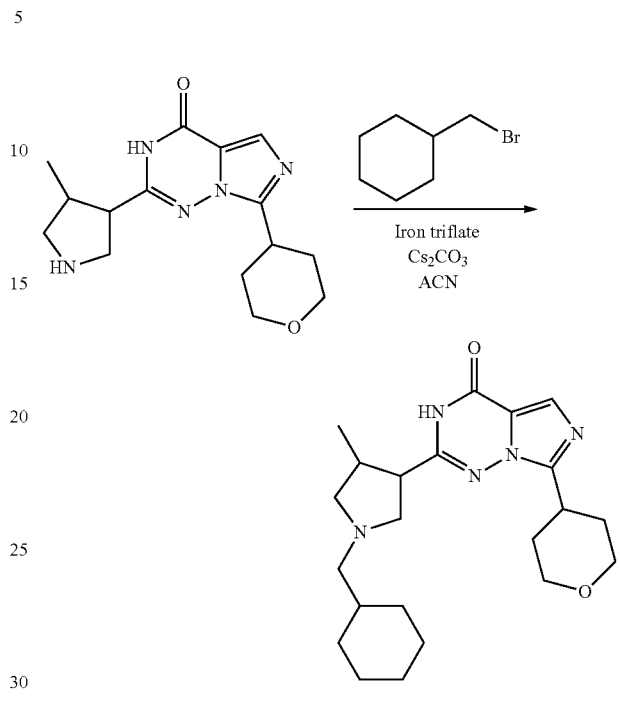

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in ACN (5 mL) were added ethanesulfonyl chloride (31.8 mg, 0.24 mmol), Iron triflate (24.9 mg, 0.04 mmol) and Et$_3$N (49.9 mg, 0.44 mmol) at −20° C. and stirred for 10 min under argon atmosphere. The reaction mixture was diluted with water and extracted with EtOAc (2×20 mL). Combined organic layer was dried over sodium sulphate, filtered and concentrated in vacuo to obtain the crude product. The crude material was purified by silica gel column chromatography to afford (+)-2-((3,4-trans)-1-(ethylsulfonyl)-4-methylpyrrolidin-3-yl)-7-(tetrahydro-2H-pyran-4-yl)imidazo[5,1-f][1,2,4]triazin-4(3H)-one (25 mg, 26%) as an off-white solid; $^1$H-NMR (DMSO-d$_6$, 500 MHz): δ 11.84 (bs, 1H), 7.68 (s, 1H), 3.94-3.92 (m, 2H), 3.78-3.75 (m, 1H), 3.64-3.59 (m, 2H), 3.52-3.45 (m, 3H), 3.17-3.14 (m, 2H), 3.05-3.01 (m, 2H), 2.68-2.62 (m, 1H), 1.86-1.82 (m, 4H), 1.28 (t, 3H), 1.12 (d, 3H); Mass (ESI): 396 [M$^+$+1]; LC-MS: 95.65%; 396.3 (M$^+$+1); (column; X-bridge C-18, (50×3.0 mm, 3.5μ); RT 2.18 min. 0.05% TFA in water: ACN; 0.8 ml/min); UPLC (purity): 97.92%; (column; Acquity BEH C-18, (50×2.1 mm, 1.7μ); RT 1.54 min. 0.025% TFA (Aq): ACN; 0.50 ml/min; Chiral HPLC: 99.41%, R$_t$=18.90 min (Chiralpak IC, 250×4.6 mm, 5μ; mobile phase (A) n-Hexane (B) DCM:Methanol (80:20) (A:B:50:50); flow Rate: 1.00 mL/min); Optical rotation [α]$_D^{20}$: +6.76° (c=0.25, DCM). TLC: 5% MeOH/DCM (Rf: 0.5).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in ACN (25 mL) were added (bromomethyl)cyclohexane (64.2 mg, 0.36 mmol), Iron triflate (33.2 mg, 0.066 mmol) and Cs$_2$CO$_3$ (214 mg, 0.66 mmol) at RT under argon atmosphere. The resultant reaction mixture was heated to 65° C. and stirred for 16 h. The reaction mixture was diluted with water (100 mL) and extracted with EtOAc (3×50 mL). Combined organic layer was dried over sodium sulphate, filtered and concentrated in vacuo to obtain the crude product. The crude material was purified by silica gel column chromatography to afford (−)-2-((3,4-trans)-1-(cyclohexylmethyl)-4-methylpyrrolidin-3-yl)-7-(tetrahydro-2H-pyran-4-yl)imidazo[5,1-f][1,2,4]triazin-4(3H)-one (40 mg, 30%) as an off-white solid; $^1$H-NMR (DMSO d$_6$, 400 MHz): δ 9.74 (bs, 1H), 7.76 (s, 1H), 4.02-3.95 (m, 4H), 3.47-3.32 (m, 7H), 3.28-3.07 (m, 3H), 2.99-2.65 (m, 2H), 1.89-1.84 (m, 3H), 1.77-1.69 (m, 5H), 1.28-1.25 (m, 2H), 1.12 (d, 3H), 1.04-0.94 (m, 2H); Mass (ESI): 400 [M$^+$+1]; LC-MS: 98.92%; 400.4 (M+1); (column; X-bridge C-18, (50×3.0 mm, 3.5μ); RT 2.21 min. 0.05% TFA in water: ACN; 0.8 ml/min); UPLC (purity): 95%; (column; Acquity BEH C-18, (50×2.1 mm, 1.7μ); RT 1.59 min. 0.025% TFA (Aq): ACN; 0.50 ml/min; Chiral HPLC: 98.74%, R$_t$=11.17 min (Chiralpak IA, 250×4.6 mm, 5μ; mobile phase (A) 0.1% DEA in n-Hexane (B) EtOH (A:B:90:10); flow Rate: 1.00 mL/min); Optical rotation [α]$_D^{20}$: −7.28° (c=0.25, DCM); TLC: 10% MeOH/DCM (Rf: 0.8).

136. (−)-2-((3,4-trans)-4-methyl-1-(4-(pyrrolidin-1-yl)benzyl)pyrrolidin-3-yl)-7-(tetrahydro-2H-pyran-4-yl)imidazo[5,1-f][1,2,4]triazin-4(3H)-one

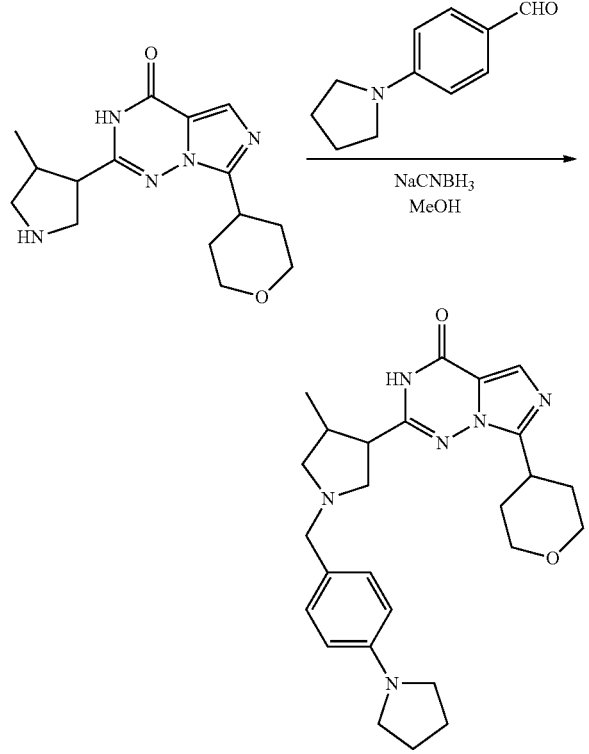

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 4-(pyrrolidin-1-yl)benzaldehyde (70 mg, 0.39 mmol) at RT under argon atmosphere. After being stirred for 2 h, NaCNBH$_3$ (63 mg, 0.99 mmol) was added to the reaction mixture and stirring was continued for another 16 h at RT. The reaction mixture was diluted with ice-cold water (100 mL) and extracted with DCM (3×50 mL). Combined organic layer was dried over sodium sulphate, filtered and concentrated in vacuo to obtain the crude product. The crude material was purified by silica gel column chromatography to afford (−)-2-((3,4-trans)-4-methyl-1-(4-(pyrrolidin-1-yl)benzyl)pyrrolidin-3-yl)-7-(tetrahydro-2H-pyran-4-yl)imidazo[5,1-f][1,2,4]triazin-4(3H)-one (45 mg, 30%) as an off-white solid; $^1$H-NMR (DMSO d$_6$, 400 MHz): δ 7.64 (s, 1H), 7.09 (d, 2H), 6.48-6.43 (m, 2H), 3.96-3.94 (m, 2H), 3.48-3.38 (m, 5H), 3.18-3.14 (m, 4H), 2.88-2.84 (m, 2H), 2.76-2.71 (m, 2H), 2.65-2.59 (m, 1H), 2.19-2.14 (m, 1H), 1.94-1.91 (m, 4H), 1.85-1.80 (m, 4H), 1.07 (d, 3H); Mass (ESI): 463.4 [M$^+$+1]; LC-MS: 95.57%; 463.4 (M+1); (column; X-bridge C-18, (50×3.0 mm, 3.5μ); RT 2.42 min. 0.05% TFA in water: ACN; 0.8 ml/min); UPLC (purity): 95.77%; (column; Acquity BEH C-18, (50×2.1 mm, 1.7μ); RT 1.71 min. 0.025% TFA (Aq): ACN; 0.50 ml/min; Chiral HPLC: 97.84%, R$_t$=11.47 min (Chiralpak IA, 250×4.6 mm, 5μ; mobile phase (A) n-Hexane (B) DCM:Methanol (80:20) (A:B:85:15); flow Rate: 1.00 mL/min); Optical rotation [α]$_D^{20}$: −4.46° (c=0.25, DCM); TLC: 10% MeOH/DCM (Rf: 0.7).

137. (+)-2-((3,4-trans)-4-methyl-1-(2-(pyrrolidin-1-yl)benzyl)pyrrolidin-3-yl)-7-(tetrahydro-2H-pyran-4-yl)imidazo[5,1-f][1,2,4]triazin-4(3H)-one

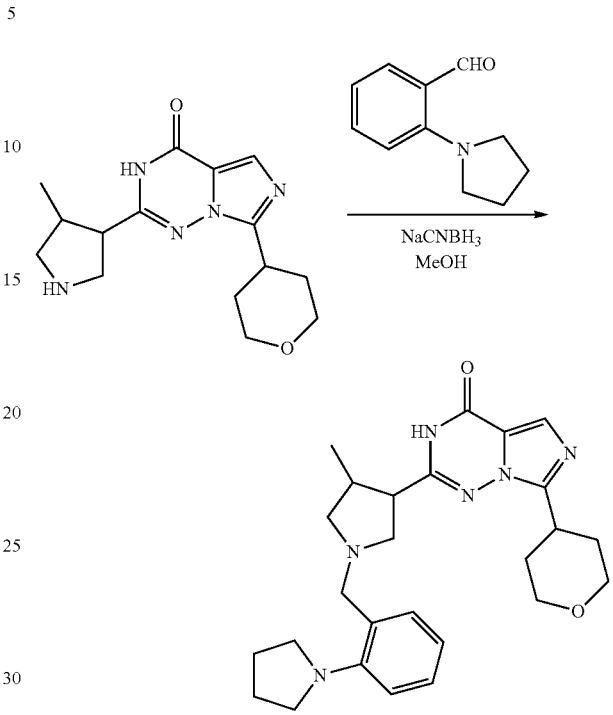

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 2-(pyrrolidin-1-yl)benzaldehyde (70 mg, 0.39 mmol) at RT under argon atmosphere. After being stirred for 2 h, NaCNBH$_3$ (63 mg, 0.99 mmol) was added to the reaction mixture and stirring was continued for another 16 h at RT. The reaction mixture was diluted with ice-cold water (100 mL) and extracted with DCM (3×50 mL). Combined organic layer was dried over sodium sulphate, filtered and concentrated in vacuo to obtain the crude product. The crude material was purified by silica gel column chromatography to afford (+)-2-((3,4-trans)-4-methyl-1-(2-(pyrrolidin-1-yl)benzyl)pyrrolidin-3-yl)-7-(tetrahydro-2H-pyran-4-yl)imidazo[5,1-f][1,2,4]triazin-4(3H)-one (40 mg, 26%) as an off-white solid; $^1$H-NMR (DMSO d$_6$, 400 MHz): δ 8.16 (bs, 1H), 7.66 (s, 1H), 7.32 (d, 1H), 7.12-7.07 (m, 1H), 6.87-6.79 (m, 2H), 3.96-3.92 (m, 2H), 3.62 (s, 2H), 3.49-3.42 (m, 3H), 3.19-3.11 (m, 4H), 2.94-2.89 (m, 2H), 2.78-2.71 (m, 2H), 2.67-2.62 (m, 1H), 2.25-2.21 (m, 1H), 1.89-1.82 (m, 8H), 1.09 (d, 3H); Mass (ESI): 463 [M$^+$+1]; LC-MS: 96.03%; 463.4 (M+1); (column; X-bridge C-18, (50×3.0 mm, 3.5μ); RT 2.40 min. 0.05% TFA in water: ACN; 0.8 ml/min); UPLC (purity): 98.39%; (column; Acquity BEH C-18, (50×2.1 mm, 1.7μ); RT 2.02 min. 0.025% TFA (Aq): ACN; 0.50 ml/min; Chiral HPLC: 100% R$_t$=9.13 min (Chiralpak IA, 250×4.6 mm, 5μ; mobile phase (A) 0.1% DEA in n-Hexane (B) Ethanol (A:B:85:15); flow Rate: 1.00 mL/min); Optical rotation [α]$_D^{20}$: +4.68° (c=0.25, DCM); TLC: 10% MeOH/DCM (Rf: 0.7).

138. (+)-2-((3,4-trans)-1-(2-(dimethylamino)benzyl)-4-methylpyrrolidin-3-yl)-7-(tetrahydro-2H-pyran-4-yl)imidazo[5,1-f][1,2,4]triazin-4(3H)-one

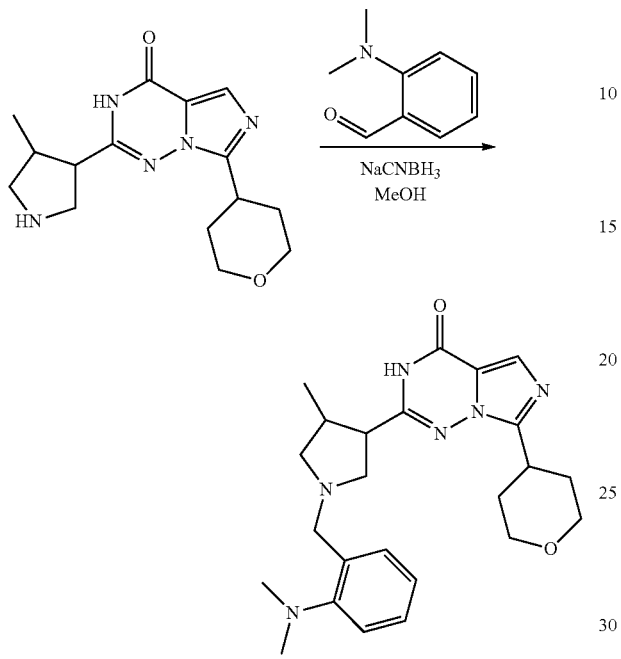

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 2-(dimethylamino)benzaldehyde (59.2 mg, 0.39 mmol) at RT under argon atmosphere. After being stirred for 2 h, NaCNBH$_3$ (62.3 mg, 0.99 mmol) was added to the reaction mixture and stirring was continued for another 16 h at RT. The reaction mixture was diluted with ice-cold water (100 mL) and extracted with DCM (3×50 mL). Combined organic layer was dried over sodium sulphate, filtered and concentrated in vacuo to obtain the crude product. The crude material was purified by silica gel column chromatography to afford (+)-2-((3,4-trans)-1-(2-(dimethylamino)benzyl)-4-methylpyrrolidin-3-yl)-7-(tetrahydro-2H-pyran-4-yl)imidazo[5,1-f][1,2,4]triazin-4(3H)-one (39 mg, 27%) as an off-white solid; $^1$H-NMR (DMSO d$_6$, 400 MHz): δ 7.67 (s, 1H), 7.38 (d, 1H), 7.18 (t, 1H), 7.08 (d, 1H), 6.96 (t, 1H), 3.96-3.94 (m, 2H), 7.65 (s, 2H), 3.49-3.42 (m, 3H), 2.98-2.94 (m, 2H), 2.83-2.79 (m, 2H), 2.69-2.68 (m, 1H), 2.65 (s, 6H), 2.31-2.27 (m, 1H), 1.89-1.81 (m, 4H), 1.09 (d, 3H); Mass (ESI): 437.4 [M$^+$+1]; LC-MS: 95.43%; 437.4 (M+1); (column; X-bridge C-18, (50×3.0 mm, 3.5μ); RT 3.13 min. 5 mM NH$_4$OAc in water: ACN; 0.8 ml/min); UPLC (purity): 98.12%; (column; Acquity BEH C-18, (50×2.1 mm, 1.7μ); RT 1.58 min. 0.025% TFA (Aq): ACN; 0.50 ml/min; Chiral HPLC: 99.23%, R$_t$=7.55 min (Chiralpak IA, 250×4.6 mm, 5μ; mobile phase (A) 0.1% DEA in n-Hexane (B) Ethanol (A:B:90:10); flow Rate: 1.00 mL/min); Optical rotation [α]$_D^{20}$: +16.16° (c=0.25, DCM); TLC: 5% MeOH/DCM (Rf: 0.4).

139. (+)-2-((3,4-trans)-1-(3-(dimethylamino)benzyl)-4-methylpyrrolidin-3-yl)-7-(tetrahydro-2H-pyran-4-yl)imidazo[5,1-f][1,2,4]triazin-4(3H)-one

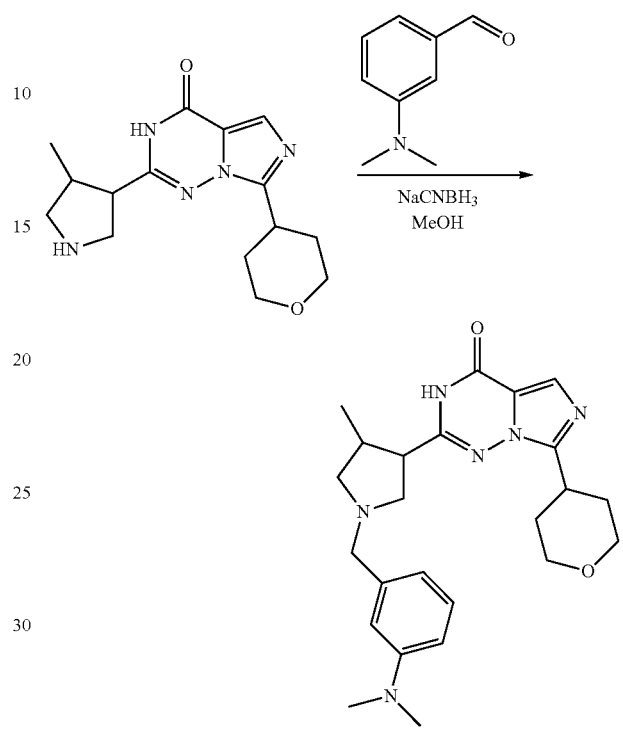

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 3-(dimethylamino)benzaldehyde (59.2 mg, 0.39 mmol) at RT under argon atmosphere. After being stirred for 2 h, NaCNBH$_3$ (62.3 mg, 0.99 mmol) was added to the reaction mixture and stirring was continued for another 16 h at RT. The reaction mixture was diluted with ice-cold water (100 mL) and extracted with DCM (3×50 mL). Combined organic layer was dried over sodium sulphate, filtered and concentrated in vacuo to obtain the crude product. The crude material was purified by silica gel column chromatography to afford (+)-2-((3,4-trans)-1-(3-(dimethylamino)benzyl)-4-methylpyrrolidin-3-yl)-7-(tetrahydro-2H-pyran-4-yl)imidazo[5,1-f][1,2,4]triazin-4(3H)-one (32 mg, 22%) as an off-white solid; $^1$H-NMR (DMSO d$_6$, 400 MHz): δ 7.64 (s, 1H), 7.12 (t, 1H), 6.68-6.59 (m, 3H), 3.96-3.94 (m, 2H), 3.58-3.47 (m, 6H), 2.89-2.84 (m, 1H), 2.83 (s, 6H), 2.79-2.77 (m, 2H), 2.68-2.65 (m, 1H), 2.23-2.21 (m, 1H), 1.89-1.84 (m, 4H), 1.09 (d, 3H); Mass (ESI): 437 [M$^+$+1]; LC-MS: 98%; 437.4 (M+1); (column; X-bridge C-18, (50×3.0 mm, 3.5μ); RT 1.84 min. 0.05% TFA in water: ACN; 0.8 ml/min); UPLC (purity): 99.38%; (column; Acquity BEH C-18, (50×2.1 mm, 1.7μ); RT 1.75 min. 0.025% TFA (Aq): ACN; 0.50 ml/min; Chiral HPLC: 99.60%, R$_t$=19.88 min (Chiralpak IC, 250×4.6 mm, 5μ; mobile phase (A) 0.1% DEA in n-Hexane (B) DCM:Methanol (80:20) (A:B:75:25); flow Rate: 1.00 mL/min); Optical rotation [α]$_D^{20}$: +12.11° (c=0.25, DCM); TLC: 5% MeOH/DCM (Rf: 0.4).

140. (+)-2-((3,4-trans)-1-(4-(dimethylamino)benzyl)-4-methylpyrrolidin-3-yl)-7-(tetrahydro-2H-pyran-4-yl)imidazo[5,1-f][1,2,4]triazin-4(3H)-one

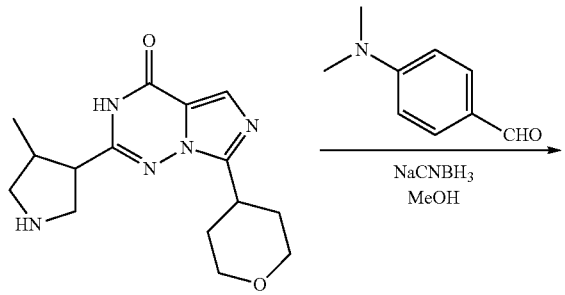

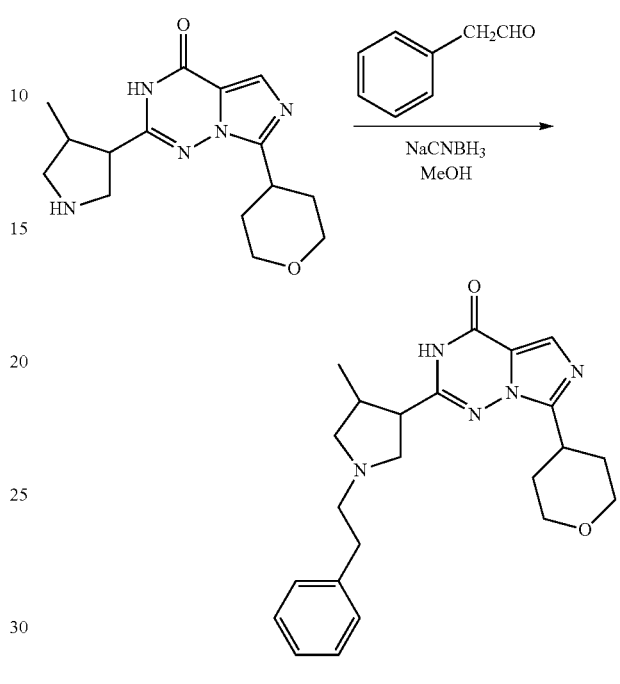

To a stirred solution of (+)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 4-(dimethylamino)benzaldehyde (59.2 mg, 0.39 mmol) at RT under argon atmosphere. After being stirred for 2 h, NaCNBH$_3$ (62.3 mg, 0.99 mmol) was added to the reaction mixture and stirring was continued for another 16 h at RT. The volatiles were evaporated under reduced pressure. The residue was diluted with ice-cold water (100 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-1-(4-(dimethylamino)benzyl)-4-methylpyrrolidin-3-yl)-7-(tetrahydro-2H-pyran-4-yl)imidazo[5,1-f][1,2,4]triazin-4(3H)-one (35 mg, 24%) as an off-white solid; $^1$H-NMR (DMSO d$_6$, 400 MHz): δ 7.65 (s, 1H), 7.12 (d, 2H), 6.67 (d, 2H), 3.97-3.95 (m, 2H), 3.57-3.51 (m, 4H), 3.38-3.36 (m, 2H), 2.89 (s, 6H), 2.86-2.85 (m, 1H), 2.78-2.75 (m, 2H), 2.64-2.61 (m, 1H), 2.22-1.99 (m, 1H), 1.89-1.82 (m, 4H), 1.07 (d, 3H); Mass (ESI): 437.4 [M$^+$+1]; LC-MS: 99.74%; 437.4 (M+1); (column; X-bridge C-18, (50×3.0 mm, 3.5μ); RT 2.29 min. 0.05% TFA in water: ACN; 0.8 ml/min); UPLC (purity): 99.50%; (column; Acquity BEH C-18, (50×2.1 mm, 1.7μ); RT 1.69 min. 0.025% TFA (Aq): ACN; 0.50 ml/min; Chiral HPLC: 100%, R$_t$=23.12 min (Chiralpak IA, 250×4.6 mm, 5μ; mobile phase (A) 0.1% TEA in n-Hexane (B) IPA (A:B:90:10); flow Rate: 1.00 mL/min); Optical rotation [α]$_D^{20}$: +9.45° (c=0.25, DCM); TLC: 5% MeOH/DCM (Rf: 0.4).

141. (+)-2-((3,4-trans)-4-methyl-1-phenethylpyrrolidin-3-yl)-7-(tetrahydro-2H-pyran-4-yl)imidazo[5,1-f][1,2,4]triazin-4(3H)-one To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 2-phenylacetaldehyde (52 mg, 0.43 mmol) at RT under argon atmosphere. After being stirred for 2 h, NaCNBH$_3$ (63 mg, 0.99 mmol) was added to the reaction mixture and stirring was continued for another 16 h at RT. The volatiles were evaporated under reduced pressure. The residue was diluted with ice-cold water (100 mL) and extracted with DCM (3×50 mL). Combined organic layer was dried over sodium sulphate, filtered and concentrated in vacuo to obtain the crude product. The crude material was purified by silica gel column chromatography to afford (+)-2-((3,4-trans)-4-methyl-1-phenethylpyrrolidin-3-yl)-7-(tetrahydro-2H-pyran-4-yl)imidazo[5,1-f][1,2,4]triazin-4(3H)-one (40 mg, 30%) as an off-white solid; $^1$H-NMR (DMSO d$_6$, 400 MHz): δ 7.65 (s, 1H), 7.25-7.17 (m, 5H), 3.96-3.94 (m, 2H), 3.50-3.48 (m, 3H), 3.01-2.98 (m, 1H), 2.95-2.93 (m, 1H), 2.87-2.85 (m, 1H), 2.69-2.61 (m, 6H), 2.34-2.29 (m, 1H), 1.87-1.82 (m, 4H), 1.09 (d, 3H); Mass (ESI): 408 [M$^+$+1]; LC-MS: 98.38%; 408 (M+1); (column; X-bridge C-18, (50×3.0 mm, 3.5μ); RT 2.85 min. 0.05% TFA (Aq): ACN; 0.8 ml/min); UPLC (purity): 96.39%; (column; Acquity BEH C-18, (50×2.1 mm, 1.7μ); RT 1.50 min. 0.025% TFA (Aq): ACN; 0.50 ml/min; Chiral HPLC: 100%, R$_t$=9.26 min (Chiralpak IA, 250×4.6 mm, 5μ; mobile phase (A) 0.1% TEA in n-Hexane (B) Ethanol (A:B:80:20); flow Rate: 1.00 mL/min); Optical rotation [α]$_D^{20}$: +19.63° (c=0.25, DCM); TLC: 10% MeOH/DCM (Rf: 0.4).

142. (+)-2-((3,4-trans)-1-((6-methoxypyridin-3-yl)methyl)-4-methylpyrrolidin-3-yl)-7-(tetrahydro-2H-pyran-4-yl)imidazo[5,1-f][1,2,4]triazin-4(3H)-one

143. (+)-2-((3,4-trans)-4-methyl-1-(pyrimidin-2-yl)pyrrolidin-3-yl)-7-(tetrahydro-2H-pyran-4-yl)imidazo[5,1-f][1,2,4]triazin-4(3H)-one

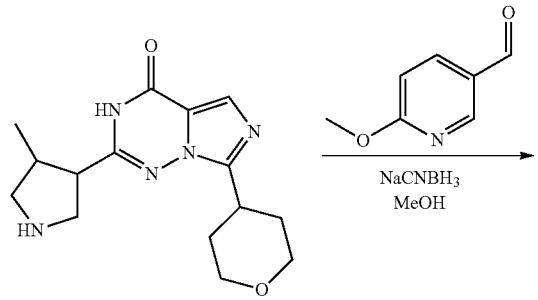

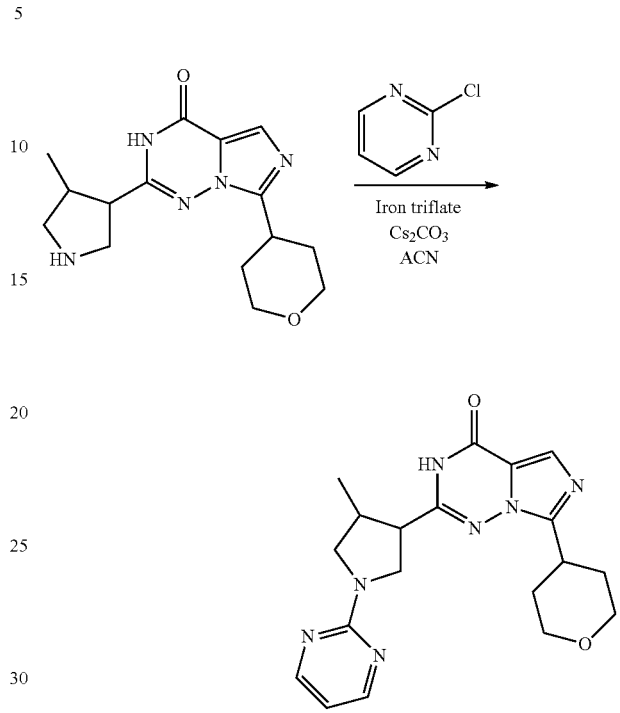

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 6-methoxynicotinaldehyde (54.2 mg, 0.39 mmol) at RT under argon atmosphere. After being stirred for 2 h, NaCNBH$_3$ (62 mg, 0.99 mmol) was added to the reaction mixture and stirring was continued for another 16 h at RT. The volatiles were evaporated under reduced pressure. The residue was diluted with ice-cold water (100 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-1-((6-methoxypyridin-3-yl)methyl)-4-methylpyrrolidin-3-yl)-7-(tetrahydro-2H-pyran-4-yl)imidazo[5,1-f][1,2,4]triazin-4(3H)-one (40 mg, 29%) as an off-white solid; $^1$H-NMR (DMSO d$_6$, 400 MHz): δ 8.09 (d, 1H), 7.65-7.62 (m, 2H), 6.78 (d, 1H), 3.96-3.94 (m, 2H), 3.84 (s, 3H), 3.61-3.54 (m, 5H), 3.37-3.35 (m, 1H), 2.96-2.94 (m, 2H), 2.78-2.74 (m, 2H), 2.65-2.61 (m, 1H), 1.89-1.82 (m, 4H), 1.09 (d, 3H); Mass (ESI): 425.4 [M$^+$+1]; LC-MS: 99.56%; 425 (M+1); (column; X-bridge C-18, (50×3.0 mm, 3.5μ); RT 2.44 min. 0.05% TFA (Aq): ACN; 0.8 ml/min); UPLC (purity): 99.5%; (column; Acquity BEH C-18, (50× 2.1 mm, 1.7μ); RT 1.29 min. 0.025% TFA (Aq): ACN; 0.50 ml/min; Chiral HPLC: 100%, R$_t$=12.11 min (Chiralpak IA, 250×4.6 mm, 5μ; mobile phase (A) 0.1% DEA in n-Hexane (B) Ethanol (A:B:80:20); flow Rate: 1.00 mL/min); Optical rotation [α]$_D^{20}$: +16.14° (c=0.25, DCM); TLC: 5% MeOH/DCM (Rf: 0.4).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (110 mg, 0.36 mmol) in ACN (10 mL) were added 2-chloropyrimidine (46 mg, 0.39 mmol), Iron triflate (37 mg, 0.072 mmol) and Cs$_2$CO$_3$ (236 mg, 0.72 mmol) at RT under argon atmosphere. The resulting reaction mixture was heated to 65° C. and stirred for 3 h. The reaction mixture was diluted with water (200 mL) and extracted with EtOAc (3×50 mL). Combined organic layer was dried over sodium sulphate, filtered and concentrated in vacuo to obtain the crude product. The crude material was purified by silica gel column chromatography to afford (+)-2-((3,4-trans)-4-methyl-1-(pyrimidin-2-yl)pyrrolidin-3-yl)-7-(tetrahydro-2H-pyran-4-yl)imidazo[5,1-f][1,2,4]triazin-4(3H)-one (45 mg, 36%) as an off-white solid; $^1$H-NMR (DMSO d$_6$, 400 MHz): δ 11.84 (bs, 1H), 8.34 (d, 2H), 7.64 (s, 1H), 6.62 (t, 1H), 3.98-3.82 (m, 1H), 3.80-3.72 (m, 4H), 3.40-3.35 (m, 1H), 3.32 (s, 3H), 3.06-3.02 (m, 1H), 2.76-2.72 (m, 1H), 1.78-1.71 (m, 4H), 1.12 (d, 3H); Mass (ESI): 382.3 [M$^+$+1]; LC-MS: 99.56%; 382.3 (M+1); (column; X-bridge C-18, (50×3.0 mm, 3.5μ); RT 1.84 min. 0.05% TFA in water: ACN; 0.8 ml/min); UPLC (purity): 99.85%; (column; Acquity BEH C-18, (50×2.1 mm, 1.7μ); RT 1.38 min. 0.025% TFA (Aq): ACN; 0.50 ml/min; Chiral HPLC: 99.59%, R$_t$=8.03 min (Chiralpak IA, 250×4.6 mm, 5μ; mobile phase (A) 0.1% DEA in n-Hexane (B) DCM:Methanol (80:20) (A:B:70:30); flow Rate: 1.00 mL/min); Optical rotation [α]$_D^{20}$: +19.31° (c=0.25, DCM); TLC: 10% MeOH/DCM (Rf: 0.6).

144. (+)-2-((3,4-trans)-1-(2,6-difluorobenzyl)-4-methylpyrrolidin-3-yl)-7-(tetrahydro-2H-pyran-4-yl)imidazo[5,1-f][1,2,4]triazin-4(3H)-one

145. (+)-2-((3,4-trans)-1-(3-cyclopropylbenzyl)-4-methylpyrrolidin-3-yl)-7-(tetrahydro-2H-pyran-4-yl)imidazo[5,1-f][1,2,4]triazin-4(3H)-one

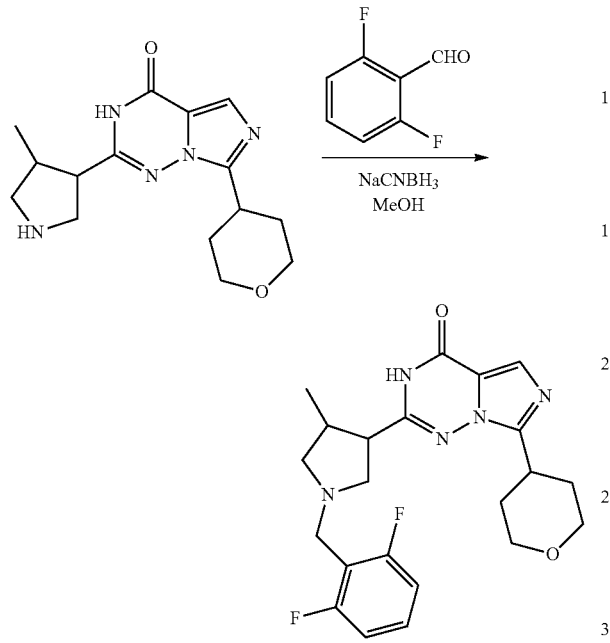

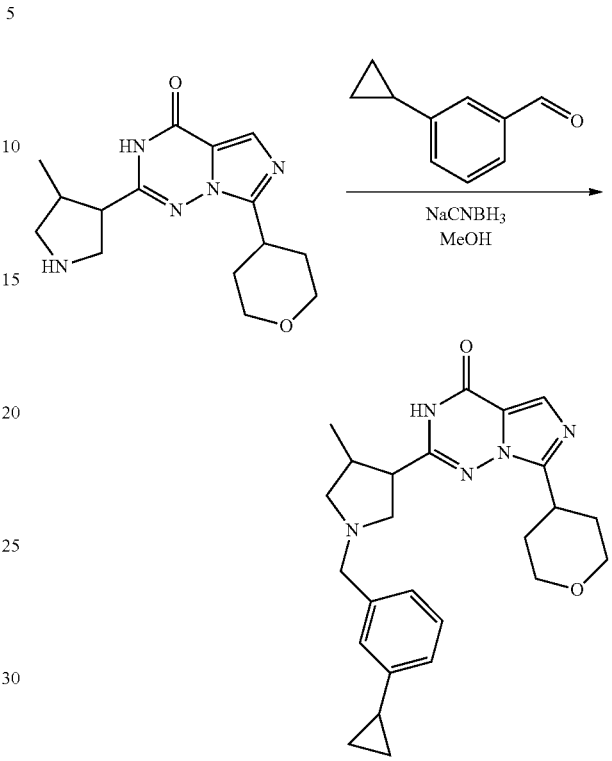

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 2,6-difluorobenzaldehyde (61 mg, 0.42 mmol) at RT under argon atmosphere. After being stirred for 2 h; NaCNBH$_3$ (63 mg, 0.99 mmol) was added to the reaction mixture and stirring was continued for another 16 h at RT. The volatiles were evaporated under reduced pressure. The residue was diluted with ice-cold water (30 mL) and extracted with DCM (3×50 mL). Combined organic layer was dried over sodium sulphate, filtered and concentrated in vacuo to obtain the crude product. The crude material was purified by silica gel column chromatography to afford (+)-2-((3,4-trans)-1-(2,6-difluorobenzyl)-4-methylpyrrolidin-3-yl)-7-(tetrahydro-2H-pyran-4-yl)imidazo[5,1-f][1,2,4]triazin-4(3H)-one (43 mg, 31%) as an off-white solid; $^1$H-NMR (DMSO d$_6$, 400 MHz): δ 11.52 (bs, 1H), 7.62 (s, 1H), 7.43-7.37 (m, 1H), 7.12-7.05 (m, 2H), 3.94-3.89 (m, 2H), 3.72 (s, 2H), 3.48-3.41 (m, 2H), 3.36-3.35 (m, 1H), 2.97-2.92 (m, 1H), 2.86-2.84 (m, 1H), 2.79-2.71 (m, 2H), 2.63-2.57 (m, 1H), 2.26-2.24 (m, 1H), 1.87-1.82 (m, 4H), 1.09 (d, 3H); Mass (ESI): 430.4 [M$^+$+1]; LC-MS: 98.27%; 430.5 (M+1); (column; X-bridge C-18, (50×3.0 mm, 3.5μ); RT 2.41 min. 0.05% TFA (Aq): ACN; 0.8 ml/min); UPLC (purity): 99.82%; (column; Acquity BEH C-18, (50×2.1 mm, 1.7μ); RT 1.37 min. 0.025% TFA (Aq): ACN; 0.50 ml/min; Chiral HPLC: 99.09%, R$_t$=8.49 min (Chiralpak IA, 250×4.6 mm, 5μ; mobile phase (A) 0.1% DEA in n-Hexane (B) DCM:Methanol (80:20) (A:B:70:30); flow Rate: 1.00 mL/min); Optical rotation [α]$_D^{20}$: +17.84° (c=0.25, DCM); TLC: 10% MeOH/DCM (Rf: 0.5).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (80 mg, 0.26 mmol) in MeOH (10 mL) was added 3-cyclopropylbenzaldehyde (45.9 mg, 0.31 mmol) at RT under argon atmosphere. After being stirred for 2 h, NaCNBH$_3$ (49.9 mg, 0.79 mmol) was added to the reaction mixture and stirring was continued for another 16 h at RT. The volatiles were evaporated under reduced pressure. The residue was diluted with ice-cold water (30 mL) and extracted with DCM (2×20 mL). Combined organic layer was dried over sodium sulphate, filtered and concentrated in vacuo to obtain the crude product. The crude material was purified by silica gel column chromatography to afford (+)-2-((3,4-trans)-1-(3-cyclopropylbenzyl)-4-methylpyrrolidin-3-yl)-7-(tetrahydro-2H-pyran-4-yl)imidazo[5,1-f][1,2,4]triazin-4(3H)-one (46.2 mg, 40%) as an off-white solid; $^1$H-NMR (DMSO d$_6$, 400 MHz): δ 7.64 (s, 1H), 7.18 (t, 1H), 7.09 (d, 1H), 7.02 (s, 1H), 6.95 (d, 1H), 3.96-3.94 (m, 2H), 3.59-3.57 (m, 2H), 3.51-3.47 (m, 2H), 3.38-3.36 (m, 1H), 2.92-2.87 (m, 2H), 2.79-2.72 (m, 2H), 2.65-2.62 (m, 1H), 2.24-2.21 (m, 1H), 1.89-1.82 (m, 5H), 1.09 (d, 3H), 0.92-0.91 (m, 2H), 0.65-0.62 (m, 2H); Mass (ESI): 434.4 [M$^+$+1]; LC-MS: 97.09%; 434 (M+1); (column; X-bridge C-18, (50×3.0 mm, 3.5μ); RT 5.18 min. 5 mM NH$_4$OAc: ACN; 0.8 ml/min); UPLC (purity): 95.58%; (column; Acquity BEH C-18, (50×2.1 mm, 1.7μ); RT 1.67 min. 0.025% TFA (Aq): ACN; 0.50 ml/min; Chiral HPLC: 95.06%, R$_t$=6.56 min (Chiralpak IA, 250×4.6 mm, 5μ; mobile phase (A) 0.1% DEA in n-Hexane (B) DCM:Methanol (80:20) (A:B:70:30); flow Rate: 1.00 mL/min); Optical rotation [α]$_D^{20}$: +23.76° (c=0.25, DCM); TLC: 10% MeOH/DCM (Rf: 0.5).

146. (+)-2-((3,4-trans)-1-(4-cyclopropylbenzyl)-4-methylpyrrolidin-3-yl)-7-(tetrahydro-2H-pyran-4-yl)imidazo[5,1-f][1,2,4]triazin-4(3H)-one

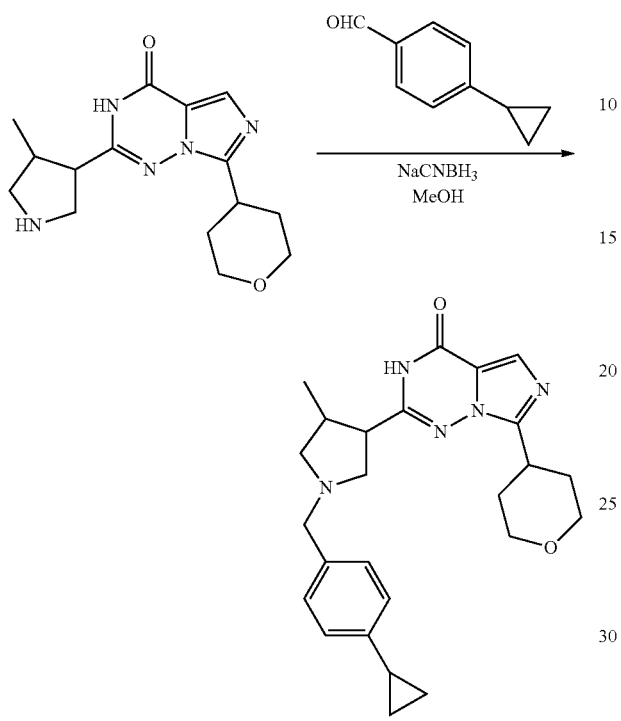

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 4-cyclopropylbenzaldehyde (63 mg, 0.43 mmol) at RT under argon atmosphere. After being stirred for 2 h, NaCNBH$_3$ (63 mg, 0.99 mmol) was added to the reaction mixture and stirring was continued for another 16 h at RT. The volatiles were evaporated under reduced pressure. The residue was diluted with ice-cold water (30 mL) and extracted with DCM (3×50 mL). Combined organic layer was dried over sodium sulphate, filtered and concentrated in vacuo to obtain the crude product. The crude material was purified by silica gel column chromatography to afford (+)-2-((3,4-trans)-1-(4-cyclopropylbenzyl)-4-methylpyrrolidin-3-yl)-7-(tetrahydro-2H-pyran-4-yl)imidazo[5,1-f][1,2,4]triazin-4(3H)-one (45 mg, 32%) as an off-white solid; $^1$H-NMR (CD$_3$OD-d$_4$, 400 MHz): δ 7.67 (s, 1H), 7.25 (d, 2H), 7.06 (d, 2H), 4.03-3.99 (m, 2H), 3.72-3.49 (m, 5H), 3.14-3.12 (m, 1H), 2.99-2.95 (m, 1H), 2.88-2.82 (m, 2H), 2.64-2.59 (m, 1H), 2.24-2.21 (m, 1H), 2.04-1.98 (m, 2H), 1.89-1.85 (m, 3H), 1.12 (d, 3H), 0.96-0.92 (m, 2H), 0.64-0.61 (m, 2H); Mass (ESI): 434.4 [M$^+$+1]; LC-MS: 98.91%; 434.6 (M+1); (column; X-bridge C-18, (50×3.0 mm, 3.5μ); RT 2.98 min. 0.05% TFA (Aq): ACN; 0.8 ml/min); UPLC (purity): 99.33%; (column; Acquity BEH C-18, (50×2.1 mm, 1.7μ); RT 1.67 min. 0.025% TFA (Aq): ACN; 0.50 ml/min; Chiral HPLC: 100%, R$_t$=7.66 min (Chiralpak IA, 250×4.6 mm, 5μ; mobile phase (A) 0.1% DEA in n-Hexane (B) DCM:Methanol (80:20) (A:B:80:20); flow Rate: 1.00 mL/min); Optical rotation [α]$_D^{20}$: +5.69° (c (0.25, DCM); TLC: 10% MeOH/DCM (Rf: 0.7).

147. (+)-((3,4-trans)-1,4-dimethylpyrrolidin-3-yl)-7-(tetrahydro-2H-pyran-4-yl)imidazo[5,1-f][1,2,4]triazin-4(3H)-one

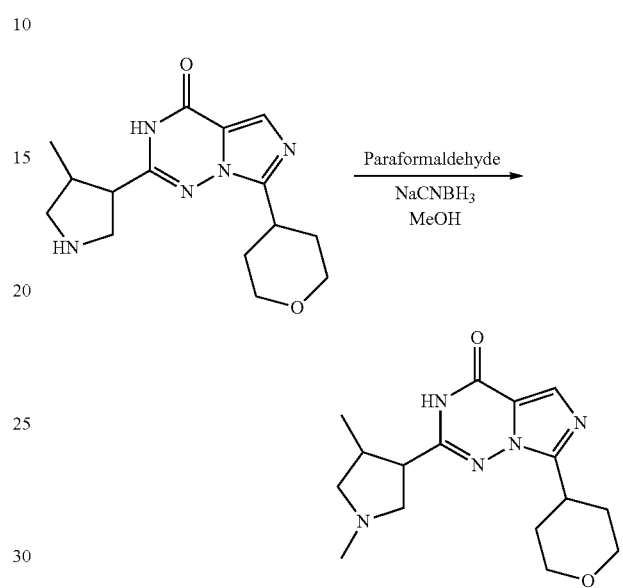

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added Paraformaldehyde (14.5 mg, 0.49 mmol) at room temperature and stirred for 2 h under argon atmosphere. To the resulting solution was added NaCNBH$_3$ (47 mg, 0.74 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-((3,4-trans)-1,4-dimethylpyrrolidin-3-yl)-7-(tetrahydro-2H-pyran-4-yl)imidazo[5,1-f][1,2,4]triazin-4(3H)-one (20 mg, 26%) as an off-white solid. $^1$H-NMR (CD$_3$OD, 400 MHz): δ 7.68 (s, 1H), 4.08-4.03 (m, 2H), 3.62-3.57 (m, 3H), 3.16-3.15 (m, 1H), 3.07-3.04 (m, 1H), 2.99-2.97 (m, 1H), 2.88-2.85 (m, 1H), 2.74-2.39 (m, 1H), 2.45 (s, 3H), 2.37-2.31 (m, 1H), 2.09-1.97 (m, 2H), 1.88-1.85 (m, 2H), 1.18 (d, 3H); Mass (ESI): 318 [M$^+$+1]; LC-MS: 95.11%; 318.3 (M$^+$+1); (column; Eclipse XDB C-18, (150×4.6 mm, 5.0μ); RT 5.51 min. 0.05% TFA (Aq): ACN; 1.0 ml/min); UPLC (purity): 96.44%; (column; Acquity UPLC HSS-T3, 100×2.1 mm, 1.8μ; RT 2.80 min. 0.025% TFA (Aq): ACN; 0.30 ml/min.; Chiral HPLC: 100%, R$_t$=39.49 min (Chiralpak IC, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +1.90° (c=0.25, DCM); TLC: 5% MeOH/DCM (R$_f$: 0.5).

148. (−)-2-((3,4-trans)-1-(2-cyclopropylbenzyl)-4-methylpyrrolidin-3-yl)-7-(tetrahydro-2H-pyran-4-yl)imidazo[5,1-f][1,2,4]triazin-4(3H)-one

149. (+)-2-((3,4-trans)-1-(3-(1H-pyrazol-1-yl)benzyl)-4-methylpyrrolidin-3-yl)-7-(tetrahydro-2H-pyran-4-yl)imidazo[5,1-f][1,2,4]triazin-4(3H)-one

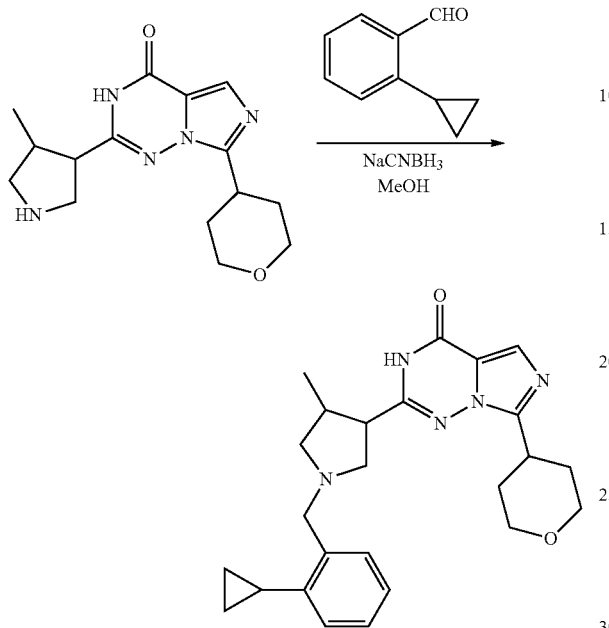

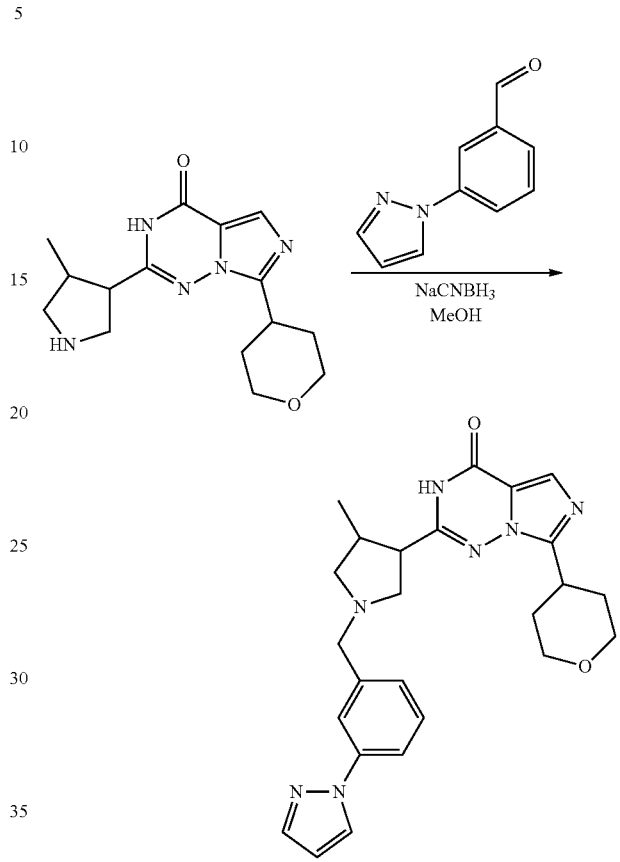

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 2-cyclopropylbenzaldehyde (63 mg, 0.42 mmol) at room temperature and stirred for 2 h under argon atmosphere. To the resulting solution was added NaCNBH$_3$ (63 mg, 0.99 mmol) and stirring was continued for another 8 h at room temperature. The volatiles were evaporated under reduced pressure. The residue was diluted with water and extracted with CH$_2$Cl$_2$ (2×30 mL). −3.21 (m, 1H), 3.14-3.12 (m, 1H), 2.94-2.91 (m, 2H), 2.62-2.57 (m, 1H), 2.25-2.19 (m, Combined organic layer was dried over sodium sulphate, filtered and concentrated in vacuo to obtain the crude product. The crude material was purified by silica gel column chromatography to afford (−)-2-((3,4-trans)-1-(2-cyclopropylbenzyl)-4-methylpyrrolidin-3-yl)-7-(tetrahydro-2H-pyran-4-yl)imidazo[5,1-f][1,2,4]triazin-4(3H)-one (50 mg, 35%) as an off-white solid; $^1$H-NMR (CD$_3$OD, 400 MHz): δ 7.68 (s, 1H), 7.31 (d, 1H), 7.21-7.14 (m, 2H), 6.98 (d, 1H), 4.08-4.02 (m, 2H), 3.92 (s, 2H), 3.65-3.54 (m, 3H), 3.242H), 2.09-1.99 (m, 2H), 1.89-1.85 (m, 2H), 1.18 (d, 3H), 1.04-0.98 (m, 2H), 0.65-0.64 (m, 2H); Mass (ESI): 434 [M$^+$+1]; LC-MS: 97%; 434.5 (M$^+$+1); (column; X-bridge C-18, (50×3.0 mm, 3.5μ); RT 2.96 min. 0.05% TFA (Aq): ACN; 0.8 ml/min); UPLC (purity): 99.74%; (column; Acquity BEH C-18, 50×2.1 mm, 1.7μ; RT 1.64 min. 0.025% TFA (Aq): ACN; 0.50 ml/min.; Chiral HPLC: 100%, R$_t$=15.46 min (Chiralpak IA, 250×4.6 mm, 5μ; mobile phase (A) 0.1% DEA in n-Hexane (B) DCM:MeOH (80:20) (A:B: 90:10); flow Rate: 1.00 mL/min); Optical rotation [α]$_D^{20}$: −10.06° (c=0.25, DCM); TLC: 10% MeOH/DCM (R$_f$: 0.7).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 3-(1H-pyrazol-1-yl)benzaldehyde (74 mg, 0.42 mmol) at room temperature and stirred for 2 h under argon atmosphere. To the resulting solution was added NaCNBH$_3$ (63 mg, 0.99 mmol) and stirring was continued for another 8 h at room temperature. The volatiles were evaporated under reduced pressure. The residue was diluted with water and extracted with CH$_2$Cl$_2$ (2×30 mL). Combined organic layer was dried over sodium sulphate, filtered and concentrated in vacuo to obtain the crude product. The crude material was purified by silica gel column chromatography to afford (+)-2-((3,4-trans)-1-(3-(1H-pyrazol-1-yl)benzyl)-4-methylpyrrolidin-3-yl)-7-(tetrahydro-2H-pyran-4-yl)imidazo[5,1-f][1,2,4]triazin-4(3H)-one (45 mg, 30%) as an off-white solid; $^1$H-NMR (CD$_3$OD-d$_4$, 400 MHz): δ 8.24 (s, 1H), 7.78 (s, 1H), 7.69-7.68 (m, 3H), 3.45 (t, 1H), 7.34 (d, 1H), 4.07-3.99 (m, 2H), 3.85-3.79 (m, 2H), 3.59-3.47 (m, 4H), 3.21-3.18 (m, 1H), 3.07-3.01 (m, 1H), 2.96-2.92 (m, 1H), 2.86-2.84 (m, 1H), 2.68-2.62 (m, 1H), 2.27 (t, 1H), 2.05-1.97 (m, 4H), 1.18 (d, 3H); Mass (ESI): 460.4 [M$^+$+1]; LC-MS: 97.41%; 460 (M$^+$+1); (column; X-bridge C-18, (50×3.0 mm, 3.5μ); RT 2.19 min. 0.05% TFA in water: ACN; 0.8 ml/min); UPLC (purity): 98.59%; (column; Acquity BEH C-18, 50×2.1 mm, 1.7μ; RT 1.47 min. 0.025% TFA (Aq): ACN; 0.50 ml/min.; Chiral HPLC: 96.19%, R$_t$=6.86 min (Chiralpak IA, 250×4.6 mm, 5μ; mobile phase (A) 0.1% DEA in n-Hexane (B) DCM:MeOH (80:20) (A:B:70:30);

flow Rate: 1.00 mL/min); Optical rotation $[\alpha]_D^{20}$: +4.73° (c=0.25, DCM); TLC: 10% MeOH/DCM (Rf: 0.6).

150. (+)-2-((3,4-trans)-4-methyl-1-(quinolin-4-ylmethyl)pyrrolidin-3-yl)-7-(tetrahydro-2H-pyran-4-yl)imidazo[5,1-f][1,2,4]triazin-4(3H)-one

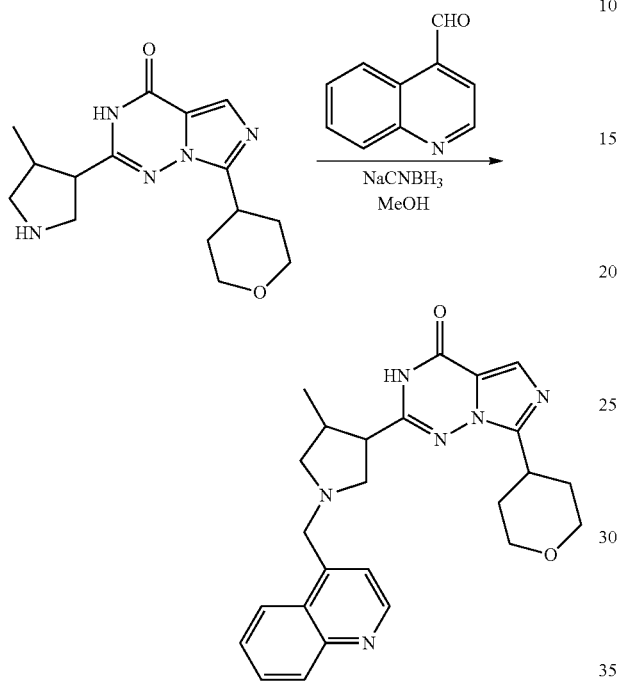

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (80 mg, 0.26 mmol) in MeOH (10 mL) was added quinoline-4-carbaldehyde (50.2 mg, 0.31 mmol) at room temperature and stirred for 2 h under argon atmosphere. To the resulting solution was added NaCNBH$_3$ (49.9 mg, 0.74 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(quinolin-4-ylmethyl)pyrrolidin-3-yl)-7-(tetrahydro-2H-pyran-4-yl)imidazo[5,1-f][1,2,4]triazin-4(3H)-one (52 mg, 44%) as an off-white solid; $^1$H-NMR (DMSO-d$_6$, 400 MHz): δ 11.57 (bs, 1H), 8.87 (d, 1H), 8.28 (d, 1H), 8.05 (d, 1H), 7.74 (t, 1H), 7.65 (s, 1H), 7.57 (t, 1H), 7.52 (d, 1H), 4.12 (s, 2H), 3.94-3.87 (m, 2H), 3.47-3.38 (m, 3H), 3.05-3.02 (m, 1H), 2.94-2.90 (m, 1H), 2.89-2.85 (m, 1H), 2.83-2.82 (m, 1H), 2.69-2.62 (m, 1H), 2.38-2.37 (m, 1H), 1.89-1.82 (m, 4H), 1.12 (d, 3H); Mass (ESI): 445 [M$^+$+1]; LC-MS: 99%; 445 (M$^+$+1); (column; X-bridge C-18, (50×3.0 mm, 3.5μ); RT 2.03 min. 0.05% TFA in water: ACN; 0.8 ml/min); UPLC (purity): 99.94%; (column; Acquity BEH C-18, 50×2.1 mm, 1.7μ; RT 1.27 min. 0.025% TFA (Aq): ACN; 0.50 ml/min.; Chiral HPLC: 99.71%, R$_t$=14.11 min (Chiralpak IA, 250×4.6 mm, 5μ; mobile phase (A) 0.1% DEA in n-Hexane (B) DCM:MeOH (80:20) (A:B:75:25); flow Rate: 1.00 mL/min); Optical rotation $[\alpha]_D^{20}$: +27.10° (c=0.25, DCM); TLC: 5% MeOH/DCM (R$_f$: 0.5).

151. (+)-2-((3,4-trans)-1-((1,3-dimethyl-1H-pyrazol-5-yl)methyl)-4-methylpyrrolidin-3-yl)-7-(tetrahydro-2H-pyran-4-yl)imidazo[5,1-f][1,2,4]triazin-4(3H)-one

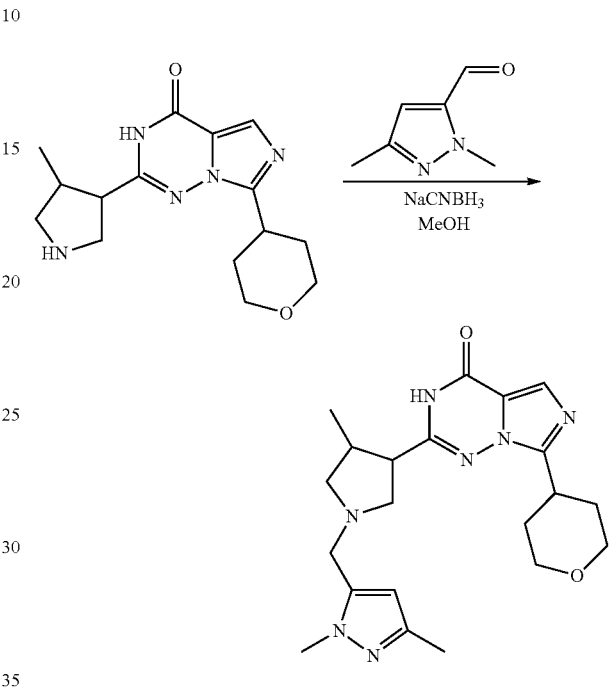

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (80 mg, 0.26 mmol) in MeOH (10 mL) was added 1,3-dimethyl-1H-pyrazole-5-carbaldehyde (39.2 mg, 0.31 mmol) at room temperature and stirred for 2 h under argon atmosphere. To the resulting solution was added NaCNBH$_3$ (49.9 mg, 0.74 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-1-((1,3-dimethyl-1H-pyrazol-5-yl)methyl)-4-methylpyrrolidin-3-yl)-7-(tetrahydro-2H-pyran-4-yl)imidazo[5,1-f][1,2,4]triazin-4(3H)-one (40 mg, 37%) as an off-white solid; $^1$H-NMR (DMSO-d$_6$, 400 MHz): δ 11.65 (bs, 1H), 7.62 (s, 1H), 5.89 (s, 1H), 3.96-3.91 (m, 2H), 3.67 (s, 3H), 3.59 (s, 2H), 3.50-3.47 (m, 2H), 3.41-3.39 (m, 1H), 2.94-2.85 (m, 2H), 2.81-2.79 (m, 2H), 2.65-2.61 (m, 1H), 2.25-2.24 (m, 1H), 2.14 (s, 3H), 1.89-1.82 (m, 4H), 1.09 (d, 3H); Mass (ESI): 412.3 [M$^+$+1]; LC-MS: 98.59%; 412 (M$^+$+1); (column; X-bridge C-18, (50×3.0 mm, 3.5μ); RT 1.74 min. 0.05% TFA in water: ACN; 0.8 ml/min); UPLC (purity): 99.67%; (column; Acquity BEH C-18, 50×2.1 mm, 1.7μ; RT 1.18 min. 0.025% TFA (Aq): ACN; 0.50 ml/min.; Chiral HPLC: 98.34%, R$_t$=11.21 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation $[\alpha]_D^{20}$: +21.85° (c=0.25, DCM); TLC: 5% MeOH/DCM (R$_f$: 0.5).

152. (+)-2-((3,4-trans)-4-methyl-1-((2-methylpyrimidin-5-yl)methyl)pyrrolidin-3-yl)-7-(tetrahydro-2H-pyran-4-yl)imidazo[5,1-f][1,2,4]triazin-4(3H)-one

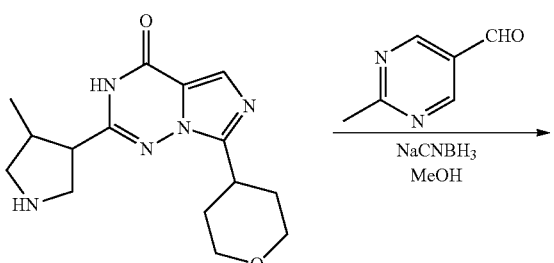

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in MeOH (10 mL) was added 2-methylpyrimidine-5-carbaldehyde (78 mg, 0.64 mmol) at room temperature and stirred for 2 h under argon atmosphere. To the resulting solution was added NaCNBH$_3$ (93 mg, 1.48 mmol) and stirring was continued for another 8 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-2-((3,4-trans)-4-methyl-1-((2-methylpyrimidin-5-yl)methyl)pyrrolidin-3-yl)-7-(tetrahydro-2H-pyran-4-yl)imidazo[5,1-f][1,2,4]triazin-4(3H)-one (50 mg, 31%) as an off-white solid. $^1$H-NMR (DMSO-d$_6$, 400 MHz): δ 11.52 (bs, 1H), 8.62 (s, 2H), 7.65 (s, 1H), 3.96-3.92 (m, 2H), 3.72-3.67 (m, 1H), 3.62-3.59 (m, 1H), 3.54-3.47 (m, 2H), 3.42-3.38 (m, 1H), 2.94-2.85 (m, 4H), 2.66-2.65 (m, 1H), 2.63 (s, 3H), 2.28-2.24 (m, 1H), 1.89-1.85 (m, 4H), 1.09 (d, 3H); Mass (ESI): 410 [M$^+$+1]; LC-MS: 97.36%; 410.4 (M$^+$+1); (column; Eclipse XDB C-18, (150×4.6 mm, 5.0μ); RT 5.74 min. 0.05% TFA (Aq): ACN; 1.0 ml/min); UPLC (purity): 99%; (column; Acquity UPLC HSS-T3, 100×2.1 mm, 1.8μ; RT 2.92 min. 0.025% TFA (Aq): ACN; 0.30 ml/min; Chiral HPLC: 100%, R$_t$=15.87 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min; Optical rotation [α]$_D^{20}$: +5.0° (c=0.25, DCM). TLC: 10% MeOH/DCM (R$_f$: 0.5).

153. (+)-2-((3,4-trans)-4-methyl-1-((2-methylthiazol-5-yl)methyl)pyrrolidin-3-yl)-7-(tetrahydro-2H-pyran-4-yl)imidazo[5,1-f][1,2,4]triazin-4(3H)-one

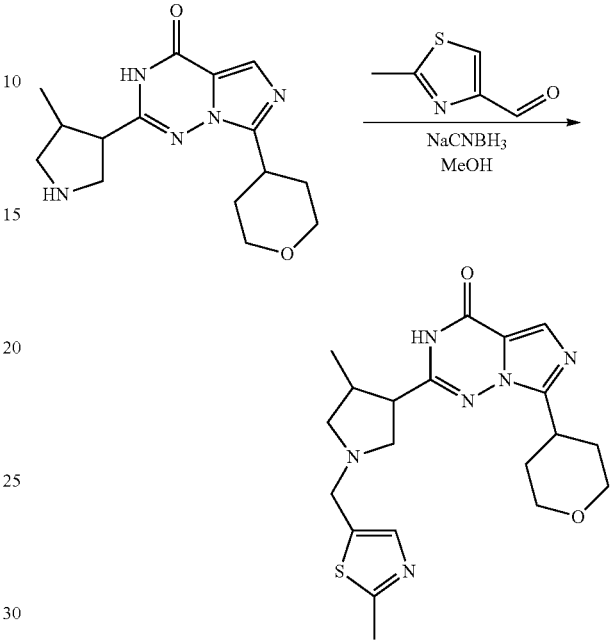

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added 2-methylthiazole-4-carbaldehyde (55 mg, 0.42 mmol) at room temperature and stirred for 2 h under argon atmosphere. To the resulting solution was added NaCNBH$_3$ (63 mg, 0.99 mmol) and stirring was continued for another 8 h at room temperature. The volatiles were evaporated under reduced pressure. The residue was diluted with water and extracted with CH$_2$Cl$_2$ (3×50 mL). Combined organic layer was dried over sodium sulphate, filtered and concentrated in vacuo to obtain the crude product. The crude material was purified by silica gel column chromatography to afford (+)-2-((3,4-trans)-4-methyl-1-((2-methylthiazol-5-yl)methyl)pyrrolidin-3-yl)-7-(tetrahydro-2H-pyran-4-yl)imidazo[5,1-f][1,2,4]triazin-4(3H)-one (40 mg, 29%) as an off-white solid. $^1$H-NMR (CD$_3$OD, 400 MHz): δ 7.73 (s, 1H), 7.49 (s, 1H), 4.09-4.02 (m, 2H), 3.97-3.87 (m, 2H), 3.64-3.57 (m, 3H), 3.17-3.14 (m, 1H), 3.04-2.97 (m, 2H), 2.90-2.87 (m, 1H), 2.71-2.69 (m, 1H), 2.65 (s, 3H), 2.32-2.28 (m, 1H), 2.08-2.00 (m, 2H), 1.95-1.89 (m, 2H), 1.18 (d, 3H); Mass (ESI): 415.2 [M$^+$+1]; LC-MS: 99%; 415 (M$^+$+1); (column; X-bridge C-18, (50×3.0 mm, 3.5μ); RT 1.69 min. 0.05% TFA in water: ACN; 0.8 ml/min); UPLC (purity): 99.77%; (column; Acquity BEH C-18, 50×2.1 mm, 1.7μ; RT 1.13 min. 0.025% TFA (Aq): ACN; 0.50 ml/min; Chiral HPLC: 99.09%, R$_t$=10.73 min (Chiralpak IA, 250×4.6 mm, 5μ; mobile phase (A) n-Hexane (B) DCM:MeOH (80:20) (A:B:80:20); flow Rate: 1.00 mL/min; Optical rotation [α]$_D^{20}$: +12.25° (c=0.25, DCM). TLC: 10% MeOH/DCM (R$_f$: 0.4).

154. (+)-2-((3,4-trans)-4-methyl-1-((6-methylpyridin-3-yl)methyl)pyrrolidin-3-yl)-7-(tetrahydro-2H-pyran-4-yl)imidazo[5,1-f][1,2,4]triazin-4(3H)-one

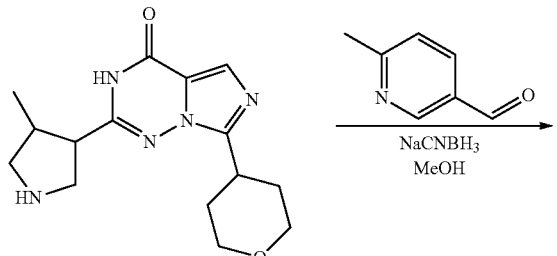

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in MeOH (10 mL) was added 6-methylnicotinaldehyde (71 mg, 0.59 mmol) at room temperature and stirred for 2 h under argon atmosphere. To the resulting solution was added NaCNBH$_3$ (93 mg, 1.48 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-((6-methylpyridin-3-yl)methyl)pyrrolidin-3-yl)-7-(tetrahydro-2H-pyran-4-yl)imidazo[5,1-f][1,2,4]triazin-4(3H)-one (43 mg, 21%) as an off-white solid. $^1$H-NMR (DMSO-d$_6$, 400 MHz): δ 8.38 (s, 1H), 7.67 (s, 1H), 7.58 (d, 1H), 7.21 (d, 1H), 3.97-3.91 (m, 2H), 3.64-3.59 (m, 2H), 3.52-3.49 (m, 1H), 2.94-2.92 (m, 1H), 2.87-2.84 (m, 2H), 2.79-2.71 (m, 2H), 2.67-2.61 (m, 2H), 2.42 (s, 3H), 2.24-2.21 (m, 1H), 1.87-1.82 (m, 4H), 1.09 (d, 3H); Mass (ESI): 409.3 [M$^+$+1]; LC-MS: 96.82%; 409.4 (M$^+$+1); (column; Eclipse XDB C-18, (150×4.6 mm, 5.0μ); RT 5.58 min. 0.05% TFA (Aq): ACN; 1.0 ml/min); UPLC (purity): 98.45%; (column; Acquity UPLC HSS-T3, 100×2.1 mm, 1.8μ; RT 2.83 min. 0.025% TFA (Aq): ACN; 0.30 ml/min; Chiral HPLC: 99.61%, R$_t$=9.69 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +18.96° (c=0.25, DCM). TLC: 5% MeOH/DCM (R$_f$: 0.3).

155. (+)-2-((3,4-trans)-4-methyl-1-((5-methylpyrazin-2-yl)methyl)pyrrolidin-3-yl)-7-(tetrahydro-2H-pyran-4-yl)imidazo[5,1-f][1,2,4]triazin-4(3H)-one

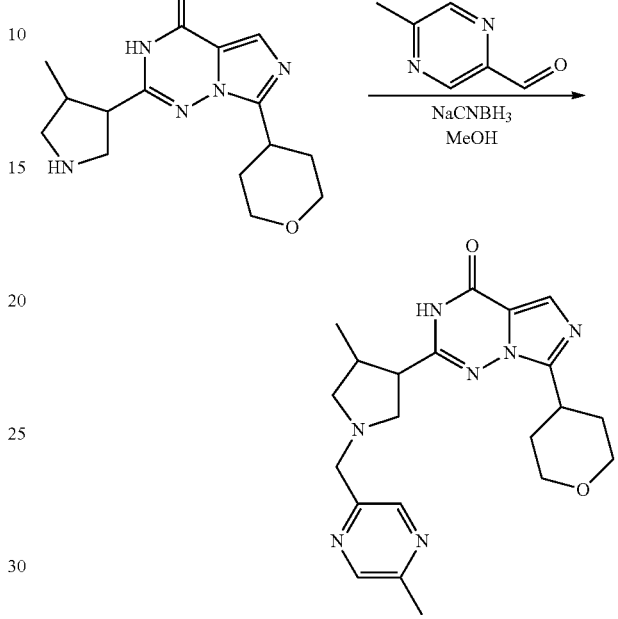

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in MeOH (10 mL) was added 5-methylpyrazine-2-carbaldehyde (72 mg, 0.59 mmol) at room temperature and stirred for 2 h under argon atmosphere. To the resulting solution was added NaCNBH$_3$ (93 mg, 1.48 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-((5-methylpyrazin-2-yl)methyl)pyrrolidin-3-yl)-7-(tetrahydro-2H-pyran-4-yl)imidazo[5,1-f][1,2,4]triazin-4(3H)-one (54 mg, 27%) as an off-white solid; $^1$H-NMR (DMSO-d$_6$, 400 MHz): δ 8.54 (s, 1H), 8.47 (s, 1H), 7.64 (s, 1H), 3.96-3.94 (m, 2H), 3.88-3.83 (m, 2H), 3.52-3.47 (m, 2H), 3.41-3.37 (m, 1H), 2.99-2.95 (m, 2H), 2.91-2.85 (m, 2H), 1.67-1.62 (m, 1H), 2.47 (s, 3H), 2.34-2.31 (m, 1H), 1.88-1.82 (m, 4H), 1.12 (d, 3H); Mass (ESI): 410 [M$^+$+1]; LC-MS: 98.17%; 410 (M$^+$+1); (column; X-bridge C-18, (50×3.0 mm, 3.5μ); RT 1.86 min. 0.05% TFA in water: ACN; 0.8 ml/min); UPLC (purity): 98.35%; (column; Acquity BEH C-18, 50×2.1 mm, 1.7μ; RT 1.16 min. 0.025% TFA (Aq): ACN; 0.50 ml/min; Chiral HPLC: 98.63%, R$_t$=9.76 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +68.65° (c=0.25, DCM). TLC: 5% MeOH/DCM (R$_f$: 0.4).

156. (+)-2-((3,4-trans)-4-methyl-1-((5-methyl-pyrazin-2-yl)methyl)pyrrolidin-3-yl)-7-(tetrahydro-2H-pyran-4-yl)imidazo[5,1-f][1,2,4]triazin-4(3H)-one

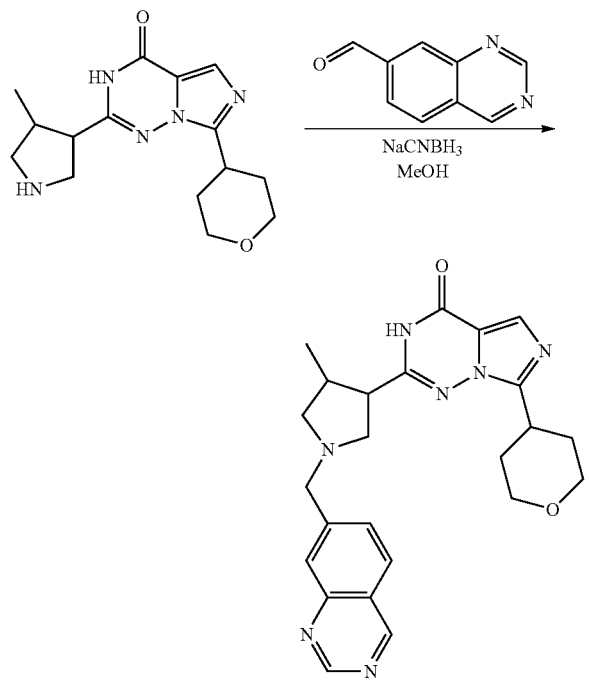

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in MeOH (10 mL) was added quinazoline-7-carbaldehyde (62 mg, 0.39 mmol) at room temperature and stirred for 2 h under argon atmosphere. To the resulting solution was added NaCNBH$_3$ (62 mg, 0.99 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-((5-methylpyrazin-2-yl)methyl)pyrrolidin-3-yl)-7-(tetrahydro-2H-pyran-4-yl)imidazo[5,1-f][1,2,4]triazin-4(3H)-one (46 mg, 31%) as an off-white solid. $^1$H-NMR (DMSO d$_6$, 400 MHz): δ 11.65 (bs, 1H), 9.56 (s, 1H), 9.24 (s, 1H), 8.14 (d, 1H), 7.94 (s, 1H), 7.77 (d, 1H), 7.68 (s, 1H), 3.98-3.87 (m, 4H), 3.54-3.48 (m, 2H), 3.41-3.37 (m, 1H), 3.04-2.99 (m, 1H), 2.96-2.94 (m, 1H), 2.89-2.81 (m, 2H), 2.71-2.67 (m, 1H), 2.37-2.31 (m, 1H), 1.87-1.82 (m, 4H), 1.12 (d, 3H); Mass (ESI): 446.3 [M$^+$+1]; LC-MS: 97.14%; 446.4 (M$^+$+1); (column; Eclipse XDB C-18, (150×4.6 mm, 5.0μ); RT 5.67 min. 0.05% TFA ACN; 1.0 ml/min); UPLC (purity): 98.79%; (column; Acquity UPLC HSS-T3, 100×2.1 mm, 1.8μ; RT 2.89 min. 0.025% TFA (Aq): ACN; 0.30 ml/min; Chiral HPLC: 99.33%, R$_t$=19.36 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +12.88° (c=0.25, DCM). TLC: 5% MeOH/DCM (Rf: 0.4)

157. (+)-2-((3,4-trans)-4-methyl-1-(3-(pyrrolidin-1-yl)benzyl)pyrrolidin-3-yl)-7-(tetrahydro-2H-pyran-4-yl)imidazo[5,1-f][1,2,4]triazin-4(3H)-one

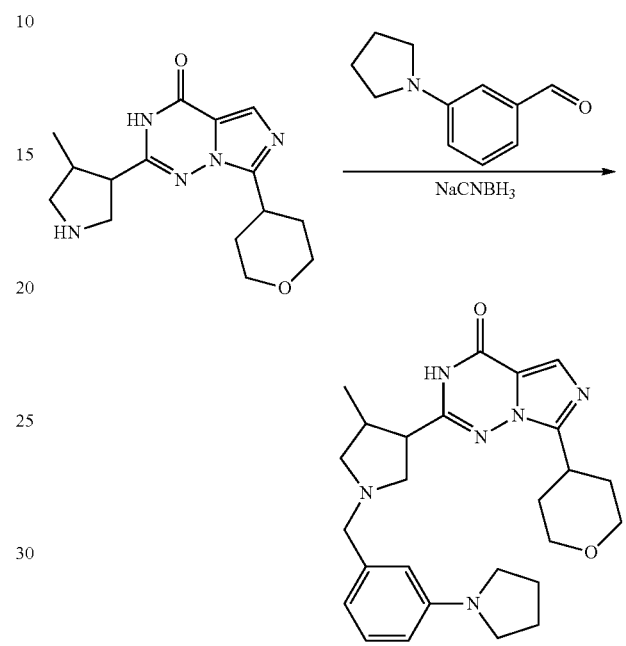

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (0.13 g, 0.42 mmol) in MeOH (10 mL) was added 3-(pyrrolidin-1-yl)benzaldehyde (0.09 g, 0.51 mmol) at room temperature and stirred for 2 h under argon atmosphere. To the resulting solution was added NaCNBH$_3$ (81 mg, 1.28 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(3-(pyrrolidin-1-yl)benzyl)pyrrolidin-3-yl)-7-(tetrahydro-2H-pyran-4-yl)imidazo[5,1-f][1,2,4]triazin-4(3H)-one (40 mg, 20%) as an off-white solid. $^1$H-NMR (DMSO-d$_6$, 400 MHz): δ 7.67 (s, 1H), 7.08 (t, 1H), 6.54 (d, 1H), 6.48 (s, 1H), 6.37 (d, 1H), 3.96-3.92 (m, 2H), 3.61-3.57 (m, 1H), 3.52-3.46 (m, 3H), 3.38-3.35 (m, 1H), 3.19-3.12 (m, 4H), 2.95-1.98 (m, 2H), 2.82-2.78 (m, 2H), 2.65-2.61 (m, 1H), 2.24-2.18 (m, 1H), 1.95-1.82 (m, 8H), 1.08 (d, 3H); Mass (ESI): 463 [M$^+$+1]; LC-MS: 99.34%; 463.4 (M$^+$+1); (column; X-bridge C-18, (50×3.0 mm, 5.0μ); RT 2.93 min. 0.05% TFA in water: ACN; 0.8 ml/min); UPLC (purity): 99.89%; (column; Acquity BEH C-18, 50×2.1 mm, 1.7μ; RT 1.72 min. 0.025% TFA (Aq): ACN; 0.50 ml/min; Chiral HPLC: 99.78%, R$_t$=7.97 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +16.35° (c=0.25, DCM). TLC: 5% MeOH/DCM (R$_f$: 0.5).

633

158. (+)-2-((3,4-trans)-4-methyl-1-((6-(trifluoromethyl)pyridin-3-yl)methyl)pyrrolidin-3-yl)-7-(tetrahydro-2H-pyran-4-yl)imidazo[5,1-f][1,2,4]triazin-4(3H)-one

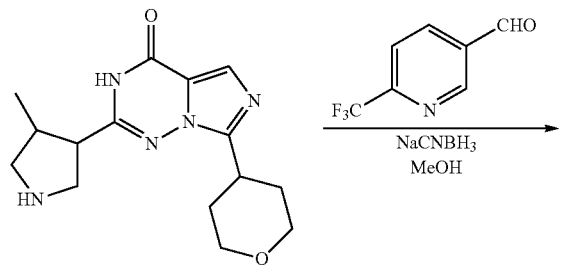

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (120 mg, 0.39 mmol) in MeOH (10 mL) was added 6-(trifluoromethyl)nicotinaldehyde (83.5 mg, 0.47 mmol) at room temperature and stirred for 2 h under argon atmosphere. To the resulting solution was added NaCNBH$_3$ (75 mg, 1.19 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-((6-(trifluoromethyl)pyridin-3-yl)methyl)pyrrolidin-3-yl)-7-(tetrahydro-2H-pyran-4-yl)imidazo[5,1-f][1,2,4]triazin-4(3H)-one (45 mg, 25%) as an off-white solid. $^1$H-NMR (DMSO-d$_6$, 400 MHz): δ 11.72 (bs, 1H), 8.74 (s, 1H), 8.02 (d, 1H), 7.89 (d, 1H), 7.64 (s, 1H), 3.94-3.91 (m, 2H), 3.82-3.76 (m, 2H), 3.51-3.47 (m, 2H), 3.40-3.37 (m, 1H), 2.98-2.83 (m, 4H), 2.69-2.62 (m, 1H), 2.34-2.29 (m, 1H), 1.89-1.82 (m, 4H), 1.08 (d, 3H); Mass (ESI): 463 [M$^+$+1]; LC-MS: 97.79%; 463.3 (M$^+$+1); (column; X-bridge C-18, (50×3.0 mm, 3.5μ); RT 2.15 min. 0.05% TFA (Aq): ACN; 0.8 ml/min); UPLC (purity): 97.98%; (column; Acquity BEH C-18, 50×2.1 mm, 1.7μ; RT 1.47 min. 0.025% TFA (Aq): ACN; 0.50 ml/min; Chiral HPLC: 98.92%, R$_t$=9.35 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +9.85° (c 0.25, DCM). TLC: 5% MeOH/DCM (R$_f$: 0.3).

634

159. (+)-2-((3,4-trans)-1-((2-ethylpyrimidin-5-yl)methyl)-4-methylpyrrolidin-3-yl)-7-(tetrahydro-2H-pyran-4-yl)imidazo[5,1-f][1,2,4]triazin-4(3H)-one

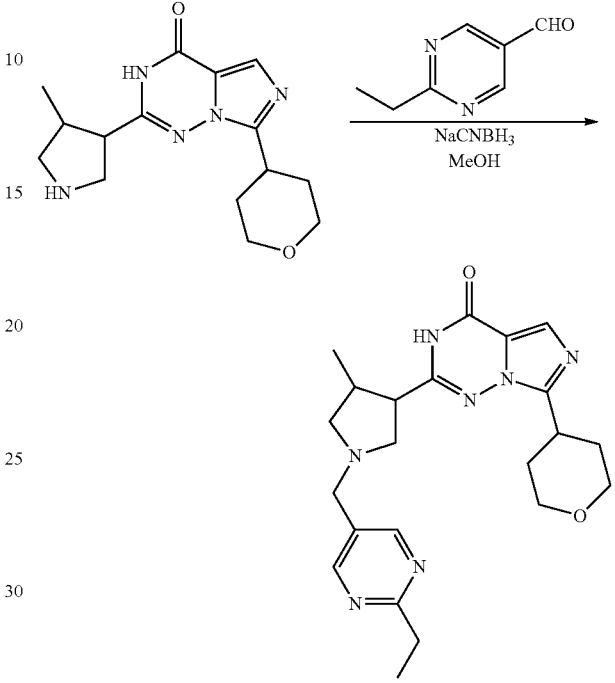

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (120 mg, 0.39 mmol) in MeOH (10 mL) was added 2-ethylpyrimidine-5-carbaldehyde (65 mg, 0.47 mmol) at room temperature and stirred for 2 h under argon atmosphere. To the resulting solution was added NaCNBH$_3$ (75 mg, 1.19 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel chromatography to afford (+)-2-((3,4-trans)-1-((2-ethylpyrimidin-5-yl)methyl)-4-methylpyrrolidin-3-yl)-7-(tetrahydro-2H-pyran-4-yl)imidazo[5,1-f][1,2,4]triazin-4(3H)-one (15 mg, 11%) as an off-white solid. $^1$H-NMR (DMSO-d$_6$, 400 MHz): δ 11.62 (bs, 1H), 6.65 (s, 2H), 7.64 (s, 1H), 3.96-3.87 (m, 2H), 3.67-3.64 (m, 1H), 3.58-3.54 (m, 1H), 3.52-3.47 (m, 2H), 3.41-3.38 (m, 2H), 2.92-2.85 (m, 5H), 2.66-2.62 (m, 1H), 2.27-2.22 (m, 1H), 1.86-1.81 (m, 4H), 1.29 (t, 3H), 1.08 (d, 3H); Mass (ESI): 424 [M$^+$+1]; LC-MS: 99.83%; 424.3 (M$^+$+1); (column; X-bridge C-18, (50×3.0 mm, 3.5μ); RT 1.72 min. 0.05% TFA (Aq): ACN; 0.8 ml/min); UPLC (purity): 98.86%; (column; Acquity BEH C-18, 50×2.1 mm, 1.7μ; RT 1.20 min. 0.025% TFA (Aq): ACN; 0.50 ml/min; Chiral HPLC: 94.80%, R$_t$=18.36 min (Chiralpak IA, 250×4.6 mm, 5μ; mobile phase (A) 0.1% DEA in n-Hexane (B) DCM:MeOH (80:20) (A:B:85:15); flow Rate: 1.00 mL/min); Optical rotation [α]$_D^{20}$: +12.22° (c=0.25, MeOH). TLC: 10% MeOH/DCM (R$_f$: 0.4).

160. (+)-2-((3,4-trans)-1-(3-bromobenzyl)-4-methyl-pyrrolidin-3-yl)-7-(tetrahydro-2H-pyran-4-yl)imidazo[5,1-f][1,2,4]triazin-4(3H)-one

161. (+)-2-((3,4-trans)-1-(2,4-dichlorobenzyl)-4-methylpyrrolidin-3-yl)-7-(tetrahydro-2H-pyran-4-yl)imidazo[5,1-f][1,2,4]triazin-4(3H)-one

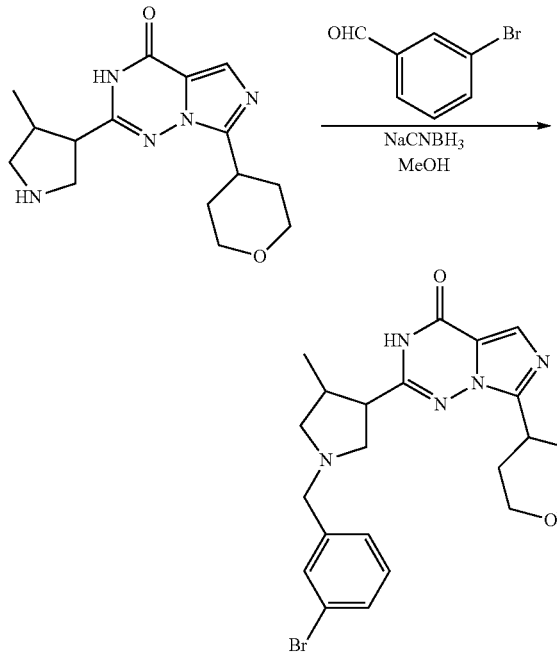

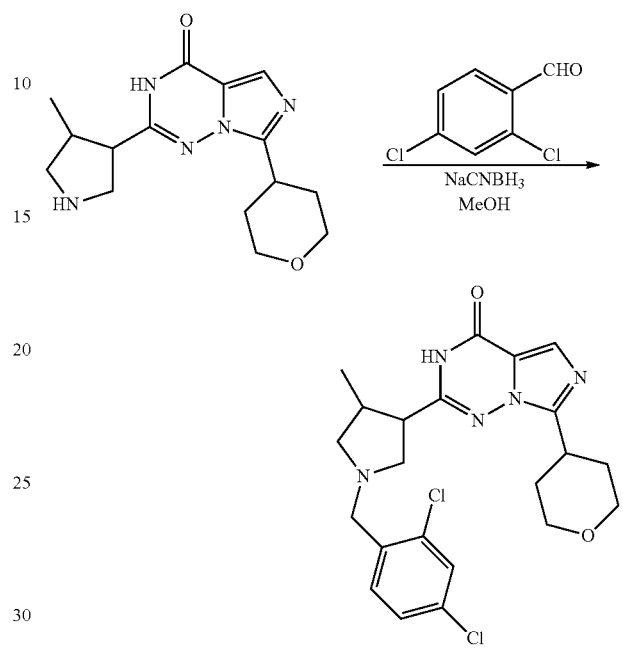

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added 3-bromobenzaldehyde (60 mg, 0.29 mmol) at room temperature and stirred for 2 h under argon atmosphere. To the resulting solution was added NaCNBH$_3$ (47 mg, 0.74 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-1-(3-bromobenzyl)-4-methylpyrrolidin-3-yl)-7-(tetrahydro-2H-pyran-4-yl)imidazo[5,1-f][1,2,4]triazin-4(3H)-one (35 mg, 30%) as an off-white solid; $^1$H-NMR (DMSO-d$_6$, 400 MHz): δ 7.62 (s, 1H), 7.47 (s, 1H), 7.42 (d, 1H), 7.25-7.21 (m, 2H), 3.96-3.94 (m, 2H), 3.59 (s, 2H), 3.55-3.51 (m, 2H), 3.49-3.48 (m, 1H), 2.95-2.94 (m, 1H), 2.84 (t, 1H), 2.77-2.72 (m, 2H), 2.68-2.63 (m, 1H), 2.27-2.21 (m, 1H), 1.84-1.79 (m, 4H), 1.08 (d, 3H); Mass (ESI): 474 [M$^+$+1]; LC-MS: 95.23%; 474.2 (M$^+$+2); (column; X-bridge C-18, (50×3.0 mm, 3.5µ); RT 2.27 min. 0.05% TFA (Aq): ACN; 0.8 ml/min); UPLC (purity): 95.48%; (column; Acquity BEH C-18, 50×2.1 mm, 1.7µ; RT 1.57 min. 0.025% TFA (Aq): ACN; 0.50 ml/min; Chiral HPLC: 97.26%, R$_t$=9.80 min (Chiralpak IA, 250×4.6 mm, 5µ; mobile phase (A) 0.1% DEA in n-Hexane (B) DCM:MeOH (80:20) (A:B:80:20); flow Rate: 1.00 mL/min); Optical rotation [α]$_D^{20}$: +16.73° (c=0.25, DCM). TLC: 10% MeOH/DCM (R$_f$: 0.5).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added 2,4-dichlorobenzaldehyde (55 mg, 0.29 mmol) at room temperature and stirred for 2 h under argon atmosphere. To the resulting solution was added NaCNBH$_3$ (43 mg, 0.74 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-1-(2,4-dichlorobenzyl)-4-methylpyrrolidin-3-yl)-7-(tetrahydro-2H-pyran-4-yl)imidazo[5,1-f][1,2,4]triazin-4(3H)-one (15 mg, 13%) as an off-white solid. $^1$H-NMR (DMSO-d$_6$, 400 MHz): δ 11.51 (bs, 1H), 7.64 (s, 1H), 7.58 (s, 1H), 7.54 (d, 1H), 7.42 (d, 1H), 3.96-3.94 (m, 2H), 3.74 (s, 2H), 3.51-3.46 (m, 2H), 3.39-3.37 (m, 1H), 3.02 (t, 1H), 2.91-2.82 (m, 3H), 2.67-2.62 (m, 1H), 2.34-2.32 (m, 1H), 1.89-1.84 (m, 4H), 1.08 (d, 3H); Mass (ESI): 462 [M$^+$]; LC-MS: 98.46%; 462.3 (M$^+$); (column; X-bridge C-18, (50×3.0 mm, 3.5µ); RT 2.40 min. 0.05% TFA (Aq): ACN; 0.8 ml/min); UPLC (purity): 99.41%; (column; Acquity BEH C-18, 50×2.1 mm, 1.7µ; RT 1.64 min. 0.025% TFA (Aq): ACN; 0.50 ml/min; Chiral HPLC: 99.84%, R$_t$=7.61 min (Chiralpak IA, 250×4.6 mm, 5µ; mobile phase (A) 0.1% DEA in n-Hexane (B) DCM:MeOH (80:20) (A:B:80:20); flow Rate: 1.00 mL/min); Optical rotation [α]$_D^{20}$: +11.45° (c=0.25, DCM). TLC: 10% MeOH/DCM (R$_f$: 0.4).

637

162. (+)-2-((3,4-trans)-1-(4-bromobenzyl)-4-methyl-pyrrolidin-3-yl)-7-(tetrahydro-2H-pyran-4-yl)imidazo[5,1-f][1,2,4]triazin-4(3H)-one

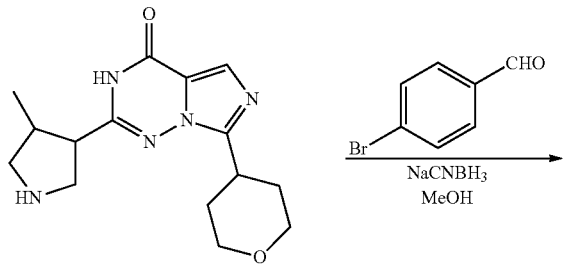

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added 4-bromobenzaldehyde (54.9 mg, 0.29 mmol) at room temperature and stirred for 2 h under argon atmosphere. To the resulting solution was added NaCNBH$_3$ (46 mg, 0.74 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-1-(4-bromobenzyl)-4-methylpyrrolidin-3-yl)-7-(tetrahydro-2H-pyran-4-yl)imidazo[5,1-f][1,2,4]triazin-4(3H)-one (20 mg, 17%) as an off-white solid. $^1$H-NMR (DMSO-d$_6$, 400 MHz): δ 7.67 (s, 1H), 7.51 (d, 2H), 7.24-7.21 (m, 2H), 3.96-3.94 (m, 2H), 3.62-3.58 (m, 2H), 3.52-3.46 (m, 3H), 2.96-2.92 (m, 1H), 2.87-2.79 (m, 3H), 2.68-2.65 (m, 1H), 2.27-2.24 (m, 1H), 1.88-1.81 (m, 4H), 1.08 (d, 3H); Mass (ESI): 472.3 [M$^+$]; LC-MS: 94.45%; 474 (M$^+$+2); (column; X-bridge C-18, (50×3.0 mm, 3.5μ); RT 2.44 min. 0.05% TFA: ACN; 0.8 ml/min); UPLC (purity): 95.91%; (column; Acquity BEH C-18, 50×2.1 mm, 1.7μ; RT 1.60 min. 0.025% TFA (Aq): ACN; 0.50 ml/min; Chiral HPLC: 95.61%, R$_t$=9.47 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +10.46° (c=0.25, DCM). TLC: 5% MeOH/DCM (Rf: 0.4).

638

163. (+)-2-((3,4-trans)-1-(3,5-dichlorobenzyl)-4-methylpyrrolidin-3-yl)-7-(tetrahydro-2H-pyran-4-yl)imidazo[5,1-f][1,2,4]triazin-4(3H)-one

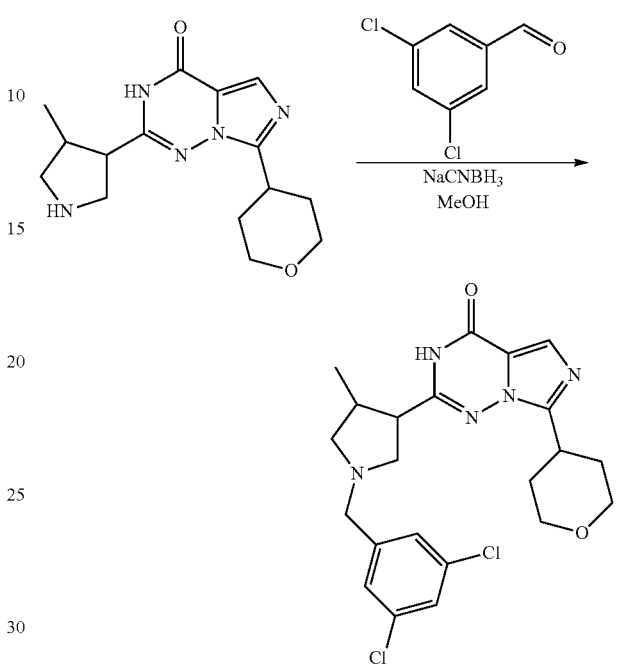

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added 3,5-dichlorobenzaldehyde (51 mg, 0.29 mmol) at room temperature and stirred for 2 h under argon atmosphere. To the resulting solution was added NaCNBH$_3$ (46 mg, 0.74 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-1-(3,5-dichlorobenzyl)-4-methylpyrrolidin-3-yl)-7-(tetrahydro-2H-pyran-4-yl)imidazo[5,1-f][1,2,4]triazin-4(3H)-one (25 mg, 22%) as an off-white solid. $^1$H-NMR (DMSO-d$_6$, 400 MHz): δ 11.62 (bs, 1H), 7.64 (s, 1H), 7.48 (s, 1H), 7.37 (s, 2H), 3.96-3.94 (m, 2H), 3.65 (s, 2H), 3.52-3.47 (m, 3H), 3.41-3.38 (m, 1H), 3.00-2.95 (m, 1H), 2.87-2.84 (m, 2H), 2.67-2.65 (m, 1H), 2.27-2.24 (m, 1H), 1.87-1.82 (m, 4H), 1.08 (d, 3H); Mass (ESI): 463.1 [M$^+$+1]; LC-MS: 96.92%; 462 (M$^+$); (column; X-bridge C-18, (50×3.0 mm, 3.5μ); RT 2.56 min. 0.05% TFA: ACN; 0.8 ml/min); UPLC (purity): 96.57%; (column; Acquity BEH C-18, 50×2.1 mm, 1.7μ; RT 1.69 min. 0.025% TFA (Aq): ACN; 0.50 ml/min; Chiral HPLC: 97.39%, R$_t$=9.37 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +10.76° (c=0.25%, DCM). TLC: 5% MeOH/DCM (R$_f$: 0.6).

164. (+)-2-((3,4-trans)-4-methyl-1-(3-(trifluoromethoxy)benzyl)pyrrolidin-3-yl)-7-(tetrahydro-2H-pyran-4-yl)imidazo[5,1-f][1,2,4]triazin-4(3H)-one

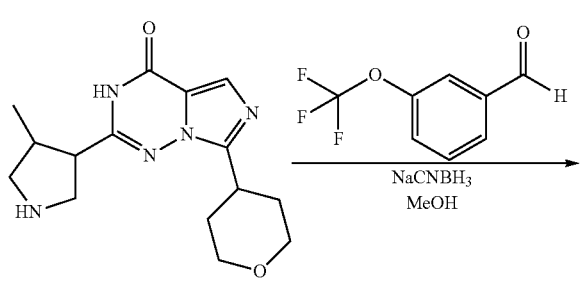

165. (+)-2-((3,4-trans)-1-(2-chloro-4-fluorobenzyl)-4-methylpyrrolidin-3-yl)-7-(tetrahydro-2H-pyran-4-yl)imidazo[5,1-f][1,2,4]triazin-4(3H)-one

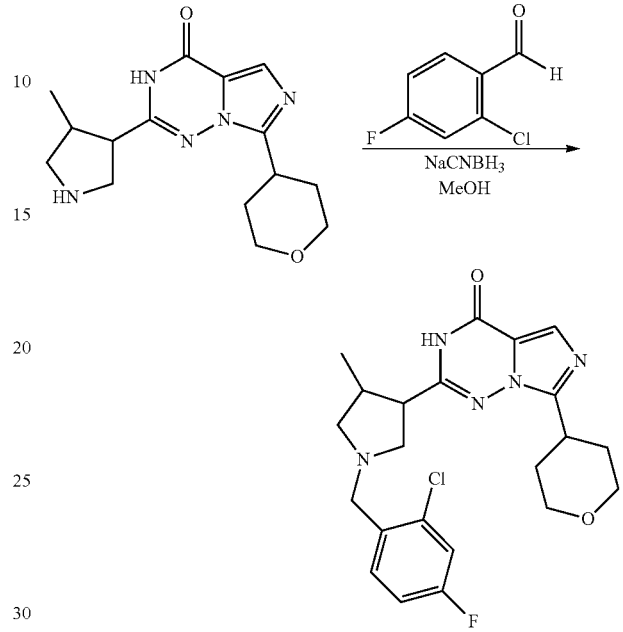

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added 3-(trifluoromethoxy)benzaldehyde (56 mg, 0.29 mmol) at room temperature and stirred for 2 h under argon atmosphere. To the resulting solution was added NaCNBH$_3$ (46 mg, 0.74 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-4-methyl-1-(3-(trifluoromethoxy)benzyl)pyrrolidin-3-yl)-7-(tetrahydro-2H-pyran-4-yl)imidazo[5,1-f][1,2,4]triazin-4(3H)-one (22 mg, 19%) as an off-white solid. $^1$H-NMR (DMSO-d$_6$, 400 MHz): δ 7.67 (s, 1H), 7.46 (t, 1H), 7.34 (d, 1H), 7.29 (s, 1H), 7.24 (d, 1H), 3.96-3.94 (m, 2H), 3.72-3.65 (m, 2H), 3.49-3.42 (m, 2H), 3.38-3.36 (m, 2H), 2.97-2.96 (m, 1H), 2.88-2.79 (m, 3H), 2.68-2.65 (m, 1H), 2.28-2.21 (m, 1H), 1.87-1.84 (m, 4H), 1.08 (d, 3H); Mass (ESI): 478 [M$^+$+1]; LC-MS: 98.60%; 478.3 (M$^+$+1); (column; X-bridge C-18, (50×3.0 mm, 3.5μ); RT 2.47 min. 0.05% TFA (Aq): ACN; 0.8 ml/min); UPLC (purity): 98.25%; (column; Acquity BEH C-18, 50×2.1 mm, 1.7μ; RT 1.69 min. 0.025% TFA (Aq): ACN; 0.50 ml/min; Chiral HPLC: 98.49%, R$_t$=7.69 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +15.66° (c=0.25, DCM). TLC: 5% MeOH/DCM (R$_f$: 0.5).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added 2-chloro-4-fluorobenzaldehyde (39 mg, 0.29 mmol) at room temperature and stirred for 2 h under argon atmosphere. To the resulting solution was added NaCNBH$_3$ (46 mg, 0.74 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-1-(2-chloro-4-fluorobenzyl)-4-methylpyrrolidin-3-yl)-7-(tetrahydro-2H-pyran-4-yl)imidazo[5,1-f][1,2,4]triazin-4(3H)-one (20 mg, 18%) as an off-white solid. $^1$H-NMR (DMSO-d$_6$, 400 MHz): δ 11.71 (bs, 1H), 7.62 (s, 1H), 7.54 (t, 1H), 7.41 (d, 1H), 7.21-7.16 (m, 1H), 3.94-3.92 (m, 2H), 3.71 (s, 2H), 3.47-3.45 (m, 2H), 3.41-3.37 (m, 1H), 3.02-2.98 (m, 1H), 2.89-2.82 (m, 3H), 2.64-2.61 (m, 1H), 2.34-2.31 (m, 1H), 1.87-1.81 (m, 4H), 1.08 (d, 3H); Mass (ESI): 446 [M$^+$+1]; LC-MS: 97.91%; 446.2 (M$^+$+1); (column; X-bridge C-18, (50×3.0 mm, 3.5μ); RT 2.20 min. 0.05% TFA (Aq): ACN; 0.8 ml/min); UPLC (purity): 99.44%; (column; Acquity BEH C-18, 50×2.1 mm, 1.7μ; RT 1.53 min. 0.025% TFA (Aq): ACN; 0.50 ml/min; Chiral HPLC: 99.70%, R$_t$=9.14 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +22.22° (c=0.25, DCM). TLC: 5% MeOH/DCM (R$_f$: 0.4).

166. (+)-2-((3,4-trans)-1-(2-bromobenzyl)-4-methyl-pyrrolidin-3-yl)-7-(tetrahydro-2H-pyran-4-yl)imidazo[5,1-f][1,2,4]triazin-4(3H)-one

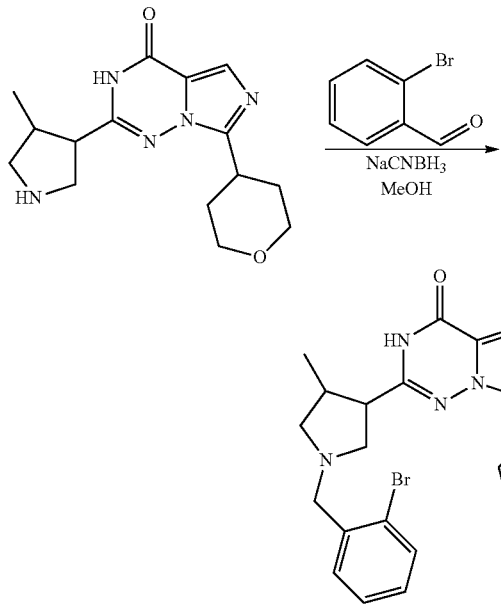

167. (+)-2-((3,4-trans)-4-methyl-1-(4-(trifluoromethoxy)benzyl)pyrrolidin-3-yl)-7-(tetrahydro-2H-pyran-4-yl)imidazo[5,1-f][1,2,4]triazin-4(3H)-one

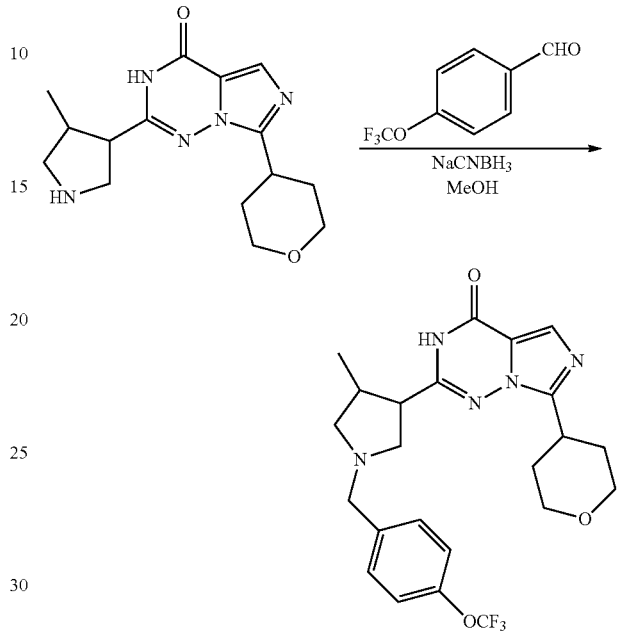

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added 2-bromobenzaldehyde (54.9 mg, 0.29 mmol) at room temperature and stirred for 2 h under argon atmosphere. To the resulting solution was added NaCNBH$_3$ (46 mg, 0.74 mmol) and stirring was continued for another 8 h at room temperature. The volatiles were evaporated under reduced pressure. The residue was diluted with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford (+)-2-((3,4-trans)-1-(2-bromobenzyl)-4-methylpyrrolidin-3-yl)-7-(tetrahydro-2H-pyran-4-yl)imidazo[5,1-f][1,2,4]triazin-4(3H)-one (18 mg, 16%) as an off-white solid. $^1$H-NMR (DMSO-d$_6$, 400 MHz): δ 11.57 (bs, 1H), 7.64 (s, 1H), 7.58 (d, 1H), 7.52 (d, 1H), 7.36 (t, 1H), 7.19 (t, 1H), 3.94-3.92 (m, 2H), 3.72 (s, 2H), 3.52-3.47 (m, 2H), 3.41-3.37 (m, 1H), 3.02-2.98 (m, 1H), 2.92-2.89 (m, 3H), 2.65-2.61 (m, 1H), 2.34-2.31 (m, 1H), 1.89-1.82 (m, 4H), 1.12 (d, 3H); Mass (ESI): 472.3 [M$^+$]; LC-MS: 93.94%; 474 (M$^+$+1); (column; X-bridge C-18, (50×3.0 mm, 3.5μ); RT 2.32 min. 0.05% TFA: ACN; 0.8 ml/min); UPLC (purity): 98.19%; (column; Acquity BEH C-18, 50×2.1 mm, 1.7μ; RT 1.51 min. 0.025% TFA (Aq): ACN; 0.50 ml/min; Chiral HPLC: 98.37%, R$_t$=20.38 min (Chiralpak IA, 250×4.6 mm, 5μ; mobile phase (A) 0.1% DEA in n-Hexane (B) DCM:MeOH (80:20) (A:B:75:25); flow Rate: 1.00 mL/min); Optical rotation [α]$_D^{20}$: +31.95° (c=0.25, DCM). TLC: 5% MeOH/DCM (R$_f$: 0.4).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (15 mL) was added 4-(trifluoromethoxy)benzaldehyde (61.17 mg, 0.32 mmol) at room temperature and stirred for 2 h under argon atmosphere. To the resulting solution was added NaCNBH$_3$ (46.78 mg, 0.74 mmol) and stirring was continued for another 8 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-2-((3,4-trans)-4-methyl-1-(4-(trifluoromethoxy)benzyl)pyrrolidin-3-yl)-7-(tetrahydro-2H-pyran-4-yl)imidazo[5,1-f][1,2,4]triazin-4(3H)-one (45 mg, 38%) as an off-white solid. $^1$H-NMR (DMSO-d$_6$, 400 MHz): δ 7.67 (s, 1H), 7.43 (d, 2H), 7.28 (d, 2H), 3.96-3.94 (m, 2H), 3.64 (s, 2H), 3.52-3.45 (m, 2H), 3.42-3.41 (m, 1H), 2.99-2.97 (m, 1H), 2.85-2.78 (m, 3H), 2.67-2.64 (m, 1H), 2.33-2.31 (m, 1H), 1.87-1.81 (m, 4H), 1.08 (d, 3H); Mass (ESI): 478 [M$^+$+1]; LC-MS: 98.20%; 478 (M$^+$+1); (column; X-bridge C-18, (50×3.0 mm, 3.5μ); RT 2.51 min. 0.05% TFA (Aq): ACN; 0.8 ml/min); HPLC (purity): 99.76%; (column; Eclipse XDB C-18, 150×4.6 mm, 5.0μ; RT 10.86 min. 5 mM NH$_4$OAc (Aq): ACN; 1.0 ml/min.; Chiral HPLC: 98.81%, R$_t$=9.15 min (Chiralpak IA, 250×4.6 mm, 5μ; mobile phase (A) 0.1% DEA in n-Hexane (B) DCM:MeOH (80:20) (A:B:85:15); flow Rate: 1.00 mL/min); Optical rotation [α]$_D^{20}$: +13.04° (c=0.25, DCM). TLC: 5% MeOH/DCM (R$_f$: 0.4).

168. (+)-2-((3,4-trans)-1-(4-chloro-3-fluorobenzyl)-4-methylpyrrolidin-3-yl)-7-(tetrahydro-2H-pyran-4-yl)imidazo[5,1-f][1,2,4]triazin-4(3H)-one

169. (+)-2-((3,4-trans)-1-(4-fluoro-3-(trifluoromethyl)benzyl)-4-methylpyrrolidin-3-yl)-7-(tetrahydro-2H-pyran-4-yl)imidazo[5,1-f][1,2,4]triazin-4(3H)-one

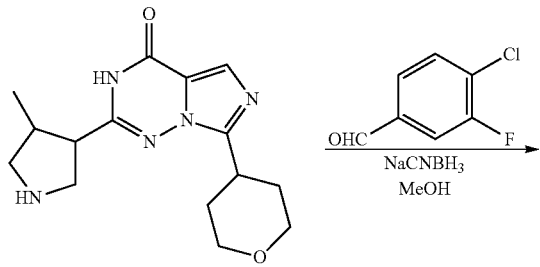

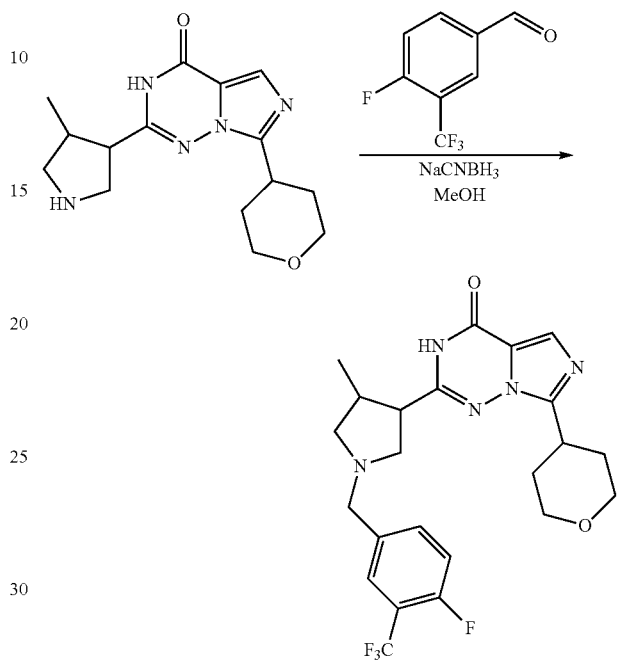

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added 4-chloro-3-fluorobenzaldehyde (51 mg, 0.32 mmol) at room temperature and stirred for 2 h under argon atmosphere. To the resulting solution was added NaCNBH$_3$ (46.78 mg, 0.74 mmol) and stirring was continued for another 8 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-2-((3,4-trans)-1-(4-chloro-3-fluorobenzyl)-4-methylpyrrolidin-3-yl)-7-(tetrahydro-2H-pyran-4-yl)imidazo[5,1-f][1,2,4]triazin-4(3H)-one (42 mg, 38%) as an off-white solid. $^1$H-NMR (DMSO-d$_6$, 400 MHz): δ 11.56 (bs, 1H), 7.64 (s, 1H), 7.53 (t, 1H), 7.34 (d, 1H), 7.18 (d, 1H), 3.96-3.94 (m, 2H), 3.67-3.65 (m, 2H), 3.51-3.48 (m, 2H), 3.42-3.41 (m, 1H), 2.98-2.97 (m, 1H), 2.83-2.79 (m, 1H), 2.74-2.72 (m, 1H), 2.67-2.64 (m, 2H), 2.33-2.31 (m, 1H), 1.87-1.81 (m, 4H), 1.08 (d, 3H); Mass (ESI): 446.5 [M$^+$+1]; LC-MS: 98.55%; 446 (M$^+$+1); (column; X-bridge C-18, (50×3.0 mm, 3.5μ); RT 2.33 min. 0.05% TFA (Aq): ACN; 0.8 ml/min); HPLC (purity): 99.11%; (column; Eclipse XDB C-18, 150×4.6 mm, 5.0μ; RT 10.56 min. 5 mM NH$_4$OAc (Aq): ACN; 1.0 ml/min.; Chiral HPLC: 98.97%, R$_t$=11.97 min (Chiralpak IA, 250×4.6 mm, 5μ; mobile phase (A) 0.1% DEA in n-Hexane (B) DCM:MeOH (80:20) (A:B: 85:15); flow Rate: 1.00 mL/min); Optical rotation [α]$_D^{20}$: +6.32° (c=0.25, DCM). TLC: 5% MeOH/DCM (Rf: 0.5).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added 4-fluoro-3-(trifluoromethyl)benzaldehyde (57 mg, 0.29 mmol) at room temperature and stirred for 2 h under argon atmosphere. To the resulting solution was added NaCNBH$_3$ (46 mg, 0.74 mmol) and stirring was continued for another 8 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-2-((3,4-trans)-1-(4-fluoro-3-(trifluoromethyl)benzyl)-4-methylpyrrolidin-3-yl)-7-(tetrahydro-2H-pyran-4-yl)imidazo[5,1-f][1,2,4]triazin-4(3H)-one (45 mg, 38%) as an off-white solid. $^1$H-NMR (DMSO-d$_6$, 400 MHz): δ 7.18-6.98 (m, 3H), 7.47 (t, 1H), 3.94-3.92 (m, 2H), 3.71 (s, 2H), 3.51-3.47 (m, 3H), 2.99-2.97 (m, 1H), 2.87-2.78 (m, 3H), 2.69-2.64 (m, 1H), 2.31-2.27 (m, 1H), 1.84-1.81 (m, 4H), 1.08 (d, 3H); Mass (ESI): 480 [M$^+$+1]; LC-MS: 98.14%; 480 (M$^+$+1); (column; X-bridge C-18, (50×3.0 mm, 3.5μ); RT 2.47 min. 0.05% TFA (Aq): ACN; 0.8 ml/min); UPLC (purity): 96.34%; (column; Acquity BEH C-18, 50×2.1 mm, 1.7μ; RT 1.70 min. 0.025% TFA (Aq): ACN; 0.50 ml/min.; Chiral HPLC: 100%, R$_t$=8.77 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +9.16° (c=0.25, DCM). TLC: 5% MeOH/DCM (Rf: 0.5).

170. (+)-2-((3,4-trans)-1-(2,5-dichlorobenzyl)-4-methylpyrrolidin-3-yl)-7-(tetrahydro-2H-pyran-4-yl)imidazo[5,1-f][1,2,4]triazin-4(3H)-one

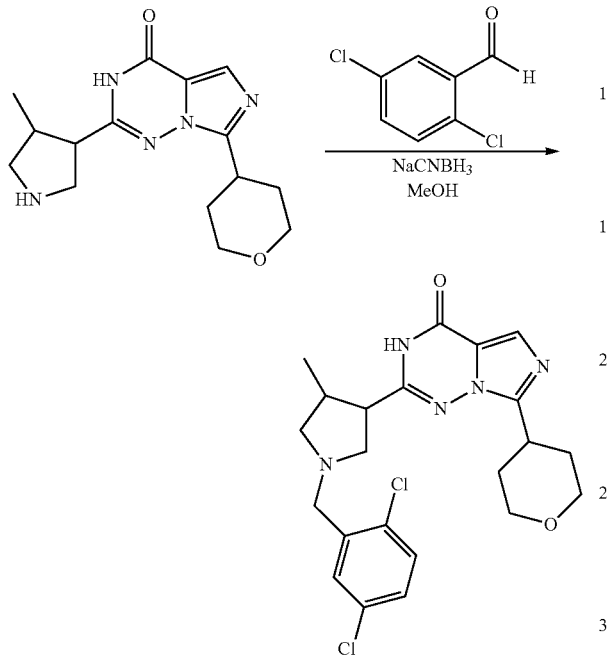

171. (+)-2-((3,4-trans)-1-(3,5-difluorobenzyl)-4-methylpyrrolidin-3-yl)-7-(tetrahydro-2H-pyran-4-yl)imidazo[1,5-f][1,2,4]triazin-4(3H)-one

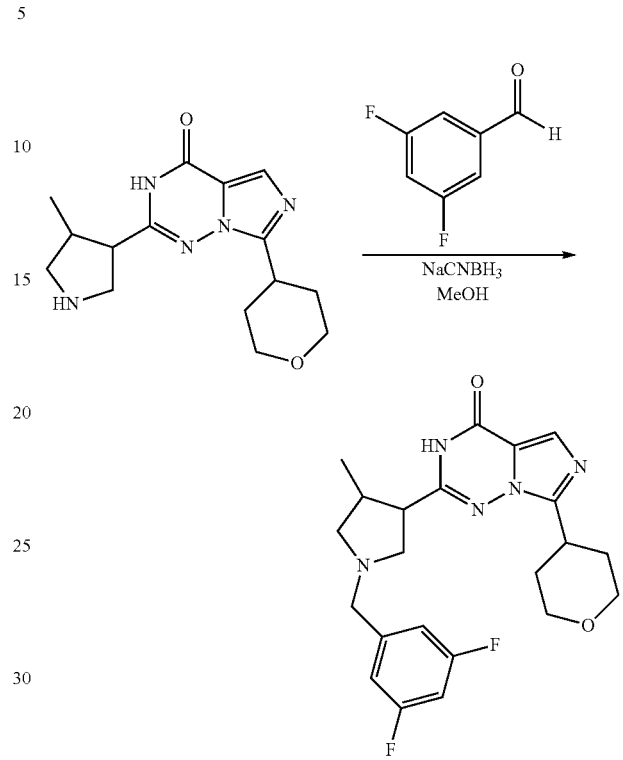

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (5 mL) was added 2,5-dichlorobenzaldehyde (56 mg, 0.32 mmol) at room temperature and stirred for 2 h under argon atmosphere. To the resulting solution was added NaCNBH$_3$ (46.7 mg, 0.74 mmol) and stirring was continued for another 8 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to (+)-2-((3,4-trans)-1-(2,5-dichlorobenzyl)-4-methylpyrrolidin-3-yl)-7-(tetrahydro-2H-pyran-4-yl)imidazo[5,1-f][1,2,4]triazin-4(3H)-one (35 mg, 31%) as an off-white solid. $^1$H-NMR (DMSO-d$_6$, 400 MHz): δ 11.72 (bs, 1H), 7.68 (s, 1H), 7.48 (d, 1H), 7.34 (d, 1H), 3.94-3.92 (m, 2H), 3.76 (s, 2H), 3.51-3.47 (m, 3H), 3.05-2.99 (m, 1H), 2.92-2.81 (m, 3H), 2.69-2.64 (m, 2H), 2.34-2.29 (m, 1H), 1.84-1.81 (m, 4H), 1.08 (d, 3H); Mass (ESI): 462 [M$^+$+1]; LC-MS: 97.49%; 462 (M$^+$+1); (column; X-bridge C-18, (50×3.0 mm, 3.5μ); RT 2.28 min. 0.05% TFA (Aq): ACN; 0.8 ml/min); UPLC (purity): 98.09%; (column; Acquity BEH C-18, 50×2.1 mm, 1.7μ; RT 1.59 min. 0.025% TFA (Aq): ACN; 0.50 ml/min.; Chiral HPLC: 99.42%, R$_t$=9.74 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +12.30° (c=0.25, DCM). TLC: 5% MeOH/DCM (Rf: 0.5).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (5 mL) was added 3,5-difluorobenzaldehyde (43 mg, 0.32 mmol) at room temperature and stirred for 2 h under argon atmosphere. To the resulting solution was added NaCNBH$_3$ (46 mg, 0.74 mmol) and stirring was continued for another 8 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-2-((3,4-trans)-1-(3,5-difluorobenzyl)-4-methylpyrrolidin-3-yl)-7-(tetrahydro-2H-pyran-4-yl)imidazo[1,5-f][1,2,4]triazin-4(3H)-one (20 mg, 19%) as an off-white solid. $^1$H-NMR (DMSO-d$_6$, 400 MHz): δ 11.67 (bs, 1H), 7.68 (s, 1H), 7.12-6.96 (m, 3H), 3.94-3.92 (m, 2H), 3.69-3.63 (m, 2H), 3.51-3.47 (m, 2H), 3.42-3.38 (m, 1H), 2.97-2.89 (m, 2H), 2.84-2.82 (m, 2H), 2.67-2.63 (m, 1H), 2.29-2.14 (m, 1H), 1.84-1.81 (m, 4H), 1.08 (d, 3H); Mass (ESI): 430 [M$^+$+1]; LC-MS: 99.72%; 430 (M$^+$+1); (column; X-bridge C-18, (50×3.0 mm, 3.5μ); RT 2.11 min. 0.05% TFA (Aq): ACN; 0.8 ml/min); UPLC (purity): 99%; (column; Acquity BEH C-18, 50×2.1 mm, 1.7μ; RT 1.48 min. 0.025% TFA (Aq): ACN; 0.50 ml/min.; Chiral HPLC: 98.58%, R$_t$=9.35 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +10.75° (c=0.25, DCM). TLC: 5% MeOH/DCM (R$_f$: 0.5).

172. (+)-2-((3,4-trans)-1-(3,4-dichlorobenzyl)-4-methylpyrrolidin-3-yl)-7-(tetrahydro-2H-pyran-4-yl)imidazo[1,5-f][1,2,4]triazin-4(3H)-one

173. (+)-(4,4-difluorocyclohexyl)-2-((3,4-trans)-1-(4-fluorobenzyl)-4-methylpyrrolidin-3-yl)imidazo[5,1-f][1,2,4]triazin-4(3H)-one

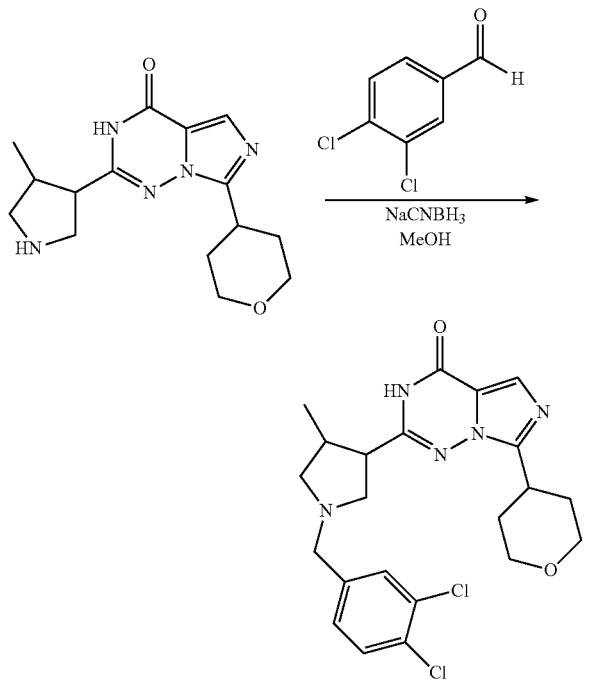

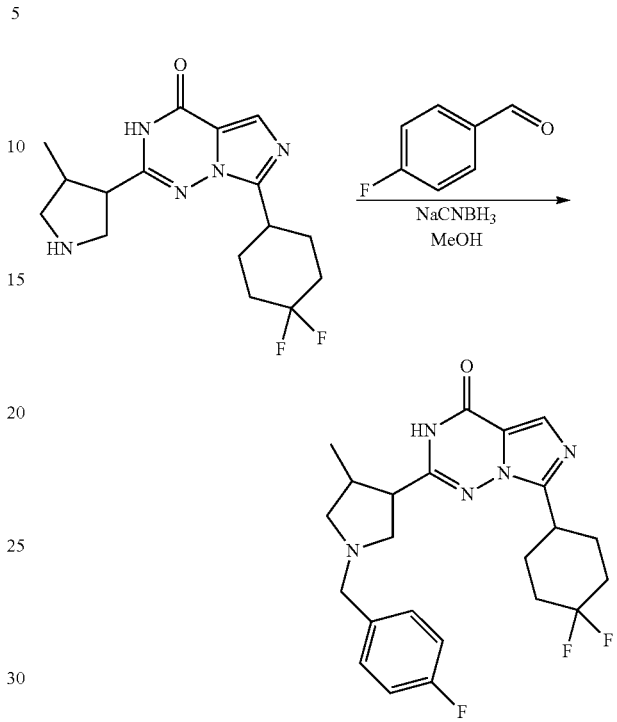

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) was added 3,4-dichlorobenzaldehyde (56.3 mg, 0.32 mmol) at room temperature and stirred for 2 h under argon atmosphere. To the resulting solution was added NaCNBH$_3$ (46 mg, 0.74 mmol) and stirring was continued for another 8 h at room temperature. The volatiles were evaporated under reduced pressure. The residue was diluted with water and extracted with CH$_2$Cl$_2$ (2×50 mL). Combined organic layer was dried over sodium sulphate, filtered and concentrated in vacuo to obtain the crude product. The crude material was purified by silica gel column chromatography to afford (+)-2-((3,4-trans)-1-(3,4-dichlorobenzyl)-4-methylpyrrolidin-3-yl)-7-(tetrahydro-2H-pyran-4-yl)imidazo[1,5-f][1,2,4]triazin-4(3H)-one (50 mg, 44%) as an off-white solid.
$^1$H-NMR (DMSO-d$_6$, 400 MHz): δ 7.68 (s, 1H), 7.58-7.52 (m, 2H), 7.32-7.29 (m, 1H), 3.94-3.92 (m, 2H), 3.64-3.62 (m, 2H), 3.51-3.45 (m, 3H), 2.97-2.92 (m, 1H), 2.89-2.78 (m, 3H), 2.69-2.65 (m, 1H), 2.29-2.14 (m, 1H), 1.84-1.81 (m, 4H), 1.08 (d, 3H); Mass (ESI): 462 [M$^+$+1]; LC-MS: 98.04%; 462 (M$^+$+1); (column; X-bridge C-18, (50×3.0 mm, 3.5μ); RT 2.44 min. 0.05% TFA (Aq): ACN; 0.8 ml/min); HPLC (purity): 99%; (column; Eclipse XDB C-18, 150×4.6 mm, 5.0μ; RT 11.12 min. 5 mM NH$_4$OAc (Aq): ACN; 1.0 ml/min.; Chiral HPLC: 97.98%, R$_t$=7.97 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +10.60° (c=0.25, DCM). TLC: 5% MeOH/DCM (Rf: 0.5).

To a stirred solution of (+)-2-((3,4-trans)-1-benzyl-4-methylpyrrolidin-3-yl)-7-(4,4-difluorocyclohexyl)imidazo[5,1-f][1,2,4]triazin-4(3H)-one (60 mg, 0.17 mmol) in MeOH (5 mL) was added 4-fluorobenzaldehyde (28.7 mg, 0.23 mmol) at room temperature and stirred for 2 h under argon atmosphere. To the resulting solution was added NaCNBH$_3$ (34 mg, 0.53 mmol) and stirring was continued for another 8 h at room temperature. The reaction mixture was quenched with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford 65 mg with 90% chemical purity. Purified by chiral preparative HPLC (Column: Chiralpak IA, 250×20 mm, 5 um (65 mg loading; (A) 0.1% DEA in n-Hexane: (B) DCM:MeOH (80:20), A:B (85:15) as mobile phase) to obtain pure (+)-(4,4-difluorocyclohexyl)-2-((3,4-trans)-1-(4-fluorobenzyl)-4-methylpyrrolidin-3-yl)imidazo[5,1-f][1,2,4]triazin-4(3H)-one (25 mg, 32%) as an off-white solid.
$^1$H-NMR (DMSO-d$_6$, 500 MHz): δ 7.67 (s, 1H), 7.37-7.35 (m, 2H), 7.15 (t, 2H), 3.63 (q, 2H), 3.34-3.22 (m, 1H), 2.97-2.95 (m, 1H), 2.85-2.75 (m, 3H), 2.67-2.62 (m, 1H), 2.27-2.23 (m, 1H), 2.19-2.15 (m, 2H), 2.02-1.97 (m, 6H), 1.12 (d, 3H); Mass (ESI): 446 [M$^+$+1]; LC-MS: 97.51%; 446 (M$^+$+1); (column; X-Bridge C-18, (50×3.0 mm, 3.5 μm); RT 2.61 min. 0.05% TFA (Aq): ACN; 0.8 ml/min); UPLC (purity): 98.13%; (column; Acquity BEH C-18, 50×2.1 mm, 1.7μ; RT 1.80 min. 0.025% TFA (Aq): ACN; 0.50 ml/min.; Chiral HPLC: 95.86%, R$_t$=6.72 min (Chiralpak IA, 250×4.6 mm, 5μ; mobile phase (A) 0.1% DEA in n-Hexane (B) DCM:MeOH (80:20) (A:B: 80:20); flow Rate: 1.00 mL/min); Optical rotation [α]$_D^{20}$: +21.47° (c=0.25, DCM). TLC: 5% MeOH/DCM (R$_f$: 0.5).

174. (+)-2-((3,4-trans)-1-(4-chlorobenzyl)-4-methyl-pyrrolidin-3-yl)-7-(4,4-difluorocyclohexyl)imidazo[5,1-f][1,2,4]triazin-4(3H)-one

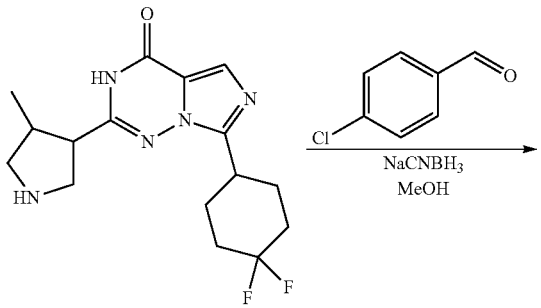

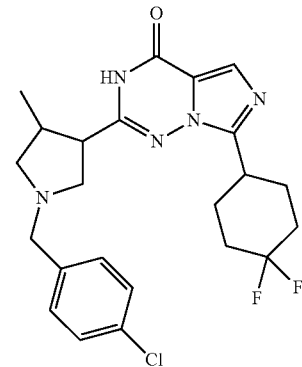

To a stirred solution of (+)-2-((3,4-trans)-1-benzyl-4-methylpyrrolidin-3-yl)-7-(4,4-difluorocyclohexyl)imidazo[5,1-f][1,2,4]triazin-4(3H)-one (60 mg, 0.17 mmol) in MeOH (5 mL) was added 4-chlorobenzaldehyde (33 mg, 0.23 mmol) at room temperature and stirred for 2 h under argon atmosphere. To the resulting solution was added NaCNBH$_3$ (34 mg, 0.53 mmol) and stirring was continued for another 8 h at room temperature. The reaction mixture was quenched with water and extracted with CH$_2$Cl$_2$ (2×20 mL). Combined organic layer was dried over sodium sulphate, filtered and concentrated in vacuo to obtain the crude product. The crude material was purified by silica gel column chromatography to afford 60 mg with 90% chemical purity. Purified by chiral preparative HPLC (Column: Chiralpak IA, 250×20 mm, 5 um (60 mg loading; (A) 0.1% DEA in n-Hexane: (B) DCM:MeOH (80:20), A:B (80:20) as mobile phase) to obtain pure (+)-2-((3,4-trans)-1-(4-chlorobenzyl)-4-methylpyrrolidin-3-yl)-7-(4,4-difluorocyclohexyl)imidazo[5,1-f][1,2,4]triazin-4(3H)-one (25 mg, 30%) as an off-white solid.

$^1$H-NMR (DMSO-d$_6$, 500 MHz): δ 7.63 (s, 1H), 7.39-7.29 (m, 4H), 3.62 (q, 2H), 2.98-2.95 (m, 2H), 2.87-2.75 (m, 3H), 2.67-2.62 (m, 1H), 2.39-2.34 (m, 1H), 2.28-2.23 (m, 2H), 2.09-1.95 (m, 6H), 1.12 (d, 3H); Mass (ESI): 462 [M$^+$+1]; LC-MS: 99.27%; 462.3 (M$^+$+1); (column; X-Bridge C-18, 50×2.1 mm, 3.5 μm); RT 2.74 min. 0.05% TFA (Aq): ACN; 0.8 ml/min.; UPLC (purity): 98.85%; (column; Acquity BEH C-18, 50×2.1 mm, 1.7μ; RT 1.91 min. 0.025% TFA (Aq): ACN; 0.50 ml/min.; Chiral HPLC: 99.51%, R$_t$=6.80 min (Chiralpak IA, 250×4.6 mm, 5μ; mobile phase (A) 0.1% DEA in n-Hexane (B) DCM:MeOH (80:20) (A:B:80:20); flow Rate: 1.00 mL/min); Optical rotation [α]$_D^{20}$: +6.62° (c=0.25, DCM). TLC: 5% MeOH/DCM (Rf: 0.4).

175. (+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)pyrimidine-5-carbonitrile

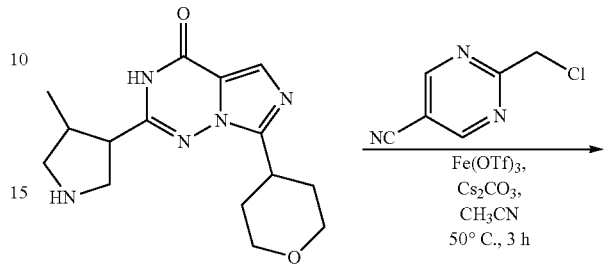

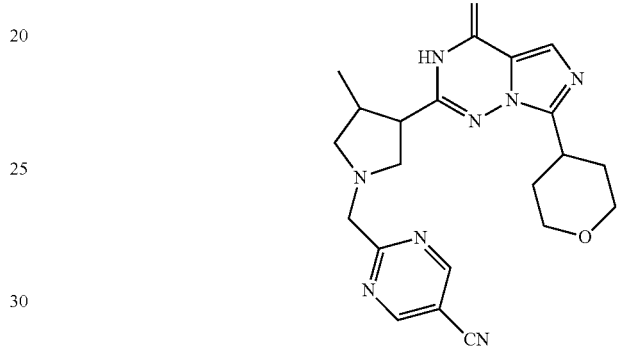

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (50 mg, 0.16 mmol) in CH$_3$CN (5 mL) under argon atmosphere were added cesium carbonate (118 mg, 0.36 mmol), iron triflate (16.6 mg, 0.03 mmol) and 2-(chloromethyl)pyrimidine-5-carbonitrile (27.8 mg, 0.18 mmol) at room temperature; heated to 50° C. and stirred for 3 h. The reaction was monitored by TLC; after completion of the reaction, the reaction mass was diluted with water (10 mL) and extracted with CH$_2$Cl$_2$ (2×20 mL). The combined organic extracts were dried over sodium sulphate, filtered and concentrated in vacuo to obtain the crude. The crude was purified through silica gel column chromatography using 3% MeOH/CH$_2$Cl$_2$ which was further purified through chiral preparative HPLC to afford (+)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)pyrimidine-5-carbonitrile (10 mg, 14%) as an off-white solid.

$^1$H-NMR (DMSO-d$_6$, 400 MHz): δ 9.25 (s, 2H), 7.66 (s, 1H), 4.11 (d, 1H), 3.99-3.90 (m, 3H), 3.48 (t, 3H), 3.12-2.94 (m, 3H), 2.80-2.78 (m, 1H), 2.61-2.59 (m, 1H), 2.41-2.39 (m, 1H), 1.90-1.78 (m, 4H), 1.10 (d, 3H); Mass (ESI): 421.3 [M$^+$+1]; LC-MS: 97.77%; 421.3 (M$^+$+1); (column; X-bridge C-18, (50×3.0 mm, 3.5 μm); RT 2.98 min. 5 mM NH$_4$OAc: ACN; 0.8 mL/min.); UPLC (purity): 98.55%; (column: Acquity UPLC HSS T3 (2.1×100 mm, 1.8μ); RT 3.01 min. ACN: 0.025% TFA (Aq); 0.3 mL/min.; Chiral HPLC: 98.96%, R$_t$=13.49 min (Chiralpak IC, 250×4.6 mm, 5 μm); mobile phase (A) 0.1% DEA in n-Hexane (B) CH$_2$Cl$_2$: MeOH (80:20) (A:B:50:50); flow Rate: 1.0 mL/min); Optical rotation [α]$_D^{20}$: +39.15° (c=0.25, CH$_2$Cl$_2$); TLC: 10% MeOH/CH$_2$Cl$_2$ (R$_f$: 0.6).

176. (+)-2-((3,4-trans)-1-((5-chloropyrimidin-2-yl)methyl)-4-methylpyrrolidin-3-yl)-7-(tetrahydro-2H-pyran-4-yl)imidazo[5,1-f][1,2,4]triazin-4(3H)-one

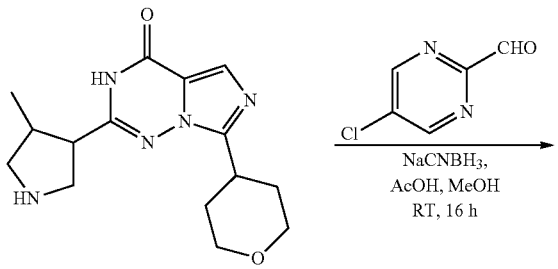

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.49 mmol) in MeOH (15 mL) under argon atmosphere was added 5-chloropyrimidine-2-carbaldehyde (141 mg, 0.99 mmol) at room temperature and stirred for 2 h. To this were added 3 drops of AcOH, sodium cyanoborohydride (93 mg, 1.48 mmol) and stirred for 16 h. The reaction was monitored by TLC; after completion of the reaction, the volatiles were removed in vacuo. The residue was diluted with water (20 mL) and extracted with $CH_2Cl_2$ (2×35 mL). The combined organic extracts dried over sodium sulphate, filtered and concentrated in vacuo to obtain the crude. The crude was purified through silica gel column chromatography using 5% MeOH/$CH_2Cl_2$ to afford (+)-2-((3,4-trans)-1-((5-chloropyrimidin-2-yl)methyl)-4-methylpyrrolidin-3-yl)-7-(tetrahydro-2H-pyran-4-yl)imidazo[5,1-f][1,2,4]triazin-4(3H)-one (50 mg, 24%) as white solid.

$^1$H-NMR (DMSO-$d_6$, 400 MHz): δ 8.90 (s, 2H), 7.68 (s, 1H), 4.00 (d, 1H), 3.98-3.86 (m, 3H), 3.50 (t, 2H), 3.41-3.40 (m, 1H), 3.12 (t, 1H), 3.02-2.94 (m, 2H), 2.78 (q, 1H), 2.64 (t, 1H), 2.38-2.32 (m, 1H), 1.90-1.74 (m, 4H), 1.10 (d, 3H); Mass (ESI): 430.4 [M$^+$+1]; LC-MS: 99.79%; 430.5 (M$^+$+1); (column; X-bridge C-18, (50×3.0 mm, 3.5 μm); RT 2.92 min. 0.05% TFA (aq.): ACN; 0.8 mL/min); UPLC (purity): 99.23%; (column: Acquity BEH C-18 (50×2.1 mm, 1.7μ); RT 1.28 min. ACN: 0.025% TFA (Aq); 0.5 mL/min.; Chiral HPLC: 99.06%, $R_t$=15.55 min (Chiralpak IC, 250×4.6 mm, 5 μm); mobile phase (A) 0.1% DEA in n-Hexane (B) $CH_2Cl_2$:MeOH (80:20) (A:B:65:35); flow Rate: 1.0 mL/min); Optical rotation $[α]_D^{20}$: +80.00° (c=0.25, $CH_2Cl_2$); TLC: 10% MeOH/$CH_2Cl_2$ ($R_f$: 0.5).

177. (+)-2-((3,4-trans)-1-((4,6-dimethylpyrimidin-2-yl)methyl)-4-methylpyrrolidin-3-yl)-7-(tetrahydro-2H-pyran-4-yl)imidazo[5,1-f][1,2,4]triazin-4(3H)-one

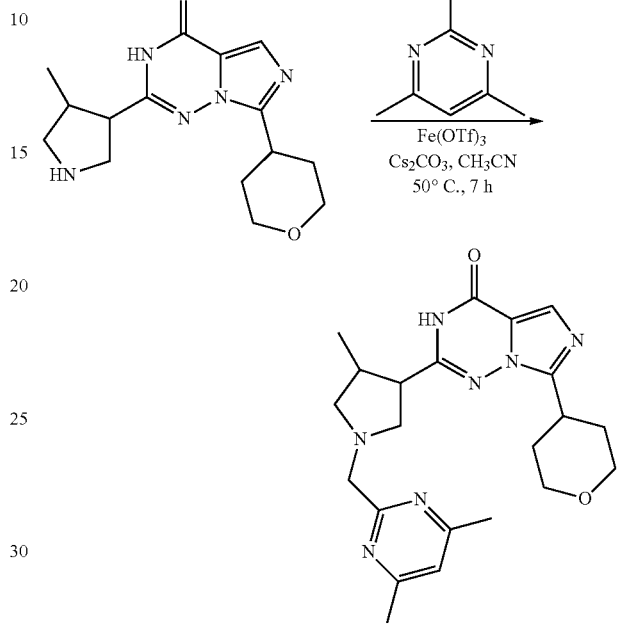

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in $CH_3CN$ (5 mL) under argon atmosphere were added iron triflate (25 mg, 0.05 mmol), cesium carbonate (161 mg, 0.49 mmol) and 2-(chloromethyl)-4,6-dimethylpyrimidine (42.7 mg, 0.27 mmol) at room temperature; heated to 50° C. and stirred for 7 h. The reaction was monitored by TLC; after completion of the starting material, the reaction mass was diluted with water (15 mL) and extracted with $CH_2Cl_2$ (3×25 mL). The combined organic extracts were dried over sodium sulphate, filtered and concentrated in vacuo to obtain the crude. The crude was purified through silica gel column chromatography using 4% MeOH/$CH_2Cl_2$ which was further purified through chiral preparative HPLC to afford (+)-2-((3,4-trans)-1-((4,6-dimethylpyrimidin-2-yl)methyl)-4-methylpyrrolidin-3-yl)-7-(tetrahydro-2H-pyran-4-yl)imidazo[5,1-f][1,2,4]triazin-4(3H)-one (10 mg, 10%) as an off-white solid.

$^1$H-NMR (DMSO-$d_6$, 400 MHz): δ 7.70 (s, 1H), 7.10 (s, 1H), 3.96-3.94 (m, 3H), 3.70 (d, 1H), 3.51-3.49 (m, 3H), 3.14-3.12 (m, 1H), 3.02-3.00 (m, 1H), 2.88 (t, 1H), 2.78-2.76 (m, 1H), 2.60-2.58 (m, 1H), 2.40 (s, 6H), 2.31-2.29 (m, 1H), 1.88-1.80 (m, 4H), 1.10 (d, 3H); Mass (ESI): 424.6 [M$^+$+1]; LC-MS: 99.38%; 424.6 (M$^+$+1); (column; X-bridge C-18, (50×3.0 mm, 3.5 μm); RT 2.56 min. 0.05% TFA (aq.): ACN; 0.8 mL/min); UPLC (purity): 98.31%; (column: Acquity BEH C-18 (50×2.1 mm, 1.7μ); RT 1.33 min. ACN: 0.025% TFA (Aq); 0.5 mL/min.; Chiral HPLC: 97.86%, $R_t$=19.61 min (Chiralpak IA, 250×4.6 mm, 5 μm); mobile phase (A) 0.1% TEA in n-Hexane (B) EtOH (A:B:50:50);

178. (+)-2-((3,4-trans)-1-((5-methoxypyrimidin-2-yl)methyl)-4-methylpyrrolidin-3-yl)-7-(tetrahydro-2H-pyran-4-yl)imidazo[5,1-f][1,2,4]triazin-4(3H)-one

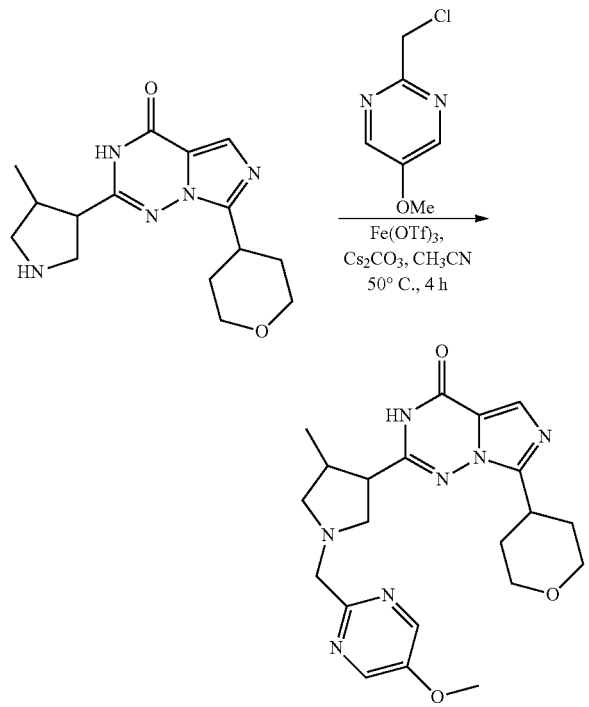

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in CH$_3$CN (8 mL) under argon atmosphere were added cesium carbonate (161 mg, 0.49 mmol), iron triflate (25 mg, 0.04 mmol) and 2-(chloromethyl)-5-methoxypyrimidine (43 mg, 0.27 mmol) at room temperature; heated to 50° C. and stirred for 4 h. The reaction was monitored by TLC; after completion of the reaction, the reaction mass was diluted with water (15 mL) and extracted with CH$_2$Cl$_2$ (3×20 mL). The combined organic extracts were dried over sodium sulphate, filtered and concentrated in vacuo to obtain the crude. The crude was purified through silica gel column chromatography using 3% MeOH/CH$_2$Cl$_2$ which was further purified through chiral preparative HPLC to afford (+)-2-((3,4-trans)-1-((5-methoxypyrimidin-2-yl)methyl)-4-methylpyrrolidin-3-yl)-7-(tetrahydro-2H-pyran-4-yl)imidazo[5,1-f][1,2,4]triazin-4(3H)-one (28 mg, 27%) as white solid.

$^1$H-NMR (DMSO-d$_6$, 400 MHz): δ 8.50 (s, 2H), 7.64 (s, 1H), 3.94-3.88 (m, 6H), 3.78 (d, 1H), 3.50-3.46 (m, 2H), 3.40-3.38 (m, 1H), 3.08 (t, 1H), 2.96-2.92 (m, 2H), 2.78-2.76 (m, 1H), 2.60-2.58 (m, 1H), 2.32-2.28 (m, 1H), 1.90-1.80 (m, 4H), 1.08 (d, 3H); Mass (ESI): 426.4 [M$^+$+1]; LC-MS: 99.15%; 426 (M$^+$+1); (column; X-bridge C-18, (50×3.0 mm, 3.5 μm); RT 1.96 min. 0.05% TFA in H$_2$O: ACN; 0.8 mL/min); UPLC (purity): 99.83%; (column: Acquity UPLC BEH C-18 (2.1×50 mm, 1.7μ); RT 1.20 min. ACN: 0.025% TFA (Aq); 0.5 mL/min.; Chiral HPLC: 98.75%, R$_t$=11.87 min (Chiralpak IA, 250×4.6 mm, 5 pt); mobile phase (A) 0.1% DEA in n-Hexane (B) CH$_2$Cl$_2$: MeOH (80:20) (A:B:80:20); flow Rate: 1.0 mL/min); Optical rotation [α]$_D^{19.98}$: +106.76° (c=0.25, CH$_2$Cl$_2$); TLC: 10% MeOH/CH$_2$Cl$_2$ (R$_f$: 0.6).

179. (+)-2-((3,4-trans)-4-methyl-1-((4-(trifluoromethyl)pyrimidin-2-yl)methyl)pyrrolidin-3-yl)-7-(tetrahydro-2H-pyran-4-yl)imidazo[5,1-f][1,2,4]triazin-4(3H)-one

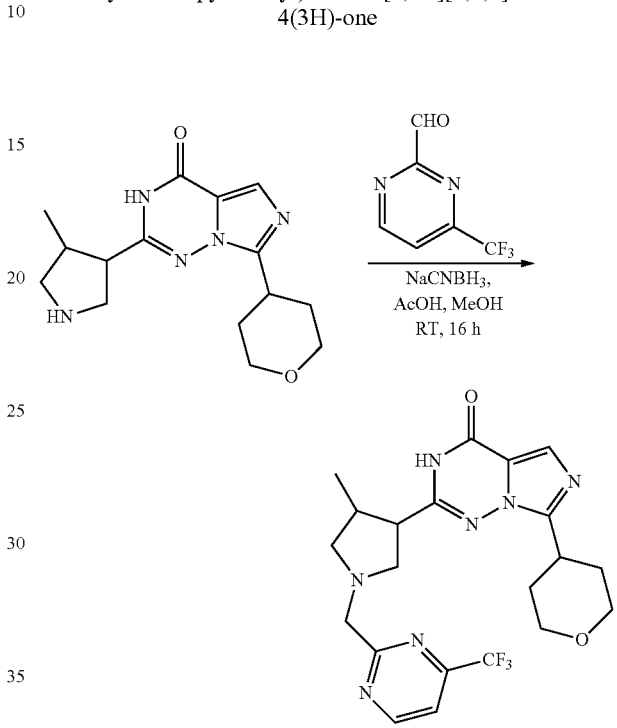

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (50 mg, 0.16 mmol) in MeOH (5 mL) under argon atmosphere was 4-(trifluoromethyl)pyrimidine-2-carbaldehyde (100 mg, crude) at room temperature and stirred for 2 h. To this were added 2 drops of AcOH, sodium cyanoborohydride (31 mg, 0.49 mmol) and stirred for 16 h. The reaction was monitored by TLC; after completion of the reaction, the reaction mass was quenched with ice cold water (10 mL) and extracted with CH$_2$Cl$_2$ (2×15 mL). The combined organic extracts were dried over sodium sulphate, filtered and concentrated in vacuo to obtain the crude. The crude was purified through silica gel column chromatography using 4% MeOH/CH$_2$Cl$_2$ which was further purified through chiral preparative HPLC to afford (+)-2-((3,4-trans)-4-methyl-1-((4-(trifluoromethyl)pyrimidin-2-yl)methyl)pyrrolidin-3-yl)-7-(tetrahydro-2H-pyran-4-yl)imidazo[5,1-f][1,2,4]triazin-4(3H)-one (10 mg, 13%) as white solid.

$^1$H-NMR (DMSO-d$_6$, 400 MHz): δ 11.66 (br s, 1H), 9.16 (d, 1H), 7.94 (d, 1H), 7.66 (s, 1H), 4.10 (d, 2H), 3.96-3.88 (m, 2H), 3.51-3.49 (m, 2H), 3.40-3.38 (m, 1H), 3.10 (d, 1H), 3.08-3.02 (m, 2H), 2.81-2.79 (m, 1H), 2.64-2.60 (m, 1H), 2.41-2.39 (m, 1H), 1.88-1.80 (m, 4H), 1.10 (d, 3H); Mass (ESI): 464.4 [M$^+$+1]; LC-MS: 96.69%; 464 (M$^+$+1); (column; X-bridge C-18, (50×3.0 mm, 3.5 μm); RT 2.18 min. 0.05% TFA (aq.): ACN; 0.8 mL/min); UPLC (purity): 96.95%; (column: Acquity BEH C-18 (50×2.1 mm, 1.7μ); RT 1.39 min. ACN: 0.025% TFA (Aq); 0.5 mL/min.; Chiral HPLC: 95.10%, R$_t$=9.09 min (Chiralpak IA, 250×4.6 mm, 5μ); mobile phase (A) 0.1% DEA in n-Hexane (B) CH$_2$Cl$_2$: MeOH (80:20) (A:B:80:20); flow Rate: 1.0 mL/min); Optical rotation [α]$_D$$^{19.98}$: +52.41° (c=0.25, CH$_2$Cl$_2$); TLC: 5% MeOH/CH$_2$Cl$_2$ (R$_f$: 0.5).

180. (+)-2-((3,4-trans)-4-methyl-1-((5-methylpyrimidin-2-yl)methyl)pyrrolidin-3-yl)-7-(tetrahydro-2H-pyran-4-yl)imidazo[5,1-f][1,2,4]triazin-4(3H)-one

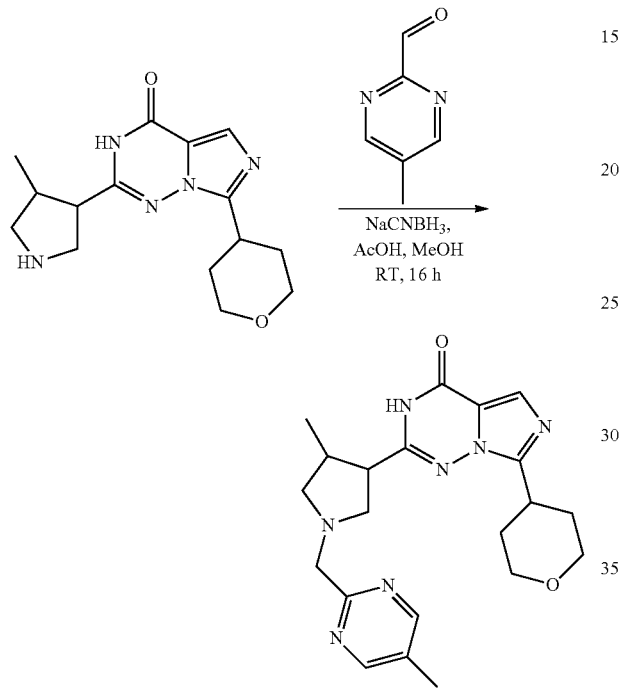

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in MeOH (10 mL) under argon atmosphere was added 5-methylpyrimidine-2-carbaldehyde (36 mg, 0.29 mmol) at room temperature and stirred for 2 h. To this were added 3 drops of AcOH, sodium cyanoborohydride (46 mg, 0.74 mmol) and stirred for 16 h. The reaction was monitored by TLC; after completion of the reaction, the reaction mass was quenched with ice cold water (10 mL) and extracted with CH$_2$Cl$_2$ (2×20 mL). The combined organic extracts were dried over sodium sulphate, filtered and concentrated in vacuo to obtain the crude. The crude was purified through silica gel column chromatography using 3% MeOH/CH$_2$Cl$_2$ which was further purified through chiral preparative HPLC to afford (+)-2-((3,4-trans)-4-methyl-1-((5-methylpyrimidin-2-yl)methyl)pyrrolidin-3-yl)-7-(tetrahydro-2H-pyran-4-yl)imidazo[5,1-f][1,2,4]triazin-4(3H)-one (30 mg, 30%) as white solid.

$^1$H-NMR (DMSO-d$_6$, 400 MHz): δ 8.60 (s, 2H), 7.78 (s, 1H), 3.96-3.90 (m, 3H), 3.80 (d, 1H), 3.52-3.46 (m, 3H), 3.10 (t, 1H), 3.00-2.92 (m, 2H), 2.78-2.76 (m, 1H), 2.60-2.58 (m, 1H), 2.34-2.32 (m, 1H), 2.24 (s, 3H), 1.90-1.80 (m, 4H), 1.10 (d, 3H); Mass (ESI): 410 [M$^+$+1]; LC-MS: 99.98%; 410 (M$^+$+1); (column: X-bridge C-18, (50×3.0 mm, 3.5 μm); RT 1.94 min. 0.05% TFA (aq.): ACN; 0.8 mL/min); UPLC (purity): 99.84%; (column: Acquity UPLC BEH C-18 (2.1×50 mm, 1.7μ); RT 1.16 min. ACN: 0.025% TFA (Aq); 0.5 mL/min.; Chiral HPLC: 97.41%, R$_{t=19.12}$ min (Chiralpak IA, 250×4.6 mm, 5 μm); mobile phase (A) 0.1% DEA in n-Hexane (B) CH$_2$Cl$_2$:MeOH (80:20) (A:B:85:15); flow Rate: 1.0 mL/min); Optical rotation [α]$_D$$^{19.99}$: +108.94° (c=0.25, CH$_2$Cl$_2$); TLC: 10% MeOH/CH$_2$Cl$_2$ (R$_f$: 0.6).

181. (+)-2-((3,4-trans)-4-methyl-1-((4-methylpyrimidin-2-yl)methyl)pyrrolidin-3-yl)-7-(tetrahydro-2H-pyran-4-yl)imidazo[5,1-f][1,2,4]triazin-4(3H)-one

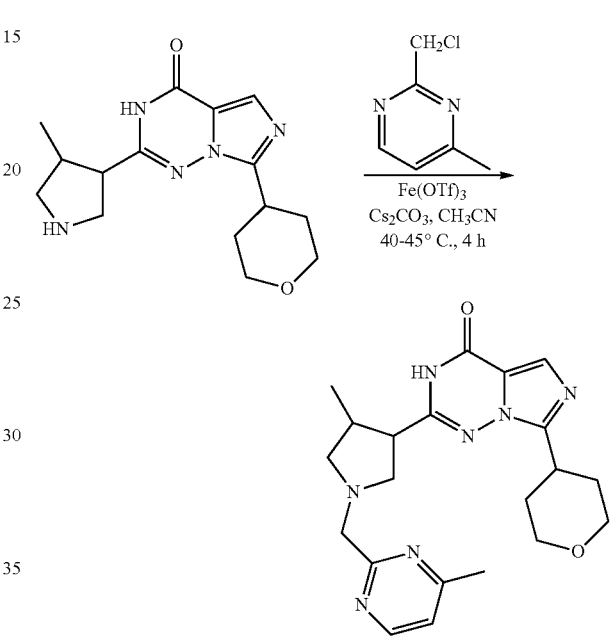

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (100 mg, 0.33 mmol) in CH$_3$CN (10 mL) under argon atmosphere were added iron triflate (33 mg, 0.06 mmol), cesium carbonate (215 mg, 0.66 mmol) and 2-(chloromethyl)-4-methylpyrimidine (51.5 mg, 0.36 mmol) at room temperature; heated to 40-45° C. and stirred for 4 h. The reaction was monitored by TLC; after completion of the starting material, the reaction mass was diluted with water (15 mL) and extracted with CH$_2$Cl$_2$ (3×25 mL). The combined organic extracts were dried over sodium sulphate, filtered and concentrated in vacuo to obtain the crude. The crude was purified through silica gel column chromatography using 2-3% MeOH/CH$_2$Cl$_2$ which was further purified through chiral preparative HPLC to afford (+)-2-((3,4-trans)-4-methyl-1-((4-methylpyrimidin-2-yl)methyl)pyrrolidin-3-yl)-7-(tetrahydro-2H-pyran-4-yl)imidazo[5,1-f][1,2,4]triazin-4(3H)-one (12 mg, 9%) as an off-white solid.

$^1$H-NMR (DMSO-d$_6$, 400 MHz): δ 8.62 (d, 1H), 7.68 (s, 1H), 7.26 (d, 1H), 3.96-3.90 (m, 3H), 3.78 (d, 1H), 3.51-3.49 (m, 3H), 3.20-3.18 (m, 1H), 3.06-3.04 (m, 1H), 2.92 (t, 1H), 2.80-2.78 (m, 1H), 2.60-2.58 (m, 1H), 2.42-2.40 (m, 3H), 2.34-2.30 (m, 1H), 1.88-1.84 (m, 4H), 1.10 (d, 3H); Mass (ESI): 410.4 [M$^+$+1]; LC-MS: 98.54%; 410 (M$^+$+1); (column; X-bridge C-18, (50×3.0 mm, 3.5 μm); RT 1.84 min. 0.05% TFA (aq.): ACN; 0.8 mL/min); UPLC (purity): 98.89%; (column: Acquity BEH C-18 (50×2.1 mm, 1.7μ); RT 1.21 min. ACN: 0.025% TFA (Aq); 0.5 mL/min.; Chiral HPLC: 97.12%, $R_t$=9.46 min (Chiralpak IA, 250×4.6 mm, 5 μm); mobile phase (A) 0.1% DEA in n-Hexane (B) $CH_2Cl_2$: MeOH (80:20) (A:B:80:20); flow Rate: 1.0 mL/min); Optical rotation $[α]_D^{19.99}$: +114.65° (c=0.25, $CH_2Cl_2$); TLC: 10% MeOH/$CH_2Cl_2$ ($R_f$: 0.6).

182. (+)-2-((3,4-trans)-1-((4-(dimethylamino)pyrimidin-2-yl)methyl)-4-methylpyrrolidin-3-yl)-7-(tetrahydro-2H-pyran-4-yl)imidazo[5,1-f][1,2,4]triazin-4(3H)-one

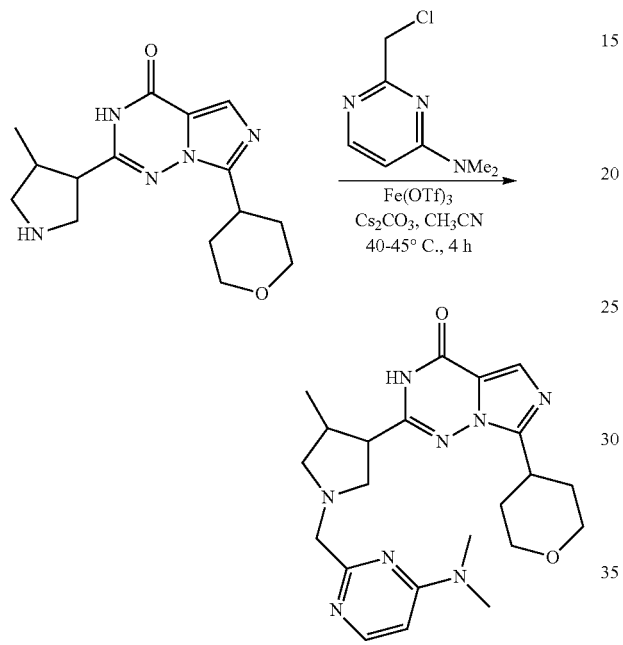

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in $CH_3CN$ (10 mL) under argon atmosphere were added iron triflate (25 mg, 0.04 mmol), cesium carbonate (161 mg, 0.49 mmol) and 2-(chloromethyl)-N,N-dimethylpyrimidin-4-amine (47 mg, 0.27 mmol) at room temperature; heated to 40-45° C. and stirred for 4 h. The reaction was monitored by TLC; after completion of the starting material, the reaction mass was diluted with water (15 mL) and extracted with $CH_2Cl_2$ (3×25 mL). The combined organic extracts were dried over sodium sulphate, filtered and concentrated in vacuo to obtain the crude. The crude was purified through silica gel column chromatography using 3-4% MeOH/$CH_2Cl_2$ which was further purified through chiral preparative HPLC to afford (+)-2-((3,4-trans)-1-((4-(dimethylamino)pyrimidin-2-yl)methyl)-4-methylpyrrolidin-3-yl)-7-(tetrahydro-2H-pyran-4-yl)imidazo[5,1-f][1,2,4]triazin-4(3H)-one (30 mg, 28%) as an off-white solid.

$^1$H-NMR (DMSO-$d_6$, 400 MHz): δ 8.14 (d, 1H), 7.76 (s, 1H), 6.54 (d, 1H), 3.96-3.90 (m, 2H), 3.78 (d, 1H), 3.60 (d, 1H), 3.51-3.49 (m, 3H), 3.14 (t, 1H), 3.10-3.08 (m, 1H), 3.02 (s, 6H), 2.90 (t, 1H), 2.76-2.74 (m, 1H), 2.61-2.59 (m, 1H), 2.34-2.30 (m, 1H), 1.90-1.80 (m, 4H), 1.10 (d, 3H); Mass (ESI): 439 [M$^+$+1]; LC-MS: 91.30%; 439 (M$^+$+1); (column; X-bridge C-18, (50×3.0 mm, 3.5 μm); RT 1.71 min. 0.05% TFA (aq.): ACN; 0.8 mL/min); UPLC (purity): 93.03%; (column: Acquity UPLC HSS-T3 (100×2.1 mm, 1.8μ); RT 2.94 min. ACN: 0.025% TFA (Aq); 0.3 mL/min.; Chiral HPLC: 96.52%, $R_t$=21.17 min (Chiralpak IA, 250×4.6 mm, 5 nm); mobile phase (A) 0.1% DEA in n-Hexane (B) $CH_2Cl_2$:MeOH (80:20) (A:B:85:15); flow Rate: 1.0 mL/min); Optical rotation $[α]_D^{20}$: +94.19° (c=0.25, $CH_2Cl_2$); TLC: 10% MeOH/$CH_2Cl_2$ ($R_f$: 0.5).

183. (+)-2-((3,4-trans)-1-((5-fluoropyrimidin-2-yl)methyl)-4-methylpyrrolidin-3-yl)-7-(tetrahydro-2H-pyran-4-yl)imidazo[5,1-f][1,2,4]triazin-4(3H)-one

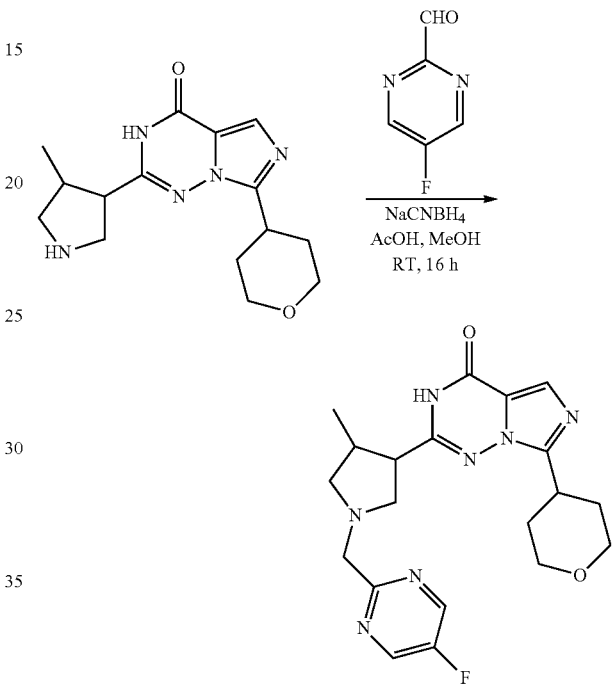

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (50 mg, 0.16 mmol) in MeOH (5 mL) under inert atmosphere was added 5-fluoropyrimidine-2-carbaldehyde (50 mg, crude) at room temperature and stirred for 2 h. To this were added 2 drops of AcOH, sodium cyanoborohydride (31 mg, 0.49 mmol) and stirred for 16 h. The reaction was monitored by TLC; after completion of the reaction, the reaction mass was diluted with water (10 mL) and extracted with $CH_2Cl_2$ (2×20 mL). The combined organic extracts dried over sodium sulphate, filtered and concentrated in vacuo to obtain the crude. The crude was purified through silica gel column chromatography using 4% MeOH/$CH_2Cl_2$ which was further purified through chiral preparative HPLC to afford (+)-2-((3,4-trans)-1-((5-fluoropyrimidin-2-yl)methyl)-4-methylpyrrolidin-3-yl)-7-(tetrahydro-2H-pyran-4-yl)imidazo[5,1-f][1,2,4]triazin-4(3H)-one (15 mg, 22%) as an off white solid.

$^1$H-NMR (DMSO-$d_6$, 400 MHz): δ 8.86 (s, 2H), 7.64 (s, 1H), 4.00-3.84 (m, 4H), 3.50-3.46 (m, 2H), 3.38-3.36 (m, 1H), 3.10 (t, 1H), 3.00-2.93 (m, 2H), 2.80-2.78 (m, 1H), 2.60-2.58 (m, 1H), 2.40-2.37 (m, 1H), 1.88-1.82 (m, 4H), 1.10 (d, 3H); Mass (ESI): 414.3 [M$^+$+1]; LC-MS: 99.58%; 414 (M$^+$+1); (column; X-bridge C-18, (50×3.0 mm, 3.5 μm); RT 2.16 min. 0.05% TFA (aq.): ACN; 0.8 mL/min); UPLC (purity): 99.72%; (column: Acquity UPLC HSS T3 (100×2.1 mm, 1.8μ); RT 3.06 min. ACN: 0.025% TFA (Aq); 0.3 mL/min.; Chiral HPLC: 99.61%, $R_t$=19.45 min (Chiralpak IA, 250×4.6 mm, 5 μm); mobile phase (A) 0.1% DEA in n-Hexane (B) $CH_2Cl_2$:MeOH (80:20) (A:B:85:15); flow Rate: 1.0 mL/min); Optical rotation $[α]_D^{20.01}$: +103.24° (c=0.25, $CH_2Cl_2$); TLC: 5% MeOH/$CH_2Cl_2$ ($R_f$: 0.6).

184. (+)-2-((3,4-trans)-1-((5-cyclopropylpyrimidin-2-yl)methyl)-4-methylpyrrolidin-3-yl)-7-(tetrahydro-2H-pyran-4-yl)imidazo[5,1-f][1,2,4]triazin-4(3H)-one

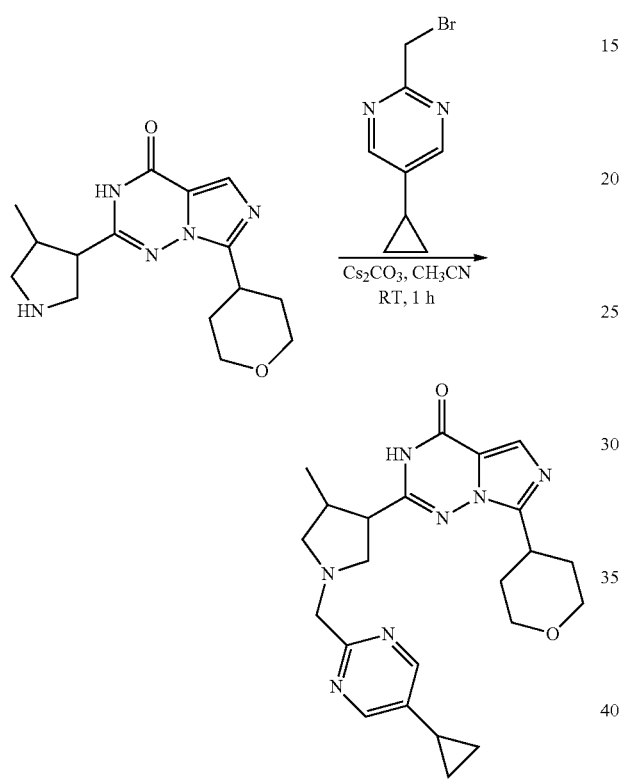

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (85 mg, 0.28 mmol) in $CH_3CN$ (10 mL) under argon atmosphere was added 2-(bromomethyl)-5-cyclopropylpyrimidine (59.75 mg, 0.28 mmol) and cesium carbonate (182.34 mg, 0.56 mmol) at room temperature and stirred for 1 h. The reaction was monitored by TLC; after completion of the reaction, the volatiles were evaporated in vacuo. The residue was diluted with water (15 mL) and the compound was extracted with $CH_2Cl_2$ (2×30 mL). The combined organic extracts dried over sodium sulfate, filtered and concentrated in vacuo to obtain the crude. The crude was purified through silica gel column chromatography which was further purified through preparative HPLC to afford (+)-2-((3,4-trans)-1-((5-cyclopropylpyrimidin-2-yl) methyl)-4-methylpyrrolidin-3-yl)-7-(tetrahydro-2H-pyran-4-yl)imidazo[5,1-f][1,2,4]triazin-4(3H)-one (25 mg, 20%) as an off-white solid.

$^1$H-NMR (DMSO-$d_6$, 400 MHz): δ 8.52 (s, 2H), 7.68 (s, 1H), 3.94-3.90 (m, 3H), 3.80 (d, 1H), 3.51-3.47 (m, 3H), 3.10 (t, 1H), 2.98-2.94 (m, 2H), 2.78-2.76 (m, 1H), 2.60-2.58 (m, 1H), 2.36-2.32 (m, 1H), 2.00-1.97 (m, 1H), 1.90-1.83 (m, 4H), 1.10 (d, 3H), 1.04-1.02 (m, 2H); 0.84-0.82 (m, 2H), 0.76-0.74 (m, 2H); Mass (ESI): 436.4 [M$^+$+1]; LC-MS: 99.86%; 436.5 (M$^+$+1); (column; X-bridge C-18, (50×3.0 mm, 3.5 μm); RT 2.15 min. 0.05% TFA (aq.): ACN; 0.8 mL/min); UPLC (purity): 99.57%; (column: Acquity BEH C-18 (50×2.1 mm, 1.7μ); RT 1.39 min. ACN: 0.025% TFA (Aq); 0.5 mL/min.; Chiral HPLC: 99.58%, $R_t$=19.82 min (Chiralpak IA, 250×4.6 mm, 5 μm); mobile phase (A) 0.1% DEA in n-Hexane (B) $CH_2Cl_2$: MeOH (80:20) (A:B:85:15); flow Rate: 1.0 mL/min); Optical rotation $[α]_D^{20}$: +84.08° (c=0.25, $CH_2Cl_2$); TLC: 10% MeOH/$CH_2Cl_2$ ($R_f$: 0.4).

185. (+)-2-((3,4-trans)-4-methyl-1-((5-(pyrrolidin-1-yl)pyrimidin-2-yl)methyl)pyrrolidin-3-yl)-7-(tetrahydro-2H-pyran-4-yl)imidazo[5,1-f][1,2,4]triazin-4(3H)-one

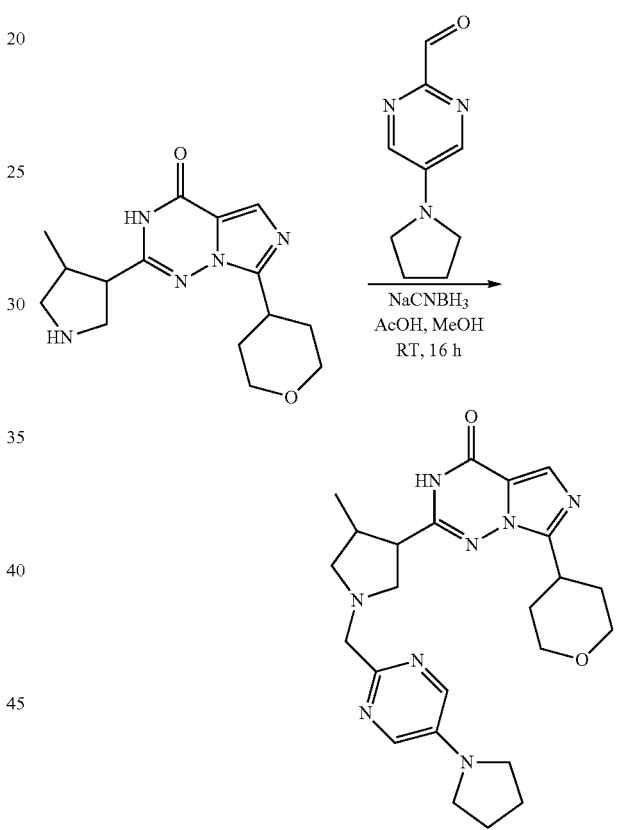

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (30 mg, 0.09 mmol) in MeOH (5 mL) under argon atmosphere was added 5-(pyrrolidin-1-yl)pyrimidine-2-carbaldehyde (45 mg crude) at room temperature and stirred for 2 h. To this were added 2 drops of AcOH, sodium cyanoborohydride (18.7 mg, 0.29 mmol) and stirred for 16 h. The reaction was monitored by TLC; after completion of the reaction, the volatiles were removed in vacuo. The residue was quenched with ice cold water (6 mL) and extracted with $CH_2Cl_2$ (3×10 mL). The combined organic extracts were dried over sodium sulphate, filtered and concentrated in vacuo to obtain the crude. The crude was purified through silica gel column chromatography using 3% MeOH/$CH_2Cl_2$ which was further purified chiral preparative HPLC to afford (+)-2-((3,4-trans)-4-methyl-1-((5-(pyrrolidin-1-yl)pyrimidin-2-yl)methyl)pyrrolidin-3-yl)-7-(tetrahydro-2H-pyran-4-yl)imidazo[5,1-f][1,2,4]triazin-4(3H)-one (13 mg, 28%) as an off-white solid.

$^1$H-NMR (CDCl$_3$, 400 MHz): δ 8.10 (s, 2H), 7.80 (s, 1H), 4.16 (d, 1H), 4.08 (t, 2H), 3.71 (d, 1H), 3.60 (t, 2H), 3.46-3.44 (m, 2H), 3.31-3.29 (m, 4H), 3.14 (d, 1H), 2.80-2.79 (m, 1H), 2.56-2.54 (m, 1H), 2.46-2.44 (m, 1H), 2.20-2.18 (m, 1H), 2.10-2.08 (m, 1H), 2.05-2.04 (m, 1H), 2.02-1.99 (m, 4H), 1.92-1.89 (m, 2H), 1.22 (d, 3H); Mass (ESI): 465.5 [M$^+$+1]; LC-MS: 98.50%; 465.4 (M$^+$+1); (column; X-bridge C-18, (50×3.0 mm, 3.5 μm); RT 3.04 min. 5 mM NH$_4$OAc: ACN; 0.8 mL/min); UPLC (purity): 98.50%; (column: Acquity BEH C-18 (50×2.1 mm, 1.7μ); RT 1.47 min. ACN: 0.025% TFA (Aq); 0.5 mL/min.; Chiral HPLC: 96.68%, R$_t$=12.40 min (Chiralpak IA, 250×4.6 mm, 5 μm); mobile phase (A) 0.1% DEA in n-Hexane (B) CH$_2$Cl$_2$: MeOH (80:20) (A:B:80:20); flow Rate: 1.0 mL/min); Optical rotation [α]$_D^{20.02}$: +81.93° (c=0.25, CH$_2$Cl$_2$); TLC: 8% MeOH/CH$_2$Cl$_2$ (R$_f$: 0.4).

186. (+)-2-((3,4-trans)-1-((5-fluoro-4-morpholinopyrimidin-2-yl)methyl)-4-methylpyrrolidin-3-yl)-7-(tetrahydro-2H-pyran-4-yl)imidazo[5,1-f][1,2,4]triazin-4(3H)-one after completion of the reaction, the volatiles were removed in vacuo to obtain the crude. The crude was purified through silica gel column chromatography using 4% MeOH/CH$_2$Cl$_2$ to afford (+)-2-((3,4-trans)-1-((5-fluoro-4-morpholinopyrimidin-2-yl)methyl)-4-methylpyrrolidin-3-yl)-7-(tetrahydro-2H-pyran-4-yl)imidazo[5,1-f][1,2,4]triazin-4(3H)-one (50 mg, 51%) as white solid.

$^1$H-NMR (CDCl$_3$, 400 MHz): δ 8.20 (d, 1H), 7.80 (s, 1H), 4.12-4.07 (m, 2H), 3.96 (d, 1H), 3.81-3.79 (m, 8H), 3.61-3.59 (m, 3H), 3.47-3.45 (m, 2H), 3.20 (d, 1H), 2.80-2.79 (m, 1H), 2.60-2.58 (m, 1H), 2.46-2.44 (m, 1H), 2.15-2.09 (m, 3H), 1.91-1.89 (m, 2H), 1.22 (d, 3H); Mass (ESI): 499.4 [M$^+$+1]; LC-MS: 95.13%; 499.6 (M$^+$+1); (column; X-bridge C-18, (50×3.0 mm, 3.5 μm); RT 2.68 min. 0.05% TFA (aq.): ACN; 0.8 mL/min); HPLC (purity): 95.46%; (column: Eclipse XDB-C18 (150 mm×4.6 mm, 5.0μ); RT 8.61 min. ACN: 5 mM NH$_4$OAc; 1.0 mL/min.; Chiral HPLC: 95.08%, R$_t$=14.00 min (Chiralpak IA, 250×4.6 mm, 5 μm); mobile phase (A) 0.1% DEA in n-Hexane (B) CH$_2$Cl$_2$:MeOH (80:20) (A:B:80:20); flow Rate: 1.0 mL/min); Optical rotation [α]$_D^{20}$: +65.44° (c=0.25, CH$_2$Cl$_2$); TLC: 8% MeOH/CH$_2$Cl$_2$ (R$_f$: 0.5).

187. (+)-2-((3,4-trans)-1-((4-cyclopropylpyrimidin-2-yl)methyl)-4-methylpyrrolidin-3-yl)-7-(tetrahydro-2H-pyran-4-yl)imidazo[5,1-f][1,2,4]triazin-4(3H)-one

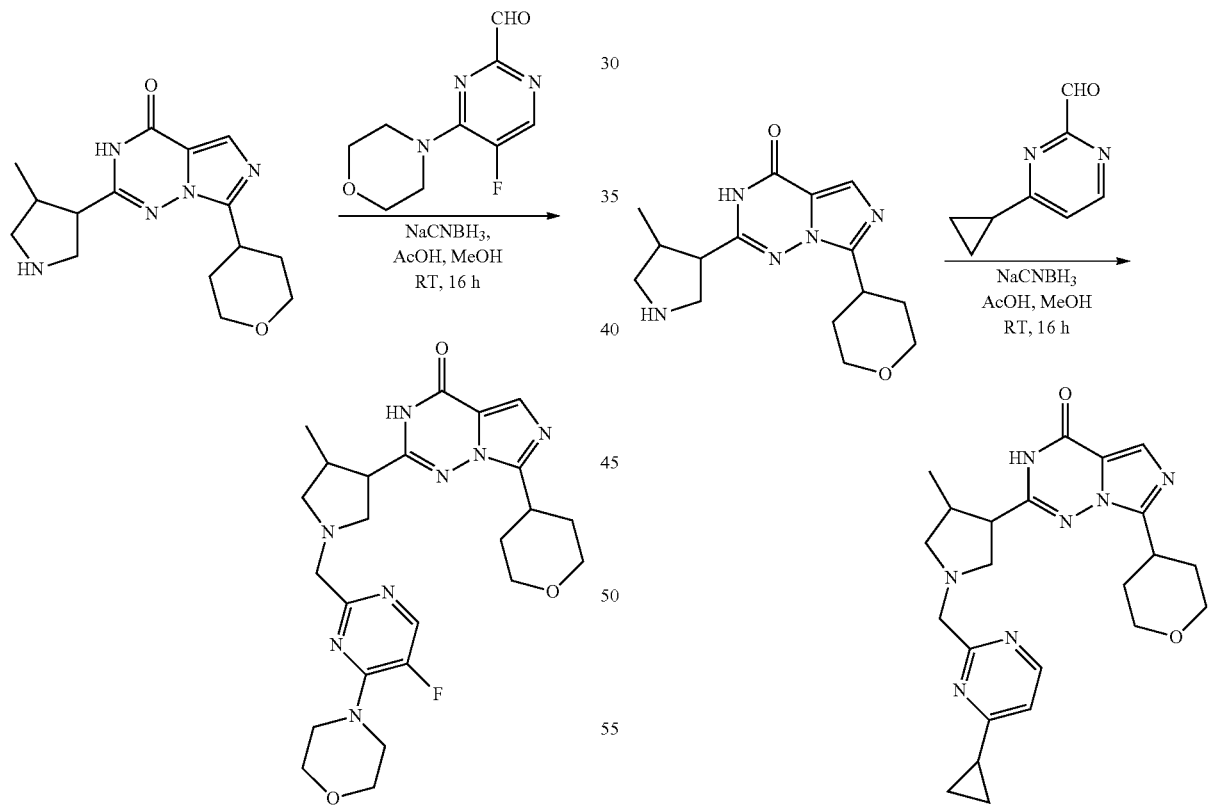

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (60 mg, 0.19 mmol) in MeOH (8 mL) under argon atmosphere was added 5-fluoro-4-morpholinopyrimidine-2-carbaldehyde (50 mg, 0.23 mmol) at room temperature and stirred for 2 h. To this were added 2 drops of AcOH, sodium cyanoborohydride (37 mg, 0.59 mmol) and stirred for 16 h. The reaction was monitored by TLC;

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (70 mg, 0.23 mmol) in MeOH (10 mL) under argon atmosphere was added 4-cyclopropylpyrimidine-2-carbaldehyde (41 mg, 0.27 mmol) at room temperature and stirred for 2 h. To this were added 3 drops of AcOH, sodium cyanoborohydride (43 mg, 0.69 mmol) and stirred for 16 h. The reaction was monitored by TLC; after completion of the reaction, the volatiles were removed in vacuo to obtain the crude. The crude was purified through silica gel column chromatography using 7% MeOH/CH$_2$Cl$_2$ to afford (+)-2-((3,4-trans)-1((4-cyclopropylpyrimidin-2-yl)methyl)-4-methylpyrrolidin-3-yl)-7-(tetrahydro-2H-pyran-4-yl)imidazo[5,1-f][1,2,4]triazin-4(3H)-one (30 mg, 30%) as pale yellow solid.

$^1$H-NMR (CDCl$_3$, 500 MHz): δ 8.62 (d, 1H), 7.90 (s, 1H), 6.98 (d, 1H), 4.16-4.08 (m, 3H), 3.78 (d, 1H), 3.61-3.59 (m, 2H), 3.44-3.40 (m, 2H), 3.16 (d, 1H), 2.91-2.90 (m, 1H), 2.60-2.58 (m, 1H), 2.46-2.44 (m, 1H), 2.20 (t, 1H), 2.10-2.08 (m, 3H), 1.98-1.95 (m, 2H), 1.22 (d, 3H), 1.12-1.08 (m, 4H); Mass (ESI): 436.4 [M$^+$+1]; LC-MS: 97.71%; 436.3 (M$^+$+1); (column; X-bridge C-18, (50×3.0 mm, 3.5 µm); RT 2.24 min. 0.05% TFA (aq.): ACN; 0.8 mL/min); UPLC (purity): 96.29%; (column: Acquity UPLC BEH C-18 (2.1× 50 mm, 1.7µ); RT 1.33 min. ACN: 0.025% TFA (Aq); 0.5 mL/min.; Chiral HPLC: 95.34%, R$_t$=20.22 min (Chiralpak IA, 250×4.6 mm, 5 µm); mobile phase (A) n-Hexane (B) CH$_2$Cl$_2$:MeOH (80:20) (A:B:85:15); flow Rate: 1.0 mL/min); Optical rotation [α]$_D^{20}$: +104.01° (c=0.25, CH$_2$Cl$_2$); TLC: 10% MeOH/CH$_2$Cl$_2$ (R$_f$: 0.4).

188. (+)-2-((3,4-trans)-4-methyl-1-((5-(methylthio) pyrimidin-2-yl)methyl)pyrrolidin-3-yl)-7-(tetrahydro-2H-pyran-4-yl)imidazo[5,1-f][1,2,4]triazin-4(3H)-one

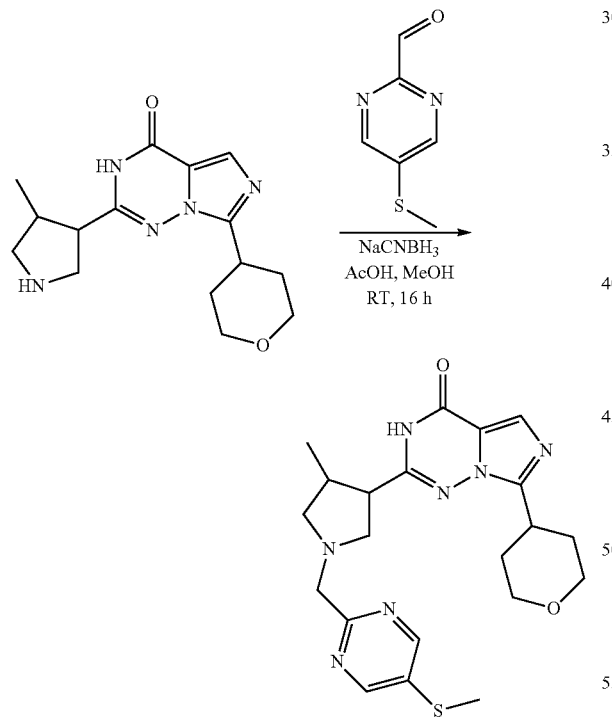

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (150 mg, 0.36 mmol) in MeOH (15 mL) under argon atmosphere were added 5-(methylthio) pyrimidine-2-carbaldehyde (150 mg) at RT and stirred for 2 h. To this were added 5 drops of acetic acid, sodium cyanoborohydride (93 mg, 1.48 mmol) and stirred for 16 h. The reaction was monitored by TLC; after completion of the reaction, the volatiles were removed in vacuo. The residue was quenched with ice cold water (20 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 3% MeOH/CH$_2$Cl$_2$ which was further purified through chiral preparative to afford (+)-2-((3,4-trans)-4-methyl-1-((5-(methylthio)pyrimidin-2-yl)methyl)pyrrolidin-3-yl)-7-(tetrahydro-2H-pyran-4-yl)imidazo[5,1-f][1,2,4]triazin-4(3H)-one (85 mg, 37%) as an off-white solid.

$^1$H-NMR (CD$_3$OD-d$_4$, 500 MHz): δ 8.78 (s, 2H), 7.78 (s, 1H), 4.50-4.36 (m, 2H), 4.12-4.06 (m, 2H), 3.66-3.58 (m, 5H), 3.10-3.04 (m, 2H), 2.78-2.68 (m, 2H), 2.60 (s, 3H), 2.10-2.04 (m, 2H), 1.96-1.92 (m, 2H), 1.26 (d, 3H); Mass (ESI): 442.2 [M$^+$+1]; LC-MS: 97.24%; 442.2 (M$^+$+1); (column; X-bridge C-18, (50×3.0 mm, 3.5µ); RT 2.14 min. 0.05% TFA (aq.): ACN; 0.8 mL/min); UPLC (purity): 97.40%; (column; Acquity UPLC BE-C18, (2.1×50 mm, 1.7µ); RT 1.29 min. ACN: 0.025% TFA (Aq); 0.5 mL/min.; Chiral HPLC: 97.86%, R$_t$=5.50 min (Chiralpak IA, 250×4.6 mm, 5µ; mobile phase (A) 0.1% DEA in n-Hexane (B) CH$_2$Cl$_2$:MeOH (80:20) (A:B:65:35); flow Rate: 1.0 mL/min); Optical rotation [α]$_D^{20}$: +78.67° (c=0.25% in CH$_2$Cl$_2$); TLC: 7% MeOH/CH$_2$Cl$_2$ (R$_f$: 0.4).

189. (+)-2-((3,4-trans)-4-methyl-1-((5-(trifluoromethyl)pyrimidin-2-yl)methyl)pyrrolidin-3-yl)-7-(tetrahydro-2H-pyran-4-yl)imidazo[5,1-f][1,2,4]triazin-4(3H)-one

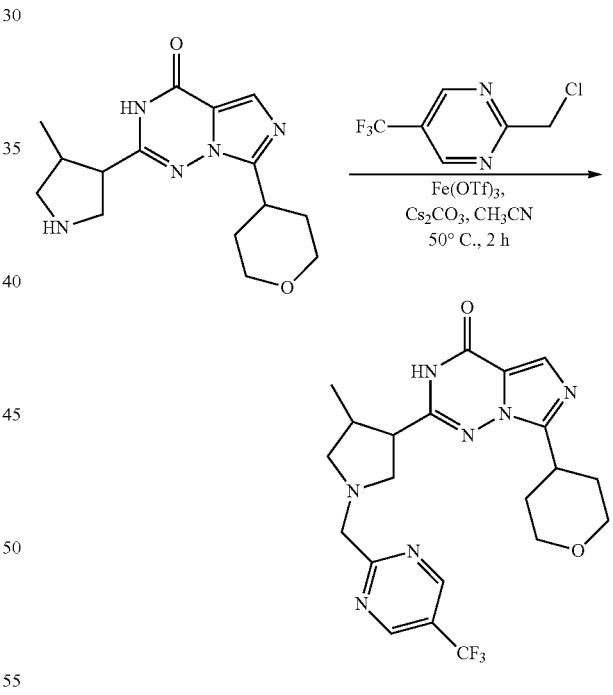

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (110 mg, 0.36 mmol) in CH$_3$CN (5 mL) under argon atmosphere were added 2-(chloromethyl)-5-(trifluoromethyl)pyrimidine (70 mg, 0.36 mmol), iron triflate (36 mg, 0.07 mmol) and cesium carbonate (236 mg, 0.72 mmol) at RT; heated to 50° C. and stirred for 2 h. The reaction was monitored by TLC; after completion of the reaction, the volatiles were removed in vacuo to obtain the crude. The crude was purified through silica gel column chromatography using 3-5% MeOH/CH$_2$Cl$_2$ which was further purified through chiral preparative HPLC to afford (+)-2-((3,4-trans)-4-methyl-1-((5-(trifluoromethyl)pyrimidin-2-yl)methyl)pyrrolidin-3-yl)-7-(tetrahydro-2H-pyran-4-yl)imidazo[5,1-f][1,2,4]triazin-4(3H)-one (75 mg, 45%) as an off-white solid.

$^1$H-NMR (CD$_3$OD-d$_4$, 500 MHz): δ 9.18 (s, 2H), 7.74 (s, 1H), 4.26 (d, 1H), 4.06-4.00 (m, 3H), 3.62-3.56 (m, 3H), 3.38 (t, 1H), 3.26-3.24 (m, 1H), 2.91-2.89 (m, 2H), 2.62-2.60 (m, 1H), 2.40 (t, 1H), 2.06-2.00 (m, 2H), 1.94-1.88 (m, 2H), 1.20 (d, 3H); Mass (ESI): 464.3 [M$^+$+1]; LC-MS: 98.85%; 464.4 (M$^+$+1); (column; X-bridge C-18, (50×3.0 mm, 3.5μ); RT 3.17 min. 5 mM NH$_4$OAc: ACN; 0.8 mL/min); UPLC (purity): 97.78%; (column; Acquity UPLC BEH C-18, (2.1×50 mm, 1.7μ); RT 1.36 min. ACN: 0.025% TFA (Aq); 0.5 mL/min.; Chiral HPLC: 99.83%, R$_t$=14.98 min (Chiralpak IA, 250×4.6 mm, 5μ; mobile phase (A) 0.1% DEA in n-Hexane (B) CH$_2$Cl$_2$:MeOH (80:20) (A:B:85:15); flow Rate: 1.0 mL/min); Optical rotation [α]$_D^{20.01}$: +87.80° (c=0.25% in CH$_2$Cl$_2$); TLC: 10% MeOH/CH$_2$Cl$_2$ (R$_f$: 0.6).

190. (+)-2-((3,4-trans)-1-((4,6-bis(trifluoromethyl)pyrimidin-2-yl)methyl)-4-methylpyrrolidin-3-yl)-7-(tetrahydro-2H-pyran-4-yl)imidazo[5,1-f][1,2,4]triazin-4(3H)-one

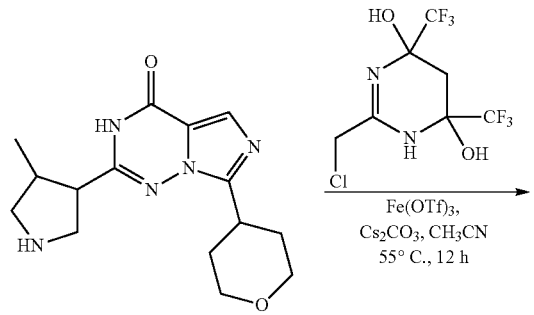

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (40 mg, 0.13 mmol) in CH$_3$CN (2 mL) under argon atmosphere were added iron triflate (6.64 mg, 0.013 mmol), cesium carbonate (85.8 mg, 0.26 mmol) and 2-(chloromethyl)-4,6-bis(trifluoromethyl)-1,4,5,6-tetrahydropyrimidine-4,6-diol (39.6 mg, 0.13 mmol) at RT; heated to 55° C. and stirred for 12 h. The reaction was monitored by TLC; after completion of the reaction, the reaction mixture was diluted with water (10 mL) and extracted with CH$_2$Cl$_2$ (2×15 mL). The combined organic extracts were dried over sodium sulfate, filtered and concentrated in vacuo to obtain the crude. The crude was purified through silica gel column chromatography using 3-5% MeOH/CH$_2$Cl$_2$ to afford (+)-2-((3,4-trans)-1-((4,6-bis(trifluoromethyl)pyrimidin-2-yl)methyl)-4-methylpyrrolidin-3-yl)-7-(tetrahydro-2H-pyran-4-yl)imidazo[5,1-f][1,2,4]triazin-4(3H)-one (10 mg, 14%) as an off-white solid.

$^1$H-NMR (CD$_3$OD-d$_4$, 400 MHz): δ 8.22 (s, 1H), 7.72 (s, 1H), 4.34 (d, 1H), 4.20 (d, 1H), 4.06-4.04 (m, 2H), 3.60-3.56 (m, 3H), 3.40-3.37 (m, 2H), 3.12 (t, 1H), 2.98-2.96 (m, 1H), 2.71-2.69 (m, 1H), 2.40 (t, 1H), 2.08-2.02 (m, 2H), 1.91-1.88 (m, 2H), 1.22 (d, 3H); Mass: m/z 532.4 [M+1]$^+$; LC-MS: 99.49%; 532.3 (M$^+$+1); (column: X-Bridge C-18, 50×3.0 mm, 3.5 μm); RT 2.54 min. 0.05% TFA (aq.): ACN; 0.8 mL/min); UPLC (purity): 98.51%; (column: Acquity UPLC BEH-C18 (50×2.1 mm, 1.7μ); RT 1.57 min. ACN: 0.025% TFA (Aq); 0.5 mL/min.; Chiral HPLC: 98.72%, R$_t$=10.40 min (Chiralpak IA, 250×4.6 mm, 5 μm); mobile phase (A) 0.1% DEA in n-Hexane (B) CH$_2$Cl$_2$:MeOH (80:20) (A:B:85:15); flow Rate: 1.0 mL/min); Optical rotation [α]$_D^{20}$: 32.11° (c=0.25, CH$_2$Cl$_2$); TLC: 5% MeOH/CH$_2$Cl$_2$ (R$_f$: 0.4).

191. (+)-2-((3,4-trans)-1-benzyl-4-methylpyrrolidin-3-yl)-7-(4-fluorophenyl)imidazo[5,1-f][1,2,4]triazin-4(3H)-one

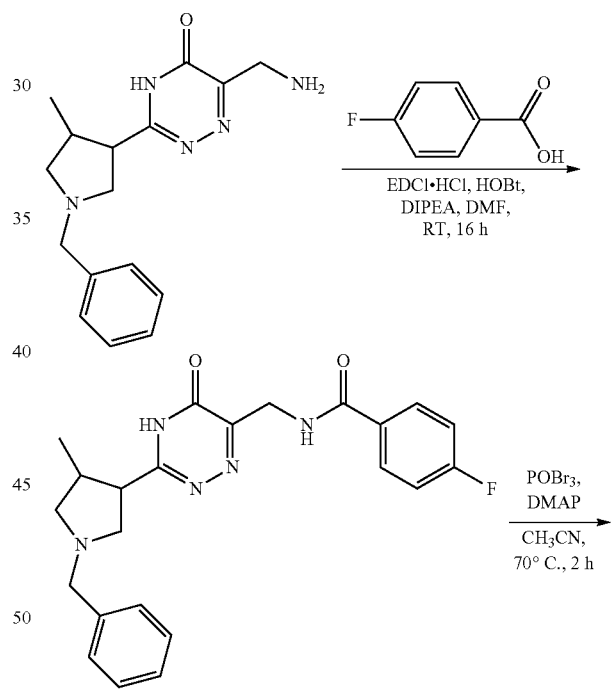

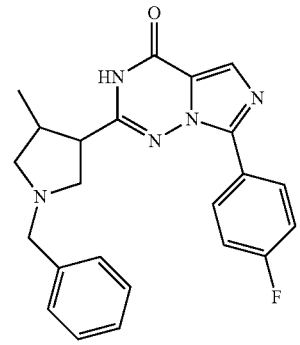

Synthesis of N-((3-((3,4-trans)-1-benzyl-4-methyl-pyrrolidin-3-yl)-5-oxo-4,5-dihydro-1,2,4-triazin-6-yl)methyl)-4-fluorobenzamide

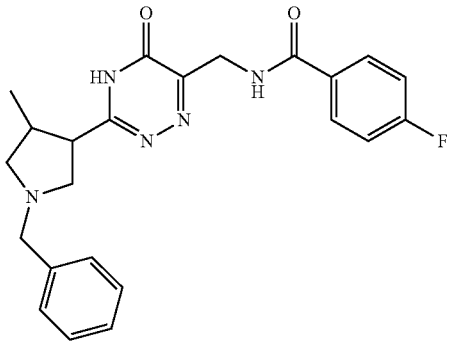 [SMILES: CC1CN(Cc2ccccc2)CC1c1nnc(CNC(=O)c2ccc(F)cc2)c(=O)[nH]1]

To a stirred solution of (+)-6-(aminomethyl)-3-((3,4-trans)-1-benzyl-4-methylpyrrolidin-3-yl)-1,2,4-triazin-5 (4H)-one (750 mg, 2.50 mmol) in DMF (7.5 mL) under argon atmosphere were added 4-fluoro benzoic acid (351 mg, 2.50 mmol), HOBt (508 mg, 3.76 mmol), EDCI. HCl (718 mg, 3.76 mmol) and N,N-diisopropyl ethyl amine (790 mg, 6.25 mmol) at RT and stirred for 16 h. The reaction was monitored by TLC; the reaction mass was diluted with water (100 mL) and extracted with $CH_2Cl_2$ (3×100 mL). The combined organic extracts were dried over sodium sulphate, filtered and concentrated in vacuo to obtain the crude. The crude was purified through silica gel column chromatography using 5% MeOH/$CH_2Cl_2$ to afford N-((3-((3,4-trans)-1-benzyl-4-methylpyrrolidin-3-yl)-5-oxo-4,5-dihydro-1,2,4-triazin-6-yl)methyl)-4-fluorobenzamide (620 mg, 58%) as yellow solid.

$^1$H-NMR ($CDCl_3$, 400 MHz): δ 7.88-7.84 (m, 2H), 7.38-7.32 (m, 5H), 7.12 (t, 2H), 4.70 (t, 2H), 3.84-3.76 (m, 2H), 3.42-3.38 (m, 1H), 3.15-3.10 (m, 1H), 2.91-2.78 (m, 1H), 2.71-2.69 (m, 1H), 2.48-2.46 (m, 1H), 2.10-2.06 (m, 1H), 1.16 (d, 3H); LC-MS: 94.36%; 422 ($M^+$+1); (column; X-Bridge C-18, 50×3.0 mm, 3.5 μm); RT 2.55 min. 0.05% TFA (Aq): ACN; 0.8 mL/min); UPLC (purity): 94.57%; (column: Acquity BEH C-18, 50×2.1 mm, 1.7μ); RT 1.58 min. ACN: 0.025% TFA (Aq); 0.5 mL/min. (IP12060692).

Synthesis of (+)-2-((3,4-trans)-1-benzyl-4-methyl-pyrrolidin-3-yl)-7-(4-fluorophenyl)imidazo[5,1-f][1,2,4]triazin-4(3H)-one

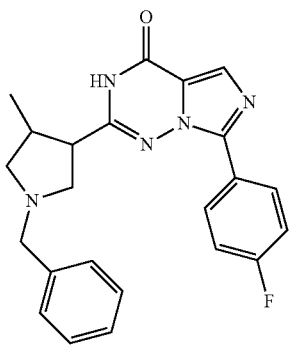 [SMILES: CC1CN(Cc2ccccc2)CC1c1nn2c(-c3ccc(F)cc3)ncc2c(=O)[nH]1]

To a stirred solution of N-((3-((3,4-trans)-1-benzyl-4-methylpyrrolidin-3-yl)-5-oxo-4,5-dihydro-1,2,4-triazin-6-yl)methyl)-4-fluorobenzamide (810 mg, 1.92 mmol) in $CHCl_3$ (24 mL) under argon atmosphere were added phosphoryl tribromide (1.65 g, 5.70 mmol) and N,N-dimethyl amino pyridine (24 mg, 0.19 mmol) at 0° C.; heated to 65-70° C. and stirred for 2 h. The reaction was monitored by TLC; the reaction mass was quenched with water (10 mL); saturated $NaHCO_3$ solution (40 mL) and extracted with $CH_2Cl_2$ (2×70 mL). The combined organic extracts were dried over sodium sulphate, filtered and concentrated in vacuo to obtain the crude. The crude was purified through silica gel column chromatography using 3% MeOH/$CH_2Cl_2$ to afford (+)-2-((3,4-trans)-1-benzyl-4-methylpyrrolidin-3-yl)-7-(4-fluorophenyl)imidazo[5,1-f][1,2,4]triazin-4(3H)-one (310 mg, 40%) as an off-white solid.

$^1$H-NMR (DMSO-$d_6$, 400 MHz): δ 8.40 (d, 2H), 7.88 (s, 1H), 7.42-7.30 (m, 7H), 3.68 (s, 2H), 3.00 (t, 1H), 2.90-2.86 (m, 3H), 2.70 (t, 1H), 2.30 (t, 1H), 1.10 (d, 3H); Mass (ESI): 404.3 [$M^+$+1]; LC-MS: 97.72%; 404.3 ($M^+$+1); (column; Eclipse XDB C-18, 150×4.6 mm, 5.0 μm); RT 2.59 min. 0.05% TFA (Aq): ACN; 1.0 mL/min); UPLC (purity): 97.64%; (column: Acquity BEH C-18, 50×2.1 mm, 1.7μ); RT 1.80 min. ACN: 0.025% TFA (Aq); 0.5 mL/min.; Chiral HPLC: 98.69%, $R_t$=7.55 min (Chiralpak IA, 250×4.6 mm, 5 μm); mobile phase (A) 0.1% DEA in n-Hexane (B) $CH_2Cl_2$: MeOH (80:20) (A:B:80:20); flow Rate: 1.0 mL/min); Optical rotation $[α]_D^{20}$: +39.29° (c=0.25, $CH_2Cl_2$); TLC: 10% MeOH/$CH_2Cl_2$ ($R_f$: 0.6).

192. (+)-2-((3,4-trans)-1-benzyl-4-methylpyrrolidin-3-yl)-7-(3-fluorophenyl)imidazo[5,1-f][1,2,4]triazin-4(3H)-one

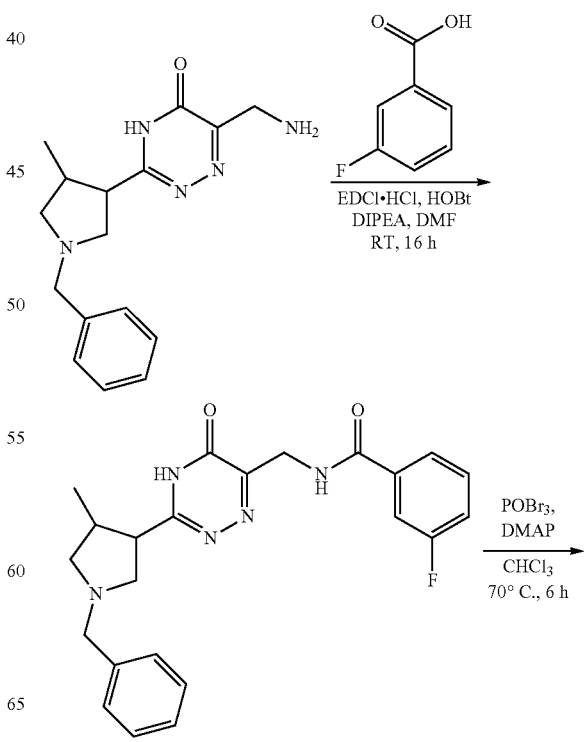

-continued

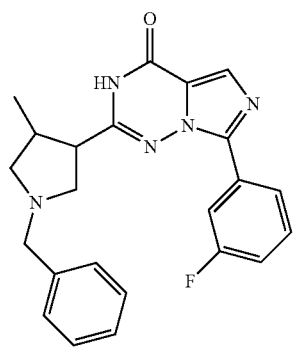

Synthesis of N-((3-((3,4-trans)-1-benzyl-4-methyl-pyrrolidin-3-yl)-5-oxo-4,5-dihydro-1,2,4-triazin-6-yl)methyl)-3-fluorobenzamide

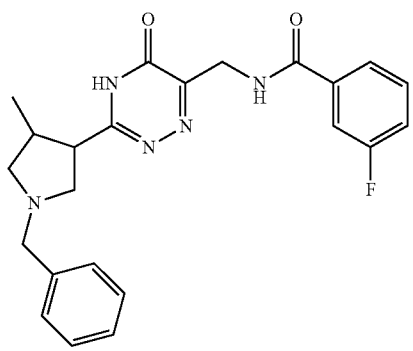 [SMILES: CC1CN(Cc2ccccc2)CC1c1nnc(CNC(=O)c2cccc(F)c2)c(=O)[nH]1]

To a stirred solution of (+)-6-(aminomethyl)-3-((3,4-trans)-1-benzyl-4-methylpyrrolidin-3-yl)-1,2,4-triazin-5(4H)-one (1 g, 3.34 mmol) in DMF (10 mL) under argon atmosphere were added EDCI.HCl (958 mg, 5.01 mmol), HOBt (677 mg, 5.01 mmol), diisopropyl ethyl amine (1.3 g, 10.00 mmol) and 3-fluorobenzoic acid (468 mg, 3.34 mmol) at room temperature and stirred for 16 h. The reaction was monitored by TLC; after completion of the reaction, the reaction mixture was diluted with ice water (50 mL) and extracted with CH$_2$Cl$_2$ (4×60 mL). The combined organic extracts were dried over sodium sulphate, filtered and concentrated in vacuo to obtain the crude. The crude was purified through silica gel column chromatography using 6-7% MeOH/CH$_2$Cl$_2$ to afford N-((3-((3,4-trans)-1-benzyl-4-methylpyrrolidin-3-yl)-5-oxo-4,5-dihydro-1,2,4-triazin-6-yl)methyl)-3-fluorobenzamide (800 mg, 57%) as an off-white solid.

$^1$H-NMR (DMSO-d$_6$, 400 MHz): δ 8.87 (t, 1H), 7.70 (d, 2H), 7.52 (q, 1H), 7.40-7.38 (m, 1H), 7.32-7.21 (m, 5H), 4.39-4.37 (m, 2H), 3.62-3.59 (m, 2H), 2.93-2.91 (m, 1H), 2.79-2.71 (m, 3H), 2.52-2.48 (m, 1H), 2.32-2.29 (m, 1H), 1.01 (d, 3H); LC-MS: 90.58%; 422 (M$^+$+1); (column: XBridge C-18, 50×3.0 mm, 3.5 μm); RT 2.45 min. 0.05% Aq TFA: ACN; 0.8 mL/min); UPLC (purity): 89.10%; (column: Acquity BEH C-18, (50×2.1 mm, 1.7μ); RT 1.58 min. ACN: 0.025% TFA (Aq); 0.5 mL/min.; TLC: 10% MeOH/CH$_2$Cl$_2$ (R$_f$: 0.5).

Synthesis of (+)-2-((3,4-trans)-1-benzyl-4-methyl-pyrrolidin-3-yl)-7-(3-fluorophenyl)imidazo[5,1-f][1,2,4]triazin-4 (3H)-one

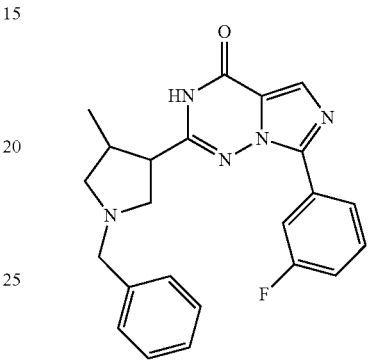

To a stirred solution of N-((3-((3,4-trans)-1-benzyl-4-methylpyrrolidin-3-yl)-5-oxo-4,5-dihydro-1,2,4-triazin-6-yl)methyl)-3-fluorobenzamide (500 mg, 1.18 mmol) in chloroform (30 mL) under argon atmosphere were added N,N-dimethyl amino pyridine (15 mg, 0.11 mmol) and phosphorus oxybromide (1 g, 3.56 mmol) at room temperature; heated to 65-70° C. and stirred for 6 h. The reaction was monitored by TLC; after completion of the reaction, the reaction mixture was diluted with water (10 mL), saturated sodium bicarbonate solution (20 mL) and extracted with CH$_2$Cl$_2$ (3×40 mL). The combined organic extracts were dried over sodium sulphate, filtered and concentrated in vacuo to obtain the crude. The crude was purified through silica gel column chromatography using 1-2% MeOH/CH$_2$Cl$_2$ to afford (+)-2-((3,4-trans)-1-benzyl-4-methylpyrrolidin-3-yl)-7-(3-fluorophenyl)imidazo[5,1-f][1,2,4]triazin-4 (3H)-one (200 mg, 43%) as an off-white solid.

$^1$H-NMR (CDCl$_3$, 400 MHz): δ 8.17-8.15 (m, 2H), 7.91 (s, 1H), 7.45-7.41 (m, 1H), 7.40-7.31 (m, 5H), 7.30-7.29 (m, 1H), 7.13-7.09 (m, 1H), 3.81 (d, 1H), 3.59 (d, 1H), 3.40 (t, 1H), 2.99 (d, 1H), 2.83-2.80 (m, 1H), 2.55-2.51 (m, 1H), 2.49-2.40 (m, 1H), 1.93 (t, 1H), 1.24 (d, 3H); Mass (ESI): 404.2 [M$^+$+1]; LC-MS: 95.16%; 404 (M$^+$+1); (column: X-bridge C-18, (50×3.0 mm, 3.5 μm); RT 2.80 min. 0.05% TFA in water:ACN; 0.8 mL/min); UPLC (purity): 94.67%; (column: Acquity BEH C-18 (50×2.1 mm, 1.7μ); RT 1.82 min. ACN: 0.025% TFA (Aq); 0.5 mL/min.; Chiral HPLC: 97.73%, R$_t$=7.02 min (Chiralpak IA, 250×4.6 mm, 5 μm); mobile phase (A) 0.1% TFA in n-Hexane (B) EtOH (A:B: 80:20); flow Rate: 1.0 mL/min); Optical rotation [α]$_D^{19.99}$: +32.97° (c=0.25, CH$_2$Cl$_2$); TLC: 5% MeOH/CH$_2$Cl$_2$ (R$_f$: 0.6).

193. (+)-2-((3,4-trans)-1-benzyl-4-methylpyrrolidin-3-yl)-7-(o-tolyl)imidazo[5,1-f][1,2,4]triazin-4(3H)-one

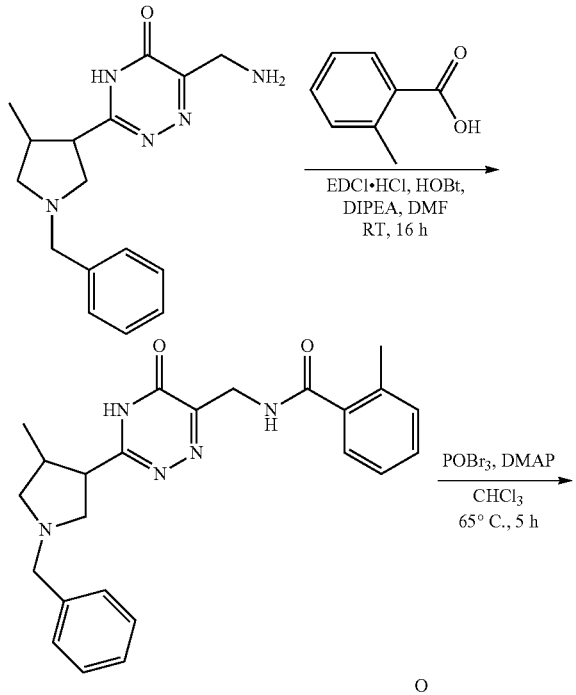

Synthesis of N-((3-((3,4-trans)-1-benzyl-4-methyl-pyrrolidin-3-yl)-5-oxo-4,5-dihydro-1,2,4-triazin-6-yl)methyl)-2-methylbenzamide

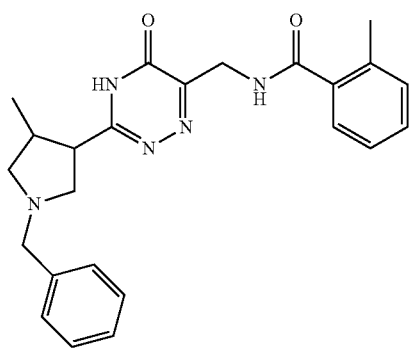

To a stirred solution of 2-methylbenzoic acid (500 mg, 3.34 mmol) in DMF (25 mL) under argon atmosphere were added EDCI.HCl (958 mg, 5.01 mmol), HOBt (677 mg, 5.01 mmol) and (+)-6-(aminomethyl)-3-((3,4-trans)-1-benzyl-4-methylpyrrolidin-3-yl)-1,2,4-triazin-5(4H)-one (1 g, 3.34 mmol) and DIPEA (1.29 g, 10.03 mmol) at 0-5° C.; warmed to RT and stirred for 16 h. The reaction was monitored by TLC; after completion of the reaction, the reaction mixture was diluted with water (25 mL) and extracted with EtOAc (2×25 mL). The combined organic extracts were dried over sodium sulfate, filtered and concentrated in vacuo to obtain the crude. The crude was purified through silica gel column chromatography using 10% MeOH/CH$_2$Cl$_2$ to afford N-((3-((3,4-trans)-1-benzyl-4-methylpyrrolidin-3-yl)-5-oxo-4,5-dihydro-1,2,4-triazin-6-yl)methyl)-2-methylbenzamide (1 g, 72%) as an off-white solid.

$^1$H-NMR (CDCl$_3$, 400 MHz): δ 7.42 (d, 1H), 7.41-7.30 (m, 6H), 7.22-7.13 (m, 3H), 6.85-6.82 (m, 1H), 4.64-4.62 (m, 2H), 3.75 (q, 2H), 3.37 (t, 1H), 3.10 (d, 1H), 2.87-2.84 (m, 1H), 2.67-2.65 (m, 2H), 2.40 (s, 3H), 2.02-2.00 (m, 1H), 1.02 (d, 3H); LC-MS: 91.50%; 418 (M$^+$+1); (column: X Bridge C-18, 50×3.0 mm, 3.5 µm); RT 2.42 min. 0.05% Aq TFA: ACN; 0.8 mL/min); UPLC (purity): 88.78%; (column: Acquity BEH C-18 (50×2.1 mm, 1.7µ); RT 1.56 min. ACN: 0.025% TFA (Aq); 0.5 mL/min. (IP12070215); TLC: 10% MeOH/CH$_2$Cl$_2$ (R$_f$: 0.6).

Synthesis of (+)-2-((3,4-trans)-1-benzyl-4-methyl-pyrrolidin-3-yl)-7-(o-tolyl)imidazo[5,1-f][1,2,4]triazin-4(3H)-one

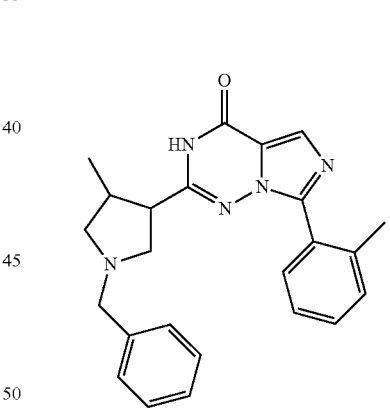

To a stirred solution of N-((3-((3,4-trans)-1-benzyl-4-methylpyrrolidin-3-yl)-5-oxo-4,5-dihydro-1,2,4-triazin-6-yl)methyl)-2-methylbenzamide (200 mg, 0.47 mmol) in CHCl$_3$ (12 mL) under argon atmosphere were added phosphoryl tribromide (412.5 mg, 1.43 mmol) and DMAP (5.84 mg, 0.04 mmol) at 0° C.; heated to 65° C. and stirred for 5 h. The reaction was monitored by TLC; after completion of the reaction, the reaction mass was quenched with ice cold water (10 mL); saturated NaHCO$_3$ solution (30 mL) and extracted with CH$_2$Cl$_2$ (2×45 mL). The combined organic extracts were dried over sodium sulphate, filtered and concentrated in vacuo to obtain the crude. The crude was purified through silica gel column chromatography using 5% MeOH/CH$_2$Cl$_2$ to afford (+)-2-((3,4-trans)-1-benzyl-4- methylpyrrolidin-3-yl)-7-(o-tolyl)imidazo[5,1-f][1,2,4]triazin-4(3H)-one (100 mg, 52%) as an off-white solid.

¹H-NMR (CDCl₃, 400 MHz): δ 8.00 (s, 1H), 7.52 (d, 1H), 7.46-7.42 (m, 5H), 7.30-7.28 (m, 3H), 3.80 (d, 1H), 3.55 (d, 1H), 3.40 (t, 1H), 2.98 (d, 1H), 2.68 (d, 1H), 2.46-2.44 (m, 2H), 2.30 (s, 3H), 1.90 (t, 1H), 1.12 (d, 3H); Mass (ESI): 400.3 [M⁺+1]; LC-MS: 96.63%; 400.4 (M⁺+1); (column; X-bridge C-18, 50×3.0 mm, 3.5 μm); RT 3.14 min. 0.05% TFA (Aq): ACN; 0.8 mL/min); UPLC (purity): 97.81%; (column: Acquity BEH C-18, 50×2.1 mm, 1.7 μm); RT 1.72 min. ACN: 0.025% TFA (Aq); 0.5 mL/min.; Chiral HPLC: 98.10%, R_t=8.06 min (Chiralpak IA, 250×4.6 mm, 5μ); mobile phase (A) 0.1% DEA in n-Hexane (B) CH₂Cl₂: MeOH (80:20) (A:B:85:15); flow Rate: 1.0 mL/min); Optical rotation [α]_D²⁰: +17.88° (c=0.25, CH₂Cl₂). TLC: 10% MeOH/CH₂Cl₂ (R_f: 0.6).

194. (+)-2-((3,4-trans)-1-benzyl-4-methylpyrrolidin-3-yl)-7-(4,5-difluoro-2-methylphenyl)imidazo[5,1-f][1,2,4]triazin-4(3H)-one

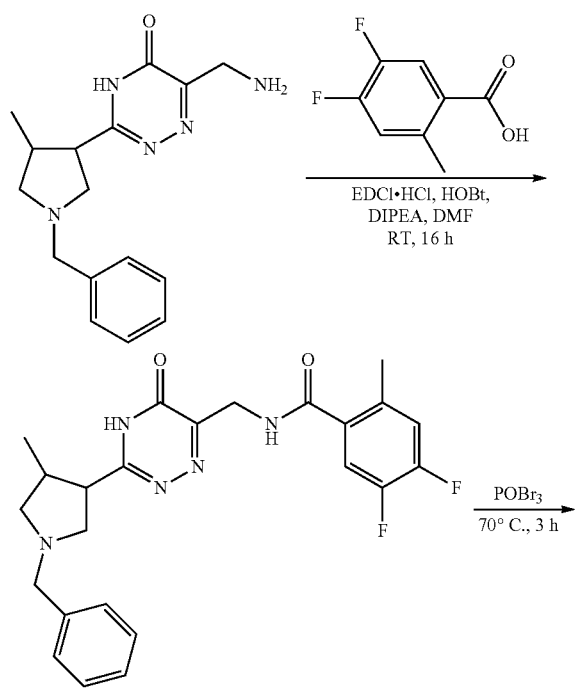

Synthesis of N-((3-((3,4-trans)-1-benzyl-4-methylpyrrolidin-3-yl)-5-oxo-4,5-dihydro-1,2,4-triazin-6-yl)methyl)-4,5-difluoro-2-methylbenzamide

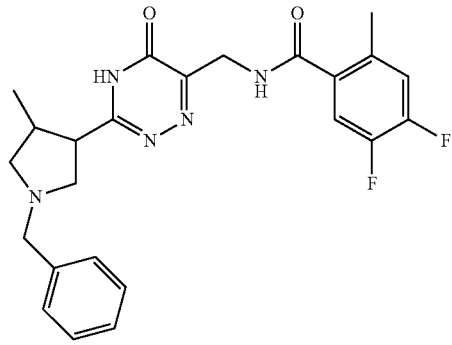 [SMILES: Cc1cc(F)c(F)cc1C(=O)NCc1nnc(C2CN(Cc3ccccc3)CC2C)[nH]c1=O]

To a stirred solution of 4,5-difluoro-2-methylbenzoic acid (632 mg, 3.67 mmol) in DMF (15 mL) under argon atmosphere were added HOBt (677 mg, 5.01 mmol), EDCI.HCl (958 mg, 5.01 mmol) and (+)-6-(aminomethyl)-3-((3,4-trans)-1-benzyl-4-methylpyrrolidin-3-yl)-1,2,4-triazin-5(4H)-one (1 g, 3.34 mmol) and DIPEA (862 mg, 6.68 mmol) at 0° C.; warmed to RT and stirred for 16 h. The reaction was monitored by TLC; after completion of the reaction, the reaction mixture was diluted with water (20 mL) and extracted with EtOAc (2×25 mL). The combined organic extracts were dried over sodium sulfate, filtered and concentrated in vacuo to obtain the crude. The crude was purified through silica gel column chromatography using 2-3% MeOH/CH₂Cl₂ to afford N-((3-((3,4-trans)-1-benzyl-4-methylpyrrolidin-3-yl)-5-oxo-4,5-dihydro-1,2,4-triazin-6-yl)methyl)-4,5-difluoro-2-methylbenzamide (750 mg, 50%) as an off-white solid.

¹H-NMR (DMSO-d₆, 400 MHz): δ 8.62-8.60 (m, 1H), 7.42-7.40 (m, 2H), 7.34-7.30 (m, 4H), 7.24-7.22 (m, 1H), 4.34 (s, 2H), 3.64-3.62 (m, 2H), 2.96-2.94 (m, 1H), 2.80-2.75 (m, 2H), 2.56-2.54 (m, 1H), 2.36-2.35 (m, 4H), 2.30-2.28 (m, 1H), 1.06 (d, 3H); LC-MS: 90.59%; 454 (M⁺+1); (column: X Bridge C-18, 50×3.0 mm, 3.5 μm); RT 3.02 min. 0.05% Aq TFA: ACN; 0.8 mL/min); TLC: 10% MeOH/CH₂Cl₂ (R_f: 0.5).

Synthesis of (+)-2-((3,4-trans)-1-benzyl-4-methylpyrrolidin-3-yl)-7-(4,5-difluoro-2-methylphenyl)imidazo[5,1-f][1,2,4]triazin-4(3H)-one

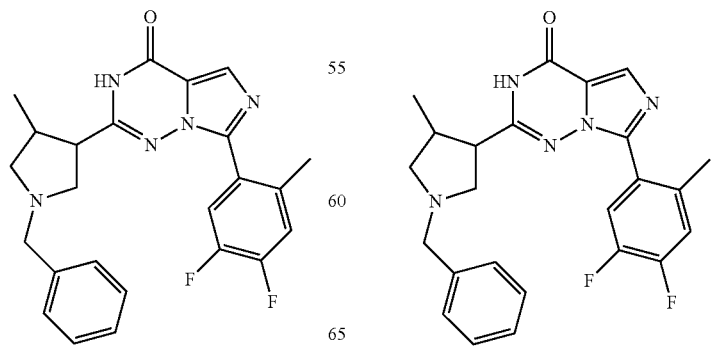

A stirred solution of N-((3-((3,4-trans)-1-benzyl-4-methylpyrrolidin-3-yl)-5-oxo-4,5-dihydro-1,2,4-triazin-6-yl)methyl)-4,5-difluoro-2-methylbenzamide (200 mg, 0.44 mmol) in phosphorous oxybromide (630 mg, 2.2 mmol) under argon atmosphere was heated to 70° C. and stirred for 3 h. The reaction was monitored by TLC; after completion of the reaction, the reaction mixture was diluted with ice cold water (5 mL), saturated NaHCO$_3$ solution (20 mL) and extracted with CH$_2$Cl$_2$ (2×25 mL). The combined organic extracts were dried over sodium sulfate, filtered and concentrated in vacuo to obtain the crude. The crude was purified through silica gel column chromatography using 2-3% MeOH/CH$_2$Cl$_2$ to afford (+)-2-((3,4-trans)-1-benzyl-4-methylpyrrolidin-3-yl)-7-(4,5-difluoro-2-methylphenyl)imidazo[5,1-f][1,2,4]triazin-4(3H)-one (120 mg, 63%) as pale yellow solid.

$^1$H-NMR (DMSO-d$_6$, 400 MHz): δ 7.90 (s, 1H), 7.68 (t, 1H), 7.50 (t, 1H), 7.30-7.20 (m, 5H), 3.60 (q, 2H), 2.92 (t, 1H), 2.80-2.68 (m, 3H), 2.58-2.56 (m, 1H), 2.34 (s, 3H), 2.24 (t, 1H), 1.08 (d, 3H); Mass (ESI): 436.4 [M$^+$+1]; LC-MS: 96.91%; 436 (M$^+$+1); (column; X-bridge C-18, (50×3.0 mm, 3.5 μm); RT 2.93 min. 0.05% TFA (Aq): ACN; 0.8 mL/min); UPLC (purity): 99.18%; (column: Acquity BEH C-18 (50×2.1 mm, 1.7 μm); RT 1.88 min. ACN: 0.025% TFA (Aq); 0.5 mL/min.; Chiral HPLC: 95.10%, R$_t$=6.65 min (Chiralpak IA, 250×4.6 mm, 5 μm); mobile phase (A) 0.1% DEA in n-Hexane (B) CH$_2$Cl$_2$:MeOH (80:20) (A:B:80:20); flow Rate: 1.0 mL/min); Optical rotation [α]$_D^{19.99}$: +20.48° (c=0.25, CH$_2$Cl$_2$); TLC: 5% MeOH/CH$_2$Cl$_2$ (R$_f$: 0.5).

195. (+)-2-((3,4-trans)-1-benzyl-4-methylpyrrolidin-3-yl)-7-phenylimidazo[5,1-f][1,2,4]triazin-4(3H)-one

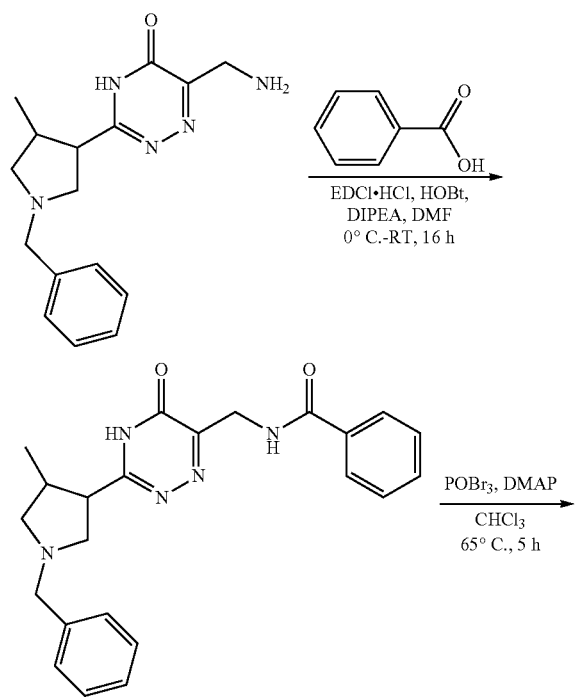

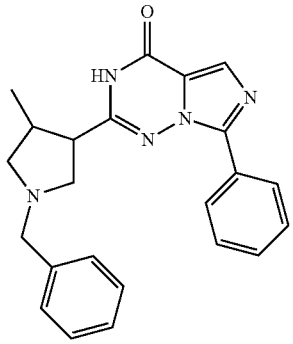

Synthesis of N-((3-((3,4-trans)-1-benzyl-4-methylpyrrolidin-3-yl)-5-oxo-4,5-dihydro-1,2,4-triazin-6-yl)methyl)benzamide

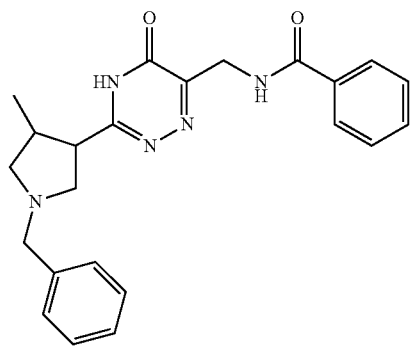 [SMILES: CC1CN(Cc2ccccc2)CC1c1nnc(CNC(=O)c2ccccc2)c(=O)[nH]1]

To a stirred solution of (+)-6-(aminomethyl)-3-((3,4-trans)-1-benzyl-4-methylpyrrolidin-3-yl)-1,2,4-triazin-5(4H)-one (250 mg, 0.83 mmol) in DMF (3 mL) under argon atmosphere were added benzoic acid (112 mg, 0.91 mmol), HOBt (170 mg, 1.25 mmol), EDCI.HCl (240 mg, 1.25 mmol), and diisopropyl ethyl amine (0.3 mL, 1.67 mmol) at 0° C.; warmed to room temperature and stirred for 16 h. The reaction was monitored by TLC; after completion of the reaction, the reaction mixture was diluted with water (15 mL) and extracted with CH$_2$Cl$_2$ (2×15 mL). The combined organic extracts were dried over sodium sulphate, filtered and concentrated in vacuo to obtain the crude. The crude was purified through silica gel column chromatography using 5% MeOH/CH$_2$Cl$_2$ to afford N-((3-((3,4-trans)-1-benzyl-4-methylpyrrolidin-3-yl)-5-oxo-4,5-dihydro-1,2,4-triazin-6-yl)methyl)benzamide (210 mg, 62%) as pale yellow solid.

$^1$H-NMR (CDCl$_3$, 400 MHz): δ 7.81 (d, 2H), 7.74 (d, 2H), 7.61-7.30 (m, 6H), 4.71-4.69 (m, 2H), 4.03-4.01 (m, 2H), 3.49-3.47 (m, 1H), 3.39-3.36 (m, 1H), 3.22-3.10 (m, 2H), 2.64-2.59 (m, 1H), 2.54-2.49 (m, 1H), 1.15 (d, 3H). LC-MS: 50.61%; 404 (M$^+$+1); (column: X-Bridge C-18, 50×3.0 mm, 3.5 μm); RT 2.33 min. 0.05% TFA (aq.): ACN; 0.8 mL/min); UPLC (purity): 56.28%; (column: Acquity BEH C-18 (50×2.1 mm, 1.7μ); RT 1.52 min. ACN: 0.025% TFA (Aq); 0.5 mL/min. (IP12050206); TLC: 10% MeOH/CH$_2$Cl$_2$ (R$_f$: 0.4).

677

Synthesis of (+)-2-((3,4-trans)-1-benzyl-4-methyl-pyrrolidin-3-yl)-7-phenylimidazo[5,1-f][1,2,4]triazin-4(3H)-one

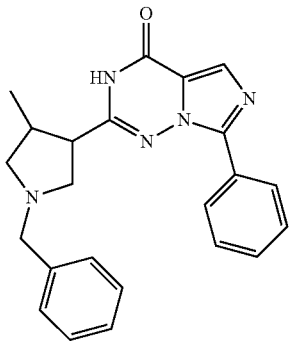 [SMILES: CC1CN(Cc2ccccc2)CC1c1nn2c(-c3ccccc3)ncc2c(=O)[nH]1]

To a stirred solution of N-((3-((3,4-trans)-1-benzyl-4-methylpyrrolidin-3-yl)-5-oxo-4,5-dihydro-1,2,4-triazin-6-yl)methyl)benzamide (450 mg, 1.11 mmol) in CHCl₃ (30 mL) were added DMAP (15.5 mg, 0.11 mmol) and phosphoryl oxybromide (958 mg, 3.34 mmol) at 0° C. and stirred for 5 min under argon atmosphere. The reaction mass was heated to 65° C. and stirred for 5 h. The reaction was monitored by TLC; the reaction mass was quenched with ice cold water (5 ml) NaHCO₃ solution (30 mL) and extracted with CH₂Cl₂ (2×50 mL). The combined organic extracts were dried over sodium sulphate, filtered and concentrated in vacuo to obtain the crude. The crude material was purified by silica gel column chromatography to afford (+)-2-((3,4-trans)-1-benzyl-4-methylpyrrolidin-3-yl)-7-phenylimidazo[5,1-f][1,2,4]triazin-4(3H)-one (180 mg, 42%) as an off-white solid.

¹H-NMR (CDCl₃, 400 MHz): δ 8.32 (d, 2H), 7.96 (s, 1H), 7.50-7.30 (m, 8H), 3.82 (d, 1H), 3.60 (d, 1H), 3.40 (t, 1H), 3.06 (d, 1H), 2.82-2.80 (m, 1H), 2.56-2.44 (m, 2H), 1.94 (t, 1H), 1.22 (d, 3H). Mass (ESI): 386.2 [M⁺+1]; LC-MS: 94.99%; 386 (M⁺+1); (column; X-bridge C-18, 50×3.0 mm, 3.5 μm); RT 2.70 min. 0.05% TFA (aq.): ACN; 0.8 mL/min); UPLC (purity): 95.74%; (column: Acquity BEH C-18; 50×2.1 mm, 1.7μ); RT 1.72 min. ACN: 0.025% TFA (Aq); 0.5 mL/min.; Chiral HPLC: 94.10%, $R_t$=7.23 min (Chiralpak IA, 250×4.6 mm, 5 μm); mobile phase (A) 0.1% DEA in n-Hexane (B) DCM:MeOH (80:20) (A:B:80:20); flow Rate: 1.0 mL/min); Optical rotation $[α]_D^{19.99}$: +38.80° (c=0.25, DCM). TLC: 10% MeOH/DCM ($R_f$: 0.7).

196. (+)-2-((3,4-trans)-1-benzyl-4-methylpyrrolidin-3-yl)-7-(4-methylpyridin-3-yl)imidazo[5,1-f][1,2,4]triazin-4(3H)-one

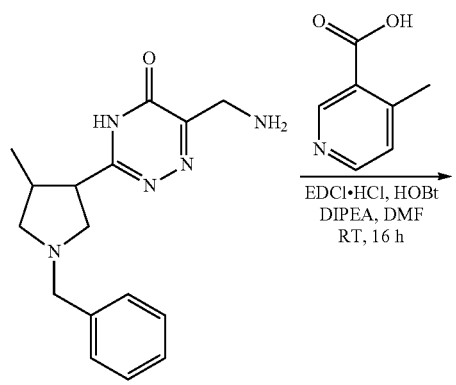

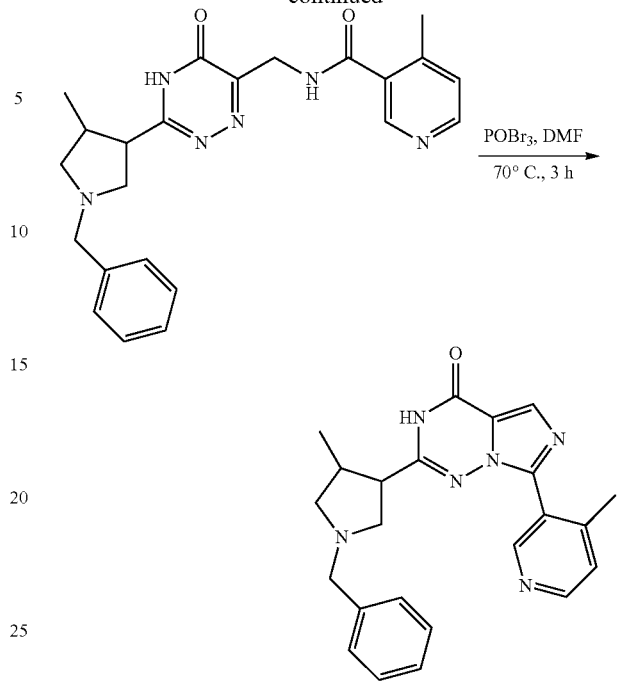

Synthesis of N-((3-((3,4-trans)-1-benzyl-4-methyl-pyrrolidin-3-yl)-5-oxo-4,5-dihydro-1,2,4-triazin-6-yl)methyl)-4-methylnicotinamide

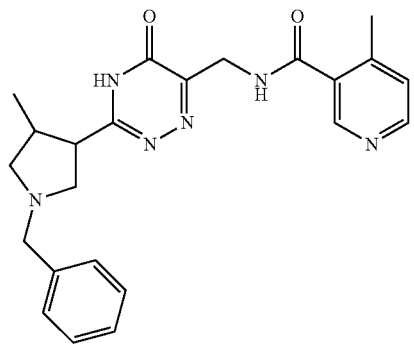 [SMILES: Cc1ccncc1C(=O)NCc1nnc(C2CN(Cc3ccccc3)CC2C)[nH]c1=O]

To a stirred solution of (+)-6-(aminomethyl)-3-((3,4-trans)-1-benzyl-4-methylpyrrolidin-3-yl)-1,2,4-triazin-5(4H)-one (75 mg, 0.25 mmol) in DMF (1.5 mL) under argon atmosphere were added EDCI.HCl (72 mg, 0.37 mmol), HOBt (34 mg, 0.25 mmol), diisopropyl ethyl amine (0.09 mL, 0.50 mmol) and 4-methylnicotinic acid (38 mg, 0.27 mmol) at room temperature and stirred for 16 h. The reaction was monitored by TLC; after completion of the reaction, the reaction mixture was diluted with water (10 mL) and extracted with 5% MeOH:CH₂Cl₂ (2×20 mL). The combined organic extracts were dried over sodium sulphate, filtered and concentrated in vacuo to obtain the crude. The crude was purified through silica gel column chromatography using 10% MeOH/CH₂Cl₂ to afford N-((3-((3,4-trans)-1-benzyl-4-methylpyrrolidin-3-yl)-5-oxo-4,5-dihydro-1,2,4-triazin-6-yl)methyl)-4-methylnicotinamide (52 mg, 50%) as an off-white solid.

¹H-NMR (DMSO-d₆, 400 MHz): δ 8.86 (t, 1H), 8.54 (s, 1H), 8.46 (d, 1H), 7.34-7.24 (m, 6H), 4.36 (d, 2H), 3.61-3.60 (m, 2H), 2.96-2.94 (m, 1H), 2.80-2.74 (m, 3H), 2.56-2.54 (m, 1H), 2.40 (s, 3H), 2.34-2.32 (m, 1H), 1.04 (d, 3H); LC-MS: 96.01%; 419.6 (M⁺+1); (column: X-Bridge C-18, 50×3.0 mm, 3.5 µm); RT 3.30 min. 0.05% TFA: ACN; 0.8 mL/min); UPLC (purity): 93.86%; (column: Acquity UPLC HSS T3, (2.1×100 mm, 1.8µ); RT 2.99 min. ACN: 0.025% TFA (Aq); 0.3 mL/min. (IP12070082); TLC: 10% MeOH/ CH₂Cl₂ (R$_f$: 0.2).

Synthesis of (+)-2-((3,4-trans)-1-benzyl-4-methyl-pyrrolidin-3-yl)-7-(4-methylpyridin-3-yl)imidazo[5, 1-f][1,2,4]triazin-4(3H)-one

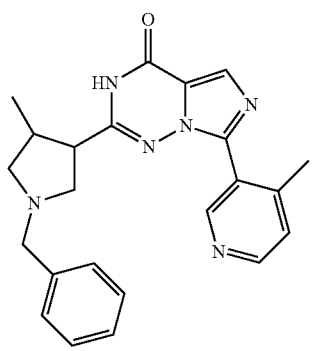

To a stirred solution of N-((3-((3,4-trans)-1-benzyl-4-methylpyrrolidin-3-yl)-5-oxo-4,5-dihydro-1,2,4-triazin-6-yl)methyl)-4-methylnicotinamide (40 mg, 0.09 mmol) in DMF (catalytic amount) under argon atmosphere was added phosphorous oxybromide (280 mg, 0.98 mmol) at room temperature; heated to 70° C. and stirred for 3 h. The reaction was monitored by TLC; after completion of the reaction, the reaction mass was quenched with ice cold water (5 ml), sodium bicarbonate solution (10 mL) and the compound was extracted with CH₂Cl₂ (2×20 mL). The combined organic extracts were dried over sodium sulfate, filtered and concentrated in vacuo to obtain the crude. The crude was purified through silica gel column chromatography using 5% MeOH/CH₂Cl₂ to afford (+)-2-((3,4-trans)-1-benzyl-4-methylpyrrolidin-3-yl)-7-(4-methylpyridin-3-yl)imidazo[5, 1-f][1,2,4]triazin-4(3H)-one (15 mg, 39%) as an off-white solid.

¹H-NMR (DMSO-d₆, 400 MHz): δ 8.76 (s, 1H), 8.56 (d, 1H), 7.98 (s, 1H), 7.42 (d, 1H), 7.32-7.20 (m, 5H), 3.62-3.58 (m, 2H), 2.94-2.72 (m, 4H), 2.61-2.59 (m, 1H), 2.40 (s, 3H), 2.31-2.29 (m, 1H), 1.04 (d, 3H); Mass (ESI): 402.1 [M⁺+2]; LC-MS: 94.49%; 401 (M⁺+1); (column; X-bridge C-18, 50×3.0 mm, 3.5 µm); RT 1.96 min. 0.05% TFA (Aq): ACN; 0.8 mL/min); UPLC (purity): 99.57%; (column: Acquity BEH C-18; 50×2.1 mm, 1.7 µm); RT 1.27 min. ACN: 0.025% TFA (Aq); 0.5 mL/min.; Chiral HPLC: 94.39%, R$_t$=8.05 min (Chiralpak IA, 250×4.6 mm, 5 µm); mobile phase (A) 0.1% DEA in n-Hexane (B) CH₂Cl₂:MeOH (80:20) (A:B: 80:20); flow Rate: 1.0 mL/min); Optical rotation [α]$_D$²⁰: +24.35° (c=0.25, CH₂Cl₂); TLC: 10% MeOH/CH₂Cl₂ (R$_f$: 0.3).

197. (+)-2-((3,4-trans)-1-benzyl-4-methylpyrrolidin-3-yl)-7-cyclopentylimidazo[5,1-f][1,2,4]triazin-4(3H)-one

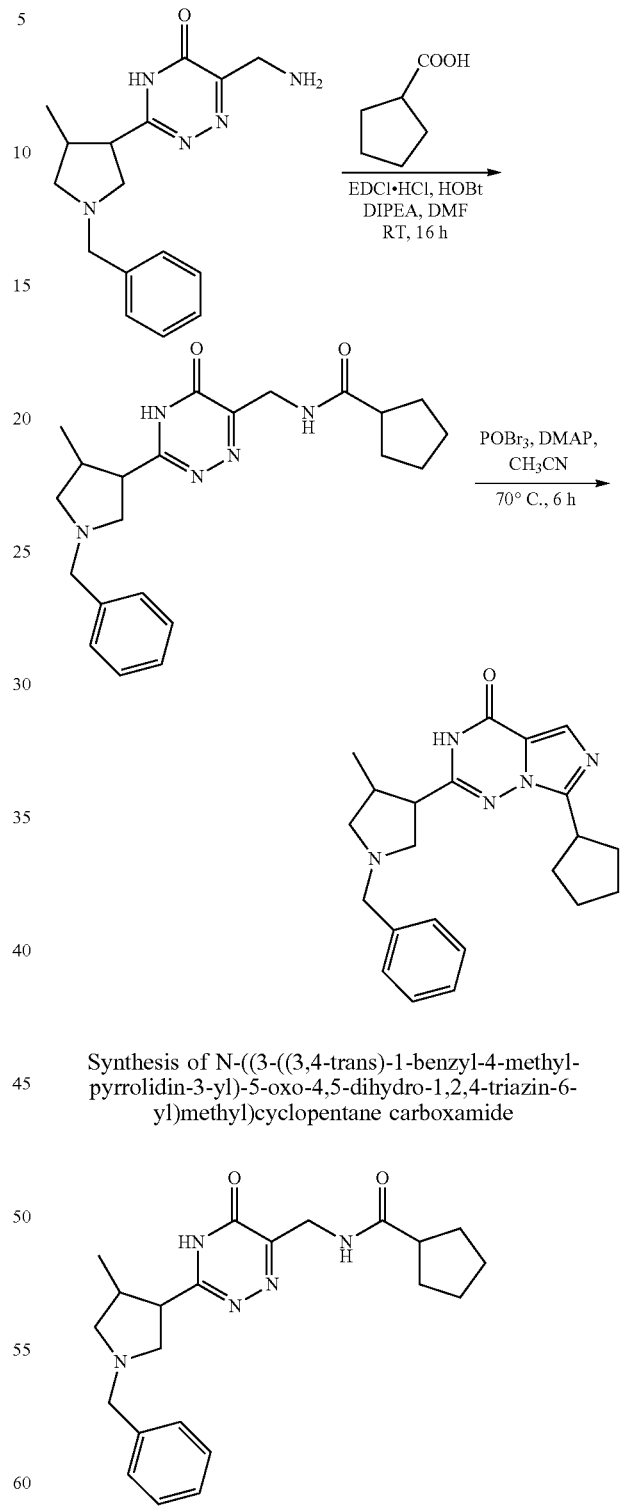

Synthesis of N-((3-((3,4-trans)-1-benzyl-4-methyl-pyrrolidin-3-yl)-5-oxo-4,5-dihydro-1,2,4-triazin-6-yl)methyl)cyclopentane carboxamide To a stirred solution of cyclopentane carboxylic acid (200 mg, 1.75 mmol) in DMF (7 mL) under argon atmosphere were added EDCI.HCl (502 mg, 2.63 mmol), HOBt (355 mg, 2.63 mmol), (+)-6-(aminomethyl)-3-((3,4-trans)-1-benzyl-4-methylpyrrolidin-3-yl)-1,2,4-triazin-5(4H)-one (524 mg, 1.75 mmol) and diisopropyl ethyl amine (0.64 mL, 3.50 mmol) at 0° C.; warmed to room temperature and stirred for 16 h. The reaction was monitored by TLC; after completion of the reaction, the reaction mixture was diluted with water (25 mL) and extracted with CH$_2$Cl$_2$ (2×35 mL). The combined organic extracts were dried over sodium sulphate, filtered and concentrated in vacuo to obtain the crude. The crude was purified through silica gel column chromatography using 2-3% MeOH/CH$_2$Cl$_2$ to afford N-((3-((3,4-trans)-1-benzyl-4-methylpyrrolidin-3-yl)-5-oxo-4,5-dihydro-1,2,4-triazin-6-yl)methyl)cyclopentane carboxamide (450 mg, 65%) as an off-white solid.

$^1$H-NMR (DMSO-d$_6$, 400 MHz): δ 8.01-8.00 (m, 1H), 7.35-7.32 (m, 5H), 4.16 (d, 2H), 3.61-3.60 (m, 2H), 2.98-2.95 (m, 1H), 2.79-2.76 (m, 3H), 2.68-2.65 (m, 1H), 2.38-2.34 (m, 1H), 1.70-1.40 (m, 9H), 1.06 (d, 3H); LC-MS: 94.53%; 396 (M$^+$+1); (column: X-Bridge C-18, 50×3.0 mm, 3.5 μm); RT 2.33 min. 0.05% TFA (aq.): ACN; 0.8 mL/min); TLC: 10% MeOH/CH$_2$Cl$_2$ (R$_f$: 0.6).

Synthesis of (+)-2-((3,4-trans)-1-benzyl-4-methylpyrrolidin-3-yl)-7-cyclopentylimidazo[5,1-f][1,2,4]triazin-4(3H)-one

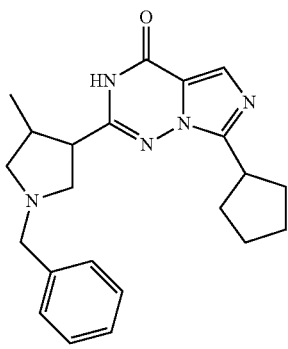 [SMILES: CC1CN(Cc2ccccc2)CC1c1nn2c(C3CCCC3)ncc2c(=O)[nH]1]

To a stirred solution of N-((3-((3,4-trans)-1-benzyl-4-methylpyrrolidin-3-yl)-5-oxo-4,5-dihydro-1,2,4-triazin-6-yl)methyl)cyclopentane carboxamide (220 mg, 0.55 mmol) in CHCl$_3$ (14 mL) under argon atmosphere were added phosphoryl tribromide (477 mg, 1.67 mmol) and DMAP (13.5 mg, 0.11 mmol) at 0° C.; heated to 65-70° C. and stirred for 6 h. The reaction was monitored by TLC; the reaction mass was quenched with water (10 mL), saturated NaHCO$_3$ solution (15 mL) and extracted with CH$_2$Cl$_2$ (3×40 mL). The combined organic extracts were dried over sodium sulphate, filtered and concentrated in vacuo to obtain the crude. The crude was purified through silica gel column chromatography using 5% MeOH/CH$_2$Cl$_2$ to afford (+)-2-((3,4-trans)-1-benzyl-4-methylpyrrolidin-3-yl)-7-cyclopentylimidazo[5,1-f][1,2,4]triazin-4(3H)-one (80 mg, 38%) as an off-white solid.

$^1$H-NMR (DMSO-d$_6$, 400 MHz): δ 7.62 (s, 1H), 7.32-7.26 (m, 5H), 3.62 (q, 2H), 3.46 (q, 1H), 2.94 (t, 1H), 2.84 (t, 1H), 2.76-2.74 (m, 2H), 2.63-2.61 (m, 1H), 2.51-2.49 (m, 1H), 2.24 (t, 1H), 2.02-1.98 (m, 2H), 1.90-1.86 (m, 3H), 1.76-1.74 (m, 2H), 1.06 (d, 3H); Mass (ESI): 378.4 [M$^+$+1]; LC-MS: 95.38%; 378 (M$^+$+1); (column: X-bridge C-18, 50×3.0 mm, 3.5 μm); RT 2.47 min. 0.05% TFA (Aq): ACN; 0.8 mL/min); UPLC (purity): 94.01%; (column: Acquity BEH C-18, 50×2.1 mm, 1.7μ); RT 1.61 min. ACN: 0.025% TFA (Aq); 0.5 mL/min.; Chiral HPLC: 93.94%, R$_t$=7.86 min (Chiralpak IA, 250×4.6 mm, 5μ); mobile phase (A) 0.1% DEA in n-Hexane (B) CH$_2$Cl$_2$:MeOH (80:20) (A:B:85:15); flow Rate: 1.0 mL/min); Optical rotation [α]$_D^{20.01}$: +23.39° (c=0.25, CH$_2$Cl$_2$); TLC: 10% MeOH/CH$_2$Cl$_2$ (R$_f$: 0.6).

198. (+)-2-((3,4-trans)-1-benzyl-4-methylpyrrolidin-3-yl)-7-(pentan-3-yl)imidazo[5,1-f][1,2,4]triazin-4(3H)-one

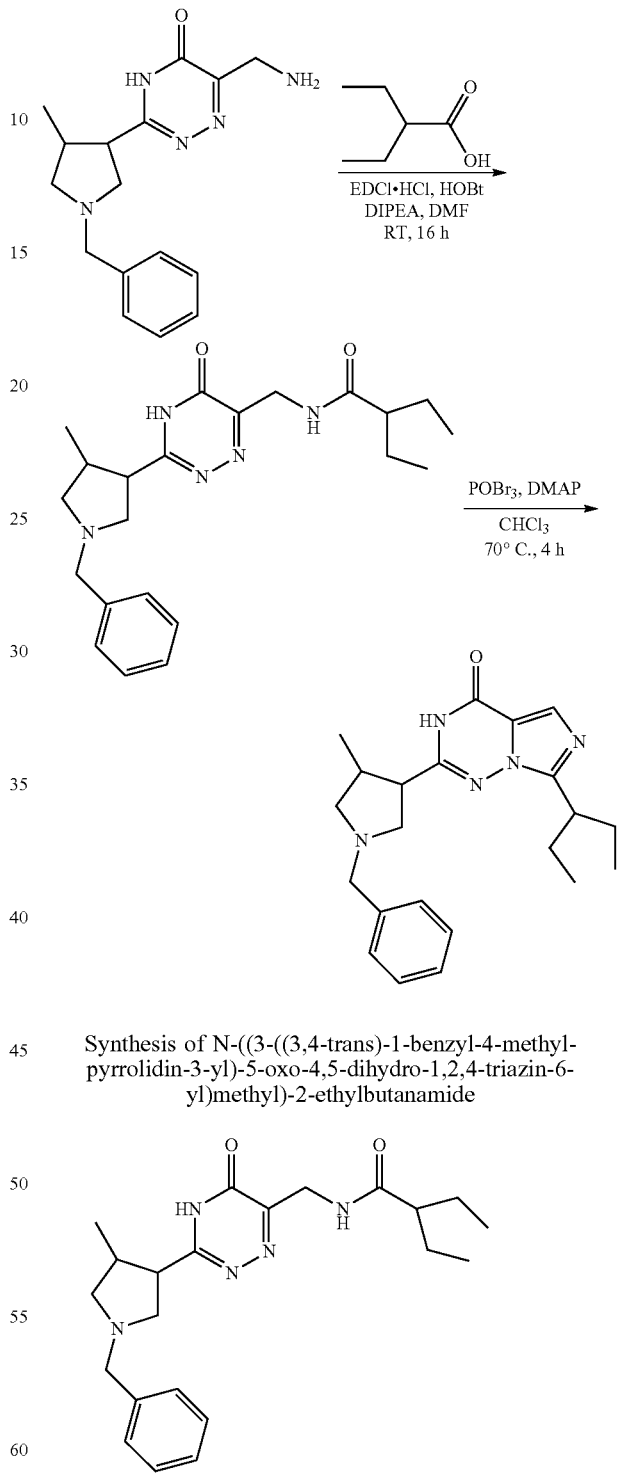

Synthesis of N-((3-((3,4-trans)-1-benzyl-4-methylpyrrolidin-3-yl)-5-oxo-4,5-dihydro-1,2,4-triazin-6-yl)methyl)-2-ethylbutanamide

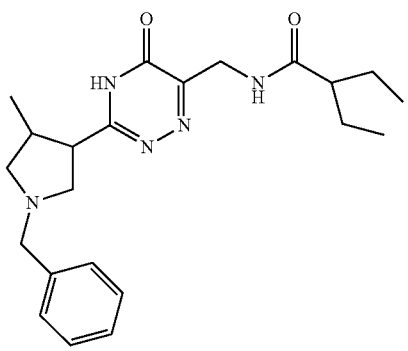 [SMILES: CCC(CC)C(=O)NCc1nnc(C2CN(Cc3ccccc3)CC2C)[nH]c1=O]

To a stirred solution of (+)-6-(aminomethyl)-3-((3,4-trans)-1-benzyl-4-methylpyrrolidin-3-yl)-1,2,4-triazin-5(4H)-one (500 mg, 0.33 mmol) in DMF (0.5 mL) under argon atmosphere were added 2-ethylbutanoic acid (213 mg, 0.36 mmol), EDCI.HCl (479 mg, 0.50 mmol), HOBt (338 mg, 0.50 mmol) and diisopropyl ethyl amine (0.6 mL, 0.66 mmol) at 0° C.; warmed to room temperature and stirred for 16 h. The reaction was monitored by TLC; after completion of the reaction, the reaction mixture was diluted with water (20 mL) and extracted with CH₂Cl₂ (2×30 mL). The combined organic extracts were dried over sodium sulphate, filtered and concentrated in vacuo to obtain the crude. The crude was purified through silica gel column chromatography using 5% MeOH/CH₂Cl₂ to afford N-((3-((3,4-trans)-1-benzyl-4-methylpyrrolidin-3-yl)-5-oxo-4,5-dihydro-1,2,4-triazin-6-yl)methyl)-2-ethylbutanamide (300 mg, 45%) as an off-white solid.

$^1$H-NMR (CDCl₃, 400 MHz): δ 7.33-7.31 (m, 5H), 6.58 (br s, 1H), 4.50 (d, 2H), 3.83-3.78 (m, 2H), 3.38 (t, 1H), 3.12 (d, 1H), 2.90-2.90 (m, 1H), 2.81-2.77 (m, 1H), 2.49-2.43 (m, 1H), 2.13-2.09 (m, 1H), 1.98-1.91 (m, 1H), 1.65-1.59 (m, 2H), 1.49-1.45 (m, 2H), 1.12 (d, 3H), 0.89-0.87 (m, 6H); LC-MS: 94.54%; 398 (M⁺+1); (column: X-Bridge C-18, 50×3.0 mm, 3.5 μm); RT 2.39 min. 0.05% TFA (aq.): ACN; 0.8 mL/min); UPLC (purity): 82.35%; (column: Acquity BEH C-18 (50×2.1 mm, 1.7μ); RT 1.52 min. ACN: 0.025% TFA (Aq); 0.5 mL/min. (IP12060256); TLC: 10% MeOH/CH₂Cl₂ (R$_f$: 0.5).

Synthesis of (+)-2-((3,4-trans)-1-benzyl-4-methyl-pyrrolidin-3-yl)-7-(pentan-3-yl)imidazo[5,1-f][1,2,4]triazin-4(3H)-one

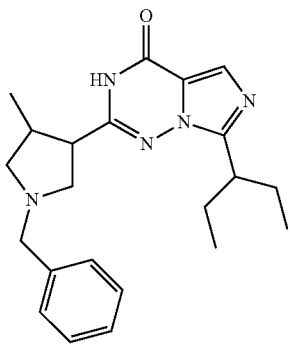 [SMILES: CCC(CC)c1ncc2c(=O)[nH]c(C3CN(Cc4ccccc4)CC3C)nn12]

A solution of N-((3-((3,4-trans)-1-benzyl-4-methylpyrrolidin-3-yl)-5-oxo-4,5-dihydro-1,2,4-triazin-6-yl)methyl)-2-ethylbutanamide (300 mg, 0.75 mmol) in phosphoryl oxybromide (648 mg, 3 eq) under argon atmosphere was heated to 70° C. and stirred for 4 h. The reaction was monitored by TLC; after completion of the reaction, the reaction was quenched with ice cold water (10 ml), NaHCO₃ solution (30 mL). The compound was extracted with CH₂Cl₂ (2×50 mL). The combined organic extracts were dried over sodium sulphate, filtered and concentrated in vacuo to obtain the crude product. The crude material was purified by silica gel column chromatography to afford (+)-2-((3,4-trans)-1-benzyl-4-methylpyrrolidin-3-yl)-7-(pentan-3-yl)imidazo[5,1-f][1,2,4]triazin-4(3H)-one (140 mg, 49%) as thick syrup.

$^1$H-NMR (CDCl₃, 500 MHz): δ 7.84 (s, 1H), 7.40-7.38 (m, 3H), 7.24 (s, 2H), 3.82 (d, 1H), 3.58 (d, 1H), 3.40 (t, 1H), 3.21-3.19 (m, 1H), 3.00 (d, 1H), 2.76-2.74 (m, 1H), 2.52-2.44 (m, 2H), 1.90 (t, 1H), 1.84-1.76 (m, 4H), 1.24 (d, 3H), 0.84-0.76 (m, 6H). Mass (ESI): 380 [M⁺+1]; LC-MS: 98.65%; 380 (M⁺+1); (column; X-bridge C-18, 50×3.0 mm, 3.5 μm); RT 2.59 min. 0.05% TFA (aq.): ACN; 0.8 mL/min); UPLC (purity): 93.19%; (column: Acquity BEH C-18; 50×2.1 mm, 1.7μ); RT 1.67 min. ACN: 0.025% TFA (Aq); 0.5 mL/min.; Chiral HPLC: 93.03%, R$_f$=19.20 min (Chiralpak IA, 250×4.6 mm, 5μ); mobile phase (A) 0.1% DEA in n-Hexane (B) DCM:MeOH (80:20) (A:B:95:5); flow Rate: 1.0 mL/min; Optical rotation [α]$_D^{19.99}$: +18.94° (c=0.25, DCM). TLC: 10% MeOH/DCM (R$_f$: 0.4).

199. (+)-2-((3,4-trans)-1-benzyl-4-methylpyrrolidin-3-yl)-7-(3-methylpyridin-4-yl)imidazo[5,1-f][1,2,4]triazin-4(3H)-one

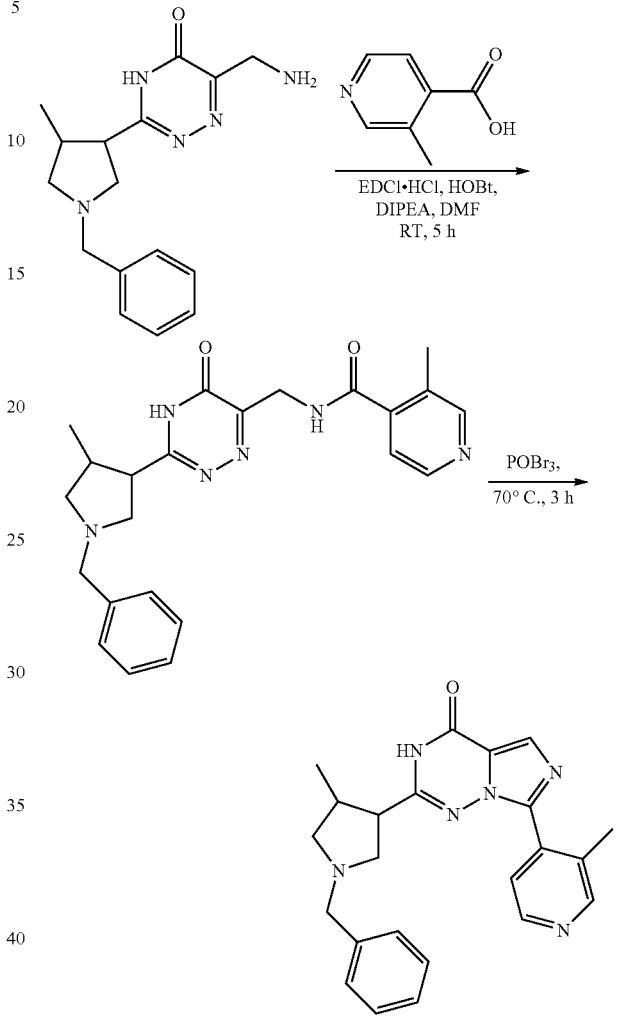

Synthesis of N-((3-((3,4-trans)-1-benzyl-4-methyl-pyrrolidin-3-yl)-5-oxo-4,5-dihydro-1,2,4-triazin-6-yl)methyl)-3-methylisonicotinamide

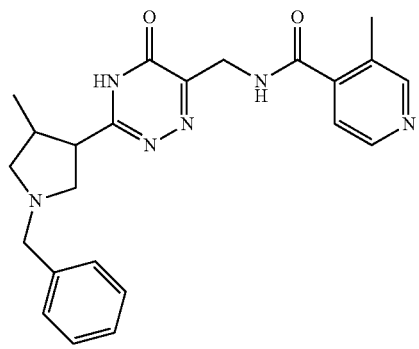 [SMILES: Cc1cnccc1C(=O)NCc1nnc(C2CN(Cc3ccccc3)CC2C)[nH]c1=O]

To a stirred solution of 3-methylisonicotinic acid (504 mg, 3.67 mmol) in CH₂Cl₂ (25 mL), DMF (2.5 mL) under argon atmosphere were added HATU (1.69 g, 4.34 mmol), (+)-6-(aminomethyl)-3-((3,4-trans)-1-benzyl-4-methylpyrrolidin-3-yl)-1,2,4-triazin-5(4H)-one (1 g, 3.34 mmol) and diisopropyl ethyl amine (862 mg, 6.68 mmol) at 0° C.; warmed to RT and stirred for 16 h. The reaction was monitored by TLC; after completion of the reaction, the reaction mixture was quenched with water (30 mL) and extracted with $CH_2Cl_2$ (2×40 mL). The combined organic extracts were dried over sodium sulfate, filtered and concentrated in vacuo to obtain the crude. The crude was purified through silica gel column chromatography using 10% $MeOH/CH_2Cl_2$ to afford N-((3-((3,4-trans)-1-benzyl-4-methylpyrrolidin-3-yl)-5-oxo-4,5-dihydro-1,2,4-triazin-6-yl)methyl)-3-methyl isonicotinamide (660 mg, 47%) as an off-white solid.

$^1$H-NMR (DMSO-$d_6$, 500 MHz): δ 8.78 (t, 1H), 8.49 (s, 1H), 8.46 (d, 1H), 7.36-7.34 (m, 5H), 7.24-7.22 (m, 1H), 4.38 (d, 2H), 3.61-3.60 (m, 2H), 2.95 (t, 2H), 2.78-2.72 (m, 3H), 2.36-2.32 (m, 5H), 1.04 (d, 3H); LC-MS: 96.71%; 419.5 (M$^+$+1); (column: X Bridge C-18, 50×3.0 mm, 3.5 μm); RT 1.79 min. 0.05% Aq TFA: ACN; 0.8 mL/min); UPLC (purity): 93.32%; (column: Acquity UPLC HSS T3 (2.1×100 mm, 1.8μ); RT 2.92 min. ACN: 0.025% TFA (Aq); 0.3 mL/min. (IP12110477); TLC: 10% $MeOH/CH_2Cl_2$ (R$_f$: 0.5).

Synthesis of (+)-2-((3,4-trans)-1-benzyl-4-methyl-pyrrolidin-3-yl)-7-(3-methylpyridin-4-yl)imidazo[5,1-f][1,2,4]triazin-4(3H)-one

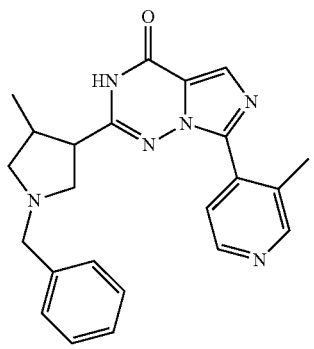

A stirred solution of N-((3-((3,4-trans)-1-benzyl-4-methylpyrrolidin-3-yl)-5-oxo-4,5-dihydro-1,2,4-triazin-6-yl)methyl)-3-methyl isonicotinamide (100 mg, 0.23 mmol) in phosphorous oxybromide (684 mg, 2.39 mmol) under argon atmosphere was heated to 70° C. and stirred for 3 h. The reaction was monitored by TLC; after completion of the reaction, the reaction mixture was quenched with saturated $NaHCO_3$ solution (20 mL) and extracted with $CH_2Cl_2$ (2×25 mL). The combined organic extracts were dried over sodium sulfate, filtered and concentrated in vacuo to obtain the crude. The crude was purified through silica gel column chromatography using 3% $MeOH/CH_2Cl_2$ which was further purified through chiral preparative HPLC to afford (+)-2-((3,4-trans)-1-benzyl-4-methylpyrrolidin-3-yl)-7-(3-methylpyridin-4-yl)imidazo[5,1-f][1,2,4]triazin-4(3H)-one (45 mg, 47%) as an off-white solid.

$^1$H-NMR (CDCl$_3$, 400 MHz): δ 8.60 (s, 1H), 8.54 (d, 1H), 8.02 (s, 1H), 7.58 (d, 1H), 7.38-7.36 (m, 4H), 7.28 (s, 1H), 3.82 (d, 1H), 3.59 (d, 1H), 3.42 (t, 1H), 3.00 (d, 1H), 2.73-2.72 (m, 1H), 2.51-2.50 (m, 1H), 2.42-2.41 (m, 1H), 2.40 (s, 3H), 1.98 (t, 1H), 1.22 (d, 3H); Mass: m/z 401.5 [M+1]$^+$; LC-MS: 98.96%; 401 (M$^+$+1); (column: X-Bridge C-18, 50×3.0 mm, 3.5 μm); RT 2.23 min. 0.05% TFA: ACN; 0.8 mL/min); UPLC (purity): 98.75%; (column: Acquity BEH-C18 (50×2.1 mm, 1.7μ); RT 1.24 min. ACN: 0.025% TFA (Aq); 0.5 mL/min.; Chiral HPLC: 99.70%, R$_t$=11.23 min (Chiralpak 1A, 250×4.6 mm, 5 μm); mobile phase (A) 0.1% DEA in n-Hexane (B) $CH_2Cl_2$:MeOH (80:20) (A:B: 85:15); flow Rate: 1.0 mL/min); Optical rotation [α]$_D^{20.01}$: +28.16° (c=0.25, $CH_2Cl_2$); TLC: 10% $MeOH/CH_2Cl_2$ (R$_f$: 0.4).

200. (+)-2-((3,4-trans)-1-benzyl-4-methylpyrrolidin-3-yl)-7-(2-fluorophenyl)imidazo[5,1-f][1,2,4]triazin-4(3H)-one

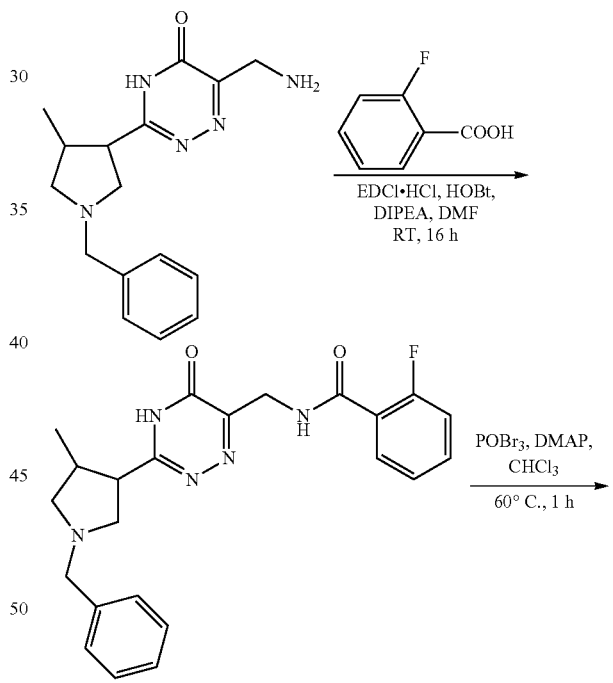

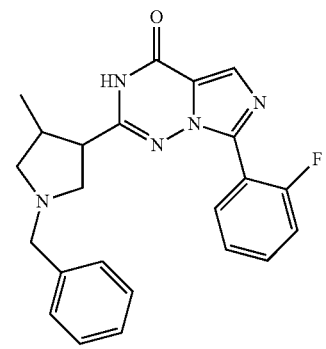 [SMILES: CC1CN(Cc2ccccc2)CC1c1nn2c(-c3ccccc3F)ncc2c(=O)[nH]1]

Synthesis of N-((3-((3,4-trans)-1-benzyl-4-methyl-pyrrolidin-3-yl)-5-oxo-4,5-dihydro-1,2,4-triazin-6-yl)methyl)-2-fluorobenzamide

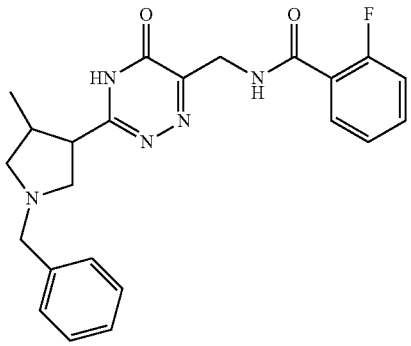

To a stirred solution of 2-fluoro benzoic acid (54 mg, 3.34 mmol) in DMF (2 mL) under argon atmosphere were added EDCI. HCl (90 mg, 0.46 mmol), HOBt (59 mg, 0.43 mmol) and (+)-6-(aminomethyl)-3-((3,4-trans)-1-benzyl-4-methyl-pyrrolidin-3-yl)-1,2,4-triazin-5(4H)-one (100 mg, 0.33 mmol) and diisopropyl ethyl amine (86 mg, 0.66 mmol) at 0° C.; warmed to RT and stirred for 16 h. The reaction was monitored by TLC; after completion of the reaction, the reaction mixture was diluted with water (15 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 10% MeOH/CH$_2$Cl$_2$ to afford N-((3-((3,4-trans)-1-benzyl-4-methylpyrrolidin-3-yl)-5-oxo-4,5-dihydro-1,2,4-triazin-6-yl)methyl)-2-fluorobenzamide (75 mg, 54%) as an off-white solid.

$^1$H-NMR (DMSO-d$_6$, 500 MHz): δ 8.50-8.48 (m, 1H), 7.72 (t, 1H), 7.60-7.58 (m, 1H), 7.23-7.17 (m, 6H), 7.14-7.12 (m, 1H), 4.40 (d, 2H), 3.66-3.64 (m, 2H), 2.98-2.96 (m, 1H), 2.80-2.77 (m, 3H), 2.56-2.53 (m, 2H), 2.28-2.26 (m, 1H), 1.04 (d, 3H); LC-MS: 95.07%; 422.4 (M$^+$+1); (column: X-Bridge C-18, 50×3.0 mm, 3.5 µm); RT 2.96 min. 0.05% Aq TFA: ACN; 0.8 mL/min); UPLC (purity): 91.44%; (column: Acquity UPLC BEH C-18 (2.1×50 mm, 1.7µ); RT 1.48 min. ACN: 0.025% TFA (Aq); 0.5 mL/min. (IP12110478); TLC: 10% MeOH/CH$_2$Cl$_2$ (R$_f$: 0.4).

Synthesis of (+)-2-((3,4-trans)-1-benzyl-4-methyl-pyrrolidin-3-yl)-7-(2-fluorophenyl)imidazo[5,1-f][1,2,4]triazin-4(3H)-one

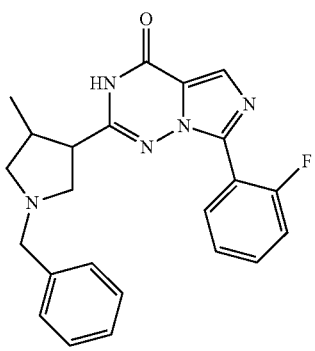

To a stirred solution of N-((3-((3,4-trans)-1-benzyl-4-methylpyrrolidin-3-yl)-5-oxo-4,5-dihydro-1,2,4-triazin-6-yl)methyl)-2-fluorobenzamide (50 mg, 0.11 mmol) in CHCl$_3$ (3.5 mL) under argon atmosphere were added phosphorous oxybromide (101 mg, 0.35 mmol) and DMAP (1.4 mg, 0.01 mmol) at room temperature; heated to 60° C. and stirred for 1 h. The reaction was monitored by TLC; after completion of the reaction, the reaction mixture was quenched with saturated NaHCO$_3$ solution (10 mL) and extracted with CH$_2$Cl$_2$ (2×20 mL). The combined organic extracts were dried over sodium sulphate, filtered and concentrated in vacuo to obtain the crude. The crude was purified through silica gel column chromatography using 3% MeOH/CH$_2$Cl$_2$ to afford (+)-2-((3,4-trans)-1-benzyl-4-methylpyrrolidin-3-yl)-7-(2-fluorophenyl)imidazo[5,1-f][1,2,4]triazin-4(3H)-one (15 mg, 32%) as pale yellow solid.

$^1$H-NMR (DMSO-d$_6$, 400 MHz): δ 7.90 (s, 1H), 7.80 (t, 1H), 7.60-7.59 (m, 1H), 7.42-7.39 (m, 2H), 7.30-7.27 (m, 5H), 3.60 (q, 2H), 2.91 (t, 1H), 2.80-2.75 (m, 3H), 2.60-2.58 (m, 1H), 2.26-2.24 (m, 1H), 1.06 (d, 3H); Mass (ESI): 404.2 [M$^+$+1]; LC-MS: 99.27%; 404.5 (M$^+$+1); (column; X-bridge C-18, (50×3.0 mm, 3.5 µm); RT 2.93 min. 0.05% TFA (aq.): ACN; 0.8 mL/min); UPLC (purity): 99.19%; (column: Acquity BEH C-18 (50×2.1 mm, 1.7µ); RT 1.66 min. ACN: 0.025% TFA (Aq); 0.5 mL/min.; Chiral HPLC: 98.65%, R$_f$=7.20 min (Chiralpak IA, 250×4.6 mm, 5 µm); mobile phase (A) n-Hexane (B) CH$_2$Cl$_2$:MeOH (80:20) (A:B:80:20); flow Rate: 1.0 mL/min); Optical rotation [α]$_D^{20}$: +36.91° (c=0.25, CH$_2$Cl$_2$); TLC: 10% MeOH/CH$_2$Cl$_2$ (R$_f$: 0.6).

201. (+)-2-((3,4-trans)-1-benzyl-4-methylpyrrolidin-3-yl)-7-(2,2,2-trifluoroethyl)imidazo[5,1-f][1,2,4]triazin-4(3H)-one

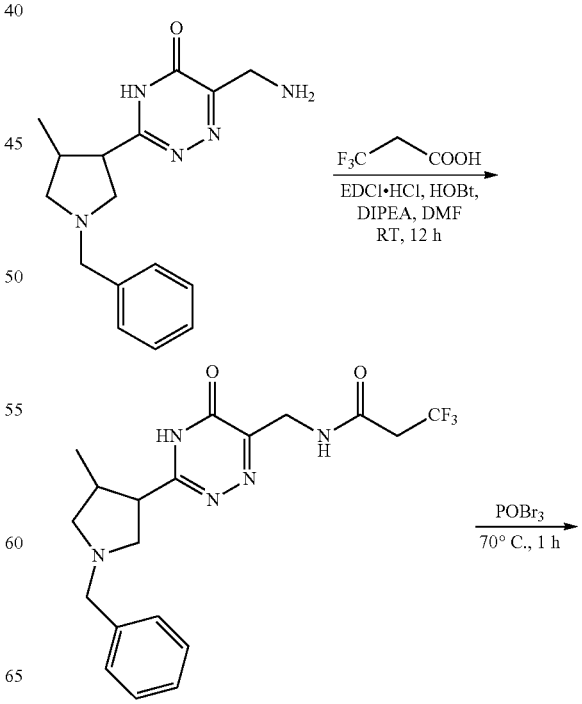

-continued

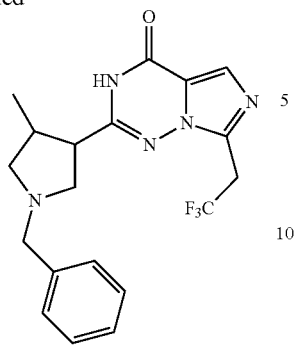

Synthesis of N-((3-((3,4-trans)-1-benzyl-4-methyl-pyrrolidin-3-yl)-5-oxo-4,5-dihydro-1,2,4-triazin-6-yl)methyl)-3,3,3-trifluoro propanamide

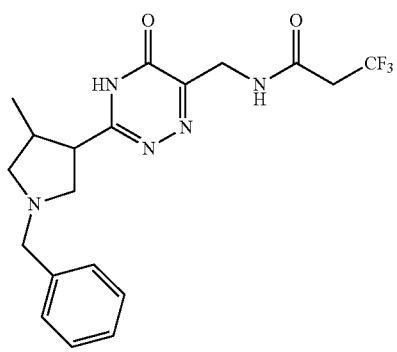 [SMILES: CC1CN(Cc2ccccc2)CC1c1nnc(CNC(=O)CC(F)(F)F)c(=O)[nH]1]

To a stirred solution of 3,3,3-trifluoropropanoic acid (214 mg, 1.67 mmol) in DMF (6 mL) under argon atmosphere were added HOBt (293.4 mg, 2.16 mmol), EDCI. HCl (323.5 mg, 2.16 mmol), (+)-6-(aminomethyl)-3-((3,4-trans)-1-benzyl-4-methylpyrrolidin-3-yl)-1,2,4-triazin-5(4H)-one (500 mg, 1.67 mmol) and diisopropyl ethyl amine (323 mg, 2.50 mmol) at RT and stirred for 12 h. The reaction was monitored by TLC; after completion of the reaction, the reaction mixture was diluted with water (20 mL) and extracted with $CH_2Cl_2$ (2×30 mL). The combined organic extracts were dried over sodium sulfate, filtered and concentrated in vacuo to obtain the crude. The crude was purified through silica gel column chromatography using 5% MeOH/$CH_2Cl_2$ to afford N-((3-((3,4-trans)-1-benzyl-4-methylpyrrolidin-3-yl)-5-oxo-4,5-dihydro-1,2,4-triazin-6-yl)methyl)-3,3,3-trifluoro propanamide (350 mg, 52%) as an off white solid.

$^1$H-NMR (CDCl$_3$, 500 MHz): δ 7.42-7.30 (m, 6H), 4.56 (s, 2H), 4.00 (dd, 2H), 3.46-3.45 (m, 1H), 3.31-3.30 (m, 1H), 3.20-3.12 (m, 4H), 2.62-2.50 (m, 2H), 1.16 (d, 3H); LC-MS: 92.06%; 410.3 (M$^+$+1); (column: X Bridge C-18, 50×3.0 mm, 3.5 μm); RT 2.17 min. 0.05% Aq TFA: ACN; 0.8 mL/min); TLC: 10% MeOH/$CH_2Cl_2$ (R$_f$: 0.5).

Synthesis of (+)-2-((3,4-trans)-1-benzyl-4-methyl-pyrrolidin-3-yl)-7-(2,2,2-trifluoroethyl)imidazo[5,1-f][1,2,4]triazin-4(3H)-one

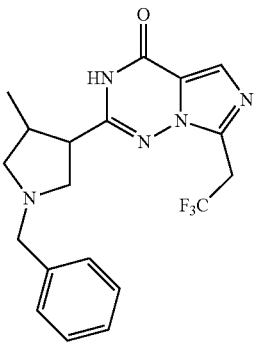 [SMILES: CC1CN(Cc2ccccc2)CC1c1nn2c(CC(F)(F)F)ncc2c(=O)[nH]1]

A stirred solution of N-((3-((3,4-trans)-1-benzyl-4-methylpyrrolidin-3-yl)-5-oxo-4,5-dihydro-1,2,4-triazin-6-yl) methyl)-3,3,3-trifluoro propanamide (300 mg, 0.07 mmol) in phosphorous oxybromide (2.1 g, 7.33 mmol) under argon atmosphere was heated to 70° C. and stirred for 1 h. The reaction was monitored by TLC; after completion of the reaction, the reaction mixture was neutralized with 20% NaHCO$_3$ solution (25 mL) and extracted with $CH_2Cl_2$ (2×30 mL). The combined organic extracts were dried over sodium sulfate, filtered and concentrated in vacuo to obtain the crude. The crude was purified through silica gel column chromatography using 3% MeOH/$CH_2Cl_2$ to afford (+)-2-((3,4-trans)-1-benzyl-4-methylpyrrolidin-3-yl)-7-(2,2,2-trifluoroethyl)imidazo[5,1-f][1,2,4]triazin-4(3H)-one (170 mg, 59%) as brown solid.

$^1$H-NMR (DMSO-d$_6$, 500 MHz): δ 7.78 (s, 1H), 7.30 (s, 5H), 4.08 (q, 2H), 3.62 (dd, 2H), 2.95 (t, 1H), 2.86-2.78 (m, 3H), 2.68 (t, 1H), 2.26 (t, 1H), 1.12 (d, 3H); LC-MS: 98.45%; 392.3 (M$^+$+1); (column: X-Bridge C-18, 50×3.0 mm, 3.5 μm); RT 3.15 min. 0.05% TFA: ACN; 0.8 mL/min); UPLC (purity): 99.03%; (column: Acquity UPLC BEH-C18 (50×2.1 mm, 1.7μ); RT 1.58 min. ACN: 0.025% TFA (Aq); 0.5 mL/min.; Chiral HPLC: 95.70%, R$_t$=20.57 min (Chiralpak IC, 250×4.6 mm, 5 μm); mobile phase (A) 0.1% DEA in n-Hexane (B) $CH_2Cl_2$:MeOH (80:20) (A:B:85:15); flow Rate: 1.0 mL/min); Optical rotation [α]$_D^{20}$:+30.96° (c=0.25, $CH_2Cl_2$); TLC: 10% MeOH/$CH_2Cl_2$ (R$_f$: 0.8).

202. (+)-2-((3,4-trans)-1-benzyl-4-methylpyrrolidin-3-yl)-7-(2-(trifluoromethyl)phenyl)imidazo[5,1-f][1,2,4]triazin-4(3H)-one

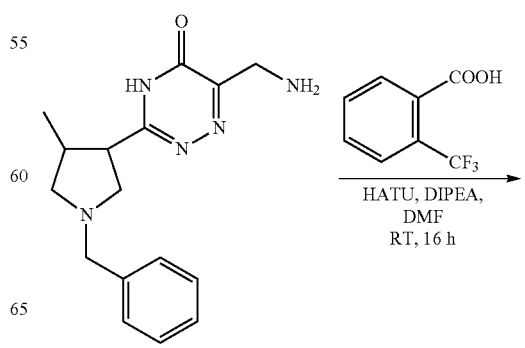

-continued

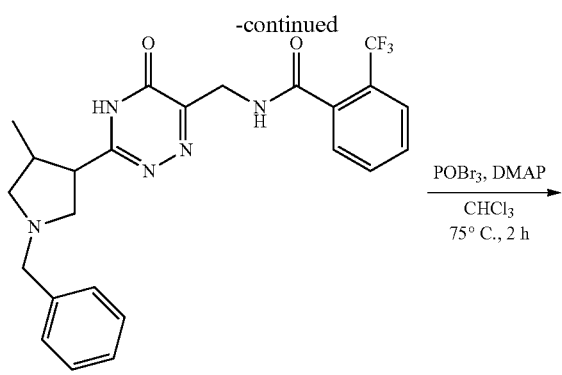

Synthesis of N-((3-((3,4-trans)-1-benzyl-4-methyl-pyrrolidin-3-yl)-5-oxo-4,5-dihydro-1,2,4-triazin-6-yl)methyl)-2-(trifluoromethyl)benzamide

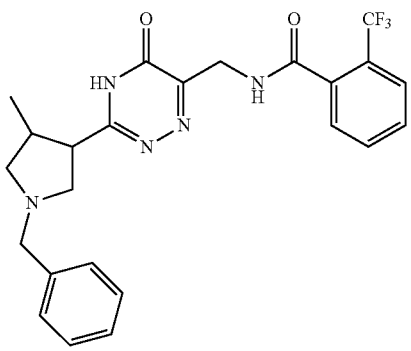 [SMILES: CC1CN(Cc2ccccc2)CC1c1nnc(CNC(=O)c2ccccc2C(F)(F)F)c(=O)[nH]1]

To a stirred solution of (+)-6-(aminomethyl)-3-((3,4-trans)-1-benzyl-4-methylpyrrolidin-3-yl)-1,2,4-triazin-5(4H)-one (1 g, 3.34 mmol) in DMF (15 mL) under argon atmosphere were added HATU (1.65 g, 4.34 mmol), 2-(trifluoromethyl)benzoic acid (762 mg, 4.00 mmol) and diisopropyl ethyl amine (1.15 mL, 6.68 mmol) at 0° C.; warmed to RT and stirred for 16 h. The reaction was monitored by TLC; after completion of the reaction, the reaction mixture was diluted with water (30 mL) and extracted with CH$_2$Cl$_2$ (2×40 mL). The combined organic extracts were dried over sodium sulfate, filtered and concentrated in vacuo to obtain the crude. The crude was purified through silica gel column chromatography using 5-7% MeOH/CH$_2$Cl$_2$ to afford N-((3-((3,4-trans)-1-benzyl-4-methylpyrrolidin-3-yl)-5-oxo-4,5-dihydro-1,2,4-triazin-6-yl)methyl)-2-(trifluoromethyl)benzamide (750 mg, 48%) as an off-white solid.

$^1$H-NMR (CDCl$_3$, 400 MHz): δ 8.72 (d, 1H), 7.60-7.58 (m, 3H), 7.40-7.34 (m, 4H), 6.90 (s, 1H), 4.70-4.68 (m, 2H), 3.86-3.74 (m, 2H), 3.40 (t, 1H), 3.20-3.16 (m, 2H), 3.02 (s, 1H), 2.90-2.89 (m, 1H), 2.80-2.78 (m, 1H), 2.50-2.49 (m, 1H), 2.13-2.10 (m, 1H), 1.20 (d, 3H); LC-MS: 88.63%; 472.5 (M$^+$+1); (column: X Bridge C-18, 50×3.0 mm, 3.5 μm); RT 2.51 min. 0.05% Aq TFA: ACN; 0.8 mL/min); UPLC (purity): 83.13%; (column: Acquity BEH C-18 (50× 2.1 mm, 1.7μ); RT 1.62 min. ACN: 0.025% TFA (Aq); 0.5 mL/min. (IP12120462); TLC: 10% MeOH/CH$_2$Cl$_2$ (R$_f$: 0.5).

Synthesis of (+)-2-((3,4-trans)-1-benzyl-4-methyl-pyrrolidin-3-yl)-7-(2-(trifluoromethyl)phenyl)imidazo[5,1-f][1,2,4]triazin-4(3H)-one

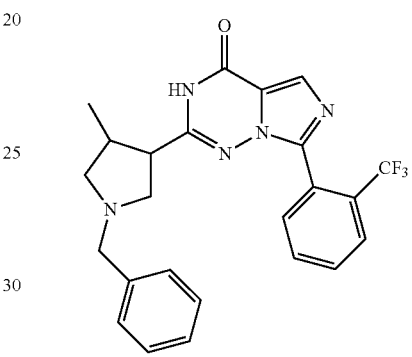

A stirred solution of N-((3-((3,4-trans)-1-benzyl-4-methylpyrrolidin-3-yl)-5-oxo-4,5-dihydro-1,2,4-triazin-6-yl)methyl)-2-(trifluoromethyl)benzamide (500 mg, 1.06 mmol) in phosphorous oxybromide (3 g, 10.61 mmol) under argon atmosphere was heated to 75° C. and stirred for 2 h. The reaction was monitored by TLC; after completion of the reaction, the reaction mixture was neutralized with saturated NaHCO$_3$ solution (25 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 3% MeOH/CH$_2$Cl$_2$ to afford (+)-2-((3,4-trans)-1-benzyl-4-methylpyrrolidin-3-yl)-7-(2-(trifluoromethyl)phenyl)imidazo[5,1-f][1,2,4]triazin-4(3H)-one (240 mg, 50%) as an off-white solid.

$^1$H-NMR (CDCl$_3$, 400 MHz): δ 7.98 (s, 1H), 7.80 (d, 1H), 7.64-7.57 (m, 3H), 7.38-7.28 (m, 4H), 7.22 (s, 1H), 3.80 (d, 1H), 3.58 (d, 1H), 3.38 (t, 1H), 2.98 (d, 1H), 2.62-2.60 (m, 1H), 2.48-2.44 (m, 2H), 1.90 (t, 1H), 1.12 (d, 3H); Mass: m/z 454.3 [M+1]$^+$; LC-MS: 99.89%; 454.2 (M$^+$+1); (column: X-Bridge C-18, 50×3.0 mm, 3.5 μm); RT 2.79 min. 5 mM NH$_4$OAc: ACN; 0.8 mL/min); UPLC (purity): 98.84%; (column: Acquity UPLC BEH-C18 (50×2.1 mm, 1.7μ); RT 1.77 min. ACN: 0.025% TFA (Aq); 0.5 mL/min.; Chiral HPLC: 89.33%, R$_t$=15.58 min (Chiralpak IA, 250×4.6 mm, 5 μm); mobile phase (A) 0.1% DEA in n-Hexane (B) CH$_2$Cl$_2$: MeOH (80:20) (A:B:90:10); flow Rate: 1.0 mL/min); Optical rotation [α]$_D^{19.99}$: +15.13° (c=0.25, CH$_2$Cl$_2$); TLC: 10% MeOH/CH$_2$Cl$_2$ (R$_f$: 0.8).

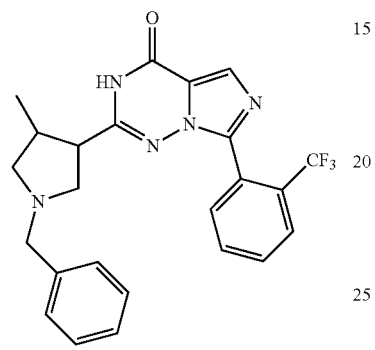

203. (+)-2-((3,4-trans)-1-benzyl-4-methylpyrrolidin-3-yl)-7-(2-(trifluoromethyl)phenyl)imidazo[5,1-f][1,2,4]triazin-4(3H)-one

204. (+)-2-((3,4-trans)-4-methyl-1-(2-(pyrimidin-5-yl)acetyl)pyrrolidin-3-yl)-7-(tetrahydro-2H-pyran-4-yl)imidazo[5,1-f][1,2,4]triazin-4(3H)-one

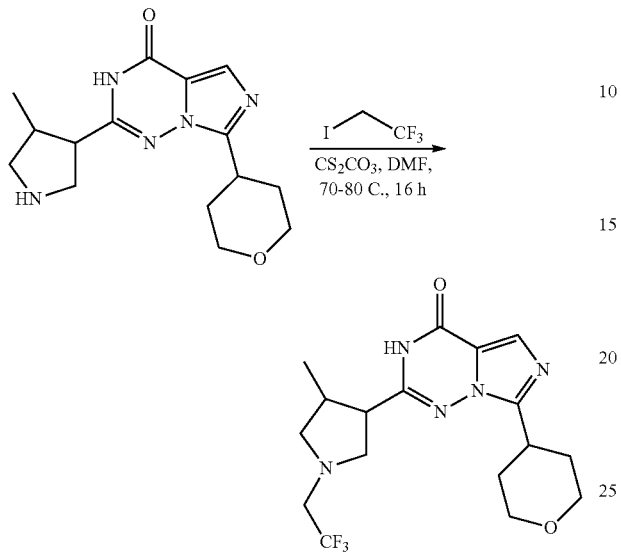

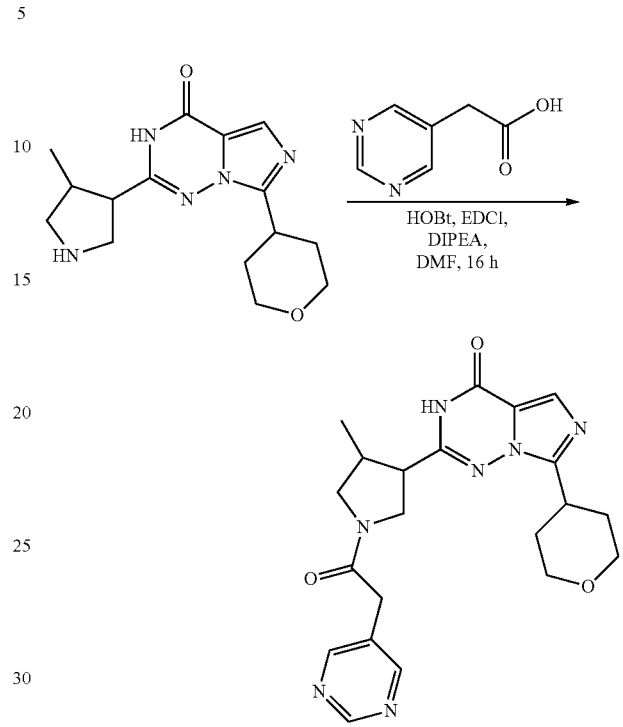

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (50 mg, 0.16 mmol) in DMF (3 mL) under argon atmosphere was added 1,1,1-trifluoro-2-iodoethane (0.14 mL, 0.66 mmol) and cesium carbonate (107 mg, 0.33 mmol) at room temperature; heated to 70-80° C. and stirred for 16 h. The reaction was monitored by TLC; after completion of the reaction, the solvent was evaporated under reduced pressure to obtain the crude product. The crude material was purified through silica gel column chromatography to afford 30 mg of (+)-2-((3,4-trans)-4-methyl-1-(2,2,2-trifluoroethyl)pyrrolidin-3-yl)-7-(tetrahydro-2H-pyran-4-yl)imidazo[5,1-f][1,2,4]triazin-4(3H)-one with UPLC: 40%; upon preparative HPLC obtained (+)-2-((3,4-trans)-1-benzyl-4-methylpyrrolidin-3-yl)-7-(2-(trifluoromethyl)phenyl)imidazo[5,1-f][1,2,4]triazin-4(3H)-one (12 mg, 19%) as white solid.

$^1$H-NMR (CDCl$_3$, 400 MHz): δ 9.90-9.50 (br s, 1H), 7.82 (s, 1H), 4.12-4.08 (m, 2H), 3.60 (t, 2H), 3.50 (t, 2H), 3.22-3.18 (m, 3H), 2.81-2.79 (m, 2H), 2.46-2.44 (m, 1H), 2.13-2.07 (m, 3H), 1.90 (d, 2H), 1.22 (d, 3H); Mass (ESI): 386.2 [M$^+$+1]; LC-MS: 96.40%; 386 (M$^+$+1); (column; X-bridge C-18, (50×3.0 mm, 3.5 μm); RT 2.28 min. 0.05% TFA (Aq): ACN; 0.8 mL/min); UPLC (purity): 95.29%; (column: Acquity BEH C-18 (50×2.1 mm, 1.7 μm); RT 1.69 min. ACN: 0.025% TFA (Aq); 0.5 mL/min.; Chiral HPLC: 97.82%, R$_t$=8.21 min (Chiralpak IA, 250×4.6 mm, 5 μm); mobile phase (A) 0.1% DEA in n-Hexane (B) CH$_2$Cl$_2$: MeOH (80:20) (A:B=80:20); flow Rate: 1.0 mL/min); Optical rotation [α]$_D^{20}$: +4.41° (c=0.25, CH$_2$Cl$_2$); TLC: 10% MeOH/CH$_2$Cl$_2$ (R$_f$: 0.6).

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (75 mg, 0.24 mmol) in DMF (6 mL) under argon atmosphere were added 2-(pyrimidin-5-yl)acetic acid (44.4 mg, 0.32 mmol), EDCI (70.9 mg, 0.37 mmol), HOBt (50 mg, 0.32 mmol) and DIPEA (95.7 mg, 0.72 mmol) at 0° C.; warmed to room temperature and stirred for 16 h. The volatiles were evaporated under reduced pressure; the residue was diluted with ice water (15 mL) and extracted with CH$_2$Cl$_2$ (2×25 mL). The combined organic extracts were dried over sodium sulphate, filtered and concentrated in vacuo to obtain the crude product. The crude material was purified through silica gel column chromatography to afford 45 mg of (+)-2-((3,4-trans)-4-methyl-1-(2-(pyrimidin-5-yl)acetyl)pyrrolidin-3-yl)-7-(tetrahydro-2H-pyran-4-yl)imidazo[5,1-f][1,2,4]triazin-4(3H)-one with HPLC: 58.36%; upon Chiral preparative HPLC purification to afford (18 mg, 17%) as an off-white solid.

$^1$H-NMR (DMSO-d$_6$, 400 MHz): δ 11.84 (br s, 1H), 9.02 (s, 1H), 8.72 (s, 2H), 7.68 (d, 1H), 4.02-3.84 (m, 4H), 3.72-3.66 (m, 2H), 3.60-3.38 (m, 3H), 3.10-2.90 (m, 2H), 2.70-2.60 (m, 2H), 1.90-1.86 (m, 4H), 1.11 (d, 3H); Mass (ESI): 424.7 [M$^+$+1]; LC-MS: 99.4%; 424.3 (M$^+$+1); (column: X-bridge C-18, 50×3.0 mm, 3.5 μm); RT 2.15 min. 5 mM NH$_4$OAc: ACN; 0.8 mL/min); UPLC (purity): 99.85%; (column: Acquity BEH C-18, (50×2.1 mm, 1.7 μm); RT 1.30 min. ACN: 0.025% TFA (Aq); 0.5 mL/min.; Chiral HPLC: 99.58%, R$_t$=15.32 min (Chiralpak IA, 250×4.6 mm, 5 μm); mobile phase (A) 0.1% DEA in n-Hexane (B) CH$_2$Cl$_2$: MeOH (80:20) (A:B=70:30); flow Rate: 1.0 mL/min); Optical rotation [α]$_D^{19.98}$: +27.42° (c=0.25, MeOH); TLC: 10% MeOH/CH$_2$Cl$_2$ (R$_f$: 0.6).

205. (+)-2-((3,4-trans)-4-methyl-1-(2-(pyrimidin-5-yl)ethyl)pyrrolidin-3-yl)-7-(tetrahydro-2H-pyran-4-yl)imidazo[5,1-f][1,2,4]triazin-4(3H)-one

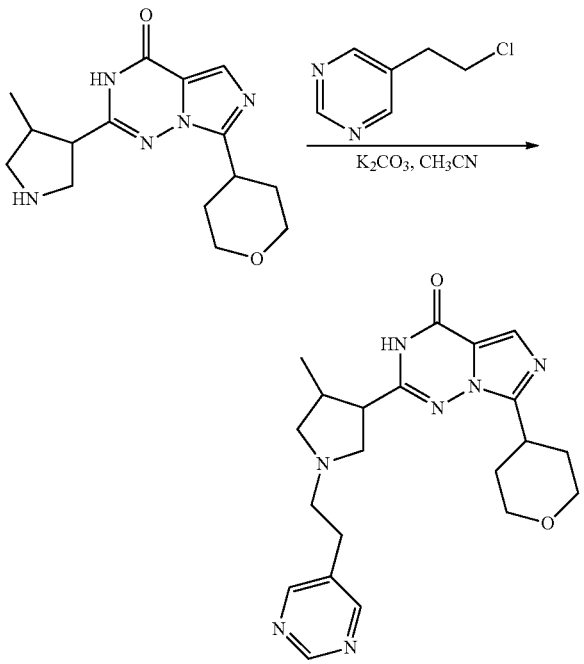

To a stirred solution of (−)-2-((3,4-trans)-4-methylpyrrolidin-3-yl)-7-(tetrahydro-2H-pyran-4-yl)imidazo[5,1-f][1,2,4]triazin-4(3H)-one (40 mg, 0.13 mmol) in CH$_3$CN (5 mL) under argon atmosphere were added potassium carbonate (27 mg, 0.19 mmol) and 5-(2-chloroethyl)pyrimidine (18 mg, 0.13 mmol) at room temperature; heated to 65-70° C. and stirred for 16 h and at 90° C. for 3 h. The reaction was monitored by TLC; the reaction mass was quenched with water (10 mL) and extracted with CH$_2$Cl$_2$ (3×20 mL). The combined organic extracts were dried over sodium sulphate, filtered and concentrated in vacuo to obtain the crude. The crude was purified through silica gel column chromatography using 3% MeOH/CH$_2$Cl$_2$ to afford (+)-2-((3,4-trans)-4-methyl-1-(2-(pyrimidin-5-yl)ethyl)pyrrolidin-3-yl)-7-(tetrahydro-2H-pyran-4-yl)imidazo[5,1-f][1,2,4]triazin-4(3H)-one (10 mg, 19%) as an off-white solid.

$^1$H-NMR (DMSO-d$_6$, 400 MHz): δ 9.00 (s, 1H), 8.68 (s, 2H), 7.62 (s, 1H), 3.94 (dd, 2H), 3.50-3.46 (m, 2H), 3.41-3.39 (m, 1H), 2.95 (t, 1H), 2.91 (t, 1H), 2.85 (t, 1H), 2.78 (d, 1H), 2.75-2.70 (m, 3H), 2.68-2.64 (m, 1H), 2.62 (t, 1H), 2.31-2.29 (m, 1H), 1.90-1.80 (m, 4H), 1.02 (d, 3H); Mass (ESI): 410.5 [M$^+$+1]; LC-MS: 88.12%; 410.3 (M$^+$+1); (column; X-bridge C-18, 50×3.0 mm, 3.5 μm); RT 2.22 min. 5 mM NH$_4$OAc: ACN; 0.8 mL/min); UPLC (purity): 88.23%; (column: Acquity UPLC HSS T3, 2.1×100 mm, 1.8 μm); RT 2.86 mM. ACN: 0.025% TFA (Aq); 0.3 mL/min.; Chiral HPLC: 89.42%, R$_t$=11.89 min (Chiralpak IA, 250×4.6 mm, 5 μm); mobile phase (A) 0.1% DEA in n-Hexane (B) CH$_2$Cl$_2$:MeOH (80:20) (A:B:70:30); flow Rate: 1.0 mL/min); Optical rotation [α]$_D^{20.01}$: +1.47° (c=0.25, CH$_2$Cl$_2$). TLC: 10% MeOH/CH$_2$Cl$_2$ (R$_f$: 0.7).

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. A compound selected from the group consisting of:
   (−)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one;
   (−)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate;
   (+)-tert-butyl 4-(2-((3,4-trans)-1-benzyl-4-methylpyrrolidin-3-yl)-4-oxo-3,4-dihydroimidazo[1,5-f][1,2,4]triazin-7-yl)piperidine-1-carboxylate;
   (+)-2-((3,4-trans)-1-benzyl-4-methylpyrrolidin-3-yl)-7-(5-fluoro-2-methylphenyl)imidazo[1,5-f][1,2,4]triazin-4(3H)-one;
   (−)-2-((3,4-trans)-1-benzyl-4-methylpyrrolidin-3-yl)-7-(5-fluoro-2-methylphenyl)imidazo[1,5-f][1,2,4]triazin-4(3H)-one;
   (+)-7-(5-fluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one;
   (−)-7-(5-fluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one;
   (−)-2-((3,4-trans)-1-benzyl-4-methylpyrrolidin-3-yl)-7-(piperidin-4-yl)imidazo[1,5-f][1,2,4]triazin-4(3H)-one;
   (+)-2-((3,4-trans)-1-benzyl-4-methylpyrrolidin-3-yl)-7-(piperidin-4-yl)imidazo[1,5-f][1,2,4]triazin-4(3H)-one;
   (+)-2-((3,4-trans)-4-methyl-1-(pyrimidin-2-ylmethyl)pyrrolidin-3-yl)-7-(tetrahydrofuran-3-yl)imidazo[5,1-f][1,2,4]triazin-4(3H)-one;
   (−)-2-(1-(3,4-trans)-benzyl-4-methylpyrrolidin-3-yl)-7-(tetrahydrofuran-3-yl)imidazo[5,1-f][1,2,4]triazin-4(3H)-one;
   (−)-3-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;
   (+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;
   (−)-2-((3,4-trans)-1-((6-methoxypyridin-2-yl)methyl)-4-methylpyrrolidin-3-yl)-7-(tetrahydro-2H-pyran-4-yl)imidazo[5,1-f][1,2,4]triazin-4(3H)-one;
   (−)-2-((3,4-trans)-1-(2-fluorobenzyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyridin-2-ylmethyl)pyrrolidin-3-yl)-7-(tetrahydro-2H-pyran-4-yl)imidazo[5,1-f][1,2,4]triazin-4(3H)-one;

(−)-2-((3,4-trans)-1-(4-fluorobenzyl)-4-methylpyrrolidin-3-yl)-7-(tetrahydro-2H-pyran-4-yl)imidazo[5,1-f][1,2,4]triazin-4(3H)-one;

(−)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)methyl)benzonitrile;

2-((3,4-trans)-1-benzyl-4-methylpyrrolidin-3-yl)-7-(1-methylpiperidin-4-yl)imidazo[5,1-f][1,2,4]triazin-4(3H)-one;

(+)-2-((3,4-trans)-4-methyl-1-((R)-1-phenylethyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-((S)-1-phenylethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(4-(trifluoromethyl)benzyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(3-(trifluoromethyl)benzyl)pyrrolidin-3-yl)-7-(tetrahydro-2H-pyran-4-yl)imidazo[5,1-f][1,2,4]triazin-4(3H)-one;

(+)-2-((3,4-trans)-1-(3-chlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2,4-difluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(2-(trifluoromethyl)benzyl)pyrrolidin-3-yl)-7-(tetrahydro-2H-pyran-4-yl)imidazo[5,1-f][1,2,4]triazin-4(3H)-one;

(+)-2-((3,4-trans)-1-(2-fluoro-5-methoxybenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(isoquinolin-7-ylmethyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinolin-6-ylmethyl)pyrrolidin-3-yl)-7-(tetrahydro-2H-pyran-4-yl)imidazo[5,1-f][1,2,4]triazin-4(3H)-one;

(+)-2-((3,4-trans)-1-(2-chlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-chlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2,5-difluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2,3-difluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrimidin-2-ylmethyl)pyrrolidin-3-yl)-7-(o-tolyl)imidazo[5,1-f][1,2,4]triazin-4(3H)-one;

(+)-2-((3,4-trans)-4-methyl-1-(pyridin-4-ylmethyl)pyrrolidin-3-yl)-7-(tetrahydro-2H-pyran-4-yl)imidazo[5,1-f][1,2,4]triazin-4(3H)-one;

(+)-2-((3,4-trans)-1-(isoquinolin-6-ylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(quinolin-7-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((2-oxo-1,2-dihydropyridin-3-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyridazin-3-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyridazin-4-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinazolin-6-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinoxalin-6-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinoxalin-2-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((1-methyl-1H-benzo[d]imidazol-2-yl)methyl)pyrrolidin-3-yl)-7-(tetrahydro-2H-pyran-4-yl)imidazo[5,1-f][1,2,4]triazin-4(3H)-one;

(−)-2-((3,4-trans)-1-((1H-benzo[d]imidazol-2-yl)methyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(imidazo[1,2-a]pyridin-2-ylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-benzoyl-4-methylpyrrolidin-3-yl)-7-(tetrahydro-2H-pyran-4-yl)imidazo[5,1-f][1,2,4]triazin-4(3H)-one;

(−)-2-((3,4-trans)-1-(2-fluorobenzoyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(3-fluorobenzoyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(4-fluorobenzoyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-nicotinoylpyrrolidin-3-yl)-7-(tetrahydro-2H-pyran-4-yl)imidazo[5,1-f][1,2,4]triazin-4(3H)-one;

(+)-2-((3,4-trans)-1-(4-fluorobenzoyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-benzoyl-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyridin-3-ylmethyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((2-methylpyrimidin-4-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrimidin-4-ylmethyl)pyrrolidin-3-yl)-7-(tetrahydro-2H-pyran-4-yl)imidazo[5,1-f][1,2,4]triazin-4(3H)-one;

(−)-2-((3,4-trans)-1-(imidazo[1,2-a]pyrimidin-2-ylmethyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(phenylsulfonyl)pyrrolidin-3-yl)-7-(tetrahydro-2H-pyran-4-yl)imidazo[5,1-f][1,2,4]triazin-4(3H)-one;

(+)-2-((3,4-trans)-1-((2-fluorophenyl)sulfonyl)-4-methyl-pyrrolidin-3-yl)-7-(tetrahydro-2H-pyran-4-yl)imidazo[5,1-f][1,2,4]triazin-4(3H)-one;

(+)-2-((3,4-trans)-1-((4-fluorophenyl)sulfonyl)-4-methyl-pyrrolidin-3-yl)-7-(tetrahydro-2H-pyran-4-yl)imidazo[5,1-f][1,2,4]triazin-4(3H)-one;

(−)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile;

(−)-2-((3,4-trans)-4-methyl-1-(phenylsulfonyl)pyrrolidin-3-yl)-7-(tetrahydro-2H-pyran-4-yl)imidazo[5,1-f][1,2,4]triazin-4(3H)-one;

(−)-2-((3,4-trans)-1-((4-fluorophenyl)sulfonyl)-4-methyl-pyrrolidin-3-yl)-7-(tetrahydro-2H-pyran-4-yl)imidazo[5,1-f][1,2,4]triazin-4(3H)-one;

(+)-2-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile;

(+)-2-((3,4-trans)-4-methyl-1-(pyrimidin-5-ylmethyl)pyrrolidin-3-yl)-7-(tetrahydro-2H-pyran-4-yl)imidazo[5,1-f][1,2,4]triazin-4(3H)-one;

(−)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile;

(+)-2-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile;

(−)-2-((3,4-trans)-4-methyl-1-(pyrimidine-2-carbonyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrimidine-2-carbonyl)pyrrolidin-3-yl)-7-(tetrahydro-2H-pyran-4-yl)imidazo[5,1-f][1,2,4]triazin-4(3H)-one;

(−)-2-((3,4-trans)-1-isonicotinoyl-4-methylpyrrolidin-3-yl)-7-(tetrahydro-2H-pyran-4-yl)imidazo[5,1-f][1,2,4]triazin-4(3H)-one;

(−)-4-((3,4-trans)-3-methyl-4-(4-oxo-7-(tetrahydro-2H-pyran-4-yl)-3,4-dihydroimidazo[5,1-f][1,2,4]triazin-2-yl)pyrrolidine-1-carbonyl)benzonitrile;

(−)-2-((3,4-trans)-4-methyl-1-(pyrimidine-5-carbonyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyrazine-2-carbonyl)pyrrolidin-3-yl)-7-(tetrahydro-2H-pyran-4-yl)imidazo[5,1-f][1,2,4]triazin-4(3H)-one;

(+)-2-((3,4-trans)-1-((3-fluorophenyl)sulfonyl)-4-methyl-pyrrolidin-3-yl)-7-(tetrahydro-2H-pyran-4-yl)imidazo[5,1-f][1,2,4]triazin-4(3H)-one;

(+)-4-(((3,4-trans)-3-methyl-4-(4-oxo-7-(tetrahydro-2H-pyran-4-yl)-3,4-dihydroimidazo[5,1-f][1,2,4]triazin-2-yl)pyrrolidin-1-yl)sulfonyl)benzonitrile;

(+)-2-((3,4-trans)-4-methyl-1-(quinolin-7-ylmethyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-picolinoylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(quinoline-2-carbonyl)pyrrolidin-3-yl)-7-(tetrahydro-2H-pyran-4-yl)imidazo[5,1-f][1,2,4]triazin-4(3H)-one;

(−)-2-((3,4-trans)-4-methyl-1-(pyrimidine-4-carbonyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyridin-3-ylsulfonyl)pyrrolidin-3-yl)-7-(tetrahydro-2H-pyran-4-yl)imidazo[5,1-f][1,2,4]triazin-4(3H)-one;

(+)-2-((3,4-trans)-1-(2-methoxybenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3-methoxybenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-methoxybenzyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(quinazoline-2-carbonyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(2-methylbenzyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(3-methylbenzyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(4-methylbenzyl)pyrrolidin-3-yl)-7-(tetrahydro-2H-pyran-4-yl)imidazo[5,1-f][1,2,4]triazin-4(3H)-one;

(−)-2-((3,4-trans)-1-(ethylsulfonyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(ethylsulfonyl)-4-methylpyrrolidin-3-yl)-7-(tetrahydro-2H-pyran-4-yl)imidazo[5,1-f][1,2,4]triazin-4(3H)-one;

(−)-2-((3,4-trans)-1-(cyclohexylmethyl)-4-methylpyrrolidin-3-yl)-7-(tetrahydro-2H-pyran-4-yl)imidazo[5,1-f][1,2,4]triazin-4(3H)-one;

(−)-2-((3,4-trans)-4-methyl-1-(4-(pyrrolidin-1-yl)benzyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(2-(pyrrolidin-1-yl)benzyl)pyrrolidin-3-yl)-7-(tetrahydro-2H-pyran-4-yl)imidazo[5,1-f][1,2,4]triazin-4(3H)-one;

(+)-2-((3,4-trans)-1-(2-(dimethylamino)benzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3-(dimethylamino)benzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-(dimethylamino)benzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-phenethylpyrrolidin-3-yl)-7-(tetrahydro-2H-pyran-4-yl)imidazo[5,1-f][1,2,4]triazin-4(3H)-one;

(+)-2-((3,4-trans)-1-((6-methoxypyridin-3-yl)methyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(pyrimidin-2-yl)pyrrolidin-3-yl)-7-(tetrahydro-2H-pyran-4-yl)imidazo[5,1-f][1,2,4]triazin-4(3H)-one;

(+)-2-((3,4-trans)-1-(2,6-difluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3-cyclopropylbenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-cyclopropylbenzyl)-4-methylpyrrolidin-3-yl)-7-(tetrahydro-2H-pyran-4-yl)imidazo[5,1-f][1,2,4]triazin-4(3H)-one;

(+)-((3,4-trans)-1,4-dimethylpyrrolidin-3-yl)-7-(tetrahydro-2H-pyran-4-yl)imidazo[5,1-f][1,2,4]triazin-4(3H)-one;

(−)-2-((3,4-trans)-1-(2-cyclopropylbenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3-(1H-pyrazol-1-yl)benzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(quinolin-4-ylmethyl)pyrrolidin-3-yl)-7-(tetrahydro-2H-pyran-4-yl)imidazo[5,1-f][1,2,4]triazin-4(3H)-one;

(+)-2-((3,4-trans)-1-((1,3-dimethyl-1H-pyrazol-5-yl)methyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-((2-methylpyrimidin-5-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((2-methylthiazol-5-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((6-methylpyridin-3-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((5-methylpyrazin-2-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((5-methylpyrazin-2-yl)methyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-(3-(pyrrolidin-1-yl)benzyl)pyrrolidin-3-yl)-7-(tetrahydro-2H-pyran-4-yl)imidazo[5,1-f][1,2,4]triazin-4(3H)-one;

(+)-2-((3,4-trans)-4-methyl-1-((6-(trifluoromethyl)pyridin-3-yl)methyl)pyrrolidin-3-yl)-7-(tetrahydro-2H-pyran-4-yl)imidazo[5,1-f][1,2,4]triazin-4(3H)-one;

(+)-2-((3,4-trans)-1-((2-ethylpyrimidin-5-yl)methyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3-bromobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2,4-dichlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(4-bromobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3,5-dichlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(3-(trifluoromethoxy)benzyl)pyrrolidin-3-yl)-7-(tetrahydro-2H-pyran-4-yl)imidazo[5,1-f][1,2,4]triazin-4(3H)-one;

(+)-2-((3,4-trans)-1-(2-chloro-4-fluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2-bromobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4,4-difluorocyclohexyl)imidazo[5,1-f][1,2,4]triazin-4(3H)-one;

(+)-2-((3,4-trans)-1-(4-chloro-3-fluorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-4-methyl-1-(4-(trifluoromethoxy)benzyl)pyrrolidin-3-yl)-7-(tetrahydro-2H-pyran-4-yl)imidazo[5,1-f][1,2,4]triazin-4(3H)-one;

(+)-2-((3,4-trans)-1-(4-fluoro-3-(trifluoromethyl)benzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(2,5-dichlorobenzyl)-4-methylpyrrolidin-3-yl)-7-(tetrahydro-2H-pyran-4-yl)imidazo[5,1-f][1,2,4]triazin-4(3H)-one;

(+)-2-((3,4-trans)-1-(3,5-difluorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(3,4-dichlorobenzyl)-4-methylpyrrolidin-3-yl)-7-(tetrahydro-2H-pyran-4-yl)imidazo[1,5-f][1,2,4]triazin-4(3H)-one;

(+)-(4,4-difluorocyclohexyl)-2-((3,4-trans)-1-(4-fluorobenzyl)-4-methylpyrrolidin-3-yl)imidazo[5,1-f][1,2,4]triazin-4(3H)-one;

(+)-2-((3,4-trans)-1-(4-chlorobenzyl)-4-methylpyrrolidin-3-yl)-7-(4,4-difluorocyclohexyl)imidazo[5,1-f][1,2,4]triazin-4(3H)-one;

(+)-7-(4,4-difluorocyclohexyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-2-((3,4-trans)-1-((3aH-benzo[d]imidazol-2-yl)methyl)-4-methylpyrrolidin-3-yl)-7-(4,4-difluorocyclohexyl)imidazo[1,5-f][1,2,4]triazin-4(3H)-one;

(+)-7-(4,4-difluorocyclohexyl)-2-((3,4-trans)-4-methyl-1-(pyridin-2-ylmethyl)pyrrolidin-3-yl)imidazo[1,5-f][1,2,4]triazin-4(3H)-one;

(+)-7-(4,4-difluorocyclohexyl)-2-((3,4-trans)-4-methyl-1-(pyridin-3-ylmethyl)pyrrolidin-3-yl)imidazo[1,5-f][1,2,4]triazin-4(3H)-one;

(+)-7-(4,4-difluorocyclohexyl)-2-((3,4-trans)-4-methyl-1-(pyrazin-2-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(5-fluoro-2-methylphenyl)imidazo[1,5-f][1,2,4]triazin-4(3H)-one;

(+)-2-((3,4-trans)-1-(4-chlorobenzyl)-4-methylpyrrolidin-3-yl)-7-(5-fluoro-2-methylphenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(5-fluoro-2-methylphenyl)imidazo[1,5-f][1,2,4]triazin-4(3H)-one;

(+)-7-(5-fluoro-2-methylphenyl)-2-((3,4-trans)-1-(4-fluorobenzyl)-4-methylpyrrolidin-3-yl)imidazo[1,5-f][1,2,4]triazin-4(3H)-one;

(+)-7-(5-fluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(5-fluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(+)-7-(5-fluoro-2-methylphenyl)-2-((3,4-trans)-4-methyl-1-(pyridin-2-ylmethyl)pyrrolidin-3-yl)imidazo[1,5-f][1,2,4]triazin-4(3H)-one;

(+)-(+)-7-(5-fluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(4-fluorocyclohexyl)imidazo[1,5-f][1,2,4]triazin-4(3H)-one;

(+)-2-((3,4-trans)-1-(4-chlorobenzyl)-4-methylpyrrolidin-3-yl)-7-(4-fluorocyclohexyl)imidazo[1,5-f][1,2,4]triazin-4(3H)-one;

(+)-2-((3,4-trans)-1-(4-fluorobenzyl)-4-methylpyrrolidin-3-yl)-7-(4-fluorocyclohexyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4-fluorocyclohexyl)imidazo[1,5-f][1,2,4]triazin-4(3H)-one;

(+)-2-((3,4-trans)-1-benzyl-4-methylpyrrolidin-3-yl)-7-(4-fluorocyclohexyl)imidazo[1,5-f][1,2,4]triazin-4(3H)-one;

(+)-2-((3,4-trans)-1-benzyl-4-methylpyrrolidin-3-yl)-7-(4-fluorocyclohexyl)imidazo[1,5-f][1,2,4]triazin-4(3H)-one;

(+)-7-(4-fluorocyclohexyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(4-fluorocyclohexyl)-2-((3,4-trans)-4-methyl-1-(pyrazin-2-ylmethyl)pyrrolidin-3-yl)imidazo[1,5-f][1,2,4]triazin-4(3H)-one;

(+)-7-(4-fluorocyclohexyl)-2-((3,4-trans)-4-methyl-1-(pyridin-2-ylmethyl)pyrrolidin-3-yl)imidazo[1,5-f][1,2,4]triazin-4(3H)-one;

(+)-7-(4-fluorocyclohexyl)-2-((3,4-trans)-4-methyl-1-(pyridin-3-ylmethyl)pyrrolidin-3-yl)imidazo[1,5-f][1,2,4]triazin-4(3H)-one;

(+)-7-(4-fluorocyclohexyl)-2-((3,4-trans)-4-methyl-1-(pyrimidin-2-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(4-fluorophenyl)imidazo[1,5-f][1,2,4]triazin-4(3H)-one;

(+)-2-((3,4-trans)-1-(4-chlorobenzyl)-4-methylpyrrolidin-3-yl)-7-(4-fluorophenyl)imidazo[1,5-f][1,2,4]triazin-4(3H)-one;

(+)-2-((3,4-trans)-1-(4-fluorobenzyl)-4-methylpyrrolidin-3-yl)-7-(4-fluorophenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4-fluorophenyl)imidazo[1,5-f][1,2,4]triazin-4(3H)-one;

(+)-2-((3,4-trans)-1-benzyl-4-methylpyrrolidin-3-yl)-7-(4-fluorophenyl)imidazo[1,5-f][1,2,4]triazin-4(3H)-one;

(+)-7-(4-fluorophenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(4-fluorophenyl)-2-((3,4-trans)-4-methyl-1-(pyrazin-2-ylmethyl)pyrrolidin-3-yl)imidazo[1,5-f][1,2,4]triazin-4(3H)-one;

(+)-7-(4-fluorophenyl)-2-((3,4-trans)-4-methyl-1-(pyridin-2-ylmethyl)pyrrolidin-3-yl)imidazo[1,5-f][1,2,4]triazin-4(3H)-one;

(+)-7-(4-fluorophenyl)-2-((3,4-trans)-4-methyl-1-(pyridin-3-ylmethyl)pyrrolidin-3-yl)imidazo[1,5-f][1,2,4]triazin-4(3H)-one;

(+)-7-(4-fluorophenyl)-2-((3,4-trans)-4-methyl-1-(pyrimidin-2-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(3-fluorophenyl)imidazo[1,5-f][1,2,4]triazin-4(3H)-one;

(+)-2-((3,4-trans)-1-(4-chlorobenzyl)-4-methylpyrrolidin-3-yl)-7-(3-fluorophenyl)imidazo[1,5-f][1,2,4]triazin-4(3H)-one;

(+)-2-((3,4-trans)-1-(4-fluorobenzyl)-4-methylpyrrolidin-3-yl)-7-(3-fluorophenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(3-fluorophenyl)imidazo[1,5-f][1,2,4]triazin-4(3H)-one;

(+)-2-((3,4-trans)-1-benzyl-4-methylpyrrolidin-3-yl)-7-(3-fluorophenyl)imidazo[1,5-f][1,2,4]triazin-4(3H)-one;

(+)-7-(3-fluorophenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(3-fluorophenyl)-2-((3,4-trans)-4-methyl-1-(pyrazin-2-ylmethyl)pyrrolidin-3-yl)imidazo[1,5-f][1,2,4]triazin-4(3H)-one;

(+)-7-(3-fluorophenyl)-2-((3,4-trans)-4-methyl-1-(pyridin-2-ylmethyl)pyrrolidin-3-yl)imidazo[1,5-f][1,2,4]triazin-4(3H)-one;

(+)-7-(3-fluorophenyl)-2-((3,4-trans)-4-methyl-1-(pyridin-3-ylmethyl)pyrrolidin-3-yl)imidazo[1,5-f][1,2,4]triazin-4(3H)-one;

(+)-7-(3-fluorophenyl)-2-((3,4-trans)-4-methyl-1-(pyrimidin-2-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-o-tolylimidazo[1,5-f][1,2,4]triazin-4(3H)-one;

(+)-2-((3,4-trans)-1-(4-chlorobenzyl)-4-methylpyrrolidin-3-yl)-7-o-tolylimidazo[1,5-f][1,2,4]triazin-4(3H)-one;

(+)-2-((3,4-trans)-1-(4-fluorobenzyl)-4-methylpyrrolidin-3-yl)-7-o-tolylimidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-o-tolylimidazo[1,5-f][1,2,4]triazin-4(3H)-one;

(+)-2-((3,4-trans)-1-(imidazo[1,2-a]pyridin-2-ylmethyl)-4-methylpyrrolidin-3-yl)-7-o-tolylimidazo[1,5-f][1,2,4]triazin-4(3H)-one;

(+)-2-((3,4-trans)-1-benzyl-4-methylpyrrolidin-3-yl)-7-o-tolylimidazo[1,5-f][1,2,4]triazin-4(3H)-one;

(+)-2-((3,4-trans)-4-methyl-1-(pyrazin-2-ylmethyl)pyrrolidin-3-yl)-7-o-tolylimidazo[1,5-f][1,2,4]triazin-4(3H)-one;

(+)-2-((3,4-trans)-4-methyl-1-(pyridin-2-ylmethyl)pyrrolidin-3-yl)-7-o-tolylimidazo[1,5-f][1,2,4]triazin-4(3H)-one;

(+)-2-((3,4-trans)-4-methyl-1-(pyridin-3-ylmethyl)pyrrolidin-3-yl)-7-o-tolylimidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(4,5-difluoro-2-methylphenyl)imidazo[1,5-f][1,2,4]triazin-4(3H)-one;

(+)-2-((3,4-trans)-1-(4-chlorobenzyl)-4-methylpyrrolidin-3-yl)-7-(4,5-difluoro-2-methylphenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4,5-difluoro-2-methylphenyl)imidazo[1,5-f][1,2,4]triazin-4(3H)-one;

(+)-2-((3,4-trans)-1-benzyl-4-methylpyrrolidin-3-yl)-7-(4,5-difluoro-2-methylphenyl)imidazo[1,5-f][1,2,4]triazin-4(3H)-one;

(+)-7-(4,5-difluoro-2-methylphenyl)-2-((3,4-trans)-1-(4-fluorobenzyl)-4-methylpyrrolidin-3-yl)imidazo[1,5-f][1,2,4]triazin-4(3H)-one;

(+)-7-(4,5-difluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(4,5-difluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(+)-7-(4,5-difluoro-2-methylphenyl)-2-((3,4-trans)-4-methyl-1-(pyridin-2-ylmethyl)pyrrolidin-3-yl)imidazo[1,5-f][1,2,4]triazin-4(3H)-one;

(+)-7-(4,5-difluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(+)-7-(4,5-difluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-phenylimidazo[1,5-f][1,2,4]triazin-4(3H)-one;

(+)-2-((3,4-trans)-1-(4-chlorobenzyl)-4-methylpyrrolidin-3-yl)-7-phenylimidazo[1,5-f][1,2,4]triazin-4(3H)-one;

(+)-2-((3,4-trans)-1-(4-fluorobenzyl)-4-methylpyrrolidin-3-yl)-7-phenylimidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-phenylimidazo[1,5-f][1,2,4]triazin-4(3H)-one;

(+)-2-((3,4-trans)-1-(imidazo[1,2-a]pyridin-2-ylmethyl)-4-methylpyrrolidin-3-yl)-7-phenylimidazo[1,5-f][1,2,4]triazin-4(3H)-one;

(+)-2-((3,4-trans)-1-benzyl-4-methylpyrrolidin-3-yl)-7-phenylimidazo[1,5-f][1,2,4]triazin-4(3H)-one;

(+)-2-((3,4-trans)-4-methyl-1-(pyrazin-2-ylmethyl)pyrrolidin-3-yl)-7-phenylimidazo[1,5-f][1,2,4]triazin-4(3H)-one;

(+)-2-((3,4-trans)-4-methyl-1-(pyridin-2-ylmethyl)pyrrolidin-3-yl)-7-phenylimidazo[1,5-f][1,2,4]triazin-4(3H)-one;

(+)-2-((3,4-trans)-4-methyl-1-(pyridin-3-ylmethyl)pyrrolidin-3-yl)-7-phenylimidazo[1,5-f][1,2,4]triazin-4(3H)-one;

(+)-2-((3,4-trans)-4-methyl-1-(pyrimidin-2-ylmethyl)pyrrolidin-3-yl)-7-phenylimidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(4-(trifluoromethyl)phenyl)imidazo[1,5-f][1,2,4]triazin-4(3H)-one;

(+)-2-((3,4-trans)-1-(4-chlorobenzyl)-4-methylpyrrolidin-3-yl)-7-(4-(trifluoromethyl)phenyl)imidazo[1,5-f][1,2,4]triazin-4(3H)-one;

(+)-2-((3,4-trans)-1-(4-fluorobenzyl)-4-methylpyrrolidin-3-yl)-7-(4-(trifluoromethyl)phenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4-(trifluoromethyl)phenyl)imidazo[1,5-f][1,2,4]triazin-4(3H)-one;

(+)-2-((3,4-trans)-1-(imidazo[1,2-a]pyridin-2-ylmethyl)-4-methylpyrrolidin-3-yl)-7-(4-(trifluoromethyl)phenyl)imidazo[1,5-f][1,2,4]triazin-4(3H)-one;

(+)-2-((3,4-trans)-1-benzyl-4-methylpyrrolidin-3-yl)-7-(4-(trifluoromethyl)phenyl)imidazo[1,5-f][1,2,4]triazin-4(3H)-one;

(+)-2-((3,4-trans)-4-methyl-1-(pyrazin-2-ylmethyl)pyrrolidin-3-yl)-7-(4-(trifluoromethyl)phenyl)imidazo[1,5-f][1,2,4]triazin-4(3H)-one;

(+)-2-((3,4-trans)-4-methyl-1-(pyridin-2-ylmethyl)pyrrolidin-3-yl)-7-(4-(trifluoromethyl)phenyl)imidazo[1,5-f][1,2,4]triazin-4(3H)-one;

(+)-2-((3,4-trans)-4-methyl-1-(pyridin-3-ylmethyl)pyrrolidin-3-yl)-7-(4-(trifluoromethyl)phenyl)imidazo[1,5-f][1,2,4]triazin-4(3H)-one;

(+)-2-((3,4-trans)-4-methyl-1-(pyrimidin-2-ylmethyl)pyrrolidin-3-yl)-7-(4-(trifluoromethyl)phenyl)imidazo[1,5-f][1,2,4]triazin-4(3H)-one;

(+)-2-((3,4-trans)-1-((1H-benzo[d]imidazol-2-yl)methyl)-4-methylpyrrolidin-3-yl)-7-(4-fluoro-2-methylphenyl)imidazo[1,5-f][1,2,4]triazin-4(3H)-one;

(+)-2-((3,4-trans)-1-(4-chlorobenzyl)-4-methylpyrrolidin-3-yl)-7-(4-fluoro-2-methylphenyl)imidazo[1,5-f][1,2,4]triazin-4(3H)-one;

(+)-2-((3,4-trans)-1-([1,2,4]triazolo[1,5-a]pyridin-2-ylmethyl)-4-methylpyrrolidin-3-yl)-7-(4-fluoro-2-methylphenyl)imidazo[1,5-f][1,2,4]triazin-4(3H)-one;

(+)-7-(4-fluoro-2-methylphenyl)-2-((3,4-trans)-1-(4-fluorobenzyl)-4-methylpyrrolidin-3-yl)imidazo[1,5-f][1,2,4]triazin-4(3H)-one;

(+)-7-(4-fluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(+)-7-(4-fluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(+)-7-(4-fluoro-2-methylphenyl)-2-((3,4-trans)-4-methyl-1-(pyridin-2-ylmethyl)pyrrolidin-3-yl)imidazo[1,5-f][1,2,4]triazin-4(3H)-one;

(+)-7-(4-fluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(+)-2-((3,4-trans)-4-methyl-1-(4-(trifluoromethyl)pyrimidin-2-yl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(2,2,2-trifluoroethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((2-methylpyridin-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(quinolin-8-ylmethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((3-methylpyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((2-methylpyridin-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((2-propylpyrimidin-5-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(2-(pyrimidin-2-yl)ethyl)pyrrolidin-3-yl)-7-(tetrahydro-2H-pyran-4-yl)imidazo[1,5-f][1,2,4]triazin-4(3H)-one;

(+)-2-((3,4-trans)-1-((1,5-naphthyridin-4-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((1,8-naphthyridin-4-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((2-(dimethylamino)pyrimidin-4-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(cinnolin-3-ylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((4,5,6,7-tetrahydropyrazolo[1,5-a]pyridin-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(2-(pyrimidin-5-yl)ethyl)pyrrolidin-3-yl)-7-(tetrahydro-2H-pyran-4-yl)imidazo[1,5-f][1,2,4]triazin-4(3H)-one;

(+)-2-((3,4-trans)-1-((8-fluoroquinolin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(benzo[c][1,2,5]thiadiazol-5-ylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-imidazol-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-imidazol-5-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-pyrazol-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-pyrazol-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-pyrazol-5-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(thiazol-2-ylmethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(quinuclidin-4-ylmethyl)pyrrolidin-3-yl)-7-(tetrahydro-2H-pyran-4-yl)imidazo[1,5-f][1,2,4]triazin-4(3H)-one;

(+)-2-((3,4-trans)-1-((1,3,5-triazin-2-yl)methyl)-4-methylpyrrolidin-3-yl)-7-(tetrahydro-2H-pyran-4-yl)imidazo[1,5-f][1,2,4]triazin-4(3H)-one;

(+)-2-fluoro-5-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzonitrile;

(+)-2-((3,4-trans)-1-((4,6-dimethylpyrimidin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chloropyrimidin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(2,3-dichlorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(3-chloro-4-fluorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((4-methylpyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((6-methylpyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(pyrido[2,3-d]pyrimidin-2-ylmethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(pyrido[3,2-b]pyrazin-3-ylmethyl)pyrrolidin-3-yl)-7-(tetrahydro-2H-pyran-4-yl)imidazo[1,5-f][1,2,4]triazin-4(3H)-one;

(+)-tert-butyl 4-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)piperidine-1-carboxylate;

(+)-2-((3,4-trans)-1-((1,2,4-oxadiazol-5-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((4,4-difluorocyclohexyl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chlorofuran-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chlorofuran-3-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chlorothiophen-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chlorothiophen-3-yl)methyl)-4-methylpyrrolidin-3-yl)-7-(tetrahydro-2H-pyran-4-yl)imidazo[1,5-f][1,2,4]triazin-4(3H)-one (+)-2-((3,4-trans)-1-(cyclopentylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(cyclopropylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(furan-2-ylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(furan-3-ylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methylpiperidin-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((tetrahydro-2H-pyran-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(piperidin-4-ylmethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(thiophen-2-ylmethyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(thiophen-3-ylmethyl)pyrrolidin-3-yl)-7-(tetrahydro-2H-pyran-4-yl)imidazo[1,5-f][1,2,4]triazin-4(3H)-one;

(+)-2-((3,4-trans)-1-((2-methoxypyridin-4-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((2-methoxypyrimidin-5-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((4-methoxypyridin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-chloropyridin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-fluoropyridin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-methoxypyridin-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-methoxypyridin-3-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(2-chloro-5-fluorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(4-chloro-3-(trifluoromethyl)benzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(4-chloro-3-methylbenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(5-chloro-2-fluorobenzyl)-4-methyl-pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((5-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((6-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(2-(trifluoromethoxy)benzyl)pyrrolidin-3-yl)-7-(tetrahydro-2H-pyran-4-yl)imidazo[1,5-f][1,2,4]triazin-4(3H)-one;

(+)-2-((3,4-trans)-1-((2-methoxypyridin-4-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((5-methoxypyridin-3-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(2-chloro-3,6-difluorobenzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(2-chloro-6-fluorobenzyl)-4-methyl-pyrrolidin-3-yl)-7-(tetrahydro-2H-pyran-4-yl)imidazo[1,5-f][1,2,4]triazin-4(3H)-one;

(+)-2-((3,4-trans)-1-(3-chloro-5-(trifluoromethyl)benzyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((3-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((4-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((5-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((6-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(+)-N,N-dimethyl-2-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(+)-N,N-dimethyl-3-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(+)-N,N-dimethyl-4-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(+)-2-((3,4-trans)-1-((1,2,4-oxadiazol-3-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-((1,3,4-oxadiazol-2-yl)methyl)-4-methylpyrrolidin-3-yl)-7-(tetrahydro-2H-pyran-4-yl)imidazo[1,5-f][1,2,4]triazin-4(3H)-one;

(+)-2-((3,4-trans)-1-(biphenyl-4-ylmethyl)-4-methylpyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-1,2,4-triazol-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((1-methyl-1H-imidazol-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((2-methylthiazol-4-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((5-(trifluoromethyl)-1,2,4-oxadiazol-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((5-methyl-1,2,4-oxadiazol-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-((5-methyl-1H-1,2,4-triazol-3-yl)methyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(4-(pyridin-4-yl)benzyl)pyrrolidin-3-yl)-7-(tetrahydro-2H-pyran-4-yl)imidazo[1,5-f][1,2,4]triazin-4(3H)-one;

(+)-2-((3,4-trans)-4-methyl-1-(oxazol-2-ylmethyl)pyrrolidin-3-yl)-7-(tetrahydro-2H-pyran-4-yl)imidazo[1,5-f][1,2,4]triazin-4(3H)-one;

(−)-7-(4,4-difluorocyclohexyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-2-((3,4-trans)-1-((3 aH-benzo [d]imidazol-2-yl)methyl)-4-methylpyrrolidin-3-yl)-7-(4,4-difluorocyclohexyl)imidazo[1,5-f][1,2,4]triazin-4(3H)-one;

(−)-7-(4,4-difluorocyclohexyl)-2-((3,4-trans)-4-methyl-1-(pyridin-2-ylmethyl)pyrrolidin-3-yl)imidazo[1,5-f][1,2,4]triazin-4(3H)-one;

(−)-7-(4,4-difluorocyclohexyl)-2-((3,4-trans)-4-methyl-1-(pyridin-3-ylmethyl)pyrrolidin-3-yl)imidazo[1,5-f][1,2,4]triazin-4(3H)-one;

(−)-7-(4,4-difluorocyclohexyl)-2-((3,4-trans)-4-methyl-1-(pyrazin-2-ylmethyl)pyrrolidin-3-yl)imidazo[1,5-f][1,2,4]triazin-4(3H)-one;

(−)-2-((3,4-trans)-1-((1H-benzo [d]imidazol-2-yl)methyl)-4-methylpyrrolidin-3-yl)-7-(5-fluoro-2-methylphenyl)imidazo[1,5-f][1,2,4]triazin-4(3H)-one;

(−)-2-((3,4-trans)-1-(4-chlorobenzyl)-4-methylpyrrolidin-3-yl)-7-(5-fluoro-2-methylphenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(5-fluoro-2-methylphenyl)imidazo[1,5-f][1,2,4]triazin-4(3H)-one;

(−)-7-(5-fluoro-2-methylphenyl)-2-((3,4-trans)-1-(4-fluorobenzyl)-4-methylpyrrolidin-3-yl)imidazo[1,5-f][1,2,4]triazin-4(3H)-one;

(−)-7-(5-fluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(5-fluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(−)-7-(5-fluoro-2-methylphenyl)-2-((3,4-trans)-4-methyl-1-(pyridin-2-ylmethyl)pyrrolidin-3-yl)imidazo[1,5-f][1,2,4]triazin-4(3H)-one;

(−)-(−)-7-(5-fluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(4-fluorocyclohexyl)imidazo[1,5-f][1,2,4]triazin-4(3H)-one;

(−)-2-((3,4-trans)-1-(4-chlorobenzyl)-4-methylpyrrolidin-3-yl)-7-(4-fluorocyclohexyl)imidazo[1,5-f][1,2,4]triazin-4(3H)-one;

(−)-2-((3,4-trans)-1-(4-fluorobenzyl)-4-methylpyrrolidin-3-yl)-7-(4-fluorocyclohexyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(4-fluorocyclohexyl)imidazo[1,5-f][1,2,4]triazin-4(3H)-one;

(−)-2-((3,4-trans)-1-benzyl-4-methylpyrrolidin-3-yl)-7-(4-fluorocyclohexyl)imidazo[1,5-f][1,2,4]triazin-4(3H)-one;

(−)-2-((3,4-trans)-1-benzyl-4-methylpyrrolidin-3-yl)-7-(4-fluorocyclohexyl)imidazo[1,5-f][1,2,4]triazin-4(3H)-one;

(−)-7-(4-fluorocyclohexyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(4-fluorocyclohexyl)-2-((3,4-trans)-4-methyl-1-(pyrazin-2-ylmethyl)pyrrolidin-3-yl)imidazo[1,5-f][1,2,4]triazin-4(3H)-one;

(−)-7-(4-fluorocyclohexyl)-2-((3,4-trans)-4-methyl-1-(pyridin-2-ylmethyl)pyrrolidin-3-yl)imidazo[1,5-f][1,2,4]triazin-4(3H)-one;

(−)-7-(4-fluorocyclohexyl)-2-((3,4-trans)-4-methyl-1-(pyridin-3-ylmethyl)pyrrolidin-3-yl)imidazo[1,5-f][1,2,4]triazin-4(3H)-one;

(−)-7-(4-fluorocyclohexyl)-2-((3,4-trans)-4-methyl-1-(pyrimidin-2-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(4-fluorophenyl)imidazo[1,5-f][1,2,4]triazin-4(3H)-one;

(−)-2-((3,4-trans)-1-(4-chlorobenzyl)-4-methylpyrrolidin-3-yl)-7-(4-fluorophenyl)imidazo[1,5-f][1,2,4]triazin-4(3H)-one;

(−)-2-((3,4-trans)-1-(4-fluorobenzyl)-4-methylpyrrolidin-3-yl)-7-(4-fluorophenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(4-fluorophenyl)imidazo[1,5-f][1,2,4]triazin-4(3H)-one;

(−)-2-((3,4-trans)-1-benzyl-4-methylpyrrolidin-3-yl)-7-(4-fluorophenyl)imidazo[1,5-f][1,2,4]triazin-4(3H)-one;

(−)-7-(4-fluorophenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(4-fluorophenyl)-2-((3,4-trans)-4-methyl-1-(pyrazin-2-ylmethyl)pyrrolidin-3-yl)imidazo[1,5-f][1,2,4]triazin-4(3H)-one;

(−)-7-(4-fluorophenyl)-2-((3,4-trans)-4-methyl-1-(pyridin-2-ylmethyl)pyrrolidin-3-yl)imidazo[1,5-f][1,2,4]triazin-4(3H)-one;

(−)-7-(4-fluorophenyl)-2-((3,4-trans)-4-methyl-1-(pyridin-3-ylmethyl)pyrrolidin-3-yl)imidazo[1,5-f][1,2,4]triazin-4(3H)-one;

(−)-7-(4-fluorophenyl)-2-((3,4-trans)-4-methyl-1-(pyrimidin-2-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(3-fluorophenyl)imidazo[1,5-f][1,2,4]triazin-4(3H)-one;

(−)-2-((3,4-trans)-1-(4-chlorobenzyl)-4-methylpyrrolidin-3-yl)-7-(3-fluorophenyl)imidazo[1,5-f][1,2,4]triazin-4(3H)-one;

(−)-2-((3,4-trans)-1-(4-fluorobenzyl)-4-methylpyrrolidin-3-yl)-7-(3-fluorophenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(3-fluorophenyl)imidazo[1,5-f][1,2,4]triazin-4(3H)-one;

(−)-2-((3,4-trans)-1-benzyl-4-methylpyrrolidin-3-yl)-7-(3-fluorophenyl)imidazo[1,5-f][1,2,4]triazin-4(3H)-one;

(−)-7-(3-fluorophenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(3-fluorophenyl)-2-((3,4-trans)-4-methyl-1-(pyrazin-2-ylmethyl)pyrrolidin-3-yl)imidazo[1,5-f][1,2,4]triazin-4(3H)-one;

(−)-7-(3-fluorophenyl)-2-((3,4-trans)-4-methyl-1-(pyridin-2-ylmethyl)pyrrolidin-3-yl)imidazo[1,5-f][1,2,4]triazin-4(3H)-one;

(−)-7-(3-fluorophenyl)-2-((3,4-trans)-4-methyl-1-(pyridin-3-ylmethyl)pyrrolidin-3-yl)imidazo[1,5-f][1,2,4]triazin-4(3H)-one;

(−)-7-(3-fluorophenyl)-2-((3,4-trans)-4-methyl-1-(pyrimidin-2-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-o-tolylimidazo[1,5-f][1,2,4]triazin-4(3H)-one;

(−)-2-((3,4-trans)-1-(4-chlorobenzyl)-4-methylpyrrolidin-3-yl)-7-o-tolylimidazo[1,5-f][1,2,4]triazin-4(3H)-one;

(−)-2-((3,4-trans)-1-(4-fluorobenzyl)-4-methylpyrrolidin-3-yl)-7-o-tolylimidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-o-tolylimidazo[1,5-f][1,2,4]triazin-4(3H)-one;

(−)-2-((3,4-trans)-1-(imidazo[1,2-a]pyridin-2-ylmethyl)-4-methylpyrrolidin-3-yl)-7-o-tolylimidazo[1,5-f][1,2,4]triazin-4(3H)-one;

(−)-2-((3,4-trans)-1-benzyl-4-methylpyrrolidin-3-yl)-7-o-tolylimidazo[1,5-f][1,2,4]triazin-4(3H)-one;

(−)-2-((3,4-trans)-4-methyl-1-(pyrazin-2-ylmethyl)pyrrolidin-3-yl)-7-o-tolylimidazo[1,5-f][1,2,4]triazin-4(3H)-one;

(−)-2-((3,4-trans)-4-methyl-1-(pyridin-2-ylmethyl)pyrrolidin-3-yl)-7-o-tolylimidazo[1,5-f][1,2,4]triazin-4(3H)-one;

(−)-2-((3,4-trans)-4-methyl-1-(pyridin-3-ylmethyl)pyrrolidin-3-yl)-7-o-tolylimidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(4,5-difluoro-2-methylphenyl)imidazo[1,5-f][1,2,4]triazin-4(3H)-one;

(−)-2-((3,4-trans)-1-(4-chlorobenzyl)-4-methylpyrrolidin-3-yl)-7-(4,5-difluoro-2-methylphenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(4,5-difluoro-2-methylphenyl)imidazo[1,5-f][1,2,4]triazin-4(3H)-one;

(−)-2-((3,4-trans)-1-benzyl-4-methylpyrrolidin-3-yl)-7-(4,5-difluoro-2-methylphenyl)imidazo[1,5-f][1,2,4]triazin-4(3H)-one;

(−)-7-(4,5-difluoro-2-methylphenyl)-2-((3,4-trans)-1-(4-fluorobenzyl)-4-methylpyrrolidin-3-yl)imidazo[1,5-f][1,2,4]triazin-4(3H)-one;

(−)-7-(4,5-difluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(4,5-difluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(−)-7-(4,5-difluoro-2-methylphenyl)-2-((3,4-trans)-4-methyl-1-(pyridin-2-ylmethyl)pyrrolidin-3-yl)imidazo[1,5-f][1,2,4]triazin-4(3H)-one (−)-7-(4,5-difluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(−)-7-(4,5-difluoro-2-methylphenyl)-2-((3,4-trans)-4-methyl-1-(pyrimidin-2-ylmethyl)pyrrolidin-3-yl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-phenylimidazo[1,5-f][1,2,4]triazin-4(3H)-one;

(−)-2-((3,4-trans)-1-(4-chlorobenzyl)-4-methylpyrrolidin-3-yl)-7-phenylimidazo[1,5-f][1,2,4]triazin-4(3H)-one;

(−)-2-((3,4-trans)-1-(4-fluorobenzyl)-4-methylpyrrolidin-3-yl)-7-phenylimidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-phenylimidazo[1,5-f][1,2,4]triazin-4(3H)-one;

(−)-2-((3,4-trans)-1-(imidazo[1,2-a]pyridin-2-ylmethyl)-4-methylpyrrolidin-3-yl)-7-phenylimidazo[1,5-f][1,2,4]triazin-4(3H)-one;

(−)-2-((3,4-trans)-1-benzyl-4-methylpyrrolidin-3-yl)-7-phenylimidazo[1,5-f][1,2,4]triazin-4(3H)-one;

(−)-2-((3,4-trans)-4-methyl-1-(pyrazin-2-ylmethyl)pyrrolidin-3-yl)-7-phenylimidazo[1,5-f][1,2,4]triazin-4(3H)-one;

(−)-2-((3,4-trans)-4-methyl-1-(pyridin-2-ylmethyl)pyrrolidin-3-yl)-7-phenylimidazo[1,5-f][1,2,4]triazin-4(3H)-one;

(−)-2-((3,4-trans)-4-methyl-1-(pyridin-3-ylmethyl)pyrrolidin-3-yl)-7-phenylimidazo[1,5-f][1,2,4]triazin-4(3H)-one;

(−)-2-((3,4-trans)-4-methyl-1-(pyrimidin-2-ylmethyl)pyrrolidin-3-yl)-7-phenylimidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(4-(trifluoromethyl)phenyl)imidazo[1,5-f][1,2,4]triazin-4(3H)-one;

(−)-2-((3,4-trans)-1-(4-chlorobenzyl)-4-methylpyrrolidin-3-yl)-7-(4-(trifluoromethyl)phenyl)imidazo[1,5-f][1,2,4]triazin-4(3H)-one (−)-2-((3,4-trans)-1-(4-fluorobenzyl)-4-methylpyrrolidin-3-yl)-7-(4-(trifluoromethyl)phenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(4-(trifluoromethyl)phenyl)imidazo[1,5-f][1,2,4]triazin-4(3H)-one;

(−)-2-((3,4-trans)-1-(imidazo[1,2-a]pyridin-2-ylmethyl)-4-methylpyrrolidin-3-yl)-7-(4-(trifluoromethyl)phenyl)imidazo[1,5-f][1,2,4]triazin-4(3H)-one;

(−)-2-((3,4-trans)-1-benzyl-4-methylpyrrolidin-3-yl)-7-(4-(trifluoromethyl)phenyl)imidazo[1,5-f][1,2,4]triazin-4(3H)-one;

(−)-2-((3,4-trans)-4-methyl-1-(pyrazin-2-ylmethyl)pyrrolidin-3-yl)-7-(4-(trifluoromethyl)phenyl)imidazo[1,5-f][1,2,4]triazin-4(3H)-one (−)-2-((3,4-trans)-4-methyl-1-(pyridin-2-ylmethyl)pyrrolidin-3-yl)-7-(4-(trifluoromethyl)phenyl)imidazo[1,5-f][1,2,4]triazin-4(3H)-one (−)-2-((3,4-trans)-4-methyl-1-(pyridin-3-ylmethyl)pyrrolidin-3-yl)-7-(4-(trifluoromethyl)phenyl)imidazo[1,5-f][1,2,4]triazin-4(3H)-one;

(−)-2-((3,4-trans)-4-methyl-1-(pyrimidin-2-ylmethyl)pyrrolidin-3-yl)-7-(4-(trifluoromethyl)phenyl)imidazo[1,5-f][1,2,4]triazin-4(3H)-one;

(−)-2-((3,4-trans)-1-((1H-benzo[d]imidazol-2-yl)methyl)-4-methylpyrrolidin-3-yl)-7-(4-fluoro-2-methylphenyl)imidazo[1,5-f][1,2,4]triazin-4(3H)-one;

(−)-2-((3,4-trans)-1-(4-chlorobenzyl)-4-methylpyrrolidin-3-yl)-7-(4-fluoro-2-methylphenyl)imidazo[1,5-f][1,2,4]triazin-4(3H)-one;

(−)-2-((3,4-trans)-1-([1,2,4]triazolo[1,5-a]pyridin-2-ylmethyl)-4-methylpyrrolidin-3-yl)-7-(4-fluoro-2-methylphenyl)imidazo[1,5-f][1,2,4]triazin-4(3H)-one;

(−)-7-(4-fluoro-2-methylphenyl)-2-((3,4-trans)-1-(4-fluorobenzyl)-4-methylpyrrolidin-3-yl)imidazo[1,5-f][1,2,4]triazin-4(3H)-one;

(−)-7-(4-fluoro-2-methylphenyl)-2-((3,4-trans)-1-(imidazo[1,2-a]pyridin-2-ylmethyl)-4-methylpyrrolidin-3-yl)imidazo[1,5-f][1,2,4]triazin-4(3H)-one;

(−)-7-(4-fluoro-2-methylphenyl)-2-((3,4-trans)-4-methyl-1-(pyrazin-2-ylmethyl)pyrrolidin-3-yl)imidazo[1,5-f][1,2,4]triazin-4(3H)-one;

(−)-7-(4-fluoro-2-methylphenyl)-2-((3,4-trans)-4-methyl-1-(pyridin-2-ylmethyl)pyrrolidin-3-yl)imidazo[1,5-f][1,2,4]triazin-4(3H)-one;

(−)-7-(4-fluoro-2-methylphenyl)-2-((3,4-trans)-4-methyl-1-(pyridin-3-ylmethyl)pyrrolidin-3-yl)imidazo[1,5-f][1,2,4]triazin-4(3H)-one;

(−)-2-((3,4-trans)-4-methyl-1-(4-(trifluoromethyl)pyrimidin-2-yl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(2,2,2-trifluoroethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((2-methylpyridin-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(quinolin-8-ylmethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((3-methylpyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((2-methylpyridin-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((2-propylpyrimidin-5-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(2-(pyrimidin-2-yl)ethyl)pyrrolidin-3-yl)-7-(tetrahydro-2H-pyran-4-yl)imidazo[1,5-f][1,2,4]triazin-4(3H)-one;

(−)-2-((3,4-trans)-1-((1,5-naphthyridin-4-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((1,8-naphthyridin-4-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((2-(dimethylamino)pyrimidin-4-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(cinnolin-3-ylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((4,5,6,7-tetrahydropyrazolo[1,5-a]pyridin-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(2-(pyrimidin-5-yl)ethyl)pyrrolidin-3-yl)-7-(tetrahydro-2H-pyran-4-yl)imidazo[1,5-f][1,2,4]triazin-4(3H)-one;

(−)-2-((3,4-trans)-1-((8-fluoroquinolin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(benzo[c][1,2,5]thiadiazol-5-ylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-imidazol-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-imidazol-5-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-pyrazol-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-pyrazol-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-pyrazol-5-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(thiazol-2-ylmethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(quinuclidin-4-ylmethyl)pyrrolidin-3-yl)-7-(tetrahydro-2H-pyran-4-yl)imidazo[1,5-f][1,2,4]triazin-4(3H)-one;

(−)-2-((3,4-trans)-1-((1,3,5-triazin-2-yl)methyl)-4-methylpyrrolidin-3-yl)-7-(tetrahydro-2H-pyran-4-yl)imidazo[1,5-f][1,2,4]triazin-4(3H)-one;

(−)-2-fluoro-5-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzonitrile;

(−)-2-((3,4-trans)-1-((4,6-dimethylpyrimidin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chloropyrimidin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(2,3-dichlorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(3-chloro-4-fluorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((4-methylpyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((6-methylpyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(pyrido[2,3-d]pyrimidin-2-ylmethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(pyrido[3,2-b]pyrazin-3-ylmethyl)pyrrolidin-3-yl)-7-(tetrahydro-2H-pyran-4-yl)imidazo[1,5-f][1,2,4]triazin-4(3H)-one;

(−)-tert-butyl 4-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)piperidine-1-carboxylate;

(−)-2-((3,4-trans)-1-((1,2,4-oxadiazol-5-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((4,4-difluorocyclohexyl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chlorofuran-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chlorofuran-3-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chlorothiophen-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chlorothiophen-3-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(cyclopentylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(cyclopropylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(furan-2-ylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(furan-3-ylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methylpiperidin-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((tetrahydro-2H-pyran-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(piperidin-4-ylmethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(thiophen-2-ylmethyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(thiophen-3-ylmethyl)pyrrolidin-3-yl)-7-(tetrahydro-2H-pyran-4-yl)imidazo[1,5-f][1,2,4]triazin-4(3H)-one;

(−)-2-((3,4-trans)-1-((2-methoxypyridin-4-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((2-methoxypyrimidin-5-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((4-methoxypyridin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-chloropyridin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-fluoropyridin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-methoxypyridin-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-methoxypyridin-3-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(2-chloro-5-fluorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(4-chloro-3-(trifluoromethyl)benzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(4-chloro-3-methylbenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(5-chloro-2-fluorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((5-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((6-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(2-(trifluoromethoxy)benzyl)pyrrolidin-3-yl)-7-(tetrahydro-2H-pyran-4-yl)imidazo[1,5-f][1,2,4]triazin-4(3H)-one;

(−)-2-((3,4-trans)-1-((2-methoxypyridin-4-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((5-methoxypyridin-3-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(2-chloro-3,6-difluorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(2-chloro-6-fluorobenzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(3-chloro-5-(trifluoromethyl)benzyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((3-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((4-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((5-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((6-(trifluoromethyl)pyridin-2-yl)methyl)pyrrolidin-3-yl)-7-(tetrahydro-2H-pyran-4-yl)imidazo[1,5-f][1,2,4]triazin-4(3H)-one;

(−)-N,N-dimethyl-2-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(−)-N,N-dimethyl-3-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(−)-N,N-dimethyl-4-(((3,4-trans)-3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzamide;

(−)-2-((3,4-trans)-1-((1,2,4-oxadiazol-3-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-((1,3,4-oxadiazol-2-yl)methyl)-4-methylpyrrolidin-3-yl)-7-(tetrahydro-2H-pyran-4-yl)imidazo[1,5-f][1,2,4]triazin-4(3H)-one;

(−)-2-((3,4-trans)-1-(biphenyl-4-ylmethyl)-4-methylpyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-1,2,4-triazol-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((1-methyl-1H-imidazol-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((2-methylthiazol-4-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((5-(trifluoromethyl)-1,2,4-oxadiazol-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((5-methyl-1,2,4-oxadiazol-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-((5-methyl-1H-1,2,4-triazol-3-yl)methyl)pyrrolidin-3-yl)-7-(tetrahydro-2H-pyran-4-yl)imidazo[1,5-f][1,2,4]triazin-4(3H)-one;

(−)-2-((3,4-trans)-4-methyl-1-(4-(pyridin-4-yl)benzyl)pyrrolidin-3-yl)-7-(tetrahydro-2H-pyran-4-yl)imidazo[1,5-f][1,2,4]triazin-4(3H)-one; and (−)-2-((3,4-trans)-4-methyl-1-(oxazol-2-ylmethyl)pyrrolidin-3-yl)-7-(tetrahydro-2H-pyran-4-yl)imidazo[1,5-f][1,2,4]triazin-4(3H)-one;

or a pharmaceutically acceptable salt thereof.

2. A pharmaceutical composition comprising a compound of claim 1 or a pharmaceutically acceptable salt thereof, and a pharmaceutically acceptable carrier or excipient.

* * * * *